(12) United States Patent
Clark et al.

(10) Patent No.: US 7,816,522 B2
(45) Date of Patent: Oct. 19, 2010

(54) TRIAZOLONE DERIVATIVES

(75) Inventors: Richard Clark, Tsukuba (JP);
Fumiyoshi Matsuura, Tsukuba (JP);
Kazunobu Kira, Tsukuba (JP);
Shinsuke Hirota, Tsukuba (JP); Hiroshi Azuma, Tsukuba (JP); Tadashi Nagakura, Tsukuba (JP); Tatsuo Horizoe, Tsukuba (JP); Kimiyo Tabata, Tsukuba (JP); Kazutomi Kusano, Tsukuba (JP); Takao Omae, Tsukuba (JP); Atsushi Inoue, Tsukuba (JP)

(73) Assignee: Eisai Co., Ltd., Tokyo (JP)

( * ) Notice: Subject to any disclaimer, the term of this patent is extended or adjusted under 35 U.S.C. 154(b) by 284 days.

(21) Appl. No.: 11/723,893

(22) Filed: Mar. 22, 2007

(65) Prior Publication Data

US 2008/0015199 A1 Jan. 17, 2008

Related U.S. Application Data

(60) Provisional application No. 60/786,687, filed on Mar. 29, 2006, provisional application No. 60/804,878, filed on Jun. 15, 2006, provisional application No. 60/838,418, filed on Aug. 18, 2006.

(30) Foreign Application Priority Data

| Mar. 24, 2006 | (JP) | ............................ P2006-083486 |
| Jun. 12, 2006 | (JP) | ............................ P2006-162594 |
| Aug. 10, 2006 | (JP) | ............................ P2006-218819 |

(51) Int. Cl.
*A61K 31/41* (2006.01)
*A61K 31/415* (2006.01)
*C07D 233/00* (2006.01)
*C07D 249/00* (2006.01)

(52) U.S. Cl. ........................ 544/242; 546/184; 548/255; 548/262.2; 548/356.1; 548/300.1; 548/400

(58) Field of Classification Search ................. 544/242; 546/184; 548/255, 262.2, 356.1, 300.1, 400
See application file for complete search history.

(56) References Cited

U.S. PATENT DOCUMENTS

| 6,916,837 | B2 | 7/2005 | Satoh et al. |
| 7,576,098 | B2 | 8/2009 | Glunz et al. |
| 2002/0004608 | A1 | 1/2002 | Alig et al. |
| 2002/0052417 | A1 | 5/2002 | Klingler et al. |
| 2003/0181766 | A1 | 9/2003 | Satoh et al. |
| 2004/0242627 | A1 | 12/2004 | Suzuki et al. |
| 2004/0254376 | A1 | 12/2004 | Suzuki et al. |
| 2005/0004197 | A1 | 1/2005 | Suzuki et al. |
| 2005/0004204 | A1 | 1/2005 | Suzuki et al. |
| 2005/0245592 | A1 | 11/2005 | Suzuki et al. |
| 2008/0015199 | A1 | 1/2008 | Clark et al. |
| 2008/0132507 | A1 | 6/2008 | Clark et al. |
| 2009/0270433 | A1 | 10/2009 | Clark et al. |

FOREIGN PATENT DOCUMENTS

| AU | 58281/80 A | 11/1980 |
| EP | 0 019 586 A | 11/1980 |
| EP | 1 020 434 A1 | 7/2000 |
| EP | 1 078 917 A1 | 2/2001 |
| EP | 1 312 602 A1 | 5/2003 |
| EP | 1 828 152 | 9/2007 |
| JP | 2002-509924 A | 4/2002 |
| JP | 2002-543176 A | 12/2002 |
| JP | 2003-212837 A | 7/2003 |
| JP | 2003-534311 A | 11/2003 |
| JP | 2003-535844 A | 12/2003 |
| SU | 1512055 A1 | 7/1992 |
| WO | WO-99/10316 A1 | 3/1999 |
| WO | WO-99/41231 A1 | 8/1999 |
| WO | WO-99/50255 A2 | 10/1999 |
| WO | WO-00/35858 A1 | 6/2000 |
| WO | WO-00/41531 A2 | 7/2000 |
| WO | WO-00/58346 | 10/2000 |
| WO | WO 00/58346 | * 10/2000 |
| WO | WO-00/66545 | 11/2000 |
| WO | WO-02/085855 | 10/2002 |
| WO | WO-2004/032846 A2 | 4/2004 |
| WO | WO-2004/101555 A1 | 11/2004 |
| WO | WO-2006/041119 A1 | 4/2006 |

(Continued)

OTHER PUBLICATIONS

Roussel et al., "Inhibition of the Tissue Factor/Factor VIIa Complex—Lead Optimisation Using Combinatorial Chemistry," Tetrahedron, vol. 55, pp. 6219-6230 (1999).

(Continued)

*Primary Examiner*—Susannah Chung
(74) *Attorney, Agent, or Firm*—Birch, Stewart, Kolasch & Birch, LLP

(57) ABSTRACT

A Compound represented by the following general formula (1), salts thereof or hydrates of the foregoing is a novel compound useful for treatment and/or prevention of diseases associated with thrombus formation, and which is safer with suitable physicochemical stability.

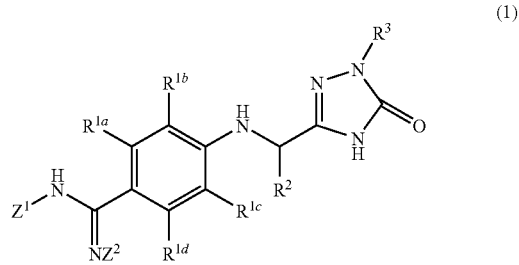

(1)

[wherein $R^{1a}$, $R^{1b}$, $R^{1c}$ and $R^{1d}$ each independently represent hydrogen, etc.; $R^2$ represents optionally substituted phenyl, etc.; $R^3$ represents optionally substituted C6-10 aryl, etc.; and $Z^1$ and $Z^2$ each independently represent hydrogen]

5 Claims, No Drawings

FOREIGN PATENT DOCUMENTS

| WO | WO-2006/062972 A2 | 6/2006 |
|---|---|---|
| WO | WO 2007/111212 | 10/2007 |

OTHER PUBLICATIONS

Database WPI Week 199323, Thomson Scientific, London, GB 1993-186830, XP002540626.

Vippagunta et al., "Crystalline Solids," *Adv. Drug Delivery Rev.*, 48, pp. 3-26 (2001).

McMahon et al., "VEGF Receptor Signaling in Tumor Angiogenesis," *The Oncologist*, 5 (suppl 1): pp. 3-10 (2000).

Fu et al., "Anti-apoptotic role . . . ," *Biochemical and Biophysical Research Comm.*, 349, pp. 504-512 (2006).

Pinedo et al., "Translational Research . . . ," *The Oncologist*, 5 (suppl 1): pp. 1-2 (2000).

Office Action of Jun. 24, 2009 in U.S. Appl. No. 11/665,385.

"Cancer." Medline Plus. (2009). Accessed Mar. 17, 2009. <http://www.nlm.nih.gov/medlineplus/cancer.html>.

Golub et al. "Molecular Classification of Cancer: Class Discovery and Class Prediction by Gene Expression Monitoring." Science (1999), vol. 286, 521-537.

Lala et al. "Role of nitric oxide in tumor progression: Lessons form experimental tumors." Cancer and Metastasis Reviews (1998), 17(1), 91-106.

Notice of Allowance of Feb. 23, 2010 in U.S. Appl. No. 11/665,385.

Notice of Allowance of Feb. 23, 2010 in U.S. Appl. No. 12/234,116.

International Preliminary Report on Patentability (Forms PCT/IB/338 and PCT/IB/373) and Written Opinion of the International Searching Authority (Form PCT/ISA/327) issued Apr. 15, 2010, in International Application No. PCT/JP2008/066944.

* cited by examiner

TRIAZOLONE DERIVATIVES

RELATED APPLICATIONS

This application claims priority to U.S. Provisional Applications 60/786,687 filed on Mar. 29, 2006, 60/804,878 filed on Jun. 15, 2006, and 60/838,418 filed on Aug. 18, 2006 as well as Japanese Patent Applications 2006-083,486 filed on Mar. 24, 2006, 2006-162,594 filed on Jun. 12, 2006 and 2006-218,819 filed on Aug. 10, 2006, all of which are herein incorporated by reference in their entirety.

BACKGROUND OF THE INVENTION

1. Field of the Invention

The present invention relates to novel triazolone derivatives which are useful as medicaments, to their pharmacologically acceptable salts, or hydrates thereof, and to therapeutic or prophylactic agents for diseases associated with thrombus formation comprising the same as active ingredients.

2. Related Background Art

Living organisms with damaged blood vessels avoid hemorrhage death by rapid production of thrombin. However, excess production of thrombin due to inflammatory reaction in damaged blood vessels causes thrombosis, which impairs the function of essential organs. Thrombin inhibitors such as heparin and warfarin, which inhibit thrombin production or directly block thrombin activity, have long been used as anticoagulants to treat or prevent thrombosis. Still, it cannot be said that such medicaments are very satisfactory from a medical standpoint, and efforts continue throughout the world toward research and development of new orally administrable anticoagulants with excellent dose response and low risk of bleeding.

The blood clotting mechanism has been classified into two pathways, the "intrinsic clotting pathway" which begins with activation of factor XII (FXII) upon contact with negative charged substances, and the "extrinsic clotting pathway" which is activated by tissue factor (TF) and factor VII (FVII). Since the pathology of thrombosis onset is associated with specific expression of TF, it has been suggested that extrinsic clotting is of major importance. Compounds that inhibit clotting factor VIIa, which is furthest upstream in the extrinsic clotting pathway of the clotting cascade, are thought to have potential use as therapeutic and/or prophylactic agents for diseases associated with thrombus formation, such as thrombosis, in which the extrinsic clotting mechanism plays a part.

As compounds that inhibit clotting factor VIIa there are known in the prior art amidinonaphthol derivatives (see Nonpatent document 1), amidino derivatives (see Patent document 1), N-sulfonyl dipeptide derivatives (see Patent document 2), 6-[[(allyl)oxy]methyl]naphthalene-2-carboxyimidamide derivatives (see Patent document 3) and phenylglycine derivatives (Patent documents 4 and 5).

However, these known compounds are inadequate from the standpoint of inhibition activity against clotting factor VIIa, blood clotting effects and thrombosis-treating effects.

[Non-patent document 1] Tetrahedron, 55, p. 6219, 1999
[Patent document 1] EP 1078917
[Patent document 2] WO 00/58346
[Patent document 3] WO 00/66545
[Patent document 4] WO 00/35858
[Patent document 5] WO 00/41531

SUMMARY OF THE INVENTION

It is an object of the present invention, which has been accomplished in light of the aforementioned problems of the prior art, to provide novel triazolone derivatives having serine protease inhibitory activity, and particularly excellent inhibitory activity against clotting factor VIIa, as well as their pharmacologically acceptable salts and hydrates thereof, and therapeutic and/or prophylactic agents for diseases associated with thrombus formation, that employ the foregoing.

As a result of much diligent research in light of the circumstances described above, the present inventors have succeeded in synthesizing novel triazolone derivatives having a specific chemical structure, and have completed this invention upon discovering that these compounds have excellent inhibitory activity against clotting factor VIIa, and particularly that they are useful as therapeutic and/or prophylactic agents for diseases associated with thrombus formation. In other words, the present invention provides the following [1]-[34].

[1] A compound represented by general formula (I), or a salt thereof or a hydrate of the foregoing:

[Chemical Formula 1]

(1)

wherein $R^{1a}$, $R^{1b}$, $R^{1c}$ and $R^{1d}$ each independently represent hydrogen, hydroxyl, C1-6 alkyl or halogen;

$R^2$ represents C6-10 aryl optionally having 1-5 substituents selected from Group A1 below, 5- to 10-membered heteroaryl optionally having 1-5 substituents selected from Group A1 below or a 9- to 12-membered benzene-fused cyclic group optionally having 1-5 substituents selected from Group A1 below;

$R^3$ represents a 5- or 6-membered non-aromatic heterocyclic group optionally having 1-5 substituents selected from Group A1 below, C6-10 aryl optionally having 1-5 substituents selected from Group A1 below or a 5- to 10-membered heteroaryl optionally having 1-5 substituents selected from Group A1 below; and $Z^1$ and $Z^2$ represent hydrogen, wherein Group A1 consists of hydroxyl, halogen, cyano, nitro, oxo, C1-6 alkyl optionally having 1-3 substituents selected from Group B1 below, C3-8 cycloalkyl optionally having 1-5 substituents selected from Group B1 below, C2-6 alkenyl, C2-6 alkynyl, C1-6 alkoxy optionally having 1-3 substituents selected from Group B1 below, C3-8 cycloalkyloxy optionally having 1-5 substituents selected from Group B1 below, C2-6 alkenyloxy, C2-6 alkynyloxy, C1-6 alkylthio, C1-6 alkylsulfinyl, C1-6 alkylsulfonyl, C1-6 alkylsulfonyloxy, C6-10 aryl optionally having 1-5 substituents selected from Group B1 below, C6-10 aryloxy optionally having 1-5 substituents selected from Group B1 below, 5- to 10-membered heteroaryl optionally having 1-5 substituents selected from Group B1 below, 5- to 10-membered heteroaryloxy optionally having 1-5 substituents selected from Group B1 below, a 5- or 6-membered non-aromatic heterocyclic group optionally having 1-5 substituents selected from Group B1 below, a 5- or 6-membered non-aromatic heterocyclooxy group optionally having 1-5 substituents selected from Group B1 below, a group represented by the formula —NR$^{1t}$—R$^{2t}$ and a group represented by the formula —CO—R$^{3t}$, where R$^{1t}$ and R$^{2t}$ each independently represent hydrogen, C1-6 alkyl optionally having 1-3 substituents selected from Group B1 below, C2-6 alkenyl, C2-7 alkylcarbonyl optionally having 1-3 substituents selected from Group B1 below, C2-7 alkoxycarbonyl optionally having 1-3 substituents selected from Group B1 below, C1-6 alkylsulfonyl optionally having 1-3 substituents selected from Group B1 below, carbamoyl, aminosulfonyl, C6-10 aryl optionally having 1-5 substituents selected from Group B1 below or 5- to 10-membered heteroaryl optionally having 1-5 substituents selected from Group B1 below, and R$^{3t}$ represents hydroxyl, C1-6 alkyl optionally having 1-3 substituents selected from Group B1 below, C1-6 alkoxy optionally having 1-3 substituents selected from Group B1 below, amino, mono(C1-6 alkyl)amino optionally having 1-3 substituents selected from Group B1 below or di(C1-6 alkyl)amino optionally having 1-3 substituents selected from Group B1 below, wherein Group B1 consists of hydroxyl, halogen, cyano, oxo, C1-6 alkoxy optionally having halogen, C3-8 cycloalkyl, amino, mono(C1-6 alkyl)amino, di(C1-6 alkyl)amino, carbamoyl, mono(C1-6 alkyl)aminocarbonyl, di(C1-6 alkyl)aminocarbonyl, C6-10 aryl optionally having 1-5 substituents selected from Group C1 below and 5- to 10-membered heteroaryl optionally having 1-5 substituents selected from Group C1 below, wherein Group C1 consists of halogen, C1-6 alkyl and C1-6 alkoxy.

[2] A compound represented by general formula (1-1), or a salt thereof or a hydrate of the foregoing:

[Chemical Formula 2]

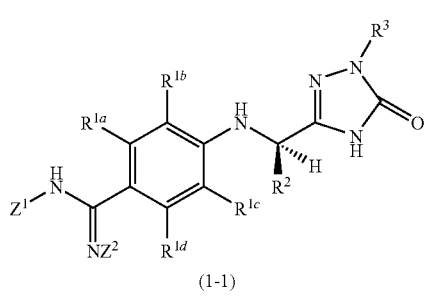

(1-1)

wherein R$^{1a}$, R$^{1b}$, R$^{1c}$, R$^{1d}$, R$^2$, R$^3$, Z$^1$ and Z$^2$ have the same definitions as R$^{1a}$, R$^{1b}$, R$^{1c}$, R$^{1d}$, R$^2$, R$^3$, Z$^1$ and Z$^2$ in claim 1.

[3] A compound represented by general formula (1-2), a salt thereof or a hydrate of the foregoing:

[Chemical Formula 3]

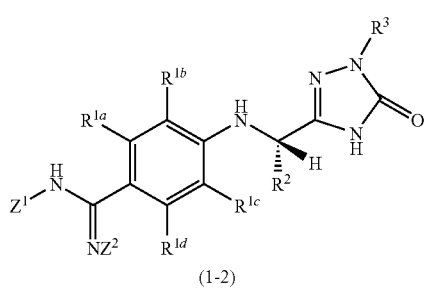

(1-2)

wherein R$^{1a}$, R$^{1b}$, R$^{1c}$, R$^{1d}$, R$^2$, R$^3$, Z$^1$ and Z$^2$ have the same definitions as R$^{1a}$, R$^{1b}$, R$^{1c}$, R$^{1d}$, R$^2$, R$^3$, Z$^1$ and Z$^2$ in claim 1.

[4] A compound according to any one of [1] to [3] above, or a salt thereof or a hydrate of the foregoing, wherein R$^{1a}$, R$^{1b}$, R$^{1c}$ and R$^{1d}$ are each independently hydrogen, fluorine or hydroxyl.

[5] A compound according to any one of [1] to [4], or a salt thereof or a hydrate of the foregoing, wherein R$^2$ is phenyl optionally having 1-4 substituents selected from Group D1 below, pyridyl optionally having 1-3 substituents selected from Group D1 below or a 9- to 12-membered benzene-fused cyclic group optionally having 1-4 substituents selected from Group D1 below, wherein Group D1 consists of hydroxyl, halogen, C1-6 alkyl optionally having 1-3 substituents selected from Group D2 below, C2-6 alkenyl, C2-6 alkynyl, C1-6 alkoxy optionally having 1-3 substituents selected from Group D2 below, C2-6 alkenyloxy, C1-6 alkylsulfonyloxy, a 5- or 6-membered non-aromatic heterocyclooxy group optionally having 1-3 substituents selected from Group D2 below and C2-7 alkylcarbonyl, wherein Group D2 consists of hydroxyl, halogen, cyano, oxo, C1-6 alkoxy optionally having halogen, mono(C1-6 alkyl)amino, di(C1-6 alkyl)amino, mono(C1-6 alkyl)aminocarbonyl and di(C1-6 alkyl)aminocarbonyl.

[6] A compound according to any one of [1] to [4], or a salt thereof or a hydrate of the foregoing, wherein R$^2$ is phenyl optionally having 1-4 substituents selected from Group D1 below, wherein Group D1 consists of hydroxyl, halogen, C1-6 alkyl optionally having 1-3 substituents selected from Group D2 below, C2-6 alkenyl, C2-6 alkynyl, C1-6 alkoxy optionally having 1-3 substituents selected from Group D2 below, C2-6 alkenyloxy, C1-6 alkylsulfonyloxy, a 5- or 6-membered non-aromatic heterocyclooxy group optionally having 1-3 substituents selected from Group D2 below and C2-7 alkylcarbonyl, wherein Group D2 consists of hydroxyl, halogen, cyano, oxo, C1-6 alkoxy optionally having halogen, mono(C1-6 alkyl)amino, di(C1-6 alkyl)amino, mono(C1-6 alkyl)aminocarbonyl and di(C1-6 alkyl)aminocarbonyl.

[7] A compound according to any one of [1] to [4], or a salt thereof or a hydrate of the foregoing, wherein R$^2$ is phenyl optionally having 2 or 3 substituents selected from Group D3 below, wherein Group D3 consists of fluorine, chlorine, methyl optionally having 1 substituent selected from Group D4 below, ethyl optionally having 1 substituent selected from Group D4 below, vinyl, ethynyl, methoxy optionally having 1 or 2 substituents selected from Group D4 below, ethoxy optionally having 1 or 2 substituents selected from Group D4 below, 1-propyloxy optionally having 1 or 2 substituents selected from Group D4 below, 2-propyloxy optionally having 1 or 2 substituents selected from Group D4 below, allyloxy, tetrahydrofuryloxy, tetrahydropyranyloxy and acetyl, wherein Group D4 consists of hydroxyl, fluorine, cyano, methoxy, methylamino, dimethylamino, methylaminocarbonyl and dimethylaminocarbonyl.

[8] A compound according to any one of [1] to [4], or a salt thereof or a hydrate of the foregoing, wherein R$^2$ is a group represented by the formula:

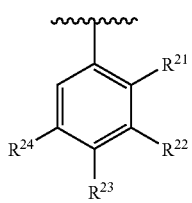

wherein R$^{21}$ represents hydrogen, fluorine or chlorine;

R$^{22}$ represents hydrogen, hydroxyl, methyl optionally having 1 substituent selected from Group D5 below, ethyl optionally having 1 substituent selected from Group D5 below, methoxy optionally having 1 substituent selected from Group D5 below, ethoxy optionally having 1 or 2 substituents selected from Group D5 below, 1-propyloxy optionally having 1 substituent selected from Group D5 below, 2-propyloxy optionally having 1 substituent selected from Group D5 below, allyloxy, tetrahydrofuryloxy, tetrahydropyranyloxy or acetyl;

R$^{23}$ represents hydrogen, fluorine, hydroxyl, methoxy optionally having 1 substituent selected from Group D6 below, ethoxy optionally having 1 substituent selected from Group D6 below or 2-propyloxy optionally having 1 substituent selected from Group D6 below; and R$^{24}$ represents hydrogen, fluorine, hydroxyl, methyl optionally having 1 substituent selected from Group D7 below, ethyl, vinyl, ethynyl, methoxy optionally having 1 substituent selected from Group D7 below, ethoxy optionally having 1 substituent selected from Group D7 below, 2-propyloxy or allyloxy, wherein Group D5 consists of hydroxyl, fluorine, cyano, methoxy, dimethylamino, dimethylaminocarbonyl, 2-fluoroethoxy and 2-hydroxyethoxy, wherein Group D6 consists of fluorine, cyano, methoxy, dimethylamino, methylaminocarbonyl and dimethylaminocarbonyl, wherein Group D7 consists of hydroxyl, fluorine, cyano and ethoxy having one methoxy.

[9] A compound according to [8], or a salt thereof or a hydrate of the foregoing, wherein R$^{21}$ is hydrogen or fluorine.

[10] A compound according to [8] or [9], or a salt thereof or a hydrate of the foregoing, wherein R$^{22}$ is hydrogen, hydroxyl, cyanomethyl, methoxymethyl, methoxy, dimethylaminocarbonylmethoxy, ethoxy, 2-fluoroethoxy, 2-hydroxyethoxy, 2-methoxyethoxy, 2-(dimethylamino)ethoxy, tetrahydrofuryloxy, tetrahydropyranyloxy, fluoromethoxy, 3-hydroxypropyloxy, 2-fluoroethoxymethyl or 2-hydroxyethoxymethyl.

[11] A compound according to any one of [8] to [10], or a salt thereof or a hydrate of the foregoing, wherein R$^{23}$ is hydrogen, fluorine, methoxy, cyanomethoxy, ethoxy, 2-propyloxy or 2-methoxyethoxy.

[12] A compound according to any one of [8] to [11], or a salt thereof or a hydrate of the foregoing, wherein R$^{24}$ is hydrogen, hydroxyl, methyl, methoxymethyl, ethyl, vinyl, ethynyl, methoxy, ethoxy or 2-fluoroethoxy.

[13] A compound according to any one of [1] to [4], or a salt thereof or a hydrate of the foregoing, wherein R$^2$ is pyridyl optionally having 1-3 substituents selected from Group D1 below, wherein Group D1 consists of hydroxyl, halogen, C1-6 alkyl optionally having 1-3 substituents selected from Group D2 below, C2-6 alkenyl, C2-6 alkynyl, C1-6 alkoxy optionally having 1-3 substituents selected from Group D2 below, C2-6 alkenyloxy, C1-6 alkylsulfonyloxy, a 5- or 6-membered non-aromatic heterocyclooxy group optionally having 1-3 substituents selected from Group D2 below and C2-7 alkylcarbonyl, wherein Group D2 consists of hydroxyl, halogen, cyano, oxo, C1-6 alkoxy optionally having halogen, mono(C1-6 alkyl)amino, di(C1-6 alkyl)amino, mono(C1-6 alkyl)aminocarbonyl and di(C1-6 alkyl)aminocarbonyl.

[14] A compound according to any one of [1] to [4], or a salt thereof or a hydrate of the foregoing, wherein R$^2$ is pyridyl having 2 substituents selected from the group consisting of C1-6 alkyl and C1-6 alkoxy.

[15] A compound according to any one of [1] to [4], or a salt thereof or a hydrate of the foregoing, wherein R$^2$ is pyridyl having 2 substituents selected from the group consisting of methyl, methoxy and ethoxy.

[16] A compound according to any one of [1] to [4], or a salt thereof or a hydrate of the foregoing, wherein R$^2$ is a group represented by the formula:

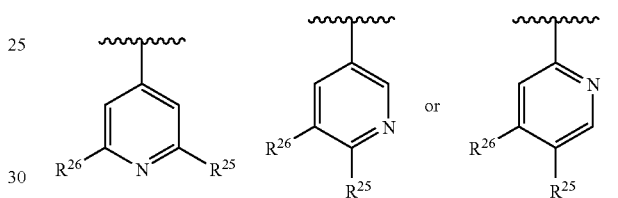

wherein R$^{25}$ represents methyl or methoxy; and R$^{26}$ represents methoxy or ethoxy.

[17] A compound according to any one of [1] to [4], or a salt thereof or a hydrate of the foregoing, wherein R$^2$ is a 9- to 12-membered benzene-fused cyclic group optionally having 1-4 substituents selected from Group D1 below, wherein Group D1 consists of hydroxyl, halogen, C1-6 alkyl optionally having 1-3 substituents selected from Group D2 below, C2-6 alkenyl, C2-6 alkynyl, C1-6 alkoxy optionally having 1-3 substituents selected from Group D2 below, C2-6 alkenyloxy, C1-6 alkylsulfonyloxy, a 5- or 6-membered non-aromatic heterocyclooxy group optionally having 1-3 substituents selected from Group D2 below and C2-7 alkylcarbonyl, wherein Group D2 consists of hydroxyl, halogen, cyano, oxo, C1-6 alkoxy optionally having halogen, mono(C1-6 alkyl)amino, di(C1-6 alkyl)amino, mono(C1-6 alkyl)aminocarbonyl and di(C1-6 alkyl)aminocarbonyl.

[18] A compound according to any one of [1] to [4], or a salt thereof or a hydrate of the foregoing, wherein R$^2$ is a group represented by the formula:

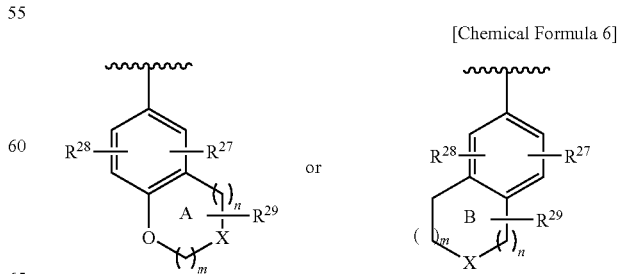

wherein R$^{27}$ represents hydrogen or halogen;

$R^{28}$ represents hydrogen, hydroxyl, halogen, C1-6 alkyl optionally having 1-3 substituents selected from Group D8 below, C2-6 alkenyl, C2-6 alkynyl, C1-6 alkoxy optionally having 1-3 substituents selected from Group D8 below or C2-7 alkylcarbonyl;

$R^{29}$ represents hydrogen, cyano, C1-6 alkyl optionally having 1-3 substituents selected from Group D8 below, C1-6 alkoxy optionally having 1-3 substituents selected from Group D8 below or carbamoyl;

X represents carbon optionally having 1 or 2 substituents selected from Group D8 below, nitrogen optionally having 1 substituent selected from Group D8 below or oxygen;

m represents an integer of 0-3 and n represents an integer of 0-2, with the proviso that the sum of m and n is 1-4; and Rings A and B optionally contain one double bond in the ring and optionally have an oxo group on the ring, wherein Group D8 consists of hydrogen, hydroxyl, halogen, C1-6 alkoxy, mono(C1-6 alkyl)amino, di(C1-6 alkyl)amino, mono(C1-6 alkyl)aminocarbonyl, di(C1-6 alkyl)aminocarbonyl and C1-6 alkyl optionally having halogen.

[19] A compound according to [18], or a salt thereof or a hydrate of the foregoing, wherein $R^2$ is a group represented by the formula:

[Chemical Formula 7]

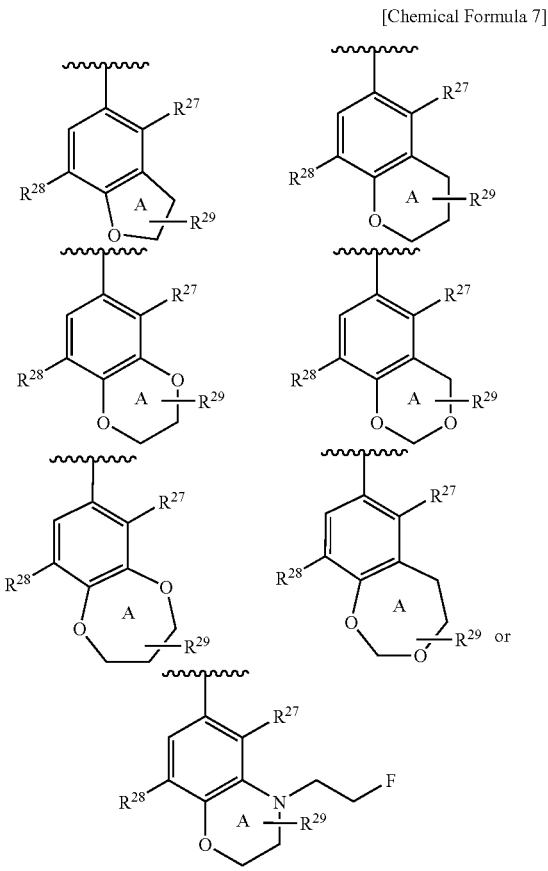

wherein $R^{27}$ represents hydrogen or halogen;

$R^{28}$ represents hydrogen, hydroxyl, C1-6 alkyl optionally having 1-3 substituents selected from Group D8 below, C2-6 alkenyl, C2-6 alkynyl, C1-6 alkoxy optionally having 1-3 substituents selected from Group D8 below or C2-7 alkylcarbonyl;

$R^{29}$ represents hydrogen, cyano, C1-6 alkyl optionally having 1-3 substituents selected from Group D8 below, C1-6 alkoxy optionally having 1-3 substituents selected from Group D8 below or aminocarbonyl; and Ring A optionally has an oxo group on the ring, wherein Group D8 consists of hydrogen, hydroxyl, halogen, C1-6 alkoxy, mono(C1-6 alkyl)amino, di(C1-6 alkyl)amino, mono(C1-6 alkyl)aminocarbonyl, di(C1-6 alkyl)aminocarbonyl, and C1-6 alkyl optionally having halogen.

[20] A compound according to [19], or a salt thereof or a hydrate of the foregoing, wherein $R^{28}$ is methyl, ethyl, methoxy, ethoxy, vinyl or ethynyl.

[21] A compound according to [19] or [20], or a salt thereof or a hydrate of the foregoing, wherein $R^{29}$ is hydrogen.

[22] A compound according to any one of [1] to [21], or a salt thereof or a hydrate of the foregoing, wherein $R^3$ is phenyl optionally having 1-3 substituents selected from Group E1 below, pyridyl optionally having 1-3 substituents selected from Group E1 below, N-oxypyridyl optionally having 1-3 substituents selected from Group E1 below, N—C1-6 alkylpyridinium optionally having 1-3 substituents selected from Group E1 below, pyrazinyl optionally having 1-3 substituents selected from Group E1 below, pyridazinyl optionally having 1-3 substituents selected from Group E1 below, pyrimidinyl optionally having 1-3 substituents selected from Group E1 below, pyrazolyl optionally having 1-3 substituents selected from Group E1 below, imidazolyl optionally having 1-3 substituents selected from Group E1 below, thiazolyl optionally having 1-3 substituents selected from Group E1 below, thienyl optionally having 1-3 substituents selected from Group E1 below or dihydropyrazinyl having an oxo group, with the proviso that when $R^3$ is N—C1-6 alkylpyridinium, $R^3$ forms an ion pair with an anion in the molecule, wherein Group E1 consists of hydroxyl, halogen, cyano, C1-6 alkyl, C1-6 alkoxy, a group represented by the formula —NH—$R^{21t}$ and a group represented by the formula —CO—$R^{31t}$:

where $R^{21t}$ represents hydrogen, C1-6 alkyl, C2-6 alkenyl, C2-7 alkylcarbonyl optionally having 1-3 substituents selected from Group E2 below, C2-7 alkoxycarbonyl optionally having 1-3 substituents selected from Group E2 below, C1-6 alkylsulfonyl, carbamoyl or aminosulfonyl, and $R^{31t}$ represents hydroxyl, C1-6 alkyl, C1-6 alkoxy, amino, mono(C1-6 alkyl)amino or di(C1-6 alkyl)amino), wherein Group E2 consists of hydroxyl, C1-6 alkoxy and C3-8 cycloalkyl.

[23] A compound according to any one of [1] to [21], or a salt thereof or a hydrate of the foregoing, wherein $R^3$ is phenyl optionally having 1 or 2 substituents selected from Group E3 below, pyridyl optionally having 1 or 2 substituents selected from Group E3 below, N-oxypyridyl optionally having 1 or 2 substituents selected from Group E3 below, pyrazinyl optionally having 1 or 2 substituents selected from Group E3 below, pyridazinyl optionally having 1 or 2 substituents selected from Group E3 below, pyrimidinyl optionally having 1 or 2 substituents selected from Group E3 below, pyrazolyl optionally having 1 or 2 substituents selected from Group E3 below, imidazolyl optionally having 1 or 2 substituents selected from Group E3 below, thiazolyl optionally having 1 or 2 substituents selected from Group E3 below, thienyl optionally having 1 or 2 substituents selected from Group E3 below or dihydropyrazinyl having an oxo group, wherein Group E3 consists of halogen, C1-6 alkyl, C1-6 alkoxy, a group represented by the formula —NH—$R^{22t}$, where $R^{22t}$ represents hydrogen or C2-7 alkoxycarbonyl, and a group represented by the formula —CO—$R^{32t}$,
where $R^{32t}$ represents hydroxyl, C1-6 alkoxy or amino.

[24] A compound according to any one of [1] to [21], or a salt thereof or a hydrate of the foregoing, wherein $R^3$ is phenyl optionally having one group selected from Group E4 below, pyridyl optionally having one group selected from Group E5 below, N-oxypyridyl, pyrazinyl, pyridazinyl, pyrimidinyl, pyrazolyl optionally having one group selected from Group E4 below, imidazolyl optionally having one group selected from Group E4 below, thiazolyl optionally having one group selected from Group E4 below, thienyl optionally having one group selected from Group E4 below or dihydropyrazinyl having an oxo group,
wherein Group E4 consists of methoxy, carboxyl, carbamoyl, methoxycarbonyl and methoxycarbonylamino,
wherein Group E5 consists of fluorine, methyl, methoxy and amino.

[25] A medicament comprising a compound according to any one of [1] to [24], or a salt thereof or a hydrate of the foregoing.

[26] A therapeutic and/or prophylactic agent for a disease associated with thrombus formation, comprising a compound according to any one of [1] to [24], or a salt thereof or a hydrate of the foregoing.

[27] A therapeutic and/or prophylactic agent for a disease selected from Group F1 below, comprising a compound according to any one of [1] to [24], or a salt thereof or a hydrate of the foregoing.

wherein Group F1 consists of thrombosis, deep vein thrombosis, pulmonary embolism, cerebral infarction, myocardial infarction, acute coronary syndrome, vascular restenosis, disseminated intravascular coagulation syndrome and malignant tumor.

[28] A therapeutic and/or prophylactic agent for a disease selected from Group F2 below, comprising a compound according to any one of [1] to [24], or a salt thereof or a hydrate of the foregoing, wherein Group F2 consists of thrombosis, deep vein thrombosis, pulmonary embolism, cerebral infarction, myocardial infarction, acute coronary syndrome, vascular restenosis and disseminated intravascular coagulation syndrome.

[29] A method for treatment and/or prevention of a disease associated with thrombus formation, which involves administration of a pharmacologically effective dose of a compound according to any one of [1] to [24], or a salt thereof or a hydrate of the foregoing.

[30] A method for treatment and/or prevention of a disease selected from Group F1 below, which involves administration of a pharmacologically effective dose of a compound according to any one of [1] to [24], or a salt thereof or a hydrate of the foregoing,
wherein Group F1 consists of thrombosis, deep vein thrombosis, pulmonary embolism, cerebral infarction, myocardial infarction, acute coronary syndrome, vascular restenosis, disseminated intravascular coagulation syndrome and malignant tumor.

[31] A method for treatment and/or prevention of a disease selected from Group F2 below, which involves administration of a pharmacologically effective dose of a compound according to any one of [1] to [24], or a salt thereof or a hydrate of the foregoing,
wherein Group F2 consists of thrombosis, deep vein thrombosis, pulmonary embolism, cerebral infarction, myocardial infarction, acute coronary syndrome, vascular restenosis and disseminated intravascular coagulation syndrome.

[32] Use of a compound according to any one of [1] to [24], or a salt thereof or a hydrate of the foregoing, for production of a therapeutic and/or prophylactic agent for a disease associated with thrombus formation.

[33] Use of a compound according to any one of [1] to [24], or a salt thereof or a hydrate of the foregoing, for production of a therapeutic and/or prophylactic agent for a disease selected from Group F1 below.
wherein Group F1 consists of thrombosis, deep vein thrombosis, pulmonary embolism, cerebral infarction, myocardial infarction, acute coronary syndrome, vascular restenosis, disseminated intravascular coagulation syndrome and malignant tumor.

[34] Use of a compound according to any one of [1] to [24], or a salt thereof or a hydrate of the foregoing, for production of a therapeutic and/or prophylactic agent for a disease selected from Group F2 below.
wherein Group F2 consists of thrombosis, deep vein thrombosis, pulmonary embolism, cerebral infarction, myocardial infarction, acute coronary syndrome, vascular restenosis and disseminated intravascular coagulation syndrome.

The compounds of the invention have excellent inhibiting effects against clotting factor VIIa and excellent anticoagulant effects, and are therefore useful as therapeutic and/or prophylactic agents for diseases associated with thrombus formation (for example, thrombosis, deep vein thrombosis, pulmonary embolism, cerebral infarction, myocardial infarction, acute coronary syndrome, vascular restenosis or disseminated intravascular coagulation syndrome) (Johannes Ruef & Hugo A Katus, New antithrombotic drugs on the horizon, Expert Opin. Investig. Drugs (2003) 12 (5): 781-797).

Substances with inhibiting effects against clotting factor VIIa have also been reported to exhibit malignant tumor metastasis suppression and reduction. Thus, the compounds of the present invention that have excellent inhibiting effects against clotting factor VIIa are also useful as therapeutic and/or prophylactic agents for malignant tumors and the like (Mattias Belting et al., Regulation of angiogenesis by tissue factor cytoplasmic domain signaling, Nature Medicine (2004) 10 (5): 502-509; X Jiang et al., Formation of tissue factor-factor VIa-factor Xa complex promotes cellular signaling and migration of human breast cancer cells, J Thromb Haemost, (2004) 2: 93-101; Hembrough T A. Swartz G M. Papathanassiu A. Vlasuk G P. Rote W E. Green S J. Pribluda V S., Tissue factor/factor VIIa inhibitors block angiogenesis and tumor growth through a nonhemostatic mechanism. Cancer Research (2003) 63 (11): 2997-3000).

Since the compounds of the invention have excellent suppressing effects against blood clotting, and are safer with suitable physicochemical stability, they are useful as medicaments, and especially as therapeutic and/or prophylactic agents for diseases associated with thrombus formation.

DESCRIPTION OF THE PREFERRED EMBODIMENTS

The present invention will now be explained in detail.
1) The compound represented by general formula (1).
Throughout the present specification, the structural formulas for the compounds will show only one specific isomer for convenience, but the invention includes all isomers such as geometric isomers, optical isomers, stereoisomers and tautomers implied by the compound structures, as well as their isomer mixtures, and the compounds may therefore be any of the isomers or their mixtures, without being limited to the formulas shown for convenience. The compounds of the invention may therefore be in optically active or racemic form, both of which are included without restrictions according to the invention. Polymorphic crystals also exist, and there may be used any crystal form or a mixture thereof without any restrictions, while the compounds of the invention include both anhydrous and hydrated forms.

2) The compound represented by general formula (1-1) and (1-2). Throughout the present specification, the structural formulas for the compounds will show only one specific isomer for convenience, but the invention includes all isomers such as geometric isomers, stereoisomers and tautomers implied by the compound structures, as well as their isomer mixtures, and the compounds may therefore be any of the isomers or their mixtures, without being limited to the formulas shown for convenience. Polymorphic crystals also exist, and there may be used any crystal form or a mixture thereof without any restrictions, while the compounds of the invention include both anhydrous and hydrated forms.

The tautomer represented by general formula (1) includes the compounds represented by general formula (1a) and (1b);

[Chemical Formula 8]

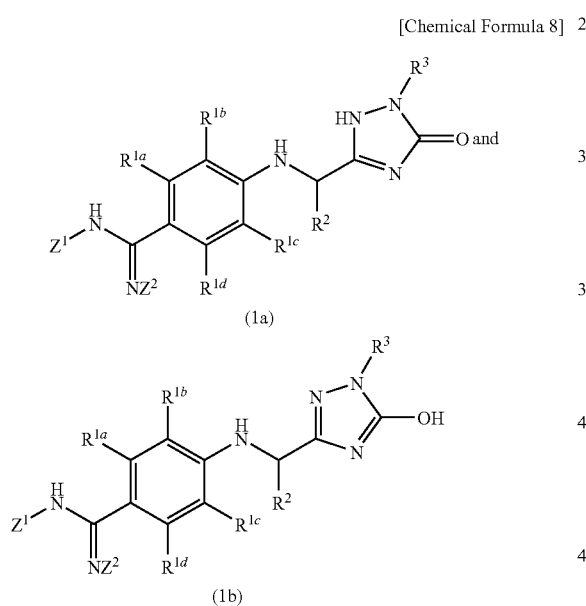

(1a)

(1b)

The tautomer represented by general formula (1-1) includes the compounds represented by general formula (1a-1) and (1b-1);

[Chemical Formula 9]

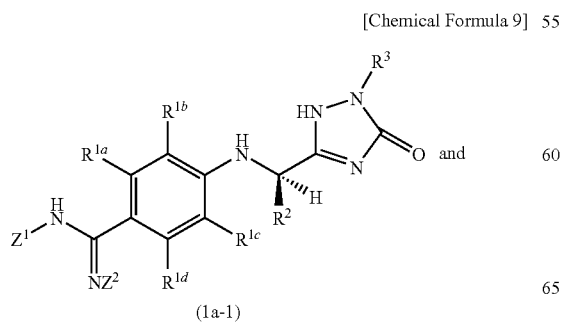

(1a-1)

(1b-1)

The tautomer represented by general formula (1-2) includes the compounds represented by general formula (1a-2) and (1b-2);

[Chemiical Formula 10]

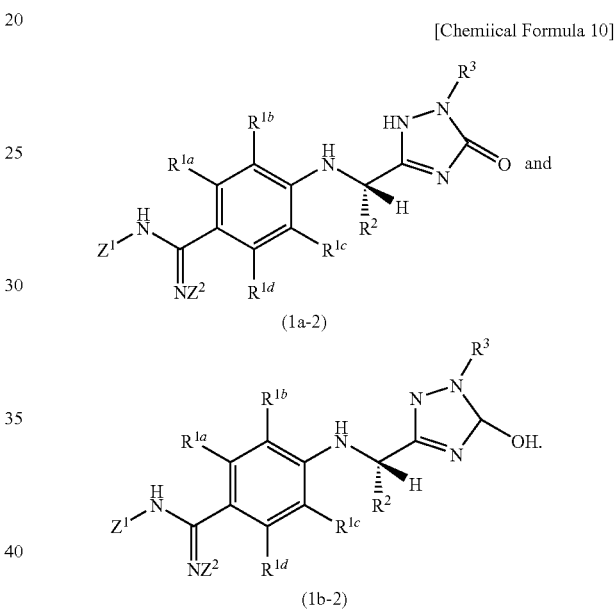

(1a-2)

(1b-2)

The definitions of the terms and symbols used throughout the present specification will now be explained, prior to a more detailed description of the invention.

The term "disease associated with thrombus formation" is not particularly restricted so long as it is a disease with onset directly or 15 indirectly caused by thrombus formation, and as specific examples there may be mentioned thrombosis, deep vein thrombosis, pulmonary embolism, cerebral infarction, myocardial infarction, acute coronary syndrome, vascular restenosis, disseminated intravascular coagulation syndrome and malignant tumor, and preferably thrombosis, deep vein thrombosis, pulmonary embolism, cerebral infarction, myocardial infarction, acute coronary syndrome, vascular restenosis and disseminated intravascular coagulation syndrome.

A "halogen" refers to fluorine, chlorine, bromine or iodine. As preferred examples of "halogen" there may be mentioned fluorine and chlorine.

The term "C1-6 alkyl" refers to a straight-chain or branched C1-6 alkyl group, and as specific examples there may be mentioned methyl, ethyl, 1-propyl (n-propyl), 2-propyl (i-propyl), 2-methyl-1-propyl (i-butyl), 2-methyl-2-propyl (t-butyl), 1-butyl (n-butyl), 2-butyl (s-butyl), 1-pentyl, 2-pentyl, 3-pentyl, 2-methyl-1-butyl, 3-methyl-1-butyl, 2-methyl-2-butyl, 3-methyl-2-butyl, 2,2-dimethyl-1-propyl, 1-hexyl, 2-hexyl, 3-hexyl, 2-methyl-1-pentyl, 3-methyl-1-pentyl, 4-methyl-1-pentyl, 2-methyl-2-pentyl, 3-methyl-2-pentyl, 4-methyl-2-pentyl, 2-methyl-3-pentyl, 3-methyl-3-pentyl, 2,3-dimethyl-1-butyl, 3,3-dimethyl-1-butyl, 2,2-dimethyl-1-butyl, 2-ethyl-1-butyl, 3,3-dimethyl-2-butyl and 2,3-dimethyl-2-butyl.

The term "C2-6 alkenyl" refers to a straight-chain or branched C2-6 alkenyl group containing one double bond, and as specific examples there may be mentioned vinyl(ethenyl), allyl(2-propenyl), 1-propenyl, isopropenyl(1-methylvinyl), 1-butenyl, 2-butenyl, 3-butenyl, pentenyl and hexenyl.

The term "C2-6 alkynyl" refers to a straight-chain or branched alkynyl group containing one triple bond, and as specific examples there may be mentioned ethynyl, 1-propynyl, 2-propynyl, butynyl, pentynyl and hexynyl.

The term "C3-8 cycloalkyl" refers to a C3-8 monocyclic saturated aliphatic hydrocarbon group, and as specific examples there may be mentioned cyclopropyl, cyclobutyl, cyclopentyl, cyclohexyl, cycloheptyl and cyclooctyl.

The term "C6-10 aryl" refers to a C6-10 aromatic hydrocarbon cyclic group, and as specific examples there may be mentioned phenyl and naphthyl.

The term "5- to 10-membered heteroaryl" refers to an aromatic cyclic group having 5-10 atoms composing the ring and containing 1-5 hetero atoms among the atoms composing the ring, and as specific examples there may be mentioned furyl, thienyl, pyrrolyl, imidazolyl, triazolyl, tetrazolyl, thiazolyl, pyrazolyl, oxazolyl, isooxazolyl, isothiazolyl, furazanyl, thiadiazolyl, oxadiazolyl, pyridyl, pyrazinyl, pyridazinyl, pyrimidinyl, triazinyl, purinyl, pteridinyl, quinolyl, isoquinolyl, naphthylidinyl, quinoxalinyl, cinnolinyl, quinazolinyl, phthaladinyl, imidazopyridyl, imidazothiazolyl, imidazooxazolyl, benzothiazolyl, benzooxazolyl, benzoimidazolyl, indolyl, isoindolyl, indazolyl, pyrrolopyridyl, thienopyridyl, furopyridyl, benzothiadiazolyl, benzooxadiazolyl, pyridopyrimidinyl, benzofuryl, benzothienyl, benzo[1,3]dioxole, thienofuryl, N-oxypyridyl and N—C1-6 alkylpyridinium.

The term "5- or 6-membered non-aromatic heterocyclic group" refers to (5) a non-aromatic cyclic group (1) having 5 or 6 atoms composing the ring, (2) containing 1 or 2 hetero atoms among the atoms composing the ring, (3) optionally containing 1 or 2 double bonds in the ring and (4) optionally containing 1 or 2 oxo (carbonyl) groups on the ring, and as specific examples there may be mentioned pyrrolidinyl, piperidinyl, morpholinyl, thiomorpholinyl, tetrahydrofuryl, tetrahydropyranyl, pyridonyl and dihydropyrazinyl.

The term "5- to 8-membered heterocycle" refers to a ring (1) having 5-8 atoms composing the ring, (2) containing 1 or 2 hetero atoms among the atoms composing the ring, (3) optionally containing 1 or 2 double bonds in the ring and (4) optionally containing 1 or 2 oxo (carbonyl) groups on the ring, and as specific examples there may be mentioned pyrrolidine ring, piperidine ring, azepane ring, azocane ring, piperazine ring, diazepane ring, diazocane ring, morpholine ring, thiomorpholine ring, tetrahydrofuran ring, tetrahydropyran ring, oxepane ring, dioxane ring, dioxepane ring, dihydrofuran ring, tetrahydrothiophene ring, tetrahydrothiopyran ring, oxazolidine ring, thiazolidine ring, pyridone ring and dihydropyrazine ring.

The term "9- to 12-membered benzene-fused cyclic group" refers to a cyclic group comprising a "5- to 8-membered heterocycle" as defined above fused with a phenyl group, and as specific preferred examples there may be mentioned groups represented by the formula:

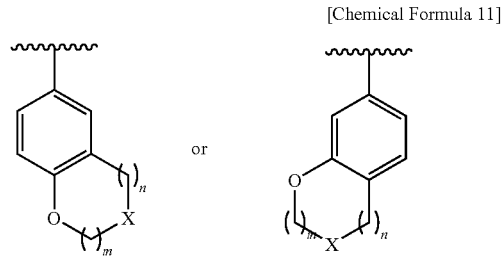

[Chemical Formula 11]

(wherein the symbols are as defined above), and more preferably groups represented by the formula:

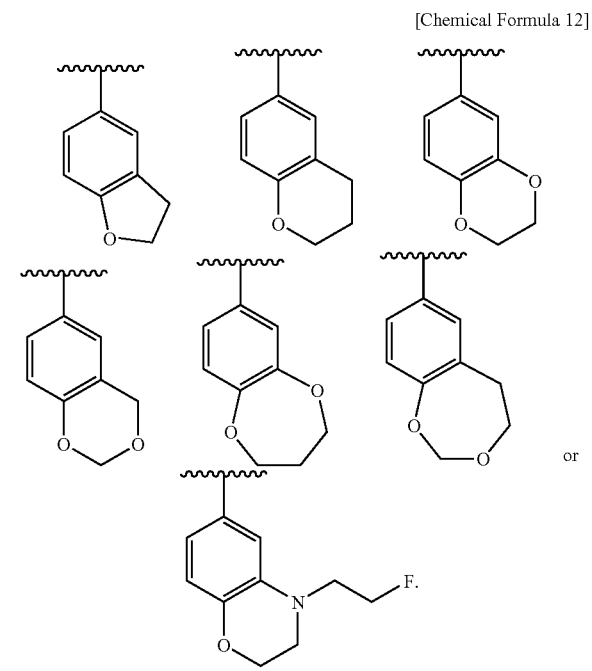

[Chemical Formula 12]

The term "C1-6 alkoxy" refers to a group consisting of an oxy group bonded to "C1-6 alkyl" as defined above, and as specific examples there may be mentioned methoxy, ethoxy, 1-propyloxy, 2-propyloxy, 2-methyl-1-propyloxy, 2-methyl-2-propyloxy, 1-butyloxy, 2-butyloxy, 1-pentyloxy, 2-pentyloxy, 3-pentyloxy, 2-methyl-1-butyloxy, 3-methyl-1-butyloxy, 2-methyl-2-butyloxy, 3-methyl-2-butyloxy, 2,2-dimethyl-1-propyloxy, 1-hexyloxy, 2-hexyloxy, 3-hexyloxy, 2-methyl-1-pentyloxy, 3-methyl-1-pentyloxy, 4-methyl-1-pentyloxy, 2-methyl-2-pentyloxy, 3-methyl-2-pentyloxy, 4-methyl-2-pentyloxy, 2-methyl-3-pentyloxy, 3-methyl-3-pentyloxy, 2,3-dimethyl-1-butyloxy, 3,3-dimethyl-1-butyloxy, 2,2-dimethyl-1-butyloxy, 2-ethyl-1-butyloxy, 3,3-dimethyl-2-butyloxy and 2,3-dimethyl-2-butyloxy.

The term "C3-8 cycloalkyloxy" refers to a group consisting of an oxy group bonded to "C3-8 cycloalkyl" as defined above, and as specific examples there may be mentioned cyclopropyloxy, cyclobutyloxy, cyclopentyloxy, cyclohexyloxy, cycloheptyloxy and cyclooctyloxy.

The term "C2-6 alkenyloxy" refers to a group consisting of an oxy group bonded to "C2-6 alkenyl as defined above, and as specific examples there may be mentioned vinyloxy (ethenyloxy), allyloxy (2-propenyloxy), 1-propenyloxy, isopropenyloxy (1-methylvinyloxy), 1-butenyloxy, 2-butenyloxy, 3-butenyloxy, pentenyloxy and hexenyloxy.

The term "C2-6 alkynyloxy" refers to a group consisting of an oxy group bonded to "C2-6 alkynyl" as defined above, and as specific examples there may be mentioned ethynyloxy, 1-propynyloxy, 2-propynyloxy, butynyloxy, pentynyloxy and hexynyloxy.

The term "C1-6 alkylthio" refers to a group consisting of a thio group bonded to "C1-6 alkyl" as defined above, and as specific examples there may be mentioned methylthio, ethylthio, 1-propylthio, 2-propylthio, butylthio and pentylthio.

The term "C1-6 alkylsulfinyl" refers to a group consisting of a sulfinyl group bonded to "C1-6 alkyl" as defined above, and as specific examples there may be mentioned methylsulfinyl, ethylsulfinyl, 1-propylsulfinyl, 2-propylsulfinyl, butylsulfinyl and pentylsulfinyl.

The term "C1-6 alkylsulfonyl" refers to a group consisting of a sulfonyl group bonded to "C1-6 alkyl" as defined above, and as specific examples there may be mentioned methylsulfonyl, ethylsulfonyl, 1-propylsulfonyl, 2-propylsulfonyl, butylsulfonyl and pentylsulfonyl.

The term "C2-7 alkylcarbonyl" refers to a group consisting of a carbonyl group bonded to "C1-6 alkyl" as defined above, and as specific examples there may be mentioned acetyl, propionyl, isopropionyl, butyryl, isobutyryl, valeryl, isovaleryl and pivaloyl.

The term "C2-7 alkoxycarbonyl" refers to a group consisting of a carbonyl group bonded to "C1-6 alkoxy" as defined above, and as specific examples there may be mentioned methoxycarbonyl, ethoxycarbonyl, 1-propyloxycarbonyl and 2-propyloxycarbonyl.

The term "C6-10 aryloxy" refers to a group consisting of an oxy group bonded to "C6-10 aryl" as defined above, and as specific examples there may be mentioned phenyloxy, 1-naphthyloxy and 2-naphthyloxy.

The term "5- to 10-membered heteroaryloxy" refers to a group consisting of an oxy group bonded to "5- to 10-membered heteroaryl" as defined above, and as specific examples there may be mentioned furyloxy, thienyloxy, pyrrolyloxy, imidazolyloxy, pyridyloxy and pyrazinyloxy.

The term "5- or 6-membered non-aromatic heterocyclooxy" refers to a group consisting of an oxy group bonded to a "5- or 6-membered non-aromatic heterocyclic group" as defined above, and as specific examples there may be mentioned pyrrolidinyloxy, piperidinyloxy, morpholinyloxy, thiomorpholinyloxy, tetrahydrofuryloxy and tetrahydropyranyloxy.

The term "C1-6 alkylsulfonyloxy" refers to a group consisting of an oxy group bonded to "C1-6 alkylsulfonyl" as defined above, and as specific examples there may be mentioned methylsulfonyloxy, ethylsulfonyloxy, 1-propylsulfonyloxy, 2-propylsulfonyloxy, butylsulfonyloxy and pentylsulfonyloxy.

The term "C6-10 arylmethyl" refers to a group consisting of methyl bonded to "C6-10 aryl" as defined above, and as specific examples there may be mentioned benzyl, 1-naphthylmethyl and 2-naphthylmethyl.

The term "C6-10 arylamino" refers to a group consisting of an amino group bonded to "C6-10 aryl" as defined above, and as specific examples there may be mentioned phenylamino, 1-naphthylamino and 2-naphthylamino.

The term "mono(C1-6 alkyl)amino" refers to a group consisting of an amino group bonded to one "C1-6 alkyl" as defined above, and as specific examples there may be mentioned methylamino and ethylamino.

The term "di(C1-6 alkyl)amino" refers to a group consisting of an amino group bonded to two "C1-6 alkyl" as defined above, and as specific examples there may be mentioned dimethylamino and methylethylamino.

The term "mono(C1-6 alkyl)aminocarbonyl" refers to a group consisting of a carbonyl group bonded to "mono(C1-6 alkyl)amino" as defined above, and as specific examples there may be mentioned methylaminocarbonyl and ethylaminocarbonyl.

The term "di(C1-6 alkyl)aminocarbonyl" refers to a group consisting of a carbonyl group bonded to "di(C1-6 alkyl) amino" as defined above, and as specific examples there may be mentioned dimethylaminocarbonyl and methylethylaminocarbonyl.

The term "pyridyl" refers to a monovalent group derived by removing one hydrogen from any desired position of a pyridine ring, and specifically there may be mentioned 2-pyridyl, 3-pyridyl and 4-pyridyl.

The term "N-oxypyridyl" refers to the aforementioned "pyridyl" having the nitrogen in the ring oxidized, and specifically there may be mentioned N-oxy-2-pyridyl, N-oxy-3-pyridyl and N-oxy-4-pyridyl.

The term "N—C1-6 alkylpyridinium" refers to a cyclic group consisting of the aforementioned "C1-6 alkyl" bonded to the nitrogen on the ring of the aforementioned "pyridyl", and specifically there may be mentioned N-methyl-2-pyridinium, N-methyl-3-pyridinium and N-methyl-4-pyridinium. The aforementioned "N—C1-6 alkylpyridinium" group forms an ion pair with anions in the molecule, and as examples of such anions there may be mentioned acetate ion and trifluoroacetate ion.

The term "pyrazinyl" refers to a monovalent group derived by removing one hydrogen from any desired position of a pyrazine ring.

The term "pyridazinyl" refers to a monovalent group derived by removing one hydrogen from any desired position of a pyridazine ring, and specifically there may be mentioned 2-pyridazinyl and 3-pyridazinyl.

The term "pyrimidinyl" refers to a monovalent group derived by removing one hydrogen from any desired position of a pyrimidine ring, and specifically there may be mentioned 2-pyrimidinyl, 4-pyrimidinyl and 5-pyrimidinyl.

The term "pyrazolyl" refers to a monovalent group derived by removing one hydrogen from any desired position of a pyrazole ring, and specifically there may be mentioned 3-pyrazolyl, 4-pyrazolyl and 5-pyrazolyl.

The term "imidazolyl" refers to a monovalent group derived by removing one hydrogen from any desired position of a imidazole ring, and specifically there may be mentioned 2-imidazolyl, 4-imidazolyl and 5-imidazolyl.

The term "thiazolyl" refers to a monovalent group derived by removing one hydrogen from any desired position of a thiazole ring, and specifically there may be mentioned 2-thiazolyl, 4-thiazolyl and 5-thiazolyl.

The term "thienyl" refers to a monovalent group derived by removing one hydrogen from any desired position of a thiophene ring, and specifically there may be mentioned 2-thienyl and 3-thienyl.

The term "pyridonyl" refers to a monovalent group derived by removing one hydrogen from any desired position of a pyridone ring, and specifically there may be mentioned groups represented by the formula:

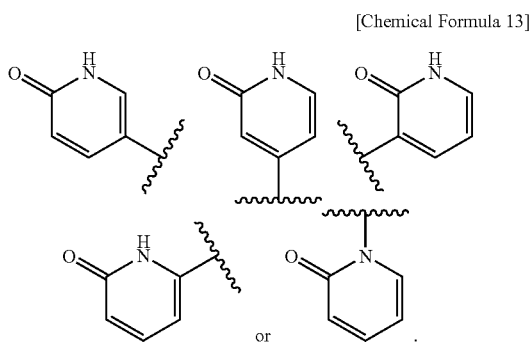

The term "dihydropyrazinyl having an oxo group" refers to a monovalent group derived by removing one hydrogen from any desired position of a dihydropyrazine ring, and having one oxo (carbonyl) group on the dihydropyrazine ring, and specifically there may be mentioned groups represented by the formula:

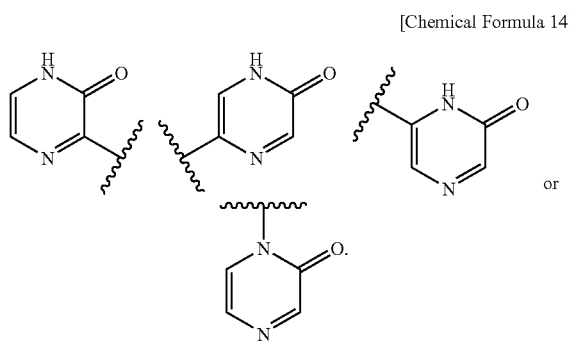

The term "tetrahydrofuryloxy" refers to a group consisting of an oxy group bonded to "a monovalent group derived by removing one hydrogen from any desired position of a tetrahydrofuran ring", and specifically there may be mentioned 2-tetrahydrofuryloxy and 3-tetrahydrofuryloxy.

The term "tetrahydropyranyloxy" refers to a group consisting of an oxy group bonded to "a monovalent group derived by removing one hydrogen from any desired position of a tetrahydropyran ring", and specifically there may be mentioned 2-tetrahydropyranyloxy, 3-tetrahydropyranyloxy and 4-tetrahydropyranyloxy.

The term "optionally having substituents" means that the compound may have one or more substituents in any desired combination at substitutable positions.

A "salt" as referred to throughout the present specification is not particularly restricted so long as it is formed with the compound of the invention and is pharmacologically acceptable, and as examples there may be mentioned inorganic acid salts, organic acid salts, inorganic base salts, organic base salts and acidic or basic amino acid salts.

As preferred examples of inorganic acid salts there may be mentioned hydrochloric acid salts, hydrobromic acid salts, sulfuric acid salts, nitric acid salts and phosphoric acid salts, and as preferred examples of organic acid salts there may be mentioned acetic acid salts, succinic acid salts, fumaric acid salts, maleic acid salts, tartaric acid salts, citric acid salts, lactic acid salts, stearic acid salts, benzoic acid salts, methanesulfonic acid salts, ethanesulfonic acid salts, p-toluenesulfonic acid salts and benzenesulfonic acid salts.

As preferred examples of inorganic base salts there may be mentioned alkali metal salts such as sodium and potassium salts, alkaline earth metal salts such as calcium and magnesium salts, and aluminum and ammonium salts, and as preferred examples of organic base salts there may be mentioned diethylamine salts, diethanolamine salts, meglumine salts and N,N'-dibenzylethylenediamine salts.

As preferred examples of acidic amino acid salts there may be mentioned aspartic acid salts and glutamic acid salts, and as examples of basic amino acid salts there may be mentioned arginine salts, lysine salts and ornithine salts.

Each substituent of the compounds of the present invention represented by the above formulas (1), (1-1) and (1-2) is explained below.

$R^{1a}$, $R^{1b}$, $R^{1c}$ and $R^{1d}$ each independently represent hydrogen, hydroxyl, C1-6 alkyl or halogen.

As preferable examples of $R^{1a}$, $R^{1b}$, $R^{1c}$ and $R^{1d}$, hydrogen, fluorine or hydroxyl is mentioned independently.

As more preferable examples of $R^{1a}$, $R^{1b}$, $R^{1c}$ and $R^{1d}$, hydrogen or fluorine is mentioned independently.

$R^{1a}$, $R^{1b}$, $R^{1c}$ and $R^{1d}$ may be either (1) all is hydrogen, (2) all is substituents other than hydrogen or (3) some are hydrogen and the others are substituents other than hydrogen, and preferably three or four of $R^{1a}$, $R^{1b}$, $R^{1c}$ and $R^{1d}$ are hydrogen.

$R^2$ represents C6-10 aryl optionally having 1-5 substituents selected from Group A1 below, 5- to 10-membered heteroaryl optionally having 1-5 substituents selected from Group A1 below or a 9- to 12-membered benzene-fused cyclic group optionally having 1-5 substituents selected from Group A1 below.

As preferable examples of $R^2$, phenyl optionally having 1-4 substituents selected from Group D1 below, pyridyl optionally having 1-3 substituents selected from Group D1 below or a 9- to 12-membered benzene-fused cyclic group optionally having 1-4 substituents selected from Group D1 below is mentioned.

As a preferable example that $R^2$ is phenyl optionally having substituents, phenyl optionally having 2 or 3 substituents selected from Group D3 below is mentioned.

As another preferable example that $R^2$ is phenyl optionally having substituents, a group represented by the following formula is mentioned:

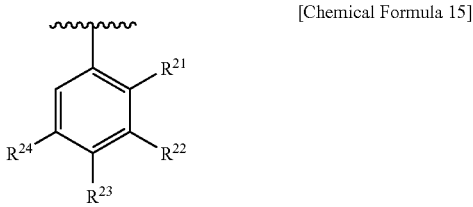

wherein $R^{21}$ represents hydrogen, fluorine or chlorine;

$R^{22}$ represents hydrogen, hydroxyl, methyl optionally having 1 substituent selected from Group D5 below, ethyl optionally having 1 substituent selected from Group D5 below, methoxy optionally having 1 substituent selected from Group D5 below, ethoxy optionally having 1 or 2 substituents selected from Group D5 below, 1-propyloxy optionally having 1 substituent selected from Group D5 below, 2-propyloxy optionally having 1 substituent selected from Group D5 below, allyloxy, tetrahydrofuryloxy, tetrahydropyranyloxy or acetyl;

$R^{23}$ represents hydrogen, fluorine, hydroxyl, methoxy optionally having 1 substituent selected from Group D6 below, ethoxy optionally having 1 substituent selected from Group D6 below or 2-propyloxy optionally having 1 substituent selected from Group D6 below; and $R^{24}$ represents hydrogen, fluorine, hydroxyl, methyl optionally having 1 substituent selected from Group D7 below, ethyl, vinyl, ethynyl, methoxy optionally having 1 substituent selected from Group D7 below, ethoxy optionally having 1 substituent selected from Group D7 below, 2-propyloxy or allyloxy.

As preferable examples of $R^{21}$, hydrogen or fluorine is mentioned; as preferable examples of $R^{22}$, hydrogen, hydroxyl, cyanomethyl, methoxymethyl, methoxy, dimethylaminocarbonylmethoxy, ethoxy, 2-fluoroethoxy, 2-hydroxyethoxy, 2-methoxyethoxy, 2-(dimethylamino)ethoxy, tetrahydrofuryloxy, tetrahydropyranyloxy, fluoromethoxy, 3-hydroxypropyloxy, 2-fluoroethoxymethyl or 2-hydroxyethoxymethyl is mentioned; as preferable examples of $R^{23}$, hydrogen, fluorine, methoxy, cyanomethoxy, ethoxy, 2-propyloxy or 2-methoxyethoxy is mentioned; and as preferable examples of $R^{24}$, hydrogen, hydroxyl, methyl, methoxymethyl, ethyl, vinyl, ethynyl, methoxy, ethoxy or 2-fluoroethoxy is mentioned.

As specific preferable examples that $R^2$ is phenyl optionally having substituents, a group represented by the following formula is mentioned:

[Chemical Formula 16]

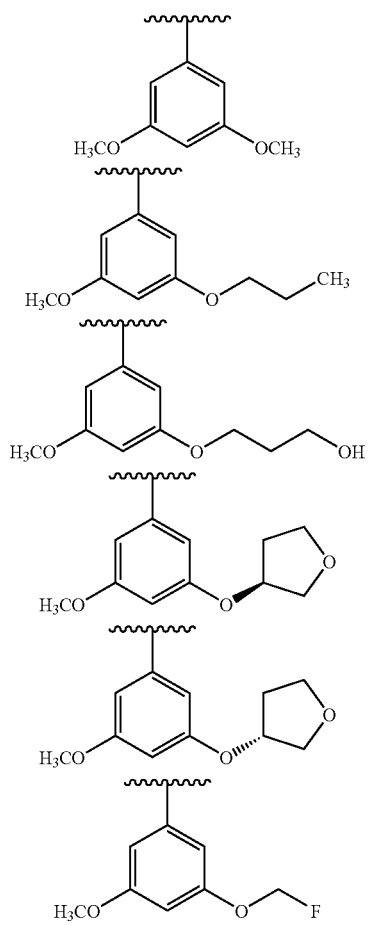

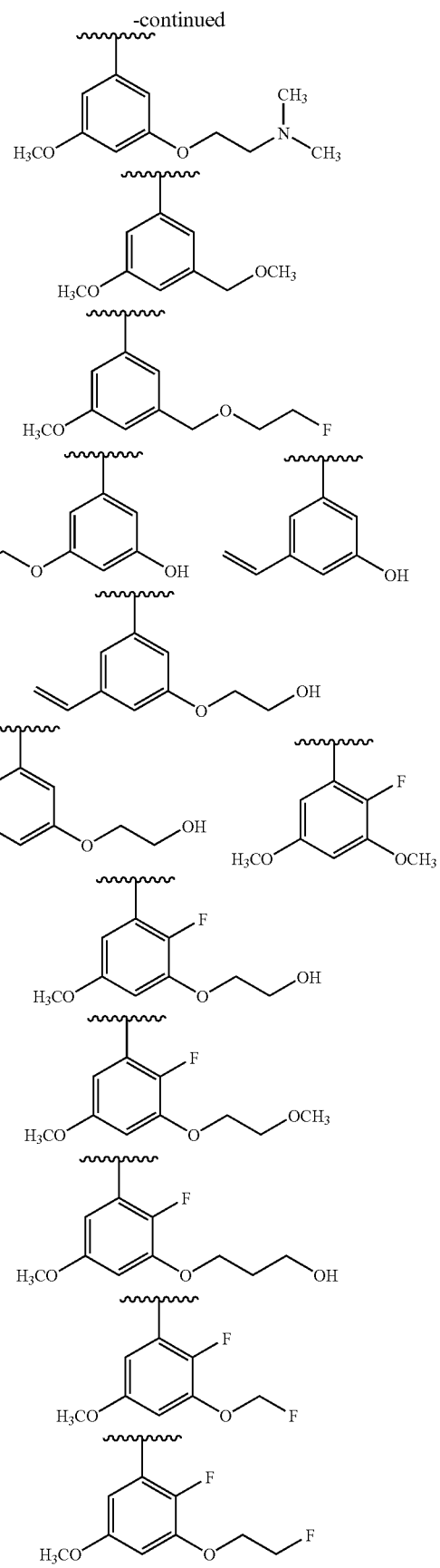

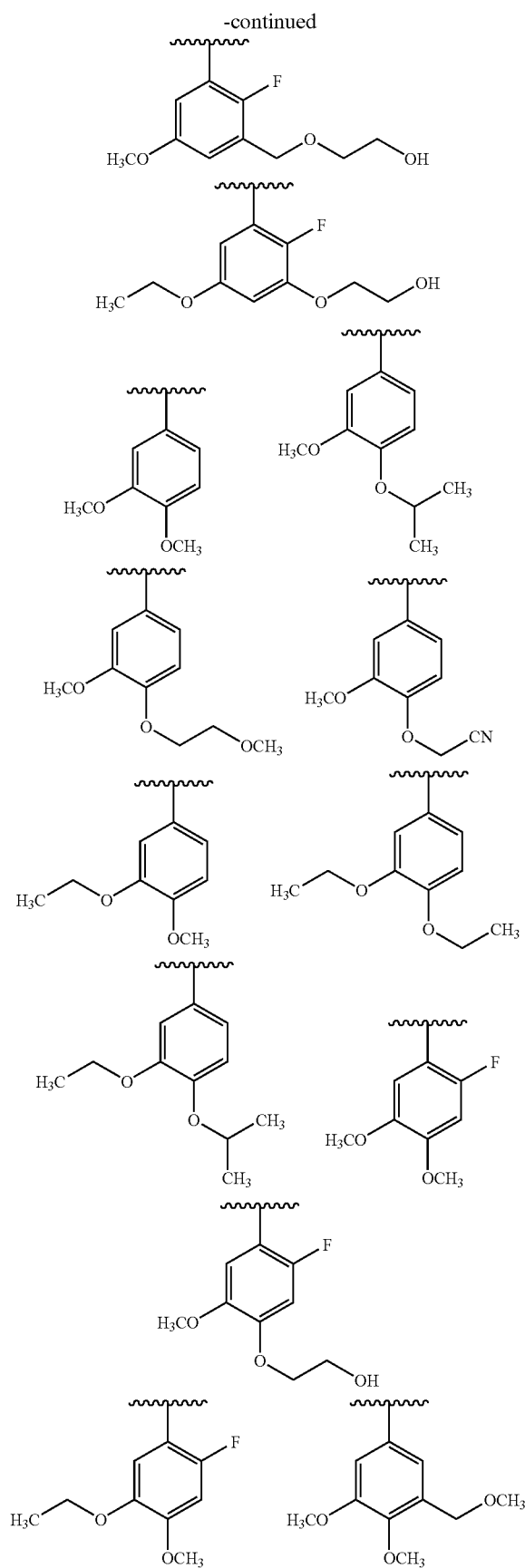

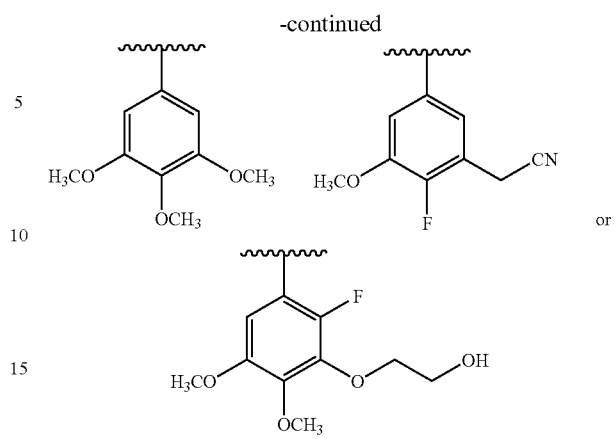

As a preferable example that $R^2$ is pyridyl optionally having substituents, pyridyl optionally having 2 substituents selected from the group consisting of C1-6 alkyl and C1-6 alkoxy is mentioned; a more preferable example is pyridyl having 2 substituents selected from the group consisting of methyl, methoxy and ethoxy; and still more preferable examples are a group represented by the following formula:

[Chemical Formula 17]

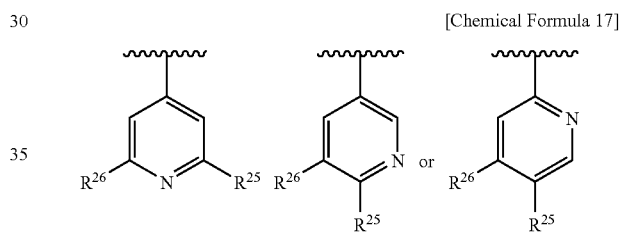

wherein $R^{25}$ represents methyl or methoxy; and $R^{26}$ represents methoxy or ethoxy.

As specific preferable examples that $R^2$ is pyridyl optionally having substituents, a group represented by the following formula is mentioned:

[Chemical Formula 18]

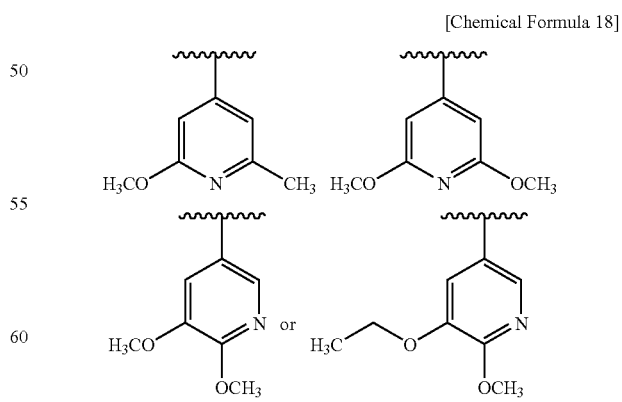

As a preferable example that $R^2$ is a 9- to 12-membered benzene-fused cyclic group optionally having substituents, a group represented by the following formula is mentioned:

[Chemical Formula 19]

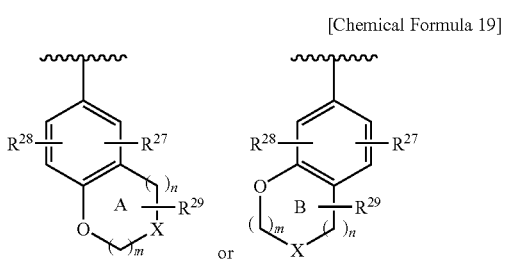

wherein $R^{27}$ represents hydrogen or halogen;

$R^{28}$ represents hydrogen, hydroxyl, halogen, C1-6 alkyl optionally having 1-3 substituents selected from Group D8 below, C2-6 alkenyl, C2-6 alkynyl, C1-6 alkoxy optionally having 1-3 substituents selected from Group D8 below or C2-7 alkylcarbonyl;

$R^{29}$ represents hydrogen, cyano, C1-6 alkyl optionally having 1-3 substituents selected from Group D8 below, C1-6 alkoxy optionally having 1-3 substituents selected from Group D8 below or carbamoyl;

X represents carbon optionally having 1 or 2 substituents selected from Group D8 below, nitrogen optionally having 1 substituent selected from Group D8 below or oxygen;

m represents an integer of 0-3 and n represents an integer of 0-2, with the proviso that the sum of m and n is 1-4; and Rings A and B optionally contain one double bond in the ring and optionally have an oxo group on the ring, and more preferable examples are a group represented by the formula:

[Chemical Formula 20]

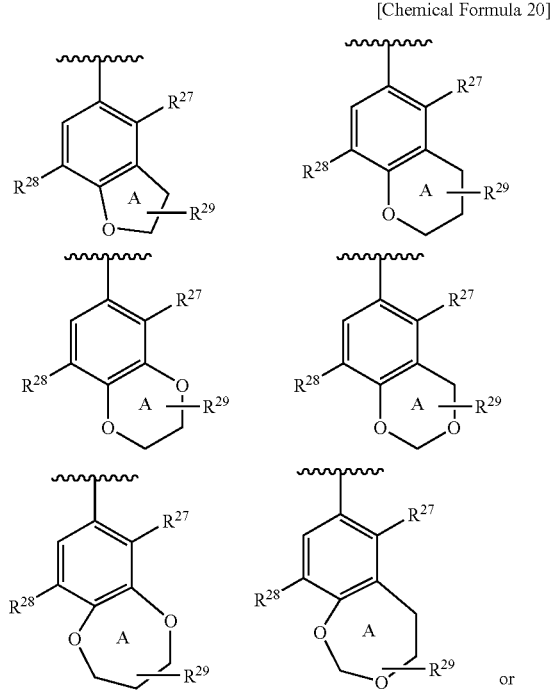

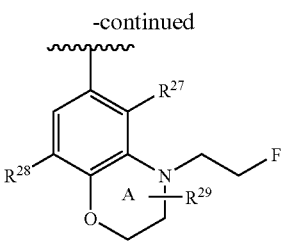

wherein $R^{27}$, $R^{28}$ and $R^{29}$ have the same definitions as above; and Ring A optionally has an oxo group on the ring.

As preferable examples of $R^{28}$, methyl, ethyl, methoxy, ethoxy, vinyl or ethynyl is mentioned; and as a preferable example of $R^{29}$, hydrogen is mentioned.

As specific preferable examples that $R^2$ is a 9- to 12-membered benzene-fused cyclic group optionally having substituents, a group represented by the following formula is mentioned:

[Chemical Formula 21]

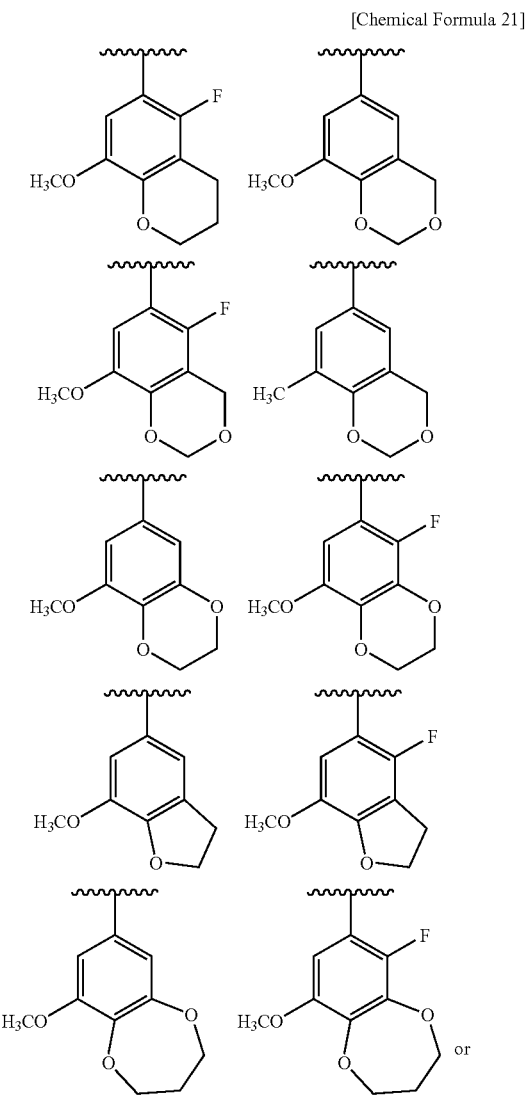

-continued

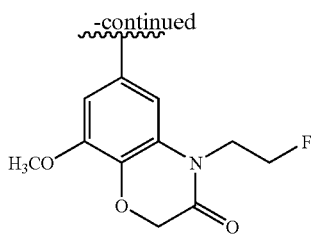

R³ represents a 5- or 6-membered non-aromatic heterocyclic group optionally having 1-5 substituents selected from Group A1 below, C6-10 aryl optionally having 1-5 substituents selected from Group A1 below or a 5- to 10-membered heteroaryl optionally having 1-5 substituents selected from Group A1 below.

As preferable examples of R³, phenyl optionally having 1-3 substituents selected from Group E1 below, pyridyl optionally having 1-3 substituents selected from Group E1 below, N-oxypyridyl optionally having 1-3 substituents selected from Group E1 below, N—C1-6 alkylpyridinium optionally having 1-3 substituents selected from Group E1 below, pyrazinyl optionally having 1-3 substituents selected from Group E1 below, pyridazinyl optionally having 1-3 substituents selected from Group E1 below, pyrimidinyl optionally having 1-3 substituents selected from Group E1 below, pyrazolyl optionally having 1 or 2 substituents selected from Group E1 below, imidazolyl optionally having 1 or 2 substituents selected from Group E1 below, thiazolyl optionally having 1 or 2 substituents selected from Group E1 below, thienyl optionally having 1-3 substituents selected from Group E1 below or dihydropyrazinyl having an oxo group, with the proviso that when R³ is N—C1-6 alkylpyridinium, R³ forms an ion pair with an anion in the molecule, is mentioned.

As more preferable examples of R³, phenyl optionally having 1 or 2 substituents selected from Group E3 below, pyridyl optionally having 1 or 2 substituents selected from Group E3 below, N-oxypyridyl optionally having 1 or 2 substituents selected from Group E3 below, pyrazinyl optionally having 1 or 2 substituents selected from Group E3 below, pyridazinyl optionally having 1 or 2 substituents selected from Group E3 below, pyrimidinyl optionally having 1 or 2 substituents selected from Group E3 below, pyrazolyl optionally having 1 or 2 substituents selected from Group E3 below, imidazolyl optionally having 1 or 2 substituents selected from Group E3 below, thiazolyl optionally having 1 or 2 substituents selected from Group E3 below, thienyl optionally having 1 or 2 substituents selected from Group E3 below or dihydropyrazinyl having an oxo group is mentioned.

As still more preferable examples of R³, phenyl optionally having one group selected from Group E4 below, pyridyl optionally having one group selected from Group E5 below, N-oxypyridyl, pyrazinyl, pyridazinyl, pyrimidinyl, pyrazolyl optionally having one group selected from Group E4 below, imidazolyl optionally having one group selected from Group E4 below, thiazolyl optionally having one group selected from Group E4 below, thienyl optionally having one group selected from Group E4 below or dihydropyrazinyl having an oxo group is mentioned.

As specific preferable examples of R³, a group represented by the following formula is mentioned:

[Chemical Formula 22]

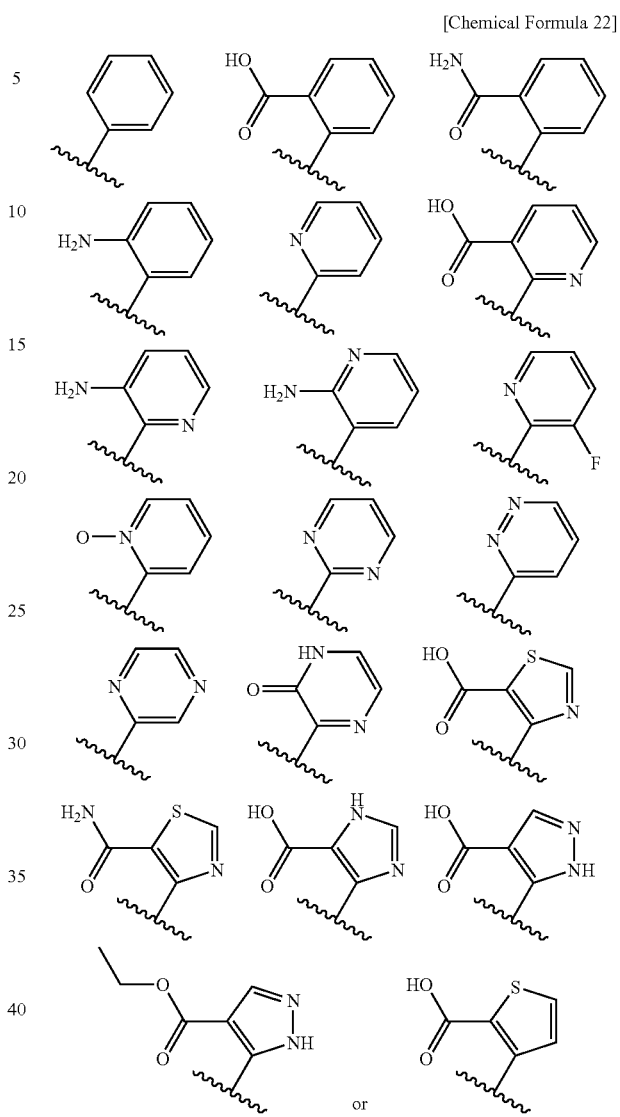

Group A1 consists of hydroxyl, halogen, cyano, nitro, oxo, C1-6 alkyl optionally having 1-3 substituents selected from Group B1 below, C3-8 cycloalkyl optionally having 1-5 substituents selected from Group B1 below, C2-6 alkenyl, C2-6 alkynyl, C1-6 alkoxy optionally having 1-3 substituents selected from Group B1 below, C3-8 cycloalkyloxy optionally having 1-5 substituents selected from Group B1 below, C2-6 alkenyloxy, C2-6 alkynyloxy, C1-6 alkylthio, C1-6 alkylsulfinyl, C1-6 alkylsulfonyl, C1-6 alkylsulfonyloxy, C6-10 aryl optionally having 1-5 substituents selected from Group B1 below, C6-10 aryloxy optionally having 1-5 substituents selected from Group B1 below, 5- to 10-membered heteroaryl optionally having 1-5 substituents selected from Group B1 below, 5- to 10-membered heteroaryloxy optionally having 1-5 substituents selected from Group B1 below, a 5- or 6-membered non-aromatic heterocyclic group optionally having 1-5 substituents selected from Group B1 below, a 5- or 6-membered non-aromatic heterocyclooxy group optionally having 1-5 substituents selected from Group B1 below, a group represented by the formula —NR$^{1ت}$—R$^{2t}$ and a group represented by the formula —CO—R$^{3t}$, where $R^{1t}$ and $R^{2t}$ each independently represent hydrogen, C1-6 alkyl optionally having 1-3 substituents selected from Group B1 below, C2-6 alkenyl, C2-7 alkylcarbonyl optionally having 1-3 substituents selected from Group B1 below, C2-7 alkoxycarbonyl optionally having 1-3 substituents selected from Group B1 below, C1-6 alkylsulfonyl optionally having 1-3 substituents selected from Group B1 below, carbamoyl, aminosulfonyl, C6-10 aryl optionally having 1-5 substituents selected from Group B1 below or 5- to 10-membered heteroaryl optionally having 1-5 substituents selected from Group B1 below, and $R^{3t}$ represents hydroxyl, C1-6 alkyl optionally having 1-3 substituents selected from Group B1 below, C1-6 alkoxy optionally having 1-3 substituents selected from Group B1 below, amino, mono(C1-6 alkyl)amino optionally having 1-3 substituents selected from Group B1 below or di(C1-6 alkyl)amino optionally having 1-3 substituents selected from Group B1 below.

Group B1 consists of hydroxyl, halogen, cyano, oxo, C1-6 alkoxy optionally having halogen, C3-8 cycloalkyl, amino, mono(C1-6 alkyl)amino, di(C1-6 alkyl)amino, carbamoyl, mono(C1-6 alkyl)aminocarbonyl, di(C1-6 alkyl)aminocarbonyl, C6-10 aryl optionally having 1-5 substituents selected from Group C1 below and 5- to 10-membered heteroaryl optionally having 1-5 substituents selected from Group C1.

Group C1 consists of halogen, C1-6 alkyl and C1-6 alkoxy.

Group D1 consists of hydroxyl, halogen, C1-6 alkyl optionally having 1-3 substituents selected from Group D2 below, C2-6 alkenyl, C2-6 alkynyl, C1-6 alkoxy optionally having 1-3 substituents selected from Group D2 below, C2-6 alkenyloxy, C1-6 alkylsulfonyloxy, a 5- or 6-membered non-aromatic heterocyclooxy group optionally having 1-3 substituents selected from Group D2 below and C2-7 alkylcarbonyl.

Group D2 consists of hydroxyl, halogen, cyano, oxo, C1-6 alkoxy optionally having halogen, mono(C1-6 alkyl)amino, di(C1-6 alkyl)amino, mono(C1-6 alkyl)aminocarbonyl and di(C1-6 alkyl)aminocarbonyl.

Group D3 consists of fluorine, chlorine, methyl optionally having 1 substituent selected from Group D4 below, ethyl optionally having 1 substituent selected from Group D4 below, vinyl, ethynyl, methoxy optionally having 1 or 2 substituents selected from Group D4 below, ethoxy optionally having 1 or 2 substituents selected from Group D4 below, 1-propyloxy optionally having 1 or 2 substituents selected from Group D4 below, 2-propyloxy optionally having 1 or 2 substituents selected from Group D4 below, allyloxy, tetrahydrofuryloxy, tetrahydropyranyloxy and acetyl.

Group D4 consists of hydroxyl, fluorine, cyano, methoxy, methylamino, dimethylamino, methylaminocarbonyl and dimethylaminocarbonyl.

Group D5 consists of hydroxyl, fluorine, cyano, methoxy, dimethylamino, dimethylaminocarbonyl, 2-fluoroethoxy and 2-hydroxyethoxy.

Group D6 consists of fluorine, cyano, methoxy, dimethylamino, methylaminocarbonyl and dimethylaminocarbonyl.

Group D7 consists of hydroxyl, fluorine, cyano and ethoxy having one methoxy.

Group D8 consists of hydrogen, hydroxyl, halogen, C1-6 alkoxy, mono(C1-6 alkyl)amino, di(C1-6 alkyl)amino, mono (C1-6 alkyl)aminocarbonyl, di(C1-6 alkyl)aminocarbonyl and C1-6 alkyl optionally having halogen.

Group E1 consists of hydroxyl, halogen, cyano, C1-6 alkyl, C1-6 alkoxy, a group represented by the formula —NH—$R^{21t}$ and a group represented by the formula —CO—$R^{31t}$, where $R^{21t}$ represents hydrogen, C1-6 alkyl, C2-6 alkenyl, C2-7 alkylcarbonyl optionally having 1-3 substituents selected from Group E2 below, C2-7 alkoxycarbonyl optionally having 1-3 substituents selected from Group E2 below, C1-6 alkylsulfonyl, carbamoyl or aminosulfonyl, and $R^{31t}$ represents hydroxyl, C1-6 alkyl, C1-6 alkoxy, amino, mono (C1-6 alkyl)amino or di(C1-6 alkyl)amino).

Group E2 consists of hydroxyl, C1-6 alkoxy and C3-8 cycloalkyl.

Group E3 consists of halogen, C1-6 alkyl, C1-6 alkoxy, a group represented by the formula —NH—$R^{22t}$, where $R^{22t}$ represents hydrogen or C2-7 alkoxycarbonyl, and a group represented by the formula —CO—$R^{32t}$, where $R^{32t}$ represents hydroxyl, C1-6 alkoxy or amino.

Group E4 consists of methoxy, carboxyl, carbamoyl, methoxycarbonyl and methoxycarbonylamino.

Group E5 consists of fluorine, methyl, methoxy and amino.

Preferable compounds of the formulas (1), (1-1) and (1-2) include the compounds obtainable by selecting and combining respective embodiments of $R^{1a}$, $R^{1b}$, $R^{1c}$, $R^{1d}$, $R^2$ and $R^3$.

Specific compounds of the formulas (1), (1-1) and (1-2) include the compounds described in Examples 1 to 238 and Examples X-1 to X-249, but it should not be understood that the present invention is limited to said compounds.

More preferable compounds of the formulas (1), (1-1) and (1-2) include the compounds described in Examples 1 to 238.

Still more preferable compounds of the formulas (1), (1-1) and (1-2) include the compounds illustrated below;

1) 4-({[2-fluoro-3-(2-fluoroethoxy)-5-methoxyphenyl]-(5-oxo-1-pyrimidin-2-yl-4,5-dihydro-1H-[1,2,4]triazol-3-yl) methyl}amino)benzamidine (ex. 3), 2) 4-({[3-methoxy-5-(2-methoxyethoxy)phenyl]-(5-oxo-1-pyrimidin-2-yl-4,5-dihydro-1H-[1,2,4]triazol-3-yl) methyl}amino)benzamidine (ex. 6), 3) 4-({[3-(2-dimethylaminoethoxy)-5-methoxyphenyl]-(5-oxo-1-pyrimidin-2-yl-4,5-dihydro-1H-[1,2,4]triazol-3-yl) methyl}amino)benzamidine (ex. 8), 4) 4-({[1-(3-aminopyridin-2-yl)-5-oxo-4,5-dihydro-1H-[1,2,4]triazol-3-yl]-(2-methoxy-6-methylpyridin-4-yl) methyl}amino)benzamidine (ex. 19), 5) 4-{[(8-methoxy-4H-benzo[1,3]dioxin-6-yl)-(5-oxo-1-pyrimidin-2-yl-4,5-dihydro-1H-[1,2,4]triazol-3-yl)methyl] amino}benzamidine (ex. 21), 6) 4-{[(3,4-dimethoxy-5-methoxymethyl-phenyl)-(5-oxo-1-pyrimidin-2-yl-4,5-dihydro-1H-[1,2,4]triazol-3-yl)methyl]amino}benzamidine (ex. 22), 7) 4-{[(3-hydroxy-5-vinylphenyl)-(5-oxo-1-pyrimidin-2-yl-4,5-dihydro-1H-[1,2,4]triazol-3-yl)methyl] amino}benzamidine (ex. 47), 8) 4-({[2-fluoro-3-(2-hydroxyethoxy)-5-methoxyphenyl]-(5-oxo-1-pyrimidin-2-yl-4,5-dihydro-1H-[1,2,4]triazol-3-yl)methyl}amino)benzamidine (ex. 153), 9) 5-{3-[(4-carbamimidoylphenylamino)-(2-fluoro-4,5-dimethoxyphenyl)methyl]-5-oxo-4,5-dihydro-[1,2,4]triazol-1-yl}-1H-pyrazole-4-carboxylic acid (ex. 157), 10) 5-{3-[(4-carbamimidoylphenylamino)-(2-fluoro-4,5-dimethoxyphenyl)methyl]-5-oxo-4,5-dihydro-[1,2,4]triazol-1-yl}-1H-pyrazole-4-carboxylic acid ethyl ester (ex. 157d), 11) 4-({[3-(3-hydroxypropoxy)-5-methoxyphenyl]-(5-oxo-1-pyrimidin-2-yl-4,5-dihydro-1H-[1,2,4]triazol-3-yl) methyl}amino)benzamidine (ex. 158), 12) 4-({[3-(2-hydroxyethoxy)-4,5-dimethoxyphenyl]-(5-oxo-1-pyrimidin-2-yl-4,5-dihydro-1H-[1,2,4]triazol-3-yl) methyl}amino)benzamidine (ex. 159), 13) 4-{[(5-ethoxy-6-methoxypyridin-3-yl)-(5-oxo-1-pyrimidin-2-yl-4,5-dihydro-1H-[1,2,4]triazol-3-yl)methyl] amino}benzamidine (ex. 160), 14) 4-{3-[(4-carbamimidoylphenylamino)-(2-fluoro-4,5-dimethoxyphenyl)methyl]-5-oxo-4,5-dihydro[1,2,4]triazol-1-yl}thiazole-5-carboxylic acid (ex. 162),
15) 4-{3-[(4-carbamimidoylphenylamino)-(5-fluoro-8-methoxy-4H-benzo[1,3]dioxin-6-yl)methyl]-5-oxo-4,5-dihydro-[1,2,4]triazol-1-yl}thiazole-5-carboxylic acid amide (ex. 164),
16) 4-{3-[(4-carbamimidoylphenylamino)-(5-fluoro-8-methoxy-4H-benzo[1,3]dioxin-6-yl)methyl]-5-oxo-4,5-dihydro-[1,2,4]triazol-1-yl}thiazole-5-carboxylic acid (ex. 165),
17) 4-{3-[(4-carbamimidoylphenylamino)-(8-methoxy-4H-benzo[1,3]dioxin-6-yl)methyl]-5-oxo-4,5-dihydro-[1,2,4]triazol-1-yl}thiazole-5-carboxylic acid (ex. 166),
18) 4-(3-{(4-carbamimidoylphenylamino)-[2-fluoro-3-(2-hydroxyethoxy)-5-methoxyphenyl]methyl}-5-oxo-4,5-dihydro[1,2,4]triazol-1-yl)thiazole-5-carboxylic acid (ex. 167),
19) 3-{3-[(4-carbamimidoylphenylamino)-(5-fluoro-8-methoxy-2,3-dihydrobenzo[1,4]dioxin-6-yl)methyl]-5-oxo-4,5-dihydro-[1,2,4]triazol-1-yl}thiophene-2-carboxylic acid (ex. 168),
20) 3-{3-[(4-carbamimidoylphenylamino)-(5,6-dimethoxypyridin-3-yl)methyl]-5-oxo-4,5-dihydro-[1,2,4]triazol-1-yl}thiophene-2-carboxylic acid (ex. 169),
21) 3-{3-[(4-carbamimidoylphenylamino)-(2-fluoro-4,5-dimethoxyphenyl)methyl]-5-oxo-4,5-dihydro[1,2,4]triazol-1-yl}thiophene-2-carboxylic acid (ex. 171),
22) 4-{3-[(4-carbamimidoylphenylamino)-(9-methoxy-3,4-dihydro-2H-benzo[b][1,4]dioxepin-7-yl)methyl]-5-oxo-4,5-dihydro-[1,2,4]triazol-1-yl}thiazole-5-carboxylic acid (ex. 180),
23) 4-{3-[(4-Carbamimidoylphenylamino)-(5-ethoxy-6-methoxypyridin-3-yl)methyl]-5-oxo-4,5-dihydro-[1,2,4]triazol-1-yl}thiazole-5-carboxylic acid (ex. 185),
24) 5-{3-[(4-Carbamimidoylphenylamino)-(2-fluoro-4,5-dimethoxyphenyl)methyl]-5-oxo-4,5-dihydro-[1,2,4]triazol-1-yl}-3H-imidazole-4-carboxylic acid (ex. 187),
25) 4-{3-[(4-Carbamimidoylphenylamino)-(5-fluoro-8-methoxy-2,3-dihydro-benzo[1,4]dioxin-6-yl)-methyl]-5-oxo-4,5-dihydro-[1,2,4]triazol-1-yl}thiazole-5-carboxylic acid (ex. 188),
26) 5-{3-[(4-Carbamimidoylphenylamino)-(5-fluoro-8-methoxychroman-6-yl)methyl]-5-oxo-4,5-dihydro-[1,2,4]triazol-1-yl}-1H-pyrazole-4-carboxylic acid (ex. 189),
27) 4-({[1-(3-Aminopyridin-2-yl)-5-oxo-4,5-dihydro-1H-[1,2,4]triazol-3-yl]-[2-fluoro-3-(2-hydroxyethoxy)-5-methoxyphenyl]methyl}amino)benzamidine (ex. 200),
28) 2-{3-[(4-Carbamimidoylphenylamino)-(8-methoxy-4H-benzo[1,3]dioxin-6-yl)methyl]-5-oxo-4,5-dihydro[1,2,4]triazol-1-yl}benzamide (ex. 211),
29) 4-{[[3-Ethynyl-5-(2-hydroxyethoxy)phenyl]-(5-oxo-1-pyrimidin-2-yl-4,5-dihydro-1H-[1,2,4]triazol-3-yl)methyl]amino}benzamidine (ex. 212),
30) 4-{[[2-Fluoro-3-(2-hydroxyethoxymethyl)-5-methoxyphenyl]-(5-oxo-1-pyrimidin-2-yl-4,5-dihydro-1H-[1,2,4]triazol-3-yl)methyl]amino}benzamidine (ex. 216),
31) 2-Fluoro-4-{[[2-fluoro-3-(2-hydroxyethoxy)-5-methoxyphenyl]-(5-oxo-1-pyrimidin-2-yl-4,5-dihydro-1H-[1,2,4]triazol-3-yl)methyl]amino}benzamidine (ex. 218),
32) 4-{[[3-Ethoxy-5-(2-hydroxyethoxy)phenyl]-(5-oxo-1-pyrimidin-2-yl-4,5-dihydro-1H-[1,2,4]triazol-3-yl)methyl]amino}benzamidine (ex. 220),
33) 4-{[(3-Ethoxy-5-hydroxyphenyl)-(5-oxo-1-pyrimidin-2-yl-4,5-dihydro-1H-[1,2,4]triazol-3-yl)methyl]amino}benzamidine (ex. 221),
34) 3-{3-[(4-Carbamimidoylphenylamino)-(5-fluoro-8-methoxychroman-6-yl)methyl]-5-oxo-4,5-dihydro-[1,2,4]triazol-1-yl}thiophene-2-carboxylic acid (ex. 222),
35) 4-{[[4-(2-Fluoroethyl)-8-methoxy-3-oxo-3,4-dihydro-2H-benzo[1,4]oxazin-6-yl]-(5-oxo-1-pyrimidin-2-yl-4,5-dihydro-1H-[1,2,4]triazol-3-yl)methyl]amino}benzamidine (ex. 223),
36) 3-{3-[(4-Carbamimidoyl-3-fluorophenylamino)-(5-fluoro-8-methoxy-2,3-dihydrobenzo[1,4]dioxin-6-yl)methyl]-5-oxo-4,5-dihydro-[1,2,4]triazol-1-yl}thiophene-2-carboxylic acid (ex. 231),
37) 4-{[(5,6-Dimethoxypyridin-3-yl)-(5-oxo-1-pyrimidin-2-yl-4,5-dihydro-1H-[1,2,4]triazol-3-yl)methyl]amino}benzamidine (ex. 234),
38) 3-{3-[(4-Carbamimidoylphenylamino)-(5-ethoxy-6-methoxypyridin-3-yl)methyl]-5-oxo-4,5-dihydro-[1,2,4]triazol-1-yl}thiophene-2-carboxylic acid (ex. 235) and
39) 3-(3-{(4-Carbamimidoylphenylamino)-[2-fluoro-4-(2-hydroxyethoxy)-5-methoxyphenyl]methyl}-5-oxo-4,5-dihydro-[1,2,4]triazol-1-yl)thiophene-2-carboxylic acid (ex. 237).

[General Production Processes for Compounds of the Invention]

The compounds of the invention may be produced by the processes described below. However, processes for production of compounds of the invention are not restricted to these alone.

The processes will now be explained.

[Production Process A] Production Process for Invention Compound Intermediate (14a)

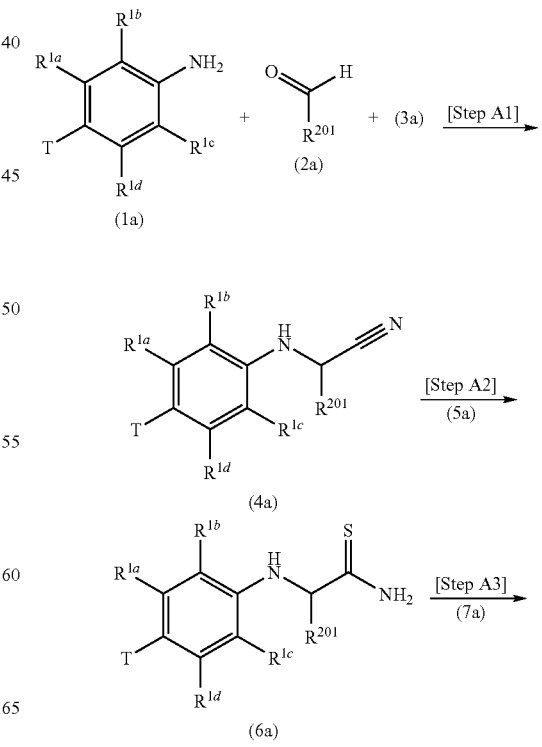

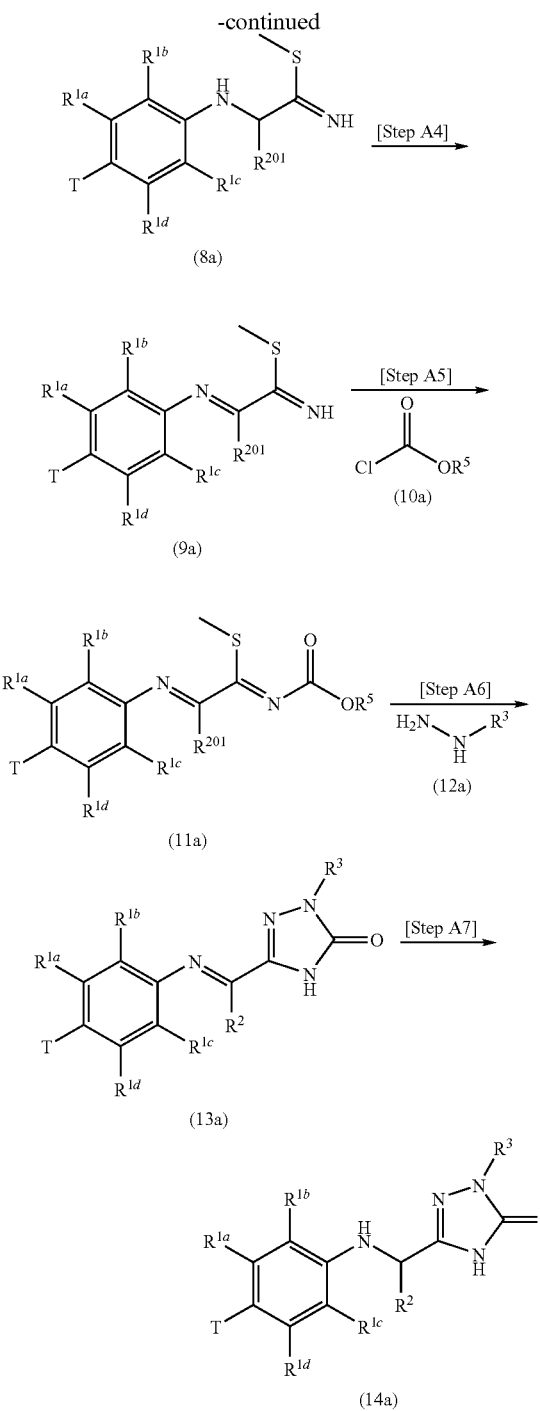

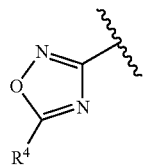

[Chemical Formula 24]

(wherein $R^4$ is C1-6 alkyl optionally substituted with halogen, C1-6 alkoxy optionally substituted with C6-10 aryl, C6-10 aryl or C6-10 aryloxy).

[Step A1]

This is a step of reacting compound (1a), compound (2a) and a cyanating agent such as trimethylsilyl cyanide or hydrogen cyanide (3a) in a solvent, in the presence or in the absence of a suitable Lewis acid catalyst and in the presence or in the absence of a suitable dehydrating agent, to produce compound (4a).

This step may be carried out by a commonly employed protocol as described in SYNLETT, 1997, 115-116 and elsewhere.

The step may also be carried out under a stream or under an atmosphere of an inert gas such as nitrogen or argon.

As compound (1a) there may be used a publicly known compound, a commercially available compound or a compound that can be produced from a commercially available compound by a process ordinarily carried out by those skilled in the art or by the processes described in the examples below.

As compound (2a) there may be used a publicly known compound, a commercially available compound or a compound that can be produced from a commercially available compound by a process ordinarily carried out by those skilled in the art or by the processes described in the examples below.

The solvent used for the reaction is not particularly restricted so long as it dissolves the starting materials to some degree and does not interfere with the reaction, and for example, there may be used halogen-based solvents such as dichloromethane, 1,2-dichloroethane and chloroform, ether-based solvents such as tetrahydrofuran, 1,2-dimethoxyethane, t-butylmethyl ether, diethyl ether and 1,4-dioxane, ester-based solvents such as ethyl acetate, nitrile-based solvents such as acetonitrile, aromatic hydrocarbon-based solvents such as benzene and toluene, aliphatic hydrocarbon-based solvents such as heptane and hexane, and solvent mixtures thereof, among which dichloromethane or tetrahydrofuran is preferred.

As examples of Lewis acids to be used for the reaction there may be mentioned ytterbium(III) trifluoromethanesulfonate hydrate, scandium(III) trifluoromethanesulfonate, bismuth (III) chloride, ruthenium(III) chloride, nickel(II) chloride and lithium perchlorate, among which ytterbium(III) trifluoromethanesulfonate hydrate is preferred.

As examples of dehydrating agents for the reaction there may be used Molecular Sieves 3A, Molecular Sieves 4A, anhydrous magnesium sulfate, anhydrous sodium sulfate and the like, among which Molecular Sieves 3A is preferred.

The reaction temperature will generally differ depending on the starting materials, solvent and other reagents used in the reaction, but it is preferably between −20° C. and 50° C., and more preferably between 10° C. and 30° C.

Here, $R^{1a}$, $R^{1b}$, $R^{1c}$, $R^{1d}$, $R^2$ and $R^3$ have the same definitions as above. $R^{201}$ represents C6-10 aryl optionally having 1-5 substituents selected from Group A1 above, 5- to 10-membered heteroaryl optionally having 1-5 substituents selected from Group A1 above or a 9- to 12-membered benzene-fused cyclic group optionally having 1-5 substituents selected from Group A1 above. When the substituent selected from Group A1 above is hydroxyl, the hydroxyl may be protected. $R^5$ represents C1-6 alkyl optionally substituted with C6-10 aryl. T is a cyano group or a group represented by the formula:

The reaction time will generally differ depending on the starting materials, solvent and other reagents used in the reaction, as well as on the reaction temperature, but preferably stirring is carried out for 1-96 hours and more preferably 12-48 hours at the aforementioned reaction temperature after addition of the reagents.

Compound (1a) may be used in a 1- to 2-fold molar amount with respect to compound (2a), but preferably it is used in a 1- to 1.2-fold molar amount and more preferably in a 1- to 1.05-fold molar amount.

The cyanating agent (3a) may be used in a 1- to 3-fold molar amount with respect to compound (2a), but preferably it is used in a 1- to 2-fold molar amount and more preferably in a 1.5- to 2-fold molar amount.

The Lewis acid catalyst may be used in a 0.01- to 2-fold molar amount with respect to compound (2a), but preferably it is used in a 0.05- to 0.2-fold molar amount and more preferably in a 0.1-fold molar amount.

[Step A2]

This is a step of reacting compound (4a) with a sulfurizing agent such as aqueous ammonium sulfide (5a) in a solvent to produce compound (6a).

The step may also be carried out under a stream or under an atmosphere of an inert gas such as nitrogen or argon.

The solvent used for the reaction is not particularly restricted so long as it dissolves the starting materials to some degree and does not interfere with the reaction, and for example, there may be used alcohol-based solvents such as methanol, ethanol and 2-propanol or ether-based solvents such as tetrahydrofuran, 1,2-dimethoxyethane, t-butylmethyl ether, diethyl ether and 1,4-dioxane, or mixtures thereof, among which methanol and tetrahydrofuran mixed solvent is preferred.

The reaction temperature will generally differ depending on the starting materials, solvent and other reagents used in the reaction, but it is preferably between 0° C. and 80° C., and more preferably between 10° C. and 50° C.

The reaction time will generally differ depending on the starting materials, solvent and other reagents used in the reaction, as well as on the reaction temperature, but preferably stirring is carried out for 1-48 hours and more preferably about 2-12 hours at the aforementioned reaction temperature after addition of the reagents.

The sulfurizing agent (5a) may be used in a 1- to 10-fold molar amount with respect to compound (4a), but preferably it is used in a 2- to 6-fold molar amount and more preferably in a 3- to 5-fold molar amount.

[Step A3]

This is a step of reacting compound (6a) with a methylating agent such as trimethyloxonium tetrafluoroborate (7a) in a solvent to produce compound (8a).

The step may also be carried out under a stream or under an atmosphere of an inert gas such as nitrogen or argon.

The solvent used for the reaction is not particularly restricted so long as it dissolves the starting materials to some degree and does not interfere with the reaction, and for example, there may be used halogen-based solvents such as dichloromethane, 1,2-dichloroethane and chloroform, aromatic hydrocarbon-based solvents such as benzene and toluene, aliphatic hydrocarbon-based solvents such as heptane and hexane, nitrile-based solvents such as acetonitrile, nitro-based solvents such as nitromethane, or mixtures thereof, among which dichloromethane or acetonitrile is preferred.

The reaction temperature will generally differ depending on the starting materials, solvent and other reagents used in the reaction, but it is preferably between −20° C. and 50° C., and more preferably between 0° C. and 30° C.

The reaction time will generally differ depending on the starting materials, solvent and other reagents used in the reaction, as well as on the reaction temperature, but preferably stirring is carried out for between 10 minutes and 14 hours and more preferably between 10 minutes and 2 hours at the aforementioned reaction temperature after addition of the reagents.

The methylating agent (7a) may be used in a 1- to 1.5-fold molar amount with respect to compound (6a), but preferably it is used in a 1- to 1.2-fold molar amount and more preferably in a 1.05-fold molar amount.

[Step A4]

This is a step of converting compound (8a) to compound (9a) with an appropriate oxidizing agent in a solvent.

The solvent used for the reaction is not particularly restricted so long as it dissolves the starting materials to some degree and does not interfere with the reaction, and for example, there may be used halogen-based solvents such as dichloromethane, 1,2-dichloroethane and chloroform, ester-based solvents such as ethyl acetate, ether-based solvents such as tetrahydrofuran, 1,2-dimethoxyethane, t-butylmethyl ether, diethyl ether and 1,4-dioxane, aromatic hydrocarbon-based solvents such as benzene and toluene, aliphatic hydrocarbon-based solvents such as heptane and hexane, ketone-based solvents such as acetone, and mixtures thereof, among which dichloromethane or ethyl acetate is preferred.

As specific examples of oxidizing agents for the reaction there may be used manganese dioxide, m-chloroperbenzoic acid and 2,3-dichloro-5,6-dicyano-p-benzoquinone, among which manganese dioxide is preferred.

The reaction temperature will generally differ depending on the starting materials, solvent and oxidizing agent used in the reaction, but it is preferably between 0° C. and 50° C., and more preferably between 10° C. and 30° C.

The reaction time will generally differ depending on the starting materials, solvent and other reagents used in the reaction, as well as on the reaction temperature, but preferably stirring is carried out for between 10 minutes and 12 hours and more preferably between 10 minutes and 2 hours at the aforementioned reaction temperature after addition of the reagents.

The oxidizing agent may be used in a 1- to 20-fold molar amount with respect to compound (8a), but preferably it is used in a 5- to 15-fold molar amount.

[Step A5]

This is a step of reacting compound (9a) with a chloroformic acid ester such as methyl chloroformate or ethyl chloroformate (10a) in a solvent, in the presence of a suitable base, to produce compound (11a).

The step may also be carried out under a stream or under an atmosphere of an inert gas such as nitrogen or argon.

The solvent used for the reaction is not particularly restricted so long as it dissolves the starting materials to some degree and does not interfere with the reaction, and for example, there may be used ether-based solvents such as tetrahydrofuran, 1,2-dimethoxyethane, t-butylmethyl ether, diethyl ether and 1,4-dioxane, halogen-based solvents such as dichloromethane, 1,2-dichloroethane and chloroform, aromatic hydrocarbon-based solvents such as benzene, toluene and xylene, aliphatic hydrocarbon-based solvents such as heptane and hexane, and mixtures thereof, among which toluene is preferred.

As specific bases for the reaction there may be used organic bases such as collidine, pyridine and lutidine, among which collidine is preferred.

The reaction temperature will generally differ depending on the starting materials, solvent and other reagents used in the reaction, but it is preferably between 0° C. and 120° C., and more preferably between 60° C. and 100° C.

The reaction time will generally differ depending on the starting materials, solvent and other reagents used in the reaction, as well as on the reaction temperature, but preferably stirring is carried out for 1-24 hours and more preferably 1-14 hours at the aforementioned reaction temperature after addition of the reagents.

The chloroformic acid ester (10a) may be used in a 1- to 3-fold molar amount with respect to compound (9a), but preferably it is used in a 1- to 2-fold molar amount and more preferably in a 1.2- to 1.6-fold molar amount.

The base may be used in a 1- to 5-fold molar amount with respect to compound (9a), but preferably it is used in a 1- to 3-fold molar amount and more preferably in a 1.5- to 2.5-fold molar amount.

[Step A6]

This is a step of reacting compound (11a) with compound (12a) in a solvent, in the presence or in the absence of a suitable base, to produce compound (13a).

As compound (12a) there may be used a publicly known compound, a commercially available compound or a compound that can be produced from a commercially available compound by a process ordinarily carried out by those skilled in the art or by the processes described in the examples below. Also, compound (12a) may be used in free form or as a salt.

The step may also be carried out under a stream or under an atmosphere of an inert gas such as nitrogen or argon.

The solvent used for the reaction is not particularly restricted so long as it dissolves the starting materials to some degree and does not interfere with the reaction, and for example, there may be used amide-based solvents such as N,N-dimethylformamide and dimethylacetamide, sulfoxide-based solvents such as dimethylsulfoxide, ether-based solvents such as tetrahydrofuran, 1,2-dimethoxyethane, t-butylmethyl ether, diethyl ether and 1,4-dioxane, aromatic hydrocarbon-based solvents such as benzene and toluene, aliphatic hydrocarbon-based solvents such as heptane and hexane, alcohol-based solvents such as methanol, ethanol and 2-propanol, halogen-based solvents such as dichloromethane, 1,2-dichloroethane and chloroform, or mixtures thereof, among which N,N-dimethylformamide is preferred.

As specific examples of bases for the reaction there may be used triethylamine, diisopropylethylamine, collidine and pyridine, among which triethylamine is preferred.

The reaction temperature will generally differ depending on the starting materials, solvent and other reagents used in the reaction, but it is preferably between 10° C. and 100° C., and more preferably between 60° C. and 90° C.

The reaction time will generally differ depending on the starting materials, solvent and other reagents used in the reaction, as well as on the reaction temperature, but preferably stirring is carried out for 1-48 hours and more preferably about 14 hours at the aforementioned reaction temperature after addition of the reagents.

Compound (12a) may be used in a 1- to 3-fold molar amount with respect to compound (11a), but preferably it is used in a 1- to 1.2-fold molar amount and more preferably in a 1- to 1.05-fold molar amount.

The base may be used in a 1- to 3-fold molar amount with respect to compound (12a), but preferably it is used in a 1- to 2-fold molar amount.

When $R^{201}$ is C6-10 aryl having a protected hydroxyl group, 5- to 10-membered heteroaryl having a protected hydroxyl group or a 9- to 12-membered benzene-fused cyclic group having a protected hydroxyl group, this step may be preceded by 1) removal of the hydroxyl-protecting group and 2) alkylation of the hydroxyl group.

Removal of the protecting group may be accomplished by a method that is generally known in the field of synthetic organic chemistry, and for example, by the methods described in T. W. Greene, (Protective Groups in Organic Synthesis), John Wiley & Sons.

For example, when the hydroxyl-protecting group is a silyl-based protecting group such as t-butyldimethylsilyl or triisopropylsilyl, the removal may be accomplished by reacting a deprotecting agent such as tetrabutylammonium fluoride with compound (11a) in a solvent such as tetrahydrofuran.

Alkylation of the hydroxyl group may be accomplished by a method that is generally known in the field of synthetic organic chemistry, and for example, it may be accomplished by reacting compound (11a) deprotected at the hydroxyl-protecting group (hereinafter referred to as "deprotected compound") with an alkylating agent such as iodoethane or 1-fluoro-2-iodoethane in a solvent such as N,N-dimethylformamide, in the presence or in the absence of a base such as potassium carbonate. It may also be accomplished by reacting the deprotected compound with an alcohol such as 3-hydroxytetrahydrofuran, 1-methylpiperidin-4-ol or 2-dimethylaminoethanol in a solvent such as tetrahydrofuran, in the presence of triphenylphosphine and in the presence of an azodicarboxylic acid diester such as diethyl azodicarboxylate or diisopropyl azodicarboxylate.

[Step A7]

This is a step of reacting compound (13a) with a suitable reducing agent in a solvent in the presence or in the absence of a suitable acid, for conversion to compound (14a).

This step may be carried out by a commonly employed method as described in Jikken Kagaku Koza 20 (4th Edition, The Chemical Society of Japan, Maruzen Publishing, pp. 282-284) and elsewhere.

The step may also be carried out under a stream or under an atmosphere of an inert gas such as nitrogen or argon.

The solvent used for the reaction is not particularly restricted so long as it dissolves the starting materials to some degree and does not interfere with the reaction, and for example, there may be used alcohol-based solvents such as methanol, ethanol and 2-propanol, amide-based solvents such as N,N-dimethylformamide and dimethylacetamide, sulfoxide-based solvents such as dimethylsulfoxide, ether-based solvents such as tetrahydrofuran, 1,2-dimethoxyethane, t-butylmethyl ether, diethyl ether and 1,4-dioxane, aromatic hydrocarbon-based solvents such as benzene and toluene, aliphatic hydrocarbon-based solvents such as heptane and hexane, halogen-based solvents such as dichloromethane, 1,2-dichloroethane and chloroform, or mixtures thereof, among which a methanol/tetrahydrofuran solvent mixture is preferred.

Examples of reducing agents to be used for the reaction include metal-hydrogen complex compounds such as sodium cyanotrihydroborate, diisobutylaluminum hydride, lithium aluminum hydride, sodium bis(2-methoxyethoxy)aluminum hydride, sodium borohydride, sodium triacetoxyborohydride, lithium borohydride, lithium triethylborohydride and lithium tri(s-butyl)borohydride, borane-tetrahydrofuran complex, borane-dimethyl sulfide complex, thexylborane, catecholborane, 9-borabicyclo[3,3,1]nonane and the like, among which sodium cyanotrihydroborate is preferred.

As examples of acids for the reaction there may be used acetic acid, formic acid, hydrochloric acid and the like, among which acetic acid is preferred.

The reaction temperature will generally differ depending on the starting materials, solvent and other reagents used in the reaction, but it is preferably between −20° C. and 80° C., and more preferably between 10° C. and 30° C.

The reaction time will generally differ depending on the starting materials, solvent and other reagents used in the reaction, as well as on the reaction temperature, but preferably stirring is carried out for 1-24 hours and more preferably about 3 hours at the aforementioned reaction temperature after addition of the reagents.

The reducing agent may be used in a 1- to 10-fold molar amount with respect to compound (13a), but preferably it is used in a 3- to 6-fold molar amount and more preferably in a 5-fold molar amount.

Alternatively, compound (13a) may be converted to compound (14a) by catalytic hydrogenation in the presence of a suitable metal catalyst.

The metal catalyst used for the reaction may be palladium-carbon, platinum(IV) oxide or the like, with palladium-carbon being preferred.

The solvent used for the reaction is not particularly restricted so long as it dissolves the starting materials to some degree and does not interfere with the reaction, and for example, there may be used alcohol-based solvents such as methanol, ethanol and 2-propanol, ester-based solvents such as ethyl acetate, ether-based solvents such as tetrahydrofuran, 1,2-dimethoxyethane, t-butylmethyl ether, diethyl ether and 1,4-dioxane, aromatic hydrocarbon-based solvents such as benzene and toluene, organic acids such as acetic acid and formic acid, water, or mixtures thereof, among which ethanol and acetic acid mixed solvent is preferred.

The reaction temperature will generally differ depending on the starting materials, solvent and other reagents used in the reaction, but it is preferably between 10° C. and 80° C., and more preferably between 10° C. and 30° C.

The reaction time will generally differ depending on the starting materials, solvent and other reagents used in the reaction, as well as on the reaction temperature, but preferably stirring is carried out for 1-24 hours and more preferably about 12 hours at the aforementioned reaction temperature after addition of the reagents.

The metal catalyst may be used in a 0.01- to 2-fold molar amount with respect to compound (13a), but preferably it is used in a 0.05- to 1-fold molar amount.

Here, $R^{1a}$, $R^{1b}$, $R^{1c}$, $R^{1d}$, $R^{201}$, $R^5$ and T have the same definitions as above.

[Step A8]

This is a step of reacting compound (8a) with a chloroformic acid ester such as methyl chloroformate or ethyl chloroformate (10a) in a solvent, in the presence of a suitable base, to produce compound (11a).

The step may also be carried out under a stream or under an atmosphere of an inert gas such as nitrogen or argon.

The solvent used for the reaction is not particularly restricted so long as it dissolves the starting materials to some degree and does not interfere with the reaction, and for example, there may be used ether-based solvents such as tetrahydrofuran, 1,2-dimethoxyethane, t-butylmethyl ether, diethyl ether and 1,4-dioxane, aromatic hydrocarbon-based solvents such as benzene and toluene, aliphatic hydrocarbon-based solvents such as heptane and hexane, halogen-based solvents such as dichloromethane, 1,2-dichloroethane and chloroform, and mixtures thereof, among which toluene is preferred.

As specific bases for the reaction there may be used collidine, pyridine and lutidine, among which collidine is preferred.

The reaction temperature will generally differ depending on the starting materials, solvent and other reagents used in the reaction, but it is preferably between 0° C. and 100° C., and more preferably between 60° C. and 80° C.

The reaction time will generally differ depending on the starting materials, solvent and other reagents used in the reaction, as well as on the reaction temperature, but preferably stirring is carried out for 1-24 hours and more preferably 1-14 hours at the aforementioned reaction temperature after addition of the reagents.

The chloroformic acid ester (10a) may be used in a 1- to 5-fold molar amount with respect to compound (8a), but preferably it is used in a 1.5- to 3.5-fold molar amount and more preferably in a 2- to 3-fold molar amount.

The base may be used in a 1- to 7-fold molar amount with respect to compound (8a), but preferably it is used in a 2- to 4-fold molar amount.

[Production Process B] Production Process (1) for Invention Compounds

[Chemical Formula 25]

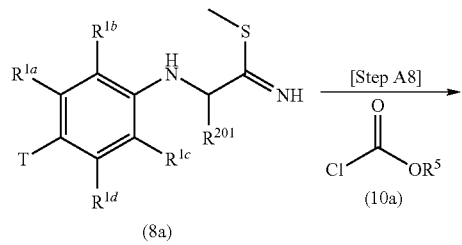

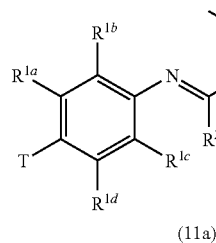

[Chemical Formula 26]

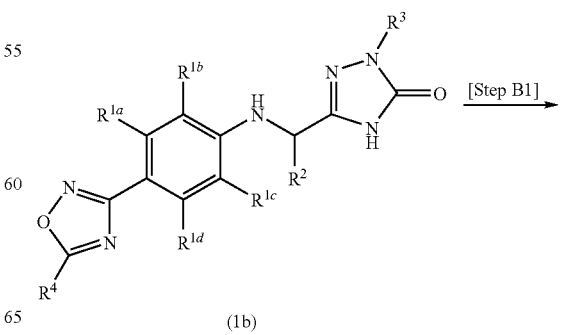

-continued

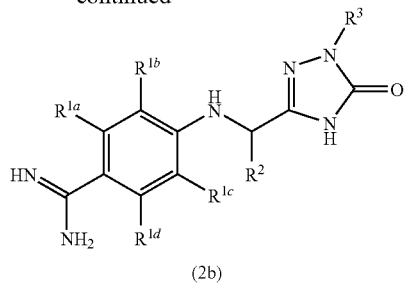

(2b)

Here, $R^{1a}$, $R^{1b}$, $R^{1c}$, $R^{1d}$, $R^2$, $R^3$ and $R^4$ have the same definitions as above.

[Step B1]

This is a step of converting compound (1b) (compound (14a) wherein T is the formula:

[Chemical Formula 27]

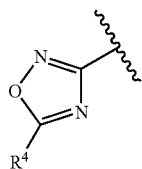

(wherein $R^4$ is as defined above)) to compound (2b) of the invention in a solvent, in the presence of a suitable metal reagent.

The step may be carried out by a commonly employed protocol as described in Tetrahedron Letters 44, (2003) 8697-8700 and elsewhere.

As compound (1b) there may be used, instead of compound (14a) obtained by [Production Process A] described above, a publicly known compound, a commercially available compound or a compound that can be produced from a commercially available compound by a process ordinarily carried out by those skilled in the art or by the processes described in the examples below.

The step may also be carried out under a stream or under an atmosphere of an inert gas such as nitrogen or argon.

The metal reagent used for the reaction may be iron powder, zinc, Raney nickel or the like, with iron powder being preferred.

The solvent used for the reaction is not particularly restricted so long as it dissolves the starting materials to some degree and does not interfere with the reaction, and for example, there may be used alcohol-based solvents such as methanol, ethanol and 2-propanol, organic acids such as acetic acid and formic acid, water, or mixtures thereof, among which methanol, acetic acid and water mixed solvent is preferred.

The reaction temperature will generally differ depending on the starting materials, solvent and other reagents used in the reaction, but it is preferably between 10° C. and 80° C., and more preferably between 50° C. and 70° C.

The reaction time will generally differ depending on the starting materials, solvent and other reagents used in the reaction, as well as on the reaction temperature, but preferably stirring is carried out for 1-24 hours and more preferably about 12 hours at the aforementioned reaction temperature after addition of the reagents.

The metal reagent may be used in a 1- to 30-fold molar amount with respect to compound (1b), but preferably it is used in a 5- to 20-fold molar amount.

Alternatively, compound (1b) may be converted to compound (2b) of the invention by catalytic hydrogenation in the presence of a suitable metal catalyst.

The step may be carried out by a commonly employed protocol as described in Tetrahedron Letters 36, (1995) 4471-4474 and elsewhere.

The metal catalyst used for the reaction may be palladium-carbon, platinum(IV) oxide or the like, with palladium-carbon being preferred.

The solvent used for the reaction is not particularly restricted so long as it dissolves the starting materials to some degree and does not interfere with the reaction, and for example, there may be used alcohol-based solvents such as methanol, ethanol and 2-propanol, acetic acid ester-based solvents such as ethyl acetate, ether-based solvents such as tetrahydrofuran, 1,2-dimethoxyethane, t-butylmethyl ether, diethyl ether and 1,4-dioxane, organic acids such as acetic acid and formic acid, water, or mixtures thereof, among which ethanol/acetic acid mixed solvents are preferred.

The reaction temperature will generally differ depending on the starting materials, solvent and other reagents used in the reaction, but it is preferably between 10° C. and 80° C., and more preferably between 10° C. and 30° C.

The reaction time will generally differ depending on the starting materials, solvent and other reagents used in the reaction, as well as on the reaction temperature, but preferably stirring is carried out for 1-24 hours and more preferably about 12 hours at the aforementioned reaction temperature after addition of the reagents.

The metal catalyst may be used in a 0.01- to 2-fold molar amount with respect to compound (1b), but preferably it is used in a 0.05- to 1-fold molar amount.

Prior to this step, the substituent on $R^3$ may also be appropriately converted by a method ordinarily employed by those skilled in the art.

For example, when the substituent is nitro it may be converted to an amino group, and when the substituent is carboxyl it may be converted to alkoxycarbonyl, aminocarbonyl, amino or the like.

[Production Process C] Production Process (2) for Invention Compounds

[Chemical Formula 28]

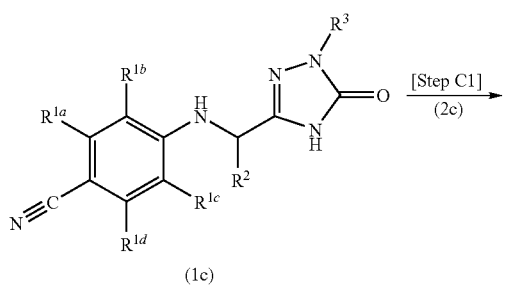

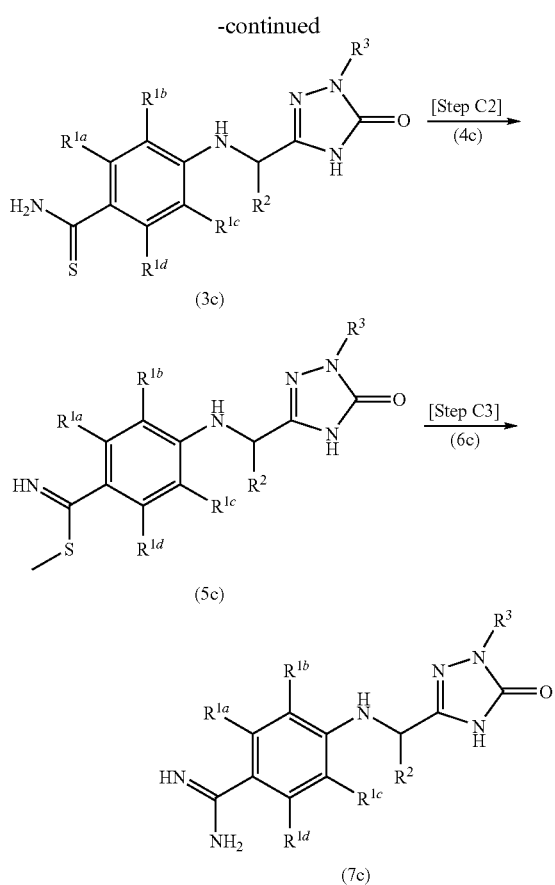

Here, $R^{1a}$, $R^{1b}$, $R^{1c}$, $R^{1d}$, $R^2$ and $R^3$ have the same definitions as above.

[Step C1]

This is a step of reacting compound (1c) (compound (14a) wherein T is a cyano group) with a sulfurizing agent such as aqueous ammonium sulfide (2c) in a solvent, in the presence or in the absence of a suitable base, to produce compound (3c).

As compound (1c) there may be used, instead of compound (14a) obtained by [Production Process A] described above, a publicly known compound, a commercially available compound or a compound that can be produced from a commercially available compound by a process ordinarily carried out by those skilled in the art or by the processes described in the examples below.

The step may also be carried out under a stream or under an atmosphere of an inert gas such as nitrogen or argon.

The solvent used for the reaction is not particularly restricted so long as it dissolves the starting materials to some degree and does not interfere with the reaction, and for example, there may be used alcohol-based solvents such as methanol, ethanol and 2-propanol, aromatic hydrocarbon-based solvents such as benzene and toluene, aliphatic hydrocarbon-based solvents such as heptane and hexane, pyridine, and mixtures thereof, among which pyridine is preferred.

As specific examples of bases for the reaction there may be used collidine, pyridine and triethylamine, among which triethylamine is preferred.

The reaction temperature will generally differ depending on the starting materials, solvent and other reagents used in the reaction, but it is preferably between 0° C. and 100° C., and more preferably between 10° C. and 80° C.

The reaction time will generally differ depending on the starting materials, solvent and other reagents used in the reaction, as well as on the reaction temperature, but preferably stirring is carried out for 2-48 hours and more preferably about 12 hours at the aforementioned reaction temperature after addition of the reagents.

The sulfurizing agent (2c) may be used in a 1- to 20-fold molar amount with respect to compound (1c), but preferably it is used in a 5- to 10-fold molar amount.

[Step C2]

This is a step of reacting compound (3c) with a methylating agent such as trimethyloxonium tetrafluoroborate (4c) in a solvent to produce compound (5c).

The step may also be carried out under a stream or under an atmosphere of an inert gas such as nitrogen or argon.

The solvent used for the reaction is not particularly restricted so long as it dissolves the starting materials to some degree and does not interfere with the reaction, and for example, there may be used halogen-based solvents such as dichloromethane, 1,2-dichloroethane and chloroform, aromatic hydrocarbon-based solvents such as benzene and toluene, aliphatic hydrocarbon-based solvents such as heptane and hexane, nitrile-based solvents such as acetonitrile, or mixtures thereof, among which acetonitrile is preferred.

The reaction temperature will generally differ depending on the starting materials, solvent and other reagents used in the reaction, but it is preferably between –20° C. and 50° C., and more preferably between 10° C. and 30° C.

The reaction time will generally differ depending on the starting materials, solvent and other reagents used in the reaction, as well as on the reaction temperature, but preferably stirring is carried out for between 10 minutes and 10 hours and more preferably for about 1 hour at the aforementioned reaction temperature after addition of the reagents.

The methylating agent (4c) may be used in a 1- to 1.5-fold molar amount with respect to compound (3c), but preferably it is used in a 1- to 1.2-fold molar amount and more preferably in a 1.05-fold molar amount.

[Step C3]

This is a step of reacting compound (5c) with an ammonia equivalent (6c) such as 1,1,3,3-tetramethyldisilazane or ammonium acetate in a solvent to produce compound (7c) of the invention.

The step may also be carried out under a stream or under an atmosphere of an inert gas such as nitrogen or argon.

The solvent used for the reaction is not particularly restricted so long as it dissolves the starting materials to some degree and does not interfere with the reaction, and for example, there may be used alcohol-based solvents such as methanol, ethanol and 2-propanol, ether-based solvents such as tetrahydrofuran, 1,2-dimethoxyethane, t-butylmethyl ether, diethyl ether and 1,4-dioxane, aromatic hydrocarbon-based solvents such as benzene and toluene, aliphatic hydrocarbon-based solvents such as heptane and hexane, nitrile-based solvents such as acetonitrile, or mixtures thereof, among which 2-propanol and acetonitrile mixed solvent is preferred.

The reaction temperature will generally differ depending on the starting materials, solvent and other reagents used in the reaction, but it is preferably between 20° C. and 100° C., and more preferably between 50° C. and 80° C.

The reaction time will generally differ depending on the starting materials, solvent and other reagents used in the reaction, as well as on the reaction temperature, but preferably stirring is carried out for 1-24 hours and more preferably about 12 hours at the aforementioned reaction temperature after addition of the reagents.

The ammonia equivalent (6c) may be used in a 1- to 5-fold molar amount with respect to compound (5c), but preferably it is used in a 1.1- to 3-fold molar amount.

[Production Process D] Production Process (3) for Invention Compounds

[Chemical Formula 29]

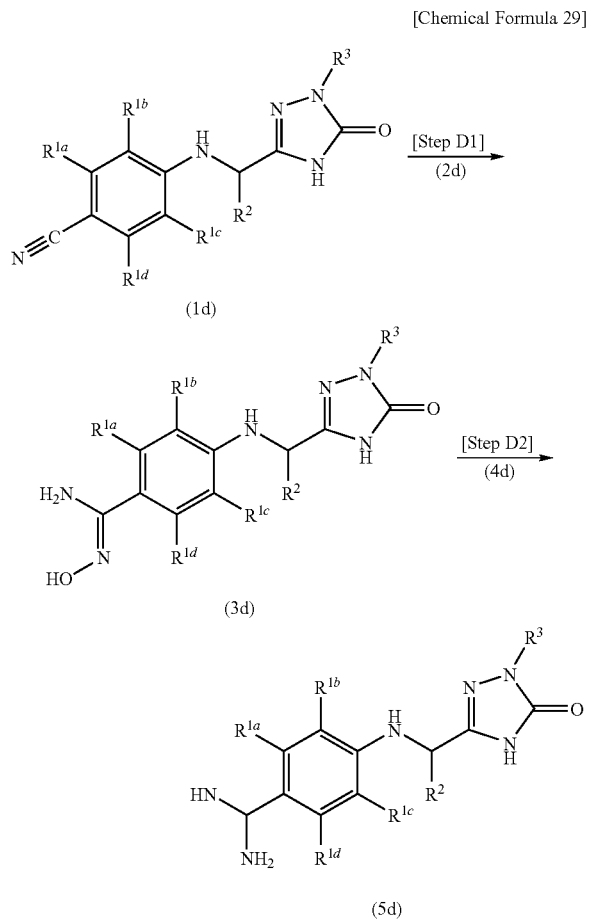

Here, $R^{1a}$, $R^{1b}$, $R^{1c}$, $R^{1d}$, $R^2$ and $R^3$ have the same definitions as above.

[Step D1]

This is a step of reacting compound (1d) (compound (14a) wherein T is a cyano group) with hydroxylamine hydrochloride (2d) in a solvent in the presence of a suitable base to produce compound (3d).

As compound (1d) there may be used, instead of compound (14a) obtained by [Production Process A] described above, a publicly known compound, a commercially available compound or a compound that can be produced from a commercially available compound by a process ordinarily carried out by those skilled in the art or by the processes described in the examples below.

The step may also be carried out under a stream or under an atmosphere of an inert gas such as nitrogen or argon.

The solvent used for the reaction is not particularly restricted so long as it dissolves the starting materials to some degree and does not interfere with the reaction, and for example, there may be used alcohol-based solvents such as methanol, ethanol, n-propanol, isopropanol, n-butanol, diethylene glycol, glycerin and octanol, amide-based solvents such as formamide, dimethylformamide and dimethylacetamide, ether-based solvents such as diethyl ether, tetrahydrofuran, 1,4-dioxane and dimethoxyethane, sulfoxide-based solvents such as dimethylsulfoxide, or mixtures thereof, among which ethanol is preferred.

As specific examples of bases for the reaction there may be used tertiary amines such as triethylamine and N-methylmorpholine, with triethylamine being preferred.

The reaction temperature will generally differ depending on the starting materials, solvent and other reagents used in the reaction, but it is preferably between 0° C. and 150° C., and more preferably between 50° C. and 100° C.

The reaction time will generally differ depending on the starting materials, solvent and other reagents used in the reaction, as well as on the reaction temperature, but preferably stirring is carried out for 1-96 hours and more preferably 2-24 hours at the aforementioned reaction temperature after addition of the reagents.

The hydroxylamine hydrochloride (2d) may be used in a 1- to 10-fold molar amount with respect to compound (1d), but preferably it is used in a 3- to 7-fold molar amount.

The base may be used in a 2- to 15-fold molar amount with respect to compound (1d), but preferably it is used in a 3- to 10-fold molar amount.

[Step D2]

This is a step of converting compound (3d) to compound (5d) by catalytic hydrogenation in a solvent, in the presence of a suitable metal catalyst and in the presence of an acid anhydride (4d).

The metal catalyst used for the reaction may be palladium-carbon or the like.

The acid anhydride used for the reaction may be acetic anhydride, trifluoroacetic acid anhydride or the like, with acetic anhydride being preferred.

The solvent used for the reaction is not particularly restricted so long as it dissolves the starting materials to some degree and does not interfere with the reaction, and for example, there may be used alcohol-based solvents such as methanol, ethanol and 2-propanol, ether-based solvents such as tetrahydrofuran, 1,2-dimethoxyethane, t-butylmethyl ether, diethyl ether and dioxane, aromatic hydrocarbon-based solvents such as benzene and toluene, organic acids such as acetic acid and formic acid, water, or mixtures thereof, with acetic acid being preferred.

The reaction temperature will generally differ depending on the starting materials, solvent and other reagents used in the reaction, but it is preferably between 10° C. and 80° C., and more preferably between 10° C. and 30° C.

The reaction time will generally differ depending on the starting materials, solvent and other reagents used in the reaction, as well as on the reaction temperature, but preferably stirring is carried out for 1-24 hours and more preferably 1-6 hours at the aforementioned reaction temperature after addition of the reagents.

The metal catalyst may be used in a 0.01- to 2-fold molar amount with respect to compound (3d), but preferably it is used in a 0.05- to 1-fold molar amount.

The acid anhydride (4d) may be used in a 1- to 50-fold molar amount with respect to compound (3d), but preferably it is used in a 3- to 10-fold molar amount.

Compound (3d) may also be converted to compound (5d) of the invention in the presence of a suitable metal reagent.

The step may also be carried out under a stream or under an atmosphere of an inert gas such as nitrogen or argon.

The metal reagent used for the reaction may be iron powder, zinc, Raney nickel or the like, with iron powder being preferred.

The solvent used for the reaction is not particularly restricted so long as it dissolves the starting materials to some degree and does not interfere with the reaction, and for example, there may be used alcohol-based solvents such as methanol, ethanol and 2-propanol, organic acids such as acetic acid and formic acid, water, or mixtures thereof, among which methanol, acetic acid and water mixed solvent is preferred.

The reaction temperature will generally differ depending on the starting materials, solvent and other reagents used in the reaction, but it is preferably between 10° C. and 80° C., and more preferably between 50° C. and 70° C.

The reaction time will generally differ depending on the starting materials, solvent and other reagents used in the reaction, as well as on the reaction temperature, but preferably stirring is carried out for 1-24 hours and more preferably about 12 hours at the aforementioned reaction temperature after addition of the reagents.

The metal reagent may be used in a 1- to 30-fold molar amount with respect to compound (1b), but preferably it is used in a 5- to 20-fold molar amount.

[Production Process E] Production Process (4) for Invention Compounds

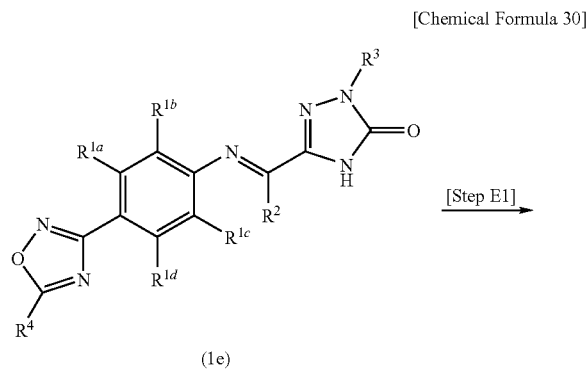

[Chemical Formula 30]

(1e)

(2e)

Here, $R^{1a}$, $R^{1b}$, $R^{1c}$, $R^{1d}$, $R^2$, $R^3$ and $R^4$ have the same definitions as above.

[Step E1]

This is a step of converting compound (1e) (compound (13a) wherein T is the formula:

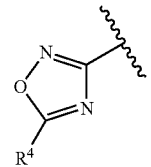

[Chemical Formula 31]

(wherein $R^4$ is as defined above)) to compound (2e) of the invention in a solvent, in the presence of a suitable metal reagent.

As compound (1e) there may be used, instead of compound (13a) obtained by [Production Process A] described above, a publicly known compound, a commercially available compound or a compound that can be produced from a commercially available compound by a process ordinarily carried out by those skilled in the art or by the processes described in the examples below.

The step may also be carried out under a stream or under an atmosphere of an inert gas such as nitrogen or argon.

The metal reagent used for the reaction may be iron powder, zinc, Raney nickel or the like, with iron powder being preferred.

The solvent used for the reaction is not particularly restricted so long as it dissolves the starting materials to some degree and does not interfere with the reaction, and for example, there may be used alcohol-based solvents such as methanol, ethanol and 2-propanol, organic acids such as acetic acid and formic acid, water, or mixtures thereof, among which methanol, acetic acid and water mixed solvent is preferred.

The reaction temperature will generally differ depending on the starting materials, solvent and other reagents used in the reaction, but it is preferably between 10° C. and 80° C., and more preferably between 50° C. and 70° C.

The reaction time will generally differ depending on the starting materials, solvent and other reagents used in the reaction, as well as on the reaction temperature, but preferably stirring is carried out for 1-48 hours and more preferably about 24 hours at the aforementioned reaction temperature after addition of the reagents.

The metal reagent may be used in a 2- to 50-fold molar amount with respect to compound (1e), but preferably it is used in a 10- to 30-fold molar amount.

Upon completion of the reaction in each step of the processes described above, the target compound of each step may be recovered from the reaction mixture by an ordinary method.

For example, when the entire reaction mixture is a solution, the reaction mixture may be returned to room temperature or cooled on ice as desired, and neutralized with an appropriate acid, alkali, oxidizing agent or reducing agent, prior to addition of water and an organic solvent that is immiscible therewith and does not react with the target compound, such as ethyl acetate, and separation of the layer containing the target compound. Next, a solvent that is immiscible with the recovered layer and does not react with the target compound may be added, and then the layer containing the target compound washed and separated. When the layer is an organic layer, it may be dried using a desiccating agent such as anhydrous magnesium sulfate or anhydrous sodium sulfate, and the solvent distilled off to recover the target compound. When the layer is an aqueous layer, it may be electrically desalted and then lyophilized to recover the target compound.

When the entire reaction mixture is a solution, it may be possible to recover the target compound simply by distilling off the components other than the target compound (for example, solvent, reagents, etc.) at ordinary pressure or under reduced pressure.

When the target compound precipitates alone as a solid, or when the entire reaction mixture is a solution and the target compound precipitates alone as a solid during the recovery process, the target compound may be first filtered by a filtration method, the filtered target compound washed with a suitable organic or inorganic solvent and drying performed for treatment of the mother liquor in the same manner as if the entire reaction mixture were a solution, in order to obtain the target compound.

On the other hand, when the reagents or catalyst are the only solids present, or when the entire reaction mixture is a solution and the reagents or catalyst alone precipitate in solid form during the recovery process, with the target compound remaining dissolved in solution, the reagents or catalyst may be first filtered by a filtration method, the filtered reagents or catalyst washed with a suitable organic or inorganic solvent, and the obtained wash combined with the mother liquor to obtain a liquid mixture, which may then be treated in the same manner as if the entire reaction mixture were a solution, in order to obtain the target compound.

The reaction mixture may be used directly for subsequent steps without isolation of the target compound in cases where components other than the target compound in the reaction mixture will not inhibit reaction in the subsequent steps.

Purity of the target compound recovered by such methods can be increased by appropriately carrying out recrystallization, various chromatography methods or distillation.

When the recovered target compound is a solid, purity of the target compound can usually be improved by recrystallization. For recrystallization there may be used a simple solvent or a multiple solvent mixture that does not react with the target compound. Specifically, the target compound may first be dissolved at room temperature or with heating in the simple solvent or solvent mixture that does not react with the target compound. The obtained mixture may then be cooled with ice water or the like or allowed to stand at room temperature to cause precipitation of the target compound from the mixture.

When the recovered target compound is a liquid, purity of the target compound can be improved by various chromatography methods. In most cases a weakly acidic silica gel such as silica gel 60 (70-230 mesh or 340-400 mesh) by Merck, Ltd. or BW-300 (300 mesh) by Fuji Silysia Chemical, Ltd. may be used. If the target compound is basic and adsorption onto the aforementioned silica gel types is too strong, there may be used propylamine-coated silica gel (200-350 mesh) by Fuji Silysia Chemical, Ltd. If the target compound is dipolar or requires elution with a highly polar solvent such as methanol, there may be used NAM-200H or NAM-300H by Nagara Science Co., Ltd. Using these silica gels, the target compound may be eluted in a simple solvent or solvent mixture that does not react with the target compound and the solvent distilled off to obtain the target compound with enhanced purity.

When the recovered target compound is a liquid, purity of the target compound can also be improved by distillation. For distillation, the target compound may be placed under reduced pressure at room temperature or with heating to achieve distillation of the target compound.

Representative examples of production processes for compounds according to the invention were described above, but the starting compounds and reagents for production of the invention compounds may form salts, hydrates or solvates, will differ depending on the starting materials and solvents used, and are not particularly restricted so long as they do not inhibit the reaction. The solvent used will also differ depending on the starting materials and reagents, and of course is not particularly restricted so long as it can dissolve the starting materials to some degree and does not inhibit the reaction. When a compound of the invention is obtained in free form, it may be converted to an acceptable salt or a hydrate of the compound by an ordinary method.

Conversely, when a compound of the invention is obtained as a salt or hydrate, it may be converted to the free form of the compound by an ordinary method.

Various isomers (for example, geometric isomers, optical isomers, rotational isomers, stereoisomers, tautomers and the like) obtained for compounds of the invention may be purified and isolated using ordinary separation means such as, for example, recrystallization, a diastereomer salt method, enzymatic resolution or chromatography methods (for example, thin-layer chromatography, column chromatography, gas chromatography, etc.).

When a compound of the invention is to be used as a medicament, the compound of the invention will usually be used after mixture and formulation with appropriate additives. However, this does not negate the use of the compounds of the invention in simple forms as medicaments.

As additives there may be mentioned excipients, binders, lubricants, disintegrators, coloring agents, taste correctives, emulsifiers, surfactants, dissolving aids, suspending agents, isotonizing agents, buffering agents, antiseptic agents, antioxidants, stabilizers, absorption accelerators and the like which are commonly used in medicaments, and these may also be used in appropriate combinations as desired.

As examples of excipients there may be mentioned lactose, saccharose, glucose, corn starch, mannitol, sorbitol, starch, pregelatinized starch, dextrin, crystalline cellulose, light anhydrous silicic acid, aluminum silicate, calcium silicate, magnesium metasilicate aluminate and calcium hydrogenphosphate.

As examples of binders there may be mentioned polyvinyl alcohol, methylcellulose, ethylcellulose, gum arabic, tragacanth, gelatin, shellac, hydroxypropylmethylcellulose, hydroxypropylcellulose, carboxymethylcellulose sodium, polyvinylpyrrolidone and macrogol.

As examples of lubricants there may be mentioned magnesium stearate, calcium stearate, sodium stearyl fumarate, talc, polyethylene glycol and colloidal silica.

As examples of disintegrators there may be mentioned crystalline cellulose, agar, gelatin, calcium carbonate, sodium hydrogen carbonate, calcium citrate, dextrin, pectin, low-substituted hydroxypropylcellulose, carboxymethylcellulose, carboxymethylcellulose calcium, croscarmellose sodium, carboxymethyl starch and carboxymethyl starch sodium.

As examples of coloring agents there may be mentioned those approved for addition to pharmaceuticals, such as iron sesquioxide, yellow iron sesquioxide, carmine, caramel, β-carotene, titanium oxide, talc, riboflavin sodium phosphate, yellow aluminum lake and the like.

As taste correctives there may be mentioned cocoa powder, menthol, aromatic powder, peppermint oil, camphor, cinnamon powder and the like.

As emulsifiers or surfactants there may be mentioned stearyltriethanolamine, sodium lauryl sulfate, laurylaminopropionic acid, lecithin, glycerin monostearate, sucrose fatty acid ester and glycerin fatty acid ester.

As dissolving aids there may be mentioned polyethylene glycol, propylene glycol, benzyl benzoate, ethanol, cholesterol, triethanolamine, sodium carbonate, sodium citrate, polysorbate 80 and nicotinic acid amide.

As suspending agents there may be mentioned the aforementioned surfactants, as well as hydrophilic polymers such as polyvinyl alcohol, polyvinylpyrrolidone, methylcellulose, hydroxymethylcellulose, hydroxyethylcellulose and hydroxypropylcellulose.

As isotonizing agents there may be mentioned glucose, sodium chloride, mannitol, sorbitol and the like.

As buffering agents there may be mentioned buffers of phosphate, acetate, carbonate, citrate and the like.

As antiseptic agents there may be mentioned methylparaben, propylparaben, chlorobutanol, benzyl alcohol, phenethyl alcohol, dehydroacetic acid and sorbic acid.

As antioxidants there may be mentioned sulfurous acid salts, ascorbic acid, α-tocopherol and the like.

As stabilizers there may be mentioned those commonly used in medicaments.

As absorption accelerators there may also be mentioned those commonly used in medicaments.

As formulations there may be mentioned oral forms such as tablets, powders, granules, capsules, syrups, lozenges and inhalants; external forms such as suppositories, ointments, eye salves, tapes, eye drops, nose drops, ear drops, poultices, lotions, and the like; and injections.

The aforementioned oral forms may be formulated with appropriate combinations of the additives mentioned above. Their surfaces may also be coated if necessary.

The aforementioned external forms may be formulated with appropriate combinations of the additives mentioned above, and especially excipients, binders, taste correctives, emulsifiers, surfactants, dissolving aids, suspending agents, isotonizing agents, antiseptic agents, antioxidants, stabilizers and absorption accelerators.

Injections may also be formulated with appropriate combinations of the additives mentioned above, and especially emulsifiers, surfactants, dissolving aids, suspending agents, isotonizing agents, buffering agents, antiseptic agents, antioxidants, stabilizers and absorption accelerators.

The dosage of a medicament according to the invention will differ depending on the severity of symptoms, patient age, gender and body weight, type of dosage form/salt, patient medicament sensitivity and specific nature of the disease, but the dosage per day for adults will generally be about 1 mg to about 1000 mg (preferably about 10 mg to about 300 mg) for oral administration, about 1 mg to about 1000 mg (preferably about 10 to about 300 mg) for external application, and in the case of an injection, about 1 μg to about 3000 μg (preferably about 3 μg to about 3000 μg) per kilogram of body weight, either administered as a single time or divided into 2 to 6 times per day.

These values are the actual administered amounts in the case of oral formulations and injections, and are the amounts actually absorbed by the body in the case of external formulations.

EXAMPLES

The compounds of the invention may be produced by the processes described in the following examples, and the effects of the compounds may be confirmed by the methods described in the following testing examples. However, these specific examples are merely illustrative and are not intended to restrict the invention in any way, and various modifications may be implemented such as are within the scope of the invention.

Compounds mentioned with reference to published documents are produced in the manner described in those documents.

Unless otherwise specified, the "silica gel" in "silica gel column chromatography" mentioned throughout the examples is either silica gel 60 (70-230 mesh or 340-400 mesh) by Merck, Ltd. or FLASH+Cartridge (KP-SIL, 60 Å, 32-63 μm) by Biotage.

Also unless otherwise specified, the "silica gel" in "silica gel column chromatography" mentioned throughout the examples may refer to Hi-Flash™ Column (40 μm 60 Å) by Yamazen Corp. in addition to the two silica gels mentioned above.

Unless otherwise specified, the "reverse phase silica gel" in "reverse phase silica gel column chromatography" mentioned throughout the examples refers to YMC*GEL ODS-A (12 nm S-50 μm) by YMC Co., Ltd.

Also unless otherwise specified, the "NH silica gel" in "NH silica gel column chromatography" mentioned throughout the examples refers to propylamine-coated silica gel (200-350 mesh) by Fuji Silysia Chemical, Ltd.

The "NAM silica gel" in "NAM silica gel column chromatography" mentioned throughout the examples refers to NAM-200H or NAM-300H by Nagara Science Co., Ltd.

Unless specifically stated otherwise, the "reverse-phase high performance liquid chromatography" mentioned throughout the examples was carried out under the following conditions.

[Column]

One of the following columns was selected for use.
Company: SHISEIDO
Name: CAPCELL PAK C18
Size: 50 mm×20 mm I.D.
Type: ACR 5 μm
Company: YMC
Name: YMC CombiPrep ODS-A
Size: 50 mm×20 mm I.D.
Type: S-5 μm
Company: WAKO
Name: WAKOpak Combi ODS-A
Size: 50 mm×20 mm I.D.

[Mobile Phase]

A combination of (1) and (2) below or a combination of (3) and (4) below was prepared with a gradient in a 100:0-0:100 proportion range for use as the mobile layer for liquid chromatography.
(1) 99.9% water (0.1% trifluoroacetic acid)
(2) 99.9% acetonitrile(0.1% trifluoroacetic acid)
(3) 99.9% water (0.1% acetic acid)
(4) 99.9% acetonitrile(0.1% acetic acid)

Unless specifically stated otherwise, the optical resolution using a SUMICHIRAL OA-2500 throughout the examples was carried out under the following conditions.

[Column]
Name: SUMICHIRAL OA-2500, 20 mmφ×25 cm
Manufacturer: Sumika Chemical Analysis Service, Ltd.

[Mobile Phase and Elution Rate]
0.05 M ammonium acetate-methanol solution, 10 ml/min Unless otherwise specified, the term "HPLC retention time" used throughout the examples is the retention time for optical resolution under the following conditions.

[Column]
Name: SUMICHIRAL OA-2500, 20 mmφ×25 cm
Manufacturer: Sumika Chemical Analysis Service, Ltd.

[Mobile Phase and Elution Rate]
0.05 M ammonium acetate-methanol solution, 10 ml/min Unless otherwise specified, the term "manganese dioxide" used throughout the examples refers to CMD-1 by Chuo Denki Kogyo Co., Ltd.

The term "room temperature" in the examples ordinarily refers to a temperature between about 10° C. and 35° C. The percentage values are weight percentages, unless otherwise specified. The other symbols used in the examples stand for the following.

¹H-NMR: Proton nuclear magnetic resonance
δ: Chemical shift
s: singlet
d: doublet
t: triplet
q: quartet
m: multiplet
br: broad
sept: septet
J: coupling constant
Hz: Hertz
M: mol/L
n-: normal
s-: secondary
t-: tertiary
N: Normality
CDCl$_3$: deutero chloroform
d$_6$-DMSO: deutero dimethylsulfoxide
CD$_3$OD: deutero methanol
CD$_3$CO$_2$D: deutero acetic acid
DMF: N,N-dimethylformamide
THF: tetrahydrofuran
DMSO: dimethylsulfoxide
DIAD: diisopropyl azodicarboxylate
DEAD: diethyl azodicarboxylate
MS3A: Molecular Sieves 3A
Yb(OTf)$_3$: ytterbium(III) trifluoromethanesulfonate hydrate
Me$_3$O$^+$BF$_4$$^-$: trimethyloxonium tetrafluoroborate
TBAF: tetrabutylammonium fluoride Example 1

(R) and (S)-2-{3-[(4-carbamimidoylphenylamino)-(2-fluoro-4,5-dimethoxyphenyl)methyl]-5-oxo-4,5-dihydro-[1,2,4]triazol-1-yl}benzoic acid acetate (1a) (2-fluoro-4,5-dimethoxyphenyl)-[4-(5-methyl-[1,2,4]oxadiazol-3-yl)phenylamino]acetonitrile

[Chemical Formula 32]

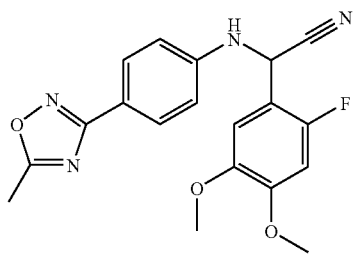

After adding 4.41 g of 4-(5-methyl-[1,2,4]oxadiazol-3-yl)phenylamine [CAS No. 10185-68-9], 4.64 g of 2-fluoro-4,5-dimethoxybenzaldehyde [CAS No. 71924-62-4], 5 g of Molecular Sieves 3A (hereinafter, "MS3A") and 6.69 ml of trimethylsilyl cyanide to a solution of 1.56 g of ytterbium(III) trifluoromethanesulfonate hydrate (hereinafter, "Yb(OTf)$_3$") in 100 ml of dichloromethane under a nitrogen atmosphere, the mixture was stirred at room temperature for 22 hours.

After then adding 500 ml of ethyl acetate to the reaction mixture, it was filtered through celite and the celite was washed with 1000 ml of ethyl acetate. The organic layers were combined and washed with water and saturated brine, and then dried over anhydrous sodium sulfate. The desiccating agent was filtered off and the filtrate was concentrated under reduced pressure. The residue was purified by silica gel column chromatography (ethyl acetate-heptane) to give the title compound (8.84 g) as a light yellow solid.

¹H-NMR (CDCl$_3$) δ 2.64 (s, 3H) 3.90 (s, 3H) 3.92 (s, 3H) 4.31 (d, J=7.6 Hz, 1H) 5.61 (d, J=7.6 Hz, 1H) 6.73 (d, J=11.2 Hz, 1H) 6.84 (d, J=8.8 Hz, 2H) 7.04 (d, J=7.2 Hz, 1H) 7.98 (d, J=8.8 Hz, 2H)

(1b) 2-(2-fluoro-4,5-dimethoxyphenyl)-2-[4-(5-methyl-[1,2,4]oxadiazol-3-yl)phenylamino]thioacetamide

[Chemical Formula 33]

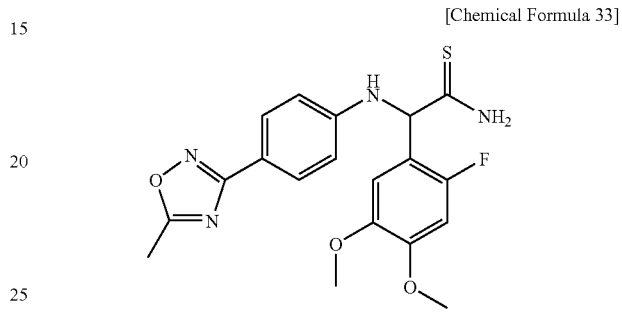

After adding 36.8 ml of a 20% aqueous solution of ammonium sulfide to a solution of 7.97 g of (2-fluoro-4,5-dimethoxyphenyl)-[4-(5-methyl-[1,2,4]oxadiazol-3-yl)phenylamino]acetonitrile in 750 ml of a methanol:tetrahydrofuran (hereinafter, "THF")=2:1 mixed solvent, the mixture was stirred at room temperature for 22 hours. Next, 1500 ml of ethyl acetate and 1000 ml of water were added to the reaction mixture, stirring was carried out at room temperature for 15 minutes, and the precipitate was filtered off. The organic layer in the filtrate was washed with saturated brine and dried over anhydrous sodium sulfate. The desiccating agent was filtered off, and the filtrate was concentrated under reduced pressure and combined with the previously obtained precipitate to give the title compound (8.59 g) as a light yellow solid.

¹H-NMR (d$_6$-DMSO) δ 2.60 (s, 3H) 3.73 (s, 3H) 3.77 (s, 3H) 5.41 (d, J=6.0 Hz, 1H) 6.75 (d, J=8.8 Hz, 2H) 6.79 (d, J=6.0 Hz, 1H) 6.92 (d, J=11.6 Hz, 1H) 7.14 (d, J=6.8 Hz, 1H) 7.74 (d, J=8.8 Hz, 2H) 9.54 (br.s, 1H) 9.80 (br.s, 1H)

(1c) 2-(2-fluoro-4,5-dimethoxyphenyl)-2-[4-(5-methyl-[1,2,4]oxadiazol-3-yl)phenylamino]thioacetimidic acid methyl ester

[Chemical Formula 34]

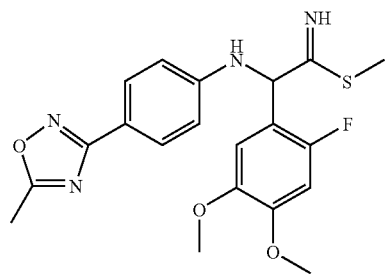

After adding 3.62 g of trimethyloxonium tetrafluoroborate (hereinafter, "Me$_3$O$^+$BF$_4$$^-$") to a solution of 8.59 g of 2-(2- fluoro-4,5-dimethoxyphenyl)-2-[4-(5-methyl-[1,2,4]oxadiazol-3-yl)phenylamino]thioacetamide in 400 ml of dichloromethane under a nitrogen atmosphere, the mixture was stirred at room temperature for 15 hours. Saturated aqueous sodium hydrogencarbonate was added to the reaction mixture and extraction was performed with dichloromethane. After washing the organic layer with saturated brine, it was dried over anhydrous sodium sulfate. The desiccating agent was filtered, and the filtrate was concentrated under reduced pressure to give the title compound (8.89 g, crude product) as an oil.

(1d) [2-(2-fluoro-4,5-dimethoxyphenyl)-2-[4-(5-methyl-[1,2,4]oxadiazol-3-yl)phenylimino]-1-methylsulfanylethylidene]carbamic acid methyl ester

[Chemical Formula 35]

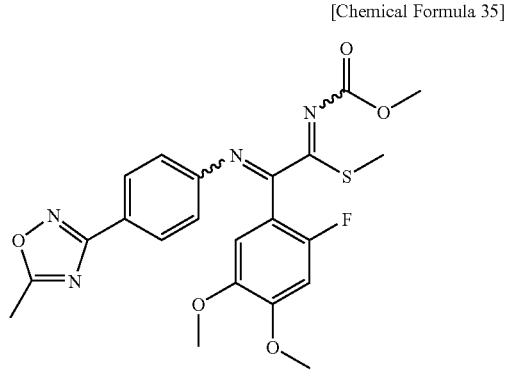

After adding 9.85 ml of 2,4,6-collidine and 4.94 ml of methyl 5 chloroformate to a solution of 8.89 g of 2-(2-fluoro-4,5-dimethoxyphenyl)-2-[4-(5-methyl-[1,2,4]oxadiazol-3-yl)phenylamino]thioacetimidic acid methyl ester in 300 ml of toluene, the mixture was stirred at 80° C. for 18 hours under a nitrogen atmosphere. After cooling the reaction mixture, dilute hydrochloric acid was added and extraction was performed with ethyl acetate. The organic layer was washed with water and saturated brine, and then dried over anhydrous sodium sulfate. The desiccating agent was filtered, and the filtrate was concentrated under reduced pressure. The residue was purified by silica gel column chromatography (ethyl acetate-heptane) to give the title compound (4.12 g, isomeric mixture) as a light yellow solid.

$^1$H-NMR (CDCl$_3$) Two isomers:

δ 2.32 (s, 3H) 2.65 (s, 3H) 3.62 (s, 3H) 3.82 (s, 3H) 3.93 (s, 3H) 6.61 (d, J=12.4 Hz, 1H) 7.10 (d, J=6.8 Hz, 2H) 7.44 (d, J=6.8 Hz, 1H) 8.01 (d, J=6.8 Hz, 2H)

δ 2.48 (s, 3H) 2.62 (s, 3H) 3.59 (s, 3H) 3.64 (s, 3H) 3.93 (s, 3H) 6.47 (d, J=10.4 Hz, 1H) 6.49 (d, J=6.0 Hz, 1H) 6.83 (d, J=8.4 Hz, 2H) 7.89 (d, J=8.41Hz, 2H)

(1e) 2-(3-{(2-fluoro-4,5-dimethoxyphenyl)-[4-(5-methyl-[1,2,4]oxadiazol-3-yl)phenylimino]methyl}-5-oxo-4,5-dihydro-[1,2,4]triazol-1-yl)benzoic acid

[Chemical Formula 36]

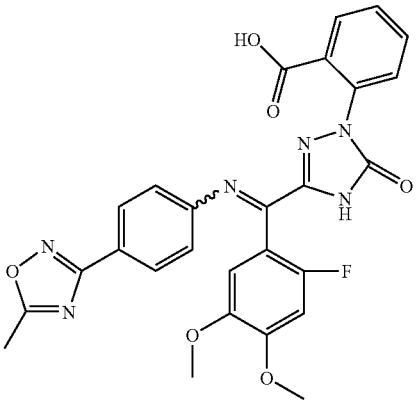

After adding 240 mg of 2-hydrazinobenzoic acid hydrochloride and 0.295 ml of triethylamine to a solution of 500 mg of [2-(2-fluoro-4,5-dimethoxyphenyl)-2-[4-(5-methyl-[1,2,4]oxadiazol-3-yl)phenylimino]-1-methylsulfanylethylidene]carbamic acid methyl ester in 10 ml of N,N-dimethylformamide (hereinafter, "DMF"), the mixture was stirred at 85° C. for 21 hours under a nitrogen atmosphere. After cooling the reaction mixture to room temperature, dilute hydrochloric acid (pH 3-4) was added and extraction was performed with ethyl acetate. The organic layer was then washed with dilute hydrochloric acid (pH 3-4) and saturated brine, and dried over anhydrous sodium sulfate. The desiccating agent was filtered, and the filtrate was concentrated under reduced pressure. The residue was purified by NAM silica gel column chromatography (methanol-ethyl acetate) to give the title compound (548 mg) as a light yellow solid.

$^1$H-NMR (CD$_3$OD) δ 2.62 (s, 3H) 3.71 (s, 3H) 3.75 (s, 3H) 6.65 (d, J=10.8 Hz, 1H) 6.93 (d, J=5.5 Hz, 1H) 6.95 (d, J=8.7 Hz, 2H) 7.53 (td, J=8.2, 1.3 Hz, 1H) 7.54 (dd, J=8.2, 1.3 Hz, 1H) 7.66 (td, J=8.2, 1.3 Hz, 1H) 7.88 (d, J=8.7 Hz, 2H) 7.97 (dd, J=8.2, 1.3 Hz, 1H)

(1f) 2-(3-{(2-fluoro-4,5-dimethoxyphenyl)-[4-(5-methyl-[1,2,4]oxadiazol-3-yl)phenylamino]methyl}-5-oxo-4,5-dihydro-[1,2,4]triazol-1-yl)benzoic acid

[Chemical Formula 37]

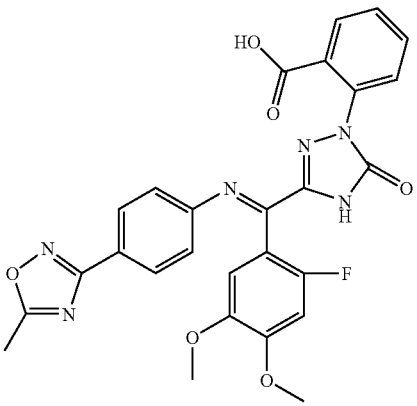

After adding 312 mg of sodium cyanotrihydroborate, 0.114 ml of acetic acid and 1.5 g of MS3A to a solution of 539 mg of 2-(3-{(2-fluoro-4,5-dimethoxyphenyl)-[4-(5-methyl-[1,2,4]oxadiazol-3-yl)phenylimino]methyl}-5-oxo-4,5-dihydro-[1,2,4]triazol-1-yl)benzoic acid in 40 ml of a methanol:THF=1:1 mixed solvent, the mixture was stirred at room temperature for 48 hours. Next, 0.7 ml of 5N hydrochloric acid was added, the reaction mixture was stirred at room temperature for 10 minutes, ethyl acetate and water were added, and filtration was performed with celite. The aqueous layer was extracted with 50 ml of ethyl acetate and dried over anhydrous sodium sulfate. The desiccating agent was filtered, and the filtrate was concentrated under reduced pressure. The residue was purified by NAM silica gel column chromatography (methanol-ethyl acetate) to give the title compound (504 mg) as a light yellow solid.

$^1$H-NMR (CD$_3$OD) δ 2.59 (s, 3H) 3.78 (s, 3H) 3.82 (s, 3H) 5.89 (s, 1H) 6.81 (d, J=8.8 Hz, 2H) 6.84 (d, J=11.1 Hz, 1H) 7.08 (d, J=6.7 Hz, 1H) 7.44-7.49 (m, 2H) 7.60 (t, J=8.1 Hz, 1H) 7.79 (d, J=8.8 Hz, 2H) 7.92 (d, J=8.1 Hz, 1H)

(1g) 2-{3-[(4-carbamimidoylphenylamino)-(2-fluoro-4,5-dimethoxyphenyl)methyl]-5-oxo-4,5-dihydro-[1,2,4]triazol-1-yl}benzoic acid trifluoroacetate

[Chemical Formula 38]

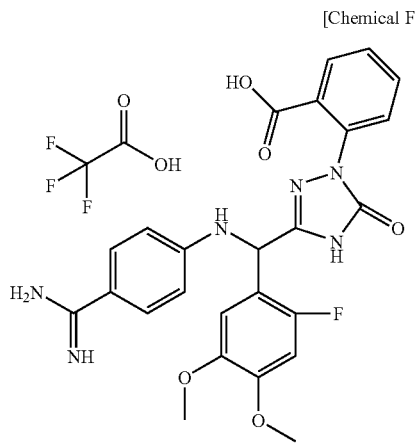

After adding 107 mg of iron powder to a solution of 70 mg of 2-(3-{(2-fluoro-4,5-dimethoxyphenyl)-[4-(5-methyl-[1,2,4]oxadiazol-3-yl)phenylamino]methyl}-5-oxo-4,5-dihydro-[1,2,4]triazol-1-yl)benzoic acid in 9 ml of a methanol:water:acetic acid=1:1:1 mixed solvent, the mixture was stirred at 55° C. for 40 hours under a nitrogen atmosphere. After filtering the reaction mixture, it was purified by reverse-phase high performance liquid chromatography (acetonitrile-water, 0.1% trifluoroacetic acid) to give 31 mg of the title compound.

$^1$H-NMR (CD$_3$OD) δ 3.80 (s, 3H) 3.84 (s, 3H) 5.95 (s, 1H) 6.86 (d, J=11.2 Hz, 1H) 6.87 (d, J=8.9 Hz, 2H) 7.05 (d, J=6.6 Hz, 1H) 7.48 (dd, J=8.1, 1.1 Hz, 1H) 7.50 (td, J=8.1, 1.1 Hz, 1H) 7.64 (d, J=8.9 Hz, 2H) 7.53 (td, J=8.1, 1.5 Hz, 1H) 7.97 (dd, J=8.1, 1.5 Hz, 1H)

Mass spectrum (ESI) m/z: 507 (M+H)$^+$ (1h) (R) and (S)-2-{3-[(4-carbamimidoylphenylamino)-(2-fluoro-4,5-dimethoxyphenyl)methyl]-5-oxo-4,5-dihydro-[1,2,4]triazol-1-yl}benzoic acid acetate

[Chemical Formula 39]

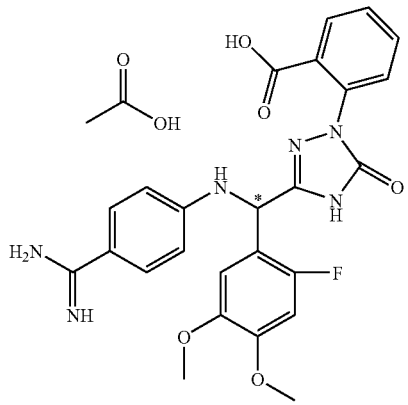

A CHIRALPAK™ AD (column size: 2 cmφ×25 cmL, Manufacturer: Daicel Chemical Industries, Ltd., Mobile phase: 2-propanol/hexane=1/3, 0.1% trifluoroacetic acid, Elution rate: 9 ml/min) was used for optical resolution of 26 mg of 2-{3-[(4-carbamimidoylphenylamino)-(2-fluoro-4,5-dimethoxyphenyl)methyl]-5-oxo-4,5-dihydro-[1,2,4]triazol-1-yl}benzoic acid trifluoroacetate (retention time for the first eluting enantiomer: 17 min, retention time for the second eluting enantiomer: 37 min). Triethylamine was added to the obtained second eluting enantiomer and the mixture was concentrated under reduced pressure. The residue was purified by reverse-phase high performance liquid chromatography (acetonitrile-water, 0.1% acetic acid) to give the second eluting enantiomer (4.4 mg) of the title compound.

Example 2

(R) and (S)-4-({(2-fluoro-3,5-dimethoxyphenyl)-[5-oxo-1-(1-oxypyridin-2-yl)-4,5-dihydro-1H-[1,2,4]triazol-3-yl]methyl}amino)benzamidine acetate (2a) 4-{[cyano-(2-fluoro-3,5-dimethoxyphenyl)methyl]amino}benzonitrile

[Chemical Formula 40]

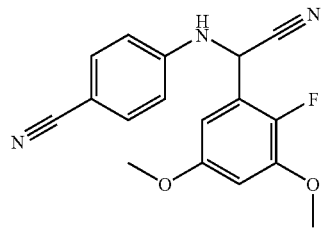

After adding 1.23 g of 4-aminobenzonitrile [CAS No. 873-74-5], 1.92 g of 2-fluoro-3,5-dimethoxybenzaldehyde [CAS No. 113984-71-7], 1.0 g of MS3A and 2.77 ml of trimethylsilyl cyanide to a solution of 0.645 g of Yb(OTf)$_3$ in 20 ml of dichloromethane under a nitrogen atmosphere, the mixture was stirred at room temperature for 20 hours. After then adding 500 ml of ethyl acetate and 300 ml of water to the reaction mixture, it was filtered through celite and the celite was washed with 500 ml of ethyl acetate. The organic layers were combined and dried over anhydrous magnesium sulfate. The desiccating agent was filtered, and the filtrate was concentrated under reduced pressure. The residue was purified by silica gel column chromatography (ethyl acetate-heptane) to give the title compound (2.59 g) as a white solid.

$^1$H-NMR (CDCl$_3$) δ 3.83 (s, 3H) 3.89 (s, 3H) 4.52 (d, J=7.5 Hz, 1H) 5.61 (d, J=7.5 Hz, 1H) 6.59-6.65 (m, 2H) 6.77 (d, J=9.0 Hz, 2H) 7.54 (d, J=9.0 Hz, 2H)

(2b) 2-(4-cyanophenylamino)-2-(2-fluoro-3,5-dimethoxyphenyl)thioacetamide

[Chemical Formula 41]

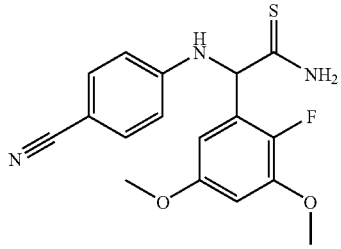

After adding 14.2 ml of a 20% aqueous solution of ammonium sulfide to a solution of 2.59 g of 4-{[cyano-(2-fluoro-3,5-dimethoxyphenyl)methyl]amino}benzonitrile in 300 ml of a methanol:THF=2:1 mixed solvent, the mixture was stirred at room temperature for 16 hours. Then, a further 14.2 ml of a 20% aqueous solution of ammonium sulfide was added, and the mixture was stirred at room temperature for 24 hours. Next, 500 ml of ethyl acetate and 800 ml of water were added to the reaction mixture, and the organic layer was washed twice with 300 ml of water and then once with 300 ml of saturated brine. The organic layer was dried over anhydrous magnesium sulfate, the desiccating agent was filtered off and the filtrate was concentrated under reduced pressure. The residue was purified by silica gel column chromatography (heptane-ethyl acetate (1:1)) to give the title compound (2.01 g) as a light yellow solid.

$^1$H-NMR (d$_6$-DMSO) δ 3.74 (s, 3H) 3.83 (s, 3H) 5.44 (d, J=5.9 Hz, 1H) 6.63-6.71 (m, 2H) 6.70 (d, J=9.0 Hz, 2H) 7.19 (d, J=5.9 Hz, 1H) 7.52 (d, J=9.0 Hz, 2H) 9.58 (br.s, 1H) 9.93 (br.s, 1H)

(2c) 2-(4-cyanophenylamino)-2-(2-fluoro-3,5-dimethoxyphenyl)thioacetimidic acid methyl ester

[Chemical Formula 42]

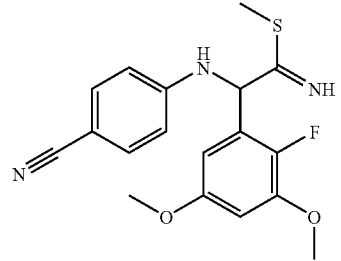

After adding 0.904 g of Me$_3$O$^+$BF$_4^-$ to a solution of 2.01 g of 2-(4-cyanophenylamino)-2-(2-fluoro-3,5-dimethoxyphenyl)thioacetamide in 150 ml of acetonitrile under a nitrogen atmosphere, the mixture was stirred at room temperature for 5 hours. Next, 400 ml of ethyl acetate and 300 ml of saturated aqueous sodium hydrogencarbonate were added and the organic layer was washed with 300 ml of water and 300 ml of saturated brine. The mixture was dried over anhydrous magnesium sulfate and the desiccating agent was filtered off. The filtrate was concentrated under reduced pressure to give the title compound (2.05 g) as a light yellow solid.

$^1$H-NMR (CDCl$_3$) δ 2.33 (s, 3H) 3.73 (s, 3H) 3.88 (s, 3H) 5.46 (d, J=5.4 Hz, 1H) 5.91 (br.s, 1H) 6.41 (dd, J=3.9, 3.2 Hz, 1H) 6.50 (dd, J=6.8, 3.2 Hz, 1H) 6.60 (d, J=9.1 Hz, 2H) 7.41 (d, J=9.1 Hz, 2H)

(2d) 2-(4-cyanophenylimino)-2-(2-fluoro-3,5-dimethoxyphenyl)thioacetimidic acid methyl ester

[Chemical Formula 43]

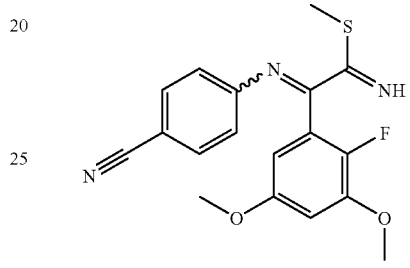

After adding 4.95 g of manganese dioxide to a solution of 2.05 g of 2-(4-cyanophenylamino)-2-(2-fluoro-3,5-dimethoxyphenyl)thioacetimidic acid methyl ester in 100 ml of ethyl acetate, the mixture was stirred at room temperature for 3 hours. The reaction mixture was filtered through celite, and the celite was washed with 500 ml of ethyl acetate. The organic layers were combined and concentrated under reduced pressure. The title compound (2.01 g) was obtained as a light yellow solid.

$^1$H-NMR (CDCl$_3$) Main isomer:

δ 2.49 (s, 3H) 3.68 (s, 3H) 3.82 (s, 3H) 6.01 (dd, J=3.5, 3.1 Hz, 1H) 6.51 (dd, J=7.0, 3.1 Hz, 1H) 6.85 (d, J=8.5 Hz, 2H) 7.50 (d, J=8.5 Hz, 2H)

(2e) [2-(4-cyanophenylimino)-2-(2-fluoro-3,5-dimethoxyphenyl)-1-methylsulfanylethylidene]carbamic acid methyl ester

[Chemical Formula 44]

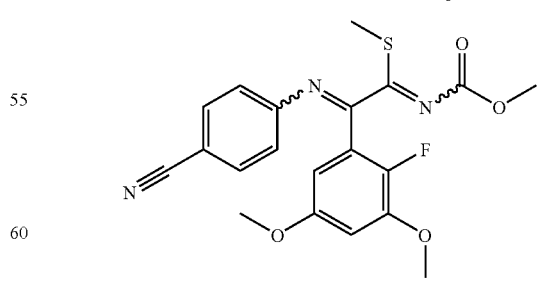

After adding 2.97 ml of 2,4,6-collidine and 1.74 ml of methyl chloroformate to a solution of 2.01 g of 2-(4-cyanophenylimino)-2-(2-fluoro-3,5-dimethoxyphenyl)thioacetimidic acid methyl ester in 80 ml of toluene, the mixture was stirred at 85° C. for 20 hours under a nitrogen atmosphere. After cooling the reaction mixture, 400 ml of ethyl acetate and 200 ml of a 2% aqueous sulfuric acid solution were added and the organic layer was washed with 300 ml of water and 300 ml of saturated brine. The organic layer was dried over anhydrous magnesium sulfate, the desiccating agent was filtered off and the filtrate was concentrated under reduced pressure. The residue was purified by silica gel column chromatography (heptane-ethyl acetate (3:2)) to give the title compound (1.89 g) as a light yellow solid.

¹H-NMR (CDCl₃) Two main isomers:

δ 2.34 (s, 3H) 3.62 (s, 3H) 3.66 (s, 3H) 3.75 (s, 3H) 6.70 (dd, J=6.6, 3.3 Hz, 1H) 6.93 (dd, J=4.0, 3.3 Hz, 1H) 7.08 (d, J=8.9 Hz, 2H) 7.62 (d, J=8.9 Hz, 2H)

δ 2.46 (s, 3H) 3.70 (s, 3H) 3.81 (s, 3H) 3.84 (s, 3H) 6.15 (t, J=3.3 Hz, 1H) 6.51 (dd, J=7.2, 3.3 Hz, 1H) 6.82 (d, J=8.7 Hz, 2H) 7.49 (d, J=8.7 Hz, 2H)

(2f) 4-({(2-fluoro-3,5-dimethoxyphenyl)-[5-oxo-1-(1-oxypyridin-2-yl)-4,5-dihydro-1H-[1,2,4]triazol-3-yl]methyl}amino)benzonitrile

[Chemical Formula 45]

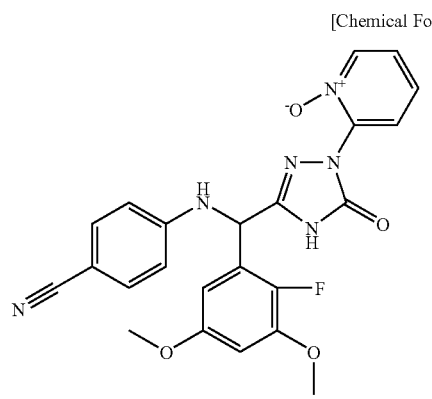

After adding 51 mg of (1-oxypyridin-2-yl)hydrazine (Example (2j)) and 0.056 ml of triethylamine to a solution of 152 mg of [2-(4-cyanophenylimino)-2-(2-fluoro-3,5-dimethoxyphenyl) 1-methylsulfanylethylidene]carbamic acid methyl ester in 6 ml of DMF, the mixture was stirred at 85° C. for 20 hours under a nitrogen atmosphere. The solvent was removed under reduced pressure, the residue was dissolved in 20 ml of a methanol:THF=1:1 mixed solvent, and then 184 mg of sodium cyanotrihydroborate and 0.063 ml of acetic acid were added prior to stirring at room temperature for 24 hours. Next, 100 ml of ethyl acetate and 50 ml of water were added and filtration was performed with celite. The aqueous layer was extracted with 50 ml of ethyl acetate, and then the organic layers were combined and dried over anhydrous magnesium sulfate, the desiccating agent was filtered off and the filtrate was concentrated under reduced pressure. The residue was purified by silica gel column chromatography (methanol-ethyl acetate (1:9)) to give the title compound (41 mg) as a brown oil.

¹H-NMR (CD₃OD) δ 3.73 (s, 3H) 3.85 (s, 3H) 5.94 (s, 1H) 6.59 (dd, J=3.3, 2.8 Hz, 1H) 6.63 (dd, J=7.1, 2.8 Hz, 1H) 6.78 (d, J=9.0 Hz, 2H) 7.45 (d, J=9.0 Hz, 2H) 7.54-7.64 (m, 2H) 7.72 (dd, J=8.5, 1.9 Hz, 1H) 8.44 (d, J=6.6 Hz, 1H)

(2g) 4-({(2-fluoro-3,5-dimethoxyphenyl)-[5-oxo-1-(1-oxypyridin-2-yl)-4,5-dihydro-1H-[1,2,4]triazol-3-yl]methyl}amino)thiobenzamide

[Chemical Formula 46]

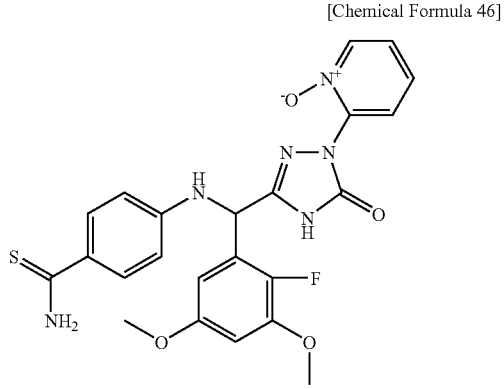

After adding 0.61 ml of a 20% aqueous solution of ammonium sulfide and 0.079 ml of triethylamine to a solution of 41 mg of 4-({(2-fluoro-3,5-dimethoxyphenyl)-[5-oxo-1-(1-oxypyridin-2-yl)-4,5-dihydro-1H-[1,2,4]triazol-3-yl] methyl}amino)benzonitrile in 1 ml of pyridine, the mixture was stirred at 60° C. for 16 hours under a nitrogen atmosphere. After cooling the reaction mixture, the solvent was removed under reduced pressure. The residue was dissolved in 3 ml of methanol and 1 ml of dimethylsulfoxide (hereinafter "DMSO"), and the solution was filtered through celite. The filtrate was purified by reverse-phase high performance liquid chromatography (acetonitrile-water, 0.1% trifluoroacetic acid) to give the title compound (21 mg) as a light yellow solid.

¹H-NMR (CD₃OD) δ 3.73 (s, 3H) 3.85 (s, 3H) 5.95 (s, 1H) 6.61-6.64 (m, 2H) 6.69 (d, J=9.5 Hz, 2H) 7.75-7.64 (m, 2H) 7.72 (dd, J=7.5, 1.8 Hz, 1H) 7.85 (d, J=9.5 Hz, 2H) 8.45 (dd, J=5.5, 1.0 Hz, 1H)

(2h) 4-({(2-fluoro-3,5-dimethoxyphenyl)-[5-oxo-1-(1-oxypyridin-2-yl)-4,5-dihydro-1H-[1,2,4]triazol-3-yl]methyl}amino)benzamidine trifluoroacetate

[Chemical Formula 47]

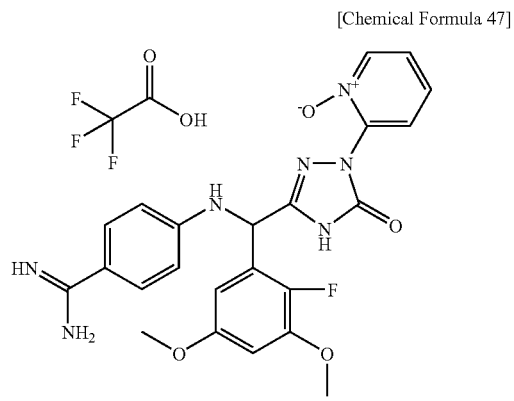

After adding 0.44 ml of a 0.1 M acetonitrile solution of Me₃O⁺BF₄⁻ to a solution of 21 mg of 4-({(2-fluoro-3,5-dimethoxyphenyl)-[5-oxo-1-(1-oxypyridin-2-yl)-4,5-dihydro-1H-[1,2,4]triazol-3-yl]methyl}amino)thiobenzamide in 5 ml of acetonitrile under a nitrogen atmosphere, the mixture was stirred at room temperature for 3 hours. The solvent was removed under reduced pressure, the residue was dissolved in 1.5 ml of acetonitrile and 1 ml of 2-propanol, and 18 µl of 1,1,3,3-tetramethyldisilazane was added. The reaction mixture was stirred at 85° C. for 16 hours under a nitrogen atmosphere and then cooled, and 20 µl of trifluoroacetic acid was added. The solvent was concentrated, and the residue was purified by reverse-phase high performance liquid chromatography (acetonitrile-water, 0.1% trifluoroacetic acid) to give the title compound (2.9 mg) as a white solid.

$^1$H-NMR (CD$_3$OD) δ 3.74 (s, 3H) 3.86 (s, 3H) 5.99 (s, 1H) 6.60 (dd, J=3.9, 3.0 Hz, 1H) 6.66 (dd, J=6.8, 3.0 Hz 1H) 6.86 (d, J=9.0 Hz, 2H) 7.58-7.65 (m, 2H) 7.63 (d, J=9.0 Hz, 2H) 7.74 (dd, J=8.0, 2.4 Hz, 1H) 8.47 (dd, J=5.2, 1.5 Hz, 1H)

Mass spectrum (ESI) m/z: 480 (M+H)$^+$ (2i) (R) and (S)-4-({(2-fluoro-3,5-dimethoxyphenyl)-[5-oxo-1-(1-oxypyridin-2-yl)-4,5-dihydro-1H-[1,2,4]triazol-3-yl]methyl}amino)benzamidine acetate

[Chemical Formula 48]

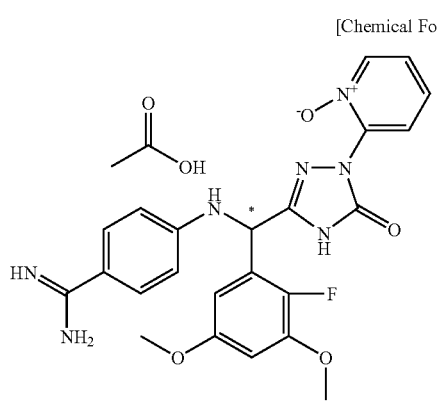

A SUMICHIRAL OA-2500 column was used for optical resolution of 35 mg of 4-({(2-fluoro-3,5-dimethoxyphenyl)-[5-oxo-1-(1-oxypyridin-2-yl)-4,5-dihydro-1H-[1,2,4]triazol-3-yl]methyl}amino)benzamidine trifluoroacetate, and the first eluting enantiomer (8.3 mg) of the title compound was obtained as a white solid.

$^1$H-NMR (CD$_3$OD) δ 3.74 (s, 3H) 3.86 (s, 3H) 5.97 (s, 1H) 6.61 (dd, J=3.9, 3.0 Hz, 1H) 6.63 (dd, J=6.8, 3.0 Hz 1H) 6.82 (d, J=9.0 Hz, 2H) 7.54 (td, J=7.2, 2.0 Hz, 1H) 7.61 (d, J=9.0 Hz, 2H) 7.61-7.63 (m, 1H) 7.69 (dd, J=7.2, 2.0 Hz, 1H) 8.43 (d, J=6.8 Hz, 1H)

HPLC retention time: 8 min (2j) (1-oxypyridin-2-yl)hydrazine

[Chemical Formula 49]

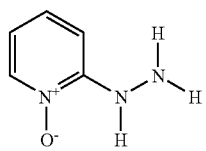

After adding 6 ml of hydrazine monohydrate to 1.66 ml of 2-chloropyridine N-oxide hydrochloride, the mixture was stirred at room temperature for 15 hours. The mixture was concentrated under reduced pressure and the residue was purified by NAM silica gel column chromatography (methanol-ethyl acetate) to give the title compound (888 mg) as a yellowish white solid.

$^1$H-NMR (CD$_3$OD) δ 6.70 (td, J=8.3, 1.5 Hz, 1H) 7.33 (ddd, J=8.3, 1.2, 0.6 Hz, 1H) 7.46 (ddd, J=8.3, 7.1, 1.2 Hz, 1H) 8.00 (ddd, J=7.1, 1.5, 0.6 Hz, 1H)

Example 3

(R) and (S)-4-({[2-fluoro-3-(2-fluoroethoxy)-5-methoxyphenyl]-(5-oxo-1-pyrimidin-2-yl-4,5-dihydro-1H-[1,2,4]triazol-3-yl)methyl}amino)benzamidine acetate (3a) (2-fluoro-5-methoxyphenoxy)triisopropylsilane

[Chemical Formula 50]

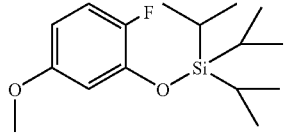

To a 200 ml THF solution containing 50.1 g of 1-fluoro-4-methoxybenzene and 70 g of N,N,N',N',N"-pentamethyldiethylenetriamine there was added dropwise 150 ml of n-butyllithium (2.66 M, hexane solution) over a period of 30 minutes, at −74° C. under a nitrogen atmosphere. After stirring for 3 hours at between −74° C. and −70° C., 100 ml of trimethyl borate was added. The temperature of the reaction mixture was then slowly allowed to rise to room temperature. Next, 70 ml of acetic acid and 75 ml of 30% aqueous hydrogen peroxide were added, and the reaction mixture was stirred overnight at room temperature. Water was then added to the reaction mixture, and then it was extracted with a mixture of hexane and ethyl acetate and dried over anhydrous magnesium sulfate. The desiccating agent was filtered off, and the filtrate was concentrated under reduced pressure to give a crude product of 1-fluoro-2-hydroxy-4-methoxybenzene (65.59 g) as a white solid.

The compound was dissolved in 500 ml of DMF, and then 40 g of imidazole and 85 g of chlorotriisopropylsilane were added and the mixture was stirred overnight at room temperature. Water was added to the reaction mixture and extraction was performed with t-butylmethyl ether. The organic layers were combined and washed with 0.5 N hydrochloric acid and saturated brine in that order. The organic layer was dried over anhydrous magnesium sulfate. The desiccating agent was filtered off and the filtrate was concentrated under reduced pressure. The residue was purified by silica gel column chromatography (t-butyl methyl ether-heptane) to give the title compound (113.04 g) as an oil.

$^1$H-NMR (CDCl$_3$) δ 1.11 (d, J=7.2 Hz, 18H) 1.23-1.32 (m, 3H) 3.75 (s, 3H) 6.39 (dt, J=2.8, 8.8 Hz, 1H) 6.50 (dd, J=3.2, 7.2 Hz, 1H) 6.93 (dd, J=8.0, 10.4 Hz, 1H)

(3b) 2-fluoro-5-methoxy-3-triisopropylsilanyloxy-benzaldehyde

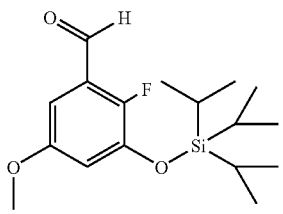

To a 240 ml THF solution containing 113 g of (2-fluoro-5-methoxyphenoxy)triisopropylsilane and 70 g of N,N,N',N',N''-pentamethyldiethylenetriamine there was added dropwise 150 ml of n-butyllithium (2.66 M, hexane solution) over a period of 50 minutes, at −74° C. After stirring for 3 hours at −60° C., 70 ml of N-formylmorpholine was added. The temperature of the reaction mixture was slowly allowed to rise to 6° C. Next, 1N hydrochloric acid was added to the reaction mixture while cooling on ice, and then the mixture was extracted with a mixture of hexane and t-butylmethyl ether and dried over anhydrous magnesium sulfate. The desiccating agent was filtered off and the filtrate was concentrated under reduced pressure. The residue was purified by silica gel column chromatography (t-butyl methyl ether-heptane) to give the title compound (113.26 g) as an oil.

$^1$H-NMR (CDCl$_3$) δ 1.11 (d, J=7.2 Hz, 18H) 1.22-1.35 (m, 3H) 3.80 (s, 3H) 6.77 (dd, J=2.8, 7.2 Hz, 1H) 6.87 (dd, J=3.2, 4.0 Hz, 1H) 10.33 (s, 1H)

(3c) (2-fluoro-5-methoxy-3-triisopropylsilanyloxyphenyl)-[4-(5-methyl-[1,2,4]oxadiazol-3-yl)phenylamino]acetonitrile

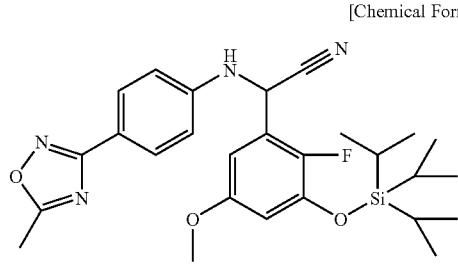

After adding 5.47 g of 4-(5-methyl-[1,2,4]oxadiazol-3-yl)phenylamine, 10.2 g of 2-fluoro-5-methoxy-3-triisopropylsilanyloxybenzaldehyde, 10 g of MS3A and 6.2 ml of trimethylsilyl cyanide to a solution of 1.94 g of Yb(OTf)$_3$ in 100 ml of dichloromethane under a nitrogen atmosphere, the mixture was stirred for 3 days at room temperature. Ethyl acetate was added to the reaction mixture, and washing was performed with water. The organic layer was dried over anhydrous magnesium sulfate. The desiccating agent was filtered off and the filtrate was concentrated under reduced pressure. The residue was purified by silica gel column chromatography (ethyl acetate-heptane) to give the title compound (9.01 g) as a light yellow solid.

$^1$H-NMR (CDCl$_3$) δ 1.10 (d, J=8.4 Hz, 18H) 1.22-1.31 (m, 3H) 2.62 (s, 3H) 3.78 (s, 3H) 4.32 (br.d, J=6.8 Hz, 1H) 5.62 (d, J=6.8 Hz, 1H) 6.57 (dd, J=3.2, 7.2 Hz, 1H) 6.67 (dd, J=2.8, 4.4 Hz, 1H) 6.82 (d, J=8.8 Hz, 2H) 7.96 (d, J=8.8 Hz, 2H)

(3d) [2-(2-fluoro-3-hydroxy-5-methoxyphenyl)-2-[4-(5-methyl-[1,2,4]oxadiazol-3-yl)phenylimino]-1-methylsulfanylethylidene]carbamic acid methyl ester

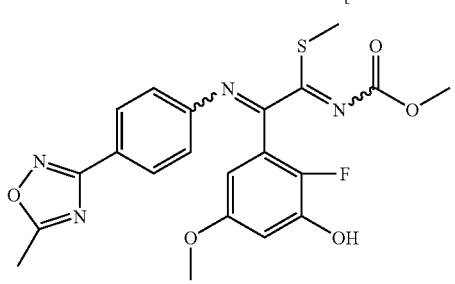

After adding 30 ml of a 20% aqueous solution of ammonium sulfide to a solution of 9.01 g of (2-fluoro-5-methoxy-3-triisopropylsilanyloxyphenyl)-[4-(5-methyl-[1,2,4]oxadiazol-3-yl)phenylamino]acetonitrile in 90 ml of an ethanol:THF=2:1 mixed solvent, the mixture was stirred at room temperature for 3 hours. Water was added to the reaction mixture and extraction was performed with ethyl acetate. The organic layer was dried over anhydrous magnesium sulfate. The desiccating agent was filtered off and the filtrate was concentrated under reduced pressure.

The residue was dissolved in 50 ml of DMF, and then 5 g of imidazole and 4 ml of chlorotriisopropylsilane were added and the mixture was stirred at room temperature until completion of the reaction. Water was added to the reaction mixture, extraction was performed with ethyl acetate, and the organic layer was dried over anhydrous magnesium sulfate. The desiccating agent was filtered off and the filtrate was concentrated under reduced pressure to give 2-(2-fluoro-5-methoxy-3-triisopropylsilanyloxyphenyl)-2-[4-(5-methyl-[1,2,4]oxadiazol-3-yl)phenylamino]thioacetamide (9.35 g, crude product).

To a solution of 9.35 g of the crude product in 100 ml of dichloromethane there was added 2 g of Me$_3$O$^+$BF$_4^-$, and the mixture was stirred at room temperature for 1 hour. Saturated aqueous sodium hydrogencarbonate was added to the reaction mixture and extraction was performed with ethyl acetate. The organic layer was washed with saturated brine and dried over anhydrous magnesium sulfate. The desiccating agent was filtered off, and the filtrate was concentrated under reduced pressure to give 2-(2-fluoro-5-methoxy-3-triisopropylsilanyloxyphenyl)-2-[4-(5-methyl-[1,2,4]oxadiazol-3-yl)phenylamino]thioacetimide acid methyl ester (crude product).

The crude product was dissolved in 50 ml of dichloromethane, and then 30 g of manganese dioxide was added and the mixture was stirred at room temperature for 3 hours. The reaction mixture was filtered and the filtrate was concentrated under reduced pressure.

The residue was dissolved in 50 ml of toluene, and then 9 ml of 2,4,6-collidine and 4 ml of methyl chloroformate were added and the mixture was stirred overnight at 85° C. under a nitrogen atmosphere. After cooling the reaction mixture, 1N hydrochloric acid was added and extraction was performed with ethyl acetate. The organic layer was dried over anhydrous magnesium sulfate. The desiccating agent was filtered off and the filtrate was concentrated under reduced pressure. The residue was purified by silica gel column chromatography (ethyl acetate-heptane) to give {2-(2-fluoro-5-methoxy-3-triisopropylsilanyloxyphenyl)-2-[4-(5-methyl-[1,2,4]oxadiazol-3-yl)phenylimino]-1-methylsulfanylethylidene}carbamic acid methyl ester (6.33 g) as a yellow solid.

6.33 g this compound was dissolved in 100 ml of THF, and then 12 ml of TBAF (1.0 M, THF solution) was added and the mixture was stirred at room temperature for 1 hour. Saturated aqueous ammonium chloride was added to the reaction mixture, extraction was performed with ethyl acetate, and the organic layer was dried over anhydrous magnesium sulfate. The desiccating agent was filtered off and the filtrate was concentrated under reduced pressure. The residue was purified by silica gel column chromatography (ethyl acetate-heptane) to give the title compound (3.9 g, isomeric mixture) as a light yellow solid.

$^1$H-NMR (CDCl$_3$) Two main isomers:

δ 2.34 (s, 3H) 2.66 (s, 3H) 3.61 (s, 3H) 3.81 (s, 3H) 6.74 (dd, J=3.6, 7.2 Hz, 1H) 6.93 (t, J=3.2 Hz, 1H) 7.13 (d, J=8.4 Hz, 2H) 8.03 (d, J=8.4 Hz, 2H) δ 2.47 (s, 3H) 2.63 (s, 3H) 3.63 (s, 3H) 3.64 (s, 3H) 6.17 (t, J=3.2 Hz, 1H) 6.53 (dd, J=2.8, 6.8 Hz, 1H) 6.84 (d, J=8.4 Hz, 2H) 7.90 (d, J=8.4 Hz, 2H)

(3e) {2-[2-fluoro-3-(2-fluoroethoxy)-5-methoxyphenyl]-2-[4-(5-methyl-[1,2,4]oxadiazol-3-yl)phenylimino]-1-methylsulfanylethylidene}carbamic acid methyl ester

[Chemical Formula 54]

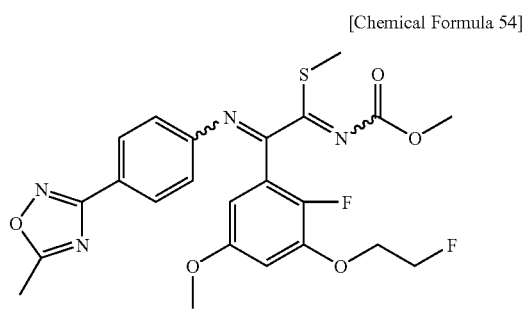

After adding 3.32 g of potassium carbonate and 3.13 g of 1-fluoro-2-iodoethane to a solution of 5.5 g of [2-(2-fluoro-3-hydroxy-5-methoxyphenyl)-2-[4-(5-methyl-[1,2,4]oxadiazol-3-yl)phenylimino]-1-methylsulfanylethylidene]carbamic acid methyl ester in 100 ml of DMF, the mixture was stirred at room temperature for 15 hours. Water was added to the reaction mixture and extraction was performed with ethyl acetate. After washing the organic layer with water and saturated brine, it was dried over anhydrous magnesium sulfate. The desiccating agent was filtered off and the filtrate was concentrated under reduced pressure. The residue was purified by silica gel column chromatography (ethyl acetate-heptane) to give the title compound (5.88 g) as a yellow solid.

$^1$H-NMR (CDCl$_3$) Two main isomers:

δ 2.46 (s, 3H) 2.62 (s, 3H) 3.62 (s, 3H) 3.62 (s, 3H) 4.10-4.20 (m, 2H) 4.60-4.75 (m, 2H) 6.16-6.20 (m, 1H) 6.47-6.51 (m, 1H) 6.83 (d, J=8.8 Hz, 2H) 7.88 (d, J=8.8 Hz, 2H)

δ 2.33 (s, 3H) 2.65 (s, 3H) 3.61 (s, 3H) 3.82 (s, 3H) 4.22-4.31 (m, 2H) 4.71-4.83 (m, 2H) 6.70-6.73 (m, 1H) 7.01-7.04 (m, 1H) 7.10 (d, J=8.8 Hz, 2H) 8.02 (d, J=8.8 Hz, 2H)

(3f) 5-{[2-fluoro-3-(2-fluoroethoxy)-5-methoxyphenyl]-[4-(5-methyl-[1,2,4]oxadiazol-3-yl)phenylamino]methyl}-2-pyrimidin-2-yl-2,4-dihydro-[1,2,4]triazol-3-one

[Chemical Formula 55]

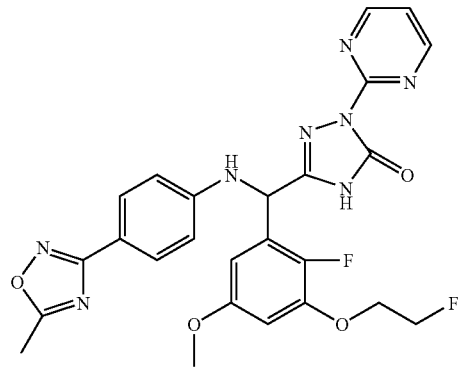

After adding 1.09 g of 2-hydrazinopyrimidine [CAS No. 7504-94-1] and 1.37 ml of triethylamine to a solution of 5.0 g of {2-[2-fluoro-3-(2-fluoroethoxy)-5-methoxyphenyl]-2-[4-(5-methyl-[1,2,4]oxadiazol-3-yl)phenylimino]-1-methylsulfanylethylidene}carbamic acid methyl ester in 50 ml of DMF, the mixture was stirred at 85° C. for 20 hours and 30 minutes under a nitrogen atmosphere. The reaction mixture was concentrated, and the residue was dissolved in 30 ml of methanol, 10 ml of THF and 3 ml of acetic acid. Next, 2.0 g of sodium cyanotrihydroborate was added to the solution, and after stirring at room temperature for 3 hours, 1.0 g of sodium cyanotrihydroborate was further added and stirring was continued for 2 hours and 30 minutes at room temperature. Water and ethyl acetate were added to the reaction mixture, and the insoluble portion was filtered off to give the title compound as a white solid. The filtrate was extracted with ethyl acetate and the organic layer was concentrated under reduced pressure. The residue was purified by NAM silica gel column chromatography (methanol-ethyl acetate) to give the title compound (total: 4.88 g) as a white solid.

$^1$H-NMR (d$_6$-DMSO) δ 2.57 (s, 3H) 3.69 (s, 3H) 4.24-4.38 (m, 2H) 4.66-4.82 (m, 2H) 5.86 (d, J=8.0 Hz, 1H) 6.60-6.68 (m, 1H) 6.73-6.75 (m, 1H) 6.79 (d, J=8.4 Hz, 2H) 7.27 (d, J=8.0 Hz, 1H) 7.38 (t, J=4.8 Hz, 1H) 7.72 (d, J=8.4 Hz, 2H) 8.79 (d, J=4.8 Hz, 2H) 12.24 (s, 1H)

(3g) 4-({[2-fluoro-3-(2-fluoroethoxy)-5-methoxyphenyl]-(5-oxo-1-pyrimidin-2-yl-4,5-dihydro-1H-[1,2,4]triazol-3-yl)methyl}amino)benzamidine acetate

[Chemical Formula 56]

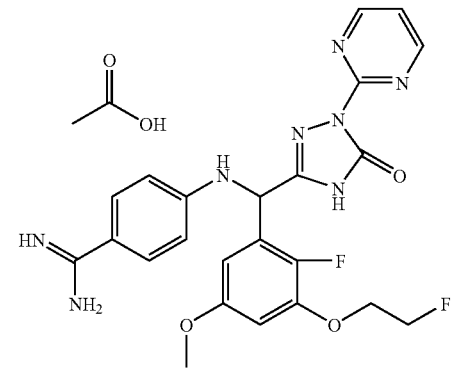

After adding 1.2 g of iron powder to a solution of 1.2 g of 5-{[2-fluoro-3-(2-fluoroethoxy)-5-methoxyphenyl]-[4-(5-methyl-[1,2,4]oxadiazol-3-yl)phenylamino]methyl}-2-pyrimidin-2-yl-2,4-dihydro-[1,2,4]triazol-3-one in 18 ml of a methanol:water:acetic acid=1:1:1 mixed solvent, the mixture was stirred at 65° C. for 24 hours and 30 minutes under a nitrogen atmosphere. After filtering the reaction mixture, it was purified by reverse-phase high performance liquid chromatography (acetonitrile-water, 0.1% acetic acid) to give the title compound (750 mg) as a light yellow solid.

$^1$H-NMR (CD$_3$OD) δ 1.94 (s, 3H) 3.70 (s, 3H) 4.21-4.31 (m, 2H) 4.65-4.79 (m, 2H) 5.99 (s, 1H) 6.62-6.66 (m, 2H) 6.86 (d, J=8.8 Hz, 2H) 7.32 (t, J=4.8 Hz, 1H) 7.61 (d, J=8.8 Hz, 2H) 8.76 (d, J=4.8 Hz, 2H)

Mass spectrum (ESI) m/z: 497 (M+H)$^+$ (3h) (R) and (S)-4-({[2-fluoro-3-(2-fluoroethoxy)-5-methoxyphenyl]-(5-oxo-1-pyrimidin-2-yl-4,5-dihydro-1H-[1,2,4]triazol-3-yl)methyl}amino)benzamidine acetate

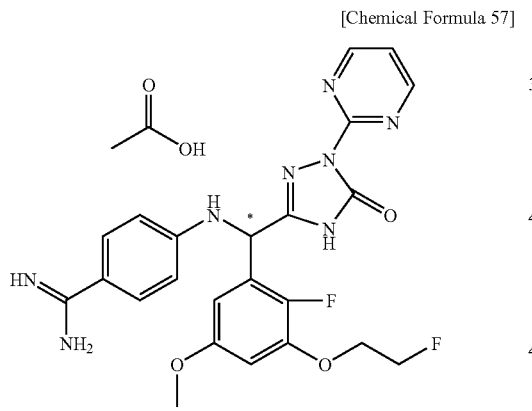

[Chemical Formula 57]

A SUMICHIRAL OA-2500 column was used for optical resolution of 750 mg of 4-({[2-fluoro-3-(2-fluoroethoxy)-5-methoxyphenyl]-(5-oxo-1-pyrimidin-2-yl-4,5-dihydro-1H-[1,2,4]triazol-3-yl)methyl}amino)benzamidine acetate, and the first eluting enantiomer (349.9 mg) of the title compound was obtained as a white solid.

$^1$H-NMR (CD$_3$OD) δ 1.93 (s, 3H) 3.72 (s, 3H) 4.22-4.32 (m, 2H) 4.65-4.80 (m, 2H) 5.97 (s, 1H) 6.63-6.68 (m, 2H) 6.87 (d, J=8.8 Hz, 2H) 7.31 (t, J=4.8 Hz, 1H) 7.62 (d, J=8.8 Hz, 2H) 8.76 (d, J=4.8 Hz, 2H)

HPLC retention time: 12 min

Example 4

4-{[(R) and (S)-{3-methoxy-5-[(S)-(tetrahydrofuran-3-yl)oxy]phenyl}-(5-oxo-1-pyrimidin-2-yl-4,5-dihydro-1H-[1,2,4]triazol-3-yl)methyl] amino}benzamidine acetate (4a) 3-methoxy-5-triisopropylsilanyloxybenzaldehyde

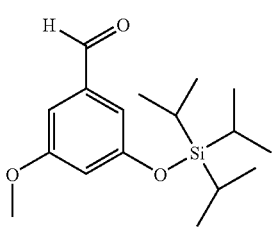

[Chemical Formula 58]

To a 50 ml DMF solution containing 2.8 g of 3-hydroxy-5-methoxybenzaldehyde [CAS No. 57179-35-8] there were added 2.5 g of imidazole and 5.9 ml of chlorotriisopropylsilane. The mixture was stirred at room temperature for 14 hours and 30 minutes. Water was added to the reaction mixture and extraction was performed with ethyl acetate. The organic layer was washed with ice-cooled 1N hydrochloric acid, water and saturated brine and then dried over anhydrous magnesium sulfate. The desiccating agent was filtered off and the filtrate was concentrated under reduced pressure. The residue was purified by silica gel column chromatography (ethyl acetate-heptane) to give the title compound (5.7 g) as a light yellow oil.

$^1$H-NMR (CDCl$_3$) δ 1.11 (d, J=7.2 Hz, 18H) 1.29 (sept, J=7.2 Hz, 3H) 3.83 (s, 3H) 6.67-6.70 (m, 1H) 6.97 (s, 1H) 6.99 (s, 1H) 9.87 (s, 1H)

(4b) {2-(3-methoxy-5-triisopropylsilanyloxyphenyl)-2-[4-(5-methyl-[1,2,4]oxadiazol-3-yl)phenylimino]-1-methylsulfanylethylidene}carbamic acid methyl ester

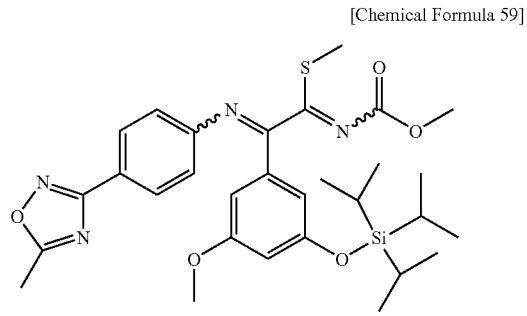

[Chemical Formula 59]

After adding 3.24 g of 4-(5-methyl-[1,2,4]oxadiazol-3-yl)phenylamine, 10 g of MS3A, 1.15 g of Yb(OTf)$_3$ and 7.0 ml of trimethylsilyl cyanide to a solution of 5.7 g of 3-methoxy-5-triisopropylsilanyloxybenzaldehyde in 150 ml of dichloromethane under a nitrogen atmosphere, the mixture was stirred at room temperature for 12 hours. The reaction mixture was filtered, and the filtrate was concentrated under reduced pressure. The residue was purified by silica gel column chromatography (ethyl acetate-heptane) to give a white solid (5.59 g).

To a solution of 5.59 g of the obtained white solid in 110 ml of a methanol:THF=8:3 mixed solvent there was added 60 ml of a 20% aqueous solution of ammonium sulfide, and the mixture was stirred at room temperature for 31 hours and 50 minutes. Water was added to the reaction mixture and extraction was performed with ethyl acetate. After washing the organic layer with water and saturated brine, it was dried over anhydrous magnesium sulfate. The desiccating agent was filtered off and the filtrate was concentrated under reduced pressure. The residue was purified by silica gel column chromatography (ethyl acetate-heptane) to give a light yellow solid (2.90 g).

To a solution of 2.90 g of the obtained light yellow solid in 30 ml of acetonitrile there was added 896 mg of $Me_3O^+BF_4^-$, and the mixture was stirred at room temperature for 2 hours. Saturated aqueous sodium hydrogencarbonate was added to the reaction mixture, and extraction was performed with ethyl acetate. After washing the organic layer with water and saturated brine, it was dried over anhydrous magnesium sulfate. The desiccating agent was filtered off, and the filtrate was concentrated under reduced pressure to give a yellow solid (3.25 g).

To a solution of 3.25 g of the obtained yellow solid in ethyl acetate there was added 10 g of manganese dioxide, and the mixture was stirred at room temperature for 2 hours. The reaction mixture was filtered, and the filtrate was concentrated under reduced pressure to give a yellow oil (2.80 g).

To a solution of 2.80 g of the obtained yellow oil in 50 ml of toluene there was added 2.4 ml of 2,4,6-collidine and 1.2 ml of methyl chloroformate, and the mixture was stirred at 80° C. for 4 hours under a nitrogen atmosphere. Water was added to the reaction mixture and extraction was performed with ethyl acetate. The organic layer was washed with ice-cooled 1N hydrochloric acid, water and saturated brine and then dried over anhydrous magnesium sulfate. The desiccating agent was filtered off and the filtrate was concentrated under reduced pressure. The residue was purified by silica gel column chromatography (ethyl acetate-heptane) to give the title compound (1.8 g) as a yellow oil.

$^1$H-NMR (CDCl$_3$) Main isomer:

δ 1.10 (d, J=7.2 Hz, 18H) 1.17-1.32 (m, 3H) 2.31 (s, 3H) 2.65 (s, 3H) 3.63 (s, 3H) 3.83 (s, 3H) 6.59 (dd, J=2.0, 2.4 Hz, 1H) 6.86-6.91 (m, 1H) 7.09-7.13 (m, 1H) 7.16 (d, J=8.8 Hz, 2H) 8.01 (d, J=8.8 Hz, 2H)

(4c) {2-(3-hydroxy-5-methoxyphenyl)-2-[4-(5-methyl-[1,2,4]oxadiazol-3-yl)phenylimino]-1-methylsulfanylethylidene}carbamic acid methyl ester

[Chemical Formula 60]

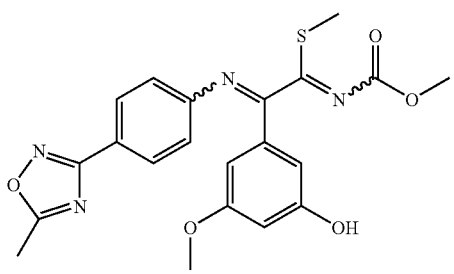

After adding 3.3 ml of TBAF (1.0 M, THF solution) to a 15 ml THF solution containing 1.8 g of {2-(3-methoxy-5-triisopropylsilanyloxyphenyl)-2-[4-(5-methyl-[1,2,4]oxadiazol-3-yl)phenylimino]-1-methylsulfanylethylidene}carbamic acid methyl ester, the mixture was stirred at 0° C. for 1 hour and 30 minutes. Saturated aqueous ammonium chloride was added to the reaction mixture and extraction was performed with ethyl acetate. The organic layer was washed with water and saturated brine and dried over anhydrous magnesium sulfate. The desiccating agent was filtered off and the filtrate was concentrated under reduced pressure. The residue was purified by silica gel column chromatography (ethyl acetate-heptane) to give the title compound (1.06 g) as a yellow solid.

$^1$H-NMR (CDCl$_3$) Main isomer:

δ 2.32 (s, 3H) 2.65 (s, 3H) 3.64 (s, 3H) 3.83 (s, 3H) 5.15 (br.s, 1H) 6.56 (dd, J=2.0, 2.4 Hz, 1H) 6.91 (dd, J=2.0, 2.4 Hz, 1H) 7.02 (dd, J=2.4, 2.4 Hz, 1H) 7.15 (d, J=8.8 Hz, 2H) 8.01 (d, J=8.8 Hz, 2H)

(4d) 4-[({3-methoxy-5-[(S)-(tetrahydrofuran-3-yl)oxy]phenyl}-(5-oxo-1-pyrimidin-2-yl-4,5-dihydro-1H-[1,2,4]triazol-3-yl)methyl)amino]benzamidine acetate

[Chemical Formula 61]

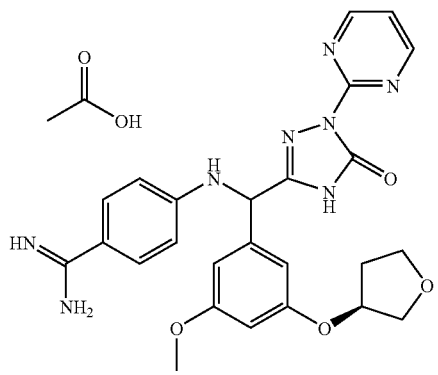

After adding 0.022 ml of (R)-(−)-3-hydroxytetrahydrofuran, 89.3 mg of triphenylphosphine and 0.155 ml of diethyl azodicarboxylate (hereinafter, "DEAD") (2.2 M toluene solution) to a 1 ml THF solution containing 100 mg of {2-(3-hydroxy-5-methoxyphenyl)-2-[4-(5-methyl-[1,2,4]oxadiazol-3-yl)phenylimino]-1-methylsulfanylethylidene}carbamic acid methyl ester at 0° C., the mixture was stirred at room temperature for 14 hours. The reaction mixture was concentrated, and the residue was crudely purified by silica gel column chromatography (ethyl acetate-heptane) to give 121 mg of a crude product.

Next, 22.5 mg of 2-hydrazinopyrimidine and 0.028 ml of triethylamine were added to a 1 ml DMF solution containing 121 mg of the obtained crude product, and the mixture was stirred at 85° C. for 11 hours under a nitrogen atmosphere. The reaction mixture was concentrated, and the residue was dissolved in 0.8 ml of methanol, 0.8 ml of THF and 0.1 ml of acetic acid. Next, 100 mg of sodium cyanotrihydroborate was added to the solution and the mixture was stirred at room temperature for 2 hours. The reaction mixture was crudely purified by reverse-phase high performance liquid chromatography (acetonitrile-water, 0.1% acetic acid) to give a crude product.

To a solution of the obtained crude product in 3 ml of a methanol:water:acetic acid=1:1:1 mixed solvent there was added 100 mg of iron powder, and the mixture was stirred at 65° C. for 14 hours under a nitrogen atmosphere. After filtering the reaction mixture, it was purified by reverse-phase high performance liquid chromatography (acetonitrile-water, 0.1% acetic acid) to give the title compound (20.75 mg) as a light yellow solid.

$^1$H-NMR (CD$_3$OD) δ 1.93 (s, 3H) 1.95-2.09 (m, 1H) 2.11-2.24 (m, 1H) 3.74 (s, 3H) 3.77-3.94 (m, 4H) 4.90-4.99 (m, 1H) 5.62 (s, 1H) 6.39 (t, J=2.0 Hz, 1H) 6.68 (s, 1H) 6.74 (s, 1H) 6.86 (d, J=8.8 Hz, 2H) 7.32 (t, J=4.8 Hz, 1H) 7.60 (d, J=8.8 Hz, 2H) 8.77 (d, J=4.8 Hz, 2H)

Mass spectrum (ESI) m/z: 503 (M+H)+

(4e) 4-[((R) and (S)-{3-methoxy-5-[(S)-(tetrahydrofuran-3-yl)oxy]phenyl}-(5-oxo-1-pyrimidin-2-yl-4,5-dihydro-1H-[1,2,4]triazol-3-yl)methyl)amino]benzamidine acetate

[Chemical Formula 62]

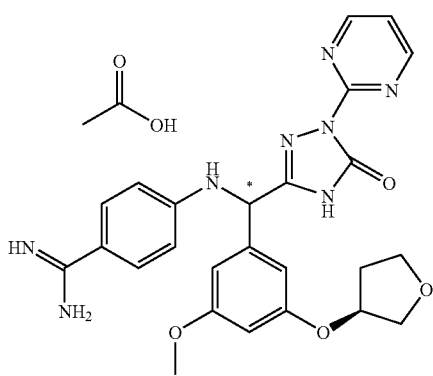

A SUMICHIRAL OA-2500 column was used for optical resolution of 20.75 mg of 4-[({3-methoxy-5-[(S)-(tetrahydrofuran-3-yl)oxy]phenyl}-(5-oxo-1-pyrimidin-2-yl-4,5-dihydro-1H-[1,2,4]triazol-3-yl)methyl)amino]benzamidine acetate, and the first eluting enantiomer (8.35 mg) of the title compound was obtained as a light yellow solid.

1H-NMR (CD3OD) δ 1.92 (s, 3H) 1.97-2.07 (m, 1H) 2.11-2.23 (m, 1H) 3.70-3.98 (m, 7H) 4.89-5.01 (m, 1H) 5.59 (s, 1H) 6.37 (dd, J=2.0, 2.4 Hz, 1H) 6.69 (s, 1H) 6.74 (s, 1H) 6.85 (d, J=8.8 Hz, 2H) 7.29 (t, J=4.8 Hz, 1H) 7.59 (d, J=8.8 Hz, 2H) 8.76 (d, J=4.8 Hz, 2H)

HPLC retention time: 14 min

Example 5

4-[((R) and (S)-{3-methoxy-5-[(R)-(tetrahydrofuran-3-yl)oxy]phenyl}-(5-oxo-1-pyrimidin-2-yl-4,5-dihydro-1H-[1,2,4]triazol-3-yl)methyl)amino]benzamidine acetate (5a) 4-[({3-methoxy-5-[(R)-(tetrahydrofuran-3-yl)oxy]phenyl}-(5-oxo-1-pyrimidin-2-yl-4,5-dihydro-1H-[1,2,4]triazol-3-yl)methyl)amino]benzamidine acetate

[Chemical Formula 63]

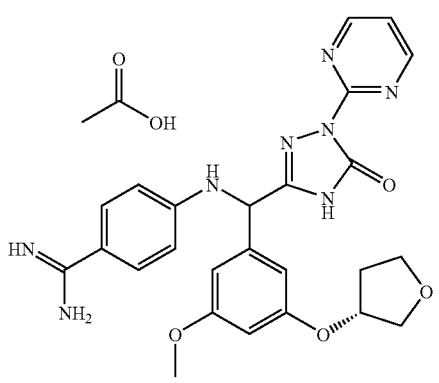

After adding 0.022 ml of (S)-(+)-3-hydroxytetrahydrofuran, 89.3 mg of triphenylphosphine and 0.155 ml of DEAD (2.2 M, toluene solution) to a 1 ml THF solution containing 100 mg of {2-(3-hydroxy-5-methoxyphenyl)-2-[4-(5-methyl-[1,2,4]oxadiazol-3-yl)phenylimino]-1-methylsulfanylethylidene}carbamic acid methyl ester (Example (4c)) at 0° C., the mixture was stirred at room temperature for 14 hours. The reaction mixture was concentrated, and the residue was crudely purified by silica gel column chromatography (ethyl acetate-heptane) to give 121 mg of a crude product.

Next, 22.5 mg of 2-hydrazinopyrimidine and 0.028 ml of triethylamine were added to a 1 ml DMF solution containing 121 mg of the obtained crude product, and the mixture was stirred at 85° C. for 11 hours under a nitrogen atmosphere. The reaction mixture was concentrated, and the residue was dissolved in 0.8 ml of methanol, 0.8 ml of THF and 0.1 ml of acetic acid. Next, 100 mg of sodium cyanotrihydroborate was added to the solution and the mixture was stirred at room temperature for 2 hours. The reaction mixture was crudely purified by reverse-phase high performance liquid chromatography (acetonitrile-water, 0.1% acetic acid) to give a crude product.

To a solution of the obtained crude product in 3 ml of a methanol:water:acetic acid=1:1:1 mixed solvent there was added 100 mg of iron powder, and the mixture was stirred at 65° C. for 14 hours under a nitrogen atmosphere. After filtering the reaction mixture, it was purified by reverse-phase high performance liquid chromatography (acetonitrile-water, 0.1% acetic acid) to give the title compound (21.38 mg) as a light yellow solid.

1H-NMR (CD3OD) δ 1.80-2.27 (m, 5H) 3.65-3.96 (m, 7H) 4.94 (br.s, 1H) 5.64 (s, 1H) 6.39 (s, 1H) 6.68 (s, 1H) 6.74 (s, 1H) 6.87 (d, J=8.8 Hz, 2H) 7.33 (t, J=4.8 Hz, 1H) 7.60 (d, J=8.8 Hz, 2H) 8.78 (d, J=4.8 Hz, 2H)

Mass spectrum (ESI) m/z: 503 (M+H)+

(5b) 4-[((R) and (S)-{3-methoxy-5-[(R)-(tetrahydrofuran-3-yl)oxy]phenyl}-(5-oxo-1-pyrimidin-2-yl-4,5-dihydro-1H-[1,2,4]triazol-3-yl)methyl)amino]benzamidine acetate

[Chemical Formula 64]

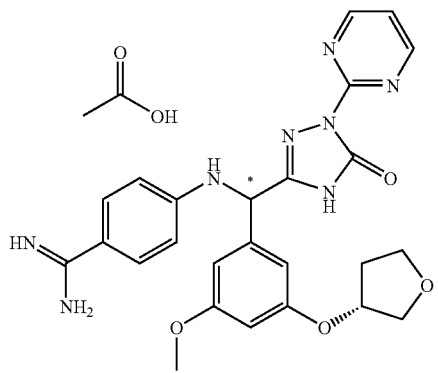

A SUMICHIRAL OA-2500 column was used for optical resolution of 21.38 mg of 4-[({3-methoxy-5-[(R)-(tetrahydrofuran-3-yl)oxy]phenyl}-(5-oxo-1-pyrimidin-2-yl-4,5-dihydro-1H-[1,2,4]triazol-3-yl)methyl)amino]benzamidine acetate, to give the first eluting enantiomer (8.79 mg) of the title compound as a light yellow solid.

1H-NMR (CD3OD) δ 1.92 (s, 3H) 2.01-2.11 (m, 1H) 2.15-2.28 (m, 1H) 3.75 (s, 3H) 3.78-3.94 (m, 4H) 4.92-5.00 (m, 1H) 5.58 (s, 1H) 6.38 (dd, J=2.0, 2.4 Hz, 1H) 6.68 (s, 1H) 6.74 (s, 1H) 6.85 (d, J=8.8 Hz, 2H) 7.30 (t, J=4.8 Hz, 1H) 7.60 (d, J=8.8 Hz, 2H) 8.76 (d, J=4.8 Hz, 2H)

HPLC retention time: 14 min

Example 6

(R) and (S)-4-({[3-methoxy-5-(2-methoxyethoxy)phenyl]-(5-oxo-1-pyrimidin-2-yl-4,5-dihydro-1H-[1,2,4]triazol-3-yl)methyl}amino)benzamidine acetate (6a) 4-({[3-methoxy-5-(2-methoxyethoxy)phenyl]-(5-oxo-1-pyrimidin-2-yl-4,5-dihydro-1H-[1,2,4]triazol-3-yl)methyl}amino)benzamidine acetate

[Chemical Formula 65]

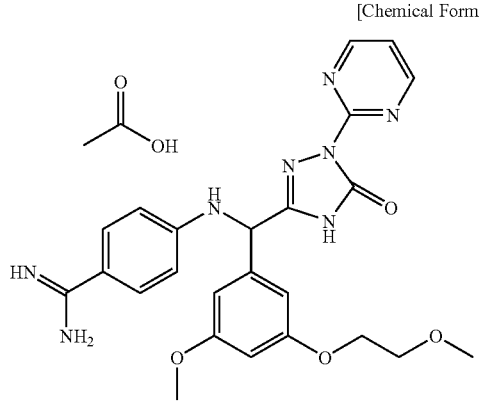

After adding 94 mg of potassium carbonate and 0.043 ml of 1-bromo-2-methoxyethane to a 1 ml DMF solution containing 100 mg of {2-(3-hydroxy-5-methoxyphenyl)-2-[4-(5-methyl-[1,2,4]oxadiazol-3-yl)phenylimino]-1-methylsulfanylethylidene}carbamic acid methyl ester (Example (4c)), the mixture was stirred at room temperature for 24 hours and 50 minutes. Water was added to the reaction mixture and extraction was performed with ethyl acetate. The organic layer was washed with water and then dried through PRESEP™. The filtrate was concentrated to give 114 mg of a crude product.

Next, 25 mg of 2-hydrazinopyrimidine and 0.031 ml of triethylamine were added to a 1 ml DMF solution containing 114 mg of the obtained crude product, and the mixture was stirred at 85° C. for 14 hours under a nitrogen atmosphere. The reaction mixture was concentrated, and the residue was dissolved in 0.8 ml of methanol, 0.8 ml of THF and 0.05 ml of acetic acid. Next, 100 mg of sodium cyanotrihydroborate was added to the solution and the mixture was stirred at room temperature for 6 hours. The reaction mixture was crudely purified by reverse-phase high performance liquid chromatography (acetonitrile-water, 0.1% acetic acid) to give a crude product.

To a solution of the obtained crude product in 3 ml of a methanol:water:acetic acid=1:1:1 mixed solvent there was added 100 mg of iron powder, and the mixture was stirred at 60° C. for 11 hours under a nitrogen atmosphere. After filtering the reaction mixture, it was purified by reverse-phase high performance liquid chromatography (acetonitrile-water, 0.1% acetic acid) to give the title compound (17.93 mg) as a white solid.

$^1$H-NMR (CD$_3$OD) δ 1.93 (s, 3H) 3.38 (s, 3H) 3.64-3.72 (m, 2H) 3.75 (s, 3H) 4.01-4.12 (m, 2H) 5.61 (s, 1H) 6.45 (t, J=2.0 Hz, 1H) 6.74 (d, J=2.0 Hz, 2H) 6.86 (d, J=8.8 Hz, 2H) 7.33 (t, J=4.8 Hz, 1H) 7.60 (d, J=8.8 Hz, 2H) 8.78 (d, J=4.8 Hz, 2H)

Mass spectrum (ESI) m/z: 491 (M+H)$^+$ (6b) (R) and (S)-4-[([3-methoxy-5-(2-methoxyethoxy)phenyl]-(5-oxo-1-pyrimidin-2-yl-4,5-dihydro-1H-[1,2,4]triazol-3-yl)methyl)amino]benzamidine acetate

[Chemical Formula 66]

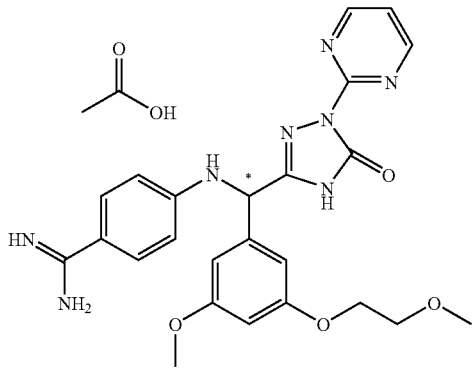

A SUMICHIRAL OA-2500 column was used for optical resolution of 17.93 mg of 4-({[3-methoxy-5-(2-methoxyethoxy)phenyl]-(5-oxo-1-pyrimidin-2-yl-4,5-dihydro-1H-[1,2,4]triazol-3-yl)methyl}amino)benzamidine acetate, to give the first eluting enantiomer (5.86 mg) of the title compound as a white solid.

$^1$H-NMR (CD$_3$OD) δ 1.91 (s, 3H) 3.38 (s, 3H) 3.64-3.72 (m, 2H) 3.75 (s, 3H) 4.02-4.12 (m, 2H) 5.59 (s, 1H) 6.44 (t, J=2.0 Hz, 1H) 6.74 (d, J=2.0 Hz, 2H) 6.86 (d, J=8.8 Hz, 2H) 7.31 (t, J=4.8 Hz, 1H) 7.60 (d, J=8.8 Hz, 2H) 8.77 (d, J=4.8 Hz, 2H)

HPLC retention time: 7 min (Column name: SUMICHIRAL OA-2500, 4.6 mmφ×25 cm, Manufacturer: Sumika Chemical Analysis Service, Ltd., Mobile phase: 0.05 M ammonium acetate-methanol solution, Elution rate: 1 ml/min)

Example 7

(R) and (S)-4-({[3-methoxy-5-(2-methoxyethoxy)phenyl]-(5-oxo-1-pyridazin-3-yl-4,5-dihydro-1H-[1,2,4]triazol-3-yl)methyl}amino)benzamidine acetate

[Chemical Formula 67]

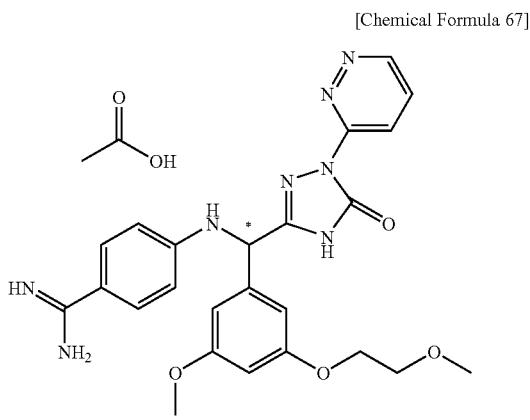

After adding 94 mg of potassium carbonate and 0.043 ml of 1-bromo-2-methoxyethane to a 1 ml DMF solution containing 100 mg of {2-(3-hydroxy-5-methoxyphenyl)-2-[4-(5- methyl-[1,2,4]oxadiazol-3-yl)phenylimino]-1-methylsulfanylethylidene}carbamic acid methyl ester (Example (4c)), the mixture was stirred at room temperature for 14 hours. Water was added to the reaction mixture and extraction was performed with ethyl acetate. The organic layer was washed with water and dried through PRESEP™. The filtrate was concentrated to give 112 mg of a crude product.

To a 1 ml DMF solution of the obtained crude product there was added 33 mg of 3-hydrazinopyridazine hydrochloride [CAS No. 117043-87-5] and 0.063 ml of triethylamine, and the mixture was stirred at 85° C. for 11 hours and 30 minutes under a nitrogen atmosphere. The reaction mixture was then concentrated.

The residue was dissolved in 0.8 ml of methanol, 0.8 ml of THF and 0.1 ml of acetic acid. Next, 100 mg of sodium cyanotrihydroborate was added to the solution and the mixture was stirred at room temperature for 3 hours and 30 minutes. The reaction mixture was crudely purified by reverse-phase high performance liquid chromatography (acetonitrile-water, 0.1% acetic acid) to give a crude product.

To a solution of the obtained crude product in 2.4 ml of a methanol:water:acetic acid=1:1:1 mixed solvent there was added 100 mg of iron powder, and the mixture was stirred at 65° C. for 18 hours and 30 minutes under a nitrogen atmosphere. After filtering the reaction mixture, it was purified by reverse-phase high performance liquid chromatography (acetonitrile-water, 0.1% acetic acid) to give 4-({[3-methoxy-5-(2-methoxyethoxy)phenyl]-(5-oxo-1-pyridazin-3-yl-4,5-dihydro-1H-[1,2,4]triazol-3-yl)methyl}amino)benzamidine acetate.

Mass spectrum (ESI) m/z: 491 (M+H)$^+$

The compound was optically resolved using a SUMICHIRAL OA-2500 column, and the first eluting enantiomer (4.57 mg) of the title compound was obtained as a light yellow solid.

$^1$H-NMR (CD$_3$OD) δ 1.93 (s, 3H) 3.37 (s, 3H) 3.65-3.71 (m, 2H) 3.74 (s, 3H) 4.02-4.09 (m, 2H) 5.57 (s, 1H) 6.41 (t, J=2.4 Hz, 1H) 6.75 (d, J=2.4 Hz, 2H) 6.85 (d, J=8.8 Hz, 2H) 7.59 (d, J=8.8 Hz, 2H) 7.74 (dd, J=4.8, 9.2 Hz, 1H) 8.56 (dd, J=1.6, 9.2 Hz, 1H) 8.99 (dd, J=1.6, 4.8 Hz, 1H)

HPLC retention time: 12 min

Example 8

(R) and (S)-4-({[3-(2-dimethylaminoethoxy)-5-methylphenyl]-(5-oxo-1-pyrimidin-2-yl-4,5-dihydro-1H-[1,2,4]triazol-3-yl)methyl}amino)benzamidine diacetate

[Chemical Formula 68]

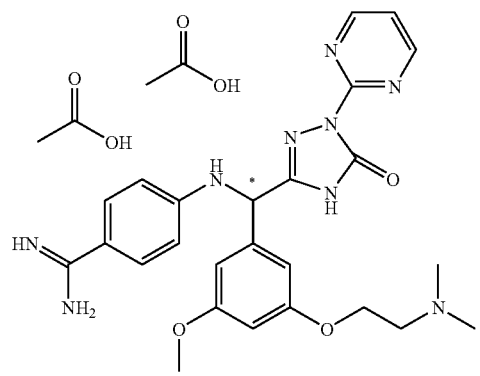

After adding 40 mg of 2-dimethylaminoethanol, 120 mg of triphenylphosphine and 0.200 ml of DEAD (2.2 M, toluene solution) to a 1 ml THF solution containing 100 mg of {2-(3-hydroxy-5-methoxyphenyl)-2-[4-(5-methyl-[1,2,4]oxadiazol-3-yl)phenylimino]-1-methylsulfanylethylidene}carbamic acid methyl ester (Example (4c)) at 0° C., the mixture was stirred at room temperature for 16 hours and 30 minutes. The reaction mixture was concentrated, and the residue was crudely purified by silica gel column chromatography (ethyl acetate-heptane) to give 55 mg of a crude product.

To a 1 ml DMF solution containing 55 mg of the obtained crude product there were added 12 mg of 2-hydrazinopyrimidine and 0.015 ml of triethylamine, and the mixture was stirred at 85° C. for 11 hours and 30 minutes under a nitrogen atmosphere. The reaction mixture was concentrated, and the residue was dissolved in 0.8 ml of methanol, 0.8 ml of THF and 0.1 ml of acetic acid. Next, 100 mg of sodium cyanotrihydroborate was added to the solution and the mixture was stirred at room temperature for 3 hours and 30 minutes. The reaction mixture was crudely purified by reverse-phase high performance liquid chromatography (acetonitrile-water, 0.1% acetic acid) to give a crude product.

To a solution of the obtained crude product in 2.4 ml of a methanol:water:acetic acid=1:1:1 mixed solvent there was added 100 mg of iron powder, and the mixture was stirred at 65° C. for 18 hours and 30 minutes under a nitrogen atmosphere. After filtering the reaction mixture, it was crudely purified by reverse-phase high performance liquid chromatography (acetonitrile-water, 0.1% acetic acid) to give a crude product.

The obtained crude product was optically resolved using a SUMICHIRAL OA-2500 column, and the first eluting enantiomer (4.35 mg) of the title compound was obtained as a light yellow solid.

$^1$H-NMR (CD$_3$OD) δ 1.92 (s, 6H) 2.49 (s, 6H) 2.96 (dd, J=5.2, 5.6 Hz, 2H) 3.76 (s, 3H) 4.14 (dd, J=5.2, 5.6 Hz, 2H) 5.58 (s, 1H) 6.47 (t, J=2.0 Hz, 1H) 6.77 (t, J=2.0 Hz, 2H) 6.85 (d, J=8.8 Hz, 2H) 7.30 (t, J=4.8 Hz, 1H) 7.60 (d, J=8.8 Hz, 2H) 8.77 (d, J=4.8 Hz, 2H)

HPLC retention time: 11 min

Example 9

(R) and (S)-4-{[(3,5-dimethoxyphenyl)-(5-oxo-1-pyrimidin-2-yl-4,5-dihydro-1H-[1,2,4]triazol-3-yl)methyl]amino}benzamidine acetate (9a) {2-(3-hydroxy-5-methoxyphenyl)-2-[4-(5-methyl-[1,2,4]oxadiazol-3-yl)phenylimino]-1-methylsulfanylethylidene}carbamic acid methyl ester

[Chemical Formula 69]

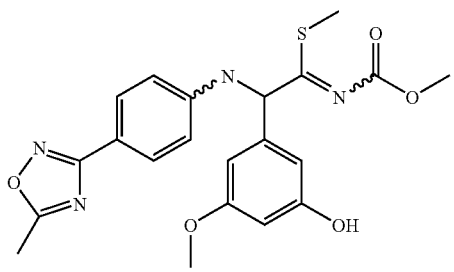

After adding 3.41 g of 4-(5-methyl-[1,2,4]oxadiazol-3-yl)phenylamine, 6.0 g of MS3A, 1.21 g of Yb(OTf)$_3$ and 4.9 ml of trimethylsilyl cyanide to a solution of 6.0 g of 3-methoxy-5-triisopropylsilanyloxybenzaldehyde (Example (4a)) in 200 ml of dichloromethane under a nitrogen atmosphere, the mixture was stirred at room temperature for 23 hours and 30 minutes. The reaction mixture was filtered, and the filtrate was concentrated under reduced pressure.

To a solution of the obtained residue in 225 ml of a methanol:THF=2:1 mixed solvent there was added 40 ml of a 20% aqueous solution of ammonium sulfide, and the mixture was stirred at room temperature for 7 hours. Water was added to the reaction mixture and extraction was performed with ethyl acetate. After washing the organic layer with water and saturated brine, it was dried over anhydrous magnesium sulfate. The desiccating agent was filtered off and the filtrate was concentrated under reduced pressure. The residue was crudely purified by silica gel column chromatography (ethyl acetate-heptane) to give a crude product.

To a solution of the obtained crude product in 100 ml of dichloromethane there was added 3.4 g of Me$_3$O$^+$BF$_4^-$, and the mixture was stirred at room temperature for 15 hours and 30 minutes. Saturated aqueous sodium hydrogencarbonate was added to the reaction mixture, and extraction was performed with ethyl acetate. After washing the organic layer with water and saturated brine, it was dried over anhydrous sodium sulfate. The desiccating agent was filtered off, and the filtrate was concentrated under reduced pressure to give a yellow oil.

To a solution of the obtained yellow oil in 200 ml of toluene there was added 10.8 ml of 2,4,6-collidine and 5.4 ml of methyl chloroformate, and the mixture was stirred at 80° C. for 46 hours under a nitrogen atmosphere. The reaction mixture was filtered, water was added to the filtrate, and extraction was performed with ethyl acetate. The organic layer was washed with ice-cooled 1N hydrochloric acid, water and saturated brine, and dried over anhydrous sodium sulfate. The desiccating agent was filtered off and the filtrate was concentrated under reduced pressure. The residue was crudely purified by silica gel column chromatography (ethyl acetate-heptane) to give a yellow oil (2.22 g).

To a 20 ml THF solution containing the obtained yellow oil there was added 4.1 ml of TBAF (1.0 M, THF solution), and the mixture was stirred at 0° C. for 2 hours. Saturated aqueous ammonium chloride was added to the reaction mixture and extraction was performed with ethyl acetate. The organic layer was washed with water and saturated brine, and then dried over anhydrous sodium sulfate. The desiccating agent was filtered off and the filtrate was concentrated under reduced pressure. The residue was purified by silica gel column chromatography (ethyl acetate-heptane) to give the title compound (1.15 g) as a yellow solid.

$^1$H-NMR (CDCl$_3$) Main isomer:

δ 2.32 (s, 3H) 2.65 (s, 3H) 3.64 (s, 3H) 3.83 (s, 3H) 5.15 (br.s, 1H) 6.56 (dd, J=2.0, 2.4 Hz, 1H) 6.91 (dd, J=2.0, 2.4 Hz, 1H) 7.02 (dd, J=2.4, 2.4 Hz, 1H) 7.15 (d, J=8.8 Hz, 2H) 8.01 (d, J=8.8 Hz, 2H)

(9b) (R) and (S)-4-{[(3,5-dimethoxyphenyl)-(5-oxo-1-pyrimidin-2-yl-4,5-dihydro-1H-[1,2,4]triazol-3-yl)methyl]amino}benzamidine acetate

[Chemical Formula 70]

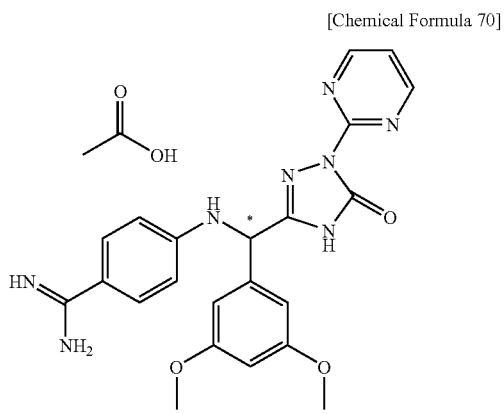

After adding 63 mg of potassium carbonate and 0.017 ml of methyl iodide to a 1 ml DMF solution containing 100 mg of {2-(3-hydroxy-5-methoxyphenyl)-2-[4-(5-methyl-[1,2,4]oxadiazol-3-yl)phenylimino]-1-methylsulfanylethylidene}carbamic acid methyl ester, the mixture was stirred at room temperature for 40 hours. Water was added to the reaction mixture and extraction was performed with ethyl acetate. The organic layer was washed with water and dried through PRESEP™. The filtrate was concentrated to give 106 mg of a crude product.

Next, 25 mg of 2-hydrazinopyrimidine and 0.031 ml of triethylamine were added to a 1 ml DMF solution containing 106 mg of the obtained crude product, and the mixture was stirred at 85° C. for 14 hours under a nitrogen atmosphere. The reaction mixture was concentrated, and the residue was dissolved in 0.8 ml of methanol, 0.8 ml of THF and 0.05 ml of acetic acid. After adding 200 mg of sodium cyanotrihydroborate to the solution, the mixture was stirred at room temperature for 19 hours. Water was added to the reaction mixture and extraction was performed with ethyl acetate. The organic layer was washed with saturated brine and dried over anhydrous sodium sulfate. The desiccating agent was filtered off and the filtrate was concentrated under reduced pressure. The residue was crudely purified by reverse-phase high performance liquid chromatography (acetonitrile-water, 0.1% acetic acid) to give a crude product.

The obtained crude product was optically resolved using a CHIRALPAK™ AD-H (column size: 2 cmφ×25 cmL, Manufacturer: Daicel Chemical Industries, Ltd., Mobile phase: 2-propanol/hexane=2/3, 0.1% trifluoroacetic acid, Elution rate: 9 ml/min) (retention time for the first eluting enantiomer: 17 min). Triethylamine was added to the obtained first eluting enantiomer and the mixture was concentrated under reduced pressure.

To a solution of the residue in 2.2 ml of a methanol:water:acetic acid=0.6:0.6:1 mixed solvent there was added 100 mg of iron powder, and the mixture was stirred at 60° C. for 14 hours under a nitrogen atmosphere. After filtering the reaction mixture, it was purified by reverse-phase high performance liquid chromatography (acetonitrile-water, 0.1% acetic acid), to give one optical isomer of the title compound (10.84 mg) as a white solid.

¹H-NMR (CD₃OD) δ 1.94 (s, 3H) 3.75 (s, 6H) 5.62 (s, 1H) 6.43 (d, J=1.6 Hz, 1H) 6.72 (s, 2H) 6.86 (d, J=8.4 Hz, 2H) 7.33 (t, J=4.8 Hz, 1H) 7.60 (d, J=8.4 Hz, 2H) 8.77 (d, J=4.8 Hz, 2H)

Mass spectrum (ESI) m/z: 447 (M+H)⁺

Example 10

(R) and (S)-4-{[(3-methoxy-5-methoxymethylphenyl)-(5-oxo-1-pyrimidin-2-yl-4,5-dihydro-1H-[1,2,4]triazol-3-yl)methyl]amino}benzamidine acetate (10a) (3-methoxy-5-methoxymethylphenyl)methanol

[Chemical Formula 71]

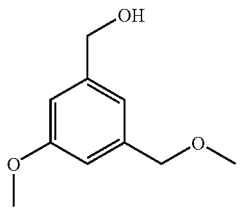

To a 50 ml THF solution containing 4 g of 5-methoxy-1,3-benzenedimethanol there was added 951 mg of sodium hydride (60% oily suspension) at 0° C. After stirring at room temperature for 1 hour, 3.58 g of t-butyldimethylsilyl chloride was added and stirring was continued at room temperature for 70 minutes. Water was added to the reaction mixture and extraction was performed with ethyl acetate. The organic layer was washed with water and saturated brine, and then dried over anhydrous sodium sulfate. The desiccating agent was filtered off and the filtrate was concentrated under reduced pressure. The residue was purified by silica gel column chromatography (ethyl acetate-heptane) to give a light yellow oil (3.74 g).

To a 10 ml THF solution containing 1 g of the obtained light yellow oil there was added 212 mg of sodium hydride (60% oily suspension) at 0° C. After stirring at room temperature for 30 minutes, 0.5 ml of methyl iodide was added and the mixture was stirred at room temperature for 2 hours. Water was added to the reaction mixture and extraction was performed with ethyl acetate. The organic layer was washed with water and saturated brine, and then dried over anhydrous sodium sulfate. The desiccating agent was filtered off and the filtrate was concentrated under reduced pressure.

To a solution of the residue in 10 ml of THF there was added 4.3 ml of TBAF (1.0 M, THF solution) at 0° C., and the mixture was stirred at room temperature for 17 hours and 30 minutes. Water was added to the reaction mixture and extraction was performed with ethyl acetate. The organic layer was washed with water and saturated brine, and then dried over anhydrous sodium sulfate. The desiccating agent was filtered off and the filtrate was concentrated under reduced pressure. The residue was purified by silica gel column chromatography (ethyl acetate-heptane) to give the title compound (618 mg) as a light yellow oil.

¹H-NMR (CDCl₃) δ 3.39 (s, 3H) 3.82 (s, 3H) 4.43 (s, 2H) 4.67 (s, 2H) 6.81 (s, 1H) 6.85 (s, 1H) 6.91 (s, 1H)

(10b) (3-methoxy-5-methoxymethylphenyl)-[4-(5-methyl-[1,2,4]oxadiazol-3-yl)phenylamino]acetonitrile

[Chemical Formula 72]

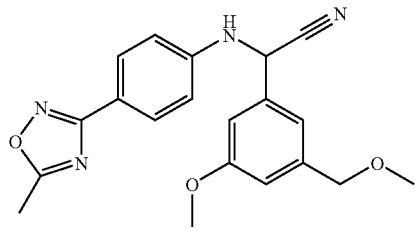

To a solution of 618 mg of (3-methoxy-5-methoxymethylphenyl)methanol in 15 ml of dichloromethane there was added 4.5 g of manganese dioxide, and the mixture was stirred at room temperature for 23 hours and 30 minutes. The reaction mixture was filtered, and the filtrate was concentrated under reduced pressure.

To a solution of the residue in 10 ml of dichloromethane there was added 550 mg of 4-(5-methyl-[1,2,4]oxadiazol-3-yl)phenylamine, 1 g of MS3A, 195 mg of Yb(OTf)₃ and 0.79 ml of trimethylsilyl cyanide, and the mixture was stirred at room temperature for 20 hours under a nitrogen atmosphere. The reaction mixture was filtered, and the filtrate was concentrated under reduced pressure. The residue was purified by silica gel column chromatography (ethyl acetate-heptane) to give the title compound (1.25 g) as a light yellow oil.

¹H-NMR (CDCl₃) δ 2.63 (s, 3H) 3.42 (s, 3H) 3.84 (s, 3H) 4.46 (s, 2H) 5.44 (br.s, 1H) 6.82 (d, J=8.8 Hz, 2H) 6.96 (s, 1H) 7.02-7.04 (m, 1H) 7.15 (s, 1H) 7.96 (d, J=8.8 Hz, 2H)

(10c) {2-(3-methoxy-5-methoxymethylphenyl)-2-[4-(5-methyl-[1,2,4]oxadiazol-3-yl)phenylimino]-1-methylsulfanylethylidene}carbamic acid methyl ester

[Chemical Formula 73]

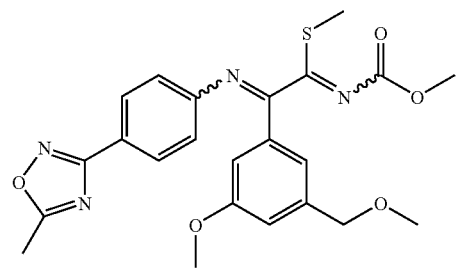

To a solution of 1.25 g of (3-methoxy-5-methoxymethylphenyl)-[4-(5-methyl-[1,2,4]oxadiazol-3-yl)phenylamino]acetonitrile in 30 ml of a methanol:THF=2:1 mixed solvent there was added 10 ml of a 20% aqueous solution of ammonium sulfide, and the mixture was stirred at room temperature for 16 hours and 30 minutes. Water was added to the reaction mixture and extraction was performed with ethyl acetate. After washing the organic layer with water and saturated brine, it was dried over anhydrous magnesium sulfate. The desiccating agent was filtered off and the filtrate was concentrated under reduced pressure.

After adding 550 mg of Me$_3$O$^+$BF$_4^-$ to a solution of the residue in 15 ml of dichloromethane, the mixture was stirred at room temperature for 3 hours. Saturated aqueous sodium hydrogencarbonate was added to the reaction mixture and extraction was performed with ethyl acetate. After washing the organic layer with water and saturated brine, it was dried over anhydrous sodium sulfate. The desiccating agent was filtered off and the filtrate was concentrated under reduced pressure.

After adding 6.5 g of manganese dioxide to a solution of the residue in 20 ml of dichloromethane, the mixture was stirred at room temperature for 17 hours. The reaction mixture was filtered and the filtrate was concentrated under reduced pressure.

After adding 1.35 ml of 2,4,6-collidine and 0.67 ml of methyl chloroformate to a solution of the residue in 20 ml of toluene, the mixture was stirred at 80° C. for 5 hours and 20 minutes under a nitrogen atmosphere. Water was added to the reaction mixture and extraction was performed with ethyl acetate. The organic layer was washed with ice-cooled 1N hydrochloric acid, water, saturated aqueous sodium hydrogencarbonate, water and saturated brine, and then dried over anhydrous sodium sulfate. The desiccating agent was filtered off and the filtrate was concentrated under reduced pressure. The residue was purified by silica gel column chromatography (ethyl acetate-heptane) to give the title compound (400 mg) as a yellow oil.

(10d) 4-{[(3-methoxy-5-methoxymethylphenyl)-(5-oxo-1-pyrimidin-2-yl-4,5-dihydro-1H-[1,2,4]triazol-3-yl)methyl]amino}benzamidine acetate

[Chemical Formula 74]

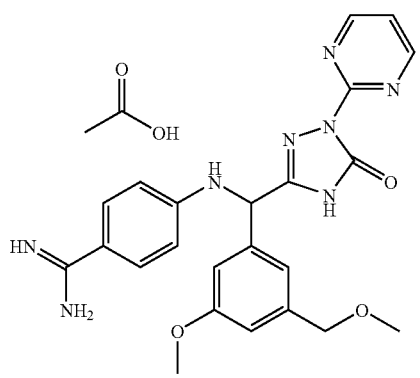

After adding 49 mg of 2-hydrazinopyrimidine and 0.062 ml of triethylamine to a 1 ml DMF solution containing 210 mg of {2-(3-methoxy-5-methoxymethylphenyl)-2-[4-(5-methyl-[1,2,4]oxadiazol-3-yl)phenylimino]-1-methylsulfanylethylidene}carbamic acid methyl ester, the mixture was stirred at 85° C. for 14 hours under a nitrogen atmosphere. The reaction mixture was concentrated, and the residue was dissolved in 1 ml of methanol, 1 ml of THF and 0.1 ml of acetic acid. After adding 250 mg of sodium cyanotrihydroborate to the solution, the mixture was stirred at room temperature for 4 hours and 30 minutes. The reaction mixture was crudely purified by reverse-phase high performance liquid chromatography (acetonitrile-water, 0.1% acetic acid) to give a crude product.

To a solution of the obtained crude product in 3 ml of a methanol:water:acetic acid=1:1:1 mixed solvent there was added 200 mg of iron powder, and the mixture was stirred at 65° C. for 13 hours under a nitrogen atmosphere. After filtering the reaction mixture, it was purified by reverse-phase high performance liquid chromatography (acetonitrile-water, 0.1% acetic acid) to give the title compound (58.4 mg).

$^1$H-NMR (CD$_3$OD) δ 1.94 (s, 3H) 3.35 (s, 3H) 3.78 (s, 3H) 4.41 (s, 2H) 5.67 (s, 1H) 6.76-6.95 (m, 3H) 7.06 (s, 1H) 7.11 (s, 1H) 7.33 (br.s, 1H) 7.60 (d, J=8.0 Hz, 2H) 8.78 (d, J=3.6 Hz, 2H)

Mass spectrum (ESI) m/z: 461 (M+H)$^+$ (10e) (R) and (S)-4-{[(3-methoxy-5-methoxymethylphenyl)-(5-oxo-1-pyrimidin-2-yl-4,5-dihydro-1H-[1,2,4]triazol-3-yl)methyl]amino}benzamidine acetate

[Chemical Formula 75]

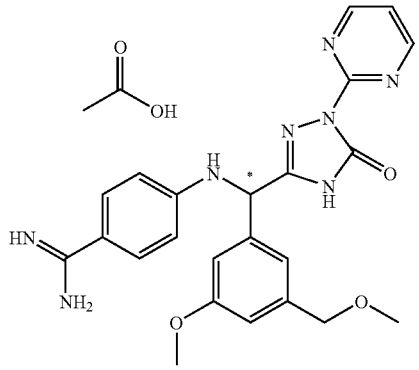

A SUMICHIRAL OA-2500 column was used for optical resolution of 58.4 mg of 4-{[(3-methoxy-5-methoxymethylphenyl)-(5-oxo-1-pyrimidin-2-yl-4,5-dihydro-1H-[1,2,4]triazol-3-yl)methyl]amino}benzamidine acetate, and the first eluting enantiomer (24.57 mg) of the title compound was obtained as a white solid.

$^1$H-NMR (CD$_3$OD) δ 1.91 (s, 3H) 3.33 (s, 3H) 3.76 (s, 3H) 4.39 (s, 2H) 5.64 (s, 1H) 6.84 (s, 1H) 6.85 (d, J=8.8 Hz, 2H) 7.06 (s, 1H) 7.10 (s, 1H) 7.29 (t, J=5.2 Hz, 1H) 7.58 (d, J=8.8 Hz, 2H) 8.75 (d, J=5.2 Hz, 2H)

HPLC retention time: 12 min

Example 11

4-{[(3-fluoromethyl-5-methoxyphenyl)-(5-oxo-1-pyrimidin-2-yl-4,5-dihydro-1H-[1,2,4]triazol-3-yl)methyl]amino}benzamidine acetate (11a) 5-triisopropylsilanyloxyisophthalic acid dimethyl ester

[Chemical Formula 76]

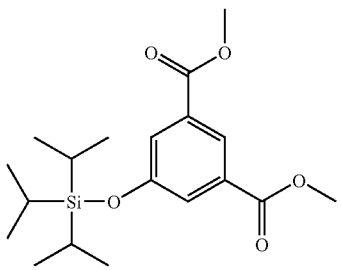

After adding 5.1 g of imidazole and 12.9 ml of chlorotriisopropylsilane to a 100 ml DMF solution containing 10.5 g of 5-hydroxyisophthalic acid dimethyl ester, the mixture was stirred at room temperature for 15 hours. Water was added to the reaction mixture and extraction was performed with ethyl acetate. The organic layer was washed with ice-cooled 1N hydrochloric acid, water and saturated brine and dried over anhydrous magnesium sulfate. The desiccating agent was filtered off and the filtrate was concentrated under reduced pressure. The residue was purified by silica gel column chromatography (ethyl acetate-heptane) to give the title compound (21.53 g) as a colorless oil.

$^1$H-NMR (CDCl$_3$) δ 1.10 (d, J=7.6 Hz, 18H) 1.26 (sept, J=7.6 Hz, 3H) 3.93 (s, 6H) 7.70 (d, J=1.2 Hz, 2H) 8.25 (t, J=1.2 Hz, 1H)

(11b) (3-hydroxymethyl-5-triisopropylsilanyloxyphenyl)methanol

[Chemical Formula 77]

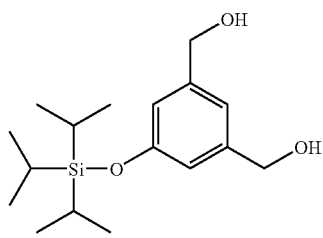

To a 100 ml THF solution containing 21.53 g of 5-triisopropylsilanyloxyisophthalic acid dimethyl ester there was added 7.1 g of lithium aluminum hydride at 0° C. After stirring at 0° C. for 1 hour, the mixture was stirred at room temperature for 3 hours and 30 minutes. Water and 1N aqueous sodium hydroxide were added to the reaction mixture which was then filtered through celite. The filtrate was extracted with ethyl acetate. The organic layer was then washed with saturated brine and dried over anhydrous sodium sulfate. The desiccating agent was filtered off and the filtrate was concentrated under reduced pressure. The residue was purified by silica gel column chromatography (ethyl acetate-heptane) to give the title compound (13.53 g) as a colorless solid.

$^1$H-NMR (CDCl$_3$) δ 1.10 (d, J=7.2 Hz, 18H) 1.29 (sept, J=7.2 Hz, 3H) 4.63 (s, 4H) 6.80 (s, 2H) 6.93 (s, 1H)

(11c) 3-(t-butyldimethylsilanyloxymethyl)-5-triisopropylsilanyloxybenzaldehyde

[Chemical Formula 78]

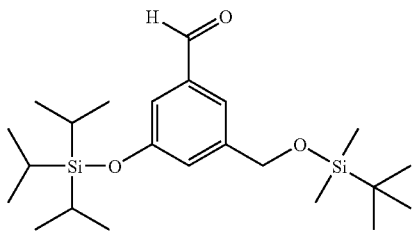

To a 50 ml THF solution containing the 13.53 g of (3-hydroxymethyl-5-triisopropylsilanyloxyphenyl)methanol there was added 1.57 g of sodium hydride (60% oily suspension) at 0° C. After stirring at room temperature for 15 minutes, 6.6 g of t-butyldimethylsilyl chloride was added and the mixture was stirred at room temperature for 3 hours and 15 minutes. Water was added to the reaction mixture and extraction was performed with ethyl acetate. The organic layer was washed with water and saturated brine, and then dried over anhydrous sodium sulfate. The desiccating agent was filtered off and the filtrate was concentrated under reduced pressure. The residue was purified by silica gel column chromatography (ethyl acetate-heptane) to give a colorless oil (9.74 g).

$^1$H-NMR (CDCl$_3$) δ 0.09 (s, 6H) 0.94 (s, 9H) 1.10 (d, J=7.2 Hz, 18H) 1.26 (sept, J=7.2 Hz, 3H) 4.61 (s, 2H) 4.67 (s, 2H) 6.76 (s, 1H) 6.81 (s, 1H) 6.84 (s, 1H)

To a solution of 9.74 g of the obtained colorless oil in 200 ml of dichloromethane there was added 28 g of manganese dioxide, and the mixture was stirred at room temperature for 17 hours. The reaction mixture was filtered and the filtrate was concentrated under reduced pressure, to give the title compound (8.05 g) as a light yellow oil.

$^1$H-NMR (CDCl$_3$) δ 0.11 (s, 6H) 0.95 (s, 9H) 1.10 (d, J=7.6 Hz, 18H) 1.28 (sept, J=7.6 Hz, 3H) 4.74 (s, 2H) 7.16 (s, 1H) 7.23 (s, 1H) 7.36 (s, 1H) 9.91 (s, 1H)

(11d) {2-(3-hydroxy-5-hydroxymethylphenyl)-2-[4-(5-methyl-[1,2,4]oxadiazol-3-yl)phenylimino]-1-methylsulfanylethylidene}carbamic acid methyl ester

[Chemical Formula 79]

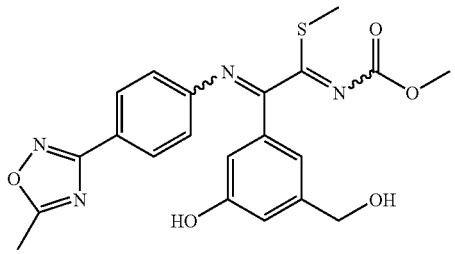

After adding 3.34 g of 4-(5-methyl-[1,2,4]oxadiazol-3-yl)phenylamine, 10 g of MS3A, 1.18 g of Yb(OTf)$_3$ and 4.8 ml of trimethylsilyl cyanide to a solution of 8.05 g of 3-(t-butyldimethylsilanyloxymethyl)-5-triisopropylsilanyloxybenzaldehyde in 100 ml of dichloromethane under a nitrogen atmosphere, the mixture was stirred at room temperature for 5 days. The reaction mixture was filtered, and the filtrate was concentrated under reduced pressure. The residue was crudely purified by silica gel column chromatography (ethyl acetate-heptane) to give a light yellow solid (6.95 g).

To a solution of 6.95 g of the obtained light yellow solid in 120 ml of a methanol:THF=2:1 mixed solvent there was added 60 ml of a 20% aqueous solution of ammonium sulfide, and the mixture was stirred at room temperature for 2 days. Water was added to the reaction mixture, which was then filtered to give a white solid (7.02 g).

To a solution of 7.02 g of the obtained white solid in 100 ml of dichloromethane there was added 1.86 g of Me$_3$O$^+$BF$_4^-$, and the mixture was stirred at room temperature for 26 hours. Saturated aqueous sodium hydrogencarbonate was added to the reaction mixture and extraction was performed with ethyl acetate. After washing the organic layer with water and saturated brine, it was dried over anhydrous sodium sulfate. The desiccating agent was filtered off and the filtrate was concentrated under reduced pressure.

After adding 1.24 g of imidazole and 1.83 g of t-butyldimethylsilyl chloride to a solution of the residue in 50 ml of DMF, the mixture was stirred at room temperature for 15 hours. Water was added to the reaction mixture and extraction was performed with ethyl acetate. The organic layer was washed with water and saturated brine, and then dried over anhydrous sodium sulfate. The desiccating agent was filtered off and the filtrate was concentrated under reduced pressure.

After adding 8 g of manganese dioxide to a solution of the residue in 100 ml of dichloromethane, the mixture was stirred at room temperature for 5 hours. The reaction mixture was filtered and the filtrate was concentrated under reduced pressure.

After adding 5 ml of 2,4,6-collidine and 2.5 ml of methyl chloroformate to a solution of the residue in 100 ml of toluene, the mixture was stirred at 80° C. for 8 hours and 40 minutes under a nitrogen atmosphere. The reaction mixture was filtered, water was added to the filtrate, and extraction was performed with ethyl acetate. The organic layer was washed with ice-cooled 1N hydrochloric acid, water and saturated brine, and dried over anhydrous sodium sulfate. The desiccating agent was filtered off and the filtrate was concentrated under reduced pressure. The residue was crudely purified by silica gel column chromatography (ethyl acetate-heptane) to give a yellow oil (6.16 g).

To a 100 ml THF solution containing 6.16 g of the obtained yellow oil there was added 19 ml of TBAF (1.0 M, THF solution), and the mixture was stirred at room temperature for 3 hours. Saturated aqueous ammonium chloride was added to the reaction mixture and extraction was performed with ethyl acetate. The organic layer was washed with water and saturated brine, and then dried over anhydrous sodium sulfate. The desiccating agent was filtered off and the filtrate was concentrated under reduced pressure. The residue was purified by silica gel column chromatography (ethyl acetate-heptane) to give the title compound (2.48 g) as a yellow solid.

(11e) {2-(3-hydroxymethyl-5-methoxyphenyl)-2-[4-(5-methyl-[1,2,4]oxadiazol-3-yl)phenylimino]-1-methylsulfanylethylidene}carbamic acid methyl ester

[Chemical Formula 80]

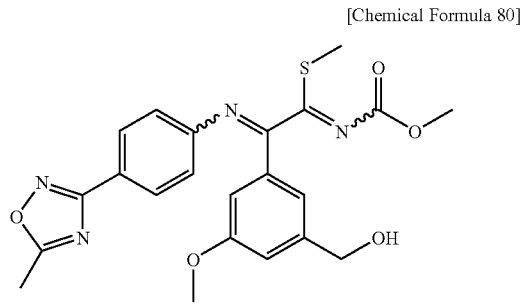

To a 3 ml DMF solution containing 700 mg of {2-(3-hydroxy-5-hydroxymethylphenyl)-2-[4-(5-methyl-[1,2,4] oxadiazol-3-yl)phenylimino]-1-methylsulfanylethylidene}carbamic acid methyl ester there was added 440 mg of potassium carbonate and 0.15 ml of methyl iodide, and the mixture was stirred at room temperature for 17 hours and 30 minutes. Water was added to the reaction mixture and extraction was performed with ethyl acetate. The organic layer was washed with water and saturated brine, and then dried over anhydrous sodium sulfate. The desiccating agent was filtered off and the filtrate was concentrated under reduced pressure. The residue was purified by silica gel column chromatography (ethyl acetate-heptane) to give the title compound (544 mg) as a yellow solid.

$^1$H-NMR (CDCl$_3$) Main isomer:

δ 2.34 (s, 3H) 2.66 (s, 3H) 3.62 (s, 3H) 3.88 (s, 3H) 4.73 (d, J=4.4 Hz, 2H) 7.12 (br.s, 1H) 7.17 (d, J=8.8 Hz, 2H) 7.36-7.42 (m, 2H) 8.03 (d, J=8.8 Hz, 2H)

(11f) {2-(3-fluoromethyl-5-methoxyphenyl)-2-[4-(5-methyl-[1,2,4]oxadiazol-3-yl)phenylimino]-1-methylsulfanylethylidene}carbamic acid methyl ester

[Chemical Formula 81]

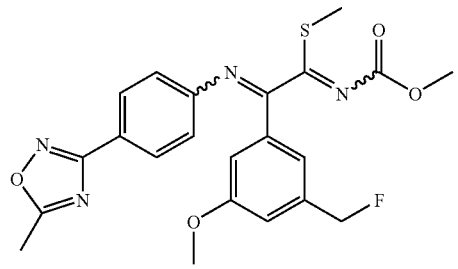

To a solution of 100 mg of {2-(3-hydroxymethyl-5-methoxyphenyl)-2-[4-(5-methyl-[1,2,4]oxadiazol-3-yl)phenylimino]-1-methylsulfanylethylidene}carbamic acid methyl ester in 1.5 ml of dichloromethane there was added 0.057 ml of [bis(2-methoxyethyl)amino]sulfur trifluoride at −78° C. After stirring at −78° C. for 5 minutes, the mixture was stirred at room temperature for 1 hour and 25 minutes. Saturated aqueous ammonium chloride was added to the reaction mixture and extraction was performed with ethyl acetate. The organic layer was washed with water and saturated brine, and then dried through PRESEP™. The filtrate was concentrated, and the residue was purified by silica gel column chromatography (ethyl acetate-heptane) to give the title compound (59 mg) as a yellow oil.

(11g) 4-{[(3-fluoromethyl-5-methoxyphenyl)-(5-oxo-1-pyrimidin-2-yl-4,5-dihydro-1H-[1,2,4]triazol-3-yl)methyl]amino}benzamidine acetate

[Chemical Formula 82]

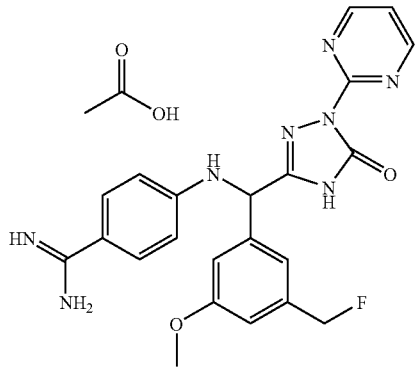

After adding 14 mg of 2-hydrazinopyrimidine and 0.015 ml of triethylamine to a 1 ml DMF solution containing 59 mg of {2-(3-fluoromethyl-5-methoxyphenyl)-2-[4-(5-methyl-[1,2,4]oxadiazol-3-yl)phenylimino]-1-methylsulfanylethylidene}carbamic acid methyl ester, the mixture was stirred at 85° C. for 22 hours and 30 minutes under a nitrogen atmosphere. The reaction mixture was concentrated, and the residue was dissolved in 0.75 ml of methanol, 0.75 ml of THF and 0.05 ml of acetic acid. After adding 100 mg of sodium cyanotrihydroborate to the solution, the mixture was stirred at room temperature for 3 hours and 40 minutes. The reaction mixture was crudely purified by reverse-phase high performance liquid chromatography (acetonitrile-water, 0.1% acetic acid) to give a crude product.

To a solution of the obtained crude product in 2.4 ml of a methanol:water:acetic acid=1:1:1 mixed solvent there was added 100 mg of iron powder, and the mixture was stirred at 65° C. for 15 hours under a nitrogen atmosphere. After filtering the reaction mixture, it was purified by reverse-phase high performance liquid chromatography (acetonitrile-water, 0.1% acetic acid) to give the title compound (14.16 mg) as a light yellow solid.

$^1$H-NMR (CD$_3$OD) δ 1.93 (s, 3H) 3.78 (s, 3H) 5.31 (d, J=47.6 Hz, 2H) 5.68 (s, 1H) 6.86 (d, J=8.4 Hz, 2H) 6.90 (s, 1H) 7.12 (s, 1H) 7.15 (s, 1H) 7.31 (t, J=4.8 Hz, 1H) 7.60 (d, J=8.4 Hz, 2H) 8.77 (d, J=4.8 Hz, 2H)

Mass spectrum (ESI) m/z: 449 (M+H)$^+$

Example 12

(R) and (S)-4-{[(3-hydroxymethyl-5-methoxyphenyl)-(5-oxo-1-pyrimidin-2-yl-4,5-dihydro-1H-[1,2,4]triazol-3-yl)methyl]amino}benzamidine trifluoroacetate (12a) 4-{[(3-hydroxymethyl-5-methoxyphenyl)-(5-oxo-1-pyrimidin-2-yl-4,5-dihydro-1H-[1,2,4]triazol-3-yl)methyl]amino}benzamidine acetate

[Chemical Formula 83]

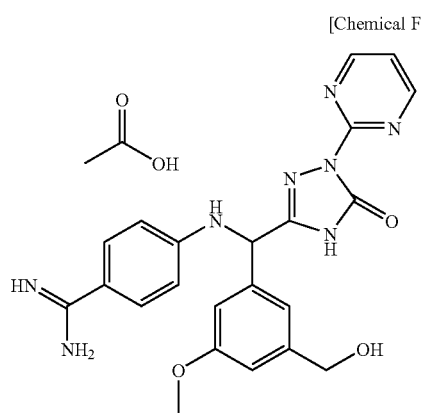

After adding 24 mg of 2-hydrazinopyrimidine and 0.030 ml of triethylamine to a 1 ml DMF solution containing 100 mg of {2-(3-hydroxymethyl-5-methoxyphenyl)-2-[4-(5-methyl-[1,2,4]oxadiazol-3-yl)phenylimino]-1-methylsulfanylethylidene}carbamic acid methyl ester (Example (11e)), the mixture was stirred at 85° C. for 14 hours and 30 minutes under a nitrogen atmosphere. The reaction mixture was concentrated, and the residue was dissolved in 1 ml of methanol, 1 ml of THF and 0.050 ml of acetic acid. After adding 100 mg of sodium cyanotrihydroborate to the reaction mixture, it was stirred at room temperature for 21 hours and 30 minutes. The reaction mixture was crudely purified by reverse-phase high performance liquid chromatography (acetonitrile-water, 0.1% acetic acid) to give a crude product.

To a solution of the obtained crude product in 3 ml of a methanol:water:acetic acid=1:1:1 mixed solvent there was added 150 mg of iron powder, and the mixture was stirred at 60° C. for 17 hours under a nitrogen atmosphere. After filtering the reaction mixture, it was purified by reverse-phase high performance liquid chromatography (acetonitrile-water, 0.1% acetic acid) to give the title compound (28.50 mg).

$^1$H-NMR (CD$_3$OD) δ 1.95 (s, 3H) 3.78 (s, 3H) 4.58 (s, 2H) 5.68 (s, 1H) 6.87 (d, J=8.8 Hz, 2H) 6.91 (s, 1H) 7.03 (s, 1H) 7.13 (s, 1H) 7.35 (t, J=4.8 Hz, 1H) 7.61 (d, J=8.8 Hz, 2H) 8.78 (d, J=4.8 Hz, 2H)

Mass spectrum (ESI) m/z: 447 (M+H)$^+$ (12b) (R) and (S)-4-{[(3-hydroxymethyl-5-methoxyphenyl)-(5-oxo-1-pyrimidin-2-yl-4,5-dihydro-1H-[1,2,4]triazol-3-yl)methyl]amino}benzamidine trifluoroacetate

[Chemical Formula 84]

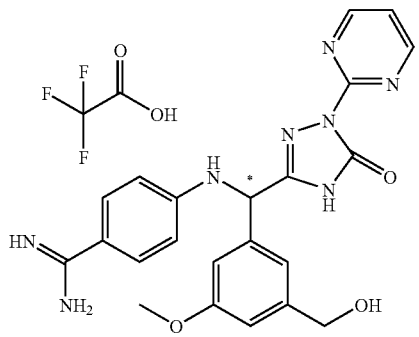

After adding trifluoroacetic acid to a suspension of 28.5 mg of 4-{[(3-hydroxymethyl-5-methoxyphenyl)-(5-oxo-1-pyrimidin-2-yl-4,5-dihydro-1H-[1,2,4]triazol-3-yl)methyl]amino}benzamidine acetate in 2.85 ml of DMSO, the mixture was concentrated under reduced pressure. The residue was optically resolved using a SUMICHIRAL OA-2500 column, and the first eluting enantiomer was obtained. This was dissolved in a trifluoroacetic acid:acetonitrile:water=1:50:50 mixed solvent and concentrated, and the first eluting enantiomer (9.80 mg) of the title compound was obtained as a white solid.

$^1$H-NMR (CD$_3$OD) δ 3.81 (s, 3H) 4.59 (s, 2H) 5.70 (s, 1H) 6.88 (d, J=9.2 Hz, 2H) 6.93 (s, 1H) 7.03 (s, 1H) 7.13 (s, 1H) 7.37 (t, J=4.8 Hz, 1H) 7.62 (d, J=9.2 Hz, 2H) 8.79 (d, J=4.8 Hz, 2H)

HPLC retention time: 11 min

Example 13

4-({[3-(2-dimethylamino-1-methylethoxy)-2-fluoro-5-methoxyphenyl]-(5-oxo-1-pyridin-2-yl-4,5-dihydro-1H-[1,2,4]triazol-3-yl)methyl}amino)benzamidine bistrifluoroacetate and 4-({[3-(2-dimethylaminopropoxy)-2-fluoro-5-methoxyphenyl]-(5-oxo-1-pyridin-2-yl-4,5-dihydro-1H-[1,2,4]triazol-3-yl)methyl}amino)benzamidine bistrifluoroacetate

[Chemical Formula 85]

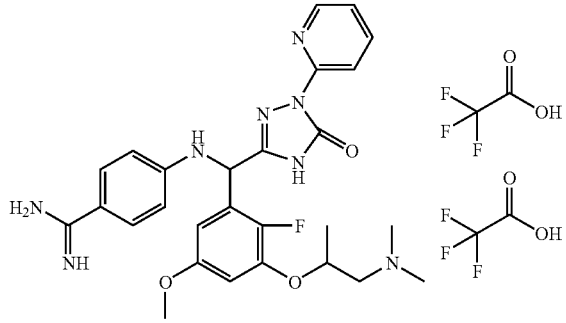

[Chemical Formula 86]

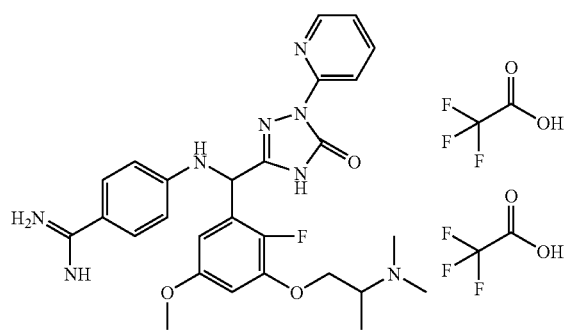

After adding 217 mg of potassium carbonate and 124 mg of (2-chloropropyl)dimethylamine hydrochloride to a 3 ml DMF solution containing 300 mg of [2-(2-fluoro-3-hydroxy-5-methoxyphenyl)-2-[4-(5-methyl-[1,2,4]oxadiazol-3-yl)phenylimino]-1-methylsulfanylethylidene]carbamic acid methyl ester (Example (3d)), the mixture was stirred at an external temperature of 80° C. for 20 hours and 30 minutes. Next, 20 mg of tetrabutylammonium iodide was added to the reaction mixture and stirring was continued at the same temperature for 5 hours and 30 minutes. The reaction mixture was concentrated, and the obtained residue was crudely purified by NAM silica gel column chromatography (chloroform-methanol) to give 210 mg of a crude product. After dissolving 50 mg of the 210 mg of obtained crude product in 2 ml of DMF, 15 mg of 2-hydrazinopyridine and 0.025 ml of triethylamine were added to the solution and the mixture was stirred at 80° C. for 10 hours under a nitrogen atmosphere. The reaction mixture was then concentrated. Next, 1 ml of methanol and 0.014 ml of acetic acid were added to dissolve the obtained residue. To this solution there was added 30 mg of sodium cyanotrihydroborate, and the mixture was stirred at room temperature for 12 hours. The reaction mixture was then concentrated.

Next, 1.5 ml of a methanol:water:acetic acid=1:1:1 mixed solvent was added to dissolve the obtained residue. After adding 50 mg of iron powder to the solution, the mixture was stirred at 60° C. for 14 hours and 45 minutes under a nitrogen atmosphere. After filtering the reaction mixture, it was purified by reverse-phase high performance liquid chromatography (acetonitrile-water, 0.1% trifluoroacetic acid), to give a mixture of the two title compounds (3.98 mg) as a light brown oil.

Mass spectrum (ESI) m/z: 535 (M+H)+

Example 14

4-({(2-fluoro-3-methoxy-5-methylphenyl)-[1-(2-methoxyphenyl)-5-oxo-4,5-dihydro-1H-[1,2,4]triazol-3-yl]methyl}amino)benzamidine trifluoroacetate (14a) 2-fluoro-5-methyl-3-triisopropylsilanyloxybenzaldehyde

[Chemical Formula 87]

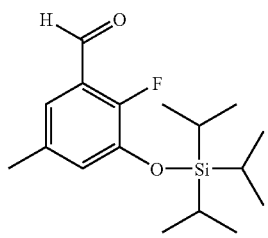

After adding 10.4 g of imidazole to a 200 ml DMF solution containing 17.6 g of 2-fluoro-5-methylphenol [CAS No. 63762-79-8], the reaction mixture was cooled to 0° C. Next, 33.5 ml of chlorotriisopropylsilane was added and the mixture was stirred at room temperature for 13 hours. Water was added to the reaction mixture and extraction was performed with diethyl ether. The organic layer was washed with water and dried over anhydrous magnesium sulfate. The desiccating agent was filtered off and the filtrate was concentrated under reduced pressure.

After adding 30 ml of N,N,N',N',N"-pentamethyldiethylenetriamine and 300 ml of THF to the obtained residue, the solution was cooled to an external temperature of −78° C. Next, 100 ml of n-butyllithium (1.6 M, hexane solution) was added dropwise over a period of 20 minutes. After stirring for 2 hours at −78° C., 18.3 ml of N-formylmorpholine was added. The temperature of the reaction mixture was allowed to rise to room temperature, and stirring was continued for 13 hours and 20 minutes. Ice was added to the reaction mixture, which was then concentrated under reduced pressure. After adding ethyl acetate and water to the residue, extraction was performed twice with ethyl acetate and the combined organic layers were washed with saturated brine. The organic layer was dried over anhydrous magnesium sulfate. The desiccating agent was filtered off and the filtrate was concentrated under reduced pressure. The residue was purified by silica gel column chromatography (ethyl acetate-heptane) to give the title compound (36.1 g) as a colorless oil.

$^1$H-NMR (CDCl$_3$) δ 1.12 (d, J=7.2 Hz, 18H) 1.24-1.33 (m, 3H) 2.31 (s, 3H) 6.99 (dd, J=2.4, 8.0 Hz, 1H) 7.20 (dd, J=1.6, 5.6 Hz, 1H) 10.30 (s, 1H)

(14b) {2-(2-fluoro-3-hydroxy-5-methylphenyl)-2-[4-(5-methyl-[1,2,4]oxadiazol-3-yl)phenylimino]-1-methylsulfanylethylidene}carbamic acid methyl ester

[Chemical Formula 88]

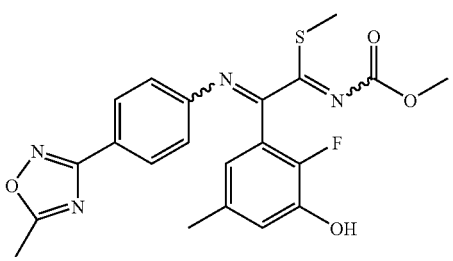

After adding 5.8 g of 4-(5-methyl-[1,2,4]oxadiazol-3-yl)phenylamine, 10 g of 2-fluoro-5-methyl-3-triisopropylsilanyloxybenzaldehyde, 10 g of MS3A and 8.9 ml of trimethylsilyl cyanide to a solution of 2.0 g of Yb(OTf)$_3$ in 200 ml of dichloromethane under a nitrogen atmosphere, the mixture was stirred overnight at room temperature. The reaction mixture was filtered through celite, and the celite was washed with ethyl acetate. The organic layer was concentrated under reduced pressure, ethyl acetate and saturated aqueous sodium hydrogencarbonate were added to the residue, and extraction was performed with ethyl acetate. The organic layer was washed with saturated brine and dried over anhydrous magnesium sulfate. The desiccating agent was filtered off and the filtrate was concentrated under reduced pressure. The residue was purified by NAM silica gel column chromatography (ethyl acetate-heptane) to give a yellow oil (13.7 g).

To a 200 ml THF solution containing 13.7 g of the obtained yellow oil there was added 45 ml of a 20% aqueous solution of ammonium sulfide, and the mixture was stirred at room temperature for 11 hours and 30 minutes. Water was added to the reaction mixture and extraction was performed with ethyl acetate. After washing the organic layer with water and saturated brine, it was dried over anhydrous magnesium sulfate. The desiccating agent was filtered off and the filtrate was concentrated under reduced pressure.

Next, 300 ml of acetonitrile was added to dissolve the obtained residue. After adding 4.3 g of $Me_3O^+BF_4^-$ to the solution, the mixture was stirred at room temperature for 1 hour. Saturated aqueous sodium hydrogencarbonate was added to the reaction mixture, and extraction was performed with ethyl acetate. After washing the organic layer with water and saturated brine, it was dried over anhydrous magnesium sulfate. The desiccating agent was filtered off and the filtrate was concentrated under reduced pressure.

After adding 200 ml of dichloromethane and 30 g of manganese dioxide to the obtained residue, the mixture was stirred at room temperature for 2 hours and 30 minutes. The reaction mixture was filtered, and the filtrate was concentrated under reduced pressure.

Next, 200 ml of toluene was added to dissolve the obtained residue. After adding 12.8 ml of 2,4,6-collidine and 6.4 ml of methyl chloroformate to the solution, the mixture was stirred at 85° C. for 24 hours under a nitrogen atmosphere. Water was added to the reaction mixture and extraction was performed with ethyl acetate. The organic layer was washed with ice-cooled 1N hydrochloric acid, ice-cooled saturated sodium hydrogen carbonate water and saturated brine, and dried over anhydrous magnesium sulfate. The desiccating agent was filtered off and the filtrate was concentrated under reduced pressure. The residue was purified by silica gel column chromatography (ethyl acetate-heptane) to give a yellow oil (12.2 g).

To a 200 ml THF solution containing 12.2 g of the obtained yellow oil there was added 16.3 ml of TBAF (1.0 M, THF solution), and the mixture was stirred at room temperature for 1 hour and 30 minutes. Saturated aqueous ammonium chloride was added to the reaction mixture, and extraction was performed with ethyl acetate. The organic layer was washed with saturated brine and dried over anhydrous magnesium sulfate. The desiccating agent was filtered off and the filtrate was concentrated under reduced pressure. The residue was purified by silica gel column chromatography (ethyl acetate-heptane) to give the title compound (3.59 g, isomeric mixture).

$^1$H-NMR (CDCl$_3$) Two main isomers:

δ 2.19 (s, 3H) 2.46 (s, 3H) 2.62 (s, 3H) 3.59 (s, 3H) 6.48 (dd, J=1.6, 5.2 Hz, 1H) 6.77-6.80 (m, 1H) 6.81 (d, J=8.4 Hz, 2H) 7.87 (d, J=8.4 Hz, 2H)

δ 2.32 (s, 6H) 2.65 (s, 3H) 3.57 (s, 3H) 6.96-6.99 (m, 1H) 7.12 (d, J=8.8 Hz, 2H) 7.18-7.19 (m, 1H) 8.02 (d, J=8.8 Hz, 2H)

(14c) 4-({(2-fluoro-3-methoxy-5-methylphenyl)-[1-(2-methoxyphenyl)-5-oxo-4,5-dihydro-1H-[1,2,4]triazol-3-yl]methyl}amino)benzamidine trifluoroacetate

[Chemical Formula 89]

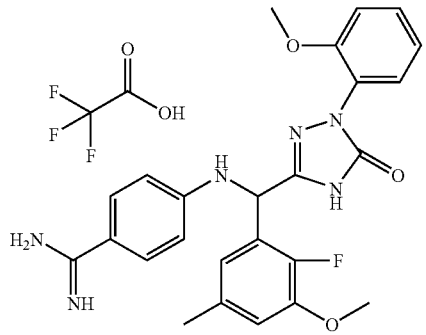

After adding 140 mg of potassium carbonate and 140 mg of iodomethane to a 3 ml DMF solution containing 220 mg of {2-(2-fluoro-3-hydroxy-5-methylphenyl)-2-[4-(5-methyl-[1,2,4]oxadiazol-3-yl)phenylimino]-1-methylsulfanylethylidene}carbamic acid methyl ester, the mixture was stirred at room temperature for 17 hours and 15 minutes. Ethyl acetate and water were added to the reaction mixture, and extraction was performed twice with ethyl acetate. The combined organic layers were washed twice with water and dried using magnesium sulfate. The desiccating agent was filtered off and the filtrate was concentrated under reduced pressure.

Half of the obtained residue was dissolved in 1 ml of DMF, and after adding 38 mg of (2-methoxyphenyl)hydrazine hydrochloride and 0.070 ml of triethylamine to the solution, the mixture was stirred at 85° C. for 7 hours and 15 minutes under a nitrogen atmosphere. The reaction mixture was then concentrated.

Next, 1 ml of methanol and 0.090 ml of acetic acid were added to dissolve the obtained residue. To this solution there was added 100 mg of sodium cyanotrihydroborate, and the mixture was stirred at room temperature for 3 hours. The reaction mixture was then concentrated.

Next, 3 ml of a methanol:water:acetic acid=1:1:1 mixed solvent was added to dissolve the obtained residue. After adding 140 mg of iron powder to the solution, the mixture was stirred at 55° C. for 17 hours and 15 minutes under a nitrogen atmosphere. After filtering the reaction mixture, it was purified by reverse-phase high performance liquid chromatography (acetonitrile-water, 0.1% trifluoroacetic acid) to give the title compound (4.15 mg) as a white solid.

$^1$H-NMR (CD$_3$OD) δ 2.31 (s, 3H) 3.82 (s, 3H) 3.87 (s, 3H) 5.95 (s, 1H) 6.83-6.86 (m, 3H) 6.94 (dd, J=2.0, 8.0 Hz, 1H) 7.02 (dt, J=0.8, 8.0 Hz, 1H) 7.14 (dd, J=1.2, 8.4 Hz, 1H) 7.30 (dd, J=1.6, 7.6 Hz, 1H) 7.43 (ddd, J=1.2, 7.2, 8.4 Hz, 1H) 7.62-7.65 (m, 2H)

Mass spectrum (ESI) m/z: 477 (M+H)$^+$

Example 15

(R) and (S)-2-{3-[(4-carbamimidoylphenylamino)-(5-oxo-1-pyrimidin-2-yl-4,5-dihydro-1H-[1,2,4]triazol-3-yl)methyl]-2-fluoro-5-methoxyphenoxy}-N,N-dimethylacetamide acetate

[Chemical Formula 90]

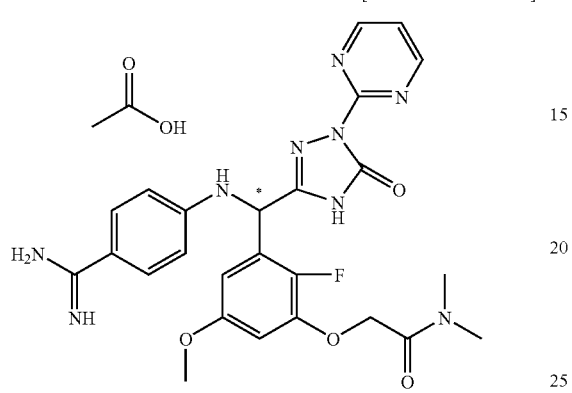

After adding 53 mg of potassium carbonate, 10 mg of tetrabutylammonium iodide and 53 mg of 2-chloro-N,N-dimethylacetamide to a 1 ml DMF solution containing 100 mg of [2-(2-fluoro-3-hydroxy-5-methoxyphenyl)-2-[4-(5-methyl-[1,2,4]oxadiazol-3-yl)phenylimino]-1-methylsulfanylethylidene]carbamic acid methyl ester (Example (3d)), the mixture was stirred at room temperature for 26 hours and 30 minutes. Ethyl acetate was added to the reaction mixture, PRESEP™ was used for filtration, and the filtrate was concentrated.

The obtained residue was dissolved in 1 ml of DMF, and then 22 mg of 2-hydrazinopyrimidine and 0.046 ml of triethylamine were added to the solution and the mixture was stirred at 85° C. for 12 hours under a nitrogen atmosphere. The reaction mixture was then concentrated.

Next, 1 ml of methanol and 0.070 ml of acetic acid were added to dissolve the obtained residue. After then adding 100 mg of sodium cyanotrihydroborate to the solution, it was stirred overnight at room temperature. The reaction mixture was then concentrated.

Next, 3 ml of a methanol:water:acetic acid=1:1:1 mixed solvent was added to dissolve the obtained residue. After then adding 121 mg of iron powder to the solution, the mixture was stirred at 60° C. for 13 hours under a nitrogen atmosphere. After filtering the reaction mixture, it was crudely purified by reverse-phase high performance liquid chromatography (acetonitrile-water, 0.1% acetic acid).

The obtained crude product was optically resolved using a SUMICHIRAL OA-2500 column, and the first eluting enantiomer (7.60 mg) of the title compound was obtained as a white solid.

$^1$H-NMR (CD$_3$OD) δ 1.91 (s, 3H) 2.96 (s, 3H) 3.08 (s, 3H) 3.69 (s, 3H) 4.87 (s, 2H) 5.95 (s, 1H) 6.57 (dd, J=2.8, 6.8 Hz, 1H) 6.67-6.69 (m, 1H) 6.85 (d J=8.8 Hz, 2H) 7.28-7.30 (m, 1H) 7.60 (d, J=8.8 Hz, 2H) 8.75 (d, J=4.4 Hz, 2H)

HPLC retention time: 19 min

Example 16

(R) and (S)-4-{[(4-cyanomethoxy-3-methoxyphenyl)-(5-oxo-1-pyrimidin-2-yl-4,5-dihydro-1H-[1,2,4]triazol-3-yl)methyl]amino}benzamidine acetate (16a) {2-(4-cyanomethoxy-3-methoxyphenyl)-2-[4-(5-methyl-[1,2,4]oxadiazol-3-yl)phenylimino]-1-methylsulfanylethylidene}carbamic acid methyl ester

[Chemical Formula 91]

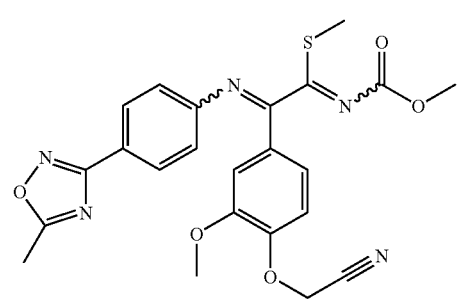

After dissolving 520 mg of {2-(4-hydroxy-3-methoxyphenyl)-2-[4-(5-methyl-[1,2,4]oxadiazol-3-yl)phenylimino]-1-methylsulfanylethylidene}carbamic acid methyl ester (Example (18d)) in 5 ml of DMF, 262 mg of potassium carbonate and 107 μl of bromoacetonitrile were added and the mixture was stirred at room temperature for 16 hours. Water was added to the reaction mixture and extraction was performed with ethyl acetate. The organic layer was washed with water and saturated brine, and then dried over anhydrous sodium sulfate. The desiccating agent was filtered off and the filtrate was concentrated under reduced pressure. The residue was purified by silica gel column chromatography (ethyl acetate-heptane) to give the title compound (514 mg, isomeric mixture) as a light yellow solid.

$^1$H-NMR (CDCl$_3$) Main isomer:
δ 2.34 (s, 3H) 2.66 (s, 3H) 3.63 (s, 3H) 3.97 (s, 3H) 4.90 (s, 2H) 7.06 (d, J=8.4 Hz, 1H) 7.18 (d, J=8.8 Hz, 2H) 7.32 (dd, J=8.4, 2.0 Hz, 1H) 7.68 (d, J=2.0 Hz, 1H) 8.03 (d, J=8.8 Hz, 2H)

(16b) 4-{[(4-cyanomethoxy-3-methoxyphenyl)-(5-oxo-1-pyrimidin-2-yl-4,5-dihydro-1H-[1,2,4]triazol-3-yl)methyl]amino}benzamidine acetate

[Chemical Formula 92]

To a solution of 535 mg of {2-(4-cyanomethoxy-3-methoxyphenyl)-2-[4-(5-methyl-[1,2,4]oxadiazol-3-yl)phenylimino]-1-methylsulfanylethylidene}carbamic acid methyl ester in 8 ml of DMF there were added 123 mg of 2-hydrazinopyrimidine and 312 μl of triethylamine, and the mixture was stirred at 85° C. for 16 hours under a nitrogen atmosphere. The reaction mixture was concentrated, and the residue was dissolved in 6 ml of a methanol:THF=1:1 mixed solvent. Next, 229 μl of acetic acid and 357 mg of sodium cyanotrihydroborate were added to the solution and the mixture was stirred at room temperature for 3 hours and 30 minutes. After adding ethyl acetate to the reaction mixture, it was filtered through a small amount of NAM silica gel, and the silica gel was washed with ethyl acetate-methanol. The filtrate was concentrated under reduced pressure, and the residue was crudely purified by NAM silica gel column chromatography (methanol-ethyl acetate), to give (2-methoxy-4-{[4-(5-methyl-[1,2,4]oxadiazol-3-yl)phenylamino]-(5-oxo-1-pyrimidin-2-yl-4,5-dihydro-1H-[1,2,4]triazol-3-yl)methyl}phenoxy)acetonitrile.

To a solution of this compound in 9 ml of a methanol:water:acetic acid=1:1:1 mixed solvent there was added 300 mg of iron powder, and the mixture was stirred at 60° C. for 16 hours under a nitrogen atmosphere. After filtering the reaction mixture, it was purified by reverse-phase high performance liquid chromatography (acetonitrile-water, 0.1% acetic acid) to give 150 mg of the title compound.

$^1$H-NMR (CD$_3$OD) δ 3.87 (s, 3H) 4.95 (s, 2H) 5.72 (s, 1H) 6.88 (d, J=8.8 Hz, 2H) 7.13 (m, 2H) 7.26 (br.s, 1H) 7.37 (t, J=4.8 Hz, 1H) 7.62 (d, J=8.8 Hz, 2H) 8.80 (d, J=4.8 Hz, 2H)

Mass spectrum (ESI) m/z: 472 (M+H)$^+$ (16c) (R) and (S)-4-{[(4-cyanomethoxy-3-methoxyphenyl)-(5-oxo-1-pyrimidin-2-yl-4,5-dihydro-1H-[1,2,4]triazol-3-yl)methyl]amino}benzamidine acetate

[Chemical Formula 93]

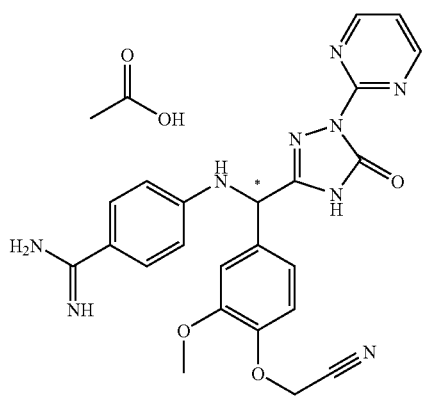

A SUMICHIRAL OA-2500 column was used for optical resolution of 120 mg of 4-{[(4-cyanomethoxy-3-methoxyphenyl)-(5-oxo-1-pyrimidin-2-yl-4,5-dihydro-1H-[1,2,4]triazol-3-yl)methyl]amino}benzamidine acetate, and the first eluting enantiomer (40.5 mg) of the title compound was obtained.

HPLC retention time: 12 min

Example 17

(R) and (S)-4-{[(3-ethoxy-4-methoxyphenyl)-(5-oxo-1-pyrimidin-2-yl-4,5-dihydro-1H-[1,2,4]triazol-3-yl)methyl]amino}benzamidine acetate (17a) (4-methoxy-3-triisopropylsilanyloxyphenyl)-[4-(5-methyl-[1,2,4]oxadiazol-3-yl)phenylamino]acetonitrile

[Chemical Formula 94]

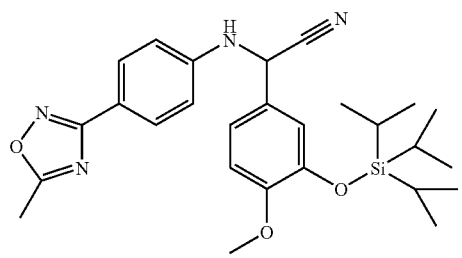

After adding 3.19 g of 4-(5-methyl-[1,2,4]oxadiazol-3-yl)phenylamine, 10 g of MS3A, 1.56 g of Yb(OTf)$_3$ and 4.84 ml of trimethylsilyl cyanide to a solution of 5.6 g of 4-methoxy-3-triisopropylsilanyloxybenzaldehyde [CAS No. 179260-96-6] in 98 ml of dichloromethane under a nitrogen atmosphere, the mixture was stirred at room temperature for 12 hours. The reaction mixture was filtered, and the filtrate was concentrated under reduced pressure. The residue was purified by silica gel column chromatography (ethyl acetate-heptane) to give a white solid (5.59 g).

(17b) 2-(4-methoxy-3-triisopropylsilanyloxyphenyl)-2-[4-(5-methyl-[1,2,4]oxadiazol-3-yl)phenylamino]thioacetamide

[Chemical Formula 95]

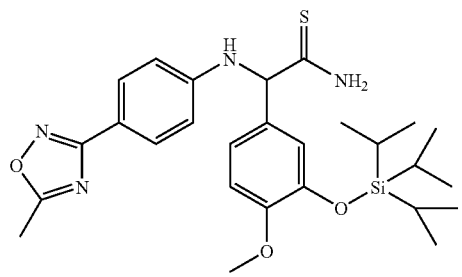

After adding 30.8 ml of a 20% aqueous solution of ammonium sulfide to a solution of 8.92 g of (4-methoxy-3-triisopropylsilanyloxyphenyl)-[4-(5-methyl-[1,2,4]oxadiazol-3-yl)phenylamino]acetonitrile in 300 ml of a methanol:THF=2:1 mixed solvent, the mixture was stirred at room temperature for 15 hours. Water was added to the reaction mixture and extraction was performed with ethyl acetate. After washing the organic layer with saturated brine, it was dried over anhydrous sodium sulfate. The desiccating agent was filtered off, and the filtrate was concentrated under reduced pressure to give the title compound (8.59 g) as a crude product.

(17c) {2-(4-methoxy-3-triisopropylsilanyloxyphenyl)-2-[4-(5-methyl-[1,2,4]oxadiazol-3-yl)phenylimino]-1-methylsulfanylethylidene}carbamic acid methyl ester

[Chemical Formula 96]

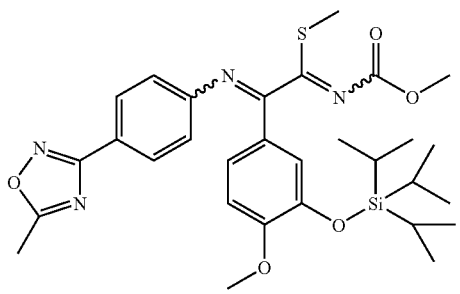

After adding 2.35 g of Me₃O⁺BF₄⁻ to a solution of 7.26 g of 2-(4-methoxy-3-triisopropylsilanyloxyphenyl)-2-[4-(5-methyl-[1,2,4]oxadiazol-3-yl)phenylamino]thioacetamide in 179 ml of dichloromethane under a nitrogen atmosphere, the mixture was stirred at room temperature for 5 hours. Saturated aqueous sodium hydrogencarbonate was added to the reaction mixture, and extraction was performed with dichloromethane. After washing the organic layer with saturated brine, it was dried over anhydrous sodium sulfate. The desiccating agent was filtered off and the filtrate was concentrated under reduced pressure.

To a solution of the obtained crude product in 300 ml of toluene there were added 6.4 ml of 2,4,6-collidine and 3.2 ml of methyl chloroformate, and the mixture was stirred at 85° C. for 16 hours under a nitrogen atmosphere. After cooling the reaction mixture, dilute hydrochloric acid was added and extraction was performed with ethyl acetate. The organic layer was washed with water and saturated brine, and then dried over anhydrous sodium sulfate. The desiccating agent was filtered off and the filtrate was concentrated under reduced pressure. The residue was purified by silica gel column chromatography (ethyl acetate-heptane) to give the title compound (3.52 g, isomeric mixture) as a light yellow oil.

¹H-NMR (CDCl₃) Main isomer:
δ 1.09 (d, J=7.2 Hz, 18H) 1.24-1.27 (m, 3H) 2.30 (s, 3H) 2.65 (s, 3H) 3.60 (s, 3H) 3.87 (s, 3H) 6.87 (d, J=8.8 Hz, 1H) 7.16 (d, J=8.8 Hz, 2H) 7.41 (m, 2H) 7.99 (d, J=8.8 Hz, 2H)

(17d) {2-(3-hydroxy-4-methoxyphenyl)-2-[4-(5-methyl-[1,2,4]oxadiazol-3-yl)phenylimino]-1-methylsulfanylethylidene}carbamic acid methyl ester

[Chemical Formula 97]

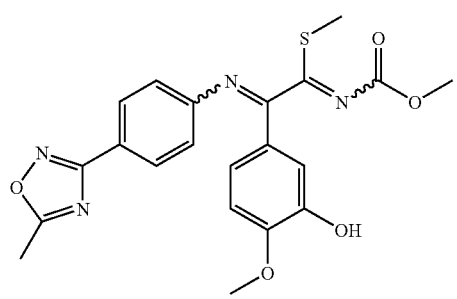

After dissolving 3.52 g of {2-(4-methoxy-3-triisopropylsilanyloxyphenyl)-2-[4-(5-methyl-[1,2,4]oxadiazol-3-yl)phenylimino]-1-methylsulfanylethylidene}carbamic acid methyl ester in 50 ml of THF, 6.49 ml of TBAF (1.0 M, THF solution) was added and the mixture was stirred at room temperature for 15 hours. Saturated aqueous ammonium chloride was added to the reaction mixture, and extraction was performed with ethyl acetate. The organic layer was dried over anhydrous sodium sulfate. The desiccating agent was filtered off and the filtrate was concentrated under reduced pressure. The residue was purified by silica gel column chromatography (ethyl acetate-heptane) to give the title compound (1.88 g, isomeric mixture) as a light yellow solid.

¹H-NMR (CDCl₃) Main isomer:
δ 2.32 (s, 3H) 2.65 (s, 3H) 3.64 (s, 3H) 3.96 (s, 3H) 5.67 (s, 1H) 6.90 (d, J=8.4 Hz, 1H) 7.16 (d, J=8.8 Hz, 2H) 7.36 (dd, J=8.4, 2.0 Hz, 1H) 7.53 (d, J=2.0 Hz, 1H) 8.01 (d, J=8.8 Hz, 2H)

(17e) {2-(3-ethoxy-4-methoxyphenyl)-2-[4-(5-methyl-[1,2,4]oxadiazol-3-yl)phenylimino]-1-methylsulfanylethylidene}carbamic acid methyl ester

[Chemical Formula 98]

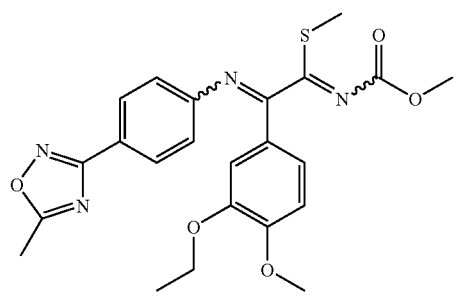

After dissolving 1.0 g of {2-(3-hydroxy-4-methoxyphenyl)-2-[4-(5-methyl-[1,2,4]oxadiazol-3-yl)phenylimino]-1-methylsulfanylethylidene}carbamic acid methyl ester in 10 ml of DMF, 473 mg of potassium carbonate and 219 μl of iodoethane were added and the mixture was stirred at room temperature for 21 hours. Water was added to the reaction mixture and extraction was performed with ethyl acetate. After washing the organic layer with water and saturated brine, it was dried over anhydrous sodium sulfate. The desiccating agent was filtered off and the filtrate was concentrated under reduced pressure. The residue was purified by silica gel column chromatography (ethyl acetate-heptane) to give the title compound (983 mg, isomeric mixture) as a light yellow solid.

¹H-NMR (CDCl₃) Main isomer:
δ 1.50 (t, J=6.8 Hz, 3H) 2.32 (s, 3H) 2.65 (s, 3H) 3.62 (s, 3H) 3.94 (s, 3H) 4.19 (q, J=6.8 Hz, 2H) 6.89 (d, J=8.4 Hz, 1H) 7.19 (d, J=8.8 Hz, 2H) 7.30 (dd, J=8.4, 2.4 Hz, 1H) 7.58 (d, J=2.4 Hz, 1H) 8.02 (d, J=8.8 Hz, 2H)

(17f) 5-{(3-ethoxy-4-methoxyphenyl)-[4-(5-methyl-[1,2,4]oxadiazol-3-yl)phenylamino]methyl}-2-pyrimidin-2-yl-2,4-dihydro-[1,2,4]triazol-3-one

[Chemical Formula 99]

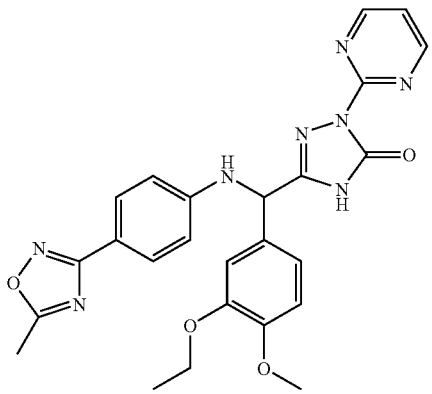

After adding 230 mg of 2-hydrazinopyrimidine and 293 μl of triethylamine to a 50 ml DMF solution containing 983 mg of {2-(3-ethoxy-4-methoxyphenyl)-2-[4-(5-methyl-[1,2,4]oxadiazol-3-yl)phenylimino]-1-methylsulfanylethylidene}carbamic acid methyl ester, the mixture was stirred at 85° C. for 10 hours under a nitrogen atmosphere. The reaction mixture was concentrated, and the residue was dissolved in 30 ml of a methanol:THF=1:1 mixed solvent. After adding 420 μl of acetic acid and 657 mg of sodium cyanotrihydroborate to the reaction mixture, it was stirred at room temperature for 5 hours. Ethyl acetate was added to the reaction mixture which was then filtered through a small amount of NAM silica gel, and the silica gel was washed with ethyl acetate-methanol. The filtrate was concentrated under reduced pressure, and the residue was purified by NAM silica gel column chromatography (methanol-ethyl acetate) to give the title compound (400 mg) as a light yellow solid.

$^1$H-NMR (CDCl$_3$) δ 1.32 (t, J=7.2 Hz, 3H) 2.58 (s, 3H) 3.80 (s, 3H) 3.90 (q, J=7.2 Hz, 2H) 5.77 (d, J=7.2 Hz, 1H) 6.77 (d, J=8.8 Hz, 1H) 6.83 (d, J=8.8 Hz, 2H) 7.12-7.17 (m, 3H) 7.81 (d, J=8.8 Hz, 2H) 8.69 (d, J=4.8 Hz, 2H)

(17g) 4-{[(3-ethoxy-4-methoxyphenyl)-(5-oxo-1-pyrimidin-2-yl-4,5-dihydro-1H-[1,2,4]triazol-3-yl)methyl]amino}benzamidine acetate

[Chemical Formula 100]

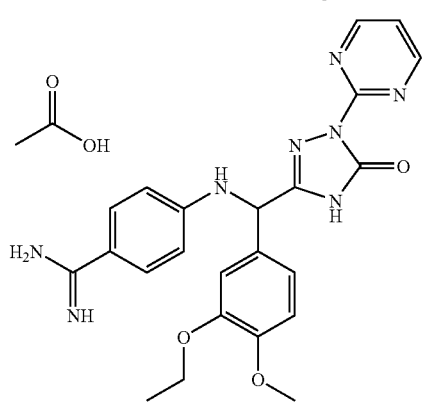

To a solution of 70 mg of 5-{(3-ethoxy-4-methoxyphenyl)-[4-(5-methyl-[1,2,4]oxadiazol-3-yl)phenylamino]methyl}-2-pyrimidin-2-yl-2,4-dihydro-[1,2,4]triazol-3-one in 3 ml of a methanol:water:acetic acid=1:1:1 mixed solvent there was added 70 mg of iron powder, and the mixture was stirred at 60° C. for 14 hours under a nitrogen atmosphere. After filtering the reaction mixture, it was purified by reverse-phase high performance liquid chromatography (acetonitrile-water, 0.1% acetic acid), to give 41 mg of the title compound.

$^1$H-NMR (CD$_3$OD) δ 1.36 (t, J=7.2 Hz, 3H) 1.91 (s, 3H) 3.81 (s, 3H) 4.05 (q, J=7.2 Hz, 2H) 5.57 (s, 1H) 6.85 (d, J=8.8 Hz, 2H) 6.95 (d, J=8.0 Hz, 1H) 7.10 (dd, J=8.0, 2.0 Hz, 1H) 7.14 (d, J=2.0 Hz, 1H) 7.30 (t, J=4.8 Hz, 1H) 7.60 (d, J=8.8 Hz, 2H) 8.77 (d, J=4.8 Hz, 2H)

Mass spectrum (ESI) m/z: 461 (M+H)$^+$ (17h) (R) and (S)-4-{[(3-ethoxy-4-methoxyphenyl)-(5-oxo-1-pyrimidin-2-yl-4,5-dihydro-1H-[1,2,4]triazol-3-yl)methyl]amino}benzamidine acetate

[Chemical Formula 101]

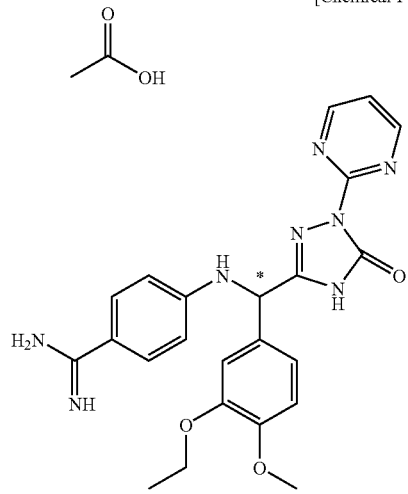

A SUMICHIRAL OA-2500 column was used for optical resolution of 250 mg of 4-{[(3-ethoxy-4-methoxyphenyl)-(5-oxo-1-pyrimidin-2-yl-4,5-dihydro-1H-[1,2,4]triazol-3-yl)methyl]amino}benzamidine acetate, and the first eluting enantiomer (103 mg) of the title compound was obtained as a white solid.

$^1$H-NMR (CD$_3$OD) δ 1.33 (t, J=7.2 Hz, 3H) 1.91 (s, 3H) 3.80 (s, 3H) 4.00 (q, J=7.2 Hz, 2H) 5.60 (s, 1H) 6.85 (d, J=8.8 Hz, 2H) 6.95 (d, J=8.0 Hz, 1H) 7.10 (dd, J=8.0, 2.0 Hz, 1H) 7.14 (d, J=2.0 Hz, 1H) 7.30 (t, J=4.8 Hz, 1H) 7.60 (d, J=8.8 Hz, 2H) 8.77 (d, J=4.8 Hz, 2H)

HPLC retention time: 12 min

Example 18

(R) and (S)-4-{[(4-ethoxy-3-methoxyphenyl)-(5-oxo-1-pyrimidin-2-yl-4,5-dihydro-1H-[1,2,4]triazol-3-yl)methyl]amino}benzamidine acetate (18a) (4-t-butyldimethylsilanyloxy-3-methoxyphenyl)-[4-(5-methyl-[1,2,4]oxadiazol-3-yl)phenylamino]acetonitrile

[Chemical Formula 102]

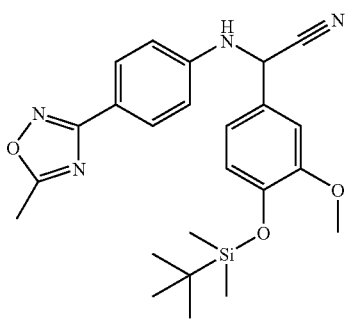

After adding 3.12 g of 4-(5-methyl-[1,2,4]oxadiazol-3-yl)phenylamine, 3.3 g of MS3A, 1.11 g of Yb(OTf)$_3$ and 4.75 ml of trimethylsilyl cyanide to a solution of 5.0 g of 4-t-butyldimethylsilanyloxy-3-methoxybenzaldehyde [CAS No. 69404-94-0] in 98 ml of dichloromethane under a nitrogen atmosphere, the mixture was stirred at room temperature for 23 hours. Next, 500 ml of ethyl acetate was added to the reaction mixture, the reaction mixture was filtered through celite, and the celite was washed with ethyl acetate. The organic layers were combined and washed with water and saturated brine, and then dried over anhydrous sodium sulfate. The desiccating agent was filtered off, and the filtrate was concentrated under reduced pressure to give the title compound (8.45 g) as a crude product.

$^1$H-NMR (CDCl$_3$) δ 0.19 (s, 6H) 1.01 (s, 9H) 2.64 (s, 3H) 3.85 (s, 3H) 4.30 (d, J=8.0 Hz, 1H) 5.40 (d, J=8.0 Hz, 1H) 6.84 (d, J=8.8 Hz, 2H) 6.91 (d, J=8.0 Hz, 1H) 7.03-7.08 (m, 2H) 7.98 (d, J=8.8 Hz, 2H)

(18b) 2-(4-t-butyldimethylsilanyloxy-3-methoxyphenyl)-2-[4-(5-methyl-[1,2,4]oxadiazol-3-yl)phenylamino]thioacetamide

[Chemical Formula 103]

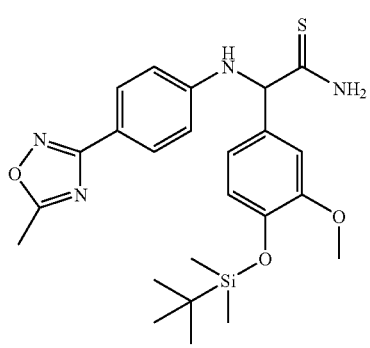

After adding 32 ml of a 20% aqueous solution of ammonium sulfide to a solution of 8.45 g of (4-t-butyldimethylsilanyloxy-3-methoxyphenyl)-[4-(5-methyl-[1,2,4]oxadiazol-3-yl)phenylamino]acetonitrile in 300 ml of a methanol:THF=2:1 mixed solvent, the mixture was stirred at room temperature for 23 hours. Water was added to the reaction mixture and extraction was performed with ethyl acetate. After washing the organic layer with saturated brine, it was dried over anhydrous sodium sulfate. The desiccating agent was filtered off, and the filtrate was concentrated under reduced pressure to give the title compound (8.26 g) as a crude product.

$^1$H-NMR (CDCl$_3$) δ 0.16 (s, 6H) 0.99 (s, 9H) 2.62 (s, 3H) 3.80 (s, 3H) 4.94 (d, J=2.4 Hz, 1H) 5.10 (d, J=2.4 Hz, 1H) 6.72 (d, J=8.8 Hz, 2H) 6.84 (d, J=8.0 Hz, 1H) 6.90-6.93 (m, 2H) 7.90 (d, J=8.8 Hz, 2H)

(18c) {2-(4-t-butyldimethylsilanyloxy-3-methoxyphenyl)-2-[4-(5-methyl-[1,2,4]oxadiazol-3-yl)phenylimino]-1-methylsulfanylethylidene}carbamic acid methyl ester

[Chemical Formula 104]

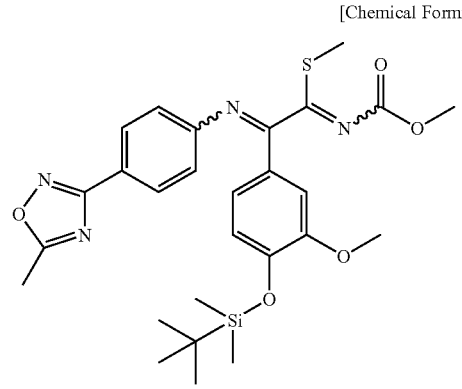

After adding 2.89 g of Me$_3$O$^+$BF$_4^-$ to a solution of 8.26 g of 2-(4-t-butyldimethylsilanyloxy-3-methoxyphenyl)-2-[4-(5-methyl-[1,2,4]oxadiazol-3-yl)phenylamino]thioacetamide in 400 ml of dichloromethane under a nitrogen atmosphere, the mixture was stirred at room temperature for 2 hours. Saturated aqueous sodium hydrogencarbonate was added to the reaction mixture, and extraction was performed with dichloromethane. After washing the organic layer with saturated brine, it was dried over anhydrous sodium sulfate. The desiccating agent was filtered off and the filtrate was concentrated under reduced pressure.

To a solution of the residue in 300 ml of toluene there were added 8.28 ml of 2,4,6-collidine and 4.15 ml of methyl chloroformate, and the mixture was stirred at 80° C. for 14 hours under a nitrogen atmosphere. After cooling the reaction mixture, dilute hydrochloric acid was added and extraction was performed with ethyl acetate. The organic layer was washed with water and saturated brine, and then dried over anhydrous sodium sulfate. The desiccating agent was filtered off and the filtrate was concentrated under reduced pressure. The residue was purified by silica gel column chromatography (ethyl acetate-heptane) to give the title compound (4.11 g, isomeric mixture) as a light yellow oil.

$^1$H-NMR (CDCl$_3$) Main isomer:
δ 0.19 (s, 6H) 1.00 (s, 9H) 2.31 (s, 3H) 2.65 (s, 3H) 3.59 (s, 3H) 3.87 (s, 3H) 6.86 (d, J=8.4 Hz, 2H) 7.18-7.20 (m, 2H) 7.54 (d, J=2.0 Hz, 1H) 8.00 (d, J=8.4 Hz, 2H)

(18d) {2-(4-hydroxy-3-methoxyphenyl)-2-[4-(5-methyl-[1,2,4]oxadiazol-3-yl)phenylimino]-1-methylsulfanylethylidene}carbamic acid methyl ester

[Chemical Formula 105]

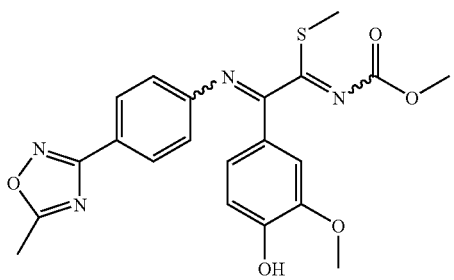

After dissolving 2.62 g of 2-(4-t-butyldimethylsilanyloxy-3-methoxyphenyl)-2-[4-(5-methyl-[1,2,4]oxadiazol-3-yl)phenylimino]-1-methylsulfanylethylidene}carbamic acid methyl ester in 52 ml of THF, 4.96 ml of TBAF (1.0 M, THF solution) was added and the mixture was stirred at room temperature for 2 hours. Saturated aqueous ammonium chloride was added to the reaction mixture, and extraction was performed with ethyl acetate. The organic layer was dried over anhydrous sodium sulfate. The desiccating agent was filtered off and the filtrate was concentrated under reduced pressure. The residue was purified by silica gel column chromatography (ethyl acetate-heptane) to give the title compound (1.87 g, isomeric mixture) as a light yellow solid.

$^1$H-NMR (CDCl$_3$) Main isomer:

δ 2.31 (s, 3H) 2.65 (s, 3H) 3.62 (s, 3H) 3.97 (s, 3H) 6.93 (d, J=8.0 Hz, 1H) 7.16 (d, J=8.4 Hz, 2H) 7.23 (br.d, J=8.0 Hz, 1H) 7.59 (br.s, 1H) 8.00 (d, J=8.4 Hz, 2H)

(18e) {2-(4-ethoxy-3-methoxyphenyl)-2-[4-(5-methyl-[1,2,4]oxadiazol-3-yl)phenylimino]-1-methylsulfanylethylidene}carbamic acid methyl ester

[Chemical Formula 106]

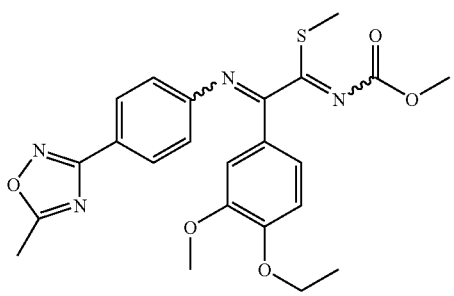

After dissolving 500 mg of {2-(4-hydroxy-3-methoxyphenyl)-2-[4-(5-methyl-[1,2,4]oxadiazol-3-yl)phenylimino]-1-methylsulfanylethylidene}carbamic acid methyl ester in 10 ml of DMF, 314 mg of potassium carbonate and 118 μl of iodoethane were added and the mixture was stirred at room temperature for 6 hours. Water was added to the reaction mixture and extraction was performed with ethyl acetate. After washing the organic layer with water and saturated brine, it was dried over anhydrous sodium sulfate. The desiccating agent was filtered off and the filtrate was concentrated under reduced pressure. The residue was purified by silica gel column chromatography (ethyl acetate-heptane) to give the title compound (435 mg, isomeric mixture) as a light yellow solid.

$^1$H-NMR (CDCl$_3$) Main isomer:

δ 1.51 (t, J=6.8 Hz, 3H) 2.32 (s, 3H) 2.65 (s, 3H) 3.62 (s, 3H) 3.95 (s, 3H) 4.15 (q, J=6.8 Hz, 2H) 6.88 (d, J=8.8 Hz, 1H) 7.19 (d, J=8.8 Hz, 2H) 7.30 (dd, J=8.8, 2.0 Hz, 1H) 7.59 (d, J=2.0 Hz, 1H) 8.02 (d, J=8.8 Hz, 2H)

(18f) 5-{(4-ethoxy-3-methoxyphenyl)-[4-(5-methyl-[1,2,4]oxadiazol-3-yl)phenylamino]methyl}-2-pyrimidin-2-yl-2,4-dihydro-[1,2,4]triazol-3-one

[Chemical Formula 107]

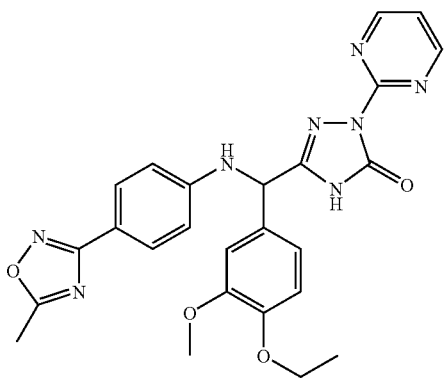

After adding 102 mg of 2-hydrazinopyrimidine and 129 μl of triethylamine to a solution of 435 mg of {2-(4-ethoxy-3-methoxyphenyl)-2-[4-(5-methyl-[1,2,4]oxadiazol-3-yl)phenylimino]-1-methylsulfanylethylidene}carbamic acid methyl ester in 15 ml of DMF, the mixture was stirred at 85° C. for 20 hours under a nitrogen atmosphere. The reaction mixture was concentrated, and the residue was dissolved in 20 ml of a methanol:THF=1:1 mixed solvent. Next, 186 μl of acetic acid and 292 mg of sodium cyanotrihydroborate were added to the solution and the mixture was stirred at room temperature for 2 hours and 30 minutes. After adding ethyl acetate to the reaction mixture, it was filtered through a small amount of NAM silica gel, and the silica gel was washed with ethyl acetate-methanol. The filtrate was concentrated under reduced pressure, and the residue was purified by NAM silica gel column chromatography (methanol-ethyl acetate) to give the title compound (152 mg).

$^1$H-NMR (CD$_3$OD) δ 1.37 (t, J=7.2 Hz, 3H) 2.57 (s, 3H) 3.83 (s, 3H) 4.03 (q, J=7.2 Hz, 2H) 5.58 (s, 1H) 6.82 (d, J=8.8 Hz, 2H) 6.93 (d, J=8.4 Hz, 1H) 7.08 (dd, J=8.4, 2.4 Hz, 1H) 7.17 (d, J=2.4 Hz, 1H) 7.34 (t, J=4.8 Hz, 1H) 7.76 (d, J=8.8 Hz, 2H) 8.78 (d, J=4.8 Hz, 2H)

(18g) 4-{[(4-ethoxy-3-methoxyphenyl)-(5-oxo-1-pyrimidin-2-yl-4,5-dihydro-1H-[1,2,4]triazol-3-yl)methyl]amino}benzamidine trifluoroacetate

[Chemical Formula 108]

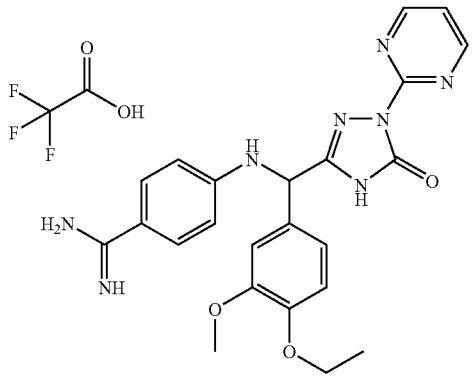

To a solution of 35 mg of 5-{(4-ethoxy-3-methoxyphenyl)-[4-(5-methyl-[1,2,4]oxadiazol-3-yl)phenylamino]methyl}-2-pyrimidin-2-yl-2,4-dihydro-[1,2,4]triazol-3-one in 3 ml of a methanol:water:acetic acid=1:1:1 mixed solvent there was added 30 mg of iron powder, and the mixture was stirred at 55° C. for 15 hours under a nitrogen atmosphere. After filtering the reaction mixture, it was purified by reverse-phase high performance liquid chromatography (acetonitrile-water, 0.1% trifluoroacetic acid) to give 18.3 mg of the title compound.

$^1$H-NMR (CD$_3$OD) δ 1.36 (t, J=7.2 Hz, 3H) 3.81 (s, 3H) 4.02 (q, J=7.2 Hz, 2H) 5.66 (s, 1H) 6.86 (d, J=7.6 Hz, 1H) 6.93 (d, J=8.4 Hz, 2H) 7.06 (br.d, J=7.6 Hz, 1H) 7.14 (br.s, 1H) 7.37 (br.s, 1H) 7.59 (d, J=8.4 Hz, 2H) 8.77 (br.s, 2H)

Mass spectrum (ESI) m/z: 461 (M+H)$^+$ (18h) (R) and (S)-4-{[(4-ethoxy-3-methoxyphenyl)-(5-oxo-1-pyrimidin-2-yl-4,5-dihydro-1H-[1,2,4]triazol-3-yl)methyl]amino}benzamidine acetate

[Chemical Formula 109]

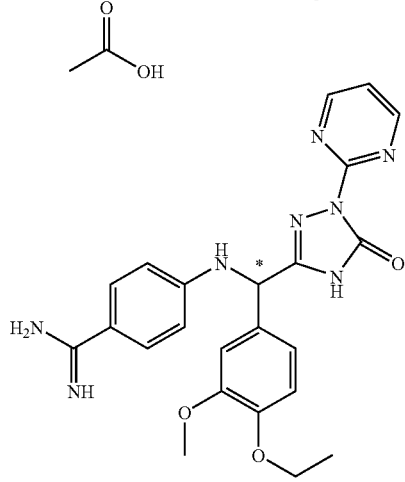

A SUMICHIRAL OA-2500 column was used for optical resolution of 75 mg of 4-{[(4-ethoxy-3-methoxyphenyl)-(5-oxo-1-pyrimidin-2-yl-4,5-dihydro-1H-[1,2,4]triazol-3-yl)methyl]amino}benzamidine acetate (produced by the same procedure as in Example (18g), using 0.1% acetic acid instead of the 0.1% trifluoroacetic acid in Example (18g)), and the first eluting enantiomer (20 mg) of the title compound was obtained as a white solid.

HPLC retention time: 12 min

Example 19

(R) and (S)-4-({[1-(3-aminopyridin-2-yl)-5-oxo-4,5-dihydro-1H-[1,2,4]triazol-3-yl]-(2-methoxy-6-methylpyridin-4-yl)methyl}amino)benzamidine acetate (19a) 2-methoxy-6-methylpyridine-4-carbaldehyde

[Chemical Formula 110]

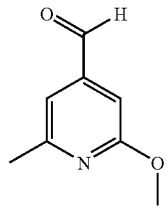

To a solution of 5.0 g of 2-chloro-6-methylisonicotinic acid [CAS No. 25462-85-5] in 50 ml of toluene there was added 3.9 ml of thionyl chloride under a nitrogen atmosphere, and the mixture was stirred for 1 hour under reflux. After cooling the reaction mixture to 0° C., 30 ml of a methanol:toluene=1:2 solvent mixture was added thereto at 0° C. over a period of 10 minutes. The reaction mixture was then stirred for 1 hour under reflux under a nitrogen atmosphere. After cooling the reaction mixture to 0° C., saturated aqueous potassium carbonate was added thereto and extraction was performed with ethyl acetate. The organic layer was washed with saturated brine and then dried over anhydrous magnesium sulfate. The desiccating agent was filtered off and the filtrate was concentrated under reduced pressure.

To a solution of the obtained residue in 10 ml of dioxane there was added 4.4 g of sodium methoxide, and the mixture was stirred for 2 hours under reflux under a nitrogen atmosphere. The reaction mixture was cooled to 0° C., and then ethyl acetate and ice-cold water were added thereto and extraction was performed with ethyl acetate. The organic layer was washed with saturated brine and then dried over anhydrous magnesium sulfate. The desiccating agent was filtered off and the filtrate was concentrated under reduced pressure. The residue was purified by silica gel column chromatography (ethyl acetate-heptane) to give 2-methoxy-6-methylisonicotinic acid methyl ester (2.5 g) as a light yellow oil.

To a solution of 2.5 g of this compound in 30 ml of THF there was added 0.53 g of lithium aluminum hydride at 0° C. under a nitrogen atmosphere, and the mixture was stirred at 0° C. for 30 minutes. After adding 0.53 ml of water, 0.53 ml of 15% aqueous sodium hydroxide and an additional 1.5 ml of water to the reaction mixture, it was stirred at room temperature for 30 minutes. The reaction mixture was filtered, and the filtrate was concentrated under reduced pressure to give 2.4 g of a crude product of (2-methoxy-6-methyl-pyridin-4-yl)methanol.

To 50 ml of dichloromethane containing 1.67 ml of oxalyl chloride there was added dropwise 1.36 ml of DMSO at −78° C. under a nitrogen atmosphere, and the mixture was stirred at -78° C. for 30 minutes. Next, 10 ml of a dichloromethane solution containing (2-methoxy-6-methyl-pyridin-4-yl)methanol was added dropwise, and the mixture was stirred at −78° C. for 30 minutes. After then adding 6.7 ml of triethylamine to the reaction mixture over a period of 10 minutes, the mixture was stirred for 30 minutes while raising the temperature from −78° C. to room temperature. Water was added to the reaction mixture, and extraction was performed with dichloromethane. The organic layer was washed with saturated brine and then dried over anhydrous magnesium sulfate. The desiccating agent was filtered off and the filtrate was concentrated under reduced pressure. The residue was purified by silica gel column chromatography (ethyl acetate-heptane) to give the title compound (1.9 g) as a light yellow oil.

$^1$H-NMR (CDCl$_3$) δ 2.53 (s, 3H) 3.97 (s, 3H) 6.93 (s, 1H) 7.13 (s, 1H) 9.96 (s, 1H)

(19b) {2-(2-methoxy-6-methylpyridin-4-yl)-2-[4-(5-methyl-[1,2,4]oxadiazol-3-yl)phenylimino]-1-methylsulfanylethylidene}carbamic acid methyl ester

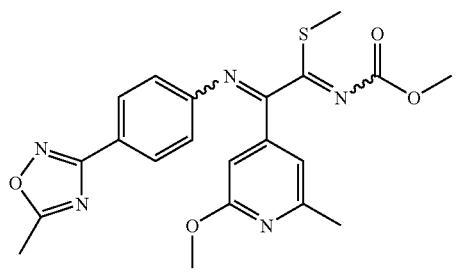

[Chemical Formula 111]

After adding 1.08 g of 4-(5-methyl-[1,2,4]oxadiazol-3-yl)phenylamine, 2 g of MS3A, 1.15 g of Yb(OTf)$_3$ and 1.65 ml of trimethylsilyl cyanide to a solution of 0.93 g of 2-methoxy-6-methylpyridine-4-carbaldehyde in 20 ml of THF under a nitrogen atmosphere, the mixture was stirred at room temperature for 16 hours. Ethyl acetate was added to the reaction mixture which was then filtered through celite, and the celite was washed with ethyl acetate. The organic layers were combined and washed with water and saturated brine, and then dried over anhydrous sodium sulfate. The desiccating agent was filtered off and the filtrate was concentrated under reduced pressure.

To a solution of the residue in 20 ml of a methanol:THF=1:1 mixed solvent there was added 10.5 ml of a 20% aqueous solution of ammonium sulfide, and the mixture was stirred at room temperature for 150 minutes. Water was added to the reaction mixture, and after stirring at room temperature for 15 minutes, the precipitate was filtered out. The filtered solid was washed with water and heptane to give 2-(2-methoxy-6-methylpyridin-4-yl)-2-[4-(5-methyl-[1,2,4]oxadiazol-3-yl)phenylimino]thioacetamide (2.3 g) as a white solid.

To a solution of 2.0 g of this compound in 40 ml of acetonitrile there was added 841 mg of Me$_3$O$^+$BF$_4^-$ under a nitrogen atmosphere, and the mixture was stirred at room temperature for 1 hour. Saturated aqueous sodium hydrogencarbonate was added to the reaction mixture, and extraction was performed with ethyl acetate. After washing the organic layer with saturated brine, it was dried over anhydrous sodium sulfate. The desiccating agent was filtered off and the filtrate was concentrated under reduced pressure.

To a solution of the obtained residue in 70 ml of ethyl acetate there was added 7.95 g of manganese dioxide, and the mixture was stirred at room temperature for 5 hours. The reaction mixture was filtered through celite, and the filtrate was concentrated under reduced pressure.

To a solution of the residue in 50 ml of toluene there were added 2.15 ml of 2,4,6-collidine and 0.84 ml of methyl chloroformate, and the mixture was stirred at 80° C. for 8 hours under a nitrogen atmosphere. After cooling the reaction mixture, dilute hydrochloric acid was added and extraction was performed with ethyl acetate. The organic layer was washed with water and saturated brine, and then dried over anhydrous sodium sulfate. The desiccating agent was filtered off and the filtrate was concentrated under reduced pressure. The residue was purified by silica gel column chromatography (ethyl acetate-heptane) to give the title compound (1.35 g, isomeric mixture) as a light yellow solid.

$^1$H-NMR (CDCl$_3$) Main isomer:

δ 2.34 (s, 3H) 2.51 (s, 3H) 2.65 (s, 3H) 3.65 (s, 3H) 3.95 (s, 3H) 6.88 (d, J=0.8 Hz, 1H) 7.13 (d, J=8.8 Hz, 2H) 7.21 (d, J=0.8 Hz, 1H) 8.02 (d, J=8.8 Hz, 2H)

(19c) 4-({[1-(3-aminopyridin-2-yl)-5-oxo-4,5-dihydro-1H-[1,2,4]triazol-3-yl]-(2-methoxy-6-methylpyridin-4-yl)methyl}amino)benzamidine acetate

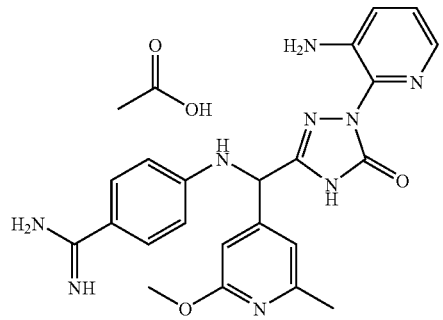

[Chemical Formula 112]

After adding 32 mg of (3-nitropyridin-2-yl)hydrazine [CAS No. 15367-16-5] and 29 μl of triethylamine to a solution of 90 mg of {2-(2-methoxy-6-methylpyridin-4-yl)-2-[4-(5-methyl-[1,2,4]oxadiazol-3-yl)phenylimino]-1-methylsulfanylethylidene}carbamic acid methyl ester in 3 ml of DMF, the mixture was stirred at 85° C. for 16 hours under a nitrogen atmosphere. The reaction mixture was concentrated, and the residue was dissolved in 2 ml of a methanol:THF=1:1 mixed solvent. After adding 42 μl of acetic acid and 64 mg of sodium cyanotrihydroborate to the reaction mixture, it was stirred at room temperature for 4 hours. After filtering the reaction mixture, it was purified by reverse-phase high performance liquid chromatography (acetonitrile-water, 0.1% acetic acid) to give 2-(3-nitropyridin-2-yl)-5-{(2-methoxy-6-methylpyridin-4-yl)-[4-(5-methyl-[1,2,4]oxadiazol-3-yl)phenylamino]methyl}-2,4-dihydro-[1,2,4]triazol-3-one (30 mg).

To a solution of this compound in 3 ml of a methanol:water:acetic acid=1:1:1 mixed solvent there was added 80 mg of iron powder, and the mixture was stirred at 55° C. for 14 hours under a nitrogen atmosphere. After filtering the reaction mixture, it was purified by reverse-phase high performance liquid chromatography (acetonitrile-water, 0.1% acetic acid), to give 20 mg of the title compound.

¹H-NMR (CD₃OD) δ 1.95 (s, 3H) 2.42 (s, 3H) 3.87 (s, 3H) 5.69 (s, 1H) 6.77 (s, 1H) 6.85 (d, J=8.8 Hz, 2H) 6.98 (s, 1H) 7.23 (dd, J=8.0, 4.0 Hz, 1H) 7.33 (d, J=8.0 Hz, 1H) 7.62 (d, J=8.8 Hz, 2H) 7.82 (d, J=4.0 Hz, 1H)

Mass spectrum (ESI) m/z: 446 (M+H)⁺

(19d) (R) and (S)-4-({[1-(3-aminopyridin-2-yl)-5-oxo-4,5-dihydro-1H-[1,2,4]triazol-3-yl]-(2-methoxy-6-methylpyridin-4-yl)methyl}amino)benzamidine acetate

[Chemical Formula 113]

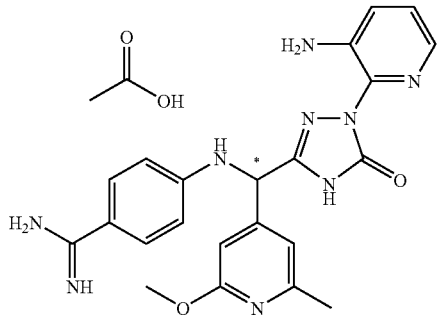

A SUMICHIRAL OA-2500 column was used for optical resolution of 20 mg of 4-({[1-(3-aminopyridin-2-yl)-5-oxo-4,5-dihydro-1H-[1,2,4]triazol-3-yl]-(2-methoxy-6-methylpyridin-4-yl)methyl}amino)benzamidine acetate, and the first eluting enantiomer (7.5 mg) of the title compound was obtained.

HPLC retention time: 7 min

Example 20

(R) and (S)-4-{[(8-methoxy-2,3-dihydro-benzo[1,4]dioxin-6-yl)-(5-oxo-1-pyrimidin-2-yl-4,5-dihydro-1H-[1,2,4]triazol-3-yl)methyl]amino}benzamidine acetate (20a) 2-(8-methoxy-2,3-dihydro-benzo[1,4]dioxin-6-yl)-2-[4-(5-methyl-[1,2,4]oxadiazol-3-yl)phenylamino]thioacetamide

[Chemical Formula 114]

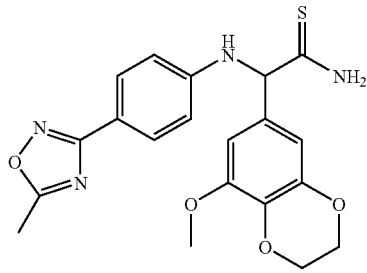

After adding 890 mg of 4-(5-methyl-[1,2,4]oxadiazol-3-yl)phenylamine, 987 mg of 8-methoxy-2,3-dihydro-benzo[1,4]dioxine-6-carbaldehyde [CAS No. 75889-54-2], 1 g of MS3A and 1.4 ml of trimethylsilyl cyanide to a solution of 315 mg of Yb(OTf)₃ in 15 ml of THF under a nitrogen atmosphere, the mixture was stirred overnight at room temperature. The reaction mixture was filtered through celite, and the celite was washed with 100 ml of ethyl acetate. The organic layer was concentrated under reduced pressure.

After adding 3 ml of a 20% aqueous solution of ammonium sulfide to a solution of the residue in 9 ml of an ethanol:THF=2:1 mixed solvent, the mixture was stirred overnight at room temperature. Water was added to the reaction mixture and extraction was performed with ethyl acetate. The organic layer was dried over anhydrous magnesium sulfate. The desiccating agent was filtered off, and the filtrate was concentrated under reduced pressure to give the title compound (1.92 g).

¹H-NMR (d₆-DMSO) δ 2.59 (s, 3H) 3.28 (s, 3H) 3.73 (s, 2H) 4.18 (s, 2H) 5.09 (d, J=6.0 Hz, 1H) 6.64 (d, J=6.0 Hz, 1H) 6.67 (d, J=2.0 Hz, 1H) 6.72 (d, J=8.8 Hz, 2H) 6.80 (d, J=1.6 Hz, 1H) 7.68 (d, J=8.4 Hz, 2H) 9.49 (br.s, 1H) 9.75 (br.s, 1H)

(20b) (R) and (S)-4-{[(8-methoxy-2,3-dihydrobenzo[1,4]dioxin-6-yl)-(5-oxo-1-pyrimidin-2-yl-4,5-dihydro-1H-[1,2,4]triazol-3-yl)methyl]amino}benzamidine acetate

[Chemical Formula 115]

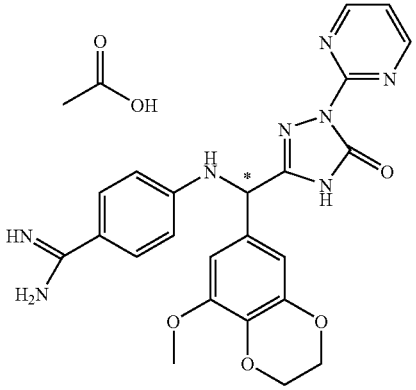

After adding 750 mg of Me₃O⁺BF₄⁻ to a solution of 1.92 g of 2-(8-methoxy-2,3-dihydrobenzo[1,4]dioxin-6-yl)-2-[4-(5-methyl-[1,2,4]oxadiazol-3-yl)phenylamino]thioacetamide in 20 ml of acetonitrile, the mixture was stirred overnight at room temperature. Saturated aqueous sodium hydrogencarbonate was added to the reaction mixture and extraction was performed with ethyl acetate. The organic layer was dried over anhydrous magnesium sulfate. The desiccating agent was filtered off, and the filtrate was concentrated under reduced pressure to give 2-(8-methoxy-2,3-dihydrobenzo[1,4]dioxin-6-yl)-2-[4-(5-methyl-[1,2,4]oxadiazol-3-yl)phenylamino]thioacetimidic acid methyl ester.

After adding 10 g of manganese dioxide to a solution of this compound in 100 ml of ethyl acetate, the mixture was stirred overnight at room temperature. The reaction mixture was filtered through celite, and the filtrate was concentrated under reduced pressure.

To a solution of the residue in 40 ml of toluene there were added 2 ml of 2,4,6-collidine and 1 ml of methyl chloroformate, and the mixture was stirred at 80° C. for 2 hours under a nitrogen atmosphere. After cooling the reaction mixture, 1N hydrochloric acid was added and extraction was performed with ethyl acetate. The organic layer was dried over anhydrous magnesium sulfate. The desiccating agent was filtered off and the filtrate was concentrated under reduced pressure. The residue was purified by silica gel column chromatography (ethyl acetate-heptane) to give {2-(8-methoxy-2,3-dihydrobenzo[1,4]dioxin-6-yl)-2-[4-(5-methyl-[1,2,4]oxadiazol-3-yl)phenylimino]-1-methylsulfanylethylidene}carbamic acid methyl ester (343 mg) as a yellow solid.

To a solution of 343 mg of this compound in 4 ml of DMF there were added 68 mg of 2-hydrazinopyrimidine and 0.1 ml of triethylamine, and the mixture was stirred overnight at 85° C. under a nitrogen atmosphere. The reaction mixture was concentrated, and the residue was dissolved in 5 ml of methanol and 0.5 ml of acetic acid. After adding 0.5 g of sodium cyanotrihydroborate to this solution, the mixture was stirred at room temperature for 1 hour. Water was added to the reaction mixture and extraction was performed with ethyl acetate. The organic layer was dried over anhydrous magnesium sulfate. The desiccating agent was filtered off and the filtrate was concentrated under reduced pressure. The residue was purified by NAM silica gel column chromatography (methanol-ethyl acetate) to give 5-{(8-methoxy-2,3-dihydrobenzo[1,4]dioxin-6-yl)-[4-(5-methyl-[1,2,4]oxadiazol-3-yl)phenylamino]methyl}-2-pyrimidin-2-yl-2,4-dihydro-[1,2,4]triazol-3-one (91 mg) as a light yellow solid.

To a solution of 91 mg of this compound in 3 ml of a methanol:water:acetic acid=1:1:1 mixed solvent there was added 100 mg of iron powder, and the mixture was stirred overnight at 60° C. under a nitrogen atmosphere. After filtering the reaction mixture, it was purified by reverse-phase high performance liquid chromatography (acetonitrile-water, 0.1% acetic acid) to give 4-{[(8-methoxy-2,3-dihydrobenzo[1,4]dioxin-6-yl)-(5-oxo-1-pyrimidin-2-yl-4,5-dihydro-1H-[1,2,4]triazol-3-yl)methyl]amino}benzamidine acetate (50 mg).

Mass spectrum (ESI) m/z: 475 (M+H)$^+$ 50 mg of this compound was optically resolved using a SUMICHIRAL OA-2500 column, and the first eluting enantiomer (21.4 mg) of the title compound was obtained as a white solid.

$^1$H-NMR (CD$_3$OD) δ 1.91 (s, 3H) 3.75 (s, 3H) 4.16-4.20 (m, 4H) 5.54 (s, 1H) 6.68 (d, J=2.0 Hz, 1H) 6.74 (d, J=2.0 Hz, 1H) 6.83 (d, J=9.2 Hz, 2H) 7.29 (t, J=4.4 Hz, 1H) 7.58 (d, J=8.8 Hz, 2H) 8.75 (d, J=4.8 Hz, 2H)

HPLC retention time: 26 min (Column name: SUMICHIRAL OA-2500, 30 mmφ×25 cm, Manufacturer: Sumika Chemical Analysis Service, Ltd., Mobile phase: 0.05 M ammonium acetate-methanol solution, Elution rate: 15 ml/min)

Example 21

(R) and (S)-4-{[(8-methoxy-4H-benzo[1,3]dioxin-6-yl)-(5-oxo-1-pyrimidin-2-yl-4,5-dihydro-1H-[1,2,4]triazol-3-yl)methyl]amino}benzamidine acetate (21a) 4-bromo-2-hydroxymethyl-6-methoxyphenol

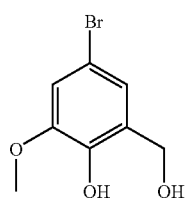

[Chemical Formula 116]

To a solution of 50 g of 5-bromo-2-hydroxy-3-methoxybenzaldehyde in 200 ml of an ethanol:THF=1:1 mixed solvent there was added 16.4 g of sodium borohydride while cooling on ice. After stirring at room temperature for 2 hours, 1N hydrochloric acid was added to the reaction mixture while cooling on ice. The organic layer was washed with ethyl acetate and dried over anhydrous magnesium sulfate. The desiccating agent was filtered off, and the filtrate was concentrated under reduced pressure to give the title compound (50 g) as a crude product.

(21b) 6-bromo-8-methoxy-4H-benzo-[1,3]dioxine

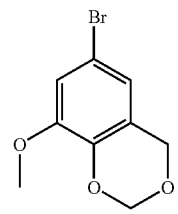

[Chemical Formula 117]

To a solution of the 50 g of 4-bromo-2-hydroxymethyl-6-methoxyphenol in 450 ml of DMF there was added 20 g of sodium hydride (60% oily suspension) while cooling on ice, and the mixture was stirred at room temperature for 30 minutes. After adding 15 ml of bromochloromethane and 3.2 g of sodium iodide to the reaction mixture, it was stirred at 80° C. for 6 hours under a nitrogen atmosphere. Saturated aqueous ammonium chloride was added to the reaction mixture, and extraction was performed with ethyl acetate. The organic layer was dried over anhydrous magnesium sulfate. The desiccating agent was filtered off and the filtrate was concentrated under reduced pressure. The residue was purified by silica gel column chromatography (ethyl acetate-heptane) to give the title compound (31.2 g) as a white solid.

$^1$H-NMR (CDCl$_3$) δ 3.87 (s, 3H) 4.85 (s, 2H) 5.28 (s, 2H) 6.73 (s, 1H) 6.88 (s, 1H)

(21c) 8-methoxy-4H-benzo[1,3]dioxine-6-carbaldehyde

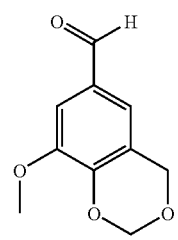

[Chemical Formula 118]

To a solution of 31.2 g of 6-bromo-8-methoxy-4H-benzo[1,3]dioxine in 500 ml of THF there was added dropwise 55 ml of n-butyllithium (2.55 M, hexane solution) at −70° C. under a nitrogen atmosphere. After stirring at −72° C. for 30 minutes, 20 ml of N-formylmorpholine was added and the temperature was raised from −78° C. to 0° C. over a period of 30 minutes. Saturated aqueous ammonium chloride was added to the reaction mixture, and extraction was performed with ethyl acetate. The organic layer was dried over anhydrous magnesium sulfate. The desiccating agent was filtered off and the filtrate was concentrated under reduced pressure. The residue was purified by silica gel column chromatography (ethyl acetate-heptane) to give the title compound (21.28 g) as a white solid.

¹H-NMR (CDCl₃) δ 3.95 (s, 3H) 4.95 (s, 2H) 5.37 (s, 2H) 7.13 (dd, J=0.8, 2.0 Hz, 1H) 7.31 (d, J=2.0 Hz, 1H) 9.82 (s, 1H)

(21d) (8-methoxy-4H-benzo[1,3]dioxin-6-yl)-[4-(5-methyl-[1,2,4]oxadiazol-3-yl)phenylamino]acetonitrile

[Chemical Formula 119]

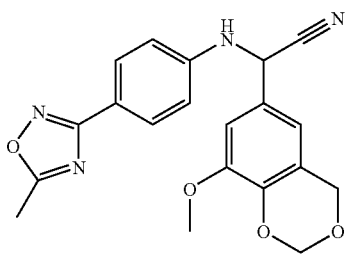

To a solution of 3.5 g of Yb(OTf)₃ in 250 ml of THF there were added 9.8 g of 4-(5-methyl-[1,2,4]oxadiazol-3-yl)phenylamine, 10.8 g of 8-methoxy-4H-benzo[1,3]dioxine-6-carbaldehyde, 10 g of MS3A and 15 ml of trimethylsilyl cyanide under a nitrogen atmosphere, and the mixture was stirred overnight at room temperature. The reaction mixture was filtered through celite, and the celite was washed with 1000 ml of ethyl acetate. The organic layer was concentrated under reduced pressure to give the title compound (29.2 g, crude product) as a light yellow solid.

¹H-NMR (CDCl₃) δ 2.64 (s, 3H) 3.92 (s, 3H) 4.28 (br.s, 1H) 4.92 (s, 2H) 5.34 (s, 2H) 5.40 (br.d, J=6.0 Hz, 1H) 6.80-6.90 (m, 3H) 6.94 (br.s, 1H) 7.98 (br.d, J=7.2 Hz, 2H)

(21e) 2-(8-methoxy-4H-benzo[1,3]dioxin-6-yl)-2[4-(5-methyl-[1,2,4]oxadiazol-3-yl)phenylamino]thioacetamide

[Chemical Formula 120]

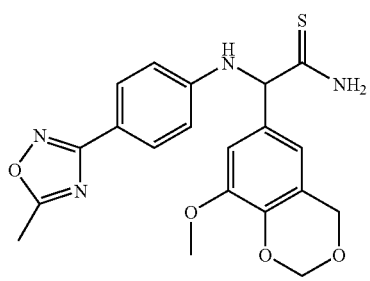

After adding 90 ml of a 20% aqueous solution of ammonium sulfide to a solution of 29.2 g of a crude (8-methoxy-4H-benzo[1,3]dioxin-6-yl)-[4-(5-methyl-[1,2,4]oxadiazol-3-yl)phenylamino]acetonitrile in 240 ml of an ethanol: THF=2:1 mixed solvent, the mixture was stirred at room temperature for 8 hours. Water was added to the reaction mixture and extraction was performed with ethyl acetate. The organic layer was dried over anhydrous magnesium sulfate. The desiccating agent was filtered off, and the filtrate was concentrated under reduced pressure to give the title compound (28.2 g, crude product) as a light yellow solid.

¹H-NMR (CDCl₃) δ 2.62 (s, 3H) 3.89 (s, 3H) 4.89 (s, 2H) 5.11 (s, 1H) 5.30 (s, 2H) 6.69 (d, J=2.0 Hz, 1H) 6.74 (d, J=8.8 Hz, 2H) 6.84 (d, J=1.6 Hz, 1H) 7.58 (br.d, J=4.8 Hz, 1H) 7.91 (d, J=8.4 Hz, 2H) 8.13 (br.d, J=4.8 Hz, 1H)

(21f) 2-(8-methoxy-4H-benzo[1,3]dioxin-6-yl)-2-[4-(5-methyl-[1,2,4]oxadiazol-3-yl)phenylamino]thioacetimidic acid methyl ester

[Chemical Formula 121]

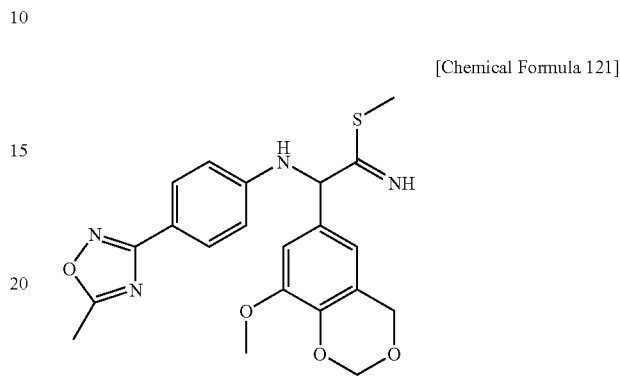

After adding 10.6 g of Me₃O⁺BF₄⁻ to a solution of 28.2 g of a crude product of 2-(8-methoxy-4H-benzo[1,3]dioxin-6-yl)-2-[4-(5-methyl-[1,2,4]oxadiazol-3-yl)phenylamino]thioacetamide in 100 ml of acetonitrile, the mixture was stirred at room temperature for 1 hour under a nitrogen atmosphere. Saturated aqueous sodium hydrogencarbonate was added to the reaction mixture, and extraction was performed with ethyl acetate. The organic layer was dried over anhydrous magnesium sulfate. The desiccating agent was filtered off, and the filtrate was concentrated under reduced pressure to give the title compound (27.2 g, crude product) as a light yellow solid.

¹H-NMR (CDCl₃) δ 2.35 (s, 3H) 2.61 (s, 3H) 3.89 (s, 3H) 4.88 (s, 2H) 4.98 (br.s, 1H) 5.29 (s, 2H) 6.64 (d, J=8.8 Hz, 2H) 6.69 (s, 1H) 6.86 (s, 1H) 7.85 (d, J=8.8 Hz, 2H)

(21g) 2-(8-methoxy-4H-benzo[1,3]dioxin-6-yl)-2-[4-(5-methyl-[1,2,4]oxadiazol-3-yl)phenylimino]thioacetimidic acid methyl ester

[Chemical Formula 122]

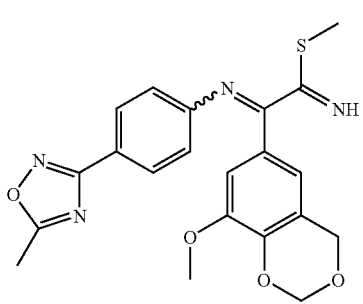

After adding 100 g of manganese dioxide to a solution of 27.2 g of the crude product of 2-(8-methoxy-4H-benzo[1,3]dioxin-6-yl)-2-[4-(5-methyl-[1,2,4]oxadiazol-3-yl)phenylamino]thioacetimidic acid methyl ester in 100 ml of ethyl acetate, the mixture was stirred at room temperature for 1 hour. The reaction mixture was filtered through celite, and the filtrate was concentrated under reduced pressure to give the title compound (23.8 g, crude product) as a brown solid.

¹H-NMR (CDCl₃) δ 2.26 (s, 3H) 2.65 (s, 3H) 3.96 (s, 3H) 4.92 (s, 2H) 5.36 (s, 2H) 6.45 (br.s, 1H) 7.02 (d, J=8.8 Hz, 2H) 7.06 (br.s, 1H) 7.52 (d, J=1.6 Hz, 1H) 7.99 (d, J=8.8 Hz, 2H)

(21h) [2-(8-methoxy-4H-benzo[1,3]dioxin-6-yl)-2-[4-(5-methyl-[1,2,4]oxadiazol-3-yl)phenylimino]-1-methylsulfanylethylidene]carbamic acid methyl ester

[Chemical Formula 123]

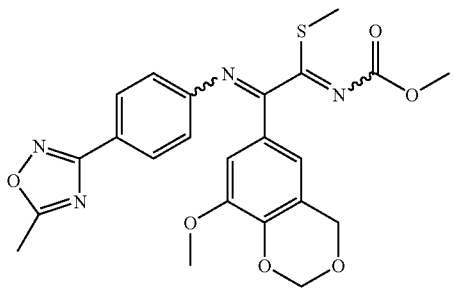

To a solution of 23.8 g of the crude product of 2-(8-methoxy-4H-benzo[1,3]dioxin-6-yl)-2-[4-(5-methyl-[1,2,4]oxadiazol-3-yl)phenylimino]thioacetimidic acid methyl ester in 100 ml of toluene there were added 32 ml of 2,4,6-collidine and 15 ml of methyl chloroformate, and the mixture was stirred at 80° C. for 1 hour under a nitrogen atmosphere. After cooling the reaction mixture, 1N hydrochloric acid was added and extraction was performed with ethyl acetate. The organic layer was dried over anhydrous magnesium sulfate. The desiccating agent was filtered off and the filtrate was concentrated under reduced pressure. The residue was purified by silica gel column chromatography (ethyl acetate-heptane) to give the title compound (12.98 g) as a yellow solid.

¹H-NMR (CDCl₃) δ 2.33 (s, 3H) 2.65 (s, 3H) 3.65 (s, 3H) 3.95 (s, 3H) 4.91 (s, 2H) 5.36 (s, 2H) 7.00 (d, J=1.6 Hz, 1H) 7.17 (d, J=8.4 Hz, 2H) 7.46 (br.s, 1H) 8.01 (d, J=8.4 Hz, 2H)

(21i) 5-{(8-methoxy-4H-benzo[1,3]dioxin-6-yl)-[4-(5-methyl-[1,2,4]oxadiazol-3-yl)phenylamino]methyl}-2-pyrimidin-2-yl-2,4-dihydro-[1,2,4]triazol-3-one

[Chemical Formula 124]

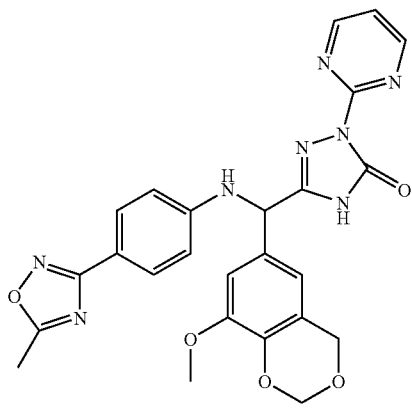

To a solution of 6.02 g of [2-(8-methoxy-4H-benzo[1,3]dioxin-6-yl)-2-[4-(5-methyl-[1,2,4]oxadiazol-3-yl)phenylimino]-1-methylsulfanylethylidene]carbamic acid methyl ester in 50 ml of DMF there were added 1.24 g of 2-hydrazinopyrimidine and 1.9 ml of triethylamine, and the mixture was stirred overnight at 85° C. under a nitrogen atmosphere. The reaction mixture was concentrated, and the residue was dissolved in 50 ml of methanol and 5 ml of acetic acid. After then adding 3.4 g of sodium cyanotrihydroborate to the reaction mixture, it was stirred at room temperature. Water was added to the reaction mixture and extraction was performed with ethyl acetate. The organic layer was dried over anhydrous magnesium sulfate. The desiccating agent was filtered off and the filtrate was concentrated under reduced pressure. The residue was purified by NAM silica gel column chromatography (methanol-ethyl acetate) to give the title compound (3.317 g) as a light yellow solid.

¹H-NMR (CDCl₃) δ 2.59 (s, 3H) 3.72 (s, 3H) 4.69 (q, J=14.8 Hz, 2H) 5.21 (s, 2H) 5.76 (br.d, J=7.6 Hz, 1H) 6.37 (br.s, 1H) 6.79 (d, J=8.4 Hz, 2H) 6.84 (s, 1H) 7.07 (s, 1H) 7.19 (t, J=4.8 Hz, 1H) 7.79 (d, J=8.8 Hz, 2H) 8.68 (d, J=4.8 Hz, 2H) 11.17 (br.s, 1H)

(21j) 4-{[(8-methoxy-4H-benzo[1,3]dioxin-6-yl)-(5-oxo-1-pyrimidin-2-yl-4,5-dihydro-1H-[1,2,4]triazol-3-yl)methyl]amino}benzamidine acetate

[Chemical Formula 125]

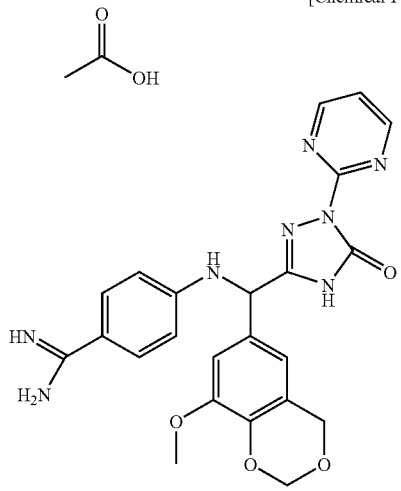

To a solution of 814 mg of 5-{(8-methoxy-4H-benzo[1,3]dioxin-6-yl)-[4-(5-methyl-[1,2,4]oxadiazol-3-yl)phenylamino]methyl}-2-pyrimidin-2-yl-2,4-dihydro-[1,2,4]triazol-3-one in 15 ml of a methanol:water:acetic acid=1:1:1 mixed solvent there was added 1 g of iron powder, and the mixture was stirred overnight at 60° C. under a nitrogen atmosphere. After adding 7.5 ml of a methanol:water:acetic acid=1:1:1 mixed solvent to the reaction mixture, the mixture was further stirred at 60° C. for 5 hours. After filtering the reaction mixture, it was purified by reverse-phase high performance liquid chromatography (acetonitrile-water, 0.1% acetic acid) to give the title compound (476 mg).

¹H-NMR (CD₃OD) δ 1.93 (s, 3H) 3.79 (s, 3H) 4.82 (m, 2H) 5.21 (s, 2H) 5.60 (s, 1H) 6.80 (s, 1H) 6.85 (d, J=8.4 Hz, 2H) 7.04 (s, 1H) 7.32 (t, J=4.8 Hz, 1H) 7.59 (d, J=8.8 Hz, 2H) 8.76 (d, J=4.8 Hz, 2H)

Mass spectrum (ESI) m/z: 475 (M+H)⁺

(21k) (R) and (S)-4-{[(8-methoxy-4H-benzo[1,3]dioxin-6-yl)-(5-oxo-1-pyrimidin-2-yl-4,5-dihydro-1H-[1,2,4]triazol-3-yl)methyl]amino}benzamidine acetate

[Chemical Formula 126]

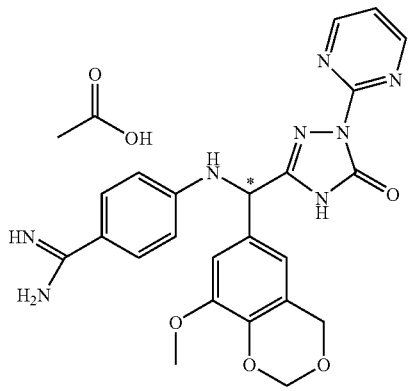

A SUMICHIRAL OA-2500 column was used for optical resolution of 120 mg of 4-{[(8-methoxy-4H-benzo[1,3]dioxin-6-yl)-(5-oxo-1-pyrimidin-2-yl-4,5-dihydro-1H-[1,2,4]triazol-3-yl)methyl]amino}benzamidine acetate, and the first eluting enantiomer (47 mg) of the title compound was obtained as a white solid.

$^1$H-NMR (CD$_3$OD) δ 1.91 (s, 3H) 3.81 (s, 3H) 4.84 (m, 2H) 5.21 (s, 2H) 5.56 (s, 1H) 6.81 (d, J=1.6 Hz, 1H) 6.84 (d, J=8.4 Hz, 2H) 7.05 (d, J=1.6 Hz, 1H) 7.30 (t, J=4.8 Hz, 1H) 7.59 (d, J=8.8 Hz, 2H) 8.76 (d, J=4.8 Hz, 2H)

HPLC retention time: 17 min

Example 22

(R) and (S)-4-{[(3,4-dimethoxy-5-methoxymethyl-phenyl)-(5-oxo-1-pyrimidin-2-yl-4,5-dihydro-1H-[1,2,4]triazol-3-yl)methyl]amino}benzamidine acetate (22a) 3,4-dimethoxy-5-triisopropylsilanyloxymethyl-benzaldehyde

[Chemical Formula 127]

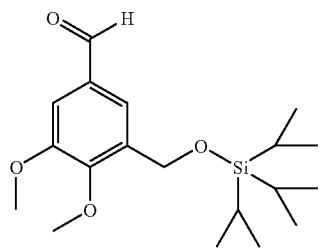

To a solution of 2.3 g of 5-bromo-2,3-dimethoxybenzaldehyde [CAS No. 71295-21-1] in 40 ml of an ethanol:THF=1:1 mixed solvent there was added 1 g of sodium borohydride while cooling on ice, and the mixture was stirred at room temperature for 3 hours. Next, 1N hydrochloric acid was added to the reaction mixture and extraction was performed with ethyl acetate. The organic layer was dried over anhydrous magnesium sulfate. The desiccating agent was filtered off and the filtrate was concentrated under reduced pressure.

The residue was dissolved in 20 ml of DMF, and then 1.5 g of imidazole and 2.4 ml of chlorotriisopropylsilane were added and the mixture was stirred overnight at room temperature. Next, 1N hydrochloric acid was added to the reaction mixture and extraction was performed with ethyl acetate. The organic layer was dried over anhydrous magnesium sulfate. The desiccating agent was filtered off and the filtrate was concentrated under reduced pressure. The residue was purified by silica gel column chromatography (ethyl acetate-heptane) to give (5-bromo-2,3-dimethoxybenzyloxy)triisopropylsilane (3.616 g) as an oil.

To a solution of the 3.616 g of (5-bromo-2,3-dimethoxybenzyloxy)triisopropylsilane in 60 ml of THF there was added dropwise 3.6 ml of n-butyllithium (2.66 M, hexane solution) at −78° C. under a nitrogen atmosphere. After stirring for 15 minutes, 2 ml of N-formylmorpholine was added and the mixture was stirred at room temperature for 20 minutes. Next, 1N hydrochloric acid was added to the reaction mixture and extraction was performed with ethyl acetate. The organic layer was dried over anhydrous magnesium sulfate. The desiccating agent was filtered off and the filtrate was concentrated under reduced pressure. The residue was purified by silica gel column chromatography (ethyl acetate-heptane) to give the title compound (2.605 g) as an oil.

$^1$H-NMR (CDCl$_3$) δ 1.12 (d, J=6.8 Hz, 18H) 1.17-1.26 (m, 3H) 3.91 (s, 3H) 3.92 (s, 3H) 4.88 (s, 2H) 7.37 (d, J=2.0 Hz, 1H) 7.69 (d, J=2.0 Hz, 1H) 9.89 (s, 1H)

(22b) [2-(3-hydroxymethyl-4,5-dimethoxyphenyl)-2-[4-(5-methyl-[1,2,4]oxadiazol-3-yl)phenylimino]-1-methylsulfanylethylidene]carbamic acid methyl ester

[Chemical Formula 128]

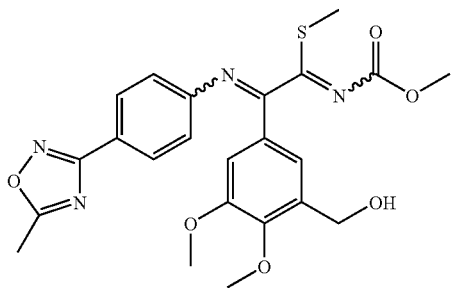

After adding 1.3 g of 4-(5-methyl-[1,2,4]oxadiazol-3-yl)phenylamine, 2.605 g of 3,4-dimethoxy-5-triisopropylsilanyloxymethylbenzaldehyde, 2.2 g of MS3A and 1.5 ml of trimethylsilyl cyanide to a solution of 460 mg of Yb(OTf)$_3$ in 18 ml of dichloromethane under a nitrogen atmosphere, the mixture was stirred at room temperature for 2 days. The reaction mixture was filtered through celite, and the celite was washed with ethyl acetate. The organic layer was concentrated under reduced pressure to give a crude product of (3,4-dimethoxy-5-triisopropylsilanyloxymethylphenyl)-[4-(5-methyl-[1,2,4]oxadiazol-3-yl)phenylamino]acetonitrile.

To a solution of this compound in 45 ml of an ethanol:THF=2:1 mixed solvent there was added 15 ml of a 20% aqueous solution of ammonium sulfide, and the mixture was stirred overnight at room temperature. Water was added to the reaction mixture and extraction was performed with ethyl acetate. The organic layer was dried over anhydrous magnesium sulfate. The desiccating agent was filtered off, and the filtrate was concentrated under reduced pressure to give a crude product of 2-(3,4-dimethoxy-5-triisopropylsilanyloxymethylphenyl)-2-[4-(5-methyl-[1,2,4]oxadiazol-3-yl)phenylamino]thioacetamide (3.79 g).

To a solution of 2.605 g of this compound in 40 ml of dichloromethane there was added 1.3 g of Me$_3$O$^+$BF$_4^-$, and the mixture was stirred at room temperature for 1 hour. Saturated aqueous sodium hydrogencarbonate was added to the reaction mixture and extraction was performed with ethyl acetate. The organic layer was dried over anhydrous magnesium sulfate. The desiccating agent was filtered off and the filtrate was concentrated under reduced pressure.

To a solution of the residue in 100 ml of dichloromethane there was added 6 g of manganese dioxide, and the mixture was stirred at room temperature for 2 hours. The reaction mixture was filtered through celite, and the filtrate was concentrated under reduced pressure.

To a solution of the residue in 50 ml of toluene there were added 5 ml of 2,4,6-collidine and 2.5 ml of methyl chloroformate, and the mixture was stirred overnight at 85° C. under a nitrogen atmosphere. After cooling the reaction mixture, 1N hydrochloric acid was added and extraction was performed with ethyl acetate. The organic layer was dried over anhydrous magnesium sulfate. The desiccating agent was filtered off and the filtrate was concentrated under reduced pressure. The residue was purified by silica gel column chromatography (ethyl acetate-heptane) to give [2-(3,4-dimethoxy-5-triisopropylsilanyloxymethyl-phenyl)-2-[4-(5-methyl-[1,2,4]oxadiazol-3-yl)-phenylimino]-1-methylsulfanylethylidene]carbamic acid methyl ester (2.03 g, isomeric mixture) as a yellow solid.

After dissolving 2.03 g of this compound in 50 ml of THF, 3.7 ml of TBAF (1.0 M, THF solution) was added and the mixture was stirred at room temperature for 15 minutes. Saturated aqueous ammonium chloride was added to the reaction mixture, and extraction was performed with ethyl acetate. The organic layer was dried over anhydrous magnesium sulfate, the desiccating agent was filtered off and the filtrate was concentrated under reduced pressure. The residue was purified by silica gel column chromatography (ethyl acetate-heptane) to give the title compound (1.41 g, isomeric mixture) as a light yellow solid.

Mass spectrum (ESI) m/z: 485 (M+H)$^+$ (22c) [2-(3,4-dimethoxy-5-methoxymethylphenyl)-2-[4-(5-methyl-[1,2,4]oxadiazol-3-yl)phenylimino]-1-methylsulfanylethylidene]carbamic acid methyl ester

[Chemical Formula 129]

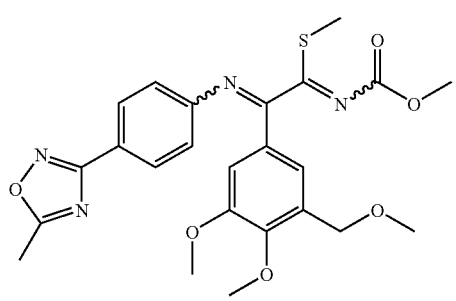

After dissolving 322 mg of [2-(3-hydroxymethyl-4,5-dimethoxyphenyl)-2-[4-(5-methyl-[1,2,4]oxadiazol-3-yl)phenylimino]-1-methylsulfanylethylidene]carbamic acid methyl ester in 5 ml of dichloromethane, 364 mg of 1,8-bis(dimethylamino)naphthalene and 240 mg of Me$_3$O$^+$BF$_4$ were added and the mixture was stirred at room temperature for 5 hours. Saturated aqueous sodium hydrogencarbonate was added to the reaction mixture and extraction was performed with ethyl acetate. The organic layer was dried over anhydrous magnesium sulfate, the desiccating agent was filtered off and the filtrate was concentrated under reduced pressure. The residue was purified by silica gel column chromatography (ethyl acetate-heptane) to give the title compound (169 mg, isomeric mixture) as a light yellow solid.

$^1$H-NMR (CDCl$_3$) δ 2.33 (s, 3H) 2.65 (s, 3H) 3.40 (s, 3H) 3.62 (s, 3H) 3.91 (s, 3H) 3.93 (s, 3H) 4.51 (s, 2H) 7.17 (d, J=8.0 Hz, 2H) 7.36 (br.d, J=2.0 Hz, 1H) 7.56 (d, J=2.4 Hz, 1H) 8.10 (d, J=8.0 Hz, 2H)

(22d) (R) and (S)-4-{[(3,4-dimethoxy-5-methoxymethylphenyl)-(5-oxo-1-pyrimidin-2-yl-4,5-dihydro-1H-[1,2,4]triazol-3-yl)methyl]amino}benzamidine acetate

[Chemical Formula 130]

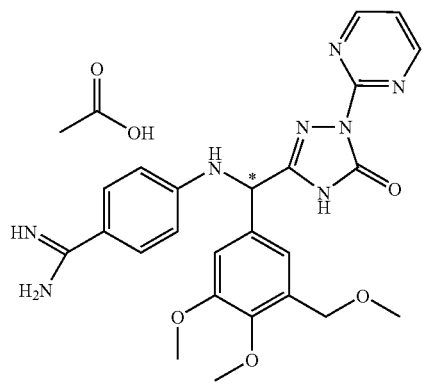

To a solution of 169 mg of [2-(3,4-dimethoxy-5-methoxymethylphenyl)-2-[4-(5-methyl-[1,2,4]oxadiazol-3-yl)phenylimino]-1-methylsulfanylethylidene]carbamic acid methyl ester in 2 ml of DMF there were added 40 mg of 2-hydrazinopyrimidine and 50 µl of triethylamine, and the mixture was stirred overnight at 85° C. under a nitrogen atmosphere. The reaction mixture was concentrated, and the residue was dissolved in 3 ml of methanol and 0.3 ml of acetic acid. After adding 100 mg of sodium cyanotrihydroborate to the solution, the mixture was stirred at room temperature for 1 hour. Water was added to the reaction mixture and extraction was performed with ethyl acetate. The organic layer was dried over anhydrous magnesium sulfate. The desiccating agent was filtered off and the filtrate was concentrated under reduced pressure. The residue was purified by NAM silica gel column chromatography (methanol-ethyl acetate) to give 5-{(3,4-dimethoxy-5-methoxymethylphenyl)-[4-(5-methyl-[1,2,4]oxadiazol-3-yl)phenylamino]methyl}-2-pyrimidin-2-yl-2,4-dihydro-[1,2,4]triazol-3-one (89 mg) as a light brown solid.

To a solution of 89 mg of this compound in 4.5 ml of a methanol:water:acetic acid=1:1:1 mixed solvent there was added 100 mg of iron powder, and the mixture was stirred overnight at 60° C. under a nitrogen atmosphere. After further adding 150 mg of iron powder, the mixture was stirred at 60° C. for 6 hours. After filtering the reaction mixture, it was purified by reverse-phase high performance liquid chromatography (acetonitrile-water, 0.1% acetic acid) to give 4-{[(3,4-dimethoxy-5-methoxymethylphenyl)-(5-oxo-1-pyrimidin-2-yl-4,5-dihydro-1H-[1,2,4]triazol-3-yl)methyl]amino}benzamidine acetate (38 mg).

Mass spectrum (ESI) m/z: 491 (M+H)$^+$ 38 mg of this compound was optically resolved using a SUMICHIRAL OA-2500 column, and the first eluting enantiomer (16.9 mg) of the title compound was obtained as a white solid.

$^1$H-NMR (CD$_3$OD) δ 1.91 (s, 3H) 3.35 (s, 3H) 3.77 (s, 3H) 3.84 (s, 3H) 4.45 (s, 2H) 5.62 (s, 1H) 6.86 (d, J=8.8 Hz, 2H) 7.16 (d, J=1.6 Hz, 1H) 7.20 (d, J=1.6 Hz, 1H) 7.30 (t, J=4.4 Hz, 1H) 7.59 (d, J=8.8 Hz, 2H) 8.77 (d, J=5.2 Hz, 2H)

HPLC retention time: 13 min

Example 23

4-{[(5-hydroxymethyl-3,4-dimethoxyphenyl)-(5-oxo-1-pyrimidin-2-yl-4,5-dihydro-1H-[1,2,4]triazol-3-yl)methyl]amino}benzamidine acetate

[Chemical Formula 131]

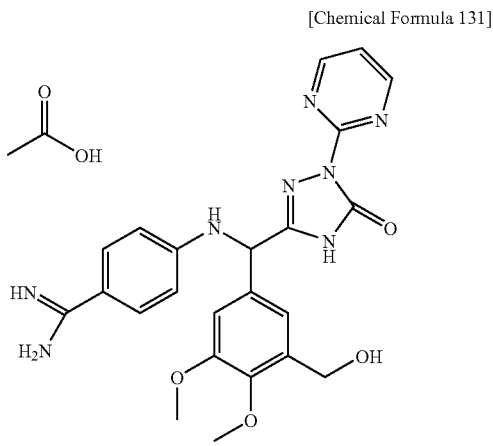

To a solution of 114 mg of [2-(3-hydroxymethyl-4,5-dimethoxyphenyl)-2-[4-(5-methyl-[1,2,4]oxadiazol-3-yl)phenylimino]-1-methylsulfanylethylidene]carbamic acid methyl ester (Example (22b)) in 2 ml of DMF there were added 25 mg of 2-hydrazinopyrimidine and 35 μl of triethylamine, and the mixture was stirred overnight at 85° C. under a nitrogen atmosphere. The reaction mixture was concentrated, and the residue was dissolved in 3 ml of methanol and 0.3 ml of acetic acid. After adding 200 mg of sodium cyanotrihydroborate to the solution, the mixture was stirred at room temperature for 1 hour. Water was added to the reaction mixture and extraction was performed with ethyl acetate. The organic layer was dried over anhydrous magnesium sulfate, the desiccating agent was filtered off and the filtrate was concentrated under reduced pressure. The residue was purified by NAM silica gel column chromatography (methanol-ethyl acetate) to give 5-{(5-hydroxymethyl-3,4-dimethoxyphenyl)-[4-(5-methyl-[1,2,4]oxadiazol-3-yl)phenylamino]methyl}-2-pyrimidin-2-yl-2,4-dihydro-[1,2,4]triazol-3-one (51 mg) as a light brown solid.

To a solution of 51 mg of this compound in 3 ml of a methanol:water:acetic acid=1:1:1 mixed solvent there was added 50 mg of iron powder, and the mixture was stirred overnight at 60° C. under a nitrogen atmosphere. After filtering the reaction mixture, it was purified by reverse-phase high performance liquid chromatography (acetonitrile-water, 0.1% acetic acid) to give the title compound (13.5 mg).

$^1$H-NMR (d$_6$-DMSO) δ 1.82 (s, 3H) 3.65 (s, 3H) 3.76 (s, 3H) 4.45 (s, 2H) 5.15 (br.s, 1H) 5.36 (d, J=6.8 Hz, 1H) 6.82 (d, J=8.4 Hz, 2H) 7.10 (t, J=4.8 Hz, 1H) 7.15 (s, 1H) 7.26 (d, J=7.2 Hz, 1H) 7.53 (d, J=8.8 Hz, 2H) 8.62 (d, J=4.8 Hz, 2H)

Mass spectrum (ESI) m/z: 477 (M+H)$^+$

Example 24

(R) and (S)-4-{[(8-methoxychroman-6-yl)-(5-oxo-1-pyrimidin-2-yl-4,5-dihydro-1H-[1,2,4]triazol-3-yl)methyl]amino}benzamidine acetate (24a) {2-(8-methoxychroman-6-yl)-2-[4-(5-methyl-[1,2,4]oxadiazol-3-yl)phenylimino]-1-methylsulfanylethylidene}carbamic acid methyl ester

[Chemical Formula 132]

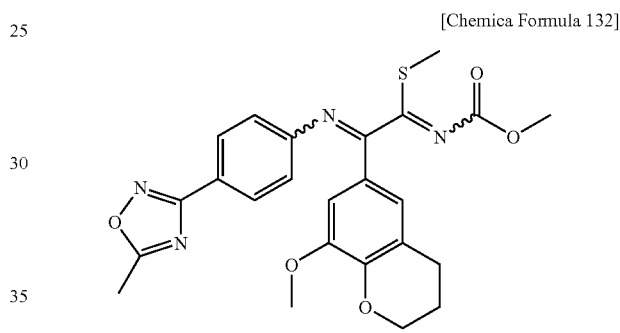

After adding 700 mg of 4-(5-methyl-[1,2,4]oxadiazol-3-yl)phenylamine, 770 mg of 8-methoxychromane-6-carbaldehyde [CAS No. 81258-23-3], 1 g of MS3A and 1.1 ml of trimethylsilyl cyanide to a solution of 250 mg of Yb(OTf)$_3$ in 5 ml of dichloromethane under a nitrogen atmosphere, the mixture was stirred overnight at room temperature. The reaction mixture was filtered through celite, and the celite was washed with 100 ml of ethyl acetate. The organic layer was concentrated under reduced pressure to give a crude product of (8-methoxychroman-6-yl)-[4-(5-methyl-[1,2,4]oxadiazol-3-yl)phenylamino]acetonitrile.

To a solution of this compound in 12 ml of an ethanol:THF=4:1 mixed solvent there was added 6 ml of a 20% aqueous solution of ammonium sulfide, and the mixture was stirred at 50° C. for 4 hours. Water was added to the reaction mixture and extraction was performed with ethyl acetate. The organic layer was dried over anhydrous magnesium sulfate. The desiccating agent was filtered off, and the filtrate was concentrated under reduced pressure to give 2-(8-methoxychroman-6-yl)-2-[4-(5-methyl-[1,2,4]oxadiazol-3-yl)phenylamino]thioacetamide (1.91 g, crude product).

To a solution of 1.91 g of this compound in 10 ml of dichloromethane there was added 719 mg of Me$_3$O$^+$BF$_4$$^-$, and the mixture was stirred at room temperature for 1 hour. Saturated aqueous sodium hydrogencarbonate was added to the reaction mixture and extraction was performed with ethyl acetate. The organic layer was dried over anhydrous magnesium sulfate. The desiccating agent was filtered off and the filtrate was concentrated under reduced pressure.

After adding 10 g of manganese dioxide to a solution of the residue in 10 ml of ethyl acetate, the mixture was stirred at room temperature for 1 hour. The reaction mixture was filtered and the filtrate was concentrated under reduced pressure.

To a solution of the residue in 30 ml of toluene there were added 2.4 ml of 2,4,6-collidine and 1.2 ml of methyl chloroformate, and the mixture was stirred at 80° C. for 1 hour under a nitrogen atmosphere. After cooling the reaction mixture, 1N hydrochloric acid was added and extraction was performed with ethyl acetate. The organic layer was dried over anhydrous magnesium sulfate. The desiccating agent was filtered off and the filtrate was concentrated under reduced pressure. The residue was purified by silica gel column chromatography (ethyl acetate-heptane) to give the title compound (960 mg, isomeric mixture) as a yellow solid.

Mass spectrum (ESI) m/z: 481 (M+H)$^+$ (24b) (R) and (S)-4-{[(8-methoxychroman-6-yl)-(5-oxo-1-pyrimidin-2-yl-4,5-dihydro-1H-[1,2,4]triazol-3-yl)methyl]amino}benzamidine acetate

[Chemical Formula 133]

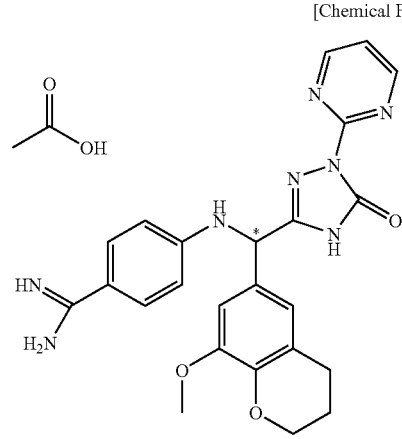

To a solution of 281 mg of {2-(8-methoxychroman-6-yl)-2-[4-(5-methyl-[1,2,4]oxadiazol-3-yl)phenylimino]-1-methylsulfanyl-ethylidene}carbamic acid methyl ester in 2 ml of DMF there were added 58 mg of 2-hydrazinopyrimidine and 130 µl of triethylamine, and the mixture was stirred overnight at 85° C. under a nitrogen atmosphere. The reaction mixture was concentrated, and the residue was dissolved in 8.75 ml of a methanol:acetic acid=10:1 mixed solvent. After adding 265 mg of sodium cyanotrihydroborate to the reaction mixture, the mixture was stirred at room temperature for 1 hour. Water was added to the reaction mixture and extraction was performed with ethyl acetate. The organic layer was dried over anhydrous magnesium sulfate. The desiccating agent was filtered off and the filtrate was concentrated under reduced pressure. The residue was purified by NAM silica gel column chromatography (methanol-ethyl acetate) to give 5-{(8-methoxychroman-6-yl)-[4-(5-methyl-[1,2,4]oxadiazol-3-yl)phenylamino]methyl}-2-pyrimidin-2-yl-2,4-dihydro-[1,2,4]triazol-3-one.

To a solution of this compound in 8 ml of a methanol:water:acetic acid=1:1:1 mixed solvent there was added 265 mg of iron powder, and the mixture was stirred overnight at 60° C. under a nitrogen atmosphere. After filtering the reaction mixture, it was purified by reverse-phase high performance liquid chromatography (acetonitrile-water, 0.1% acetic acid) to give 4-{[(8-methoxychroman-6-yl)-(5-oxo-1-pyrimidin-2-yl-4,5-dihydro-1H-[1,2,4]triazol-3-yl)methyl]amino}benzamidine acetate (88 mg).

Mass spectrum (ESI) m/z: 473 (M+H)$^+$ 88 mg of this compound was optically resolved using a SUMICHIRAL OA-2500 column, and the first eluting enantiomer (44 mg) of the title compound was obtained as a white solid.

$^1$H-NMR (CD$_3$OD) δ 1.90 (s, 3H) 1.95-1.99 (m, 2H) 2.75 (t, J=6.4 Hz, 2H) 3.78 (s, 3H) 4.16 (t, J=5.2 Hz, 2H) 5.46 (s, 1H) 6.83 (d, J=8.8 Hz, 2H) 6.85 (d, J=1.2 Hz, 1H) 6.97 (d, J=2.4 Hz, 1H) 7.25 (t, J=5.2 Hz, 1H) 7.57 (d, J=9.2 Hz, 2H) 8.74 (d, J=5.2 Hz, 2H)

HPLC retention time: 15 min

Example 25

4-({[3-(1-hydroxyethyl)-4,5-dimethoxyphenyl]-(5-oxo-1-pyrimidin-2-yl-4,5-dihydro-1H-[1,2,4]triazol-3-yl)methyl}amino)benzamidine acetate (25a) 3,4-dimethoxy-5-(1-triisopropylsilanyloxy-ethyl)benzaldehyde

[Chemical Formula 134]

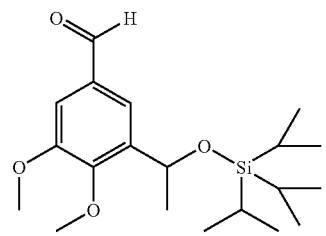

To a solution of 4 g of 5-bromo-2,3-dimethoxybenzaldehyde in 75 ml of THF there was added dropwise 20 ml of methylmagnesium bromide (0.93 M, THF solution) under a nitrogen atmosphere. After stirring at room temperature for 1 hour, 1N hydrochloric acid was added to the reaction mixture and extraction was performed with ethyl acetate. The organic layer was dried over anhydrous magnesium sulfate. The desiccating agent was filtered off and the filtrate was concentrated under reduced pressure.

The residue was dissolved in DMF, and then imidazole and chlorotriisopropylsilane were added and the mixture was stirred at room temperature overnight and at 60° C. for 3 hours. Next, 1N hydrochloric acid was added to the reaction mixture and extraction was performed with ethyl acetate. The organic layer was dried over anhydrous magnesium sulfate. The desiccating agent was filtered off and the filtrate was concentrated under reduced pressure. The residue was purified by silica gel column chromatography (ethyl acetate-heptane) to give [1-(5-bromo-2,3-dimethoxyphenyl)ethoxy]triisopropylsilane (5.423 g) as an oil.

To a solution of 5.423 g of this compound in 60 ml of THF there was added dropwise 5.3 ml of n-butyllithium (2.66 M, hexane solution) at −78° C. under a nitrogen atmosphere. After stirring for 15 minutes, 2 ml of N-formylmorpholine was added and the mixture was stirred at room temperature for 20 minutes. Next, 1N hydrochloric acid was added to the reaction mixture and extraction was performed with ethyl acetate. The organic layer was dried over anhydrous magnesium sulfate. The desiccating agent was filtered off and the filtrate was concentrated under reduced pressure. The residue was purified by silica gel column chromatography (ethyl acetate-heptane) to give the title compound (4.348 g) as an oil.

$^1$H-NMR (CDCl$_3$) δ 1.01 (d, J=7.2 Hz, 9H) 1.05 (d, J=6.4 Hz, 9H) 1.06-1.16 (m, 3H) 1.41 (d, J=6.0 Hz, 3H) 3.92 (s, 6H) 5.32 (dd, J=6.4, 12.4 Hz, 1H) 7.34 (d, J=2.0 Hz, 1H) 7.74 (d, J=2.0 Hz, 1H) 9.88 (s, 1H)

(25b) {2-[3-(1'-hydroxyethyl)-4,5-dimethoxyphenyl]-2-[4-(5-methyl-[1,2,4]oxadiazol-3-yl)phenylimino]-1-methylsulfanylethylidene}carbamic acid methyl ester

[Chemica Formula 135]

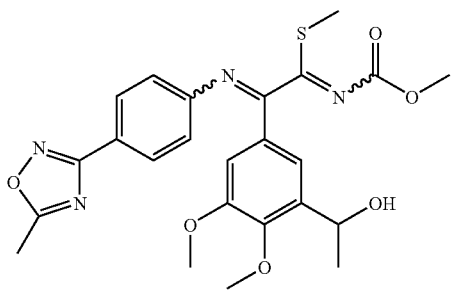

After adding 0.99 g of 4-(5-methyl-[1,2,4]oxadiazol-3-yl) phenylamine, 2.607 g of 3,4-dimethoxy-5-(1'-triisopropylsilanyloxyethyl)benzaldehyde, 1.7 g of MS3A and 1.6 ml of trimethylsilyl cyanide to a solution of 350 mg of Yb(OTf)$_3$ in 14 ml of dichloromethane under a nitrogen atmosphere, the mixture was stirred at room temperature for 2 days. The reaction mixture was filtered through celite, and the celite was washed with ethyl acetate. The organic layer was concentrated under reduced pressure to give a crude product of [3,4-dimethoxy-5-(1'-triisopropylsilanyloxyethyl)phenyl]-[4-(5-methyl-[1,2,4]oxadiazol-3-yl)phenylamino]acetonitrile.

To a solution of this compound in 45 ml of an ethanol: THF=2:1 mixed solvent there was added 15 ml of a 20% aqueous solution of ammonium sulfide, and the mixture was stirred overnight at room temperature. Water was added to the reaction mixture and extraction was performed with ethyl acetate. The organic layer was dried over anhydrous magnesium sulfate. The desiccating agent was filtered off, and the filtrate was concentrated under reduced pressure to give 2-[3,4-dimethoxy-5-(1-triisopropylsilanyloxyethyl)phenyl]-2-[4-(5-methyl-[1,2,4]oxadiazol-3-yl)phenylamino]thioacetamide (4.8 g, crude product).

To a solution of 4.8 g of this compound in 40 ml of dichloromethane there was added 1 g of Me$_3$O$^+$BF$_4^-$, and the mixture was stirred at room temperature for 1 hour. Saturated aqueous sodium hydrogencarbonate was added to the reaction mixture and extraction was performed with ethyl acetate. The organic layer was dried with anhydrous magnesium sulfate, the desiccating agent was filtered off and the filtrate was concentrated under reduced pressure.

To a solution of the residue in 154 ml of dichloromethane there was added 7 g of manganese dioxide, and the mixture was stirred at room temperature for 2 hours. The reaction mixture was filtered through celite, and the filtrate was concentrated under reduced pressure.

To a solution of the residue in 40 ml of toluene there were added 2.2 ml of 2,4,6-collidine and 1.1 ml of methyl chloroformate, and the mixture was stirred overnight at 85° C. under a nitrogen atmosphere. After cooling the reaction mixture, 1N hydrochloric acid was added and extraction was performed with ethyl acetate. The organic layer was dried over anhydrous magnesium sulfate. The desiccating agent was filtered off and the filtrate was concentrated under reduced pressure. The residue was purified by silica gel column chromatography (ethyl acetate-heptane) to give {2-[3,4-dimethoxy-5-(1-triisopropylsilanyloxyethyl)phenyl]-2-[4-(5-methyl-[1,2,4] oxadiazol-3-yl)phenylimino]-1-methylsulfanylethylidene}carbamic acid methyl ester (336 mg, isomeric mixture) as a yellow solid.

336 mg of this compound was dissolved in 8 ml of THF, and then 0.65 ml of TBAF (1.0 M, THF solution) was added and the mixture was stirred at room temperature for 15 minutes. Saturated aqueous ammonium chloride was added to the reaction mixture, and extraction was performed with ethyl acetate. The organic layer was dried over anhydrous magnesium sulfate. The desiccating agent was filtered off and the filtrate was concentrated under reduced pressure. The residue was purified by silica gel column chromatography (ethyl acetate-heptane) to give the title compound (132 mg, isomeric mixture) as a light yellow solid.

Mass spectrum (ESI) m/z: 499 (M+H)$^+$ (25c) 4-({[3-(1-hydroxyethyl)-4,5-dimethoxyphenyl]-(5-oxo-1-pyrimidin-2-yl-4,5-dihydro-1H-[1,2,4]triazol-3-yl)methyl}amino)benzamidine acetate

[Chemical Formula 136]

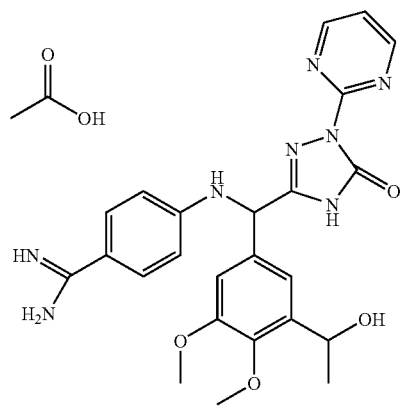

After adding 22 mg of 2-hydrazinopyrimidine and 50 μl of triethylamine to a solution of 112 mg of {2-[3-(1-hydroxyethyl)-4,5-dimethoxyphenyl]-2-[4-(5-methyl-[1,2,4]oxadiazol-3-yl)phenylimino]-1-methylsulfanylethylidene}carbamic acid methyl ester in 2 ml of DMF, the mixture was stirred overnight at 85° C. under a nitrogen atmosphere. The reaction mixture was concentrated, and the residue was dissolved in 3 ml of methanol and 0.3 ml of acetic acid. After adding 100 mg of sodium cyanotrihydroborate to the solution, the mixture was stirred at room temperature for 1 hour. Water was added to the reaction mixture and extraction was performed with ethyl acetate. The organic layer was dried over anhydrous magnesium sulfate. The desiccating agent was filtered off and the filtrate was concentrated under reduced pressure. The residue was purified by NAM silica gel column chromatography (methanol-ethyl acetate) to give 5-{[3-(1-hydroxyethyl)-4,5-dimethoxyphenyl]-[4-(5-methyl-[1,2,4]oxadiazol-3-yl)phenylamino]

methyl}-2-pyrimidin-2-yl-4,5-dihydro-1H-[1,2,4]triazol-3-one (93 mg) as a light brown solid.

To a solution of 93 mg of this compound in 3 ml of a methanol:water:acetic acid=1:1:1 mixed solvent there was added 100 mg of iron powder, and the mixture was stirred overnight at 60° C. under a nitrogen atmosphere. After filtering the reaction mixture, it was purified by reverse-phase high performance liquid chromatography (acetonitrile-water, 0.1% acetic acid) to give the title compound (35.7 mg).

$^1$H-NMR (CD$_3$OD) δ 1.35, 1.40 (each d, J=6.4 Hz, total 3H) 1.94 (s, 3H) 3.80 (s, 3H) 3.84, 3.86 (each s, total 3H) 5.14, 5.14 (each q, J=6.4 Hz, total 1H) 5.64, 5.66 (each s, total 1H) 6.87, 6.88 (each d, J=9.2 Hz, total 2H) 7.12, 7.13 (each d, J=4.8 Hz, total 1H) 7.26, 7.26 (each d, J=4.4 Hz, total 1H) 7.34 (t, J=4.8 Hz, 1H) 7.60, 7.61 (each d, J=8.4 Hz, total 2H) 8.77, 8.78 (each d, J=4.8 Hz, total 2H)

Mass spectrum (ESI) m/z: 491 (M+H)$^+$

Example 26

(R) and (S)-4-{[(3-cyanomethyl-4,5-dimethoxyphenyl)-(5-oxo-1-pyrimidin-2-yl-4,5-dihydro-1H-[1,2,4]triazol-3-yl)methyl]amino}benzamidine acetate (26a) {2-(3-cyanomethyl-4,5-dimethoxyphenyl)-2-[4-(5-methyl-[1,2,4]oxadiazol-3-yl)phenylimino]-1-methylsulfanylethylidene}carbamic acid methyl ester

[Chemica Formula 137]

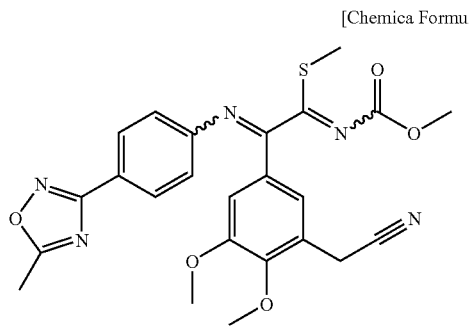

After dissolving 194 mg of [2-(3-hydroxymethyl-4,5-dimethoxyphenyl)-2-[4-(5-methyl-[1,2,4]oxadiazol-3-yl)phenylimino]-1-methylsulfanylethylidene]carbamic acid methyl ester (Example (22b)), 315 mg of triphenylphosphine and 0.11 ml of acetone cyanohydrin in 4 ml of THF under a nitrogen atmosphere, the solution was cooled to −78° C. Next, 0.23 ml of diisopropyl azodicarboxylate (hereinafter, "DIAD") was added and the mixture was stirred at room temperature for 1 hour. The reaction mixture was concentrated under reduced pressure, and the residue was purified by silica gel column chromatography (ethyl acetate-heptane) to give the title compound (197 mg, isomeric mixture) as a light yellow solid.

Mass spectrum (ESI) m/z: 494 (M+H)$^+$ (26b) (R) and (S)-4-{[(3-cyanomethyl-4,5-dimethoxyphenyl)-(5-oxo-1-pyrimidin-2-yl-4,5-dihydro-1H-[1,2,4]triazol-3-yl)methyl]amino}benzamidine acetate

[Chemical Formula 138]

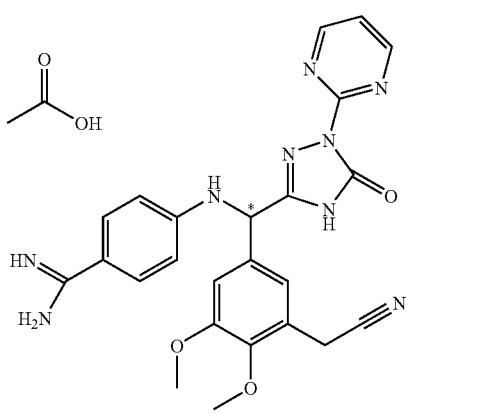

After adding 30 mg of 2-hydrazinopyrimidine and 50 μl of triethylamine to a solution of 152 mg of {2-(cyanomethyl-4,5-dimethoxyphenyl)-2-[4-(5-methyl-[1,2,4]oxadiazol-3-yl)phenylimino]-1-methylsulfanylethylidene}carbamic acid methyl ester in 2 ml of DMF, the mixture was stirred overnight at 85° C. under a nitrogen atmosphere. The reaction mixture was concentrated, and the residue was dissolved in 3 ml of methanol and 0.3 ml of acetic acid. After adding 100 mg of sodium cyanotrihydroborate to the solution, the mixture was stirred at room temperature for 1 hour. Water was added to the reaction mixture and extraction was performed with ethyl acetate. The organic layer was dried over anhydrous magnesium sulfate. The desiccating agent was filtered off and the filtrate was concentrated under reduced pressure. The residue was purified by NAM silica gel column chromatography (methanol-ethyl acetate) to give (2,3-dimethoxy-5-{[4-(5-methyl-[1,2,4]oxadiazol-3-yl)phenylamino]-(5-oxo-1-pyrimidin-2-yl-4,5-dihydro-1H-[1,2,4]triazol-3-yl)methyl}phenyl)acetonitrile (72 mg) as a light brown solid.

To a solution of 72 mg of this compound in 3 ml of a methanol:water:acetic acid=1:1:1 mixed solvent there was added 100 mg of iron powder, and the mixture was stirred overnight at 60° C. under a nitrogen atmosphere. After filtering the reaction mixture, it was purified by reverse-phase high performance liquid chromatography (acetonitrile-water, 0.1% acetic acid) to give 4-{[(3-cyanomethyl-4,5-dimethoxyphenyl)-(5-oxo-1-pyrimidin-2-yl-4,5-dihydro-1H-[1,2,4]triazol-3-yl)methyl]amino}benzamidine acetate (48 mg).

Mass spectrum (ESI) m/z: 486 (M+H)$^+$ 48 mg of this compound was optically resolved using a SUMICHIRAL OA-2500 column, and the first eluting enantiomer (19.3 mg) of the title compound was obtained as a white solid.

$^1$H-NMR (CD$_3$OD) δ 1.92 (s, 3H) 3.77 (s, 2H) 3.86 (s, 6H) 5.60 (s, 1H) 6.85 (d, J=8.8 Hz, 2H) 7.13 (d, J=2.0 Hz, 1H) 7.24 (d, J=2.4 Hz, 1H) 7.28 (t, J=4.8 Hz, 1H) 7.59 (d, J=8.8 Hz, 2H) 8.75 (d, J=4.4 Hz, 2H)

HPLC retention time: 12 min

Example 27

(R) and (S)-4-{[(8-ethyl-4H-benzo[1,3]dioxin-6-yl)-(5-oxo-1-pyrimidin-2-yl-4,5-dihydro-1H-[1,2,4]triazol-3-yl)methyl]amino}benzamidine acetate

(27a) 8-ethyl-4H-benzo[1,3]dioxine-6-carbaldehyde

[Chemical Formula 139]

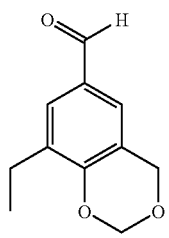

To a solution of 1.88 g of 5-bromo-3-ethyl-2-hydroxybenzaldehyde in 40 ml of an ethanol:THF=1:1 mixed solvent there was added 1 g of sodium borohydride while cooling on ice. After stirring at room temperature for 2 hours, 1N hydrochloric acid was added to the reaction mixture while cooling on ice. The reaction mixture was extracted with ethyl acetate and dried over anhydrous magnesium sulfate. The desiccating agent was filtered off, and the filtrate was concentrated under reduced pressure to give 4-bromo-8-ethyl-6-hydroxymethylphenol as a white solid.

After adding 0.83 g of sodium hydride (60% oily suspension) to a solution of 1.91 g of this compound in 30 ml of DMF while cooling on ice, the mixture was stirred at room temperature for 30 minutes. After then adding 0.67 ml of bromochloromethane and 0.25 g of sodium iodide to the reaction mixture, it was stirred at 80° C. for 6 hours under a nitrogen atmosphere. Saturated aqueous ammonium chloride was added to the reaction mixture, and extraction was performed with ethyl acetate. The organic layer was dried over anhydrous magnesium sulfate. The desiccating agent was filtered off and the filtrate was concentrated under reduced pressure. The residue was purified by silica gel column chromatography (ethyl acetate-heptane) to give 6-bromo-8-ethyl-4H-benzo[1,3]dioxine (1.50 g).

To a solution of 1.50 g of this compound in 30 ml of THF there was added dropwise 4.5 ml of n-butyllithium (1.58 M, hexane solution) at −70° C. under a nitrogen atmosphere. After stirring at −70° C. for 30 minutes, 1 ml of N-formylmorpholine was added and the temperature was raised from −70° C. to 0° C. over a period of 30 minutes. Saturated aqueous ammonium chloride was added to the reaction mixture, and extraction was performed with ethyl acetate. The organic layer was dried over anhydrous magnesium sulfate. The desiccating agent was filtered off and the filtrate was concentrated under reduced pressure. The residue was purified by silica gel column chromatography (ethyl acetate-heptane) to give the title compound (871 mg).

(27b) [2-(8-ethyl-4H-benzo[1,3]dioxin-6-yl)-2-[4-(5-methyl-[1,2,4]oxadiazol-3-yl)phenylimino]-1-methylsulfanylethylidene]carbamic acid methyl ester

[Chemical Formula 140]

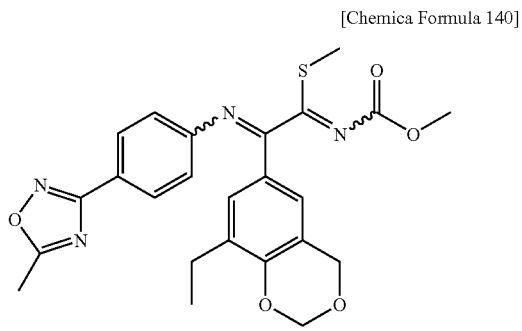

After adding 794 mg of 4-(5-methyl-[1,2,4]oxadiazol-3-yl)phenylamine, 871 mg of 8-ethyl-4H-benzo[1,3]dioxine-6-carbaldehyde, 1 g of MS3A and 1 ml of trimethylsilyl cyanide to a solution of 281 mg of Yb(OTf)$_3$ in 20 ml of dichloromethane under a nitrogen atmosphere, the mixture was stirred at room temperature for 2 days. The reaction mixture was filtered through celite, and the celite was washed with 100 ml of ethyl acetate. The organic layer was concentrated under reduced pressure to give (8-ethyl-4H-benzo[1,3]dioxin-6-yl)-[4-(5-methyl-[1,2,4]oxadiazol-3-yl)phenylamino]acetonitrile(crude product) as a light yellow solid.

To a solution of this compound in 45 ml of an ethanol:THF=2:1 mixed solvent there was added 15 ml of a 20% aqueous solution of ammonium sulfide, and the mixture was stirred overnight at room temperature. Water was added to the reaction mixture and extraction was performed with ethyl acetate. The organic layer was dried over anhydrous magnesium sulfate. The desiccating agent was filtered off, and the filtrate was concentrated under reduced pressure to give a crude product of 2-(8-ethyl-4H-benzo[1,3]dioxin-6-yl)-2-[4-(5-methyl-[1,2,4]oxadiazol-3-yl)phenylamino]thioacetamide.

After adding 0.8 g of Me$_3$O$^+$BF$_4^-$ to a solution of this compound in 30 ml of dichloromethane under a nitrogen atmosphere, the mixture was stirred at room temperature for 1 hour. Saturated aqueous sodium hydrogencarbonate was added to the reaction mixture, and extraction was performed with ethyl acetate. The organic layer was dried over anhydrous magnesium sulfate. The desiccating agent was filtered off and the filtrate was concentrated under reduced pressure.

After adding 4 g of manganese dioxide to a solution of the residue in ethyl acetate, the mixture was stirred at room temperature for 1 hour. Next, 8 g of manganese dioxide was further added and the mixture was stirred at room temperature for 2 hours. The reaction mixture was filtered through celite, and the filtrate was concentrated under reduced pressure.

To a solution of the residue in 30 ml of toluene there were added 2 ml of 2,4,6-collidine and 1 ml of methyl chloroformate, and the mixture was stirred at 80° C. for 2 hours under a nitrogen atmosphere. After cooling the reaction mixture, 1N hydrochloric acid was added and extraction was performed with ethyl acetate. The organic layer was dried over anhydrous magnesium sulfate. The desiccating agent was filtered off and the filtrate was concentrated under reduced pressure. The residue was purified by silica gel column chromatography (ethyl acetate-heptane) to give the title compound (773 mg) as a yellow solid.

Mass spectrum (ESI) m/z: 481 (M+H)$^+$ (27c) (R) and (S)-4-{[(8-ethyl-4H-benzo[1,3]dioxin-6-yl)-(5-oxo-1-pyrimidin-2-yl-4,5-dihydro-1H-[1,2,4]triazol-3-yl)methyl]amino}benzamidine acetate

[Chemical Formula 141]

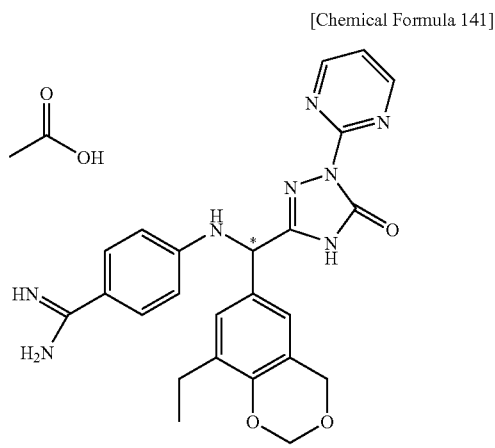

To a solution of 101 mg of [2-(8-ethyl-4H-benzo[1,3]dioxin-6-yl)-2-[4-(5-methyl-[1,2,4]oxadiazol-3-yl)phenylimino]-1-methylsulfanylethylidene]carbamic acid methyl ester in 2 ml of DMF there were added 21 mg of 2-hydrazinopyrimidine and 50 μl of triethylamine, and the mixture was stirred overnight at 85° C. under a nitrogen atmosphere. The reaction mixture was concentrated, and the residue was dissolved in 3 ml of methanol and 0.3 ml of acetic acid. After adding 200 mg of sodium cyanotrihydroborate to the solution, the mixture was stirred at room temperature for 1 hour. Water was added to the reaction mixture and extraction was performed with ethyl acetate. The organic layer was dried over anhydrous magnesium sulfate. The desiccating agent was filtered off and the filtrate was concentrated under reduced pressure. The residue was purified by NAM silica gel column chromatography (methanol-ethyl acetate) to give 5-{(8-ethyl-4H-benzo[1,3]dioxin-6-yl)-[4-(5-methyl-[1,2,4]oxadiazol-3-yl)phenylamino]methyl}-2-pyrimidin-2-yl-2,4-dihydro-[1,2,4]triazol-3-one.

To a solution of this compound in 3 ml of a methanol:water:acetic acid=1:1:1 mixed solvent there was added 70 mg of iron powder, and the mixture was stirred overnight at 60° C. under a nitrogen atmosphere. After filtering the reaction mixture, it was purified by reverse-phase high performance liquid chromatography (acetonitrile-water, 0.1% acetic acid) to give 4-{[(8-ethyl-4H-benzo[1,3]dioxin-6-yl)-(5-oxo-1-pyrimidin-2-yl-4,5-dihydro-1H-[1,2,4]triazol-3-yl)methyl]amino}benzamidine acetate (26 mg).

Mass spectrum (ESI) m/z: 473 (M+H)$^+$ 26 mg of this compound was optically resolved using a SUMICHIRAL OA-2500 column, and the first eluting enantiomer (9.7 mg) of the title compound was obtained as a white solid.

$^1$H-NMR (CD$_3$OD) δ 1.13 (t, J=7.6 Hz, 3H) 1.89 (s, 3H) 2.57 (q, J=7.6 Hz, 2H) 4.82-4.90 (m, 2H) 5.22 (s, 2H) 5.49 (s, 1H) 6.83 (d, J=8.8 Hz, 2H) 7.03 (br.s, 1H) 7.21 (br.s, 1H) 7.25 (t, J=5.2 Hz, 1H) 7.58 (d, J=9.2 Hz, 2H) 8.74 (d, J=4.8 Hz, 2H)

HPLC retention time: 12 min

Example 28

(R) and (S)-4-{[(8-ethoxy-4H-benzo[1,3]dioxin-6-yl)-(5-oxo-1-pyrimidin-2-yl-4,5-dihydro-1H-[1,2,4]triazol-3-yl)methyl]amino}benzamidine acetate (28a)
8-ethoxy-4H-benzo[1,3]dioxine-6-carbaldehyde

[Chemical Formula 142]

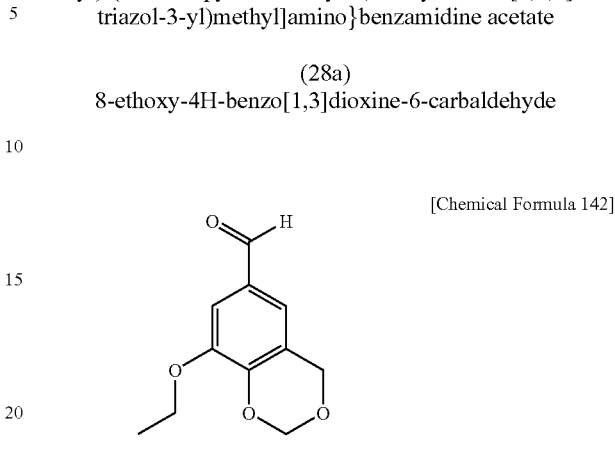

After adding 5.59 g of N-bromosuccinimide to a solution of 5.11 g of 3-ethoxy-2-hydroxybenzaldehyde in 100 ml of acetonitrile, the mixture was stirred at room temperature for 3 hours. The reaction mixture was concentrated, water was added to the residue, and extraction was performed with ethyl acetate. The organic layer was dried over anhydrous magnesium sulfate. The desiccating agent was filtered off and the filtrate was concentrated under reduced pressure. The residue was recrystallized using t-butyl methyl ether-heptane to give 5-bromo-3-ethoxy-2-hydroxybenzaldehyde (2.53 g).

$^1$H-NMR (CDCl$_3$) δ 1.49 (t, J=7.2 Hz, 3H) 4.11 (q, J=7.2 Hz, 2H) 7.16 (d, J=2.4 Hz, 1H) 7.29 (d, J=2.0 Hz, 1H) 9.84 (s, 1H) 10.91 (s, 1H)

To a solution of 2.53 g of this compound in 40 ml of an ethanol:THF=1:1 mixed solvent there was added 1 g of sodium borohydride while cooling on ice. After stirring at room temperature for 3 hours, 1N hydrochloric acid was added to the reaction mixture while cooling on ice. The organic layer was washed with ethyl acetate and dried over anhydrous magnesium sulfate. The desiccating agent was filtered off, and the filtrate was concentrated under reduced pressure to give 4-bromo-8-ethoxy-6-hydroxymethylphenol.

To a solution of this compound in 40 ml of DMF there was added 1 g of sodium hydride (60% oily suspension) while cooling on ice, and the mixture was stirred at room temperature for 30 minutes. After then adding 1 ml of bromochloromethane and 0.25 g of sodium iodide to the reaction mixture, it was stirred at 80° C. for 6 hours under a nitrogen atmosphere. Saturated aqueous ammonium chloride was added to the reaction mixture, and extraction was performed with ethyl acetate. The organic layer was dried over anhydrous magnesium sulfate. The desiccating agent was filtered off and the filtrate was concentrated under reduced pressure. The residue was purified by silica gel column chromatography (ethyl acetate-heptane) to give 6-bromo-8-ethoxy-4H-benzo[1,3]dioxine (1.62 g).

To a solution of 1.62 g of this compound in 30 ml of THF there was added dropwise 2.8 ml of n-butyllithium (2.62 M, hexane solution) at −70° C. under a nitrogen atmosphere. After stirring at −70° C. for 30 minutes, 1 ml of N-formylmorpholine was added and the temperature was raised from −70° C. to 0° C. over a period of 30 minutes. Saturated aqueous ammonium chloride was added to the reaction mixture, and extraction was performed with ethyl acetate. The organic layer was dried over anhydrous magnesium sulfate. The desiccating agent was filtered off and the filtrate was concentrated under reduced pressure. The residue was purified by silica gel column chromatography (ethyl acetate-heptane) to give the title compound (773 mg).

(28b) {2-(8-ethoxy-4H-benzo[1,3]dioxin-6-yl)-2-[4-(5-methyl-[1,2,4]oxadiazol-3-yl)phenylimino]-1-methylsulfanylethylidene}carbamic acid methyl ester

[Chemica Formula 143]

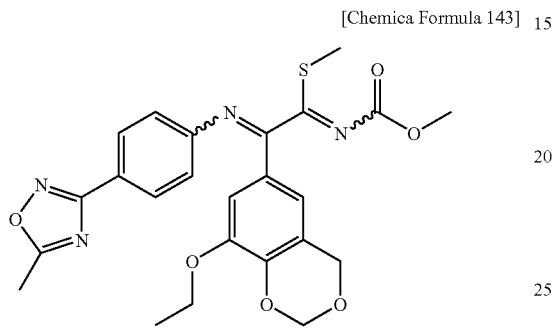

To a solution of 230 mg of Yb(OTf)$_3$ in 20 ml of dichloromethane there were added 650 mg of 4-(5-methyl-[1,2,4]oxadiazol-3-yl)phenylamine, 773 mg of 8-ethyl-4H-benzo[1,3]dioxine-6-carbaldehyde, 1 g of MS3A and 0.8 ml of trimethylsilyl cyanide under a nitrogen atmosphere, and the mixture was stirred overnight at room temperature. The reaction mixture was filtered through celite, and the celite was washed with 100 ml of ethyl acetate. The organic layer was concentrated under reduced pressure to give (8-ethoxy-4H-benzo[1,3]dioxin-6-yl)-[4-(5-methyl-[1,2,4]oxadiazol-3-yl)phenylamino]acetonitrile (crude product).

To a solution of this compound in an ethanol:THF=2:1 mixed solvent there was added a 20% aqueous solution of ammonium sulfide, and the mixture was stirred overnight at room temperature. Water was added to the reaction mixture and extraction was performed with ethyl acetate. The organic layer was dried over anhydrous magnesium sulfate. The desiccating agent was filtered off, and the filtrate was concentrated under reduced pressure to give 2-(8-ethoxy-4H-benzo[1,3]dioxin-6-yl)-2-[4-(5-methyl-[1,2,4]oxadiazol-3-yl)phenylamino]thioacetamide (1.74 g, crude product).

After adding 650 mg of Me$_3$O$^+$BF$_4^-$ to a solution of 1.7 g of this compound in 40 ml of dichloromethane under a nitrogen atmosphere, the mixture was stirred at room temperature for 1 hour. Saturated aqueous sodium hydrogencarbonate was added to the reaction mixture, and extraction was performed with ethyl acetate. The organic layer was dried over anhydrous magnesium sulfate. The desiccating agent was filtered off and the filtrate was concentrated under reduced pressure.

After adding manganese dioxide to a solution of the residue in ethyl acetate, the mixture was stirred at room temperature for 1 hour. The reaction mixture was filtered, and the filtrate was concentrated under reduced pressure.

To a solution of the residue in toluene there were added 2,4,6-collidine and methyl chloroformate, and the mixture was stirred at 80° C. under a nitrogen atmosphere. After cooling the reaction mixture, 1N hydrochloric acid was added and extraction was performed with ethyl acetate. The organic layer was dried over anhydrous magnesium sulfate. The desiccating agent was filtered off and the filtrate was concentrated under reduced pressure. The residue was purified by silica gel column chromatography (ethyl acetate-heptane) to give the title compound (1.7 g) as a yellow solid.

Mass spectrum (ESI) m/z: 497 (M+H)$^+$ (28c) (R) and (S)-4-{[(8-ethoxy-4H-benzo[1,3]dioxin-6-yl)-(5-oxo-1-pyrimidin-2-yl-4,5-dihydro-1H-[1,2,4]triazol-3-yl)methyl]amino}benzamidine acetate

[Chemical Formula 144]

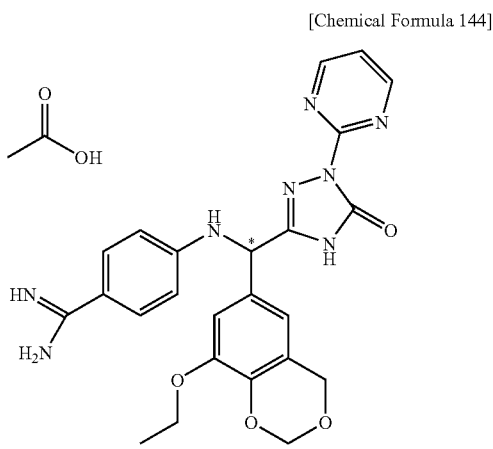

To a solution of 105 mg of {2-(8-ethoxy-4H-benzo[1,3]dioxin-6-yl)-2-[4-(5-methyl-[1,2,4]oxadiazol-3-yl)phenylimino]-1-methylsulfanylethylidene}carbamic acid methyl ester in 2 ml of DMF there were added 20.9 mg of 2-hydrazinopyrimidine and 50 μl of triethylamine, and the mixture was stirred overnight at 85° C. under a nitrogen atmosphere. The reaction mixture was concentrated, and the residue was dissolved in 3 ml of methanol and 0.3 ml of acetic acid. After adding 100 mg of sodium cyanotrihydroborate to the solution, the mixture was stirred at room temperature for 1 hour. Water was added to the reaction mixture and extraction was performed with ethyl acetate. The organic layer was dried over anhydrous magnesium sulfate. The desiccating agent was filtered off and the filtrate was concentrated under reduced pressure. The residue was purified by NAM silica gel column chromatography (methanol-ethyl acetate) to give 5-{(8-ethoxy-4H-benzo[1,3]dioxin-6-yl)-[4-(5-methyl-[1,2,4]oxadiazol-3-yl)phenylamino]methyl}-2-pyrimidin-2-yl-2,4-dihydro-[1,2,4]triazol-3-one (46 mg).

To a solution of 46 mg of this compound in 3 ml of a methanol:water:acetic acid=1:1:1 mixed solvent there was added 65 mg of iron powder, and the mixture was stirred overnight at 60° C. under a nitrogen atmosphere. After filtering the reaction mixture, it was purified by reverse-phase high performance liquid chromatography (acetonitrile-water, 0.1% acetic acid) to give 4-{[(8-ethoxy-4H-benzo[1,3]dioxin-6-yl)-(5-oxo-1-pyrimidin-2-yl-4,5-dihydro-1H-[1,2,4]triazol-3-yl)methyl]amino}benzamidine acetate (26 mg).

Mass spectrum (ESI) m/z: 489 (M+H)$^+$ 26 mg of this compound was optically resolved using a SUMICHIRAL OA-2500 column, and the first eluting enantiomer (9.7 mg) of the title compound was obtained as a white solid.

$^1$H-NMR (CD$_3$OD) δ 1.34 (t, J=6.8 Hz, 3H) 1.91 (s, 3H) 3.97-4.07 (m, 2H) 4.79-4.90 (m, 2H) 5.22 (s, 2H) 5.54 (s, 1H)

6.80 (s, 1H) 6.84 (d, J=8.8 Hz, 2H) 7.03 (s, 1H) 7.30 (t, J=5.2 Hz, 1H) 7.59 (d, J=8.8 Hz, 2H) 8.77 (d, J=4.8 Hz, 2H)

HPLC retention time: 16 min

Example 29

(R) and (S)-4-({[1-(3-fluoropyridin-2-yl)-5-oxo-4,5-dihydro-1H-[1,2,4]triazol-3-yl]-(8-methoxychroman-6-yl)methyl}amino)benzamidine acetate (29a) (3-fluoropyridin-2-yl)hydrazine

[Chemical Formula 145]

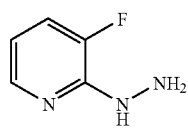

To a solution of 9.59 g of 2-chloro-3-fluoropyridine in 6 ml of ethanol there was added 6 ml of hydrazine monohydrate, and the mixture was stirred at 60° C. for 3 days. The solution was adsorbed onto 50 g of NH silica gel and purified by NH silica gel column chromatography (ethyl acetate-heptane) to give the title compound (403 mg) as a yellow solid.

$^1$H-NMR (DMSO-d$_6$) δ 4.10 (s, 2H) 6.54-6.58 (m, 1H) 7.27-7.32 (m, 1H) 7.72 (s, 1H) 7.86 (d, J=5.2 Hz, 1H)

(29b) (R) and (S)-4-({[1-(3-fluoropyridin-2-yl)-5-oxo-4,5-dihydro-1H-[1,2,4]triazol-3-yl]-(8-methoxychroman-6-yl)methyl}amino)benzamidine acetate

[Chemical Formula 146]

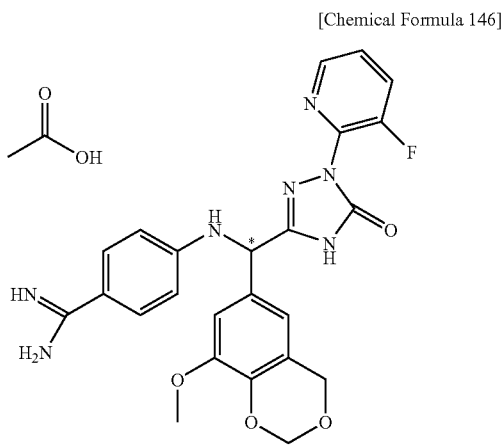

After adding 25 mg of (3-fluoropyridin-2-yl)hydrazine and 50 μl of triethylamine to a solution of 100 mg of {2-(8-methoxychroman-6-yl)-2-[4-(5-methyl-[1,2,4]oxadiazol-3-yl)phenylimino]-1-methylsulfanylethylidene}carbamic acid methyl ester (Example (24a)) in 2 ml of DMF, the mixture was stirred overnight at 85° C. under a nitrogen atmosphere. The reaction mixture was concentrated, and the residue was dissolved in 3 ml of methanol and 0.3 ml of acetic acid. After adding 100 mg of sodium cyanotrihydroborate to the reaction mixture, it was stirred at room temperature for 2 hours. Water was added to the reaction mixture and extraction was performed with ethyl acetate. The organic layer was dried over anhydrous magnesium sulfate. The desiccating agent was filtered off and the filtrate was concentrated under reduced pressure. The residue was purified by NAM silica gel column chromatography (methanol-ethyl acetate) to give 2-(3-fluoro-pyridin-2-yl)-5-{(8-methoxychroman-6-yl)-[4-(5-methyl-[1,2,4]oxadiazol-3-yl)phenylamino]methyl}-2,4-dihydro-[1,2,4]triazol-3-one (60 mg).

To a solution of 60 mg of this compound in 3 ml of a methanol:water:acetic acid=1:1:1 mixed solvent there was added 70 mg of iron powder, and the mixture was stirred overnight at 60° C. under a nitrogen atmosphere. After filtering the reaction mixture, it was purified by reverse-phase high performance liquid chromatography (acetonitrile-water, 0.1% acetic acid) to give 4-({[1-(3-fluoropyridin-2-yl)-5-oxo-4,5-dihydro-1H-[1,2,4]triazol-3-yl]-(8-methoxychroman-6-yl)methyl}amino)benzamidine acetate (29 mg).

Mass spectrum (ESI) m/z: 490 (M+H)$^+$ 29 mg of this compound was optically resolved using a SUMICHIRAL OA-2500 column, and the first eluting enantiomer (10.1 mg) of the title compound was obtained as a white solid.

$^1$H-NMR (CD$_3$OD) δ 1.92 (s, 3H) 1.94-2.01 (m, 2H) 2.78 (t, J=6.4 Hz, 2H) 3.80 (s, 3H) 4.18 (t, J=5.2 Hz, 2H) 5.53 (s, 1H) 6.83-6.87 (m, 3H) 6.95 (d, J=2.0 Hz, 1H) 7.53 (sept, J=4.8 Hz, 1H) 7.60 (d, J=9.2 Hz, 2H) 7.81 (dt, J=1.2, 8.4 Hz, 1H) 8.37 (d, J=4.4 Hz, 1H)

HPLC retention time: 8 min

Example 30

(R) and (S)-4-({[1-(3-fluoropyridin-2-yl)-5-oxo-4,5-dihydro-1H-[1,2,4]triazol-3-yl]-(9-methoxy-3,4-dihydro-2H-benzo[b][1,4]dioxepin-7-yl)methyl}amino)benzamidine acetate (30a) 9-methoxy-3,4-dihydro-2H-benzo[b][1,4]dioxepin-7-carbaldehyde

[Chemical Formula 147]

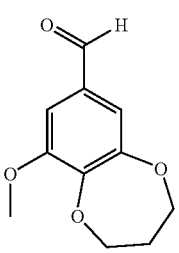

After adding 1.5 g of potassium carbonate and 1.2 g of 1,3-dibromopropane to a solution of 920 mg of 3,4-dihydroxy-5-methoxybenzaldehyde [CAS No. 859785-71-0] in 10 ml of DMF, the mixture was stirred at 60° C. for 3 hours. Water was added to the reaction mixture, and extraction was performed with ethyl acetate. The organic layer was dried over anhydrous magnesium sulfate. The desiccating agent was filtered off and the filtrate was concentrated under reduced pressure. The residue was purified by silica gel column chromatography (ethyl acetate-heptane) to give the title compound (604 mg) as an oil.

$^1$H-NMR (CDCl$_3$) δ 2.29 (quint, J=6.0 Hz, 2H) 3.92 (s, 3H) 4.33 (t, J=5.6 Hz, 2H) 4.45 (t, J=5.6 Hz, 2H) 7.10-7.11 (m, 1H) 7.12 (br.s, 1H) 9.78 (d, J=1.6 Hz, 1H)

(30b) 2-(9-methoxy-3,4-dihydro-2H-benzo[b][1,4]dioxepin-7-yl)-2-[4-(5-methyl-[1,2,4]oxadiazol-3-yl)phenylamino]thioacetamide

[Chemical Formula 148]

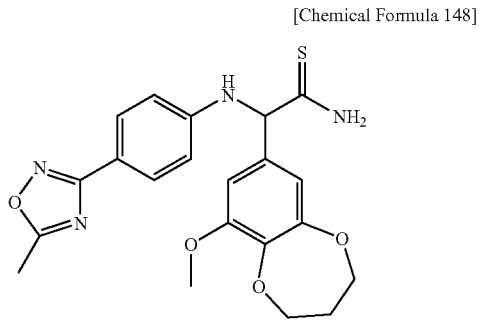

To a solution of 626 mg of Yb(OTf)₃ in 30 ml of dichloromethane there were added 1.77 g of 4-(5-methyl-[1,2,4]oxadiazol-3-yl)phenylamine, 2.11 g of 9-methoxy-3,4-dihydro-2H-benzo[b][1,4]dioxepin-7-carbaldehyde, 2 g of MS3A and 2.6 ml of trimethylsilyl cyanide under a nitrogen atmosphere, and the mixture was stirred overnight at room temperature. The reaction mixture was filtered through celite, and the celite was washed with 100 ml of ethyl acetate. The organic layer was concentrated under reduced pressure.

To a solution of the residue in 100 ml of an ethanol:THF=6:4 mixed solvent there was added 50 ml of a 20% aqueous solution of ammonium sulfide, and the mixture was stirred at 40° C. for 2 hours. Water was added to the reaction mixture and extraction was performed with ethyl acetate. The organic layer was dried over anhydrous magnesium sulfate. The desiccating agent was filtered off, and the filtrate was concentrated under reduced pressure to give the title compound (4.7 g, crude product) as a light yellow solid.

¹H-NMR (d₆-DMSO) δ 2.02-2.11 (m, 2H) 2.58 (s, 3H) 3.73 (s, 3H) 4.01-4.12 (m, 4H) 5.12 (d, J=6.0 Hz, 1H) 6.67 (d, J=5.6 Hz, 1H) 6.73 (d, J=8.8 Hz, 2H) 6.76 (d, J=2.0 Hz, 1H) 6.92 (s, 1H) 7.69 (d, J=8.8 Hz, 2H) 9.50 (br.s, 1H) 9.77 (br.s, 1H)

(30c) {2-(9-methoxy-3,4-dihydro-2H-benzo[b][1,4]dioxepin-7-yl)-2-[4-(5-methyl-[1,2,4]oxadiazol-3-yl)phenylimino]-1-methylsulfanylethylidene}carbamic acid methyl ester

[Chemical Formula 149]

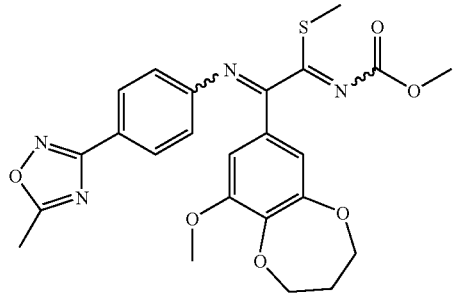

After adding 1.63 g of Me₃O⁺BF₄⁻ to a solution of 4.7 g of 2-(9-methoxy-3,4-dihydro-2H-benzo[b][1,4]dioxepin-7-yl)-2-[4-(5-methyl-[1,2,4]oxadiazol-3-yl)phenylamino]thioacetamide in 50 ml of acetonitrile, the mixture was stirred at room temperature. Saturated aqueous sodium hydrogencarbonate was added to the reaction mixture, and extraction was performed with ethyl acetate. The organic layer was dried over anhydrous magnesium sulfate. The desiccating agent was filtered off, and the filtrate was concentrated under reduced pressure to give 2-(9-methoxy-3,4-dihydro-2H-benzo[b][1,4]dioxepin-7-yl)-2-[4-(5-methyl-[1,2,4]oxadiazol-3-yl)phenylamino]thioacetimidic acid methyl ester.

To a solution of this compound in 60 ml of ethyl acetate there was added 16 g of manganese dioxide, and the mixture was stirred at room temperature. The reaction mixture was filtered through celite, and the filtrate was concentrated under reduced pressure.

To a solution of the residue in 50 ml of toluene there were added 4 ml of 2,4,6-collidine and 2 ml of methyl chloroformate, and the mixture was stirred at 80° C. under a nitrogen atmosphere. After cooling the reaction mixture, 1N hydrochloric acid was added and extraction was performed with ethyl acetate. The organic layer was dried over anhydrous magnesium sulfate. The desiccating agent was filtered off and the filtrate was concentrated under reduced pressure. The residue was purified by silica gel column chromatography (ethyl acetate-heptane) to give the title compound (1.997 g) as a yellow solid.

¹H-NMR (CDCl₃) δ 2.26-2.50 (m, 2H) 2.32 (s, 3H) 2.65 (s, 3H) 3.65 (s, 3H) 3.92 (s, 3H) 4.29 (t, J=5.6 Hz, 2H) 4.40 (t, J=6.0 Hz, 2H) 7.01 (d, J=2.0 Hz, 1H) 7.15 (d, J=8.0 Hz, 2H) 7.27 (d, J=1.6 Hz, 1H) 8.00 (d, J=8.0 Hz, 2H)

(30d) (R) and (S)-4-({[1-(3-fluoropyridin-2-yl)-5-oxo-4,5-dihydro-1H-[1,2,4]triazol-3-yl]-(9-methoxy-3,4-dihydro-2H-benzo[b][1,4]dioxepin-7-yl)methyl}amino)benzamidine acetate

[Chemical Formula 150]

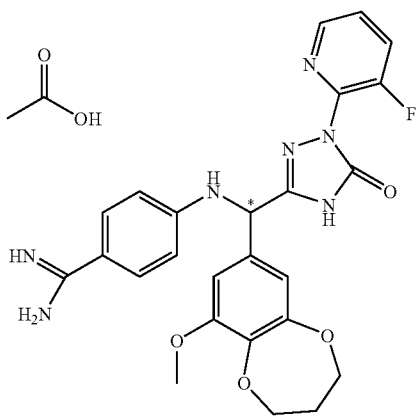

After adding 28 mg of (3-fluoropyridin-2-yl)hydrazine and 50 μl of triethylamine to a solution of 119 mg of {2-(9-methoxy-3,4-dihydro-2H-benzo[b][1,4]dioxepin-7-yl)-2-[4-(5-methyl-[1,2,4]oxadiazol-3-yl)phenylimino]-1-methylsulfanylethylidene}carbamic acid methyl ester in 2 ml of DMF, the mixture was stirred overnight at 85° C. under a nitrogen atmosphere. The reaction mixture was concentrated, and the residue was dissolved in 3 ml of methanol and 0.3 ml of acetic acid. After adding 100 mg of sodium cyanotrihydroborate to the reaction mixture, it was stirred at room temperature for 1 hour. Water was added to the reaction mixture and extraction was performed with ethyl acetate. The organic layer was dried over anhydrous magnesium sulfate. The desiccating agent was filtered off and the filtrate was concentrated under reduced pressure. The residue was purified by NAM silica gel column chromatography (methanol-ethyl acetate) to give 2-(3-fluoropyridin-2-yl)-5-{(9-methoxy-3,4-dihydro-2H-benzo[b][1,4]dioxepin-7-yl)-[4-(5-methyl-[1,2,4]oxadiazol-3-yl)phenylamino]methyl}-2,4-dihydro-[1,2,4]triazol-3-one.

To a solution of this compound in 3 ml of a methanol:water:acetic acid=1:1:1 mixed solvent, 100 mg of iron powder was added and the mixture was stirred overnight at 60° C. under a nitrogen atmosphere. After filtering the reaction mixture, it was purified by reverse-phase high performance liquid chromatography (acetonitrile-water, 0.1% acetic acid) to give 4-({[1-(3-fluoropyridin-2-yl)-5-oxo-4,5-dihydro-1H-[1,2,4]triazol-3-yl]-(9-methoxy-3,4-dihydro-2H-benzo[b][1,4]dioxepin-7-yl)methyl}amino)benzamidine acetate (60 mg).

Mass spectrum (ESI) m/z: 506 (M+H)$^+$ 60 mg of this compound was optically resolved using a SUMICHIRAL OA-2500 column, and the first eluting enantiomer (21 mg) of the title compound was obtained.

$^1$H-NMR (CD$_3$OD) δ 1.90 (s, 3H) 2.13 (t, J=5.2 Hz, 2H) 3.77 (s, 3H) 4.05-4.15 (m, 4H) 5.54 (s, 1H) 6.79 (d, J=2.4 Hz, 1H) 6.84 (d, J=8.8 Hz, 2H) 6.89 (d, J=1.6 Hz, 1H) 7.51 (sept, J=4.0 Hz, 1H) 7.59 (d, J=8.8 Hz, 2H) 7.80 (dt, J=1.2, 9.6 Hz, 1H) 8.36 (d, J=4.4 Hz, 1H)

HPLC retention time: 9 min

Example 31

(R) and (S)-4-{[(7-methoxy-2,3-dihydrobenzofuran-5-yl)-(5-oxo-1-pyrimidin-2-yl-4,5-dihydro-1H-[1,2,4]triazol-3-yl)methyl]amino}benzamidine acetate (31a) {2-(7-methoxy-2,3-dihydrobenzofuran-5-yl)-2-[4-(5-methyl-[1,2,4]oxadiazol-3-yl)phenylimino]-1-methylsulfanylethylidene}carbamic acid methyl ester

[Chemical Formula 151]

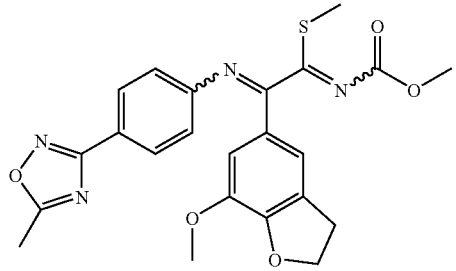

To a solution of 426 mg of Yb(OTf)$_3$ in 30 ml of THF there were added 1.2 g of 4-(5-methyl-[1,2,4]oxadiazol-3-yl)phenylamine, 1.22 g of 7-methoxy-2,3-dihydrobenzofuran-5-carbaldehyde [CAS No. 363185-46-0], 1 g of MS3A and 1.9 ml of trimethylsilyl cyanide under a nitrogen atmosphere, and the mixture was stirred at room temperature. The reaction mixture was filtered through celite, and the celite was washed with 100 ml of ethyl acetate. The organic layer was concentrated under reduced pressure to give a crude product of (7-methoxy-2,3-dihydrobenzofuran-5-yl)-[4-(5-methyl-[1,2,4]oxadiazol-3-yl)phenylamino]acetonitrile.

To a solution of this compound in 45 ml of an ethanol:THF=2:1 mixed solvent there was added 15 ml of a 20% aqueous solution of ammonium sulfide, and the mixture was stirred at room temperature. Water was added to the reaction mixture and extraction was performed with ethyl acetate. The organic layer was dried over anhydrous magnesium sulfate. The desiccating agent was filtered off, and the filtrate was concentrated under reduced pressure to give a crude product of 2-(7-methoxy-2,3-dihydrobenzofuran-5-yl)-2-[4-(5-methyl-[1,2,4]oxadiazol-3-yl)phenylamino]thioacetamide.

To a solution of this compound in 50 ml of acetonitrile there was added 1.12 g of Me$_3$O$^+$BF$_4^-$, and the mixture was stirred at room temperature for 1 hour. Saturated aqueous sodium hydrogencarbonate was added to the reaction mixture, and extraction was performed with ethyl acetate. The organic layer was dried over anhydrous magnesium sulfate. The desiccating agent was filtered off and the filtrate was concentrated under reduced pressure.

To a solution of the residue in 50 ml of toluene there were added 2 ml of 2,4,6-collidine and 1 ml of methyl chloroformate, and the mixture was stirred at 80° C. for 1 hour under a nitrogen atmosphere. After cooling the reaction mixture, 1N hydrochloric acid was added and extraction was performed with ethyl acetate. The organic layer was dried over anhydrous magnesium sulfate. The desiccating agent was filtered off and the filtrate was concentrated under reduced pressure. The residue was purified by silica gel column chromatography (ethyl acetate-heptane) to give the title compound (369 mg, isomeric mixture) as a yellow solid.

Mass spectrum (ESI) m/z: 467 (M+H)$^+$ (31b) (R) and (S)-4-{[(7-methoxy-2,3-dihydrobenzofuran-5-yl)-(5-oxo-1-pyrimidin-2-yl-4,5-dihydro-1H-[1,2,4]triazol-3-yl)methyl]amino}benzamidine acetate

[Chemical Formula 152]

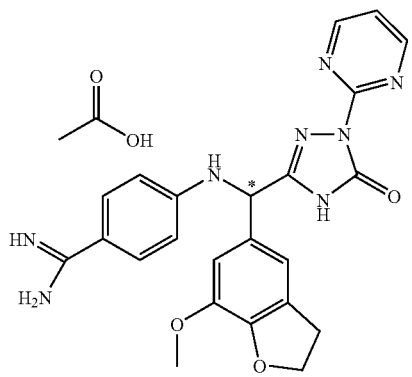

After adding 27 mg of 2-hydrazinopyrimidine and 50 μl of triethylamine to a solution of 128 mg of [2-(7-methoxy-2,3-dihydrobenzofuran-5-yl)-2-[4-(5-methyl-[1,2,4]oxadiazol-3-yl)phenylimino]-1-methylsulfanylethylidene]carbamic acid methyl ester in 2 ml of DMF, the mixture was stirred overnight at 85° C. under a nitrogen atmosphere. The reaction mixture was concentrated, and the residue was dissolved in 3 ml of methanol and 0.3 ml of acetic acid. After adding 100 mg of sodium cyanotrihydroborate to the reaction mixture, the mixture was stirred at room temperature for 1 hour. Water was added to the reaction mixture and extraction was performed with ethyl acetate. The organic layer was dried over anhydrous magnesium sulfate. The desiccating agent was filtered off and the filtrate was concentrated under reduced pressure. The residue was purified by NAM silica gel column chromatography (methanol-ethyl acetate) to give 5-{[(7-methoxy-2,3-dihydrobenzofuran-5-yl)-[4-(5-methyl-[1,2,4]oxadiazol-3-yl)phenylamino]methyl}-2-pyrimidin-2-yl-2,4-dihydro-[1,2,4]triazol-3-one.

To a solution of this compound in 3 ml of a methanol:water:acetic acid=1:1:1 mixed solvent there was added 100 mg of iron powder, and the mixture was stirred overnight at 60° C. under a nitrogen atmosphere. After filtering the reaction mixture, it was purified by reverse-phase high performance liquid chromatography (acetonitrile-water, 0.1% acetic acid) to give 4-{[(7-methoxy-2,3-dihydrobenzofuran-5-yl)-(5-oxo-1-pyrimidin-2-yl-4,5-dihydro-1H-[1,2,4]triazol-3-yl)methyl]amino}benzamidine acetate (18.1 mg).

Mass spectrum (ESI) m/z: 459 (M+H)$^+$ 18.1 mg of this compound was optically resolved using a SUMICHIRAL OA-2500 column, and the first eluting enantiomer (7.6 mg) of the title compound was obtained as a white solid.

$^1$H-NMR (CD$_3$OD) δ 1.91 (s, 3H) 3.19 (t, J=8.4 Hz, 2H) 3.82 (s, 3H) 4.56 (t, J=8.8 Hz, 2H) 5.54 (s, 1H) 6.85 (d, J=8.8 Hz, 2H) 7.01 (s, 1H) 7.03 (s, 1H) 7.29 (t, J=4.8 Hz, 1H) 7.59 (d, J=8.8 Hz, 2H) 8.76 (d, J=4.8 Hz, 2H)

HPLC retention time: 17 min

Example 32

(R) and (S)-4-{[(5-fluoro-8-methoxy-4H-benzo[1,3]dioxin-6-yl)-(5-oxo-1-pyrimidin-2-yl-4,5-dihydro-1H-[1,2,4]triazol-3-yl)methyl]amino}benzamidine acetate (32a) 5-fluoro-8-methoxy-4H-benzo[1,3]dioxine

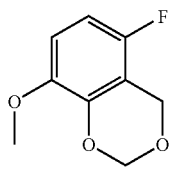

[Chemical Formula 153]

To a solution of 6.85 g of 6-fluoro-2-hydroxy-3-methoxybenzaldehyde [CAS No. 457628-15-8] in 200 ml of an ethanol:THF=1:1 mixed solvent there was added 1.52 g of sodium borohydride while cooling on ice. After stirring at room temperature for 30 minutes, 1N hydrochloric acid was added to the reaction mixture while cooling on ice. The reaction mixture was extracted with ethyl acetate and dried over anhydrous magnesium sulfate. The desiccating agent was filtered off, and the filtrate was concentrated under reduced pressure to give 3-fluoro-2-hydroxymethyl-6-methoxyphenol (6.1 g, crude product).

To a solution of the 6.1 g of 3-fluoro-2-hydroxymethyl-6-methoxyphenol in 90 ml of DMF there was added 3 g of sodium hydride (60% oily suspension) while cooling on ice, and the mixture was stirred at room temperature for 30 minutes. After adding 2.55 ml of bromochloromethane and 510 mg of sodium iodide to the reaction mixture, it was stirred at 80° C. for 6 hours under a nitrogen atmosphere. Saturated aqueous ammonium chloride was added to the reaction mixture, and extraction was performed with ethyl acetate. The organic layer was dried over anhydrous magnesium sulfate. The desiccating agent was filtered off and the filtrate was concentrated under reduced pressure. The residue was purified by silica gel column chromatography (ethyl acetate-heptane) to give the title compound (1.086 g).

$^1$H-NMR (CDCl$_3$) δ 3.85 (s, 3H) 4.91 (s, 2H) 5.29 (s, 2H) 6.59 (t, J=9.2 Hz, 1H) 6.70 (dd, J=5.2, 9.2 Hz, 1H)

(32b) 5-fluoro-8-methoxy-4H-benzo[1,3]dioxine-6-carbaldehyde

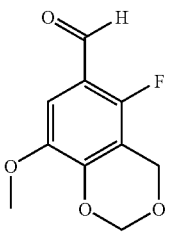

[Chemical Formula 154]

To a solution of the 1.086 g of 5-fluoro-8-methoxy-4H-benzo[1,3]dioxine and 1.28 ml of N,N,N',N',N''-pentamethyldiethylenetriamine in 10 ml of THF there was added dropwise 2.4 ml of n-butyllithium (2.55 M, hexane solution) at −74° C. The mixture was stirred at −74° C. for 1 hour, and then 0.7 ml of N-formylmorpholine was added. After stirring at room temperature for 1 hour, 1N hydrochloric acid was added thereto while cooling on ice, and the mixture was extracted with ethyl acetate and dried over anhydrous magnesium sulfate. The desiccating agent was filtered off and the filtrate was concentrated under reduced pressure. The residue was purified by silica gel column chromatography (ethyl acetate-heptane) to give the title compound (153 mg) as an oil.

$^1$H-NMR (CDCl$_3$) δ 3.91 (s, 3H) 4.95 (s, 2H) 5.36 (s, 2H) 7.22 (d, J=6.4 Hz, 1H) 10.21 (s, 1H)

(32c) {2-(5-fluoro-8-methoxy-4H-benzo[1,3]dioxin-6-yl)-2-[4-(5-methyl-[1,2,4]oxadiazol-3-yl)phenylimino]-1-methylsulfanylethylidene}carbamic acid methyl ester

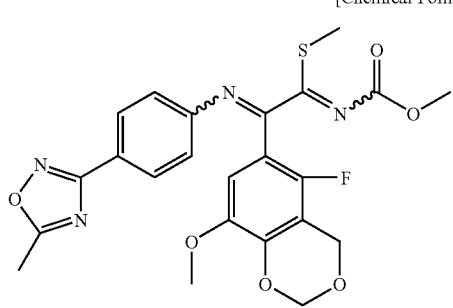

[Chemical Formula 155]

To a solution of 45 mg of Yb(OTf)$_3$ in 3 ml of THF there were added 126 mg of 4-(5-methyl-[1,2,4]oxadiazol-3-yl)phenylamine, 153 mg of 5-fluoro-8-methoxy-4H-benzo[1,3]dioxine-6-carbaldehyde, 0.2 g of MS3A and 192 µl of trimethylsilyl cyanide under a nitrogen atmosphere, and the mixture was stirred overnight at room temperature. The reaction mixture was filtered through celite, and the celite was washed with THF. The organic layer was concentrated under reduced pressure to give (5-fluoro-8-methoxy-4H-benzo[1,3]dioxin-6-yl)-[4-(5-methyl-[1,2,4]oxadiazol-3-yl)phenylamino]acetonitrile (crude product).

To a solution of this compound in 9 ml of an ethanol:THF=2:1 mixed solvent there was added 3 ml of a 20% aqueous solution of ammonium sulfide, and the mixture was stirred at 50° C. for 6 hours. Water was added to the reaction mixture and extraction was performed with ethyl acetate. The organic layer was dried over anhydrous magnesium sulfate. The desiccating agent was filtered off, and the filtrate was concentrated under reduced pressure to give 2-(5-fluoro-8-methoxy-4H-benzo[1,3]dioxin-6-yl)-2-[4-(5-methyl-[1,2,4]oxadiazol-3-yl)phenylamino]thioacetamide (310 mg, crude product).

To a solution of 310 mg of this compound in 4 ml of acetonitrile there was added 120 mg of $Me_3O^+BF_4^-$, and the mixture was stirred at room temperature for 30 minutes. Saturated aqueous sodium hydrogencarbonate was added to the reaction mixture, and extraction was performed with ethyl acetate. The organic layer was dried over anhydrous magnesium sulfate. The desiccating agent was filtered off and the filtrate was concentrated under reduced pressure.

To a solution of the residue in 2 ml of ethyl acetate there was added 1.5 g of manganese dioxide, and the mixture was stirred at room temperature for 1 hour. The reaction mixture was filtered, and the filtrate was concentrated under reduced pressure.

To a solution of the residue in 4 ml of toluene there were added 0.8 ml of 2,4,6-collidine and 0.4 ml of methyl chloroformate, and the mixture was stirred at 80° C. for 1 hour under a nitrogen atmosphere. After cooling the reaction mixture, 1N hydrochloric acid was added and extraction was performed with ethyl acetate. The organic layer was dried over anhydrous magnesium sulfate. The desiccating agent was filtered off and the filtrate was concentrated under reduced pressure. The residue was purified by silica gel column chromatography (ethyl acetate-heptane) to give the title compound (213 mg, isomeric mixture) as a yellow solid.

$^1$H-NMR (CDCl$_3$) Two main isomers:
δ 2.32 (s, 3H) 2.65 (s, 3H) 3.63 (s, 3H) 3.93 (s, 3H) 4.92 (s, 2H) 5.34 (s, 2H) 7.08 (d, J=8.4 Hz, 2H) 7.39 (d, J=6.4 Hz, 1H) 8.01 (d, J=8.8 Hz, 2H) δ 2.48 (s, 3H) 2.63 (s, 3H) 3.61 (s, 3H) 3.63 (s, 3H) 4.77 (s, 2H) 5.25 (s, 2H) 6.42 (d, J=6.4 Hz, 1H) 6.83 (d, J=8.4 Hz, 2H) 7.91 (d, J=8.8 Hz, 2H)

(32d) (R) and (S)-4-{[(5-fluoro-8-methoxy-4H-benzo[1,3]dioxin-6-yl)-(5-oxo-1-pyrimidin-2-yl-4,5-dihydro-1H-[1,2,4]triazol-3-yl)methyl]amino}benzamidine acetate

[Chemical Formula 156]

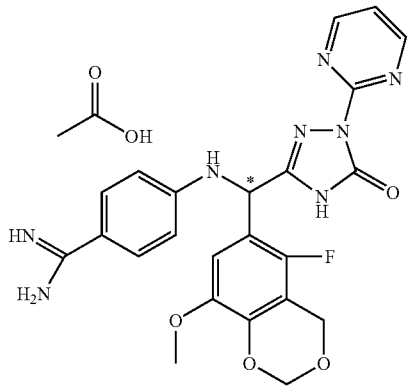

After adding 21 mg of 2-hydrazinopyrimidine and 50 μl of triethylamine to a solution of 105 mg of {2-(5-fluoro-8-methoxy-4H-benzo[1,3]dioxin-6-yl)-2-[4-(5-methyl-[1,2,4]oxadiazol-3-yl)phenylimino]-1-methylsulfanylethylidene}carbamic acid methyl ester in 2 ml of DMF, the mixture was stirred overnight at 85° C. under a nitrogen atmosphere. The reaction mixture was concentrated, and the residue was dissolved in 3 ml of methanol and 0.3 ml of acetic acid. After adding 100 mg of sodium cyanotrihydroborate to the reaction mixture, the mixture was stirred at room temperature for 1 hour. Water was added to the reaction mixture and extraction was performed with ethyl acetate. The organic layer was dried over anhydrous magnesium sulfate. The desiccating agent was filtered off and the filtrate was concentrated under reduced pressure. The residue was purified by NAM silica gel column chromatography (methanol-ethyl acetate) to give 5-{(5-fluoro-8-methoxy-4H-benzo[1,3]dioxin-6-yl)-[4-(5-methyl-[1,2,4]oxadiazol-3-yl)phenylamino]methyl}-2-pyrimidin-2-yl-2,4-dihydro-[1,2,4]triazol-3-one (74 mg) as a light brown solid.

To a solution of 74 mg of this compound in 3.5 ml of a methanol:water:acetic acid=1:1:1.5 mixed solvent there was added 100 mg of iron powder, and the mixture was stirred overnight at 60° C. under a nitrogen atmosphere. After filtering the reaction mixture, it was purified by reverse-phase high performance liquid chromatography (acetonitrile-water, 0.1% acetic acid) to give 4-{[(5-fluoro-8-methoxy-4H-benzo[1,3]dioxin-6-yl)-(5-oxo-1-pyrimidin-2-yl-4,5-dihydro-1H-[1,2,4]triazol-3-yl)methyl]amino}benzamidine acetate (47 mg).

Mass spectrum (ESI) m/z: 493 (M+H)$^+$ 47 mg of this compound was optically resolved using a SUMICHIRAL OA-2500 column, and the first eluting enantiomer (16.5 mg) of the title compound was obtained as a white solid.

$^1$H-NMR (CD$_3$OD) δ 1.92 (s, 3H) 3.75 (s, 3H) 4.92 (m, 2H) 5.23 (d, J=1.6 Hz, 2H) 5.87 (s, 1H) 6.84 (d, J=8.8 Hz, 2H) 7.03 (d, J=7.2 Hz, 1H) 7.29 (t, J=4.8 Hz, 1H) 7.60 (d, J=8.8 Hz, 2H) 8.75 (d, J=4.8 Hz, 2H)

HPLC retention time: 17 min

Example 33

(R) and (S)-4-{[(5-fluoro-8-methoxychroman-6-yl)-(5-oxo-1-pyrimidin-2-yl-4,5-dihydro-1H-[1,2,4]triazol-3-yl)methyl]amino}benzamidine acetate (33a)
3-fluoro-2-(3-hydroxypropyl)-6-methoxyphenol

[Chemical Formula 157]

To a solution of 4.46 g of 6-fluoro-2-hydroxy-3-methoxybenzaldehyde in 50 ml of dichloromethane there was added 10 g of (triphenyl phosphoranilidene)acetic acid ethyl ester while cooling on ice. After stirring at room temperature for 30 minutes, the reaction mixture was poured into a silica gel column and elution was performed with heptane-ethyl acetate=3:1. The eluate was concentrated under reduced pressure. The residue was dissolved in 100 ml of ethyl acetate, 1 g of 10% palladium-carbon was added, and the mixture was stirred at room temperature for 7 hours under a hydrogen atmosphere. The reaction mixture was filtered through celite, and the filtrate was concentrated under reduced pressure. The residue was dissolved in 100 ml of THF, and then 2 g of lithium borohydride was added while cooling on ice and the mixture was stirred overnight at room temperature. After adding 1N hydrochloric acid to the reaction mixture while cooling on ice, extraction was performed with ethyl acetate. The organic layer was dried over anhydrous magnesium sulfate. The desiccating agent was filtered off and the filtrate was concentrated under reduced pressure. The residue was purified by silica gel column chromatography (ethyl acetate-heptane) to give the title compound (4.78 g) as a solid.

$^1$H-NMR (CDCl$_3$) δ 1.85 (sept, J=6.8 Hz, 2H) 2.80 (dt, J=1.6, 6.8 Hz, 2H) 3.59 (t, J=6.0 Hz, 2H) 3.86 (s, 3H) 6.54 (t, J=9.2 Hz, 1H) 6.64 (dd, J=4.8, 8.8 Hz, 1H)

(33b) 5-fluoro-8-methoxychromane

[Chemical Formula 158]

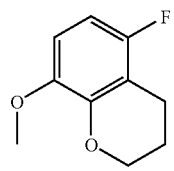

After dissolving 4.78 g of 3-fluoro-2-(3-hydroxypropyl)-6-methoxyphenol and 9.4 g of triphenylphosphine in 70 ml of THF under a nitrogen atmosphere, the solution was cooled to −74° C. Next, 7 ml of DIAD was added to the reaction mixture, and the temperature was allowed to rise to room temperature prior to stirring overnight. The reaction mixture was concentrated, and the residue was purified by silica gel column chromatography (ethyl acetate-heptane) to give the title compound (3.6 g) as an oil.

(33c) 5-fluoro-8-methoxychromane-6-carbaldehyde

[Chemical Formula 159]

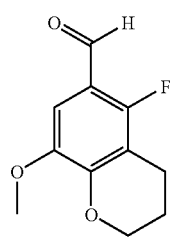

To a solution of 3.6 g of 5-fluoro-8-methoxychromane and 4.2 ml of N,N,N',N',N"-pentamethyldiethylenetriamine in 130 ml of THF there was added dropwise 8 ml of n-butyl-lithium (2.55 M, hexane solution) at −74° C. After stirring at −74° C. for 1 hour, N-formylmorpholine was added. After further stirring at room temperature for 1 hour, 1N hydrochloric acid was added to the reaction mixture while cooling on ice, and the mixture was extracted with ethyl acetate and dried over anhydrous magnesium sulfate. The desiccating agent was filtered off and the filtrate was concentrated under reduced pressure. The residue was purified by silica gel column chromatography (ethyl acetate-heptane) to give the title compound (1.50 g) as a white solid.

$^1$H-NMR (CDCl$_3$) δ 2.03-2.10 (m, 2H) 2.80 (t, J=6.4 Hz, 2H) 3.90 (s, 3H) 4.36 (t, J=5.2 Hz, 2H) 7.16 (d, J=6.4 Hz, 1H) 10.24 (s, 1H)

(33d) [2-(5-fluoro-8-methoxychroman-6-yl)-2-[4-(5-methyl-[1,2,4]oxadiazol-3-yl)phenylimino]-1-methylsulfanylethylidene]carbamic acid methyl ester

[Chemical Formula 160]

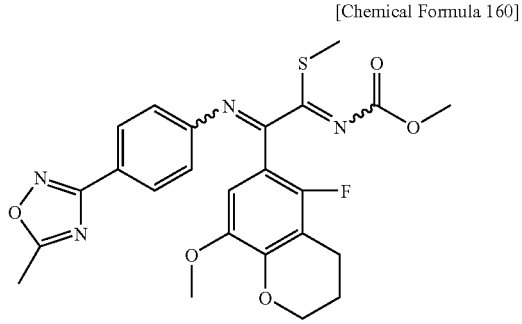

After adding 940 mg of 4-(5-methyl-[1,2,4]oxadiazol-3-yl)phenylamine, 1.125 g of 5-fluoro-8-methoxychromane-6-carbaldehyde, 1 g of MS3A and 1.43 ml of trimethylsilyl cyanide to a solution of 330 mg of Yb(OTf)$_3$ in 20 ml of THF under a nitrogen atmosphere, the mixture was stirred overnight at room temperature. The reaction mixture was filtered through celite, and the celite was washed with ethyl acetate. The organic layer was concentrated under reduced pressure to give (5-fluoro-8-methoxychroman-6-yl)-[4-(5-methyl-[1,2,4]oxadiazol-3-yl)phenylamino]acetonitrile (crude product).

$^1$H-NMR (CDCl$_3$) δ 2.00-2.09 (m, 2H) 2.64 (s, 3H) 2.78 (t, J=6.4 Hz, 2H) 3.90 (s, 3H) 4.30 (t, J=4.8 Hz, 2H) 5.58 (d, J=6.4 Hz, 1H) 6.84 (d, J=8.4 Hz, 2H) 6.89 (d, J=6.8 Hz, 1H) 7.98 (d, J=8.4 Hz, 2H)

To a solution of this compound in 45 ml of an ethanol:THF=2:1 mixed solvent there was added 15 ml of a 20% aqueous solution of ammonium sulfide, and the mixture was stirred overnight at room temperature. Water was added to the reaction mixture and extraction was performed with ethyl acetate. The organic layer was dried over anhydrous magnesium sulfate. The desiccating agent was filtered off, and the filtrate was concentrated under reduced pressure to give 2-(5-fluoro-8-methoxychroman-6-yl)-2-[4-(5-methyl-[1,2,4]oxadiazol-3-yl)-2-phenylamino]thioacetamide (crude product).

$^1$H-NMR (d$_6$-DMSO) δ 1.85-1.93 (m, 2H) 2.59 (s, 3H) 2.66 (t, J=6.0 Hz, 2H) 3.69 (s, 3H) 4.12 (t, J=6.0 Hz, 2H) 5.38 (d, J=6.4 Hz, 1H) 6.70-6.81 (m, 3H) 6.95 (d, J=6.8 Hz, 1H) 7.73 (d, J=8.4 Hz, 2H) 9.50 (s, 1H) 9.89 (s, 1H)

To a solution of this compound in 40 ml of acetonitrile there was added 900 mg of Me$_3$O$^+$BF$_4^-$, and the mixture was stirred at room temperature for 1 hour. Saturated aqueous sodium hydrogencarbonate was added to the reaction mixture and extraction was performed with ethyl acetate. The organic layer was dried over anhydrous magnesium sulfate. The desiccating agent was filtered off, and the filtrate was concentrated under reduced pressure to give 2-(5-fluoro-8-methoxy-chroman-6-yl)-2-[4-(5-methyl-[1,2,4]oxadiazol-3-yl)-2-phenylamino]thioacetamide acid methyl ester (crude product).

$^1$H-NMR (CDCl$_3$) δ 1.90-2.06 (m, 2H) 2.35 (s, 3H) 2.61 (s, 3H) 2.79 (t, J=6.4 Hz, 2H) 3.80 (s, 3H) 4.26 (t, J=5.2 Hz, 2H) 5.36 (br.s, 2H) 6.64-6.70 (m, 3H) 6.86 (d, J=8.8 Hz, 2H) 7.98 (d, J=8.4 Hz, 2H)

To a solution of this compound in 50 ml of ethyl acetate there was added 10 g of manganese dioxide, and the mixture was stirred at room temperature for 1 hour. The reaction mixture was filtered, and the filtrate was concentrated under reduced pressure.

To a solution of the residue in 40 ml of toluene there were added 4 ml of 2,4,6-collidine and 2 ml of methyl chloroformate, and the mixture was stirred at 80° C. for 1 hour under a nitrogen atmosphere. After cooling the reaction mixture, 1N hydrochloric acid was added and extraction was performed with ethyl acetate. The organic layer was dried over anhydrous magnesium sulfate. The desiccating agent was filtered off and the filtrate was concentrated under reduced pressure. The residue was purified by silica gel column chromatography (ethyl acetate-heptane) to give the title compound (1.09 g, isomeric mixture) as a yellow solid.

$^1$H-NMR (CDCl$_3$) Two main isomers:

δ 2.01-2.06 (m, 2H) 2.33 (s, 3H) 2.65 (s, 3H) 2.76 (t, J=6.4 Hz, 2H) 3.58 (s, 3H) 3.91 (s, 3H) 4.32 (t, J=4.8 Hz, 2H) 7.30 (d, J=7.2 Hz, 1H) 7.09 (d, J=8.0 Hz, 2H) 8.00 (d, J=8.4 Hz, 2H)

δ 1.93-2.00 (m, 2H) 2.48 (s, 3H) 2.63 (s, 3H) 2.61-2.64 (m, 2H) 3.58 (s, 3H) 3.62 (s, 3H) 4.23 (t, J=4.8 Hz, 2H) 6.30 (d, J=6.0 Hz, 1H) 6.84 (d, J=8.4 Hz, 2H) 7.90 (d, J=8.0 Hz, 2H)

(33e) (R) and (S)-4-{[(5-fluoro-8-methoxychroman-6-yl)-(5-oxo-1-pyrimidin-2-yl-4,5-dihydro-1H-[1,2,4]triazol-3-yl)methyl]amino}benzamidine acetate

[Chemical Formula 161]

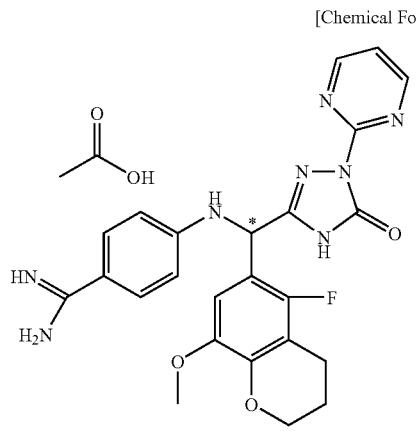

After adding 23 mg of 2-hydrazinopyrimidine and 35 μl of triethylamine to a solution of 113 mg of [2-(5-fluoro-8-methoxychroman-6-yl)-2-[4-(5-methyl-[1,2,4]oxadiazol-3-yl)phenylimino]-1-methylsulfanylethylidene]carbamic acid methyl ester in 2 ml of DMF, the mixture was stirred overnight at 85° C. under a nitrogen atmosphere. The reaction mixture was concentrated, and the residue was dissolved in 5 ml of methanol and 0.5 ml of acetic acid. After adding 100 mg of sodium cyanotrihydroborate to the reaction mixture it was stirred at room temperature for 1 hour. Water was added to the reaction mixture and extraction was performed with ethyl acetate. The organic layer was dried over anhydrous magnesium sulfate. The desiccating agent was filtered off and the filtrate was concentrated under reduced pressure. The residue was purified by NAM silica gel column chromatography (methanol-ethyl acetate) to give 5-{(5-fluoro-8-methoxychroman-6-yl)-[4-(5-methyl-[1,2,4]oxadiazol-3-yl)phenylamino]methyl}-2-pyrimidin-2-yl-2,4-dihydro-[1,2,4]triazol-3-one (82 mg) as a light brown solid.

$^1$H-NMR (CDCl$_3$) δ 1.94-2.00 (m, 2H) 2.58 (s, 3H) 2.71 (t, J=6.4 Hz, 2H) 3.60 (s, 3H) 4.21 (t, J=4.4 Hz, 2H) 6.00 (br.s, 2H) 6.78 (d, J=8.8 Hz, 2H) 6.94 (d, J=6.8 Hz, 1H) 7.15 (t, J=4.4 Hz, 1H) 7.80 (d, J=8.8 Hz, 2H) 8.70 (d, J=4.8 Hz, 2H) 10.57 (br.s, 1H)

To a solution of 82 mg of this compound in 3.5 ml of a methanol:water:acetic acid=1:1:1.5 mixed solvent there was added 100 mg of iron powder, and the mixture was stirred overnight at 60° C. under a nitrogen atmosphere. After filtering the reaction mixture, it was purified by reverse-phase high performance liquid chromatography (acetonitrile-water, 0.1% acetic acid) to give 4-{[(5-fluoro-8-methoxychroman-6-yl)-(5-oxo-1-pyrimidin-2-yl-4,5-dihydro-1H-[1,2,4]triazol-3-yl)methyl]amino}benzamidine acetate (47 mg).

Mass spectrum (ESI) m/z: 491 (M+H)$^+$ 47 mg of this compound was optically resolved using a SUMICHIRAL OA-2500 column, and the first eluting enantiomer (17.0 mg) of the title compound was obtained as a white solid.

$^1$H-NMR (CD$_3$OD) δ 1.92 (s, 3H) 1.96-2.00 (m, 2H) 2.76 (t, J=6.4 Hz, 2H) 3.72 (s, 3H) 4.18 (t, J=5.6 Hz, 2H) 5.88 (s, 1H) 6.85 (d, J=9.2 Hz, 2H) 6.93 (d, J=7.2 Hz, 1H) 7.30 (t, J=4.8 Hz, 1H) 7.60 (d, J=9.2 Hz, 2H) 8.75 (d, J=4.4 Hz, 2H)

HPLC retention time: 15 min

Example 34

(R) and (S)-4-({[1-(3-aminopyridin-2-yl)-5-oxo-4,5-dihydro-1H-[1,2,4]triazol-3-yl]-(9-methoxy-3,4-dihydro-2H-benzo[b][1,4]oxepin-7-yl)methyl}amino)benzamidine acetate (34a) 5-{(9-methoxy-3,4-dihydro-2H-benzo[b][1,4]dioxepin-7-yl)-[4-(5-methyl-[1,2,4]oxadiazol-3-yl)phenylamino]methyl]-2-(3-nitropyridin-2-yl)-2,4-dihydro-[1,2,4]triazol-3-one

[Chemical Formula 162]

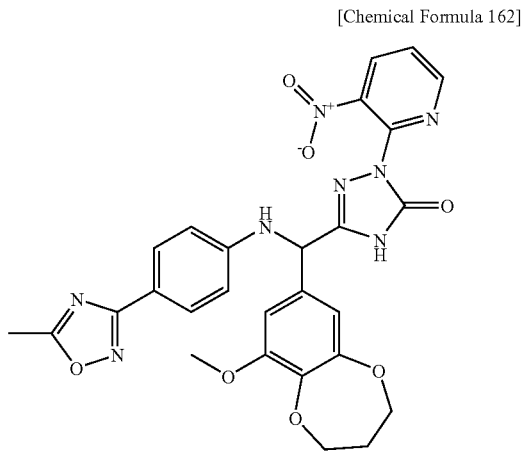

After adding 37.3 mg of (3-nitropyridin-2-yl)hydrazine and 37 μl of triethylamine to a solution of 109 mg of [2-(9-methoxy-3,4-dihydro-2H-benzo[b][1,4]dioxepin-7-yl)-2-[4-(5-methyl-[1,2,4]oxadiazol-3-yl)phenylimino]-1-methylsulfanylethylidene]carbamic acid methyl ester (Example (30c)) in 5 ml of DMF under a nitrogen atmosphere, the mixture was heated at 85° C. for 20 hours. The reaction mixture was concentrated under reduced pressure, the residue was dissolved in 20 ml of a methanol:THF=1:1 mixed solvent, 83 mg of sodium cyanotrihydroborate and 32 μl of acetic acid were added and the mixture was stirred at room temperature for 24 hours. After adding 100 ml of ethyl acetate and 50 ml of water, filtration was performed with celite. The aqueous layer was extracted with 50 ml of ethyl acetate, and then the organic layers were combined and dried over anhydrous magnesium sulfate, the desiccating agent was filtered off and the filtrate was concentrated under reduced pressure. The residue was purified by NAM silica gel column chromatography (methanol-ethyl acetate (1:40)) to give the title compound (59 mg) as a light yellow solid.

$^1$H-NMR (CDCl$_3$) δ 2.18 (quint, J=5.9 Hz, 2H) 2.60 (s, 3H) 3.58 (s, 3H) 4.44 (t, J=5.9 Hz, 2H) 4.57 (t, J=5.9 Hz, 2H) 5.52 (s, 1H) 6.72 (d, J=2.3 Hz, 1H) 6.75 (d, J=2.3 Hz, 1H) 6.75 (d, J=8.2 Hz, 2H) 7.53 (dd, J=7.6, 5.3 Hz, 1H) 7.75 (d, J=8.2 Hz, 2H) 8.36 (dd, J=7.6, 0.9 Hz, 1H) 8.52 (dd, J=5.3, 0.9 Hz, 1H)

(34b) 4-({[1-(3-aminopyridin-2-yl)-5-oxo-4,5-dihydro-1H-[1,2,4]triazol-3-yl]-(9-methoxy-3,4-dihydro-2H-benzo[b][1,4]dioxepin-7-yl)methyl}amino)benzamidine trifluoroacetate

[Chemical Formula 163]

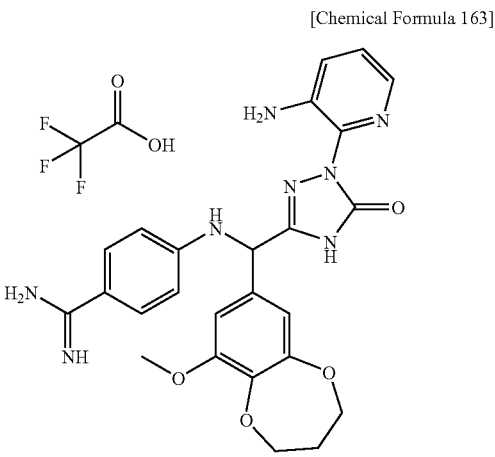

To a solution of 59 mg of 5-{(9-methoxy-3,4-dihydro-2H-benzo[b][1,4]dioxepin-7-yl)-[4-(5-methyl-[1,2,4]oxadiazol-3-yl)phenylamino]methyl]-2-(3-nitropyridin-2-yl)-2,4-dihydro-[1,2,4]triazol-3-one in 4.5 ml of a methanol:water:acetic acid=1:1:1 mixed solvent there was added 69 mg of iron powder, and the mixture was stirred at 55° C. for 15 hours under a nitrogen atmosphere. After filtering the reaction mixture, it was purified by reverse-phase high performance liquid chromatography (acetonitrile-water, 0.1% trifluoroacetic acid) to give the title compound (22 mg) as a white solid.

$^1$H-NMR (CD$_3$OD) δ 2.16 (quint, J=5.8 Hz, 2H) 3.83 (s, 3H) 4.15 (q, J=5.8 Hz, 4H) 5.65 (s, 1H) 6.80 (d, J=2.1 Hz, 1H) 6.87 (d, J=8.8 Hz, 2H) 6.88 (d, J=2.1 Hz, 1H) 7.31 (dd, J=8.0, 5.5 Hz, 1H) 7.44 (d, J=8.0 Hz, 1H) 7.64 (d, J=8.8 Hz, 2H) 7.84 (d, J=5.5 Hz, 1H)

(34c) (R) and (S)-4-({[1-(3-aminopyridin-2-yl)-5-oxo-4,5-dihydro-1H-[1,2,4]triazol-3-yl]-(9-methoxy-3,4-dihydro-2H-benzo[b][1,4]dioxepin-7-yl)methyl}amino)benzamidine acetate

[Chemical Formula 164]

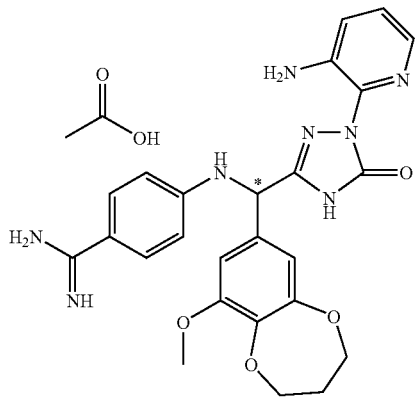

A SUMICHIRAL OA-2500 column was used for optical resolution of 22 mg of 4-({[1-(3-aminopyridin-2-yl)-5-oxo-4,5-dihydro-1H-[1,2,4]triazol-3-yl]-(9-methoxy-3,4-dihydro-2H-benzo[b][1,4]dioxepin-7-yl)methyl}amino)benzamidine trifluoroacetate, and the first eluting enantiomer (5.9 mg) of the title compound was obtained as a white solid.

$^1$H-NMR (CD$_3$OD) δ 1.93 (s, 3H) 2.16 (quint, J=5.8 Hz, 2H) 3.82 (s, 3H) 4.15 (q, J=5.8 Hz, 4H) 5.59 (s, 1H) 6.81 (d, J=2.3 Hz, 1H) 6.86 (d, J=8.8 Hz, 2H) 6.89 (d, J=2.3 Hz, 1H) 7.22 (dd, J=8.4, 4.9 Hz, 1H) 7.33 (dd, J=8.4, 1.9 Hz, 1H) 7.61 (d, J=8.8 Hz, 2H) 7.83 (dd, J=4.9, 1.9 Hz, 1H)

HPLC retention time: 8 min

Example 35

(R) and (S)-4-({[1-(3-aminopyridin-2-yl)-5-oxo-4,5-dihydro-1H-[1,2,4]triazol-3-yl]-(3-ethoxy-4-methoxyphenyl)methyl}amino)benzamidine acetate (35a) 4-({[1-(3-aminopyridin-2-yl)-5-oxo-4,5-dihydro-1H-[1,2,4]triazol-3-yl]-(3-ethoxy-4-methoxyphenyl)methyl}amino)benzamidine trifluoroacetate

[Chemical Formula 165]

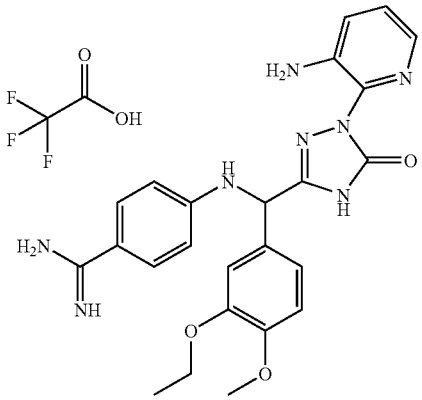

After adding 28 mg of (3-nitropyridin-2-yl)hydrazine and 32 μl of triethylamine to a solution of 105 mg of {2-(3- ethoxy-4-methoxyphenyl)-2-[4-(5-methyl-[1,2,4]oxadiazol-3-yl)phenylimino]-1-methylsulfanylethylidene}carbamic acid methyl ester (Example (17e)) in 3 ml of DMF, the mixture was stirred at 85° C. for 16 hours under a nitrogen atmosphere. The reaction mixture was concentrated, and the residue was dissolved in 4 ml of a methanol:THF=1:1 mixed solvent. After adding 46 μl of acetic acid and 71 mg of sodium cyanotrihydroborate to the solution, the mixture was stirred at room temperature for 6 hours. After filtering the reaction mixture, it was purified by reverse-phase high performance liquid chromatography (acetonitrile-water, 0.1% acetic acid) to give 59 mg of 5-{(3-ethoxy-4-methoxyphenyl)-[4-(5-methyl-[1,2,4]oxadiazol-3-yl)phenylamino]methyl]-2-(3-nitropyridin-2-yl)-2,4-dihydro-[1,2,4]triazol-3-one.

To a solution of this compound in 3 ml of a methanol:water:acetic acid=1:1:1 mixed solvent there was added 30 mg of iron powder, and the mixture was stirred at 55° C. for 20 hours under a nitrogen atmosphere. After filtering the reaction mixture, it was purified by reverse-phase high performance liquid chromatography (acetonitrile-water, 0.1% trifluoroacetic acid) to give the title compound (13 mg) as a white solid.

$^1$H-NMR (CD$_3$OD) δ 1.38 (t, J=7.8 Hz, 3H) 3.83 (s, 3H) 4.03-4.10 (m, 2H) 5.66 (s, 1H) 6.88 (d, J=8.4 Hz, 2H) 6.99 (d, J=8.2 Hz, 1H) 7.09 (dd, J=8.2, 1.3 Hz, 1H) 7.12 (d, J=1.3 Hz, 1H) 7.27 (dd, J=8.4, 4.7 Hz, 1H) 7.39 (dd, J=8.4, 1.6 Hz, 1H) 7.62 (d, J=8.4 Hz, 2H) 7.83 (dd, J=4.7, 1.6 Hz, 1H)

(35b) (R) and (S)-4-({[1-(3-aminopyridin-2-yl)-5-oxo-4,5-dihydro-1H-[1,2,4]triazol-3-yl]-(3-ethoxy-4-methoxyphenyl)methyl}amino)benzamidine acetate

[Chemical Formula 166]

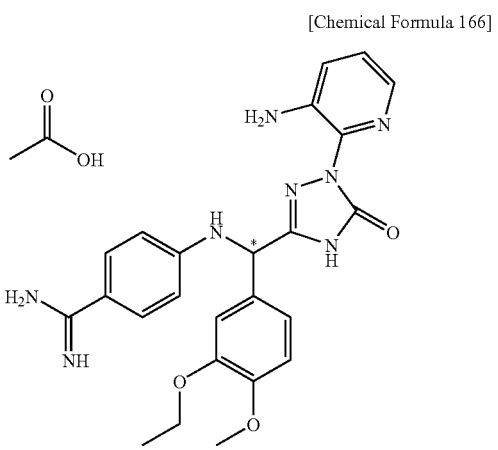

A SUMICHIRAL OA-2500 column was used for optical resolution of 13 mg of 4-({[1-(3-aminopyridin-2-yl)-5-oxo-4,5-dihydro-1H-[1,2,4]triazol-3-yl]-(3-ethoxy-4-methoxyphenyl)methyl}amino)}benzamidine trifluoroacetate, and the first eluting enantiomer (2.2 mg) of the title compound was obtained as a white solid.

$^1$H-NMR (CD$_3$OD) δ 1.37 (t, J=7.8 Hz, 3H) 1.91 (s, 3H) 3.83 (s, 3H) 4.03-4.10 (m, 2H) 5.58 (s, 1H) 6.85 (d, J=8.8 Hz, 2H) 6.95 (d, J=8.4 Hz, 1H) 7.09 (dd, J=8.4, 1.3 Hz, 1H) 7.13 (d, J=1.3 Hz, 1H) 7.21 (dd, J=8.3, 4.4 Hz, 1H) 7.33 (dd, J=8.3, 1.6 Hz, 1H) 7.63 (d, J=8.8 Hz, 2H) 7.83 (dd, J=4.4, 1.6 Hz, 1H)

HPLC retention time: 7 min

Example 36

(R) and (S)-2-{3-[(4-carbamimidoylphenylamino)-(3,4-dimethoxyphenyl)methyl]-5-oxo-4,5-dihydro-[1,2,4]triazol-1-yl}benzoic acid acetate (36a) (3,4-dimethoxyphenyl)-[4-(5-methyl-[1,2,4]oxadiazol-3-yl)phenylamino]acetonitrile

[Chemical Formula 167]

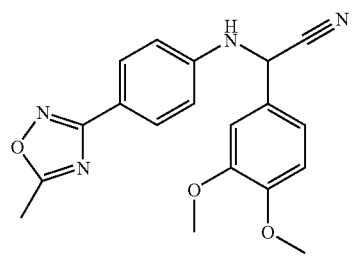

After adding 0.887 g of 4-(5-methyl-[1,2,4]oxadiazol-3-yl)phenylamine, 0.831 g of 3,4-dimethoxybenzaldehyde, 1 g of MS3A and 1 ml of trimethylsilyl cyanide to a solution of 0.31 g of Yb(OTf)$_3$ in 20 ml of dichloromethane under a nitrogen atmosphere, the mixture was stirred at room temperature for 22 hours. After then adding 200 ml of ethyl acetate to the reaction mixture, it was filtered through celite and the celite was washed with 200 ml of ethyl acetate. The organic layers were combined and washed with water and saturated brine, and then dried over anhydrous magnesium sulfate. The desiccating agent was filtered off and the filtrate was concentrated under reduced pressure. The residue was purified by silica gel column chromatography (ethyl acetate-heptane) to give the title compound (1.75 g) as a light yellow solid.

$^1$H-NMR (CDCl$_3$) δ 2.63 (s, 3H) 3.91 (s, 3H) 3.92 (s, 3H) 4.30 (d, J=5.5 Hz, 1H) 5.44 (d, J=5.5 Hz, 1H) 6.84 (d, J=8.8 Hz, 2H) 6.93 (d, J=7.8 Hz, 1H) 7.06 (d, J=2.0 Hz, 1H) 7.18 (dd, J=7.8, 2.0 Hz, 1H) 7.98 (d, J=8.8 Hz, 2H)

(36b) 2-(3,4-dimethoxyphenyl)-2-[4-(5-methyl-[1,2,4]oxadiazol-3-yl)phenylamino]thioacetamide

[Chemical Formula 168]

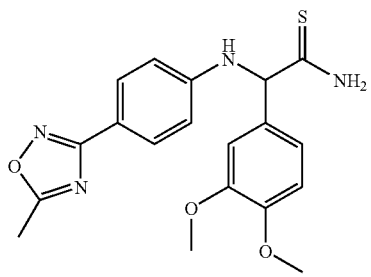

To a solution of 1.25 g of (3,4-dimethoxyphenyl)-[4-(5-methyl-[1,2,4]oxadiazol-3-yl)phenylamino]acetonitrile in 120 ml of an ethanol:THF=2:1 mixed solvent there was added 10 ml of a 20% aqueous solution of ammonium sulfide, and the mixture was stirred at room temperature for 60 hours. Next, 500 ml of ethyl acetate and 400 ml of water were added to the reaction solution, and the organic layer was washed twice with 300 ml of water and once with 300 ml of saturated brine, and was then dried over anhydrous magnesium sulfate. The desiccating agent was filtered off, and after concentrating the filtrate under reduced pressure, 10 ml of t-butyl methyl ether was added to the residue prior to filtration. The solid was washed with 10 ml of t-butyl methyl ether to give the title compound (1.34 g) as a white solid.

$^1$H-NMR (CDCl$_3$) δ 2.63 (s, 3H) 3.88 (s, 3H) 3.89 (s, 3H) 4.95 (br.s, 1H) 5.15 (s, 1H) 6.72 (d, J=8.8 Hz, 2H) 6.88 (d, J=7.8 Hz, 1H) 6.96 (d, J=2.0 Hz, 1H) 7.04 (dd, J=7.8, 2.0 Hz, 1H) 7.57 (br.s, 1H) 7.90 (d, J=8.8 Hz, 2H) 8.10 (br.s, 1H)

(36c) 2-(3,4-dimethoxyphenyl)-2-[4-(5-methyl-[1,2,4]oxadiazol-3-yl)phenylamino]thioacetimidic acid methyl ester

[Chemical Formula 169]

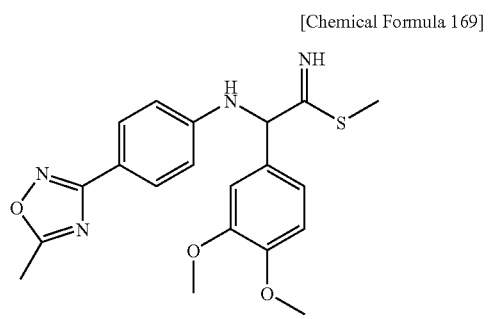

After adding 170 mg of Me$_3$O$^+$BF$_4$$^-$ to a solution of 385 mg of 2-(3,4-dimethoxyphenyl)-2-[4-(5-methyl-[1,2,4]oxadiazol-3-yl)phenylamino]thioacetamide in 30 ml of dichloromethane under a nitrogen atmosphere, the mixture was stirred at room temperature for 18 hours. Next, 200 ml of ethyl acetate and 100 ml of a 5% aqueous sodium hydrogen carbonate solution were added to the reaction mixture. The organic layer was washed 100 ml of saturated brine and dried over anhydrous magnesium sulfate. The desiccating agent was filtered, and the filtrate was concentrated under reduced pressure to give the title compound (371 mg, crude product).

$^1$H-NMR (CDCl$_3$) δ 2.30 (br.s, 3H) 2.61 (s, 3H) 3.88 (s, 6H) 5.1 (br.s, 1H) 6.66 (d, J=8.8 Hz, 2H) 6.87 (d, J=7.8 Hz, 1H) 6.90-7.05 (br.s, 2H) 7.86 (d, J=8.8 Hz, 2H)

(36d) [2-(3,4-dimethoxyphenyl)-2-[4-(5-methyl-[1,2,4]oxadiazol-3-yl)phenylimino]-1-methylsulfanylethylidene]carbamic acid methyl ester

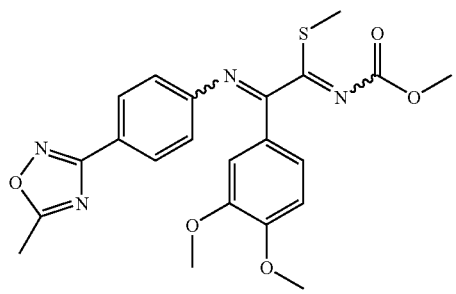

To a solution of 0.784 g of 2-(3,4-dimethoxyphenyl)-2-[4-(5-methyl-[1,2,4]oxadiazol-3-yl)phenylamino]thioacetim-idic acid methyl ester in 21.1 ml of toluene there were added 0.393 ml of 2,4,6-collidine and 0.304 ml of methyl chloroformate under a nitrogen atmosphere, and the mixture was stirred at 80° C. for 15 hours. After cooling the reaction mixture, 150 ml of ethyl acetate and 50 ml of water were added and the pH was adjusted to 4 with a few drops of sulfuric acid. The organic layer was washed with 50 ml of water and 50 ml of saturated brine, and dried over anhydrous magnesium sulfate. The desiccating agent was filtered, and the filtrate was concentrated under reduced pressure. The residue was purified by silica gel column chromatography (ethyl acetate-heptane) to give the title compound (0.436 g) as a light yellow solid.

$^1$H-NMR (CDCl$_3$) δ 2.35 (s, 3H) 2.66 (s, 3H) 3.64 (s, 3H) 3.95 (s, 3H) 3.96 (s, 3H) 6.90 (d, J=7.8 Hz, 1H) 7.09 (dd, J=8.8 Hz, 2H) 7.31 (dd, J=7.8, 2.0 Hz, 1H) 7.61 (d, J=2.0 Hz, 1H) 8.03 (d, J=8.8 Hz, 2H)

(36e) 2-(3-{(3,4-dimethoxyphenyl)-[4-(5-methyl-[1,2,4]oxadiazol-3-yl)phenylimino]methyl}-5-oxo-4,5-dihydro-[1,2,4]triazol-1-yl)benzoic acid

[Chemical Formula 170]

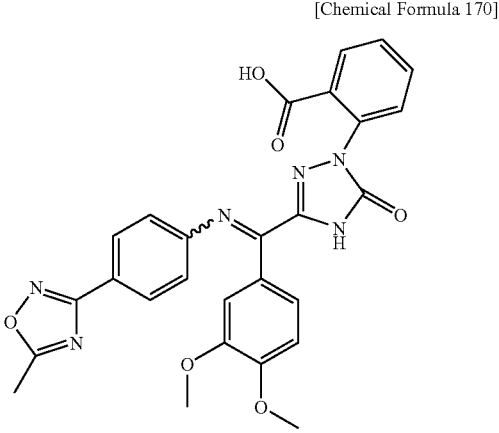

After adding 38 mg of 2-hydrazinobenzoic acid hydrochloride and 0.056 ml of triethylamine to a solution of 91 mg of [2-(3,4-dimethoxyphenyl)-2-[4-(5-methyl-[1,2,4]oxadiazol-3-yl)phenylimino]-1-methylsulfanylethylidene]carbamic acid methyl ester in 5 ml of DMF, the mixture was stirred at 90° C. for 20 hours under a nitrogen atmosphere. After cooling the reaction mixture to room temperature, 30 ml of water was added, hydrochloric acid was added (for adjustment to pH 3-4), and extraction was performed with 50 ml of ethyl acetate. The organic layer was washed twice with 30 ml of water and once with 30 ml of saturated brine, and then dried over anhydrous magnesium sulfate. The desiccating agent was filtered, and the filtrate was concentrated under reduced pressure. The residue was purified by NAM silica gel column chromatography (methanol-dichloromethane) to give the title compound (34 mg) as a light yellow solid.

$^1$H-NMR (CD$_3$OD) δ 2.63 (s, 3H) 3.58 (s, 3H) 3.79 (s, 3H) 6.85-6.88 (m, 2H) 6.92 (d, J=8.8 Hz, 2H) 7.03 (dd, J=7.8, 2.0 Hz, 1H) 7.54 (t, J=7.5 Hz, 1H) 7.59 (d, J=7.5 Hz, 1H) 7.68 (t, J=7.5 Hz, 1H) 7.90 (d, J=8.8 Hz, 2H) 7.99 (d, J=7.5 Hz, 1H)

Mass spectrum (ESI) m/z: 527 (M+H)$^+$ (36f) 2-(3-{(3,4-dimethoxyphenyl)-[4-(5-methyl-[1,2,4]oxadiazol-3-yl)phenylamino]methyl}-5-oxo-4,5-dihydro-[1,2,4]triazol-1-yl)benzoic acid

[Chemical Formula 171]

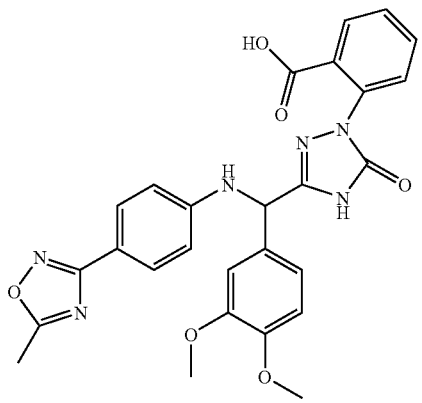

After adding 16.3 mg of sodium cyanotrihydroborate and 0.0074 ml of acetic acid to a solution of 34 mg of 2-(3-{(3,4-dimethoxyphenyl)-[4-(5-methyl-[1,2,4]oxadiazol-3-yl)phenylimino]methyl}-5-oxo-4,5-dihydro-[1,2,4]triazol-1-yl)benzoic acid in 6 ml of a methanol:THF=2:1 mixed solvent, the mixture was stirred at room temperature for 20 hours. Next, 0.1 ml of 5N hydrochloric acid was added to the reaction mixture and the mixture was stirred at room temperature for 10 minutes, after which 10 ml of ethyl acetate and 5 ml of water were added and filtration was performed with celite. The aqueous layer was extracted with 10 ml of ethyl acetate, and the organic layers were combined and dried over anhydrous magnesium sulfate. The desiccating agent was filtered, and the filtrate was concentrated under reduced pressure. The residue was purified by NAM silica gel column chromatography (methanol-dichloromethane) to give the title compound (25 mg) as a white solid.

$^1$H-NMR (CD$_3$OD) δ 2.59 (s, 3H) 3.83 (s, 3H) 3.86 (s, 3H) 5.58 (s, 1H) 6.84 (d, J=8.8 Hz, 2H) 6.98 (d, J=7.8 Hz, 1H) 7.09 (dd, J=7.8, 2.0 Hz, 1H) 7.15 (d, J=2.0 Hz, 1H) 7.52 (t, J=7.5 Hz, 1H) 7.53 (d, J=7.5 Hz, 1H) 7.65 (t, J=7.5 Hz, 1H) 7.80 (d, J=8.8 Hz, 2H) 7.96 (d, J=7.5 Hz, 1H)

(36g) (R) and (S)-2-{3-[(4-carbamimidoylphenylamino)-(3,4-dimethoxyphenyl)methyl]-5-oxo-4,5-dihydro-[1,2,4]triazol-1-yl}benzoic acid acetate

[Chemical Formula 172]

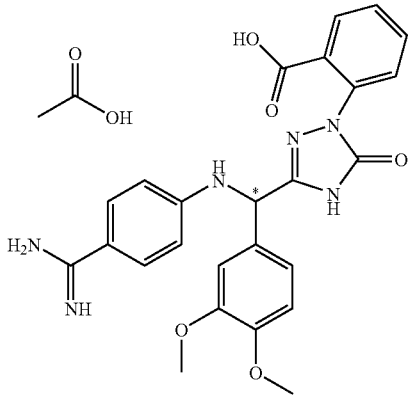

To a solution of 25 mg of 2-(3-{(3,4-dimethoxyphenyl)-[4-(5-methyl-[1,2,4]oxadiazol-3-yl)phenylamino]methyl}-5-oxo-4,5-dihydro-[1,2,4]triazol-1-yl)benzoic acid in 6 ml of a methanol:water:acetic acid=1:1:1 mixed solvent there was added 26 mg of iron powder under a nitrogen atmosphere, and the mixture was stirred at 45° C. for 15 hours and at 55° C. for 6 hours. After filtering the reaction mixture, it was purified by reverse-phase high performance liquid chromatography (acetonitrile-water, 0.1% trifluoroacetic acid) to give 14 mg of 2-{3-[(4-carbamimidoylphenylamino)-(3,4-dimethoxyphenyl)methyl]-5-oxo-4,5-dihydro-[1,2,4]triazol-1-yl}benzoic acid trifluoroacetate.

Mass spectrum (ESI) m/z: 527 (M+H)$^+$

A 10 mg portion of this compound was optically resolved using a SUMICHIRAL OA-2500 column, and the first eluting enantiomer (1.3 mg) of the title compound was obtained as a white solid.

$^1$H-NMR (CD$_3$OD) δ 1.95 (s, 3H) 3.83 (s, 3H) 3.85 (s, 3H) 5.57 (s, 1H) 6.88 (d, J=9.0 Hz, 2H) 6.98 (d, J=8.2 Hz, 1H) 7.10 (dd, J=8.2, 2.1 Hz, 1H) 7.16 (d, J=2.1 Hz, 1H) 7.35-7.45 (m, 3H) 7.61 (d, J=9.0 Hz, 2H) 7.71 (dd, J=7.7, 2.0 Hz, 1H)

HPLC retention time: 14 min

Example 37

(R) and (S)-2-{3-[(4-carbamimidoyl-3-fluorophenylamino)-(3,4-dimethoxyphenyl)methyl]-5-oxo-4,5-dihydro-[1,2,4]triazol-1-yl}benzoic acid acetate (37a) [2-(4-cyano-3-fluorophenylimino)-2-(3,4-dimethoxyphenyl)-1-methylsulfanylethylidene]carbamic acid methyl ester

[Chemical Formula 173]

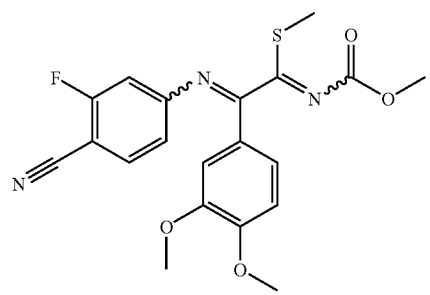

After adding 541 mg of 2-fluoro-4-aminobenzonitrile [CAS No. 53312-80-4], 500 mg of MS3A, 493 mg of Yb(OTf)$_3$ and 1.1 ml of trimethylsilyl cyanide to a solution of 795 mg of 3,4-dimethoxybenzaldehyde in 20 ml of THF under a nitrogen atmosphere, the mixture was stirred at room temperature for 14 hours. The reaction mixture was filtered through celite, and the celite was washed with ethyl acetate. The organic layer was concentrated under reduced pressure to give a crude product of 4-{[cyano-(3,4-dimethoxyphenyl)methyl]amino}-2-fluorobenzonitrile.

To a solution of this compound in 40 ml of a methanol:THF=1:1 mixed solvent there was added 6.8 ml of a 20% aqueous solution of ammonium sulfide, and the mixture was stirred at room temperature for 6 hours. Water was added to the reaction mixture and extraction was performed with ethyl acetate. After washing the organic layer with water and saturated brine, it was dried over anhydrous sodium sulfate. The desiccating agent was filtered off, and the filtrate was concentrated under reduced pressure to give a crude product of 2-(4-cyano-3-fluorophenylamino)-2-(3,4-dimethoxyphenyl)thioacetamide.

To a solution of this compound in 20 ml of acetonitrile there was added 618 mg of $Me_3O^+BF_4^-$, and the mixture was stirred at room temperature for 30 minutes. Saturated aqueous sodium hydrogencarbonate was added to the reaction mixture, and extraction was performed with ethyl acetate. The organic layer was washed with saturated brine and dried over anhydrous magnesium sulfate. The desiccating agent was filtered off and the filtrate was concentrated under reduced pressure.

After adding 3.46 g of manganese dioxide to a solution of the residue in 20 ml of ethyl acetate, the mixture was stirred at room temperature for 35 minutes. The reaction mixture was filtered through celite, and the filtrate was concentrated under reduced pressure.

After adding 1.57 ml of 2,4,6-collidine and 0.62 ml of methyl chloroformate to a solution of the residue in 30 ml of toluene, the mixture was stirred at 80° C. for 4 hours and 30 minutes under a nitrogen atmosphere. After cooling the reaction mixture, 0.5N hydrochloric acid was added and extraction was performed with ethyl acetate. The organic layer was washed with saturated brine and dried over anhydrous magnesium sulfate. The desiccating agent was filtered off and the filtrate was concentrated under reduced pressure. The residue was purified by silica gel column chromatography (ethyl acetate-heptane) to give the title compound (1.3 g, isomeric mixture) as a light yellow solid.

$^1$H-NMR (CDCl$_3$) Main isomer:

δ 2.37 (s, 3H) 3.62 (s, 3H) 3.95 (s, 3H) 3.96 (s, 3H) 6.88 (d, J=8.4 Hz, 1H) 6.96-7.00 (m, 2H) 7.27 (m, 1H) 7.54 (t, J=8.0 Hz, 2H)

(37b) 2-{3-[(4-cyano-3-fluorophenylamino)-(3,4-dimethoxyphenyl)methyl]-5-oxo-4,5-dihydro-[1,2,4]triazol-1-yl}benzoic acid

[Chemical Formula 174]

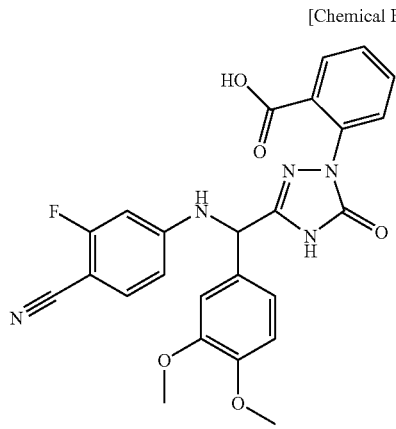

After adding 55 mg of 2-hydrazinobenzoic acid hydrochloride and 101 μl of triethylamine to a solution of 120 mg of [2-(4-cyano-3-fluorophenylimino)-2-(3,4-dimethoxyphenyl)-1-methylsulfanylethylidene]carbamic acid methyl ester in 3 ml of DMF, the mixture was stirred at 85° C. for 16 hours under a nitrogen atmosphere. The reaction mixture was concentrated, and the residue was dissolved in 3 ml of a methanol:THF=1:1 mixed solvent. After adding 58 μl of acetic acid and 91 mg of sodium cyanotrihydroborate to the solution, the mixture was stirred at room temperature for 15 hours. Ethyl acetate was then added to the reaction mixture. The organic layer was washed with dilute hydrochloric acid and saturated brine and then dried over anhydrous magnesium sulfate. The desiccating agent was filtered off and the filtrate was concentrated under reduced pressure. The residue was purified by NAM silica gel column chromatography (methanol-ethyl acetate) to give the title compound (100 mg) as a light yellow solid.

$^1$H-NMR (CD$_3$OD) δ 3.75 (s, 3H) 3.78 (s, 3H) 5.43 (s, 1H) 6.30 (d, J=11.2 Hz, 1H) 6.38 (d, J=8.4 Hz, 1H) 6.78 (d, J=8.4 Hz, 1H) 6.91-6.94 (m, 2H) 7.21 (t, J=8.0 Hz, 1H) 7.50-7.57 (m, 2H) 7.69 (t, J=7.2 Hz, 1H) 7.88 (d, J=7.6 Hz, 1H)

(37c) (R) and (S)-2-{3-[(4-carbamimidoyl-3-fluorophenylamino)-(3,4-dimethoxyphenyl)methyl]-5-oxo-4,5-dihydro-[1,2,4]triazol-1-yl}benzoic acid acetate

[Chemical Formula 175]

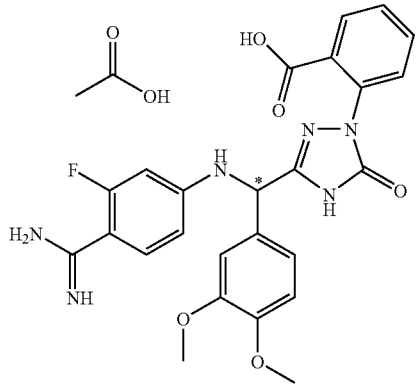

After adding 131 mg of hydroxylammonium chloride and 367 μl of triethylamine to a solution of 175 mg of 2-{3-[(4-cyano-3-fluorophenylamino)-(3,4-dimethoxyphenyl)methyl]-5-oxo-4,5-dihydro-[1,2,4]triazol-1-yl}benzoic acid in 10 ml of ethanol, the mixture was stirred at 75° C. for 23 hours under a nitrogen atmosphere. The reaction mixture was concentrated, and the residue was dissolved in 3 ml of acetic acid. After adding 0.2 ml of acetic anhydride and 50 mg of palladium-carbon to the solution, the mixture was stirred for 2 hours and 30 minutes under a hydrogen atmosphere. The reaction mixture was filtered through celite, and the filtrate was concentrated under reduced pressure. The residue was purified by reverse-phase high performance liquid chromatography (acetonitrile-water, 0.1% trifluoroacetic acid) to give 70 mg of 2-{3-[(4-carbamimidoyl-3-fluorophenylamino)-(3,4-dimethoxyphenyl)methyl]-5-oxo-4,5-dihydro-[1,2,4]triazol-1-yl}benzoic acid trifluoroacetate as a light yellow solid.

Mass spectrum (ESI) m/z: 507 (M+H)$^+$

A 60 mg portion of this compound was optically resolved using a SUMICHIRAL OA-2500 column, and the first eluting enantiomer (19.5 mg) of the title compound was obtained as a white solid.

$^1$H-NMR (CD$_3$OD) δ 3.82 (s, 3H) 3.85 (s, 3H) 5.58 (s, 1H) 6.59 (dd, J=14.4, 2.0 Hz, 1H) 6.72 (dd, J=8.8, 2.0 Hz, 1H) 6.98 (d, J=8.0 Hz, 1H) 7.09 (dd, J=8.4, 2.0 Hz, 1H) 7.14 (d, J=2.0 Hz, 1H) 7.35-7.50 (m, 4H) 7.71 (dd, J=7.6, 1.6 Hz, 1H)

HPLC retention time: 17 min (Column name: SUMICHIRAL OA-2500, 30 mmφ×25 cm, Manufacturer: Sumika Chemical Analysis Service, Ltd., Mobile phase: 0.05 M ammonium acetate-methanol solution, Elution rate: 20 ml/min)

Example 38

(R) and (S)-2-{3-[(4-carbamimidoylphenylamino)-(2-methoxy-6-methylpyridin-4-yl)methyl]-5-oxo-4,5-dihydro-[1,2,4]triazol-1-yl}benzoic acid acetate

[Chemical Formula 176]

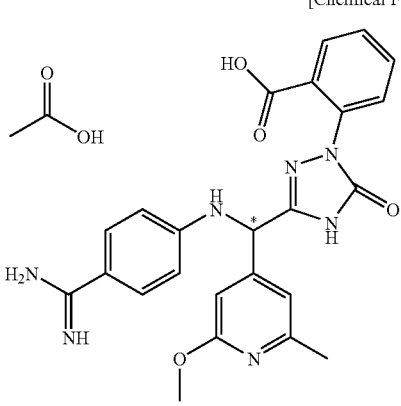

After adding 39 mg of 2-hydrazinobenzoic acid hydrochloride and 57 µl of triethylamine to a solution of 90 mg of 2-(2-methoxy-6-methylpyridin-4-yl)-2-[4-(5-methyl-[1,2,4]oxadiazol-3-yl)phenylimino]thioacetamide (Example (19b)) in 3 ml of DMF, the mixture was stirred at 85° C. for 16 hours under a nitrogen atmosphere. The reaction mixture was concentrated, and the residue was dissolved in 2 ml of a methanol:THF=1:1 mixed solvent. After adding 41 µl of acetic acid and 64 mg of sodium cyanotrihydroborate to the reaction mixture, the mixture was stirred at room temperature for 4 hours. After filtering the reaction mixture, it was purified by reverse-phase high performance liquid chromatography (acetonitrile-water, 0.1% acetic acid) to give 2-(3{(2-methoxy-6-methylpyridin-4-yl)-[4-(5-methyl-[1,2,4]oxadiazol-3-yl) phenylamino]methyl}-5-oxo-4,5-dihydro-[1,2,4]triazol-1-yl}benzoic acid (35 mg).

To a solution of this compound in 2.4 ml of a methanol:water:acetic acid=1:1:1 mixed solvent there was added 40 mg of iron powder, and the mixture was stirred at 55° C. for 16 hours under a nitrogen atmosphere. After filtering the reaction mixture, it was purified by reverse-phase high performance liquid chromatography (acetonitrile-water, 0.1% acetic acid) to give 15 mg of 2-{3[(4-carbamimidoylphenylamino)-(2-methoxy-6-methylpyridin-4-yl)methyl]-5-oxo-4,5-dihydro-[1,2,4]triazol-1-yl}benzoic acid acetate.

$^1$H-NMR (d$_6$-DMSO) δ 2.37 (s, 3H) 3.81 (s, 3H) 5.45 (br.s, 1H) 6.74 (d, J=8.4 Hz, 2H) 6.79 (s, 1H) 7.01 (s, 1H) 7.29-7.35 (m, 3H) 7.45 (d, J=8.4 Hz, 2H) 7.64 (d, J=7.2 Hz, 1H) 8.34 (br.s, 2H)

Mass spectrum (ESI) m/z: 474 (M+H)$^+$ 15 mg of this compound was optically resolved using a SUMICHIRAL OA-2500 column, and the first eluting enantiomer (6.1 mg) of the title compound was obtained.

HPLC retention time: 13 min

Example 39

(R) and (S)-4-{[(2-methoxy-6-methyl-pyridin-4-yl)-(5-oxo-1-pyrimidin-2-yl-4,5-dihydro-1H-[1,2,4]triazol-3-yl)methyl]amino}benzamidine acetate

[Chemical Formula 177]

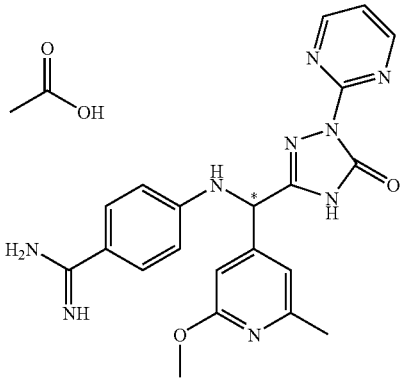

The same procedure was carried out as in Examples (17f)-(17g), except that 2-(2-methoxy-6-methylpyridin-4-yl)-2-[4-(5-methyl-[1,2,4]oxadiazol-3-yl)phenylimino]-1-methylsulfanylethylidene}carbamic acid methyl ester (Example (19b)) was used instead of the 2-(3-ethoxy-4-methoxyphenyl)-2-[4-(5-methyl-[1,2,4]oxadiazol-3-yl)phenylimino]-1-methylsulfanylethylidene}carbamic acid methyl ester in Example (17f), to give 4-{[(2-methoxy-6-methyl-pyridin-4-yl)-(5-oxo-1-pyrimidin-2-yl-4,5-dihydro-1H-[1,2,4]triazol-3-yl)methyl]amino}benzamidine acetate.

$^1$H-NMR (CD$_3$OD) δ 1.94 (s, 3H) 2.40 (s, 3H) 3.86 (s, 3H) 5.65 (s, 1H) 6.77 (s, 1H) 6.85 (d, J=8.4 Hz, 2H) 6.98 (s, 1H) 7.32 (t, J=5.2 Hz, 1H) 7.61 (d, J=8.4 Hz, 2H) 8.78 (d, J=5.2 Hz, 2H)

Mass spectrum (ESI) m/z: 432 (M+H)$^+$

A 6.0 mg portion of this compound was optically resolved using a SUMICHIRAL OA-2500 column, and the first eluting enantiomer (2.2 mg) of the title compound was obtained.

HPLC retention time: 14 min

Example 40

(R) and (S)-4-{[(4-fluoro-7-methoxy-2,3-dihydrobenzofuran-5-yl)-(5-oxo-1-pyrimidin-2-yl-4,5-dihydro-1H-[1,2,4]triazol-3-yl)methyl]amino}benzamidine acetate (40a) 4-fluoro-7-methoxy-2,3-dihydrobenzofuran

[Chemical Formula 178]

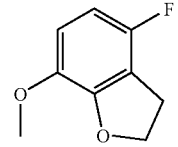

To a suspension of 50 g of methyltriphenylphosphonium bromide in 300 ml of toluene there was added 45 ml of n-butyllithium (2.55 M, hexane solution) while cooling on ice under a nitrogen atmosphere. After stirring at room temperature for 2 hours, the reaction mixture was allowed to stand. A 150 ml portion of the supernatant was added dropwise to a solution of 5.00 g of 6-fluoro-2-hydroxy-3-methoxybenzaldehyde [CAS No. 457628-15-8] in 90 ml of toluene while cooling on ice. After stirring the mixture at room temperature for 1 hour, saturated aqueous ammonium chloride was added to the reaction mixture. The reaction mixture was extracted with ethyl acetate The organic layer was dried over anhydrous magnesium sulfate. The desiccating agent was filtered off and the filtrate was concentrated under reduced pressure. The residue was purified by silica gel column chromatography (ethyl acetate-heptane) to give 3-fluoro-6-methoxy-2-vinylphenol (4.33 g) as a solid.

This compound was dissolved in 20 ml of DMF, and then 3.00 g of imidazole and 5.50 g of chlorotriisopropylsilane were added and the mixture was stirred overnight at 50° C. Water was added to the reaction mixture and extraction was performed with ethyl acetate. The organic layer was dried over anhydrous magnesium sulfate. The desiccating agent was filtered off and the filtrate was concentrated under reduced pressure. The residue was purified by silica gel column chromatography (ethyl acetate-heptane) to give (3-fluoro-6-methoxy-2-vinylphenoxy)triisopropylsilane (3.35 g) as an oil.

To a solution of this compound in 20 ml of THF there was added 10 ml of borane-tetrahydrofuran complex (1.0 M, THF solution) while cooling on ice. After stirring overnight at room temperature, 10 ml of saturated aqueous sodium hydrogencarbonate and 10 ml of 30% hydrogen peroxide water were added to the reaction mixture while cooling on ice, and the mixture was stirred at room temperature for 4 hours. Water was added to the reaction mixture and extraction was performed with ethyl acetate. The organic layer was dried over anhydrous magnesium sulfate. The desiccating agent was filtered off and the filtrate was concentrated under reduced pressure.

The residue was dissolved in 20 ml of THF, and then 20 ml of TBAF (1.0 M, THF solution) was added and the mixture was stirred at room temperature for 1 hour. Saturated aqueous ammonium chloride was added to the reaction mixture, and extraction was performed with ethyl acetate. The organic layer was dried over anhydrous magnesium sulfate. The desiccating agent was filtered off and the filtrate was concentrated under reduced pressure. The residue was purified by silica gel column chromatography (ethyl acetate-heptane) to give 3-fluoro-2-(2-hydroxyethyl)-6-methoxyphenol (1.09 g) as an oil.

This compound and 2.10 g of triphenylphosphine were dissolved in 20 ml of THF, and the mixture was cooled to −74° C. Next, 1.8 ml of DIAD was added to the reaction mixture, and the temperature was allowed to rise to room temperature prior to stirring overnight. The reaction mixture was concentrated, and the residue was purified by silica gel column chromatography (ethyl acetate-heptane) to give the title compound (802 mg) as an oil.

$^1$H-NMR (CDCl$_3$) δ 3.27 (t, J=8.8 Hz, 2H) 3.84 (s, 3H) 4.67 (t, J=8.8 Hz, 2H) 6.49 (t, J=8.8 Hz, 1H) 6.66 (dd, J=4.4, 8.8 Hz, 1H)

(40b) 4-fluoro-7-methoxy-2,3-dihydrobenzofuran-5-carbaldehyde

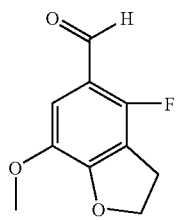

[Chemical Formula 179]

To a solution of 665 mg of 4-fluoro-7-methoxy-2,3-dihydrobenzofuran and 740 mg of N,N,N',N',N''-pentamethyldiethylenetriamine in 15 ml of THF there was added dropwise 1.66 ml of n-butyllithium (2.55 M, hexane solution) at −74° C. The mixture was stirred at −74° C. for 1 hour, and then 500 µl of N-formylmorpholine was added. After further stirring at room temperature for 1 hour, 1N hydrochloric acid was added to the reaction mixture while cooling on ice, and the mixture was extracted with ethyl acetate and dried over anhydrous magnesium sulfate. The desiccating agent was filtered off and the filtrate was concentrated under reduced pressure. The residue was purified by silica gel column chromatography (ethyl acetate-heptane) to give the title compound (321 mg) as an oil.

$^1$H-NMR (CDCl$_3$) δ 3.34 (t, J=9.2 Hz, 2H) 3.89 (s, 3H) 4.83 (t, J=9.2 Hz, 2H) 7.24 (d, J=5.6 Hz, 1H) 10.18 (s, 1H)

(40c) {2-(4-fluoro-7-methoxy-2,3-dihydrobenzofuran-5-yl)-2-[4-(5-methyl-[1,2,4]oxadiazol-3-yl)phenylimino]-1-methylsulfanylethylidene}carbamic acid methyl ester

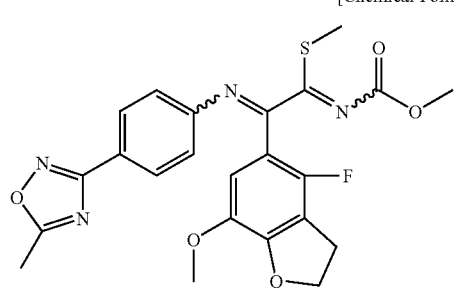

[Chemical Formula 180]

After adding 287 mg of 4-(5-methyl-[1,2,4]oxadiazol-3-yl)phenylamine [CAS No. 10185-68-9], 321 mg of 4-fluoro-7-methoxy-2,3-dihydrobenzofuran-5-carbaldehyde, 300 mg of MS3A and 0.44 ml of trimethylsilyl cyanide to a solution of 102 mg of Yb(OTf)$_3$ in 5 ml of THF under a nitrogen atmosphere, the mixture was stirred overnight at room temperature. The reaction mixture was filtered through celite, and the celite was washed with ethyl acetate. The organic layer was concentrated under reduced pressure to give (4-fluoro-7-methoxy-2,3-dihydrobenzofuran-5-yl)-[4-(5-methyl-[1,2,4]oxadiazol-3-yl)phenylamino]acetonitrile (crude product).

To a solution of this compound in 150 ml of an ethanol: THF=2:1 mixed solvent there was added 50 ml of a 20% aqueous solution of ammonium sulfide, and the mixture was stirred at 50° C. for 2 hours. Water was added to the reaction mixture and extraction was performed with ethyl acetate. The organic layer was dried over anhydrous magnesium sulfate. The desiccating agent was filtered off, and the filtrate was concentrated under reduced pressure to give 2-(4-fluoro-7-methoxy-2,3-dihydrobenzofuran-5-yl)-2-[4-(5-methyl-[1,2,4]oxadiazol-3-yl)phenylamino]thioacetamide (700 mg, crude product).

To a solution of this compound in 20 ml of dichloromethane there was added 300 mg of Me$_3$O$^+$BF$_4^-$, and the mixture was stirred at room temperature for 3 hours. Saturated aqueous sodium hydrogencarbonate was added to the reaction mixture and extraction was performed with ethyl acetate. The organic layer was dried over anhydrous magnesium sulfate. The desiccating agent was filtered off, and the filtrate was concentrated under reduced pressure to give 2-(4-fluoro-7-methoxy-2,3-dihydrobenzofuran-5-yl)-2-[4-(5-methyl-[1,2,4]oxadiazol-3-yl)phenylamino]thioacetamide acid methyl ester (crude product).

To a solution of this compound in 20 ml of ethyl acetate there was added 3 g of manganese dioxide, and the mixture was stirred at room temperature for 1 hour. The reaction mixture was filtered, and the filtrate was concentrated under reduced pressure.

To a solution of the residue in 10 ml of toluene there were added 1 ml of 2,4,6-collidine and 500 μl of methyl chloroformate, and the mixture was stirred at 80° C. for 1 hour under a nitrogen atmosphere. After cooling the reaction mixture, 1N hydrochloric acid was added and extraction was performed with ethyl acetate. The organic layer was dried over anhydrous magnesium sulfate. The desiccating agent was filtered off and the filtrate was concentrated under reduced pressure. The residue was purified by silica gel column chromatography (ethyl acetate-heptane) to give the title compound (595 mg, isomeric mixture) as a yellow solid.

$^1$H-NMR (CDCl$_3$) Two main isomers:

δ 2.32 (s, 3H) 2.65 (s, 3H) 3.31 (t, J=9.2 Hz, 2H) 3.63 (s, 3H) 3.90 (s, 3H) 4.78 (t, J=8.8 Hz, 2H) 7.37 (d, J=5.2 Hz, 1H) 7.10 (d, J=8.8 Hz, 2H) 7.90 (d, J=8.8 Hz, 2H)

δ 2.48 (s, 3H) 2.63 (s, 3H) 3.17 (t, J=9.2 Hz, 2H) 3.60 (s, 3H) 3.63 (s, 3H) 4.67 (t, J=8.8 Hz, 2H) 6.41 (d, J=5.2 Hz, 1H) 6.84 (d, J=8.8 Hz, 2H) 7.90 (d, J=8.8 Hz, 2H)

(40d) (R) and (S)-4-{[(4-fluoro-7-methoxy-2,3-dihydrobenzofuran-5-yl)-(5-oxo-1-pyrimidin-2-yl-4,5-dihydro-1H-[1,2,4]triazol-3-yl)methyl]amino}benzamidine acetate

[Chemical Formula 181]

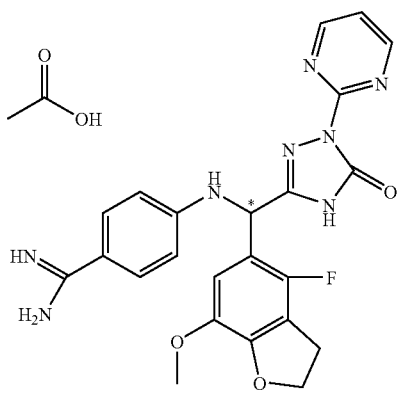

After adding 22 mg of 2-hydrazinopyrimidine and 50 ul of triethylamine to a solution of 105 mg of {2-(4-fluoro-7-methoxy-2,3-dihydrobenzofuran-5-yl)-2-[4-(5-methyl-[1,2,4]oxadiazol-3-yl)-phenylimino]-1-methylsulfanylethylidene}carbamic acid methyl ester in 2 ml of DMF, the mixture was stirred overnight at 85° C. under a nitrogen atmosphere. The reaction mixture was concentrated, and the residue was dissolved in 5 ml of methanol and 0.5 ml of acetic acid. After adding 100 mg of sodium cyanotrihydroborate to the reaction mixture, it was stirred at room temperature for 1 hour. Water was added to the reaction mixture and extraction was performed with ethyl acetate. The organic layer was dried over anhydrous magnesium sulfate. The desiccating agent was filtered off and the filtrate was concentrated under reduced pressure. The residue was purified by silica gel column chromatography (methanol-ethyl acetate) to give 5-{(4-fluoro-7-methoxy-2,3-dihydrobenzofuran-5-yl)-[4-(5-methyl-[1,2,4]oxadiazol-3-yl)phenylamino]methyl}-2-pyrimidin-2-yl-2,4-dihydro-[1,2,4]triazol-3-one (76 mg) as a light brown solid.

To a solution of this compound in 3.0 ml of a methanol:water:acetic acid=1:1:1 mixed solvent there was added 86 mg of iron powder, and the mixture was stirred overnight at 60° C. under a nitrogen atmosphere. After filtering the reaction mixture, it was purified by reverse-phase high performance liquid chromatography (acetonitrile-water, 0.1% acetic acid) to give 4-{[(4-fluoro-7-methoxy-2,3-dihydrobenzofuran-5-yl)-(5-oxo-1-pyrimidin-2-yl-4,5-dihydro-1H-[1,2,4]triazol-3-yl)methyl]amino}benzamidine acetate (44 mg).

Mass spectrum (ESI) m/z: 477 (M+H)$^+$ 44 mg of this compound was optically resolved using a SUMICHIRAL OA-2500 column, and the first eluting enantiomer (16.5 mg) of the title compound was obtained as a white solid.

$^1$H-NMR (CD$_3$OD) δ 1.91 (s, 3H) 3.22 (t, J=8.8 Hz, 2H) 3.69 (s, 3H) 4.61 (t, J=8.8 Hz, 2H) 5.88 (s, 1H) 6.84 (d, J=9.2 Hz, 2H) 6.93 (d, J=6.4 Hz, 1H) 7.28 (t, J=4.8 Hz, 1H) 7.59 (d, J=9.2 Hz, 2H) 8.72 (d, J=4.8 Hz, 2H)

HPLC retention time: 11 min

Example 41

(R) and (S)-4-{[(5-fluoro-8-methoxy-2,3-dihydrobenzo[1,4]dioxin-6-yl)-(5-oxo-1-pyrimidin-2-yl-4,5-dihydro-1H-[1,2,4]triazol-3-yl)methyl]amino}benzamidine acetate (41a) 4-bromo-3-fluoro-6-methoxybenzene-1,2-diol

[Chemical Formula 182]

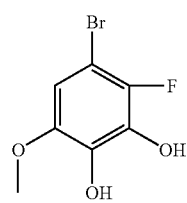

After adding 3.11 g of N-bromosuccinimide to a solution of 2.98 g of 6-fluoro-2-hydroxy-3-methoxybenzaldehyde [CAS No. 457628-15-8] in 15 ml of acetonitrile, the mixture was stirred overnight at room temperature. Water was added to the reaction mixture and extraction was performed with ethyl acetate. The organic layer was dried over anhydrous magnesium sulfate. The desiccating agent was filtered off, and the filtrate was concentrated under reduced pressure to give 3.13 g of 5-bromo-6-fluoro-2-hydroxy-3-methoxybenzaldehyde (crude product).

To a solution of this compound in 60 ml of chloroform there was added 4.00 g of 60% metachloroperbenzoic acid, and the mixture was stirred at 50° C. for 2 hours. The reaction mixture was concentrated, the residue was dissolved in 20 ml of methanol, 5 ml of 5N aqueous sodium hydroxide was added and the mixture was stirred overnight at room temperature. After adding 1N hydrochloric acid to render the reaction mixture acidic, the precipitated crystals were filtered out. The filtrate was extracted with ethyl acetate. The organic layer was dried over anhydrous magnesium sulfate. The desiccating agent was filtered off, and the filtrate was concentrated under reduced pressure to give the title compound (1.82 g, crude product).

(41b) 6-bromo-5-fluoro-8-methoxy-2,3-dihydrobenzo[1,4]dioxine

[Chemical Formula 183]

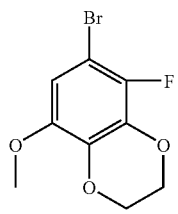

After adding 830 mg of 1,2-dibromoethane and 1.4 g of potassium carbonate to a solution of 880 mg of 4-bromo-3-fluoro-6-methoxybenzene-1,2-diol in 10 ml of DMF, the mixture was stirred at 80° C. for 6 hours. Next, 1N hydrochloric acid was added to the reaction mixture and the reaction mixture was extracted with ethyl acetate. The organic layer was dried over anhydrous magnesium sulfate. The desiccating agent was filtered off and the filtrate was concentrated under reduced pressure. The residue was purified by NH silica gel column chromatography (ethyl acetate-heptane) to give the title compound (549 mg) as a solid.

$^1$H-NMR (CDCl$_3$) δ 3.84 (s, 3H) 4.32-4.38 (m, 4H) 6.60 (d, J=5.6 Hz, 1H)

(41c) 5-fluoro-8-methoxy-2,3-dihydrobenzo[1,4]dioxine-6-carbaldehyde

[Chemical Formula 184]

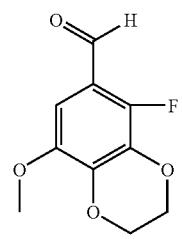

To a solution of 549 mg of 6-bromo-5-fluoro-8-methoxy-2,3-dihydrobenzo[1,4]dioxine in 15 ml of THF there was added dropwise 0.86 ml of n-butyllithium (2.55 M, hexane solution) at −70° C. under a nitrogen atmosphere. After stirring at −72° C. for 30 minutes, 0.3 ml of N-formylmorpholine was added and the temperature was raised from −78° C. to 0° C. over a period of 30 minutes. Saturated aqueous ammonium chloride was added to the reaction mixture, and extraction was performed with ethyl acetate. The organic layer was dried over anhydrous magnesium sulfate. The desiccating agent was filtered off and the filtrate was concentrated under reduced pressure. The residue was purified by silica gel column chromatography (ethyl acetate-heptane) to give the title compound (247 mg) as a solid.

$^1$H-NMR (CDCl$_3$) δ 3.90 (s, 3H) 4.35-4.38 (m, 2H) 4.43-4.45 (m, 2H) 6.92 (d, J=5.6 Hz, 1H) 10.24 (s, 1H)

(41d) [2-(5-fluoro-8-methoxy-2,3-dihydrobenzo[1,4]dioxin-6-yl)-2-[4-(5-methyl-[1,2,4]oxadiazol-3-yl)phenylimino]-1-methylsulfanylethylidene]carbamic acid methyl ester

[Chemical Formula 185]

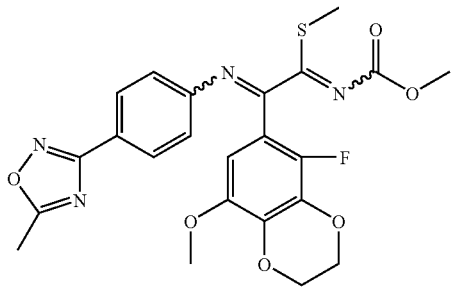

To a solution of 71 mg of Yb(OTf)$_3$ in 4 ml of THF there were added 204 mg of 4-(5-methyl-[1,2,4]oxadiazol-3-yl)phenylamine, 247 mg of 5-fluoro-8-methoxy-2,3-dihydrobenzo[1,4]dioxine-6-carbaldehyde, 250 mg of MS3A and 0.30 ml of trimethylsilyl cyanide under a nitrogen atmosphere, and the mixture was stirred overnight at room temperature. The reaction mixture was filtered through celite, and the celite was washed with ethyl acetate. The organic layer was concentrated under reduced pressure to give (5-fluoro-8-methoxy-2,3-dihydrobenzo[1,4]dioxin-6-yl)-[4-(5-methyl-[1,2,4]oxadiazol-3-yl)phenylamino]acetonitrile (crude product).

To a solution of this compound in 12 ml of an ethanol:THF=2:1 mixed solvent there was added 4 ml of a 20% aqueous solution of ammonium sulfide, and the mixture was stirred at 50° C. for 4 hours. Water was added to the reaction mixture and extraction was performed with ethyl acetate. The organic layer was dried over anhydrous magnesium sulfate. The desiccating agent was filtered off, and the filtrate was concentrated under reduced pressure to give 2-(5-fluoro-8-methoxy-2,3-dihydrobenzo[1,4]dioxin-6-yl)-2-[4-(5-methyl-[1,2,4]oxadiazol-3-yl)phenylamino]thioacetamide (crude product).

To a solution of this compound in 7 ml of acetonitrile there was added 220 mg of Me$_3$O$^+$BF$_4^-$, and the mixture was stirred at room temperature for 0.5 hour. Saturated aqueous sodium hydrogencarbonate was added to the reaction mixture and extraction was performed with ethyl acetate. The organic layer was dried over anhydrous magnesium sulfate. The desiccating agent was filtered off, and the filtrate was concentrated under reduced pressure to give 2-(5-fluoro-8-methoxy- 2,3-dihydrobenzo[1,4]dioxin-6-yl)-2-[4-(5-methyl-[1,2,4]oxadiazol-3-yl)phenylamino]thioacetamide acid methyl ester (crude product).

To a solution of this compound in 10 ml of ethyl acetate there was added 3 g of manganese dioxide, and the mixture was stirred at room temperature for 1 hour. The reaction mixture was filtered, and the filtrate was concentrated under reduced pressure.

To a solution of the residue in 5 ml of toluene there were added 0.6 ml of 2,4,6-collidine and 0.3 ml of methyl chloroformate, and the mixture was stirred at 80° C. for 1 hour under a nitrogen atmosphere. After cooling the reaction mixture, 1N hydrochloric acid was added and extraction was performed with ethyl acetate. The organic layer was dried over anhydrous magnesium sulfate. The desiccating agent was filtered off and the filtrate was concentrated under reduced pressure. The residue was purified by silica gel column chromatography (ethyl acetate-heptane) to give the title compound (266 mg, isomeric mixture) as a yellow solid.

Mass spectrum (ESI) m/z: 501 (M+H)$^+$ (41e) (R) and (S)-4-{[(5-fluoro-8-methoxy-2,3-dihydrobenzo[1,4]dioxin-6-yl)-(5-oxo-1-pyrimidin-2-yl-4,5-dihydro-1H-[1,2,4]triazol-3-yl)methyl]amino}benzamidine acetate

[Chemical Formula 186]

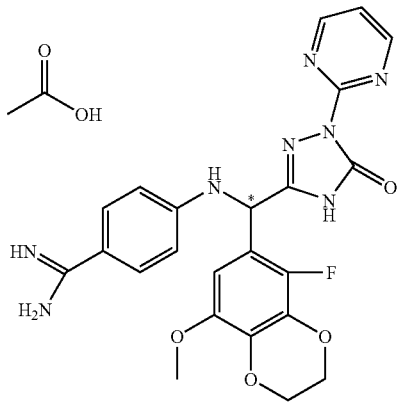

After adding 21 mg of 2-hydrazinopyrimidine and 50 ul of triethylamine to a solution of 105 mg of [2-(5-fluoro-8-methoxy-2,3-dihydrobenzo[1,4]dioxin-6-yl)-2-[4-(5-methyl-[1,2,4]oxadiazol-3-yl)phenylimino]-1-methylsulfanylethylidene]carbamic acid methyl ester in 2 ml of DMF, the mixture was stirred overnight at 85° C. under a nitrogen atmosphere. The reaction mixture was concentrated, and the residue was dissolved in 3 ml of methanol and 0.3 ml of acetic acid. After adding 200 mg of sodium cyanotrihydroborate to the reaction mixture it was stirred at room temperature for 1 hour. Water was added to the reaction mixture and extraction was performed with ethyl acetate. The organic layer was dried over anhydrous magnesium sulfate. The desiccating agent was filtered off and the filtrate was concentrated under reduced pressure. The residue was purified by NAM silica gel column chromatography (methanol-ethyl acetate) to give 5-{(5-fluoro-8-methoxy-2,3-dihydrobenzo[1,4]dioxin-6-yl)-[4-(5-methyl-[1,2,4]oxadiazol-3-yl)phenylamino]methyl}-2-pyrimidin-2-yl-2,4-dihydro-[1,2,4]triazol-3-one (58 mg) as a light brown solid.

To a solution of this compound in 3.0 ml of a methanol:water:acetic acid=1:1:1 mixed solvent there was added 70 mg of iron powder, and the mixture was stirred overnight at 60° C. under a nitrogen atmosphere. After filtering the reaction mixture, it was purified by reverse-phase high performance liquid chromatography (acetonitrile-water, 0.1% acetic acid) to give 4-{[(5-fluoro-8-methoxy-2,3-dihydrobenzo[1,4]dioxin-6-yl)-(5-oxo-1-pyrimidin-2-yl-4,5-dihydro-1H-[1,2,4]triazol-3-yl)methyl]amino}benzamidine acetate (32 mg).

Mass spectrum (ESI) m/z: 493 (M+H)$^+$ 32 mg of this compound was optically resolved using a SUMICHIRAL OA-2500 column, and the first eluting enantiomer (11.4 mg) of the title compound was obtained as a white solid.

$^1$H-NMR (CD$_3$OD) δ 1.91 (s, 3H) 3.69 (s, 3H) 4.21-4.35 (m, 4H) 5.91 (s, 1H) 6.65 (d, J=6.0 Hz, 1H) 6.85 (d, J=9.2 Hz, 2H) 7.31 (t, J=4.8 Hz, 1H) 7.61 (d, J=9.2 Hz, 2H) 8.76 (d, J=4.8 Hz, 2H)

HPLC retention time: 17 min

Example 42

(R) and (S)-4-{[(6-fluoro-9-methoxy-3,4-dihydro-2H-benzo[b][1,4]dioxepin-7-yl)-(5-oxo-1-pyrimidin-2-yl-4,5-dihydro-1H-[1,2,4]triazol-3-yl)methyl]amino}benzamidine acetate (42a) 7-bromo-6-fluoro-9-methoxy-3,4-dihydro-2H-benzo[b][1,4]dioxepine

[Chemical Formula 187]

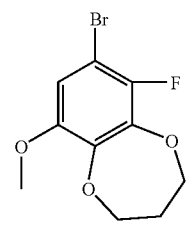

After adding 830 mg of 1,3-dibromopropane and 1.4 g of potassium carbonate to a solution of 880 mg of 4-bromo-3-fluoro-6-methoxybenzene-1,2-diol (Example (41a)) in 10 ml of DMF, the mixture was stirred at 80° C. for 6 hours. After adding 1N hydrochloric acid to the reaction mixture, the reaction mixture was extracted with ethyl acetate. The organic layer was dried over anhydrous magnesium sulfate. The desiccating agent was filtered off and the filtrate was concentrated under reduced pressure. The residue was purified by NH silica gel column chromatography (ethyl acetate-heptane) to give the title compound (548 mg) as a solid.

$^1$H-NMR (CDCl$_3$) δ 2.26 (Sept, J=5.6 Hz, 2H) 3.82 (s, 3H) 4.32 (dd, J=4.8, 10.4 Hz, 4H) 6.09 (d, J=6.0 Hz, 1H)

(42b) 6-fluoro-9-methoxy-3,4-dihydro-2H-benzo[b][1,4]dioxepin-7-carbaldehyde

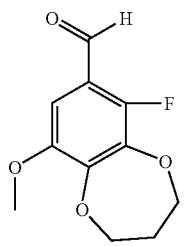

[Chemical Formula 188]

To a solution of 548 mg of 7-bromo-6-fluoro-9-methoxy-3,4-dihydro-2H-benzo[b][1,4]dioxepine in 15 ml of THF there was added dropwise 0.81 ml of n-butyllithium (2.55 M, hexane solution) at −70° C. under a nitrogen atmosphere. After stirring at −72° C. for 30 minutes, 0.3 ml of N-formylmorpholine was added and the temperature was raised from −78° C. to 0° C. over a period of 30 minutes. Saturated aqueous ammonium chloride was added to the reaction mixture, and extraction was performed with ethyl acetate. The organic layer was dried over anhydrous magnesium sulfate. The desiccating agent was filtered off and the filtrate was concentrated under reduced pressure. The residue was purified by silica gel column chromatography (ethyl acetate-heptane) to give the title compound (239 mg) as a solid.

$^1$H-NMR (CDCl$_3$) δ 2.33 (Sept, J=6.0 Hz, 2H) 3.87 (s, 3H) 4.40 (t, J=6.0 Hz, 2H) 4.48 (t, J=6.0 Hz, 2H) 6.98 (d, J=5.6 Hz, 1H) 10.24 (s, 1H)

(42c) [2-(6-fluoro-9-methoxy-3,4-dihydro-2H-benzo[b][1,4]dioxepin-7-yl)-2-[4-(5-methyl-[1,2,4]oxadiazol-3-yl)phenylimino]-1-methylsulfanylethylidene]carbamic acid methyl ester

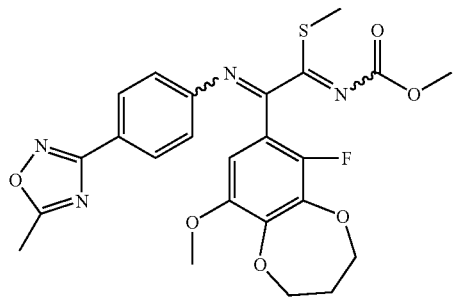

[Chemical Formula 189]

After adding 185 mg of 4-(5-methyl-[1,2,4]oxadiazol-3-yl)phenylamine, 239 mg of 6-fluoro-9-methoxy-3,4-dihydro-2H-benzo[b][1,4]dioxepin-7-carbaldehyde, 250 mg of MS3A and 0.28 ml of trimethylsilyl cyanide to a solution of 65 mg of Yb(OTf)$_3$ in 4 ml of THF under a nitrogen atmosphere, the mixture was stirred overnight at room temperature. The reaction mixture was filtered through celite, and the celite was washed with ethyl acetate. The organic layer was concentrated under reduced pressure to give (6-fluoro-9-methoxy-3,4-dihydro-2H-benzo[b][1,4]dioxepin-7-yl)-[4-(5-methyl-[1,2,4]oxadiazol-3-yl)phenylamino]acetonitrile (crude product).

To a solution of this compound in 12 ml of an ethanol:THF=2:1 mixed solvent there was added 4 ml of a 20% aqueous solution of ammonium sulfide, and the mixture was stirred at 50° C. for 4 hours. Water was added to the reaction mixture and extraction was performed with ethyl acetate. The organic layer was dried over anhydrous magnesium sulfate. The desiccating agent was filtered off, and the filtrate was concentrated under reduced pressure to give 2-(6-fluoro-9-methoxy-3,4-dihydro-2H-benzo[b][1,4]dioxepin-7-yl)-2-[4-(5-methyl-[1,2,4]oxadiazol-3-yl)phenylamino]thioacetamide (crude product).

To a solution of this compound in 7 ml of acetonitrile there was added 220 mg of Me$_3$O$^+$BF$_4^-$, and the mixture was stirred at room temperature for 0.5 hour. Saturated aqueous sodium hydrogencarbonate was added to the reaction mixture and extraction was performed with ethyl acetate. The organic layer was dried over anhydrous magnesium sulfate. The desiccating agent was filtered off, and the filtrate was concentrated under reduced pressure to give 2-(6-fluoro-9-methoxy-3,4-dihydro-2H-benzo[b][1,4]dioxepin-7-yl)-2-[4-(5-methyl-[1,2,4]oxadiazol-3-yl)phenylamino]thioacetamide acid methyl ester (crude product).

To a solution of this compound in 10 ml of ethyl acetate there was added 3 g of manganese dioxide, and the mixture was stirred at room temperature for 1 hour. The reaction mixture was filtered, and the filtrate was concentrated under reduced pressure.

To a solution of the residue in 5 ml of toluene there were added 0.6 ml of 2,4,6-collidine and 0.3 ml of methyl chloroformate, and the mixture was stirred at 80° C. for 1 hour under a nitrogen atmosphere. After cooling the reaction mixture, 1N hydrochloric acid was added and extraction was performed with ethyl acetate. The organic layer was dried over anhydrous magnesium sulfate. The desiccating agent was filtered off and the filtrate was concentrated under reduced pressure. The residue was purified by silica gel column chromatography (ethyl acetate-heptane) to give the title compound (297 mg, isomeric mixture) as a yellow solid.

Mass spectrum (ESI) m/z: 515 (M+H)$^+$

(42d) (R) and (S)-4-{[(6-fluoro-9-methoxy-3,4-dihydro-2H-benzo[b][1,4]dioxepin-7-yl)-(5-oxo-1-pyrimidin-2-yl-4,5-dihydro-1H-[1,2,4]triazol-3-yl)methyl]amino}benzamidine acetate

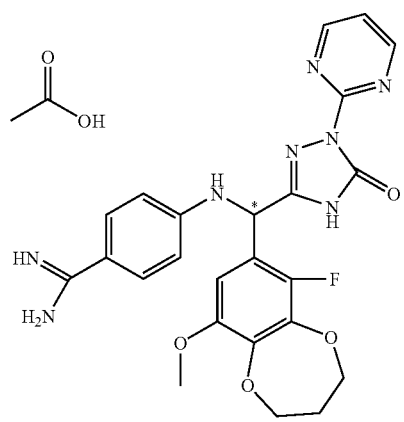

[Chemical Formula 190]

After adding 20 mg of 2-hydrazinopyrimidine and 50 ul of triethylamine to a solution of 103 mg of [2-(6-fluoro-9-methoxy-3,4-dihydro-2H-benzo[b][1,4]dioxepin-7-yl)-2-[4-(5-methyl-[1,2,4]oxadiazol-3-yl)phenylimino]-1-methylsulfanylethylidene]carbamic acid methyl ester in 2 ml of DMF, the mixture was stirred overnight at 85° C. under a nitrogen atmosphere. The reaction mixture was concentrated, and the residue was dissolved in 3 ml of methanol and 0.3 ml of acetic acid. After adding 200 mg of sodium cyanotrihydroborate to the reaction mixture, it was stirred at room temperature for 1 hour. Water was added to the reaction mixture and extraction was performed with ethyl acetate. The organic layer was dried over anhydrous magnesium sulfate. The desiccating agent was filtered off and the filtrate was concentrated under reduced pressure. The residue was purified by NAM silica gel column chromatography (methanol-ethyl acetate) to give 5-{(6-fluoro-9-methoxy-3,4-dihydro-2H-benzo[b][1,4]dioxepin-7-yl)-[4-(5-methyl-[1,2,4]oxadiazol-3-yl)phenylamino]methyl}-2-pyrimidin-2-yl-2,4-dihydro-[1,2,4]triazol-3-one (67 mg) as a light brown solid.

To a solution of this compound in 3.0 ml of a methanol:water:acetic acid=1:1:1 mixed solvent there was added 70 mg of iron powder, and the mixture was stirred overnight at 60° C. under a nitrogen atmosphere. After filtering the reaction mixture, it was purified by reverse-phase high performance liquid chromatography (acetonitrile-water, 0.1% acetic acid), to give 4-{[(6-fluoro-9-methoxy-3,4-dihydro-2H-benzo[b][1,4]dioxepin-7-yl)-(5-oxo-1-pyrimidin-2-yl-4,5-dihydro-1H-[1,2,4]triazol-3-yl)methyl]amino}benzamidine acetate (35 mg).

Mass spectrum (ESI) m/z: 507 (M+H)$^+$ 35 mg of this compound was optically resolved using a SUMICHIRAL OA-2500 column, and the first eluting enantiomer (11.1 mg) of the title compound was obtained as a white solid.

$^1$H-NMR (CD$_3$OD) δ 1.91 (s, 3H) 2.16-2.22 (m, 2H) 3.71 (s, 3H) 4.09-4.27 (m, 4H) 5.92 (s, 1H) 6.81 (d, J=6.4 Hz, 1H) 6.85 (d, J=9.2 Hz, 2H) 7.30 (t, J=4.8 Hz, 1H) 7.61 (d, J=9.2 Hz, 2H) 8.76 (d, J=4.8 Hz, 2H)

HPLC retention time: 15 min

Example 43

(R) and (S)-4-({[3-methyl-5-(1-methylpiperidin-4-yloxy)phenyl]-(5-oxo-1-pyrimidin-2-yl-4,5-dihydro-1H-[1,2,4]triazol-3-yl)methyl}amino)benzamidine diacetate (43a) 3-methyl-5-triisopropylsilanyloxybenzaldehyde

[Chemical Formula 191]

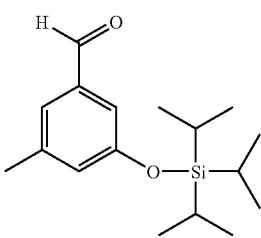

After adding 1.11 g of imidazole to a solution of 2.02 g of 3-hydroxy-5-methylbenzaldehyde [CAS No. 60549-26-0] in 20 ml of DMF, the reaction mixture was cooled to 0° C. Next, 3.56 ml of chlorotriisopropylsilane was added and the mixture was stirred at room temperature for 19 hours and 10 minutes. Water was added to the reaction mixture, and extraction was performed twice with diethyl ether. The organic layer was washed twice with water and then dried over anhydrous magnesium sulfate. The desiccating agent was filtered off and the filtrate was concentrated under reduced pressure. The residue was purified by silica gel column chromatography (hexane-diethyl ether) to give the title compound (3.86 g) as a yellow oil.

$^1$H-NMR (CDCl$_3$) δ 1.12 (d, J=7.6 Hz, 18H) 1.24-1.33 (m, 3H) 2.39 (s, 3H) 6.97 (s, 1H) 7.16 (s, 1H) 7.27 (s, 1H) 9.90 (s, 1H)

(43b) {2-(3-hydroxy-5-methylphenyl)-2-[4-(5-methyl-[1,2,4]oxadiazol-3-yl)phenylimino]-1-methylsulfanylethylidene}carbamic acid methyl ester

[Chemical Formula 192]

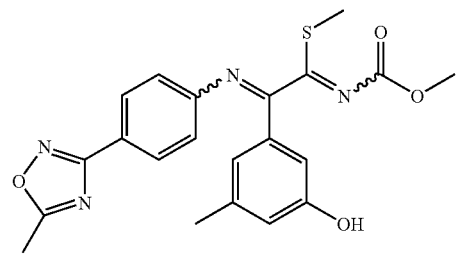

To a solution of 819 mg of Yb(OTf)$_3$ in 80 ml of dichloromethane there were added 2.43 g of 4-(5-methyl-[1,2,4]oxadiazol-3-yl)phenylamine, 3.86 g of 3-methyl-5-triisopropylsilanyloxybenzaldehyde, 3.8 g of MS3A and 3.67 ml of trimethylsilyl cyanide under a nitrogen atmosphere, and the mixture was stirred at room temperature for 19 hours. The reaction mixture was filtered through celite, and the celite was washed with ethyl acetate. The organic layer was concentrated under reduced pressure, ethyl acetate and saturated aqueous sodium hydrogencarbonate were added to the residue, and extraction was performed with ethyl acetate. After washing the organic layer with water and saturated brine, it was dried over anhydrous magnesium sulfate. The desiccating agent was filtered off and the filtrate was concentrated under reduced pressure. The residue was purified by silica gel column chromatography (heptane-ethyl acetate) to give a white sticky solid (4.05 g).

To a solution of 4.05 g of the obtained white sticky solid in 100 ml of ethanol there was added 14.5 ml of a 20% aqueous solution of ammonium sulfide, and the mixture was stirred at room temperature for 14 hours and 30 minutes. Water was added to the reaction mixture, and extraction was performed twice with ethyl acetate. After washing the organic layer with water and saturated brine, it was dried over anhydrous magnesium sulfate. The desiccating agent was filtered off and the filtrate was concentrated under reduced pressure.

Next, 100 ml of dichloromethane was added to the obtained residue for dissolution. After adding 1.38 g of Me$_3$O$^+$BF$_4^-$ to the solution, the mixture was stirred at room temperature for 2 hours. Saturated aqueous sodium hydrogencarbonate was added to the reaction mixture and extraction was performed with dichloromethane. The organic layer was washed with water and then dried over anhydrous magnesium sulfate. The desiccating agent was filtered off and the filtrate was concentrated under reduced pressure.

To a solution of the obtained residue in 80 ml of toluene there were added 3.93 ml of 2,4,6-collidine and 1.97 ml of methyl chloroformate, and the mixture was stirred at 85° C. for 5 hours under a nitrogen atmosphere. Water was added to the reaction mixture and extraction was performed with ethyl acetate. The organic layer was washed with ice-cooled 0.5N hydrochloric acid, water, saturated aqueous sodium hydrogencarbonate and saturated brine, and then dried over anhydrous magnesium sulfate. The desiccating agent was filtered off and the filtrate was concentrated under reduced pressure. The residue was purified by silica gel column chromatography (heptane-ethyl acetate) to give a yellow oil (1.9 g).

To a solution of 1.9 g of the obtained yellow oil in 20 ml of THF there was added 3.6 ml of TBAF (1.0 M, THF solution), and the mixture was stirred at room temperature for 2 hours. After adding saturated aqueous ammonium chloride to the reaction mixture, the solvent was distilled off under reduced pressure. Water was added to the residue and extraction was performed with ethyl acetate. The organic layer was washed with saturated brine and dried over anhydrous magnesium sulfate. The desiccating agent was filtered off and the filtrate was concentrated under reduced pressure. The residue was purified by silica gel column chromatography (heptane-ethyl acetate) to give the title compound (1.1 g, isomeric mixture).

$^1$H-NMR (CDCl$_3$) Main isomer:

δ 2.32 (s, 3H) 2.35 (s, 3H) 2.65 (s, 3H) 3.62 (s, 3H) 5.14 (br.s, 1H) 6.83 (br.s, 1H) 7.15-7.17 (m, 3H) 7.23 (br.s, 1H) 8.00-8.03 (m, 2H)

(43c) (R) and (S)-4-({[3-methyl-5-(1-methylpiperidin-4-yloxy)phenyl]-(5-oxo-1-pyrimidin-2-yl-4,5-dihydro-1H-[1,2,4]triazol-3-yl)methyl}amino)benzamidine diacetate

[Chemical Formula 193]

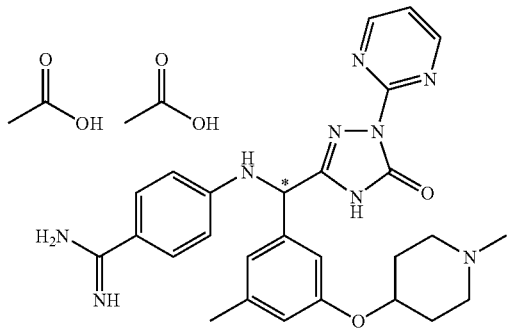

After adding 32.6 mg of 1-methylpiperidin-4-ol and 93 mg of triphenylphosphine to a solution of 100 mg of {2-(3-hydroxy-5-methylphenyl)-2-[4-(5-methyl-[1,2,4]oxadiazol-3-yl)phenylimino]-1-methylsulfanylethylidene}carbamic acid methyl ester in 1 ml of THF, the mixture was stirred for 35 minutes while cooling on ice. After adding 0.100 ml of DIAD to the reaction mixture and stirring for 30 minutes while cooling on ice, the mixture was stirred at room temperature for 3 hours. The reaction mixture was concentrated and the residue was crudely purified by NAM silica gel column chromatography (ethyl acetate-methanol) to give 78 mg of a crude product.

To a solution of 78 mg of the obtained crude product in 2 ml of DMF there were added 14.8 mg of 2-hydrazinopyrimidine and 0.031 ml of triethylamine, and the mixture was stirred at 85° C. for 10 hours under a nitrogen atmosphere. The reaction mixture was concentrated under reduced pressure.

The obtained residue was dissolved in 2 ml of methanol, 1 ml of THF and 0.070 ml of acetic acid. After adding 100 mg of sodium cyanotrihydroborate to the reaction mixture it was stirred at room temperature for 3 hours. The reaction mixture was crudely purified by reverse-phase high performance liquid chromatography (acetonitrile-water, 0.1% acetic acid) to give a crude product.

To a solution of the obtained crude product in 1.8 ml of a methanol:water:acetic acid=1:1:1 mixed solvent there was added 80 mg of iron powder, and the mixture was stirred at 60° C. for 10 hours under a nitrogen atmosphere. After filtering the reaction mixture, it was purified by reverse-phase high performance liquid chromatography (acetonitrile-water, 0.1% acetic acid).

The obtained product was optically resolved using a SUMICHIRAL OA-2500 column, and the first eluting enantiomer (3.16 mg) of the title compound was obtained as a white solid.

$^1$H-NMR (CD$_3$OD) δ 1.88 (br.s, 2H) 1.92 (s, 6H) 2.02 (br.s, 2H) 2.30 (s, 3H) 2.51 (s, 3H) 2.71 (br.s, 2H) 2.94 (br.s, 2H) 4.50 (br.s, 1H) 5.58 (s, 1H) 6.73 (br.s, 1H) 6.85 (d, J=9.2 Hz, 2H) 6.96 (br.s, 1H) 6.98 (br.s, 1H) 7.31 (t, J=4.8 Hz, 1H) 7.60 (d, J=9.2 Hz, 2H) 8.77 (d, J=4.8 Hz, 2H)

HPLC retention time: 7 min (Column name: SUMICHIRAL OA-2500, 30 mmφ×25 cm, Manufacturer: Sumika Chemical Analysis Service, Ltd., Mobile phase: 0.05 M ammonium acetate-methanol solution, Elution rate: 40 ml/min)

Example 44

(R) and (S)-2-{3-[(4-carbamimidoylphenylamino)-(5-oxo-1-pyrimidin-2-yl-4,5-dihydro-1H-[1,2,4]triazol-3-yl)methyl]-5-methylphenoxy}-N,N-dimethylacetamide acetate

[Chemical Formula 194]

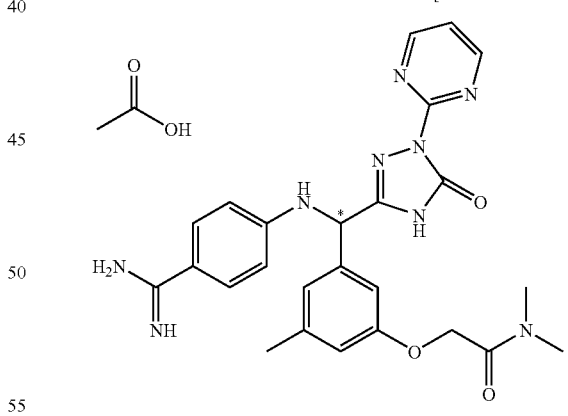

To a solution of 100 mg of {2-(3-hydroxy-5-methylphenyl)-2-[4-(5-methyl-[1,2,4]oxadiazol-3-yl)phenylimino]-1-methylsulfanylethylidene}carbamic acid methyl ester (Example (43b)) in 2 ml of DMF there were added 65 mg of potassium carbonate, 18 mg of tetrabutylammonium iodide and 0.049 ml of 2-chloro-N,N-dimethylacetamide, and the mixture was stirred at room temperature for 6 hours and 30 minutes. Ethyl acetate and water were added to the reaction mixture, and extraction was performed three times with ethyl acetate. The organic layer was filtered through PRESEP™ and the filtrate was concentrated.

To a solution of the obtained residue in 2 ml of DMF there were added 23.4 mg of 2-hydrazinopyrimidine and 0.050 ml of triethylamine, and the mixture was stirred at 85° C. for 10 hours under a nitrogen atmosphere. The reaction mixture was concentrated under reduced pressure.

The obtained residue was dissolved in 2 ml of methanol, 1 ml of THF and 0.070 ml of acetic acid. After adding 100 mg of sodium cyanotrihydroborate to the reaction mixture it was stirred at room temperature for 3 hours. The reaction mixture was crudely purified by reverse-phase high performance liquid chromatography (acetonitrile-water, 0.1% acetic acid) to give a crude product.

To a solution of the obtained crude product in 1.8 ml of a methanol:water:acetic acid=1:1:1 mixed solvent there was added 80 mg of iron powder, and the mixture was stirred at 60° C. for 10 hours under a nitrogen atmosphere. After filtering the reaction mixture, it was purified by reverse-phase high performance liquid chromatography (acetonitrile-water, 0.1% acetic acid).

The obtained product was optically resolved using a SUMICHIRAL OA-2500 column, and the first eluting enantiomer (1.4 mg) of the title compound was obtained as a white solid.

$^1$H-NMR (CD$_3$OD) δ 1.91 (s, 3H) 2.30 (s, 3H) 2.92 (s, 3H) 3.05 (s, 3H) 4.77 (s, 2H) 5.57 (s, 1H) 6.74 (s, 1H) 6.84 (d, J=8.8 Hz, 2H) 6.94 (s, 1H) 7.00 (s, 1H) 7.30 (t, J=4.4 Hz, 1H) 7.59 (d, J=8.8 Hz, 2H) 8.77 (d, J=4.4 Hz, 2H)

HPLC retention time: 9 min (Column name: SUMICHIRAL OA-2500, 30 mmφ×25 cm, Manufacturer: Sumika Chemical Analysis Service, Ltd., Mobile phase: 0.05 M ammonium acetate-methanol solution, Elution rate: 40 ml/min)

Example 45

(1) 4-[((R) and (S)-(5-oxo-1-pyrimidin-2-yl-4,5-dihydro-1H-[1,2,4]triazol-3-yl)-{3-[(S)-(tetrahydrofuran-3-yl)oxy]-5-vinylphenyl}methyl)amino]benzamidine acetate and (2) 4-[((R) and (S)-{3-ethynyl-5-[(S)-(tetrahydrofuran-3-yl)oxy]phenyl}-(5-oxo-1-pyrimidin-2-yl-4,5-dihydro-1H-[1,2,4]triazol-3-yl)methyl)amino]benzamidine acetate (45a)
3-ethynyl-5-triisopropylsilanyloxybenzaldehyde

[Chemical Formula 195]

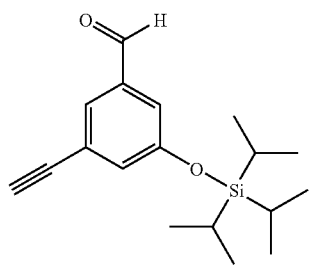

To a solution of 2.0 g of 3-ethynyl-5-hydroxybenzaldehyde [CAS No. 871345-34-5] in 20 ml of DMF there were added 1.87 g of imidazole and 4.4 ml of chlorotriisopropylsilane. The mixture was stirred overnight at room temperature. Water was added to the reaction mixture and extraction was performed with ethyl acetate. The organic layer was washed with ice-cooled 1N hydrochloric acid, water and saturated brine, and dried over anhydrous magnesium sulfate. The desiccating agent was filtered off and the filtrate was concentrated under reduced pressure. The residue was purified by silica gel column chromatography (ethyl acetate-heptane) to give the title compound (3.92 g) as a light yellow oil.

$^1$H-NMR (CDCl$_3$) δ 1.11 (d, J=6.8 Hz, 18H) 1.23-1.32 (m, 3H) 3.13 (s, 1H) 7.21-7.23 (m, 1H) 7.34 (d, J=1.2 Hz, 1H) 7.55 (dd, J=1.2, 1.6 Hz, 1H) 9.90 (s, 1H)

(45b) {2-(3-ethynyl-5-hydroxyphenyl)-2-[4-(5-methyl-[1,2,4]oxadiazol-3-yl)phenylimino]-1-methylsulfanylethylidene}carbamic acid methyl ester

[Chemical Formula 196]

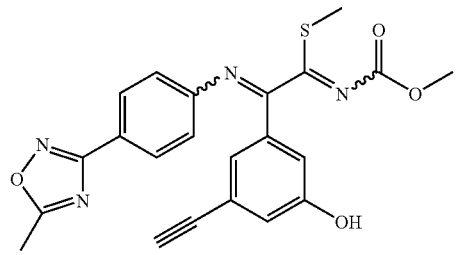

After adding 2.51 g of 4-(5-methyl-[1,2,4]oxadiazol-3-yl)phenylamine, 8 g of MS3A, 806 mg of Yb(OTf)$_3$ and 4.9 ml of trimethylsilyl cyanide to a solution of 3.92 g of 3-ethynyl-5-triisopropylsilanyloxybenzaldehyde in 100 ml of dichloromethane under a nitrogen atmosphere, the mixture was stirred at room temperature for 12 hours. The reaction mixture was filtered, and the filtrate was concentrated under reduced pressure. The residue was purified by silica gel column chromatography (ethyl acetate-heptane) to give a light yellow solid (6.06 g).

To a solution of 6.06 g of the obtained light yellow solid in 150 ml of a methanol:THF=2:1 mixed solvent there was added 100 ml of a 20% aqueous solution of ammonium sulfide, and the mixture was stirred at room temperature for 25 hours and 30 minutes. The reaction mixture was concentrated under reduced pressure. Water was added to the residue and extraction was performed with ethyl acetate. After washing the organic layer with water and saturated brine, it was dried over anhydrous sodium sulfate. The desiccating agent was filtered off and the filtrate was concentrated under reduced pressure.

To a solution of the residue in 20 ml of DMF there were added 383 mg of imidazole and 1.2 ml of chlorotriisopropylsilane. The mixture was stirred at room temperature for 2 hours. Water was added to the reaction mixture and extraction was performed with ethyl acetate. The organic layer was washed with water and saturated brine, and then dried over anhydrous sodium sulfate. The desiccating agent was filtered off and the filtrate was concentrated under reduced pressure. The residue was purified by silica gel column chromatography (ethyl acetate-heptane) to give a light yellow solid (5.58 g).

To a solution of 5.58 g of the obtained light yellow solid in 50 ml of acetonitrile there was added 1.74 g of Me$_3$O$^+$BF$_4^-$, and the mixture was stirred at 0° C. for 10 minutes. Saturated aqueous sodium hydrogencarbonate was added to the reaction mixture, and extraction was performed with ethyl acetate. After washing the organic layer with water and saturated brine, it was dried over anhydrous magnesium sulfate. The desiccating agent was filtered off, and the filtrate was concentrated under reduced pressure to give a yellow oil (5.87 g).

To a solution of 5.87 g of the obtained yellow oil in 100 ml of ethyl acetate there was added 15 g of manganese dioxide, and the mixture was stirred at room temperature for 2 hours. The reaction mixture was filtered, and the filtrate was concentrated under reduced pressure to give an orange oil (5.6 g).

To a solution of 5.6 g of the obtained orange oil in 60 ml of toluene there were added 4.84 ml of 2,4,6-collidine and 2.42 ml of methyl chloroformate, and the mixture was stirred at 80° C. for 1 hour and 30 minutes under a nitrogen atmosphere. Water was added to the reaction mixture and extraction was performed with ethyl acetate. The organic layer was washed with ice-cooled 1N hydrochloric acid, water and saturated brine and then dried over anhydrous magnesium sulfate. The desiccating agent was filtered off and the filtrate was concentrated under reduced pressure. The residue was purified by silica gel column chromatography (ethyl acetate-heptane) to give a yellow oil (4.71 g).

To a solution of 4.71 g of the obtained yellow oil in 60 ml of THF there was added 8.77 ml of TBAF (1.0 M, THF solution), and the mixture was stirred at 0° C. for 1 hour. Saturated aqueous ammonium chloride was added to the reaction mixture and extraction was performed with ethyl acetate. The organic layer was washed with water and saturated brine and dried over anhydrous magnesium sulfate. The desiccating agent was filtered off and the filtrate was concentrated under reduced pressure. The residue was purified by silica gel column chromatography (ethyl acetate-heptane) to give the title compound (3.28 g) as a yellow solid.

¹H-NMR (CDCl₃) Main isomer:

δ 2.32 (s, 3H) 2.66 (s, 3H) 3.10 (s, 1H) 3.65 (s, 3H) 7.12 (dd, J=1.2, 2.4 Hz, 1H) 7.15 (d, J=8.8 Hz, 2H) 7.38 (dd, J=1.6, 2.4 Hz, 1H) 7.51 (d, J=1.2, 1.6 Hz, 1H) 8.03 (d, J=8.8 Hz, 2H)

(45c) 4-[((R) and (S)-(5-oxo-1-pyrimidin-2-yl-4,5-dihydro-1H-[1,2,4]triazol-3-yl)-{3-[(S)-(tetrahydrofuran-3-yl)oxy]-5-vinylphenyl}methyl)amino]benzamidine acetate (45C-1) and 4-[((R) and (S)-{3-ethynyl-5-[(tetrahydrofuran-3-yl)oxy]phenyl}-(5-oxo-1-pyrimidin-2-yl-4,5-dihydro-1H-[1,2,4]triazol-3-yl)methyl)amino]benzamidine acetate (45C-2)

[Chemical Formula 197]

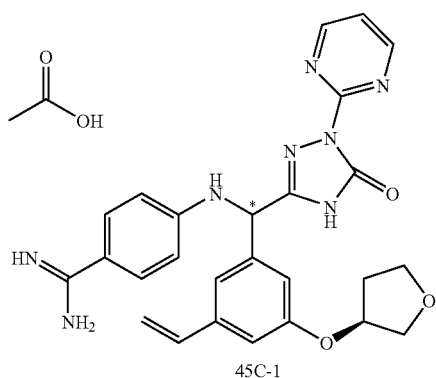

45C-1

[Chemical Formula 198]

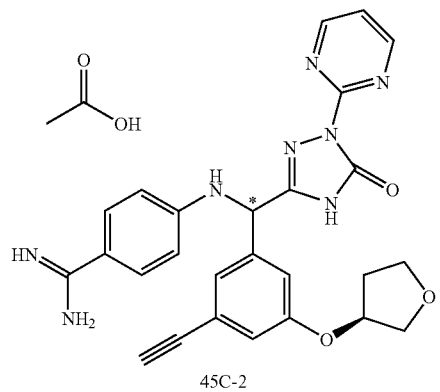

45C-2

After adding 0.0744 ml of (R)-(−)-3-hydroxytetrahydrofuran, 121 mg of triphenylphosphine and 0.0891 ml of diisopropyl azodicarboxylate to a solution of 100 mg of {2-(3-ethynyl-5-hydroxyphenyl)-2-[4-(5-methyl-[1,2,4]oxadiazol-3-yl)phenylimino]-1-methylsulfanylethylidene}carbamic acid methyl ester in 1 ml of THF at 0° C., the mixture was stirred at room temperature for 16 hours and 30 minutes. The reaction mixture was concentrated, and the residue was crudely purified by silica gel column chromatography (ethyl acetate-heptane) to give 116 mg of a crude product.

To a solution of 105 mg of the obtained crude product in 1 ml of DMF there were added 23 mg of 2-hydrazinopyrimidine and 0.029 ml of triethylamine, and the mixture was stirred at 85° C. for 19 hours under a nitrogen atmosphere. The reaction mixture was concentrated, and the residue was dissolved in 0.8 ml of methanol, 0.8 ml of THF and 0.08 ml of acetic acid. After adding 100 mg of sodium cyanotrihydroborate to the solution, the mixture was stirred at room temperature for 3 hours. The reaction mixture was crudely purified by reverse-phase high performance liquid chromatography (acetonitrile-water, 0.1% acetic acid) to give a crude product.

To a solution of the obtained crude product in 3 ml of a methanol:water:acetic acid=1:1:1 mixed solvent there was added 100 mg of iron powder, and the mixture was stirred at 65° C. for 47 hours under a nitrogen atmosphere. After filtering the reaction mixture, it was purified by reverse-phase high performance liquid chromatography (acetonitrile-water, 0.1% acetic acid) to give 4-[((5-oxo-1-pyrimidin-2-yl-4,5-dihydro-1H-[1,2,4]triazol-3-yl)-{3-[(S)-(tetrahydrofuran-3-yl)oxy]-5-vinylphenyl}methyl)amino]benzamidine acetate and 4-[({3-ethynyl-5-[(S)-(tetrahydrofuran-3-yl)oxy]phenyl}-(5-oxo-1-pyrimidin-2-yl-4,5-dihydro-1H-[1,2,4]triazol-3-yl)methyl)amino]benzamidine acetate.

Mass spectrum (ESI) m/z: 499 (M+H)⁺
Mass spectrum (ESI) m/z: 497 (M+H)⁺

The 4-[((5-oxo-1-pyrimidin-2-yl-4,5-dihydro-1H-[1,2,4]triazol-3-yl)-{3-[(S)-(tetrahydrofuran-3-yl)oxy]-5-vinylphenyl}methyl)amino]benzamidine acetate was optically resolved using a SUMICHIRAL OA-2500 column, and the first eluting enantiomer (2.05 mg) of the title compound (45C-1) was obtained as a light yellow solid.

¹H-NMR (CD₃OD) δ 1.91 (s, 3H) 1.99-2.08 (m, 1H) 2.14-2.25 (m, 1H) 3.78-3.98 (m, 4H) 4.98-5.05 (m, 1H) 5.24 (dd, J=0.8, 10.8 Hz, 1H) 5.62 (s, 1H) 5.79 (dd, J=0.8, 17.6 Hz, 1H) 6.69 (dd, J=10.8, 17.6 Hz, 1H) 6.86 (d, J=8.8 Hz, 2H) 6.89-6.92 (m, 1H) 6.98-7.03 (m, 1H) 7.25 (br.s, 1H) 7.30 (t, J=4.8 Hz, 1H) 7.60 (d, J=8.8 Hz, 2H) 8.77 (d, J=4.8 Hz, 2H)

HPLC retention time: 14 min

The 4-[({3-ethynyl-5-[(S)-(tetrahydrofuran-3-yl)oxy]phenyl}-(5-oxo-1-pyrimidin-2-yl-4,5-dihydro-1H-[1,2,4]triazol-3-yl)methyl)amino]benzamidine acetate was optically resolved using a SUMICHIRAL OA-2500 column, and the first eluting enantiomer (1.43 mg) of the title compound (45C-2) was obtained as a light yellow solid.

$^1$H-NMR (CD$_3$OD) δ 1.92 (s, 3H) 1.97-2.07 (m, 1H) 2.14-2.26 (m, 1H) 3.50 (s, 1H) 3.79-3.97 (m, 4H) 4.97-5.03 (m, 1H) 5.62 (s, 1H) 6.85 (d, J=9.2 Hz, 2H) 6.92-6.93 (m, 1H) 7.12-7.13 (m, 1H) 7.27 (br.s, 1H) 7.30 (t, J=4.8 Hz, 1H) 7.61 (d, J=9.2 Hz, 2H) 8.77 (d, J=4.8 Hz, 2H)

HPLC retention time: 15 min

Example 46

(R) and (S)-4-({[3-(2-hydroxyethoxy)-5-vinylphenyl]-(5-oxo-1-pyrimidin-2-yl-4,5-dihydro-1H-[1,2,4]triazol-3-yl)methyl}amino)benzamidine acetate

[Chemical Formula 199]

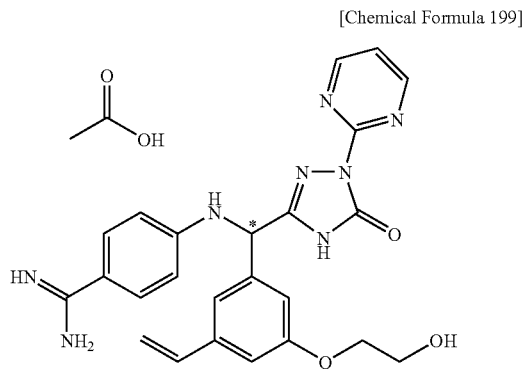

After adding 200 mg of potassium carbonate and 0.1 ml of 2-(2-bromoethoxy)tetrahydro-2H-pyran to a solution of 80 mg of {2-(3-ethynyl-5-hydroxyphenyl)-2-[4-(5-methyl-[1,2,4]oxadiazol-3-yl)phenylimino]-1-methylsulfanylethylidene}carbamic acid methyl ester (Example (45b)) in 1 ml of DMF, the mixture was stirred at room temperature for 14 hours. Water was added to the reaction mixture and extraction was performed with ethyl acetate. The organic layer was washed with water and dried through PRE-SEP™. The filtrate was concentrated, and the residue was purified by silica gel column chromatography (ethyl acetate-heptane) to give 95 mg of a yellow oil.

To a solution of 95 mg of the obtained yellow oil in 1 ml of DMF there were added 19 mg of 2-hydrazinopyrimidine and 0.024 ml of triethylamine, and the mixture was stirred at 85° C. for 16 hours under a nitrogen atmosphere. The reaction mixture was concentrated, and the residue was dissolved in 1 ml of methanol, 1 ml of THF and 0.1 ml of acetic acid. After adding 100 mg of sodium cyanotrihydroborate to the solution, the mixture was stirred at room temperature for 3 hours. The reaction mixture was crudely purified by reverse-phase high performance liquid chromatography (acetonitrile-water, 0.1% acetic acid) to give a crude product.

To a solution of the obtained crude product in 3 ml of a methanol:water:acetic acid=1:1:1 mixed solvent there was added 100 mg of iron powder, and the mixture was stirred at 60° C. for 2 days under a nitrogen atmosphere. After filtering the reaction mixture, it was purified by reverse-phase high performance liquid chromatography (acetonitrile-water, 0.1% acetic acid) to give 5.63 mg of 4-({[3-(2-hydroxyethoxy)-5-vinylphenyl]-(5-oxo-1-pyrimidin-2-yl-4,5-dihydro-1H-[1,2,4]triazol-3-yl)methyl}amino)benzamidine acetate.

Mass spectrum (ESI) m/z: 473 (M+H)$^+$

This compound was optically resolved using a SUMICHIRAL OA-2500 column, and the first eluting enantiomer (1.99 mg) of the title compound was obtained as a white solid.

$^1$H-NMR (CD$_3$OD) δ 1.91 (s, 3H) 3.84 (t, J=4.8 Hz, 2H) 4.04 (m, 2H) 5.23 (dd, J=0.8, 10.8 Hz, 1H) 5.59 (s, 1H) 5.78 (dd, J=0.8, 17.6 Hz, 1H) 6.69 (dd, J=10.8, 17.6 Hz, 1H) 6.85 (d, J=9.2 Hz, 2H) 6.92-6.99 (m, 1H) 7.03-7.10 (m, 1H) 7.24 (s, 1H) 7.27 (t, J=4.8 Hz, 1H) 7.59 (d, J=9.2 Hz, 2H) 8.76 (d, J=4.8 Hz, 2H)

HPLC retention time: 15 min (Column name: SUMICHIRAL OA-2500, 30 mmφ×25 cm, Manufacturer: Sumika Chemical Analysis Service, Ltd., Mobile phase: 0.05 M ammonium acetate-methanol solution, Elution rate: 20 ml/min)

Example 47

(R) and (S)-4-{[(3-hydroxy-5-vinylphenyl)-(5-oxo-1-pyrimidin-2-yl-4,5-dihydro-1H-[1,2,4]triazol-3-yl)methyl]amino}benzamidine acetate

[Chemical Formula 200]

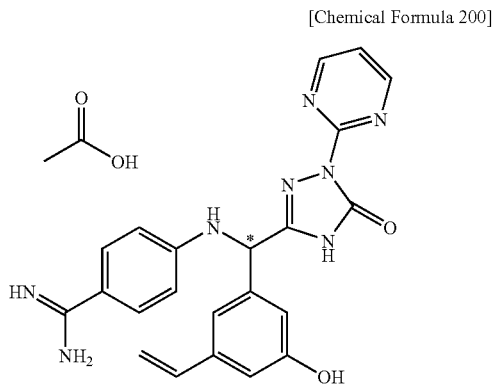

After adding 11 mg of 2-hydrazinopyrimidine and 0.014 ml of triethylamine to a solution of 43 mg of {2-(3-ethynyl-5-hydroxyphenyl)-2-[4-(5-methyl-[1,2,4]oxadiazol-3-yl)phenylimino]-1-methylsulfanylethylidene}carbamic acid methyl ester (Example (45b)) in 1 ml of DMF, the mixture was stirred at 85° C. for 16 hours under a nitrogen atmosphere. The reaction mixture was concentrated, and the residue was dissolved in 1 ml of methanol, 1 ml of THF and 0.1 ml of acetic acid. After adding 100 mg of sodium cyanotrihydroborate to the solution, the mixture was stirred at room temperature for 3 hours. The reaction mixture was crudely purified by reverse-phase high performance liquid chromatography (acetonitrile-water, 0.1% acetic acid) to give a crude product.

To a solution of the obtained crude product in 3 ml of a methanol:water:acetic acid=1:1:1 mixed solvent there was added 100 mg of iron powder, and the mixture was stirred at 60° C. for 2 days under a nitrogen atmosphere. After filtering the reaction mixture, it was purified by reverse-phase high performance liquid chromatography (acetonitrile-water, 0.1% acetic acid) to give 6.05 mg of 4-{[(3-hydroxy-5-vinylphenyl)-(5-oxo-1-pyrimidin-2-yl-4,5-dihydro-1H-[1,2,4]triazol-3-yl)methyl]amino}benzamidine acetate.

Mass spectrum (ESI) m/z: 429 (M+H)$^+$

This compound was optically resolved using a SUM-ICHIRAL OA-2500 column, and the first eluting enantiomer (2.13 mg) of the title compound was obtained as a white solid.

$^1$H-NMR (CD$_3$OD) δ 1.91 (s, 3H) 5.20 (d, J=11.2 Hz, 1H) 5.56 (s, 1H) 5.74 (d, J=17.6 Hz, 1H) 6.65 (dd, J=11.2, 17.6 Hz, 1H) 6.81-6.88 (m, 4H) 7.11 (s, 1H) 7.29 (br.s, 1H) 7.60 (d, J=8.8 Hz, 2H) 8.77 (d, J=4.8 Hz, 2H)

HPLC retention time: 11 min (Column name: SUM-ICHIRAL OA-2500, 30 mmφ×25 cm, Manufacturer: Sumika Chemical Analysis Service, Ltd., Mobile phase: 0.05 M ammonium acetate-methanol solution, Elution rate: 30 ml/min)

Example 48

4-{[(2-fluoro-4,5-dimethoxyphenyl)-(5-oxo-1-pyrimidin-2-yl-4,5-dihydro-1H-[1,2,4]triazol-3-yl)methyl]amino}-N-methylbenzamidine acetate (48a) 4-{[(2-fluoro-4,5-dimethoxyphenyl)-(5-oxo-1-pyrimidin-2-yl-4,5-dihydro-1H-[1,2,4]triazol-3-yl)methyl]amino}thiobenzamide

[Chemical Formula 201]

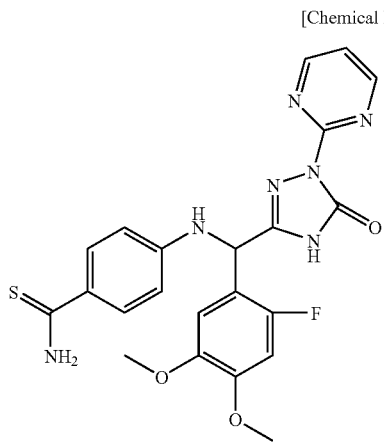

The same procedure was carried out as in Examples (2a)-(2g), except that 2-fluoro-3,4-dimethoxybenzaldehyde and 2-hydrazinopyrimidine were used instead of respectively 2-fluoro-3,5-dimethoxybenzaldehyde in Example (2a) and (1-oxypyridin-2-yl)hydrazine in Example (2f), to give the title compound.

$^1$H-NMR (d$_6$-DMSO) δ 3.70 (s, 3H) 3.77 (s, 3H) 6.31 (d, J=6.9 Hz, 1H) 6.68 (d, J=8.9 Hz, 2H) 6.96 (d, J=11.5 Hz, 1H) 7.15 (d, J=6.5 Hz, 1H) 7.02 (d, J=6.9 Hz, 1H) 7.37 (t, J=4.9 Hz, 1H) 7.83 (d, J=8.9 Hz, 2H) 8.79 (d, J=4.9 Hz, 2H) 9.05 (s, 1H) 9.34 (s, 1H) 12.24 (s, 1H)

(48b) 4-{[(2-fluoro-4,5-dimethoxyphenyl)-(5-oxo-1-pyrimidin-2-yl-4,5-dihydro-1H-[1,2,4]triazol-3-yl)methyl]amino}-N-methylbenzamidine acetate

[Chemical Formula 202]

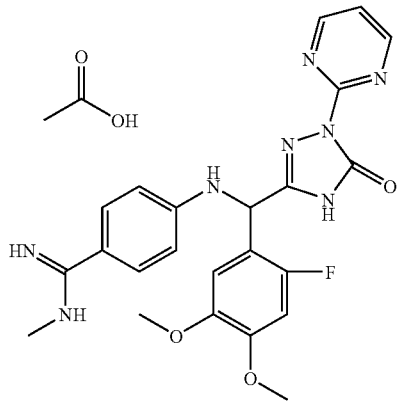

After adding 24.4 mg of Me$_3$O$^+$BF$_4^-$ to a solution of 72.2 mg of 4-{[(2-fluoro-4,5-dimethoxyphenyl)-(5-oxo-1-pyrimidin-2-yl-4,5-dihydro-1H-[1,2,4]triazol-3-yl)methyl]amino}thiobenzamide in 10 ml of acetonitrile under a nitrogen atmosphere, the mixture was stirred at room temperature for 3 hours. The solvent was removed under reduced pressure, the residue was dissolved in 2 ml of acetonitrile and 2 ml of 2-propanol, and 15.2 mg of methylamine hydrochloride and 31.4 μl of triethylamine were added. The reaction mixture was stirred at 85° C. for 16 hours under a nitrogen atmosphere and then cooled. The solvent was concentrated, and the residue was purified by reverse-phase high performance liquid chromatography (acetonitrile-water, 0.1% acetic acid) to give the title compound (10.9 mg) as a white solid.

$^1$H-NMR (CD$_3$OD) δ 1.95 (s, 3H) 3.03 (s, 3H) 3.75 (s, 3H) 3.82 (s, 3H) 5.93 (s, 1H) 6.85 (d, J=11.2 Hz, 1H) 6.87 (d, J=9.0 Hz, 2H) 7.08 (d, J=6.6 Hz, 1H) 7.35 (t, J=4.6 Hz, 1H) 7.55 (d, J=9.0 Hz, 2H) 8.78 (d, J=4.6 Hz, 2H)

Example 49

4-{[(2-fluoro-4,5-dimethoxyphenyl)-(5-oxo-1-pyrimidin-2-yl-4,5-dihydro-1H-[1,2,4]triazol-3-yl)methyl]amino}-N,N-dimethylbenzamidine acetate

[Chemical Formula 203]

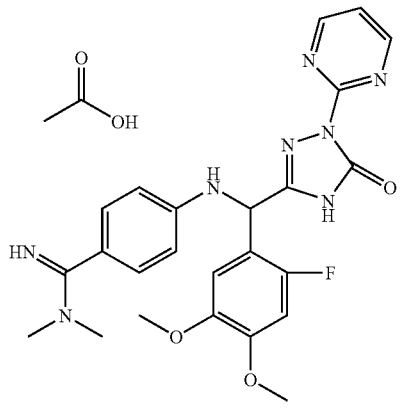

The same procedure was carried out as in Example (48b), except that dimethylamine hydrochloride was used instead of the methylamine hydrochloride, to give the title compound as a white solid.

$^1$H-NMR (CD$_3$OD) δ 1.95 (s, 3H) 3.13 (s, 3H) 3.22 (s, 3H) 3.77 (s, 3H) 3.83 (s, 3H) 5.92 (s, 1H) 6.86 (d, J=11.6 Hz, 1H) 6.89 (d, J=8.9 Hz, 2H) 7.08 (d, J=6.8 Hz, 1H) 7.35 (t, J=4.6 Hz, 1H) 7.37 (d, J=9.0 Hz, 2H) 8.78 (d, J=4.6 Hz, 2H)

Example 50

(R) and (S)-4-({[1-(2-aminopyridin-3-yl)-5-oxo-4,5-dihydro-1H-[1,2,4]triazol-3-yl]-[2-fluoro-3-(2-fluoroethoxy)-5-methoxyphenyl]methyl}amino)benzamidine diacetate (50a) 4-({[1-(2-aminopyridin-3-yl)-5-oxo-4,5-dihydro-1H-[1,2,4]triazol-3-yl]-[2-fluoro-3-(2-fluoroethoxy)-5-methoxyphenyl]methyl}amino)benzamidine bistrifluoroacetate

[Chemical Formula 204]

The same procedure was carried out as in Examples (3f)-(3g), except that (2-nitropyridin-3-yl)hydrazine [CAS No. 57115-43-2] was used instead of the 2-hydrazinopyrimidine in Example (3f), to give the title compound as a brown solid.

$^1$H-NMR (CD$_3$OD) δ 3.73 (s, 3H) 4.25 (m, 1H) 4.34 (m, 1H) 4.67 (m, 1H) 4.79 (m, 1H) 6.03 (s, 1H) 6.62 (dd, J=5.2, 3.1 Hz, 1H) 6.69 (dd, J=7.0, 3.1 Hz, 1H) 6.75 (dd, J=8.1, 5.4 Hz, 1H) 6.87 (d, J=8.9 Hz, 2H) 7.64 (d, J=8.9 Hz, 2H) 7.66 (dd, J=8.1, 1.0 Hz, 1H) 7.96 (dd, J=5.4, 1.0 Hz, 1H)

(50b) (R) and (S)-4-({[1-(2-aminopyridin-3-yl)-5-oxo-4,5-dihydro-1H-[1,2,4]triazol-3-yl]-[2-fluoro-3-(2-fluoroethoxy)-5-methoxyphenyl]methyl}amino) benzamidine diacetate

[Chemical Formula 205]

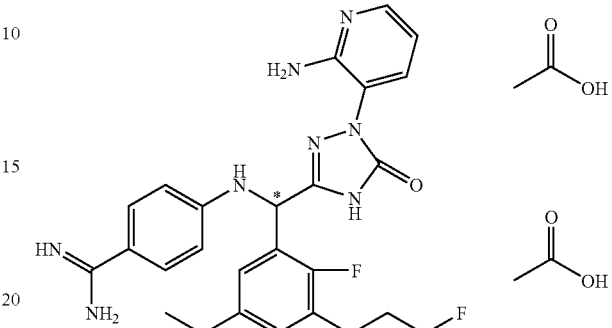

A SUMICHIRAL OA-2500 column was used for optical resolution of 28 mg of 4-({[1-(2-aminopyridin-3-yl)-5-oxo-4,5-dihydro-1H-[1,2,4]triazol-3-yl]-[2-fluoro-3-(2-fluoroethoxy)-5-methoxyphenyl]methyl}amino)benzamidine bistrifluoroacetate, and the first eluting enantiomer (11.7 mg) of the title compound was obtained as a white solid.

$^1$H-NMR (CD$_3$OD) δ 1.93 (s, 6H) 3.72 (s, 3H) 4.25 (m, 1H) 4.33 (m, 1H) 4.67 (m, 1H) 4.78 (m, 1H) 5.99 (s, 1H) 6.63 (dd, J=5.4, 3.2 Hz, 1H) 6.66 (dd, J=7.3, 3.2 Hz, 1H) 6.75 (dd, J=8.0, 5.1 Hz, 1H) 6.85 (d, J=8.9 Hz, 2H) 7.63 (d, J=8.9 Hz, 2H) 7.66 (dd, J=8.0, 1.4 Hz, 1H) 7.94 (dd, J=5.1, 1.4 Hz, 1H)

HPLC retention time: 12 min (Column name: SUMICHIRAL OA-2500, 30 mmφ×25 cm, Manufacturer: Sumika Chemical Analysis Service, Ltd., Mobile phase: 0.05 M ammonium acetate-methanol solution, Elution rate: 15 ml/min)

Example 51

4-({[1-(6-aminopyridin-2-yl)-5-oxo-4,5-dihydro-1H-[1,2,4]triazol-3-yl]-[2-fluoro-3-(2-fluoroethoxy)-5-methoxyphenyl]methyl}amino)benzamidine trifluoroacetate (51a) 6-hydrazinopyridine-2-carboxylic acid methyl ester hydrochloride

[Chemical Formula 206]

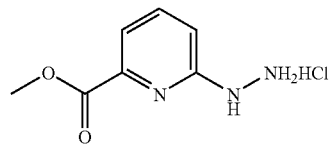

To a solution of 1.7 g of 6-bromopyridine-2-carboxylic acid methyl ester [CAS No. 26218-75-7] in 10 ml of toluene there were added 522 mg of 1,1'-bis(diphenylphosphino)ferrocene, 288 mg of tris(dibenzylideneacetone)dipalladium(0), 2.56 g of cesium carbonate and 1.04 g of t-butyl carbazinate under a nitrogen atmosphere, and the mixture was stirred while heating at 100° C. for 20 hours. The reaction mixture was cooled and the solvent was concentrated under reduced pressure, and then 40 ml of a 10% solution of hydrogen chloride in methanol was added and the reaction mixture was stirred at room temperature for 20 hours and under reflux for 10 hours. After cooling the reaction mixture, the solvent was concentrated under reduced pressure. Next, 60 ml of water and 30 ml of ethyl acetate were added to the residue and the mixture was filtered. The organic layer was extracted with 30 ml of 1N hydrochloric acid, and the aqueous layers were combined and rendered alkaline with a 5N aqueous sodium hydroxide solution. The solution was extracted twice with 250 ml of ethyl acetate, and then the organic layers were combined and dried over anhydrous magnesium sulfate. The desiccating agent was filtered off and the filtrate was concentrated under reduced pressure. The residue was dissolved in ethyl acetate, and a 4N solution of hydrogen chloride in ethyl acetate was added. The solid was filtered out and dried under reduced pressure to give 458 mg of the title compound as a brown solid.

$^1$H-NMR (CD$_3$OD) δ 3.98 (s, 3H) 7.11 (dd, J=8.5, 1.0 Hz, 1H) 7.72 (dd, J=7.5, 1.0 Hz, 1H) 7.88 (dd, J=8.5, 7.5 Hz, 1H)

(51b) 6-(3-{[2-fluoro-3-(2-fluoroethoxy)-5-methoxyphenyl]-4-(5-methyl-[1,2,4]oxadiazol-3-yl)phenylamino]methyl}-5-oxo-4,5-dihydro-1H-[1,2,4]triazol-1-yl)pyridine-2-carboxylic acid methyl ester

[Chemical Formula 207]

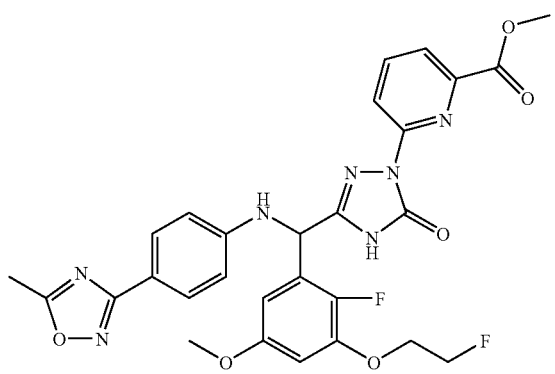

The same procedure was carried out as in Example (3f), except that 6-hydrazinopyridine-2-carboxylic acid methyl ester hydrochloride was used instead of the 2-hydrazinopyrimidine, to give the title compound as a brown solid.

$^1$H-NMR (CD$_3$OD) δ 2.57 (s, 3H) 3.71 (s, 3H) 3.95 (s, 3H) 4.22 (m, 1H) 4.29 (m, 1H) 4.66 (m, 1H) 4.77 (m, 1H) 5.94 (s, 1H) 6.62-6.67 (m, 2H) 6.80 (d, J=8.9 Hz, 2H) 7.77 (d, J=8.9 Hz, 2H) 7.98 (dd, J=8.1, 1.2 Hz, 1H) 8.05 (t, J=8.1 Hz, 1H) 8.23 (dd, J=8.1, 1.2 Hz, 1H)

(51c) 6-(3-{[2-fluoro-3-(2-fluoroethoxy)-5-methoxyphenyl]-4-(5-methyl-[1,2,4]oxadiazol-3-yl)phenylamino]methyl}-5-oxo-4,5-dihydro-1H-[1,2,4]triazol-1-yl)pyridine-2-carboxylic acid

[Chemical Formula 208]

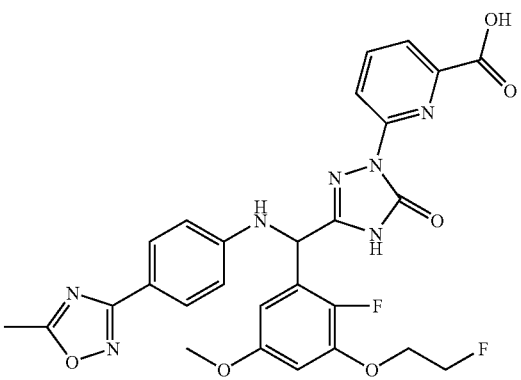

After dissolving 167 mg of 6-(3-{[2-fluoro-3-(2-fluoroethoxy)-5-methoxyphenyl]-4-(5-methyl-[1,2,4]oxadiazol-3-yl)phenylamino]methyl}-5-oxo-4,5-dihydro-1H-[1,2,4]triazol-1-yl)pyridine-2-carboxylic acid methyl ester in 2 ml of THF and 4 ml of methanol, 0.56 ml of a 5N aqueous sodium hydroxide solution was added and the mixture was stirred overnight at room temperature. After adding acetic acid and concentrating the mixture under reduced pressure, the residue was dissolved in methanol and purified by reverse-phase high performance liquid chromatography (acetonitrile-water, 0.1% trifluoroacetic acid) to give the title compound (81 mg) as a light yellow solid.

$^1$H-NMR (CD$_3$OD) δ 2.58 (s, 3H) 3.74 (s, 3H) 4.25 (m, 1H) 4.33 (m, 1H) 4.77 (m, 1H) 4.89 (m, 1H) 5.98 (s, 1H) 6.68-6.70 (m, 2H) 6.83 (d, J=8.9 Hz, 2H) 7.80 (d, J=8.9 Hz, 2H) 8.05 (dd, J=7.8, 0.9 Hz, 1H) 8.08 (t, J=7.8 Hz, 1H) 8.32 (dd, J=7.8, 0.9 Hz, 1H)

(51d) 2-(6-aminopyridin-2-yl)-5-{[2-fluoro-3-(2-fluoroethoxy)-5-methoxyphenyl]-[4-(5-methyl-[1,2,4]oxadiazol-3-yl)phenylamino]methyl}-2,4-dihydro-[1,2,4]triazol-3-one

[Chemical Formula 209]

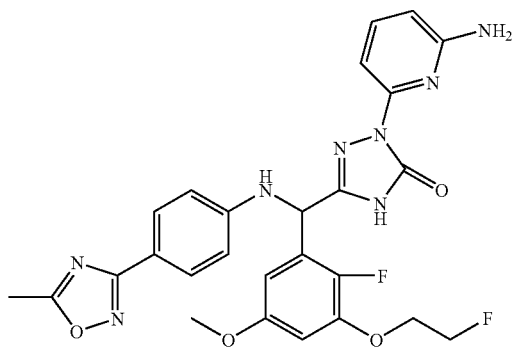

After adding 0.041 ml of triethylamine and 0.063 ml of diphenylphosphorylazide to a solution of 81 mg of 6-(3-{[2- fluoro-3-(2-fluoroethoxy)-5-methoxyphenyl]-4-(5-methyl-[1,2,4]oxadiazol-3-yl)phenylamino]methyl}-5-oxo-4,5-dihydro-1H-[1,2,4]triazol 1-yl)pyridine-2-carboxylic acid in 4 ml of 1,4-dioxane, the mixture was heated at 80° C. for 20 hours under a nitrogen atmosphere. The reaction mixture was then cooled and filtered. It was purified by reverse-phase high performance liquid chromatography (acetonitrile-water, 0.1% trifluoroacetic acid) to give the title compound (33 mg) as a white solid.

$^1$H-NMR (CD$_3$OD) δ 2.59 (s, 3H) 3.75 (s, 3H) 4.25 (m, 1H) 4.33 (m, 1H) 4.67 (m, 1H) 4.79 (m, 1H) 5.98 (s, 1H) 6.66-6.73 (m, 3H) 6.83 (d, J=9.0 Hz, 2H) 7.30 (dd, J=8.3, 1.1 Hz, 1H) 7.81 (d, J=9.0 Hz, 2H) 7.87 (t, J=8.3 Hz, 1H)

(51e) 4-({[1-(6-aminopyridin-2-yl)-5-oxo-4,5-dihydro-1H-[1,2,4]triazol-3-yl]-[2-fluoro-3-(2-fluoroethoxy)-5-methoxyphenyl]methyl}amino)benzamidine trifluoroacetate

[Chemical Formula 210]

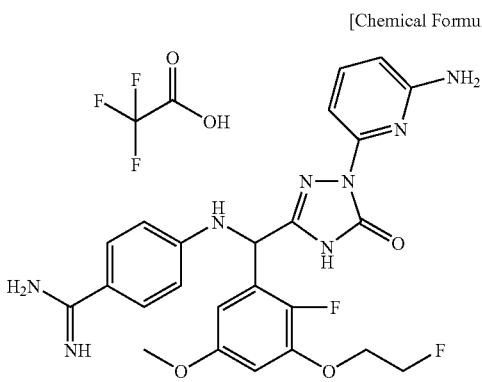

The same procedure was carried out as in Example (1g), except that 33 mg of 2-(6-aminopyridin-2-yl)-5-{[2-fluoro-3-(2-fluoroethoxy)-5-methoxyphenyl]-[4-(5-methyl-[1,2,4]oxadiazol-3-yl)phenylamino]methyl}-2,4-dihydro-[1,2,4]triazol-3-one was used instead of the 2-(3-{(2-fluoro-4,5-dimethoxyphenyl)-[4-(5-methyl-[1,2,4]oxadiazol-3-yl)phenylamino]methyl}-5-oxo-4,5-dihydro-[1,2,4]triazol-1-yl)benzoic acid, to give the title compound (11 mg) as a brown solid.

$^1$H-NMR (CD$_3$OD) δ 3.74 (s, 3H) 4.25 (m, 1H) 4.32 (m, 1H) 4.67 (m, 1H) 4.79 (m, 1H) 6.04 (s, 1H) 6.61-6.64 (m, 2H) 6.72 (dd, J=6.8, 3.3 Hz, 1H) 6.87 (d, J=9.0 Hz, 2H) 7.24 (d, J=8.0 Hz, 1H) 7.65 (d, J=9.0 Hz, 2H) 7.78 (t, J=8.0 Hz, 1H)

Example 52

(R) and (S)-4-({[1-(3-aminopyridin-2-yl)-5-oxo-4,5-dihydro-1H-[1,2,4]triazol-3-yl]-(4-fluoro-7-methoxy-2,3-dihydrobenzofuran-5-yl)methyl}amino)benzamidine diacetate

[Chemical Formula 211]

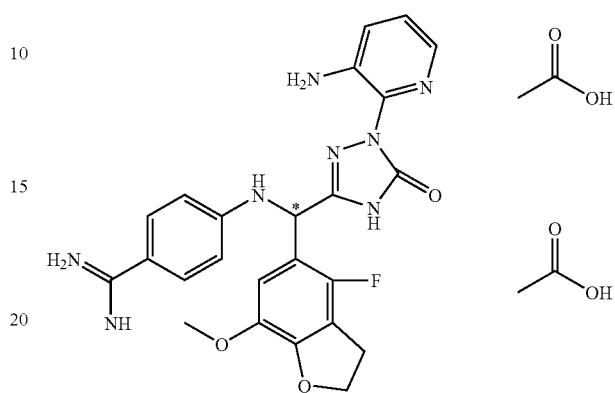

The same procedure was carried out as in Example (40d), except that (3-nitropyridin-2-yl)hydrazine was used instead of the 2-hydrazinopyrimidine, to give the first eluting enantiomer of the title compound.

$^1$H-NMR (CD$_3$OD) δ 1.93 (s, 6H) 3.27 (t, J=9.2 Hz, 2H) 3.75 (s, 3H) 4.66 (t, J=9.2 Hz, 2H) 5.91 (s, 1H) 6.86 (d, J=9.0 Hz, 2H) 6.95 (d, J=6.1 Hz, 1H) 7.21 (dd, J=8.0, 4.8 Hz, 1H) 7.33 (dd, J=8.0, 1.3 Hz, 1H) 7.62 (d, J=9.0 Hz, 2H) 7.81 (dd, J=4.8, 1.3 Hz, 1H)

HPLC retention time: 12 min (Column name: SUMICHIRAL OA-2500, 30 mmφ×25 cm, Manufacturer: Sumika Chemical Analysis Service, Ltd., Mobile phase: 0.05 M ammonium acetate-methanol solution, Elution rate: 15 ml/min)

Example 53

(R) and (S)-4-{[(4-fluoromethoxy-3-methoxyphenyl)-(5-oxo-1-pyrimidin-2-yl-4,5-dihydro-1H-[1,2,4]triazol-3-yl)methyl]amino}benzamidine acetate

[Chemical Formula 212]

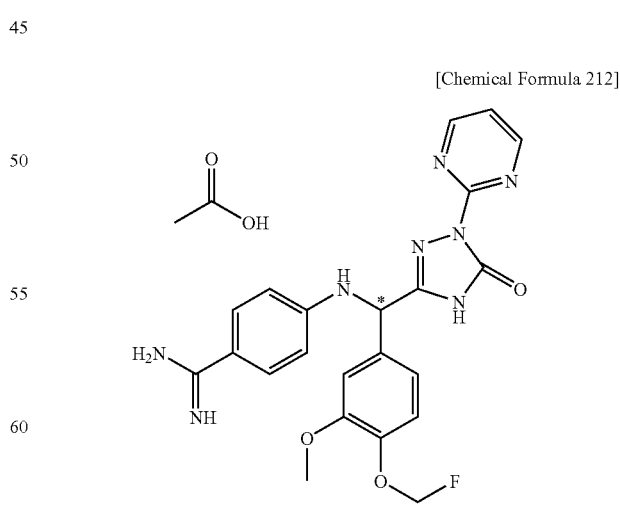

The same procedure was carried out as in Examples (16a)-(16b) except that toluene-4-sulfonic acid fluoromethyl ester was used instead of the bromoacetonitrile in Example (16a), to give 4-{[(4-fluoromethoxy-3-methoxyphenyl)-(5-oxo-1-pyrimidin-2-yl-4,5-dihydro-1H-[1,2,4]triazol-3-yl)methyl]amino}benzamidine acetate.

$^1$H-NMR (CD$_3$OD) δ 1.93 (s, 3H) 3.83 (s, 3H) 5.64 (s, 1H) 5.66 (d, J=54.4 Hz, 2H) 6.86 (d, J=8.8 Hz, 2H) 7.04 (d, J=8.4 Hz, 1H) 7.29 (d, J=8.4 Hz, 1H) 7.31-7.34 (m, 2H) 7.61 (d, J=8.8 Hz, 2H) 8.77 (d, J=4.8 Hz, 2H)

Mass spectrum (ESI) m/z: 465 (M+H)$^+$

A 13 mg portion of this compound was optically resolved using a SUMICHIRAL OA-2500 column, and the first eluting enantiomer (5.3 mg) of the title compound was obtained as a white solid.

HPLC retention time: 13 min

Example 54

(R) and (S)-4-{[(2,6-dimethoxypyridin-4-yl)-(5-oxo-1-pyrimidin-2-yl-4,5-dihydro-1H-[1,2,4]triazol-3-yl)methyl]amino}benzamidine acetate

[Chemical Formula 213]

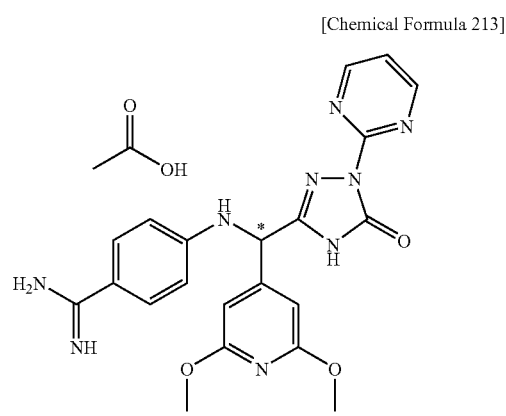

The same procedure was carried out as in Examples (17f)-(17g), except that 2-(2,6-dimethoxypyridin-4-yl)-2-[4-(5-methyl-[1,2,4]oxadiazol-3-yl)phenylimino]-1-methylsulfanylethylidene}carbamic acid methyl ester (Example (55a)) was used instead of the 2-(3-ethoxy-4-methoxyphenyl)-2-[4-(5-methyl-[1,2,4]oxadiazol-3-yl)phenylimino]-1-methylsulfanylethylidene}carbamic acid methyl ester in Example (17f), to give 4-{[(2,6-dimethoxypyridin-4-yl)-(5-oxo-1-pyrimidin-2-yl-4,5-dihydro-1H-[1,2,4]triazol-3-yl)methyl]amino}benzamidine acetate.

$^1$H-NMR (CD$_3$OD) δ 1.93 (s, 3H) 3.86 (s, 6H) 5.62 (s, 1H) 6.50 (s, 2H) 6.84 (d, J=8.8 Hz, 2H) 7.32 (t, J=5.2 Hz, 1H) 7.61 (d, J=8.8 Hz, 2H) 8.77 (d, J=5.2 Hz, 2H)

Mass spectrum (ESI) m/z: 448 (M+H)$^+$

A 9.4 mg portion of this compound was optically resolved using a SUMICHIRAL OA-2500 column, and the first eluting enantiomer (3.6 mg) of the title compound was obtained as a white solid.

HPLC retention time: 16 min

Example 55

(R) and (S)-4-({[1-(3-aminopyridin-2-yl)-5-oxo-4,5-dihydro-1H-[1,2,4]triazol-3-yl]-(2,6-dimethoxypyridin-4-yl)methyl}amino)benzamidine acetate (55a) 2-(2,6-dimethoxypyridin-4-yl)-2-[4-(5-methyl-[1,2,4]oxadiazol-3-yl)phenylimino]-1-methylsulfanylethylidene}carbamic acid methyl ester

[Chemical Formula 214]

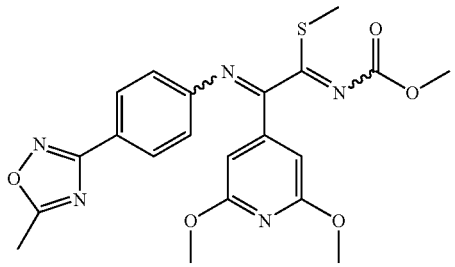

The same procedure was carried out as in Example (19b), except that 2,6-dimethoxypyridine-4-carbaldehyde [CAS No. 52606-01-6] was used instead of the 2-methoxy-6-methylpyridine-4-carbaldehyde, to give the title compound.

$^1$H-NMR (CDCl$_3$) Main isomer:

δ 2.34 (s, 3H) 2.65 (s, 3H) 3.68 (s, 3H) 3.96 (s, 6H) 6.75 (s, 2H) 7.13 (d, J=8.8 Hz, 2H) 8.02 (d, J=8.8 Hz, 2H)

(55b) (R) and (S)-4-({[1-(3-aminopyridin-2-yl)-5-oxo-4,5-dihydro-1H-[1,2,4]triazol-3-yl]-(2,6-dimethoxypyridin-4-yl)methyl}amino)benzamidine acetate

[Chemical Formula 215]

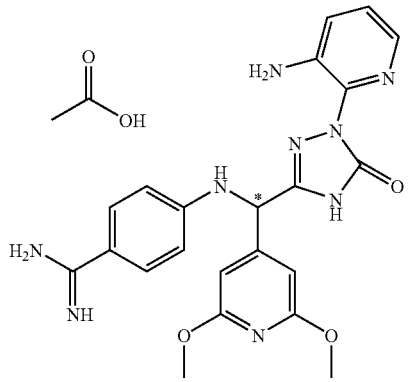

The same procedure was carried out as in Example (19c), except that 2-(2,6-dimethoxypyridin-4-yl)-2-[4-(5-methyl-[1,2,4]oxadiazol-3-yl)phenylimino]-1-methylsulfanylethylidene}carbamic acid methyl ester was used instead of the 2-(2-methoxy-6-methylpyridin-4-yl)-2-[4-(5-methyl-[1,2,4]oxadiazol-3-yl)phenylimino]-1-methylsulfanylethylidene}carbamic acid methyl ester, to give 4-({[1-(3-aminopyridin-2-yl)-5-oxo-4,5-dihydro-1H-

[1,2,4]triazol-3-yl]-(2,6-dimethoxypyridin-4-yl)methyl}amino)benzamidine acetate.

$^1$H-NMR (CD$_3$OD) δ 1.93 (s, 3H) 3.88 (s, 6H) 5.65 (s, 1H) 6.50 (s, 2H) 6.85 (d, J=8.8 Hz, 2H) 7.22 (dd, J=8.0, 4.8 Hz, 1H) 7.32 (dd, J=8.0, 1.2 Hz, 1H) 7.62 (d, J=8.8 Hz, 2H) 7.82 (dd, J=4.8, 1.2 Hz, 1H)

Mass spectrum (ESI) m/z: 462 (M+H)$^+$

A 20 mg portion of this compound was optically resolved using a SUMICHIRAL OA-2500 column, and the first eluting enantiomer (7.5 mg) of the title compound was obtained.

HPLC retention time: 7 min

Example 56

(R) and (S)-4-{[(2,6-dimethoxypyridin-4-yl)-[1-(3-fluoropyridin-2-yl)-5-oxo-4,5-dihydro-1H-[1,2,4]triazol-3-yl)methyl]amino}benzamidine acetate

[Chemical Formula 216]

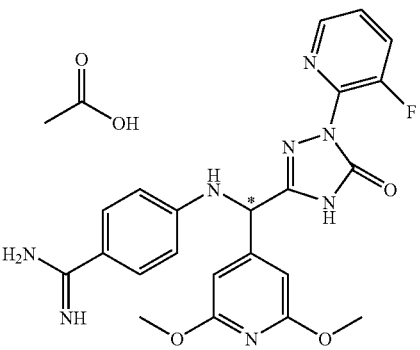

The same procedure was carried out as in Example (19c), except that {2-(2,6-dimethoxypyridin-4-yl)-2-[4-(5-methyl-[1,2,4]oxadiazol-3-yl)phenylimino]-1-methylsulfanylethylidene}carbamic acid methyl ester and (3-fluoropyridin-2-yl)hydrazine were used instead of respectively the {2-(2-methoxy-6-methylpyridin-4-yl)-2-[4-(5-methyl-[1,2,4]oxadiazol-3-yl)phenylimino]-1-methylsulfanylethylidene}carbamic acid methyl ester and the (3-nitropyridin-2-yl)hydrazine, to give 4-{[(2,6-dimethoxypyridin-4-yl)-[1-(3-fluoropyridin-2-yl)-5-oxo-4,5-dihydro-1H-[1,2,4]triazol-3-yl)methyl]amino}benzamidine acetate.

$^1$H-NMR (CD$_3$OD) δ 1.96 (s, 3H) 3.89 (s, 6H) 5.66 (s, 1H) 6.49 (s, 2H) 6.85 (d, J=8.4 Hz, 2H) 7.55 (br.s, 1H) 7.62 (d, J=8.4 Hz, 2H) 7.82 (br.t, J=8.8 Hz, 1H) 8.37 (br.s, 1H)

Mass spectrum (ESI) m/z: 465 (M+H)$^+$

A 21 mg portion of this compound was optically resolved using a SUMICHIRAL OA-2500 column, and the first eluting enantiomer (5.4 mg) of the title compound was obtained.

HPLC retention time: 8 min

Example 57

4-({[1-(3-aminopyridin-2-yl)-5-oxo-4,5-dihydro-1H-[1,2,4]triazol-3-yl]-(8-methoxy-4H-benzo[1,3]dioxin-6-yl)methyl}amino)benzamidine acetate

[Chemical Formula 217]

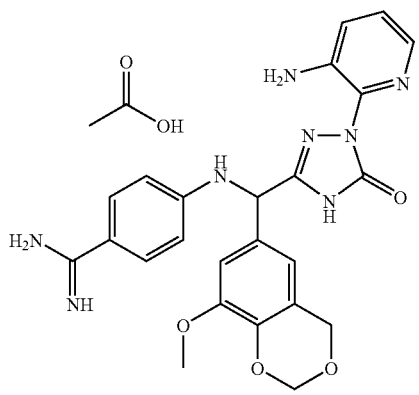

The same procedure was carried out as in Example (19c), except that [2-(8-methoxy-4H-benzo[1,3]dioxin-6-yl)-2-[4-(5-methyl-[1,2,4]oxadiazol-3-yl)phenylimino]-1-methylsulfanylethylidene]carbamic acid methyl ester (Example (21h)) was used instead of the {2-(2-methoxy-6-methylpyridin-4-yl)-2-[4-(5-methyl-[1,2,4]oxadiazol-3-yl)phenylimino]-1-methylsulfanylethylidene}carbamic acid methyl ester, to give the title compound.

$^1$H-NMR (CD$_3$OD) δ 1.95 (s, 3H) 3.83 (s, 3H) 4.86 (m, 2H) 5.24 (s, 2H) 5.64 (s, 1H) 6.81 (d, J=1.6 Hz, 1H) 6.86 (d, J=8.8 Hz, 2H) 7.04 (d, J=1.6 Hz, 1H) 7.23 (dd, J=8.0, 4.4 Hz, 1H) 7.34 (dd, J=8.0, 1.6 Hz, 1H) 7.62 (d, J=8.8 Hz, 2H) 7.83 (dd, J=4.4, 1.2 Hz, 1H)

Mass spectrum (ESI) m/z: 489 (M+H)$^+$

Example 58

4-[((R) and (S)-{3-methyl-5-[(S)-(tetrahydrofuran-3-yl)oxy]phenyl}-(5-oxo-1-pyrimidin-2-yl-4,5-dihydro-1H-[1,2,4]triazol-3-yl)methyl)amino]benzamidine acetate

[Chemical Formula 218]

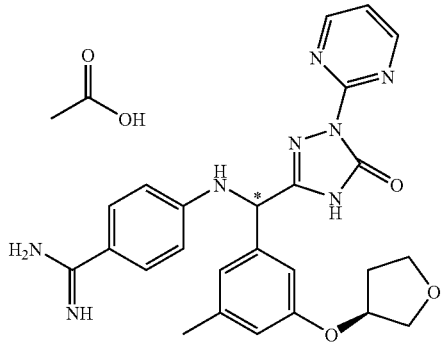

The same procedure was carried out as in Example (43c), except that (R)-(−)-3-hydroxytetrahydrofuran was used instead of the 1-methylpiperidin-4-ol, to give the first eluting enantiomer of the title compound as a white solid.

¹H-NMR (CD₃OD) δ 1.92 (s, 3H) 1.97-2.03 (m, 1H) 2.11-2.21 (m, 1H) 2.29 (s, 3H) 3.77-3.93 (m, 4H) 4.94-4.96 (m, 1H) 5.61 (s, 1H) 6.66 (s, 1H) 6.85 (d, J=8.8 Hz, 2H) 6.88 (s, 1H) 6.97 (s, 1H) 7.31 (t, J=4.8 Hz, 1H) 7.59 (d, J=8.8 Hz, 2H) 8.77 (d, J=4.8 Hz, 2H)

HPLC retention time: 13 min

Example 59

4-[((R) and (S)-{3-methyl-5-[(R)-(tetrahydrofuran-3-yl)oxy]phenyl}-(5-oxo-1-pyrimidin-2-yl-4,5-dihydro-1H-[1,2,4]triazol-3-yl)methyl)amino]benzamidine acetate

[Chemical Formula 219]

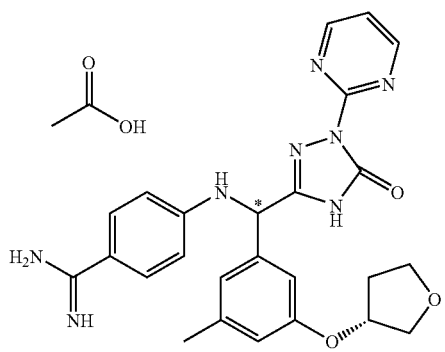

The same procedure was carried out as in Example (43c), except that (S)-(+)-3-hydroxytetrahydrofuran was used instead of the 1-methylpiperidin-4-ol, to give the first eluting enantiomer of the title compound as a white solid.

¹H-NMR (CD₃OD) δ 1.92 (s, 3H) 2.01-2.08 (m, 1H) 2.13-2.23 (m, 1H) 2.29 (s, 3H) 3.78-3.91 (m, 4H) 4.93-4.96 (m, 1H) 5.61 (s, 1H) 6.66 (s, 1H) 6.85 (d, J=8.8 Hz, 2H) 6.87 (s, 1H) 6.97 (s, 1H) 7.32 (t, J=4.8 Hz, 1H) 7.59 (d, J=8.8 Hz, 2H) 8.77 (d, J=4.8 Hz, 2H)

HPLC retention time: 12 min

Example 60

(R) and (S)-4-({[3-methyl-5-(tetrahydropyran-4-yloxy)phenyl]-(5-oxo-1-pyrimidin-2-yl-4,5-dihydro-1H-[1,2,4]triazol-3-yl)methyl}amino)benzamidine acetate

[Chemical Formula 220]

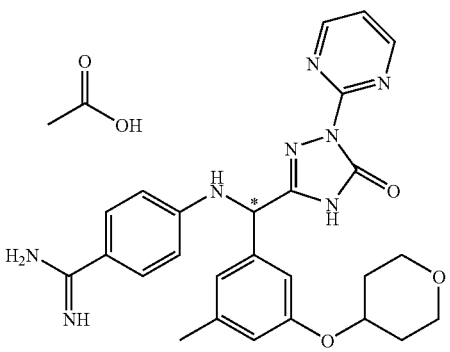

The same procedure was carried out as in Example (43c), except that tetrahydropyran-4-ol was used instead of the 1-methylpiperidin-4-ol, to give the first eluting enantiomer of the title compound as a white solid.

¹H-NMR (CD₃OD) δ 1.58-1.69 (m, 2H) 1.89-2.00 (m, 2H) 1.92 (s, 3H) 2.29 (s, 3H) 3.48-3.55 (m, 2H) 3.84-3.91 (m, 2H) 4.49-4.55 (m, 1H) 5.61 (s, 1H) 6.72 (s, 1H) 6.86 (d, J=8.8 Hz, 2H) 6.96 (s, 2H) 7.32 (t, J=4.8 Hz, 1H) 7.60 (d, J=8.8 Hz, 2H) 8.77 (d, J=4.8 Hz, 2H)

HPLC retention time: 12 min

Example 61

(R) and (S)-4-({[3-(2-fluoroethoxy)-5-methoxyphenyl]-(5-oxo-1-pyrimidin-2-yl-4,5-dihydro-1H-[1,2,4]triazol-3-yl)methyl}amino)benzamidine acetate

[Chemical Formula 221]

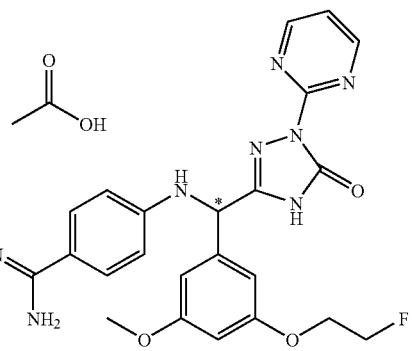

The same procedure was carried out as in Examples (6a)-(6b), except that 1-fluoro-2-iodoethane was used instead of the 1-bromo-2-methoxyethane in Example (6a), to give the first eluting enantiomer of the title compound.

¹H-NMR (CD₃OD) δ 1.91 (s, 3H) 3.74 (s, 3H) 4.10-4.20 (m, 2H) 4.58-4.72 (m, 2H) 5.60 (s, 1H) 6.44 (t, J=2.0 Hz, 1H) 6.75 (d, J=2.0 Hz, 2H) 6.86 (d, J=8.8 Hz, 2H) 7.30 (t, J=4.8 Hz, 1H) 7.59 (d, J=8.8 Hz, 2H) 8.76 (d, J=4.8 Hz, 2H)

HPLC retention time: 13 min

Example 62

(R) and (S)-2-{3-[(4-carbamimidoylphenylamino)-(5-oxo-1-pyrimidin-2-yl-4,5-dihydro-1H-[1,2,4]triazol-3-yl)methyl]-5-methoxyphenoxy}-N,N-dimethylacetamide acetate

[Chemical Formula 222]

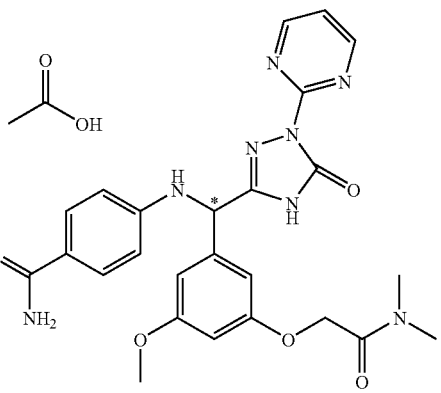

The same procedure was carried out as in Examples (6a)-(6b), except that 2-chloro-N,N-dimethylacetamide was used instead of the 1-bromo-2-methoxyethane in Example (6a), to give the first eluting enantiomer of the title compound.

¹H-NMR (CD₃OD) δ 1.92 (s, 3H) 2.91 (s, 3H) 3.02 (s, 3H) 3.74 (s, 3H) 4.68-4.78 (m, 2H) 5.62 (s, 1H) 6.47 (t, J=2.0 Hz, 1H) 6.74 (d, J=2.0 Hz, 1H) 6.76 (d, J=2.0 Hz, 1H) 6.84 (d, J=8.8 Hz, 2H) 7.31 (t, J=4.8 Hz, 1H) 7.59 (d, J=8.8 Hz, 2H) 8.77 (d, J=4.8 Hz, 2H)

HPLC retention time: 15 min

Example 63

(R) and (S)-4-({[3-methoxy-5-(tetrahydropyran-4-yloxy)phenyl]-(5-oxo-1-pyrimidin-2-yl-4,5-dihydro-1H-[1,2,4]triazol-3-yl)methyl}amino)benzamidine acetate

[Chemical Formula 223]

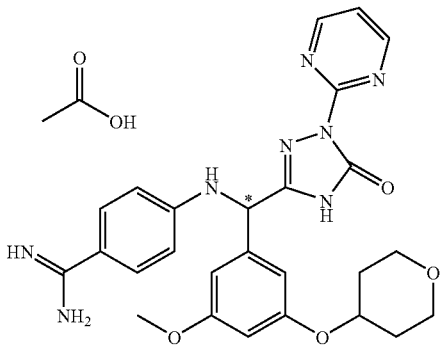

The same procedure was carried out as in Examples (4d)-(4e), except that tetrahydropyran-4-ol was used instead of the (R)-(−)-3-hydroxytetrahydrofuran in Example (4d), to give the first eluting enantiomer of the title compound.

¹H-NMR (CD₃OD) δ 1.54-1.73 (m, 2H) 1.80-2.03 (m, 5H) 3.44-3.60 (m, 2H) 3.74 (s, 3H) 3.80-3.95 (m, 2H) 4.43-4.58 (m, 1H) 5.60 (s, 1H) 6.43 (s, 1H) 6.73 (s, 1H) 6.75 (s, 1H) 6.85 (d, J=8.8 Hz, 2H) 7.30 (br.s, 1H) 7.59 (d, J=8.8 Hz, 2H) 8.76 (d, J=4.8 Hz, 2H)

HPLC retention time: 14 min

Example 64

(R) and (S)-4-({[3-(2-fluoroethoxy)-5-methoxyphenyl]-(5-oxo-1-pyridazin-3-yl-4,5-dihydro-1H-[1,2,4]triazol-3-yl)methyl}amino)benzamidine acetate

[Chemical Formula 224]

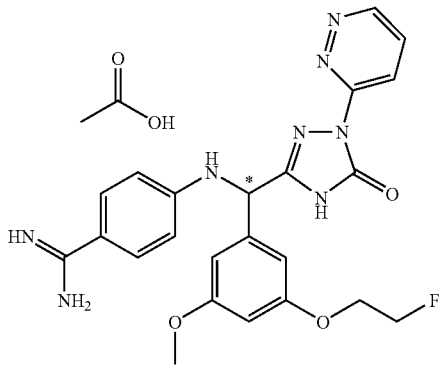

The same procedure was carried out as in Example 7, except that 1-fluoro-2-iodoethane was used instead of the 1-bromo-2-methoxyethane, to give the first eluting enantiomer of the title compound.

¹H-NMR (CD₃OD) δ 1.92 (s, 3H) 3.75 (s, 3H) 4.10-4.23 (m, 2H) 4.58-4.75 (m, 2H) 5.57 (s, 1H) 6.43 (t, J=2.0 Hz, 1H) 6.77 (d, J=2.0 Hz, 2H) 6.86 (d, J=8.8 Hz, 2H) 7.59 (d, J=8.8 Hz, 2H) 7.74 (dd, J=4.8, 9.2 Hz, 1H) 8.56 (dd, J=1.2, 9.2 Hz, 1H) 8.99 (dd, J=1.2, 4.8 Hz, 1H)

HPLC retention time: 12 min

Example 65

(R) and (S)-4-{[(3-ethoxy-5-methoxyphenyl)-(5-oxo-1-pyridazin-3-yl-4,5-dihydro-1H-[1,2,4]triazol-3-yl)methyl]amino}benzamidine acetate

[Chemical Formula 225]

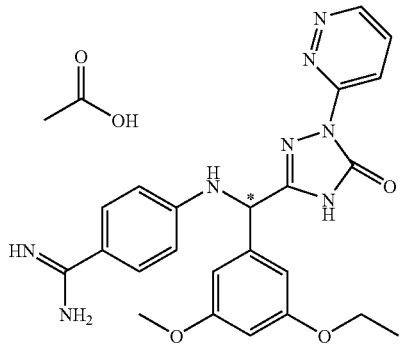

The same procedure was carried out as in Example 7, except that bromoethane was used instead of the 1-bromo-2-methoxyethane, to give the first eluting enantiomer of the title compound.

¹H-NMR (CD₃OD) δ 1.33 (t, J=7.2 Hz, 3H) 1.91 (s, 3H) 3.75 (s, 3H) 3.99 (q, J=7.2 Hz, 2H) 5.56 (s, 1H) 6.38 (dd, J=2.0, 2.4 Hz, 1H) 6.73 (br.s, 2H) 6.86 (d, J=8.8 Hz, 2H) 7.59 (d, J=8.8 Hz, 2H) 7.74 (dd, J=4.8, 8.8 Hz, 1H) 8.56 (d, J=8.8 Hz, 1H) 8.99 (dd, J=4.8 Hz, 1H)

HPLC retention time: 8 min (Column name: SUMICHIRAL OA-2500, 4.6 mmφ×25 cm, Manufacturer: Sumika Chemical Analysis Service, Ltd., Mobile phase: 0.05 M ammonium acetate-methanol solution, Elution rate: 1 ml/min)

Example 66

(R) and (S)-4-{[(2-fluoro-3,5-dimethoxyphenyl)-(5-oxo-1-pyrimidin-2-yl-4,5-dihydro-1H-[1,2,4]triazol-3-yl)methyl]amino}benzamidine acetate

[Chemical Formula 226]

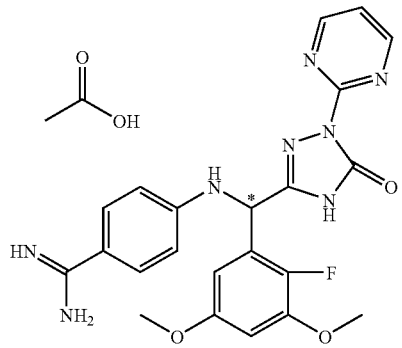

The same procedure was carried out as in Examples (3e)-(3h), except that methyl iodide was used instead of the 1-fluoro-2-iodoethane in Example (3e), to give the first eluting enantiomer of the title compound.

$^1$H-NMR (CD$_3$OD) δ 1.93 (s, 3H) 3.72 (s, 3H) 3.85 (s, 3H) 5.94 (s, 1H) 6.57-6.66 (m, 2H) 6.85 (d, J=8.8 Hz, 2H) 7.29 (t, J=4.8 Hz, 1H) 7.61 (d, J=8.8 Hz, 2H) 8.75 (d, J=4.8 Hz, 2H)

HPLC retention time: 13 min

Example 67

(R) and (S)-4-{[(2-fluoro-3,4,5-trimethoxyphenyl)-(5-oxo-1-pyrimidin-2-yl-4,5-dihydro-1H-[1,2,4]triazol-3-yl)methyl]amino}benzamidine acetate (67a) 2-fluoro-4,5-dimethoxy-3-triisopropylsilanyloxybenzaldehyde

[Chemical Formula 227]

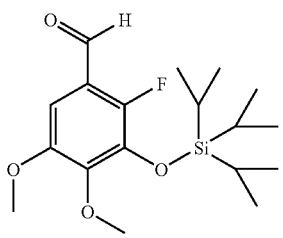

The same procedure was carried out as in Examples (3a)-(3b), except that 4-fluoro-1,2-dimethoxybenzene was used instead of the 1-fluoro-4-methoxybenzene in Example (3a), to give the title compound.

$^1$H-NMR (CDCl$_3$) δ 1.11 (d, J=7.2 Hz, 18H) 1.32 (sept, J=7.2 Hz, 3H) 3.86 (s, 3H) 3.90 (s, 3H) 6.95 (d, J=5.6 Hz, 1H) 10.25 (s, 1H)

(67b) {2-(2-fluoro-3-hydroxy-4,5-dimethoxyphenyl)-2-[4-(5-methyl-[1,2,4]oxadiazol-3-yl)phenylimino]-1-methylsulfanylethylidene}carbamic acid methyl ester

[Chemical Formula 228]

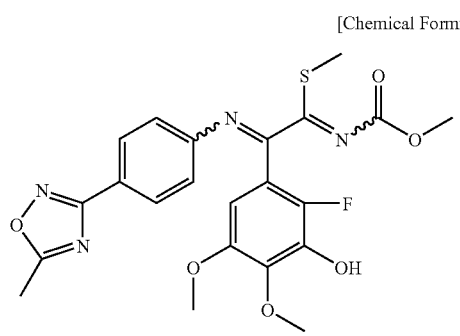

The same procedure was carried out as in Example (9a), except that 2-fluoro-4,5-dimethoxy-3-triisopropylsilanyloxybenzaldehyde was used instead of the 3-methoxy-5-triisopropylsilanyloxybenzaldehyde, to give the title compound.

$^1$H-NMR (CDCl$_3$) Two main isomers:

δ 2.34 (s, 3H) 2.66 (s, 3H) 3.63 (s, 3H) 3.91 (s, 3H) 4.01 (s, 3H) 5.62 (br.s, 1H) 7.07 (d, J=6.4 Hz, 1H) 7.10 (d, J=8.4 Hz, 2H) 8.03 (d, J=8.4 Hz, 2H)

δ 2.47 (s, 3H) 2.63 (s, 3H) 3.63 (s, 3H) 3.66 (s, 3H) 3.92 (s, 3H) 5.50 (br.s, 1H) 6.15 (d, J=5.2 Hz, 1H) 6.85 (d, J=8.4 Hz, 2H) 7.91 (d, J=8.4 Hz, 2H)

(67c) (R) and (S)-4-{[(2-fluoro-3,4,5-trimethoxyphenyl)-(5-oxo-1-pyrimidin-2-yl-4,5-dihydro-1H-[1,2,4]triazol-3-yl)methyl]amino}benzamidine acetate

[Chemical Formula 229]

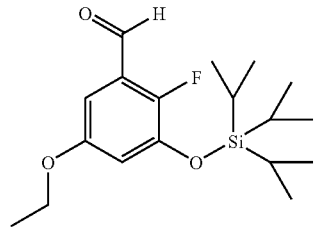

The same procedure was carried out as in Examples (3e)-(3h), except that {2-(2-fluoro-3-hydroxy-4,5-dimethoxyphenyl)-2-[4-(5-methyl-[1,2,4]oxadiazol-3-yl)phenylimino]-1-methylsulfanylethylidene}carbamic acid methyl ester and methyl iodide were used instead of respectively the [2-(2-fluoro-3-hydroxy-5-methoxyphenyl)-2-[4-(5-methyl-[1,2,4]oxadiazol-3-yl)-phenylimino]-1-methylsulfanylethylidene] carbamic acid methyl ester in Example (3e) and 1-fluoro-2-iodoethane in Example (3e), to give the first eluting enantiomer of the title compound.

$^1$H-NMR (CD$_3$OD) δ 1.92 (s, 3H) 3.74 (s, 3H) 3.81 (s, 3H) 3.91 (s, 3H) 5.93 (s, 1H) 6.85 (d, J=8.8 Hz, 2H) 6.90 (d, J=6.8 Hz, 1H) 7.30 (t, J=4.8 Hz, 1H) 7.61 (d, J=8.8 Hz, 2H) 8.75 (d, J=4.8 Hz, 2H)

HPLC retention time: 13 min

Example 68

(R) and (S)-4-({[2-fluoro-3-(2-fluoroethoxy)-5-ethoxyphenyl]-(5-oxo-1-pyrimidin-2-yl-4,5-dihydro-1H-[1,2,4]triazol-3-yl)methyl}amino)benzamidine acetate (68a) 5-ethoxy-2-fluoro-3-triisopropylsilanyloxybenzaldehyde

[Chemical Formula 230]

The same procedure was carried out as in Examples (3a)-(3b), except that 1-ethoxy-4-fluorobenzene was used instead of the 1-fluoro-4-methoxybenzene in Example (3a), to give the title compound.

¹H-NMR (CDCl₃) δ 1.11 (d, J=7.2 Hz, 18H) 1.30 (sept, J=7.2 Hz, 3H) 1.40 (t, J=6.8 Hz, 3H) 3.99 (q, J=6.8 Hz, 2H) 6.75 (dd, J=3.2, 7.2 Hz, 1H) 6.84 (dd, J=3.2, 4.4 Hz, 1H) 10.30 (s, 1H)

(68b) {2-(5-ethoxy-2-fluoro-3-hydroxyphenyl)-2-[4-(5-methyl-[1,2,4]oxadiazol-3-yl)phenylimino]-1-methylsulfanylethylidene}carbamic acid methyl ester

[Chemical Formula 231]

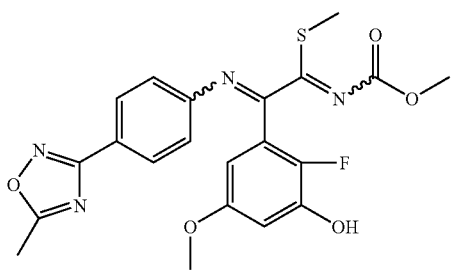

The same procedure was carried out as in Examples (3c)-(3d), except that 5-ethoxy-2-fluoro-3-triisopropylsilanyloxybenzaldehyde was used instead of the 2-fluoro-5-methoxy-3-triisopropylsilanyloxybenzaldehyde in Example (3c), to give the title compound.

¹H-NMR (CDCl₃) Two main isomers:
δ 1.31 (t, J=6.8 Hz, 3H) 2.46 (s, 3H) 2.60 (s, 3H) 3.62 (s, 3H) 3.83 (q, J=6.8 Hz, 2H) 5.22 (br.s, 1H) 6.18 (dd, J=3.2, 4.4 Hz, 1H) 6.52 (dd, J=3.2, 7.2 Hz, 1H) 6.83 (d, J=8.4 Hz, 2H) 7.89 (d, J=8.4 Hz, 2H)
δ 1.39 (t, J=7.2 Hz, 3H) 2.32 (s, 3H) 2.65 (s, 3H) 3.60 (s, 3H) 4.02 (q, J=7.2 Hz, 2H) 5.35 (br.s, 1H) 6.72 (dd, J=3.2, 7.2 Hz, 1H) 6.91 (dd, J=3.2, 4.8 Hz, 1H) 7.12 (d, J=8.8 Hz, 2H) 8.02 (d, J=8.8 Hz, 2H)

(68c) (R) and (S)-4-({[5-ethoxy-2-fluoro-3-(2-fluoroethoxy)phenyl]-(5-oxo-1-pyrimidin-2-yl-4,5-dihydro-1H-[1,2,4]triazol-3-yl)methyl}amino)benzamidine acetate

[Chemical Formula 232]

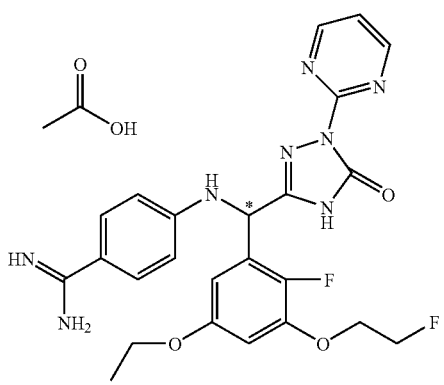

The same procedure was carried out as in Examples (6a)-(6b), except that {2-(5-ethoxy-2-fluoro-3-hydroxyphenyl)-2-[4-(5-methyl-[1,2,4]oxadiazol-3-yl)-phenylimino]-1-methylsulfanylethylidene}carbamic acid methyl ester and 1-fluoro-2-iodoethane were used instead of respectively the {2-(3-hydroxy-5-methoxyphenyl)-2-[4-(5-methyl-[1,2,4]oxadiazol-3-yl)phenylimino]-1-methylsulfanylethylidene}carbamic acid methyl ester in Example (6a) and 1-bromo-2-methoxyethane in Example (6a), to give the first eluting enantiomer of the title compound.

¹H-NMR (CD₃OD) δ 1.28 (t, J=6.8 Hz, 3H) 1.91 (s, 3H) 3.91 (q, J=6.8 Hz, 2H) 4.17-4.32 (m, 2H) 4.62-4.80 (m, 2H) 5.94 (s, 1H) 6.60 (dd, J=2.8, 6.8 Hz, 1H) 6.65 (dd, J=2.8, 4.8 Hz, 1H) 6.86 (d, J=8.8 Hz, 2H) 7.29 (t, J=4.8 Hz, 1H) 7.61 (d, J=8.8 Hz, 2H) 8.75 (d, J=4.8 Hz, 2H)

HPLC retention time: 13 min

Example 69

(R) and (S)-4-{[(5-ethoxy-2-fluoro-3-methoxyphenyl)-(5-oxo-1-pyrimidin-2-yl-4,5-dihydro-1H-[1,2,4]triazol-3-yl)methyl]amino}benzamidine acetate

[Chemical Formula 233]

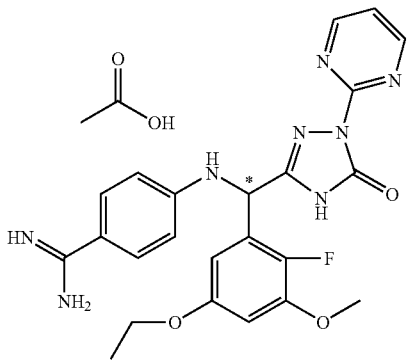

The same procedure was carried out as in Examples (6a)-(6b), except that {2-(5-ethoxy-2-fluoro-3-hydroxyphenyl)-2-[4-(5-methyl-[1,2,4]oxadiazol-3-yl)phenylimino]-1-methylsulfanylethylidene}carbamic acid methyl ester (Example (68b)) and methyl iodide were used instead of respectively the {2-(3-hydroxy-5-methoxyphenyl)-2-[4-(5-methyl-[1,2,4]oxadiazol-3-yl)phenylimino]-1-methylsulfanylethylidene}carbamic acid methyl ester in Example (6a) and 1-bromo-2-methoxyethane in Example (6a), to give the first eluting enantiomer of the title compound.

¹H-NMR (CD₃OD) δ 1.28 (t, J=7.2 Hz, 3H) 1.91 (s, 3H) 3.83 (s, 3H) 3.91 (q, J=7.2 Hz, 2H) 5.94 (s, 1H) 6.54-6.64 (m, 2H) 6.85 (d, J=8.8 Hz, 2H) 7.29 (t, J=4.8 Hz, 1H) 7.60 (d, J=8.8 Hz, 2H) 8.75 (d, J=4.8 Hz, 2H)

HPLC retention time: 13 min

Example 70

4-({(R) and (S)-[5-ethoxy-2-fluoro-3-(2-fluoroethoxy)phenyl]-(5-oxo-1-pyridazin-3-yl-4,5-dihydro-1H-[1,2,4]triazol-3-yl)methyl}amino)benzamidine acetate

[Chemical Formula 234]

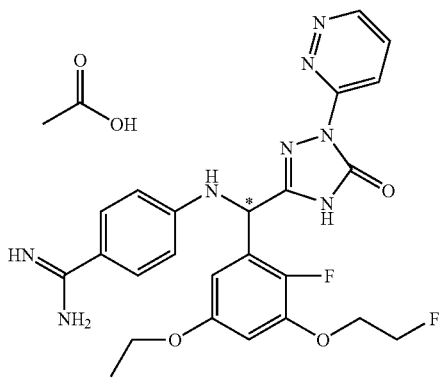

The same procedure was carried out as in Example 7, except that {2-(5-ethoxy-2-fluoro-3-hydroxyphenyl)-2-[4-(5-methyl-[1,2,4]oxadiazol-3-yl)-phenylimino]-1-methylsulfanylethylidene}carbamic acid methyl ester (Example (68b)) and 1-fluoro-2-iodoethane were used instead of respectively the {2-(3-hydroxy-5-methoxyphenyl)-2-[4-(5-methyl-[1,2,4]oxadiazol-3-yl)phenylimino]-1-methylsulfanylethylidene}carbamic acid methyl ester and 1-bromo-2-methoxyethane, to give the first eluting enantiomer of the title compound.

$^1$H-NMR (CD$_3$OD) δ 1.28 (t, J=7.2 Hz, 3H) 1.92 (s, 3H) 3.91 (q, J=7.2 Hz, 2H) 4.18-4.32 (m, 2H) 4.63-4.81 (m, 2H) 5.95 (s, 1H) 6.58 (dd, J=2.8, 6.8 Hz, 1H) 6.66 (dd, J=2.8, 5.2 Hz, 1H) 6.86 (d, J=9.2 Hz, 2H) 7.60 (d, J=9.2 Hz, 2H) 7.74 (dd, J=4.8, 8.8 Hz, 1H) 8.54 (dd, J=1.2, 8.8 Hz, 1H) 8.99 (dd, J=1.2, 4.8 Hz, 1H)

HPLC retention time: 7 min (Column name: SUMICHIRAL OA-2500, 4.6 mmφ×25 cm, Manufacturer: Sumika Chemical Analysis Service, Ltd., Mobile phase: 0.05 M ammonium acetate-methanol solution, Elution rate: 1 ml/min)

Example 71

(R) and (S)-4-{[(5-ethoxy-2-fluoro-3-methoxyphenyl)-(5-oxo-1-pyridazin-3-yl-4,5-dihydro-1H-[1,2,4]triazol-3-yl)methyl]amino}benzamidine acetate

[Chemical Formula 235]

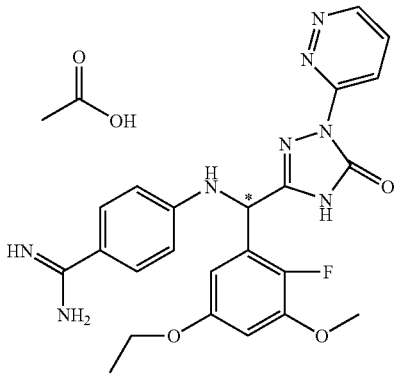

The same procedure was carried out as in Example 7, except that {2-(5-ethoxy-2-fluoro-3-hydroxyphenyl)-2-[4-(5-methyl-[1,2,4]oxadiazol-3-yl)phenylimino]-1-methylsulfanylethylidene}carbamic acid methyl ester (Example (68b)) and methyl iodide were used instead of respectively the {2-(3-hydroxy-5-methoxyphenyl)-2-[4-(5-methyl-[1,2,4]oxadiazol-3-yl)phenylimino]-1-methylsulfanylethylidene}carbamic acid methyl ester and 1-bromo-2-methoxyethane, to give the first eluting enantiomer of the title compound.

$^1$H-NMR (CD$_3$OD) δ 1.28 (t, J=6.8 Hz, 3H) 1.92 (s, 3H) 3.83 (s, 3H) 3.91 (q, J=6.8 Hz, 2H) 5.94 (s, 1H) 6.56 (dd, J=2.8, 7.2 Hz, 1H) 6.61 (dd, J=2.8, 4.4 Hz, 1H) 6.85 (d, J=8.8 Hz, 2H) 7.60 (d, J=8.8 Hz, 2H) 7.74 (dd, J=4.8, 9.2 Hz, 1H) 8.54 (dd, J=1.2, 9.2 Hz, 1H) 8.99 (dd, J=1.2, 4.8 Hz, 1H)

HPLC retention time: 7 min (Column name: SUMICHIRAL OA-2500, 4.6 mmφ×25 cm, Manufacturer: Sumika Chemical Analysis Service, Ltd., Mobile phase: 0.05 M ammonium acetate-methanol solution, Elution rate: 1 ml/min)

Example 72

(R) and (S)-4-({[3-(2-fluoroethoxymethyl)-5-methoxyphenyl]-(5-oxo-1-pyrimidin-2-yl-4,5-dihydro-1H-[1,2,4]triazol-3-yl)methyl}amino)benzamidine acetate (72a)
[3-(2-fluoroethoxymethyl)-5-methoxyphenyl]methanol

[Chemical Formula 236]

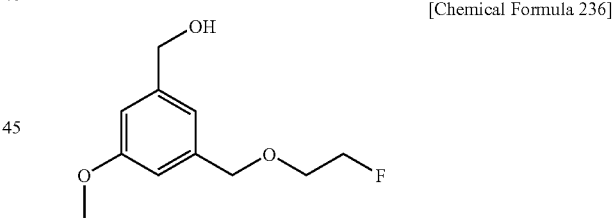

To a solution of 1 g of 5-methoxy-1,3-benzenedimethanol in 10 ml of DMF there was added 238 mg of sodium hydride (60% oily suspension) at 0° C. After stirring at room temperature for 30 minutes, 1.04 g of 1-fluoro-2-iodoethane was added and the mixture was stirred at room temperature for 22 hours. Water was added to the reaction mixture and extraction was performed with ethyl acetate. The organic layer was washed with water and saturated brine, and then dried over anhydrous sodium sulfate. The desiccating agent was filtered off and the filtrate was concentrated under reduced pressure. The residue was purified by silica gel column chromatography (ethyl acetate-heptane) to give the title compound (145 mg) as a colorless oil.

(72b) [3-(2-fluoroethoxymethyl)-5-methoxyphenyl]-[4-(5-methyl-[1,2,4]oxadiazol-3-yl)phenylamino]acetonitrile

[Chemical Formula 237]

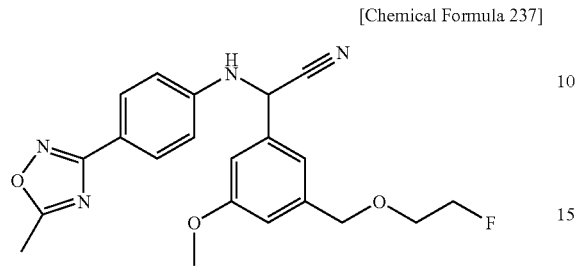

The same procedure was carried out as in Example (10b), except that [3-(2-fluoroethoxymethyl)-5-methoxyphenyl]methanol was used instead of (3-methoxy-5-methoxymethylphenyl)methanol, to give the title compound.

$^1$H-NMR (CDCl$_3$) δ 2.62 (s, 3H) 3.71-3.83 (m, 2H) 3.85 (s, 3H) 4.54-4.68 (m, 2H) 4.61 (s, 2H) 5.45 (br.s, 1H) 6.83 (d, J=8.8 Hz, 2H) 7.00 (s, 1H) 7.05 (s, 1H) 7.17 (s, 1H) 7.98 (d, J=8.8 Hz, 2H)

(72c) (R) and (S)-4-({[3-(2-fluoroethoxymethyl)-5-methoxyphenyl]-(5-oxo-1-pyrimidin-2-yl-4,5-dihydro-1H-[1,2,4]triazol-3-yl)methyl}amino)benzamidine acetate

[Chemical Formula 238]

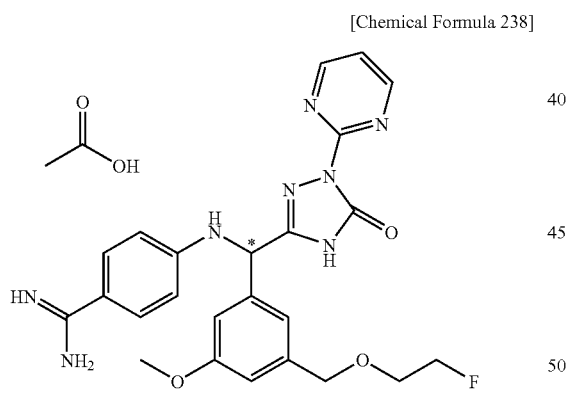

The same procedure was carried out as in Examples (10c)-(10e), except that [3-(2-fluoroethoxymethyl)-5-methoxyphenyl]-[4-(5-methyl-[1,2,4]oxadiazol-3-yl)phenylamino]acetonitrile was used instead of the (3-methoxy-5-methoxymethylphenyl)-[4-(5-methyl-[1,2,4]oxadiazol-3-yl)phenylamino]acetonitrile in Example (10c), to give the first eluting enantiomer of the title compound.

$^1$H-NMR (CD$_3$OD) δ 1.91 (s, 3H) 3.62-3.74 (m, 2H) 3.78 (s, 3H) 4.42-4.61 (m, 2H) 4.53 (s, 2H) 5.62 (s, 1H) 6.85 (d J=8.8 Hz, 2H) 6.88 (s, 1H) 7.02-7.09 (m, 1H) 7.13 (s, 1H) 7.29 (t, J=4.8 Hz, 1H) 7.59 (d, J=8.8 Hz, 2H) 8.76 (d, J=4.8 Hz, 2H)

HPLC retention time: 13 min

Example 73

(R) and (S)-4-{[(3-methoxy-5-methoxymethylphenyl)-(5-oxo-1-pyridazin-3-yl-4,5-dihydro-1H-[1,2,4]triazol-3-yl)methyl]amino}benzamidine trifluoroacetate (73a) 4-{[(3-methoxy-5-methoxymethylphenyl)-(5-oxo-1-pyridazin-3-yl-4,5-dihydro-1H-[1,2,4]triazol-3-yl)methyl]amino}benzamidine acetate

[Chemical Formula 239]

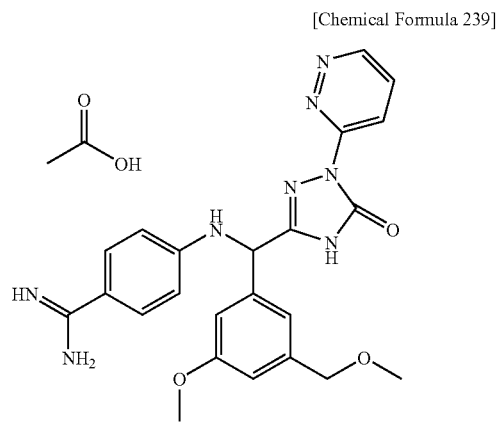

The same procedure was carried out as in Example (10d), except that 3-hydrazinopyridazine hydrochloride was used instead of the 2-hydrazinopyrimidine, to give the title compound.

$^1$H-NMR (CD$_3$OD) δ 1.95 (s, 3H) 3.35 (s, 3H) 3.78 (s, 3H) 4.41 (s, 2H) 5.70 (s, 1H) 6.82-6.94 (m, 3H) 7.07 (s, 1H) 7.12 (s, 1H) 7.60 (d, J=8.8 Hz, 2H) 7.77 (dd, J=4.8, 9.2 Hz, 1H) 8.49 (dd, J=1.2, 9.2 Hz, 1H) 9.04 (dd, J=1.2, 4.8 Hz, 1H)

Mass spectrum (ESI) m/z: 461 (M+H)$^+$ (73b) (R) and (S)-4-{[(3-methoxy-5-methoxymethylphenyl)-(5-oxo-1-pyridazin-3-yl-4,5-dihydro-1H-[1,2,4]triazol-3-yl)methyl]amino}benzamidine trifluoroacetate

[Chemical Formula 240]

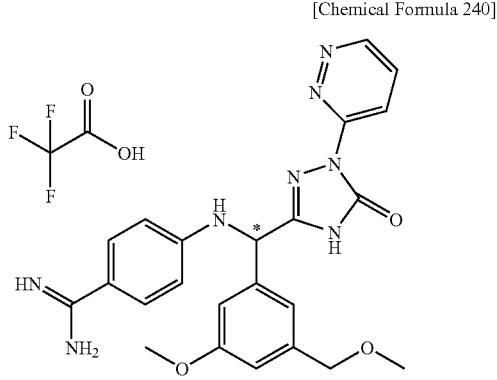

The same procedure was carried out as in Example (12b), except that 4-{[(3-methoxy-5-methoxymethylphenyl)-(5-oxo-1-pyridazin-3-yl-4,5-dihydro-1H-[1,2,4]triazol-3-yl)methyl]amino}benzamidine acetate was used instead of the 4-{[(3-hydroxymethyl-5-methoxyphenyl)-(5-oxo-1-pyrimidin-2-yl-4,5-dihydro-1H-[1,2,4]triazol-3-yl)methyl]amino}benzamidine acetate, to give the first eluting enantiomer of the title compound.

¹H-NMR (CD₃OD) δ 3.38 (s, 3H) 3.80 (s, 3H) 4.44 (s, 2H) 5.75 (s, 1H) 6.89 (d, J=8.8 Hz, 2H) 6.91 (s, 1H) 7.07 (s, 1H) 7.12 (s, 1H) 7.62 (d, J=8.8 Hz, 2H) 7.81 (dd, J=4.4, 8.8 Hz, 1H) 8.44 (d, J=8.8 Hz, 1H) 9.08 (d, J=4.4 Hz, 1H)

HPLC retention time: 12 min

Example 74

(R) and (S)-4-({[3-ethyl-5-(2-fluoroethoxy)phenyl]-(5-oxo-1-pyrimidin-2-yl-4,5-dihydro-1H-[1,2,4]triazol-3-yl)methyl}amino)benzamidine acetate (74a) {2-(3-ethyl-5-hydroxyphenyl)-2-[4-(5-methyl-[1,2,4]oxadiazol-3-yl)phenylimino]-1-methylsulfanylethylidene}carbamic acid methyl ester

[Chemical Formula 241]

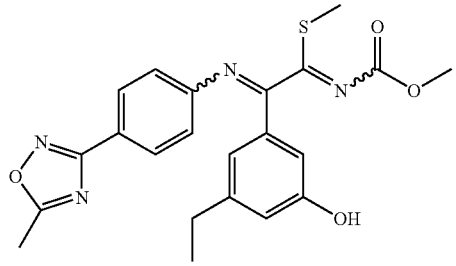

The same procedure was carried out as in Examples (4a)-(4c), except that 3-ethyl-5-hydroxybenzaldehyde [CAS No. 532966-64-6] was used instead of the 3-hydroxy-5-methoxybenzaldehyde in Example (4a), to give the title compound.

¹H-NMR (CDCl₃) Main isomer:
δ 1.24 (t, J=7.6 Hz, 3H) 2.33 (s, 3H) 2.60-2.70 (m, 5H) 3.61 (s, 3H) 5.00 (br.s, 1H) 6.84-6.88 (m, 1H) 7.14-7.19 (m, 3H) 7.23 (br.s, 1H) 8.01 (d, J=8.8 Hz, 2H)

(74b) (R) and (S)-4-({[3-ethyl-5-(2-fluoroethoxy)phenyl]-(5-oxo-1-pyrimidin-2-yl-4,5-dihydro-1H-[1,2,4]triazol-3-yl)methyl}amino)benzamidine acetate

[Chemical Formula 242]

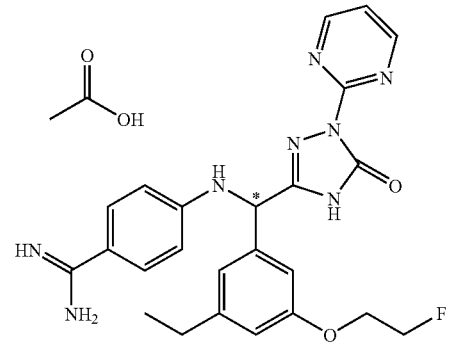

The same procedure was carried out as in Examples (6a)-(6b), except that {2-(3-ethyl-5-hydroxyphenyl)-2-[4-(5-methyl-[1,2,4]oxadiazol-3-yl)phenylimino]-1-methylsulfanylethylidene}carbamic acid methyl ester and 1-fluoro-2-iodoethane were used instead of respectively the {2-(3-hydroxy-5-methoxyphenyl)-2-[4-(5-methyl-[1,2,4]oxadiazol-3-yl)phenylimino]-1-methylsulfanylethylidene}carbamic acid methyl ester in Example (6a) and 1-bromo-2-methoxyethane, to give the first eluting enantiomer of the title compound.

¹H-NMR (CD₃OD) δ 1.17 (t, J=7.6 Hz, 3H) 1.91 (s, 3H) 2.58 (q, J=7.6 Hz, 2H) 4.08-4.25 (m, 2H) 4.55-4.78 (m, 2H) 5.62 (s, 1H) 6.74 (s, 1H) 6.85 (d, J=8.8 Hz, 2H) 6.97 (s, 1H) 7.01 (s, 1H) 7.29 (t, J=5.2 Hz, 1H) 7.59 (d, J=8.8 Hz, 2H) 8.76 (d, J=5.2 Hz, 2H)

HPLC retention time: 11 min

Example 75

(R) and (S)-4-{[(3-ethyl-5-methoxyphenyl)-(5-oxo-1-pyrimidin-2-yl-4,5-dihydro-1H-[1,2,4]triazol-3-yl)methyl]amino}benzamidine acetate

[Chemical Formula 243]

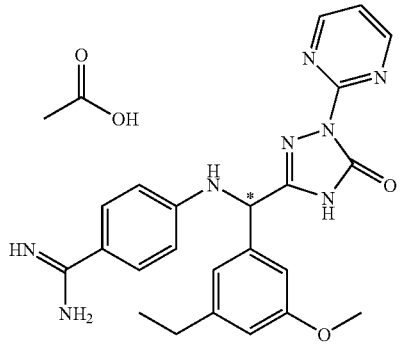

The same procedure was carried out as in Examples (6a)-(6b), except that {2-(3-ethyl-5-hydroxyphenyl)-2-[4-(5-methyl-[1,2,4]oxadiazol-3-yl)phenylimino]-1-methylsulfanylethylidene}carbamic acid methyl ester (Example (74a)) and methyl iodide were used instead of respectively the {2-(3-hydroxy-5-methoxyphenyl)-2-[4-(5-methyl-[1,2,4]oxadiazol-3-yl)phenylimino]-1-methylsulfanylethylidene}carbamic acid methyl ester in Example (6a) and 1-bromo-2-methoxyethane in Example (6a), to give the first eluting enantiomer of the title compound.

¹H-NMR (CD₃OD) δ 1.19 (t, J=7.6 Hz, 3H) 1.92 (s, 3H) 2.60 (q, J=7.6 Hz, 2H) 3.75 (s, 3H) 5.62 (s, 1H) 6.72 (s, 1H) 6.86 (d, J=9.2 Hz, 2H) 6.94 (s, 1H) 6.98 (s, 1H) 7.32 (t, J=4.8 Hz, 1H) 7.60 (d, J=9.2 Hz, 2H) 8.77 (d, J=4.8 Hz, 2H)

HPLC retention time: 11 min

Example 76

(R) and (S)-4-({[3-ethyl-5-(2-methoxyethoxy)phenyl]-(5-oxo-1-pyrimidin-2-yl-4,5-dihydro-1H-[1,2,4]triazol-3-yl)methyl}amino)benzamidine trifluoroacetate (76a) 4-({[3-ethyl-5-(2-methoxyethoxy)phenyl]-(5-oxo-1-pyrimidin-2-yl-4,5-dihydro-1H-[1,2,4]triazol-3-yl)methyl}amino)benzamidine acetate

[Chemical Formula 244]

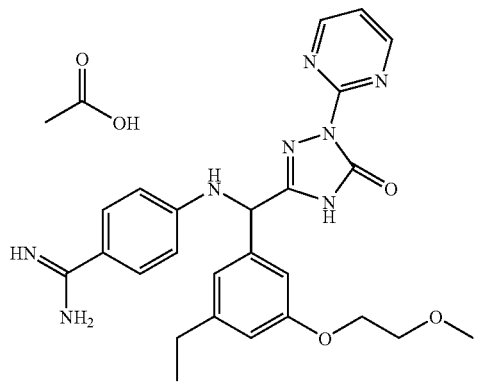

The same procedure was carried out as in Example (6a), except that {2-(3-ethyl-5-hydroxyphenyl)-2-[4-(5-methyl-[1,2,4]oxadiazol-3-yl)phenylimino]-1-methylsulfanylethylidene}carbamic acid methyl ester (Example (74a)) was used instead of the {2-(3-hydroxy-5-methoxyphenyl)-2-[4-(5-methyl-[1,2,4]oxadiazol-3-yl)phenylimino]-1-methylsulfanylethylidene}carbamic acid methyl ester, to give the title compound.

$^1$H-NMR (CD$_3$OD) δ 1.21 (t, J=7.6 Hz, 3H) 1.96 (s, 3H) 2.61 (q, J=7.6 Hz, 2H) 3.38 (s, 3H) 3.65-3.75 (m, 2H) 4.02-4.15 (m, 2H) 5.66 (s, 1H) 6.78 (s, 1H) 6.87 (d, J=8.8 Hz, 2H) 6.96 (s, 1H) 6.99 (s, 1H) 7.36 (t, J=4.8 Hz, 1H) 7.61 (d, J=8.8 Hz, 2H) 8.78 (d, J=4.8 Hz, 2H)

Mass spectrum (ESI) m/z: 489 (M+H)$^+$ (76b) (R) and (S)-4-({[3-ethyl-5-(2-methoxyethoxy)phenyl]-(5-oxo-1-pyrimidin-2-yl-4,5-dihydro-1H-[1,2,4]triazol-3-yl)methyl}amino)benzamidine trifluoroacetate

[Chemical Formula 245]

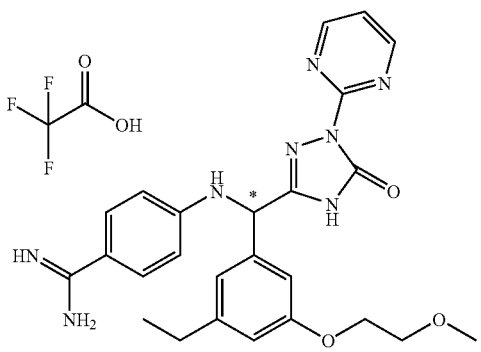

The same procedure was carried out as in Example (12b), except that 4-({[3-ethyl-5-(2-methoxyethoxy)phenyl]-(5-oxo-1-pyrimidin-2-yl-4,5-dihydro-1H-[1,2,4]triazol-3-yl)methyl}amino)benzamidine acetate was used instead of the 4-{[(3-hydroxymethyl-5-methoxyphenyl)-(5-oxo-1-pyrimidin-2-yl-4,5-dihydro-1H-[1,2,4]triazol-3-yl)methyl]amino}benzamidine acetate, to give the first eluting enantiomer of the title compound.

$^1$H-NMR (CD$_3$OD) δ 1.20 (t, J=7.6 Hz, 3H) 2.63 (q, J=7.6 Hz, 2H) 3.39 (s, 3H) 3.63-3.77 (m, 2H) 4.03-4.17 (m, 2H) 5.67 (s, 1H) 6.79 (s, 1H) 6.88 (d, J=8.8 Hz, 2H) 6.96 (s, 1H) 7.00 (s, 1H) 7.37 (t, J=4.8 Hz, 1H) 7.62 (d, J=8.8 Hz, 2H) 8.79 (d, J=4.8 Hz, 2H)

HPLC retention time: 11 min

Example 77

4-{[(3-cyanomethoxy-5-ethylphenyl)-(5-oxo-1-pyrimidin-2-yl-4,5-dihydro-1H-[1,2,4]triazol-3-yl)methyl]amino}benzamidine acetate

[Chemical Formula 246]

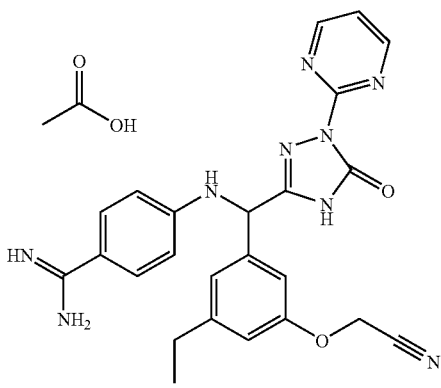

The same procedure was carried out as in Example (6a), except that {2-(3-ethyl-5-hydroxyphenyl)-2-[4-(5-methyl-[1,2,4]oxadiazol-3-yl)phenylimino]-1-methylsulfanylethylidene}carbamic acid methyl ester (Example (74a)) and bromoacetonitrile were used instead of respectively the {2-(3-hydroxy-5-methoxyphenyl)-2-[4-(5-methyl-[1,2,4]oxadiazol-3-yl)phenylimino]-1-methylsulfanylethylidene}carbamic acid methyl ester and 1-bromo-2-methoxyethane, to give the title compound.

$^1$H-NMR (CD$_3$OD) δ 1.21 (t, J=7.6 Hz, 3H) 1.92 (s, 3H) 2.65 (q, J=7.6 Hz, 2H) 4.96 (s, 2H) 5.63 (s, 1H) 6.77-6.93 (m, 3H) 7.06 (s, 1H) 7.13 (s, 1H) 7.31 (t, J=4.8 Hz, 1H) 7.60 (d, J=8.8 Hz, 2H) 8.77 (d, J=4.8 Hz, 2H)

Mass spectrum (ESI) m/z: 470 (M+H)$^+$

Example 78

(R) and (S)-4-({[3-ethoxy-5-(2-fluoroethoxy)phenyl]-(5-oxo-1-pyrimidin-2-yl-4,5-dihydro-1H-[1,2,4]triazol-3-yl)methyl}amino)benzamidine trifluoroacetate

(78a) {2-(3-ethoxy-5-hydroxyphenyl)-2-[4-(5-methyl-[1,2,4]oxadiazol-3-yl)phenylimino]-1-methylsulfanylethylidene}carbamic acid methyl ester

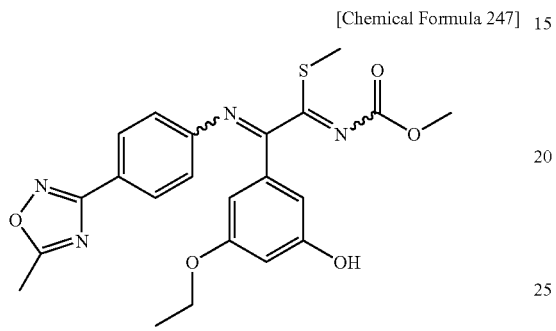

[Chemical Formula 247]

The same procedure was carried out as in Examples (4a)-(4c), except that 3-ethoxy-5-hydroxybenzaldehyde was used instead of the 3-hydroxy-5-methoxybenzaldehyde in Example (4a), to give the title compound.

$^1$H-NMR (CDCl$_3$) Main isomer:
δ 1.41 (t, J=6.8 Hz, 3H) 2.32 (s, 3H) 2.65 (s, 3H) 3.65 (s, 3H) 4.06 (q, J=6.8 Hz, 2H) 6.56 (t, J=2.4 Hz, 1H) 6.92 (dd, J=1.6, 2.4 Hz, 1H) 7.01 (t, J=1.6 Hz, 1H) 7.16 (d, J=8.8 Hz, 2H) 8.02 (d, J=8.8 Hz, 2H)

(78b) 4-({[3-ethoxy-5-(2-fluoroethoxy)phenyl]-(5-oxo-1-pyrimidin-2-yl-4,5-dihydro-1H-[1,2,4]triazol-3-yl)methyl}amino)benzamidine acetate

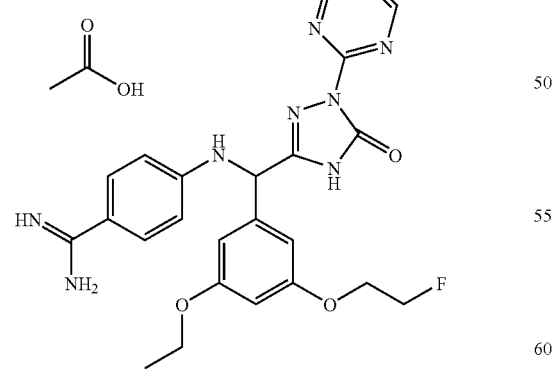

[Chemical Formula 248]

The same procedure was carried out as in Example (6a), except that {2-(3-ethoxy-5-hydroxyphenyl)-2-[4-(5-methyl-[1,2,4]oxadiazol-3-yl)phenylimino]-1-methylsulfanylethylidene}carbamic acid methyl ester and 1-fluoro-2-iodoethane were used instead of respectively the {2-(3-hydroxy-5-methoxyphenyl)-2-[4-(5-methyl-[1,2,4]oxadiazol-3-yl)phenylimino]-1-methylsulfanylethylidene}carbamic acid methyl ester and 1-bromo-2-methoxyethane, to give the title compound.

$^1$H-NMR (CD$_3$OD) δ 1.32 (t, J=7.2 Hz, 3H) 1.93 (s, 3H) 3.97 (q, J=7.2 Hz, 2H) 4.06-4.25 (m, 2H) 4.56-4.77 (m, 2H) 5.61 (s, 1H) 6.44 (dd, J=2.0, 2.4 Hz, 1H) 6.68-6.78 (m, 2H) 6.87 (d, J=8.8 Hz, 2H) 7.32 (t, J=4.8 Hz, 1H) 7.60 (d, J=8.8 Hz, 2H) 8.78 (d, J=4.8 Hz, 2H)

Mass spectrum (ESI) m/z: 493 (M+H)$^+$

(78c) (R) and (S)-4-({[3-ethoxy-5-(2-fluoroethoxy)phenyl]-(5-oxo-1-pyrimidin-2-yl-4,5-dihydro-1H-[1,2,4]triazol-3-yl)methyl}amino)benzamidine trifluoroacetate

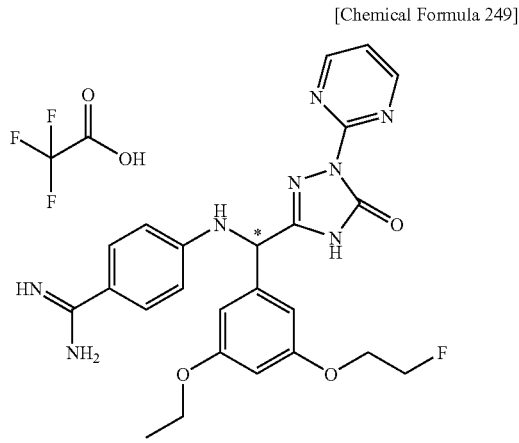

[Chemical Formula 249]

The same procedure was carried out as in Example (12b), except that 4-({[3-ethoxy-5-(2-fluoroethoxy)phenyl]-(5-oxo-1-pyrimidin-2-yl-4,5-dihydro-1H-[1,2,4]triazol-3-yl)methyl}amino)benzamidine acetate was used instead of the 4-{[(3-hydroxymethyl-5-methoxyphenyl)-(5-oxo-1-pyrimidin-2-yl-4,5-dihydro-1H-[1,2,4]triazol-3-yl)methyl]amino}benzamidine acetate, to give the first eluting enantiomer of the title compound.

$^1$H-NMR (CD$_3$OD) δ 1.36 (t, J=6.8 Hz, 3H) 4.02 (q, J=6.8 Hz, 2H) 4.12-4.29 (m, 2H) 4.60-4.80 (m, 2H) 5.65 (s, 1H) 6.50 (dd, J=2.0, 2.4 Hz, 1H) 6.70-6.79 (m, 2H) 6.88 (d, J=8.8 Hz, 2H) 7.38 (t, J=4.8 Hz, 1H) 7.62 (d, J=8.8 Hz, 2H) 8.80 (d, J=4.8 Hz, 2H)

HPLC retention time: 12 min

Example 79

(R) and (S)-4-{[(3,5-diethoxyphenyl)-(5-oxo-1-pyrimidin-2-yl-4,5-dihydro-1H-[1,2,4]triazol-3-yl)methyl]amino}benzamidine trifluoroacetate (79a) 4-{[(3,5-diethoxyphenyl)-(5-oxo-1-pyrimidin-2-yl-4,5-dihydro-1H-[1,2,4]triazol-3-yl)methyl]amino}benzamidine acetate

[Chemical Formula 250]

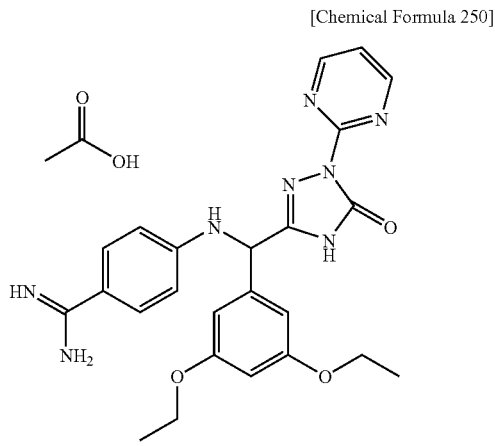

The same procedure was carried out as in Example (6a), except that {2-(3-ethoxy-5-hydroxyphenyl)-2-[4-(5-methyl-[1,2,4]oxadiazol-3-yl)phenylimino]-1-methylsulfanylethylidene}carbamic acid methyl ester (Example (78a)) and bromoethane were used instead of respectively the {2-(3-hydroxy-5-methoxyphenyl)-2-[4-(5-methyl-[1,2,4]oxadiazol-3-yl)phenylimino]-1-methylsulfanylethylidene}carbamic acid methyl ester and 1-bromo-2-methoxyethane, to give the title compound.

$^1$H-NMR (CD$_3$OD) δ 1.34 (t, J=7.2 Hz, 6H) 1.93 (s, 3H) 3.98 (q, J=7.2 Hz, 4H) 5.59 (s, 1H) 6.41 (t, J=2.0 Hz, 1H) 6.69 (d, J=2.0 Hz, 2H) 6.87 (d, J=8.8 Hz, 2H) 7.34 (t, J=4.8 Hz, 1H) 7.61 (d, J=8.8 Hz, 2H) 8.78 (d, J=4.8 Hz, 2H)

Mass spectrum (ESI) m/z: 475 (M+H)$^+$ (79b) (R) and (S)-4-{[(3,5-diethoxyphenyl)-(5-oxo-1-pyrimidin-2-yl-4,5-dihydro-1H-[1,2,4]triazol-3-yl)methyl]amino}benzamidine trifluoroacetate

[Chemical Formula 251]

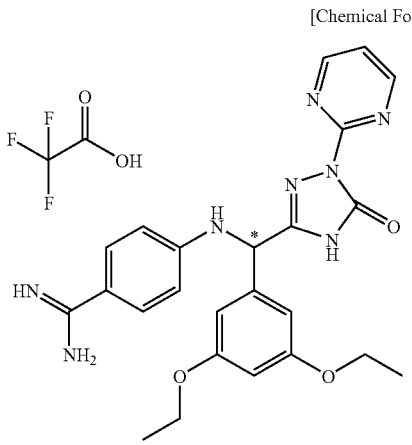

The same procedure was carried out as in Example (12b), except that 4-{[(3,5-diethoxyphenyl)-(5-oxo-1-pyrimidin-2-yl-4,5-dihydro-1H-[1,2,4]triazol-3-yl)methyl]amino}benzamidine acetate was used instead of the 4-{[(3-hydroxymethyl-5-methoxyphenyl)-(5-oxo-1-pyrimidin-2-yl-4,5-dihydro-1H-[1,2,4]triazol-3-yl)methyl]amino}benzamidine acetate, to give the first eluting enantiomer of the title compound.

$^1$H-NMR (CD$_3$OD) δ 1.36 (t, J=6.8 Hz, 6H) 4.01 (q, J=6.8 Hz, 4H) 5.63 (s, 1H) 6.44 (t, J=2.0 Hz, 1H) 6.68 (d, J=2.0 Hz, 2H) 6.87 (d, J=8.8 Hz, 2H) 7.38 (t, J=4.8 Hz, 1H) 7.62 (d, J=8.8 Hz, 2H) 8.80 (d, J=4.8 Hz, 2H)

HPLC retention time: 12 min

Example 80

(R) and (S)-4-({[3-ethoxy-5-(2-fluoroethoxy)phenyl]-(5-oxo-1-pyridazin-3-yl-4,5-dihydro-1H-[1,2,4]triazol-3-yl)methyl}amino)benzamidine acetate

[Chemical Formula 252]

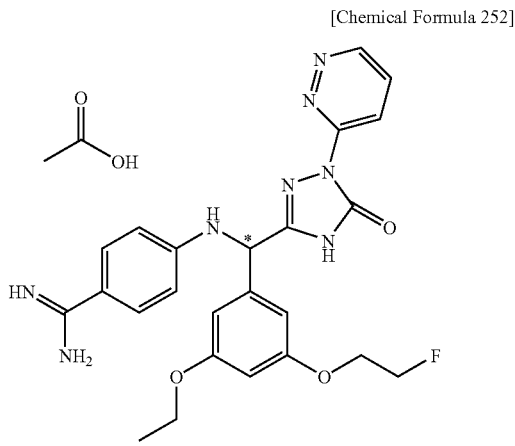

The same procedure was carried out as in Example 7, except that {2-(3-ethoxy-5-hydroxyphenyl)-2-[4-(5-methyl-[1,2,4]oxadiazol-3-yl)phenylimino]-1-methylsulfanylethylidene}carbamic acid methyl ester (Example (78a)) and 1-fluoro-2-iodoethane were used instead of respectively the {2-(3-hydroxy-5-methoxyphenyl)-2-[4-(5-methyl-[1,2,4]oxadiazol-3-yl)phenylimino]-1-methylsulfanylethylidene}carbamic acid methyl ester and 1-bromo-2-methoxyethane, to give the first eluting enantiomer of the title compound.

$^1$H-NMR (CD$_3$OD) δ 1.24 (t, J=6.8 Hz, 3H) 1.84 (s, 3H) 3.89 (q, J=6.8 Hz, 2H) 4.00-4.17 (m, 2H) 4.47-4.69 (m, 2H) 5.50 (s, 1H) 6.33 (dd, J=2.0, 2.4 Hz, 1H) 6.62-6.70 (m, 2H) 6.78 (d, J=9.2 Hz, 2H) 7.51 (d, J=9.2 Hz, 2H) 7.66 (dd, J=4.8, 9.2 Hz, 1H) 8.47 (dd, J=1.6, 9.2 Hz, 1H) 8.92 (dd, J=1.6, 4.8 Hz, 1H)

HPLC retention time: 12 min

Example 81

(R) and (S)-4-({[4-(2-fluoroethoxy)-3-methoxyphenyl]-(5-oxo-1-pyrimidin-2-yl-4,5-dihydro-1H-[1,2,4]triazol-3-yl)methyl}amino)benzamidine acetate

[Chemical Formula 253]

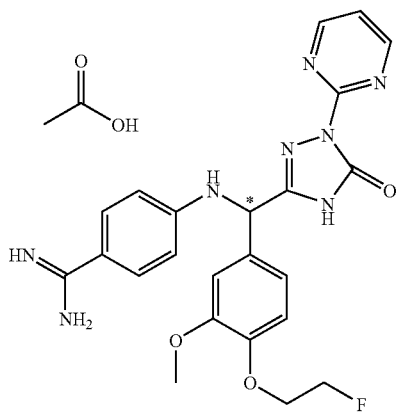

The same procedure was carried out as in Examples (6a)-(6b), except that {2-(4-hydroxy-3-methoxyphenyl)-2-[4-(5-methyl-[1,2,4]oxadiazol-3-yl)phenylamino]-1-methylsulfanylethylidene}carbamic acid methyl ester(18d) and 1-fluoro-2-iodoethane were used instead of respectively the {2-(3-hydroxy-5-methoxyphenyl)-2-[4-(5-methyl-[1,2,4]oxadiazol-3-yl)phenylimino]-1-methylsulfanylethylidene}carbamic acid methyl ester in Example (6a) and 1-bromo-2-methoxyethane in Example (6a), to give the first eluting enantiomer of the title compound.

$^1$H-NMR (CD$_3$OD) δ 1.90 (s, 3H) 3.82 (s, 3H) 4.12-4.27 (m, 2H) 4.58-4.79 (m, 2H) 5.87 (s, 1H) 6.85 (d, J=8.8 Hz, 2H) 6.94 (d, J=8.4 Hz, 1H) 7.08 (dd, J=2.0, 8.4 Hz, 1H) 7.20 (d, J=2.0 Hz, 1H) 7.27 (t, J=4.8 Hz, 1H) 7.59 (d, J=8.8 Hz, 2H) 8.76 (d, J=4.8 Hz, 2H)

HPLC retention time: 8 min (Column name: SUMICHIRAL OA-2500, 4.6 mmφ×25 cm, Manufacturer: Sumika Chemical Analysis Service, Ltd., Mobile phase: 0.05 M ammonium acetate-methanol solution, Elution rate: 1 ml/min)

Example 82

(R) and (S)-4-({(3,7-dimethoxy-2,3-dihydrobenzofuran-5-yl)-(5-oxo-1-pyrimidin-2-yl-4,5-dihydro-1H-[1,2,4]triazol-3-yl)methyl}amino)benzamidine acetate

(82a) 7-methoxy-3-triisopropylsilanyloxy-2,3-dihydrobenzofuran-5-carbaldehyde

[Chemical Formula 254]

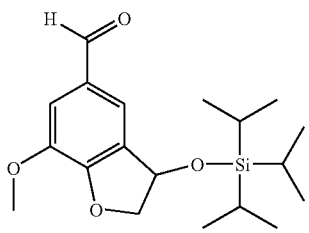

After adding 4.3 g of potassium carbonate and 2.35 ml of methyl bromoacetate to a solution of 5.39 g of 5-bromo-2-hydroxy-3-methoxybenzoic acid methyl ester in 40 ml of DMF, the mixture was stirred for a day at room temperature. Water was added to the reaction mixture and extraction was performed with ethyl acetate. The organic layer was washed with water and saturated brine and then dried over anhydrous magnesium sulfate. The desiccating agent was filtered off and the filtrate was concentrated under reduced pressure. To a solution of 4.41 g of the residue in 60 ml of a methanol:water=1:1 mixed solvent there was added 12 ml of a 5N aqueous sodium hydroxide solution, and the mixture was stirred at room temperature for 21 hours. Water was added to the reaction mixture, and filtration was performed to give a light yellow solid (3.75 g). After adding 3 ml of acetic acid and 1.51 g of sodium acetate to a solution of the obtained light yellow solid in 26 ml of acetic anhydride, the mixture was heated to reflux for 6 hours. Water was added to the reaction mixture and extraction was performed with ethyl acetate. The organic layer was washed with water and saturated brine and then dried over anhydrous magnesium sulfate. The desiccating agent was filtered off and the filtrate was concentrated under reduced pressure. The residue was purified by silica gel column chromatography (ethyl acetate-heptane) to give a light yellow solid (2.26 g).

To a solution of the obtained light yellow solid in 20 ml of methanol there were added 7.5 ml of water and 5 ml of 1N hydrochloric acid, and the mixture was stirred at 75° C. for 10 hours. Water was added to the reaction mixture, and filtration was performed to give 5-bromo-7-methoxy-benzofuran-3-one as a light brown solid (1.78 g).

$^1$H-NMR (CDCl$_3$) δ 3.96 (s, 3H) 4.71 (s, 2H) 7.19 (d, J=1.2 Hz, 1H) 7.39 (d, J=1.2 Hz, 1H)

To a solution of the obtained light brown solid in 30 ml of methanol there was added 554 mg of sodium borohydride at 0° C., and the mixture was stirred for 3 hours and 30 minutes. Saturated aqueous ammonium chloride was added to the reaction mixture and extraction was performed with ethyl acetate. The organic layer was washed with water and saturated brine, and then dried over anhydrous sodium sulfate. The desiccating agent was filtered off and the filtrate was concentrated under reduced pressure.

To a solution of the residue in 30 ml of DMF there were added 956 mg of imidazole and 2.7 ml of chlorotriisopropylsilane, and the mixture was stirred at room temperature for 2 days. Water was added to the reaction mixture and extraction was performed with ethyl acetate. The organic layer was washed with ice-cooled 1N hydrochloric acid, water, saturated aqueous sodium hydrogencarbonate, water and saturated brine, and then dried over anhydrous sodium sulfate. The desiccating agent was filtered off and the filtrate was concentrated under reduced pressure. The residue was purified by silica gel column chromatography (ethyl acetate-heptane) to give 2.59 g of a light yellow solid.

To a solution of the obtained light yellow solid in 30 ml of THF there was added 2.71 ml of n-butyllithium (2.62 M, hexane solution) at −78° C. under a nitrogen atmosphere. After stirring for 3 hours, 0.843 ml of N-formylmorpholine was added and the mixture was stirred at room temperature for 2 hours and 30 minutes. Saturated aqueous ammonium chloride was added to the reaction mixture and extraction was performed with ethyl acetate. The organic layer was washed with water and saturated brine and then dried over anhydrous magnesium sulfate. The desiccating agent was filtered off and the filtrate was concentrated under reduced pressure. The residue was purified by silica gel column chromatography (ethyl acetate-heptane) to give the title compound (1.83 g) as a light yellow oil.

¹H-NMR (CDCl₃) δ 0.95-1.25 (m, 21H) 3.95 (s, 3H) 4.55 (dd, J=3.6, 10.4 Hz, 1H) 4.72 (dd, J=6.8, 10.4 Hz, 1H) 5.66 (dd, J=3.6, 6.8 Hz, 1H) 7.40 (d, J=1.2 Hz, 1H) 7.51 (d, J=1.2 Hz, 1H) 9.85 (s, 1H)

(82b) {2-(3-hydroxy-7-methoxy-2,3-dihydrobenzofuran-5-yl)-2-[4-(5-methyl-[1,2,4]oxadiazol-3-yl)phenylimino]-1-methylsulfanylethylidene}carbamic acid methyl ester

[Chemical Formula 255]

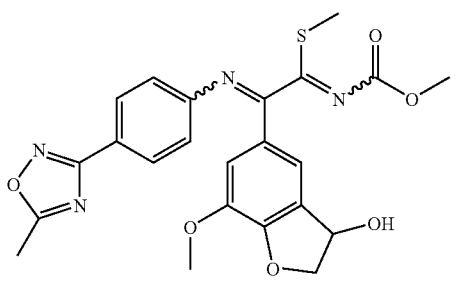

The same procedure was carried out as in Examples (4b)-(4c), except that 7-methoxy-3-triisopropylsilanyloxy-2,3-dihydrobenzofuran-5-carbaldehyde was used instead of the 3-methoxy-5-triisopropylsilanyloxybenzaldehyde in Example (4b), to give the title compound.

¹H-NMR (CDCl₃) Main isomer:

δ 2.34 (s, 3H) 2.66 (s, 3H) 3.64 (s, 3H) 3.97 (s, 3H) 4.62 (dd, J=2.4, 10.8 Hz, 1H) 4.71 (dd, J=6.4, 10.8 Hz, 1H) 5.45 (dt, J=2.4, 6.4 Hz, 1H) 7.17 (d, J=8.8 Hz, 2H) 7.45 (d, J=1.6 Hz, 1H) 7.60 (d, J=1.6 Hz, 1H) 8.02 (d, J=8.8 Hz, 2H)

(82c) {2-(3,7-dimethoxy-2,3-dihydrobenzofuran-5-yl)-2-[4-(5-methyl-[1,2,4]oxadiazol-3-yl)phenylimino]-1-methylsulfanylethylidene}carbamic acid methyl ester

[Chemical Formula 256]

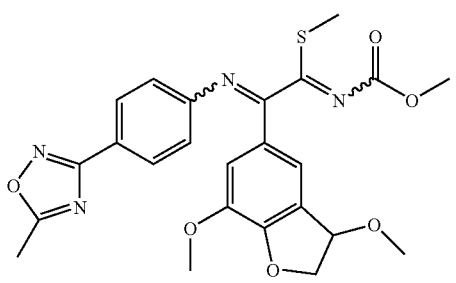

After adding 201 mg of 1,8-bis(dimethylamino)naphthalene and 138 mg of trimethyloxonium tetrafluoroborate to a solution of 150 mg of {2-(3-hydroxy-7-methoxy-2,3-dihydrobenzofuran-5-yl)-2-[4-(5-methyl-[1,2,4]oxadiazol-3-yl)phenylimino]-1-methylsulfanylethylidene}carbamic acid methyl ester in 3 ml of acetonitrile at 0° C., the mixture was stirred for 2 hours. Saturated aqueous sodium hydrogencarbonate was added to the reaction mixture, and extraction was performed with ethyl acetate. After washing the organic layer with water and saturated brine, it was dried over anhydrous magnesium sulfate. The desiccating agent was filtered off and the filtrate was concentrated under reduced pressure. The residue was purified by silica gel column chromatography (ethyl acetate-heptane) to give the title compound (80 mg) as a yellow oil.

(82d) (R) and (S)-4-({(3,7-dimethoxy-2,3-dihydrobenzofuran-5-yl)-(5-oxo-1-pyrimidin-2-yl-4,5-dihydro-1H-[1,2,4]triazol-3-yl)methyl}amino)benzamidine acetate

[Chemical Formula 257]

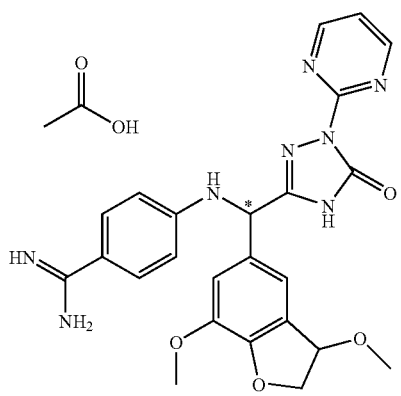

The same procedure was carried out as in Examples (10d)-(10e), except that {2-(3,7-dimethoxy-2,3-dihydrobenzofuran-5-yl)-2-[4-(5-methyl-[1,2,4]oxadiazol-3-yl)phenylimino]-1-methylsulfanylethylidene}carbamic acid methyl ester was used instead of the {2-(3-methoxy-5-methoxymethylphenyl)-2-[4-(5-methyl-[,2,4]oxadiazol-3-yl)phenylimino]-1-methylsulfanylethylidene}carbamic acid methyl ester in Example (10d), to give the first eluting enantiomer of the title compound.

¹H-NMR (CD₃OD) isomer mixture

δ 1.91 (s, 3H) 3.28, 3.34 (each s, total 3H) 3.84, 3.85 (each s, total 3H) 4.45 (dd, J=6.4, 10.8 Hz, 1H) 4.54, 4.55 (each dd, J=2.4, 10.8 Hz, total 1H) 4.99 (dd, J=2.4, 6.4 Hz, 1H) 5.61 (s, 1H) 6.87 (d, J=8.8 Hz, 2H) 7.13-7.28 (m, 2H) 7.30 (t, J=4.8 Hz, 1H) 7.60 (d, J=8.8 Hz, 2H) 8.77 (d, J=4.8 Hz, 2H)

HPLC retention time: 16 min

Example 83

4-{[(3-ethoxy-5-methoxymethylphenyl)-(5-oxo-1-pyrimidin-2-yl-4,5-dihydro-1H-[1,2,4]triazol-3-yl)methyl]amino}benzamidine acetate (83a) {2-(3-ethoxy-5-hydroxymethylphenyl)-2-[4-(5-methyl-[1,2,4]oxadiazol-3-yl)phenylimino]-1-methylsulfanylethylidene}carbamic acid methyl ester

[Chemical Formula 258]

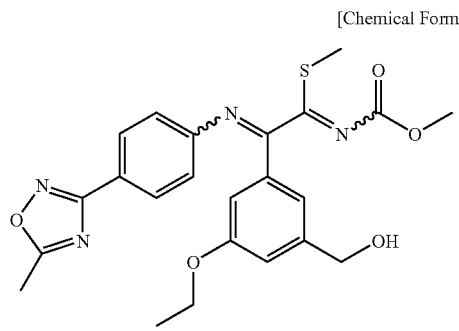

The same procedure was carried out as in Example (11e), except that bromoethane was used instead of the methyl iodide, to give the title compound.

$^1$H-NMR (CDCl$_3$) Main isomer:
δ 1.43 (t, J=7.2 Hz, 3H) 2.34 (s, 3H) 2.66 (s, 3H) 3.62 (s, 3H) 4.10 (q, J=7.2 Hz, 2H) 4.72 (s, 2H) 7.10 (br.s, 1H) 7.16 (d, J=8.4 Hz, 2H) 7.36 (br.t, J=2.0 Hz, 1H) 7.39 (s, 1H) 8.02 (d, J=8.4 Hz, 2H)

(83b) {2-(3-ethoxy-5-methoxymethylphenyl)-2-[4-(5-methyl-[1,2,4]oxadiazol-3-yl)phenylimino]-1-methylsulfanylethylidene}carbamic acid methyl ester

[Chemical Formula 259]

The same procedure was carried out as in Example (82c), except that {2-(3-ethoxy-5-hydroxymethylphenyl)-2-[4-(5-methyl-[1,2,4]oxadiazol-3-yl)phenylimino]-1-methylsulfanylethylidene}carbamic acid methyl ester was used instead of the {2-(3-hydroxy-7-methoxy-2,3-dihydrobenzofuran-5-yl)-2-[4-(5-methyl-[1,2,4]oxadiazol-3-yl)phenylimino]-1-methylsulfanylethylidene}carbamic acid methyl ester, to give the title compound.

(83c) 4-{[(3-ethoxy-5-methoxymethylphenyl)-(5-oxo-1-pyrimidin-2-yl-4,5-dihydro-1H-[1,2,4]triazol-3-yl)methyl]amino}benzamidine acetate

[Chemical Formula 260]

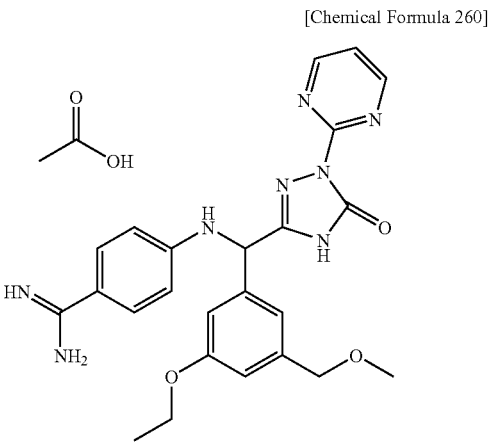

The same procedure was carried out as in Example (10d), except that {2-(3-ethoxy-5-methoxymethylphenyl)-2-[4-(5-methyl-[1,2,4]oxadiazol-3-yl)phenylimino]-1-methylsulfanylethylidene}carbamic acid methyl ester was used instead of the {2-(3-methoxy-5-methoxymethylphenyl)-2-[4-(5-methyl-[1,2,4]oxadiazol-3-yl)phenylimino]-1-methylsulfanylethylidene}carbamic acid methyl ester, to give the title compound.

$^1$H-NMR (CD$_3$OD) δ 1.33 (t, J=6.8 Hz, 3H) 1.92 (s, 3H) 3.33 (s, 3H) 4.00 (q, J=6.8 Hz, 2H) 4.39 (s, 2H) 5.65 (s, 1H) 6.83 (s, 1H) 6.86 (d, J=8.8 Hz, 2H) 7.04 (s, 1H) 7.09 (s, 1H) 7.31 (t, J=4.8 Hz, 1H) 7.59 (d, J=8.8 Hz, 2H) 8.77 (d, J=4.8 Hz, 2H)

Mass spectrum (ESI) m/z: 475 (M+H)$^+$

Example 84

4-{[(3-ethoxy-5-fluoromethylphenyl)-(5-oxo-1-pyrimidin-2-yl-4,5-dihydro-1H-[1,2,4]triazol-3-yl)methyl]amino}benzamidine acetate

[Chemical Formula 261]

The same procedure was carried out as in Examples (11f)-(11g), except that {2-(3-ethoxy-5-hydroxymethylphenyl)-2-

[4-(5-methyl-[1,2,4]oxadiazol-3-yl)phenylimino]-1-methylsulfanylethylidene}carbamic acid methyl ester (Example (83a)) was used instead of the {2-(3-hydroxymethyl-5-methoxyphenyl)-2-[4-(5-methyl-[1,2,4]oxadiazol-3-yl)phenylimino]-1-methylsulfanylethylidene}carbamic acid methyl ester in Example (11f), to give the title compound.

¹H-NMR (CD₃OD) δ 1.37 (t, J=6.8 Hz, 3H) 1.97 (s, 3H) 4.06 (q, J=6.8 Hz, 2H) 5.35 (d, J=47.6 Hz, 2H) 5.72 (s, 1H) 6.86 (d, J=8.8 Hz, 2H) 6.94 (s, 1H) 7.11 (s, 1H) 7.15 (s, 1H) 7.37 (t, J=4.8 Hz, 1H) 7.62 (d, J=8.8 Hz, 2H) 8.80 (d, J=4.8 Hz, 2H)

Mass spectrum (ESI) m/z: 463 (M+H)⁺

Example 85

4-{[(R) and (S)-(3-allyloxy-5-methoxymethylphenyl)-(5-oxo-1-pyrimidin-2-yl-4,5-dihydro-1H-[1,2,4]triazol-3-yl)methyl]amino}benzamidine acetate (85a) {2-(3-allyloxy-5-hydroxymethylphenyl)-2-[4-(5-methyl-[1,2,4]oxadiazol-3-yl)phenylimino]-1-methylsulfanylethylidene}carbamic acid methyl ester

[Chemical Formula 262]

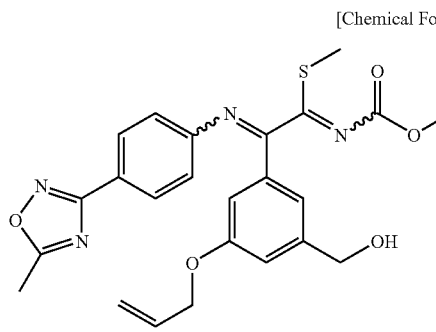

The same procedure was carried out as in Example (11e), except that allyl bromide was used instead of the methyl iodide, to give the title compound.

(85b) {2-(3-allyloxy-5-methoxymethylphenyl)-2-[4-(5-methyl-[1,2,4]oxadiazol-3-yl)phenylimino]-1-methylsulfanylethylidene}carbamic acid methyl ester

[Chemical Formula 263]

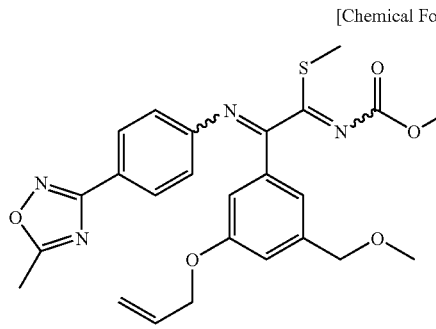

The same procedure was carried out as in Example (82c), except that {2-(3-allyloxy-5-hydroxymethylphenyl)-2-[4-(5-methyl-[1,2,4]oxadiazol-3-yl)phenylimino]-1-methylsulfanylethylidene}carbamic acid methyl ester was used instead of the {2-(3-hydroxy-7-methoxy-2,3-dihydrobenzofuran-5-yl)-2-[4-(5-methyl-[1,2,4]oxadiazol-3-yl)phenylimino]-1-methylsulfanylethylidene}carbamic acid methyl ester, to give the title compound.

(85c) 4-{[(R) and (S)-(3-allyloxy-5-methoxymethylphenyl)-(5-oxo-1-pyrimidin-2-yl-4,5-dihydro-1H-[1,2,4]triazol-3-yl)methyl]amino}benzamidine acetate

[Chemical Formula 264]

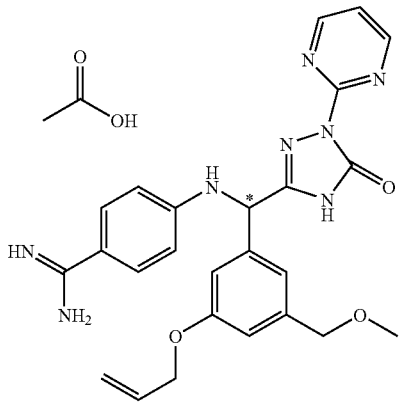

The same procedure was carried out as in Examples (10d)-(10e), except that {2-(3-allyloxy-5-methoxymethylphenyl)-2-[4-(5-methyl-[1,2,4]oxadiazol-3-yl)phenylimino]-1-methylsulfanylethylidene}carbamic acid methyl ester was used instead of the {2-(3-methoxy-5-methoxymethylphenyl)-2-[4-(5-methyl-[1,2,4]oxadiazol-3-yl)phenylimino]-1-methylsulfanylethylidene}carbamic acid methyl ester in Example (10d), to give the first eluting enantiomer of the title compound.

¹H-NMR (CD₃OD) δ 1.90 (s, 3H) 3.34 (s, 3H) 4.40 (s, 2H) 4.53 (ddd, J=1.6, 1.6, 5.2 Hz, 2H) 5.20 (tdd, J=1.6, 1.6, 10.8 Hz, 1H) 5.36 (tdd, J=1.6, 1.6, 17.2 Hz, 1H) 5.58 (s, 1H) 6.01 (tdd, J=5.2, 10.8, 17.2 Hz, 1H) 6.84 (s, 1H) 6.85 (d, J=8.8 Hz, 2H) 7.08 (s, 1H) 7.12 (s, 1H) 7.26 (t, J=4.8 Hz, 1H) 7.59 (d, J=8.8 Hz, 2H) 8.75 (d, J=4.8 Hz, 2H)

HPLC retention time: 6 min (Column name: SUMICHIRAL OA-2500, 4.6 mmφ×25 cm, Manufacturer: Sumika Chemical Analysis Service, Ltd., Mobile phase: 0.05 M ammonium acetate-methanol solution, Elution rate: 1 ml/min)

Example 86

4-{[(5-oxo-1-pyrimidin-2-yl-4,5-dihydro-1H-[1,2,4]triazol-3-yl)-(3,4,5-trimethoxyphenyl)methyl]amino}benzamidine acetate (86a) {2-(4-hydroxy-3,5-dimethoxyphenyl)-2-[4-(5-methyl-[1,2,4]oxadiazol-3-yl)phenylimino]-1-methylsulfanylethylidene}carbamic acid methyl ester

[Chemical Formula 265]

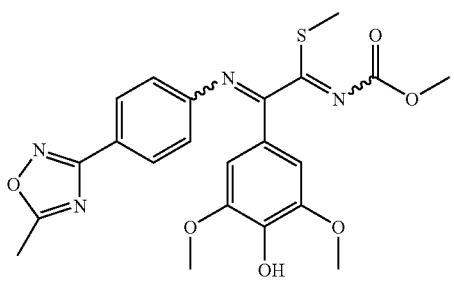

The same procedure was carried out as in Example (9a), except that 4-(t-butyldimethylsilanyloxy)-3,5-dimethoxybenzaldehyde [CAS No. 106852-80-6] was used instead of the 3-methoxy-5-triisopropylsilanyloxybenzaldehyde, to give the title compound.

$^1$H-NMR (CDCl$_3$) Main isomer:
δ 2.32 (s, 3H) 2.65 (s, 3H) 3.63 (s, 3H) 3.94 (s, 6H) 5.89 (s, 1H) 7.15 (s, 2H) 7.19 (d, J=8.4 Hz, 2H) 8.01 (d, J=8.4 Hz, 2H)

(86b) 4-{[(5-oxo-1-pyrimidin-2-yl-4,5-dihydro-1H-[1,2,4]triazol-3-yl)-(3,4,5-trimethoxyphenyl)methyl]amino}benzamidine acetate

[Chemical Formula 266]

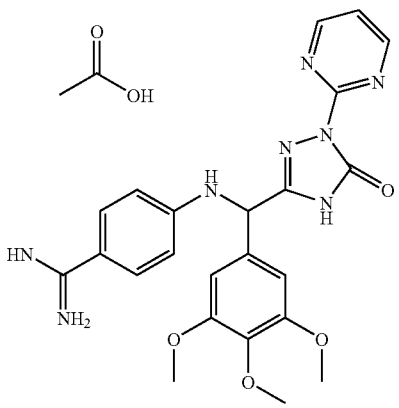

The same procedure was carried out as in Example (6a), except that {2-(4-hydroxy-3,5-dimethoxyphenyl)-2-[4-(5-methyl-[1,2,4]oxadiazol-3-yl)phenylimino]-1-methylsulfanylethylidene}carbamic acid methyl ester and methyl iodide were used instead of respectively the {2-(3-hydroxy-5-methoxyphenyl)-2-[4-(5-methyl-[1,2,4]oxadiazol-3-yl)phenylimino]-1-methylsulfanylethylidene}carbamic acid methyl ester and 1-bromo-2-methoxyethane, to give the title compound.

$^1$H-NMR (CD$_3$OD) δ 1.93 (s, 3H) 3.73 (s, 3H) 3.80 (s, 6H) 5.64 (s, 1H) 6.88 (d, J=8.8 Hz, 2H) 6.90 (s, 2H) 7.34 (t, J=5.2 Hz, 1H) 7.61 (d, J=8.8 Hz, 2H) 8.78 (d, J=5.2 Hz, 2H)

Mass spectrum (ESI) m/z: 477 (M+H)$^+$

Example 87

4-({[3,5-dimethoxy-4-(2-methoxyethoxy)phenyl]-[1-(2-methoxyphenyl)-5-oxo-4,5-dihydro-1H-[1,2,4]triazol-3-yl]methyl}amino)benzamidine acetate

[Chemical Formula 267]

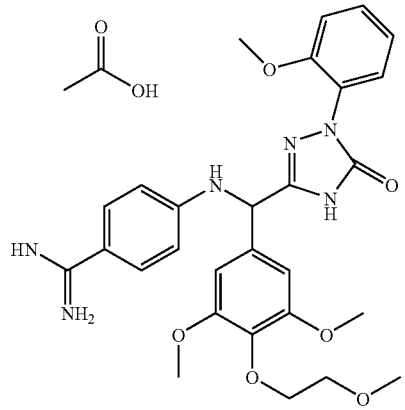

The same procedure was carried out as in Example (6a), except that {2-(4-hydroxy-3,5-dimethoxyphenyl)-2-[4-(5-methyl-[1,2,4]oxadiazol-3-yl)phenylimino]-1-methylsulfanylethylidene}carbamic acid methyl ester (Example (86a)) and 2-methoxyphenylhydrazine hydrochloride were used instead of respectively the {2-(3-hydroxy-5-methoxyphenyl)-2-[4-(5-methyl-[1,2,4]oxadiazol-3-yl)phenylimino]-1-methylsulfanylethylidene}carbamic acid methyl ester and 2-hydrazinopyrimidine, to give the title compound.

$^1$H-NMR (CD$_3$OD) δ 1.91 (s, 3H) 3.39 (s, 3H) 3.62-3.69 (m, 2H) 3.81 (s, 3H) 3.84 (s, 6H) 4.01-4.09 (m, 2H) 5.62 (s, 1H) 6.86 (s, 2H) 6.87 (d, J=8.8 Hz, 2H) 7.03 (ddd, J=1.2, 7.6, 8.0 Hz, 1H) 7.15 (dd, J=1.2, 8.4 Hz, 1H) 7.31 (dd, J=2.0, 8.0 Hz, 1H) 7.44 (ddd, J=2.0, 7.6, 8.4 Hz, 1H) 7.64 (d, J=8.8 Hz, 2H)

Mass spectrum (ESI) m/z: 549 (M+H)$^+$

Example 88

4-{[(R) and (S)-(5-oxo-1-pyridazin-3-yl-4,5-dihydro-1H-[1,2,4]triazol-3-yl)-(3,4,5-trimethoxyphenyl)methyl]amino}benzamidine trifluoroacetate (88a) {2-(3-hydroxy-4,5-dimethoxyphenyl)-2-[4-(5-methyl-[1,2,4]oxadiazol-3-yl)phenylimino]-1-methylsulfanylethylidene}carbamic acid methyl ester

[Chemical Formula 268]

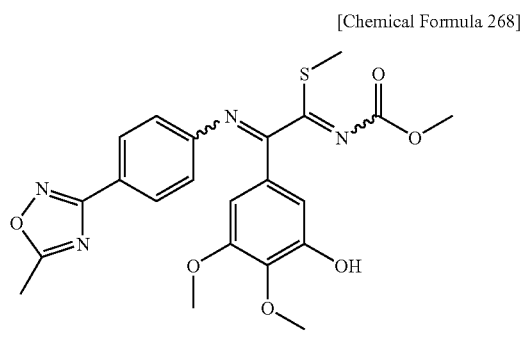

The same procedure was carried out as in Examples (4a)-(4c), except that 3-hydroxy-4,5-dimethoxybenzaldehyde was used instead of the 3-hydroxy-5-methoxybenzaldehyde in Example (4a), to give the title compound.

$^1$H-NMR (CDCl$_3$) Main isomer:

δ 2.32 (s, 3H) 2.65 (s, 3H) 3.65 (s, 3H) 3.93 (s, 3H) 3.97 (s, 3H) 5.82 (s, 1H) 7.00 (d, J=2.0 Hz, 1H) 7.14 (d, J=8.8 Hz, 2H) 7.19 (d, J=2.0 Hz, 1H) 8.00 (d, J=8.8 Hz, 2H)

(88b) 4-{[(5-oxo-1-pyridazin-3-yl-4,5-dihydro-1H-[1,2,4]triazol-3-yl)-(3,4,5-trimethoxyphenyl)methyl]amino}benzamidine acetate

[Chemical Formula 269]

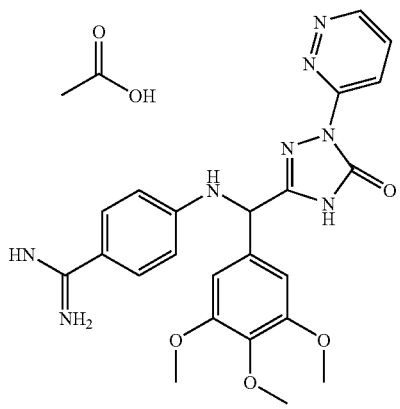

The same procedure was carried out as in Example (6a), except that {2-(3-hydroxy-4,5-dimethoxyphenyl)-2-[4-(5-methyl-[1,2,4]oxadiazol-3-yl)phenylimino]-1-methylsulfanylethylidene}carbamic acid methyl ester, methyl iodide and 3-hydrazinopyridazine hydrochloride were used instead of respectively the {2-(3-hydroxy-5-methoxyphenyl)-2-[4-(5-methyl-[1,2,4]oxadiazol-3-yl)phenylimino]-1-methylsulfanylethylidene}carbamic acid methyl ester, 1-bromo-2-methoxyethane and 2-hydrazinopyrimidine, to give the title compound.

$^1$H-NMR (CD$_3$OD) δ 1.95 (s, 3H) 3.73 (s, 3H) 3.83 (s, 6H) 5.65 (s, 1H) 6.89 (d, J=9.2 Hz, 2H) 6.91 (s, 2H) 7.62 (d, J=9.2 Hz, 2H) 7.78 (dd, J=4.8, 8.8 Hz, 1H) 8.51 (dd, J=1.6, 8.8 Hz, 1H) 9.04 (dd, J=1.6, 4.8 Hz, 1H)

Mass spectrum (ESI) m/z: 477 (M+H)$^+$ (88c) 4-{[(R) and (S)-(5-oxo-1-pyridazin-3-yl-4,5-dihydro-1H-[1,2,4]triazol-3-yl)-(3,4,5-trimethoxyphenyl)methyl]amino}benzamidine trifluoroacetate

[Chemical Formula 270]

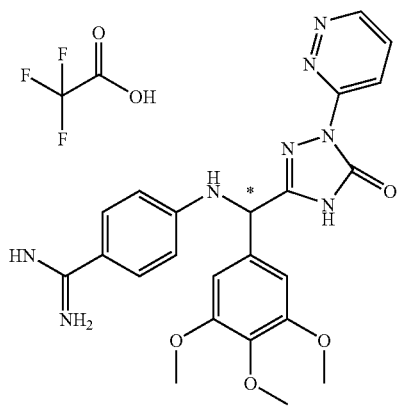

The same procedure was carried out as in Example (12b), except that 4-{[(5-oxo-1-pyridazin-3-yl-4,5-dihydro-1H-[1,2,4]triazol-3-yl)-(3,4,5-trimethoxyphenyl)methyl]amino}benzamidine acetate was used instead of the 4-{[(3-hydroxymethyl-5-methoxyphenyl)-(5-oxo-1-pyrimidin-2-yl-4,5-dihydro-1H-[1,2,4]triazol-3-yl)methyl]amino}benzamidine acetate, to give the first eluting enantiomer of the title compound.

$^1$H-NMR (CD$_3$OD) δ 3.75 (s, 3H) 3.85 (s, 6H) 5.70 (s, 1H) 6.90 (s, 2H) 6.91 (d, J=8.8 Hz, 2H) 7.63 (d, J=8.8 Hz, 2H) 7.81 (dd, J=4.8, 9.2 Hz, 1H) 8.45 (d, J=9.2 Hz, 1H) 9.08 (d, J=4.8 Hz, 1H)

HPLC retention time: 11 min

Example 89

4-{[(R) and (S)-[3-(2-fluoroethoxy)-4,5-dimethoxyphenyl]-(5-oxo-1-pyridazin-3-yl-4,5-dihydro-1H-[1,2,4]triazol-3-yl)methyl]amino}benzamidine acetate

[Chemical Formula 271]

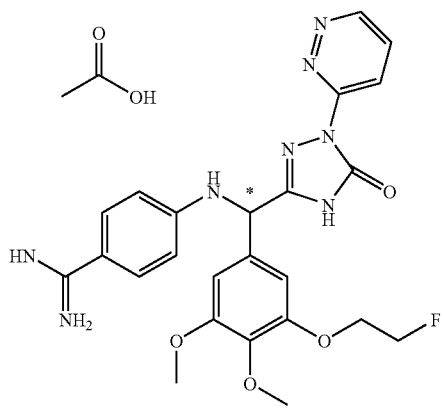

The same procedure was carried out as in Example 7, except that {2-(3-hydroxy-4,5-dimethoxyphenyl)-2-[4-(5- methyl-[1,2,4]oxadiazol-3-yl)phenylimino]-1-methylsulfanylethylidene}carbamic acid methyl ester (Example (88a)) and 1-fluoro-2-iodoethane were used instead of respectively the {2-(3-hydroxy-5-methoxyphenyl)-2-[4-(5-methyl-[1,2,4]oxadiazol-3-yl)phenylimino]-1-methylsulfanylethylidene}carbamic acid methyl ester and 1-bromo-2-methoxyethane, to give the first eluting enantiomer of the title compound.

$^1$H-NMR (CD$_3$OD) δ 1.92 (s, 3H) 3.75 (s, 3H) 3.82 (s, 3H) 4.12-4.32 (m, 2H) 4.58-4.78 (m, 2H) 5.58 (s, 1H) 6.86 (d, J=8.8 Hz, 2H) 6.90 (d, J=2.0 Hz, 1H) 6.93 (d, J=2.0 Hz, 1H) 7.60 (d, J=8.8 Hz, 2H) 7.75 (dd, J=4.8, 9.2 Hz, 1H) 8.56 (dd, J=1.6, 9.2 Hz, 1H) 9.00 (dd, J=1.6, 4.8 Hz, 1H)

HPLC retention time: 6 min (Column name: SUMICHIRAL OA-2500, 4.6 mmφ×25 cm, Manufacturer: Sumika Chemical Analysis Service, Ltd., Mobile phase: 0.05 M ammonium acetate-methanol solution, Elution rate: 1 ml/min)

Example 90

4-{[(3-ethoxyphenyl)-(5-oxo-1-pyrimidin-2-yl-4,5-dihydro-1H-[1,2,4]triazol-3-yl)methyl]amino}benzamidine acetate (90a) {2-(3-hydroxyphenyl)-2-[4-(5-methyl-[1,2,4]oxadiazol-3-yl)phenylimino]-1-methylsulfanylethylidene}carbamic acid methyl ester

[Chemical Formula 272]

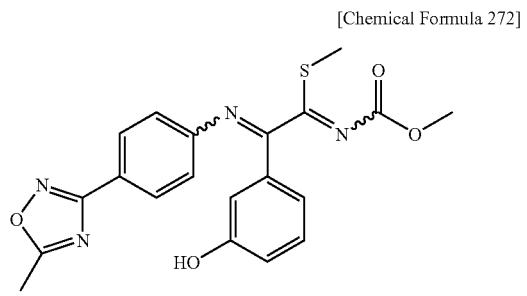

The same procedure was carried out as in Examples (4a)-(4c), except that 3-hydroxybenzaldehyde was used instead of the 3-hydroxy-5-methoxybenzaldehyde in Example (4a), to give the title compound.

$^1$H-NMR (CDCl$_3$) Main isomer:
δ 2.33 (s, 3H) 2.65 (s, 3H) 3.61 (s, 3H) 5.61 (br.s, 1H) 6.96-7.05 (m, 1H) 7.16 (d, J=8.4 Hz, 2H) 7.28 (m, 3H) 8.01 (d, J=8.4 Hz, 2H)

(90b) 4-{[(3-ethoxyphenyl)-(5-oxo-1-pyrimidin-2-yl-4,5-dihydro-1H-[1,2,4]triazol-3-yl)methyl]amino}benzamidine acetate

[Chemical Formula 273]

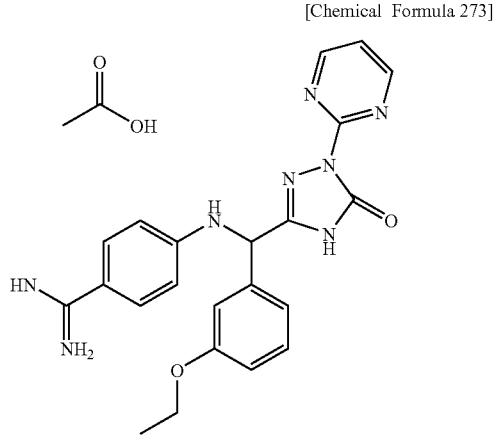

The same procedure was carried out as in Example (6a), except that {2-(3-hydroxyphenyl)-2-[4-(5-methyl-[1,2,4]oxadiazol-3-yl)phenylimino]-1-methylsulfanylethylidene}carbamic acid methyl ester and bromoethane were used instead of respectively the {2-(3-hydroxy-5-methoxyphenyl)-2-[4-(5-methyl-[1,2,4]oxadiazol-3-yl)phenylimino]-1-methylsulfanylethylidene}carbamic acid methyl ester and 1-bromo-2-methoxyethane, to give the title compound.

$^1$H-NMR (CD$_3$OD) δ 1.34 (t, J=6.8 Hz, 3H) 1.94 (s, 3H) 4.00 (q, J=6.8 Hz, 2H) 5.66 (s, 1H) 6.80-6.95 (m, 3H) 7.03-7.18 (m, 2H) 7.27 (t, J=8.4 Hz, 1H) 7.32 (t, J=4.8 Hz, 1H) 7.60 (d, J=8.4 Hz, 2H) 8.76 (d, J=4.8 Hz, 2H)

Mass spectrum (ESI) m/z: 431 (M+H)$^+$

Example 91

4-({[2-fluoro-3-(2-fluoroethoxy)-5-methylphenyl]-[1-(2-methoxyphenyl)-5-oxo-4,5-dihydro-1H-[1,2,4]triazol-3-yl]methyl}amino)benzamidine trifluoroacetate

[Chemical Formula 274]

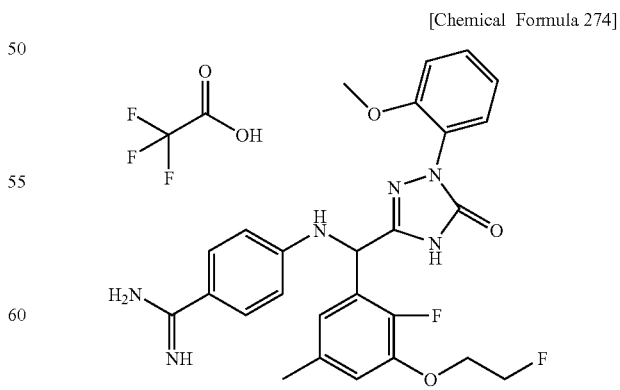

The same procedure was carried out as in Example (14c), except that 1-fluoro-2-iodoethane was used instead of the iodomethane, to give the title compound as a white solid.

$^1$H-NMR (CD$_3$OD) δ 2.30 (s, 3H) 3.81 (s, 3H) 4.23-4.32 (m, 2H) 4.66-4.80 (m, 2H) 5.96 (s, 1H) 6.84-6.89 (m, 3H) 6.95 (dd, J=1.6, 7.6 Hz, 1H) 7.02 (dt, J=1.2, 7.6 Hz, 1H) 7.13 (dd, J=1.2, 8.4 Hz, 1H) 7.30 (dd, J=1.6, 7.6 Hz, 1H) 7.43 (ddd, J=1.6, 7.6, 8.4 Hz, 1H) 7.62-7.65 (m, 2H)

Mass spectrum (ESI) m/z: 509 (M+H)$^+$

Example 92

4-{[(R) and (S)-[2-fluoro-5-methoxy-3-(2-methoxyethoxy)phenyl]-(5-oxo-1-pyrimidin-2-yl-4,5-dihydro-1H-[1,2,4]triazol-3-yl)methyl]amino}benzamidine acetate

[Chemical Formula 275]

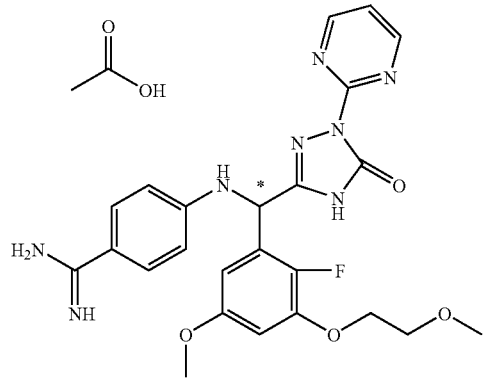

The same procedure was carried out as in Example 15, except that 1-bromo-2-methoxyethane was used instead of the 2-chloro-N,N-dimethylacetamide, to give the first eluting enantiomer of the title compound as a white solid.

$^1$H-NMR (CD$_3$OD) δ 1.91 (s, 3H) 3.42 (s, 3H) 3.71 (s, 3H) 3.74-3.76 (m, 2H) 4.15-4.17 (m, 2H) 5.92 (s, 1H) 6.60-6.62 (m, 1H) 6.65-6.67 (m, 1H) 6.85 (d, J=8.8 Hz, 2H) 7.27 (t, J=4.8 Hz, 1H) 7.60 (d, J=8.8 Hz, 2H) 8.75 (d, J=4.8 Hz, 2H)

Mass spectrum (ESI) m/z: 509 (M+H)$^+$ (mass of racemic mixture)

HPLC retention time: 15 min

Example 93

4-{[(R) and (S)-(3-methoxy-5-methylphenyl)-(5-oxo-1-pyrimidin-2-yl-4,5-dihydro-1H-[1,2,4]triazol-3-yl)methyl]amino}benzamidine acetate

[Chemical Formula 276]

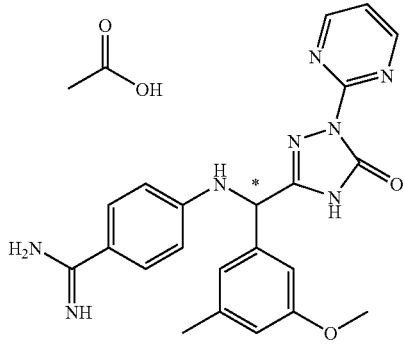

The same procedure was carried out as in Examples (3e)-(3h), except that {2-(3-hydroxy-5-methylphenyl)-2-[4-(5-methyl-[1,2,4]oxadiazol-3-yl)phenylimino]-1-methylsulfanylethylidene}carbamic acid methyl ester (Example (43b)) and iodomethane were used instead of respectively the [2-(2-fluoro-3-hydroxy-5-methoxyphenyl)-2-[4-(5-methyl-[1,2,4]oxadiazol-3-yl)phenylimino]-1-methylsulfanylethylidene]carbamic acid methyl ester in Example (3e) and 1-fluoro-2-iodoethane in Example (3e), to give the first eluting enantiomer of the title compound as a white solid.

$^1$H-NMR (CD$_3$OD) δ 1.91 (s, 3H) 2.29 (s, 3H) 3.75 (s, 3H) 5.57 (s, 1H) 6.69 (br.s, 1H) 6.85 (d, J=8.8 Hz, 2H) 6.92 (br.s, 1H) 6.95 (br.s, 1H) 7.30 (t, J=4.8 Hz, 1H) 7.59 (d, J=8.8 Hz, 2H) 8.77 (d, J=4.8 Hz, 2H)

HPLC retention time: 12 min

Example 94

4-{[(R) and (S)-[3-(2-methoxyethoxy)-5-methylphenyl]-(5-oxo-1-pyrimidin-2-yl-4,5-dihydro-1H-[1,2,4]triazol-3-yl)methyl]amino}benzamidine acetate

[Chemical Formula 277]

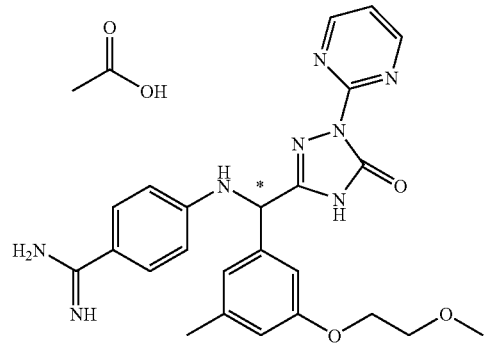

The same procedure was carried out as in Examples (3e)-(3h), except that {2-(3-hydroxy-5-methylphenyl)-2-[4-(5-methyl-[1,2,4]oxadiazol-3-yl)phenylimino]-1-methylsulfanylethylidene}carbamic acid methyl ester (Example (43b)) and 1-bromo-2-methoxyethane were used instead of respectively the [2-(2-fluoro-3-hydroxy-5-methoxyphenyl)-2-[4-(5-methyl-[1,2,4]oxadiazol-3-yl)phenylimino]-1-methylsulfanylethylidene]carbamic acid methyl ester in Example (3e) and 1-fluoro-2-iodoethane in Example (3e), to give the first eluting enantiomer of the title compound as a white solid.

$^1$H-NMR (CD$_3$OD) δ 1.90 (s, 3H) 2.29 (s, 3H) 3.38 (s, 3H) 3.67-3.70 (m, 2H) 4.05-4.07 (m, 2H) 5.56 (s, 1H) 6.70 (br.s, 1H) 6.84 (d, J=8.8 Hz, 2H) 6.94 (br.s, 1H) 6.97 (br.s, 1H) 7.27 (t, J=4.8 Hz, 1H) 7.59 (d, J=8.8 Hz, 2H) 8.76 (d, J=4.8 Hz, 2H)

HPLC retention time: 12 min

Example 95

4-({(R) and (S)-(8-methoxy-4H-benzo[1,3]dioxin-6-yl)-[1-(2-methoxyphenyl)-5-oxo-4,5-dihydro-1H-[1,2,4]triazol-3-yl]methyl}amino)benzamidine acetate

[Chemical Formula 278]

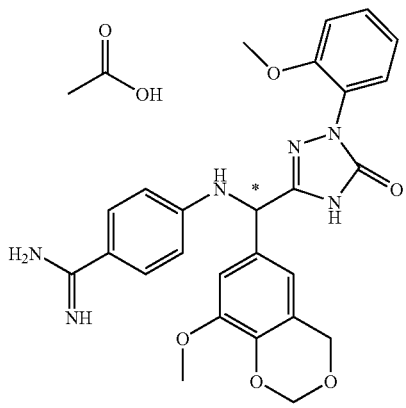

The same procedure was carried out as in Examples (21i)-(21k), except that (2-methoxyphenyl)hydrazine hydrochloride was used instead of the 2-hydrazinopyrimidine in Example (21i), to give the first eluting enantiomer of the title compound as a white solid.

$^1$H-NMR (CD$_3$OD) δ 1.89 (s, 3H) 3.79 (s, 3H) 3.80 (s, 3H) 4.84 (s, 2H) 5.23 (s, 2H) 5.55 (s, 1H) 6.78 (d, J=1.2 Hz, 1H) 6.84 (d, J=8.8 Hz, 2H) 7.00-7.04 (m, 2H) 7.13 (dd, J=1.2, 7.6 Hz, 1H) 7.30 (dd, J=1.2, 7.6 Hz, 1H) 7.42 (m, 1H) 7.61 (d, J=8.8 Hz, 2H)

HPLC retention time: 15 min (Column name: SUMICHIRAL OA-2500, 20 mmϕ×25 cm, Manufacturer: Sumika Chemical Analysis Service, Ltd., Mobile phase: 0.05 M ammonium acetate-methanol solution, Elution rate: 5 ml/min)

Example 96

4-{[(R) and (S)-(5-ethoxy-2-fluorophenyl)-(5-oxo-1-pyrimidin-2-yl-4,5-dihydro-1H-[1,2,4]triazol-3-yl)methyl]amino}benzamidine acetate (96a) {2-[2-fluoro-5-hydroxyphenyl]-2-[4-(5-methyl-[1,2,4]oxadiazol-3-yl)phenylimino]-1-methylsulfanylethylidene}carbamic acid methyl ester

[Chemical Formula 279]

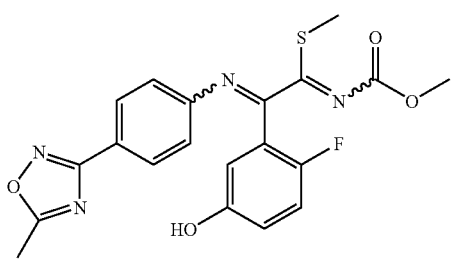

The same procedure was carried out as in Examples (4b)-(4c), except that 5-(t-butyldimethylsilanyloxy)-2-fluorobenzaldehyde [CAS No. 113984-67-1] was used instead of the 3-methoxy-5-triisopropylsilanyloxybenzaldehyde in Example (4b), to give the title compound (isomeric mixture) as a yellow solid.

$^1$H-NMR (CDCl$_3$) Two main isomers:

δ 2.31 (s, 3H) 2.65 (s, 3H) 3.58 (s, 3H) 6.75-6.83 (m, 1H) 6.96-7.00 (m, 1H) 7.10 (d, J=8.0 Hz, 2H) 7.32-7.35 (m, 1H) 8.00 (d, J=8.0 Hz, 2H) δ 2.45 (s, 3H) 2.61 (s, 3H) 3.61 (s, 3H) 6.56-6.61 (m, 1H) 6.75-6.83 (m, 3H) 6.96-7.00 (m, 1H) 7.85 (d, J=8.0 Hz, 2H)

(96b) 4-{[(R) and (S)-(5-ethoxy-2-fluorophenyl)-(5-oxo-1-pyrimidin-2-yl-4,5-dihydro-1H-[1,2,4]triazol-3-yl)methyl]amino}benzamidine acetate

[Chemical Formula 280]

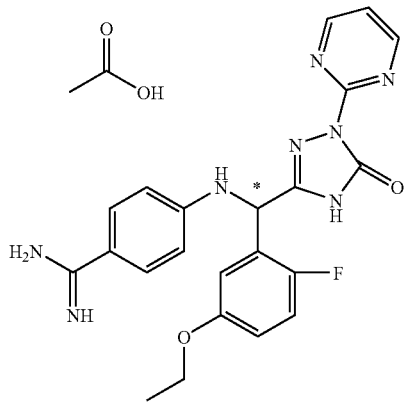

The same procedure was carried out as in Examples (3e)-(3h), except that {2-[2-fluoro-5-hydroxyphenyl]-2-[4-(5-methyl-[1,2,4]oxadiazol-3-yl)phenylimino]-1-methylsulfanylethylidene}carbamic acid methyl ester and iodoethane were used instead of respectively the [2-(2-fluoro-3-hydroxy-5-methoxyphenyl)-2-[4-(5-methyl-[1,2,4]oxadiazol-3-yl)-phenylimino]-1-methylsulfanylethylidene]carbamic acid methyl ester in Example (3e) and 1-fluoro-2-iodoethane in Example (3e), to give the first eluting enantiomer of the title compound as a white solid.

$^1$H-NMR (CD$_3$OD) δ 1.27 (t, J=6.8 Hz, 3H) 1.90 (s, 3H) 3.90 (q, J=6.8 Hz, 2H) 5.90 (s, 1H) 6.79-6.85 (m, 1H) 6.84 (d, J=8.8 Hz, 2H) 7.02 (t, J=9.2 Hz, 1H) 7.08 (dd, J=3.2, 6.0 Hz, 1H) 7.26 (t, J=4.8 Hz, 1H) 7.59 (d, J=8.8 Hz, 2H) 8.73 (d, J=4.8 Hz, 2H)

HPLC retention time: 12 min

Example 97

4-{[(R) and (S)-(8-methyl-4H-benzo[1,3]dioxin-6-yl)-(5-oxo-1-pyrimidin-2-yl-4,5-dihydro-1H-[1,2,4]triazol-3-yl)methyl]amino}benzamidine acetate (97a) 6-bromo-8-methyl-4H-benzo[1,3]dioxine

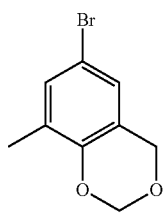

[Chemical Formula 281]

To a solution of 10 g of 2-hydroxy-3-methylbenzoic acid in 200 ml of DMF there was added 11.7 g of N-bromosuccinimide at room temperature. After the reaction mixture was stirred for 23 hours, water was added, and extraction was performed twice with ethyl acetate. The combined organic layers were dried over anhydrous magnesium sulfate. The desiccating agent was filtered off, and the filtrate was concentrated under reduced pressure to give a crude product (14.7 g).

A 5 g portion of the 14.7 g of obtained crude product was dissolved in 80 ml of THF, and the mixture was cooled and stirred at an external temperature of 0° C. To this solution there was added 22 ml of borane-THF complex (1M, THF solution) over a period of 30 minutes. After stirring the reaction mixture at room temperature for 8 hours, it was again cooled to an external temperature of 0° C., and 4.2 ml of borane-methyl sulfide complex (10 M, methyl sulfide solution) was added over a period of 15 minutes. The reaction mixture was stirred at room temperature for 18 hours and 45 minutes, and then 5 ml of water was carefully added and the mixture was stirred at room temperature for 30 minutes. After adding saturated aqueous ammonium chloride to the solution, it was concentrated under reduced pressure. Ethyl acetate was added to the residue and extraction was performed with ethyl acetate. The organic layer was washed with saturated brine and then dried over anhydrous magnesium sulfate. The desiccating agent was filtered off and the filtrate was concentrated under reduced pressure. The obtained residue was crudely purified by silica gel column chromatography (ethyl acetate-heptane) to give a crude product (3.17 g).

A 1.5 g portion of 3.17 g of the obtained crude product was slowly added to a solution of 830 mg of sodium hydride (60% oily suspension) in 50 ml of DMF which had been cooled and stirred at an external temperature of 0° C. The reaction mixture was stirred at room temperature for 30 minutes, and then 0.51 ml of chlorobromomethane and 210 mg of sodium iodide were added at room temperature. The reaction mixture was heated at an external temperature of 80° C., stirred overnight, and then air-cooled. After carefully adding water, extraction was performed twice with t-butyl methyl ether. The combined organic layers were washed with water and saturated brine, and then dried over anhydrous magnesium sulfate. The desiccating agent was filtered off and the filtrate was concentrated under reduced pressure. The residue was purified by silica gel column chromatography (ethyl acetate-heptane) to give the title compound (1.3 g) as a light yellow solid.

$^1$H-NMR (CDCl$_3$) δ 2.17 (s, 3H) 4.85 (s, 2H) 5.24 (s, 2H) 6.92-6.94 (m, 1H) 7.13-7.15 (m, 1H)

(97b) 8-methyl-4H-benzo[1,3]dioxine-6-carbaldehyde

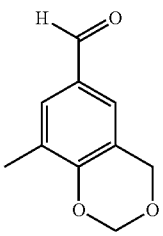

[Chemical Formula 282]

The same procedure was carried out as in Example (21c), except that 6-bromo-8-methyl-4H-benzo[1,3]dioxine was used instead of 6-bromo-8-methoxy-4H-benzo[1,3]dioxine, to give the title compound as a light yellow solid.

$^1$H-NMR (CDCl$_3$) δ 2.26 (s, 3H) 4.94 (s, 2H) 5.34 (s, 2H) 7.37 (br.s, 1H) 7.57 (br.s, 1H) 9.83 (s, 1H)

(97c) 4-{[(R) and (S)-(8-methyl-4H-benzo[1,3]dioxin-6-yl)-(5-oxo-1-pyrimidin-2-yl-4,5-dihydro-1H-[1,2,4]triazol-3-yl)methyl]amino}benzamidine acetate

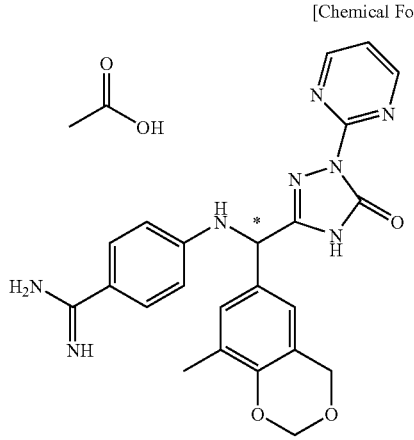

[Chemical Formula 283]

The same procedure was carried out as in Examples (21d)-(21k), except that 8-methyl-4H-benzo[1,3]dioxine-6-carbaldehyde was used instead of the 8-methoxy-4H-benzo[1,3]dioxine-6-carbaldehyde in Example (21d), to give the first eluting enantiomer of the title compound as a white solid.

$^1$H-NMR (CD$_3$OD) δ 1.91 (s, 3H) 2.13 (s, 3H) 4.80 (s, 2H) 5.21 (s, 2H) 5.53 (s, 1H) 6.83 (d, J=8.8 Hz, 2H) 7.01 (br.s, 1H) 7.19 (br.s, 1H) 7.29 (t, J=4.4 Hz, 1H) 7.58 (d, J=8.8 Hz, 2H) 8.75 (d, J=4.4 Hz, 2H)

HPLC retention time: 13 min

Example 98

4-{[(R) and (S)-[2-fluoro-3,5-bis-(2-fluoroethoxy)phenyl]-(5-oxo-1-pyrimidin-2-yl-4,5-dihydro-1H-[1,2,4]triazol-3-yl)methyl]amino}benzamidine acetate

(98a) 1-fluoro-4-(2-fluoroethoxy)benzene

[Chemical Formula 284]

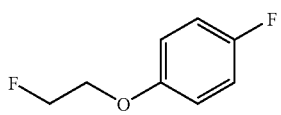

After adding 7.34 g of potassium carbonate and 8.31 g of 1-fluoro-2-iodoethane to a solution of 4.5 g of 4-fluorophenol in 50 ml of DMF, the mixture was stirred at room temperature for 27 hours. Water was added to the reaction mixture, and extraction was performed with diethyl ether. The organic layer was washed with saturated brine and dried over anhydrous magnesium sulfate. The desiccating agent was filtered off and the filtrate was concentrated under reduced pressure. The obtained residue was purified by silica gel column chromatography (ethyl acetate-heptane) to give the title compound (4.6 g) as a colorless liquid.

$^1$H-NMR (CDCl$_3$) δ 4.13-4.22 (m, 2H) 4.67-4.81 (m, 2H) 6.84-6.90 (m, 2H) 6.95-7.01 (m, 2H)

(98b) 2-fluoro-5-(2-fluoroethoxy)-3-triisopropylsilanyloxybenzaldehyde

[Chemical Formula 285]

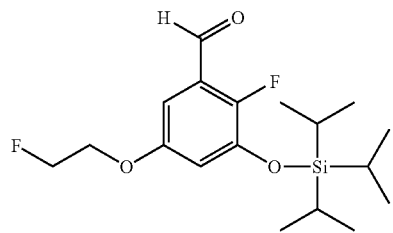

The same procedure was carried out as in Examples (3a)-(3b), except that 1-fluoro-4-(2-fluoroethoxy)benzene was used instead of the 1-fluoro-4-methoxybenzene in Example (3a), to give the title compound as a colorless oil.

$^1$H-NMR (CDCl$_3$) δ 1.11 (d, J=7.2 Hz, 18H) 1.24-1.34 (m, 3H) 4.14-4.23 (m, 2H) 4.68-4.81 (m, 2H) 6.81-6.87 (m, 2H) 10.32 (s, 1H)

(98c) {2-[2-fluoro-3-hydroxy-5-(2-fluoroethoxy)phenyl]-2-[4-(5-methyl-[1,2,4]oxadiazol-3-yl)phenylimino]-1-methylsulfanylethylidene}carbamic acid methyl ester

[Chemical Formula 286]

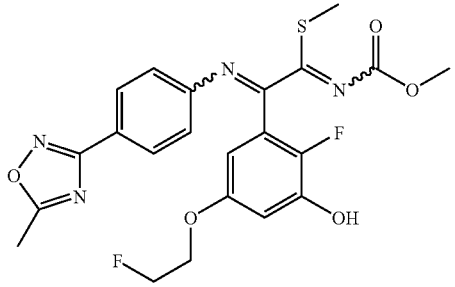

The same procedure was carried out as in Examples (3c)-(3d), except that 2-fluoro-5-(2-fluoroethoxy)-3-triisopropylsilanyloxybenzaldehyde was used instead of the 2-fluoro-5-methoxy-3-triisopropylsilanyloxybenzaldehyde in Example (3c), to give the title compound (isomeric mixture).

$^1$H-NMR (CDCl$_3$) Two main isomers:

δ 2.34 (s, 3H) 2.66 (s, 3H) 3.61 (s, 3H) 4.17-4.28 (m, 2H) 4.67-4.81 (m, 2H) 5.34 (d, J=5.2 Hz, 1H) 6.79 (dd, J=3.2, 6.4 Hz, 1H) 6.96 (dd, J=3.2, 4.8 Hz, 1H) 7.08-7.13 (m, 2H) 8.01-8.05 (m, 2H)

δ 2.47 (s, 3H) 2.63 (s, 3H) 3.63 (s, 3H) 3.99-4.08 (m, 2H) 4.59-4.74 (m, 2H) 5.20 (d, J=4.0 Hz, 1H) 6.24 (dd, J=3.2, 4.0 Hz, 1H) 6.58 (dd, J=3.2, 7.2 Hz, 1H) 6.81-6.85 (m, 2H) 7.88-7.92 (m, 2H)

(98d) 4-{[(R) and (S)-[2-fluoro-3,5-bis-(2-fluoroethoxy)phenyl]-(5-oxo-1-pyrimidin-2-yl-4,5-dihydro-1H-[1,2,4]triazol-3-yl)methyl]amino}benzamidine acetate

[Chemical Formula 287]

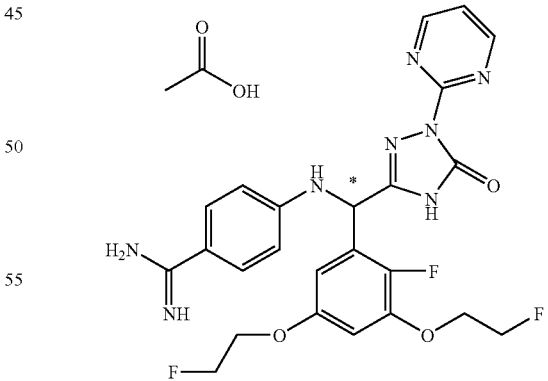

The same procedure was carried out as in Examples (3e)-(3h), except that {2-[2-fluoro-3-hydroxy-5-(2-fluoroethoxy)phenyl]-2-[4-(5-methyl-[1,2,4]oxadiazol-3-yl)phenylimino]-1-methylsulfanylethylidene}carbamic acid methyl ester was used instead of the [2-(2-fluoro-3-hydroxy-5-methoxy-phenyl)-2-[4-(5-methyl-[1,2,4]oxadiazol-3-yl)-phenylimino]-1-methylsulfanylethylidene]carbamic acid methyl ester in Example (3e), to give the first eluting enantiomer of the title compound as a white solid.

$^1$H-NMR (CD$_3$OD) δ 1.91 (s, 3H) 4.06-4.32 (m, 4H) 4.55-4.80 (m, 4H) 5.93 (s, 1H) 6.67-6.72 (m, 2H) 6.85 (d, J=8.8 Hz, 2H) 7.25-7.30 (m, 1H) 7.60 (d, J=8.8 Hz, 2H) 8.75 (d, J=4.4 Hz, 2H)

HPLC retention time: 13 min

Example 99

4-{[(R) and (S)-[3-(2,2-difluoroethoxy)-2-fluoro-5-methoxyphenyl]-(5-oxo-1-pyrimidin-2-yl-4,5-dihydro-1H-[1,2,4]triazol-3-yl)methyl]amino}benzamidine acetate

[Chemical Formula 288]

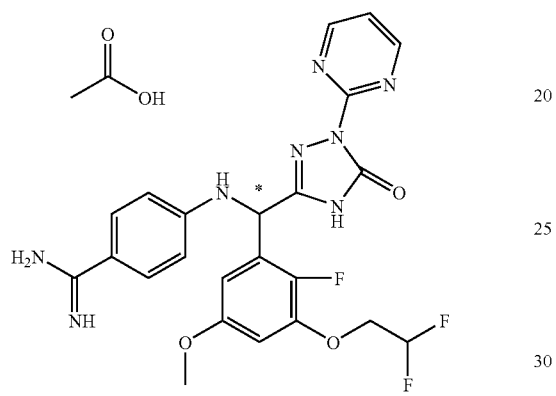

The same procedure was carried out as in Examples (3e)-(3h), except that 1,1-difluoro-2-iodoethane was used instead of the 1-fluoro-2-iodoethane in Example (3e), to give the first eluting enantiomer of the title compound as a white solid.

$^1$H-NMR (CD$_3$OD) δ 1.91 (s, 3H) 3.71 (s, 3H) 4.29 (dt, J=4.0, 13.6 Hz, 2H) 5.96 (s, 1H) 6.18 (tt, J=4.0, 54.8 Hz, 1H) 6.67 (dd, J=2.8, 6.8 Hz, 1H) 6.72 (d, J=2.8, 4.8 Hz, 1H) 6.86 (d, J=8.8 Hz, 2H) 7.31 (t, J=4.8 Hz, 1H) 7.62 (d, J=8.8 Hz, 2H) 8.76 (d, J=4.8 Hz, 2H)

HPLC retention time: 12 min

Example 100

4-{[(R) and (S)-[2-fluoro-3-(2-fluoroethoxy)-5-methoxyphenyl]-(5-oxo-1-pyrazin-2-yl-4,5-dihydro-1H-[1,2,4]triazol-3-yl)methyl]amino}benzamidine acetate

[Chemical Formula 289]

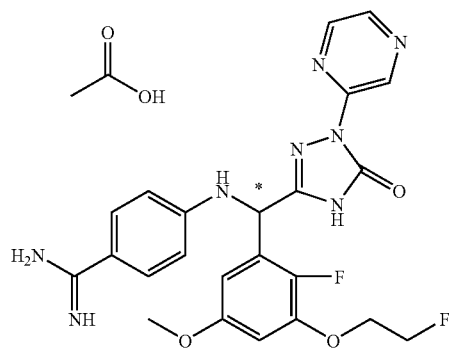

The same procedure was carried out as in Examples (3f)-(3h), except that 2-hydrazinopyrazine [CAS No. 54608-52-5] was used instead of the 2-hydrazinopyrimidine in Example (3f), to give the first eluting enantiomer of the title compound as a white solid.

$^1$H-NMR (CD$_3$OD) δ 1.92 (s, 3H) 3.70 (s, 3H) 4.21-4.31 (m, 2H) 4.65-4.79 (m, 2H) 5.93 (s, 1H) 6.61 (dd, J=2.8, 6.8 Hz, 1H) 6.69 (d, J=2.8, 4.8 Hz, 1H) 6.85 (d, J=8.8 Hz, 2H) 7.60 (d, J=8.8 Hz, 2H) 8.37 (d, J=2.4 Hz, 1H) 8.45 (s, 1H) 9.44 (s, 1H)

HPLC retention time: 25 min (Column name: SUMICHIRAL OA-2500, 20 mmφ×25 cm, Manufacturer: Sumika Chemical Analysis Service, Ltd., Mobile phase: 0.05 M ammonium acetate-methanol solution, Elution rate: 5 ml/min)

Example 101

4-{[(R) and (S)-(2-fluoro-4,5-dimethoxyphenyl)-(5-oxo-1-pyrazin-2-yl-4,5-dihydro-1H-[1,2,4]triazol-3-yl)methyl]amino}benzamidine acetate

[Chemical Formula 290]

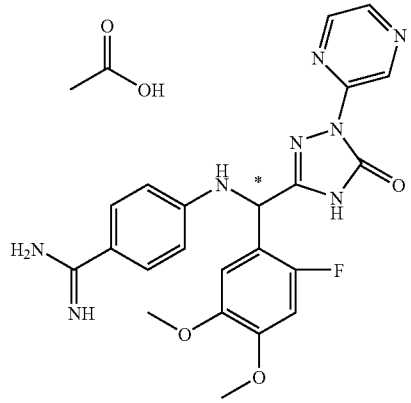

The same procedure was carried out as in Examples (119a)-(119b), except that 2-hydrazinopyrazine [CAS No. 54608-52-5] was used instead of the 3-hydrazinopyridazine hydrochloride in Example (119a), to give the first eluting enantiomer of the title compound as a white solid.

$^1$H-NMR (CD$_3$OD) δ 1.92 (s, 3H) 3.74 (s, 3H) 3.81 (s, 3H) 5.90 (s, 1H) 6.82 (d, J=11.6 Hz, 1H) 6.86 (d, J=8.8 Hz, 2H) 7.11 (d, J=6.8 Hz, 1H) 7.60 (d, J=8.8 Hz, 2H) 8.39 (d, J=2.8 Hz, 1H) 8.46 (m, 1H) 9.41 (d, J=1.2 Hz, 1H)

HPLC retention time: 27 min (Column name: SUMICHIRAL OA-2500, 20 mmφ×25 cm, Manufacturer: Sumika Chemical Analysis Service, Ltd., Mobile phase: 0.05 M ammonium acetate-methanol solution, Elution rate: 5 ml/min)

Example 102

4-{[(R) and (S)-(8-methoxy-4H-benzo[1,3]dioxin-6-yl)-(5-oxo-1-pyrazin-2-yl-4,5-dihydro-1H-[1,2,4]triazol-3-yl)methyl]amino}benzamidine acetate

[Chemical Formula 291]

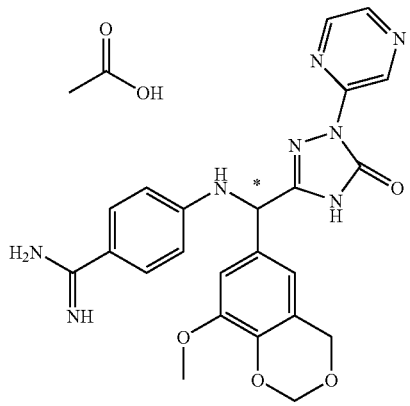

The same procedure was carried out as in Examples (21i)-(21k), except that 2-hydrazinopyrazine was used instead of the 2-hydrazinopyrimidine in Example (21i), to give the first eluting enantiomer of the title compound as a white solid.

$^1$H-NMR (CD$_3$OD) δ 1.92 (s, 3H) 3.82 (s, 3H) 4.86 (s, 2H) 5.22 (s, 2H) 5.53 (s, 1H) 6.82 (s, 1H) 6.85 (d, J=8.8 Hz, 2H) 7.06 (s, 1H) 7.59 (d, J=8.8 Hz, 2H) 8.38 (d, J=2.4 Hz, 1H) 8.47 (s, 1H) 9.45 (s, 1H)

HPLC retention time: 16 min

Example 103

4-{[(R) and (S)-(2-fluoro-3-fluoromethoxy-5-methoxyphenyl)-(5-oxo-1-pyrimidin-2-yl-4,5-dihydro-1H-[1,2,4]triazol-3-yl)methyl]amino}benzamidine acetate

[Chemical Formula 292]

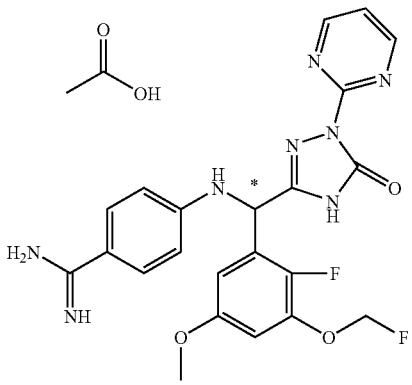

The same procedure was carried out as in Examples (3e)-(3h), except that toluene-4-sulfonic acid fluoromethyl ester [CAS No. 114435-86-8] was used instead of the 1-fluoro-2-iodoethane in Example (3e), to give the first eluting enantiomer of the title compound as a white solid.

$^1$H-NMR (CD$_3$OD) δ 1.91 (s, 3H) 3.72 (s, 3H) 5.75 (d, J=54.0 Hz, 2H) 5.93 (s, 1H) 6.76 (dd, J=2.8, 6.4 Hz, 1H) 6.82-6.86 (m, 1H) 6.85 (d, J=8.8 Hz, 2H) 7.27 (t, J=4.8 Hz, 1H) 7.61 (d, J=8.8 Hz, 2H) 8.75 (d, J=4.8 Hz, 2H)

HPLC retention time: 14 min

Example 104

4-{[(R) and (S)-(3-fluoromethoxy-5-methoxyphenyl)-(5-oxo-1-pyrimidin-2-yl-4,5-dihydro-1H-[1,2,4]triazol-3-yl)methyl]amino}benzamidine acetate

[Chemical Formula 293]

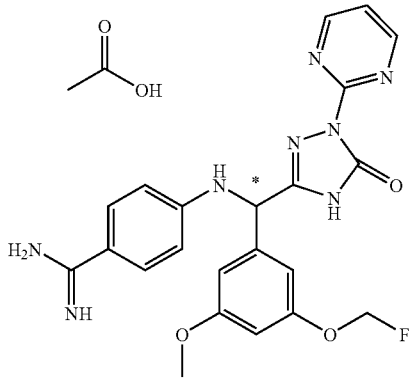

The same procedure was carried out as in Examples (6a)-(6b), except that toluene-4-sulfonic acid fluoromethyl ester was used instead of the 1-bromo-2-methoxyethane in Example (6a), to give the first eluting enantiomer of the title compound as a white solid.

$^1$H-NMR (CD$_3$OD) δ 1.92 (s, 3H) 3.77 (s, 3H) 5.61 (s, 1H) 5.71 (d, J=54.4 Hz, 2H) 6.59 (t, J=2.4 Hz, 1H) 6.86 (d, J=9.2 Hz, 2H) 6.89-6.90 (m, 2H) 7.30 (t, J=4.8 Hz, 1H) 7.60 (d, J=9.2 Hz, 2H) 8.77 (d, J=4.8 Hz, 2H)

HPLC retention time: 14 min

Example 105

2-{3-[(4-carbamimidoyl-phenylamino)-(4-dimethylcarbamoylmethoxy-3-methoxyphenyl)methyl]-5-oxo-4,5-dihydro-1H-[1,2,4]triazol-1-yl}benzamide trifluoroacetate (105a) {2-(4-dimethylcarbamoylmethoxy-3-methoxyphenyl)-2-[4-(5-methyl-[1,2,4]oxadiazol-3-yl)phenylimino]-1-methylsulfanylethylidene}carbamic acid methyl ester

[Chemical Formula 294]

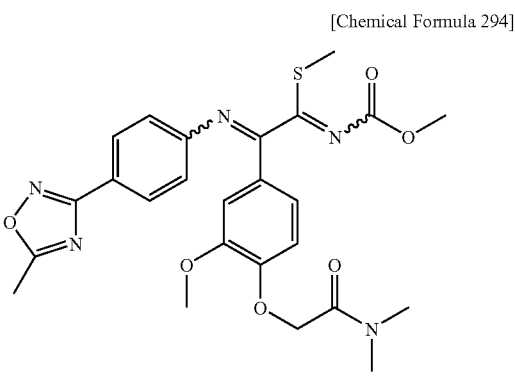

The same procedure was carried out as in Example (18e), except that 2-chloro-N,N-dimethylacetamide was used instead of the iodoethane in Example (18e), to give the title compound.

(105b) 2-{3-[(4-carbamimidoyl-phenylamino)-(4-dimethylcarbamoylmethoxy-3-methoxy-phenyl)methyl]-5-oxo-4,5-dihydro-1H-[1,2,4]triazol-1-yl}benzoic acid trifluoroacetate

[Chemical Formula 295]

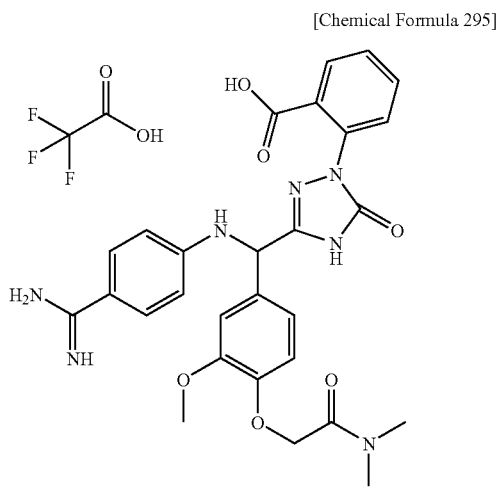

The same procedure was carried out as in Example (16b), except that {2-(4-dimethylcarbamoylmethoxy-3-methoxyphenyl)-2-[4-(5-methyl-[1,2,4]oxadiazol-3-yl)phenylimino]-1-methylsulfanylethylidene}carbamic acid methyl ester was used instead of the {2-(4-cyanomethoxy-3-methoxyphenyl)-2-[4-(5-methyl-[1,2,4]oxadiazol-3-yl)phenylimino]-1-methylsulfanylethylidene}carbamic acid methyl ester, to give the title compound.
Mass spectrum (ESI) m/z: 560 (M+H)$^+$

(105c) 2-{3-[(4-carbamimidoyl-phenylamino)-(4-dimethylcarbamoylmethoxy-3-methoxy-phenyl)methyl]-5-oxo-4,5-dihydro-1H-[1,2,4]triazol-1-yl}benzamide trifluoroacetate

[Chemical Formula 296]

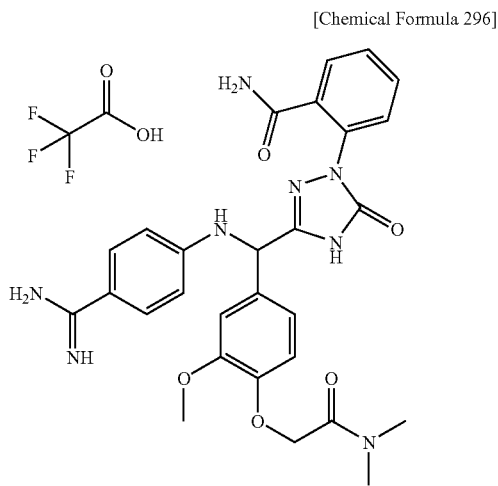

After adding 20.4 mg of BOP reagent, 5.3 mg of 1-hydroxybenzotriazole, 20.5 μl of N,N-diisopropylethylamine and 3.1 mg of ammonium chloride to a solution of 11.5 mg of 2-{3-[(4-carbamimidoyl-phenylamino)-(4-dimethylcarbam-oylmethoxy-3-methoxy-phenyl)methyl]-5-oxo-4,5-dihydro-1H-[1,2,4]triazol-1-yl}benzoic acid trifluoroacetate in 1 ml of DMF, the mixture was stirred at room temperature for 22 hours. After filtering the reaction mixture, it was purified by reverse-phase high performance liquid chromatography (acetonitrile-water, 0.1% trifluoroacetic acid) to give 4.3 mg of the title compound.
$^1$H-NMR (CD$_3$OD) δ 2.96 (s, 3H) 3.09 (s, 3H) 3.87 (s, 3H) 4.81 (s, 2H) 5.63 (s, 1H) 6.87 (d, J=8.8 Hz, 2H) 6.94 (d, J=8.4 Hz, 1H) 7.10 (dd, J=8.4, 2.4 Hz, 1H) 7.17 (d, J=2.4 Hz, 1H) 7.44-7.68 (m, 5H) 8.28 (br.s, 1H) 8.79 (br.s, 1H)
Mass spectrum (ESI) m/z: 559 (M+H)$^+$

Example 106

2-{3[(4-carbamimidoylphenylamino)-phenyl-methyl]-5-oxo-4,5-dihydro-1H-[1,2,4]triazol-1-yl}benzoic acid trifluoroacetate

[Chemical Formula 297]

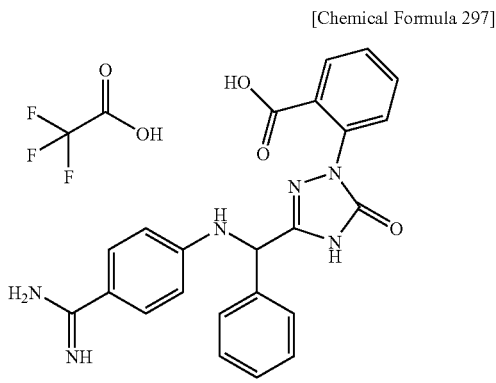

The same procedure was carried out as in Examples (1a)-(1g), except that benzaldehyde was used instead of the 2-fluoro-4,5-dimethoxybenzaldehyde in Example (1a), to give the title compound.
$^1$H-NMR (CD$_3$OD) δ 5.72 (s, 1H) 6.88 (d, J=8.8 Hz, 2H) 7.26-7.34 (m, 8H) 7.63 (d, J=8.8 Hz, 2H) 7.95 (d, J=8.0, 1.6 Hz, 1H)

Example 107

4-({[1-(2-aminophenyl)-5-oxo-4,5-dihydro-1H-[1,2,4]triazol-3-yl]-(2-fluoro-4,5-dimethoxyphenyl)methyl}amino)benzamidine trifluoroacetate

[Chemical Formula 298]

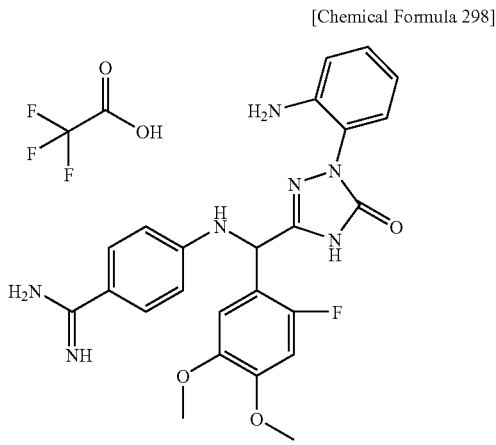

The same procedure was carried out as in Examples (135h)-(135i), except that 2-(3-{(2-fluoro-4,5-dimethoxyphenyl)-[4-(5-methyl-[1,2,4]oxadiazol-3-yl)phenylamino]

methyl}-5-oxo-4,5-dihydro-1H-[1,2,4]triazol-1-yl)benzoic acid (Example (1f)) was used instead of the 2-(3-{(3-dimethylcarbamoylmethoxy-5-ethyl-2-fluorophenyl)-[4-(5-methyl-[1,2,4]oxadiazol-3-yl)phenylamino]methyl}-5-oxo-4,5-dihydro-1H-[1,2,4]triazol-1-yl)benzoic acid in Example (135h), to give 2-(2-aminophenyl)-5-{(2-fluoro-4,5-dimethoxyphenyl)-[4-(5-methyl-[1,2,4]oxadiazol-3-yl)phenylamino]methyl}-2,4-dihydro-[1,2,4]triazol-3-one.

The same procedure was carried out as in Example (1g), except that this compound was used instead of the 2-(3-{(2-fluoro-4,5-dimethoxyphenyl)-[4-(5-methyl-[1,2,4]oxadiazol-3-yl)phenylamino]methyl}-5-oxo-4,5-dihydro-1H-[1,2,4]triazol-1-yl)benzoic acid, to give the title compound.

$^1$H-NMR (CD$_3$OD) δ 3.78 (s, 3H) 3.84 (s, 3H) 5.98 (s, 1H) 6.85-7.37 (m, 6H) 6.87 (d, J=8.8 Hz, 2H) 7.64 (d, J=8.8 Hz, 2H)

Mass spectrum (ESI) m/z: 478 (M+H)$^+$

Example 108

(R) and (S)-2-{3-[(4-carbamimidoylphenylamino)-(2-fluoro-4,5-dimethoxyphenyl)methyl]-5-oxo-4,5-dihydro-[1,2,4]triazol-1-yl}benzoic acid methyl ester acetate (108a) 2-{3-[(4-carbamimidoylphenylamino)-(2-fluoro-4,5-dimethoxyphenyl)methyl]-5-oxo-4,5-dihydro-[1,2,4]triazol-1-yl}benzoic acid methyl ester trifluoroacetate

[Chemical Formula 299]

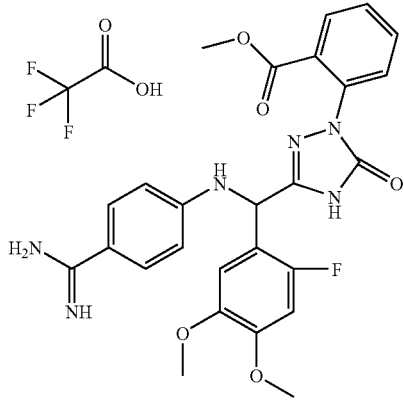

To a solution of 150 mg of 2-(3-{(2-fluoro-4,5-dimethoxyphenyl)-[4-(5-methyl-[1,2,4]oxadiazol-3-yl)phenylamino]methyl}-5-oxo-4,5-dihydro-1H-[1,2,4]triazol-1-yl)benzoic acid (Example (1f)) in 4.5 ml of a THF:methanol=2:1 mixed solvent there was added 150 μl of trimethylsilyldiazomethane (2.0 M, hexane solution) in an ice bath under a nitrogen atmosphere, and the mixture was stirred for 14 hours while raising the temperature to room temperature. Next, 70 μl of trimethylsilyldiazomethane (2.0 M, hexane solution) was added in an ice bath and the mixture was stirred for 90 minutes. After adding 5 drops of acetic acid, the reaction mixture was concentrated under reduced pressure. To a solution of the residue in 4.5 ml of a methanol:water:acetic acid=1:1:1 mixed solvent there was added 100 mg of iron powder, and the mixture was stirred overnight at 60° C. under a nitrogen atmosphere. After filtering the reaction mixture, it was purified by reverse-phase high performance liquid chromatography (acetonitrile-water, 0.1% trifluoroacetic acid) to give 46 mg of the title compound.

$^1$H-NMR (CD$_3$OD) δ 3.76 (s, 3H) 3.85 (s, 3H) 3.88 (s, 3H) 5.99 (s, 1H) 6.92 (d, J=8.8 Hz, 2H) 6.93 (m, 1H) 7.10 (d, J=6.8 Hz, 1H) 7.68 (d, J=8.8 Hz, 2H) 7.52-7.70 (m, 3H) 7.90 (dd, J=7.6, 1.6 Hz, 1H)

Mass spectrum (ESI) m/z: 521 (M+H)$^+$ (108b) (R) and (S)-2-{3-[(4-carbamimidoylphenylamino)-(2-fluoro-4,5-dimethoxyphenyl)methyl]-5-oxo-4,5-dihydro-[1,2,4]triazol-1-yl}benzoic acid methyl ester acetate

[Chemical Formula 300]

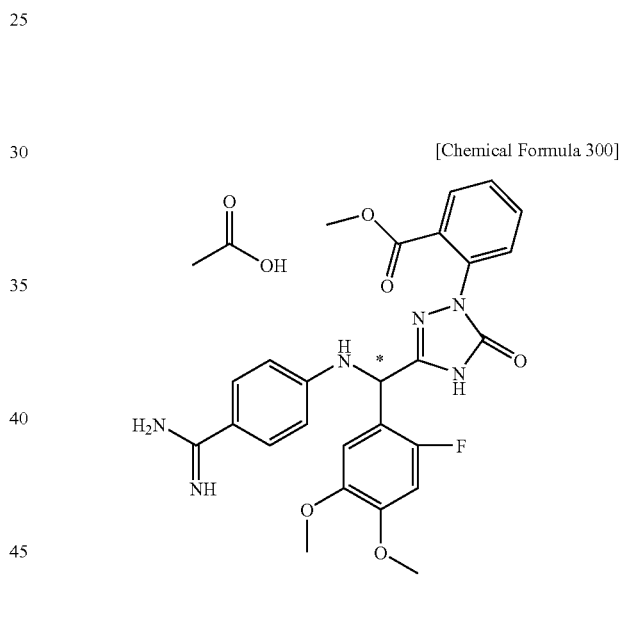

A CHIRALPAK™ AD (column size: 2 cmφ×25 cm, Manufacturer: Daicel Chemical Industries, Ltd., Mobile phase: 2-propanol/hexane=1/4, 0.1% trifluoroacetic acid, Elution rate: 9 ml/min) was used for optical resolution of 12 mg of 2-{3-[(4-carbamimidoylphenylamino)-(2-fluoro-4,5-dimethoxyphenyl)methyl]-5-oxo-4,5-dihydro-[1,2,4]triazol-1-yl}benzoic acid methyl ester trifluoroacetate (retention time for the first eluting enantiomer: 30 min, retention time for the second eluting enantiomer: 50 min). Triethylamine was added to the obtained second eluting enantiomer and the mixture was concentrated under reduced pressure. The residue was purified by reverse-phase high performance liquid chromatography (acetonitrile-water, 0.1% acetic acid) to give the second eluting enantiomer (4.7 mg) of the title compound.

Example 109

(R) and (S)-2-{3-[(4-carbamimidoylphenylamino)-(2-fluoro-4,5-dimethoxyphenyl)methyl]-5-oxo-4,5-dihydro-1H-[1,2,4]triazol-1-yl}benzamide acetate (109a) 2-{3-[(4-carbamimidoylphenylamino)-(2-fluoro-4,5-dimethoxyphenyl)methyl]-5-oxo-4,5-dihydro-1H-[1,2,4]triazol-1-yl}benzamide trifluoroacetate

[Chemical Formula 301]

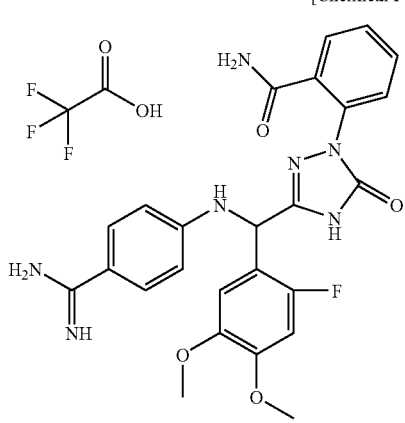

After adding 152 mg of BOP reagent, 39.5 mg of 1-hydroxybenzotriazole, 153 µl of N,N-diisopropylethylamine and 23.5 mg of ammonium chloride to a solution of 80 mg of 2-(3-{(2-fluoro-4,5-dimethoxyphenyl)-[4-(5-methyl-[1,2,4]oxadiazol-3-yl)phenylamino]methyl}-5-oxo-4,5-dihydro-1H-[1,2,4]triazol-1-yl)benzoic acid (Example (1f)) in 3 ml of DMF, the mixture was stirred at room temperature for 17 hours. Water was added to the reaction mixture, extraction was performed with ethyl acetate, and the organic layer was concentrated under reduced pressure. To a solution of the residue in 4.5 ml of a methanol:water:acetic acid=1:1:1 mixed solvent there was added 80 mg of iron powder, and the mixture was stirred at 55° C. for 14 hours under a nitrogen atmosphere. After filtering the reaction mixture, it was purified by reverse-phase high performance liquid chromatography (acetonitrile-water, 0.1% trifluoroacetic acid) to give 41 mg of the title compound.

$^1$H-NMR (CD$_3$OD) δ 3.84 (s, 3H) 3.87 (s, 3H) 5.97 (s, 1H) 6.90 (d, J=11.6 Hz, 1H) 6.91 (d, J=8.8 Hz, 2H) 7.10 (d, J=6.8 Hz, 1H) 7.68 (d, J=8.8 Hz, 2H) 7.47-7.70 (m, 4H)

Mass spectrum (ESI) m/z: 506 (M+H)$^+$ (109b) (R) and (S)-2-{3-[(4-carbamimidoylphenylamino)-(2-fluoro-4,5-dimethoxyphenyl)methyl]-5-oxo-4,5-dihydro-1H-[1,2,4]triazol-1-yl}benzamide acetate

[Chemical Formula 302]

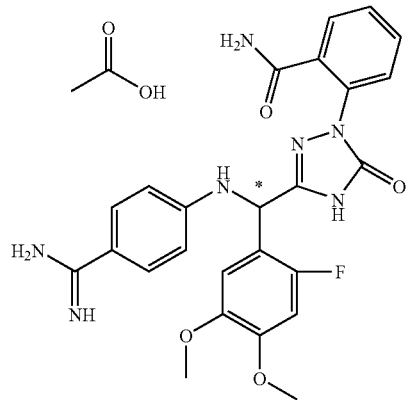

A SUMICHIRAL OA-2500 column was used for optical resolution of 58 mg of 2-{3-[(4-carbamimidoylphenylamino)-(2-fluoro-4,5-dimethoxyphenyl)methyl]-5-oxo-4,5-dihydro-[1,2,4]triazol-1-yl}benzamide trifluoroacetate, and the first eluting enantiomer (13.1 mg) of the title compound was obtained as a white solid.

$^1$H-NMR (CD$_3$OD) δ 1.90 (s, 3H) 3.79 (s, 3H) 3.83 (s, 3H) 5.89 (s, 1H) 6.84 (d, J=11.6 Hz, 1H) 6.85 (d, J=8.8 Hz, 2H) 7.07 (d, J=6.8 Hz, 1H) 7.62 (d, J=8.8 Hz, 2H) 7.44-7.68 (m, 4H)

HPLC retention time: 10 min (Column name: SUMICHIRAL OA-2500, 30 mmφ×25 cm, Manufacturer: Sumika Chemical Analysis Service, Ltd., Mobile phase: 0.05 M ammonium acetate-methanol solution, Elution rate: 15 ml/min)

Example 110

(R) and (S)-2-{3-[(4-carbamimidoylphenylamino)-(3,4-dimethoxyphenyl)methyl]-5-oxo-4,5-dihydro-1H-[1,2,4]triazol-1-yl}benzamide acetate

[Chemical Formula 303]

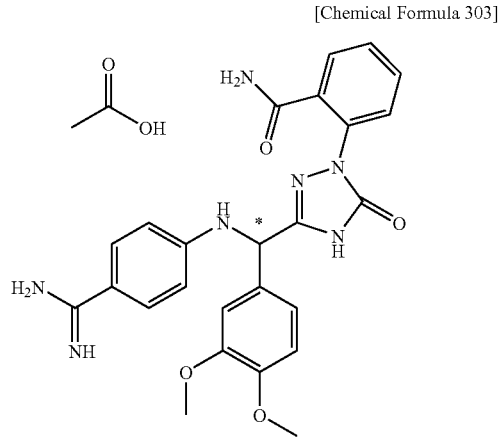

The same procedure was carried out as in Examples (109a)-(109b), except that 2-(3-{(3,4-dimethoxyphenyl)-[4-(5-methyl-[1,2,4]oxadiazol-3-yl)phenylamino]methyl}-5-oxo-4,5-dihydro-1H-[1,2,4]triazol-1-yl)benzoic acid (Example (36f)) was used instead of the 2-(3-{(2-fluoro-4,5-dimethoxyphenyl)-[4-(5-methyl-[1,2,4]oxadiazol-3-yl)phenylamino]methyl}-5-oxo-4,5-dihydro-1H-[1,2,4]triazol-1-yl)benzoic acid in Example (109a), to give the first eluting enantiomer of the title compound.

$^1$H-NMR (CD$_3$OD) δ 1.90 (s, 3H) 3.83 (s, 3H) 3.85 (s, 3H) 5.60 (s, 1H) 6.87 (d, J=8.8 Hz, 2H) 6.98 (d, J=8.4 Hz, 1H) 7.09 (dd, J=8.4, 2.4 Hz, 1H) 7.14 (d, J=2.4 Hz, 1H) 7.62 (d, J=8.8 Hz, 2H) 7.46-7.68 (m, 4H)

HPLC retention time: 10 min (Column name: SUMICHIRAL OA-2500, 30 mmϕ×25 cm, Manufacturer: Sumika Chemical Analysis Service, Ltd., Mobile phase: 0.05 M ammonium acetate-methanol solution, Elution rate: 15 ml/min)

Example 111

4-{[(R) and (S)-(2-fluoro-4,5-dimethoxyphenyl)-(5-oxo-1-pyrimidin-2-yl-4,5-dihydro-1H-[1,2,4]triazol-3-yl)methyl]amino}benzamidine acetate

[Chemical Formula 304]

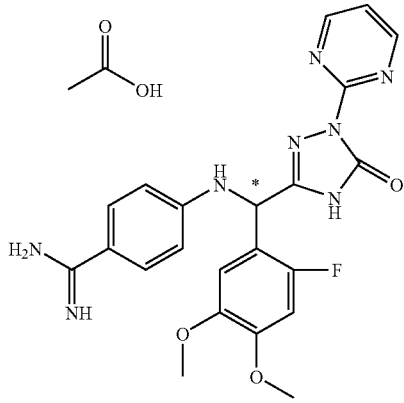

The same procedure was carried out as in Examples (17f)-(17g), except that [2-(2-fluoro-4,5-dimethoxyphenyl)-2-[4-(5-methyl-[1,2,4]oxadiazol-3-yl)phenylimino]-1-methylsulfanylethylidene]carbamic acid methyl ester (Example (1f)) was used instead of the {2-(3-ethoxy-4-methoxyphenyl)-2-[4-(5-methyl-[1,2,4]oxadiazol-3-yl)phenylimino]-1-methylsulfanylethylidene}carbamic acid methyl ester in Example (17f), to give 5-{(2-fluoro-4,5-dimethoxyphenyl)-[4-(5-methyl-[1,2,4]oxadiazol-3-yl)phenylamino]methyl}-2-pyrimidin-2-yl-2,4-dihydro-[1,2,4]triazol-3-one. A 40 mg portion of this compound was optically resolved using a CHIRALPAK™ AD-H (column size: 2 cmϕ×25 cm, Manufacturer: Daicel Chemical Industries, Ltd., Mobile phase: 2-propanol/hexane=2/3, 0.1% trifluoroacetic acid, Elution rate: 9 ml/min) (retention time for the first eluting enantiomer: 19 min, retention time for the second eluting enantiomer: 21 min). Triethylamine was added to the obtained first eluting enantiomer and the mixture was concentrated under reduced pressure.

To a solution of the residue in 2.4 ml of a methanol:water:acetic acid=1:1:1 mixed solvent there was added 20 mg of iron powder, and the mixture was stirred at 60° C. for 14 hours under a nitrogen atmosphere. After filtering the reaction mixture, it was purified by reverse-phase high performance liquid chromatography (acetonitrile-water, 0.1% acetic acid) to give one optical isomer (1.94 mg) of the title compound.

$^1$H-NMR (CD$_3$OD) δ 1.93 (s, 3H) 3.75 (s, 3H) 3.82 (s, 3H) 5.95 (s, 1H) 6.82-6.89 (m, 3H) 7.07 (d, J=6.8 Hz, 1H) 7.63 (t, J=5.2 Hz, 1H) 7.62 (d, J=8.8 Hz, 2H) 8.78 (d, J=5.2 Hz, 2H)

Mass spectrum (ESI) m/z: 465 (M+H)

Example 112

4-({(4-methoxy-3,5-dimethylphenyl)-[1-(2-methoxyphenyl)-5-oxo-4,5-dihydro-1H-[1,2,4]triazol-3-yl]methyl}amino)benzamidine acetate

[Chemical Formula 305]

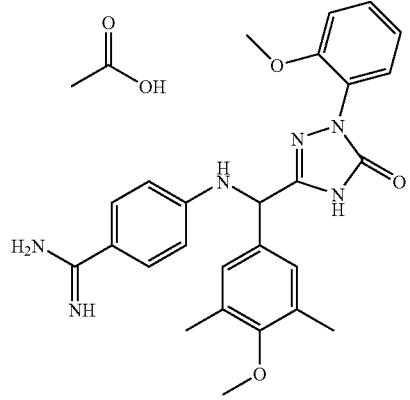

The same procedure was carried out as in Examples (1a)-(1g), except that 3,5-dimethyl-4-methoxybenzaldehyde [CAS No. 39250-90-3] was used instead of the 2-fluoro-4,5-dimethoxybenzaldehyde in Example (1a), and 2-methoxyphenylhydrazine hydrochloride was used instead of the 2-hydrazinobenzoic acid hydrochloride in Example (1e).

$^1$H-NMR (CD$_3$OD) δ 1.93 (s, 3H) 2.29 (s, 6H) 3.71 (s, 3H) 3.81 (s, 3H) 5.55 (s, 1H) 6.84 (d, J=8.8 Hz, 2H) 7.61 (td, J=7.6, 1.2 Hz, 1H) 7.14 (dd, J=8.4, 1.2 Hz, 1H) 7.17 (s, 2H) 7.31 (dd, J=7.6, 2.0 Hz, 1H) 7.43 (ddd, J=8.4, 7.6, 2.0 Hz, 1H) 7.63 (d, J=8.8 Hz, 2H)

Mass spectrum (ESI) m/z: 473 (M+H)$^+$

Example 113

(R) and (S)-4-{[(2-fluoro-5-(2-fluoroethoxy)-4-methoxyphenyl)-(5-oxo-1-pyrimidin-2-yl-4,5-dihydro-1H[1,2,4]triazol-3-yl)methyl]amino}benzamidine acetate

[Chemical Formula 306]

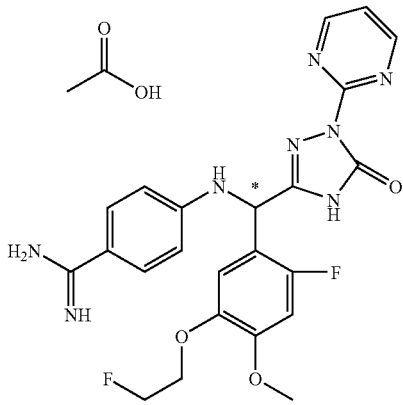

The same procedure was carried out as in Examples (17e)-(17g), except that {2-(2-fluoro-5-hydroxy-4-methoxyphenyl)-2-[4-(5-methyl-[1,2,4]oxadiazol-3-yl)phenylimino]-1-methylsulfanylethylidene}carbamic acid methyl ester (Example (120c)) and 1-fluoro-2-iodoethane were used instead of respectively the {2-(3-hydroxy-4-methoxyphenyl)-2-[4-(5-methyl-[1,2,4]oxadiazol-3-yl)phenylimino]-1-methylsulfanylethylidene}carbamic acid methyl ester in Example (17e) and iodoethane in Example (17e), to give the first eluting enantiomer of the title compound.

$^1$H-NMR (CD$_3$OD) δ 1.92 (s, 3H) 3.81 (s, 3H) 4.10 (dm, J=28.8 Hz, 2H) 4.60 (dm, J=47.6 Hz, 2H) 5.91 (s, 1H) 6.83 (d, J=11.6 Hz, 1H) 6.86 (d, J=8.8 Hz, 2H) 7.13 (d, J=7.2 Hz, 1H) 7.30 (t, J=4.8 Hz, 1H) 7.60 (d, J=8.8 Hz, 2H) 8.75 (d, J=4.8 Hz, 2H)

Mass spectrum (ESI) m/z: 497 (M+H)$^+$

Example 114

4-{[(4-cyanomethoxy-3-ethoxyphenyl)-(5-oxo-1-pyrimidin-2-yl-4,5-dihydro-1H-[1,2,4]triazol-3-yl)methyl]amino}benzamidine trifluoroacetate (114a) {2-(4-hydroxy-3-ethoxyphenyl)-2-[4-(5-methyl-[1,2,4]oxadiazol-3-yl)phenylimino]-1-methylsulfanylethylidene}carbamic acid methyl ester

[Chemical Formula 307]

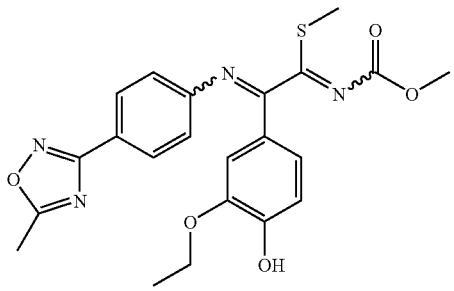

The same procedure was carried out as in Examples (18a)-(18d), except that 4-t-butyldimethylsilanyloxy-3-ethoxybenzaldehyde [CAS No. 581800-64-8] was used instead of the 4-t-butyldimethylsilanyloxy-3-5 methoxybenzaldehyde in Example (18a), to give the title compound.

(114b) 4-{[(4-cyanomethoxy-3-ethoxyphenyl)-(5-oxo-1-pyrimidin-2-yl-4,5-dihydro-1H-[1,2,4]triazol-3-yl)methyl]amino}benzamidine trifluoroacetate

[Chemical Formula 308]

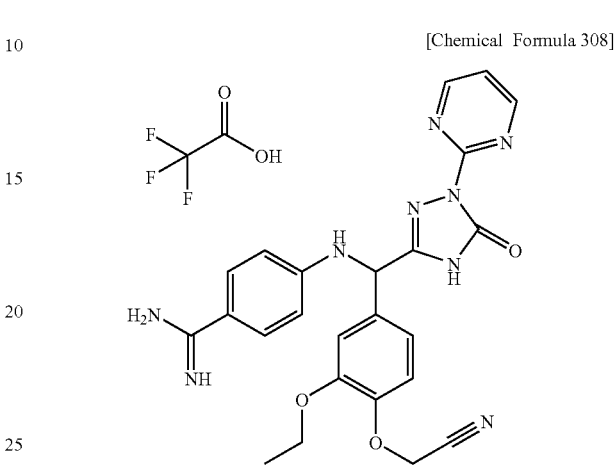

The same procedure was carried out as in Examples (16a)-(16b), except that {2-(4-hydroxy-3-ethoxyphenyl)-2-[4-(5-methyl-[1,2,4]oxadiazol-3-yl)phenylamino]-1-methylsulfanylethylidene}carbamic acid methyl ester was used instead of the {2-(4-hydroxy-3-methoxyphenyl)-2-[4-(5-methyl-[1,2,4]oxadiazol-3-yl)phenylamino]-1-methylsulfanylethylidene}carbamic acid methyl ester in Example (16a), to give the title compound.

$^1$H-NMR (CD$_3$OD) δ 1.41 (t, J=7.2 Hz, 3H) 4.10 (q, J=7.2 Hz, 2H) 4.96 (s, 2H) 5.71 (s, 1H) 6.88 (d, J=9.2 Hz, 2H) 7.13 (br.s, 2H) 7.24 (br.s, 1H) 7.38 (t, J=4.8 Hz, 1H) 7.62 (d, J=9.2 Hz, 2H) 8.80 (d, J=4.8 Hz, 2H)

Mass spectrum (ESI) m/z: 486 (M+H)$^+$

Example 115

(R) and (S)-4-{[(5-ethoxy-2-fluoro-4-methoxyphenyl)-(5-oxo-1-pyrimidin-2-yl-4,5-dihydro-1H-[1,2,4]triazol-3-yl)methyl]amino}benzamidine acetate (115a) 5-ethoxy-2-fluoro-4-methoxybenzaldehyde

[Chemical Formula 309]

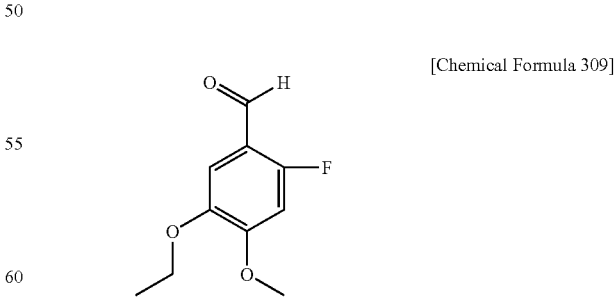

To a solution of 2.62 ml of morpholine in 50 ml of THF there was added 11.2 ml of n-butyllithium (2.71 M, hexane solution) at −78° C. under a nitrogen atmosphere, and the mixture was stirred at −40° C. for 30 minutes. To this solution there was added dropwise a solution of 6.5 g of 2-bromo-5- ethoxy-4-methoxybenzaldehyde [CAS No. 56517-30-7] in 40 ml of THF at −78° C., and the mixture was stirred at −78° C. for 1 hour. After further adding 14.8 ml of n-butyllithium (2.71 M, hexane solution) at −78° C., the mixture was stirred at −78° C. for 40 minutes, and then a solution of 15.8 g of N-fluorobenzenesulfonamide in 40 ml of THF was added dropwise at −78° C. and the mixture was stirred overnight while raising the temperature to room temperature. Saturated aqueous ammonium chloride was added to the reaction mixture and extraction was performed with ethyl acetate. The organic layer was washed with water and saturated brine and then dried over anhydrous sodium sulfate. The desiccating agent was filtered off and the filtrate was concentrated under reduced pressure. The residue was purified by silica gel column chromatography (ethyl acetate-heptane) to give the title compound (3.33 g) as a light yellow solid.

$^1$H-NMR (CDCl$_3$) δ 1.47 (t, J=7.2 Hz, 3H) 3.94 (s, 3H) 4.11 (q, J=7.2 Hz, 2H) 6.63 (d, J=11.6 Hz, 1H) 7.26 (d, J=6.4 Hz, 1H) 10.29 (s, 1H)

(115b) 4-{[(5-ethoxy-2-fluoro-4-methoxyphenyl)-(5-oxo-1-pyrimidin-2-yl-4,5-dihydro-1H-[1,2,4]triazol-3-yl)methyl]amino}benzamidine trifluoroacetate

[Chemical Formula 310]

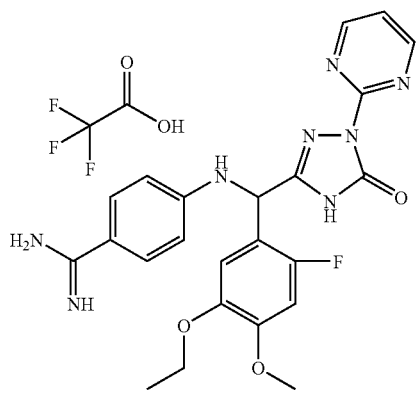

The same procedure was carried out as in Examples (1a)-(1d), except that 5-ethoxy-2-fluoro-4-methoxybenzaldehyde was used instead of the 2-fluoro-4,5-dimethoxybenzaldehyde in Example (1a), to give {2-(5-ethoxy-2-fluoro-4-methoxyphenyl)-2-[4-(5-methyl-[1,2,4]oxadiazol-3-yl)phenylimino]-1-methylsulfanyl-ethylidene}carbamic acid methyl ester. The same procedure was carried out as in Example (16b), except that this compound was used instead of the {2-(4-cyanomethoxy-3-methoxyphenyl)-2-[4-(5-methyl-[1,2,4]oxadiazol-3-yl)phenylimino]-1-methylsulfanylethylidene}carbamic acid methyl ester in Example (16b), to give the title compound.

$^1$H-NMR (CD$_3$OD) δ 1.33 (t, J=7.2 Hz, 3H) 3.83 (s, 3H) 3.99 (q, J=7.2 Hz, 2H) 5.95 (s, 1H) 6.86 (d, J=9.6 Hz, 1H) 6.87 (d, J=8.8 Hz, 2H) 7.04 (d, J=7.2 Hz, 1H) 7.38 (t, J=4.8 Hz, 1H) 7.63 (d, J=8.8 Hz, 2H) 8.79 (d, J=4.8 Hz, 2H)

Mass spectrum (ESI) m/z: 479 (M+H)$^+$ (115c) (R) and (S)-4-{[(5-ethoxy-2-fluoro-4-methoxyphenyl)-(5-oxo-1-pyrimidin-2-yl-4,5-dihydro-1H-[1,2,4]triazol-3-yl)methyl]amino}benzamidine acetate

[Chemical Formula 311]

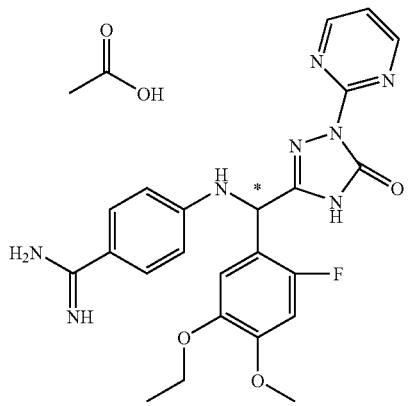

A SUMICHIRAL OA-2500 column was used for optical resolution of 12 mg of 4-{[(5-ethoxy-2-fluoro-4-methoxyphenyl)-(5-oxo-1-pyrimidin-2-yl-4,5-dihydro-1H-[1,2,4]triazol-3-yl)methyl]amino}benzamidine acetate, and the first eluting enantiomer (5.1 mg) of the title compound was obtained.

HPLC retention time: 13 min

Example 116

(R) and (S)-4-{[(3-fluoro-4,5-dimethoxyphenyl)-(5-oxo-1-pyrimidin-2-yl-4,5-dihydro-1H-[1,2,4]triazol-3-yl)methyl]amino}benzamidine acetate (116a) 3-fluoro-5-methoxy-4-triisopropylsilanyloxy-benzaldehyde

[Chemical Formula 312]

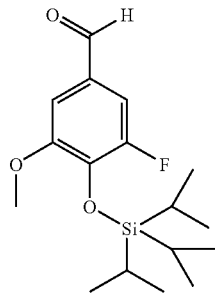

After adding 0.52 g of imidazole and 1.49 ml of chlorotriisopropylsilane to a solution of 1.0 g of 3-fluoro-5-methoxy-4-hydroxybenzaldehyde [CAS No. 79418-78-3] in 15 ml of DMF, the mixture was stirred at room temperature for 17 hours. Water was added to the reaction mixture and extraction was performed with ethyl acetate. The organic layer was washed with dilute hydrochloric acid and saturated brine, and then dried over anhydrous sodium sulfate. The desiccating agent was filtered off and the filtrate was concentrated under reduced pressure. The residue was purified by silica gel column chromatography (ethyl acetate-heptane) to give the title compound (1.67 g) as a colorless oil.

$^1$H-NMR (CDCl$_3$) δ 1.09 (d, J=7.6 Hz, 18H) 1.30 (m, 3H) 3.89 (s, 3H) 7.21-7.25 (m, 2H) 9.80 (d, J=1.2 Hz, 1H)

(116b) (R) and (S)-4-{[(3-fluoro-4,5-dimethoxyphenyl)-(5-oxo-1-pyrimidin-2-yl-4,5-dihydro-1H-[1,2,4]triazol-3-yl)methyl]amino}benzamidine acetate

[Chemical Formula 313]

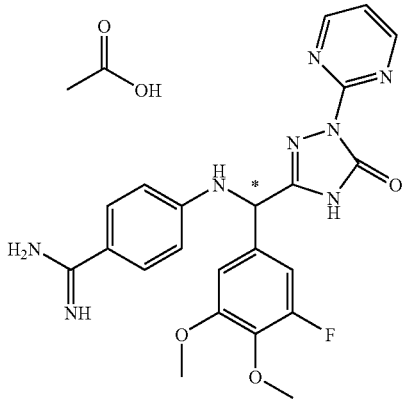

The same procedure was carried out as in Examples (18a)-(18h), except that 3-fluoro-5-methoxy-4-triisopropylsilanyloxybenzaldehyde and iodomethane were used instead of respectively the 4-t-butyldimethylsilanyloxy-3-methoxybenzaldehyde in Example (18a) and iodoethane in Example (18e), to give the first eluting enantiomer of the title compound.

HPLC retention time: 12 min

Example 117

(R) and (S)-4-({[3-(2-fluoroethoxy)-4-methoxyphenyl]-(5-oxo-1-pyrimidin-2-yl-4,5-dihydro-1H-[1,2,4]triazol-3-yl)methyl}amino)benzamidine acetate

[Chemical Formula 314]

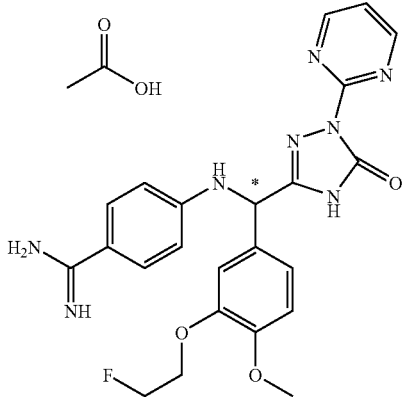

The same procedure was carried out as in Examples (16a)-(16c), except that {2-(3-hydroxy-4-methoxyphenyl)-2-[4-(5-methyl-[1,2,4]oxadiazol-3-yl)phenylimino]-1-methylsulfanylethylidene}carbamic acid methyl ester (Example (17d)) and 1-fluoro-2-iodoethane were used instead of respectively the {2-(4-hydroxy-3-methoxyphenyl)-2-[4-(5-methyl-[1,2,4]oxadiazol-3-yl)phenylimino]-1-methylsulfanylethylidene}carbamic acid methyl ester in Example (16a) and iodoethane in Example (16a), to give the first eluting enantiomer of the title compound.

$^1$H-NMR (CD$_3$OD) δ 3.73 (s, 3H) 4.13 (m, 2H) 4.59 (m, 2H) 5.56 (s, 1H) 6.76 (d, J=9.2 Hz, 2H) 6.90 (d, J=8.4 Hz, 1H) 7.02 (dd, J=8.4, 2.0 Hz, 1H) 7.07 (d, J=2.0 Hz, 1H) 7.26 (t, J=4.8 Hz, 1H) 7.51 (d, J=9.2 Hz, 2H) 8.68 (d, J=4.8 Hz, 2H) (racemic mixture, trifluoroacetate data)

Mass spectrum (ESI) m/z: 479 (M+H)$^+$ (data for racemic mixture)

HPLC retention time: 13 min

Example 118

(R) and (S)-4-{[(3-allyloxy-4-methoxyphenyl)-(5-oxo-1-pyrimidin-2-yl-4,5-dihydro-1H-[1,2,4]triazol-3-yl)methyl]amino}benzamidine acetate (118a) 4-{[(3-allyloxy-4-methoxyphenyl)-(5-oxo-1-pyrimidin-2-yl-4,5-dihydro-1H-[1,2,4]triazol-3-yl)methyl]amino}benzamidine acetate

[Chemical Formula 315]

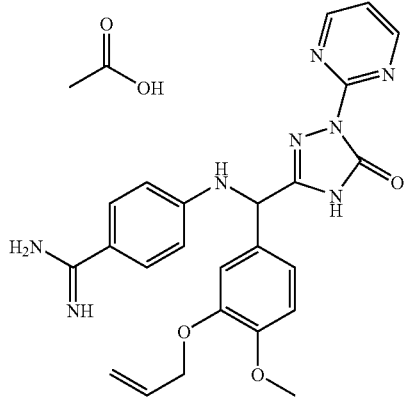

The same procedure was carried out as in Examples (17e)-(17g), except that allyl bromide was used instead of the iodoethane in Example (17e), to give the title compound.

$^1$H-NMR (CD$_3$OD) δ 1.93 (s, 3H) 3.82 (s, 3H) 4.54 (d, J=5.2 Hz, 2H) 5.17 (dd, J=10.4, 1.6 Hz, 1H) 5.33 (dd, J=17.2, 1.6 Hz, 1H) 5.62 (s, 1H) 6.00 (m, 1H) 6.86 (d, J=8.8 Hz, 2H) 6.96 (d, J=8.4 Hz, 1H) 7.10 (dd, J=8.4, 2.0 Hz, 1H) 7.15 (d, J=2.0 Hz, 1H) 7.34 (t, J=5.2 Hz, 1H) 7.60 (d, J=8.8 Hz, 2H) 8.78 (d, J=5.2 Hz, 2H)

Mass spectrum (ESI) m/z: 473 (M+H)$^+$ (118b) (R) and (S)-4-{[(3-allyloxy-4-methoxyphenyl)-(5-oxo-1-pyrimidin-2-yl-4,5-dihydro-1H-[1,2,4]triazol-3-yl)methyl]amino}benzamidine acetate

[Chemical Formula 316]

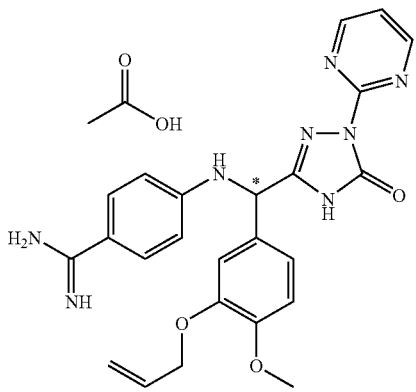

A SUMICHIRAL OA-2500 column was used for optical resolution of 11.0 mg of 4-{[(3-allyloxy-4-methoxyphenyl)-(5-oxo-1-pyrimidin-2-yl-4,5-dihydro-1H-[1,2,4]triazol-3-yl)methyl]amino}benzamidine acetate, and the first eluting enantiomer (3.9 mg) of the title compound was obtained as a white solid.

HPLC retention time: 13 min

Example 119

(R) and (S)-4-{[(2-fluoro-4,5-dimethoxyphenyl)-(5-oxo-1-pyridazin-3-yl-4,5-dihydro-1H-[1,2,4]triazol-3-yl)methyl]amino}benzamidine acetate (119a) 4-{[(2-fluoro-4,5-dimethoxyphenyl)-(5-oxo-1-pyridazin-3-yl-4,5-dihydro-1H-[1,2,4]triazol-3-yl)methyl]amino}benzamidine acetate

[Chemical Formula 317]

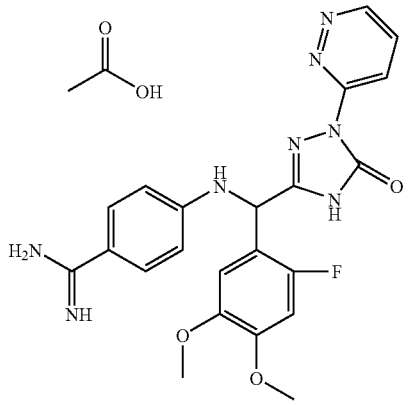

To a solution of 98 mg of [2-(2-fluoro-4,5-dimethoxyphenyl)-2-[4-(5-methyl-[1,2,4]oxadiazol-3-yl)phenylimino]-1-methylsulfanylethylidene]carbamic acid methyl ester (Example (1d)) in 3 ml of DMF there were added 30.5 mg of 3-hydrazinopyridazine hydrochloride [CAS No. 117043-87-5] and 29 μl of triethylamine, and the mixture was stirred at 85° C. for 18 hours under a nitrogen atmosphere. The reaction mixture was concentrated, and the residue was dissolved in 3 ml of a methanol:THF=1:1 mixed solvent. After adding 44 μl of acetic acid and 65 mg of sodium cyanotrihydroborate to the reaction mixture, it was stirred at room temperature for 6 hours. After filtering the reaction mixture, it was purified by reverse-phase high performance liquid chromatography (acetonitrile-water, 0.1% trifluoroacetic acid) to give 5-{(2-fluoro-4,5-dimethoxyphenyl)-[4-(5-methyl-[1,2,4]oxadiazol-3-yl)phenylamino]methyl}-2-pyridazin-3-yl-2,4-dihydro-[1,2,4]triazol-3-one (60 mg).

To a solution of this compound in 3 ml of a methanol:water:acetic acid=1:1:1 mixed solvent there was added 80 mg of iron powder, and the mixture was stirred at 55° C. for 15 hours under a nitrogen atmosphere. After filtering the reaction mixture, it was purified by reverse-phase high performance liquid chromatography (acetonitrile-water, 0.1% acetic acid) to give 39 mg of the title compound.

$^1$H-NMR (CD$_3$OD) δ 1.97 (s, 3H) 3.76 (s, 3H) 3.82 (s, 3H) 5.98 (s, 1H) 6.84-6.90 (m, 3H) 7.08 (d, J=7.2 Hz, 1H) 7.63 (d, J=8.8 Hz, 2H) 7.80 (dd, J=8.8, 4.8 Hz, 1H) 8.45 (dd, J=8.8, 1.6 Hz, 1H) 9.06 (dd, J=4.8, 1.6 Hz, 1H)

Mass spectrum (ESI) m/z: 465 (M+H)$^+$ (119b) (R) and (S)-4-{[(2-fluoro-4,5-dimethoxyphenyl)-(5-oxo-1-pyridazin-3-yl-4,5-dihydro-1H-[1,2,4]triazol-3-yl)methyl]amino}benzamidine acetate

[Chemical Formula 318]

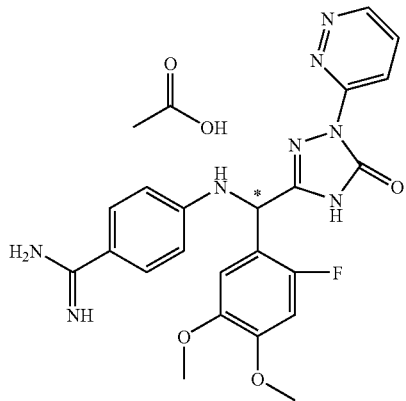

A SUMICHIRAL OA-2500 column was used for optical resolution of 39 mg of 4-{[(2-fluoro-4,5-dimethoxyphenyl)-(5-oxo-1-pyridazin-3-yl-4,5-dihydro-1H-[1,2,4]triazol-3-yl)methyl]amino}benzamidine acetate, and the first eluting enantiomer (13.1 mg) of the title compound was obtained.

HPLC retention time: 13 min

Example 120

(R) and (S)-4-{[(3-allyloxy-2-fluoro-4-methoxyphenyl)-(5-oxo-1-pyrimidin-2-yl-4,5-dihydro-1H-[1,2,4]triazol-3-yl)methyl]amino}benzamidine acetate (120a) 2-bromo-4-methoxy-5-triisopropylsilanyloxy-benzaldehyde

[Chemical Formula 319]

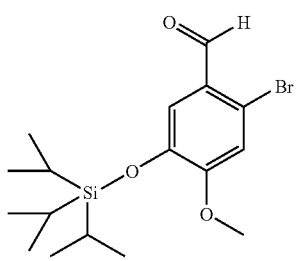

After adding 10.9 g of sodium hydrogen carbonate and 2.32 ml of bromine to a solution of 10 g of 4-methoxy-3-triisopropylsilanyloxybenzaldehyde [CAS No. 179260-96-6] in 200 ml of chloroform at 0° C., the mixture was stirred at room temperature for 15 hours. Saturated aqueous sodium sulfite was then added to the reaction mixture, and extraction was performed with dichloromethane. The organic layer was washed with saturated brine and dried over anhydrous sodium sulfate. The desiccating agent was filtered, and the filtrate was concentrated under reduced pressure. The residue was purified by silica gel column chromatography (ethyl acetate-heptane) to give the title compound (11.7 g) as a light yellow oil.
$^1$H-NMR (CDCl$_3$) δ 1.08 (d, J=7.2 Hz, 18H) 1.22-1.27 (m, 3H) 3.88 (s, 3H) 7.01 (s, 1H) 7.40 (s, 1H) 10.13 (s, 1H)

(120b) 2-fluoro-4-methoxy-5-triisopropylsilanyloxy-benzaldehyde

[Chemical Formula 320]

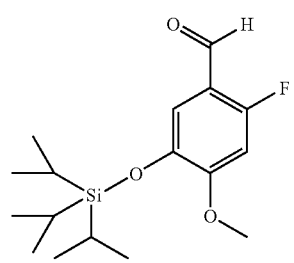

To a solution of 2.01 ml of morpholine in 50 ml of THF there was added 8.69 ml of n-butyllithium (2.66 M, hexane solution) at −78° C. under a nitrogen atmosphere, and the mixture was stirred at −40° C. for 30 minutes. A solution of 2-bromo-4-methoxy-5-triisopropylsilanyloxybenzaldehyde in 15 ml of THF was then added dropwise at −78° C., and the mixture was further stirred at −78° C. for 40 minutes. After further adding 11.1 ml of n-butyllithium (2.66 M, hexane solution) at −78° C., the mixture was stirred at −78° C. for 40 minutes, and then a solution of 10.6 g of N-fluorobenzenesulfonamide in 40 ml of THF was added dropwise at −78° C. and the reaction mixture was stirred overnight while raising the temperature to room temperature. Dilute hydrochloric acid was added to the reaction mixture, and extraction was performed with diethyl ether. The organic layer was washed with saturated aqueous sodium hydrogencarbonate, water and saturated brine and then dried over anhydrous sodium sulfate. The desiccating agent was filtered off and the filtrate was concentrated under reduced pressure. The residue was purified by silica gel column chromatography (ethyl acetate-heptane) to give the title compound (2.96 g) as a light yellow solid.
$^1$H-NMR (CDCl$_3$) δ 1.09 (d, J=7.2 Hz, 18H) 1.22-1.27 (m, 3H) 3.87 (s, 3H) 6.59 (d, J=11.6 Hz, 1H) 7.27 (d, J=6.8 Hz, 1H) 10.16 (s, 1H)

(120c) {2-(2-fluoro-5-hydroxy-4-methoxyphenyl)-2-[4-(5-methyl-[1,2,4]oxadiazol-3-yl)phenylimino]-1-methylsulfanylethylidene}carbamic acid methyl ester

[Chemical Formula 321]

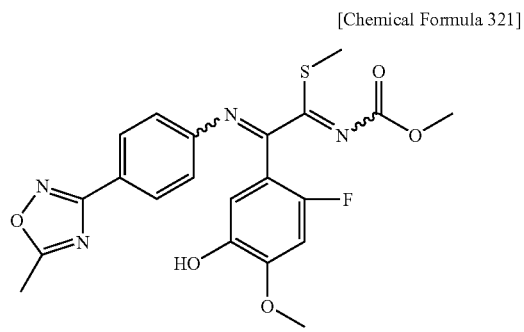

The same procedure was carried out as in Examples (17a)-(17d), except that 2-fluoro-4-methoxy-5-triisopropylsilanyloxybenzaldehyde was used instead of the 4-methoxy-3-triisopropylsilanyloxybenzaldehyde in Example (17a), to give the title compound.

(120d) (R) and (S)-4-{[(3-allyloxy-2-fluoro-4-methoxyphenyl)-(5-oxo-1-pyrimidin-2-yl-4,5-dihydro-1H-[1,2,4]triazol-3-yl)methyl]amino}benzamidine acetate

[Chemical Formula 322]

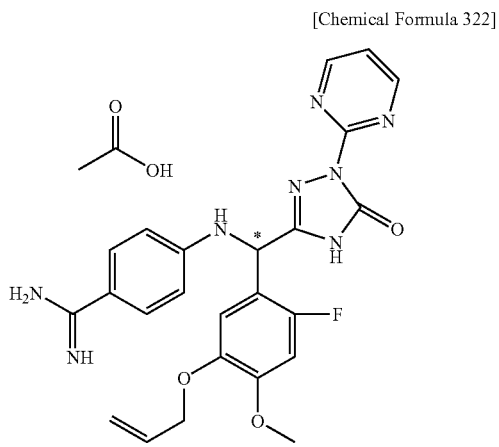

The same procedure was carried out as in Examples (17e)-(17g), except that {2-(2-fluoro-5-hydroxy-4-methoxyphenyl)-2-[4-(5-methyl-[1,2,4]oxadiazol-3-yl)phenylimino]-1-methylsulfanylethylidene}carbamic acid methyl ester and allyl bromide were used instead of respectively the {2-(3-hydroxy-4-methoxyphenyl)-2-[4-(5-methyl-[1,2,4]oxadiazol-3-yl)phenylimino]-1-methylsulfanylethylidene}carbamic acid methyl ester in Example (17e) and iodoethane in Example (17e), to give 4-{[(3-allyloxy-2-fluoro-4-methoxyphenyl)-(5-oxo-1-pyrimidin-2-yl-4,5-dihydro-1H-[1,2,4]triazol-3-yl)methyl]amino}benzamidine acetate.

$^1$H-NMR (CD$_3$OD) δ 1.93 (s, 3H) 3.82 (s, 3H) 4.46 (d, J=5.6 Hz, 2H) 5.11 (dd, J=10.8, 1.6 Hz, 1H) 5.27 (dd, J=17.6, 1.6 Hz, 1H) 5.92 (s, 1H) 5.95 (m, 1H) 6.83 (d, J=11.6 Hz, 1H) 6.86 (d, J=8.8 Hz, 2H) 7.08 (d, J=7.2 Hz, 1H) 7.33 (t, J=4.8 Hz, 1H) 7.61 (d, J=8.8 Hz, 2H) 8.77 (d, J=4.8 Hz, 2H)

Mass spectrum (ESI) m/z: 491 (M+H)$^+$

An 84 mg portion of this compound was optically resolved using a SUMICHIRAL OA-2500 column, and the first eluting enantiomer (31.4 mg) of the title compound was obtained.

HPLC retention time: 12 min

Example 121

(R) and (S)-4-{[(3-ethoxy-4-methoxyphenyl)-(5-oxo-1-pyridazin-3-yl-4,5-dihydro-1H-[1,2,4]triazol-3-yl)methyl]amino}benzamidine acetate

[Chemical Formula 323]

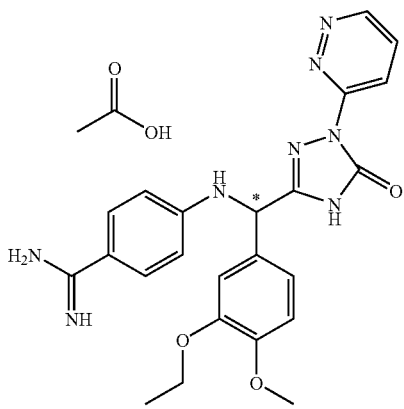

The same procedure was carried out as in Examples (119a)-(119b) except that {2-(3-ethoxy-4-methoxyphenyl)-2-[4-(5-methyl-[1,2,4]oxadiazol-3-yl)phenylimino]-1-methylsulfanylethylidene}carbamic acid methyl ester (Example (17e)) was used instead of [2-(2-fluoro-4,5-dimethoxyphenyl)-2-[4-(5-methyl-[1,2,4]oxadiazol-3-yl)phenylimino]-1-methylsulfanylethylidene]carbamic acid methyl ester in Example (119a), to give the first eluting enantiomer of the title compound.

$^1$H-NMR (CD$_3$OD) δ 1.34 (t, J=6.8 Hz, 3H) 1.93 (s, 3H) 3.79 (s, 3H) 4.01 (q, J=6.8 Hz, 2H) 5.64 (s, 1H) 6.86 (d, J=8.8 Hz, 2H) 6.91 (d, J=8.4 Hz, 1H) 7.08 (dd, J=8.4, 2.4 Hz, 1H) 7.14 (d, J=2.0 Hz, 1H) 7.59 (d, J=8.8 Hz, 2H) 7.76 (dd, J=9.2, 4.8 Hz, 1H) 8.45 (dd, J=9.2, 1.6 Hz, 1H) 9.03 (dd, J=4.8, 1.6 Hz, 1H) (data for racemic mixture)

Mass spectrum (ESI) m/z: 461 (M+H)$^+$ (data for racemic mixture)

HPLC retention time: 12 min

Example 122

(R) and (S)-2-{3[(4-carbamimidoylphenylamino)-(5-ethoxy-2-fluoro-4-methoxyphenyl)methyl]-5-oxo-4,5-dihydro-[1,2,4]triazol-1-yl}benzoic acid acetate

[Chemical Formula 324]

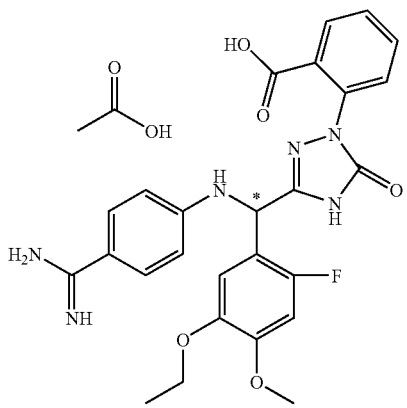

After adding 16 mg of 2-hydrazinobenzoic acid hydrochloride and 25 µl of triethylamine to a solution of 85 mg of {2-(5-ethoxy-2-fluoro-4-methoxyphenyl)-2-[4-(5-methyl-[1,2,4]oxadiazol-3-yl)phenylimino]-1-methylsulfanylethylidene}carbamic acid methyl ester (see Example (115b)) in 3 ml of DMF, the mixture was stirred at 90° C. for 14 hours under a nitrogen atmosphere. The reaction mixture was concentrated, and the residue was dissolved in 3 ml of a methanol:THF=2:1 mixed solvent. After adding 35 µl of acetic acid and 55 mg of sodium cyanotrihydroborate to the reaction mixture, it was stirred at room temperature for 6 hours. After filtering the reaction mixture, it was purified by reverse-phase high performance liquid chromatography (acetonitrile-water, 0.1% trifluoroacetic acid) to give 2-(3-{(5-ethoxy-2-fluoro-4-methoxyphenyl)-[4-(5-methyl-[1,2,4]oxadiazol-3-yl)phenylamino]methyl}-5-oxo-4,5-dihydro-1H-[1,2,4]triazol-1-yl)benzoic acid (30 mg).

To a solution of this compound in 3 ml of a methanol:water:acetic acid=1:1:1 mixed solvent there was added 30 mg of iron powder, and the mixture was stirred at 60° C. for 12 hours under a nitrogen atmosphere. After filtering the reaction mixture, it was purified by reverse-phase high performance liquid chromatography (acetonitrile-water, 0.1% trifluoroacetic acid) to give 6.0 mg of 2-{3-[(4-carbamimidoylphenylamino)-(5-ethoxy-2-fluoro-4-methoxyphenyl)methyl]-5-oxo-4,5-dihydro-1H-[1,2,4]triazol-1-yl}benzoic acid trifluoroacetate.

$^1$H-NMR (CD$_3$OD) δ 1.34 (t, J=7.2 Hz, 3H) 3.84 (s, 3H) 3.98 (q, J=7.2 Hz, 2H) 5.93 (s, 1H) 6.85 (d, J=12 Hz, 1H) 6.87 (d, J=8.8 Hz, 2H) 7.03 (d, J=7.2 Hz, 1H) 7.46-7.74 (m, 3H) 7.64 (d, J=8.8 Hz, 2H) 7.97 (dd, J=8.0, 1.2 Hz, 1H)

Mass spectrum (ESI) m/z: 521 (M+H)$^+$ 6 mg of this compound was optically resolved using a SUMICHIRAL OA-2500 column, and the first eluting enantiomer (1.9 mg) of the title compound was obtained.

HPLC retention time: 12 min

Example 123

(R) and (S)-4-({[1-(3-fluoropyridin-2-yl)-5-oxo-4,5-dihydro-1H-[1,2,4]triazol-3-yl]-(7-methoxy-2,3-dihydrobenzofuran-5-yl)methyl}amino)benzamidine acetate

[Chemical Formula 325]

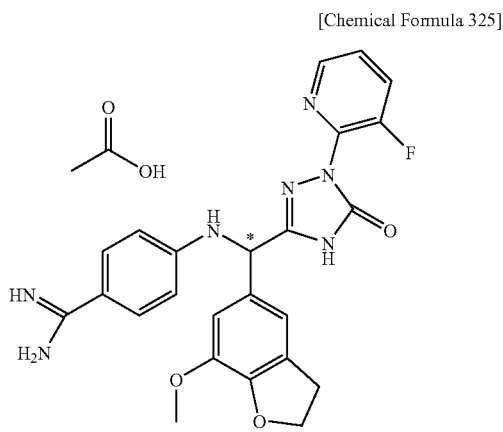

The same procedure was carried out as in Example (30d), except that {2-(7-methoxy-2,3-dihydro-benzofuran-5-yl)-2-[4-(5-methyl-[1,2,4]oxadiazol-3-yl)phenylimino]-1-methylsulfanylethylidene}carbamic acid methyl ester (Example (31a)) was used instead of the {2-(9-methoxy-3,4-dihydro-2H-benzo[b][1,4]dioxepin-7-yl)-2-[4-(5-methyl-[1,2,4]oxadiazol-3-yl)phenylimino]-1-methylsulfanylethylidene}carbamic acid methyl ester, to give the first eluting enantiomer of the title compound.

$^1$H-NMR (CD$_3$OD) δ 1.91 (s, 3H) 3.20 (t, J=8.4 Hz, 2H) 3.83 (s, 3H) 4.57 (t, J=8.4 Hz, 2H) 5.55 (s, 1H) 6.84 (d, J=8.8 Hz, 2H) 7.01 (d, J=9.6 Hz, 2H) 7.49-7.54 (m, 1H) 7.60 (d, J=9.2 Hz, 2H) 7.80 (t, J=10.0 Hz, 1H) 8.36 (d, J=4.8 Hz, 1H)

Mass spectrum (ESI) m/z: 494 (M+H)$^+$ (data for racemic mixture)

HPLC retention time: 9 min

Example 124

4-({(2-fluoro-4,5-dimethoxyphenyl)-[1-(3-methoxypyridin-2-yl)-5-oxo-4,5-dihydro-1H-[1,2,4]triazol-3-yl]methyl}amino)benzamidine acetate

[Chemical Formula 326]

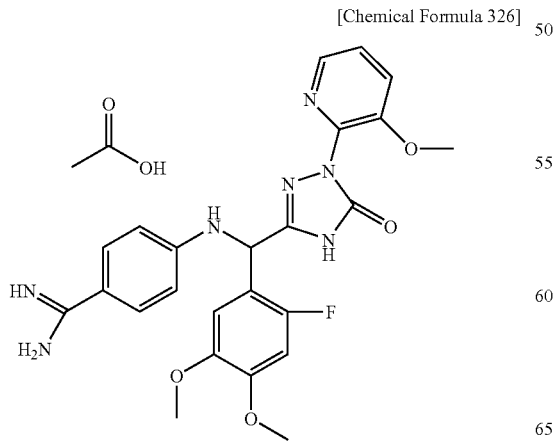

The same procedure was carried out as in Examples (1e)-(1g), except that (3-methoxypyridin-2-yl)hydrazine was used instead of the 2-hydrazinobenzoic acid hydrochloride in Example (1e), to give the title compound.

$^1$H-NMR (CD$_3$OD) δ 1.96 (s, 3H) 3.77 (s, 3H) 3.83 (s, 3H) 3.87 (s, 3H) 5.94 (s, 1H) 6.85 (d, J=4.0 Hz, 1H) 6.86 (d, J=9.2 Hz, 2H) 7.05 (d, J=7.2 Hz, 1H) 7.53 (dd, J=4.8, 8.4 Hz, 1H) 7.63 (d, J=9.2 Hz, 2H) 7.68 (dd, J=1.2, 8.4 Hz, 1H) 8.10 (dd, J=1.2, 4.8 Hz, 1H)

Mass spectrum (ESI) m/z: 494 (M+H)$^+$

Example 125

4-({(2-fluoro-4,5-dimethoxyphenyl)-[1-(3-fluoropyridin-2-yl)-5-oxo-4,5-dihydro-1H-[1,2,4]triazol-3-yl]methyl}amino)benzamidine acetate

[Chemical Formula 327]

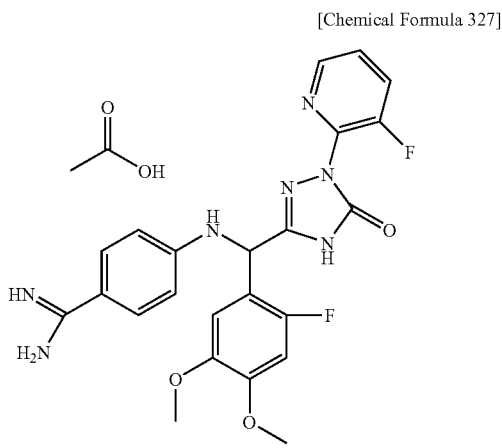

The same procedure was carried out as in Examples (1e)-(1g), except that (3-fluoropyridin-2-yl)hydrazine was used instead of the 2-hydrazinobenzoic acid hydrochloride in Example (1e), to give the title compound.

$^1$H-NMR (CD$_3$OD) δ 1.92 (s, 3H) 3.74 (s, 3H) 3.81 (s, 3H) 5.93 (s, 1H) 6.83 (d, J=11.6 Hz, 1H) 6.85 (d, J=9.2 Hz, 2H) 7.09 (d, J=7.2 Hz, 1H) 7.51-7.56 (m, 1H) 7.61 (d, J=8.8 Hz, 2H) 7.82 (ddd, J=1.2, 8.4, 10.8 Hz, 1H) 8.36 (d, J=4.4 Hz, 1H)

Mass spectrum (ESI) m/z: 482 (M+H)$^+$

Example 126

2-(4-{(4-carbamimidoylphenylamino)-[1-(3-methoxypyridin-2-yl)-5-oxo-4,5-dihydro-1H-[1,2,4]triazol-3-yl]methyl}-2-ethoxyphenoxy)-N-methyl-acetamide acetate (126a) {2-(3-ethoxy-4-hydroxyphenyl)-2-[4-(5-methyl-[1,2,4]oxadiazol-3-yl)phenylimino]-1-methylsulfanylethylidene}carbamic acid methyl ester

[Chemical Formula 328]

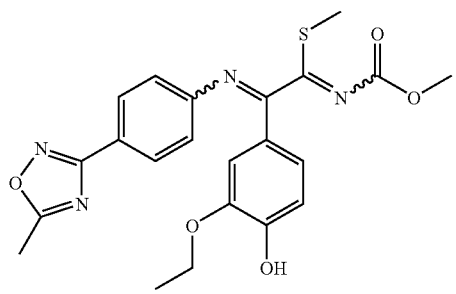

The same procedure was carried out as in Examples (18a)-(18d), except that 4-t-butyldimethylsilanyloxy-3-ethoxybenzaldehyde [CAS No. 581800-64-8] was used instead of the 4-t-butyldimethylsilanyloxy-3-methoxybenzaldehyde in Example (18a), to give the title compound.

(126b) {2-(3-ethoxy-4-methylcarbamoylmethoxyphenyl)-2-[4-(5-methyl-[1,2,4]oxadiazol-3-yl)phenylimino]-1-methylsulfanylethylidene}carbamic acid methyl ester

[Chemical Formula 329]

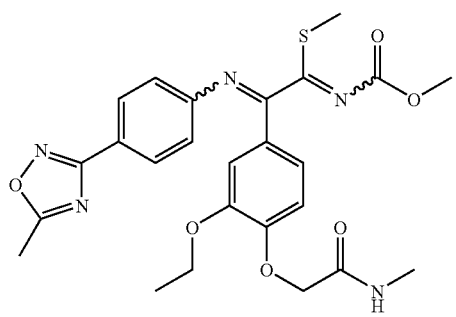

After adding 200 mg of potassium carbonate and 78 mg of 2-bromo-N-methyl-acetamide to a solution of 154 mg of {2-(3-ethoxy-4-hydroxyphenyl)-2-[4-(5-methyl-[1,2,4]oxadiazol-3-yl)phenylimino]-1-methylsulfanylethylidene}carbamic acid methyl ester in 1 ml of acetone, the mixture was stirred overnight at room temperature. Water was added to the reaction mixture, extraction was performed with ethyl acetate, and the organic layer was washed with 0.5N hydrochloric acid and saturated brine in that order. The organic layer was dried over anhydrous magnesium sulfate. The desiccating agent was filtered off and the filtrate was concentrated under reduced pressure. The residue was purified by silica gel column chromatography (ethyl acetate-heptane) to give the title compound (161 mg) as a yellow solid.

Mass spectrum (ESI) m/z: 526 (M+H)$^+$ (126c) 2-(4-{(4-carbamimidoyl-phenylamino)-[1-(3-methoxy-pyridin-2-yl)-5-oxo-4,5-dihydro-1H-[1,2,4]triazol-3-yl]methyl}-2-ethoxy-phenoxy)-N-methyl-acetamide acetate

[Chemical Formula 330]

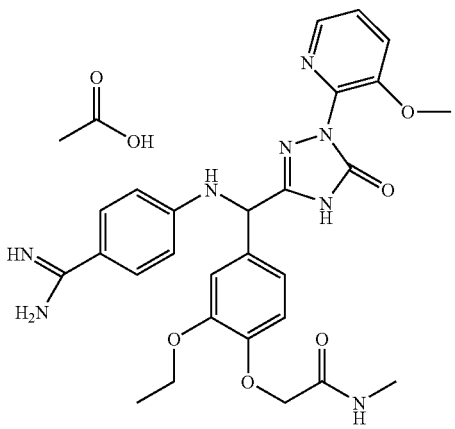

The same procedure was carried out as in Examples (21i)-(21j), except that {2-(3-ethoxy-4-methylcarbamoylmethoxyphenyl)-2-[4-(5-methyl-[1,2,4]oxadiazol-3-yl)phenylimino]-1-methylsulfanylethylidene}carbamic acid methyl ester and (3-methoxy-pyridin-2-yl)hydrazine were used instead of respectively the {2-(8-methoxy-4H-benzo[1,3]dioxin-6-yl)-2-[4-(5-methyl-[1,2,4]oxadiazol-3-yl)-phenylimino]-1-methylsulfanylethylidene}carbamic acid methyl ester in Example (21i) and 2-hydrazinopyrimidine in Example (21i), to give the title compound.

$^1$H-NMR (CD$_3$OD) δ 1.41 (t, J=6.8 Hz, 3H) 1.96 (s, 3H) 2.81 (s, 3H) 3.86 (s, 3H) 4.08-4.15 (m, 2H) 4.50 (s, 2H) 5.66 (s, 1H) 6.86 (d, J=8.8 Hz, 2H) 7.02 (d, J=8.4 Hz, 1H) 7.07 (dd, J=2.0, 8.4 Hz, 1H) 7.19 (d, J=2.0 Hz, 1H) 7.53 (dd, J=4.8, 8.4 Hz, 1H) 7.62 (d, J=8.8 Hz, 2H) 7.68 (dd, J=1.6, 8.4 Hz, 1H) 8.10 (dd, J=1.2, 4.8 Hz, 1H)

Mass spectrum (ESI) m/z: 547 (M+H)$^+$

Example 127

2-(4-{(4-carbamimidoylphenylamino)-[1-(3-methylpyridin-2-yl)-5-oxo-4,5-dihydro-1H-[1,2,4]triazol-3-yl]methyl}-2-ethoxyphenoxy)-N-methylacetamide acetate

[Chemical Formula 331]

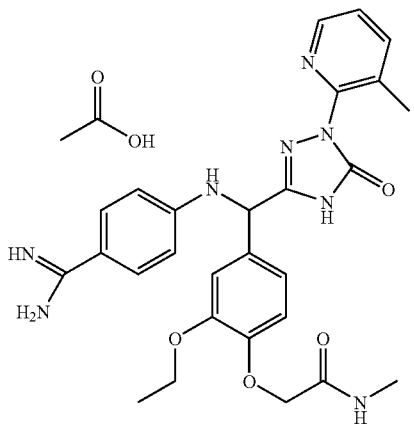

The same procedure was carried out as in Examples (21i)-(21j), except that {2-(3-ethoxy-4-methylcarbamoylmethoxyphenyl)-2-[4-(5-methyl-[1,2,4]oxadiazol-3-yl)phe-nylimino]-1-methylsulfanylethylidene}carbamic acid methyl ester (Example (126a)) and (3-methylpyridin-2-yl) hydrazine were used instead of respectively the {2-(8-methoxy-4H-benzo[1,3]dioxin-6-yl)-2-[4-(5-methyl-[1,2,4]oxadiazol-3-yl)-phenylimino]-1-methylsulfanylethylidene}carbamic acid methyl ester in Example (21i) and 2-hydrazinopyrimidine in Example (21i), to give the title compound.

$^1$H-NMR (CD$_3$OD) δ 1.41 (t, J=7.2 Hz, 3H) 1.98 (s, 3H) 2.27 (s, 3H) 2.81 (s, 3H) 4.08-4.14 (m, 2H) 4.50 (s, 2H) 5.69 (s, 1H) 6.87 (d, J=8.8 Hz, 2H) 7.03 (d, J=8.4 Hz, 1H) 7.08 (dd, J=2.0, 8.4 Hz, 1H) 7.20 (d, J=2.0 Hz, 1H) 7.41-7.47 (m, 1H) 7.63 (d, J=8.8 Hz, 2H) 7.87 (d, J=7.6 Hz, 1H) 8.38 (br.s, 1H)

Mass spectrum (ESI) m/z: 531 (M+H)$^+$

Example 128

4-({[3-ethoxy-4-(2-methoxyethoxy)phenyl]-[1-(3-methylpyridin-2-yl)-5-oxo-4,5-dihydro-1H-[1,2,4]triazol-3-yl]methyl}amino)benzamidine acetate (128a) {2-[3-ethoxy-4-(2-methoxyethoxy)phenyl]-2-[4-(5-methyl-[1,2,4]oxadiazol-3-yl)phenylimino]-1-methylsulfanylethylidene}carbamic acid methyl ester

[Chemical Formula 332]

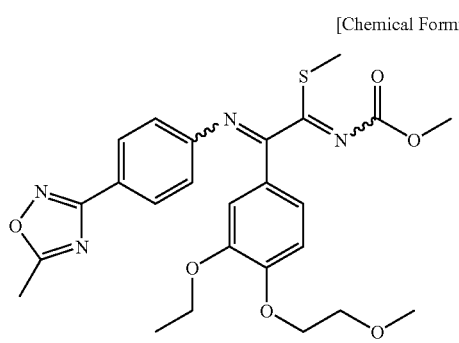

After adding 200 mg of potassium carbonate, 10 mg of tetrabutylammonium iodide and 200 mg of 1-bromo-2-methoxyethane to a solution of {2-(3-ethoxy-4-hydroxyphenyl)-2-[4-(5-methyl-[1,2,4]oxadiazol-3-yl)phenylimino]-1-methylsulfanylethylidene}carbamic acid methyl ester (Example 126a) in 1 ml of DMF, the mixture was stirred overnight at room temperature. Water was added to the reaction mixture, extraction was performed with ethyl acetate, and the organic layer was washed with 0.5 N hydrochloric acid and saturated brine in that order. The organic layer was dried over anhydrous magnesium sulfate. The desiccating agent was filtered off and the filtrate was concentrated under reduced pressure. The residue was purified by silica gel column chromatography (ethyl acetate-heptane) to give the title compound (193 mg) as a yellow solid.

Mass spectrum (ESI) m/z: 513 (M+H)$^+$ (128b) 4-({[3-ethoxy-4-(2-methoxyethoxy)phenyl]-[1-(3-methyl-pyridin-2-yl)-5-oxo-4,5-dihydro-1H-[1,2,4]triazol-3-yl]methyl}amino)benzamidine acetate

[Chemical Formula 333]

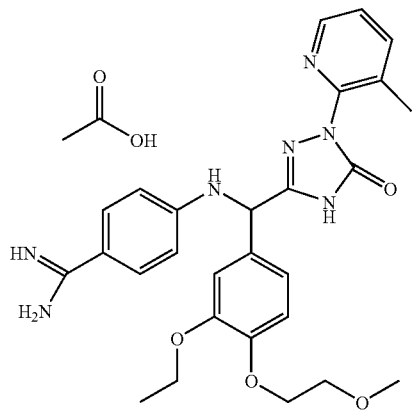

The same procedure was carried out as in Examples (21i)-(21j), except that {2-(3-ethoxy-4-(2-methoxyethoxy)phenyl]-2-[4-(5-methyl-[1,2,4]oxadiazol-3-yl)phenylimino]-1-methylsulfanylethylidene}carbamic acid methyl ester and (3-methylpyridin-2-yl)hydrazine were used instead of respectively the {2-(8-methoxy-4H-benzo[1,3]dioxin-6-yl)-2-[4-(5-methyl-[1,2,4]oxadiazol-3-yl)phenylimino]-1-methylsulfanylethylidene}carbamic acid methyl ester in Example (21i) and 2-hydrazinopyrimidine in Example (21i), to give the title compound.

$^1$H-NMR (CD$_3$OD) δ 1.37 (t, J=6.8 Hz, 3H) 1.90 (s, 3H) 2.26 (s, 3H) 3.41 (s, 3H) 3.71-3.77 (m, 2H) 4.06-4.11 (m, 2H) 4.12-4.14 (m, 2H) 5.60 (s, 1H) 6.86 (d, J=8.8 Hz, 2H) 6.98 (d, J=8.0 Hz, 1H) 7.06 (dd, J=2.0, 8.0 Hz, 1H) 7.14 (d, J=1.6 Hz, 1H) 7.42 (dd, J=5.2, 7.6 Hz, 1H) 7.61 (d, J=8.8 Hz, 2H) 7.85 (d, J=8.0 Hz, 1H) 8.36 (d, J=4.8 Hz, 1H)

Mass spectrum (ESI) m/z: 518 (M+H)$^+$

Example 129

(R) and (S)-4-({[3,4-dimethoxy-5-(2-methoxyethyl)-phenyl]-(5-oxo-1-pyrimidin-2-yl-4,5-dihydro-1H-[1,2,4]triazol-3-yl)methyl}amino)benzamidine acetate (129a)
5-bromo-1,2-dimethoxy-3-(2-methoxyethyl)benzene

[Chemical Formula 334]

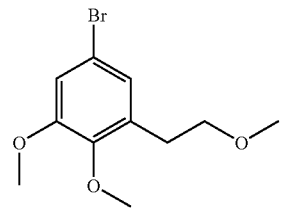

After dissolving 3 g of 2-allyl-4-bromo-6-methoxy-phenol [CAS No. 352019-92-2] in 10 ml of DMF, 1.3 g of imidazole and 2 g of chlorotriisopropylsilane were added and the mixture was stirred at 50° C. for 4 hours. Next, 1N hydrochloric acid was added to the reaction mixture and extraction was performed with ethyl acetate. The organic layer was dried over anhydrous magnesium sulfate. The desiccating agent was filtered off, and the filtrate was concentrated under reduced pressure to give (2-allyl-4-bromo-6-methoxyphenoxy)triisopropylsilane.

Ozone gas was blown into a solution of this compound in 140 ml of a dichloromethane:methanol=1:1 mixed solvent for 40 minutes at −78° C. After blowing oxygen gas for 5 minutes to remove the dissolved ozone, 2 g of sodium borohydride was added. After stirring the mixture at room temperature for 2 hours, saturated aqueous ammonium chloride was added to the reaction mixture while cooling on ice. The reaction mixture was extracted with ethyl acetate and dried over anhydrous magnesium sulfate. The desiccating agent was filtered off, and the filtrate was concentrated under reduced pressure to give 2-(5-bromo-3-methoxy-2-triisopropylsilanyloxyphenyl)ethanol (3.808 g) as an oil.

After dissolving 2.2 g of this compound in 20 ml of THF, 7 ml of TBAF (1.0 M, THF solution) was added and the mixture was stirred at room temperature. Saturated aqueous ammonium chloride was added to the reaction mixture, and extraction was performed with ethyl acetate. The organic layer was dried over anhydrous magnesium sulfate. The desiccating agent was filtered off and the filtrate was concentrated under reduced pressure. The residue was purified by silica gel column chromatography (ethyl acetate-heptane) to give 4-bromo-2-(2-hydroxyethyl)-6-methoxyphenol as an oil.

To a solution of this compound in 30 ml of t-butyl methyl ether there were added 20 ml of 40% aqueous sodium hydroxide, 200 mg of tetrabutylammonium iodide and 5 ml of iodomethane, and the mixture was stirred at 50° C. for 5 hours and at room temperature for 48 hours. Water was added to the reaction mixture, and extraction was performed with t-butyl methyl ether. The organic layer was dried over anhydrous magnesium sulfate. The desiccating agent was filtered off and the filtrate was concentrated under reduced pressure. The residue was purified by silica gel column chromatography (ethyl acetate-heptane) to give the title compound (493 mg) as an oil.

$^1$H-NMR (CDCl$_3$) δ 2.86 (t, J=7.2 Hz, 2H) 3.35 (s, 3H) 3.55 (t, J=7.2 Hz, 2H) 3.79 (s, 3H) 3.83 (s, 3H) 6.89 (d, J=2.0 Hz, 1H) 6.95 (d, J=2.0 Hz, 1H)

(129b) 3,4-dimethoxy-5-(2-methoxyethyl)benzaldehyde

[Chemical Formula 335]

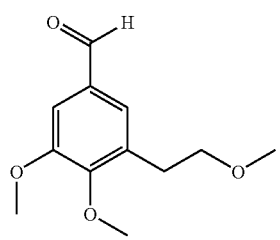

To a solution of 1.3 g of 5-bromo-1,2-dimethoxy-3-(2-methoxyethyl)benzene in 20 ml of THF there was added dropwise 2 ml of n-butyllithium (2.66 M, hexane solution) at −70° C. under a nitrogen atmosphere. After stirring at −70° C. for 30 minutes, 0.7 ml of N-formylmorpholine was added and the temperature was raised from −70° C. to 0° C. over a period of 30 minutes. Saturated aqueous ammonium chloride was added to the reaction mixture, and extraction was performed with ethyl acetate. The organic layer was dried over anhydrous magnesium sulfate. The desiccating agent was filtered off and the filtrate was concentrated under reduced pressure. The residue was purified by silica gel column chromatography (ethyl acetate-heptane) to give the title compound (806 mg) as an oil.

$^1$H-NMR (CDCl$_3$) δ 2.97 (t, J=6.4 Hz, 2H) 3.36 (s, 3H) 3.61 (t, J=6.8 Hz, 2H) 3.91 (s, 3H) 3.92 (s, 3H) 7.33 (d, J=2.0 Hz, 1H) 7.35 (d, J=2.0 Hz, 1H), 9.86 (s, 1H)

(129c) {2-[3,4-dimethoxy-5-(2-methoxyethyl)phenyl]-2-[4-(5-methyl-[1,2,4]oxadiazol-3-yl)phenylimino]-1-methylsulfanylethylidene}carbamic acid methyl ester

[Chemical Formula 336]

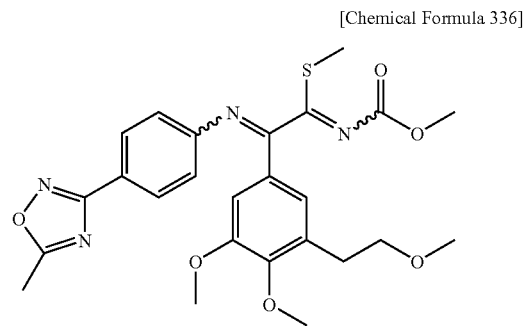

The same procedure was carried out as in Examples (21d)-(21h), except that 3,4-dimethoxy-5-(2-methoxyethyl)benzaldehyde was used instead of the 8-methoxy-4H-benzo[1,3]dioxine-6-carbaldehyde in Example (21d), to give the title compound.

Mass spectrum (ESI) m/z: 513 (M+H)$^+$ (129d) 4-({[3,4-dimethoxy-5-(2-methoxyethyl)phenyl]-(5-oxo-1-pyrimidin-2-yl-4,5-dihydro-1H-[1,2,4]triazol-3-yl)methyl}amino)benzamidine acetate

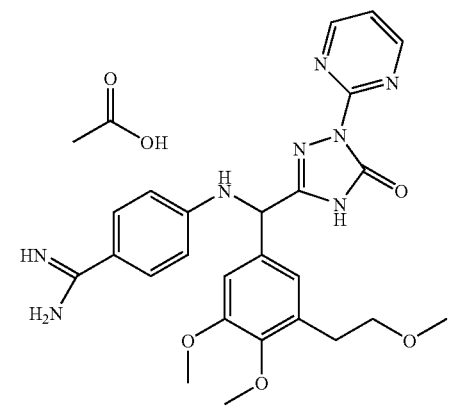

The same procedure was carried out as in Examples (21i)-(21j), except that {2-[3,4-dimethoxy-5-(2-methoxyethyl)phenyl]-2-[4-(5-methyl-[1,2,4]oxadiazol-3-yl)phenylimino]-1-methylsulfanylethylidene}carbamic acid methyl ester was used instead of the {2-(8-methoxy-4H-benzo[1,3]dioxin-6-yl)-2-[4-(5-methyl-[1,2,4]oxadiazol-3-yl)phenylimino]-1-methylsulfanylethylidene}carbamic acid methyl ester in Example (21i), to give the title compound.

$^1$H-NMR (d$_6$-DMSO) δ 1.73 (s, 3H) 2.73 (t, J=6.8 Hz, 2H) 3.18 (s, 3H) 3.43 (t, J=6.8 Hz, 2H) 3.66 (s, 3H) 3.74 (s, 3H)

5.28 (d, J=6.8 Hz, 1H) 6.83 (d, J=8.8 Hz, 2H) 6.97 (s, 1H) 7.08 (t, J=4.4 Hz, 1H) 7.12 (s, 1H) 7.20 (d, J=6.8 Hz, 1H) 7.55 (d, J=8.8 Hz, 2H) 8.61 (d, J=4.8 Hz, 2H)

Mass spectrum (ESI) m/z: 505 (M+H)⁺

(129e) (R) and (S)-4-({[3,4-dimethoxy-5-(2-methoxyethyl)-phenyl]-(5-oxo-1-pyrimidin-2-yl-4,5-dihydro-1H-[1,2,4]triazol-3-yl)methyl}amino)benzamidine acetate

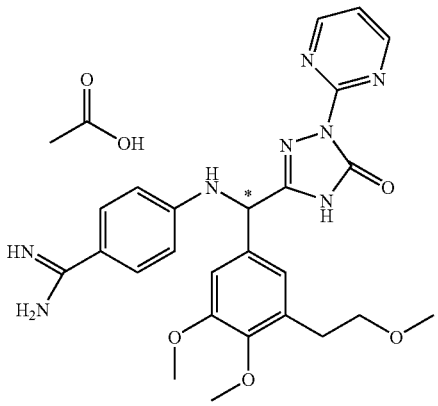

[Chemical Formula 337]

A SUMICHIRAL OA-2500 column was used for optical resolution of 63 mg of 4-({[3,4-dimethoxy-5-(methoxyethyl)phenyl]-(5-oxo-1-pyrimidin-2-yl-4,5-dihydro-1H-[1,2,4]triazol-3-yl)methyl}amino)benzamidine acetate, and the first eluting enantiomer (26.7 mg) of the title compound was obtained as a white solid.

¹H-NMR (CD₃OD) δ 1.91 (s, 3H) 2.85 (t, J=6.8 Hz, 2H) 3.28 (s, 3H) 3.55 (t, J=6.8 Hz, 2H) 3.77 (s, 3H) 3.83 (s, 3H) 5.78 (s, 1H) 6.85 (d, J=8.8 Hz, 2H) 7.00 (d, J=1.6 Hz, 1H) 7.09 (t, J=1.6 Hz, 1H) 7.30 (t, J=4.8 Hz, 1H) 7.59 (d, J=8.8 Hz, 2H) 8.76 (d, J=4.8 Hz, 2H)

HPLC retention time: 11 min

Example 130

(R) and (S)-4-{[(4-methoxy-8,9-dihydro-5,7-dioxabenzocyclohepten-2-yl)-(5-oxo-1-pyrimidin-2-yl-4,5-dihydro-1H-[1,2,4]triazol-3-yl)methyl]amino}benzamidine acetate (130a) 2-bromo-4-methoxy-8,9-dihydro-5,7-dioxabenzocycloheptene

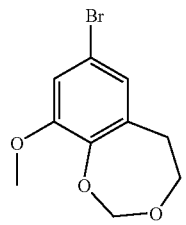

[Chemical Formula 338]

After dissolving 3 g of 2-allyl-4-bromo-6-methoxyphenol in 10 ml of DMF, 1.3 g of imidazole and 2 g of chlorotriisopropylsilane were added and the mixture was stirred at 50° C. for 4 hours. Next, 1N hydrochloric acid was added to the reaction mixture and extraction was performed with ethyl acetate. The organic layer was dried over anhydrous magnesium sulfate. The desiccating agent was filtered off, and the filtrate was concentrated under reduced pressure to give (2-allyl-4-bromo-6-methoxyphenoxy)triisopropylsilane.

Ozone gas was blown into a solution of this compound in 140 ml of a dichloromethane:methanol=1:1 mixed solvent for 40 minutes at −78° C. After blowing oxygen gas for 5 minutes to remove the dissolved ozone, 2 g of sodium borohydride was added. After stirring the mixture at room temperature for 2 hours, saturated aqueous ammonium chloride was added to the reaction mixture while cooling on ice. The reaction mixture was extracted with ethyl acetate and dried over anhydrous magnesium sulfate. The desiccating agent was filtered off, and the filtrate was concentrated under reduced pressure to give 2-(5-bromo-3-methoxy-2-triisopropylsilanyloxyphenyl)ethanol (3.808 g) as an oil.

After dissolving 1.6 g of this compound in 10 ml of THF, 5 ml of TBAF (1.0 M, THF solution) was added and the mixture was stirred at room temperature. Saturated aqueous ammonium chloride was added to the reaction mixture, and extraction was performed with ethyl acetate. The organic layer was dried over anhydrous magnesium sulfate. The desiccating agent was filtered off and the filtrate was concentrated under reduced pressure. The residue was purified by silica gel column chromatography (ethyl acetate-heptane) to give 4-bromo-2-(2-hydroxyethyl)-6-methoxyphenol as an oil.

To a solution of 898 mg of 4-bromo-2-(2-hydroxyethyl)-6-methoxyphenol in 10 ml of DMF there was added 1 g of sodium bistrimethylsilylamide while cooling on ice, and the mixture was stirred at room temperature for 30 minutes. After adding 1 ml of bromochloromethane to the reaction mixture, it was stirred at 80° C. for 20 hours under a nitrogen atmosphere. Saturated aqueous ammonium chloride was added to the reaction mixture, and extraction was performed with ethyl acetate. The organic layer was dried over anhydrous magnesium sulfate. The desiccating agent was filtered off and the filtrate was concentrated under reduced pressure. The residue was purified by silica gel column chromatography (ethyl acetate-heptane) to give the title compound (420 mg) as an oil.

¹H-NMR (CDCl₃) δ 2.96-2.99 (m, 2H) 3.78-3.82 (m, 2H) 3.84 (s, 3H) 5.04 (s, 2H) 6.89 (d, J=2.0 Hz, 1H) 6.92 (d, J=2.0 Hz, 1H)

(130b) 4-methoxy-8,9-dihydro-5,7-dioxabenzocycloheptene-2-carbaldehyde

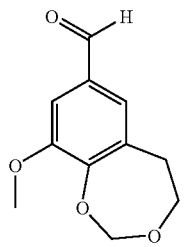

[Chemical Formula 339]

To a solution of 420 mg of 2-bromo-4-methoxy-8,9-dihydro-5,7-dioxa-benzocycloheptene in 10 ml of THF there was added dropwise 0.7 ml of n-butyllithium (2.66 M, hexane solution) at −70° C. under a nitrogen atmosphere. After stirring at −70° C. for 10 minutes, 0.5 ml of N-formylmorpholine was added and the temperature was raised from −70° C. to 0° C. over a period of 30 minutes. Saturated aqueous ammonium chloride was added to the reaction mixture, and extraction was performed with ethyl acetate. The organic layer was dried over anhydrous magnesium sulfate. The desiccating agent was filtered off and the filtrate was concentrated under reduced pressure. The residue was purified by silica gel column chromatography (ethyl acetate-heptane) to give the title compound (235 mg) as an oil.

$^1$H-NMR (CDCl$_3$) δ 3.11 (t, J=5.2 Hz, 2H) 3.87-3.89 (m, 2H) 3.92 (s, 3H) 5.12 (s, 2H) 7.27 (d, J=2.0 Hz, 1H) 7.33 (d, J=2.0 Hz, 1H) 9.86 (s, 1H)

(130c) (R) and (S)-4-{[(4-methoxy-8,9-dihydro-5,7-dioxa-benzocyclohepten-2-yl)-(5-oxo-1-pyrimidin-2-yl-4,5-dihydro-1H-[1,2,4]triazol-3-yl)methyl]amino}benzamidine acetate

[Chemical Formula 340]

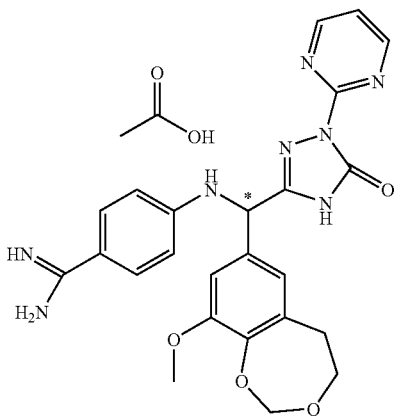

The same procedure was carried out as in Examples (21d)-(21k), except that 4-methoxy-8,9-dihydro-5,7-dioxa-benzocycloheptene-2-carbaldehyde was used instead of the 8-methoxy-4H-benzo[1,3]dioxine-6-carbaldehyde in Example (21d), to give the first eluting enantiomer of the title compound.

$^1$H-NMR (CD$_3$OD) δ 1.92 (s, 3H) 2.97 (t, J=4.0 Hz, 2H) 3.77 (dd, J=3.6, 6.0 Hz, 2H) 3.81 (s, 3H) 4.95 (s, 2H) 5.59 (s, 1H) 6.85 (d, J=8.8 Hz, 2H) 6.98 (d, J=2.0 Hz, 1H) 7.11 (d, J=2.0 Hz, 1H) 7.31 (t, J=5.2 Hz, 1H) 7.60 (d, J=8.8 Hz, 2H) 8.76 (d, J=5.2 Hz, 2H)

HPLC retention time: 13 min

Example 131

(R) and (S)-4-{[(3-cyanomethyl-4-fluoro-5-methoxyphenyl)-(5-oxo-1-pyrimidin-2-yl-4,5-dihydro-1H-[1,2,4]triazol-3-yl)methyl]amino}benzamidine acetate (131a) 4-fluoro-3-methoxy-5-triisopropylsilanyloxymethylbenzaldehyde

[Chemical Formula 341]

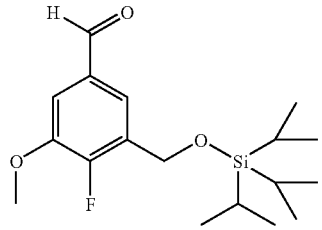

After dissolving 9.17 g of (4-fluoro-3-methoxyphenyl) methanol [CAS No. 128495-45-4] in 100 ml of DMF, 5 g of imidazole and 17 g of t-butyl-chlorodiphenylsilane were added and the mixture was stirred overnight at room temperature. Next, 1N hydrochloric acid was added to the reaction mixture, and extraction was performed with ethyl acetate. The organic layer was dried over anhydrous magnesium sulfate. The desiccating agent was filtered off and the filtrate was concentrated under reduced pressure. The residue was purified by silica gel column chromatography (ethyl acetate-heptane) to give t-butyl-(4-fluoro-3-methoxybenzyloxy)diphenylsilane as an oil.

To a solution of 20.4 g of this compound and 9.4 g of N,N,N',N',N''-pentamethyldiethylenetriamine in 60 ml of THF there was added dropwise 20 ml of n-butyllithium (2.66 M, hexane solution) at −78° C. under a nitrogen atmosphere. After stirring for 15 minutes, 6.5 ml of N-formylmorpholine was added and the mixture was stirred at room temperature for 20 minutes. Next, 1N hydrochloric acid was added to the reaction mixture and extraction was performed with ethyl acetate. The organic layer was dried over anhydrous magnesium sulfate. The desiccating agent was filtered off and the filtrate was concentrated under reduced pressure. The residue was purified by silica gel column chromatography (ethyl acetate-heptane) to give 5-(t-butyl-diphenylsilanyloxymethyl)-2-fluoro-3-methoxy-benzaldehyde as an oil.

$^1$H-NMR (CDCl$_3$) δ 1.10 (s, 9H) 3.86 (s, 3H) 4.75 (s, 2H) 7.23-7.27 (m, 2H) 7.35-7.45 (m, 6H) 7.64-7.66 (m, 4H) 10.33 (s, 1H)

To a solution of this compound in 150 ml of an ethanol:THF=1:1 mixed solvent there was added 2 g of sodium borohydride while cooling on ice. After stirring overnight at room temperature, 1N hydrochloric acid was added to the reaction mixture while cooling on ice. The reaction mixture was extracted with ethyl acetate and dried over anhydrous magnesium sulfate. The desiccating agent was filtered off, and the filtrate was concentrated under reduced pressure to give [5-(t-butyl-diphenylsilanyloxymethyl)-2-fluoro-3-methoxyphenyl]methanol (18.7 g) as an oil.

$^1$H-NMR (CDCl$_3$) δ 1.10 (s, 9H) 3.21 (s, 1H) 3.84 (s, 3H) 4.71 (s, 4H) 6.85 (d, J=4.8 Hz, 1H) 6.94 (d, J=8.6 Hz, 1H) 7.35-7.44 (m, 6H) 7.65-7.68 (m, 4H)

This compound was dissolved in 10 ml of DMF, and then 1 g of imidazole and 1 g of chlorotriisopropylsilane were added and the mixture was stirred at room temperature for 2 days. Next, 1N hydrochloric acid was added to the reaction mixture and extraction was performed with ethyl acetate. The organic layer was dried over anhydrous magnesium sulfate. The desiccating agent was filtered off and the filtrate was concentrated under reduced pressure.

After dissolving the residue in 200 ml of THF, 7.1 ml of tetrabutylammonium hydroxide (40%, aqueous solution) was added and the mixture was stirred at room temperature for 2 hours. Extraction was performed with t-butyl methyl ether. The organic layer was dried over anhydrous magnesium sulfate. The desiccating agent was filtered off and the filtrate was concentrated under reduced pressure. The residue was purified by silica gel column chromatography (ethyl acetate-heptane) to give (4-fluoro-3-methoxy-5-triisopropylsilanyloxymethyl-phenyl)-methanol (2.435 g) as an oil.

After dissolving this compound in 30 ml of dichloromethane, there were added 2 g of MS3A, 1.3 g of N-methylmorpholine-N-oxide and 130 mg of tetrabutylammonium perruthenate in that order and the mixture was stirred at room temperature for 2 hours. The reaction mixture was purified by silica gel chromatography (ethyl acetate-heptane) to give the title compound (2.103 g).

271

(131b) {2-(4-fluoro-3-hydroxymethyl-5-methoxyphenyl)-2-[4-(5-methyl-[1,2,4]oxadiazol-3-yl)phenylimino]-1-methylsulfanylethylidene}carbamic acid methyl ester

[Chemical Formula 342]

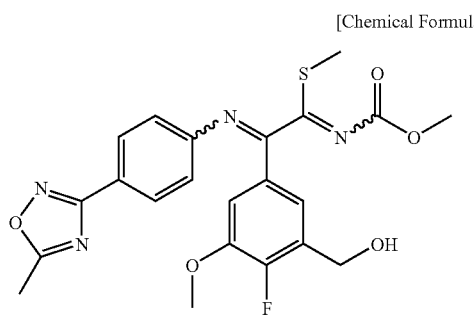

The same procedure was carried out as in Example (22b), except that 4-fluoro-3-methoxy-5-triisopropylsilanyloxymethylbenzaldehyde was used instead of the 3,4-dimethoxy-5-triisopropylsilanyloxymethylbenzaldehyde, to give the title compound.

Mass spectrum (ESI) m/z: 473 (M+H)$^+$ (131c) {2-(4-fluoro-3-cyanomethyl-5-methoxyphenyl)-2-[4-(5-methyl-[1,2,4]oxadiazol-3-yl)phenylimino]-1-methylsulfanylethylidene}carbamic acid methyl ester

[Chemical Formula 343]

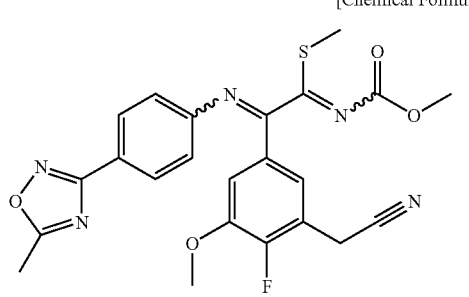

The same procedure was carried out as in Example (26a), except that {2-(4-fluoro-3-hydroxymethyl-5-methoxyphenyl)-2-[4-(5-methyl-[1,2,4]oxadiazol-3-yl)phenylimino]-1-methylsulfanylethylidene}carbamic acid methyl ester was used instead of the {2-(3,4-dimethoxy-5-hydroxymethylphenyl)-2-[4-(5-methyl-[1,2,4]oxadiazol-3-yl)phenylimino]-1-methylsulfanylethylidene}carbamic acid methyl ester, to give the title compound.

Mass spectrum (ESI) m/z: 482 (M+H)$^+$

272

(131d) (R) and (S)-4-{[(3-cyanomethyl-4-fluoro-5-methoxyphenyl)-(5-oxo-1-pyrimidin-2-yl-4,5-dihydro-1H-[1,2,4]triazol-3-yl)methyl]amino}benzamidine acetate

[Chemical Formula 344]

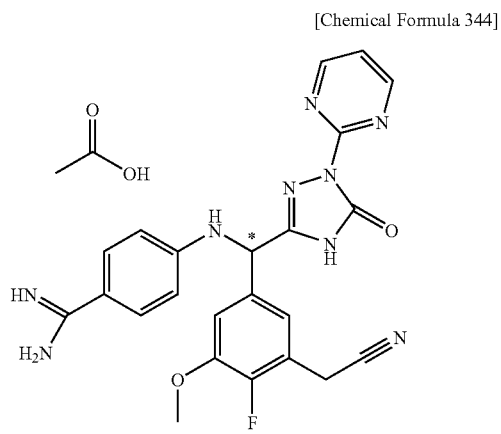

The same procedure was carried out as in Examples (21i)-(21k), except that {2-(4-fluoro-3-cyanomethyl-5-methoxyphenyl)-2-[4-(5-methyl-[1,2,4]oxadiazol-3-yl)phenylimino]-1-methylsulfanylethylidene}carbamic acid methyl ester was used instead of the {2-(8-methoxy-4H-benzo[1,3]dioxin-6-yl)-2-[4-(5-methyl-[1,2,4]oxadiazol-3-yl)phenylimino]-1-methylsulfanylethylidene}carbamic acid methyl ester in Example (21i), to give the first eluting enantiomer of the title compound.

$^1$H-NMR (CD$_3$OD) δ 1.92 (s, 3H) 3.88 (m, 5H) 5.62 (s, 1H) 6.85 (d, J=8.8 Hz, 2H) 7.19 (dd, J=2.0, 5.2 Hz, 1H) 7.27 (t, J=4.8 Hz, 1H) 7.33 (dd, J=2.0, 8.8 Hz, 1H) 7.60 (d, J=8.8 Hz, 2H) 8.76 (d, J=4.8 Hz, 2H)

HPLC retention time: 13 min

Example 132

(R) and (S)-4-({{(3-ethoxy-4-methoxyphenyl)-[1-(3-fluoro-pyridin-2-yl)-5-oxo-4,5-dihydro-1H-[1,2,4]triazol-3-yl]methyl}amino}benzamidine acetate

[Chemical Formula 345]

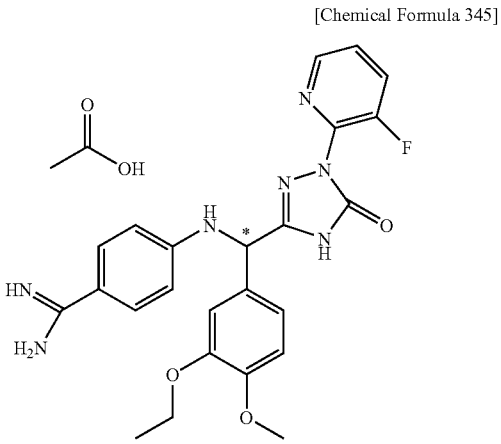

The same procedure was carried out as in Example (30d), except that {2-(3-ethoxy-4-methoxyphenyl)-2-[4-(5-methyl-

[1,2,4]oxadiazol-3-yl)phenylamino]-1-methylsulfanylethylidene}carbamic acid methyl ester (Example (17e)) was used instead of the {2-(9-methoxy-3,4-dihydro-2H-benzo[b][1,4]dioxepin-7-yl)-2-[4-(5-methyl-[1,2,4]oxadiazol-3-yl)phenylimino]-1-methylsulfanylethylidene}carbamic acid methyl ester, to give the first eluting enantiomer of the title compound.

$^1$H-NMR (CD$_3$OD) δ 1.38 (t, J=6.8 Hz, 3H) 1.92 (s, 3H) 3.82 (s, 3H) 4.05 (q, J=6.8 Hz, 2H) 5.60 (s, 1H) 6.85 (d, J=8.8 Hz, 2H) 6.96 (d, J=8.4 Hz, 1H) 7.07 (dd, J=2.4, 8.4 Hz, 1H) 7.12 (d, J=1.6 Hz, 1H) 7.53 (quint, J=4.8 Hz, 1H) 7.60 (d, J=8.8 Hz, 2H) 7.82 (dt, J=1.2, 8.4 Hz, 1H) 8.37 (d, J=4.4 Hz, 1H)

HPLC retention time: 8 min

Example 133

(R) and (S)-4-({[1-(3-fluoropyridin-2-yl)-5-oxo-4,5-dihydro-1H-[1,2,4]triazol-3-yl]-(8-methoxy-4H-benzo[1,3]dioxin-6-yl)methyl}amino)benzamidine acetate

[Chemical Formula 346]

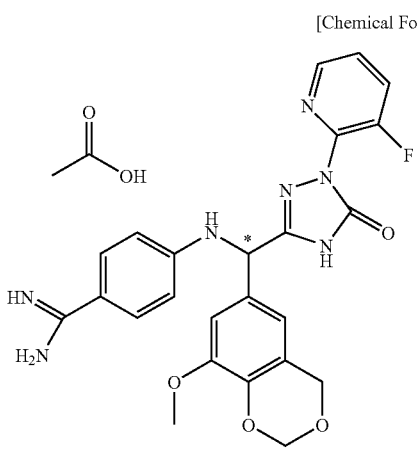

The same procedure was carried out as in Example (30d), except that {2-(8-methoxy-4H-benzo[1,3]dioxin-6-yl)-2-[4-(5-methyl-[1,2,4]oxadiazol-3-yl)phenylimino]-1-methylsulfanylethylidene}carbamic acid methyl ester (Example (21h)) was used instead of the {2-(9-methoxy-3,4-dihydro-2H-benzo[b][1,4]dioxepin-7-yl)-2-[4-(5-methyl-[1,2,4]oxadiazol-3-yl)phenylimino]-1-methylsulfanylethylidene}carbamic acid methyl ester, to give the first eluting enantiomer of the title compound.

$^1$H-NMR (CD$_3$OD) δ 1.88 (s, 3H) 3.81 (s, 3H) 4.85 (m, 2H) 5.23 (s, 2H) 5.56 (s, 1H) 6.80 (d, J=2.0 Hz, 1H) 6.84 (d, J=8.8 Hz, 2H) 7.04 (d, J=2.0 Hz, 1H) 7.50-7.55 (m, 1H) 7.60 (d, J=8.8 Hz, 2H) 7.81 (dt, J=1.2, 8.4 Hz, 1H) 8.37 (d, J=4.4 Hz, 1H)

HPLC retention time: 8 min

Example 134

4-({[1-(3-bromopyridin-2-yl)-5-oxo-4,5-dihydro-1H-[1,2,4]triazol-3-yl]-(2-fluoro-4,5-dimethoxyphenyl)methyl}amino)benzamidine acetate

[Chemical Formula 347]

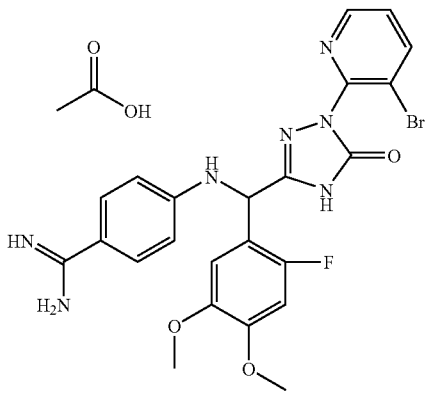

The same procedure was carried out as in Examples (1e)-(1g), except that (3-bromopyridin-2-yl)hydrazine was used instead of the 2-hydrazinobenzoic acid hydrochloride in Example (1e), to give the title compound.

$^1$H-NMR (CD$_3$OD) δ 1.92 (s, 3H) 3.77 (s, 3H) 3.82 (s, 3H) 5.91 (s, 1H) 6.85 (d, J=11.2 Hz, 1H) 6.86 (d, J=8.8 Hz, 2H) 7.07 (d, J=7.2 Hz, 1H) 7.43 (dd, J=4.8, 8.0 Hz, 1H) 7.62 (d, J=8.8 Hz, 2H) 8.23 (dd, J=1.6, 8.0 Hz, 1H) 8.52 (dd, J=1.6, 4.8 Hz, 1H)

Mass spectrum (ESI) m/z: 542 (M+H)$^+$

Example 135

(2-{3-[(4-carbamimidoylphenylamino)-(3-dimethylcarbamoylmethoxy-5-ethyl-2-fluorophenyl)methyl]-5-oxo-4,5-dihydro-1H-[1,2,4]triazol-1-yl}phenyl)carbamic acid methyl ester trifluoroacetate (135a) 5-ethyl-2-fluorophenol

[Chemical Formula 348]

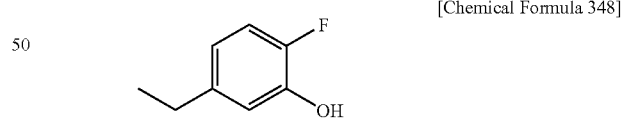

A solution of 15.5 g of 4-ethylfluorobenzene and 14.6 g of N,N,N'N'-tetramethylethylenediamine in 500 ml of THF was cooled to −75° C. under a nitrogen atmosphere, and then 126 ml of s-butyllithium (0.99M, cyclohexane solution) was added and the mixture was stirred for 2 hours. After then adding 28 ml of trimethyl borate, the reaction mixture was warmed to room temperature and 14.4 ml of acetic acid was added. After stirring for 30 minutes, the reaction mixture was cooled to 0° C., and then 28.4 ml of 30% aqueous hydrogen peroxide was added and the mixture was stirred at room temperature for 18 hours. Next, 500 ml of saturated aqueous sodium sulfite was added to the reaction mixture and extraction was performed with 1 liter of diethyl ether. The organic layer was washed with 500 ml of water and 500 ml of saturated aqueous sodium chloride in that order and dried over anhydrous magnesium sulfate, the desiccating agent was filtered, and the filtrate was concentrated under reduced pressure. The residue was subjected to distillation to give the title compound (16.35 g) as a colorless liquid (boiling point: 76-80° C., 17 mmHg).

$^1$H-NMR (CDCl$_3$) δ 1.30 (t, J=7.7 Hz, 3H) 2.57 (q, J=7.7 Hz, 2H) 6.65 (ddd, J=8.5, 4.7, 2.1 Hz, 1H) 6.83 (dd, J=8.5, 2.1 Hz, 1H) 6.95 (dd, J=10.6, 8.5 Hz, 1H)

(135b) t-butyl-(5-ethyl-2-fluorophenoxy)dimethylsilane

[Chemical Formula 349]

After adding 9.16 g of imidazole and 19.4 g of t-butyldimethylchlorosilane to a solution of 16.4 g of 5-ethyl-2-fluorophenol in 40 ml of DMF, the reaction mixture was stirred at room temperature for 18 hours. After then adding 500 ml of diethyl ether and 500 ml of water to the reaction mixture, the organic layer was washed twice with 100 ml of water and once with 100 ml of saturated aqueous sodium chloride in that order and then dried over anhydrous magnesium sulfate, the desiccating agent was filtered off, and the filtrate was concentrated under reduced pressure. The residue was subjected to distillation to give the title compound (25.38 g) as a colorless liquid (boiling point: 133-135° C., 20 mmHg).

$^1$H-NMR (CDCl$_3$) δ 0.19 (s, 6H) 1.01 (s, 9H) 1.38 (t, J=7.7 Hz, 3H) 2.55 (q, J=7.7 Hz, 2H) 6.67 (ddd, J=8.3, 4.3, 2.2 Hz, 1H) 6.72 (dd, J=8.3, 2.2 Hz, 1H) 6.94 (dd, J=10.8, 8.3 Hz, 1H)

(135c) 3-(t-butyldimethylsilanyloxy)-5-ethyl-2-fluorobenzaldehyde

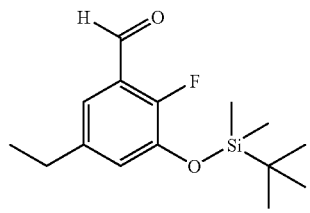

[Chemical Formula 350]

A solution of 12.7 g of t-butyl-(5-ethyl-2-fluorophenoxy)dimethylsilane and 7.5 g of N,N,N'N'-tetramethylethylenediamine in 250 ml of THF was cooled to −75° C. under a nitrogen atmosphere, and then 55.6 ml of s-butyllithium (0.99 M, cyclohexane solution) was added and the mixture was stirred for 2 hours. After adding 7.74 ml of DMF and stirring at −75° C. for 1 hour, the temperature was allowed to rise to room temperature. Next, 500 ml of diethyl ether and 500 ml of a 5% aqueous ammonium chloride were added to the reaction mixture, the organic layer was washed twice with 500 ml of water and once with 500 ml of saturated aqueous sodium chloride in that order, and the aqueous layer was extracted with 100 ml of diethyl ether. The organic layers were combined and dried over anhydrous magnesium sulfate, the desiccating agent was filtered off, and the filtrate was concentrated under reduced pressure. The residue was purified by silica gel column chromatography (ethyl acetate-heptane) to give the title compound (12.6 g) as a white solid.

$^1$H-NMR (CDCl$_3$) δ 0.24 (s, 6H) 1.01 (s, 9H) 1.24 (t, J=7.7 Hz, 3H) 2.60 (q, J=7.7 Hz, 2H) 6.99 (dd, J=10.0, 2.2 Hz, 1H) 7.25 (dd, J=4.8, 2.2 Hz, 1H) 10.30 (s, 1H)

(135d) {2-[3-(t-butyldimethylsilanyloxy)-5-ethyl-2-fluorophenyl]-2-[4-(5-methyl-[1,2,4]oxadiazol-3-yl)phenylimino]-1-methylsulfanylethylidene}carbamic acid methyl ester

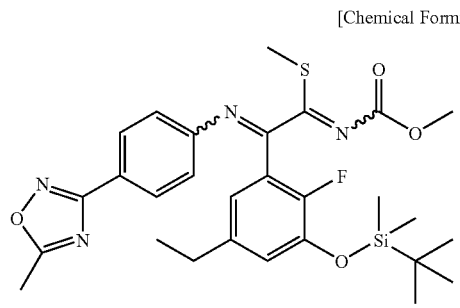

[Chemical Formula 351]

The same procedure was carried out as in Examples (1a)-(1d), except that 3-(t-butyldimethylsilanyloxy)-5-ethyl-2-fluorobenzaldehyde was used instead of the 2-fluoro-4,5-dimethoxybenzaldehyde in Example (1a), to give the title compound (0.76 g) as a light yellow oil.

$^1$H-NMR (CDCl$_3$) Two main isomers:

δ 0.20 (s, 6H) 0.98 (s, 9H) 1.10 (t, J=7.8 Hz, 3H) 2.49 (s, 3H) 2.50 (q, J=7.8 Hz, 2H) 2.64 (s, 3H) 3.63 (s, 3H) 6.55 (dd, J=5.6, 2.3 Hz, 1H) 6.71 (d, J=8.3, 2.3 Hz, 1H) 6.83 (d, J=8.3 Hz, 2H) 7.88 (d, J=8.3 Hz, 2H)

δ 0.19 (s, 6H) 0.97 (s, 9H) 1.10 (t, J=7.8 Hz, 3H) 2.36 (s, 3H) 2.50 (q, J=7.8 Hz, 2H) 2.68 (s, 3H) 3.57 (s, 3H) 6.43 (dd, J=5.6, 2.3 Hz, 1H) 6.92 (d, J=8.3, 2.3 Hz, 1H) 7.16 (d, J=8.3 Hz, 2H) 8.04 (d, J=8.3 Hz, 2H)

(135e) {2-(5-ethyl-2-fluoro-3-hydroxyphenyl)-2-[4-(5-methyl-[1,2,4]oxadiazol-3-yl)phenylimino]-1-methylsulfanylethylidene}carbamic acid methyl ester

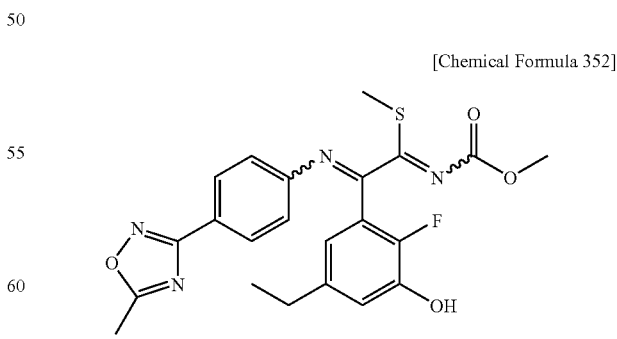

[Chemical Formula 352]

To a solution of 0.76 g of {2-[3-(t-butyldimethylsilanyloxy)-5-ethyl-2-fluorophenyl]-2-[4-(5-methyl-[1,2,4]oxadiazol-3-yl)phenylimino]-1-methylsulfanylethylidene}carbamic acid methyl ester in 30 ml of THF there was added 1.6 ml of TBAF (1.0 M, THF solution) under a nitrogen atmosphere. The reaction mixture was stirred at room temperature for 4 hours, and then 200 ml of ethyl acetate and 100 ml of water were added. The organic layer was washed twice with 100 ml of water and once with 100 ml of saturated aqueous sodium chloride in that order and dried over anhydrous magnesium sulfate, the desiccating agent was filtered, and the filtrate was concentrated under reduced pressure. The residue was purified by silica gel column chromatography (ethyl acetate-heptane) to give the title compound (0.41 g) as a white solid.

$^1$H-NMR (CDCl$_3$) Two main isomers:

δ 1.26 (t, J=7.8 Hz, 3H) 2.46 (s, 3H) 2.48 (q, J=7.8 Hz, 2H) 2.63 (s, 3H) 3.58 (s, 3H) 6.48 (dd, J=5.6, 2.1 Hz, 1H) 6.81 (d, J=8.1, 2.1 Hz, 1H) 6.82 (d, J=8.3 Hz, 2H) 7.89 (d, J=8.3 Hz, 2H)

δ 1.24 (t, J=7.8 Hz, 3H) 2.34 (s, 3H) 2.65 (q, J=7.8 Hz, 2H) 2.66 (s, 3H) 3.58 (s, 3H) 7.02 (dd, J=8.2, 2.2 Hz, 1H) 7.14 (d, J=8.3 Hz, 2H) 7.16 (dd, J=6.2, 2.2 Hz, 1H) 8.03 (d, J=8.3 Hz, 2H)

(135f) {2-(3-dimethylcarbamoylmethoxy-5-ethyl-2-fluorophenyl)-2-[4-(5-methyl-[1,2,4]oxadiazol-3-yl)phenylimino]-1-methylsulfanylethylidene}carbamic acid methyl ester

[Chemical Formula 353]

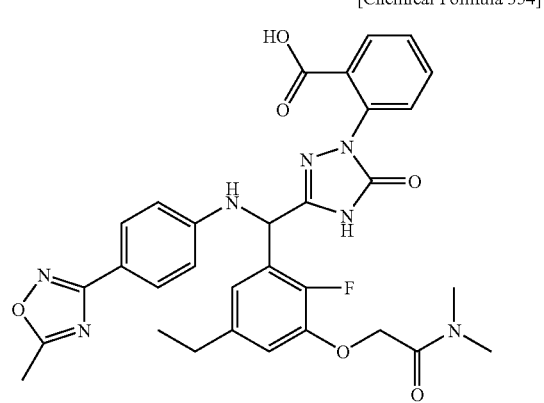

After adding 0.163 g of potassium carbonate and 0.14 ml of 2-chloro-N,N-dimethylacetamide to a solution of 0.41 g of {2-(5-ethyl-2-fluoro-3-hydroxyphenyl)-2-[4-(5-methyl-[1,2,4]oxadiazol-3-yl)phenylimino]-1-methylsulfanylethylidene}carbamic acid methyl ester in 15 ml of DMF, the reaction mixture was stirred at room temperature for 60 hours, and then 200 ml of ethyl acetate and 100 ml of water were added. The organic layer was washed twice with 100 ml of water and once with 100 ml of saturated aqueous sodium chloride in that order, and dried over anhydrous magnesium sulfate. The desiccating agent was filtered, and the filtrate was concentrated under reduced pressure. The residue was purified by silica gel column chromatography (ethyl acetate-heptane) to give the title compound (0.41 g) as a light yellow solid.

$^1$H-NMR (CDCl$_3$) Two main isomers:

δ 1.26 (t, J=7.8 Hz, 3H) 2.46 (s, 3H) 2.48 (q, J=7.8 Hz, 2H) 2.63 (s, 3H) 2.91 (s, 3H) 2.96 (s, 3H) 3.58 (s, 3H) 4.64 (s, 2H) 6.57 (dd, J=5.6, 2.1 Hz, 1H) 6.82 (d, J=8.3 Hz, 2H) 6.87 (dd, J=8.1, 2.1 Hz, 1H) 7.88 (d, J=8.3 Hz, 2H)

δ 1.24 (t, J=7.8 Hz, 3H) 2.34 (s, 3H) 2.65 (q, J=7.8 Hz, 2H) 2.67 (s, 3H) 2.99 (s, 3H) 3.12 (s, 3H) 3.56 (s, 3H) 4.78 (s, 2H) 7.07 (dd, J=8.2, 2.2 Hz, 1H) 7.14 (d, J=8.3 Hz, 2H) 7.33 (dd, J=6.2, 2.2 Hz, 1H) 8.04 (d, J=8.3 Hz, 2H)

(135g) 2-(3-{(3-dimethylcarbamoylmethoxy-5-ethyl-2-fluorophenyl)-[4-(5-methyl-[1,2,4]oxadiazol-3-yl)phenylamino]methyl}-5-oxo-4,5-dihydro-1H-[1,2,4]triazol-1-yl)benzoic acid

[Chemical Formula 354]

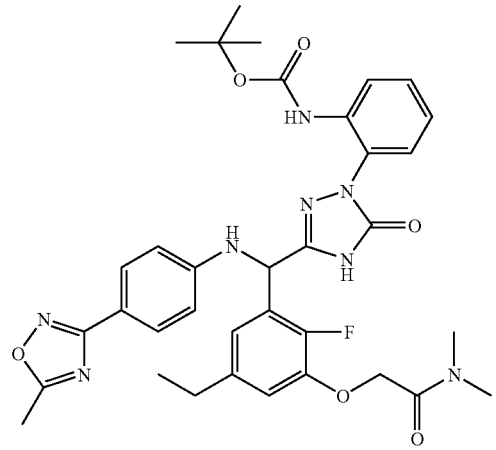

The same procedure was carried out as in Example (2f), except that 0.409 g of {2-(3-dimethylcarbamoylmethoxy-5-ethyl-2-fluorophenyl)-2-[4-(5-methyl-[1,2,4]oxadiazol-3-yl)phenylimino]-1-methylsulfanylethylidene}carbamic acid methyl ester and 0.160 g of 2-hydrazinobenzoic acid hydrochloride were used instead of respectively the [2-(4-cyanophenylimino)-2-(2-fluoro-3,5-dimethoxyphenyl)-1-methylsulfanylethylidene]carbamic acid methyl ester and (1-oxypyridin-2-yl)hydrazine, to give the title compound (0.280 g) as a white solid.

$^1$H-NMR (CD$_3$OD) δ 1.17 (t, J=7.7 Hz, 3H) 2.58 (q, J=7.7 Hz, 2H) 2.59 (s, 3H) 2.95 (s, 3H) 3.07 (s, 3H) 4.89 (s, 2H) 5.93 (s, 1H) 6.81 (d, J=8.4 Hz, 2H) 6.89 (dd, J=8.0, 2.2 Hz, 1H) 6.98 (dd, J=5.5, 2.2 Hz, 1H) 7.48 (td, J=7.3, 1.5 Hz, 1H) 7.49 (ddd, J=7.6, 1.5, 0.8 Hz, 1H) 7.63 (ddd, J=7.6, 7.3, 1.8 Hz, 1H) 7.79 (d, J=8.4 Hz, 2H) 7.95 (ddd, J=7.3, 1.8, 0.8 Hz, 1H)

(135h) [2-(3-{(3-dimethylcarbamoylmethoxy-5-ethyl-2-fluorophenyl)-[4-(5-methyl-[1,2,4]oxadiazol-3-yl)phenylamino]methyl}-5-oxo-4,5-dihydro-1H-[1,2,4]triazol-1-yl)phenyl]carbamic acid t-butyl ester

[Chemical Formula 355]

A solution of 0.320 g of 2-(3-{(3-dimethylcarbamoyl-methoxy-5-ethyl-2-fluorophenyl)-[4-(5-methyl-[1,2,4]oxadiazol-3-yl)phenylamino]methyl}-5-oxo-4,5-dihydro-1H-[1,2,4]triazol-1-yl)benzoic acid, 0.098 ml of triethylamine and 0.151 ml of diphenylphosphorylazide in 10 ml of t-butanol was stirred under a nitrogen atmosphere at room temperature for 20 hours and then at 70° C. for 36 hours. After adding 100 ml of ethyl acetate and 50 ml of water to the reaction mixture, the organic layer was dried over anhydrous magnesium sulfate, the desiccating agent was filtered off and the filtrate was concentrated under reduced pressure. The residue was purified by silica gel column chromatography (methanol-ethyl acetate) to give the title compound (0.135 g) as a white solid.

$^1$H-NMR (CD$_3$OD) δ 1.17 (t, J=7.7 Hz, 3H) 1.48 (s, 9H) 2.59 (q, J=7.7 Hz, 2H) 2.60 (s, 3H) 2.96 (s, 3H) 3.09 (s, 3H) 4.90 (s, 2H) 5.98 (s, 1H) 6.81 (d, J=8.4 Hz, 2H) 6.90 (dd, J=8.3, 2.2 Hz, 1H) 6.98 (dd, J=5.7, 2.2 Hz, 1H) 7.18 (td, J=8.0, 1.7 Hz, 1H) 7.35 (td, J=8.0, 1.7 Hz, 1H) 7.40 (dd, J=8.0, 1.7 Hz, 1H) 7.79 (d, J=8.4 Hz, 2H) 7.79 (dd, J=8.0, 1.7 Hz, 1H)

(135i) 2-(3-{[1-(2-aminophenyl)-5-oxo-4,5-dihydro-1H-[1,2,4]triazol-3-yl]-[4-(5-methyl-[1,2,4]oxadiazol-3-yl)phenylamino]methyl}-5-ethyl-2-fluorophenoxy-N,N-dimethylacetamide

[Chemical Formula 356]

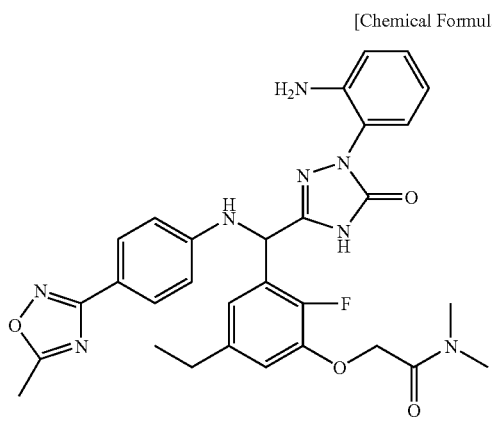

After adding 2 ml of trifluoroacetic acid to a solution of 0.135 g of [2-(3-{(3-dimethylcarbamoylmethoxy-5-ethyl-2-fluorophenyl)-[4-(5-methyl-[1,2,4]oxadiazol-3-yl)phenylamino]methyl}-5-oxo-4,5-dihydro-1H-[1,2,4]triazol-1-yl)phenyl]carbamic acid t-butyl ester in 10 ml of dichloromethane, the reaction mixture was stirred at room temperature for 4 hours, and the solvent was removed under reduced pressure. Next, 50 ml of ethyl acetate and 5 ml of 5% aqueous potassium carbonate were added to the residue, and the organic layer was washed with 20 ml of water and 20 ml of saturated aqueous sodium chloride in that order. The aqueous layer was extracted with 50 ml of ethyl acetate, and then the organic layers were combined and dried over anhydrous magnesium sulfate, the desiccating agent was filtered off and the filtrate was concentrated under reduced pressure. The title compound (0.100 g) was obtained as a white solid.

$^1$H-NMR (CD$_3$OD) δ 1.17 (t, J=7.7 Hz, 3H) 2.58 (q, J=7.7 Hz, 2H) 2.59 (s, 3H) 2.96 (s, 3H) 3.09 (s, 3H) 4.90 (s, 2H) 5.96 (s, 1H) 6.75 (td, J=7.8, 1.5 Hz, 1H) 6.81 (d, J=8.5 Hz, 2H) 6.87 (dd, J=7.8, 1.5 Hz, 1H) 6.89 (dd, J=8.5, 2.2 Hz, 1H) 6.98 (td, J=5.6, 2.2 Hz, 1H) 7.13 (td, J=7.8, 1.5 Hz, 1H) 7.22 (dd, J=7.8, 1.5 Hz, 1H) 7.79 (d, J=8.5 Hz, 2H)

(135j) (2-{3-[4-(carbamimidoylphenylamino)-(3-dimethylcarbamoylmethoxy-5-ethyl-2-fluorophenyl)methyl]-5-oxo-4,5-dihydro-1H-[1,2,4]triazol-1-yl}phenyl)carbamic acid methyl ester trifluoroacetate

[Chemical Formula 357]

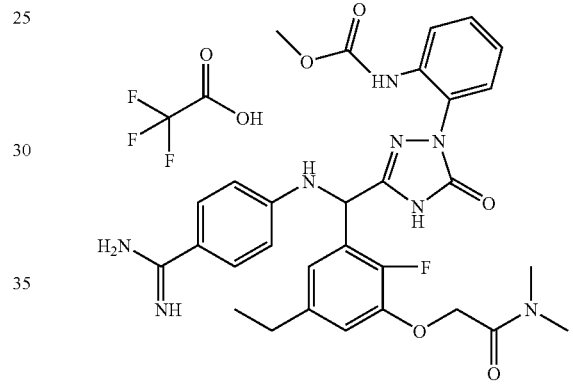

A solution of 36 mg of 2-(3-{[1-(2-aminophenyl)-5-oxo-4,5-dihydro-1H-[1,2,4]triazol-1-yl]-[4-(5-methyl-[1,2,4]oxadiazol-3-yl)phenylamino]methyl}-5-ethyl-2-fluorophenoxy-N,N-dimethylacetamide in 6 ml of dichloromethane was cooled to 0° C., and then 12 µl of 2,4,6-collidine and 6 µl of methyl chloroformate were added and the reaction mixture was stirred at room temperature for 15 hours. The solvent was removed under reduced pressure, the residue was dissolved in 2 ml of methanol, 2 ml of water and 2 ml of acetic acid, 50 mg of iron powder was added, and the mixture was heated at 60° C. for 20 hours. After filtering the reaction mixture, it was purified by reverse-phase high performance liquid chromatography (acetonitrile-water, 0.1% trifluoroacetic acid) to give the title compound (0.015 g) as a white solid.

$^1$H-NMR (CD$_3$OD) δ 1.18 (t, J=7.8 Hz, 3H) 2.59 (q, J=7.8 Hz, 2H) 2.98 (s, 3H) 3.10 (s, 3H) 3.69 (s, 3H) 4.91 (s, 2H) 6.03 (s, 1H) 6.87 (d, J=8.4 Hz, 2H) 6.90 (dd, J=7.3, 1.2 Hz, 1H) 6.93 (dd, J=6.3, 1.2 Hz, 1H) 7.19 (td, J=8.2, 1.4 Hz, 1H) 7.36 (td, J=8.2, 1.4 Hz, 1H) 7.43 (dd, J=8.2, 1.4 Hz, 1H) 7.65 (d, J=8.4 Hz, 2H) 7.66 (dd, J=8.2, 1.4 Hz, 1H)

Example 136

(R) and (S)-4-({[1-(3-aminopyridin-2-yl)-5-oxo-4,5-dihydro-1H-[1,2,4]triazol-3-yl]-[2-fluoro-3-(2-fluoroethoxy)-5-methoxyphenyl]methyl}amino)benzamidine acetate (136a) {2-(4-cyanophenylimino)-2-[2-fluoro-3-(2-fluoroethoxy)-5-methoxyphenyl]-1-methylsulfanylethylidene)carbamic acid methyl ester

[Chemical Formula 358]

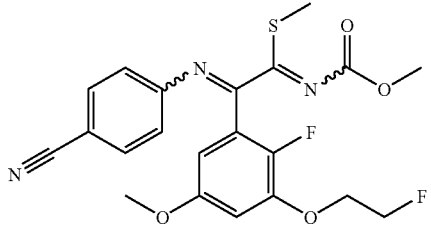

The same procedure was carried out as in Examples (2a)-(2e), except that 2.16 g of 2-fluoro-3-(2-fluoroethoxy)-5-methoxybenzaldehyde was used instead of the 2-fluoro-3,5-dimethoxybenzaldehyde in Example (2a), to give the title compound as a white solid.

$^1$H-NMR (CDCl$_3$) Two isomers:

δ 2.34 and 2.47 (s, 3H) 3.61 and 3.64 (s, 3H) 3.67 and 3.82 (s, 3H) 4.14 and 4.20 (m, 1H) 4.25 and 4.31 (m, 1H) 4.64 and 4.71 (m, 1H) 4.76 and 4.83 (m, 1H) 6.20 and 6.99 (t, J=3.6 Hz, 1H) 6.54 and 6.73 (dd, J=6.3, 3.6 Hz, 1H) 6.82 and 7.09 (d, J=8.4 Hz, 2H) 7.50 and 7.61 (d, J=8.4 Hz, 2H)

(136b) 4-({[1-(3-aminopyridin-2-yl)-5-oxo-4,5-dihydro-1H-[1,2,4]triazol-3-yl]-[2-fluoro-3-(2-fluoroethoxy)-5-methoxyphenyl]methyl}amino)benzamidine trifluoroacetate

[Chemical Formula 359]

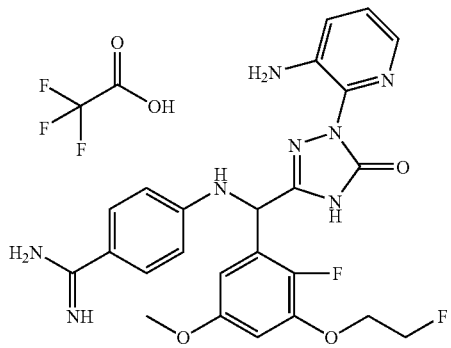

The same procedure was carried out as in Examples (2f)-(2h), except that {2-(4-cyanophenylimino)-2-[2-fluoro-3-(2-fluoroethoxy)-5-methoxyphenyl]-1-methylsulfanylethylidene}carbamic acid methyl ester and (3-nitropyridin-2-yl)hydrazine [CAS No. 15367-16-5] were used instead of respectively the [2-(4-cyanophenylimino)-2-(2-fluoro-3,5-dimethoxyphenyl)-1-methylsulfanylethylidene]carbamic acid methyl ester in Example (2f) and (1-oxypyridin-2-yl)hydrazine in Example (2f), to give the title compound.

$^1$H-NMR (CD$_3$OD) δ 3.74 (s, 3H) 4.25 (m, 1H) 4.32 (m, 1H) 4.67 (m, 1H) 4.79 (m, 1H) 6.05 (s, 1H) 6.65 (dd, J=5.3, 2.1 Hz, 1H) 6.69 (dd, J=7.0, 2.1 Hz, 1H) 6.88 (d, J=8.7 Hz, 2H) 7.29 (dd, J=8.0, 5.9 Hz, 1H) 7.41 (dd, J=8.0, 1.3 Hz, 1H) 7.65 (d, J=8.7 Hz, 2H) 7.84 (dd, J=5.9, 1.3 Hz, 1H)

(136c) (R) and (S)-4-({[1-(3-aminopyridin-2-yl)-5-oxo-4,5-dihydro-1H-[1,2,4]triazol-3-yl]-[2-fluoro-3-(2-fluoroethoxy)-5-methoxyphenyl]methyl}amino) benzamidine acetate

[Chemical Formula 360]

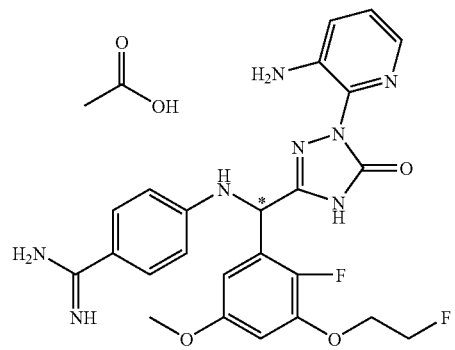

A SUMICHIRAL OA-2500 column was used for optical resolution of 18 mg of 4-({[1-(3-aminopyridin-2-yl)-5-oxo-4,5-dihydro-1H-[1,2,4]triazol-3-yl]-[2-fluoro-3-(2-fluoroethoxy)-5-methoxyphenyl]methyl}amino)benzamidine trifluoroacetate, and the first eluting enantiomer (5.9 mg) of the title compound was obtained as a white solid.

$^1$H-NMR (CD$_3$OD) δ 1.91 (s, 3H) 3.72 (s, 3H) 4.23 (m, 1H) 4.30 (m, 1H) 4.67 (m, 1H) 4.79 (m, 1H) 5.97 (s, 1H) 6.63 (dd, J=7.1, 2.4 Hz, 1H) 6.68 (dd, J=4.8, 2.4 Hz, 1H) 6.85 (d, J=8.7 Hz, 2H) 7.20 (dd, J=8.1, 4.7 Hz, 1H) 7.32 (dd, 8.1, 1.2 Hz, 1H) 7.61 (d, J=8.7 Hz, 2H) 7.81 (dd, 4.7, 1.2 Hz, 1H)

HPLC retention time: 7 min

Example 137

(R) and (S)-4-({[1-(3-aminopyridin-2-yl)-5-oxo-4,5-dihydro-1H-[1,2,4]triazol-3-yl]-(2-fluoro-3,5-dimethoxyphenyl)methyl}amino)benzamidine acetate (137a) 4-({[1-(3-aminopyridin-2-yl)-5-oxo-4,5-dihydro-1H-[1,2,4]triazol-3-yl]-(2-fluoro-3,5-dimethoxyphenyl)methyl}amino)benzamidine trifluoroacetate

[Chemical Formula 361]

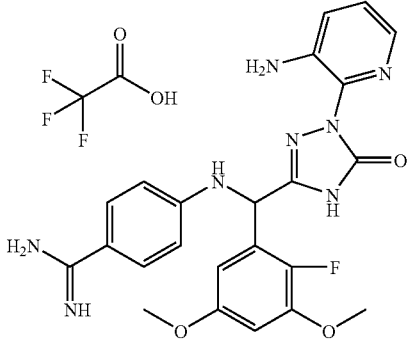

The same procedure was carried out as in Examples (2f)-(2h), except that (3-nitropyridin-2-yl)hydrazine was used instead of the (1-oxypyridin-2-yl)hydrazine in Example (2f), to give the title compound.

$^1$H-NMR (CD$_3$OD) δ 3.74 (s, 3H) 3.86 (s, 3H) 6.04 (s, 1H) 6.59 (dd, J=5.2, 2.4 Hz, 1H) 6.66 (dd, J=6.8, 2.4 Hz, 1H) 6.87

(d, J=8.7 Hz, 2H) 7.29 (dd, J=8.0, 5.6 Hz, 1H) 7.41 (dd, J=8.0, 1.2 Hz, 1H) 7.64 (d, J=8.7 Hz, 2H) 7.84 (dd, J=5.6, 1.2 Hz, 1H)

(137b) (R) and (S)-4-({[1-(3-aminopyridin-2-yl)-5-oxo-4,5-dihydro-1H-[1,2,4]triazol-3-yl]-(2-fluoro-3,5-dimethoxyphenyl)methyl}amino)benzamidine trifluoroacetate

[Chemical Formula 362]

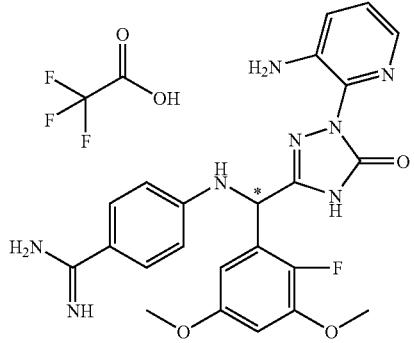

A SUMICHIRAL OA-2500 column was used for optical resolution of 8 mg of 4-({[1-(3-aminopyridin-2-yl)-5-oxo-4,5-dihydro-1H-[1,2,4]triazol-3-yl]-(2-fluoro-3,5-dimethoxyphenyl)methyl}amino)benzamidine trifluoroacetate, and the first eluting enantiomer (2.8 mg) of the title compound was obtained as a white solid.

$^1$H-NMR (CD$_3$OD) δ 3.74 (s, 3H) 3.86 (s, 3H) 6.04 (s, 1H) 6.59 (dd, J=5.2, 2.4 Hz, 1H) 6.66 (dd, J=6.8, 2.4 Hz, 1H) 6.87 (d, J=8.7 Hz, 2H) 7.29 (dd, J=8.0, 5.6 Hz, 1H) 7.41 (dd, J=8.0, 1.2 Hz, 1H) 7.64 (d, J=8.7 Hz, 2H) 7.84 (dd, J=5.6, 1.2 Hz, 1H)

HPLC retention time: 7 min

Example 138

4-({[1-(3-aminopyridin-2-yl)-5-oxo-4,5-dihydro-1H-[1,2,4]triazol-3-yl]-(2-fluoro-4,5-dimethoxyphenyl)methyl}amino)benzamidine trifluoroacetate (138a) 5-{(2-fluoro-4,5-dimethoxyphenyl)-[4-(5-methyl-[1,2,4]oxadiazol-3-yl)phenylamino]methyl}-2-(3-nitropyridin-2-yl)-2,4-dihydro-1H-[1,2,4]triazol-3-one

[Chemical Formula 363]

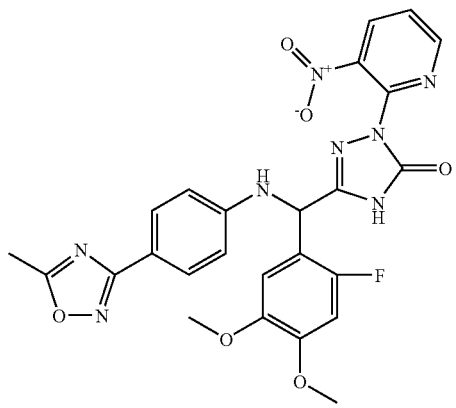

The same procedure was carried out as in Example (2f), except that (3-nitropyridin-2-yl)hydrazine and 182 mg of {2-(2-fluoro-4,5-dimethoxyphenyl)-2-[4-(5-methyl-[1,2,4]oxadiazol-3-yl)phenylimino]-1-methanesulfanylethylidene}carbamic acid methyl ester (Example (1d)) were used instead of respectively the (1-oxypyridin-2-yl)hydrazine and [2-(4-cyanophenylimino)-2-(2-fluoro-3,5-dimethoxyphenyl) 1-methylsulfanylethylidene] carbamic acid methyl ester, to give the title compound (104 mg).

$^1$H-NMR (CD$_3$OD) δ 2.59 (s, 3H) 3.81 (s, 3H) 3.84 (s, 3H) 5.93 (s, 1H) 6.83 (d, J=8.8 Hz, 2H) 6.85 (d, J=10.4 Hz, 1H) 7.07 (d, J=7.6 Hz, 1H) 7.65 (dd, J=8.1, 4.5 Hz, 1H) 7.80 (d, J=8.8 Hz, 2H) 8.49 (dd, J=8.1, 1.3 Hz, 1H) 8.77 (dd, J=4.5, 1.3 Hz, 1H)

(138b) 4-({[1-(3-aminopyridin-2-yl)-5-oxo-4,5-dihydro-1H-[1,2,4]triazol-3-yl]-(2-fluoro-4,5-dimethoxyphenyl)methyl}amino)benzamidine trifluoroacetate

[Chemical Formula 364]

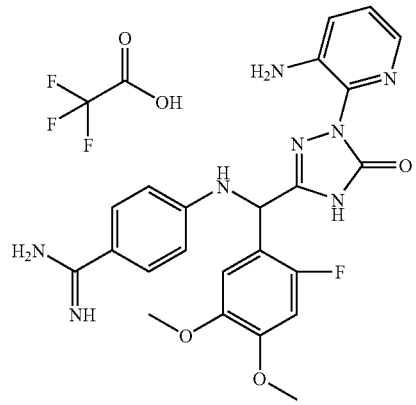

The same procedure was carried out as in Example (1g), except that 104 mg of 5-{(2-fluoro-4,5-dimethoxyphenyl)-[4-(5-methyl-[1,2,4]oxadiazol-3-yl)phenylamino]methyl}-2-(3-nitropyridin-2-yl)-2,4-dihydro-1H-[1,2,4]triazol-3-one was used instead of the 2-(3-{(2-fluoro-4,5-dimethoxyphenyl)-[4-(5-methyl-[1,2,4]oxadiazol-3-yl)phenylamino]methyl}-5-oxo-4,5-dihydro-[1,2,4]triazol-1-yl)benzoic acid, to give the title compound (34 mg).

$^1$H-NMR (CD$_3$OD) δ 3.73 (s, 3H) 3.81 (s, 3H) 5.98 (s, 1H) 6.86 (d, J=11.4 Hz, 1H) 6.87 (d, J=8.6 Hz, 2H) 7.05 (d, J=7.8 Hz, 1H) 7.60 (br.s, 1H) 7.83 (br.s, 1H) 7.64 (d, J=8.6 Hz, 2H) 7.85 (br.s, 1H) 8.38 (br.s, 2H) 8.79 (br.s, 2H)

Example 139

4-({[1-(2-aminophenyl)-5-oxo-4,5-dihydro-1H-[1,2,4]triazol-3-yl]-[3-(2-dimethylaminoethoxy)-5-ethyl-2-fluorophenyl]methyl}amino)benzamidine bistrifluoroacetate (139a) {2-[3-(2-dimethylaminoethoxy)-5-ethyl-2-fluorophenyl]-2-[4-(5-methyl-[1,2,4]oxadiazol-3-yl)phenylimino]-1-methylsulfanylethylidene}carbamic acid methyl ester

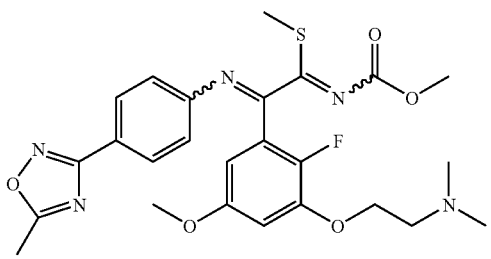

[Chemical Formula 365]

The same procedure was carried out as in Example (135f), except that (2-chloroethyl)dimethylamine hydrochloride was used instead of the 2-chloro-N,N-dimethylacetamide, to give the title compound.

$^1$H-NMR (CDCl$_3$) Two isomers:

δ 1.08 (t, J=7.8 Hz, 3H) 2.32 (s, 6H) 2.38 (s, 3H) 2.49 (q, J=7.8 Hz, 2H) 2.61 (s, 3H) 2.70 (d, J=5.5 Hz, 2H) 3.59 (s, 3H) 4.02 (d, J=5.5 Hz, 2H) 6.46 (dd, J=5.5, 2.2 Hz, 1H) 6.75 (dd, J=8.1, 2.2 Hz, 1H) 6.81 (d, J=8.6 Hz, 2H) 7.86 (d, J=8.6 Hz, 2H)

δ 1.23 (t, J=7.8 Hz, 3H) 2.34 (s, 3H) 2.58 (s, 6H) 2.63 (q, J=7.8 Hz, 2H) 2.66 (s, 3H) 2.79 (d, J=5.5 Hz, 2H) 3.56 (s, 3H) 4.14 (d, J=5.5 Hz, 2H) 6.96 (dd, J=8.1, 2.2 Hz, 1H) 7.12 (d, J=8.6 Hz, 2H) 7.28 (dd, J=5.5, 2.2 Hz, 1H) 8.01 (d, J=8.6 Hz, 2H)

(139b) 2-(3-{[3-(2-dimethylaminoethoxy)-5-ethyl-2-fluorophenyl]-[4-(5-methyl-[1,2,4]oxadiazol-3-yl)phenylamino]methyl}-5-oxo-4,5-dihydro-1H-[1,2,4]triazol-1-yl)benzoic acid trifluoroacetate

[Chemical Formula 366]

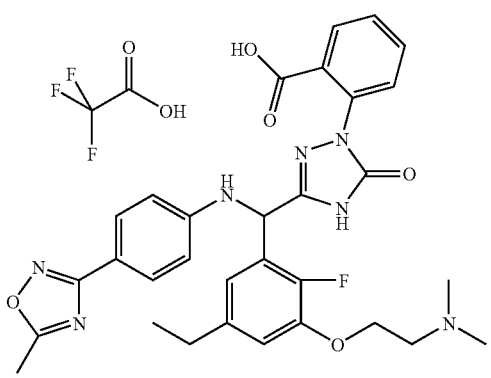

The same procedure was carried out as in Example (2f), except that 2-hydrazinobenzoic acid hydrochloride and 505 mg of {2-[3-(2-dimethylaminoethoxy)-5-ethyl-2-fluorophenyl]-2-[4-(5-methyl-[1,2,4]oxadiazol-3-yl)phenylimino]-1-methylsulfanylethylidene}carbamic acid methyl ester were used respectively instead of (1-oxypyridin-2-yl)hydrazine and [2-(4-cyanophenylimino)-2-(2-fluoro-3,5-dimethoxyphenyl)-1-methylsulfanylethylidene]carbamic acid methyl ester, to give the title compound (433 mg).

$^1$H-NMR (CD$_3$OD) δ 1.19 (t, J=7.7 Hz, 3H) 2.60 (s, 3H) 2.62 (q, J=7.7 Hz, 2H) 3.00 (s, 6H) 3.62 (t, J=5.8 Hz, 2H) 4.43 (t, J=5.8 Hz, 2H) 5.95 (s, 1H) 6.82 (d, J=8.8 Hz, 2H) 7.03 (dd, J=8.0, 1.5 Hz, 1H) 7.07 (dd, J=5.7, 1.5 Hz, 1H) 7.48 (dd, J=7.3, 1.0 Hz, 1H) 7.50 (td, J=7.3, 1.0 Hz, 1H) 7.64 (td, J=7.3, 1.0 Hz, 1H) 7.79 (d, J=8.8 Hz, 2H) 7.95 (dd, J=7.3, 1.0 Hz, 1H)

(139c) 2-(2-aminophenyl)-5-{[3-(2-dimethylaminoethoxy)-5-ethyl-2-fluorophenyl]-[4-(5-methyl-[1,2,4]oxadiazol-3-yl)-phenylamino]-methyl}-2,4-dihydro-1H-[1,2,4]triazol-3-one trifluoroacetate

[Chemical Formula 367]

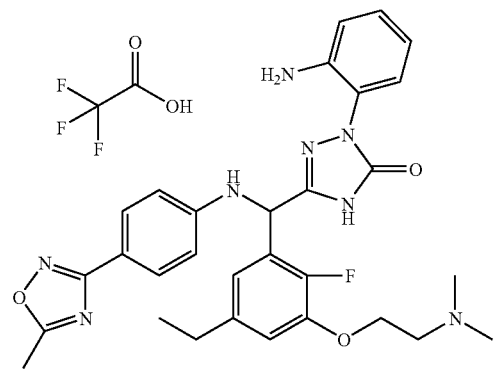

The same procedure was carried out as in Examples (135h)-(135i), except that 2-(3-{[3-(2-dimethylaminoethoxy)-5-ethyl-2-fluorophenyl]-[4-(5-methyl-[1,2,4]oxadiazol-3-yl)phenylamino]methyl}-5-oxo-4,5-dihydro-1H-[1,2,4]triazol-1-yl)benzoic acid was used instead of the 2-(3-{(3-dimethylcarbamoylmethoxy-5-ethyl-2-fluorophenyl)-[4-(5-methyl-[1,2,4]oxadiazol-3-yl)phenylamino]methyl}-5-oxo-4,5-dihydro-[1,2,4]triazol-1-yl)benzoic acid in Example (135h), to give the title compound.

$^1$H-NMR (CD$_3$OD) δ 1.20 (t, J=7.5 Hz, 3H) 2.60 (s, 3H) 2.63 (q, J=7.5 Hz, 2H) 3.00 (s, 6H) 3.62 (t, J=5.2 Hz, 2H) 4.43 (t, J=5.2 Hz, 2H) 5.99 (s, 1H) 6.81 (d, J=8.8 Hz, 2H) 6.82 (t, J=7.5 Hz, 1H) 6.95 (d, J=8.3 Hz, 1H) 7.02-7.07 (m, 2H) 7.18 (t, J=7.5 Hz, 1H) 7.25 (d, J=7.5 Hz, 1H) 7.78 (d, J=8.8 Hz, 2H)

(139d) 4-({[1-(2-aminophenyl)-5-oxo-4,5-dihydro-1H-[1,2,4]triazol-3-yl]-[3-(2-dimethylaminoethoxy)-5-ethyl-2-fluorophenyl]methyl}amino)benzamidine bistrifluoroacetate

[Chemical Formula 368]

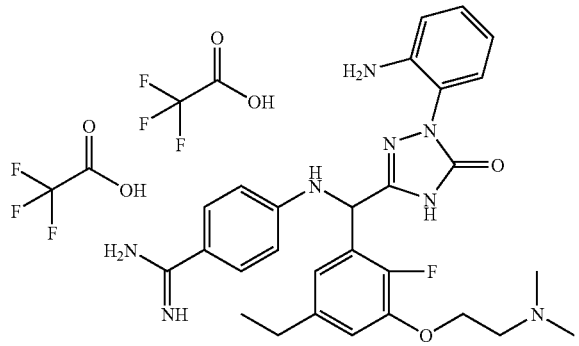

The same procedure was carried out as in Example (1g), except that 13.2 mg of 2-(2-aminophenyl)-5-{[3-(2-dimethylaminoethoxy)-5-ethyl-2-fluorophenyl]-[4-(5-methyl-[1,2,4]oxadiazol-3-yl)phenylamino]methyl}-2,4-dihydro-1H-[1,2,4]triazol-3-one trifluoroacetate was used instead of the 2-(3-{(2-fluoro-4,5-dimethoxyphenyl)-[4-(5-methyl-[1,2,4]oxadiazol-3-yl)phenylamino]methyl}-5-oxo-4,5-dihydro-[1,2,4]triazol-1-yl)benzoic acid, to give 4.7 mg of the title compound as a colorless oil.

$^1$H-NMR (CD$_3$OD) δ 1.20 (t, J=7.8 Hz, 3H) 2.63 (q, J=7.8 Hz, 2H) 3.01 (s, 6H) 3.64 (t, J=5.6 Hz, 2H) 4.44 (t, J=5.6 Hz, 2H) 6.05 (s, 1H) 6.88 (d, J=8.7 Hz, 2H) 6.93 (t, J=7.5 Hz, 1H) 7.04 (d, J=7.5 Hz, 1H) 7.05 (dd, J=5.4, 2.2 Hz, 1H) 7.07 (dd, J=7.8, 2.2 Hz, 1H) 7.22 (t, J=7.5 Hz, 1H) 7.29 (d, J=7.5 Hz, 1H) 7.65 (d, J=8.7 Hz, 2H)

Example 140

4-({[3-(2-dimethylaminoethoxy)-5-ethyl-2-fluorophenyl]-(5-oxo-1-pyridin-2-yl-4,5-dihydro-1H-[1,2,4]triazol-3-yl)methyl}amino)benzamidine bistrifluoroacetate (140a) 5-{[3-(2-dimethylaminoethoxy)-5-ethyl-2-fluorophenyl]-[4-(5-methyl-[1,2,4]oxadiazol-3-yl)phenylamino]methyl}-2-pyridin-2-yl-2,4-dihydro-1H-[1,2,4]triazol-3-one trifluoroacetate

[Chemical Formula 369]

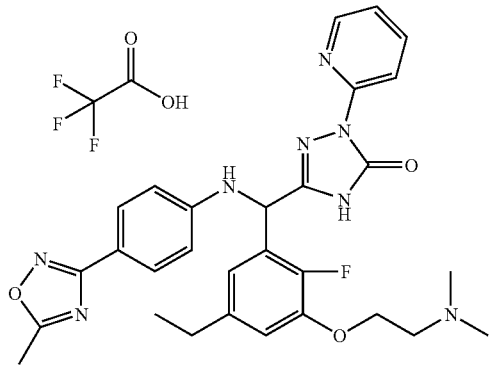

The same procedure was carried out as in Example (2f), except that (pyridin-2-yl)hydrazine and 30 mg of 2-[3-(2-dimethylaminoethoxy)-5-ethyl-2-fluorophenyl]-2-[4-(5-methyl-[1,2,4]oxadiazol-3-yl)phenylimino]-1-methylsulfanylethylidene}carbamic acid methyl ester (Example (139a)) were used instead of respectively (1-oxy-pyridin-2-yl)hydrazine and [2-(4-cyanophenylimino)-2-(2-fluoro-3,5-dimethoxyphenyl)-1-methylsulfanylethylidene]carbamic acid methyl ester, to give the title compound (20 mg) as a white solid.

$^1$H-NMR (CD$_3$OD) δ 1.19 (t, J=7.7 Hz, 3H) 2.59 (s, 3H) 2.61 (q, J=7.7 Hz, 2H) 3.01 (s, 6H) 3.63 (d, J=5.1 Hz, 2H) 4.42 (d, J=5.1 Hz, 2H) 5.98 (s, 1H) 6.81 (d, J=8.8 Hz, 2H) 7.02 (dd, J=7.7, 2.1 Hz, 1H) 7.06 (dd, J=6.5, 2.1 Hz, 1H) 7.31 (dd, J=7.9, 5.1 Hz, 1H) 7.78 (d, J=8.8 Hz, 2H) 7.95 (t, J=7.9 Hz, 1H) 8.06 (d, J=7.9 Hz, 1H) 8.42 (d, J=5.1 Hz, 1H)

(140b) 4-({[3-(2-dimethylaminoethoxy)-5-ethyl-2fluorophenyl]-(5-oxo-1-pyridin-2-yl-4,5-dihydro-1H-[1,2,4]triazol-3-yl)methyl}amino)benzamidine bistrifluoroacetate

[Chemical Formula 370]

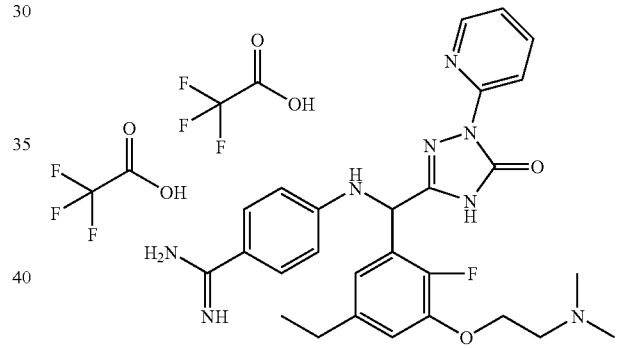

The same procedure was carried out as in Example (1g), except that 20 mg of 5-{[3-(2-dimethylaminoethoxy)-5-ethyl-2-fluorophenyl]-[4-(5-methyl-[1,2,4]oxadiazol-3-yl)phenylamino]methyl}-2-pyridin-2-yl-2,4-dihydro-1H-[1,2,4]triazol-3-one trifluoroacetate was used instead of the 2-(3-{(2-fluoro-4,5-dimethoxyphenyl)-[4-(5-methyl-[1,2,4]oxadiazol-3-yl)phenylamino]methyl}-5-oxo-4,5-dihydro-[1,2,4]triazol-1-yl)benzoic acid, to give the title compound (6.5 mg) as a colorless oil.

$^1$H-NMR (CD$_3$OD) δ 1.22 (t, J=7.7 Hz, 3H) 2.65 (q, J=7.7 Hz, 2H) 3.01 (s, 6H) 3.63 (d, J=5.3 Hz, 2H) 4.44 (d, J=5.3 Hz, 2H) 6.01 (s, 1H) 6.88 (d, J=8.8 Hz, 2H) 7.05 (dd, J=6.0, 2.1 Hz, 1H) 7.07 (dd, J=7.6, 2.1 Hz, 1H) 7.31 (dd, J=7.6, 5.0 Hz, 1H) 7.65 (d, J=8.8 Hz, 2H) 7.94 (t, J=7.6 Hz, 1H) 8.05 (d, J=7.6 Hz, 1H) 8.43 (d, J=5.0 Hz, 1H)

Example 141

4-({[3-(2-dimethylamino-1-methylethoxy)-5-ethyl-2-fluorophenyl]-(5-oxo-1-pyridin-2-yl-4,5-dihydro-1H-[1,2,4]triazol-3-yl)methyl}amino)benzamidine bistrifluoroacetate (141a) {2-[3-(2-dimethylamino-1-methylethoxy)-5-ethyl-2-fluorophenyl]-2-[4-(5-methyl-[1,2,4]oxadiazol-3-yl)phenylimino]-1-methylsulfanylethylidene}carbamic acid methyl ester

[Chemical Formula 371]

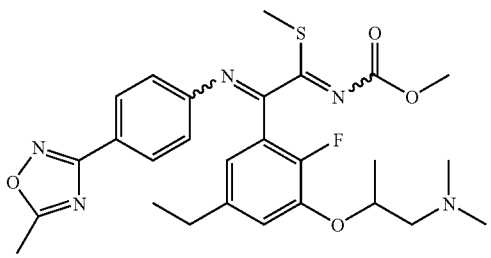

The same procedure was carried out as in Example (135f), except that (2-chloropropyl)dimethylamine hydrochloride was used instead of the 2-chloro-N,N-dimethylacetamide, to give the title compound (41 mg) as a light yellow oil.

$^1$H-NMR (CDCl$_3$) Two isomers:

δ 1.17 (t, J=7.6 Hz, 3H) 1.23 (d, J=6.3 Hz, 3H) 2.24 (s, 6H) 2.30-2.61 (m, 2H) 2.46 (s, 3H) 2.47 (q, J=7.6 Hz, 2H) 2.61 (s, 3H) 3.59 (s, 3H) 4.51 (sext, J=6.3 Hz, 1H) 6.52 (dd, J=5.1, 2.1 Hz, 1H) 6.82 (d, J=8.8 Hz, 2H) 6.83 (dd, J=7.6, 2.1 Hz, 1H) 7.87 (d, J=8.8 Hz, 2H)

δ 1.24 (t, J=7.6 Hz, 3H) 1.31 (d, J=6.3 Hz, 3H) 2.30-2.61 (m, 2H) 2.31 (s, 3H) 2.33 (s, 6H) 2.64 (q, J=7.6 Hz, 2H) 2.65 (s, 3H) 3.55 (s, 3H) 4.32 (sext, J=6.3 Hz, 1H) 7.02 (dd, J=7.6, 2.1 Hz, 1H) 7.15 (d, J=8.8 Hz, 2H) 7.29 (dd, J=5.1, 2.1 Hz, 1H) 8.02 (d, J=8.8 Hz, 2H)

(141b) 5-{[3-(2-dimethylamino-1-methylethoxy)-5-ethyl-2-fluorophenyl]-[4-(5-methyl-[1,2,4]oxadiazol-3-yl)-phenylamino]methyl}-2-pyridin-2-yl-2,4-dihydro-1H-[1,2,4]triazol-3-one trifluoroacetate

[Chemical Formula 372]

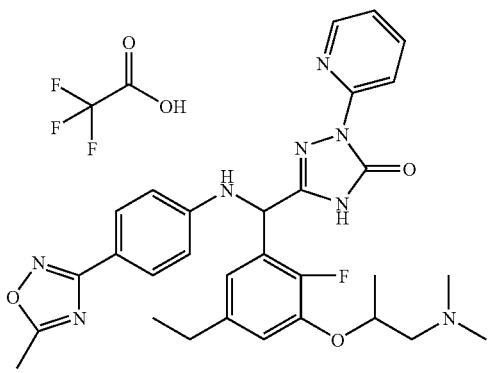

The same procedure was carried out as in Example (2f), except that (pyridin-2-yl)hydrazine and 26 mg of {2-[3-(2-dimethylamino-1-methylethoxy)-5-ethyl-2-fluorophenyl]-2-[4-(5-methyl-[1,2,4]oxadiazol-3-yl)phenylimino]-1-methylsulfanylethylidene}carbamic acid methyl ester were used instead of respectively the (1-oxypyridin-2-yl)hydrazine and [2-(4-cyanophenylimino)-2-(2-fluoro-3,5-dimethoxyphenyl)-1-methylsulfanylethylidene]carbamic acid methyl ester, to give the title compound (18 mg) as a white solid.

$^1$H-NMR (CD$_3$OD) Two isomers:

δ 1.20 and 1.21 (t, J=7.8 Hz, 3H) 1.31 and 1.32 (d, J=6.4 Hz, 3H) 2.60 (s, 3H) 2.63 (q, J=7.8 Hz, 2H) 3.00 (s, 6H) 3.40 (dd, J=13.7, 3.1 Hz, 1H) 3.53 (dd, J=13.7, 10.0 Hz, 1H) 4.94 (m, 1H) 5.98 and 5.99 (s, 1H) 6.81 and 6.82 (d, J=8.8 Hz, 2H) 7.01 (d, J=7.6 Hz, 1H) 7.03 (d, J=5.5 Hz, 1H) 7.31 (ddd, J=7.7, 5.3, 0.8 Hz, 1H) 7.79 (d, J=8.8 Hz, 2H) 7.95 (td, J=7.7, 1.3 Hz, 1H) 8.06 (dd, J=7.7, 0.8 Hz, 1H) 8.44 (dd, J=5.3, 1.3 Hz, 1H)

(141c) 4-({[3-(2-dimethylamino-1-methylethoxy)-5-ethyl-2-fluorophenyl]-(5-oxo-1-pyridin-2-yl-4,5-dihydro-1H-[1,2,4]triazol-3-yl)methyl}amino)benzamidine bistrifluoroacetate

[Chemical Formula 373]

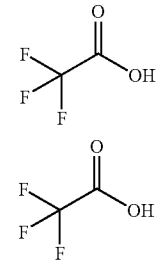

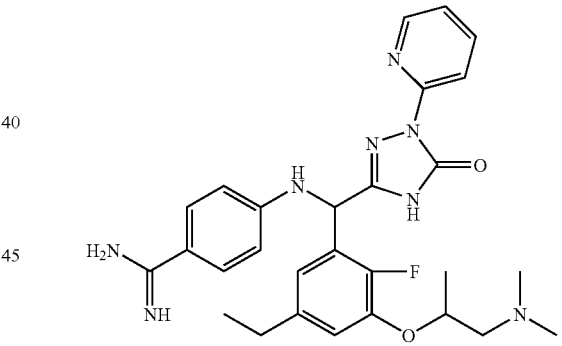

The same procedure was carried out as in Example (1g), except that 15.2 mg of 5-{[3-(2-dimethylamino-1-methylethoxy)-5-ethyl-2-fluorophenyl]-[4-(5-methyl-[1,2,4]oxadiazol-3-yl)phenylamino]methyl}-2-pyridin-2-yl-2,4-dihydro-1H-[1,2,4]triazol-3-one trifluoroacetate was used instead of the 2-(3-{(2-fluoro-4,5-dimethoxyphenyl)-[4-(5-methyl-[1,2,4]oxadiazol-3-yl)phenylamino]methyl}-5-oxo-4,5-dihydro-[1,2,4]triazol-1-yl)benzoic acid, to give the title compound (8.18 mg) as a colorless oil.

$^1$H-NMR (CD$_3$OD) Two isomers:

δ 1.20 and 1.21 (t, J=7.8 Hz, 3H) 1.31 and 1.32 (d, J=6.4 Hz, 3H) 2.64 and 2.65 (q, J=7.8 Hz, 2H) 3.00 (s, 6H) 3.42 (dd, J=13.6, 2.4 Hz, 1H) 3.54 (dd, J=13.6, 10.2 Hz, 1H) 4.94 (m, 1H) 6.02 and 6.03 (s, 1H) 6.88 and 6.89 (d, J=8.8 Hz, 2H) 7.01-7.04 (m, 2H) 7.32 (ddd, J=7.4, 5.2, 1.0 Hz, 1H) 7.65 (d, J=8.8 Hz, 2H) 7.95 (td, J=7.4, 1.3 Hz, 1H) 8.05 (dd, J=7.4, 1.0 Hz, 1H) 8.44 (dd, J=5.2, 1.3 Hz, 1H)

Example 142

2-(3{(4-carbamimidoyl-phenylamino)-[3-(3-dimethylamino-2,2-dimethylpropoxy)-5-ethyl-2-fluorophenyl]methyl}-5-oxo-4,5-dihydro-1H-[1,2,4]triazol-1-yl}benzoic acid bistrifluoroacetate (142a) {2-[3-(3-dimethylamino-2,2-dimethylpropoxy)-5-ethyl-2-fluorophenyl]-2-[4-(5-methyl-[1,2,4]oxadiazol-3-yl)phenylimino]-1-methylsulfanylethylidene}carbamic acid methyl ester

[Chemical Formula 374]

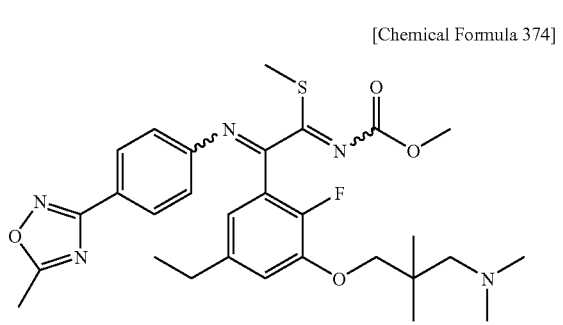

The same procedure was carried out as in Example (135f), except that (3-chloro-2,2-dimethylpropyl)dimethylamine was used instead of the 2-chloro-N,N-dimethylacetamide, to give the title compound.

$^1$H-NMR (CDCl$_3$) δ 0.94 (s, 6H) 1.07 (t, J=7.8 Hz, 3H) 2.27 (s, 6H) 2.29 (s, 2H) 2.34 (s, 3H) 2.55 (q, J=7.8 Hz, 2H) 2.63 (s, 3H) 3.57 (s, 3H) 3.75 (s, 2H) 6.43 (dd, J=5.4, 1.8 Hz, 1H) 6.76 (dd, J=8.0, 1.8 Hz, 1H) 6.82 (d, J=8.9 Hz, 2H) 7.87 (d, J=8.9 Hz, 2H)

(142b) 2-(3-{[3-(3-dimethylamino-2,2-dimethylpropoxy-5-ethyl-2-fluorophenyl)-[4-(5-methyl-[1,2,4]oxadiazol-3-yl)phenylamino]methyl}-5-oxo-4,5-dihydro-1H-[1,2,4]triazol-1-yl)benzoic acid trifluoroacetate

[Chemical Formula 375]

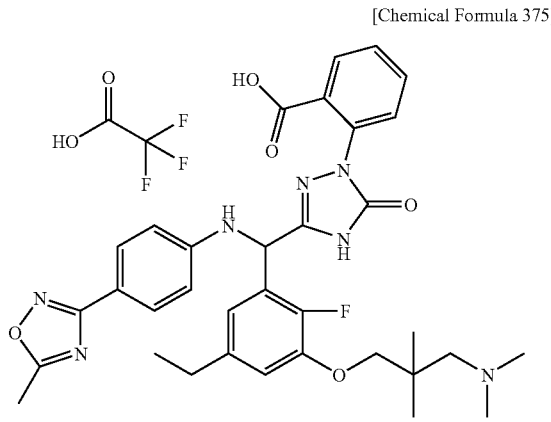

The same procedure was carried out as in Example (2f), except that 2-hydrazinobenzoic acid hydrochloride and 35 mg of {2-[3-(3-dimethylamino-2,2-dimethylpropoxy)-5-ethyl-2-fluorophenyl]-2-[4-(5-methyl-[[1,2,4]oxadiazol-3-yl)phenylimino]-1-methylsulfanylethylidene}carbamic acid methyl ester were used instead of respectively the (1-oxypyridin-2-yl)hydrazine and [2-(4-cyanophenylimino)-2-(2-fluoro-3,5-dimethoxyphenyl)-1-methylsulfanylethylidene] carbamic acid methyl ester, to give the title compound (33 mg) as a colorless oil.

$^1$H-NMR (CD$_3$OD) δ 1.20 (t, J=7.8 Hz, 3H) 1.24 (s, 3H) 1.25 (s, 3H) 2.60 (s, 3H) 2.63 (q, J=7.8 Hz, 2H) 2.99 (s, 6H) 3.35 (s, 2H) 4.00 (s, 2H) 5.95 (s, 1H) 6.81 (d, J=9.0 Hz, 2H) 7.00 (d, J=7.5 Hz, 1H) 7.02 (d, J=5.0 Hz, 1H) 7.48 (d, J=7.6 Hz, 1H) 7.49 (t, J=7.6 Hz, 1H) 7.63 (td, J=7.6, 1.2 Hz, 1H) 7.89 (d, J=9.0 Hz, 2H) 7.94 (dd, J=7.6, 1.2 Hz, 1H)

(142c) 2-(3 {(4-carbamimidoylphenylamino)-[3-(3-dimethylamino-2,2-dimethylpropoxy)-5-ethyl-2-fluorophenyl]methyl}-5-oxo-4,5-dihydro-1H-[1,2,4]triazol-1-yl}benzoic acid bistrifluoroacetate

[Chemical Formula 376]

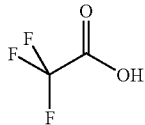

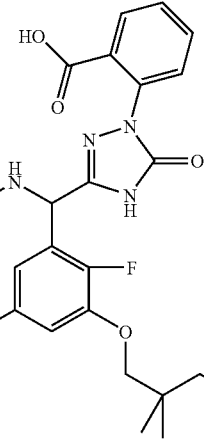

The same procedure was carried out as in Example (1g), except that 33 mg of (3-{[3-(3-dimethylamino-2,2-dimethyl-propoxy-5-ethyl-2-fluorophenyl)-[4-(5-methyl-[1,2,4]oxadiazol-3-yl)phenylamino]methyl}-5-oxo-4,5-dihydro-1H-[1,2,4]triazol-1-yl)benzoic acid trifluoroacetate was used instead of the 2-(3-{(2-fluoro-4,5-dimethoxyphenyl)-[4-(5-methyl-[1,2,4]oxadiazol-3-yl)phenylamino]methyl}-5-oxo-4,5-dihydro-[1,2,4]triazol-1-yl)benzoic acid, to give the title compound (12 mg) as a white oil.

$^1$H-NMR (CD$_3$OD) δ 1.20 (t, J=7.8 Hz, 3H) 1.22 (s, 3H) 1.24 (s, 3H) 2.61 (q, J=7.8 Hz, 2H) 2.97 (s, 6H) 3.30 (s, 2H) 3.96 (s, 2H) 5.97 (s, 1H) 6.85 (d, J=8.7 Hz, 2H) 6.98 (d, J=5.0

Hz, 1H) 7.01 (d, J=7.3 Hz, 1H) 7.45 (d, J=7.6 Hz, 1H) 7.48 (t, J=7.6 Hz, 1H) 7.62 (t, J=7.6 Hz, 1H) 7.63 (d, J=8.7 Hz, 2H) 7.93 (d, J=7.6 Hz, 1H)

Example 143

(R) and (S)-2-fluoro-4-{[(2-fluoro-4,5-dimethoxyphenyl)-(5-oxo-1-pyrimidin-2-yl-4,5-dihydro-1H-[1,2,4]triazol-3-yl)methyl]amino}benzamidine acetate (143a) {2-[4-cyano-3-fluorophenylimino]-2-(2-fluoro-4,5-dimethoxyphenyl)-1-methylsulfanylethylidene}carbamic acid methyl ester

[Chemical Formula 377]

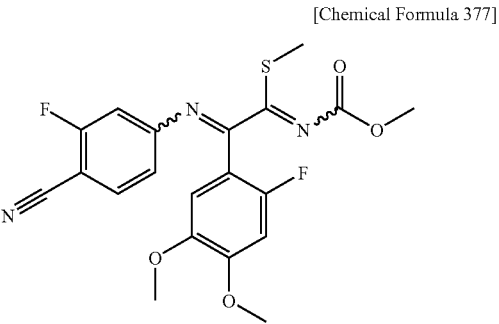

The same procedure was carried out as in Example (37a), except that 2-fluoro-4,5-dimethoxybenzaldehyde was used instead of 3,4-dimethoxybenzaldehyde, to give the title compound.

$^1$H-NMR (CDCl$_3$) δ 2.36 (s, 3H) 3.63 (s, 3H) 3.92 (s, 3H) 3.94 (s, 3H) 6.60 (m, 1H) 6.62 (d, J=12.4 Hz, 1H) 6.88 (d, J=8.8 Hz, 1H) 7.38 (d, J=6.8 Hz, 1H) 7.54 (t, J=7.2 Hz, 1H)
Mass spectrum (ESI) m/z: 434 (M+H)$^+$ (143b) 2-fluoro-4-{[(2-fluoro-4,5-dimethoxyphenyl)-(5-oxo-1-pyrimidin-2-yl-4,5-dihydro-1H-[1,2,4]triazol-3-yl)methyl]amino}benzonitrile

[Chemical Formula 378]

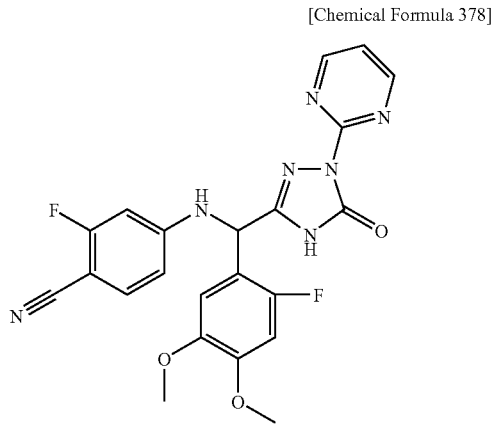

The same procedure was carried out as in Example (17f), except that {2-[4-cyano-3-fluorophenylimino]-2-(2-fluoro-4,5-dimethoxyphenyl)-1-methylsulfanylethylidene}carbamic acid methyl ester was used instead of the {2-(3-ethoxy-4-methoxyphenyl)-2-[4-(5-methyl-[1,2,4]oxadiazol-3-yl)phenylimino]-1-methylsulfanylethylidene}carbamic acid methyl ester, to give the title compound.

$^1$H-NMR (CD$_3$OD) δ 3.77 (s, 3H) 3.84 (s, 3H) 5.91 (s, 1H) 6.57 (dd, J=12.4, 2.0 Hz, 1H) 6.63 (dd, J=8.4, 2.0 Hz, 1H) 6.87 (d, J=11.6 Hz, 1H) 7.00 (d, J=7.2 Hz, 1H) 7.37 (t, J=4.8 Hz, 1H) 7.42 (dd, J=8.8, 7.6 Hz, 1H) 8.79 (d, J=4.8 Hz, 2H)

(143c) (R) and (S)-2-fluoro-4-{[(2-fluoro-4,5-dimethoxyphenyl)-(5-oxo-1-pyrimidin-2-yl-4,5-dihydro-1H-[1,2,4]triazol-3-yl)methyl]amino}benzamidine acetate

[Chemical Formula 379]

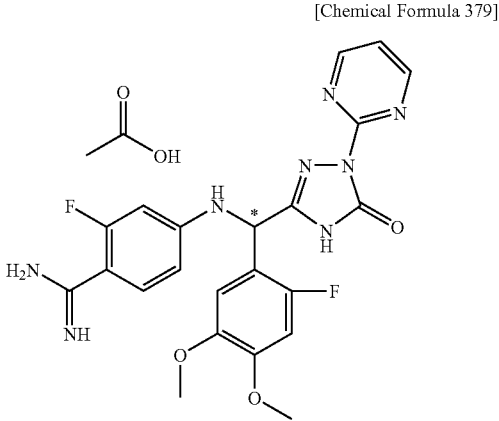

The same procedure was carried out as in Examples (2g)-(2h), except that [2-fluoro-4-{[(2-fluoro-4,5-dimethoxyphenyl)-(5-oxo-1-pyrimidin-2-yl-4,5-dihydro-1H-[1,2,4]triazol-3-yl)methyl]amino}benzonitrile and 0.1% acetic acid were used instead of respectively the 4-({(2-fluoro-3,5-dimethoxyphenyl)-[5-oxo-1-(1-oxypyridin-2-yl)-4,5-dihydro-1H-[1,2,4]triazol-3-yl]methyl}amino)benzonitrile in Example (2g) and the 0.1% trifluoroacetic acid in Example (2h), to give 2-fluoro-4-{[(2-fluoro-4,5-dimethoxyphenyl)-(5-oxo-1-pyrimidin-2-yl-4,5-dihydro-1H-[1,2,4]triazol-3-yl)methyl]amino}benzamidine acetate.

$^1$H-NMR (CD$_3$OD) δ 3.67 (s, 3H) 3.73 (s, 3H) 5.78 (s, 1H) 6.50 (dd, J=14.4, 2.4 Hz, 1H) 6.61 (dd, J=8.8, 2.4 Hz, 1H) 6.75 (d, J=11.6 Hz, 1H) 7.01 (d, J=6.8 Hz, 1H) 7.22 (t, J=4.8 Hz, 1H) 7.37 (t, J=8.4 Hz, 1H) 8.68 (d, J=4.8 Hz, 2H)
Mass spectrum (ESI) m/z: 483 (M+H)$^+$ A 3.5 mg portion of this compound was optically resolved using a SUMICHIRAL OA-2500 column, and the first eluting enantiomer (1.0 mg) of the title compound was obtained.

HPLC retention time: 15 min

Example 144

(R) and (S)-4-{[(4-cyanomethoxy-3-methoxyphenyl)-(5-oxo-1-pyridazin-3-yl-4,5-dihydro-1H-[1,2,4]triazol-3-yl)methyl]amino}benzamidine acetate

[Chemical Formula 380]

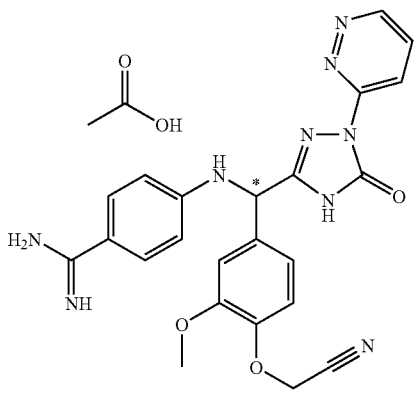

The same procedure was carried out as in Examples (119a)-(119b), except that {2-(4-cyanomethoxy-3-methoxyphenyl)-2-[4-(5-methyl-[1,2,4]oxadiazol-3-yl)phenylimino]-1-methylsulfanylethylidene}carbamic acid methyl ester (Example (16a)) was used instead of the {2-(2-fluoro-4,5-dimethoxyphenyl)-2-[4-(5-methyl-[1,2,4]oxadiazol-3-yl)phenylimino]-1-methylsulfanylethylidene}carbamic acid methyl ester in Example (119a), to give the first eluting enantiomer of the title compound.

$^1$H-NMR (CD$_3$OD) δ 1.93 (s, 3H) 3.84 (s, 3H) 4.91 (s, 2H) 5.65 (s, 1H) 6.87 (d, J=8.8 Hz, 2H) 7.06 (d, J=8.4 Hz, 1H) 7.13 (dd, J=8.4, 2.0 Hz, 1H) 7.28 (d, J=2.0 Hz, 1H) 7.60 (d, J=8.8 Hz, 2H) 7.75 (dd, J=9.2, 4.8 Hz, 1H) 8.53 (dd, J=9.2, 1.2 Hz, 1H) 9.01 (dd, J=4.8, 1.2 Hz, 1H)

HPLC retention time: 12 min

Example 145

(R) and (S)-4-{[(2-fluoro-3,5-dimethoxyphenyl)-(5-oxo-1-pyridazin-3-yl-4,5-dihydro-1H-[1,2,4]triazol-3-yl)methyl]amino}benzamidine acetate

[Chemical Formula 381]

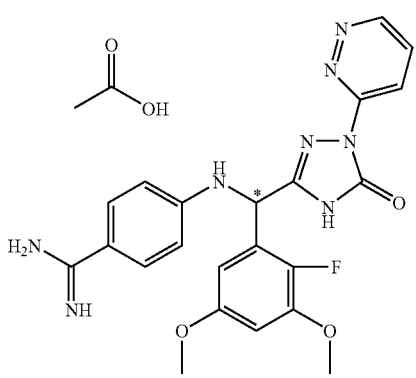

The same procedure was carried out as in Examples (3e)-(3g), except that methyl iodide and 3-hydrazinopyridazine hydrochloride were used instead of respectively the 1-fluoro-2-iodoethane in Example (3e) and the 2-hydrazinopyrimidine in Example (3f), to give 4-{[(2-fluoro-3,5-dimethoxyphenyl)-(5-oxo-1-pyridazin-3-yl-4,5-dihydro-1H-[1,2,4]triazol-3-yl)methyl]amino}benzamidine acetate.

$^1$H-NMR (CD$_3$OD) δ 1.93 (s, 3H) 3.71 (s, 3H) 3.84 (s, 3H) 5.97 (s, 1H) 6.59-6.64 (m, 2H) 6.86 (d, J=8.8 Hz, 2H) 7.61 (d, J=8.8 Hz, 2H) 7.76 (dd, J=8.8, 4.8 Hz, 1H) 8.50 (dd, J=8.8, 1.2 Hz, 1H) 9.01 (dd, J=4.8, 1.2 Hz, 1H)

Mass spectrum (ESI) m/z: 465 (M+H)$^+$

A 5.5 mg portion of this compound was optically resolved using a SUMICHIRAL OA-2500 column, and the first eluting enantiomer (2.4 mg) of the title compound was obtained.

HPLC retention time: 14 min

Example 146

(R) and (S)-4-{[(3-cyanomethyl-4-fluoro-5-methoxyphenyl)-(5-oxo-1-pyridazin-3-yl-4,5-dihydro-1H-[1,2,4]triazol-3-yl)methyl]amino}benzamidine acetate

[Chemical Formula 382]

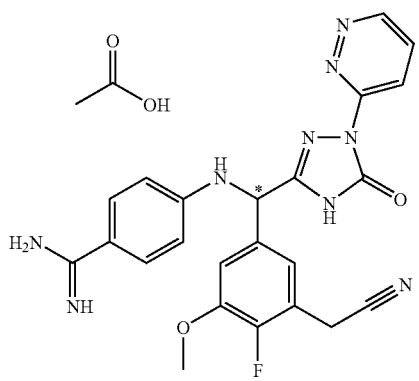

The same procedure was carried out as in Example (119a), except that {2-(4-fluoro-3-cyanomethyl-5-methoxyphenyl)-2-[4-(5-methyl-[1,2,4]oxadiazol-3-yl)phenylimino]-1-methylsulfanylethylidene}carbamic acid methyl ester (Example (131c)) was used instead of the {2-(2-fluoro-4,5-dimethoxyphenyl)-2-[4-(5-methyl-[1,2,4]oxadiazol-3-yl)phenylimino]-1-methylsulfanylethylidene}carbamic acid methyl ester, to give 4-{[(3-cyanomethyl-4-fluoro-5-methoxyphenyl)-(5-oxo-1-pyridazin-3-yl-4,5-dihydro-1H-[1,2,4]triazol-3-yl)methyl]amino}benzamidine acetate.

$^1$H-NMR (CD$_3$OD) δ 1.94 (s, 3H) 3.85 (s, 3H) 3.86 (s, 2H) 5.72 (s, 1H) 6.87 (d, J=8.8 Hz, 2H) 7.20 (dd, J=6.0, 2.0 Hz, 1H) 7.33 (dd, J=7.6, 2.0 Hz, 1H) 7.61 (d, J=8.8 Hz, 2H) 7.77 (dd, J=9.2, 4.8 Hz, 1H) 8.52 (dd, J=9.2, 1.6 Hz, 1H) 9.03 (dd, J=4.8, 1.6 Hz, 1H)

Mass spectrum (ESI) m/z: 474 (M+H)$^+$

A 12 mg portion of this compound was optically resolved using a SUMICHIRAL OA-2500 column, and the first eluting enantiomer (4.5 mg) of the title compound was obtained.

HPLC retention time: 10 min

Example 147

4-{[(9-methoxy-3,4-dihydro-2H-benzo[b][1,4]dioxepin-7-yl)-(5-oxo-1-pyridazin-3-yl-4,5-dihydro-1H-[1,2,4]triazol-3-yl)methyl]amino}benzamidine acetate

[Chemical Formula 383]

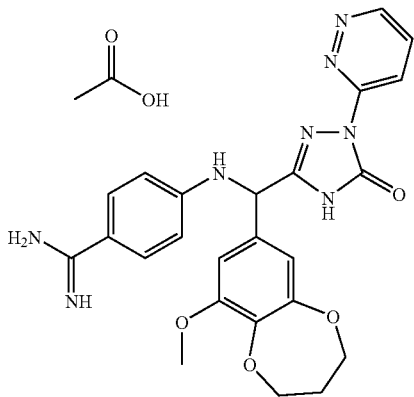

The same procedure was carried out as in Example (119a), except that {2-(9-methoxy-3,4-dihydro-2H-benzo[b][1,4]dioxepin-7-yl)-2-[4-(5-methyl-[1,2,4]oxadiazol-3-yl)phenylimino]-1-methylsulfanylethylidene}carbamic acid methyl ester (Example (30c)) was used instead of the {2-(2-fluoro-4,5-dimethoxyphenyl)-2-[4-(5-methyl-[1,2,4]oxadiazol-3-yl)phenylimino]-1-methylsulfanyl-ethylidene}carbamic acid methyl ester, to give the title compound.

$^1$H-NMR (CD$_3$OD) δ 1.94 (s, 3H) 2.13 (m, 2H) 3.79 (s, 3H) 4.11 (m, 4H) 5.61 (s, 1H) 6.81 (d, J=2.0 Hz, 1H) 6.87 (d, J=8.8 Hz, 2H) 6.91 (d, J=2.0 Hz, 1H) 7.61 (d, J=8.8 Hz, 2H) 7.77 (dd, J=9.2, 5.2 Hz, 1H) 8.49 (dd, J=9.2, 1.6 Hz, 1H) 9.03 (dd, J=5.2, 1.6 Hz, 1H)

Mass spectrum (ESI) m/z: 489 (M+H)$^+$

Example 148

(R) and (S)-{[(3-cyanomethoxy-2-fluoro-5-methoxyphenyl)-(5-oxo-1-pyridazin-3-yl-4,5-dihydro-1H-[1,2,4]triazol-3-yl)methyl]amino}benzamidine acetate

[Chemical Formula 384]

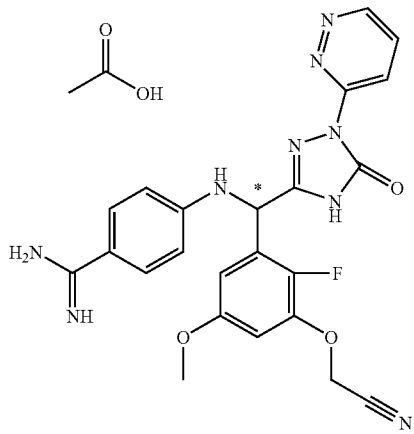

The same procedure was carried out as in Example (16a), except that {2-(2-fluoro-3-hydroxy-5-methoxyphenyl)-2-[4-(5-methyl-[1,2,4]oxadiazol-3-yl)phenylimino]-1-methylsulfanylethylidene}carbamic acid methyl ester (Example (3d)) was used instead of the {2-(4-hydroxy-3-methoxyphenyl)-2-[4-(5-methyl-[1,2,4]oxadiazol-3-yl) phenylimino]-1-methylsulfanylethylidene}carbamic acid methyl ester, to give {2-(3-cyanomethoxy-2-fluoro-5-methoxyphenyl)-2-[4-(5-methyl-[1,2,4]oxadiazol-3-yl)phenylimino]-1-methylsulfanylethylidene}carbamic acid methyl ester.

The same procedure was carried out as in Example (119a), except that this compound was used instead of the {2-(2-fluoro-4,5-dimethoxyphenyl)-2-[4-(5-methyl-[1,2,4]oxadiazol-3-yl)phenylimino]-1-methylsulfanylethylidene}carbamic acid methyl ester, to give {[(3-cyanomethoxy-2-fluoro-5-methoxyphenyl)-(5-oxo-1-pyridazin-3-yl-4,5-dihydro-1H-[1,2,4]triazol-3-yl)methyl]amino}benzamidine acetate.

$^1$H-NMR (CD$_3$OD) δ 1.95 (s, 3H) 3.73 (s, 3H) 5.05 (s, 2H) 6.02 (s, 1H) 6.76-6.79 (m, 2H) 6.87 (d, J=9.2 Hz, 2H) 7.63 (d, J=9.2 Hz, 2H) 7.77 (dd, J=9.2, 4.8 Hz, 1H) 8.47 (dd, J=9.2, 1.6 Hz, 1H) 9.03 (dd, J=4.8, 1.6 Hz, 1H)

Mass spectrum (ESI) m/z: 490 (M+H)$^+$

A 14 mg portion of this compound was optically resolved using a SUMICHIRAL OA-2500 column, and the first eluting enantiomer (5.1 mg) of the title compound was obtained.

HPLC retention time: 10 min

Example 149

(R) and (S)-4-{[(3,4-dimethoxyphenyl)-(5-oxo-1-pyridazin-3-yl-4,5-dihydro-1H-[1,2,4]triazol-3-yl)methyl]amino}benzamidine acetate

[Chemical Formula 385]

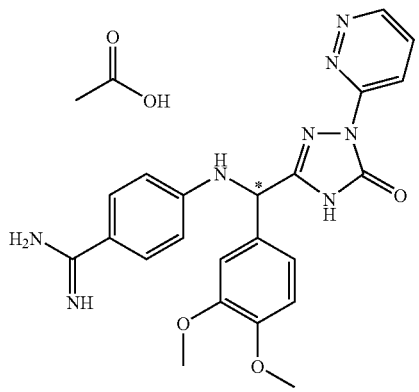

The same procedure was carried out as in Example (119a), except that {2-(3,4-dimethoxyphenyl)-2-[4-(5-methyl-[1,2,4]oxadiazol-3-yl)phenylimino]-1-methylsulfanylethylidene}carbamic acid methyl ester (Example (36d)) was used instead of the {2-(2-fluoro-4,5-dimethoxyphenyl)-2-[4-(5-methyl-[1,2,4]oxadiazol-3-yl)phenylimino]-1-methylsulfanylethylidene}carbamic acid methyl ester, to give 4-{[(3,4-dimethoxyphenyl)-(5-oxo-1-pyridazin-3-yl-4,5-dihydro-1H-[1,2,4]triazol-3-yl)methyl]amino}benzamidine acetate.

$^1$H-NMR (CD$_3$OD) δ 1.93 (s, 3H) 3.79 (s, 3H) 3.80 (s, 3H) 5.65 (s, 1H) 6.87 (d, J=9.2 Hz, 2H) 6.92 (d, J=8.4 Hz, 1H) 7.08 (dd, J=8.4, 2.0 Hz, 1H) 7.16 (d, J=2.0 Hz, 1H) 7.59 (d, J=9.2 Hz, 2H) 7.76 (dd, J=9.2, 4.8 Hz, 1H) 8.47 (dd, J=9.2, 1.6 Hz, 1H) 9.03 (dd, J=4.8, 1.6 Hz, 1H)

Mass spectrum (ESI) m/z: 447 (M+H)$^+$

A 13 mg portion of this compound was optically resolved using a SUMICHIRAL OA-2500 column, and the first eluting enantiomer (2.7 mg) of the title compound was obtained.
HPLC retention time: 14 min Example 150

(R) and (S)-4-{[(8-methoxy-4H-benzo[1,3]dioxin-6-yl)-(5-oxo-1-pyridazin-3-yl-4,5-dihydro-1H[1,2,4]triazol-3-yl)methyl]amino}benzamidine acetate

[Chemical Formula 386]

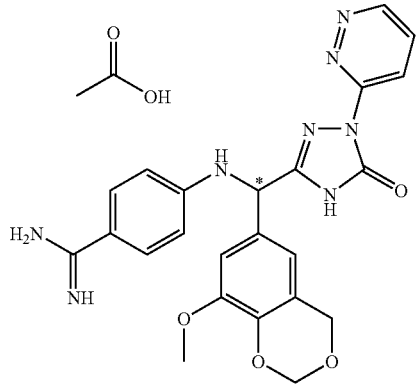

The same procedure was carried out as in Examples (119a)-(119b), except that {2-(8-methoxy-4H-benzo[1,3]dioxin-6-yl)-2-[4-(5-methyl-[1,2,4]oxadiazol-3-yl)phenylimino]-1-methylsulfanylethylidene}carbamic acid methyl ester (Example (21h)) was used instead of the {2-(2-fluoro-4,5-dimethoxyphenyl)-2-[4-(5-methyl-[1,2,4]oxadiazol-3-yl)phenylimino]-1-methylsulfanylethylidene}carbamic acid methyl ester in Example (119a), to give the first eluting enantiomer of the title compound.
$^1$H-NMR (CD$_3$OD) δ 1.92 (s, 3H) 3.81 (s, 3H) 4.84 (d, J=2.4 Hz, 2H) 5.21 (s, 2H) 5.54 (s, 1H) 6.82-6.90 (m, 3H) 7.06 (d, J=2.0 Hz, 1H) 7.58 (d, J=9.2 Hz, 2H) 7.73 (dd, J=9.2, 4.8 Hz, 1H) 8.55 (dd, J=9.2, 1.2 Hz, 1H) 8.98 (dd, J=4.8, 1.2 Hz, 1H)
HPLC retention time: 16 min Example 151

(R) and (S)-4-{[(2-fluoro-3-(2-fluoroethoxy)-5-methoxyphenyl)-(5-oxo-1-pyridazin-3-yl-4,5-dihydro-1H-[1,2,4]triazol-3-yl)methyl]amino}benzamidine acetate

[Chemical Formula 387]

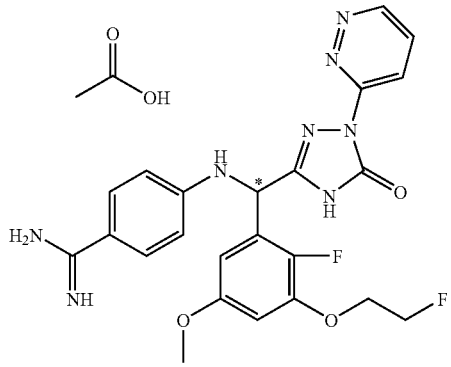

The same procedure was carried out as in Examples (119a)-(119b), except that {2-[2-fluoro-3-(2-fluoroethoxy)-5-methoxyphenyl]-2-[4-(5-methyl-[1,2,4]oxadiazol-3-yl)phenylimino]-1-methylsulfanylethylidene}carbamic acid methyl ester (Example (3e)) was used instead of the {2-(2-fluoro-4,5-dimethoxyphenyl)-2-[4-(5-methyl-[1,2,4]oxadiazol-3-yl)phenylimino]-1-methylsulfanylethylidene}carbamic acid methyl ester in Example (119a), to give the first eluting enantiomer of the title compound.
$^1$H-NMR (CD$_3$OD) δ 1.94 (s, 3H) 3.70 (s, 3H) 4.22-4.29 (m, 2H) 4.66-4.77 (m, 2H) 6.00 (s, 1H) 6.62-6.67 (m, 2H) 6.86 (d, J=8.0 Hz, 2H) 7.61 (d, J=8.0 Hz, 2H) 7.76 (dd, J=8.8, 4.0 Hz, 1H) 8.47 (d, J=8.8 Hz, 1H) 9.03 (d, J=4.0 Hz, 1H) (data for racemic mixture)
HPLC retention time: 13 min Example 152

(R) and (S)-3-{3-[(4-carbamimidoylphenylamino)-(8-methoxy-4H-benzo[1,3]dioxin-6-yl)methyl]-5-oxo-4,5-dihydro[1,2,4]triazol-1-yl}thiophene-2-carboxylic acid methyl ester acetate (152a) 3-{3-[(4-carbamimidoylphenylamino)-(8-methoxy-4H-benzo[1,3]dioxin-6-yl)methyl]-5-oxo-4,5-dihydro[1,2,4]triazol-1-yl}thiophene-2-carboxylic acid methyl ester acetate

[Chemical Formula 388]

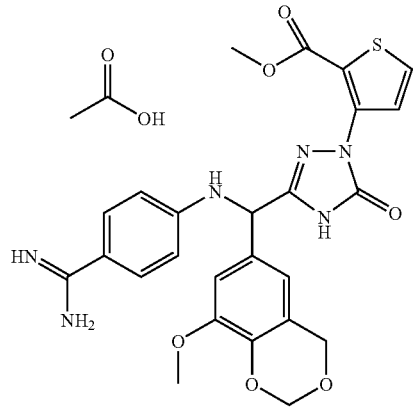

After adding 32 mg of 3-hydrazinothiophene-2-carboxylic acid methyl ester [CAS No. 75681-13-9] and 0.030 ml of triethylamine to a solution of 90 mg of {2-(8-methoxy-4H-benzo[1,3]dioxin-6-yl)-2-[4-(5-methyl-[1,2,4]oxadiazol-3-yl)phenylimino]-1-methylsulfanylethylidene}carbamic acid methyl ester (Example (21h)) in 1 ml of DMF, the mixture was stirred at 85° C. for 20 hours under a nitrogen atmosphere. The reaction mixture was concentrated, and the residue was dissolved in 0.8 ml of methanol, 0.8 ml of THF and 0.1 ml of acetic acid. After adding 100 mg of sodium cyanotrihydroborate to the solution, the mixture was stirred at room temperature for 18 hours and 30 minutes. The reaction mixture was crudely purified by reverse-phase high performance liquid chromatography (acetonitrile-water, 0.1% acetic acid) to give a crude product.
To a solution of the obtained crude product in 3 ml of a methanol:water:acetic acid=1:1:1 mixed solvent there was added 100 mg of iron powder, and the mixture was stirred at 65° C. for 16 hours under a nitrogen atmosphere. After filtering the reaction mixture, it was purified by reverse-phase high performance liquid chromatography (acetonitrile-water, 0.1% acetic acid) to give 27.99 mg of the title compound as a white solid.

$^1$H-NMR (CD$_3$OD) δ 1.93 (s, 3H) 3.75 (s, 3H) 3.83 (s, 3H) 4.86 (s, 2H) 5.24 (s, 2H) 5.61 (s, 1H) 6.81 (d, J=1.6 Hz, 1H) 6.87 (d, J=8.8 Hz, 2H) 7.03 (d, J=1.6 Hz, 1H) 7.20 (d, J=4.8 Hz, 1H) 7.63 (d, J=8.8 Hz, 2H) 7.76 (d, J=4.8 Hz, 1H)

Mass spectrum (ESI) m/z: 537 (M+H)$^+$ (152b) (R) and (S)-3-{3-[(4-carbamimidoylphenylamino)-(8-methoxy-4H-benzo[1,3]dioxin-6-yl)methyl]-5-oxo-4,5-dihydro[1,2,4]triazol-1-yl}thiophene-2-carboxylic acid methyl ester acetate

[Chemical Formula 389]

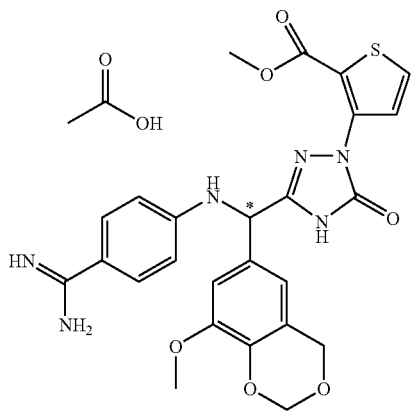

A SUMICHIRAL OA-2500 column was used for optical resolution of 27.99 mg of 3-{3-[(4-carbamimidoylphenylamino)-(8-methoxy-4H-benzo[1,3]dioxin-6-yl)methyl]-5-oxo-4,5-dihydro[1,2,4]triazol 1-yl}thiophene-2-carboxylic acid methyl ester acetate, and the first eluting enantiomer (10.25 mg) of the title compound was obtained as a white solid.

$^1$H-NMR (CD$_3$OD) δ 1.91 (s, 3H) 3.75 (s, 3H) 3.84 (s, 3H) 4.87 (s, 2H) 5.24 (s, 2H) 5.58 (s, 1H) 6.81 (d, J=1.2 Hz, 1H) 6.86 (d, J=8.8 Hz, 2H) 7.03 (br.s, 1H) 7.20 (d, J=5.6 Hz, 1H) 7.62 (d, J=8.8 Hz, 2H) 7.76 (d, J=5.2 Hz, 1H)

HPLC retention time: 9 min (Column name: SUMICHIRAL OA-2500, 30 mmφ×25 cm, Manufacturer: Sumika Chemical Analysis Service, Ltd., Mobile phase: 0.05 M ammonium acetate-methanol solution, Elution rate: 20 ml/min)

Example 153

(R) and (S)-4-({[2-fluoro-3-(2-hydroxyethoxy)-5-methoxyphenyl]-(5-oxo-1-pyrimidin-2-yl-4,5-dihydro-1H-[1,2,4]triazol-3-yl)methyl}amino)benzamidine acetate (153a) 4-({[2-fluoro-3-(2-hydroxyethoxy)-5-methoxyphenyl]-(5-oxo-1-pyrimidin-2-yl-4,5-dihydro-1H-[1,2,4]triazol-3-yl)methyl}amino)benzamidine acetate

[Chemical Formula 390]

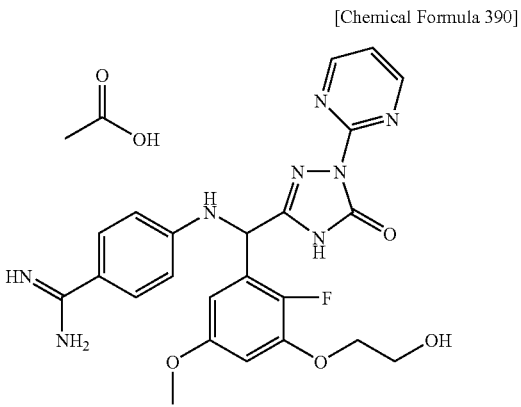

After adding 200 mg of potassium carbonate and 0.1 ml of 2-(2-bromoethoxy)tetrahydro-2H-pyran to a solution of 80 mg of [2-(2-fluoro-3-hydroxy-5-methoxyphenyl)-2-[4-(5-methyl-[1,2,4]oxadiazol-3-yl)phenylimino]-1-methylsulfanylethylidene]carbamic acid methyl ester (Example (3d)) in 1 ml of DMF, the mixture was stirred at room temperature for 14 hours. Water was added to the reaction mixture and extraction was performed with ethyl acetate. The organic layer was washed with water and dried through PRESEP™. The filtrate was concentrated, and the residue was purified by silica gel column chromatography (ethyl acetate-heptane) to give 69 mg of a yellow oil.

To a solution of the obtained 69 mg of yellow oil in 1 ml of DMF there were added 13 mg of 2-hydrazinopyrimidine and 0.016 ml of triethylamine, and the mixture was stirred at 85° C. for 16 hours under a nitrogen atmosphere. The reaction mixture was concentrated, and the residue was dissolved in 1 ml of methanol, 1 ml of THF and 0.1 ml of acetic acid. After adding 100 mg of sodium cyanotrihydroborate to the solution, the mixture was stirred at room temperature for 3 hours. The reaction mixture was crudely purified by reverse-phase high performance liquid chromatography (acetonitrile-water, 0.1% acetic acid) to give a crude product.

To a solution of the obtained crude product in 3 ml of a methanol:water:acetic acid=1:1:1 mixed solvent there was added 100 mg of iron powder, and the mixture was stirred at 60° C. for 2 days under a nitrogen atmosphere. After filtering the reaction mixture, it was purified by reverse-phase high performance liquid chromatography (acetonitrile-water, 0.1% acetic acid) to give the title compound (13.89 mg).

$^1$H-NMR (CD$_3$OD) δ 1.94 (s, 3H) 3.71 (s, 3H) 3.88 (t, J=4.8 Hz, 2H) 4.10 (t, J=4.8 Hz, 2H) 5.99 (s, 1H) 6.55-6.72 (m, 2H) 6.86 (d, J=8.8 Hz, 2H) 7.34 (t, J=4.8 Hz, 1H) 7.62 (d, J=8.8 Hz, 2H) 8.77 (d, J=4.8 Hz, 2H).

Mass spectrum (ESI) m/z: 495 (M+H)$^+$

(153b) (R) and (S)-4-({[2-fluoro-3-(2-hydroxy-ethoxy)-5-methoxyphenyl]-(5-oxo-1-pyrimidin-2-yl-4,5-dihydro-1H-[1,2,4]triazol-3-yl)methyl}amino)benzamidine acetate

[Chemical Formula 391]

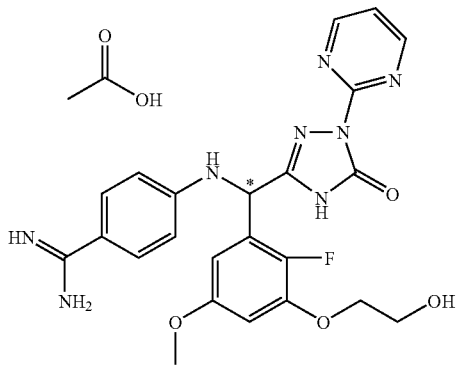

A SUMICHIRAL OA-2500 column was used for optical resolution of 13.89 mg of 4-({[2-fluoro-3-(2-hydroxy-ethoxy)-5-methoxyphenyl]-(5-oxo-1-pyrimidin-2-yl-4,5-dihydro-1H-[1,2,4]triazol-3-yl)methyl}amino)benzamidine acetate, and the first eluting enantiomer (5.89 mg) of the title compound was obtained as a white solid.

$^1$H-NMR (CD$_3$OD) δ 1.91 (s, 3H) 3.71 (s, 3H) 3.82-3.94 (m, 2H) 4.02-4.16 (m, 2H) 5.95 (s, 1H) 6.57-6.70 (m, 2H) 6.85 (d, J=8.8 Hz, 2H) 7.30 (t, J=5.2 Hz, 1H) 7.61 (d, J=8.8 Hz, 2H) 8.76 (d, J=5.2 Hz, 2H).

HPLC retention time: 8 min (Column name: SUMICHIRAL OA-2500, 30 mmφ×25 cm, Manufacturer: Sumika Chemical Analysis Service, Ltd., Mobile phase: 0.05 M ammonium acetate-methanol solution, Elution rate: 40 ml/min)

Example 154

(R) and (S)-4-({(2-fluoro-3,5-dimethoxyphenyl)-[5-oxo-1-(3-oxo-3,4-dihydropyrazin-2-yl)]-4,5-dihydro-1H-[1,2,4]triazol-3-yl]methyl}amino)benzamidine acetate (154a) (3-t-butoxypyrazin-2-yl)hydrazine

[Chemical Formula 392]

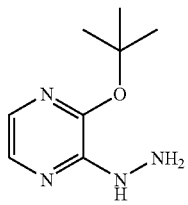

To a solution of 5.64 g of diisopropylamine in 100 ml of THF there was added 21.1 ml of n-butyllithium (2.55M, n-hexane solution) at −75° C. under a nitrogen atmosphere, and after stirring the mixture for 30 minutes, a solution of 6.78 g of 3-t-butoxypyrazine [CAS No. 70090-30-1] in 30 ml of THF was added dropwise. After stirring at the same temperature for 4 hours, a solution of 17.9 g of iodine in 100 ml of THF was added dropwise and the mixture was stirred overnight at room temperature. Next, 800 ml of saturated aqueous sodium sulfite and 800 ml of ethyl acetate were added, and the organic layer was washed with 300 ml of saturated aqueous sodium chloride and dried over anhydrous magnesium sulfate. The desiccating agent was filtered off and the filtrate was concentrated under reduced pressure. The residue was purified by silica gel column chromatography (heptane-ethyl acetate) to give 2-t-butoxy-3-iodopyrazine (0.77 g) as a yellow oil.

This compound was dissolved in 10 ml of THF, and then 1 ml of hydrazine monohydrate was added and the mixture was heated to reflux for 5 days. Next, 200 ml of ethyl acetate and 50 ml of water were added, and the organic layer was washed with 50 ml of water and 50 ml of saturated aqueous sodium chloride in that order and then dried over anhydrous magnesium sulfate. The desiccating agent was filtered off and the filtrate was concentrated under reduced pressure. The residue was purified by silica gel column chromatography (ethyl acetate-heptane) to give the title compound (0.28 g) as a gold-colored solid.

$^1$H-NMR (CDCl$_3$) δ 1.59 (s, 9H) 3.87 (br.s, 2H) 6.22 (br.s, 1H) 7.33 (d, J=3.3 Hz, 1H) 7.56 (d, J=3.3 Hz, 1H)

(154b) 3-(3-{(2-fluoro-3,5-dimethoxyphenyl)-[4-(5-methyl-[1,2,4]oxadiazol-3-yl)phenylamino]methyl}-5-oxo-4,5-dihydro-1H-[1,2,4]triazol-1-yl)-1H-pyrazin-2-one

[Chemical Formula 393]

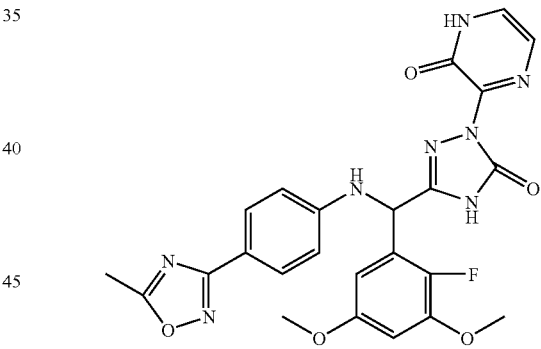

After adding 2 ml of trifluoroacetic acid to a solution of 139 mg of (3-t-butoxypyrazin-2-yl)hydrazine in 2 ml of dichloromethane, the mixture was stirred at room temperature for 2 hours. Next, 50 ml of toluene was added, the mixture was concentrated under reduced pressure, and then 50 ml of methanol was added and the mixture was concentrated under reduced pressure. The residue was dissolved in 20 ml of DMF.

The same procedure was carried out as in Examples (3e)-(3f), except that methyl iodide and the aforementioned 4 ml DMF solution were used instead of respectively the 1-fluoro-2-iodoethane in Example (3e) and the 2-hydrazinopyrimidine in Example (3f), to give the title compound (34 mg) as a yellow solid.

$^1$H-NMR (CD$_3$OD) δ 2.59 (s, 3H) 3.73 (s, 3H) 3.85 (s, 3H) 5.94 (s, 1H) 6.61 (s, 1H) 6.63 (s, 1H) 6.79 (d, J=9.1 Hz, 2H) 7.38 (d, J=3.6 Hz, 1H) 7.50 (d, J=3.6 Hz, 1H) 7.78 (d, J=9.1 Hz, 2H)

(154c) (R) and (S)-4-({(2-fluoro-3,5-dimethoxyphenyl)-[5-oxo-1-(3-oxo-3,4-dihydropyrazin-2-yl)]-4,5-dihydro-1H-[1,2,4]triazol-3-yl]methyl}amino)benzamidine acetate

[Chemical Formula 394]

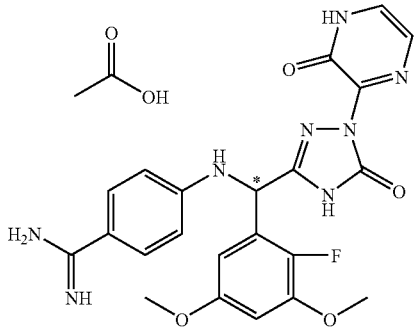

The same procedure was carried out as in Examples (3g)-(3h), except that 3-(3-{(2-fluoro-3,5-dimethoxyphenyl)-[4-(5-methyl-[1,2,4]oxadiazol-3-yl)phenylamino]-methyl}-5-oxo-4,5-dihydro-1H-[1,2,4]triazol-1-yl)-1H-pyrazin-2-one was used instead of the 5-{[2-fluoro-3-(2-fluoroethoxy)-5-methoxyphenyl]-[4-(5-methyl-[1,2,4]oxadiazol-3-yl)phenylamino]methyl}-2-pyrimidin-2-yl-2,4-dihydro-[1,2,4]triazol-3-one in Example (3g), to give the first eluting enantiomer of the title compound as a white solid.

$^1$H-NMR (CD$_3$OD) δ 1.95 (s, 3H) 3.72 (s, 3H) 3.85 (s, 3H) 5.92 (s, 1H) 6.59-6.64 (m, 2H) 6.83 (d, J=8.8 Hz, 2H) 7.50 (br.s, 1H) 7.61 (d, J=8.8 Hz, 2H) 7.70 (br.s, 1H)

Example 155

(R) and (S)-3-{3-[(4-carbamimidoylphenylamino)-(3,4-dimethoxyphenyl)methyl]-5-oxo-4,5-dihydro[1,2,4]triazol-1-yl}thiophene-2-carboxylic acid acetate

[Chemical Formula 395]

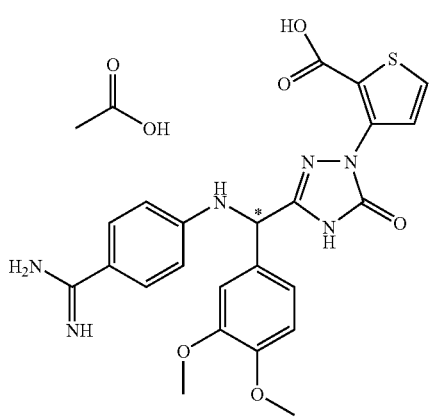

After adding 30 mg of 3-hydrazinothiophene-2-carboxylic acid methyl ester and 25 μl of triethylamine to a solution of 80 mg of {2-(3,4-dimethoxyphenyl)-2-[4-(5-methyl-[1,2,4]oxadiazol-3-yl)phenylimino]-1-methylsulfanylethylidene}carbamic acid methyl ester (Example (36d)) in 3 ml of DMF, the mixture was stirred at 85° C. for 18 hours under a nitrogen atmosphere. The reaction mixture was concentrated, and the residue was dissolved in 2 ml of methanol and 2 ml of THF. After adding 35 μl of acetic acid and 56 mg of sodium cyanotrihydroborate to the solution, the mixture was stirred at room temperature for 15 hours. Next, 2 ml of an aqueous 1N sodium hydroxide solution was added to the reaction mixture, and stirring was continued at room temperature for 2 hours. After adding 2 ml of 1N hydrochloric acid to the reaction mixture, extraction was performed with ethyl acetate. The organic layer was washed with saturated brine and dried over anhydrous magnesium sulfate. The desiccating agent was filtered off and the filtrate was concentrated under reduced pressure. The residue was purified by NAM silica gel column chromatography (methanol-ethyl acetate) to give 70 mg of 3-(3-{(3,4-dimethoxyphenyl)-[4-(5-methyl-[1,2,4]oxadiazol-3-yl)phenylamino]methyl}-5-oxo-4,5-dihydro-[1,2,4]triazol-1-yl)thiophene-2-carboxylic acid.

To a solution of this compound in 3 ml of a methanol:water:acetic acid=1:1:1 mixed solvent there was added 70 mg of iron powder, and the mixture was stirred at 60° C. for 16 hours under a nitrogen atmosphere. After filtering the reaction mixture, it was purified by reverse-phase high performance liquid chromatography (acetonitrile-water, 0.1% trifluoroacetic acid) to give 40 mg of 3-{3-[(4-carbamimidoylphenylamino)-(3,4-dimethoxyphenyl)methyl]-5-oxo-4,5-dihydro[1,2,4]triazol-1-yl}thiophene-2-carboxylic acid trifluoroacetate.

Mass spectrum (ESI) m/z: 495 (M+H)$^+$ 40 mg of this compound was optically resolved using a SUMICHIRAL OA-2500 column, and the first eluting enantiomer (17.25 mg) of the title compound was obtained as a white solid.

$^1$H-NMR (CD$_3$OD) δ 1.95 (s, 3H) 3.83 (s, 3H) 3.85 (s, 3H) 5.55 (s, 1H) 6.87 (d, J=8.8 Hz, 2H) 6.98 (d, J=8.4 Hz, 1H) 7.07-7.09 (m, 2H) 7.15 (d, J=2.0 Hz, 1H) 7.43 (d, J=5.2 Hz, 1H) 7.62 (d, J=8.8 Hz, 2H)

HPLC retention time: 19 min (Column name: SUMICHIRAL OA-2500, 30 mmφ×25 cm, Manufacturer: Sumika Chemical Analysis Service, Ltd., Mobile phase: 0.05 M ammonium acetate-methanol solution, Elution rate: 20 ml/min)

Example 156

(R) and (S)-4-{[(9-methoxy-3,4-dihydro-2H-benzo[b][1,4]dioxepin-7-yl)-(5-oxo-1-pyrimidin-2-yl-4,5-dihydro-1H-[1,2,4]triazol-3-yl)methyl]amino}benzamidine acetate

[Chemical Formula 396]

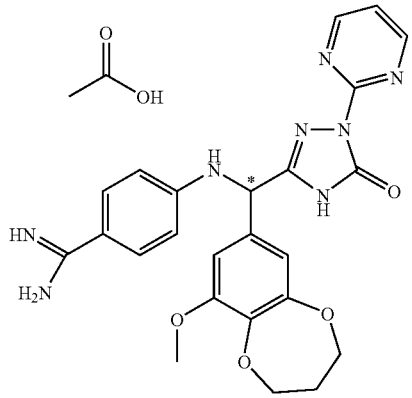

The same procedure was carried out as in Example (30d), except that 2-hydrazinopyrimidine was used instead of the (3-fluoropyridin-2-yl)hydrazine, to give the first eluting enantiomer of the title compound.

¹H-NMR (CD₃OD) δ 1.93 (s, 3H) 2.12-2.19 (m, 2H) 3.81 (s, 3H) 4.10-4.15 (m, 4H) 5.54 (s, 1H) 6.80 (d, J=1.6 Hz, 1H) 6.85 (d, J=8.8 Hz, 2H) 6.90 (d, J=2.4 Hz, 1H) 7.31 (t, J=5.2 Hz, 1H) 7.60 (d, J=9.2 Hz, 2H) 8.77 (d, J=5.2 Hz, 2H)

Mass spectrum (ESI) m/z: 489 (M+H)⁺ (data for racemic mixture)

HPLC retention time: 15 min

Example 157

5-{3-[(4-carbamimidoylphenylamino)-(2-fluoro-4,5-dimethoxyphenyl)methyl]-5-oxo-4,5-dihydro-[1,2,4]triazol-1-yl}-1H-pyrazole-4-carboxylic acid acetate (157a) 3-(N'-t-butoxycarbonylhydrazino)-1H-pyrazole-4-carboxylic acid ethyl ester

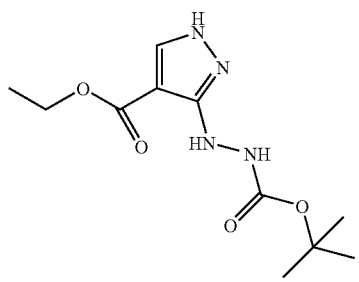

[Chemical Formula 397]

After adding 10 ml of an aqueous solution containing 6.66 g of sodium nitrite and 100 ml of a 35% hydrochloric acid solution containing 64.3 g of stannous chloride dihydrate in that order to 65 ml of a 35% hydrochloric acid solution containing 15.7 g of 3-amino-1H-pyrazole-4-carboxylic acid ethyl ester while cooling on ice, the mixture was stirred for 2 hours. The precipitate was filtered off and dissolved in 150 ml of water. After then adding 300 ml of dichloromethane, the mixture was adjusted to alkalinity with potassium carbonate, and then 33.1 g of di-t-butyl dicarbonate was added and the mixture was stirred for 60 hours at room temperature. The solution was separated, the aqueous solution was extracted twice with 200 ml of dichloromethane, and the organic layers were combined and dried over anhydrous magnesium sulfate. The desiccating agent was filtered off and the filtrate was concentrated under reduced pressure. The residue was purified by silica gel column chromatography (heptane-ethyl acetate) to give the title compound (4.35 g) as a white solid.

¹H-NMR (CDCl₃) δ 1.34 (t, J=7.3 Hz, 3H) 1.43 (s, 9H) 1.67 (br.s, 2H) 4.29 (q, J=7.3 Hz, 2H) 6.92 (br.s, 1H) 7.79 (s, 1H)

(157b) 3-hydrazino-1H-pyrazole-4-carboxylic acid ethyl ester bishydrochloride

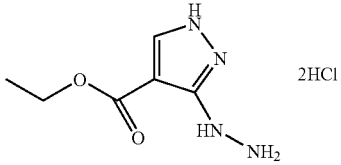

[Chemical Formula 398]

After adding 25 ml of trifluoroacetic acid to a solution of 3.30 g of 3-(N'-t-butoxycarbonylhydrazino)-1H-pyrazole-4-carboxylic acid ethyl ester in 50 ml of dichloromethane, the mixture was stirred for 2 hours at room temperature. Next, 100 ml of toluene was added and the solvent was removed under reduced pressure. The residue was dissolved in a small amount of methanol, and after adding a 4N solution containing hydrochloric acid in ethyl acetate until the solution reached acidic, the solvent was removed under reduced pressure. The residue was treated with 50 ml of t-butyl methyl ether, and the solid was filtered off and dried under reduced pressure to give the title compound (3.30 g) as a white solid.

¹H-NMR (d₆-DMSO) δ 1.25 (t, J=7.3 Hz, 3H) 4.19 (q, J=7.3 Hz, 2H) 8.18 (br.s, 1H) 8.23 (s, 1H) 9.90 (br.s, 4H) 12.55 (br.s, 1H)

(157c) 5-(3-{(2-fluoro-4,5-dimethoxyphenyl)-[4-(5-methyl-[1,2,4]oxadiazol-3-yl)phenylamino]methyl}-5-oxo-4,5-dihydro-[1,2,4]triazol-1-yl)-1H-pyrazole-4-carboxylic acid ethyl ester

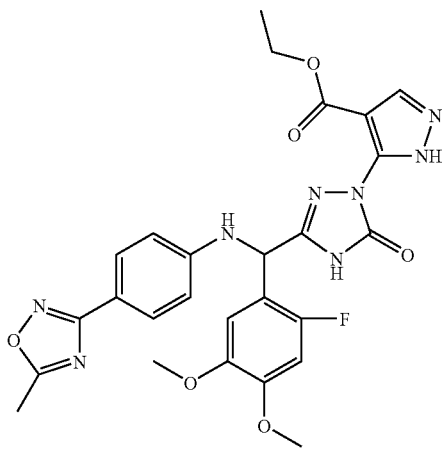

[Chemical Formula 399]

A solution of 0.140 g of 3-hydrazino-1H-pyrazole-4-carboxylic acid ethyl ester, 0.236 g of [2-(2-fluoro-4,5-dimethoxyphenyl)-2-[4-(5-methyl-[1,2,4]oxadiazol-3-yl) phenylimino]-1-methylsulfanylethylidene]carbamic acid methyl ester (Example 1d) and 0.209 ml of triethylamine in 6 ml of DMF was heated at 85° C. for 15 hours under a nitrogen atmosphere. After cooling the reaction mixture to room temperature, the solvent was removed under reduced pressure, the residue was dissolved in 7 ml of methanol, and then 0.251 g of sodium cyanotrihydroborate, 0.086 ml of acetic acid and 0.5 g of MS3A were added and the mixture was stirred at room temperature for 20 hours. Next, 100 ml of ethyl acetate and 50 ml of water were added, and the organic layer was washed with 50 ml of water and 50 ml of saturated brine in that order and then dried over anhydrous magnesium sulfate. The desiccating agent was filtered off, the filtrate was concentrated under reduced pressure, and the residue was purified by silica gel column chromatography (ethyl acetate-methanol) to give the title compound (0.152 g) as a light green solid.

$^1$H-NMR (CD$_3$OD) δ 1.16 (t, J=7.4 Hz, 3H) 2.58 (s, 3H) 3.78 (s, 3H) 3.82 (s, 3H) 4.11-4.18 (m, 2H) 5.94 (s, 1H) 6.82 (d, J=9.0 Hz, 2H) 6.85 (d, J=8.2 Hz, 1H) 7.10 (d, J=5.9 Hz, 1H) 7.79 (d, J=9.0 Hz, 2H) 8.24 (s, 1H)

(157d) 5-{3-[(4-carbamimidoylphenylamino)-(2-fluoro-4,5-dimethoxyphenyl)methyl]-5-oxo-4,5-dihydro-[1,2,4]triazol-1-yl}-1H-pyrazole-4-carboxylic acid ethyl ester acetate

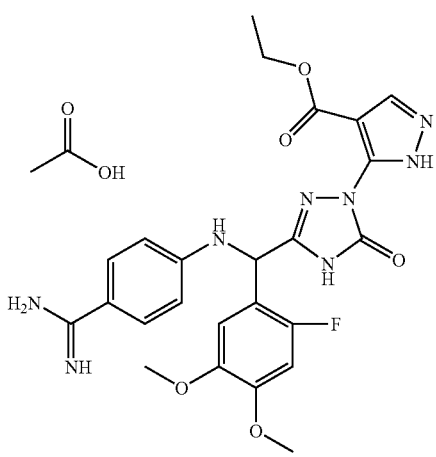

[Chemical Formula 400]

To a solution of 0.152 g of 5-(3-{(2-fluoro-4,5-dimethoxyphenyl)-[4-(5-methyl-[1,2,4]oxadiazol-3-yl)phenylamino]methyl}-5-oxo-4,5-dihydro-[1,2,4]triazol-1-yl)-1H-pyrazole-4-carboxylic acid ethyl ester in 15 ml of a methanol:water:acetic acid=1:1:1 mixed solvent there was added 0.150 g of iron powder, and the mixture was heated and stirred at 60° C. for 20 hours. After filtering the reaction mixture, it was purified by reverse-phase high performance liquid chromatography (acetonitrile-water, 0.1% acetic acid) to give 0.091 g of the title compound.

$^1$H-NMR (CD$_3$OD) δ 1.19 (t, J=7.4 Hz, 3H) 1.97 (s, 3H) 3.80 (s, 3H) 3.84 (s, 3H) 4.17 (m, 2H) 5.93 (s, 1H) 6.87 (d, J=8.7 Hz, 2H) 6.88 (d, J=10.3 Hz, 1H) 7.08 (d, J=6.9 Hz, 1H) 7.63 (d, J=8.7 Hz, 2H) 8.25 (s, 1H)

(157e) 5-{3-[(4-carbamimidoylphenylamino)-(2-fluoro-4,5-dimethoxyphenyl)methyl]-5-oxo-4,5-dihydro-[1,2,4]triazol-1-yl}-1H-pyrazole-4-carboxylic acid acetate

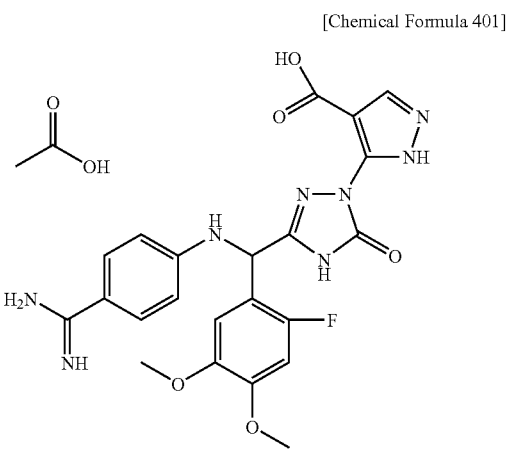

[Chemical Formula 401]

After adding 0.056 ml of triethylamine, 0.0015 g of 4-dimethylaminopyridine and 71 mg of di-t-butyl dicarbonate to a solution of 0.068 g of 5-{3-[(4-carbamimidoylphenylamino)-(2-fluoro-4,5-dimethoxyphenyl)methyl]-5-oxo-4,5-dihydro-[1,2,4]triazol-1-yl}-1H-pyrazole-4-carboxylic acid ethyl ester acetate in 4 ml of acetonitrile, the mixture was stirred at room temperature for 15 minutes. The solvent was removed under reduced pressure, and then 1 ml of methanol and 1 ml of a 5N aqueous solution of sodium hydroxide were added and the mixture was further stirred at room temperature for 6 hours. Next, 2 ml of acetic acid, 1 ml of water and 1 ml of methanol were added to the reaction mixture, which was then stirred and heated at 50° C. for 15 hours. After cooling, purification was performed by reverse-phase high performance liquid chromatography (acetonitrile-water, 0.1% acetic acid) to give 0.034 g of the title compound.

$^1$H-NMR (CD$_3$OD) δ 1.98 (s, 3H) 3.79 (s, 3H) 3.83 (s, 3H) 5.94 (s, 1H) 6.86 (d, J=10.6 Hz, 1H) 6.86 (d, J=9.1 Hz, 2H) 7.04 (d, J=6.8 Hz, 1H) 7.64 (d, J=9.1 Hz, 2H) 8.23 (s, 1H)

Example 158

4-({(R) and (S)-[3-(3-hydroxypropoxy)-5-methoxyphenyl]-(5-oxo-1-pyrimidin-2-yl-4,5-dihydro-1H-[1,2,4]triazol-3-yl)methyl}amino)benzamidine acetate

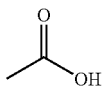

[Chemical Formula 402]

-continued

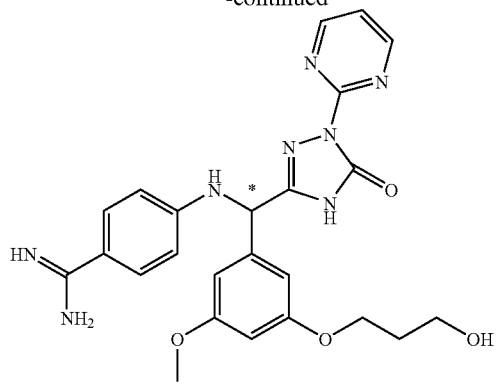

After adding 200 mg of potassium carbonate and 0.1 ml of (3-bromopropoxy)-t-butyldimethylsilane to a solution of 100 mg of {2-(3-hydroxy-5-methoxyphenyl)-2-[4-(5-methyl-[1,2,4]oxadiazol-3-yl)phenylimino]-1-methylsulfanylethylidene}carbamic acid methyl ester (Example 4c) in 1 ml of DMF, the mixture was stirred at room temperature for 17 hours. Water was added to the reaction mixture and extraction was performed with ethyl acetate. The organic layer was washed with water and saturated brine in that order, and dried through PRESEP™. The filtrate was concentrated to give a yellow oil (123 mg).

To a solution of the obtained 123 mg of yellow oil in 1 ml of DMF there were added 22 mg of 2-hydrazinopyrimidine and 0.028 ml of triethylamine, and the mixture was stirred at 85° C. for 12 hours under a nitrogen atmosphere. The reaction mixture was concentrated, and the residue was dissolved in 1.5 ml of methanol and 0.1 ml of acetic acid. After adding 100 mg of sodium cyanotrihydroborate to the solution, the mixture was stirred at room temperature for 3 days. The reaction mixture was crudely purified by reverse-phase high performance liquid chromatography (acetonitrile-water, 0.1% acetic acid) to give a crude product of 5-({3-[3-(t-butyldimethylsilanyloxy)propoxy]-5-methoxyphenyl}-[4-(5-methyl-[1,2,4]oxadiazol-3-yl)phenylamino]methyl)-2-pyrimidin-2-yl-2,4-dihydro-[1,2,4]triazol-3-one.

To a solution of the obtained crude product in 3 ml of a methanol:water:acetic acid=1:1:1 mixed solvent there was added 100 mg of iron powder, and the mixture was stirred at 60° C. for 18 hours under a nitrogen atmosphere. After filtering the reaction mixture, it was purified by reverse-phase high performance liquid chromatography (acetonitrile-water, 0.1% acetic acid) to give 4-({[3-(3-hydroxypropoxy)-5-methoxyphenyl]-(5-oxo-1-pyrimidin-2-yl-4,5-dihydro-1H-[1,2,4]triazol-3-yl)methyl}amino)benzamidine acetate.

Mass spectrum (ESI) m/z: 491 (M+H)$^+$

This compound was optically resolved using a SUMICHIRAL OA-2500 column, and the first eluting enantiomer (7.65 mg) of the title compound was obtained as a white solid.

$^1$H-NMR (CD$_3$OD) δ 1.92 (s, 3H) 3.23-3.37 (m, 2H) 3.63-3.81 (m, 5H) 4.04 (t, J=6.0 Hz, 2H) 5.60 (s, 1H) 6.45 (s, 1H) 6.72 (s, 2H) 6.86 (d, J=8.4 Hz, 2H) 7.34 (t, J=4.4 Hz, 1H) 7.60 (d, J=8.4 Hz, 2H) 8.78 (d, J=4.4 Hz, 2H)

HPLC retention time: 7 min (Column name: SUMICHIRAL OA-2500, 30 mmφ×25 cm, Manufacturer: Sumika Chemical Analysis Service, Ltd., Mobile phase: 0.05 M ammonium acetate-methanol solution, Elution rate: 40 ml/min)

Example 159

4-({(R) and (S)-[3-(2-hydroxyethoxy)-4,5-dimethoxyphenyl]-(5-oxo-1-pyrimidin-2-yl-4,5-dihydro-1H-[1,2,4]triazol-3-yl)methyl}amino)benzamidine acetate (159a) {2-(3-hydroxy-4,5-dimethoxyphenyl)-2-[4-(5-methyl-[1,2,4]oxadiazol-3-yl)phenylimino]-1-methylsulfanylethylidene}carbamic acid methyl ester

[Chemical Formula 403]

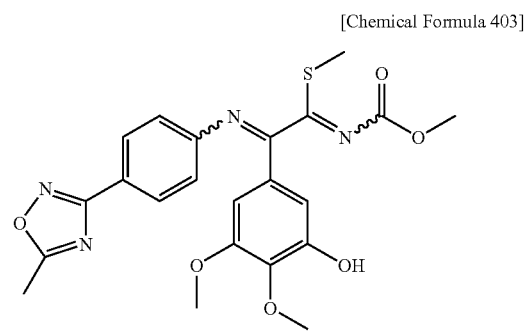

To a solution of 3.2 g of 3-hydroxy-4,5-dimethoxybenzaldehyde in 50 ml of DMF there were added 1.49 g of imidazole and 4.5 ml of chlorotriisopropylsilane. The mixture was stirred at room temperature for 21 hours and 30 minutes. Water was added to the reaction mixture and extraction was performed with ethyl acetate. The organic layer was washed with ice-cooled 1N hydrochloric acid, water, saturated aqueous sodium hydrogencarbonate, water and saturated brine in that order, and dried over anhydrous magnesium sulfate. The desiccating agent was filtered off and the filtrate was concentrated under reduced pressure. The residue was purified by silica gel column chromatography (ethyl acetate-heptane) to give 3,4-dimethoxy-5-triisopropylsilanyloxybenzaldehyde (6.08 g) as a light yellow oil.

To a solution of the obtained 6.08 g of light yellow oil in 200 ml of dichloromethane there were added 3.14 g of 4-(5-methyl-[1,2,4]oxadiazol-3-yl)phenylamine, 6 g of MS3A, 1.12 g of Yb(OTf)$_3$ and 4.5 ml of trimethylsilyl cyanide under a nitrogen atmosphere, and the mixture was stirred at room temperature for 15 hours and 30 minutes. The reaction mixture was filtered, and the filtrate was concentrated under reduced pressure. The residue was crudely purified by NH silica gel column chromatography (ethyl acetate) to give a crude product of (3,4-dimethoxy-5-triisopropylsilanyloxyphenyl)-[4-(5-methyl-[1,2,4]oxadiazol-3-yl)phenylamino]acetonitrile.

To a solution of the obtained crude product in 225 ml of a methanol:THF=2:1 mixed solvent there was added 40 ml of a 20% aqueous solution of ammonium sulfide, and the mixture was stirred at room temperature for 7 hours. Water was added to the reaction mixture and extraction was performed with ethyl acetate. The organic layer was washed with water and saturated brine in that order and dried over anhydrous magnesium sulfate. The desiccating agent was filtered off and the filtrate was concentrated under reduced pressure. The residue was crudely purified by silica gel column chromatography (heptane-ethyl acetate) to give a crude product of 2-(3,4-dimethoxy-5-triisopropylsilanyloxyphenyl)-2-[4-(5-methyl-[1,2,4]oxadiazol-3-yl)phenylamino]thioacetamide.

To a solution of the obtained crude product in 70 ml of dichloromethane there was added 2.2 g of Me$_3$O$^+$BF$_4^-$, and the mixture was stirred at room temperature for 16 hours and 30 minutes. Saturated aqueous sodium hydrogencarbonate was added to the reaction mixture, and extraction was performed with dichloromethane. The organic layer was washed with water and saturated brine in that order and dried over anhydrous sodium sulfate. The desiccating agent was filtered off and the filtrate was concentrated under reduced pressure.

To a solution of the residue in 100 ml of toluene there were added 4.6 ml of 2,4,6-collidine and 2.3 ml of methyl chloroformate, and the mixture was stirred at 80° C. for 19 hours under a nitrogen atmosphere. Water was added to the reaction mixture and extraction was performed with ethyl acetate. The organic layer was washed with ice-cooled 1N hydrochloric acid, water, saturated aqueous sodium hydrogencarbonate, water and saturated brine in that order and dried over anhydrous sodium sulfate. The desiccating agent was filtered off and the filtrate was concentrated under reduced pressure. The residue was crudely purified by silica gel column chromatography (heptane-ethyl acetate) to give {2-(3,4-dimethoxy-5-triisopropylsilanyloxyphenyl)-2-[4-(5-methyl-[1,2,4]oxadiazol-3-yl)phenylamino]-1-methylsulfanylethylidene}carbamic acid methyl ester (2.53 g) as a yellow oil.

To a solution of 2.53 g of the obtained yellow oil in 20 ml of THF there was added 4.2 ml of TBAF (1.0 M, THF solution), and the mixture was stirred at 0° C. for 2 hours. Saturated aqueous ammonium chloride was added to the reaction mixture and extraction was performed with ethyl acetate. The organic layer was washed with water and saturated brine in that order and dried over anhydrous sodium sulfate. The desiccating agent was filtered off and the filtrate was concentrated under reduced pressure. The residue was purified by silica gel column chromatography (heptane-ethyl acetate) to give the title compound (1.22 g) as a yellow solid.

$^1$H-NMR (CDCl$_3$) Main isomer:

δ 2.32 (s, 3H) 2.65 (s, 3H) 3.65 (s, 3H) 3.93 (s, 3H) 3.97 (s, 3H) 5.82 (s, 1H) 7.00 (d, J=2.0 Hz, 1H) 7.14 (d, J=8.8 Hz, 2H) 7.19 (d, J=2.0 Hz, 1H) 8.00 (d, J=8.8 Hz, 2H)

(159b) 4-({(R) and (S)-[3-(2-hydroxyethoxy)-4,5-dimethoxyphenyl]-(5-oxo-1-pyrimidin-2-yl-4,5-dihydro-1H-[1,2,4]triazol-3-yl)methyl}amino)benzamidine acetate

[Chemical Formula 404]

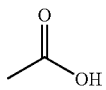

-continued

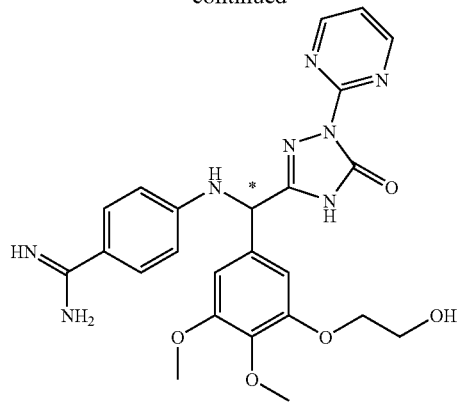

After adding 300 mg of potassium carbonate and 0.1 ml of 2-(2-bromoethoxy)tetrahydro-2H-pyran to a solution of 100 mg of {2-(3-hydroxy-4,5-dimethoxyphenyl)-2-[4-(5-methyl-[1,2,4]oxadiazol-3-yl)phenylimino]-1-methylsulfanylethylidene}carbamic acid methyl ester in 1 ml of DMF, the mixture was stirred at room temperature for 20 hours. Water was added to the reaction mixture and extraction was performed with ethyl acetate. The organic layer was washed with water and saturated brine in that order, and dried through PRESEP™. The filtrate was concentrated, and the residue was purified by silica gel column chromatography (ethyl acetate-heptane) to give (2-{3,4-dimethoxy-5-[2-(tetrahydropyran-2-yloxy)ethoxy]phenyl}-2-[4-(5-methyl-[1,2,4]oxadiazol-3-yl)phenylamino]-1-methylsulfanylethylidene)carbamic acid methyl ester (80 mg) as a yellow oil.

To a solution of the obtained 80 mg of yellow oil in 1 ml of DMF there were added 15 mg of 2-hydrazinopyrimidine and 0.019 ml of triethylamine, and the mixture was stirred at 85° C. for 12 hours under a nitrogen atmosphere. The reaction mixture was concentrated, and the residue was dissolved in 1.5 ml of methanol and 0.1 ml of acetic acid. After adding 100 mg of sodium cyanotrihydroborate to the solution, the mixture was stirred at room temperature for 3 days. The reaction mixture was crudely purified by reverse-phase high performance liquid chromatography (acetonitrile-water, 0.1% acetic acid) to give a crude product of 5-({3,4-dimethoxy-5-[2-(tetrahydropyran-2-yloxy)ethoxy]phenyl}-[4-(5-methyl-[1,2,4]oxadiazol-3-yl)phenylamino]methyl)-2-pyrimidin-2-yl-2,4-dihydro-[1,2,4]triazol-3-one.

To a solution of the obtained crude product in 3 ml of a methanol:water:acetic acid=1:1:1 mixed solvent there was added 100 mg of iron powder, and the mixture was stirred at 60° C. for 18 hours under a nitrogen atmosphere. After filtering the reaction mixture, it was purified by reverse-phase high performance liquid chromatography (acetonitrile-water, 0.1% acetic acid) to give 4-({[3-(2-hydroxyethoxy)-4,5-dimethoxyphenyl]-(5-oxo-1-pyrimidin-2-yl-4,5-dihydro-1H-[1,2,4]triazol-3-yl)methyl}amino)benzamidine acetate.

Mass spectrum (ESI) m/z: 507 (M+H)$^+$

This compound was optically resolved using a SUMICHIRAL OA-2500 column, and the first eluting enantiomer (7.23 mg) of the title compound was obtained as a light yellow solid.

$^1$H-NMR (CD$_3$OD) δ 1.92 (s, 3H) 3.77 (s, 3H) 3.82 (s, 3H) 3.84 (t, J=4.8 Hz, 2H) 3.97-4.12 (m, 2H) 5.60 (s, 1H) 6.86 (d, J=8.8 Hz, 2H) 6.90 (s, 2H) 7.31 (t, J=4.8 Hz, 1H) 7.60 (d, J=8.8 Hz, 2H) 8.77 (d, J=4.8 Hz, 2H)

HPLC retention time: 7 min (Column name: SUM-ICHIRAL OA-2500, 30 mmφ×25 cm, Manufacturer: Sumika Chemical Analysis Service, Ltd., Mobile phase: 0.05 M ammonium acetate-methanol solution, Elution rate: 40 ml/min)

Example 160

4-{[(R) and (S)-(5-ethoxy-6-methoxypyridin-3-yl)-(5-oxo-1-pyrimidin-2-yl-4,5-dihydro-1H-[1,2,4]triazol-3-yl)methyl]amino}benzamidine acetate (160a) {2-(5-ethoxy-6-methoxypyridin-3-yl)-2-[4-(5-methyl-[1,2,4]oxadiazol-3-yl)phenylimino]-1-methylsulfanylethylidene}carbamic acid methyl ester

[Chemical Formula 405]

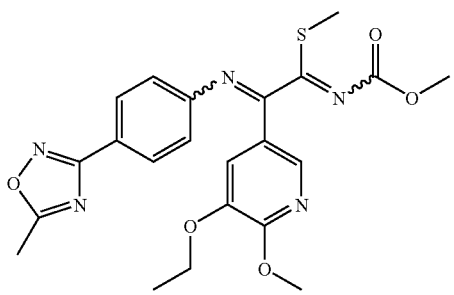

After adding 7.5 g of potassium carbonate and 6 ml of ethyl iodide to a solution of 3.9 g of 2-chloropyridin-3-ol in 60 ml of DMF, the mixture was stirred at 80° C. for 1 hour and 30 minutes. Water was added to the reaction mixture and extraction was performed with ethyl acetate. The organic layer was washed with water and saturated brine in that order and then dried over anhydrous magnesium sulfate The desiccating agent was filtered off and the filtrate was concentrated under reduced pressure.

After adding a 28% sodium methoxide-methanol solution to the residue and stirring at 80° C. for 3 hours, the mixture was further stirred at 100° C. for 3 hours. Water was added to the reaction mixture and extraction was performed with ethyl acetate. The organic layer was washed with water and saturated brine in that order and then dried over anhydrous magnesium sulfate. The desiccating agent was filtered off and the filtrate was concentrated under reduced pressure. The residue was purified by silica gel column chromatography (heptane-ethyl acetate) to give 3-ethoxy-2-methoxypyridine (4.1 g) as a colorless oil.

To a solution of 4.1 g of the obtained colorless oil and 4.25 g of sodium acetate in 40 ml of acetic acid there was added a solution of 2.83 ml of bromine in 10 ml of acetic acid at 10° C. The reaction mixture was stirred at 10° C. for 1 hour, and then at room temperature for 3 hours. The reaction mixture was poured into ice water and neutralized with an aqueous 5N sodium hydroxide solution. It was then extracted with ethyl acetate. The organic layer was washed with water and saturated brine in that order and then dried over anhydrous magnesium sulfate. The desiccating agent was filtered off and the filtrate was concentrated under reduced pressure. The residue was purified by silica gel column chromatography (heptane-ethyl acetate) to give 5-bromo-3-ethoxy-2-methoxypyridine (5.28 g) as a light yellow oil.

To a solution of the 5.28 g of light yellow oil in 80 ml of THF there was added dropwise 9.07 ml of n-butyllithium (2.64 M, hexane solution) at −78° C. over a period of 20 minutes. After stirring at −78° C. for 3 hours, 4.59 ml of N-formylmorpholine was added. After further stirring at −78° C. for 20 minutes, the temperature was slowly allowed to rise to room temperature. Saturated aqueous ammonium chloride was added to the reaction mixture and extraction was performed with ethyl acetate. The organic layer was washed with saturated brine and then dried over anhydrous magnesium sulfate. The desiccating agent was filtered off and the filtrate was concentrated under reduced pressure. The residue was purified by silica gel column chromatography (heptane-ethyl acetate) to give 5-ethoxy-6-methoxypyridine-3-carbaldehyde (2.23 g) as a light yellow oil.

After adding 533 mg of 4-(5-methyl-[1,2,4]oxadiazol-3-yl)phenylamine, 1.5 g of MS3A and 171 mg of Yb(OTf)$_3$ to a solution of 500 mg of the obtained light yellow oil in 10 ml of THF under a nitrogen atmosphere, the mixture was stirred at room temperature for 2 hours, and then 0.69 ml of trimethylsilyl cyanide was added and the mixture was stirred at room temperature for 1 day. The reaction mixture was filtered, and the filtrate was concentrated under reduced pressure.

To a solution of the residue in 20 ml of a methanol:THF=3:1 mixed solvent there was added 20 ml of a 20% aqueous solution of ammonium sulfide, and the mixture was stirred at room temperature for 1 day. Water was added to the reaction mixture and filtration was performed to give 2-(5-ethoxy-6-methoxypyridin-3-yl)-2-[4-(5-methyl-[1,2,4]oxadiazol-3-yl)phenylamino]thioacetamide (1.06 g) as a white solid.

To a solution of the obtained 1.06 g of white solid in 20 ml of acetonitrile there was added 431 mg of Me$_3$O$^+$BF$_4^-$, and the mixture was stirred at room temperature for 1 hour and 30 minutes. Saturated aqueous sodium hydrogencarbonate was added to the reaction mixture, and extraction was performed with ethyl acetate. The organic layer was washed with water and saturated brine in that order and then dried over anhydrous magnesium sulfate. The desiccating agent was filtered off and the filtrate was concentrated under reduced pressure.

To a solution of the residue in 20 ml of ethyl acetate there was added 2.5 g of manganese dioxide, and the mixture was stirred at room temperature for 1 hour. The reaction mixture was filtered, and the filtrate was concentrated under reduced pressure.

To a solution of the residue in 20 ml of toluene there were added 1.22 ml of 2,4,6-collidine and 0.61 ml of methyl chloroformate, and the mixture was stirred at 80° C. for 3 hours under a nitrogen atmosphere. Ice-cooled 1N hydrochloric acid was added to the reaction mixture and extraction was performed with ethyl acetate. The organic layer was washed with water and saturated brine in that order and then dried over anhydrous magnesium sulfate. The desiccating agent was filtered off and the filtrate was concentrated under reduced pressure. The residue was purified by silica gel column chromatography (heptane-ethyl acetate) to give the title compound (750 mg) as a yellow solid.

Mass spectrum (ESI) m/z: 470 (M+H)$^+$ (160b) 4-{[(R) and (S)-(5-ethoxy-6-methoxypyridin-3-yl)-(5-oxo-1-pyrimidin-2-yl-4,5-dihydro-1H-[1,2,4]triazol-3-yl)methyl]amino}benzamidine acetate

[Chemical Formula 406]

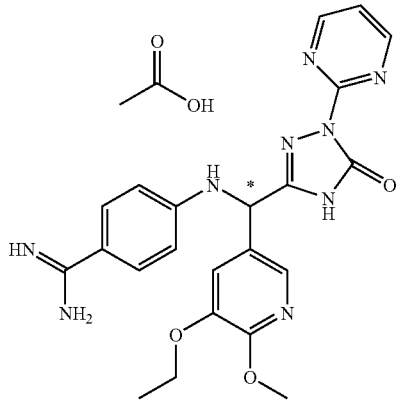

After adding 23.5 mg of 2-hydrazinopyrimidine and 0.030 ml of triethylamine to a solution of 100 mg of {2-(5-ethoxy-6-methoxypyridin-3-yl)-2-[4-(5-methyl-[1,2,4]oxadiazol-3-yl)phenylimino]-1-methylsulfanylethylidene}carbamic acid methyl ester in 1 ml of DMF, the mixture was stirred at 85° C. for 21 hours under a nitrogen atmosphere. The reaction mixture was concentrated, and the residue was dissolved in 2.0 ml of methanol and 0.1 ml of acetic acid. After adding 100 mg of sodium cyanotrihydroborate to the solution, the mixture was stirred at room temperature for 23 hours. The reaction mixture was crudely purified by reverse-phase high performance liquid chromatography (acetonitrile-water, 0.1% acetic acid) to give a crude product of 5-{(5-ethoxy-6-methoxypyridin-3-yl)-[4-(5-methyl-[1,2,4]oxadiazol-3-yl)phenylamino]methyl}-2-pyrimidin-2-yl-2,4-dihydro-[1,2,4]triazol-3-one. To a solution of the obtained crude product in 3 ml of a methanol:water:acetic acid=1:1:1 mixed solvent there was added 100 mg of iron powder, and the mixture was stirred at 60° C. for 11 hours and 30 minutes under a nitrogen atmosphere. After filtering the reaction mixture, it was purified by reverse-phase high performance liquid chromatography (acetonitrile-water, 0.1% acetic acid) to give 4-{[(5-ethoxy-6-methoxypyridin-3-yl)-(5-oxo-1-pyrimidin-2-yl-4,5-dihydro-1H-[1,2,4]triazol-3-yl)methyl]amino}benzamidine acetate.

Mass spectrum (ESI) m/z: 462 (M+H)$^+$

This compound was optically resolved using a SUMICHIRAL OA-2500 column, and the first eluting enantiomer (5.37 mg) of the title compound was obtained as a white solid.

$^1$H-NMR (CD$_3$OD) δ 1.33 (t, J=5.8 Hz, 3H) 1.92 (s, 3H) 3.91 (s, 3H) 3.99 (q, J=5.8 Hz, 2H) 5.69 (s, 1H) 6.88 (d, J=8.4 Hz, 2H) 7.30 (d, J=4.8 Hz, 1H) 7.38 (s, 1H) 7.60 (d, J=8.4 Hz, 2H) 7.83 (s, 1H) 8.76 (d, J=4.8 Hz, 2H)

HPLC retention time: 12 min (Column name: SUMICHIRAL OA-2500, 30 mmφ×25 cm, Manufacturer: Sumika Chemical Analysis Service, Ltd., Mobile phase: 0.05 M ammonium acetate-methanol solution, Elution rate: 30 ml/min)

Example 161

(R) and (S)-4-{[(4-fluoro-7-methoxy-2,3-dihydrobenzofuran-5-yl)-(5-oxo-1-pyrimidin-2-yl-4,5-dihydro-1H-[1,2,4]triazol-3-yl)methyl]amino}benzamidine acetate (161a) 4-fluoro-7-methoxy-2,3-dihydrobenzofuran-5-carbaldehyde

[Chemical Formula 407]

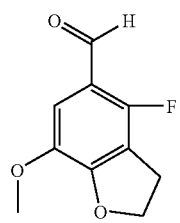

To a suspension of 50 g of methyltriphenylphosphonium bromide in 300 ml of toluene there was added dropwise 45 ml of n-butyllithium (2.55 M, hexane solution) at 0° C. under a nitrogen atmosphere. The mixture was stirred at room temperature for 2 hours and allowed to stand. Next, 150 ml of the supernatant was added to a solution of 5 g of 6-fluoro-2-hydroxy-3-methoxybenzaldehyde [CAS No. 457628-15-8] in 90 ml of toluene. The mixture was stirred at room temperature for 1 hour, 1N hydrochloric acid was added to the reaction mixture, and extraction was performed with ethyl acetate. The organic layer was dried over anhydrous magnesium sulfate and filtered, and the filtrate was concentrated. The residue was purified by silica gel column chromatography (ethyl acetate-heptane) to give 3-fluoro-6-methoxy-2-vinylphenol (4.33 g).

After dissolving 4.33 g of this compound in 20 ml of DMF, there were added 3 g of imidazole and 5.5 g of chlorotriisopropylsilane, and the mixture was stirred overnight at 50° C. Ethyl acetate was added to the reaction mixture, and washing was performed with water. The organic layer was dried over anhydrous magnesium sulfate. The desiccating agent was filtered off and the filtrate was concentrated under reduced pressure. The residue was purified by silica gel column chromatography (ethyl acetate-heptane) to give (3-fluoro-6-methoxy-2-vinylphenoxy)triisopropylsilane (3.35 g).

After dissolving 3.35 g of this compound in 20 ml of THF, there was added 5 dropwise 10 ml of borane-tetrahydrofuran complex (1M, THF solution) while cooling on ice. The mixture was stirred overnight at room temperature, and then 10 ml of saturated aqueous sodium hydrogencarbonate and 10 ml of 30% aqueous hydrogen peroxide were added and the mixture was stirred at room temperature for 4 hours. The reaction mixture was extracted with ethyl acetate, the organic layer was dried over anhydrous magnesium sulfate and filtered, and the filtrate was concentrated.

The residue was dissolved in 20 ml of THF, and then 20 ml of TBAF (1M, THF solution) was added and the mixture was stirred at room temperature for 1 hour. Ethyl acetate was added to the reaction mixture, and washing was performed with water. The organic layer was dried over anhydrous magnesium sulfate. The desiccating agent was filtered off and the filtrate was concentrated under reduced pressure. The residue was purified by silica gel column chromatography (ethyl acetate-heptane) to give 3-fluoro-2-(2-hydroxyethyl)-6-methoxyphenol (1.01 g).

After dissolving 1.01 g of this compound in 20 ml of THF, 2.1 g of triphenylphosphine was added and the mixture was cooled to −70° C. Next, 1.6 ml of diisopropylazodicarboxylate was added and the mixture was stirred overnight at room temperature. The reaction mixture was concentrated, and the residue was purified by silica gel column chromatography (ethyl acetate-heptane) to give 4-fluoro-7-methoxy-2,3-dihydrobenzofuran (802 mg).

To a solution of 665 mg of this compound and 740 mg of N,N,N',N',N''-pentamethyldiethylenetriamine in 15 ml of THF there was added dropwise 1.66 ml of n-butyllithium (2.55 M, hexane solution) at −74° C. After stirring at −70° C. for 1 hour, 0.5 ml of N-formylmorpholine was added. The temperature of the reaction mixture was slowly allowed to rise to 6° C. Next, 1N hydrochloric acid was added to the reaction mixture while cooling on ice, and then it was extracted with a mixture of hexane and t-butyl methyl ether and dried over anhydrous magnesium sulfate. The desiccating agent was filtered off and the filtrate was concentrated under reduced pressure. The residue was purified by silica gel column chromatography (ethyl acetate-heptane) to give the title compound (321 mg) as an oil.

$^{1}$H-NMR (CDCl$_{3}$) δ 3.34 (t, J=8.8 Hz, 2H) 3.89 (s, 3H) 4.82 (t, J=8.8 Hz, 2H) 7.24 (d, J=5.6 Hz, 1H) 10.18 (s, 1H)

(161b) [2-(4-cyanophenylimino)-2-(4-fluoro-7-methoxy-2,3-dihydrobenzofuran-5-yl)-1-methylsulfanylethylidene]carbamic acid methyl ester

[Chemical Formula 408]

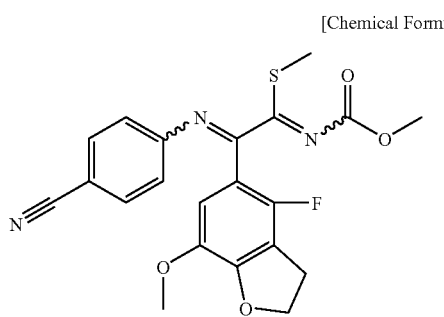

After adding 966 mg of 4-aminobenzonitrile, 1 g of MS3A, 507 mg of Yb(OTf)$_{3}$ and 2 ml of trimethylsilyl cyanide to a solution of 1.6 g of 4-fluoro-7-methoxy-2,3-dihydrobenzofuran-5-carbaldehyde in 25 ml of THF under a nitrogen atmosphere, the mixture was stirred at room temperature for 14 hours. The reaction mixture was filtered through celite, and the celite was washed with ethyl acetate. The organic layer was concentrated under reduced pressure.

To a solution of the residue in 30 ml of an ethanol:THF=2:1 mixed solvent there was added 10 ml of a 20% aqueous solution of ammonium sulfide, and the mixture was stirred at room temperature for 6 hours. Water was added to the reaction mixture and extraction was performed with ethyl acetate. After washing the organic layer with water and saturated brine, it was dried over anhydrous sodium sulfate. The desiccating agent was filtered off, and the filtrate was concentrated under reduced pressure to give a crude product of 2-(4-cyanophenylamino)-2-(4-fluoro-7-methoxy-2,3-dihydrobenzofuran-5-yl)thioacetamide.

To a solution of this compound in 10 ml of acetonitrile there was added 1 g of Me$_{3}$O$^{+}$BF$_{4}^{-}$, and the mixture was stirred at room temperature for 30 minutes. Saturated aqueous sodium hydrogencarbonate was added to the reaction mixture, and extraction was performed with ethyl acetate. After washing the organic layer with saturated brine, it was dried over anhydrous magnesium sulfate. The desiccating agent was filtered off and the filtrate was concentrated under reduced pressure.

To a solution of the residue in 30 ml of ethyl acetate there was added 1.5 g of manganese dioxide, and the mixture was stirred at room temperature for 1 hour. The reaction mixture was filtered through celite, and the filtrate was concentrated under reduced pressure.

After then adding 4 ml of 2,4,6-collidine and 2 ml of methyl chloroformate to a solution of the residue in 50 ml of toluene, the mixture was stirred at 80° C. for 1 hour under a nitrogen atmosphere. After cooling the reaction mixture, 0.5 N hydrochloric acid was added and extraction was performed with ethyl acetate. After washing the organic layer with saturated brine, it was dried over anhydrous magnesium sulfate. The desiccating agent was filtered off and the filtrate was concentrated under reduced pressure. The residue was purified by silica gel column chromatography (ethyl acetate-heptane) to give the title compound (1.68 g, isomeric mixture) as a light yellow solid.

$^{1}$H-NMR (CDCl$_{3}$) Two main isomers:

δ 2.33 (s, 3H) 3.31 (t, J=8.8 Hz, 2H) 3.63 (s, 3H) 3.90 (s, 3H) 4.79 (t, J=8.8 Hz, 2H) 6.82 (d, J=7.2 Hz, 1H) 7.07 (d, J=8.0 Hz, 2H) 7.59 (d, J=8.0 Hz, 2H)

δ 2.48 (s, 3H) 3.17 (t, J=7.6 Hz, 2H) 3.61 (s, 3H) 3.69 (s, 3H) 4.70 (t, J=7.6 Hz, 2H) 6.43 (d, J=5.6 Hz, 1H) 7.33 (d, J=5.6 Hz, 2H) 7.51 (d, J=8.8 Hz, 2H)

(161c) (R) and (S)-4-{[(4-fluoro-7-methoxy-2,3-dihydrobenzofuran-5-yl)-(5-oxo-1-pyrimidin-2-yl-4,5-dihydro-1H-[1,2,4]triazol-3-yl)methyl]amino}benzamidine acetate

[Chemical Formula 409]

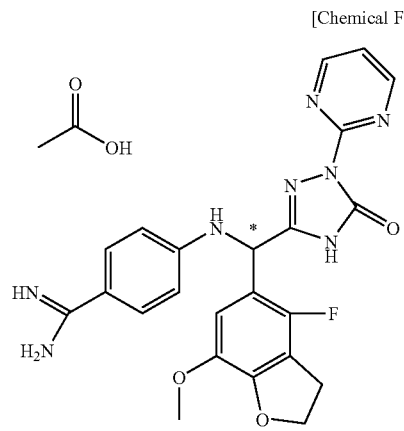

After adding 144 mg of 2-hydrazinopyrimidine and 900 μl of triethylamine to a solution of 624 mg of [2-(4-cyanophenylimino)-2-(4-fluoro-7-methoxy-2,3-dihydrobenzofuran-5-yl)-1-methylsulfanylethylidene]carbamic acid methyl ester in 12 ml of DMF, the mixture was stirred overnight at 85° C. under a nitrogen atmosphere. The reaction mixture was concentrated, and the residue was dissolved in 6.6 ml of a methanol:acetic acid=10:1 mixed solvent. After adding 1 g of sodium cyanotrihydroborate to the solution, the mixture was stirred at room temperature for 1 hour. Ethyl acetate was added to the reaction mixture. The organic layer was washed with dilute hydrochloric acid and saturated brine and then dried over anhydrous magnesium sulfate. The desiccating agent was filtered off and the filtrate was concentrated under reduced pressure. The residue was purified by NAM silica gel column chromatography (methanol-ethyl acetate) to give 4-{[(4-fluoro-7-methoxy-2,3-dihydrobenzofuran-5-yl)-(5-oxo-1-pyrimidin-2-yl-4,5-dihydro-1H-[1,2,4]triazol-3-yl)methyl]amino}benzonitrile (414 mg) as a light yellow solid.

To a solution of 414 mg of this compound in 9 ml of pyridine there were added 1.2 ml of triethylamine and 9 ml of a 20% aqueous solution of ammonium sulfide, and the mixture was stirred overnight at 60° C. under a nitrogen atmosphere. The reaction mixture was concentrated, and the residue was purified by reverse-phase high performance liquid chromatography (acetonitrile-water, 0.1% acetic acid) to give 4-{[(4-fluoro-7-methoxy-2,3-dihydrobenzofuran-5-yl)-(5-oxo-1-pyrimidin-2-yl-4,5-dihydro-1H-[1,2,4]triazol-3-yl)methyl]amino}thiobenzamide (207 mg) as a light yellow solid.

To a suspension of 207 mg of this compound in 10 ml of acetonitrile there was added 68.2 mg of $Me_3O^+BF_4^-$, and the mixture was stirred at room temperature for 15 minutes. After adding 5 ml of isopropanol and 0.1 ml of 1,1,3,3-tetramethyldisilazane to the reaction mixture, it was stirred at 60° C. for 36 hours. The reaction mixture was concentrated, and the residue was purified by reverse-phase high performance liquid chromatography (acetonitrile-water, 0.1% acetic acid) to give 4-{[(4-fluoro-7-methoxy-2,3-dihydrobenzofuran-5-yl)-(5-oxo-1-pyrimidin-2-yl-4,5-dihydro-1H-[1,2,4]triazol-3-yl)methyl]amino}benzamidine acetate (173 mg).

A SUMICHIRAL OA-2500 column was used for optical resolution of 173 mg of this compound, and the first eluting enantiomer (71 mg) of the title compound was obtained as a white solid.

$^1$H-NMR (CD$_3$OD) δ 1.92 (s, 3H) 3.27 (t, J=8.8 Hz, 2H) 3.76 (s, 3H) 4.66 (t, J=8.8 Hz, 2H) 5.88 (s, 1H) 6.86 (d, J=8.8 Hz, 2H) 6.97 (d, J=5.6 Hz, 1H) 7.31 (t, J=4.8 Hz, 1H) 7.62 (d, J=8.8 Hz, 2H) 8.77 (d, J=4.8 Hz, 2H)

HPLC retention time: 28 min

Example 162

(R) and (S)-4-{3-[(4-carbamimidoylphenylamino)-(2-fluoro-4,5-dimethoxyphenyl)methyl]-5-oxo-4,5-dihydro[1,2,4]triazol-1-yl}thiazole-5-carboxylic acid (162a) 4-amino-2-methanesulfonylthiazole-5-carboxylic acid methyl ester

[Chemical Formula 410]

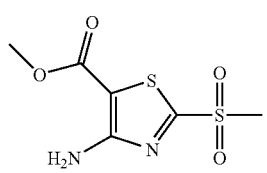

After adding 45.2 g of 4-amino-2-methylsulfanylthiazole-5-carboxylic acid methyl ester [CAS No. 60093-05-2] to 2 liters of a water:methanol=1:1 mixed solvent at room temperature, 408 g of Oxone was added in small portions over a period of 30 minutes with stirring. The mixture was stirred at room temperature for 24 hours, and then poured into a mixture of 10 liters of ethyl acetate and 10 liters of water. After washing the organic layer with 5 liters of saturated brine, it was dried over anhydrous magnesium sulfate. The desiccating agent was filtered off, and the filtrate was concentrated under reduced pressure to give the title compound (37.6 g) as a white solid.

$^1$H-NMR (CDCl$_3$) δ 3.29 (s, 3H) 3.90 (s, 3H) 6.00 (br.s, 2H)

(162b) 4-aminothiazole-5-carboxylic acid methyl ester

[Chemical Formula 411]

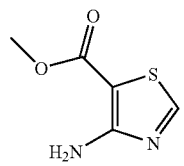

To a solution of 37.6 g of 4-amino-2-methanesulfonylthiazole-5-carboxylic acid methyl ester in 1 liter of a methanol:THF=1:1 mixed solvent at room temperature there was added 15 g of sodium borohydride in small portions over a period of 10 hours. The reaction mixture was stirred at room temperature for 40 hours, and then poured into a mixture of 6 liters of ethyl acetate and 3 liters of water. The organic layer was washed with 3 liters of water and 3 liters of saturated brine, and the aqueous layer was extracted again with ethyl acetate. The organic layers were combined and dried over anhydrous magnesium sulfate. The desiccating agent was filtered off and the filtrate was concentrated under reduced pressure. The residue was purified by silica gel column chromatography (ethyl acetate-heptane) to give the title compound (15.3 g) as a light yellow solid.

$^1$H-NMR (CDCl$_3$) δ 3.85 (s, 3H) 5.87 (br.s, 2H) 8.54 (s, 1H)

(162c) 4-hydrazinothiazole-5-carboxylic acid methyl ester

[Chemical Formula 412]

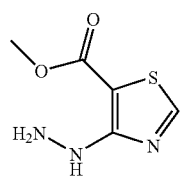

To a solution of 4-aminothiazole-5-carboxylic acid methyl ester (15.3 g) in concentrated hydrochloric acid (90 ml) there was added dropwise an aqueous solution (10 ml) containing sodium nitrite (7.32 g) at 0-10° C. The mixture was then stirred at 0° C. for 30 minutes. To this mixture there was added dropwise a concentrated hydrochloric acid solution (100 ml) containing stannous chloride (73.2 g) at 0-10° C., and the mixture was stirred at the same temperature for 2 hours. The mixture was filtered, and the filtrate was carefully added to a suspension of potassium carbonate and celite in ethyl acetate (3 liters) with stirring, with regular addition of potassium carbonate to prevent solution acidic. After adding the filtered substance to a solution of this mixture in ethyl acetate, it was rendered basic with a 5N aqueous sodium hydroxide solution. The mixture was allowed to stand, and then most of the supernatant (organic layer A) was separated off. The remaining suspension was filtered through celite and the filtrate was separated into organic layer B and aqueous layer A. Ethyl acetate (500 ml) and anhydrous magnesium sulfate were added to the filtered substance, and the mixture was stirred and then filtered. Aqueous layer A was re-extracted with the resulting filtrate. Washing of the filtered substance and re-extraction of aqueous layer A were repeated 4 times in the same manner. Organic layer A and organic layer B were combined with the obtained organic layer, and the mixture was dried over anhydrous magnesium sulfate. The desiccating agent was filtered off and the filtrate was concentrated under reduced pressure. The residue was purified by silica gel column chromatography (ethyl acetate-methanol) to give the title compound (11.6 g) as a light yellow solid.

$^1$H-NMR (CDCl$_3$) δ 3.83 (s, 3H) 4.14 (br.s, 2H) 7.55 (br.s, 1H) 8.61 (s, 1H)

(162d) (R) and (S)-4-{3-[(4-carbamimidoylphenylamino)-(2-fluoro-4,5-dimethoxyphenyl)methyl]-5-oxo-4,5-dihydro[1,2,4]triazol-1-yl}thiazole-5-carboxylic acid

[Chemical Formula 413]

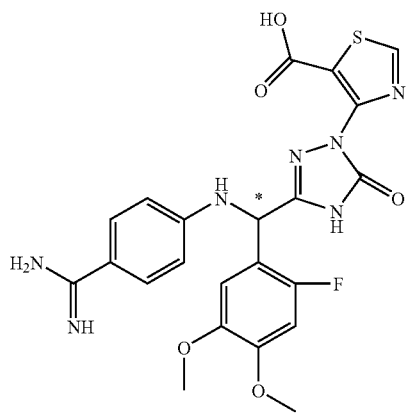

After adding 115 mg of 4-hydrazinothiazole-5-carboxylic acid methyl ester and 93 µl of triethylamine to a solution of 315 mg of [2-(2-fluoro-3,4-dimethoxyphenyl)-2-[4-(5-methyl-[1,2,4]oxadiazol-3-yl)phenylimino]-1-methylsulfanylethylidene]carbamic acid methyl ester (Example 1d) in 50 ml of DMF, the mixture was stirred at 85° C. for 24 hours under a nitrogen atmosphere. The reaction mixture was then concentrated.

The residue was dissolved in 5 ml of THF, and then 534 µl of 5N aqueous sodium hydroxide was added and the mixture was stirred at room temperature for 14 hours. After adding 10 ml of water and 700 µl of 5N hydrochloric acid to the reaction mixture, it was extracted with ethyl acetate. After washing the organic layer with saturated brine, it was dried over anhydrous magnesium sulfate. The desiccating agent was filtered off and the filtrate was concentrated under reduced pressure.

To a solution of the residue in 9 ml of a methanol:water: acetic acid=1:1:1 mixed solvent there was added 300 mg of iron powder, and the mixture was stirred at 60° C. for 20 hours under a nitrogen atmosphere. After filtering the reaction mixture, it was purified by reverse-phase high performance liquid chromatography (acetonitrile-water, 0.1% trifluoroacetic acid) to give 150 mg of 4-{3-[(4-carbamimidoylphenylamino)-(2-fluoro-4,5-dimethoxyphenyl)methyl]-5-oxo-4,5-dihydro[1,2,4]triazol-1-yl}thiazole-5-carboxylic acid trifluoroacetate.

Mass spectrum (ESI) m/z: 514 (M+H)$^+$

This compound was optically resolved using a SUMICHIRAL OA-2500 column, and the first eluting enantiomer (50 mg) of the title compound was obtained as a white solid.

$^1$H-NMR (CD$_3$OD) δ 3.78 (s, 3H) 3.83 (s, 3H) 5.91 (s, 1H) 6.82-6.87 (m, 3H) 7.07 (d, J=7.2 Hz, 1H) 7.62 (d, J=8.8 Hz, 2H) 8.89 (s, 1H)

HPLC retention time: 24 min (Column name: SUMICHIRAL OA-2500, 30 mmφ×25 cm, Manufacturer: Sumika Chemical Analysis Service, Ltd., Mobile phase: 0.5 mM ammonium acetate-methanol solution, Elution rate: 25 ml/min)

Example 163

(R) and (S)-4-(3-{(4-carbamimidoylphenylamino)-[2-fluoro-3-(3-hydroxypropoxy)-5-methoxyphenyl]methyl}-5-oxo-4,5-dihydro-[1,2,4]triazol-1-yl)thiazole-5-carboxylic acid (163a) 2-(4-cyanophenylamino)-2-(2-fluoro-5-methoxy-3-triisopropylsilanyloxyphenyl)thioacetamide

[Chemical Formula 414]

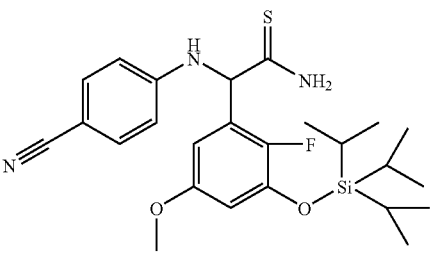

After adding 18 g of 4-aminobenzonitrile, 50 g of MS3A, 6.65 g of Yb(OTf)$_3$ and 28.6 ml of trimethylsilyl cyanide to a solution of 50.04 g of 2-fluoro-5-methoxy-3-triisopropylsilanyloxybenzaldehyde (Example 3b) in 300 ml of THF under a nitrogen atmosphere, the mixture was stirred at room temperature for 4 hours. The reaction mixture was filtered through celite, and the celite was washed with ethyl acetate. The organic layer was concentrated under reduced pressure. The residue was dissolved in ethyl acetate, and the organic layer was washed with water and saturated brine and then dried over anhydrous sodium sulfate. The desiccating agent was filtered off and the filtrate was concentrated under reduced pressure. The obtained solid was suspended in ethyl acetate-heptane (1:2) and the solid was filtered to give 4-{[cyano-(2-fluoro-5-methoxy-3-triisopropylsilanyloxyphenyl)methyl]amino}benzonitrile (59.32 g).

To a solution of the 59.32 g of this compound in 690 ml of a methanol:THF=2:1 mixed solvent there was added 230 ml of a 20% aqueous solution of ammonium sulfide, the mixture was stirred at room temperature for 6 hours. After adding ethyl acetate (1000 ml) and water (1000 ml) to the reaction mixture, extraction was performed with ethyl acetate, and the organic layer was washed with saturated brine and dried over anhydrous magnesium sulfate. The desiccating agent was filtered off and the filtrate was concentrated under reduced pressure.

The residue was dissolved in 200 ml of DMF, and then 6.3 g of imidazole and 15.1 g of chlorotriisopropylsilane were added and the mixture was stirred at room temperature for 6 hours. The reaction mixture was diluted with ethyl acetate, washed with water and saturated brine and dried over anhydrous magnesium sulfate. The desiccating agent was filtered off and the filtrate was concentrated under reduced pressure. The residue was purified by silica gel column chromatography (ethyl acetate-heptane) to give the title compound (57.97 g) as a light yellow solid.

$^1$H-NMR (CDCl$_3$) δ 1.10-1.16 (m, 18H) 1.25-1.35 (m, 3H) 3.67 (s, 3H) 5.42 (d, J=4.8 Hz, 1H) 6.03 (d, J=4.8 Hz, 1H) 6.43-6.48 (m, 2H) 6.55 (d, J=8.8 Hz, 2H) 7.34-7.38 (m, 1H) 7.38 (d, J=8.8 Hz, 2H) 7.42-7.46 (m, 1H)

(163b) [2-(4-cyanophenylimino)-2-(2-fluoro-3-hydroxy-5-methoxyphenyl)-1-methylsulfanylethylidene]carbamic acid methyl ester

[Chemical Formula 415]

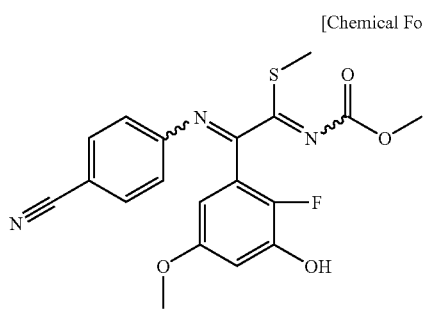

To a suspension of 57.96 g of 2-(4-cyanophenylamino)-2-(2-fluoro-5-methoxy-3-triisopropylsilanyloxyphenyl)thioacetamide in 200 ml of acetonitrile there was added 18.5 g of Me$_3$O$^+$BF$_4^-$, and the mixture was stirred at room temperature for 3 hours. After adding 2.1 g of Me$_3$O$^+$BF$_4^-$ to the reaction mixture, it was further stirred at room temperature for 1 hour. Saturated aqueous sodium hydrogencarbonate was added to the reaction mixture, and extraction was performed with ethyl acetate. After washing the organic layer with saturated brine, it was dried over anhydrous magnesium sulfate. The desiccating agent was filtered off, and the filtrate was concentrated under reduced pressure to give 2-(4-cyanophenylamino)-2-(2-fluoro-5-methoxy-3-triisopropylsilanyloxyphenyl)thioacetimidic acid methyl ester (crude product).

The crude product was dissolved in 500 ml of ethyl acetate, 112 g of manganese dioxide was added and the mixture was stirred at room temperature for 4 hours. The reaction mixture was filtered and the filtrate was concentrated under reduced pressure.

After dissolving the residue in 500 ml of toluene, 39 ml of 2,4,6-collidine and 23 ml of methyl chloroformate were added, and the mixture was stirred at 80° C. for 4 hours under a nitrogen atmosphere. After cooling the reaction mixture, 1N hydrochloric acid was added and extraction was performed with ethyl acetate. The organic layer was dried over anhydrous magnesium sulfate. The desiccating agent was filtered off and the filtrate was concentrated under reduced pressure. The residue was purified by silica gel column chromatography (heptane-ethyl acetate) to give [2-(4-cyanophenylimino)-2-(2-fluoro-5-methoxy-3-triisopropylsilanyloxyphenyl)-1-methylsulfanylethylidene]carbamic acid methyl ester (45.78 g) as a yellow solid.

After dissolving the 45.78 g of this compound in 400 ml of THF, 90 ml of TBAF (1.0 M, THF solution) was added and the mixture was stirred at room temperature for 1 hour. Saturated aqueous ammonium chloride was added to the reaction mixture, and extraction was performed with ethyl acetate. The organic layer was dried over anhydrous magnesium sulfate. The desiccating agent was filtered off and the filtrate was concentrated under reduced pressure. The residue was purified by silica gel column chromatography (heptane-ethyl acetate) to give the title compound (27.83 g, isomeric mixture) as a light yellow solid.

$^1$H-NMR (CDCl$_3$) Two main isomers:

δ 2.34 (s, 3H) 3.62 (s, 3H) 3.67 (s, 3H) 5.37 (d, J=4.8 Hz, 1H) 6.88-6.91 (m, 1H) 6.56 (dd, J=3.2, 7.2 Hz, 1H) 7.10 (d, J=8.4 Hz, 2H) 7.50 (d, J=8.4 Hz, 2H)

δ 2.48 (s, 3H) 3.61 (s, 3H) 3.80 (s, 3H) 5.26 (d, J=3.6 Hz, 1H) 6.17-6.19 (m, 1H) 6.75 (dd, J=2.8, 6.8 Hz, 1H) 6.81 (d, J=8.4 Hz, 2H) 7.61 (d, J=8.4 Hz, 2H)

(163c) (2-{3-[3-(t-butyldimethylsilanyloxy)propoxy]-2-fluoro-5-methoxyphenyl}-2-(4-cyanophenylimino)-1-methylsulfanylethylidene)carbamic acid methyl ester

[Chemical Formula 416]

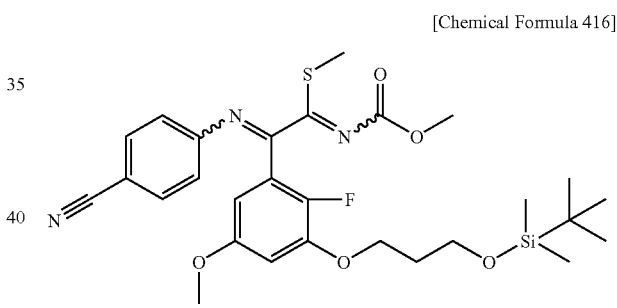

After adding 0.489 g of cesium carbonate and 0.348 ml of (3-bromopropoxy)-t-butyldimethylsilane to a solution of 0.401 g of [2-(4-cyanophenylimino)-2-(2-fluoro-3-hydroxy-5-methoxyphenyl)-1-methylsulfanylethylidene]carbamic acid methyl ester in 10 ml of DMF, the mixture was stirred at room temperature for 24 hours. Next, 50 ml of water was added to the reaction mixture and extraction was performed with 100 ml of ethyl acetate. The organic layer was washed with 50 ml of water and 50 ml of saturated brine in that order and then dried over anhydrous magnesium sulfate. The desiccating agent was filtered off and the filtrate was concentrated under reduced pressure. The residue was purified by silica gel column chromatography (ethyl acetate-heptane) to give 0.517 g of the title compound.

$^1$H-NMR (CDCl$_3$) Two main isomers:

δ 0.01 and 0.04 (s, 6H) 0.87 and 0.90 (s, 9H) 1.94 and 2.01 (quint, J=6.0 Hz, 2H) 2.34 and 2.46 (s, 3H) 3.60 and 3.63 (s, 3H) 3.66 and 3.81 (s, 3H) 3.74 and 3.79 (t, J=6.0 Hz, 2H) 4.01 and 4.10 (t, J=6.0 Hz, 2H) 6.11 and 6.89 (t, J=3.4 Hz, 1H) 6.52 and 6.61 (dd, J=6.7, 3.4 Hz, 1H) 6.81 and 7.08 (d, J=8.5 Hz, 2H) 7.47 and 7.60 (d, J=8.5 Hz, 2H)

(163d) (R) and (S)-4-(3-{(4-carbamimidoylphenylamino)-[2-fluoro-3-(3-hydroxypropoxy)-5-methoxyphenyl]methyl}-5-oxo-4,5-dihydro-[1,2,4]triazol-1-yl)thiazole-5-carboxylic acid

[Chemical Formula 417]

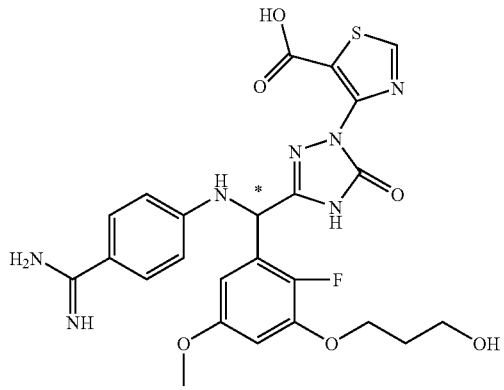

After adding 172 mg of 4-hydrazinothiazole-5-carboxylic acid methyl ester (Example 162c) and 138 µl of triethylamine to a solution of 517 mg of (2-{3-[3-(t-butyldimethylsilanyloxy)propoxy]-2-fluoro-5-methoxyphenyl}-2-(4-cyanophenylimino)-1-methylsulfanylethylidene)carbamic acid methyl ester in 15 ml of DMF, the mixture was stirred at 85° C. for 24 hours under a nitrogen atmosphere.

The reaction mixture was concentrated, and the residue was dissolved in 30 ml of a methanol:THF=2:1 mixed solvent. After adding 181 µl of acetic acid and 566 mg of sodium cyanotrihydroborate to the solution, the mixture was stirred at room temperature for 20 hours. Next, 100 ml of water was added to the reaction mixture and extraction was performed with 200 ml of ethyl acetate. The organic layer was washed with 100 ml of water and 100 ml of saturated brine in that order and then dried over anhydrous magnesium sulfate. The desiccating agent was filtered off and the filtrate was concentrated under reduced pressure.

The residue was dissolved in 20 ml of methanol, and then 4 ml of 5N aqueous sodium hydroxide was added and the mixture was stirred at room temperature for 5 hours. Acetic acid was added to the reaction mixture, which was then concentrated under reduced pressure. The residue was dissolved in 10 ml of methanol, and then 138 µl of triethylamine and 313 mg of hydroxylammonium chloride were added and the mixture was heated at 60° C. for 20 hours under a nitrogen atmosphere. After cooling, 10 ml of acetic acid, 10 ml of water and 1.01 g of iron powder were added to the reaction mixture, and heating was continued at 60° C. for 20 hours under a nitrogen atmosphere. After cooling the reaction mixture, it was filtered through celite and purified by reverse-phase high performance liquid chromatography (acetonitrile-water, 0.1% trifluoroacetic acid) to give 4-(3-{(4-carbamimidoylphenylamino)-[2-fluoro-3-(3-hydroxypropoxy)-5-methoxyphenyl]methyl}-5-oxo-4,5-dihydro-[1,2,4]triazol-1-yl)thiazole-5-carboxylic acid trifluoroacetate.

This compound was optically resolved using a SUMICHIRAL OA-2500 column, and the first eluting enantiomer (10.2 mg) of the title compound was obtained as a white solid.

$^1$H-NMR (CD$_3$OD) δ 2.00 (quint, 6.3 Hz, 2H) 3.74 (s, 3H) 3.75 (t, J=6.3 Hz, 2H) 4.13 (t, J=6.3 Hz, 2H) 5.94 (s, 1H) 6.52 (dd, J=6.7, 3.0, 1H) 6.56 (dd, J=5.5, 3.0, 1H) 6.75 (d, J=8.9 Hz, 2H) 7.64 (d, J=8.9 Hz, 2H) 8.88 (s, 1H)

HPLC retention time: 16 min (Column name: SUMICHIRAL OA-2500, 30 mmφ×25 cm, Manufacturer: Sumika Chemical Analysis Service, Ltd., Mobile phase: 0.5 mM ammonium acetate-methanol solution, Elution rate: 30 ml/min)

Example 164

(R) and (S)-4-{3-[(4-carbamimidoylphenylamino)-(5-fluoro-8-methoxy-4H-benzo[1,3]dioxin-6-yl)methyl]-5-oxo-4,5-dihydro-[1,2,4]triazol-1-yl}thiazole-5-carboxylic acid amide (164a) 4-{3-[(5-fluoro-8-methoxy-4H-benzo[1,3]dioxin-6-yl)-(4-thiocarbamoylphenylamino)methyl]-5-oxo-4,5-dihydro-[1,2,4]triazol-1-yl}thiazole-5-carboxylic acid amide

[Chemical Formula 418]

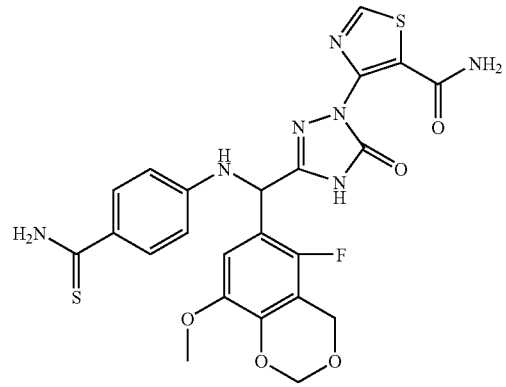

To a solution of 235 mg of 4-{3-[(4-cyanophenylamino)-(5-fluoro-8-methoxy-4H-benzo[1,3]dioxin-6-yl)methyl]-5-oxo-4,5-dihydro-[1,2,4]triazol-1-yl}thiazole-5-carboxylic acid methyl ester (Example 165b) in 4 ml of pyridine there were added 0.2 ml of triethylamine and 4 ml of a 20% aqueous solution of ammonium sulfide, and the mixture was stirred overnight at 60° C. under a nitrogen atmosphere. The reaction mixture was concentrated, and the residue was purified by reverse-phase high performance liquid chromatography (acetonitrile-water, 0.1% acetic acid) to give the title compound (109 mg) as a light yellow solid.

Mass spectrum (ESI) m/z: 558 (M+H)$^+$ (164b) (R) and (S)-4-{3-[(4-carbamimidoylphenylamino)-(5-fluoro-8-methoxy-4H-benzo[1,3]dioxin-6-yl)methyl]-5-oxo-4,5-dihydro-[1,2,4]triazol-1-yl}thiazole-5-carboxylic acid amide

[Chemical Formula 419]

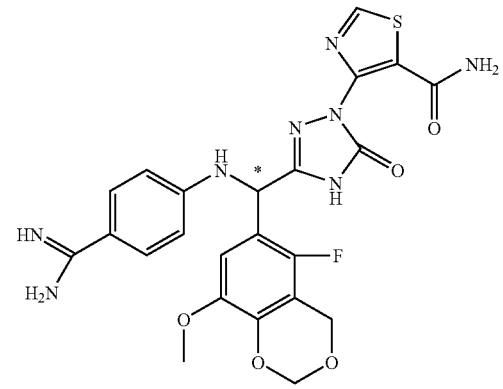

After adding 33 mg of $Me_3O^+BF_4^-$ to a suspension of 109 mg of 4-{3-[(5-fluoro-8-methoxy-4H-benzo[1,3]dioxin-6-yl)-(4-thiocarbamoylphenylamino)methyl]-5-oxo-4,5-dihydro-[1,2,4]triazol-1-yl}thiazole-5-carboxylic acid amide in 1 ml of acetonitrile, the mixture was stirred at room temperature for 30 minutes. Next, 4 ml of isopropanol and 0.055 ml of 1,1,3,3-tetramethyldisilazane were added to the reaction mixture, which was then stirred overnight at 60° C. The reaction mixture was concentrated, and the residue was purified by reverse-phase high performance liquid chromatography (acetonitrile-water, 0.1% acetic acid) to give 4-{3-[(4-carbamimidoylphenylamino)-(5-fluoro-8-methoxy-4H-benzo[1,3]dioxin-6-yl)methyl]-5-oxo-4,5-dihydro-[1,2,4]triazol-1-yl}thiazole-5-carboxylic acid amide (36 mg).

A SUMICHIRAL OA-2500 column was used for optical resolution of 36 mg of this compound, and the first eluting enantiomer (12.26 mg) of the title compound was obtained as a white solid.

$^1$H-NMR (CD$_3$OD) δ 3.75 (s, 3H) 4.81-4.92 (m, 2H) 5.23 (s, 2H) 5.79 (s, 1H) 6.79 (d, J=8.8 Hz, 2H) 7.03 (d, J=6.8 Hz, 1H) 7.58 (d, J=8.8 Hz, 2H) 9.01 (s, 1H)

HPLC retention time: 12 min (Column name: SUMICHIRAL OA-2500, 30 mmφ×25 cm, Manufacturer: Sumika Chemical Analysis Service, Ltd., Mobile phase: 0.5 mM ammonium acetate-methanol solution, Elution rate: 20 ml/min)

Example 165

(R) and (S)-4-{3-[(4-carbamimidoylphenylamino)-(5-fluoro-8-methoxy-4H-benzo[1,3]dioxin-6-yl)methyl]-5-oxo-4,5-dihydro-[1,2,4]triazol-1-yl}thiazole-5-carboxylic acid (165a) [2-(4-cyanophenylimino)-2-(5-fluoro-8-methoxy-4H-benzo[1,3]dioxin-6-yl)-1-methylsulfanylethylidene]carbamic acid methyl ester

[Chemical Formula 420]

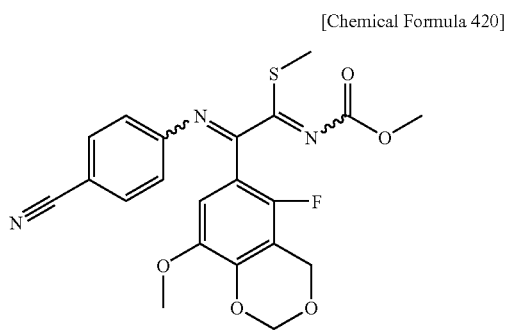

To a solution of 931 mg of 5-fluoro-8-methoxy-4H-benzo[1,3]dioxine-6-carbaldehyde (Example 32b) in 20 ml of THF there were added 520 mg of 4-aminobenzonitrile, 1 g of MS3A, 270 mg of Yb(OTf)$_3$ and 1 ml of trimethylsilyl cyanide, and the mixture was stirred overnight at room temperature. The reaction mixture was filtered through celite, and the celite was washed with ethyl acetate. The organic layer was concentrated under reduced pressure.

To a solution of the residue in 15 ml of a methanol:THF=2:1 mixed solvent there was added 5 ml of a 20% aqueous solution of ammonium sulfide, and the mixture was stirred overnight at room temperature. Water was added to the reaction mixture and extraction was performed with ethyl acetate. After washing the organic layer with water and saturated brine, it was dried over anhydrous magnesium sulfate. The desiccating agent was filtered off, and the filtrate was concentrated under reduced pressure to give a crude product of 2-(4-cyanophenylamino)-2-(5-fluoro-8-methoxy-4H-benzo[1,3]dioxin-6-yl)thioacetamide (1.31 g).

To a solution of this compound in 10 ml of acetonitrile there was added 545 mg of $Me_3O^+BF_4^-$, and the mixture was stirred at room temperature for 30 minutes. Saturated aqueous sodium hydrogencarbonate was added to the reaction mixture, and extraction was performed with ethyl acetate. After washing the organic layer with saturated brine, it was dried over anhydrous magnesium sulfate. The desiccating agent was filtered off and the filtrate was concentrated under reduced pressure.

To a solution of the residue in 15 ml of ethyl acetate there was added 2.8 g of manganese dioxide, and the mixture was stirred at room temperature for 1 hour. The reaction mixture was filtered through celite, and the filtrate was concentrated under reduced pressure.

After then adding 0.93 ml of 2,4,6-collidine and 0.54 ml of methyl chloroformate to a solution of the residue in 10 ml of toluene, the mixture was stirred at 80° C. for 1 hour under a nitrogen atmosphere. After cooling the reaction mixture, 0.5 N hydrochloric acid was added and extraction was performed with ethyl acetate. After washing the organic layer with saturated brine, it was dried over anhydrous magnesium sulfate. The desiccating agent was filtered off and the filtrate was concentrated under reduced pressure. The residue was purified by silica gel column chromatography (ethyl acetate-heptane) to give the title compound (0.89 g, isomeric mixture) as a light yellow solid.

$^1$H-NMR (CDCl$_3$) Two main isomers:

δ 2.34 (s, 3H) 3.64 (s, 3H) 3.92 (s, 3H) 4.91 (s, 2H) 5.34 (s, 2H) 6.82 (d, 5 J=8.0 Hz, 1H) 7.06 (d, J=8.0 Hz, 2H) 7.60 (d, J=8.0 Hz, 2H)

δ 2.49 (s, 3H) 3.62 (s, 3H) 3.70 (s, 3H) 4.75 (s, 2H) 5.27 (s, 2H) 6.45 (d, J=5.6 Hz, 1H) 7.35 (d, J=6.4 Hz, 2H) 7.52 (d, J=6.4 Hz, 2H)

(165b) 4-{3-[(4-cyanophenylamino)-(5-fluoro-8-methoxy-4H-benzo[1,3]dioxin-6-yl)methyl]-5-oxo-4,5-dihydro-[1,2,4]triazol-1-yl}thiazole-5-carboxylic acid methyl ester

[Chemical Formula 421]

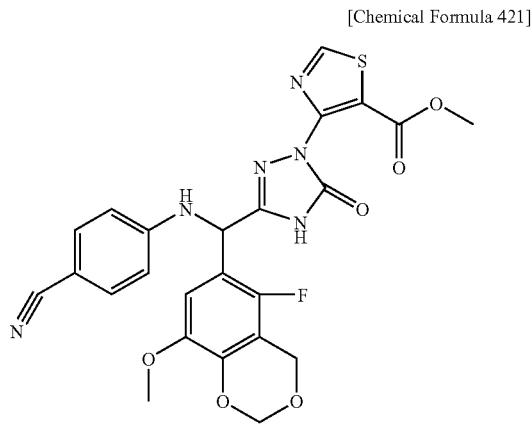

After adding 93 mg of 4-hydrazinothiazole-5-carboxylic acid methyl ester (Example 162c) and 150 µl of triethylamine to a solution of 252 mg of [2-(4-cyanophenylimino)-2-(5-fluoro-8-methoxy-4H-benzo[1,3]dioxin-6-yl)-1-methylsulfanylethylidene]carbamic acid methyl ester in 5 ml of DMF, the mixture was stirred overnight at 85° C. under a nitrogen atmosphere. The reaction mixture was then concentrated.

The residue was dissolved in 8.8 ml of a THF:methanol:acetic acid=5:5:1 mixed solvent. After adding 1 g of sodium cyanotrihydroborate to the solution, the mixture was stirred at room temperature for 1 hour. Ethyl acetate was added to the reaction mixture. After washing the organic layer with water and saturated brine, it was dried over anhydrous magnesium sulfate. The desiccating agent was filtered off and the filtrate was concentrated under reduced pressure. The residue was purified by NAM silica gel column chromatography (methanol-ethyl acetate) to give the title compound (239 mg) as a light yellow solid.

$^1$H-NMR (CD$_3$OD) δ 3.79 (s, 3H) 3.82 (s, 3H) 4.93 (s, 2H) 5.26 (s, 2H) 5.90 (s, 1H) 6.80 (d, J=9.2 Hz, 2H) 6.98 (d, J=6.8 Hz, 1H) 7.46 (d, J=9.2 Hz, 2H) 9.16 (s, 1H)

(165c) 4-{3-[(4-carbamimidoylphenylamino)-(5-fluoro-8-methoxy-4H-benzo[1,3]dioxin-6-yl)methyl]-5-oxo-4,5-dihydro-[1,2,4]triazol-1-yl}thiazole-5-carboxylic acid trifluoroacetate overnight at 60° C. under a nitrogen atmosphere. The reaction mixture was concentrated, acetic acid was added to the residue and the mixture was again concentrated. This was purified by NAM silica gel column chromatography (methanol-ethyl acetate) to give 4-{3-[(5-fluoro-8-methoxy-4H-benzo[1,3]dioxin-6-yl)-(4-thiocarbamoylphenylamino)methyl]-5-oxo-4,5-dihydro-[1,2,4]triazol-1-yl}thiazole-5-carboxylic acid (106 mg) as a light yellow solid.

To a suspension of 106 mg of this compound in 1 ml of acetonitrile there was added 31 mg of Me$_3$O$^+$BF$_4^-$, and the mixture was stirred at room temperature for 30 minutes. After adding 2 ml of isopropanol and 0.075 ml of 1,1,3,3-tetramethyldisilazane to the reaction mixture, it was stirred at 60° C. for 36 hours. The reaction mixture was concentrated, and the residue was purified by reverse-phase high performance liquid chromatography (acetonitrile-water, 0.1% trifluoroacetic acid) to give the title compound (65 mg).

Mass spectrum (ESI) m/z: 542 (M+H)$^+$ (165d) (R) and (S)-4-{3-[(4-carbamimidoylphenylamino)-(5-fluoro-8-methoxy-4H-benzo[1,3]dioxin-6-yl)methyl]-5-oxo-4,5-dihydro-[1,2,4]triazol-1-yl}thiazole-5-carboxylic acid

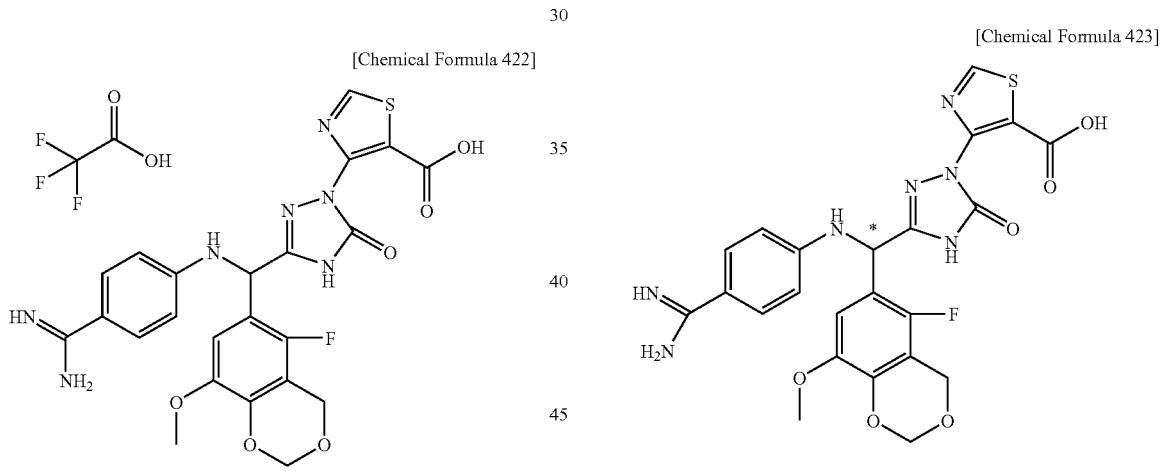

[Chemical Formula 422]

[Chemical Formula 423]

To a solution of 135 mg of 4-{3-[(4-cyanophenylamino)-(5-fluoro-8-methoxy-4H-benzo[1,3]dioxin-6-yl)methyl]-5-oxo-4,5-dihydro-[1,2,4]triazol-1-yl}thiazole-5-carboxylic acid methyl ester in 2 ml of methanol there was added 0.5 ml of a 5N aqueous sodium hydroxide solution, and the mixture was stirred at room temperature for 1 hour. After adding 0.45 ml of 5N hydrochloric acid and 1 ml of 1N hydrochloric acid to the reaction mixture, extraction was performed with ethyl acetate. After washing the organic layer with saturated brine, it was dried over anhydrous magnesium sulfate. The desiccating agent was filtered off and the filtrate was concentrated under reduced pressure.

To a solution of the residue in 2 ml of pyridine there were added 0.1 ml of triethylamine and 2 ml of a 20% aqueous solution of ammonium sulfide, and the mixture was stirred A SUMICHIRAL OA-2500 column was used for optical resolution of 65 mg of 4-{3-[(4-carbamimidoylphenylamino)-(5-fluoro-8-methoxy-4H-benzo[1,3]dioxin-6-yl)methyl]-5-oxo-4,5-dihydro-[1,2,4]triazol-1-yl}thiazole-5-carboxylic acid trifluoroacetate, and the first eluting enantiomer (19.86 mg) of the title compound was obtained as a white solid.

$^1$H-NMR (CD$_3$OD) δ 3.79 (s, 3H) 4.80-4.87 (m, 2H) 5.25 (s, 2H) 5.88 (s, 1H) 6.84 (d, J=8.8 Hz, 2H) 7.01 (d, J=6.4 Hz, 1H) 7.62 (d, J=8.8 Hz, 2H) 8.87 (s, 1H)

HPLC retention time: 29 min (Column name: SUMICHIRAL OA-2500, 30 mmφ×25 cm, Manufacturer: Sumika Chemical Analysis Service, Ltd., Mobile phase: 0.5 mM ammonium acetate-methanol solution, Elution rate: 30 ml/min)

Example 166

(R) and (S)-4-{3-[(4-carbamimidoylphenylamino)-(8-methoxy-4H-benzo[1,3]dioxin-6-yl)methyl]-5-oxo-4,5-dihydro-[1,2,4]triazol-1-yl}thiazole-5-carboxylic acid (166a) 4-(3-{(8-methoxy-4H-benzo[1,3]dioxin-6-yl)-[4-(5-methyl-[1,2,4]oxadiazol-3-yl)phenylamino]methyl}-5-oxo-4,5-dihydro-[1,2,4]triazol-1-yl)thiazole-5-carboxylic acid methyl ester

[Chemical Formula 424]

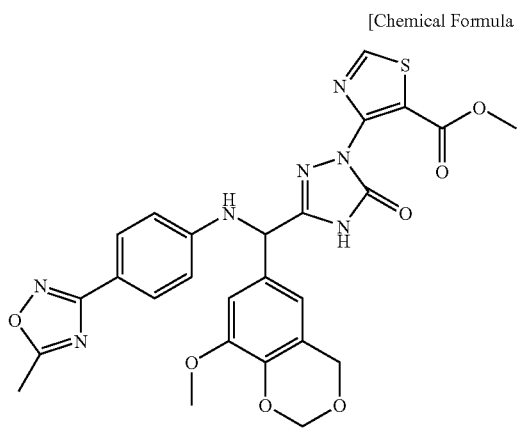

To a solution of 300 mg of [2-(8-methoxy-4H-benzo[1,3]dioxin-6-yl)-2-[4-(5-methyl-[1,2,4]oxadiazol-3-yl)phenylimino]-1-methylsulfanylethylidene]carbamic acid methyl ester (Example 21h) in 7.5 ml of THF there were added 110.4 mg of 4-hydrazinothiazole-5-carboxylic acid methyl ester (Example 162c) and 180 μl of triethylamine, and the mixture was stirred overnight at 60° C. under a nitrogen atmosphere. The reaction mixture was concentrated, the residue was dissolved in 5 ml of DMF, 0.15 ml of triethylamine was added and the mixture was stirred at 80° C. for 6 hours. The reaction mixture was then concentrated.

The residue was dissolved in 8.8 ml of a THF:methanol:acetic acid=5:5:1 mixed solvent. After adding 1 g of sodium cyanotrihydroborate to the solution, the mixture was stirred at room temperature for 1 hour. Ethyl acetate was added to the reaction mixture. After washing the organic layer with water and saturated brine, it was dried over anhydrous magnesium sulfate. The desiccating agent was filtered off and the filtrate was concentrated under reduced pressure. The residue was purified by NAM silica gel column chromatography (methanol-ethyl acetate) to give the title compound (290 mg) as a light yellow solid.

Mass spectrum (ESI) m/z: 578 (M+H)+

(166b) 4-{3-[(4-carbamimidoylphenylamino)-(8-methoxy-4H-benzo[1,3]dioxin-6-yl)methyl]-5-oxo-4,5-dihydro-[1,2,4]triazol-1-yl}thiazole-5-carboxylic acid trifluoroacetate

[Chemical Formula 425]

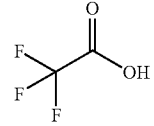

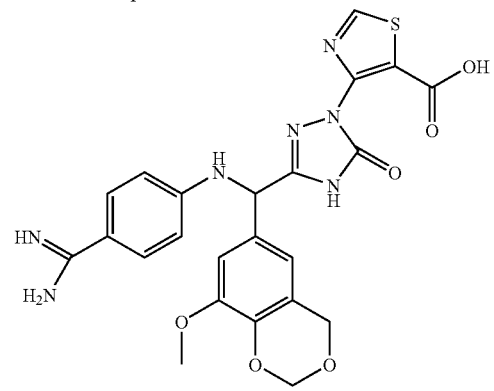

After dissolving 290 mg of 4-(3-{(8-methoxy-4H-benzo[1,3]dioxin-6-yl)-[4-(5-methyl-[1,2,4]oxadiazol-3-yl)phenylamino]methyl}-5-oxo-4,5-dihydro-[1,2,4]triazol-1-yl) thiazole-5-carboxylic acid methyl ester in 3 ml of methanol, 1 ml of a 5N aqueous sodium hydroxide solution was added and the mixture was stirred at room temperature for 0.5 hour.

After then adding 0.95 ml of 5N hydrochloric acid, 3 ml of acetic acid, 1 ml of water and 300 mg of iron powder to the reaction mixture, it was stirred overnight at 60° C. Next, 1 ml of acetic acid was added to the reaction mixture and stirring was continued at 60° C. for 6 hours. After cooling to room temperature, 0.4 ml of trifluoroacetic acid was added to the reaction mixture. After filtering the reaction mixture, it was purified by reverse-phase high performance liquid chromatography (acetonitrile-water, 0.1% trifluoroacetic acid) to give 175 mg of the title compound as a white solid.

Mass spectrum (ESI) m/z: 524 (M+H)+

(166c) (R) and (S)-4-{3-[(4-carbamimidoylphenylamino)-(8-methoxy-4H-benzo[1,3]dioxin-6-yl)methyl]-5-oxo-4,5-dihydro-[1,2,4]triazol-1-yl}thiazole-5-carboxylic acid

[Chemical Formula 426]

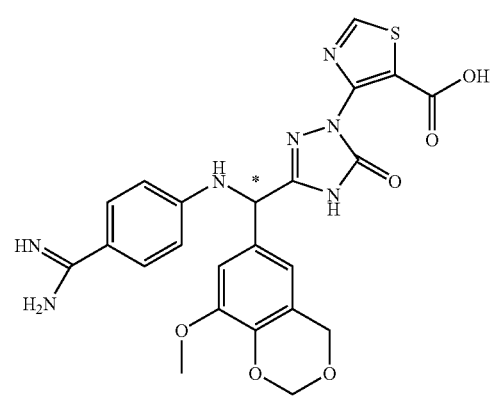

A SUMICHIRAL OA-2500 column was used for optical resolution of 70 mg of 4-{3-[(4-carbamimidoylphenylamino)-(8-methoxy-4H-benzo[1,3]dioxin-6-yl)methyl]-5-oxo-4,5-dihydro-[1,2,4]triazol-1-yl}thiazole-5-carboxylic acid trifluoroacetate, and the first eluting enantiomer (21.51 mg) of the title compound was obtained as a white solid.

$^1$H-NMR (CD$_3$OD) δ 3.85 (s, 3H) 4.82-4.90 (m, 2H) 5.24 (s, 2H) 5.54 (s, 1H) 6.81 (s, 1H) 6.85 (d, J=8.8 Hz, 2H) 7.04 (s, 1H) 7.61 (d, J=8.8 Hz, 2H) 8.87 (s, 1H)

HPLC retention time: 26 min (Column name: SUMICHIRAL OA-2500, 30 mmφ×25 cm, Manufacturer: Sumika Chemical Analysis Service, Ltd., Mobile phase: 0.5 mM ammonium acetate-methanol solution, Elution rate: 30 ml/min)

Example 167

(R) and (S)-4-(3-{(4-carbamimidoylphenylamino)-[2-fluoro-3-(2-hydroxyethoxy)-5-methoxyphenyl]methyl}-5-oxo-4,5-dihydro[1,2,4]triazol-1-yl)thiazole-5-carboxylic acid

[Chemical Formula 427]

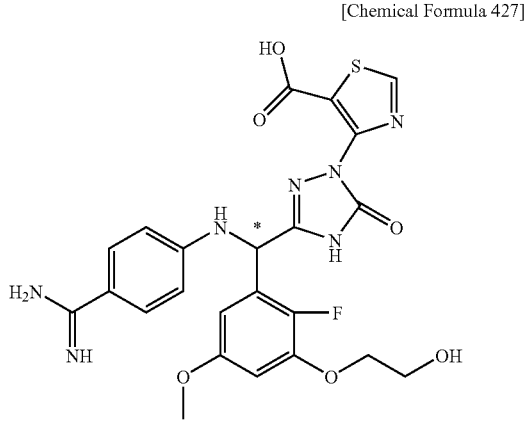

After adding 313 mg of potassium carbonate and 222 μl of 2-(2-bromoethoxy)tetrahydro-2H-pyran to a solution of 520 mg of [2-(2-fluoro-3-hydroxy-5-methoxyphenyl)-2-[4-(5-methyl-[1,2,4]oxadiazol-3-yl)phenylimino]-1-methylsulfanylethylidene]carbamic acid methyl ester (Example 3d) in 10 ml of DMF, the mixture was stirred at room temperature for 29 hours. Water was added to the reaction mixture and extraction was performed with ethyl acetate. After washing the organic layer with water and saturated brine, it was dried over anhydrous magnesium sulfate. The desiccating agent was filtered off and the filtrate was concentrated under reduced pressure.

After dissolving 280 mg of the obtained residue in 10 ml of DMF, 83 mg of 4-hydrazinothiazole-5-carboxylic acid methyl ester (Example 162c) and 67 μl of triethylamine were added to the solution and the mixture was stirred at 85° C. for 24 hours under a nitrogen atmosphere. The reaction mixture was then concentrated.

The residue was dissolved in 5 ml of THF, and then 479 μl of 5N aqueous sodium hydroxide was added and the mixture was stirred at room temperature for 16 hours. After adding 10 ml of water and 500 μl of 5N hydrochloric acid to the reaction mixture, it was extracted with ethyl acetate. After washing the organic layer with saturated brine, it was dried over anhydrous magnesium sulfate. The desiccating agent was filtered off and the filtrate was concentrated under reduced pressure.

To a solution of the residue in 9 ml of a methanol:water:acetic acid=1:1:1 mixed solvent there was added 300 mg of iron powder, and the mixture was stirred at 60° C. for 24 hours under a nitrogen atmosphere. After filtering the reaction mixture, it was purified by reverse-phase high performance liquid chromatography (acetonitrile-water, 0.1% trifluoroacetic acid) to give 80 mg of 4-(3-{(4-carbamimidoylphenylamino)-[2-fluoro-3-(2-hydroxyethoxy)-5-methoxyphenyl]methyl}-5-oxo-4,5-dihydro[1,2,4]triazol-1-yl)thiazole-5-carboxylic acid trifluoroacetate.

Mass spectrum (ESI) m/z: 544 (M+H)$^+$

This compound was optically resolved using a SUMICHIRAL OA-2500 column, and the first eluting enantiomer (10 mg) of the title compound was obtained as a white solid.

$^1$H-NMR (CD$_3$OD) δ 3.74 (s, 3H) 3.88 (dd, J=5.2, 4.4 Hz, 2H) 4.10 (dd, J=5.2, 4.4 Hz, 2H) 5.95 (s, 1H) 6.62-6.68 (m, 2H) 6.85 (d, J=9.2 Hz, 2H) 7.63 (d, J=9.2 Hz, 2H) 8.90 (s, 1H)

HPLC retention time: 20 min (Column name: SUMICHIRAL OA-2500, 30 mmφ×25 cm, Manufacturer: Sumika Chemical Analysis Service, Ltd., Mobile phase: 0.5 mM ammonium acetate-methanol solution, Elution rate: 30 ml/min)

Example 168

(R) and (S)-3-{3-[(4-carbamimidoylphenylamino)-(5-fluoro-8-methoxy-2,3-dihydrobenzo[1,4]dioxin-6-yl)methyl]-5-oxo-4,5-dihydro-[1,2,4]triazol-1-yl}thiophene-2-carboxylic acid (168a) [2-(4-cyanophenylimino)-2-(5-fluoro-8-methoxy-2,3-dihydrobenzo[1,4]dioxin-6-yl)-1-methylsulfanylethylidene]carbamic acid methyl ester

[Chemical Formula 428]

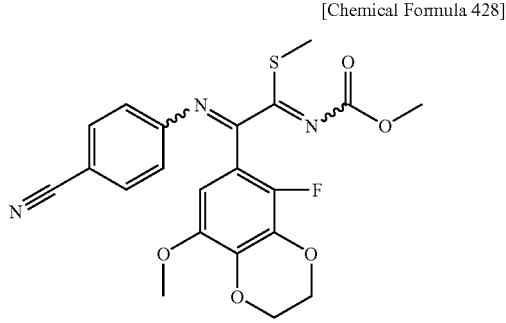

After adding 17 ml of trimethylsilyl cyanide to a suspension of 17.4 g of 5-fluoro-8-methoxy-2,3-dihydrobenzo[1,4]dioxine-6-carbaldehyde (Example 41c), 9.68 g of 4-aminobenzonitrile, 17 g of MS3A, 5 g of Yb(OTf)$_3$ in 400 ml of THF, the mixture was stirred at room temperature for 14 hours. The reaction mixture was filtered through celite, and the celite was washed with ethyl acetate. The organic layer was concentrated under reduced pressure. The residue was washed with an ethyl acetate and heptane mixed solvent to give 4-{[cyano-(5-fluoro-8-methoxy-2,3-dihydrobenzo[1,4]dioxin-6-yl)methyl]amino}benzonitrile (28.01 g).

To a solution of 28 g of this compound in 375 ml of a methanol:THF=2:1 mixed solvent there was added 250 ml of a 20% aqueous solution of ammonium sulfide, and the mixture was stirred overnight at room temperature. Next, 500 ml of water was added to the reaction mixture and the precipitated solid was filtered out. The solid was washed with water and dried to give 2-(4-cyanophenylamino)-2-(5-fluoro-8-methoxy-2,3-dihydrobenzo[1,4]dioxin-6-yl)thioacetamide (28 g).

$^1$H-NMR (CDCl$_3$) δ 3.90 (s, 3H) 4.36 (d, J=8.8 Hz, 4H) 4.46 (d, J=6.0 Hz, 1H) 5.57 (d, J=4.4 Hz, 1H) 6.64 (d, J=4.4 Hz, 1H) 6.77 (d, J=7.2 Hz, 2H) 7.55 (d, J=7.2 Hz, 2H)

To a solution of 1.02 g of this compound in 10 ml of acetonitrile there was added 0.426 g of Me$_3$O$^+$BF$_4^-$, and the mixture was stirred at room temperature for 30 minutes. Saturated aqueous sodium hydrogencarbonate was added to the reaction mixture, and extraction was performed with ethyl acetate. The organic layer was washed with saturated brine and then dried over anhydrous magnesium sulfate. The desiccating agent was filtered off and the filtrate was concentrated under reduced pressure.

To a solution of the residue in 10 ml of ethyl acetate there was added 2 g of manganese dioxide, and the mixture was stirred at room temperature for 1 hour. The reaction mixture was filtered through celite, and the filtrate was concentrated under reduced pressure.

After then adding 0.73 ml of 2,4,6-collidine and 0.42 ml of methyl chloroformate to a solution of the residue in 10 ml of toluene, the mixture was stirred at 80° C. for 1 hour under a nitrogen atmosphere. After cooling the reaction mixture, 0.5 N hydrochloric acid was added and extraction was performed with ethyl acetate. The organic layer was washed with saturated brine and then dried over anhydrous magnesium sulfate. The desiccating agent was filtered off and the filtrate was concentrated under reduced pressure. The residue was designated as "Residue 1".

Next, 5.03 g of 2-(4-cyanophenylamino)-2-(5-fluoro-8-methoxy-2,3-dihydrobenzo[1,4]dioxin-6-yl)thioacetamide was used for follow-up synthesis. Here, the reaction procedure was the same as described above, but the reagents used were 2.1 g of Me$_3$O$^+$BF$_4^-$, 10 g of manganese dioxide, 3.6 ml of 2,4,6-collidine and 2.1 ml of methyl chloroformate.

The obtained residue was combined with "Residue 1" and purified by silica gel column chromatography (ethyl acetate-heptane) to give the title compound (3.08 g, isomeric mixture) as a light yellow solid.

$^1$H-NMR (CDCl$_3$) Two main isomers:
δ 2.34 (s, 3H) 3.65 (s, 3H) 3.91 (s, 3H) 4.27-4.29 (m, 2H) 4.32-4.37 (m, 2H) 6.81 (d, J=8.4 Hz, 1H) 7.02-7.08 (m, 2H) 7.59 (d, J=8.0 Hz, 2H)
δ 2.48 (s, 3H) 3.65 (s, 3H) 3.72 (s, 3H) 4.32-4.37 (m, 2H) 4.40-4.44 (m, 2H) 6.17 (d, J=4.8 Hz, 1H) 7.02-7.08 (m, 2H) 7.50 (d, J=8.0 Hz, 2H)

(168b) 3-{3-[(4-cyanophenylamino)-(5-fluoro-8-methoxy-2,3-dihydrobenzo[1,4]dioxin-6-yl)methyl]-5-oxo-4,5-dihydro-[1,2,4]triazol-1-yl}thiophene-2-carboxylic acid methyl ester

[Chemical Formula 429]

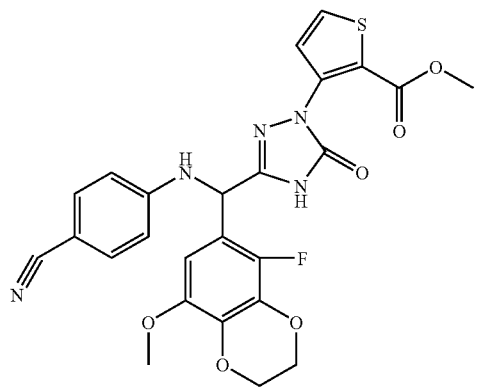

To a solution of 2 g of [2-(4-cyanophenylimino)-2-(5-fluoro-8-methoxy-2,3-dihydrobenzo[1,4]dioxin-6-yl)-1-methylsulfanylethylidene]carbamic acid methyl ester in 24 ml of DMF there were added 720 mg of 3-hydrazinothiophene-2-carboxylic acid methyl ester and 1.2 ml of triethylamine, and the mixture was stirred overnight at 85° C. under a nitrogen atmosphere.

The reaction mixture was concentrated, and the residue was dissolved in 21 ml of a methanol:THF:acetic acid=10:10:1 mixed solvent. After adding 2 g of sodium cyanotrihydroborate to the solution, the mixture was stirred overnight at room temperature. Ethyl acetate was then added to the reaction mixture. The organic layer was washed with dilute hydrochloric acid and saturated brine and then dried over anhydrous magnesium sulfate. The desiccating agent was filtered off and the filtrate was concentrated under reduced pressure. The residue was purified by NAM silica gel column chromatography (methanol-ethyl acetate) to give the title compound (1.72 g) as a light yellow solid.

(168c) 3-{3-[(4-carbamimidoylphenylamino)-(5-fluoro-8-methoxy-2,3-dihydrobenzo[1,4]dioxin-6-yl)methyl]-5-oxo-4,5-dihydro-[1,2,4]triazol-1-yl}thiophene-2-carboxylic acid trifluoroacetate

[Chemical Formula 430]

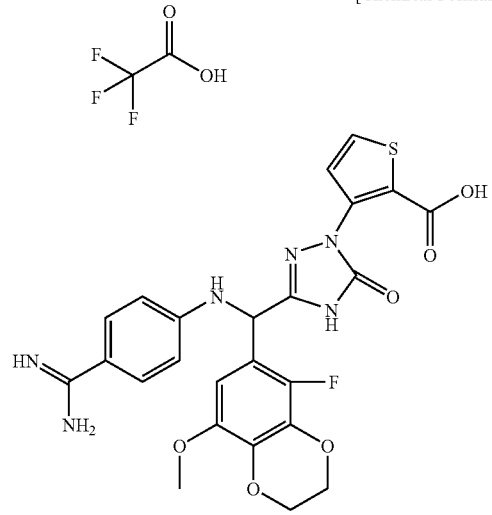

To a solution of 472 mg of 3-{3-[(4-cyanophenylamino)-(5-fluoro-8-methoxy-2,3-dihydrobenzo[1,4]dioxin-6-yl)methyl]-5-oxo-4,5-dihydro-[1,2,4]triazol-1-yl}thiophene-2-carboxylic acid methyl ester in 10 ml of ethanol there were added 488 mg of hydroxylammonium chloride and 1.22 ml of triethylamine, and the mixture was stirred overnight at 68° C. under a nitrogen atmosphere.

The reaction mixture was concentrated, and the residue was dissolved in 10 ml of acetic acid. After adding 1 ml of acetic anhydride and 500 mg of 10% palladium-carbon (hydrous) to the solution, the mixture was stirred for 3 hours under a hydrogen atmosphere. The reaction mixture was filtered through celite, and the filtrate was concentrated under reduced pressure. The residue was dissolved in 4 ml of methanol and 7 ml of a 5N aqueous sodium hydroxide solution, and the mixture was stirred at room temperature for 1 hour. After adding 2.5 ml of trifluoroacetic acid, the solution was purified by reverse phase silica gel column chromatography (acetonitrile-water, 0.1% trifluoroacetic acid) to give the title compound (350 mg) as a light yellow solid.

Mass spectrum (ESI) m/z: 541 (M+H)$^+$

339

(168d) (R) and (S)-3-{3-[(4-carbamimidoylphenylamino)-(5-fluoro-8-methoxy-2,3-dihydrobenzo[1,4]dioxin-6-yl)methyl]-5-oxo-4,5-dihydro-[1,2,4]triazol-1-yl}thiophene-2-carboxylic acid

[Chemical Formula 431]

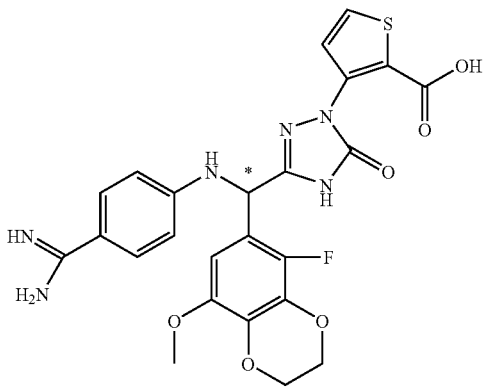

A SUMICHIRAL OA-2500 column was used for optical resolution of 120 mg of 3-{3-[(4-carbamimidoylphenylamino)-(5-fluoro-8-methoxy-2,3-dihydrobenzo[1,4]dioxin-6-yl)methyl]-5-oxo-4,5-dihydro-[1,2,4]triazol-1-yl}thiophene-2-carboxylic acid trifluoroacetate, and the first eluting enantiomer (38.5 mg) of the title compound was obtained as a white solid.

$^1$H-NMR (CD$_3$OD) δ 3.76 (s, 3H) 4.29 (s, 4H) 5.87 (s, 1H) 6.65 (d, J=6.0 Hz, 1H) 6.84 (d, J=8.8 Hz, 2H) 7.09 (d, J=5.2 Hz, 1H) 7.44 (d, J=5.2 Hz, 1H) 7.61 (d, J=8.8 Hz, 2H)

HPLC retention time: 21 min (Column name: SUMICHIRAL OA-2500, 30 mmφ×25 cm, Manufacturer: Sumika Chemical Analysis Service, Ltd., Mobile phase: 0.05 M ammonium acetate-methanol solution, Elution rate: 20 ml/min)

Example 169

3-{3-[(R) and (S)-(4-carbamimidoylphenylamino)-(5,6-dimethoxypyridin-3-yl)methyl]-5-oxo-4,5-dihydro-[1,2,4]triazol-1-yl}thiophene-2-carboxylic acid acetate (169a) {2-(5,6-dimethoxypyridin-3-yl)-2-[4-(5-methyl-[1,2,4]oxadiazol-3-yl)phenylimino]-1-methylsulfanylethylidene}carbamic acid methyl ester

[Chemical Formula 432]

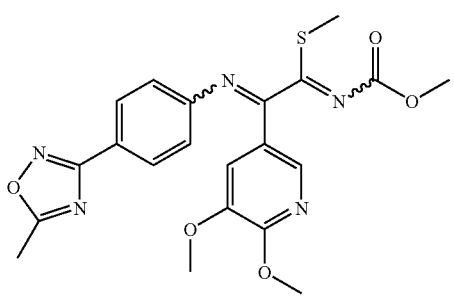

To a solution of 1.0 g of 5,6-dimethoxypyridine-3-carbaldehyde [CAS No. 52605-99-9] in 10 ml of THF there were added 1.15 g of 4-(5-methyl-[1,2,4]oxadiazol-3-yl)phenylamine, 5 g of MS3A and 371 mg of Yb(OTf)$_3$ under a nitrogen atmosphere, and after stirring at room temperature for 2 hours, 4.5 ml of trimethylsilyl cyanide was added and the mixture was stirred at room temperature for 12 hours and 30 minutes. The reaction mixture was filtered, and the filtrate was concentrated under reduced pressure. A dichloromethane, heptane and ethyl acetate mixed solvent was added and the mixture was filtered to give (5,6-dimethoxypyridin-3-yl)-[4-(5-methyl[1,2,4]oxadiazol-3-yl)phenylamino]acetonitrile (2.19 g) as a white solid.

$^1$H-NMR (CDCl$_3$) δ 2.64 (s, 3H) 3.93 (s, 3H) 4.06 (s, 3H) 4.28 (d, J=8.0 Hz, 1H) 5.45 (d, J=8.0 Hz, 1H) 6.86 (d, J=8.8 Hz, 2H) 7.20 (d, J=2.0 Hz, 1H) 7.95-8.05 (m, 3H)

To a solution of 2.19 g of the obtained white solid in 40 ml of a methanol:THF=3:1 mixed solvent there was added 40 ml of a 20% aqueous solution of ammonium sulfide, and the mixture was stirred at room temperature for 8 hours. After adding water to the reaction mixture, it was filtered to give 2-(5,6-dimethoxypyridin-3-yl)-2-[4-(5-methyl[1,2,4]oxadiazol-3-yl)phenylamino]thioacetamide (2.18 g) as a white solid.

To a solution of 2.18 g of the obtained white solid in 20 ml of acetonitrile there was added 920 mg of Me$_3$O$^+$BF$_4^-$, and the mixture was stirred at room temperature for 30 minutes. Saturated aqueous sodium hydrogencarbonate was added to the reaction mixture, and extraction was performed with ethyl acetate. The organic layer was washed with water and saturated brine in that order and then dried over anhydrous magnesium sulfate. The desiccating agent was filtered off and the filtrate was concentrated under reduced pressure.

After adding 6 g of manganese dioxide to a solution of the residue in 80 ml of ethyl acetate, the mixture was stirred at room temperature for 30 minutes. The reaction mixture was filtered, and the filtrate was concentrated under reduced pressure.

After then adding 1.86 ml of 2,4,6-collidine and 0.87 ml of methyl chloroformate to a solution of the residue in 20 ml of toluene, the mixture was stirred at 80° C. for 1 hour under a nitrogen atmosphere. Water was added to the reaction mixture and extraction was performed with ethyl acetate. The organic layer was washed with ice-cooled 0.5N hydrochloric acid, water, saturated aqueous sodium hydrogencarbonate, water and saturated brine in that order, and then dried over anhydrous magnesium sulfate. The desiccating agent was filtered off and the filtrate was concentrated under reduced pressure. The residue was purified by silica gel column chromatography (heptane-ethyl acetate) to give the title compound (1.36 g) as a yellow solid.

$^1$H-NMR (CDCl$_3$) Main isomer:
δ 2.34 (s, 3H) 2.66 (s, 3H) 3.67 (s, 3H) 3.97 (s, 3H) 4.09 (s, 3H) 7.16 (d, J=8.8 Hz, 2H) 7.74 (d, J=2.0 Hz, 1H) 7.98-8.07 (m, 3H)

(169b) 3-{3-[(R) and (S)-(4-carbamimidoylphenylamino)-(5,6-dimethoxypyridin-3-yl)methyl]-5-oxo-4,5-dihydro-[1,2,4]triazol-1-yl}thiophene-2-carboxylic acid acetate

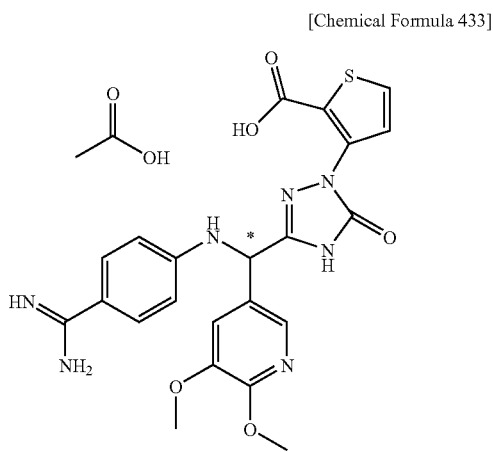

[Chemical Formula 433]

After adding 38 mg of 3-hydrazinothiophene-2-carboxylic acid methyl ester and 0.030 ml of triethylamine to a solution of 100 mg of {2-(5,6-dimethoxypyridin-3-yl)-2-[4-(5-methyl-[1,2,4]oxadiazol-3-yl)phenylimino]-1-methylsulfanylethylidene}carbamic acid methyl ester in 1 ml of DMF, the mixture was stirred at 90° C. for 12 hours under a nitrogen atmosphere. The reaction mixture was concentrated, and the residue was dissolved in 1.5 ml of methanol and 0.1 ml of acetic acid. After adding 100 mg of sodium cyanotrihydroborate to the solution, the mixture was stirred at room temperature for 3 hours. Next, 1.0 ml of a 5N aqueous sodium hydroxide solution was added and the mixture was stirred at room temperature for 2 hours. After then adding 0.3 ml of acetic acid, the reaction mixture was crudely purified by reverse-phase high performance liquid chromatography (acetonitrile-water, 0.1% acetic acid) to give a crude product of 3-(3-{(5,6-dimethoxypyridin-3-yl)-[4-(5-methyl-[1,2,4]oxadiazol-3-yl)phenylamino]methyl}-5-oxo-4,5-dihydro-[1,2,4]triazol-1-yl)thiophene-2-carboxylic acid.

To a solution of this compound in 3 ml of a methanol:water:acetic acid=1:1:1 mixed solvent there was added 100 mg of iron powder, and the mixture was stirred at 60° C. for 12 hours under a nitrogen atmosphere. After filtering the reaction mixture, it was purified by reverse-phase high performance liquid chromatography (acetonitrile-water, 0.1% trifluoroacetic acid) to give 3-{3-[(4-carbamimidoylphenylamino)-(5,6-dimethoxypyridin-3-yl)methyl]-5-oxo-4,5-dihydro-[1,2,4]triazol-1-yl}thiophene-2-carboxylic acid trifluoroacetate.

Mass spectrum (ESI) m/z: 496 (M+H)$^+$

This compound was optically resolved using a SUMICHIRAL OA-2500 column, and the first eluting enantiomer (16.55 mg) of the title compound was obtained as a white solid.

$^1$H-NMR (CD$_3$OD) δ 1.93 (s, 3H) 3.84 (s, 3H) 3.92 (s, 3H) 5.68 (s, 1H) 6.87 (d, J=8.8 Hz, 2H) 7.07 (d, J=5.2 Hz, 1H) 7.41 (d, J=2.0 Hz, 1H) 7.43 (d, J=5.2 Hz, 1H) 7.61 (d, J=8.8 Hz, 2H) 7.83 (d, J=2.0 Hz, 1H)

HPLC retention time: 16 min (Column name: SUMICHIRAL OA-2500, 30 mmφ×25 cm, Manufacturer: Sumika Chemical Analysis Service, Ltd., Mobile phase: 0.05 M ammonium acetate-methanol solution, Elution rate: 25 ml/min)

Example 170

3-{3-[(R) and (S)-(4-carbamimidoylphenylamino)-(4,5-dimethoxypyridin-2-yl)methyl]-5-oxo-4,5-dihydro-[1,2,4]triazol-1-yl}thiophene-2-carboxylic acid (170a) {2-(4,5-dimethoxypyridin-2-yl)-2-[4-(5-methyl-[1,2,4]oxadiazol-3-yl)phenylimino]-1-methylsulfanylethylidene}carbamic acid methyl ester

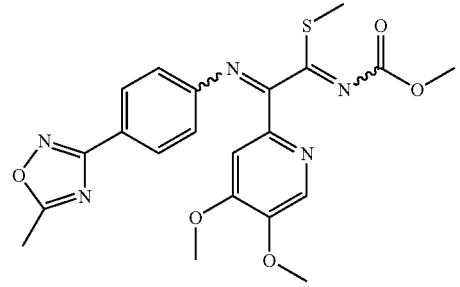

[Chemical Formula 434]

The same procedure was carried out as in Example (19b), except that 4,5-dimethoxypyridine-2-carbaldehyde [CAS No. 62885-51-2] was used instead of the 2-methoxy-6-methylpyridine-4-carbaldehyde, to give the title compound.

$^1$H-NMR (CD$_3$OD) Main isomer:

δ 2.36 (s, 3H) 2.66 (s, 3H) 3.68 (s, 3H) 4.00 (s, 3H) 4.02 (s, 3H) 7.19 (d, J=8.8 Hz, 2H) 7.81 (s, 1H) 8.04 (d, J=8.8 Hz, 2H) 8.18 (s, 1H)

(170b) 3-{3-[(R) and (S)-(4-carbamimidoylphenylamino)-(4,5-dimethoxypyridin-2-yl)methyl]-5-oxo-4,5-dihydro-[1,2,4]triazol-1-yl}thiophene-2-carboxylic acid

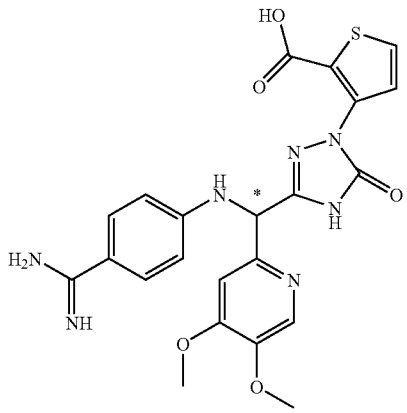

[Chemical Formula 435]

The same procedure was carried out as in Example 155, except that {2-(4,5-dimethoxypyridin-2-yl)-2-[4-(5-methyl-

[1,2,4]oxadiazol-3-yl)phenylimino]-1-methylsulfanylethylidene}carbamic acid methyl ester was used instead of the {2-(3,4-dimethoxyphenyl)-2-[4-(5-methyl-[1,2,4]oxadiazol-3-yl)phenylimino]-1-methylsulfanylethylidene}carbamic acid methyl ester, to give 3-{3-[(4-carbamimidoylphenylamino)-(4,5-dimethoxypyridin-2-yl)methyl]-5-oxo-4,5-dihydro-[1,2,4]triazol-1-yl}thiophene-2-carboxylic acid trifluoroacetate.

Mass spectrum (ESI) m/z: 496 (M+H)$^+$

A 20 mg portion of this compound was optically resolved using a SUMICHIRAL OA-2500 column, and the first eluting enantiomer (3.68 mg) of the title compound was obtained.

$^1$H-NMR (CD$_3$OD) δ 3.90 (s, 3H) 3.91 (s, 3H) 5.66 (s, 1H) 6.92 (d, J=8.8 Hz, 2H) 7.09 (d, J=5.2 Hz, 1H) 7.25 (s, 1H) 7.43 (d, J=5.2 Hz, 1H) 7.64 (d, J=8.8 Hz, 2H) 8.13 (s, 1H)

HPLC retention time: 20 min (Column name: SUMICHIRAL OA-2500, 30 mmφ×25 cm, Manufacturer: Sumika Chemical Analysis Service, Ltd., Mobile phase: 0.05 M ammonium acetate-methanol solution, Elution rate: 20 ml/min)

Example 171

(R) and (S)-3-{3-[(4-carbamimidoylphenylamino)-(2-fluoro-4,5-dimethoxyphenyl)methyl]-5-oxo-4,5-dihydro[1,2,4]triazol-1-yl}thiophene-2-carboxylic acid

[Chemical Formula 436]

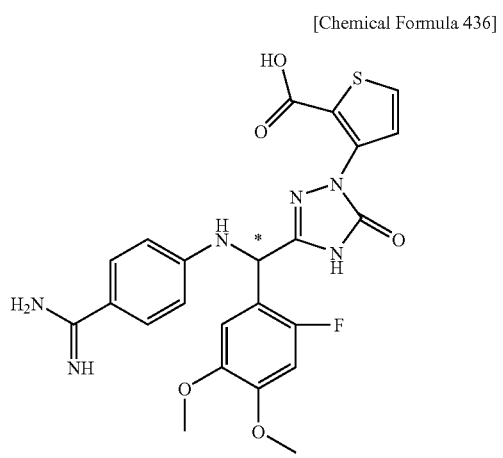

After adding 566 mg of 3-hydrazinothiophene-2-carboxylic acid methyl ester and 457 µl of triethylamine to a solution of 1.55 g of [2-(2-fluoro-4,5-dimethoxyphenyl)-2-[4-(5-methyl-[1,2,4]oxadiazol-3-yl)phenylimino]-1-methylsulfanylethylidene]carbamic acid methyl ester (Example 1d) in 50 ml of DMF, the mixture was stirred at 85° C. for 23 hours under a nitrogen atmosphere. The reaction mixture was then concentrated.

A 400 mg portion of the residue was dissolved in 10 ml of methanol, 708 µl of a 5N aqueous sodium hydroxide solution was added, and the mixture was stirred at room temperature for 24 hours. After then adding 800 µl of 5N hydrochloric acid and water to the reaction mixture, extraction was performed with ethyl acetate. The organic layer was washed with saturated brine and then dried over anhydrous magnesium sulfate. The desiccating agent was filtered off and the filtrate was concentrated under reduced pressure.

To a solution of the residue in 12 ml of a methanol:water: acetic acid=1:1:1 mixed solvent there was added 400 mg of iron powder, and the mixture was stirred at 60° C. for 16 hours under a nitrogen atmosphere. After filtering the reaction mixture, it was purified by reverse-phase high performance liquid chromatography (acetonitrile-water, 0.1% trifluoroacetic acid) to give 110 mg of 3-{3-[(4-carbamimidoylphenylamino)-(2-fluoro-4,5-dimethoxyphenyl)methyl]-5-oxo-4,5-dihydro[1,2,4]triazol-1-yl}thiophene-2-carboxylic acid trifluoroacetate.

Mass spectrum (ESI) m/z: 513 (M+H)$^+$

This compound was optically resolved using a SUMICHIRAL OA-2500 column, and the first eluting enantiomer (30.02 mg) of the title compound was obtained as a white solid.

$^1$H-NMR (CD$_3$OD) δ 3.78 (s, 3H) 3.82 (s, 3H) 5.88 (s, 1H) 6.82-6.87 (m, 3H) 7.08 (d, J=7.2 Hz, 2H) 7.42 (d, J=5.2 Hz, 1H) 7.62 (d, J=8.8 Hz, 2H)

HPLC retention time: 16 min (Column name: SUMICHIRAL OA-2500, 30 mmφ×25 cm, Manufacturer: Sumika Chemical Analysis Service, Ltd., Mobile phase: 0.5 mM ammonium acetate-methanol solution, Elution rate: 35 ml/min)

Example 172

(R) and (S)-4-({[2-fluoro-3-(2-hydroxyethoxy)-5-methoxyphenyl]-(5-oxo-1-pyrimidin-2-yl-4,5-dihydro-1H-[1,2,4]triazol-3-yl)methyl}amino)benzamidine acetate (172a) (2-{2-fluoro-5-methoxy-3-[2-(tetrahydropyran-2-yloxy)ethoxy]phenyl}-2-[4-(5-methyl-[1,2,4]oxadiazol-3-yl)phenylimino]-1-methylsulfanylethylidene)carbamic acid methyl ester

[Chemical Formula 437]

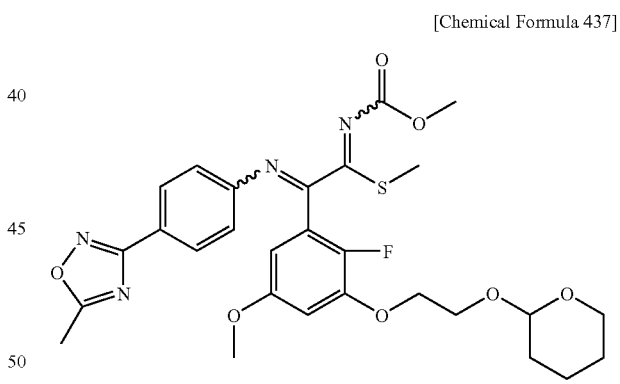

After adding 200 mg of potassium carbonate and 0.1 ml of 2-(2-bromoethoxy)tetrahydro-2H-pyran to a solution of 80 mg of [2-(2-fluoro-3-hydroxy-5-methoxyphenyl)-2-[4-(5-methyl-[1,2,4]oxadiazol-3-yl)phenylimino]-1-methylsulfanylethylidene]carbamic acid methyl ester (Example 3d) in 1 ml of DMF, the mixture was stirred at room temperature for 14 hours. Water was added to the reaction mixture and extraction was performed with ethyl acetate. The organic layer was washed with water and dried through PRESEP™. The filtrate was concentrated, and the residue was purified by silica gel column chromatography (ethyl acetate-heptane) to give the title compound (69 mg) as a yellow oil.

$^1$H-NMR (CDCl$_3$) δ 1.40-1.90 (m, 6H) 2.32 and 2.46 (s, 3H) 2.62 and 2.65 (s, 3H) 3.42-4.28 (m, 12H) 4.65 and 4.71 (br.t, J=3.2 Hz, 1H) 6.10-6.17 and 6.95-7.01 (m, 1H) 6.54 and 6.75 (dd, J=2.8, 6.8 Hz, 1H) 6.84 and 7.11 (d, J=8.4 Hz, 2H) 7.89 and 8.03 (d, J=8.4 Hz, 2H)

Mass spectrum (ESI) m/z: 587 (M+H)$^+$ (172b) 4-({[2-fluoro-3-(2-hydroxyethoxy)-5-methoxyphenyl]-(5-oxo-1-pyrimidin-2-yl-4,5-dihydro-1H-[1,2,4]triazol-3-yl)methyl}amino)benzamidine acetate

[Chemical Formula 438]

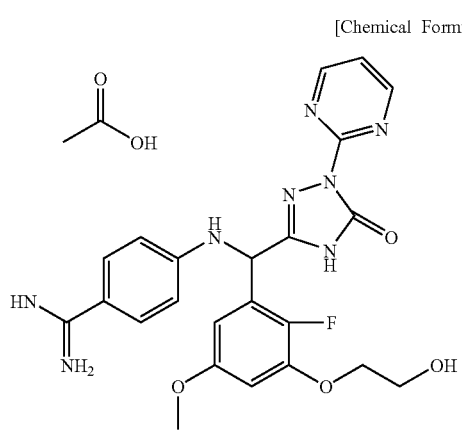

After adding 13 mg of 2-hydrazinopyrimidine and 0.016 ml of triethylamine to a solution of 69 mg of (2-{2-fluoro-5-methoxy-3-[2-(tetrahydropyran-2-yloxy)ethoxy]phenyl}-2-[4-(5-methyl-[1,2,4]oxadiazol-3-yl)phenylimino]-1-methylsulfanylethylidene)carbamic acid methyl ester in 1 ml of DMF, the mixture was stirred at 85° C. for 16 hours under a nitrogen atmosphere. The reaction mixture was concentrated to give a crude product of 5-({2-fluoro-5-methoxy-3-[2-(tetrahydropyran-2-yloxy)ethoxy]phenyl}-[4-(5-methyl-[1,2,4]oxadiazol-3-yl)phenylimino]methyl)-2-pyrimidin-2-yl-2,4-dihydro-[1,2,4]triazol-3-one.

Mass spectrum (ESI) m/z: 639 (M+Na)$^+$

This compound was dissolved in 1 ml of methanol, 1 ml of THF and 0.1 ml of acetic acid. After adding 100 mg of sodium cyanotrihydroborate to the solution, the mixture was stirred at room temperature for 3 hours. The reaction mixture was crudely purified by reverse-phase high performance liquid chromatography (acetonitrile-water, 0.1% acetic acid) to give a crude product of 5-({2-fluoro-5-methoxy-3-[2-(tetrahydropyran-2-yloxy)ethoxy]phenyl}-[4-(5-methyl-[1,2,4]oxadiazol-3-yl)phenylamino]methyl)-2-pyrimidin-2-yl-2,4-dihydro-[1,2,4]triazol-3-one.

$^1$H-NMR (CD$_3$OD) δ 1.40-1.90 (m, 6H) 2.59 (s, 3H) 3.43-4.30 (m, 9H) 4.70 (br.s, 1H) 5.96 (s, 1H) 6.62-6.75 (m, 2H) 6.82 (d, J=8.8 Hz, 2H) 7.36 (t, J=4.8 Hz, 1H) 7.79 (d, J=8.8 Hz, 2H) 8.79 (d, J=4.8 Hz, 2H)

Mass spectrum (ESI) m/z: 641 (M+Na)$^+$

To a solution of this compound in 3 ml of a methanol:water:acetic acid=1:1:1 mixed solvent there was added 100 mg of iron powder, and the mixture was stirred at 60° C. for 2 days under a nitrogen atmosphere. After filtering the reaction mixture, it was purified by reverse-phase high performance liquid chromatography (acetonitrile-water, 0.1% acetic acid) to give the title compound (13.89 mg).

$^1$H-NMR (CD$_3$OD) δ 1.94 (s, 3H) 3.71 (s, 3H) 3.88 (t, J=4.8 Hz, 2H) 4.10 (t, J=4.8 Hz, 2H) 5.99 (s, 1H) 6.55-6.72 (m, 2H) 6.86 (d, J=8.8 Hz, 2H) 7.34 (t, J=4.8 Hz, 1H) 7.62 (d, J=8.8 Hz, 2H) 8.77 (d, J=4.8 Hz, 2H)

Mass spectrum (ESI) m/z: 495 (M+H)$^+$ (172c) {[4-({[2-fluoro-3-(2-hydroxyethoxy)-5-methoxyphenyl]-(5-oxo-1-pyrimidin-2-yl-4,5-dihydro-1H-[1,2,4]triazol-3-yl)methyl}amino)phenyl]iminomethyl}carbamic acid ethyl ester, or {1-amino-1-[4-({[2-fluoro-3-(2-hydroxyethoxy)-5-methoxyphenyl]-(5-oxo-1-pyrimidin-2-yl-4,5-dihydro-1H-[1,2,4]triazol-3-yl)methyl}amino)phenyl]methylidene}carbamic acid ethyl ester To a solution of 500 mg of 4-({[2-fluoro-3-(2-hydroxyethoxy)-5-methoxyphenyl]-(5-oxo-1-pyrimidin-2-yl-4,5-dihydro-1H-[1,2,4]triazol-3-yl)methyl}amino)benzamidine acetate in 8 ml of DMF there were added 280 mg of ethyl 4-nitrophenylcarbonate [CAS No. 6132-45-2] and 0.75 ml of triethylamine, and the mixture was stirred at 50° C. for 4 hours and 30 minutes. After adding 1 ml of acetic acid to the reaction mixture, it was concentrated under reduced pressure. The obtained residue was purified by NAM silica gel column chromatography (methanol-ethyl acetate) to give the title compound (474 mg).

$^1$H-NMR (CD$_3$OD) δ 1.30 (t, J=7.2 Hz, 3H) 3.78 (s, 3H) 3.88 (t, J=4.8 Hz, 2H) 4.11 (t, J=4.8 Hz, 2H) 4.18 (q, J=7.2 Hz, 2H) 5.98 (s, 1H) 6.64 (dd, J=3.2, 4.8 Hz, 1H) 6.67 (dd, J=3.2, 6.8 Hz, 1H) 6.80 (d, J=8.8 Hz, 2H) 7.36 (t, J=4.8 Hz, 1H) 7.70 (d, J=8.8 Hz, 2H) 8.78 (d, J=4.8 Hz, 2H)

(172d) (R) and (S)-{[4-({[2-fluoro-3-(2-hydroxyethoxy)-5-methoxyphenyl]-(5-oxo-1-pyrimidin-2-yl-4,5-dihydro-1H-[1,2,4]triazol-3-yl)methyl}amino)phenyl]iminomethyl}carbamic acid ethyl ester, or (R) and (S)-{1-amino-1-[4-({[2-fluoro-3-(2-hydroxyethoxy)-5-methoxyphenyl]-(5-oxo-1-pyrimidin-2-yl-4,5-dihydro-1H-[1,2,4]triazol-3-yl)methyl}amino)phenyl]methylidene}carbamic acid ethyl ester A SUMICHIRAL OA-2500 column was used for optical resolution of 40 mg of this compound obtained in Example (172c), and the first eluting enantiomer (17.6 mg) of the title compound was obtained.

HPLC retention time: 21 min (Column name: SUMICHIRAL OA-2500, 30 mmφ×25 cm, Manufacturer: Sumika Chemical Analysis Service, Ltd., Mobile phase: 0.05 M ammonium acetate-methanol solution, Elution rate: 30 ml/min)

(172e) (R) or (S)-4-({[2-fluoro-3-(2-hydroxy-ethoxy)-5-methoxyphenyl]-(5-oxo-1-pyrimidin-2-yl-4,5-dihydro-1H-[1,2,4]triazol-3-yl)methyl}amino)benzamidine acetate

[Chemical Formula 439]

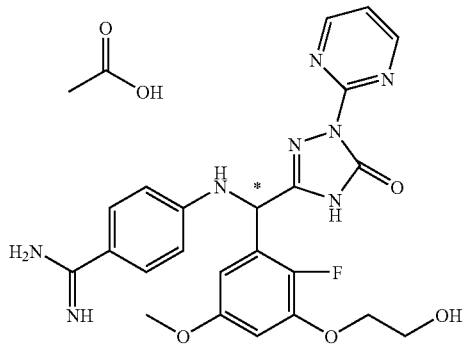

To a solution of 17.6 mg of the first eluting enantiomer compound obtained in Example (172d) in 0.5 ml of methanol there was added 0.5 ml of a 2N aqueous sodium hydroxide solution, and the mixture was stirred at room temperature for 1 hour. After adding 0.5 ml of 2N hydrochloric acid to the reaction mixture, it was purified by reverse-phase high performance liquid chromatography (acetonitrile-water, 0.1% acetic acid) to give the title compound (6.7 mg) as a white solid.

$^1$H-NMR (CD$_3$OD) δ 1.93 (s, 3H) 3.71 (s, 3H) 3.88 (t, J=4.8 Hz, 2H) 4.09 (t, J=4.8 Hz, 2H) 5.97 (s, 1H) 6.63-6.66 (m, 2H) 6.86 (d, J=8.8 Hz, 2H) 7.32 (t, J=4.8 Hz, 1H) 7.61 (d, J=8.8 Hz, 2H) 8.77 (d, J=4.8 Hz, 2H)

HPLC retention time: 8 min (Column name: SUMICHIRAL OA-2500, 4.6 mmφ×25 cm, Manufacturer: Sumika Chemical Analysis Service, Ltd., Mobile phase: 0.05 M ammonium acetate-methanol solution, Elution rate: 1 ml/min)

Example 173

2-{3-[(R) and (S)-(4-carbamimidoyl-3-fluorophenylamino)-(2-methoxy-6-methylpyridin-4-yl)methyl]-5-oxo-4,5-dihydro-[1,2,4]triazol-1-yl}benzoic acid

[Chemical Formula 440]

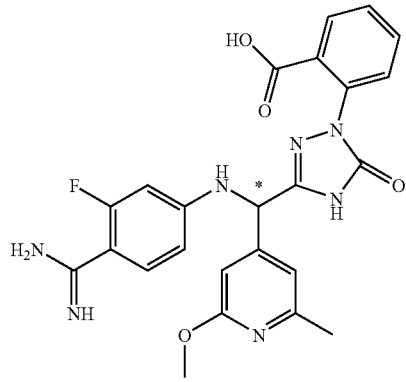

The same procedure was carried out as in Examples (37a)-(37c), except that 2-methoxy-6-methylpyridine-4-carbaldehyde (Example (19a)) was used instead of the 3,4-dimethoxybenzaldehyde in Example (37a), to give the title compound.

Mass spectrum (ESI) m/z: 492 (M+H)$^+$ $^1$H-NMR (CD$_3$OD) δ 2.43 (s, 3H) 3.88 (s, 3H) 5.64 (s, 1H) 6.60 (dd, J=14.4, 2.4 Hz, 1H) 6.69 (dd, J=8.8, 2.4 Hz, 1H) 6.76 (s, 1H) 6.98 (s, 1H) 7.35-7.52 (m, 4H) 7.70 (dd, J=7.2, 1.6 Hz, 1H)

HPLC retention time: 13 min (Column name: SUMICHIRAL OA-2500, 30 mmφ×25 cm, Manufacturer: Sumika Chemical Analysis Service, Ltd., Mobile phase: 0.05 M ammonium acetate-methanol solution, Elution rate: 25 ml/min)

Example 174

(R) and (S)-4-({[1-(6-aminopyridin-2-yl)-5-oxo-4,5-dihydro-1H-[1,2,4]triazol-3-yl]-[2-fluoro-3-(2-fluoroethoxy)-5-methoxyphenyl]methyl}amino)benzamidine acetate (174a) 6-hydrazinopyridine-2-carboxylic acid methyl ester hydrochloride

[Chemical Formula 441]

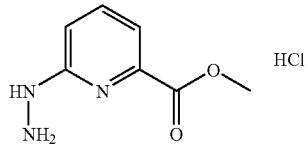

A solution of 2.12 g of 6-bromopyridine-2-carboxylic acid methyl ester, 0.65 g of 1,1'-bis(diphenylphosphino)ferrocene, 0.358 g of tris(dibenzylideneacetone) dipalladium(0), 3.19 g of cesium carbonate and 1.29 g of t-butyl carbazate in 15 ml of toluene was stirred at 100° C. for 20 hours under a nitrogen atmosphere.

The solvent was concentrated under reduced pressure, 40 ml of a 10% solution of hydrogen chloride in methanol was added to the residue, and the mixture was heated to reflux for 20 hours. After cooling, the reaction mixture was crudely purified by reverse-phase high performance liquid chromatography (acetonitrile-water, 0.1% trifluoroacetic acid) to give the title compound (0.48 g) as a yellow solid.

$^1$H-NMR (CD$_3$OD) δ 3.98 (s, 3H) 4.90 (br.s, 4H) 7.11 (d, J=7.5 Hz, 1H) 7.72 (d, J=7.7 Hz, 1H) 7.88 (dd, J=7.7, 7.5 Hz, 1H)

(174b) 6-(3-{[2-fluoro-3-(2-fluoroethoxy)-5-methoxyphenyl]-[4-(5-methyl-[1,2,4]oxadiazol-3-yl)phenylamino]methyl}-5-oxo-4,5-dihydro-[1,2,4]triazol-1-yl)pyridine-2-carboxylic acid methyl ester

[Chemical Formula 442]

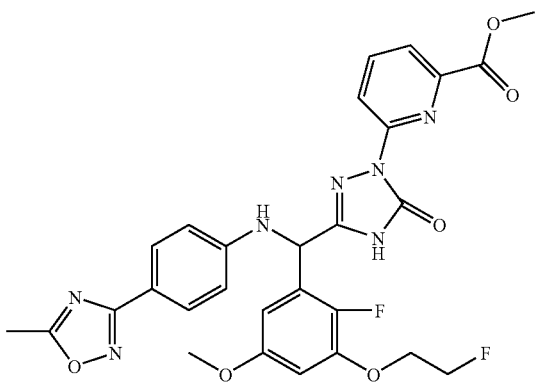

After adding 149 mg of 6-hydrazinopyridine-2-carboxylic acid methyl ester hydrochloride and 92 μl of triethylamine to a solution of 255 mg of {2-[2-fluoro-3-(2-fluoroethoxy)-5- methoxyphenyl]-2-[4-(5-methyl-[1,2,4]oxadiazol-3-yl)phenylimino]-1-methylsulfanylethylidene}carbamic acid methyl ester (Example (3e)) in 5 ml of DMF, the mixture was stirred at 85° C. for 24 hours under a nitrogen atmosphere.

The reaction mixture was concentrated, and the residue was dissolved in 10 ml of methanol. After adding 87 μl of acetic acid and 317 mg of sodium cyanotrihydroborate to the solution, the mixture was stirred at room temperature for 20 hours. Water was added to the reaction mixture and extraction was performed with ethyl acetate. The organic layer was washed with saturated brine and then dried over anhydrous magnesium sulfate. The desiccating agent was filtered off and the filtrate was concentrated under reduced pressure. Purification was then performed by reverse-phase high performance liquid chromatography (acetonitrile-water, 0.1% trifluoroacetic acid) to give the title compound (167 mg) as a white solid.

$^1$H-NMR (CD$_3$OD) δ 2.57 (s, 3H) 3.72 (s, 3H) 3.94 (s, 3H) 4.22 (m, 1H) 4.28 (m, 1H) 4.65 (m, 1H) 4.78 (m, 1H) 5.98 (s, 1H) 6.61 (m, 1H) 6.65 (m, 1H) 6.80 (d, J=9.0 Hz, 2H) 7.77 (d, J=9.0 Hz, 2H) 7.98 (dd, J=7.8, 1.0 Hz, 1H) 8.05 (t, J=7.8 Hz, 1H) 8.23 (dd, J=7.8, 1.0 Hz, 1H)

(174c) 6-(3-{[2-fluoro-3-(2-fluoroethoxy)-5-methoxyphenyl]-[4-(5-methyl-[1,2,4]oxadiazol-3-yl)phenylamino]methyl}-5-oxo-4,5-dihydro-[1,2,4]triazol-1-yl)pyridine-2-carboxylic acid

[Chemical Formula 443]

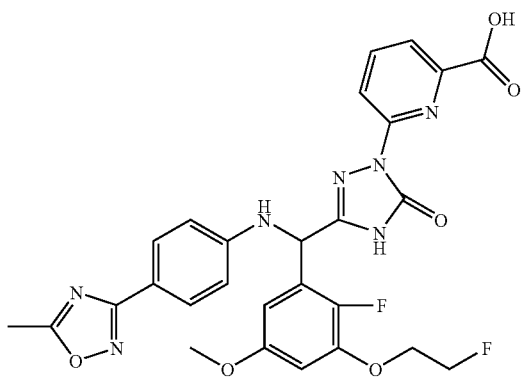

After dissolving 167 mg of 6-(3-{[2-fluoro-3-(2-fluoroethoxy)-5-methoxyphenyl]-[4-(5-methyl-[1,2,4]oxadiazol-3-yl)phenylamino]methyl}-5-oxo-4,5-dihydro-[1,2,4]triazol-1-yl)pyridine-2-carboxylic acid methyl ester in 6 ml of a methanol:THF=2:1 mixed solvent, there was added 562 μl of a 5N aqueous sodium hydroxide solution and the mixture was stirred at room temperature for 15 hours. The mixture was adjusted to acidic with acetic acid and then concentrated under reduced pressure. The residue was dissolved in methanol, and the solution was filtered through celite and then purified by reverse-phase high performance liquid chromatography (acetonitrile-water, 0.1% trifluoroacetic acid) to give the title compound (81 mg) as a light yellow solid.

$^1$H-NMR (CD$_3$OD) δ 2.59 (s, 3H) 3.74 (s, 3H) 4.25 (m, 1H) 4.32 (m, 1H) 4.67 (m, 1H) 4.79 (m, 1H) 5.98 (s, 1H) 6.68 (s, 1H) 6.69 (s, 1H) 6.83 (d, J=8.9 Hz, 2H) 7.80 (d, J=8.9 Hz, 2H) 8.05 (dd, J=7.4, 1.0 Hz, 1H) 8.07 (t, J=7.4 Hz, 1H) 8.32 (dd, J=7.4, 1.0 Hz, 1H)

(174d) 2-(6-aminopyridin-2-yl)-5-{[2-fluoro-3-(2-fluoroethoxy)-5-methoxyphenyl]-[4-(5-methyl-[1,2,4]oxadiazol-3-yl)phenylamino]methyl}-2,4-dihydro-[1,2,4]triazol-3-one

[Chemical Formula 444]

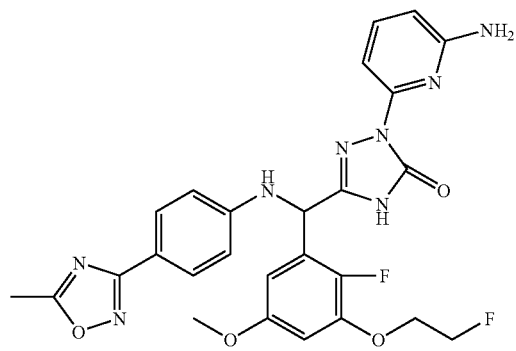

After adding 41 μl of triethylamine and 63 μl of diphenylphosphorylazide to a solution of 81 mg of 6-(3-{[2-fluoro-3-(2-fluoroethoxy)-5-methoxyphenyl]-[4-(5-methyl-[1,2,4]oxadiazol-3-yl)phenylamino]methyl}-5-oxo-4,5-dihydro-[1,2,4]triazol-1-yl)pyridine-2-carboxylic acid in 4 ml of 1,4-dioxane under a nitrogen atmosphere, the mixture was heated for 20 hours at 80° C. After cooling, the reaction mixture was filtered and purified by reverse-phase high performance liquid chromatography (acetonitrile-water, 0.1% trifluoroacetic acid) to give the title compound (33 mg) as a white solid.

$^1$H-NMR (CD$_3$OD) δ 2.59 (s, 3H) 3.75 (s, 3H) 4.25 (m, 1H) 4.33 (m, 1H) 4.67 (m, 1H) 4.79 (m, 1H) 5.98 (s, 1H) 6.67 (d, J=8.3 Hz, 1H) 6.68 (dd, J=5.1, 3.1 Hz, 1H) 6.72 (dd, 6.5, 3.1 Hz, 1H) 6.83 (d, J=8.9 Hz, 2H) 7.30 (d, J=8.3 Hz, 1H) 7.81 (d, J=8.9 Hz, 2H) 7.87 (t, J=8.3 Hz, 1H)

(174e) 4-({[1-(6-aminopyridin-2-yl)-5-oxo-4,5-dihydro-1H-[1,2,4]triazol-3-yl]-[2-fluoro-3-(2-fluoroethoxy)-5-methoxyphenyl]methyl}amino)benzamidine trifluoroacetate

[Chemical Formula 445]

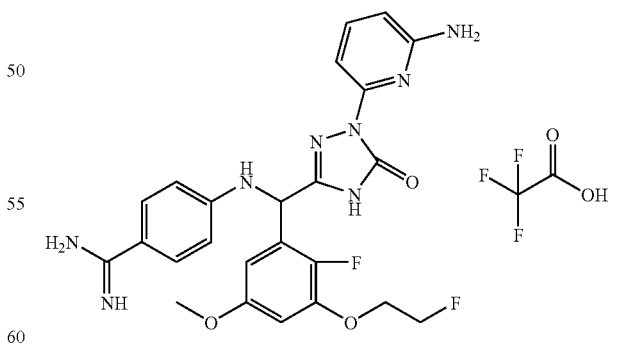

To a solution of 33 mg of 2-(6-aminopyridin-2-yl)-5-{[2-fluoro-3-(2-fluoroethoxy)-5-methoxyphenyl]-[4-(5-methyl-[1,2,4]oxadiazol-3-yl)phenylamino]methyl}-2,4-dihydro-[1,2,4]triazol-3-one in 3 ml of a methanol:water:acetic acid=1:1:1 mixed solvent there was added 34 mg of iron powder, and the mixture was stirred at 60° C. for 20 hours under a nitrogen atmosphere. After filtering the reaction mixture, it was purified by reverse-phase high performance liquid chromatography (acetonitrile-water, 0.1% trifluoroacetic acid) to give the title compound (11 mg) as a light brown solid.

$^1$H-NMR (CD$_3$OD) δ 3.74 (s, 3H) 4.25 (m, 1H) 4.32 (m, 1H) 4.67 (m, 1H) 4.79 (m, 1H) 6.04 (s, 1H) 6.61 (d, J=8.2 Hz, 1H) 6.63 (dd, J=5.1, 3.1 Hz, 1H) 6.71 (dd, 6.6, 3.1 Hz, 1H) 6.88 (d, J=8.9 Hz, 2H) 7.24 (d, J=8.2 Hz, 1H) 7.65 (d, J=8.9 Hz, 2H) 7.78 (t, J=8.2 Hz, 1H)

(174f) (R) and (S)-4-({[1-(6-aminopyridin-2-yl)-5-oxo-4,5-dihydro-1H-[1,2,4]triazol-3-yl]-[2-fluoro-3-(2-fluoroethoxy)-5-methoxyphenyl]methyl}amino) benzamidine acetate

[Chemical Formula 446]

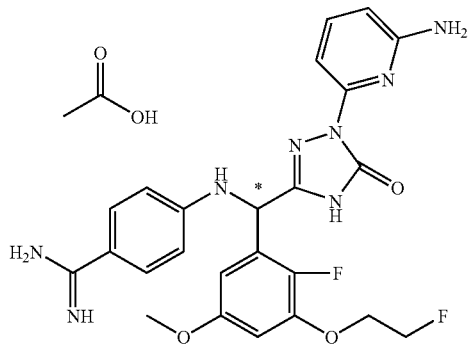

11 mg of 4-({[1-(6-aminopyridin-2-yl)-5-oxo-4,5-dihydro-1H-[1,2,4]triazol-3-yl]-[2-fluoro-3-(2-fluoroethoxy)-5-methoxyphenyl]methyl}amino)benzamidine trifluoroacetate was optically resolved using a SUMICHIRAL OA-2500 column, and the first eluting enantiomer (3 mg) of the title compound was obtained as a white solid.

$^1$H-NMR (CD$_3$OD) δ 1.90 (s, 3H) 3.71 (s, 3H) 4.23 (m, 1H) 4.31 (m, 1H) 4.66 (m, 1H) 4.78 (m, 1H) 5.93 (s, 1H) 6.38 (d, J=8.0 Hz, 1H) 6.63 (dd, J=6.8, 3.1 Hz, 1H) 6.68 (dd, 5.1, 3.1 Hz, 1H) 6.85 (d, J=8.9 Hz, 2H) 7.21 (d, J=8.0 Hz, 1H) 7.48 (t, J=8.0 Hz, 1H) 7.61 (d, J=8.9 Hz, 2H)

HPLC retention time: 8 min (Column name: SUMICHIRAL OA-2500, 20 mmφ×25 cm, Manufacturer: Sumika Chemical Analysis Service, Ltd., Mobile phase: 0.05 M ammonium acetate-methanol solution, Elution rate: 10 ml/min)

Example 175

5-{3-[(4-carbamimidoylphenylamino)-(5-fluoro-8-methoxy-2,3-dihydrobenzo[1,4]dioxin-6-yl)methyl]-5-oxo-4,5-dihydro-[1,2,4]triazol-1-yl}-1H-pyrazole-4-carboxylic acid ethyl ester acetate (175a) 5-(3-{(5-fluoro-8-methoxy-2,3-dihydrobenzo[1,4]dioxin-6-yl)-[4-(5-methyl-[1,2,4]oxadiazol-3-yl)phenylamino]methyl}-5-oxo-4,5-dihydro-[1,2,4]triazol-1-yl)-1H-pyrazole-4-carboxylic acid ethyl ester

[Chemical Formula 447]

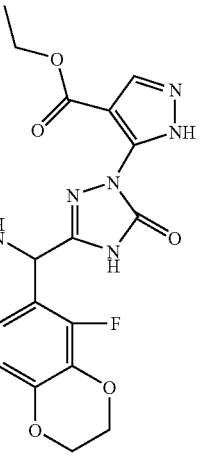

A solution of 62 mg of 3-hydrazino-1H-pyrazole-4-carboxylic acid ethyl ester bishydrochloride (Example (157b)), 106 mg of [2-(5-fluoro-8-methoxy-2,3-dihydrobenzo[1,4]dioxin-6-yl)-2-[4-(5-methyl-[1,2,4]oxadiazol-3-yl)phenylimino]-1-methylsulfanylethylidene]carbamic acid methyl ester (Example 41d) and 88 μl of triethylamine in 5 ml of DMF was heated at 85° C. for 15 hours under a nitrogen atmosphere with stirring. After cooling the reaction mixture to room temperature, the solvent was removed under reduced pressure. The residue was dissolved in 8 ml of methanol, and then 133 mg of sodium cyanotrihydroborate, 49 μl of acetic acid and 0.5 g of MS3A were added and the mixture was stirred at room temperature for 20 hours. Next, 100 ml of ethyl acetate and 50 ml of water were added, and the organic layer was washed with 50 ml of water and 50 ml of saturated brine in that order and then dried over anhydrous magnesium sulfate. The desiccating agent was filtered off, the filtrate was concentrated under reduced pressure, and the residue was purified by silica gel column chromatography (ethyl acetate-methanol) to give the title compound (68 mg) as a light green solid.

Mass spectrum (ESI) m/z: 615 (M+H)$^+$

353

(175b) 5-{3-[(4-carbamimidoylphenylamino)-(5-fluoro-8-methoxy-2,3-dihydrobenzo[1,4]dioxin-6-yl)methyl]-5-oxo-4,5-dihydro-[1,2,4]triazol-1-yl}-1H-pyrazole-4-carboxylic acid ethyl ester acetate

[Chemical Formula 448]

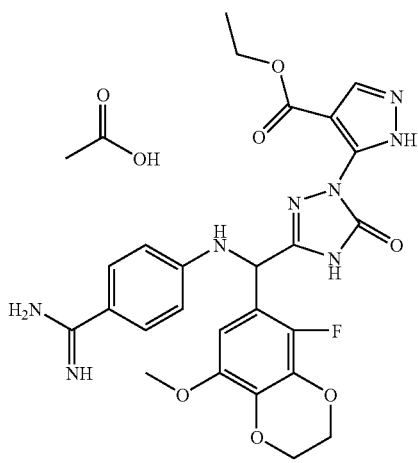

To a solution of 68 mg of 5-(3-{(5-fluoro-8-methoxy-2,3-dihydrobenzo[1,4]dioxin-6-yl)-[4-(5-methyl-[1,2,4]oxadiazol-3-yl)phenylamino]methyl}-5-oxo-4,5-dihydro-[1,2,4]triazol-1-yl)-1H-pyrazole-4-carboxylic acid ethyl ester in 6 ml of a methanol:water:acetic acid=1:1:1 mixed solvent there was added 68 mg of iron powder, and the mixture was stirred at 62.5° C. for 40 hours under a nitrogen atmosphere. After cooling, the reaction mixture was filtered through celite and purified by reverse-phase high performance liquid chromatography (acetonitrile-water, 0.1% acetic acid). The title compound (16.0 mg) was obtained as a white solid.

$^1$H-NMR (CD$_3$OD) δ 1.20 (t, J=7.3 Hz, 3H) 1.97 (s, 3H) 3.79 (s, 3H) 4.14-4.21 (m, 2H) 4.30 (s, 4H) 5.93 (s, 1H) 6.66 (d, J=6.6 Hz, 1H) 6.87 (d, J=8.8 Hz, 2H) 7.65 (d, J=8.8 Hz, 2H) 8.26 (s, 1H)

Example 176

(R) and (S)-2-{3-[(4-carbamimidoylphenylamino)-(6-fluoro-9-methoxy-3,4-dihydro-2H-benzo[b][1,4]dioxepin-7-yl)methyl]-5-oxo-4,5-dihydro-[1,2,4]triazol-1-yl}nicotinic acid (176a) [2-(4-cyanophenylimino)-2-(5-fluoro-9-methoxy-3,4-dihydro-2H-benzo[b][1,4]dioxepin-7-yl)-1-methylsulfanylethylidene]carbamic acid methyl ester

[Chemical Formula 449]

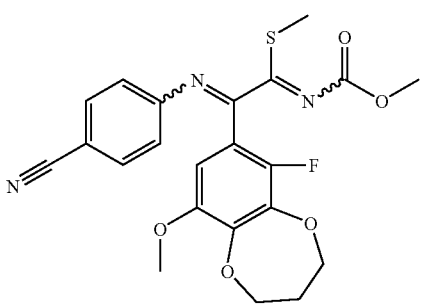

354

To a solution of 1.294 g of 6-fluoro-9-methoxy-3,4-dihydro-2H-benzo[b][1,4]dioxepin-7-carbaldehyde (Example 42b), 680 mg of 4-aminobenzonitrile, 1.3 g of MS3A and 355 mg of Yb(OTf)$_3$ in 20 ml of THF there was added 1.2 ml of trimethylsilyl cyanide, and the mixture was stirred overnight at room temperature. The reaction mixture was filtered through celite, and the celite was washed with ethyl acetate. The organic layer was concentrated under reduced pressure.

To a solution of this compound in 15 ml of a methanol:THF=2:1 mixed solvent there was added 5 ml of a 20% aqueous solution of ammonium sulfide, and the mixture was stirred at room temperature for 4 hours. Water was added to the reaction mixture and extraction was performed with ethyl acetate. The organic layer was washed with saturated brine and then dried over anhydrous magnesium sulfate. The desiccating agent was filtered off, and the filtrate was concentrated under reduced pressure to give 2-(4-cyanophenylamino)-2-(6-fluoro-9-methoxy-3,4-dihydrobenzo[b][1,4]dioxepin-7-yl)thioacetamide.

To a solution of this compound in 20 ml of acetonitrile there was added 1 g of Me$_3$O$^+$BF$_4^-$, and the mixture was stirred at room temperature for 30 minutes. Saturated aqueous sodium hydrogencarbonate was added to the reaction mixture, and extraction was performed with ethyl acetate. The organic layer was washed with saturated brine and then dried over anhydrous magnesium sulfate. The desiccating agent was filtered off and the filtrate was concentrated under reduced pressure.

After adding 6 g of manganese dioxide to a solution of the residue in 10 ml of ethyl acetate, the mixture was stirred at room temperature for 45 minutes. The reaction mixture was filtered through celite, and the filtrate was concentrated under reduced pressure.

To a solution of the residue in 20 ml of toluene there were added 3 ml of 2,4,6-collidine and 1.5 ml of methyl chloroformate, and the mixture was stirred at 80° C. for 30 minutes under a nitrogen atmosphere. After cooling the reaction mixture, 0.5 N hydrochloric acid was added and extraction was performed with ethyl acetate. The organic layer was washed with saturated brine and then dried over anhydrous magnesium sulfate. The desiccating agent was filtered off and the filtrate was concentrated under reduced pressure. The residue was purified by silica gel column chromatography (ethyl acetate-heptane) to give the title compound (1.263 g, isomeric mixture) as a light yellow solid.

$^1$H-NMR (CDCl$_3$) Two main isomers:

δ 2.31-2.34 (m, 2H) 2.34 (s, 3H) 3.63 (s, 3H) 3.88 (s, 3H) 4.36 (t, J=5.6 Hz, 2H) 4.45 (t, J=5.6 Hz, 2H) 7.06 (d, J=8.4 Hz, 2H) 7.10 (d, J=5.6 Hz, 1H) 7.60 (d, J=8.4 Hz, 2H)

δ 2.23-2.27 (m, 2H) 2.48 (s, 3H) 3.63 (s, 3H) 3.69 (s, 3H) 4.26 (t, J=5.6 Hz, 2H) 4.32-4.38 (m, 2H) 6.23 (d, J=5.6 Hz, 1H) 6.81 (d, J=8.4 Hz, 2H) 7.50 (d, J=8.4 Hz, 2H)

(176b) 2-{3-[(4-cyanophenylamino)-(6-fluoro-9-methoxy-3,4-dihydro-2H-benzo[b][1,4]dioxepin-7-yl)methyl]-5-oxo-4,5-dihydro-[1,2,4]triazol-1-yl}nicotinic acid

[Chemical Formula 450]

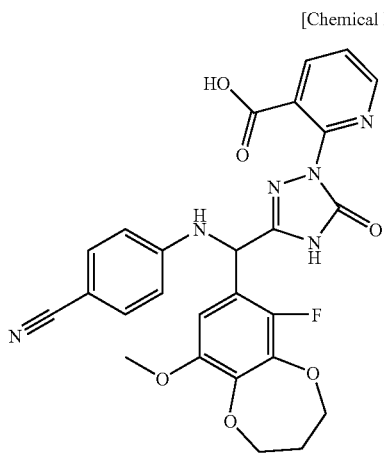

After adding 84 mg of 2-hydrazinonicotinic acid and 153 µl of triethylamine to a solution of 229 mg of [2-(4-cyanophenylimino)-2-(6-fluoro-9-methoxy-3,4-dihydro-2H-benzo[b][1,4]dioxepin-7-yl)-1-methylsulfanylethylidene]carbamic acid methyl ester in 15 ml of THF, the mixture was heated for 48 hours at 60° C. under a nitrogen atmosphere. After cooling, the mixture was concentrated under reduced pressure. The residue was dissolved in 8 ml of DMF, and then 153 µl of triethylamine was added and the mixture was heated for 24 hours at 85° C. under a nitrogen atmosphere. After cooling, the mixture was concentrated under reduced pressure.

The residue was then dissolved in 10 ml of methanol. After adding 144 µl of acetic acid and 251 mg of sodium cyanotrihydroborate to the solution, the mixture was stirred at room temperature for 24 hours. Next, 50 ml of water was added to the reaction mixture and extraction was performed with 200 ml of ethyl acetate. The organic layer was washed with 50 ml of water and 50 ml of saturated brine in that order and then dried over anhydrous magnesium sulfate. The desiccating agent was filtered off and the filtrate was concentrated under reduced pressure. The residue was purified by NAM silica gel column chromatography (methanol-ethyl acetate) to give the title compound (146 mg) as a light yellow solid.

$^1$H-NMR (CD$_3$OD) δ 2.18-2.25 (m, 2H) 3.77 (s, 3H) 4.13-4.28 (m, 4H) 5.93 (s, 1H) 6.78 (d, J=6.6 Hz, 1H) 6.80 (d, J=8.9 Hz, 2H) 7.45 (d, J=8.9 Hz, 2H) 7.56 (dd, J=7.9, 4.7 Hz, 1H) 8.49 (dd, J=7.9, 1.8 Hz, 1H) 8.66 (dd, J=4.7, 1.8 Hz, 1H)

(176c) 2-(3-{(6-fluoro-9-methoxy-3,4-dihydro-2H-benzo[b][1,4]dioxepin-7-yl)-[4-(N-hydroxycarbamimidoyl)phenylamino]methyl}-5-oxo-4,5-dihydro-[1,2,4]triazol-1-yl)nicotinic acid

[Chemical Formula 451]

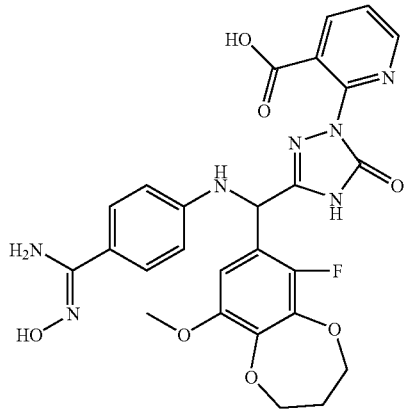

After adding 114 mg of hydroxylammonium chloride and 267 µl of triethylamine to a solution of 146 mg of 2-{3-[(4-cyanophenylamino)-(6-fluoro-9-methoxy-3,4-dihydro-2H-benzo[b][1,4]dioxepin-7-yl)methyl]-5-oxo-4,5-dihydro-[1,2,4]triazol-1-yl}nicotinic acid in 10 ml of methanol, the mixture was heated for 28 hours at 60° C. After cooling the reaction mixture, it was purified by reverse-phase high performance liquid chromatography (acetonitrile-water, 0.1% acetic acid) to give the title compound (61 mg) as a light yellow solid.

$^1$H-NMR (CD$_3$OD) δ 2.18-2.25 (m, 2H) 3.77 (s, 3H) 4.13-4.28 (m, 4H) 5.96 (s, 1H) 6.77 (d, J=6.1 Hz, 1H) 6.87 (d, J=9.1 Hz, 2H) 7.51 (d, J=9.1 Hz, 2H) 7.59 (dd, J=8.1, 4.3 Hz, 1H) 8.41 (dd, J=8.1, 1.5 Hz, 1H) 8.68 (dd, J=4.3, 1.5 Hz, 1H)

(176d) (R) and (S)-2-{3-[(4-carbamimidoylphenylamino)-(6-fluoro-9-methoxy-3,4-dihydro-2H-benzo[b][1,4]dioxepin-7-yl)methyl]-5-oxo-4,5-dihydro-[1,2,4]triazol-1-yl}nicotinic acid

[Chemical Formula 452]

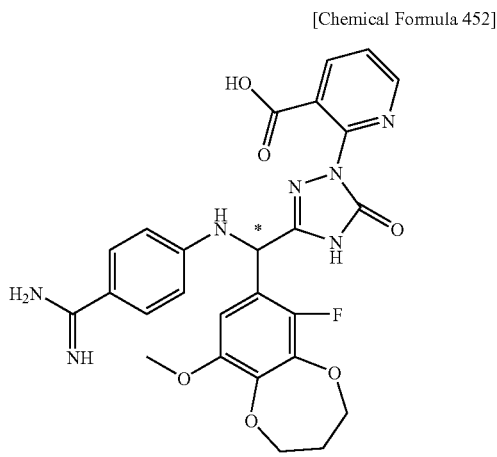

To a solution of 61 mg of 2-(3-{(6-fluoro-9-methoxy-3,4-dihydro-2H-benzo[b][1,4]dioxepin-7-yl)-[4-(N-hydroxycarbamimidoyl)phenylamino]methyl}-5-oxo-4,5-dihydro-[1,2,4]triazol-1-yl)nicotinic acid in 6 ml of a methanol:water:acetic acid=1:1:1 mixed solvent there was added 60 mg of iron powder, and the mixture was stirred at 60° C. for 30 hours under a nitrogen atmosphere. Upon cooling, the reaction mixture was filtered through celite and purified by reverse-phase high performance liquid chromatography (acetonitrile-water, 0.1% trifluoroacetic acid) to give 2-{3-[(4-carbamimidoylphenylamino)-(6-fluoro-9-methoxy-3,4-dihydro-2H-benzo[b][1,4]dioxepin-7-yl)methyl]-5-oxo-4,5-dihydro-[1,2,4]triazol-1-yl}nicotinic acid.

Mass spectrum (ESI) m/z: 550 (M+H)$^+$

This compound was optically resolved using a SUMICHIRAL OA-2500 column, and the first eluting enantiomer (9.6 mg) of the title compound was obtained as a white solid.

$^1$H-NMR (CD$_3$OD) δ 2.17-2.25 (m, 2H) 3.78 (s, 3H) 4.10-4.30 (m, 4H) 5.96 (s, 1H) 6.79 (d, J=6.2 Hz, 1H) 6.86 (d, J=9.0 Hz, 2H) 7.54 (dd, J=8.3, 4.3 Hz, 1H) 7.65 (d, J=9.0 Hz, 2H) 8.30 (dd, J=8.3, 1.3 Hz, 1H) 8.66 (dd, J=4.3, 1.3 Hz, 1H)

HPLC retention time: 24 min (Column name: SUMICHIRAL OA-2500, 30 mmφ×25 cm, Manufacturer: Sumika Chemical Analysis Service, Ltd., Mobile phase: 0.5 mM ammonium acetate-methanol solution, Elution rate: 20 ml/min)

Example 177

5-(3-{(4-carbamimidoylphenylamino)-[2-fluoro-3-(3-hydroxypropoxy)-5-methoxyphenyl]methyl}-5-oxo-4,5-dihydro-[1,2,4]triazol-1-yl)-1H-pyrazole-4-carboxylic acid acetate (177a) (2-{3-[3-(t-butyldimethylsilanyloxy)propoxy]-2-fluoro-5-methoxyphenyl}-2-[4-(5-methyl-[1,2,4]oxadiazol-3-yl)phenylimino]-1-methylsulfanylethylidene)carbamic acid methyl ester

[Chemical Formula 453]

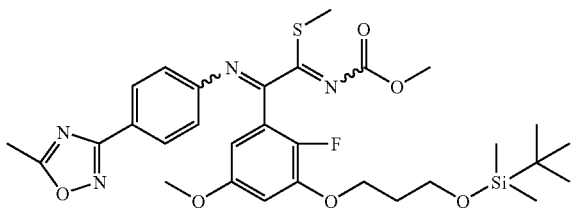

After adding 313 mg of cesium carbonate and 0.257 ml of (3-bromopropoxy)-t-butyldimethylsilane to a solution of 339 mg of [2-(2-fluoro-3-hydroxy-5-methoxyphenyl)-2-[4-(5-methyl-[1,2,4]oxadiazol-3-yl)phenylimino]-1-methylsulfanylethylidene]carbamic acid methyl ester (Example (3d)) in 8 ml of DMF, the mixture was stirred at room temperature for 15 hours. Next, 100 ml of water was added to the reaction mixture and extraction was performed with 300 ml of ethyl acetate. The organic layer was washed with 50 ml of water and 50 ml of saturated brine in that order and then dried over anhydrous magnesium sulfate. The desiccating agent was filtered off and the filtrate was concentrated under reduced pressure. The residue was purified by silica gel column chromatography (ethyl acetate-heptane) to give the title compound (413 mg).

$^1$H-NMR (CDCl$_3$) Two main isomers:

δ 0.01 (s, 6H) 0.87 (s, 9H) 1.95 (quint, J=6.6 Hz, 2H) 2.57 (s, 3H) 2.64 (s, 3H) 3.65 (s, 3H) 3.66 (s, 3H) 3.75 (t, J=6.6 Hz, 2H) 4.03 (t, J=6.6 Hz, 2H) 6.12 (dd, J=4.5, 3.6 Hz, 1H) 6.51 (dd, J=6.9, 3.6 Hz, 1H) 6.86 (d, J=8.5 Hz, 2H) 7.91 (d, J=8.5 Hz, 2H)

δ 0.06 (s, 6H) 0.92 (s, 9H) 2.04 (quint, J=6.6 Hz, 2H) 2.35 (s, 3H) 2.67 (s, 3H) 3.52 (s, 3H) 3.83 (t, J=6.6 Hz, 2H) 3.85 (s, 3H) 4.13 (t, J=6.6 Hz, 2H) 6.72 (dd, J=7.1, 3.5 Hz, 1H) 6.97 (dd, J=4.5, 3.5 Hz, 1H) 7.13 (d, J=8.7 Hz, 2H) 8.04 (d, J=8.7 Hz, 2H)

(177b) 5-[3-({3-[3-(t-butyldimethylsilanyloxy)propoxy]-2-fluoro-5-methoxyphenyl}-[4-(5-methyl-[1,2,4]oxadiazol-3-yl)phenylamino]methyl)-5-oxo-4,5-dihydro-[1,2,4]triazol-1-yl]-1H-pyrazole-4-carboxylic acid ethyl ester and 5-(3-{[2-fluoro-3-(3-hydroxypropoxy)-5-methoxyphenyl]-[4-(5-methyl-[1,2,4]oxadiazol-3-yl)phenylamino]methyl}-5-oxo-4,5-dihydro-[1,2,4]triazol-1-yl)-1H-pyrazole-4-carboxylic acid ethyl ester

[Chemical Formula 454]

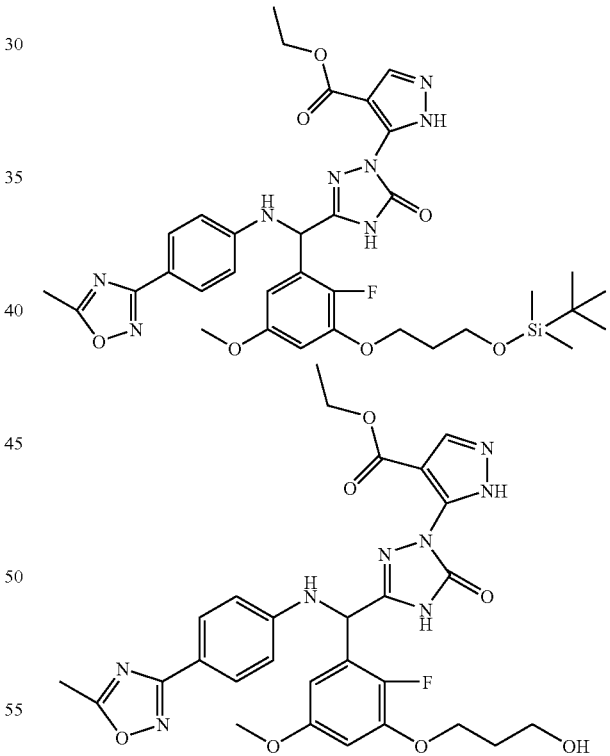

A solution of 87 mg of 3-hydrazino-1H-pyrazole-4-carboxylic acid ethyl ester bishydrochloride (Example (157b)), 206 mg of (2-{3-[3-(t-butyldimethylsilanyloxy)propoxy]-2-fluoro-5-methoxyphenyl}-2-[4-(5-methyl-[1,2,4]oxadiazol-3-yl)phenylimino]-1-methylsulfanylethylidene)carbamic acid methyl ester and 0.160 ml of triethylamine in 10 ml of DMF was stirred at 85° C. for 15 hours under a nitrogen atmosphere. The solvent was concentrated under reduced pressure.

The residue was dissolved in 7 ml of methanol, and then 205 mg of sodium cyanotrihydroborate, 0.113 ml of acetic acid and 0.5 g of MS3A were added and the mixture was stirred at room temperature for 20 hours. Next, 100 ml of ethyl acetate and 50 ml of water were added, and the organic layer was washed with 50 ml of water and 50 ml of saturated brine in that order and then dried over anhydrous magnesium sulfate. The desiccating agent was filtered off, the filtrate was concentrated under reduced pressure, and the residue was purified by NAM silica gel column chromatography (ethyl acetate-methanol) to give the title compounds (53 mg, 64 mg, respectively).

$^1$H-NMR (CD$_3$OD) δ 0.01 (s, 6H) 0.84 (s, 9H) 1.14 (t, J=7.5 Hz, 3H) 1.95 (quint, J=6.5 Hz, 2H) 2.55 (s, 3H) 3.60 (s, 3H) 3.71 (t, J=6.5 Hz, 2H) 4.04-4.15 (m, 4H) 5.90 (s, 1H) 6.59 (dd, J=7.2, 2.9 Hz, 1H) 6.62 (dd, J=5.4, 2.9 Hz, 1H) 6.79 (d, J=9.0 Hz, 2H) 7.77 (d, J=9.0 Hz, 2H) 8.21 (s, 1H)

$^1$H-NMR (CD$_3$OD) δ 1.19 (t, J=7.5 Hz, 3H) 1.97 (quint, J=6.5 Hz, 2H) 2.55 (s, 3H) 3.70 (s, 3H) 3.71 (t, J=6.5 Hz, 2H) 4.06-4.15 (m, 4H) 5.88 (s, 1H) 6.60 (s, 1H) 6.61 (s, 1H) 6.78 (d, J=9.0 Hz, 2H) 7.75 (d, J=9.0 Hz, 2H) 8.21 (s, 1H)

(177c) 5-(3-{(4-carbamimidoylphenylamino)-[2-fluoro-3-(3-hydroxypropoxy)-5-methoxyphenyl]methyl}-5-oxo-4,5-dihydro-[1,2,4]triazol-1-yl)-1H-pyrazole-4-carboxylic acid ethyl ester trifluoroacetate

[Chemical Formula 455]

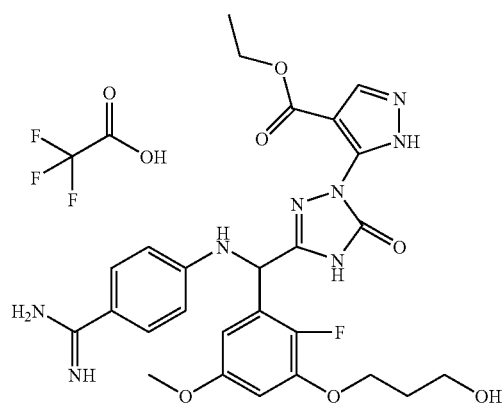

To a solution of 53 mg of 5-[3-({3-[3-(t-butyldimethylsilanyloxy)propoxy]-2-fluoro-5-methoxyphenyl}-[4-(5-methyl-[1,2,4]oxadiazol-3-yl)phenylamino]methyl)-5-oxo-4,5-dihydro-[1,2,4]triazol-1-yl]-1H-pyrazole-4-carboxylic acid ethyl ester and 64 mg of 5-(3-{[2-fluoro-3-(3-hydroxypropoxy)-5-methoxyphenyl]-[4-(5-methyl-[1,2,4]oxadiazol-3-yl)phenylamino]methyl}-5-oxo-4,5-dihydro-[1,2,4]triazol-1-yl)-1H-pyrazole-4-carboxylic acid ethyl ester in 6 ml of a methanol:water:acetic acid=1:1:1 mixed solvent there was added 150 mg of iron powder, and the mixture was stirred at 62.5° C. for 20 hours under a nitrogen atmosphere. After cooling, the reaction mixture was filtered through celite and purified by reverse-phase high performance liquid chromatography (acetonitrile-water, 0.1% trifluoroacetic acid). The title compound (54.9 mg) was obtained as a white solid.

$^1$H-NMR (CD$_3$OD) δ 1.17 (t, J=7.1 Hz, 3H) 1.99 (quint, J=6.2 Hz, 2H) 3.74 (t, J=6.2 Hz, 2H) 3.75 (s, 3H) 4.14 (t, J=6.2 Hz, 2H) 4.15-4.20 (m, 2H) 5.88 (s, 1H) 6.61 (dd, J=4.9, 2.9 Hz, 1H) 6.67 (dd, J=6.8, 2.9 Hz, 1H) 6.87 (d, J=9.0 Hz, 2H) 7.64 (d, J=9.0 Hz, 2H) 8.25 (s, 1H)

(177d) 5-(3-{(4-carbamimidoylphenylamino)-[2-fluoro-3-(3-hydroxypropoxy)-5-methoxyphenyl]methyl}-5-oxo-4,5-dihydro-[1,2,4]triazol-1-yl)-1H-pyrazole-4-carboxylic acid

[Chemical Formula 456]

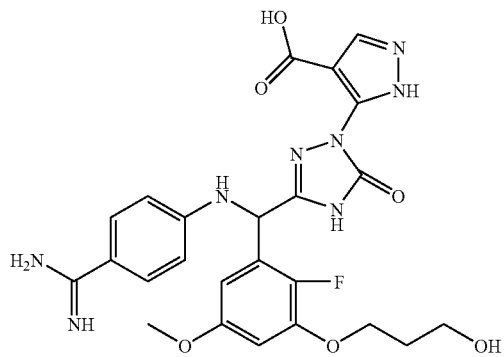

After adding 38 μl of triethylamine, 0.3 mg of 4-dimethylaminopyridine and 46 mg of di-t-butyl dicarbonate to a solution of 55 mg of 5-(3-{(4-carbamimidoylphenylamino)-[2-fluoro-3-(3-hydroxypropoxy)-5-methoxyphenyl]methyl}-5-oxo-4,5-dihydro-[1,2,4]triazol-1-yl)-1H-pyrazole-4-carboxylic acid ethyl ester trifluoroacetate in 6 ml of an acetonitrile:DMF=2:1 mixed solvent, the mixture was stirred at room temperature for 15 hours. The solvent was removed under reduced pressure, and then 1 ml of methanol and 1 ml of a 1N aqueous sodium hydroxide solution were added and the mixture was stirred at room temperature for 8 hours. After adding 5 ml of a methanol:water:acetic acid=1:1:1 mixed solvent to the reaction mixture, it was stirred and heated at 50° C. for 15 hours. The mixture was cooled and then directly purified by reverse-phase high performance liquid chromatography (acetonitrile-water, 0.1% acetic acid) to give 16 mg of the title compound.

$^1$H-NMR (CD$_3$OD) δ 1.99 (quint, J=6.2 Hz, 2H) 3.71 (s, 3H) 3.74 (t, J=6.2 Hz, 2H) 4.12 (t, J=6.2 Hz, 2H) 5.93 (s, 1H) 6.61 (dd, J=4.9, 2.9 Hz, 1H) 6.63 (dd, J=6.7, 2.9 Hz, 1H) 6.83 (d, J=9.0 Hz, 2H) 7.61 (d, J=9.0 Hz, 2H) 8.03 (s, 1H)

Example 178

(R) and (S)-2-(3-{(4-carbamimidoylphenylamino)-[2-fluoro-4-(2-hydroxyethoxy)-5-methoxyphenyl]methyl}-5-oxo-4,5-dihydro-[1,2,4]triazol-1-yl)benzoic acid

(178a) 4-(t-butyldimethylsilanyloxy)-2-fluoro-5-methoxybenzaldehyde

[Chemical Formula 457]

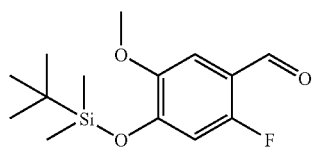

The same procedure was carried out as in Example (4a), except that 2-fluoro-4-hydroxy-5-methoxybenzaldehyde [CAS No. 79418-77-2] and t-butylchlorodimethylsilane were used instead of respectively the 3-hydroxy-5-methoxybenzaldehyde and chlorotriisopropylsilane, to give the title compound as a colorless oil.

$^1$H-NMR (CDCl$_3$) δ 0.15 (s, 6H) 0.99 (s, 9H) 3.87 (s, 3H) 6.60 (d, J=11.6 Hz, 1H) 7.26 (d, J=8.4 Hz, 1H) 10.17 (s, 1H)

(178b) {2-(2-fluoro-4-hydroxy-5-methoxyphenyl)-2-[4-(5-methyl-[1,2,4]oxadiazol-3-yl)phenylimino]-1-methylsulfanylethylidene}carbamic acid methyl ester

[Chemical Formula 458]

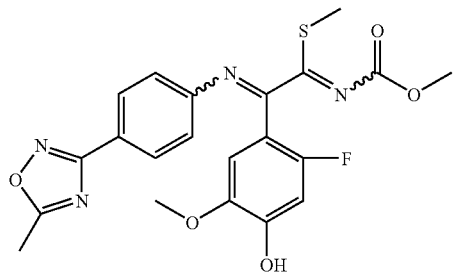

The same procedure was carried out as in Examples (4b)-(4c), except that 4-(t-butyldimethylsilanyloxy)-2-fluoro-5-methoxybenzaldehyde was used instead of the 3-methoxy-5-triisopropylsilanyloxybenzaldehyde in Example (4b), to give the title compound as a yellow solid.

$^1$H-NMR (CDCl$_3$) Two main isomers:

δ 2.31 (s, 3H) 2.62 (s, 3H) 3.61 (s, 3H) 3.84 (s, 3H) 5.32 (s, 1H) 6.44 (d, J=10.0 Hz, 1H) 6.67 (d, J=6.4 Hz, 1H) 7.07-7.10 (m, 2H) 7.86-7.89 (m, 2H)

δ 2.46 (s, 3H) 2.65 (s, 3H) 3.61 (s, 3H) 3.94 (s, 3H) 5.39 (s, 1H) 6.61 (d, J=11.6 Hz, 1H) 6.81-6.83 (m, 2H) 7.46 (d, J=7.2 Hz, 1H) 7.98-8.01 (m, 2H)

(178c) (2-{4-[2-(t-butyldimethylsilanyloxy)ethoxy]-2-fluoro-5-methoxyphenyl}-2-[4-(5-methyl-[1,2,4]oxadiazol-3-yl)phenylimino]-1-methylsulfanylethylidene)carbamic acid methyl ester

[Chemical Formula 459]

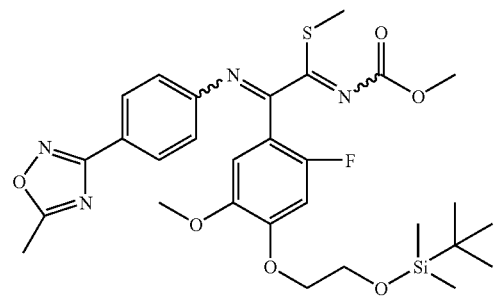

The same procedure was carried out as in Example (3e), except that {2-(2-fluoro-4-hydroxy-5-methoxyphenyl)-2-[4-(5-methyl-[1,2,4]oxadiazol-3-yl)phenylimino]-1-methylsulfanylethylidene}carbamic acid methyl ester and (2-bromoethoxy)-t-butyldimethylsilane were used instead of respectively the [2-(2-fluoro-3-hydroxy-5-methoxyphenyl)-2-[4-(5-methyl-[1,2,4]oxadiazol-3-yl)phenylimino]-1-methylsulfanylethylidene]carbamic acid methyl ester and 1-fluoro-2-iodoethane, to give the title compound as a yellow solid.

1H-NMR (CDCl$_3$) Two main isomers:

δ 0.05 (s, 6H) 0.88 (s, 9H) 2.47 (s, 3H) 2.62 (s, 3H) 3.59 (s, 3H) 3.79 (s, 3H) 3.82-3.86 (m, 4H) 6.46 (d, J=10.8 Hz, 1H) 6.58 (d, J=8.0 Hz, 1H) 6.83 (d, J=8.4 Hz, 2H) 7.90 (d, J=8.4 Hz, 2H)

δ 0.09 (s, 6H) 0.89 (s, 9H) 2.32 (s, 3H) 2.65 (s, 3H) 3.61 (s, 3H) 3.90 (s, 3H) 4.00 (t, J=5.2 Hz, 2H) 4.13 (t, J=5.2 Hz, 2H) 6.60 (d, J=12.4 Hz, 1H) 7.10 (d, J=8.4 Hz, 2H) 7.49 (d, J=7.2 Hz, 1H) 8.01 (d, J=8.4 Hz, 2H)

(178d) (R) and (S)-2-(3-{(4-carbamimidoylphenylamino)-[2-fluoro-4-(2-hydroxyethoxy)-5-methoxyphenyl]methyl}-5-oxo-4,5-dihydro-[1,2,4]triazol-1-yl)benzoic acid

[Chemical Formula 460]

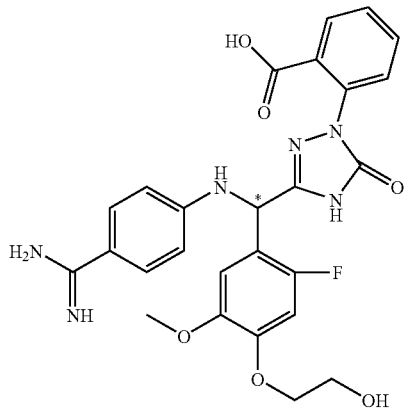

The same procedure was carried out as in Examples (3f)-(3h), except that (2-{4-[2-(t-butyldimethylsilanyloxy)ethoxy]-2-fluoro-5-methoxyphenyl}-2-[4-(5-methyl-[1,2,4]oxadiazol-3-yl)phenylimino]-1-methylsulfanylethylidene)carbamic acid methyl ester and 2-hydrazinobenzoic acid hydrochloride were used instead of respectively the {2-[2-fluoro-3-(2-fluoroethoxy)-5-methoxyphenyl]-2-[4-(5-methyl-[1,2,4]oxadiazol-3-yl)phenylimino]-1-methylsulfanylethylidene}carbamic acid methyl ester in Example (3f) and 2-hydrazinopyrimidine in Example (3f), to give the title compound as a white solid.

$^1$H-NMR (CD$_3$OD) δ 3.78-3.84 (m, 2H) 3.82 (s, 3H) 3.96-4.12 (m, 2H) 5.89 (s, 1H) 6.80-6.88 (m, 3H) 7.13 (d, J=7.2 Hz, 1H) 7.34-7.46 (m, 3H) 7.54-7.62 (m, 2H) 7.70 (d, J=7.2 Hz, 1H)

HPLC retention time: 16 min (Column name: SUMICHIRAL OA-2500, 30 mmφ×25 cm, Manufacturer: Sumika Chemical Analysis Service, Ltd., Mobile phase: 0.05 M ammonium acetate-methanol solution, Elution rate: 20 ml/min)

Example 179

(R) and (S)-4-{3-[(4-carbamimidoylphenylamino)-(8-ethyl-4H-benzo[1,3]dioxin-6-yl)methyl]-5-oxo-4,5-dihydro-[1,2,4]triazol-1-yl}thiazole-5-carboxylic acid (179a) 4-(3-{(8-ethyl-4H-benzo[1,3]dioxin-6-yl)-[4-(5-methyl-[1,2,4]oxadiazol-3-yl)phenylamino]methyl}-5-oxo-4,5-dihydro-[1,2,4]triazol-1-yl)thiazole-5-carboxylic acid methyl ester

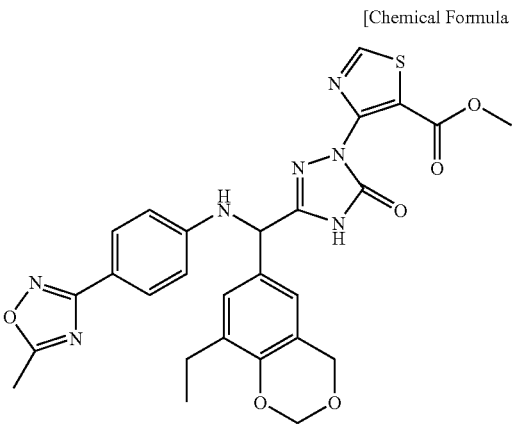

[Chemical Formula 461]

After adding 71 mg of 4-hydrazinothiazole-5-carboxylic acid methyl ester (Example (162c)) and 300 μl of triethylamine to a solution of 198 mg of [2-(8-ethyl-4H-benzo[1,3]dioxin-6-yl)-2-[4-(5-methyl-[1,2,4]oxadiazol-3-yl)phenylimino]-1-methylsulfanylethylidene]carbamic acid methyl ester (Example (27b)) in 6 ml of THF, the mixture was stirred overnight at 60° C. under a nitrogen atmosphere. The reaction mixture was then concentrated. The residue was dissolved in 6 ml of DMF, and then 0.3 ml of triethylamine was added and the mixture was stirred at 80° C. for 6 hours.

The reaction mixture was concentrated, and the residue was dissolved in 2.2 ml of a THF:methanol:acetic acid=5:5:1 mixed solvent. After adding 0.2 g of sodium cyanotrihydroborate to the solution, the mixture was stirred at room temperature for 4 hours. Ethyl acetate was added to the reaction mixture. After washing the organic layer with water and saturated brine, it was dried over anhydrous magnesium sulfate. The desiccating agent was filtered off and the filtrate was concentrated under reduced pressure. The residue was purified by NAM silica gel column chromatography (methanol-ethyl acetate) to give the title compound (179 mg) as a light yellow solid.

Mass spectrum (ESI) m/z: 576 (M+H)$^+$ (179b) 4-{3-[(4-carbamimidoylphenylamino)-(8-ethyl-4H-benzo[1,3]dioxin-6-yl)methyl]-5-oxo-4,5-dihydro-[1,2,4]triazol-1-yl}thiazole-5-carboxylic acid trifluoroacetate

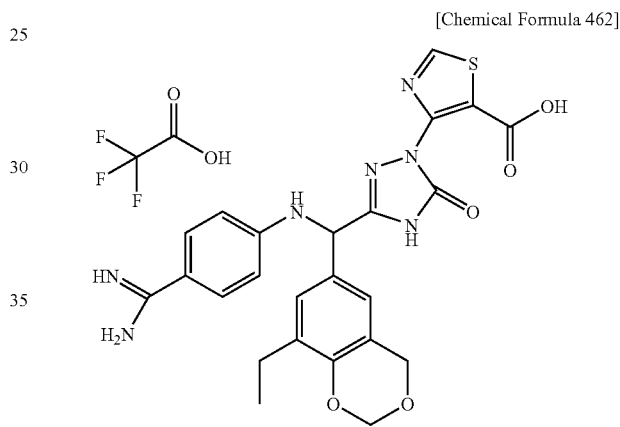

[Chemical Formula 462]

After dissolving 179 mg of 4-(3-{(8-ethyl-4H-benzo[1,3]dioxin-6-yl)-[4-(5-methyl-[1,2,4]oxadiazol-3-yl)phenylamino]methyl}-5-oxo-4,5-dihydro-[1,2,4]triazol-1-yl)thiazole-5-carboxylic acid methyl ester in 2 ml of methanol, there was added 0.5 ml of a 5N aqueous sodium hydroxide solution and the mixture was stirred at room temperature for 1 hour. After adding 0.5 ml of 5N hydrochloric acid to the reaction mixture, extraction was performed with ethyl acetate. The organic layer was dried over anhydrous magnesium sulfate. The desiccating agent was filtered off and the filtrate was concentrated under reduced pressure.

The residue was dissolved in 1 ml of methanol, 1.3 ml of acetic acid and 1 ml of water, and then 200 mg of iron powder was added and the mixture was stirred at 60° C. for 20 hours. After adding 0.4 ml of trifluoroacetic acid to the reaction mixture, it was filtered and then purified by reverse-phase high performance liquid chromatography (acetonitrile-water, 0.1% trifluoroacetic acid) to give 143 mg of the title compound as a white solid.

Mass spectrum (ESI) m/z: 522 (M+H)$^+$ (179c) (R) and (S)-4-{3-[(4-carbamimidoylphenylamino)-(8-ethyl-4H-benzo[1,3]dioxin-6-yl)methyl]-5-oxo-4,5-dihydro-[1,2,4]triazol-1-yl}thiazole-5-carboxylic acid

[Chemical Formula 463]

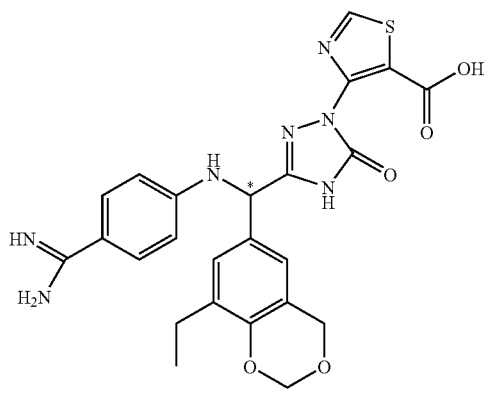

A SUMICHIRAL OA-2500 column was used for optical resolution of 143 mg of 4-{3-[(4-carbamimidoylphenylamino)-(8-ethyl-4H-benzo[1,3]dioxin-6-yl)methyl]-5-oxo-4,5-dihydro-[1,2,4]triazol-1-yl}thiazole-5-carboxylic acid trifluoroacetate, and the first eluting enantiomer (30.36 mg) of the title compound was obtained as a white solid.

$^1$H-NMR (CD$_3$OD) δ 1.18 (t, J=7.2 Hz, 3H) 2.61 (q, J=7.2 Hz, 2H) 4.85-4.89 (m, 2H) 5.25 (s, 2H) 5.53 (s, 1H) 6.85 (d, J=8.8 Hz, 2H) 7.03 (s, 1H) 7.21 (s, 1H) 7.61 (d, J=8.8 Hz, 2H) 8.88 (s, 1H)

HPLC retention time: 17 min (Column name: SUMICHIRAL OA-2500, 30 mmφ×25 cm, Manufacturer: Sumika Chemical Analysis Service, Ltd., Mobile phase: 0.5 mM ammonium acetate-methanol solution, Elution rate: 30 ml/min)

Example 180

(R) and (S)-4-{3-[(4-carbamimidoylphenylamino)-(9-methoxy-3,4-dihydro-2H-benzo[b][1,4]dioxepin-7-yl)methyl]-5-oxo-4,5-dihydro-[1,2,4]triazol-1-yl}thiazole-5-carboxylic acid (180a) 4-(3-{(9-methoxy-3,4-dihydro-2H-benzo[b][1,4]dioxepin-7-yl)-[4-(5-methyl-[1,2,4]oxadiazol-3-yl)phenylamino]methyl}-5-oxo-4,5-dihydro-[1,2,4]triazol-1-yl)thiazole-5-carboxylic acid methyl ester

[Chemical Formula 464]

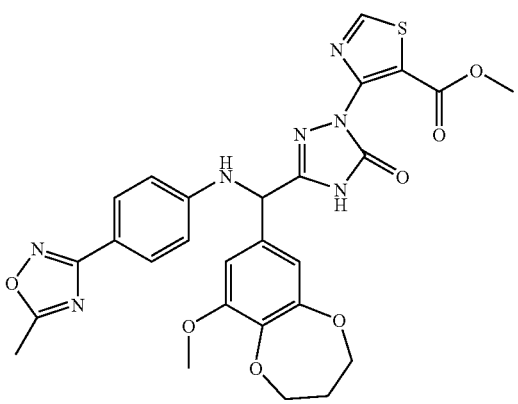

After adding 55 mg of 4-hydrazinothiazole-5-carboxylic acid methyl ester (Example (162c)) and 300 μl of triethylamine to a solution of 160 mg of {2-(9-methoxy-3,4-dihydro-2H-benzo[b][1,4]dioxepin-7-yl)-2-[4-(5-methyl-[1,2,4]oxadiazol-3-yl)phenylimino]-1-methylsulfanylethylidene}carbamic acid methyl ester (Example 30c) in 5 ml of THF, the mixture was stirred overnight at 60° C. under a nitrogen atmosphere. The reaction mixture was then concentrated. The residue was dissolved in 5 ml of DMF, and then 0.3 ml of triethylamine was added and the mixture was stirred at 80° C. for 6 hours.

The reaction mixture was concentrated, and the residue was dissolved in 2.2 ml of a THF:methanol:acetic acid=5:5:1 mixed solvent. After adding 0.2 g of sodium cyanotrihydroborate to the solution, the mixture was stirred at room temperature for 4 hours. Ethyl acetate was added to the reaction mixture. After washing the organic layer with water and saturated brine, it was dried over anhydrous magnesium sulfate. The desiccating agent was filtered off and the filtrate was concentrated under reduced pressure. The residue was purified by NAM silica gel column chromatography (methanol-ethyl acetate) to give the title compound (135 mg) as a light yellow solid.

Mass spectrum (ESI) m/z: 592 (M+H)$^+$ (180b) 4-{3-[(4-carbamimidoylphenylamino)-(9-methoxy-3,4-dihydro-2H-benzo[b][1,4]dioxepin-7-yl)methyl]-5-oxo-4,5-dihydro-[1,2,4]triazol-1-yl}thiazole-5-carboxylic acid trifluoroacetate

[Chemical Formula 465]

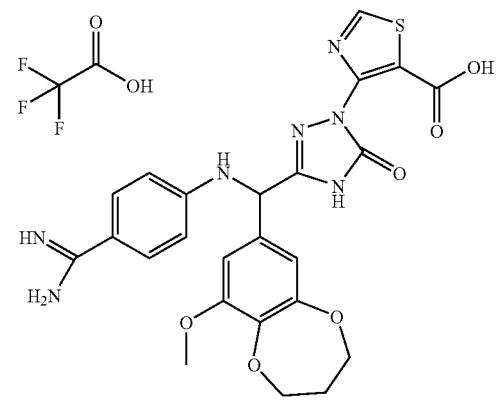

After dissolving 135 mg of 4-(3-{(9-methoxy-3,4-dihydro-2H-benzo[b][1,4]dioxepin-7-yl)-[4-(5-methyl-[1,2,4]oxadiazol-3-yl)phenylamino]methyl}-5-oxo-4,5-dihydro-[1,2,4]triazol-1-yl)thiazole-5-carboxylic acid methyl ester in 2 ml of methanol, 0.5 ml of a 5N aqueous sodium hydroxide solution was added and the mixture was stirred at room temperature for 1 hour. After adding 0.5 ml of 5N hydrochloric acid to the reaction mixture, extraction was performed with ethyl acetate. The organic layer was dried over anhydrous magnesium sulfate. The desiccating agent was filtered off and the filtrate was concentrated under reduced pressure.

The residue was dissolved in 1 ml of methanol, 1.3 ml of acetic acid and 1 ml of water, and then 150 mg of iron powder was added and the mixture was stirred at 60° C. for 20 hours. After adding 0.4 ml of trifluoroacetic acid to the reaction mixture, it was filtered and then purified by reverse-phase high performance liquid chromatography (acetonitrile-water, 0.1% trifluoroacetic acid) to give 109 mg of the title compound as a white solid.

Mass spectrum (ESI) m/z: 538 (M+H)$^+$

367

(180c) (R) and (S)-4-{3-[(4-carbamimidoylphenylamino)-(9-methoxy-3,4-dihydro-2H-benzo[b][1,4]dioxepin-7-yl)methyl]-5-oxo-4,5-dihydro-[1,2,4]triazol-1-yl}thiazole-5-carboxylic acid

[Chemical Formula 466]

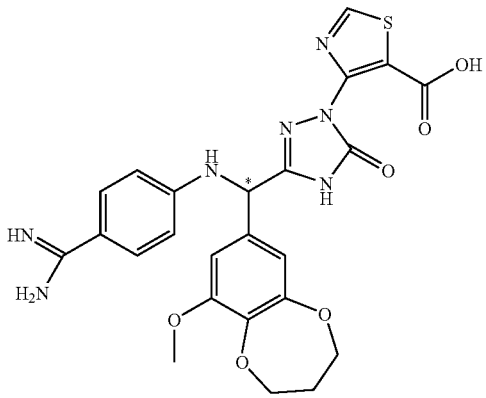

A SUMICHIRAL OA-2500 column was used for optical resolution of 109 mg of 4-{3-[(4-carbamimidoylphenylamino)-(9-methoxy-3,4-dihydro-2H-benzo[b][1,4]dioxepin-7-yl)methyl]-5-oxo-4,5-dihydro-[1,2,4]triazol-1-yl}thiazole-5-carboxylic acid trifluoroacetate, and the first eluting enantiomer (30.53 mg) of the title compound was obtained as a white solid.

$^1$H-NMR (CD$_3$OD) δ 2.11-2.20 (m, 2H) 3.83 (s, 3H) 4.10-4.19 (m, 4H) 5.52 (s, 1H) 6.80 (d, J=2.0 Hz, 1H) 6.85 (d, J=8.8 Hz, 2H) 6.89 (d, J=2.0 Hz, 1H) 7.61 (d, J=8.8 Hz, 2H) 8.88 (s, 1H)

HPLC retention time: 22 min (Column name: SUMICHIRAL OA-2500, 30 mmφ×25 cm, Manufacturer: Sumika Chemical Analysis Service, Ltd., Mobile phase: 0.5 mM ammonium acetate-methanol solution, Elution rate: 30 ml/min)

Example 181

4-({[2-fluoro-3-(2-hydroxyethoxy)-5-methoxyphenyl]-(5-oxo-1-pyrimidin-2-yl-4,5-dihydro-1H-[1,2,4]triazol-3-yl)methyl}amino)benzamidine acetate (181a) (2-{3-[2-(t-butyldimethylsilanyloxy)ethoxy]-2-fluoro-5-methoxyphenyl}-2-(4-cyanophenylimino)-1-methylsulfanylethylidene)carbamic acid methyl ester

[Chemical Formula 467]

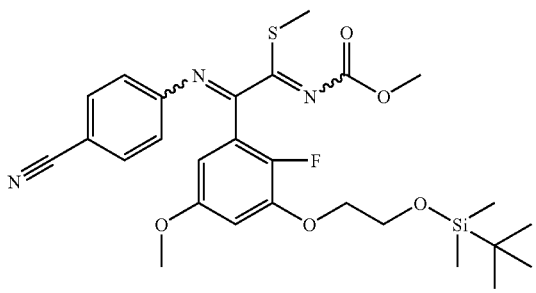

After adding 1.8 g of potassium carbonate and 3 g of (2-bromoethoxy)-t-butyldimethylsilane to a solution of 3.45 g of [2-(4-cyanophenylimino)-2-(2-fluoro-3-hydroxy-5-methoxyphenyl)-1-methylsulfanylethylidene]carbamic acid methyl ester (Example (163b)) in 10 ml of DMF, the mixture was stirred at 50° C. for 5 hours. Water was added to the reaction mixture and extraction was performed with ethyl acetate. The organic layer was washed with water and dried over anhydrous magnesium sulfate. The desiccating agent was filtered off and the filtrate was concentrated under reduced pressure. The residue was purified by silica gel column chromatography (heptane-ethyl acetate) to give the title compound (3.73 g, isomeric mixture) as a light yellow solid.

$^1$H-NMR (CDCl$_3$) Two main isomers:

δ 0.05 (s, 6H) 0.88 (s, 9H) 2.47 (s, 3H) 3.64 (s, 3H) 3.67 (s, 3H) 3.92 (t, J=4.8 Hz, 2H) 3.98 (t, J=4.8 Hz, 2H) 6.13-6.17 (m, 1H) 6.53 (dd, J=2.8, 6.8 Hz, 1H) 6.81 (d, J=8.4 Hz, 2H) 7.48 (d, J=8.4 Hz, 2H)

δ 0.10 (s, 6H) 0.90 (s, 9H) 2.33 (s, 3H) 3.60 (s, 3H) 3.81 (s, 3H) 3.98 (t, J=4.8 Hz, 2H) 4.08 (t, J=4.8 Hz, 2H) 6.74 (dd, J=2.8, 6.8 Hz, 1H) 6.90-6.94 (m, 1H) 7.08 (d, J=8.4 Hz, 2H) 7.60 (d, J=8.4 Hz, 2H)

Mass spectrum (ESI) m/z: 560 (M+H)$^+$ (181b) 4-[({3-[2-(t-butyldimethylsilanyloxy)ethoxy]-2-fluoro-5-methoxyphenyl}-(5-oxo-1-pyrimidin-2-yl-4,5-dihydro-1H-[1,2,4]triazol-3-yl)methyl)amino]benzonitrile

[Chemical Formula 468]

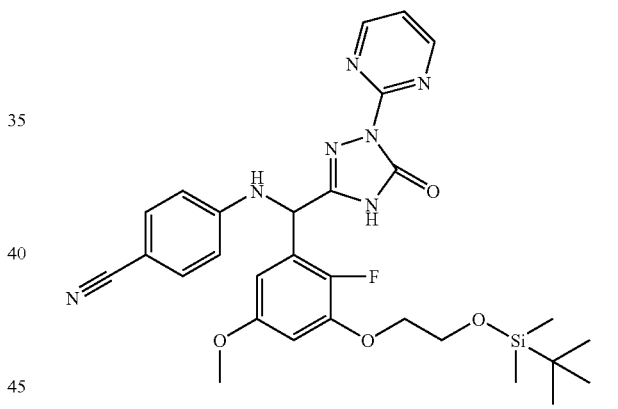

After adding 600 mg of 2-hydrazinopyrimidine and 1.5 ml of triethylamine to a solution of 3.2 g of (2-{3-[2-(t-butyldimethylsilanyloxy)ethoxy]-2-fluoro-5-methoxyphenyl}-2-(4-cyanophenylimino)-1-methylsulfanylethylidene)carbamic acid methyl ester in 30 ml of THF, the mixture was stirred overnight at 60° C. under a nitrogen atmosphere. Next, 30 ml of methanol and 4.5 ml of acetic acid were added to the reaction mixture. After then adding 3 g of sodium cyanotrihydroborate to the solution, the mixture was stirred at room temperature for 5 hours. Ethyl acetate was added to the reaction mixture. After washing the organic layer with water and saturated brine, it was dried over anhydrous magnesium sulfate. The desiccating agent was filtered off and the filtrate was concentrated under reduced pressure to give the title compound (3.4 g, crude product) as a light yellow solid.

$^1$H-NMR (CD$_3$OD) δ 0.08 (s, 6H) 0.87 (s, 9H) 3.65 (s, 3H) 3.94-4.01 (m, 2H) 4.07-4.12 (m, 2H) 5.95 (s, 1H) 6.61 (dd, J=2.8, 4.8 Hz, 1H) 6.67 (dd, J=2.8, 6.8 Hz, 1H) 6.80 (d, J=9.2 Hz, 2H) 7.36 (t, J=4.8 Hz, 1H) 7.45 (d, J=9.2 Hz, 2H) 8.78 (d, J=4.8 Hz, 2H)

Mass spectrum (ESI) m/z: 592 (M+H)$^+$ (181c) 4-({[2-fluoro-3-(2-hydroxyethoxy)-5-methoxyphenyl]-(5-oxo-1-pyrimidin-2-yl-4,5-dihydro-1H-[1,2,4]triazol-3-yl)methyl}amino)benzonitrile

[Chemical Formula 469]

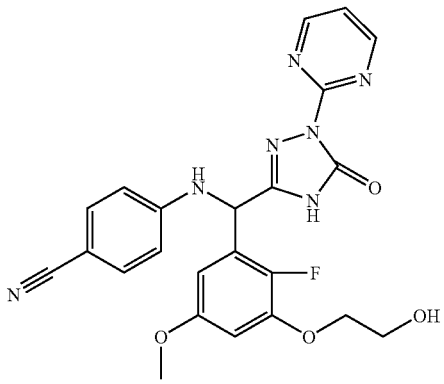

After dissolving 3.4 g of 4-[({3-[2-(t-butyldimethylsilanyloxy)ethoxy]-2-fluoro-5-methoxyphenyl}-(5-oxo-1-pyrimidin-2-yl-4,5-dihydro-1H-[1,2,4]triazol-3-yl)methyl)amino]benzonitrile in 100 ml of acetic acid, 5 ml of water was added and the mixture was stirred overnight at 50° C. The reaction mixture was concentrated, and the residue was purified by NAM silica gel column chromatography (methanol-ethyl acetate) to give the title compound (2.25 g) as a light yellow solid.

$^1$H-NMR (CD$_3$OD) δ 3.73 (s, 3H) 3.88 (t, J=4.8 Hz, 2H) 4.11 (t, J=4.8 Hz, 2H) 5.95 (s, 1H) 6.61 (dd, J=2.8, 4.8 Hz, 1H) 6.68 (dd, J=2.8, 6.8 Hz, 1H) 6.80 (d, J=8.8 Hz, 2H) 7.36 (t, J=4.8 Hz, 1H) 7.45 (d, J=8.8 Hz, 2H) 8.78 (d, J=4.8 Hz, 2H)

Mass spectrum (ESI) m/z: 478 (M+H)$^+$ (181d) 4-({[2-fluoro-3-(2-hydroxyethoxy)-5-methoxyphenyl]-(5-oxo-1-pyrimidin-2-yl-4,5-dihydro-1H-[1,2,4]triazol-3-yl)methyl}amino)benzamidine acetate

[Chemical Formula 470]

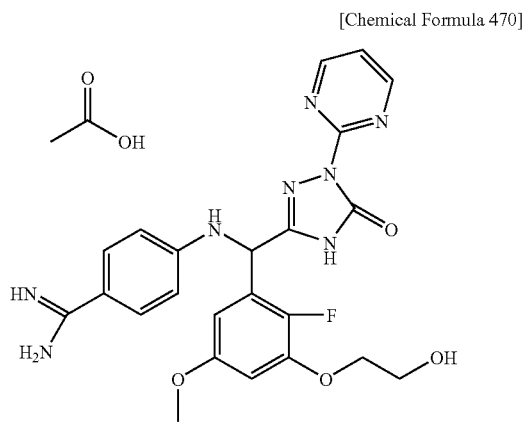

To a solution of 2.25 g of 4-({[2-fluoro-3-(2-hydroxyethoxy)-5-methoxyphenyl]-(5-oxo-1-pyrimidin-2-yl-4,5-dihydro-1H-[1,2,4]triazol-3-yl)methyl}amino)benzonitrile in 30 ml of pyridine there were added 1.5 ml of triethylamine and 30 ml of a 20% aqueous solution of ammonium sulfide, and the mixture was stirred overnight at 60° C. under a nitrogen atmosphere. The reaction mixture was concentrated, acetic acid was added to the residue, and the mixture was again concentrated.

The residue was washed with an ethyl acetate-methanol mixed solvent to give 4-({[2-fluoro-3-(2-hydroxyethoxy)-5-methoxyphenyl]-(5-oxo-1-pyrimidin-2-yl-4,5-dihydro-1H-[1,2,4]triazol-3-yl)methyl}amino)thiobenzamide (2.00 g) as a light yellow solid.

After suspending 2 g of this compound in 25 ml of acetonitrile, 652 mg of Me$_3$O$^+$BF$_4^-$ was added and the mixture was stirred at room temperature for 30 minutes. Next, 315 mg of Me$_3$O$^+$BF$_4^-$ was further added and stirring was continued for 30 minutes. Next, 20 ml of isopropanol and 0.83 ml of 1,1,3,3-tetramethyldisilazane were added to the reaction mixture, which was then stirred overnight at 60° C. The reaction mixture was concentrated, and the residue was purified by reverse-phase silica gel chromatography (acetonitrile-water, 0.1% acetic acid) to give the title compound (1.128 g).

$^1$H-NMR (CD$_3$OD) δ 1.91 (s, 3H) 3.71 (s, 3H) 3.82-3.94 (m, 2H) 4.02-4.16 (m, 2H) 5.95 (s, 1H) 6.57-6.70 (m, 2H) 6.85 (d, J=8.8 Hz, 2H) 7.30 (t, J=5.2 Hz, 1H) 7.61 (d, J=8.8 Hz, 2H) 8.76 (d, J=5.2 Hz, 2H)

Mass spectrum (ESI) m/z: 495 (M+H)$^+$

Example 182

4-(3-{(4-carbamimidoylphenylamino)-[2-fluoro-3-(2-hydroxyethoxy)-5-methoxyphenyl]methyl}-5-oxo-4,5-dihydro[1,2,4]triazol-1-yl)thiazole-5-carboxylic acid trifluoroacetate (182a) {2-(4-cyanophenylimino)-2-[2-fluoro-3-(2-hydroxyethoxy)-5-methoxyphenyl]-1-methylsulfanylethylidene}carbamic acid methyl ester

[Chemical Formula 471]

After adding 0.09 ml of acetic acid and 1.3 ml of TBAF (1.0 M, THF solution) to a solution of 616 mg of (2-{3-[2-(t-butyldimethylsilanyloxy)ethoxy]-2-fluoro-5-methoxyphenyl}-2-(4-cyanophenylimino)-1-methylsulfanylethylidene)carbamic acid methyl ester (Example (181a)) in 5 ml of THF, the mixture was stirred overnight at room temperature. Saturated aqueous ammonium chloride was added to the reaction mixture, and extraction was performed with ethyl acetate. The organic layer was dried over anhydrous magnesium sulfate. The desiccating agent was filtered off and the filtrate was concentrated under reduced pressure. The residue was purified by silica gel column chromatography (heptane-ethyl acetate) to give the title compound (394 mg, isomeric mixture) as a light yellow solid.

$^1$H-NMR (CDCl$_3$) Two main isomers:

δ 2.47 (s, 3H) 3.64 (s, 3H) 3.67 (s, 3H) 3.90-3.96 (m, 2H) 4.13 (t, J=4.4 Hz, 2H) 6.16 (t, J=3.2 Hz, 1H) 6.54 (dd, J=3.2, 6.4 Hz, 1H) 6.82 (d, J=8.4 Hz, 2H) 7.51 (d, J=8.4 Hz, 2H)

δ 2.34 (s, 3H) 3.61 (s, 3H) 3.82 (s, 3H) 3.96-4.01 (m, 2H) 4.04 (t, J=4.4 Hz, 2H) 6.73 (dd, J=3.2, 6.4 Hz, 1H) 6.97 (t, J=3.2 Hz, 1H) 7.09 (d, J=8.4 Hz, 2H) 7.62 (d, J=8.4 Hz, 2H)

(182b) 4-(3-{(4-cyanophenylamino)-[2-fluoro-3-(2-hydroxyethoxy)-5-methoxyphenyl]methyl}-5-oxo-4,5-dihydro-[1,2,4]triazol-1-yl)thiazole-5-carboxylic acid methyl ester

[Chemical Formula 472]

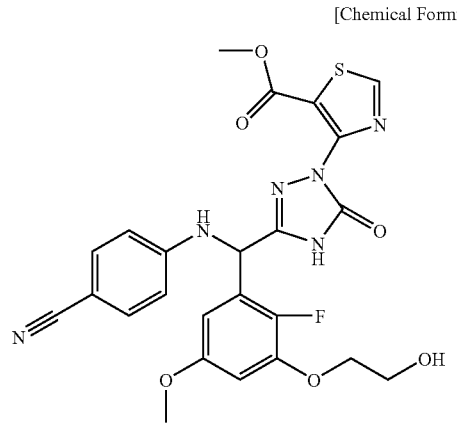

After adding 153 mg of 4-hydrazinothiazole-5-carboxylic acid methyl ester (Example (162c)) and 600 µl of triethylamine to a solution of 394 mg of {2-(4-cyanophenylimino)-2-[2-fluoro-3-(2-hydroxyethoxy)-5-methoxyphenyl]-1-methylsulfanylethylidene}carbamic acid methyl ester in 6 ml of THF, the mixture was stirred at 60° C. for 4 hours under a nitrogen atmosphere. The reaction mixture was concentrated, the residue was dissolved in 5 ml of DMF, 600 µl of triethylamine was added and the mixture was stirred overnight at 85° C.

The reaction mixture was concentrated, and the residue was dissolved in 10 ml of a methanol:THF=1:1 mixed solvent. After adding 500 µl of acetic acid and 700 mg of sodium cyanotrihydroborate to the solution, the mixture was stirred at room temperature for 19 hours. Water was added to the reaction mixture and extraction was performed with ethyl acetate. The organic layer was washed with saturated brine and then dried over anhydrous magnesium sulfate. The desiccating agent was filtered off and the filtrate was concentrated under reduced pressure. The residue was purified by NAM silica gel column chromatography (methanol-ethyl acetate) to give the title compound (375 mg).

$^1$H-NMR (CD$_3$OD) δ 3.74 (s, 3H) 3.82 (s, 3H) 3.88 (t, J=4.8 Hz, 2H) 4.10 (t, J=4.8 Hz, 2H) 5.95 (s, 1H) 6.60-6.62 (m, 1H) 6.66-6.70 (m, 1H) 6.80 (d, J=8.8 Hz, 2H) 7.45 (d, J=8.8 Hz, 2H) 9.15 (s, 1H)

(182c) 4-(3-{(4-carbamimidoylphenylamino)-[2-fluoro-3-(2-hydroxyethoxy)-5-methoxyphenyl]methyl}-5-oxo-4,5-dihydro[1,2,4]triazol-1-yl)thiazole-5-carboxylic acid trifluoroacetate

[Chemical Formula 473]

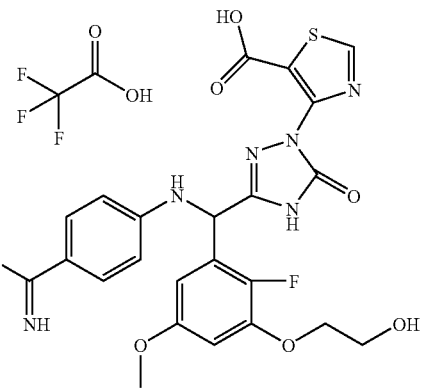

After dissolving 375 mg of 4-(3-{(4-cyanophenylamino)-[2-fluoro-3-(2-hydroxyethoxy)-5-methoxyphenyl]methyl}-5-oxo-4,5-dihydro-[1,2,4]triazol-1-yl)thiazole-5-carboxylic acid methyl ester in 10 ml of THF, 694 µl of a 5N aqueous sodium hydroxide solution was added and the mixture was stirred at room temperature for 5 hours. After further adding 800 µl of 5N hydrochloric acid and water to the reaction mixture, extraction was performed with ethyl acetate. The organic layer was washed with saturated brine and then dried over anhydrous magnesium sulfate. The desiccating agent was filtered off and the filtrate was concentrated under reduced pressure.

To a solution of the residue in 8 ml of ethanol there were added 241 mg of hydroxylammonium chloride and 677 µl of triethylamine, and the mixture was stirred at 70° C. for 18 hours under a nitrogen atmosphere.

The reaction mixture was concentrated, and the residue was dissolved in 10 ml of acetic acid. After adding 0.5 ml of acetic anhydride and 100 mg of 10% palladium-carbon (hydrous) to the solution, the mixture was stirred for 2 hours under a hydrogen atmosphere. The reaction mixture was filtered through celite, and the filtrate was concentrated under reduced pressure. The residue was purified by reverse-phase high performance liquid chromatography (acetonitrile-water, 0.1% trifluoroacetic acid) to give the title compound (260 mg).

Mass spectrum (ESI) m/z: 544 (M+H)$^+$ $^1$H-NMR (CD$_3$OD) δ 3.74 (s, 3H) 3.88 (br.s, 2H) 4.10 (br.s, 2H) 6.00 (s, 1H) 6.59-6.61 (br.s, 1H) 6.68 (br.d, J=6.8 Hz, 1H) 6.86 (d, J=8.4 Hz, 2H) 7.63 (d, J=8.4 Hz, 2H) 8.28 (br.s, 1H) 8.80 (br.s, 1H) 9.13 (s, 1H)

Example 183

2-{3-[(R) and (S)-(4-carbamimidoyl-3-hydroxyphenylamino)-(3,4-dimethoxyphenyl)methyl]-5-oxo-4,5-dihydro-[1,2,4]triazol-1-yl}benzoic acid (183a) 2-{3-[(3-benzyloxy-4-cyanophenylamino)-(3,4-dimethoxyphenyl)methyl]-5-oxo-4,5-dihydro-[1,2,4]triazol-1-yl}benzoic acid

[Chemical Formula 474]

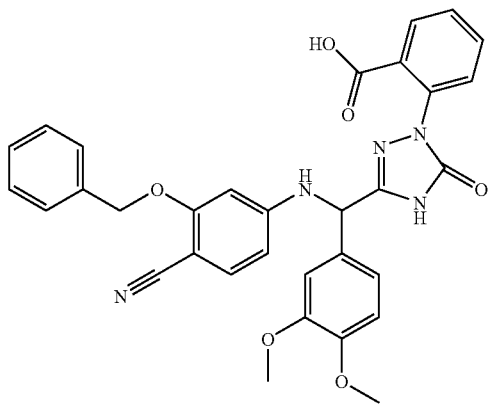

The same procedure was carried out as in Examples (37a)-(37b), except that 2-benzyloxy-4-aminobenzonitrile [CAS No. 284044-40-2] was used instead of the 2-fluoro-4-aminobenzonitrile in Example (37a), to give the title compound.

$^1$H-NMR (d$_6$-DMSO) δ 3.76 (s, 3H) 3.77 (s, 3H) 5.11 (d, J=3.6 Hz, 2H) 5.63 (d, J=6.4 Hz, 1H) 6.43 (dd, J=8.4, 1.6 Hz, 1H) 6.59 (d, J=1.6 Hz, 1H) 6.97 (d, J=8.4 Hz, 1H) 7.05 (dd, J=8.4, 2.0 Hz, 1H) 7.16 (d, J=2.0 Hz, 1H) 7.30-7.47 (m, 9H) 7.62 (td, J=7.6, 1.6 Hz, 1H) 7.78 (dd, J=8.4, 2.0 Hz, 1H)

(183b) 2-{3-[(R) and (S)-(4-carbamimidoyl-3-hydroxyphenylamino)-(3,4-dimethoxyphenyl)methyl]-5-oxo-4,5-dihydro-[1,2,4]triazol-1-yl}benzoic acid

[Chemical Formula 475]

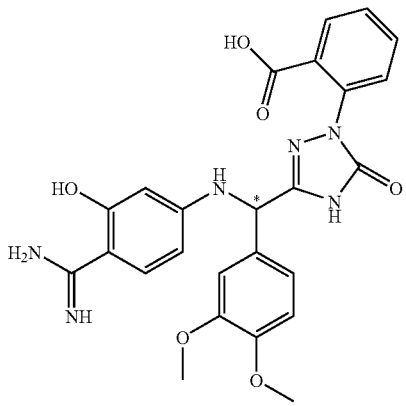

After adding 72 mg of hydroxylammonium chloride and 203 μl of triethylamine to a solution of 120 mg of 2-{3-[(3-benzyloxy-4-cyanophenylamino)-(3,4-dimethoxyphenyl)methyl]-5-oxo-4,5-dihydro-[1,2,4]triazol-1-yl}benzoic acid in 3 ml of ethanol, the mixture was stirred at 70° C. for 36 hours under a nitrogen atmosphere. The reaction mixture was then concentrated.

The residue was dissolved in 4 ml of acetic acid. After adding 0.4 ml of acetic anhydride and 25 mg of 10% palladium-carbon (hydrous) to this solution, the mixture was stirred at room temperature for 9 hours under a hydrogen atmosphere. Next, 25 mg of 10% palladium-carbon (hydrous) was added to the reaction mixture, and the mixture was stirred at room temperature for 19 hours under a hydrogen atmosphere. The reaction mixture was filtered through celite, and the filtrate was concentrated under reduced pressure. The residue was purified by reverse-phase high performance liquid chromatography (acetonitrile-water, 0.1% trifluoroacetic acid) to give 30 mg of 2-{3-[(4-carbamimidoyl-3-hydroxyphenylamino)-(3,4-dimethoxyphenyl)methyl]-5-oxo-4,5-dihydro-[1,2,4]triazol-1-yl}benzoic acid trifluoroacetate as a light yellow solid.

Mass spectrum (ESI) m/z: 505 (M+H)$^+$

This compound was optically resolved using a SUMICHIRAL OA-2500 column, and the first eluting enantiomer (1.59 mg) of the title compound was obtained as a white solid.

$^1$H-NMR (CD$_3$OD) δ 3.84 (s, 3H) 3.88 (s, 3H) 5.39 (s, 1H) 6.44 (dd, J=9.2, 2.0 Hz, 1H) 6.75 (br.s, 1H) 6.99 (d, J=8.4 Hz, 1H) 7.05 (dd, J=8.4, 2.4 Hz, 1H) 7.22 (d, J=2.4 Hz, 1H) 7.39-7.47 (m, 4H) 7.68 (m, 1H)

HPLC retention time: 23 min (Column name: SUMICHIRAL OA-2500, 30 mmφ×25 cm, Manufacturer: Sumika Chemical Analysis Service, Ltd., Mobile phase: 0.05 M ammonium acetate-methanol solution, Elution rate: 20 ml/min)

Example 184

(R) and (S)-4-({(2-fluoro-4,5-dimethoxyphenyl)-[1-(3-fluoropyridin-2-yl)-5-oxo-4,5-dihydro-1H-[1,2,4]triazol-3-yl]methyl}amino)benzamidine acetate

[Chemical Formula 476]

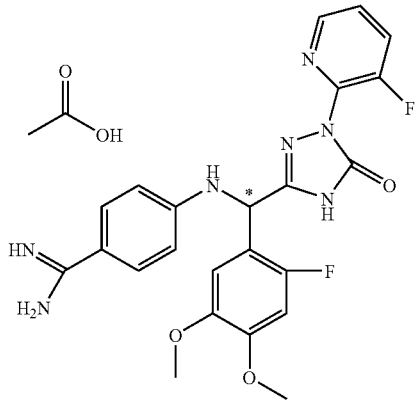

76 mg of 4-({(2-fluoro-4,5-dimethoxyphenyl)-[1-(3-fluoropyridin-2-yl)-5-oxo-4,5-dihydro-1H-[1,2,4]triazol-3-yl]methyl}amino)benzamidine acetate (Example 125) was optically resolved using a SUMICHIRAL OA-2500 column, and the first eluting enantiomer (33.78 mg) of the title compound was obtained as a white solid.

$^1$H-NMR (CD$_3$OD) δ 1.91 (s, 3H) 3.69 (s, 3H) 3.80 (s, 3H) 5.94 (s, 1H) 6.81 (d, J=11.2 Hz, 1H) 6.85 (d, J=8.8 Hz, 2H)

7.08 (d, J=7.2 Hz, 1H) 7.51 (Sept, J=4.0 Hz, 1H) 7.59 (d, J=8.8 Hz, 2H) 7.80 (t, J=8.4 Hz, 1H) 8.35 (d, J=4.8 Hz, 1H)
HPLC retention time: 12 min Example 185

4-{3-[(R) and (S)-(4-Carbamimidoylphenylamino)-(5-ethoxy-6-methoxypyridin-3-yl)methyl]-5-oxo-4,5-dihydro-[1,2,4]triazol-1-yl}thiazole-5-carboxylic acid (185a) 4-Amino-2-methanesulfonylthiazole-5-carboxylic acid ethyl ester

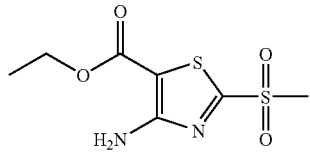

[Chemical Formula 477]

After adding 41.8 g of 4-amino-2-methylsulfanylthiazole-5-carboxylic acid ethyl ester [CAS No. 39736-29-3] to 3 liters of a water:methanol=1:1 mixed solvent at room temperature, 352 g of Oxone™ was added thereto in small portions over a period of 15 minutes with stirring. The mixture was stirred at room temperature for 16 hours and then poured into a mixture of 8 liters of ethyl acetate and 5 liters of water. The organic layer was washed with 5 liters of water and 3 liters of saturated brine and then dried over anhydrous magnesium sulfate. The desiccating agent was removed by filtration, and the filtrate was concentrated under reduced pressure to give the title compound (34.5 g) as a light yellow solid.
$^1$H-NMR (CDCl$_3$) δ 1.36 (t, J=7.5 Hz, 3H) 3.29 (s, 3H) 4.34 (q, J=7.5 Hz, 2H) 6.00 (br.s, 2H)

(185b) 4-Aminothiazole-5-carboxylic acid ethyl ester

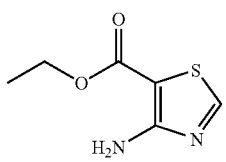

[Chemical Formula 478]

To 1 liter of a methanol:THF=1:1 mixed solvent solution containing 34.5 g of 4-amino-2-methanesulfonylthiazole-5-carboxylic acid ethyl ester, 10.4 g of sodium borohydride was added in small portions over a period of 20 minutes at room temperature. The reaction mixture was stirred at room temperature for 2 hours, and then was poured into 8 liters of ethyl acetate and 4 liters of water. The organic layer was washed with 3 liters of water and 3 liters of saturated brine, and the aqueous layer was extracted with ethyl acetate again. The organic layers were combined and dried over anhydrous magnesium sulfate. The desiccating agent was removed by filtration, and the filtrate was concentrated under reduced pressure to give the title compound (19.3 g) as a light yellow solid.
$^1$H-NMR (CDCl$_3$) δ 1.37 (t, J=7.5 Hz, 3H) 4.30 (t, J=7.5 Hz, 2H) 5.87 (br.s, 2H) 8.54 (s, 1H)

(185c) 4-Hydrazinothiazole-5-carboxylic acid ethyl ester

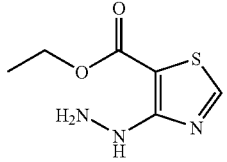

[Chemical Formula 479]

To 100 ml of a concentrated hydrochloric acid solution containing 19.3 g of 4-aminothiazole-5-carboxylic acid ethyl ester, 12 ml of an aqueous solution of 8.5 g of sodium nitrite was added dropwise at 0 to 5° C. This mixture was stirred at 0° C. for 30 minutes, and then 120 ml of a concentrated hydrochloric acid solution containing 84.9 g of stannous chloride was added dropwise thereto at 0 to 10° C. The mixture was further stirred at the same temperature for 2 hours and then stirred at room temperature for 30 minutes. The reaction mixture was filtered, and the filtrate was carefully added to 2 liters of an ethyl acetate suspension containing 500 g of potassium carbonate and 100 g of celite with stirring. Further, the filtered substance was added to this ethyl acetate suspension, and then the suspension was made basic with 150 ml of a 5 N sodium hydroxide aqueous solution. The mixture was allowed to stand, and then most of the supernatant (organic layer A: 1.5 liters) was collected. The remaining suspension was filtered through celite, and the celite was washed with 1 liter of ethyl acetate and 500 ml of water. The filtrate was separated into organic layer B and aqueous layer A. Ethyl acetate (1 liter) and anhydrous magnesium sulfate were added to the filtered substance, and the mixture was stirred and then filtered. Aqueous layer A was re-extracted with the resulting filtrate. Washing of the filtered substance and re-extraction of aqueous layer A were repeated 4 times in the same manner. Organic layer A and organic layer B were combined with the obtained organic layers, and the mixture was dried over anhydrous magnesium sulfate. The desiccating agent was removed by filtration, and the filtrate was concentrated under reduced pressure. The residue was purified by silica gel column chromatography (ethyl acetate-methanol) to give the title compound (11.9 g) as a light yellow solid.
$^1$H-NMR (CDCl$_3$) δ 1.35 (t, J=7.5 Hz, 3H) 4.14 (br.s, 2H) 4.30 (q, J=7.5 Hz, 2H) 7.55 (br.s, 1H) 8.60 (s, 1H)

377

(185d) 4-(3-{(5-ethoxy-6-methoxypyridin-3-yl)-[4-(5-methyl-[1,2,4]oxadiazol-3-yl)phenylamino]methyl}-5-oxo-4,5-dihydro-[1,2,4]triazol-1-yl)thiazole-5-carboxylic acid ethyl ester

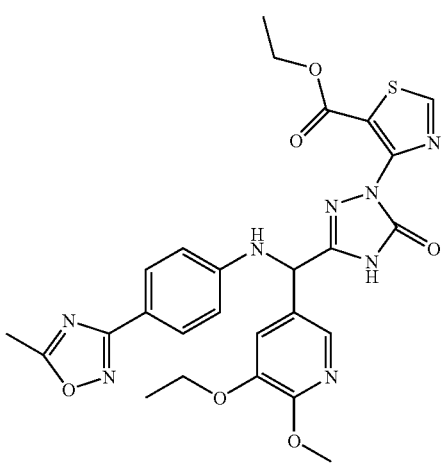

[Chemical Formula 480]

To 4 ml of a DMF solution containing 117 mg of {2-(5-ethoxy-6-methoxypyridin-3-yl)-2-[4-(5-methyl-[1,2,4]oxadiazol-3-yl)phenylimino]-1-methylsulfanylethylidene}carbamic acid methyl ester (Example 160a), 52 mg of 4-hydrazinothiazole-5-carboxylic acid ethyl ester and 0.038 ml of triethylamine were added. The mixture was stirred at 85° C. for 16 hours under a nitrogen atmosphere. The reaction mixture was concentrated. The residue was dissolved in 10 ml of methanol and 0.05 ml of acetic acid, and then 125 mg of sodium cyanotrihydroborate was further added thereto. The mixture was stirred at room temperature for 15 hours, and then 100 ml of ethyl acetate and 50 ml of water were added thereto. The organic layer was washed with 50 ml of water and then with 50 ml of saturated brine and then dried over anhydrous magnesium sulfate. The desiccating agent was removed by filtration, and the filtrate was concentrated under reduced pressure. The residue was purified by NAM silica gel column chromatography (methanol-ethyl acetate) to give the title compound (65 mg).

$^1$H-NMR (CDCl$_3$) δ 1.22 (t, J=7.3 Hz, 3H) 1.40 (t, J=6.8 Hz, 3H) 2.59 (s, 3H) 3.94 (s, 3H) 4.08 (q, J=7.3 Hz, 2H) 4.25 (q, J=6.8 Hz, 2H) 5.69 (s, 1H) 6.85 (d, J=9.2 Hz, 2H) 7.38 (s, 1H) 7.80 (d, J=9.2 Hz, 2H) 7.84 (s, 1H) 9.16 (s, 1H)

378

(185e) 4-{3-[(R) and (S)-(4-Carbamimidoylphenylamino)-(5-ethoxy-6-methoxypyridin-3-yl)methyl]-5-oxo-4,5-dihydro-[1,2,4]triazol-1-yl}thiazole-5-carboxylic acid

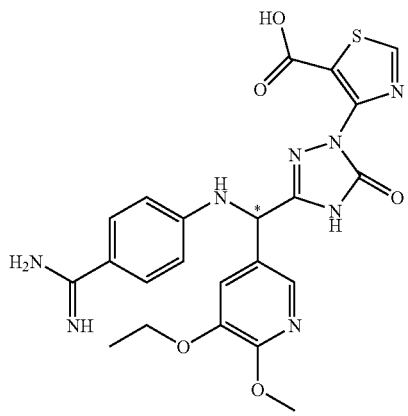

[Chemical Formula 481]

To 2 ml of a methanol solution containing 64 mg of 4-(3-{(5-ethoxy-6-methoxypyridin-3-yl)-[4-(5-methyl-[1,2,4]oxadiazol-3-yl)phenylamino]methyl}-5-oxo-4,5-dihydro-[1,2,4]triazol-1-yl)thiazole-5-carboxylic acid ethyl ester, 500 μl of a 5 N sodium hydroxide aqueous solution was added. The mixture was stirred at room temperature for 4 hours, and 6 ml of a methanol:water:acetic acid=1:1:1 mixed solvent and 62 mg of iron powder were added thereto. The mixture was stirred at 60° C. for 15 hours under a nitrogen atmosphere. The reaction mixture was filtered and then was purified by reverse-phase high performance liquid chromatography (acetonitrile-water, 0.1% trifluoroacetic acid) to give 4-{3-[(4-carbamimidoylphenylamino)-(5-ethoxy-6-methoxypyridin-3-yl)methyl]-5-oxo-4,5-dihydro-[1,2,4]triazol-1-yl}thiazole-5-carboxylic acid trifluoroacetate.

This compound was optically resolved using a SUMICHIRAL OA-2500 column, and the first eluting enantiomer (10.3 mg) of the title compound was obtained as a white solid.

$^1$H-NMR (CD$_3$OD) δ 1.39 (t, J=7.2 Hz, 3H) 3.94 (s, 3H) 4.09 (q, J=7.2 Hz, 2H) 5.78 (s, 1H) 6.88 (d, J=8.9 Hz, 2H) 7.36 (d, J=1.2 Hz, 1H) 7.64 (d, J=8.9 Hz, 2H) 7.83 (d, J=1.2 Hz, 1H) 8.90 (s, 1H)

HPLC retention time: 27 min (Column name: SUMICHIRAL OA-2500, 30 mmφ×25 cm, Manufacturer: Sumika Chemical Analysis Service, Ltd., Mobile phase: 0.5 mM ammonium acetate-methanol solution, Elution rate: 30 ml/min)

Example 186

4-{[(R) and (S)-[1-(3-Aminopyridin-2-yl)-5-oxo-4,5-dihydro-1H-[1,2,4]triazol-3-yl]-(5,6-dimethoxypyridin-3-yl)methyl]amino}benzamidine acetate (186a) 5-{(5,6-dimethoxypyridin-3-yl)-[4-(5-methyl-[1,2,4]oxadiazol-3-yl)phenylamino]methyl}-2-(3-nitropyridin-2-yl)-2,4-dihydro-[1,2,4]triazol-3-one

[Chemical Formula 482]

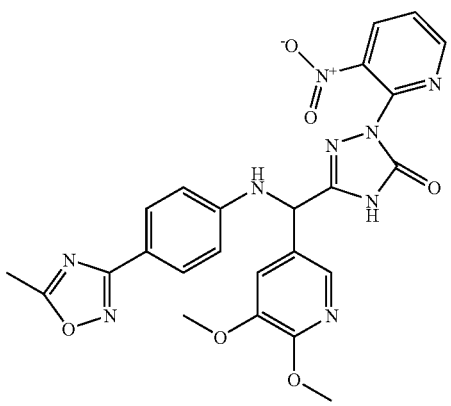

The same procedure was carried out as in Example (34a), except that {2-(5,6-dimethoxypyridin-3-yl)-2-[4-(5-methyl-[1,2,4]oxadiazol-3-yl)phenylimino]-1-methylsulfanylethylidene}carbamic acid methyl ester (Example (169a)) was used instead of the [2-(9-methoxy-3,4-dihydro-2H-benzo[b][1,4]dioxepin-7-yl)-2-[4-(5-methyl-[1,2,4]oxadiazol-3-yl)phenylimino]-1-methylsulfanylethylidene]carbamic acid methyl ester, to give the title compound.

$^1$H-NMR (CD$_3$OD) δ 2.58 (s, 3H) 3.97 (s, 3H) 4.05 (s, 3H) 5.73 (s, 1H) 6.85 (d, J=8.9 Hz, 2H) 7.39 (d, J=1.5 Hz, 1H) 7.65 (dd, J=7.5, 3.4 Hz, 1H) 7.80 (d, J=8.9 Hz, 2H) 7.85 (d, J=1.5 Hz, 1H) 8.48 (dd, J=7.5, 0.8 Hz, 1H) 8.77 (dd, J=3.4, 0.8 Hz, 1H)

(186b) 4-{[(R) and (S)-[1-(3-Aminopyridin-2-yl)-5-oxo-4,5-dihydro-1H-[1,2,4]triazol-3-yl]-(5,6-dimethoxypyridin-3-yl)methyl]amino}benzamidine acetate

[Chemical Formula 483]

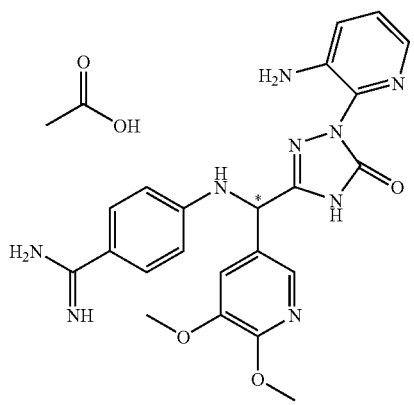

The same procedure was carried out as in Example (34a), except that 5-{(5,6-dimethoxypyridin-3-yl)-[4-(5-methyl-[1,2,4]triazol-3-yl)phenylamino]methyl}-2-(3-nitropyridin-2-yl)-2,4-dihydro-[1,2,4]triazol-3-one was used instead of the 5-{(9-methoxy-3,4-dihydro-2H-benzo[b][1,4]dioxepin-7-yl)-[4-(5-methyl-[1,2,4]oxadiazol-3-yl)phenylamino]methyl}-2-(3-nitropyridin-2-yl)-2,4-dihydro-[1,2,4]triazol-3-one, to give 4-{[[1-(3-Aminopyridin-2-yl)-5-oxo-4,5-dihydro-1H-[1,2,4]triazol-3-yl]-(5,6-dimethoxypyridin-3-yl)methyl]amino}benzamidine trifluoroacetate.

This compound was optically resolved using a SUMICHIRAL OA-2500 column, and the first eluting enantiomer (16.0 mg) of the title compound was obtained as a white solid.

$^1$H-NMR (CD$_3$OD) δ 1.91 (s, 3H) 3.84 (s, 3H) 3.93 (s, 3H) 5.67 (s, 1H) 6.88 (d, J=8.9 Hz, 2H) 7.21 (dd, J=7.9, 4.5 Hz, 1H) 7.33 (dd, J=7.9, 1.3 Hz, 1H) 7.40 (d, J=1.5 Hz, 1H) 7.62 (d, J=8.9 Hz, 2H) 7.83 (dd, J=4.5, 1.3 Hz, 1H) 7.84 (d, J=1.5 Hz, 1H)

HPLC retention time: 8 min (Column name: SUMICHIRAL OA-2500, 30 mmφ×25 cm, Manufacturer: Sumika Chemical Analysis Service, Ltd., Mobile phase: 0.5 mM ammonium acetate-methanol solution, Elution rate: 20 ml/min)

Example 187

5-{3-[(R) or (S)-(4-Carbamimidoylphenylamino)-(2-fluoro-4,5-dimethoxyphenyl)methyl]-5-oxo-4,5-dihydro-[1,2,4]triazol-1-yl}-3H-imidazole-4-carboxylic acid (187a) 3-Benzyl-5-(N'-t-butoxycarbonylhydrazino)-3H-imidazole-4-carboxylic acid ethyl ester

[Chemical Formula 484]

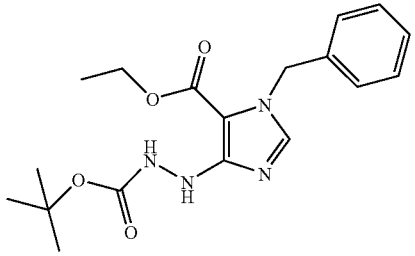

An aqueous solution (2 ml) of sodium nitrite (869 mg) was added dropwise to 10 ml of a 35% hydrochloric acid solution containing 2.94 g of 5-amino-3-benzyl-3H-imidazole-4-carboxylic acid ethyl ester [CAS No. 169616-29-9] at 0 to 5° C. This mixture solution was stirred at 0° C. for 30 minutes, and then 10 ml of a concentrated hydrochloric acid solution containing 9.1 g of stannous chloride was added dropwise thereto at 0 to 10° C. The mixture was further stirred at the same temperature for 2 hours. The precipitate was collected by filtration and washed with a small amount of water. To this solid, 100 ml of water and 100 ml of dichloromethane were added. The resulting mixture was made basic with potassium carbonate, and then 3.9 g of di-t-butyl dicarbonate was added thereto. The mixture was stirred at room temperature for 48 hours, and 400 ml of ethyl acetate and 200 ml of water were added. The layers were separated and the aqueous layer was extracted with 200 ml of ethyl acetate twice. The organic layers were combined and dried over anhydrous magnesium sulfate. The desiccating agent was removed by filtration, and the filtrate was concentrated under reduced pressure. The residue was purified by silica gel column chromatography (methanol-ethyl acetate) to give the title compound (3.71 g) as a white solid.

¹H-NMR (CDCl₃) δ 1.33 (t, J=7.6 Hz, 3H) 1.49 (s, 9H) 4.28 (q, J=7.6 Hz, 2H) 5.37 (s, 2H) 6.59 (br.s, 1H) 7.15 (m, 2H) 7.27-7.35 (m, 3H)

(187b)
3-Benzyl-5-hydrazino-3H-imidazole-4-carboxylic acid ethyl ester

[Chemical Formula 485]

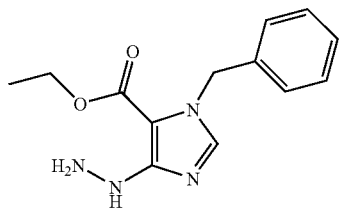

To 50 ml of a dichloromethane solution containing 3.7 g of 3-benzyl-5-(N'-t-butoxycarbonylhydrazino)-3H-imidazole-4-carboxylic acid ethyl ester, 20 ml of trifluoroacetic acid was added. The resulting mixture was stirred at room temperature for 4 hours, and 100 ml of toluene was added thereto. The mixture was concentrated under reduced pressure. The residue was dissolved in 400 ml of ethyl acetate, and the solution was washed with 200 ml of a 2 N sodium hydroxide solution. The aqueous layer was extracted with 200 ml of ethyl acetate, and the organic layers were combined and dried over anhydrous magnesium sulfate. The desiccating agent was removed by filtration, and the filtrate was concentrated under reduced pressure. The residue was purified by silica gel column chromatography (methanol-ethyl acetate) to give the title compound (1.65 g) as a light yellow solid.

¹H-NMR (CDCl₃) δ 1.34 (t, J=7.2 Hz, 3H) 4.22 (q, J=7.2 Hz, 2H) 5.39 (s, 2H) 6.50 (br.s, 1H) 7.15 (d, J=7.7 Hz, 2H) 7.28-7.36 (m, 3H)

(187c) 3-Benzyl-5-{3-[(R) and (S)-(4-cyanophenylamino)-(2-fluoro-4,5-dimethoxyphenyl)methyl]-5-oxo-4,5-dihydro-[1,2,4]triazol-1-yl}-3H-imidazole-4-carboxylic acid ethyl ester

[Chemical Formula 486]

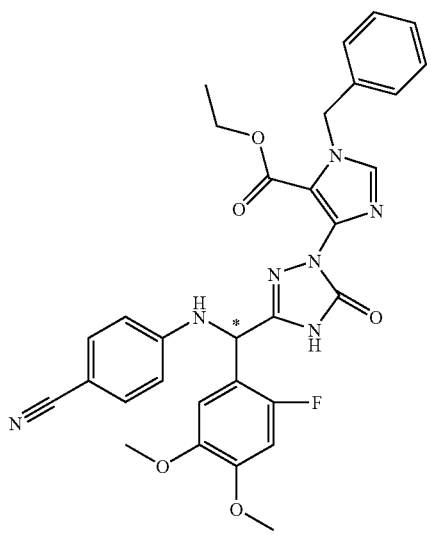

The same procedure was carried out as in Example (2a) to (2e), except that 2-fluoro-4,5-dimethoxybenzaldehyde was used instead of the 2-fluoro-3,5-dimethoxybenzaldehyde in Example (2a), to give [2-(4-Cyanophenylimino)-2-(2-fluoro-4,5-dimethoxyphenyl)-1-methylsulfanylethylidene]carbamic acid methyl ester.

To 8 ml of a DMF solution containing 415 mg of this compound, 286 mg of 3-benzyl-5-hydrazino-3H-imidazole-4-carboxylic acid ethyl ester and 0.153 ml of triethylamine were added. The resulting mixture was stirred at 85° C. for 16 hours under a nitrogen atmosphere. The reaction mixture was concentrated. The residue was dissolved in 15 ml of methanol and 0.23 ml of acetic acid, and then 628 mg of sodium cyanotrihydroborate was added thereto. The mixture was stirred at room temperature for 15 hours, and then 100 ml of ethyl acetate and 50 ml of water were added thereto. The organic layer was washed with 20 ml of water and then with 20 ml of saturated brine and was dried over anhydrous magnesium sulfate. The desiccating agent was removed by filtration, and the filtrate was concentrated under reduced pressure. The residue was purified by NAM silica gel column chromatography (methanol-ethyl acetate) to give 3-benzyl-5-{3-[(4-cyanophenylamino)-(2-fluoro-4,5-dimethoxyphenyl)methyl]-5-oxo-4,5-dihydro-[1,2,4]triazol-1-yl}-3H-imidazole-4-carboxylic acid ethyl ester (153 mg).

This compound was optically resolved using a CHIRALPAK AD-H column, and the first eluting enantiomer (46 mg) of the title compound was obtained as a light yellow solid.

¹H-NMR (CD₃OD) δ 1.01 (t, J=7.6 Hz, 3H) 3.76 (s, 3H) 3.83 (s, 3H) 4.10 (m, 2H) 5.59 (s, 2H) 5.87 (s, 1H) 6.79 (d, J=8.8 Hz, 2H) 6.85 (d, J=10.2 Hz, 1H) 7.06 (d, J=7.4 Hz, 1H) 7.22 (br.d, J=8.8 Hz, 2H) 7.26-7.34 (m, 3H) 7.44 (d, J=8.8 Hz, 2H) 8.01 (s, 1H)

HPLC retention time: 23 min (Column name: CHIRALPAK AD-H, 20 mmφ×25 cm, Manufacturer: Daicel Chemical Industries, Ltd., Mobile phase: ethyl acetate/heptane=1/1, Elution rate: 10 ml/min)

(187d) 3-Benzyl-5-(3-{(R) or (S)-(2-fluoro-4,5-dimethoxyphenyl)-[(4-(N-hydroxycarbamimidoyl)phenylamino]-methyl}-5-oxo-4,5-dihydro-[1,2,4]triazol-1-yl)-3H-imidazole-4-carboxylic acid

[Chemical Formula 487]

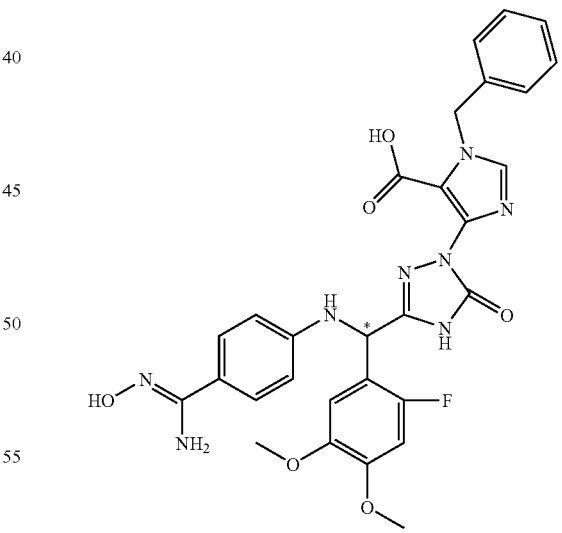

To 3 ml of a methanol solution containing 45 mg of 3-benzyl-5-{(R) or (S)-3-[(4-cyanophenylamino)-(2-fluoro-4,5-dimethoxyphenyl)methyl]-5-oxo-4,5-dihydro-[1,2,4]triazol-1-yl}-3H-imidazole-4-carboxylic acid ethyl ester (Example (187c)), 0.4 ml of a 5 N sodium hydroxide solution was added. The resulting mixture was stirred at room temperature for 5 hours, and then 0.4 ml of 5 N hydrochloric acid was added thereto. The mixture was concentrated under reduced pressure.

The residue was dissolved in 3 ml of methanol, and 52 mg of hydroxylammonium chloride and 0.126 ml of triethylamine were added thereto. The mixture was stirred at 65° C. for 16 hours under a nitrogen atmosphere. After the addition of the same amounts of the reagents, the mixture was further stirred at 65° C. for 24 hours. After cooling, the reaction mixture was purified by reverse-phase high performance liquid chromatography (acetonitrile-water, 0.1% trifluoroacetic acid) to give the title compound (34 mg) as a white solid.

$^1$H-NMR (CD$_3$OD) δ 3.76 (s, 3H) 3.81 (s, 3H) 5.65 (d, J=14.9 Hz, 1H) 5.70 (d, J=14.9 Hz, 1H) 5.84 (s, 1H) 6.79 (d, J=9.1 Hz, 2H) 6.82 (d, J=11.2 Hz, 1H) 7.05 (d, J=7.1 Hz, 1H) 7.23-7.31 (m, 5H) 7.45 (d, J=9.1 Hz, 2H) 7.74 (s, 1H)

(187e) 5-{3-[(R) or (S)-(4-Carbamimidoylphenylamino)-(2-fluoro-4,5-dimethoxyphenyl)methyl]-5-oxo-4,5-dihydro-[1,2,4]triazol-1-yl}-3H-imidazole-4-carboxylic acid

[Chemical Formula 488]

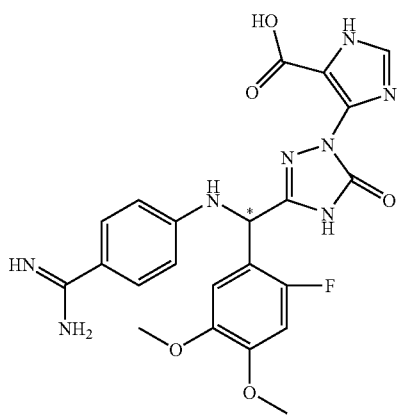

To 6 ml of an ethanol solution containing 30 mg of 3-benzyl-5-(3-{(R) or (S)-(2-fluoro-4,5-dimethoxyphenyl)-[(4-(N-hydroxycarbamimidoyl)phenylamino]-methyl}-5-oxo-4,5-dihydro-[1,2,4]triazol-1-yl)-3H-imidazole-4-carboxylic acid (Example (187d)), 10 mg of 5% palladium carbon powder and 94 mg of ammonium formate were added. The resulting mixture was stirred at 80° C. for 60 hours under a nitrogen atmosphere. After cooling, the reaction mixture was purified by reverse-phase high performance liquid chromatography (acetonitrile-water, 0.1% acetic acid) to give the title compound (0.36 mg) as a brown solid.

$^1$H-NMR (CD$_3$OD) δ 3.77 (s, 3H) 3.85 (s, 3H) 5.88 (s, 1H) 6.85 (m, 3H) 7.07 (d, J=7.0 Hz, 1H) 7.62 (m, 3H)

Example 188

4-{3-[(R) and (S)-(4-Carbamimidoylphenylamino)-(5-fluoro-8-methoxy-2,3-dihydrobenzo[1,4]dioxin-6-yl)methyl]-5-oxo-4,5-dihydro-[1,2,4]triazol-1-yl}thiazole-5-carboxylic acid (188a) 4-(5-Trifluoromethyl-[1,2,4]oxadiazol-3-yl)phenylamine

[Chemical Formula 489]

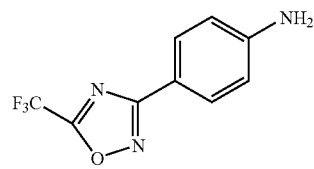

To 500 ml of a dichloromethane solution containing 10.2 g of [4-(N-hydroxycarbamimidoyl)phenyl]carbamic acid t-butyl ester (Tetrahedron Lett. 2003, 44, 8697), 8.8 ml of diisopropylethylamine and 8.6 ml of trifluoroacetic anhydride were added at 0° C. under a nitrogen atmosphere. The resulting mixture was stirred for 20 hours, and then 500 ml of ethyl acetate and 500 ml of water were added thereto. The organic layer was washed with 200 ml of water and then with 200 ml of saturated brine and dried over anhydrous magnesium sulfate. The desiccating agent was removed by filtration, and the filtrate was concentrated under reduced pressure. The residue was purified by silica gel column chromatography (ethyl acetate-heptane) to give [4-(5-trifluoromethyl-[1,2,4]oxadiazol-3-yl)phenyl]carbamic acid t-butyl ester (9.6 g).

$^1$H-NMR (CDCl$_3$) δ 1.55 (s, 9H) 6.66 (s, 1H) 7.54 (d, J=8.5 Hz, 2H) 8.03 (d, J=8.5 Hz, 2H)

To 30 ml of a dichloromethane solution containing 9.6 g of this compound, 30 ml of trifluoroacetic acid was added. The resulting mixture was stirred at room temperature for 3 hours, and then 500 ml of ethyl acetate and 300 ml of a saturated sodium hydrogen carbonate aqueous solution were added thereto. The organic layer was washed with 300 ml of water and dried over anhydrous magnesium sulfate. The desiccating agent was removed by filtration, and the filtrate was concentrated under reduced pressure to give the title compound (6.8 g) as a pink solid.

$^1$H-NMR (CDCl$_3$) δ 6.75 (d, J=8.5 Hz, 2H) 7.90 (d, J=8.5 Hz, 2H)

(188b) [2-(5-Fluoro-8-methoxy-2,3-dihydrobenzo[1,4]dioxin-6-yl)-2-[4-(5-trifluoromethyl-[1,2,4]oxadiazol-3-yl)phenylimino]-1-methylsulfanylethylidene]carbamic acid methyl ester

[Chemical Formula 490]

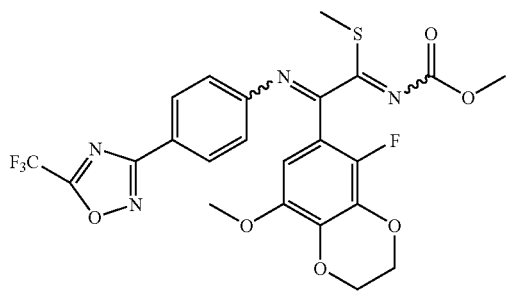

The same procedure was carried out as in Example (41d), except that 4-(5-trifluoromethyl-[1,2,4]oxadiazol-3-yl)phenylamine was used instead of the 4-(5-methyl-[1,2,4]oxadiazol-3-yl)phenylamine, to give the title compound as a light yellow compound.

$^1$H-NMR (CDCl$_3$) Main isomer:

δ 2.34 (s, 3H) 3.65 (s, 3H) 3.93 (s, 3H) 4.36 (m, 2H) 4.44 (m, 2H) 6.89 (d, J=9.2 Hz, 1H) 7.10 (d, J=8.9 Hz, 2H) 8.09 (d, J=8.9 Hz, 2H)

(188c) 4-(3-{(5-Fluoro-8-methoxy-2,3-dihydrobenzo[1,4]dioxin-6-yl)-[4-(5-trifluoromethyl-[1,2,4]oxadiazol-3-yl)phenylamino]methyl}-5-oxo-4,5-dihydro-[1,2,4]triazol-1-yl)thiazole-5-carboxylic acid ethyl ester

(188d) 4-{3-[(R) and (S)-(4-Carbamimidoylphenylamino)-(5-fluoro-8-methoxy-2,3-dihydrobenzo[1,4]dioxin-6-yl)methyl]-5-oxo-4,5-dihydro-[1,2,4]triazol-1-yl}thiazole-5-carboxylic acid

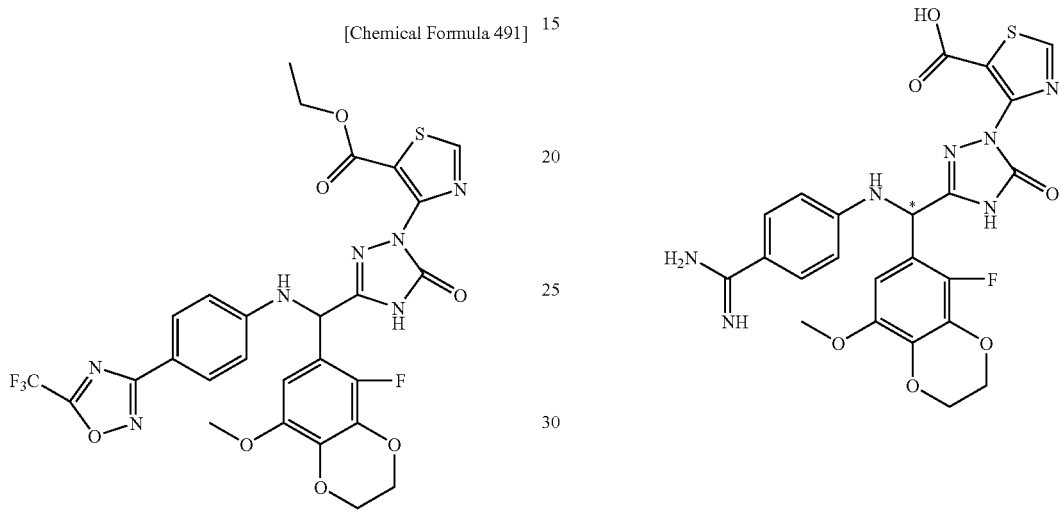

[Chemical Formula 491]

[Chemical Formula 492]

To 5 ml of a DMF solution containing 113 mg of [2-(5-fluoro-8-methoxy-2,3-dihydrobenzo[1,4]dioxin-6-yl)-2-[4-(5-trifluoromethyl-[1,2,4]oxadiazol-3-yl)phenylimino]-1-methylsulfanylethylidene]carbamic acid methyl ester, 40 mg of 4-hydrazinothiazole-5-carboxylic acid ethyl ester (Example (185c)) and 0.030 ml of triethylamine were added. The resulting mixture was stirred at 85° C. for 16 hours under a nitrogen atmosphere. The reaction mixture was concentrated under reduced pressure. The residue was dissolved in 5 ml of methanol and 0.035 ml of acetic acid, and 103 mg of sodium cyanotrihydroborate was added thereto. The mixture was stirred at room temperature for 15 hours, and then 100 ml of ethyl acetate and 50 ml of water were added thereto. The organic layer was washed with 50 ml of water and then with 50 ml of saturated brine and was dried over anhydrous magnesium sulfate. The desiccating agent was removed by filtration, and the filtrate was concentrated under reduced pressure. The residue was purified by silica gel column chromatography (methanol-ethyl acetate) to give the title compound (57 mg).

$^1$H-NMR (CD$_3$OD) δ 1.25 (t, J=7.3 Hz, 3H) 3.78 (s, 3H) 4.27 (q, J=7.3 Hz, 2H) 4.29 (s, 4H) 5.93 (s, 1H) 6.68 (d, J=5.5 Hz, 1H) 6.86 (d, J=8.9 Hz, 2H) 7.89 (d, J=8.9 Hz, 2H) 9.15 (s, 1H)

To 2 ml of a methanol solution containing 57 mg of 4-(3-{(5-fluoro-8-methoxy-2,3-dihydrobenzo[1,4]dioxin-6-yl)-[4-(5-trifluoromethyl-[1,2,4]oxadiazol-3-yl)phenylamino]methyl}-5-oxo-4,5-dihydro-[1,2,4]triazol-1-yl)thiazole-5-carboxylic acid ethyl ester, 0.2 ml of a 5 N sodium hydroxide aqueous solution was added. The resulting mixture was stirred at room temperature for 18 hours, and then 2 ml of methanol, 2 ml of acetic acid, and 38 mg of iron powder were added thereto. The mixture was stirred at 60° C. for 18 hours and then at 65° C. for 6 hours, under a nitrogen atmosphere. After cooling, the reaction mixture was purified by reverse-phase high performance liquid chromatography (acetonitrile-water, 0.1% acetic acid) to give 4-{3-[(4-carbamimidoylphenylamino)-(5-fluoro-8-methoxy-2,3-dihydrobenzo[1,4]dioxin-6-yl)methyl]-5-oxo-4,5-dihydro-[1,2,4]triazol-1-yl}thiazole-5-carboxylic acid.

This compound was optically resolved using a SUMICHIRAL OA-2500 column, and the first eluting enantiomer (2.9 mg) of the title compound was obtained as a white solid.

$^1$H-NMR (CD$_3$OD) δ 3.77 (s, 3H) 4.29 (s, 4H) 5.85 (s, 1H) 6.66 (d, J=6.4 Hz, 1H) 6.84 (d, J=8.4 Hz, 2H) 7.63 (d, J=8.4 Hz, 2H) 8.86 (s, 1H)

HPLC retention time: 29 min (Column name: SUMICHIRAL OA-2500, 30 mmφ×25 cm, Manufacturer: Sumika Chemical Analysis Service, Ltd., Mobile phase: 0.5 mM ammonium acetate-methanol solution, Elution rate: 30 ml/min)

Example 189

5-{3-[(4-Carbamimidoylphenylamino)-(5-fluoro-8-methoxychroman-6-yl)methyl]-5-oxo-4,5-dihydro-[1,2,4]triazol-1-yl}-1H-pyrazole-4-carboxylic acid (189a) [2-(5-Fluoro-8-methoxychroman-6-yl)-2-[4-(5-trifluoromethyl-[1,2,4]oxadiazol-3-yl)phenylimino]-1-methylsulfanylethylidene]carbamic acid methyl ester

[Chemical Formula 493]

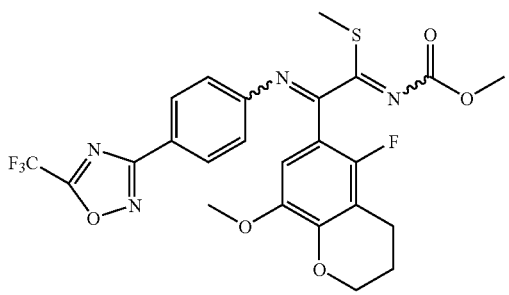

The same procedure was carried out as in Example (33d), except that 4-(5-trifluoromethyl-[1,2,4]oxadiazol-3-yl)phenylamine (Example (188a)) was used instead of the 4-(5-methyl-[1,2,4]oxadiazol-3-yl)phenylamine, to give the title compound as a light yellow solid.

$^1$H-NMR (CDCl$_3$) Main isomer:
δ 2.05 (m, 2H) 2.34 (s, 3H) 2.77 (t, J=6.8 Hz, 2H) 3.64 (s, 3H) 3.92 (s, 3H) 4.34 (t, J=5.5 Hz, 2H) 7.14 (d, J=8.6 Hz, 2H) 8.08 (d, J=8.6 Hz, 2H)

(189b) 5-(3-{(5-Fluoro-8-methoxychroman-6-yl)-[4-(5-trifluoromethyl-[1,2,4]oxadiazol-3-yl)phenylamino]methyl}-5-oxo-4,5-dihydro-[1,2,4]triazol-1-yl)-1H-pyrazole-4-carboxylic acid ethyl ester

[Chemical Formula 494]

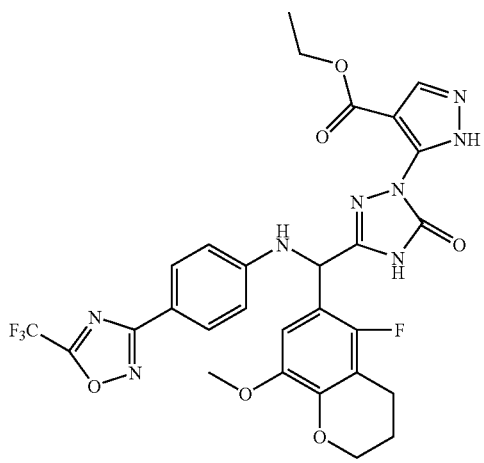

To 5 ml of a DMF solution containing 160 mg of [2-(5-fluoro-8-methoxychroman-6-yl)-2-[4-(5-trifluoromethyl-[1,2,4]oxadiazol-3-yl)phenylimino]-1-methylsulfanylethylidene]carbamic acid methyl ester, 87 mg of 3-hydrazino-1H-pyrazole-4-carboxylic acid ethyl ester bishydrochloride (Example (157b)) and 0.124 ml of triethylamine were added. The resulting mixture was stirred at 85° C. for 16 hours under a nitrogen atmosphere. The reaction mixture was concentrated. The residue was dissolved in 8 ml of methanol and 0.068 ml of acetic acid, and then 187 mg of sodium cyanotrihydroborate was added thereto. The mixture was stirred at room temperature for 15 hours, and then 100 ml of ethyl acetate and 50 ml of water were added thereto. The organic layer was washed with 50 ml of water and then with 50 ml of saturated brine and was dried over anhydrous magnesium sulfate. The desiccating agent was removed by filtration, and the filtrate was concentrated under reduced pressure. The residue was purified by NAM silica gel column chromatography (methanol-ethyl acetate) to give the title compound (39 mg).

$^1$H-NMR (CD$_3$OD) δ 1.25 (t, J=7.3 Hz, 3H) 1.97 (quint, J=6.7 Hz, 2H) 2.75 (t, J=6.7 Hz, 2H) 3.66 (s, 3H) 4.12-4.19 (m, 4H) 5.88 (s, 1H) 6.85 (d, J=8.8 Hz, 2H) 6.94 (d, J=6.3 Hz, 1H) 7.87 (d, J=8.8 Hz, 2H) 8.24 (s, 1H)

(189c) 5-{3-[(4-Carbamimidoylphenylamino)-(5-fluoro-8-methoxychroman-6-yl)methyl]-5-oxo-4,5-dihydro-[1,2,4]triazol-1-yl}-1H-pyrazole-4-carboxylic acid

[Chemical Formula 495]

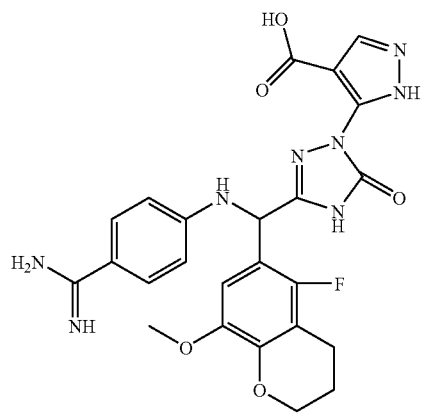

Iron powder (64 mg) was added to 6 ml of a methanol:water:acetic acid=1:1:1 mixed solvent solution containing 74 mg of 5-(3-{(5-fluoro-8-methoxychroman-6-yl)-[4-(5-trifluoromethyl-[1,2,4]oxadiazol-3-yl)phenylamino]methyl}-5-oxo-4,5-dihydro-[1,2,4]triazol-1-yl)-1H-pyrazole-4-carboxylic acid ethyl ester. The resulting mixture was stirred at 60° C. for 20 hours under a nitrogen atmosphere. After filtration, the reaction mixture was purified by reverse-phase high performance liquid chromatography (acetonitrile-water, 0.1% acetic acid) to give 22 mg of 5-{3-[(4-carbamimidoylphenylamino)-(5-fluoro-8-methoxychroman-6-yl)methyl]-5-oxo-4,5-dihydro-[1,2,4]triazol-1-yl}-1H-pyrazole-4-carboxylic acid ethyl ester.

To a solution of 22 mg of this compound in 1 ml of acetonitrile and 0.5 ml of DMF, 0.016 ml of triethylamine, 0.3 mg of 4-dimethylaminopyridine, and 0.091 ml of an acetonitrile solution of 1M di-t-butyl dicarbonate were added. The resulting mixture was stirred at room temperature for 15 hours. The solvent was removed under reduced pressure. To the residue, 1 ml of methanol and 1 ml of a 5 N sodium hydroxide aqueous solution were added. The mixture was stirred at room temperature for 8 hours, and then 2 ml of acetic acid, 1 ml of water, and 1 ml of methanol were added to this reaction mixture. The mixture was stirred at 50° C. for 15 hours. The reaction mixture was cooled and then purified by reverse-phase high performance liquid chromatography (acetonitrile-water, 0.1% acetic acid) to give the title compound (7 mg).

$^1$H-NMR (CD$_3$OD) δ 2.00 (m, 2H) 2.76 (t, J=6.6 Hz, 2H) 3.75 (s, 3H) 4.18 (t, J=5.6 Hz, 2H) 5.86 (s, 1H) 6.84 (d, J=8.6 Hz, 2H) 6.91 (d, J=6.5 Hz, 1H) 7.62 (d, J=8.6 Hz, 2H) 7.99 (s, 1H)

Example 190

4-{3-[(R) and (S)-(4-Carbamimidoylphenylamino)-(5-fluoro-8-methoxychroman-6-yl)methyl]-5-oxo-4,5-dihydro-[1,2,4]triazol-1-yl}thiazole-5-carboxylic acid (190a) 4-(3-{(5-Fluoro-8-methoxychroman-6-yl)-[4-(5-trifluoromethyl-[1,2,4]oxadiazol-3-yl)phenylamino]methyl}-5-oxo-4,5-dihydro-[1,2,4]triazol-1-yl)thiazole-5-carboxylic acid ethyl ester

[Chemical Formula 496]

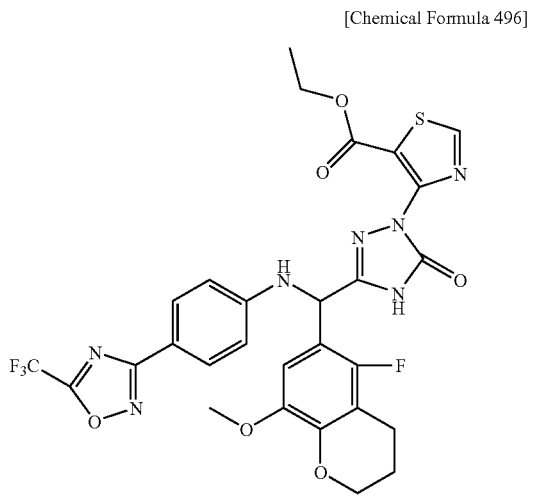

To 4 ml of a DMF solution containing 111 mg of [2-(5-fluoro-8-methoxychroman-6-yl)-2-[4-(5-trifluoromethyl-[1,2,4]oxadiazol-3-yl)phenylimino]-1-methylsulfanylethylidene]carbamic acid methyl ester (Example (189a)), 37 mg of 4-hydrazinothiazole-5-carboxylic acid ethyl ester (Example (185c)) and 0.031 ml of triethylamine were added. The resulting mixture was stirred at 85° C. for 20 hours under a nitrogen atmosphere. The reaction mixture was concentrated. The residue was dissolved in 4 ml of methanol and 0.032 ml of acetic acid, and then 83 mg of sodium cyanotrihydroborate was added thereto. The mixture was stirred at room temperature for 15 hours, and then 100 ml of ethyl acetate and 50 ml of water were added thereto. The organic layer was washed with 50 ml of water and then with 50 ml of saturated brine and was dried over anhydrous magnesium sulfate. The desiccating agent was removed by filtration, and the filtrate was concentrated under reduced pressure. The residue was purified by NAM silica gel column chromatography (methanol-ethyl acetate) to give the title compound (74 mg).

$^1$H-NMR (CD$_3$OD) 1.24 (t, J=7.3 Hz, 3H) 2.00 (tt, J=7.0, 5.6 Hz, 2H) 2.78 (t, J=7.0 Hz, 2H) 3.77 (s, 3H) 4.20 (t, J=5.6 Hz, 2H) 4.25 (q, J=7.3 Hz, 2H) 5.91 (s, 1H) 6.85 (d, J=9.0 Hz, 2H) 6.94 (d, J=7.3 Hz, 1H) 7.87 (d, J=9.0 Hz, 2H) 9.15 (s, 1H)

(190b) 4-{3-[(4-Carbamimidoylphenylamino)-(5-fluoro-8-methoxychroman-6-yl)methyl]-5-oxo-4,5-dihydro-[1,2,4]triazol-1-yl}thiazole-5-carboxylic acid trifluoroacetate

[Chemical Formula 497]

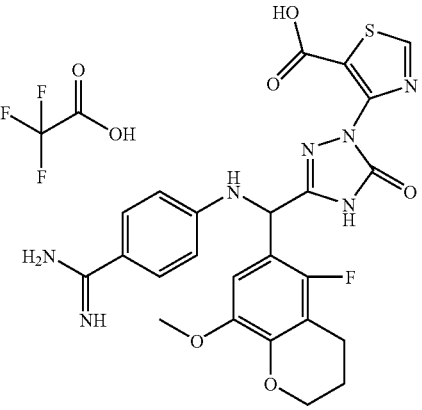

To 2 ml of a methanol solution containing 74 mg of 4-(3-{(5-fluoro-8-methoxychroman-6-yl)-[4-(5-trifluoromethyl-[1,2,4]oxadiazol-3-yl)phenylamino]methyl}-5-oxo-4,5-dihydro-[1,2,4]triazol-1-yl)thiazole-5-carboxylic acid ethyl ester, 0.5 ml of a 5 N sodium hydroxide aqueous solution was added. The resulting mixture was stirred at room temperature for 18 hours, and then 2 ml of acetic acid, 1.5 ml of water, and 74 mg of iron powder were added thereto. The mixture was stirred at 60° C. for 15 hours under a nitrogen atmosphere. The reaction mixture was filtered and purified by reverse-phase high performance liquid chromatography (acetonitrile-water, 0.1% trifluoroacetic acid) to give the title compound (34 mg).

$^1$H-NMR (CD$_3$OD) δ 2.00 (tt, J=7.0, 5.6 Hz, 2H) 2.76 (t, J=7.0 Hz, 2H) 3.76 (s, 3H) 4.20 (t, J=5.6 Hz, 2H) 5.94 (s, 1H) 6.86 (d, J=8.9 Hz, 2H) 6.88 (d, J=7.5 Hz, 1H) 7.64 (d, J=9.0 Hz, 2H) 8.29 (br.s, 1H) 8.78 (br.s, 1H) 9.14 (s, 1H)

(190c) 4-{3-[(R) and (S)-(4-Carbamimidoylphenylamino)-(5-fluoro-8-methoxychroman-6-yl)methyl]-5-oxo-4,5-dihydro-[1,2,4]triazol-1-yl}thiazole-5-carboxylic acid

[Chemical Formula 498]

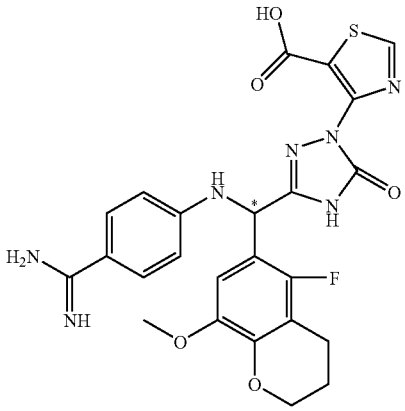

4-{3-[(4-Carbamimidoylphenylamino)-(5-fluoro-8-methoxychroman-6-yl)methyl]-5-oxo-4,5-dihydro-[1,2,4]triazol- 1-yl}thiazole-5-carboxylic acid trifluoroacetate (33 mg) was optically resolved using a SUMICHIRAL OA-2500 column, and the first eluting enantiomer (5.0 mg) of the title compound was obtained as a white solid.

$^1$H-NMR (CD$_3$OD) δ 2.00 (tt, J=7.0, 5.3 Hz, 2H) 2.76 (t, J=7.0 Hz, 2H) 3.76 (s, 3H) 4.20 (t, J=5.3 Hz, 2H) 5.87 (s, 1H) 6.84 (d, J=8.9 Hz, 2H) 6.91 (d, J=7.0 Hz, 1H) 7.64 (d, J=8.9 Hz, 2H) 8.87 (s, 1H)

HPLC retention time: 26 min (Column name: SUMICHIRAL OA-2500, 30 mmφ×25 cm, Manufacturer: Sumika Chemical Analysis Service, Ltd., Mobile phase: 0.5 mM ammonium acetate-methanol solution, Elution rate: 30 ml/min)

Example 191

5-{3-[(R) or (S)-(4-Carbamimidoylphenylamino)-(5-fluoro-8-methoxy-2,3-dihydrobenzo[1,4]dioxin-6-yl) methyl]-5-oxo-4,5-dihydro-[1,2,4]triazol-1-yl}-3H-imidazole-4-carboxylic acid trifluoroacetate (191a) 3-Benzyl-5-{3-[(4-cyanophenylamino)-(5-fluoro-8-methoxy-2,3-dihydrobenzo[1,4]dioxin-6-yl) methyl]-5-oxo-4,5-dihydro-[1,2,4]triazol-1-yl}-3H-imidazole-4-carboxylic acid ethyl ester

[Chemical Formula 499]

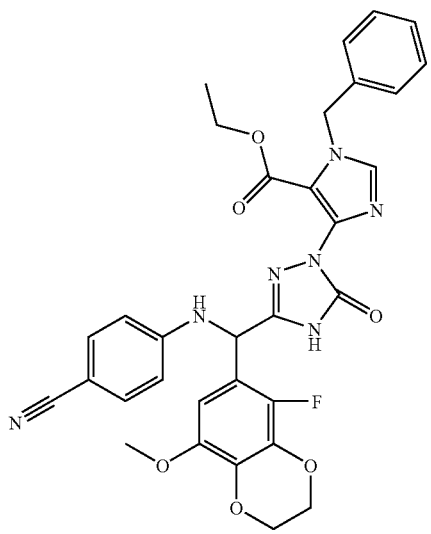

The same procedure was carried out as in Example (168b), except that 3-benzyl-5-hydrazino-3H-imidazole-4-carboxylic acid ethyl ester (Example (187b)) was used instead of the 3-hydrazinothiophene-2-carboxylic acid methyl ester, to give the title compound as a light yellow solid.

$^1$H-NMR (CDCl$_3$) δ 1.05 (t, J=7.2 Hz, 3H) 3.72 (s, 3H) 4.14 (m, 2H) 4.35 (s, 4H) 5.50 (s, 2H) 5.63 (d, J=5.3 Hz, 1H) 5.75 (d, J=5.3 Hz, 1H) 6.45 (d, J=6.9 Hz, 1H) 6.59 (d, J=8.8 Hz, 2H) 7.23-7.25 (m, 3H) 7.37 (d, J=7.8 Hz, 2H) 7.39 (d, J=8.8 Hz, 2H) 7.54 (s, 1H)

(191b) 3-Benzyl-5-{3-[(R) and (S)-(4-cyanophenylamino)-(5-fluoro-8-methoxy-2,3-dihydrobenzo[1,4]dioxin-6-yl)methyl]-5-oxo-4,5-dihydro-[1,2,4]triazol-1-yl}-3H-imidazole-4-carboxylic acid ethyl ester

[Chemical Formula 500]

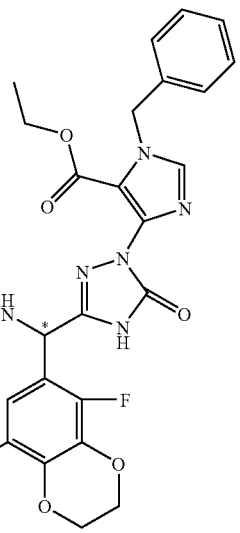

3-Benzyl-5-{3-[(4-cyanophenylamino)-(5-fluoro-8-methoxy-2,3-dihydrobenzo[1,4]dioxin-6-yl)methyl]-5-oxo-4,5-dihydro-[1,2,4]triazol-1-yl}-3H-imidazole-4-carboxylic acid ethyl ester (306 mg) was optically resolved using a CHIRALPAK AD-H column, and the second eluting enantiomer (97 mg) of the title compound was obtained as a light yellow solid.

$^1$H-NMR (CDCl$_3$) δ 0.98 (t, J=7.2 Hz, 3H) 3.74 (s, 3H) 4.12 (m, 2H) 4.30 (m, 4H) 5.48 (d, J=15.3 Hz, 1H) 5.53 (d, J=15.3 Hz, 1H) 5.73 (s, 1H) 6.47 (d, J=6.9 Hz, 1H) 6.55 (d, J=8.8 Hz, 2H) 7.23 (m, 2H) 7.31-7.39 (m, 3H) 7.39 (d, J=8.8 Hz, 2H) 7.54 (s, 1H)

HPLC retention time: 35 min (Column name: CHIRALPAK AD-H, 20 mmφ×25 cm, Manufacturer: Daicel Chemical Industries, Ltd., Mobile phase: ethyl acetate/heptane=6/4, Elution rate: 10 ml/min)

(191c) 3-Benzyl-5-(3-{(R) or (S)-(5-fluoro-8-methoxy-2,3-dihydrobenzo[1,4]dioxin-6-yl)-[4-(N-hydroxycarbamimidoyl)phenylamino]methyl}-5-oxo-4,5-dihydro-[1,2,4]triazol-1-yl}-3H-imidazole-4-carboxylic acid

[Chemical Formula 501]

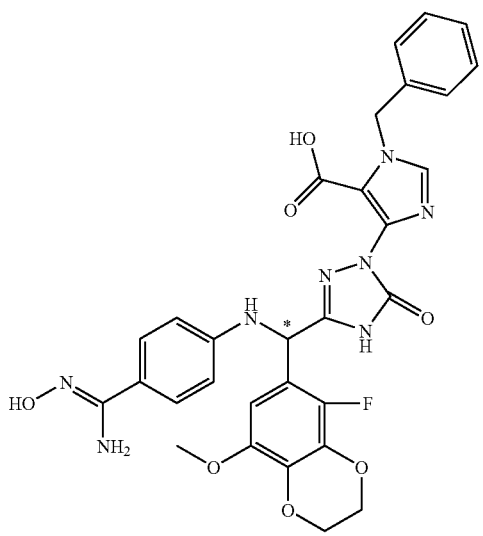

The same procedure was carried out as in Example (187d), except that 3-benzyl-5-{3-[(R) or (S)-(4-cyanophenylamino)-(5-fluoro-8-methoxy-2,3-dihydrobenzo[1,4]dioxin-6-yl)methyl]-5-oxo-4,5-dihydro-[1,2,4]triazol-1-yl}-3H-imidazole-4-carboxylic acid ethyl ester (Example (191b)) was used instead of the 3-benzyl-5-{(R) or (S)-3-[(4-cyanophenylamino)-(2-fluoro-4,5-dimethoxyphenyl)methyl]-5-oxo-4,5-dihydro-[1,2,4]triazol-1-yl}-3H-imidazole-4-carboxylic acid ethyl ester in Example (187d), to give the title compound.

$^1$H-NMR (CD$_3$OD) δ 3.75 (s, 3H) 4.28 (s, 4H) 5.65 (d, J=14.5 Hz, 1H) 5.69 (d, J=14.5 Hz, 1H) 5.84 (s, 1H) 6.63 (d, J=5.7 Hz, 1H) 6.79 (d, J=8.8 Hz, 2H) 7.22-7.30 (m, 5H) 7.45 (d, J=8.8 Hz, 2H) 7.75 (s, 1H)

(191d) 5-{3-[(R) or (S)-(4-Carbamimidoylphenylamino)-(5-fluoro-8-methoxy-2,3-dihydrobenzo[1,4]dioxin-6-yl)methyl]-5-oxo-4,5-dihydro-[1,2,4]triazol-1-yl}-3H-imidazole-4-carboxylic acid trifluoroacetate

[Chemical Formula 502]

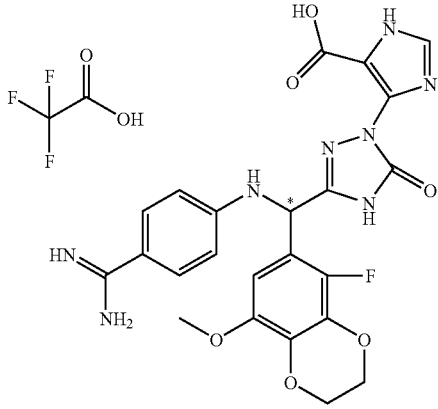

The same procedure was carried out as in Example (187e), except that 3-benzyl-5-(3-{(R) or (S)-(5-fluoro-8-methoxy-2,3-dihydrobenzo[1,4]dioxin-6-yl)-[4-(N-hydroxycarbamimidoyl)phenylamino]methyl}-5-oxo-4,5-dihydro-[1,2,4]triazol-1-yl)-3H-imidazole-4-carboxylic acid (Example (191c)) and 0.1% trifluoroacetic acid were used instead of respectively 3-benzyl-5-(3-{(R) or (S)-(2-fluoro-4,5-dimethoxyphenyl)-[(4-(N-hydroxycarbamimidoyl)phenylamino]-methyl}-5-oxo-4,5-dihydro-[1,2,4]triazol-1-yl)-3H-imidazole-4-carboxylic acid and 0.1% acetic acid, to give the title compound as a brown solid.

$^1$H-NMR (CD$_3$OD) δ 3.76 (s, 3H) 4.30 (s, 4H) 5.88 (s, 1H) 6.65 (d, J=6.0 Hz, 1H) 6.84 (d, J=9.1 Hz, 2H) 7.60 (s, 1H) 7.62 (d, J=9.1 Hz, 2H)

Example 192

5-{3-[(4-Carbamimidoylphenylamino)-(6-fluoro-9-methoxy-3,4-dihydro-2H-benzo[b][1,4]dioxepin-7-yl)methyl]-5-oxo-4,5-dihydro-[1,2,4]triazol-1-yl}-1H-pyrazole-4-carboxylic acid ethyl ester acetate

(192a) 5-{3-{(6-Fluoro-9-methoxy-3,4-dihydro-2H-benzo[b][1,4]dioxepin-7-yl)-[4-(5-methyl[1,2,4]oxadiazol-3-yl)phenylamino]methyl}-5-oxo-4,5-dihydro-[1,2,4]triazol-1-yl)-1H-pyrazole-4-carboxylic acid ethyl ester

[Chemical Formula 503]

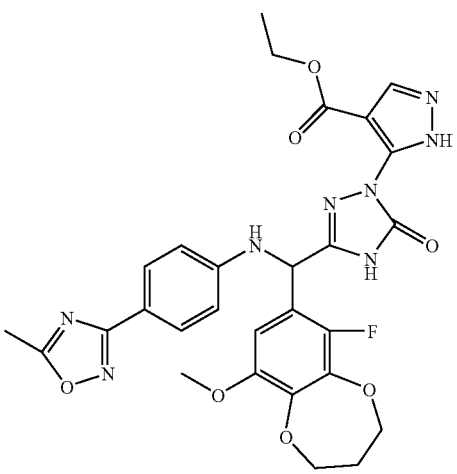

The same procedure was carried out as in Examples (1e) to (1f), except that {2-(9-methoxy-3,4-dihydro-2H-benzo[b][1,4]dioxepin-7-yl)-2-[4-(5-methyl-[1,2,4]oxadiazol-3-yl)phenylimino]-1-methylsulfanylethylidene}carbamic acid methyl ester (Example (30c)) and 3-hydrazino-1H-pyrazole-4-carboxylic acid ethyl ester bishydrochloride (Example (157b)) were used instead of respectively the [2-(2-fluoro-4,5-dimethoxyphenyl)-2-[4-(5-methyl-[1,2,4]oxadiazol-3-yl)phenylimino]-1-methylsulfanylethylidene]carbamic acid methyl ester and 2-hydrazinobenzoic acid hydrochloride in Example (1e), to give the title compound.

Mass spectrum (ESI) m/z: 629 (M+Na)$^+$ (192b) 5-{3-[(4-Carbamimidoylphenylamino)-(6-fluoro-9-methoxy-3,4-dihydro-2H-benzo[b][1,4]dioxepin-7-yl)methyl]-5-oxo-4,5-dihydro-[1,2,4]triazol-1-yl}-1H-pyrazole-4-carboxylic acid ethyl ester acetate

[Chemical Formula 504]

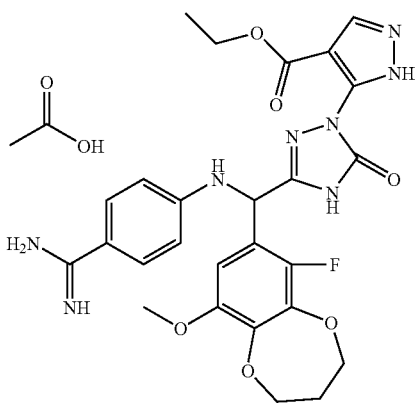

The same procedure was carried out as in Example (1g), except that 5-(3-{(6-fluoro-9-methoxy-3,4-dihydro-2H-benzo[b][1,4]dioxepin-7-yl)-[4-(5-methyl[1,2,4]oxadiazol-3-yl)phenylamino]methyl}-5-oxo-4,5-dihydro-[1,2,4]triazol-1-yl)-1H-pyrazole-4-carboxylic acid ethyl ester and 0.1% acetic acid were used instead of respectively 2-(3-{(2-fluoro-4,5-dimethoxyphenyl)-[4-(5-methyl-[1,2,4]oxadiazol-3-yl)phenylamino]methyl}-5-oxo-4,5-dihydro-[1,2,4]triazol-1-yl)benzoic acid and 0.1% trifluoroacetic acid, to give the title compound as a light yellow solid.

$^1$H-NMR (CD$_3$OD) δ 1.20 (t, J=7.1 Hz, 3H) 1.97 (s, 3H) 2.22 (m, 2H) 3.78 (s, 3H) 4.12-4.30 (m, 6H) 5.95 (s, 1H) 6.80 (d, J=6.2 Hz, 1H) 6.87 (d, J=9.0 Hz, 2H) 7.65 (d, J=9.0 Hz, 2H) 8.26 (s, 1H)

Example 193

(R) and (S)-4-{3-[(4-Carbamimidoylphenylamino)-(3,4-dimethoxyphenyl)methyl]-5-oxo-4,5-dihydro-[1,2,4]triazol-1-yl}-thiazole-5-carboxylic acid (193a) {2-(3,4-dimethoxyphenyl)-1-methylsulfanyl-2-[4-(5-trifluoromethyl-[1,2,4]oxadiazol-3-yl)phenylimino]ethylidene}carbamic acid methyl ester

[Chemical Formula 505]

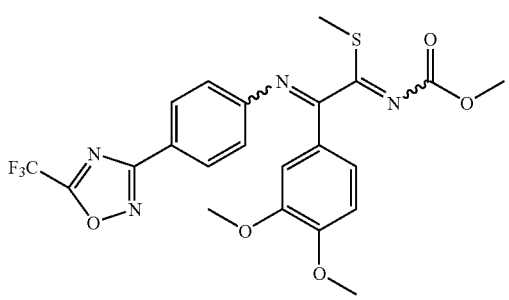

The same procedure was carried out as in Example (1a) to (1d), except that 4-(5-trifluoromethyl-[1,2,4]oxadiazol-3-yl)phenylamine (Example (188a)) and 3,4-dimethoxybenzaldehyde were used instead of respectively 4-(5-methyl-[1,2,4]oxadiazol-3-yl)phenylamine and 2-fluoro-4,5-dimethoxybenzaldehyde in Example (1a), to give the title compound as a light yellow solid.

$^1$H-NMR (CDCl$_3$) δ 2.34 (s, 3H) 3.65 (s, 3H) 3.96 (s, 3H) 3.97 (s, 3H) 6.90 (d, J=8.6 Hz, 1H) 7.23 (d, J=8.3 Hz, 2H) 7.30 (dd, J=8.6, 2.3 Hz, 1H) 7.61 (d, J=2.3 Hz, 1H) 8.09 (d, J=8.3 Hz, 2H)

(193b) 4-(3-{(3,4-Dimethoxyphenyl)-[4-(5-trifluoromethyl-[1,2,4]oxadiazol-3-yl)phenylamino]methyl}-5-oxo-4,5-dihydro-[1,2,4]triazol-1-yl)thiazole-5-carboxylic acid ethyl ester

[Chemical Formula 506]

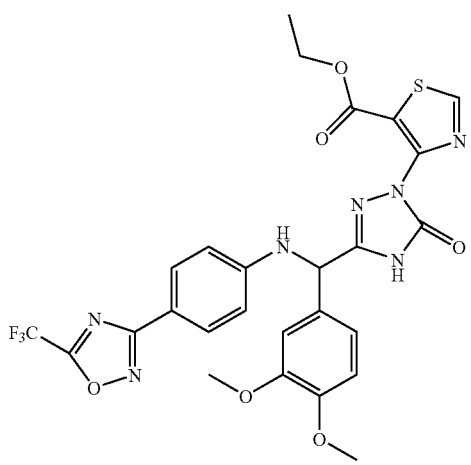

The same procedure was carried out as in Example (185d), except that {2-(3,4-dimethoxyphenyl)-1-methylsulfanyl-2-[4-(5-trifluoromethyl-[1,2,4]oxadiazol-3-yl)phenylimino]ethylidene}carbamic acid methyl ester was used instead of the {2-(5-ethoxy-6-methoxypyridin-3-yl)-2-[4-(5-methyl-[1,2,4]oxadiazol-3-yl)phenylimino]-1-methylsulfanylethylidene}carbamic acid methyl ester, to give the title compound.

$^1$H-NMR (CD$_3$OD) δ 1.19 (t, J=7.3 Hz, 3H) 3.84 (s, 3H) 3.86 (s, 3H) 4.44 (q, J=7.3 Hz, 2H) 5.62 (s, 1H) 6.87 (d, J=8.7 Hz, 2H) 6.98 (d, J=8.2 Hz, 1H) 7.11 (dd, J=8.2, 1.8 Hz, 1H) 7.15 (d, J=1.8 Hz, 1H) 7.87 (d, J=8.7 Hz, 2H) 9.16 (s, 1H)

(193c) 4-{3-[(4-Carbamimidoylphenylamino)-(3,4-dimethoxyphenyl)methyl]-5-oxo-4,5-dihydro-[1,2,4]triazol-1-yl}thiazole-5-carboxylic acid trifluoroacetate

[Chemical Formula 507]

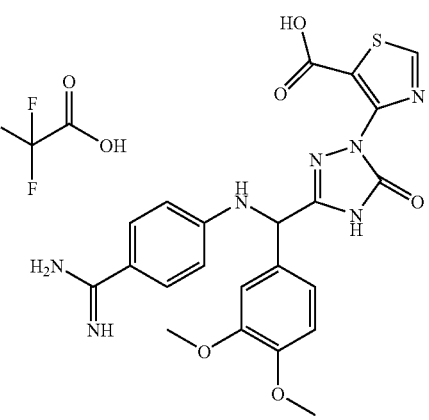

The same procedure was carried out as in Example (190b), except that 4-(3-{(3,4-dimethoxyphenyl)-[4-(5-trifluoromethyl-[1,2,4]oxadiazol-3-yl)phenylamino]methyl}-5-oxo-4,5-dihydro-[1,2,4]triazol-1-yl)thiazole-5-carboxylic acid ethyl ester was used instead of the 4-(3-{(5-fluoro-8-methoxychroman-6-yl)-[4-(5-trifluoromethyl-[1,2,4]oxadiazol-3-yl)phenylamino]methyl}-5-oxo-4,5-dihydro-[1,2,4]triazol-1-yl)thiazole-5-carboxylic acid ethyl ester, to give the title compound.

$^1$H-NMR (CD$_3$OD) δ 3.82 (s, 3H) 3.85 (s, 3H) 5.60 (s, 1H) 6.86 (d, J=8.9 Hz, 2H) 6.97 (d, J=8.3 Hz, 1H) 7.09 (dd, J=8.3, 1.8 Hz, 1H) 7.15 (d, J=1.8 Hz, 1H) 7.61 (d, J=8.9 Hz, 2H) 8.90 (s, 1H)

(193d) (R) and (S)-4-{3-[(4-Carbamimidoylphenylamino)-(3,4-dimethoxyphenyl)methyl]-5-oxo-4,5-dihydro-[1,2,4]triazol-1-yl}thiazole-5-carboxylic acid

[Chemical Formula 508]

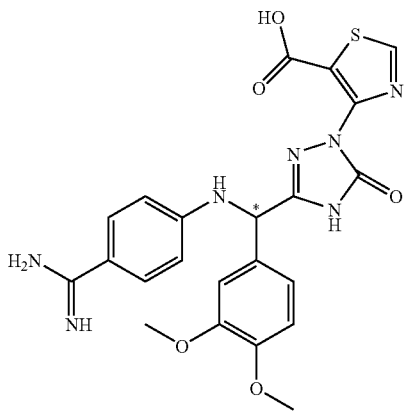

4-{3-[(4-Carbamimidoylphenylamino)-(3,4-dimethoxyphenyl)methyl]-5-oxo-4,5-dihydro-[1,2,4]triazol-1-yl}thiazole-5-carboxylic acid (15 mg) was optically resolved using a SUMICHIRAL OA-2500 column, and the first eluting enantiomer (3.1 mg) of the title compound was obtained as a white solid.

$^1$H-NMR (CD$_3$OD) δ 3.82 (s, 3H) 3.85 (s, 3H) 5.57 (s, 1H) 6.86 (d, J=8.9 Hz, 2H) 6.97 (d, J=8.3 Hz, 1H) 7.09 (dd, J=8.3, 1.8 Hz, 1H) 7.15 (d, J=1.8 Hz, 1H) 7.62 (d, J=8.9 Hz, 2H) 8.88 (s, 1H)

HPLC retention time: 23 min (Column name: SUMICHIRAL OA-2500, 30 mmφ×25 cm, Manufacturer: Sumika Chemical Analysis Service, Ltd., Mobile phase: 0.5 mM ammonium acetate-methanol solution, Elution rate: 30 ml/min)

Example 194

(R) and (S)-5-{3-[(4-Carbamimidoylphenylamino)-(2-fluoro-4,5-dimethoxyphenyl)methyl]-5-oxo-4,5-dihydro-[1,2,4]triazol-1-yl}-1H-pyrazole-4-carboxylic acid acetate

[Chemical Formula 509]

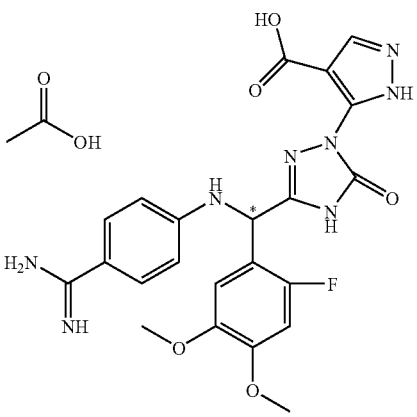

5-{3-[(4-Carbamimidoylphenylamino)-(2-fluoro-4,5-dimethoxyphenyl)methyl]-5-oxo-4,5-dihydro-[1,2,4]triazol-1-yl}-1H-pyrazole-4-carboxylic acid acetate (Example (157e), 0.8 mg) was optically resolved using a SUMICHIRAL OA-2500 column, and the first eluting enantiomer (0.3 mg) of the title compound was obtained.

$^1$H-NMR (CD$_3$OD) δ 1.98 (s, 3H) 3.78 (s, 3H) 3.82 (s, 3H) 5.92 (s, 1H) 6.84 (d, J=10.6 Hz, 1H) 6.86 (d, J=9.1 Hz, 2H) 7.07 (d, J=6.8 Hz, 1H) 7.63 (d, J=9.1 Hz, 2H) 7.98 (s, 1H)

HPLC retention time: 20 min (Column name: SUMICHIRAL OA-2500, 30 mmφ×25 cm, Manufacturer: Sumika Chemical Analysis Service, Ltd., Mobile phase: 0.5 mM ammonium acetate-methanol solution, Elution rate: 15 ml/min)

Example 195

3-(3-{(R) and (S)-(4-Carbamimidoylphenylamino)-[3-methoxy-4-(2-methoxyethoxy)phenyl]methyl}-5-oxo-4,5-dihydro-[1,2,4]triazol-1-yl)thiophene-2-carboxylic acid (195a) {2-[3-Methoxy-4-(2-methoxyethoxy)phenyl]-2-[4-(5-methyl-[1,2,4]oxadiazol-3-yl)phenylimino]-1-methylsulfanylethylidene}carbamic acid methyl ester

[Chemical Formula 510]

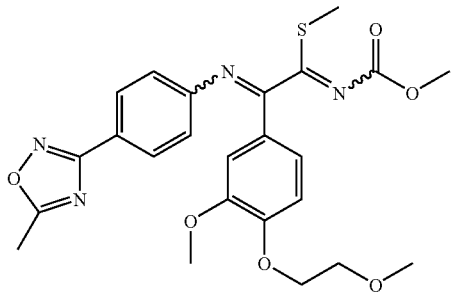

The same procedure was carried out as in Example (18e), except that 1-bromo-2-methoxyethane was used instead of the iodoethane, to give the title compound.

(195b) 3-(3-{(R) and (S)-(4-Carbamimidoylphenylamino)-[3-methoxy-4-(2-methoxyethoxy)phenyl]methyl}-5-oxo-4,5-dihydro-[1,2,4]triazol-1-yl)thiophene-2-carboxylic acid

[Chemical Formula 511]

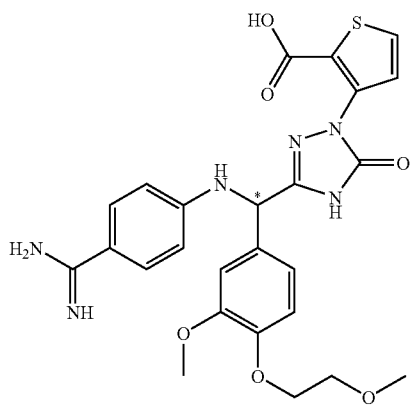

The same procedure was carried out as in Example (169b), except that {2-[3-methoxy-4-(2-methoxyethoxy)phenyl]-2-[4-(5-methyl-[1,2,4]oxadiazol-3-yl)phenylimino]-1-methylsulfanylethylidene}carbamic acid methyl ester was used instead of {2-(5,6-dimethoxypyridin-3-yl)-2-[4-(5-methyl-[1,2,4]oxadiazol-3-yl)phenylimino]-1-methylsulfanylethylidene}carbamic acid methyl ester, to give the first eluting enantiomer of the title compound.

$^1$H-NMR (CD$_3$OD) δ 3.41 (s, 3H) 3.72-3.74 (m, 2H) 3.84 (s, 3H) 4.11-4.13 (m, 2H) 5.56 (s, 1H) 6.86 (d, J=8.8 Hz, 2H) 6.98 (d, J=8.4 Hz, 1H) 7.06 (dd, J=2.0, 8.4 Hz, 1H) 7.07 (d, J=5.6 Hz, 1H) 7.16 (d, J=2.0 Hz, 1H) 7.43 (d, J=5.6 Hz, 1H) 7.60 (d, J=8.8 Hz, 2H)

HPLC retention time: 12 min (Column name: SUMICHIRAL OA-2500, 30 mmφ×25 cm, Manufacturer: Sumika Chemical Analysis Service, Ltd., Mobile phase: 0.05 M ammonium acetate-methanol solution, Elution rate: 30 ml/min)

Example 196

5-{3-[(4-Carbamimidoylphenylamino)-(6-fluoro-9-methoxy-3,4-dihydro-2H-benzo[b][1,4]dioxepin-7-yl)methyl]-5-oxo-4,5-dihydro-[1,2,4]triazol-1-yl}-1H-pyrazole-4-carboxylic acid acetate

[Chemical Formula 512]

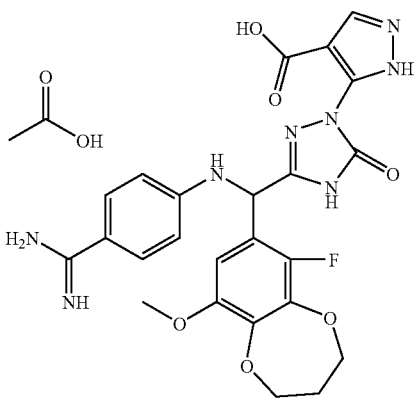

The same procedure was carried out as in Example (157e), except that 5-{3-[(4-carbamimidoylphenylamino)-(6-fluoro-9-methoxy-3,4-dihydro-2H-benzo[b][1,4]dioxepin-7-yl)methyl]-5-oxo-4,5-dihydro-[1,2,4]triazol-1-yl}-1H-pyrazole-4-carboxylic acid ethyl ester acetate (Example (192b)) was used instead of 5-{3-[(4-carbamimidoylphenylamino)-(2-fluoro-4,5-dimethoxyphenyl)methyl]-5-oxo-4,5-dihydro-[1,2,4]triazol-1-yl}-1H-pyrazole-4-carboxylic acid ethyl ester acetate, to give the title compound.

$^1$H-NMR (CD$_3$OD) δ 1.95 (s, 3H) 2.21 (m, 2H) 3.75 (s, 3H) 4.08-4.30 (m, 4H) 5.90 (s, 1H) 6.79 (d, J=6.2 Hz, 1H) 6.84 (d, J=8.6 Hz, 2H) 7.62 (d, J=8.6 Hz, 2H) 8.01 (s, 1H)

Example 197

5-{3-[(4-Carbamimidoylphenylamino)-(5-fluoro-8-methoxy-2,3-dihydrobenzo[1,4]dioxin-6-yl)methyl]-5-oxo-4,5-dihydro-[1,2,4]triazol-1-yl}-1H-pyrazole-4-carboxylic acid ethyl ester trifluoroacetate (197a) 5-{3-[(4-Cyanophenylamino)-(5-fluoro-8-methoxy-2,3-dihydrobenzo[1,4]dioxin-6-yl)methyl]-5-oxo-4,5-dihydro-[1,2,4]triazol-1-yl}-1H-pyrazole-4-carboxylic acid ethyl ester

[Chemical Formula 513]

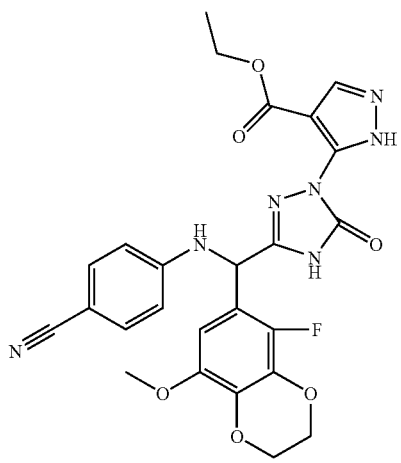

The same procedure was carried out as in Example (168b), except that 3-hydrazino-1H-pyrazole-4-carboxylic acid ethyl ester bishydrochloride (Example (157b)) was used instead of 3-hydrazinothiophene-2-carboxylic acid methyl ester, to give the title compound as a light yellow solid.

$^1$H-NMR (CDCl$_3$) δ 1.20 (t, J=7.2 Hz, 3H) 3.82 (s, 3H) 4.15 (m, 2H) 4.21 (s, 4H) 5.80 (s, 1H) 6.50 (br.s, 1H) 6.62 (d, J=8.5 Hz, 2H) 7.35 (d, J=8.5 Hz, 2H) 8.04 (s, 1H)

(197b) 5-(3-{(5-Fluoro-8-methoxy-2,3-dihydrobenzo[1,4]dioxin-6-yl)-4-(N-hydroxycarbamimidoyl)phenylamino]methyl}-5-oxo-4,5-dihydro-[1,2,4]triazol-1-yl)-1H-pyrazole-4-carboxylic acid ethyl ester

[Chemical Formula 514]

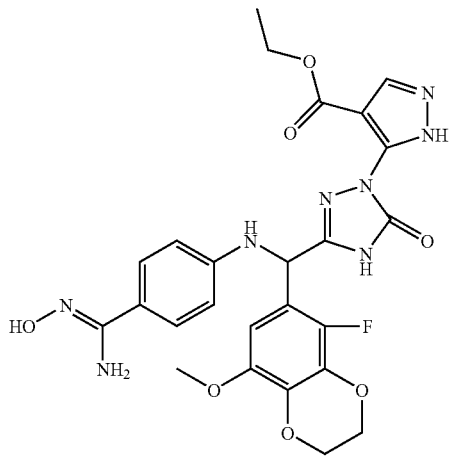

The same procedure was carried out as in Example (176c), except that 5-{3-[(4-cyanophenylamino)-(5-fluoro-8-methoxy-2,3-dihydrobenzo[1,4]dioxin-6-yl)methyl]-5-oxo-4,5-dihydro-[1,2,4]triazol-1-yl}-1H-pyrazole-4-carboxylic acid ethyl ester was used instead of 2-{3-[(4-cyanophenylamino)-(6-fluoro-9-methoxy-3,4-dihydro-2H-benzo[b][1,4]dioxepin-7-yl)methyl]-5-oxo-4,5-dihydro-[1,2,4]triazol-1-yl}nicotinic acid, to give the title compound as a brown solid.
$^1$H-NMR (CD$_3$OD) δ 1.17 (t, J=7.3 Hz, 3H) 3.77 (s, 3H) 4.15 (m, 2H) 4.19 (m, 4H) 5.83 (s, 1H) 6.68 (d, J=6.2 Hz, 1H) 6.75 (d, J=8.8 Hz, 2H) 7.43 (d, J=8.8 Hz, 2H) 8.25 (s, 1H)

(197c) 5-{3-[(4-Carbamimidoylphenylamino)-(5-fluoro-8-methoxy-2,3-dihydrobenzo[1,4]dioxin-6-yl)methyl]-5-oxo-4,5-dihydro-[1,2,4]triazol-1-yl}-1H-pyrazole-4-carboxylic acid ethyl ester trifluoroacetate

[Chemical Formula 515]

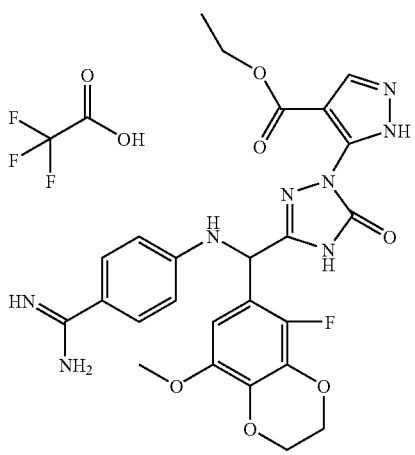

The same procedure was carried out as in Example (1g), except that 15 mg of 5-(3-{(5-fluoro-8-methoxy-2,3-dihydrobenzo[[1,4]dioxin-6-yl)-4-(N-hydroxycarbamimidoyl)phenylamino]methyl}-5-oxo-4,5-dihydro-[1,2,4]triazol-1-yl)-1H-pyrazole-4-carboxylic acid ethyl ester and 0.1% acetic acid were used instead of respectively 2-(3-{(2-fluoro-4,5-dimethoxyphenyl)-[4-(5-methyl-[1,2,4]oxadiazol-3-yl)phenylamino]methyl}-5-oxo-4,5-dihydro-[1,2,4]triazol-1-yl)benzoic acid and 0.1% trifluoroacetic acid, to give the title compound as a light yellow solid.
$^1$H-NMR (d$_6$-DMSO) δ 1.05 (t, J=7.1 Hz, 3H) 3.64 (s, 3H) 4.00 (q, J=7.1 Hz, 2H) 4.21-4.80 (m, 4H) 5.62 (s, 1H) 6.77 (d, J=6.2 Hz, 1H) 6.79 (d, J=8.7 Hz, 2H) 7.44 (br.s, 1H) 7.56 (d, J=8.7 Hz, 2H)

Example 198

(R) or (S)-5-(3-{(4-Carbamimidoylphenylamino)-[2-fluoro-3-(3-hydroxypropoxy)-5-methoxyphenyl]methyl}-5-oxo-4,5-dihydro-[1,2,4]triazol-1-yl)-1H-pyrazole-4-carboxylic acid acetate

(198a) 3-(N'-t-Butoxycarbonylhydrazino)pyrazole-1,4-dicarboxylic acid 4-benzyl ester 1-t-butyl ester

[Chemical Formula 516]

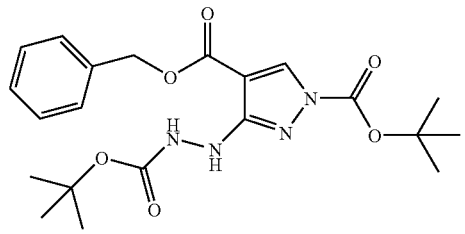

The same procedure was carried out as in Example (157a), except that 3-amino-1H-pyrazole-4-carboxylic acid benzyl ester was used instead of 3-amino-1H-pyrazole-4-carboxylic acid ethyl ester, to give the title compound as a white solid.
$^1$H-NMR (CDCl$_3$) δ 1.60 (s, 18H) 5.29 (s, 2H) 6.56 (br.s, 1H) 7.21 (br.s, 1H) 7.43-7.42 (m, 5H) 8.32 (s, 1H)

(198b) 5-Hydrazino-1H-pyrazole-4-carboxylic acid benzyl ester bishydrochloride

[Chemical Formula 517]

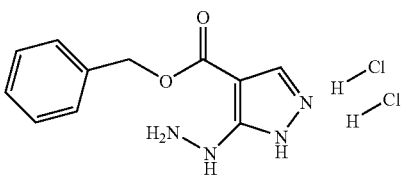

The same procedure was carried out as in Example (157b), except that 3-(N'-t-butoxycarbonylhydrazino)pyrazole-1,4-dicarboxylic acid 4-benzyl ester 1-t-butyl ester was used instead of the 3-(N'-t-butoxycarbonylhydrazino)-1H-pyrazole-4-carboxylic acid ethyl ester, to give the title compound as a white solid.
$^1$H-NMR (CD$_3$OD) δ 5.29 (s, 2H) 7.30-7.44 (m, 5H) 8.08 (s, 1H)

403

(198c) 5-{3-[{3-[3-(t-Butyldimethylsilanyloxy)propoxy]-2-fluoro-5-methoxyphenyl}-(4-cyanophenylamino)methyl]-5-oxo-4,5-dihydro-[1,2,4]triazol-1-yl}-1H-pyrazole-4-carboxylic acid benzyl ester

404

(198d) 3-{3-[{3-[3-(t-Butyldimethylsilanyloxy)propoxy]-2-fluoro-5-methoxyphenyl}-(4-cyanophenylamino)methyl]-5-oxo-4,5-dihydro-[1,2,4]triazol-1-yl}-1-trityl-1H-pyrazole-4-carboxylic acid benzyl ester

[Chemical Formula 518]

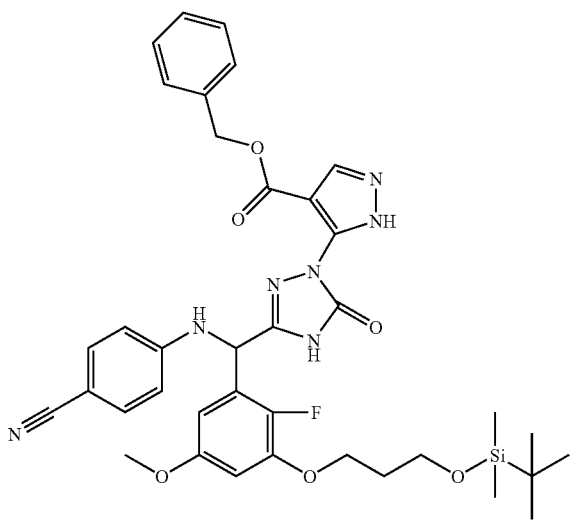

[Chemical Formula 519]

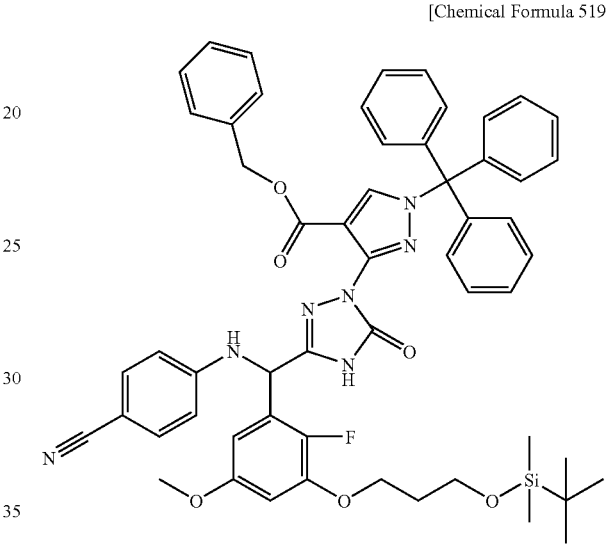

The same procedure was carried out as in Example (177b), except that (2-{3-[3-(t-butyldimethylsilanyloxy)propoxy]-2-fluoro-5-methoxyphenyl}-2-(4-cyanophenylimino)-1-methylsulfanylethylidene)carbamic acid methyl ester (Example (163c)) and 5-hydrazino-1H-pyrazole-4-carboxylic acid benzyl ester bishydrochloride were used instead of respectively (2-{3-[3-(t-butyldimethylsilanyloxy)propoxy]-2-fluoro-5-methoxyphenyl}-2-[4-(5-methyl-[1,2,4]oxadiazol-3-yl)phenylimino]-1-methylsulfanylethylidene)carbamic acid methyl ester and 3-hydrazino-1H-pyrazole-4-carboxylic acid ethyl ester bishydrochloride, to give the title compound as a light yellow solid.

$^1$H-NMR (CD$_3$OD) δ 0.06 (s, 6H) 0.84 (s, 9H) 1.94 (quint, J=6.5 Hz, 2H) 3.68 (s, 3H) 3.80 (t, J=6.5 Hz, 2H) 4.08 (t, J=6.5 Hz, 2H) 5.12 (d, J=12.8 Hz, 1H) 5.15 (d, J=12.8 Hz, 1H) 5.76 (s, 1H) 6.54 (t, J=2.9 Hz, 1H) 6.58 (dd, J=7.5, 2.9 Hz, 1H) 6.72 (d, J=8.9 Hz, 2H) 7.27 (s, 5H) 7.49 (d, J=8.9 Hz, 2H) 8.25 (s, 1H)

To 10 ml of dichloromethane solution containing 259 mg of 5-{3-[{3-[3-(t-butyldimethylsilanyloxy)propoxy]-2-fluoro-5-methoxyphenyl}-(4-cyanophenylamino)methyl]-5-oxo-4,5-dihydro-[1,2,4]triazol-1-yl}-1H-pyrazole-4-carboxylic acid benzyl ester, 0.060 ml of triethylamine and 109 mg of α-chlorotriphenylmethane were added at 0° C. The resulting mixture was stirred at 0° C. for 1 hour and then at room temperature for 3 hours. Then, 150 ml of ethyl acetate and 50 ml of water were added to the reaction mixture. The organic layer was washed with 50 ml of water and then with 50 ml of saturated brine and then dried over anhydrous magnesium sulfate. The desiccating agent was removed by filtration, and the filtrate was concentrated under reduced pressure. The residue was purified by silica gel column chromatography (ethyl acetate-heptane) to give the title compound (177 mg).

$^1$H-NMR (CDCl$_3$) δ 0.06 (s, 6H) 0.90 (s, 9H) 2.04 (m, 2H) 3.64 (s, 3H) 3.83 (t, J=6.1 Hz, 2H) 4.08 (t, J=6.1 Hz, 2H) 5.05 (d, J=12.7 Hz, 1H) 5.14 (d, J=12.7 Hz, 1H) 5.42 (d, J=4.8 Hz, 1H) 5.45 (d, J=4.8 Hz, 1H) 6.30 (m, 1H) 6.50 (m, 1H) 6.52 (d, J=9.0 Hz, 2H) 7.11-7.25 (s, 20H) 7.38 (d, J=9.0 Hz, 2H) 7.98 (s, 1H)

(198e) (R) and (S)-3-{3-[{3-[3-(t-Butyldimethylsilanyloxy)propoxy]-2-fluoro-5-methoxyphenyl}-(4-cyanophenylamino)methyl]-5-oxo-4,5-dihydro-[1,2,4]triazol-1-yl}-1-trityl-1H-pyrazole-4-carboxylic acid benzyl ester

[Chemical Formula 520]

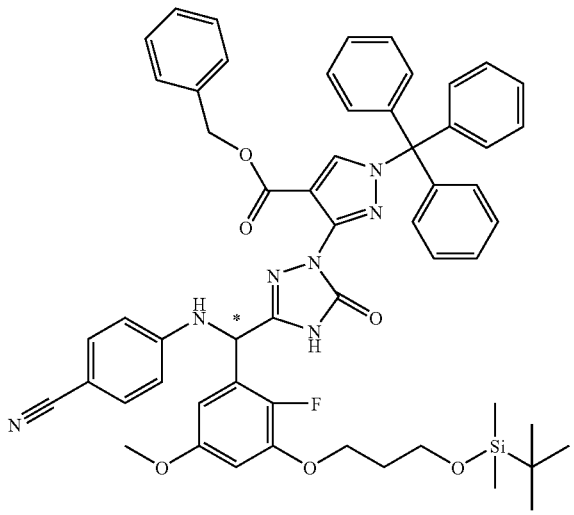

3-{3-[{3-[3-(t-Butyldimethylsilanyloxy)propoxy]-2-fluoro-5-methoxyphenyl}-(4-cyanophenylamino)methyl]-5-oxo-4,5-dihydro-[1,2,4]triazol-1-yl}-1-trityl-1H-pyrazole-4-carboxylic acid benzyl ester (177 mg) was optically resolved using a CHIRALPAK IA column, and the second eluting enantiomer (44 mg) of the title compound was obtained as a light yellow solid.

$^1$H-NMR (CD$_3$OD) δ 0.00 (s, 6H) 0.84 (s, 9H) 1.93 (quint, J=6.1 Hz, 2H) 3.64 (s, 3H) 3.79 (t, J=6.1 Hz, 2H) 4.07 (t, J=6.1 Hz, 2H) 5.07 (d, J=12.4 Hz, 1H) 5.11 (d, J=12.4 Hz, 1H) 5.73 (s, 1H) 6.50 (dd, J=4.5, 2.9 Hz, 1H) 6.50 (dd, J=7.4, 2.9 Hz, 1H) 6.69 (d, J=8.8 Hz, 2H) 7.11-7.34 (s, 20H) 7.37 (d, J=8.8 Hz, 2H) 7.92 (s, 1H)

HPLC retention time: 35 min (Column name: CHIRALPAK IA, 20 mmφ×25 cm, Manufacturer: Daicel Chemical Industries, Ltd., Mobile phase: ethyl acetate/heptane=2/8, Elution rate: 10 ml/min)

(198f) (R) or (S)-5-(3-{(4-Carbamimidoylphenylamino)-[2-fluoro-3-(3-hydroxypropoxy)-5-methoxyphenyl]methyl}-5-oxo-4,5-dihydro-[1,2,4]triazol-1-yl)-1H-pyrazole-4-carboxylic acid acetate

[Chemical Formula 521]

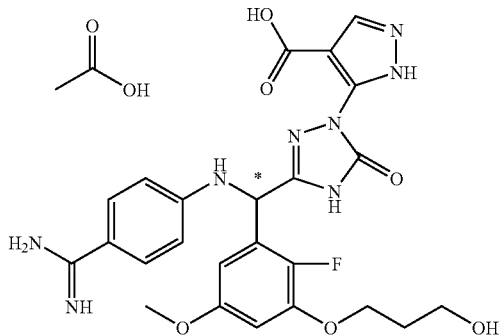

To 4 ml of a methanol solution containing 44 mg of (R) or (S)-3-{3-[{3-[3-(t-butyldimethylsilanyloxy)propoxy]-2-fluoro-5-methoxyphenyl}-(4-cyanophenylamino)methyl]-5-oxo-4,5-dihydro-[1,2,4]triazol-1-yl}-1-trityl-1H-pyrazole-4-carboxylic acid benzyl ester (Example (198e)), 32 mg of hydroxylammonium chloride and 0.063 ml of triethylamine were added. The resulting mixture was stirred at 60° C. for 15 hours under a nitrogen atmosphere.

The solvent was removed under reduced pressure. The residue was dissolved in 6 ml of a methanol:water:acetic acid=1:1:1 mixed solvent. The resulting solution was stirred at 60° C. for 24 hours under a nitrogen atmosphere.

The solvent was removed under reduced pressure. The residue was dissolved in 5 ml of methanol, and then 0.04 g of 10% palladium carbon was added thereto. The mixture was stirred at room temperature under a hydrogen atmosphere of 4.5 kg/cm$^2$ for 12 hours. The reaction mixture was filtered through celite, and the filtrate was concentrated under reduced pressure. The residue was purified by reverse-phase high performance liquid chromatography (acetonitrile-water, 0.1% acetic acid) to give the title compound (4 mg) as a brown solid.

$^1$H-NMR (CD$_3$OD) δ 1.95 (s, 3H) 2.00 (quint, J=6.1 Hz, 2H) 3.74 (s, 3H) 3.76 (t, J=6.1 Hz, 2H) 4.13 (t, J=6.1 Hz, 2H) 5.93 (s, 1H) 6.60 (dd, J=4.8, 2.9 Hz, 1H) 6.65 (dd, J=7.2, 2.9 Hz, 1H) 6.85 (d, J=8.9 Hz, 2H) 7.62 (d, J=8.9 Hz, 2H) 8.04 (s, 1H)

Example 199

(R) and (S)-4-({[2-Fluoro-3-(2-hydroxyethoxy)-5-methoxyphenyl]-[5-oxo-1-(3-oxo-3,4-dihydropyrazin-2-yl)-4,5-dihydro-1H-[1,2,4]triazol-3-yl]methyl}amino)benzamidine acetate (199a) 3-(3-{{3-[2-(t-Butyldimethylsilanyloxy)ethoxy]-2-fluoro-5-methoxyphenyl}-[4-(5-methyl-[1,2,4]oxadiazol-3-yl)phenylamino]methyl}-5-oxo-4,5-dihydro-1H-[1,2,4]triazol-1-yl)-1H-pyrazin-2-one

[Chemical Formula 522]

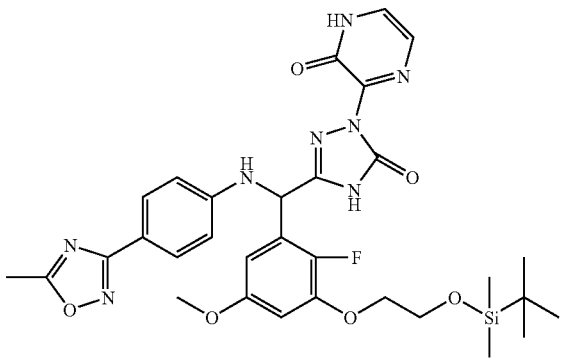

To 2 ml of a dichloromethane solution containing 139 mg of (3-t-butoxypyrazin-2-yl)hydrazine (Example (154a)), 2 ml of trifluoroacetic acid was added. The resulting mixture was stirred at room temperature for 2 hours, and then 50 ml of toluene was added thereto. The mixture was concentrated under reduced pressure, and 50 ml of methanol was added thereto. Then, the mixture was concentrated under reduced pressure. The residue was treated with 10 ml of diethylether and a 4 N hydrogen chloride-ethyl acetate solution, and 3-hydrazino-1H-pyrazin-2-one hydrochloride was collected by filtration.

3-Hydrazino-1H-pyrazin-2-one hydrochloride (24 mg) and triethylamine (0.033 ml) were added to 3 ml of a DMF solution containing 70 mg of (2-{3-[2-(t-butyldimethylsilanyloxy)ethoxy]-2-fluoro-5-methoxyphenyl}-2-[4-(5-methyl-[1,2,4]oxadiazol-3-yl)phenylimino]-1-methylsulfanylethylidene)carbamic acid methyl ester (Example (200a)). The resulting mixture was stirred at 85° C. for 16 hours and then concentrated under reduced pressure. The residue was dissolved in 5 ml of methanol, and 58 mg of sodium cyanotrihydroborate and 0.056 ml of acetic acid were further added thereto. The mixture was stirred at room temperature for 15 hours. To this reaction mixture, 40 ml of ethyl acetate and 20 ml of water were added. The organic layer was washed with 20 ml of water and then with 20 ml of saturated brine and then dried over anhydrous magnesium sulfate. The desiccating agent was removed by filtration, and the filtrate was concentrated under reduced pressure. The residue was purified by NAM silica gel column chromatography (methanol-ethyl acetate) to give the title compound (34 mg).

$^{1}$H-NMR (CD$_{3}$OD) δ 0.01 (s, 6H) 0.80 (s, 9H) 2.50 (s, 3H) 3.64 (s, 3H) 3.89 (t, J=4.6 Hz, 2H) 4.01 (t, J=4.6 Hz, 2H) 5.86 (s, 1H) 6.52-6.57 (m, 2H) 6.81 (d, J=9.1 Hz, 2H) 7.30 (d, J=4.1 Hz, 1H) 7.42 (d, J=4.1 Hz, 1H) 7.70 (d, J=9.1 Hz, 2H)

(199b) (R) and (S)-4-({[2-Fluoro-3-(2-hydroxyethoxy)-5-methoxyphenyl]-[5-oxo-1-(3-oxo-3,4-dihydropyrazin-2-yl)-4,5-dihydro-1H-[1,2,4]triazol-3-yl]methyl}amino)benzamidine acetate

[Chemical Formula 523]

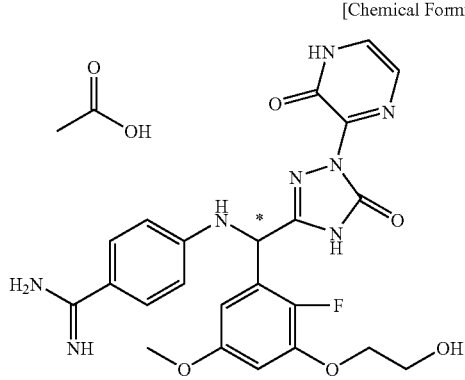

Iron powder (55 mg) was added to 4.5 ml of a methanol:water:acetic acid=1:1:1 mixed solvent solution containing 34 mg of 3-(3-{{3-[2-(t-butyldimethylsilanyloxy)ethoxy]-2-fluoro-5-methoxyphenyl}-[4-(5-methyl-[1,2,4]oxadiazol-3-yl)phenylamino]methyl}-5-oxo-4,5-dihydro-1H-[1,2,4]triazol-1-yl)-1H-pyrazin-2-one. The mixture was stirred at 65° C. for 24 hours under a nitrogen atmosphere. The reaction mixture was filtered and then purified by reverse-phase high performance liquid chromatography (acetonitrile-water, 0.1% acetic acid) to give 4-({[2-fluoro-3-(2-hydroxyethoxy)-5-methoxyphenyl]-[5-oxo-1-(3-oxo-3,4-dihydropyrazin-2-yl)-4,5-dihydro-1H-[1,2,4]triazol-3-yl]methyl}amino)benzamidine acetate (5.9 mg).

This compound (5.9 mg) was optically resolved using a SUMICHIRAL OA-2500 column, and the first eluting enantiomer (1.8 mg) of the title compound was obtained as a white solid.

$^{1}$H-NMR (CD$_{3}$OD) δ 1.95 (s, 3H) 3.71 (s, 3H) 3.87 (t, J=4.7 Hz, 2H) 4.08 (t, J=4.7 Hz, 2H) 5.94 (s, 1H) 6.63-6.65 (m, 2H) 6.83 (d, J=8.8 Hz, 2H) 7.47 (br.s, 1H) 7.61 (d, J=8.8 Hz, 2H) 7.65 (br.s, 1H)

HPLC retention time: 21 min (Column name: SUMICHIRAL OA-2500, 30 mmφ×25 cm, Manufacturer: Sumika Chemical Analysis Service, Ltd., Mobile phase: 0.5 mM ammonium acetate-methanol solution, Elution rate: 15 ml/min)

Example 200

4-({[1-(3-Aminopyridin-2-yl)-5-oxo-4,5-dihydro-1H-[1,2,4]triazol-3-yl]-[2-fluoro-3-(2-hydroxyethoxy)-5-methoxyphenyl]methyl}amino)benzamidine acetate (200a) (2-{3-[2-(t-Butyldimethylsilanyloxy)ethoxy]-2-fluoro-5-methoxyphenyl}-2-[4-(5-methyl-[1,2,4]oxadiazol-3-yl)phenylimino]-1-methylsulfanylethylidene)carbamic acid methyl ester

[Chemical Formula 524]

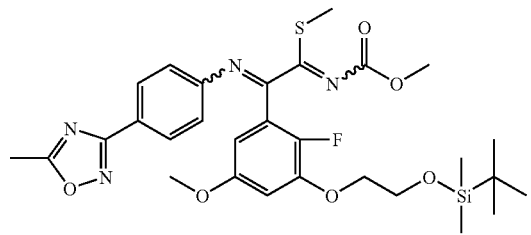

To 15 ml of a DMF solution containing 522 mg of [2-(2-fluoro-3-hydroxy-5-methoxyphenyl)-2-[4-(5-methyl-[1,2,4]oxadiazol-3-yl)phenylimino]-1-methylsulfanylethylidene] carbamic acid methyl ester (Example (3d)), 173 mg of potassium carbonate and 0.269 ml of (2-bromoethoxy)-t-butyldimethylsilane were added. The resulting mixture was stirred at room temperature for 15 hours, and then 25 ml of water and 25 ml of saturated ammonium chloride aqueous solution were added thereto. The mixture was extracted with 150 ml of ethyl acetate. The organic layer was washed with 50 ml of water and then with 50 ml of saturated brine and dried over anhydrous magnesium sulfate. The desiccating agent was removed by filtration, and the filtrate was concentrated under reduced pressure. The residue was purified by silica gel column chromatography (ethyl acetate-heptane) to give the title compound (210 mg).

$^{1}$H-NMR (CDCl$_{3}$) Two main isomers:

δ 0.03 (s, 6H) 0.85 (s, 9H) 2.46 (s, 3H) 2.52 (s, 3H) 3.63 (s, 3H) 3.64 (s, 3H) 3.91 (t, J=4.9 Hz, 2H) 3.98 (t, J=4.9 Hz, 2H) 6.13 (dd, J=3.8, 2.8 Hz, 1H) 6.51 (dd, J=7.2, 2.8 Hz, 1H) 6.84 (d, J=8.5 Hz, 2H) 7.89 (d, J=8.5 Hz, 2H)

δ 0.09 (s, 6H) 0.90 (s, 9H) 2.33 (s, 3H) 2.65 (s, 3H) 3.60 (s, 3H) 3.82 (s, 3H) 3.99 (t, J=4.9 Hz, 2H) 4.08 (t, J=4.9 Hz, 2H) 6.73 (dd, J=7.2, 2.8 Hz, 1H) 6.97 (dd, J=3.8, 2.8 Hz, 1H) 7.11 (d, J=8.5 Hz, 2H) 8.03 (d, J=8.5 Hz, 2H)

(200b) 5-{{3-[2-(t-Butyldimethylsilanyloxy)ethoxy]-2-fluoro-5-methoxyphenyl}-[4-(5-methyl-[1,2,4]oxadiazol-3-yl)phenylamino]methyl}-2-(3-nitropyridin-2-yl)-2,4-dihydro-[1,2,4]triazol-3-one

[Chemical Formula 525]

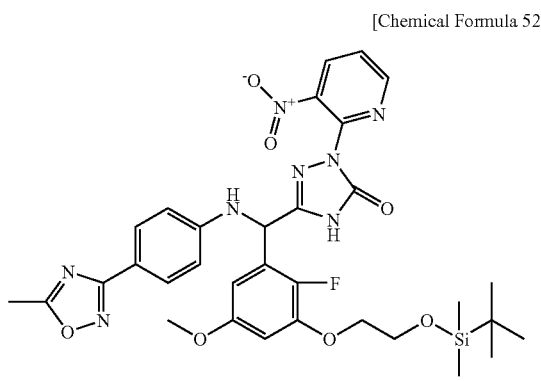

To 3 ml of a DMF solution containing 70 mg of (2-{3-[2-(t-butyldimethylsilanyloxy)ethoxy]-2-fluoro-5-methoxyphenyl}-2-[4-(5-methyl-[1,2,4]oxadiazol-3-yl)phenylimino]-1-methylsulfanylethylidene)carbamic acid methyl ester, 19 mg of (3-Nitropyridin-2-yl)hydrazine and 0.017 ml of triethylamine were added. The resulting mixture was stirred at 85° C. for 16 hours and concentrated under reduced pressure. The residue was dissolved in 5 ml of methanol, and 58 mg of sodium cyanotrihydroborate and 0.056 ml of acetic acid were added thereto. The mixture was stirred at room temperature for 15 hours. To this reaction mixture, 40 ml of ethyl acetate and 20 ml of water were added. The organic layer was washed with 20 ml of water and then with 20 ml of saturated brine and dried over anhydrous magnesium sulfate. The desiccating agent was removed by filtration, and the filtrate was concentrated under reduced pressure. The residue was purified by NAM silica gel column chromatography (methanol-ethyl acetate) to give the title compound (55 mg).

$^1$H-NMR (CD$_3$OD) δ 0.01 (s, 6H) 0.82 (s, 9H) 2.51 (s, 3H) 3.67 (s, 3H) 3.91 (m, 2H) 4.13 (m, 2H) 5.92 (s, 1H) 6.55-6.59 (m, 2H) 6.85 (d, J=8.8 Hz, 2H) 7.53 (dd, J=7.8, 4.7 Hz, 1H) 7.73 (d, J=8.8 Hz, 2H) 8.48 (dd, J=7.8, 1.5 Hz, 1H) 8.66 (dd, J=4.7, 1.5 Hz, 1H)

(200c) 4-({[1-(3-Aminopyridin-2-yl)-5-oxo-4,5-dihydro-1H-[1,2,4]triazol-3-yl]-[2-fluoro-3-(2-hydroxyethoxy)-5-methoxyphenyl]methyl}amino)benzamidine acetate

[Chemical Formula 526]

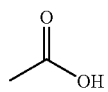

-continued

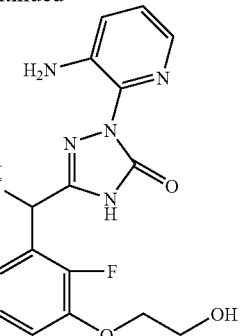

Iron powder (55 mg) was added to 4.5 ml of a methanol:water:acetic acid=1:1:1 mixed solvent solution containing 55 mg of 5-{{3-[2-(t-butyldimethylsilanyloxy)ethoxy]-2-fluoro-5-methoxyphenyl}-[4-(5-methyl-[1,2,4]oxadiazol-3-yl)phenylamino]methyl}-2-(3-nitropyridin-2-yl)-2,4-dihydro-[1,2,4]triazol-3-one. The mixture was stirred at 65° C. for 24 hours under a nitrogen atmosphere. The reaction mixture was filtered and then purified by reverse-phase high performance liquid chromatography (acetonitrile-water, 0.1% acetic acid) to give the title compound (21 mg).

$^1$H-NMR (CD$_3$OD) δ 1.96 (s, 3H) 3.72 (s, 3H) 3.89 (t, J=4.9 Hz, 2H) 4.11 (t, J=4.9 Hz, 2H) 6.02 (s, 1H) 6.62 (dd, J=4.8, 3.1 Hz, 1H) 6.68 (dd, J=7.5, 3.1 Hz, 1H) 6.87 (d, J=9.2 Hz, 2H) 7.23 (dd, J=8.0, 4.6 Hz, 1H) 7.33 (dd, J=8.0, 1.5 Hz, 1H) 7.63 (d, J=9.2 Hz, 2H) 7.81 (dd, J=4.6, 1.5 Hz, 1H)

Example 201

4-({(R) and (S)-[1-(3-Aminopyridin-2-yl)-5-oxo-4,5-dihydro-1H-[1,2,4]triazol-3-yl]-[2-fluoro-3-(2-hydroxyethoxy)-5-methoxyphenyl]methyl}amino)benzamidine acetate

[Chemical Formula 527]

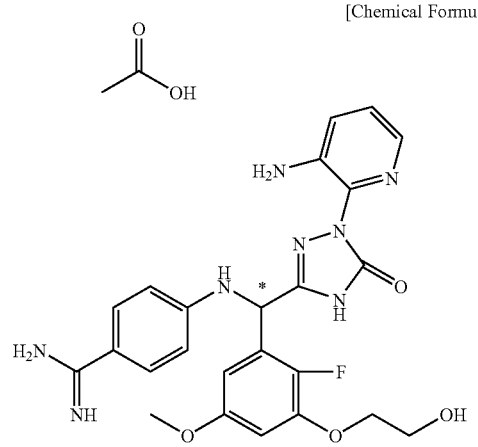

[1276]

4-({[1-(3-Aminopyridin-2-yl)-5-oxo-4,5-dihydro-1H-[1,2,4]triazol-3-yl]-[2-fluoro-3-(2-hydroxyethoxy)-5-methoxyphenyl]methyl}amino)benzamidine acetate (Example (200c), 21 mg) was optically resolved using a SUMICHIRAL OA-2500 column, and the first eluting enantiomer (9.1 mg) of the title compound was obtained as a white solid.

¹H-NMR (CD₃OD) δ 1.96 (s, 3H) 3.72 (s, 3H) 3.88 (t, J=4.9 Hz, 2H) 4.09 (t, J=4.9 Hz, 2H) 5.99 (s, 1H) 6.62-6.67 (m, 2H) 6.85 (d, J=9.2 Hz, 2H) 7.21 (dd, J=8.0, 4.6 Hz, 1H) 7.32 (dd, J=8.0, 1.5 Hz, 1H) 7.62 (d, J=9.2 Hz, 2H) 7.81 (dd, J=4.6, 1.5 Hz, 1H)

HPLC retention time: 10 min (Column name: SUMICHIRAL OA-2500, 30 mmφ×25 cm, Manufacturer: Sumika Chemical Analysis Service, Ltd., Mobile phase: 0.5 mM ammonium acetate-methanol solution, Elution rate: 15 ml/min)

Example 202

4-({[1-(3-Aminopyridin-2-yl)-5-oxo-4,5-dihydro-1H-[1,2,4]triazol-3-yl]-[2-fluoro-5-methoxy-3-(2-methoxyethoxy)phenyl]methyl}amino)benzamidine acetate (202a)
2-Fluoro-5-methoxy-3-(2-methoxyethoxy)benzaldehyde

[Chemical Formula 528]

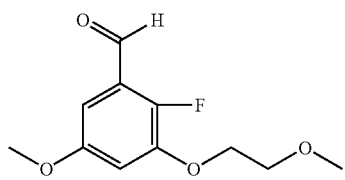

The same procedure was carried out as in Example (3e), except that 2-25 fluoro-3-hydroxy-5-methoxybenzaldehyde [CAS No. 883576-31-6] and 2-bromoethylmethyl ether were used instead of respectively [2-(2-fluoro-3-hydroxy-5-methoxyphenyl)-2-[4-(5-methyl-[1,2,4]oxadiazol-3-yl)phenylimino]-1-methylsulfanylethylidene]carbamic acid methyl ester and 1-fluoro-2-iodoethane, to give the title compound was obtained as a white solid.

¹H-NMR (CDCl₃) δ 3.47 (s, 3H) 3.79 (m, 2H) 4.20 (m, 2H) 3.80 (s, 3H) 6.80-6.84 (m, 2H) 10.35 (s, 1H)

(202b) {2-[2-Fluoro-5-methoxy-3-(2-methoxyethoxy)phenyl]-1-methylsulfanyl-2-[4-(5-trifluoromethyl-[1,2,4]oxadiazol-3-yl)phenylimino]ethylidene}carbamic acid methyl ester

[Chemical Formula 529]

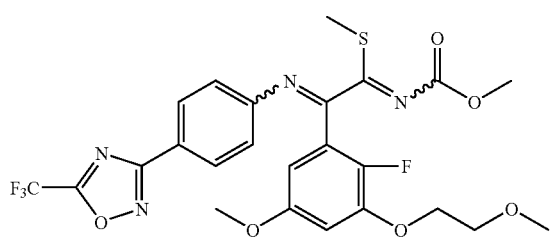

The same procedure was carried out as in Examples (1a) to (1d), except that 4-(5-trifluoromethyl-[1,2,4]oxadiazol-3-yl)phenylamine (Example (188a)) and 2-fluoro-5-methoxy-3-(2-methoxyethoxy)benzaldehyde were used instead of respectively the 4-(5-methyl-[1,2,4]oxadiazol-3-yl)phenylamine and 2-fluoro-4,5-dimethoxybenzaldehyde in Example (1a), to give the title compound as a light yellow solid.

¹H-NMR (CDCl₃) Main isomer:
δ 2.47 (s, 3H) 3.46 (s, 3H) 3.64 (s, 3H) 3.69 (t, J=4.8 Hz, 2H) 3.84 (s, 3H) 4.06 (t, J=4.8 Hz, 2H) 6.16 (t, J=3.3 Hz, 1H) 6.52 (dd, J=7.1, 3.3 Hz, 1H) 6.88 (d, J=9.2 Hz, 2H) 7.95 (d, J=9.2 Hz, 2H)

(202c) 5-{[2-Fluoro-5-methoxy-3-(2-methoxyethoxy)phenyl]-[4-(5-trifluoromethyl-[1,2,4]oxadiazol-3-yl)phenylamino]methyl}-2-(3-nitropyridin-2-yl)-2,4-dihydro-[1,2,4]triazol-3-one

[Chemical Formula 530]

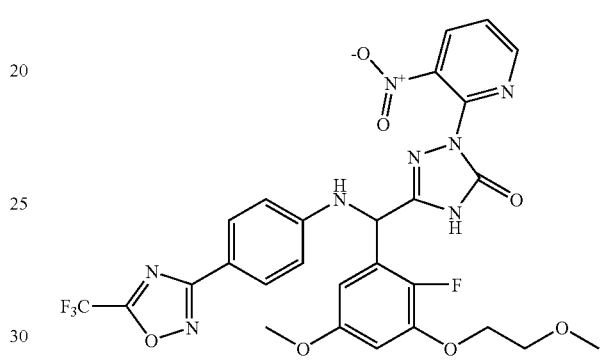

To 3 ml of a DMF solution containing 86 mg of {2-[2-fluoro-5-methoxy-3-(2-methoxyethoxy)phenyl]-1-methylsulfanyl-2-[4-(5-trifluoromethyl-[1,2,4]oxadiazol-3-yl)phenylimino]ethylidene}carbamic acid methyl ester, 25 mg of (3-nitropyridin-2-yl)hydrazine and 0.023 ml of triethylamine were added. The resulting mixture was stirred at 85° C. for 16 hours and concentrated under reduced pressure. The residue was dissolved in 5 ml of methanol, and 66 mg of sodium cyanotrihydroborate and 0.085 ml of acetic acid were added thereto. The mixture was stirred at room temperature for 15 hours. To this reaction mixture, 50 ml of ethyl acetate and 20 ml of water were added. The organic layer was washed with 20 ml of water and then with 20 ml of saturated brine and dried over anhydrous magnesium sulfate. The desiccating agent was removed by filtration, and the filtrate was concentrated under reduced pressure. The residue was purified by NAM silica gel column chromatography (methanol-ethyl acetate) to give the title compound (55 mg).

¹H-NMR (CD₃OD) δ 3.41 (s, 3H) 3.73 (s, 3H) 3.74 (m, 2H) 4.15 (m, 2H) 6.00 (s, 1H) 6.61-6.64 (m, 2H) 6.85 (d, J=8.9 Hz, 2H) 7.60 (dd, J=8.0, 4.5 Hz, 1H) 7.85 (d, J=8.9 Hz, 2H) 8.46 (dd, J=8.0, 1.6 Hz, 1H) 8.72 (dd, J=4.5, 1.6 Hz, 1H)

(202d) 4-({[1-(3-Aminopyridin-2-yl)-5-oxo-4,5-dihydro-1H-[1,2,4]triazol-3-yl]-[2-fluoro-5-methoxy-3-(2-methoxyethoxy)phenyl]methyl}amino)benzamidine acetate

[Chemical Formula 531]

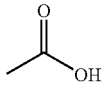

-continued

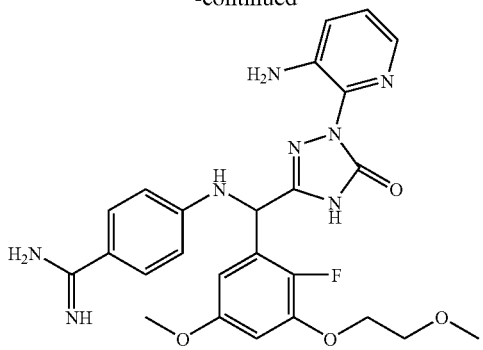

Iron powder (55 mg) was added to 4.5 ml of a methanol: water:acetic acid=1:1:1 mixed solvent solution containing 38 mg of 5-{[2-fluoro-5-methoxy-3-(2-methoxyethoxy)phenyl]-[4-(5-trifluoromethyl-[1,2,4]oxadiazol-3-yl)phenylamino]methyl}-2-(3-nitropyridin-2-yl)-2,4-dihydro-[1,2,4]triazol-3-one. The mixture was stirred at 65° C. for 24 hours under a nitrogen atmosphere. The reaction mixture was filtered and then purified by reverse-phase high performance liquid chromatography (acetonitrile-water, 0.1% acetic acid) to give the title compound (25 mg).

$^1$H-NMR (CD$_3$OD) δ 1.95 (s, 3H) 3.41 (s, 3H) 3.72 (s, 3H) 3.75 (m, 2H) 4.17 (m, 2H) 6.02 (s, 1H) 6.62 (dd, J=4.0, 2.9 Hz, 1H) 6.67 (dd, J=6.6, 2.9 Hz, 1H) 6.86 (d, J=8.8 Hz, 2H) 7.22 (dd, 8.0, 4.7 Hz, 1H) 7.33 (dd, J=8.0, 1.3 Hz, 1H) 7.63 (d, J=8.8 Hz, 2H) 7.81 (dd, J=4.7, 1.3 Hz, 1H)

Example 203

4-({(R) and (S)-[1-(3-Aminopyridin-2-yl)-5-oxo-4,5-dihydro-1H-[1,2,4]triazol-3-yl]-[2-fluoro-5-methoxy-3-(2-methoxyethoxy)phenyl]methyl}amino)benzamidine acetate

[Chemical Formula 532]

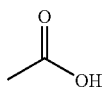
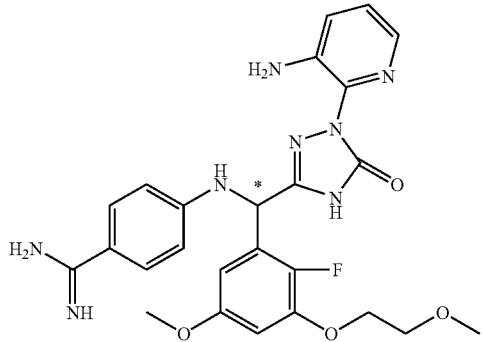

4-({[1-(3-Aminopyridin-2-yl)-5-oxo-4,5-dihydro-1H-[1,2,4]triazol-3-yl]-[2-fluoro-3-(2-methoxyethoxy)-5-methoxyphenyl]methyl}amino)benzamidine acetate (24 mg) was optically resolved using a SUMICHIRAL OA-2500 column, and the first eluting enantiomer (9.5 mg) of the title compound was obtained as a white solid.

$^1$H-NMR (CD$_3$OD) δ 1.95 (s, 3H) 3.41 (s, 3H) 3.70 (s, 3H) 3.74 (m, 2H) 4.15 (m, 2H) 5.97 (s, 1H) 6.61-6.65 (m, 2H) 6.84 (d, J=9.2 Hz, 2H) 7.20 (dd, 8.1, 4.5 Hz, 1H) 7.31 (dd, J=8.1, 1.3 Hz, 1H) 7.62 (d, J=9.2 Hz, 2H) 7.81 (dd, J=4.5, 1.3 Hz, 1H)

HPLC retention time: 11 min (Column name: SUMICHIRAL OA-2500, 30 mmφ×25 cm, Manufacturer: Sumika Chemical Analysis Service, Ltd., Mobile phase: 0.5 mM ammonium acetate-methanol solution, Elution rate: 15 ml/min)

Example 204

4-({[1-(3-Aminopyridin-2-yl)-5-oxo-4,5-dihydro-1H-[1,2,4]triazol-3-yl]-[5-ethyl-2-fluoro-3-(3-hydroxypropoxy)phenyl]methyl}amino)benzamidine acetate (204a) 5-{{3-[3-(t-Butyldimethylsilanyloxy)propoxy]-5-ethyl-2-fluorophenyl}-[4-(5-methyl-[1,2,4]oxadiazol-3-yl)phenylamino]methyl}-2-(3-nitropyridin-2-yl)-2,4-dihydro-[1,2,4]triazol-3-one

[Chemical Formula 533]

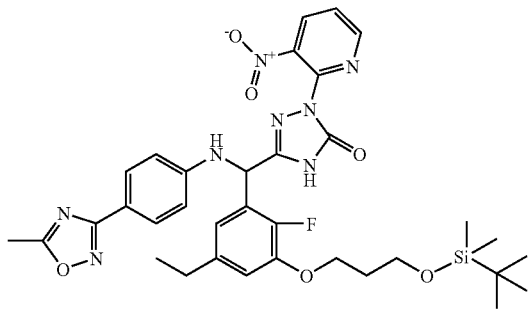

The same procedure was carried out as in Example (135f), except that (3-bromopropoxy)-t-butyldimethylsilane was used instead of 2-chloro-N,N-dimethylacetamide, to give {2-{3-[3-(t-Butyldimethylsilanyloxy)propoxy]-5-ethyl-2-fluorophenyl}-2-[4-(5-methyl-[1,2,4]oxadiazol-3-yl)phenylimino]-1-methylsulfanylethylidene}carbamic acid methyl ester.

The same procedure was carried out as in Example (34a), except that this compound was used instead of [2-(9-methoxy-3,4-dihydro-2H-benzo[b][1,4]dioxepin-7-yl)-2-[4-(5-methyl-[1,2,4]oxadiazol-3-yl)phenylimino]-1-methylsulfanylethylidene]carbamic acid methyl ester, to give the title compound as a light yellow solid.

$^1$H-NMR (CD$_3$OD) δ 0.01 (s, 6H) 0.84 (s, 9H) 1.15 (t, J=7.3 Hz, 3H) 1.95 (quint, J=6.3 Hz, 2H) 2.54 (s, 3H) 2.55 (q, J=7.3 Hz, 2H) 3.80 (t, J=6.3 Hz, 2H) 4.11 (t, J=6.3 Hz, 2H) 5.94 (s, 1H) 6.80 (d, J=8.8 Hz, 2H) 6.87-6.92 (m, 2H) 7.56 (dd, J=8.0, 4.2 Hz, 1H) 7.77 (d, J=8.8 Hz, 2H) 8.41 (dd, J=8.0, 2.0 Hz, 1H) 8.69 (dd, J=4.2, 2.0 Hz, 1H)

(204b) 4-({[1-(3-Aminopyridin-2-yl)-5-oxo-4,5-dihydro-1H-[1,2,4]triazol-3-yl]-[5-ethyl-2-fluoro-3-(3-hydroxypropoxy)phenyl]methyl}amino)benzamidine acetate

[Chemical Formula 534]

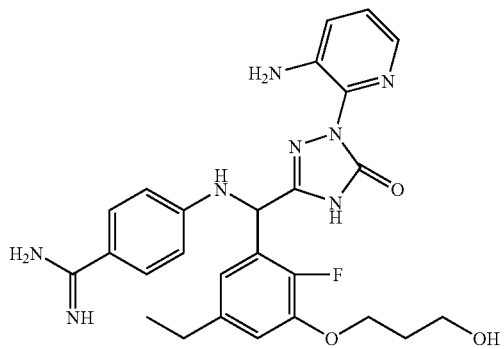

The same procedure was carried out as in Example (3g), except that 5-{{3-[3-(t-butyldimethylsilanyloxy)propoxy]-5-ethyl-2-fluorophenyl}-[4-(5-methyl-[1,2,4]oxadiazol-3-yl)phenylamino]methyl}-2-(3-nitropyridin-2-yl)-2,4-dihydro-[1,2,4]triazol-3-one was used instead of 5-{[2-fluoro-3-(2-fluoroethoxy)-5-methoxyphenyl]-[4-(5-methyl-[1,2,4]oxadiazol-3-yl)phenylamino]methyl}-2-pyrimidin-2-yl-2,4-dihydro-[1,2,4]triazol-3-one, to give the title compound.

¹H-NMR (CD₃OD) δ1.16 (t, J=7.1 Hz, 3H) 1.95 (s, 3H) 2.01 (quint, J=6.3 Hz, 2H) 2.57 (q, J=7.1 Hz, 2H) 3.75 (t, J=6.3 Hz, 2H) 4.16 (t, J=6.3 Hz, 2H) 5.98 (s, 1H) 6.85 (d, J=9.0 Hz, 2H) 6.89-6.96 (m, 2H) 7.22 (dd, J=8.3, 4.6 Hz, 1H) 7.32 (dd, J=8.3, 1.7 Hz, 1H) 7.62 (d, J=9.0 Hz, 2H) 7.82 (dd, J=4.6, 1.7 Hz, 1H)

Example 205

(R) and (S)-4-({[1-(3-Aminopyridin-2-yl)-5-oxo-4,5-dihydro-1H-[1,2,4]triazol-3-yl]-[5-ethyl-2-fluoro-3-(3-hydroxypropoxy)phenyl]methyl}amino)benzamidine acetate

[Chemical Formula 535]

-continued

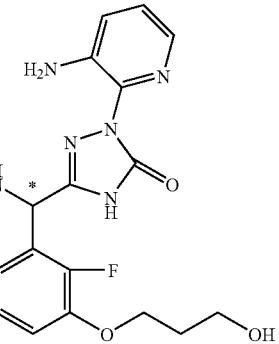

4-({[1-(3-Aminopyridin-2-yl)-5-oxo-4,5-dihydro-1H-[1,2,4]triazol-3-yl]-[5-ethyl-2-fluoro-3-(3-hydroxypropoxy)phenyl]methyl}amino)benzamidine acetate (Example (204b), 34 mg) was optically resolved using a SUMICHIRAL OA-2500 column, and the first eluting enantiomer (15.6 mg) of the title compound was obtained as a white solid.

¹H-NMR (CD₃OD) δ1.16 (t, J=7.1 Hz, 3H) 1.95 (s, 3H) 2.01 (quint, J=6.3 Hz, 2H) 2.57 (q, J=7.1 Hz, 2H) 3.75 (t, J=6.3 Hz, 2H) 4.16 (t, J=6.3 Hz, 2H) 5.98 (s, 1H) 6.85 (d, J=9.0 Hz, 2H) 6.89-6.96 (m, 2H) 7.22 (dd, J=8.3, 4.6 Hz, 1H) 7.32 (dd, J=8.3, 1.7 Hz, 1H) 7.62 (d, J=9.0 Hz, 2H) 7.82 (br.s, 1H)

HPLC retention time: 6 min (Column name: SUMICHIRAL OA-2500, 30 mmφ×25 cm, Manufacturer: Sumika Chemical Analysis Service, Ltd., Mobile phase: 0.5 mM ammonium acetate-methanol solution, Elution rate: 15 ml/min)

Example 206

3-(3-{(R) and (S)-(4-Carbamimidoylphenylamino)-[4-(3-hydroxypropoxy)-3-methoxyphenyl]methyl}-5-oxo-4,5-dihydro-[1,2,4]triazol-1-yl)thiophene-2-carboxylic acid (206a) {2-{4-[3-(t-Butyldimethylsilanyloxy)propoxy]-3-methoxyphenyl}-2-[4-(5-methyl-[1,2,4]oxadiazol-3-yl)phenylimino]-1-methylsulfanylethylidene}carbamic acid methyl ester

[Chemical Formula 536]

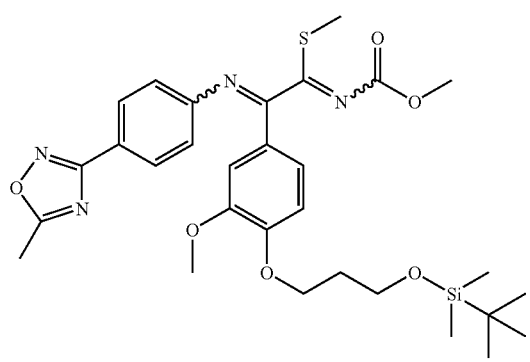

The same procedure was carried out as in Example (18e), except that 3-bromopropoxy-t-butyldimethylsilane was used instead of iodoethane, to give the title compound.

(206b) 3-(3-{(R) and (S)-(4-Carbamimidoylphenylamino)-[4-(3-hydroxypropoxy)-3-methoxyphenyl]methyl}-5-oxo-4,5-dihydro-[1,2,4]triazol-1-yl)thiophene-2-carboxylic acid

[Chemical Formula 537]

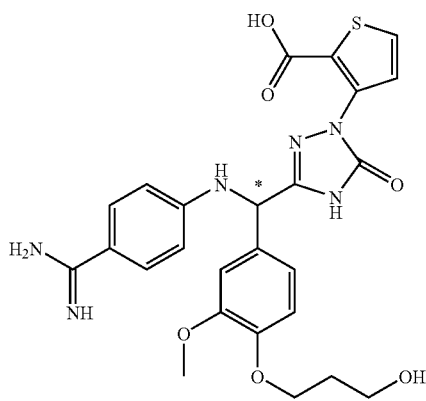

The same procedure was carried out as in Example (169b), except that {2-{4-[3-(t-butyldimethylsilanyloxy)propoxy]-3-methoxyphenyl}-2-[4-(5-methyl-[1,2,4]oxadiazol-3-yl)phenylimino]-1-methylsulfanylethylidene}carbamic acid methyl ester was used instead of {2-(5,6-dimethoxypyridin-3-yl)-2-[4-(5-methyl-[1,2,4]oxadiazol-3-yl)phenylimino]-1-methylsulfanylethylidene}carbamic acid methyl ester, to give the first eluting enantiomer of the title compound.

$^1$H-NMR (CD$_3$OD) δ 1.95-2.02 (m, 2H) 3.74 (t, J=6.4 Hz, 2H) 3.84 (s, 3H) 4.10 (t, J=6.4 Hz, 2H) 5.54 (s, 1H) 6.86 (d, J=8.8 Hz, 2H) 6.98 (d, J=8.4 Hz, 1H) 7.05-7.08 (m, 2H) 7.15 (d, J=1.6 Hz, 1H) 7.42 (d, J=5.2 Hz, 1H) 7.61 (d, J=8.8 Hz, 2H)

HPLC retention time: 12 min (Column name: SUMICHIRAL OA-2500, 30 mmφ×25 cm, Manufacturer: Sumika Chemical Analysis Service, Ltd., Mobile phase: 0.5 mM ammonium acetate-methanol solution, Elution rate: 40 ml/min)

Example 207

4-({[1-(3-Aminopyridin-2-yl)-5-oxo-4,5-dihydro-1H-[1,2,4]triazol-3-yl]-[3-(2-hydroxyethoxy)-5-methoxyphenyl]methyl}amino)benzamidine acetate

[Chemical Formula 538]

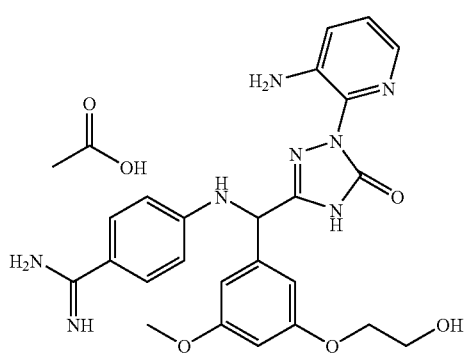

The same procedure was carried out as in Examples (200a) to (200c), except that {2-(3-hydroxy-5-methoxyphenyl)-2-[4-(5-methyl-[1,2,4]oxadiazol-3-yl)phenylimino]-1-methylsulfanylethylidene}carbamic acid methyl ester (Example (4c)) was used instead of [2-(2-fluoro-3-hydroxy-5-methoxyphenyl)-2-[4-(5-methyl-[1,2,4]oxadiazol-3-yl)phenylimino]-1-methylsulfanylethylidene]carbamic acid methyl ester in Example (200a), to give the title compound.

$^1$H-NMR (CD$_3$OD) δ 1.91 (s, 3H) 3.77 (s, 3H) 3.83 (t, J=4.9 Hz, 2H) 4.12 (t, J=4.9 Hz, 2H) 5.66 (s, 1H) 6.51 (s, 1H) 6.67 (m, 2H) 6.85 (d, J=9.1 Hz, 2H) 7.23 (m, 1H) 7.34 (br.d, J=7.7 Hz, 1H) 7.62 (d, J=9.1 Hz, 2H) 7.83 (br.s, 1H)

Example 208

4-{[(R) and (S)-[2-Fluoro-4-(2-hydroxyethoxy)-5-methoxyphenyl]-(5-oxo-1-pyrimidin-2-yl-4,5-dihydro-1H-[1,2,4]triazol-3-yl)methyl]amino}benzamidine acetate

[Chemical Formula 539]

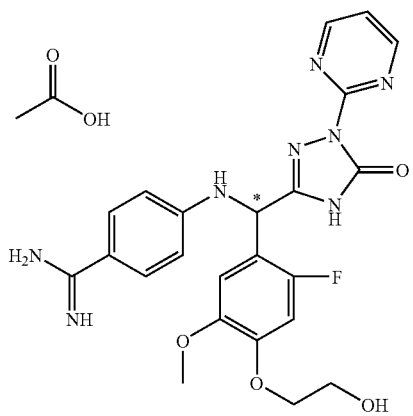

The same procedure was carried out as in Examples (3f) to (3h), except that (2-{4-[2-(t-butyldimethyl silanyloxy)ethoxy]-2-fluoro-5-methoxyphenyl}-2-[4-(5-methyl-[1,2,4]oxadiazol-3-yl)phenylimino]-1-methylsulfanylethylidene)carbamic acid methyl ester (Example (178c)) was used instead of {2-[2-fluoro-3-(2-fluoroethoxy)-5-methoxyphenyl]-2-[4-(5-methyl-[1,2,4]oxadiazol-3-yl)phenylimino]-1-methylsulfanylethylidene}carbamic acid methyl ester in Example (3f), to give the first eluting enantiomer of the title compound as a white solid.

$^1$H-NMR (CD$_3$OD) δ 1.92 (s, 3H) 3.76-3.79 (m, 2H) 3.82 (s, 3H) 3.93-3.96 (m, 2H) 5.91 (s, 1H) 6.83 (d, J=11.6 Hz, 1H) 6.85 (d, J=8.8 Hz, 2H) 7.12 (d, J=7.2 Hz, 1H) 7.31 (t, J=4.8 Hz, 1H) 7.60 (d, J=8.8 Hz, 2H) 8.75 (d, J=4.8 Hz, 2H)

HPLC retention time: 16 min (Column name: SUMICHIRAL OA-2500, 30 mmφ×25 cm, Manufacturer: Sumika Chemical Analysis Service, Ltd., Mobile phase: 0.05 M ammonium acetate-methanol solution, Elution rate: 20 ml/min)

Example 209

4-{[[1-(3-Aminopyridin-2-yl)-5-oxo-4,5-dihydro-1H-[1,2,4]triazol-3-yl]-(5-fluoro-8-methoxychroman-6-yl)methyl]amino}benzamidine trifluoroacetate

[Chemical Formula 540]

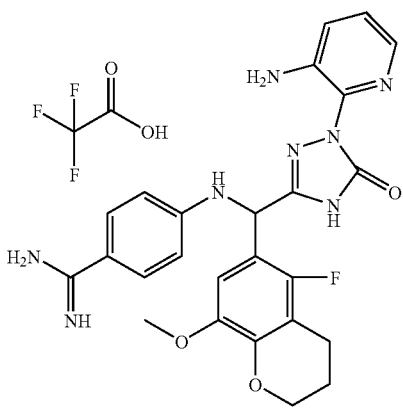

The same procedure was carried out as in Examples (200b) to (200c), except that [2-(5-fluoro-8-methoxychroman-6-yl)-2-[4-(5-methyl-[1,2,4]oxadiazol-3-yl)phenylimino]-1-methylsulfanylethylidene]carbamic acid methyl ester (Example (33d)) and 0.1% trifluoroacetic acid were used instead of respectively the (2-{3-[2-(t-butyldimethylsilanyloxy)ethoxy]-2-fluoro-5-methoxyphenyl}-2-[4-(5-methyl-[1,2,4]oxadiazol-3-yl)phenylimino]-1-methylsulfanylethylidene)carbamic acid methyl ester in Example (200b) and 0.1% acetic acid in Example (200c), to give the title compound.

$^1$H-NMR (CD$_3$OD) δ 1.98 (quint, J=6.8 Hz, 2H) 2.76 (t, J=6.8 Hz, 2H) 3.75 (s, 3H) 4.19 (t, J=6.8 Hz, 2H) 5.94 (s, 1H) 6.85 (d, J=9.0 Hz, 2H) 6.90 (d, J=5.9 Hz, 1H) 7.23 (dd, J=7.6, 4.9 Hz, 1H) 7.33 (d, J=7.6 Hz, 1H) 7.63 (d, J=9.0 Hz, 2H) 7.81 (d, J=4.9 Hz, 1H)

Example 210

6-{3-[(4-Carbamimidoylphenylamino)-(2-fluoro-3,5-dimethoxyphenyl)methyl]-5-oxo-4,5-dihydro-[1,2,4]triazol-1-yl}pyridine-2-carboxylic acid trifluoroacetate

[Chemical Formula 541]

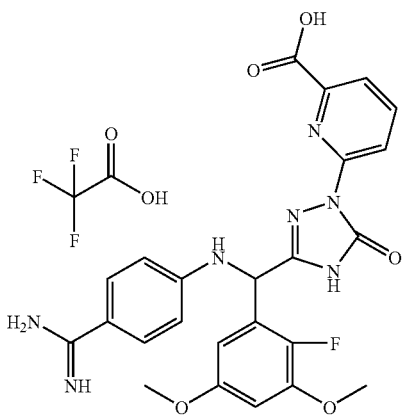

The same procedure was carried out as in Example (3e), except that methyl iodide was used instead of 1-fluoro-2-iodoethane, to give [2-(2-Fluoro-4,5-dimethoxyphenyl)-2-[4-(5-methyl-[1,2,4]oxadiazol-3-yl)phenylimino]-1-methylsulfanylethylidene]carbamic acid methyl ester.

The same procedure was carried out as in Examples (180a) to (180b), except that [2-(2-fluoro-4,5-dimethoxyphenyl)-2-[4-(5-methyl-[1,2,4]oxadiazol-3-yl)phenylimino]-1-methylsulfanylethylidene]carbamic acid methyl ester and 6-hydrazinopyridine-2-carboxylic acid methyl ester hydrochloride (Example (174a)) were used instead of respectively {2-(9-methoxy-3,4-dihydro-2H-benzo[b][1,4]dioxepin-7-yl)-2-[4-(5-methyl-[1,2,4]oxadiazol-3-yl)phenylimino]-1-methylsulfanylethylidene}carbamic acid methyl ester and 4-hydrazinothiazole-5-carboxylic acid methyl ester in Example (180a), to give the title compound as a yellow solid.

$^1$H-NMR (CD$_3$OD) δ 3.70 (s, 3H) 3.84 (s, 3H) 5.83 (s, 1H) 6.63 (br.s, 2H) 6.85 (d, J=8.5 Hz, 2H) 7.63 (d, J=8.5 Hz, 2H) 8.05-8.30 (m, 3H)

Mass spectrum (ESI) m/z: 508 (M+H)$^+$

Example 211

(R) and (S)-2-{3-[(4-Carbamimidoylphenylamino)-(8-methoxy-4H-benzo[1,3]dioxin-6-yl)methyl]-5-oxo-4,5-dihydro[1,2,4]triazol-1-yl}benzoic acid amide acetate

[Chemical Formula 542]

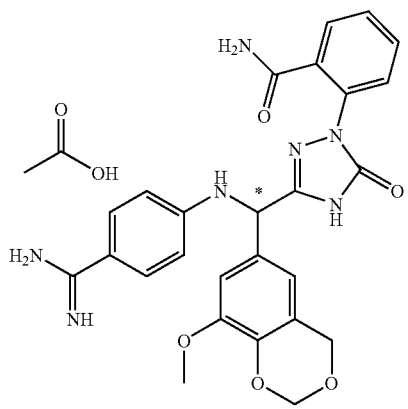

To 2 ml of a DMF solution containing 130 mg of [2-(8-methoxy-4H-benzo[1,3]dioxin-6-yl)-2-[4-(5-methyl-[1,2,4]oxadiazol-3-yl)phenylimino]-1-methylsulfanylethylidene]carbamic acid methyl ester (Example (21h)), 46 mg of 2-hydrazinobenzoic acid hydrochloride and 0.200 ml of triethylamine were added. The resulting mixture was stirred at 80° C. for 8 hours under a nitrogen atmosphere, and then the reaction mixture was concentrated. The residue was dissolved in 3 ml of methanol and 0.3 ml of acetic acid, and 250 mg of sodium cyanotrihydroborate was added thereto. The mixture was stirred at room temperature overnight. To this reaction mixture, water was added and extracted with ethyl acetate. The organic layer was dried over anhydrous magnesium sulfate. The desiccating agent was removed by filtration, and the filtrate was concentrated under reduced pressure. The residue was purified by NAM silica gel column chromatography (methanol-ethyl acetate) to give 2-(3-{(8-methoxy-4H-benzo[1,3]dioxin-6-yl)-[4-(5-methyl-[1,2,4]oxadiazol-3-yl)phenylamino]methyl}-5-oxo-4,5-dihydro[1,2,4]triazol-1-yl)benzoic acid.

To 2 ml of a DMF solution of this compound, 500 mg of benzotriazol-1-yloxytris(pyrrolidino)phosphinium hexafluorophosphate, 130 mg of 1-hydroxybenzotriazole, 0.33 ml of N,N-diisopropylethylamine, and 50 mg of ammonium chloride were added. The mixture was stirred at room temperature for 3 hours, and water was added thereto and extracted with ethyl acetate. The organic layer was dried over anhydrous magnesium sulfate. The desiccating agent was removed by filtration, and the filtrate was concentrated under reduced pressure. The residue was purified by silica gel column chromatography (methanol-ethyl acetate) to give 2-(3-{(8-methoxy-4H-benzo[1,3]dioxin-6-yl)-[4-(5-methyl-[1,2,4]oxadiazol-3-yl)phenylamino]methyl}-5-oxo-4,5-dihydro[1,2,4]triazol-1-yl)benzoic acid amide.

Iron powder (200 mg) was added to 3 ml of a methanol:water:acetic acid=1:1:1 mixed solvent solution of this compound. The resulting mixture was stirred at 60° C. overnight under a nitrogen atmosphere. The reaction mixture was filtered and purified by reverse-phase high performance liquid chromatography (acetonitrile-water, 0.1% acetic acid) to give 2-{3-[(4-carbamimidoylphenylamino)-(8-methoxy-4H-benzo[1,3]dioxin-6-yl)methyl]-5-oxo-4,5-dihydro[1,2,4]triazol-1-yl}benzoic acid amide acetate (16 mg).

This compound (16 mg) was optically resolved using a SUMICHIRAL OA-2500 column, and the first eluting enantiomer (5.93 mg) of the title compound was obtained as a white solid.

$^1$H-NMR (CD$_3$OD) δ 1.92 (s, 3H) 3.84 (s, 3H) 4.84-4.93 (m, 2H) 5.24 (s, 2H) 5.58 (s, 1H) 6.80 (d, J=2.0 Hz, 1H) 6.86 (d, J=8.8 Hz, 2H) 7.03 (d, J=2.0 Hz, 1H) 7.46 (dt, J=2.0, 7.8 Hz, 1H) 7.51-7.59 (m, 2H) 7.63 (d, J=8.8 Hz, 2H) 7.65-7.68 (m, 1H)

HPLC retention time: 11 min (Column name: SUMICHIRAL OA-2500, 30 mmϕ×25 cm, Manufacturer: Sumika Chemical Analysis Service, Ltd., Mobile phase: 0.05 M ammonium acetate-methanol solution, Elution rate: 20 ml/min)

Example 212

(R) and (S)-4-{[[3-Ethynyl-5-(2-hydroxyethoxy)phenyl]-(5-oxo-1-pyrimidin-2-yl-4,5-dihydro-1H-[1,2,4]triazol-3-yl)methyl]amino}benzamidine acetate

[Chemical Formula 543]

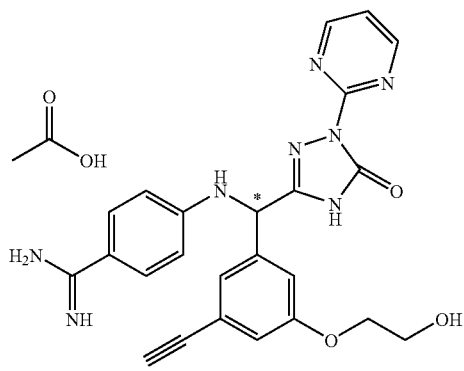

To 6 ml of a DMF solution containing 512 mg of {2-(3-ethynyl-5-hydroxyphenyl)-2-[4-(5-methyl-[1,2,4]oxadiazol-3-yl)phenylimino]-1-methylsulfanylethylidene}carbamic acid methyl ester (Example (45b)), 1.3 g of potassium carbonate and 0.64 ml of 2-(2-bromoethoxy)tetrahydropyran were added. The resulting mixture was stirred at room temperature overnight, and then water was added thereto and extracted with ethyl acetate. The organic layer was washed with water and dried over anhydrous magnesium sulfate. The desiccating agent was removed by filtration, and the filtrate was concentrated under reduced pressure. The residue was purified by silica gel column chromatography (heptane-ethyl acetate) to give [2-{3-ethynyl-5-[2-(tetrahydropyran-2-yloxy)ethoxy]phenyl}-2-[4-(5-methyl-[1,2,4]oxadiazol-3-yl)phenylimino]-1-methylsulfanylethylidene]carbamic acid methyl ester (491 mg, isomer mixture) as a light yellow solid.

To 7 ml of a DMF solution containing 451 mg of this compound, 75 mg of 2-hydrazinopyrimidine and 0.5 ml of triethylamine were added. The resulting mixture was stirred at 85° C. overnight under a nitrogen atmosphere. The reaction mixture was concentrated, and the residue was dissolved in 6 ml of methanol and 0.6 ml of acetic acid. After adding 600 mg of sodium cyanotrihydroborate to this reaction mixture, the resulting mixture was stirred at room temperature for 2 hours. Water was added to the reaction mixture, and then the mixture was extracted with ethyl acetate. The organic layer was dried over anhydrous magnesium sulfate. The desiccating agent was removed by filtration, and the filtrate was concentrated under reduced pressure. The residue was purified by NAM silica gel column chromatography (methanol-ethyl acetate) to give 5-{{3-ethynyl-5-[2-(tetrahydropyran-2-yloxy)ethoxy]phenyl}-[4-(5-methyl-[1,2,4]oxadiazol-3-yl)phenylamino]methyl}-2-pyrimidin-2-yl-2,4-dihydro-[1,2,4]triazol-3-one (236 mg) as a light yellow solid.

Iron powder (136 mg) was added to 4 ml of a methanol:water:acetic acid=1.5:1.5:1 mixed solvent solution containing this compound. The mixture was stirred at 60° C. for 2 days under a nitrogen atmosphere. The reaction mixture was filtered and then purified by reverse-phase high performance liquid chromatography (acetonitrile-water, 0.1% acetic acid) to give 4-{[[3-ethynyl-5-(2-hydroxyethoxy)phenyl]-(5-oxo-1-pyrimidin-2-yl-4,5-dihydro-1H-[1,2,4]triazol-3-yl)methyl]amino}benzamidine acetate (26 mg).

This compound (26 mg) was optically resolved using a SUMICHIRAL OA-2500 column, and the first eluting enantiomer (10.15 mg) of the title compound was obtained as a white solid.

$^1$H-NMR (CD$_3$OD) δ 1.92 (s, 3H) 3.48 (s, 1H) 3.82 (t, J=4.4 Hz, 2H) 3.98-4.03 (m, 2H) 5.64 (s, 1H) 6.84 (d, J=8.8 Hz, 2H) 6.96-6.98 (m, 1H) 7.17 (t, J=2.0 Hz, 1H) 7.25 (s, 1H) 7.29 (t, J=4.8 Hz, 1H) 7.59 (d, J=8.8 Hz, 2H) 8.76 (d, J=4.8 Hz, 2H)

HPLC retention time: 20 min (Column name: SUMICHIRAL OA-2500, 30 mmϕ×25 cm, Manufacturer: Sumika Chemical Analysis Service, Ltd., Mobile phase: 0.05 M ammonium acetate-methanol solution, Elution rate: 20 ml/min)

Example 213

(R) and (S)-4-{[(8-Methoxy-4H-benzo[1,3]dioxin-6-yl)-(5-oxo-1-pyridin-2-yl-4,5-dihydro-1H-[1,2,4]triazol-3-yl)methyl]amino}benzamidine acetate

[Chemical Formula 544]

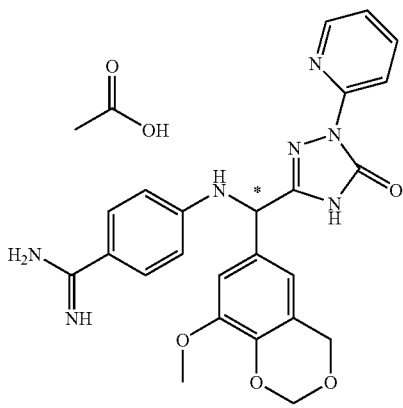

The same procedure was carried out as in Examples (21i) to (21k), except that 2-hydrazinopyridine dihydrochloride was used instead of 2-hydrazinopyrimidine in Example (21i), to give the first eluting enantiomer of the title compound.

$^1$H-NMR (CD$_3$OD) δ 1.93 (s, 3H) 3.81 (s, 3H) 4.84-4.93 (m, 2H) 5.22 (s, 2H) 5.61 (s, 1H) 6.81 (s, 1H) 6.86 (dd, J=2.0, 8.8 Hz, 2H) 7.04 (br.s, 1H) 7.27 (br.t, J=5.2 Hz, 1H) 7.60 (dd, J=2.0, 8.8 Hz, 2H) 7.89 (t, J=8.0 Hz, 1H) 8.08 (d, J=7.6 Hz, 1H) 8.44 (br.d, J=4.8 Hz, 1H)

HPLC retention time: 11 min (Column name: SUMICHIRAL OA-2500, 30 mmφ×25 cm, Manufacturer: Sumika Chemical Analysis Service, Ltd., Mobile phase: 0.05 M ammonium acetate-methanol solution, Elution rate: 20 ml/min)

Example 214

(R) and (S)-2-{3-[(4-Carbamimidoylphenylamino)-(9-methoxy-3,4-dihydro-2H-benzo[b][1,4]dioxepin-7-yl)methyl]-5-oxo-4,5-dihydro[1,2,4]triazol-1-yl}benzoic acid amide acetate

[Chemical Formula 545]

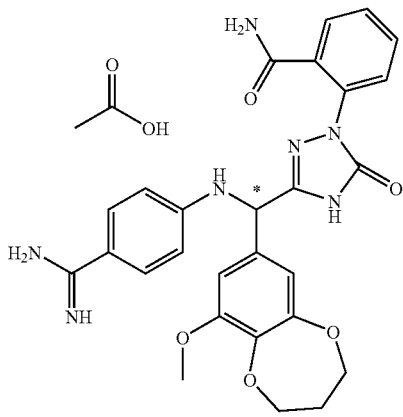

The same procedure was carried out as in Example (211), except that {2-(9-methoxy-3,4-dihydro-2H-benzo[b][1,4]dioxepin-7-yl)-2-[4-(5-methyl-[1,2,4]oxadiazol-3-yl)phenylimino]-1-methylsulfanylethylidene}carbamic acid methyl ester (Example (30c)) was used instead of [2-(8-methoxy-4H-benzo[1,3]dioxin-6-yl)-2-[4-(5-methyl-[1,2,4]oxadiazol-3-yl)phenylimino]-1-methylsulfanylethylidene]carbamic acid methyl ester (Example (21h)), to give the first eluting enantiomer of the title compound.

$^1$H-NMR (CD$_3$OD) δ 1.91 (s, 3H) 2.11-2.19 (m, 2H) 3.83 (s, 3H) 4.14 (dd, J=6.0, 11.2 Hz, 4H) 5.56 (s, 1H) 6.79 (d, J=2.0 Hz, 1H) 6.83-6.86 (m, 1H) 6.85-6.88 (m, 2H) 7.43-7.49 (m, 1H) 7.51-7.59 (m, 2H) 7.62 (d, J=8.8 Hz, 2H) 7.61-7.67 (m, 1H)

HPLC retention time: 11 min (Column name: SUMICHIRAL OA-2500, 30 mmφ×25 cm, Manufacturer: Sumika Chemical Analysis Service, Ltd., Mobile phase: 0.05 M ammonium acetate-methanol solution, Elution rate: 20 ml/min)

Example 215

(R) and (S)-3-{3-[(4-Carbamimidoylphenylamino)-(4-fluoro-7-methoxy-2,3-dihydrobenzofuran-5-yl)methyl]-5-oxo-4,5-dihydro[1,2,4]triazol-1-yl}thiophene-2-carboxylic acid

[Chemical Formula 546]

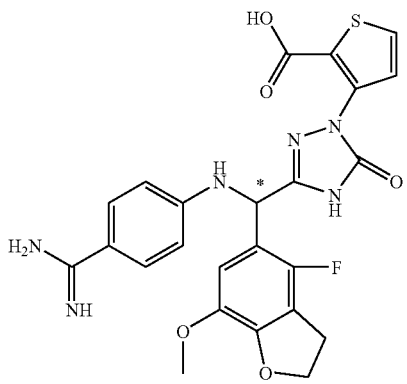

The same procedure was carried out as in Examples (168b) to (168d), except that [2-(4-cyanophenylimino)-2-(4-fluoro-7-methoxy-2,3-dihydrobenzofuran-5-yl)-1-methylsulfanylethylidene]carbamic acid methyl ester (Example (161b)) was used instead of [2-(4-cyanophenylimino)-2-(5-fluoro-8-methoxy-2,3-dihydrobenzo[1,4]dioxin-6-yl)-1-methylsulfanylethylidene]carbamic acid methyl ester in Example (168b), to give the first eluting enantiomer of the title compound.

$^1$H-NMR (CD$_3$OD) δ 3.25-3.35 (m, 2H) 3.78 (s, 3H) 4.66 (t, J=8.8 Hz, 2H) 5.83 (s, 1H) 6.84 (d, J=8.8 Hz, 2H) 6.94 (d, J=6.4 Hz, 1H) 7.07 (d, J=5.2 Hz, 1H) 7.42 (d, J=5.2 Hz, 1H) 7.61 (d, J=8.8 Hz, 2H)

HPLC retention time: 13 min (Column name: SUMICHIRAL OA-2500, 30 mmφ×25 cm, Manufacturer: Sumika Chemical Analysis Service, Ltd., Mobile phase: 0.05 M ammonium acetate-methanol solution, Elution rate: 20 ml/min)

Example 216

(R) and (S)-4-{[[2-Fluoro-3-(2-hydroxyethoxymethyl)-5-methoxyphenyl]-(5-oxo-1-pyrimidin-2-yl-4,5-dihydro-1H-[1,2,4]triazol-3-yl)methyl]amino}benzamidine acetate

(216a) (3-Dimethoxymethyl-2-fluoro-5-methoxyphenyl)methanol

[Chemical Formula 547]

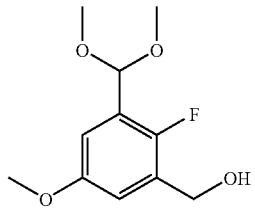

To 15 ml of a THF solution containing 3.665 g of 2-dimethoxymethyl-1-fluoro-4-methoxybenzene [CAS No. 883576-30-5] and 3.48 g of N,N,N',N',N''-pentamethyldiethylenetriamine, 7.1 ml of n-butyllithium (2.66 M, hexane solution) was added dropwise at −74° C. The resulting mixture was stirred at −60° C. for 3 hours, and then 3 ml of N-formylmorpholine was added thereto. The temperature of the reaction mixture was slowly allowed to rise to room temperature. Then, water was added to the reaction mixture while cooling on ice, and then the mixture was extracted with a mixture of hexane and t-butylmethyl ether and dried over anhydrous magnesium sulfate. The desiccating agent was removed by filtration, and the filtrate was concentrated under reduced pressure to give a crude product of 3-dimethoxymethyl-2-fluoro-5-methoxybenzaldehyde.

Then, this compound was dissolved in 30 ml of THF and 30 ml of water, and 3 g of sodium tetrahydroborate was further added thereto. The resulting mixture was stirred at room temperature for 1 hour, and then water was added thereto. The mixture was extracted with ethyl acetate. The organic layer was dried over anhydrous magnesium sulfate. The desiccating agent was removed by filtration, and the filtrate was concentrated under reduced pressure. The residue was purified by silica gel column chromatography (heptane-ethyl acetate) to give the title compound (3.889 g).

$^1$H-NMR (CD$_3$OD) δ 3.45 (s, 6H) 3.78 (s, 3H) 4.63 (s, 2H) 5.56 (s, 1H) 6.96 (dd, J=3.2, 4.8 Hz, 1H) 7.01 (dd, J=3.2, 6.0 Hz, 1H)

(216b) 2-[2-(3-Dimethoxymethyl-2-fluoro-5-methoxybenzyloxy)ethoxy]tetrahydropyran

[Chemical Formula 548]

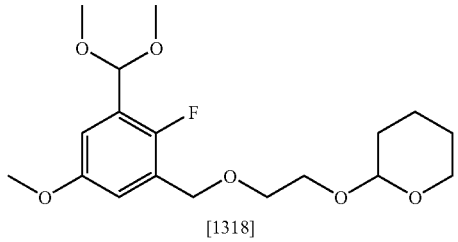

[1318]

(3-Dimethoxymethyl-2-fluoro-5-methoxyphenyl)methanol (1.861 g) was dissolved in 10 ml of DMF, and 390 mg of sodium hydride, 300 mg of tetrabutylammonium iodide, and 1.8 ml of 2-(2-bromoethoxy)tetrahydropyran were added thereto. The mixture was stirred at room temperature for 2 hours, and then water was added thereto. The mixture was extracted with ethyl acetate. The organic layer was dried over anhydrous magnesium sulfate. The desiccating agent was removed by filtration, and the filtrate was concentrated under reduced pressure. The residue was purified by silica gel column chromatography (heptane-ethyl acetate) to give the title compound (1.035 g).

$^1$H-NMR (CD$_3$OD) δ 1.45-1.62 (m, 4H) 1.66-1.74 (m, 1H) 1.78-1.88 (m, 1H) 3.35 (s, 6H) 3.46-3.54 (m, 1H) 3.58-3.64 (m, 1H) 3.69 (t, J=4.8 Hz, 2H) 3.78 (s, 3H) 3.83-3.90 (m, 2H) 4.59-4.62 (m, 2H) 4.64 (t, J=4.8 Hz, 1H) 5.55 (s, 1H) 6.97-7.03 (m, 2H)

(216c) 2-Fluoro-3-(2-hydroxyethoxymethyl)-5-methoxybenzaldehyde

[Chemical Formula 549]

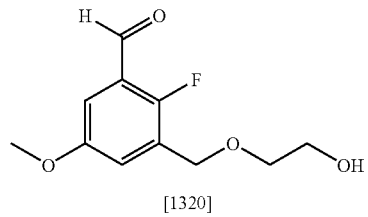

[1320]

2-[2-(3-Dimethoxymethyl-2-fluoro-5-methoxybenzyloxy)ethoxy]tetrahydropyran (1.035 g) was dissolved in 10 ml of THF and 3 ml of water, and 1 g of p-toluenesulfonic acid was added thereto. The resulting mixture was stirred at room temperature overnight, and then water was added thereto. The mixture was extracted with ethyl acetate. The organic layer was dried over anhydrous magnesium sulfate. The desiccating agent was removed by filtration, and the filtrate was concentrated under reduced pressure. The residue was purified by silica gel column chromatography (heptane-ethyl acetate) to give the title compound (305 mg).

$^1$H-NMR (CDCl$_3$) δ 3.67 (t, J=4.4 Hz, 2H) 3.80 (t, J=4.4 Hz, 2H) 3.83 (s, 3H) 4.65 (s, 2H) 7.23-7.25 (m, 2H) 10.33 (s, 1H)

(216d) 2-Fluoro-5-methoxy-3-(2-triisopropylsilanyloxyethoxymethyl)benzaldehyde

[Chemical Formula 550]

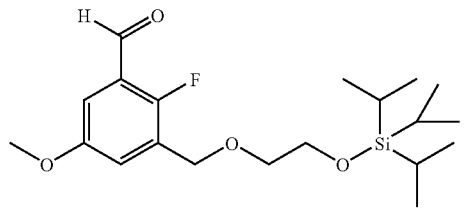

2-Fluoro-3-(2-hydroxyethoxymethyl)-5-methoxybenzaldehyde (305 mg) was dissolved in 3 ml of DMF, and 300 mg of imidazole and 283 mg of chlorotriisopropylsilane were added thereto. The resulting mixture was stirred at 50° C. for 2 hours, and then water was added thereto. The mixture was extracted with ethyl acetate. The organic layer was dried over anhydrous magnesium sulfate. The desiccating agent was removed by filtration, and the filtrate was concentrated under reduced pressure to give a crude product of the title compound (533 mg).

(216e) {2-(4-Cyanophenylimino)-2-[2-fluoro-3-(2-hydroxyethoxymethyl)-5-methoxyphenyl]-1-methylsulfanylethylidene}carbamic acid methyl ester

[Chemical Formula 551]

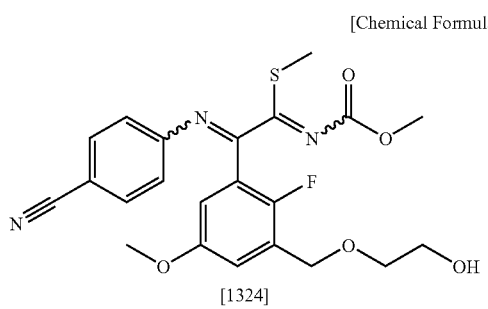

[1324]

The same procedure was carried out as in Examples (163a) to (163b), except that 2-fluoro-5-methoxy-3-(2-triisopropyl-silanyloxyethoxymethyl)benzaldehyde was used instead of 2-fluoro-5-methoxy-3-triisopropylsilanyloxybenzaldehyde in Example (163a), to give the title compound.

(216f) 4-{[[2-Fluoro-3-(2-hydroxyethoxymethyl)-5-methoxyphenyl]-(5-oxo-1-pyrimidin-2-yl-4,5-dihydro-1H-[1,2,4]triazol-3-yl)methyl]amino}benzonitrile

[Chemical Formula 552]

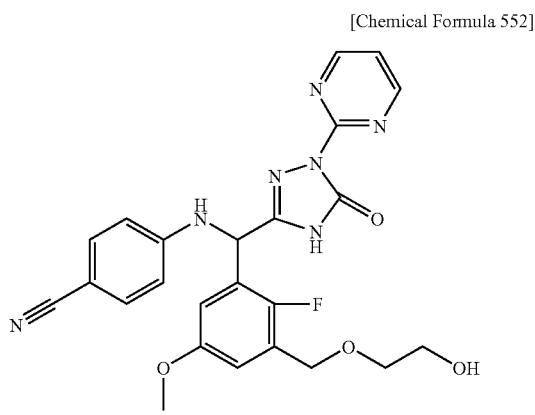

The same procedure was carried out as in Example (3f), except that {2-(4-cyanophenylimino)-2-[2-fluoro-3-(2-hydroxyethoxymethyl)-5-methoxyphenyl]-1-methylsulfanylethylidene}carbamic acid methyl ester was used instead of {2-[2-fluoro-3-(2-fluoroethoxy)-5-methoxyphenyl]-2-[4-(5-methyl-[1,2,4]oxadiazol-3-yl)phenylimino]-1-methylsulfanylethylidene}carbamic acid methyl ester, to give the title compound.

(216g) 4-{[[2-Fluoro-3-(2-hydroxyethoxymethyl)-5-methoxyphenyl]-(5-oxo-1-pyrimidin-2-yl-4,5-dihydro-1H-[1,2,4]triazol-3-yl)methyl]amino}benzamidine acetate

[Chemical Formula 553]

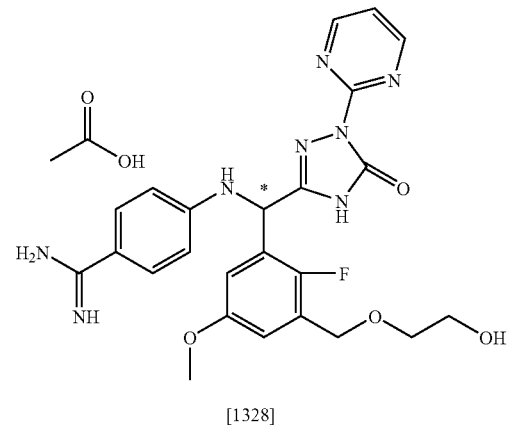

[1328]

The same procedure was carried out as in Example (181d), except that 4-{[[2-fluoro-3-(2-hydroxyethoxymethyl)-5-methoxyphenyl]-(5-oxo-1-pyrimidin-2-yl-4,5-dihydro-1H-[1,2,4]triazol-3-yl)methyl]amino}benzonitrile was used instead of 4-({[2-fluoro-3-(2-hydroxyethoxy)-5-methoxyphenyl]-(5-oxo-1-pyrimidin-2-yl-4,5-dihydro-1H-[1,2,4]triazol-3-yl)methyl}amino)benzonitrile, to give the first eluting enantiomer of the title compound.

$^1$H-NMR (CD$_3$OD) δ 1.92 (s, 3H) 3.60 (t, J=4.8 Hz, 2H) 3.70 (t, J=4.8 Hz, 2H) 3.74 (s, 3H) 4.62-4.64 (m, 2H) 5.94 (s, 1H) 6.85 (d, J=8.8 Hz, 2H) 7.03 (d, J=5.6 Hz, 2H) 7.30 (t, J=4.8 Hz, 1H) 7.61 (d, J=8.8 Hz, 2H) 8.76 (d, J=4.8 Hz, 2H)

HPLC retention time: 8 min (Column name: SUMICHIRAL OA-2500, 30 mmφ×25 cm, Manufacturer: Sumika Chemical Analysis Service, Ltd., Mobile phase: 0.05 M ammonium acetate-methanol solution, Elution rate: 20 ml/min)

Example 217

(R) and (S)-4-{[[2-Fluoro-3-((S)-2-hydroxy-1-methylethoxy)-5-methoxyphenyl]-(5-oxo-1-pyrimidin-2-yl-4,5-dihydro-1H-[1,2,4]triazol-3-yl)methyl]amino}benzamidine acetate (217a) {2-{3-[(S)-2-(t-Butyldimethylsilanyloxy)-1-methylethoxy]-2-fluoro-5-methoxyphenyl}-2-[4-(5-methyl-[1,2,4]oxadiazol-3-yl)phenylimino]-1-methylsulfanylethylidene}carbamic acid methyl ester

[Chemical Formula 554]

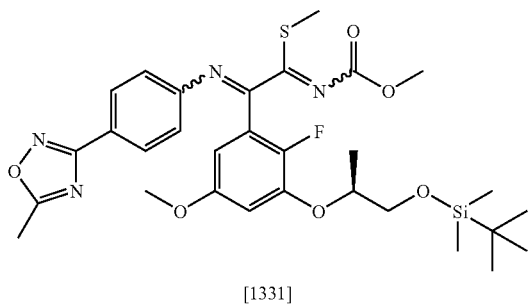

[1331]

[2-(2-Fluoro-3-hydroxy-5-methoxyphenyl)-2-[4-(5-methyl-[1,2,4]oxadiazol-3-yl)phenylimino]-1-methylsulfanylethylidene]carbamic acid methyl ester (Example (3d), 275 mg), (R)-1-(t-butyldimethylsilanyloxy)propan-2-ol [CAS No. 136918-07-5] (171 mg), and triphenylphosphine (236 mg) were dissolved in 3 ml of THF under a nitrogen atmosphere, and the resulting mixture was cooled to −78° C. After the addition of 0.177 ml of N,N'-diisopropylazodicarboxylate, the mixture was allowed to warm to room temperature with stirring overnight. The reaction mixture was concentrated, and the residue was purified by silica gel column chromatography (heptane-ethyl acetate) to give the title compound (343 mg).

(217b) 4-{[[2-Fluoro-3-((S)-2-hydroxy-1-methylethoxy)-5-methoxyphenyl]-(5-oxo-1-pyrimidin-2-yl-4,5-dihydro-1H-[1,2,4]triazol-3-yl)methyl]amino}benzamidine acetate

[Chemical Formula 555]

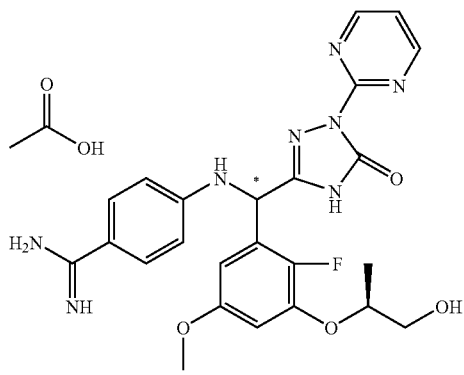

The same procedure was carried out as in Examples (3e) to (3h), except that {2-{3-[(S)-2-(t-butyldimethylsilanyloxy)-1-methylethoxy]-2-fluoro-5-methoxyphenyl}-2-[4-(5-methyl-[1,2,4]oxadiazol-3-yl)phenylimino]-1-methylsulfanylethylidene}carbamic acid methyl ester was used instead of [2-(2-fluoro-3-hydroxy-5-methoxyphenyl)-2-[4-(5-methyl-[1,2,4]oxadiazol-3-yl)phenylimino]-1-methylsulfanylethylidene]carbamic acid methyl ester in Example (3e), to give the first eluting enantiomer of the title compound.

$^1$H-NMR (CD$_3$OD) δ 1.26 (d, J=6.0 Hz, 3H) 1.91 (s, 3H) 3.60-3.69 (m, 2H) 3.66 (s, 3H) 4.41-4.48 (m, 1H) 5.96 (s, 1H) 6.61-6.66 (m, 2H) 6.83 (d, J=8.8 Hz, 2H) 7.28 (t, J=4.8 Hz, 1H) 7.59 (d, J=8.8 Hz, 2H) 8.73 (d, J=4.8 Hz, 2H)

HPLC retention time: 14 min (Column name: SUMICHIRAL OA-2500, 30 mmφ×25 cm, Manufacturer: Sumika Chemical Analysis Service, Ltd., Mobile phase: 0.05 M ammonium acetate-methanol solution, Elution rate: 20 ml/min)

Example 218

(R) and (S)-2-Fluoro-4-{[[2-fluoro-3-(2-hydroxyethoxy)-5-methoxyphenyl]-(5-oxo-1-pyrimidin-2-yl-4,5-dihydro-1H-[1,2,4]triazol-3-yl)methyl]amino}benzamidine acetate (218a) [2-(4-Cyano-3-fluorophenylimino)-2-(2-fluoro-3-hydroxy-5-methoxyphenyl)-1-methylsulfanylethylidene]carbamic acid methyl ester

[Chemical Formula 556]

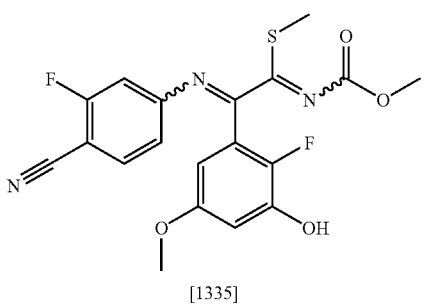

[1335]

2-Fluoro-4-aminobenzonitrile [CAS No. 53312-80-4] (1.02 g), MS3A (7 g), and Yb(OTf)$_3$ (465 mg) were added to 30 ml of a THF solution containing 2.45 g of 2-fluoro-5-methoxy-3-triisopropylsilanyloxybenzaldehyde (Example (3b)) under a nitrogen atmosphere. The resulting mixture was stirred at room temperature for 2 hours, and then 1.1 ml of trimethylsilyl cyanide was added thereto. The mixture was stirred at room temperature for 3 days. The reaction mixture was filtered, and the filtrate was concentrated under reduced pressure. The residue was purified by silica gel column chromatography (ethyl acetate-heptane) to give 4-{[cyano-(2-fluoro-5-methoxy-3-triisopropylsilanyloxyphenyl)methyl]amino}-2-fluorobenzonitrile (2.05 g) as a yellow oil.

To 30 ml of a methanol:THF=2:1 mixed solvent solution containing this compound, 30 ml of a 20% ammonium sulfide aqueous solution was added. The resulting mixture was stirred at room temperature overnight, and then water was added thereto. The mixture was extracted with ethyl acetate. The organic layer was washed with water and saturated brine and dried over anhydrous sodium sulfate. The desiccating agent was removed by filtration, and the filtrate was concentrated under reduced pressure. The residue was purified by silica gel column chromatography (ethyl acetate-heptane) to give 2-(4-cyano-3-fluorophenylamino)-2-(2-fluoro-5-methoxy-3-triisopropylsilanyloxyphenyl)thioacetamide (1.55 g) as a white solid. Me$_3$O$^+$BF$_4^-$ (498 mg) was added to 15 ml of an acetonitrile solution of this compound. The resulting mixture was stirred at room temperature for 40 minutes under a nitrogen atmosphere, and then a saturated sodium hydrogen carbonate aqueous solution was added thereto. The mixture was extracted with ethyl acetate. The organic layer was washed with water and saturated brine and dried over anhydrous magnesium sulfate. The desiccating agent was removed by filtration, and the filtrate was concentrated under reduced pressure.

To 15 ml of an ethyl acetate solution containing the residue, 3 g of manganese dioxide was added, and the resulting mixture was stirred at room temperature for 30 minutes. The reaction mixture was filtered, and the filtrate was concentrated under reduced pressure.

To 10 ml of a toluene solution of the residue, 1.4 ml of 2,4,6-collidine and 0.7 ml of methyl chloroformate were added. The resulting mixture was stirred at 80° C. for 4 hours under a nitrogen atmosphere. The reaction mixture was filtered, and 1N hydrochloric acid was added to the filtrate. The mixture was extracted with ethyl acetate. The organic layer was washed with water and saturated brine and dried over anhydrous magnesium sulfate. The desiccating agent was removed by filtration, and the filtrate was concentrated under reduced pressure. The residue was purified by silica gel column chromatography (ethyl acetate-heptane) to give [2-[4-cyano-3-fluorophenylimino]-2-(2-fluoro-5-methoxy-3-triisopropylsilanyloxyphenyl)-1-methylsulfanylethylidene]carbamic acid methyl ester (824 mg) as a yellow oil.

To 15 ml of a THF solution of this compound, 1.5 ml of TBAF (1.0 M, THF solution) was added. The resulting mixture was stirred at room temperature for 1 hour, and a saturated ammonium chloride aqueous solution was added thereto. The mixture was extracted with ethyl acetate. The organic layer was washed with water and saturated brine and dried over anhydrous magnesium sulfate. The desiccating agent was removed by filtration, and the filtrate was concentrated under reduced pressure. The residue was purified by silica gel column chromatography (ethyl acetate-heptane) to give the title compound (466 mg) as a yellow solid.

Mass spectrum (ESI) m/z: 420 (M+H)$^+$ (218b) (R) and (S)-2-Fluoro-4-{[[2-fluoro-3-(2-hydroxyethoxy)-5-methoxyphenyl]-(5-oxo-1-pyrimidin-2-yl-4,5-dihydro-1H-[1,2,4]triazol-3-yl)methyl]amino}benzamidine acetate

[Chemical Formula 557]

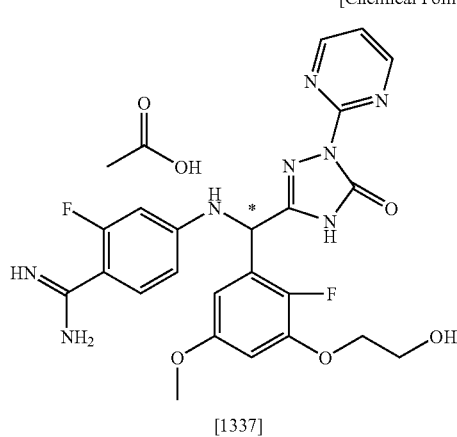

[1337]

To 2 ml of a DMF solution containing 200 mg of [2-(4-cyano-3-fluorophenylimino)-2-(2-fluoro-3-hydroxy-5-methoxyphenyl)-1-methylsulfanylethylidene]carbamic acid methyl ester, 300 mg of potassium carbonate and 0.2 ml of 2-(2-bromoethoxy)tetrahydro-2H-pyran were added. The resulting mixture was stirred at room temperature for 18 hours, and then water was added thereto. The mixture was extracted with ethyl acetate. The organic layer was washed with water and then with 5 saturated brine and dried over anhydrous sodium sulfate. The desiccating agent was removed by filtration, and the filtrate was concentrated under reduced pressure. The residue was purified by silica gel column chromatography (ethyl acetate-heptane) to give (2-(4-cyano-3-fluorophenylimino)-2-{2-fluoro-5-methoxy-3-[2-(tetrahydropyran-2-yloxy)ethoxy]phenyl}-1-methylsulfanylethylidene)carbamic acid methyl ester (150 mg) as a yellow oil.

To 1.5 ml of a DMF solution of this compound, 30 mg of 2-hydrazinopyrimidine and 0.038 ml of triethylamine were added. The resulting mixture was stirred at 70° C. for 23 hours under a nitrogen atmosphere. The reaction mixture was concentrated. The residue was dissolved in 1.5 ml of THF, 1.5 ml of methanol, and 0.1 ml of acetic acid, and 200 mg of sodium cyanotrihydroborate was added to this mixture. The mixture was stirred at room temperature for 4 hours. The reaction mixture was concentrated, and the residue was crudely purified by NAM silica gel column chromatography (methanol-ethyl acetate) to give a crude product of 2-fluoro-4-{[{2-fluoro-5-methoxy-3-[2-(tetrahydropyran-2-yloxy)ethoxy]phenyl}-(5-oxo-1-pyrimidin-2-yl-4,5-dihydro-1H-[1,2,4]triazol-3-yl)methyl]amino}benzonitrile.

To 1.9 ml of pyridine solution of this crude product, 0.306 ml of triethylamine and 1.9 ml of a 20% ammonium sulfide aqueous solution were added. The resulting mixture was stirred at 50° C. for 2 hours under a nitrogen atmosphere and then purified by reverse-phase high performance liquid chromatography (acetonitrile-water, 0.1% acetic acid) to give 2-fluoro-4-{[{2-fluoro-5-methoxy-3-[2-(tetrahydropyran-2-yloxy)ethoxy]phenyl}-(5-oxo-1-pyrimidin-2-yl-4,5-dihydro-1H-[1,2,4]triazol-3-yl)methyl]amino}thiobenzamide (44 mg) as a light yellow solid.

To 1.5 ml of an acetonitrile solution of this compound, 12 mg of Me$_3$O$^+$BF$_4^-$ was added. The resulting mixture was stirred at room temperature for 3 hours under a nitrogen atmosphere, and then 1 ml of acetonitrile, 1 ml of isopropanol, and 0.04 ml of 1,1,3,3-tetramethyldisilazane were added thereto. The mixture was stirred at 70° C. for 2 hours under a nitrogen atmosphere and then concentrated. To the residue, 1.5 ml of a methanol:water:acetic acid=1:1:1 mixed solvent was added. The mixture was stirred at 60° C. for 3 hours and purified by reverse-phase high performance liquid chromatography (acetonitrile-water, 0.1% acetic acid) to give 2-fluoro-4-{[[2-fluoro-3-(2-hydroxyethoxy)-5-methoxyphenyl]-(5-oxo-1-pyrimidin-2-yl-4,5-dihydro-1H-[1,2,4]triazol-3-yl)methyl]amino}benzamidine acetate.

Mass spectrum (ESI) m/z: 513 (M+H)$^+$

This compound was optically resolved using a SUMICHIRAL OA-2500 column, and the first eluting enantiomer (6.79 mg) of the title compound was obtained as a white solid.

$^1$H-NMR (CD$_3$OD) δ 1.92 (s, 3H) 3.71 (s, 3H) 3.88 (t, J=4.8 Hz, 2H) 4.09 (t, J=4.8 Hz, 2H) 5.91 (s, 1H) 6.50-6.74 (m, 4H) 7.29 (t, J=4.8 Hz, 1H) 7.46 (t, J=8.4 Hz, 1H) 8.75 (d, J=4.8 Hz, 2H)

HPLC retention time: 11 min (Column name: SUMICHIRAL OA-2500, 30 mmφ×25 cm, Manufacturer: Sumika Chemical Analysis Service, Ltd., Mobile phase: 0.05 M ammonium acetate-methanol solution, Elution rate: 30 ml/min)

Example 219

(R) and (S)-4-{[[5-Ethoxy-2-fluoro-3-(2-hydroxy-ethoxy)phenyl]-(5-oxo-1-pyrimidin-2-yl-4,5-dihydro-1H-[1,2,4]triazol-3-yl)methyl]amino}benzamidine acetate

(219a) {2-(5-Ethoxy-2-fluoro-3-hydroxyphenyl)-2-[4-(5-methyl-[1,2,4]oxadiazol-3-yl)phenylimino]-1-methylsulfanylethylidene}carbamic acid methyl ester

[Chemical Formula 558]

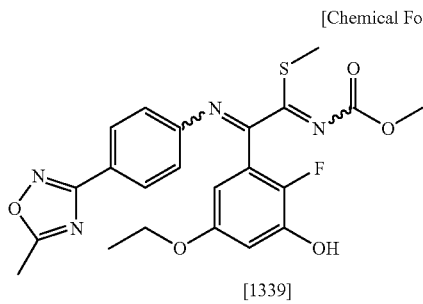

[1339]

To 150 ml of a THF solution containing 10.5 g of 1-ethoxy-4-fluorobenzene, 50 ml of n-butyllithium (1.58 M, hexane solution) was added dropwise at −78° C. under a nitrogen atmosphere. The resulting mixture was stirred for 4 and a half hours, then 8.9 ml of trimethoxy boron was added thereto. Then, the temperature of the mixture was slowly allowed to rise to room temperature. The reaction mixture was stirred for 3 and a half hours, then 12.9 ml of acetic acid and 12.7 ml of a 30% hydrogen peroxide aqueous solution were added thereto at 0° C. The mixture was stirred at room temperature overnight, and then a saturated sodium sulfite aqueous solution was added thereto. The mixture was extracted with ethyl acetate. The organic layer was washed with water and saturated brine and dried over anhydrous magnesium sulfate. The desiccating agent was removed by filtration, and the filtrate was concentrated under reduced pressure. The residue was crudely purified by silica gel column chromatography (ethyl acetate-heptane) to give a crude product of 5-ethoxy-2-fluorophenol.

To 100 ml of a DMF solution of this crude product, 3.06 g of imidazole and 6.4 ml of chlorotriisopropylsilane were added. The resulting mixture was stirred at room temperature overnight, and water was added thereto. The mixture was extracted with diethyl ether. The organic layer was washed with 1 N hydrochloric acid cooled with ice, water, a saturated sodium hydrogen carbonate aqueous solution, water, and saturated brine in this order. The organic layer was dried over anhydrous magnesium sulfate. The desiccating agent was removed by filtration, and the filtrate was concentrated under reduced pressure. The residue was purified by silica gel column chromatography (ethyl acetate-heptane) to give (5-ethoxy-2-fluorophenoxy)triisopropylsilane (4.06 g) as a colorless oil.

To 50 ml of a THF solution containing this compound and 2.85 ml of N,N,N',N',N''-pentamethyldiethylene triamine, 8.6 ml of n-butyllithium (1.58 M, hexane solution) was added dropwise at −78° C. under a nitrogen atmosphere. The resulting mixture was stirred for 7 hours at a temperature range of −60 to −65° C., and then 1.7 ml of N-formylmorpholine was added thereto. The temperature of the mixture was allowed to rise to room temperature. The reaction mixture was stirred overnight, and saturated ammonium chloride aqueous solution was added thereto. The mixture was extracted with ethyl acetate. The organic layer was washed with water and saturated brine and dried over anhydrous magnesium sulfate. The desiccating agent was removed by filtration, and the filtrate was concentrated under reduced pressure. The residue was purified by silica gel column chromatography (ethyl acetate-heptane) to give 5-ethoxy-2-fluoro-3-triisopropylsilanyloxy-benzaldehyde (4.04 g) as a light yellow oil. To 100 ml of a dichloromethane solution of this compound, 2.01 g of 4-(5-methyl-[1,2,4]oxadiazol-3-yl)phenylamine, 10 g of MS3A, 738 mg of Yb(OTf)$_3$, and 3.0 ml of trimethylsilyl cyanide were added under a nitrogen atmosphere. The resulting mixture was stirred at room temperature for 3 days and then filtered. The filtrate was concentrated under reduced pressure. The residue was purified by silica gel column chromatography (ethyl acetate-heptane) to give (5-ethoxy-2-fluoro-3-triisopropylsilanyloxyphenyl)-[4-(5-methyl-[1,2,4]oxadiazol-3-yl)phenylamino]acetonitrile (1.68 g) was a yellow oil.

To 60 ml of a methanol:THF=2:1 mixed solvent solution containing this compound, 20 ml of a 20% ammonium sulfide aqueous solution was added. The resulting mixture was stirred at room temperature overnight, and then water was added thereto. The mixture was extracted from ethyl acetate. The organic layer was washed with water and saturated brine and then dried over anhydrous sodium sulfate. The desiccating agent was removed by filtration, and the filtrate was concentrated under reduced pressure.

To 5 ml of a DMF solution of the residue, 327 mg of imidazole and 0.51 ml of chlorotriisopropylsilane were added. The resulting mixture was stirred at room temperature for 7 and a half hours, and then water was added thereto. The mixture was extracted with ethyl acetate. The organic layer was washed with water and saturated brine and then dried over anhydrous sodium sulfate. The desiccating agent was removed by filtration, and the filtrate was concentrated under reduced pressure. The residue was purified by silica gel column chromatography (ethyl acetate-heptane) to give 2-(5-ethoxy-2-fluoro-3-triisopropylsilanyloxyphenyl)-2-[4-(5-methyl-[1,2,4]oxadiazol-3-yl)phenylamino]thioacetamide (1.49 g) as a light yellow oil.

To 20 ml of a dichloromethane solution of this compound, 454 mg of Me$_3$O$^+$BF$_4^-$ was added. The resulting mixture was stirred at room temperature for 4 hours under a nitrogen atmosphere, and then water was added thereto. The mixture was extracted with ethyl acetate. The organic layer was washed with a saturated sodium hydrogen carbonate aqueous solution, water, and saturated brine and then dried over anhydrous sodium sulfate. The desiccating agent was removed by filtration, and the filtrate was concentrated under reduced pressure.

To 20 ml of a dichloromethane solution of the residue, 5 g of manganese dioxide was added, and the resulting mixture was stirred at room temperature for 2 hours. The reaction mixture was filtered, and the filtrate was concentrated under reduced pressure.

To 10 ml of a toluene solution of the residue, 1.28 ml of 2,4,6-collidine and 0.64 ml of methyl chloroformate were added. The resulting mixture was stirred at 80° C. overnight under a nitrogen atmosphere. The reaction mixture was filtered, and water was added to the filtrate. The mixture was extracted with ethyl acetate. The organic layer was washed with 1 N hydrochloric acid cooled with ice, water, a saturated sodium hydrogen carbonate aqueous solution, water, and saturated brine in this order, and then dried over anhydrous sodium sulfate. The desiccating agent was removed by filtration, and the filtrate was concentrated under reduced pressure. The residue was purified by silica gel column chromatography (ethyl acetate-heptane) to give 2-(5-ethoxy-2-fluoro-3-triisopropylsilanyloxyphenyl)-2-[4-(5-methyl-[1,2,4]oxadiazol-3-yl)phenylimino]-1-methylsulfanylethylidene}carbamic acid methyl ester (1.45 g) as a yellow oil.

To 20 ml of a THF solution of this compound, 2.42 ml of TBAF (1.0 M, THF solution) was added. The resulting mixture was stirred at 0° C. for 3 hours, and then a saturated ammonium chloride aqueous solution was added thereto. The mixture was extracted with ethyl acetate. The organic layer was washed with water and saturated brine and then dried over anhydrous sodium sulfate. The desiccating agent was removed by filtration, and the filtrate was concentrated under reduced pressure. The residue was purified by silica gel column chromatography (ethyl acetate-heptane) to give the title compound (866 mg) as a yellow solid.

$^1$H-NMR (CDCl$_3$) Two main isomers:
δ 1.31 (t, J=7.2 Hz, 3H) 2.47 (s, 3H) 2.62 (s, 3H) 3.62 (s, 3H) 3.84 (q, J=7.2 Hz, 2H) 5.17 (br.d, J=3.6 Hz, 1H) 6.19 (dd, J=2.8, 4.8 Hz, 1H) 6.53 (dd, J=2.8, 6.8 Hz, 1H) 6.84 (d, J=8.8 Hz, 2H) 7.90 (d, J=8.8 Hz, 2H)
δ 1.40 (t, J=6.8 Hz, 3H) 2.33 (s, 3H) 2.66 (s, 3H) 3.60 (s, 3H) 4.02 (q, J=6.8 Hz, 2H) 5.30 (br.d, J=4.8 Hz, 1H) 6.73 (dd, J=3.2, 6.8 Hz, 1H) 6.92 (dd, J=3.2, 5.2 Hz, 1H) 7.12 (d, J=8.8 Hz, 2H) 8.03 (d, J=8.8 Hz, 2H)

(219b) (R) and (S)-4-{[[5-Ethoxy-2-fluoro-3-(2-hydroxyethoxy)phenyl]-(5-oxo-1-pyrimidin-2-yl-4,5-dihydro-1H-[1,2,4]triazol-3-yl)methyl]amino}benzamidine acetate

[Chemical Formula 559]

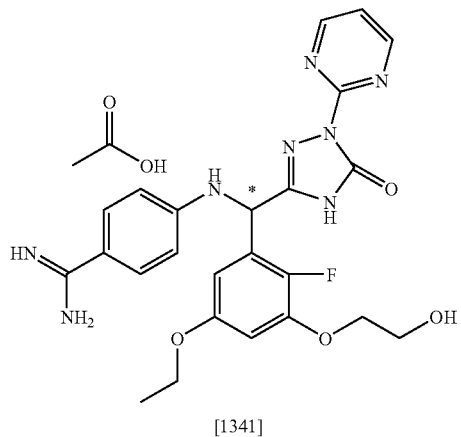

[1341]

To 2 ml of a DMF solution containing 75 mg of {2-(5-ethoxy-2-fluoro-3-hydroxyphenyl)-2-[4-(5-methyl-[1,2,4]oxadiazol-3-yl)phenylimino]-1-methylsulfanylethylidene}carbamic acid methyl ester, 100 mg of potassium carbonate and 0.1 ml of 2-(2-bromoethoxy)tetrahydro-2H-pyran were added. The resulting mixture was stirred at room temperature for 10 hours, and then water was added thereto. The mixture was extracted with ethyl acetate. The organic layer was washed with water and then dried through PRESEP™. The filtrate was concentrated, and the residue was purified by silica gel column chromatography (ethyl acetate-heptane) to give {2-{5-ethoxy-2-fluoro-3-[2-(tetrahydropyran-2-yloxy)ethoxy]phenyl}-2-[4-(5-methyl-[1,2,4]oxadiazol-3-yl)phenylimino]-1-methylsulfanylethylidene}carbamic acid methyl ester (51 mg) as a yellow oil.

To 1 ml of a DMF solution of this compound, 9.3 mg of 2-hydrazinopyrimidine and 0.012 ml of triethylamine were added. The resulting mixture was stirred at 85° C. for 18 hours under a nitrogen atmosphere. The reaction mixture was concentrated, and the residue was dissolved in 2 ml of methanol and 0.05 ml of acetic acid. To this mixture, 100 mg of sodium cyanotrihydroborate was added. The mixture was stirred at room temperature overnight and crudely purified by reverse-phase high performance liquid chromatography (acetonitrile-water, 0.1% acetic acid) to give a crude product of 5-{{5-ethoxy-2-fluoro-3-[2-(tetrahydropyran-2-yloxy)ethoxy]phenyl}-[4-(5-methyl-[1,2,4]oxadiazol-3-yl)phenylamino]methyl}-2-pyrimidin-2-yl-2,4-dihydro-[1,2,4]triazol-3-one. Iron powder (100 mg) was added to 3 ml of a methanol:water:acetic acid=1:1:1 mixed solvent solution containing this crude product. The mixture was stirred at 60° C. overnight under a nitrogen atmosphere. The reaction mixture was filtered and then purified by reverse-phase high performance liquid chromatography (acetonitrile-water, 0.1% acetic acid) to give 4-{[[5-ethoxy-2-fluoro-3-(2-hydroxyethoxy)phenyl]-(5-oxo-1-pyrimidin-2-yl-4,5-dihydro-1H-[1,2,4]triazol-3-yl)methyl]amino}benzamidine acetate.

Mass spectrum (ESI) m/z: 509 (M+H)$^+$

This compound was optically resolved using a SUMICHIRAL OA-2500 column, and the first eluting enantiomer (1.73 mg) of the title compound was obtained as a white solid.

$^1$H-NMR (CD$_3$OD) δ 1.30 (t, J=6.8 Hz, 3H) 1.91 (s, 3H) 3.87 (t, J=4.8 Hz, 2H) 3.93 (q, J=6.8 Hz, 2H) 4.08 (t, J=4.8 Hz, 2H) 5.92 (s, 1H) 6.56-6.68 (m, 2H) 6.85 (d, J=8.8 Hz, 2H) 7.28 (t, J=4.8 Hz, 1H) 7.60 (d, J=8.8 Hz, 2H) 8.75 (d, J=4.8 Hz, 2H)

HPLC retention time: 8 min (Column name: SUMICHIRAL OA-2500, 30 mmφ×25 cm, Manufacturer: Sumika Chemical Analysis Service, Ltd., Mobile phase: 0.05 M ammonium acetate-methanol solution, Elution rate: 40 ml/min)

Example 220

(R) and (S)-4-{[[3-Ethoxy-5-(2-hydroxyethoxy)phenyl]-(5-oxo-1-pyrimidin-2-yl-4,5-dihydro-1H-[1,2,4]triazol-3-yl)methyl]amino}benzamidine acetate

[Chemical Formula 560]

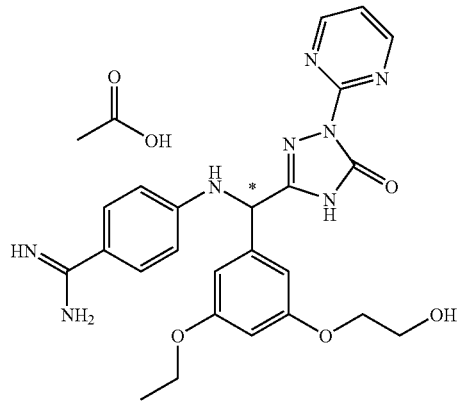

[1343]

To 1 ml of a DMF solution containing 80 mg of {2-(3-ethoxy-5-hydroxyphenyl)-2-[4-(5-methyl-[1,2,4]oxadiazol- 3-yl)phenylimino]-1-methylsulfanylethylidene}carbamic acid methyl ester (Example (78a)), 200 mg of potassium carbonate and 0.1 ml of 2-(2-bromoethoxy)tetrahydro-2H-pyran were added. The resulting mixture was stirred at room temperature overnight, and then water was added thereto. The mixture was extracted with ethyl acetate. The organic layer was washed with water and saturated brine and then concentrated. The residue was purified by silica gel column chromatography (ethyl acetate-heptane) to give {2-{3-ethoxy-5-[2-(tetrahydropyran-2-yloxy)ethoxy]phenyl}-2-[4-(5-methyl-[1,2,4]oxadiazol-3-yl)phenylimino]-1-methylsulfanylethylidene}carbamic acid methyl ester (76 mg) as a yellow oil.

To 1 ml of a DMF solution of this compound, 14 mg of 2-hydrazinopyrimidine and 0.018 ml of triethylamine were added. The resulting mixture was stirred at 85° C. for 28 hours under a nitrogen atmosphere, and the mixture was then concentrated. The residue was dissolved in 1 ml of methanol, 1 ml of THF, and 0.1 ml of acetic acid. Then, 100 mg of sodium cyanotrihydroborate was further added to the mixture. The resulting mixture was stirred at room temperature for 3 hours and then crudely purified by reverse-phase high performance liquid chromatography (acetonitrile-water, 0.1% acetic acid) to give a crude product of 5-{{3-ethoxy-5-[2-(tetrahydropyran-2-yloxy)ethoxy]phenyl}-[4-(5-methyl-[1,2,4]oxadiazol-3-yl)phenylamino]methyl}-2-pyrimidin-2-yl-2,4-dihydro-[1,2,4]triazol-3-one.

Iron powder (100 mg) was added to 3 ml of a methanol:water:acetic acid=1:1:1 mixed solvent solution containing this crude product. The resulting mixture was stirred at 60° C. for 2 days under a nitrogen atmosphere. The reaction mixture was filtered and purified by reverse-phase high performance liquid chromatography (acetonitrile-water, 0.1% acetic acid) to give 4-{[[3-ethoxy-5-(2-hydroxyethoxy)phenyl]-(5-oxo-1-pyrimidin-2-yl-4,5-dihydro-1H-[1,2,4]triazol-3-yl)methyl]amino}benzamidine acetate.

$^1$H-NMR (CD$_3$OD) δ 1.34 (t, J=6.8 Hz, 3H) 1.94 (s, 3H) 3.82 (t, J=4.4 Hz, 2H) 3.92-4.07 (m, 4H) 5.62 (s, 1H) 6.46 (t, J=2.0 Hz, 1H) 6.71 (br.s, 1H) 6.73 (br.s, 1H) 6.87 (d, J=8.8 Hz, 2H) 7.35 (t, J=4.8 Hz, 1H) 7.61 (d, J=8.8 Hz, 2H) 8.79 (d, J=4.8 Hz, 2H)

Mass spectrum (ESI) m/z: 491 (M+H)$^+$

This compound was optically resolved using a SUMICHIRAL OA-2500 column, and the first eluting enantiomer (3.17 mg) of the title compound was obtained as a white solid.

$^1$H-NMR (CD$_3$OD) δ 1.33 (t, J=7.2 Hz, 3H) 1.91 (s, 3H) 3.82 (t, J=4.8 Hz, 2H) 3.92-4.06 (m, 4H) 5.55 (s, 1H) 6.43 (t, J=1.6 Hz, 1H) 6.72 (t, J=1.6 Hz, 1H) 6.74 (t, J=1.6 Hz, 1H) 6.85 (d, J=9.2 Hz, 2H) 7.28 (t, J=4.8 Hz, 1H) 7.59 (d, J=9.2 Hz, 2H) 8.76 (d, J=4.8 Hz, 2H)

HPLC retention time: 7 min (Column name: SUMICHIRAL OA-2500, 30 mmφ×25 cm, Manufacturer: Sumika Chemical Analysis Service, Ltd., Mobile phase: 0.05 M ammonium acetate-methanol solution, Elution rate: 40 ml/min)

Example 221

(R) and (S)-4-{[(3-Ethoxy-5-hydroxyphenyl)-(5-oxo-1-pyrimidin-2-yl-4,5-dihydro-1H-[1,2,4]triazol-3-yl)methyl]amino}benzamidine acetate

[Chemical Formula 561]

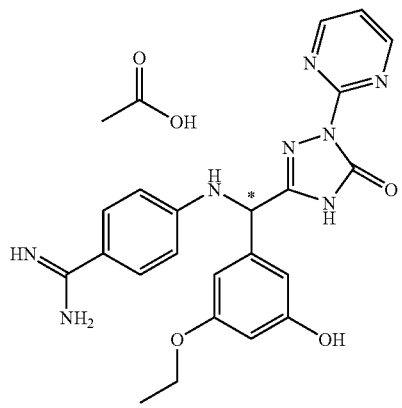

To 1 ml of a DMF solution containing 45 mg of {2-(3-ethoxy-5-hydroxyphenyl)-2-[4-(5-methyl-[1,2,4]oxadiazol-3-yl)phenylimino]-1-methylsulfanylethylidene}carbamic acid methyl ester (Example (78a)), 11 mg of 2-hydrazinopyrimidine and 0.014 ml of triethylamine were added. The resulting mixture was stirred at 85° C. for one day under a nitrogen atmosphere and then concentrated. The residue was dissolved in 1 ml of methanol, 1 ml of THF, and 0.1 ml of acetic acid, and 100 mg of sodium cyanotrihydroborate was further added thereto. The mixture was stirred at room temperature for 3 hours. The reaction mixture was crudely purified by reverse-phase high performance liquid chromatography (acetonitrile-water, 0.1% acetic acid) to give a crude product of 5-{(3-ethoxy-5-hydroxyphenyl)-[4-(5-methyl-[1,2,4]oxadiazol-3-yl)phenylamino]methyl}-2-pyrimidin-2-yl-2,4-dihydro-[1,2,4]triazol-3-one.

Iron powder (100 mg) was added to 3 ml of a methanol:water:acetic acid=1:1:1 mixed solvent solution containing this crude compound. The resulting mixture was stirred at 60° C. for 2 days under a nitrogen atmosphere. The reaction mixture was filtered and purified by reverse-phase high performance liquid chromatography (acetonitrile-water, 0.1% acetic acid) to give 4-{[(3-ethoxy-5-hydroxyphenyl)-(5-oxo-1-pyrimidin-2-yl-4,5-dihydro-1H-[1,2,4]triazol-3-yl)methyl]amino}benzamidine acetate.

Mass spectrum (ESI) m/z: 447 (M+H)$^+$

This compound was optically resolved using a SUMICHIRAL OA-2500 column, and the first eluting enantiomer (5.06 mg) of the title compound was obtained as a white solid.

$^1$H-NMR (CD$_3$OD) δ 1.33 (t, J=7.2 Hz, 3H) 1.91 (s, 3H) 3.96 (q, J=7.2 Hz, 2H) 5.52 (s, 1H) 6.29 (t, J=1.6 Hz, 1H) 6.56 (t, J=1.6 Hz, 1H) 6.60 (t, J=1.6 Hz, 1H) 6.85 (d, J=9.2 Hz, 2H) 7.29 (br.t, J=4.8 Hz, 1H) 7.60 (d, J=9.2 Hz, 2H) 8.77 (d, J=4.8 Hz, 2H)

HPLC retention time: 8 min (Column name: SUMICHIRAL OA-2500, 30 mmφ+25 cm, Manufacturer: Sumika

Example 222

(R) and (S)-3-{3-[(4-Carbamimidoylphenylamino)-(5-fluoro-8-methoxychroman-6-yl)methyl]-5-oxo-4,5-dihydro[1,2,4]triazol-1-yl}thiophene-2-carboxylic acid

[Chemical Formula 562]

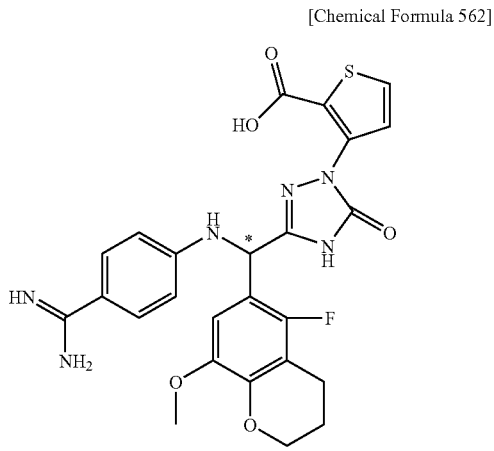

To 1 ml of a DMF solution containing 100 mg of [2-(5-fluoro-8-methoxychroman-6-yl)-2-[4-(5-methyl-[1,2,4]oxadiazol-3-yl)phenylimino]-1-methylsulfanylethylidene]carbamic acid methyl ester (Example (33d)), 35 mg of 3-hydrazinothiophene-2-carboxylic acid methyl ester and 0.028 ml of triethylamine were added. The resulting mixture was stirred at 85° C. for 12 hours under a nitrogen atmosphere and then concentrated. The residue was dissolved in 1.5 ml of methanol, 1.5 ml of THF, and 0.1 ml of acetic acid, and 100 mg of sodium cyanotrihydroborate was further added thereto. The mixture was stirred at room temperature for 3 hours, and 1 ml of a 5 N sodium hydroxide aqueous solution was added thereto. The mixture was stirred at room temperature overnight. Acetic acid (0.3 ml) was added to the reaction mixture, and the resulting mixture was crudely purified by reverse-phase high performance liquid chromatography (acetonitrile-water, 0.1% acetic acid) to give a crude product of 3-(3-{(5-fluoro-8-methoxychroman-6-yl)-[4-(5-methyl-[1,2,4]oxadiazol-3-yl)phenylamino]methyl}-5-oxo-4,5-dihydro-[1,2,4]triazol-1-yl)thiophene-2-carboxylic acid.

Iron powder (100 mg) was added to 3 ml of a methanol:water:acetic acid=1:1:1 mixed solvent solution containing this crude product. The resulting mixture was stirred at 60° C. overnight under a nitrogen atmosphere. The reaction mixture was filtered and purified by reverse-phase high performance liquid chromatography (acetonitrile-water, 0.1% trifluoroacetic acid) to give 3-{3-[(4-carbamimidoylphenylamino)-(5-fluoro-8-methoxychroman-6-yl)methyl]-5-oxo-4,5-dihydro[1,2,4]triazol-1-yl)thiophene-2-carboxylic acid trifluoroacetate.

$^1$H-NMR (CD$_3$OD) δ 1.85-2.05 (m, 2H) 2.60-2.85 (m, 2H) 3.73 (s, 3H) 4.05-4.25 (m, 2H) 5.89 (s, 1H) 6.78-6.90 (m, 3H) 7.17 (d, J=5.2 Hz, 1H) 7.61 (d, J=8.8 Hz, 2H) 7.71 (d, J=5.2 Hz, 1H)

Mass spectrum (ESI) m/z: 539 (M+H)$^+$

This compound was optically resolved using a SUMICHIRAL OA-2500 column, and the first eluting enantiomer (19.16 mg) of the title compound was obtained as a white solid.

HPLC retention time: 19 min (Column name: SUMICHIRAL OA-2500, 30 mmφ×25 cm, Manufacturer: Sumika Chemical Analysis Service, Ltd., Mobile phase: 0.05 M ammonium acetate-methanol solution, Elution rate: 20 ml/min)

Example 223

(R) and (S)-4-{[[4-(2-Fluoroethyl)-8-methoxy-3-oxo-3,4-dihydro-2H-benzo[1,4]oxazin-6-yl]-(5-oxo-1-pyrimidin-2-yl-4,5-dihydro-1H-[1,2,4]triazol-3-yl)methyl]amino}benzamidine acetate (223a) 4-(2-Fluoroethyl)-8-methoxy-3-oxo-3,4-dihydro-2H-benzo[1,4]oxazine-6-carboaldehyde

[Chemical Formula 563]

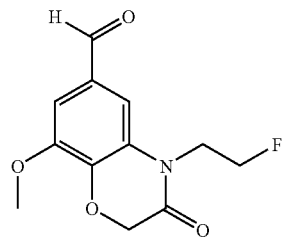

To 3 ml of a DMF solution containing 233 mg of 8-methoxy-3-oxo-3,4-dihydro-2H-benzo[1,4]oxazine-6-carboaldehyde [CAS No. 711021-34-0], 312 mg of potassium carbonate and 236 mg of 1-fluoro-2-iodoethane were added. The resulting mixture was stirred at room temperature for one day, and water was added thereto. The mixture was extracted with ethyl acetate. The organic layer was washed with water and saturated brine and then dried over anhydrous sodium sulfate. The desiccating agent was removed by filtration, and the filtrate was concentrated under reduced pressure. The residue was purified by silica gel column chromatography (ethyl acetate-heptane) to give 4-(2-fluoroethyl)-8-methoxy-3-oxo-3,4-dihydro-2H-benzo[1,4]oxazine-6-carboaldehyde (151 mg) as a white solid.

(223b) [4-(2-Fluoroethyl)-8-methoxy-3-oxo-3,4-dihydro-2H-benzo[1,4]oxazin-6-yl]-[4-(5-methyl[1,2,4]oxadiazol-3-yl)phenylamino]acetonitrile

[Chemical Formula 564]

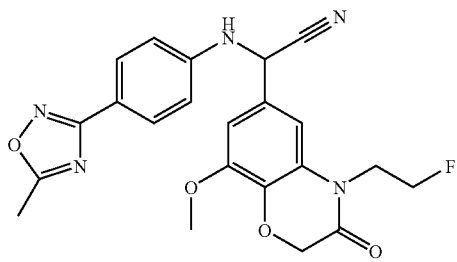

The same procedure was carried out as in Example (1a), except that 4-(2-fluoroethyl)-8-methoxy-3-oxo-3,4-dihydro-2H-benzo[1,4]oxazine-6-carboaldehyde was used instead of 2-fluoro-4,5-dimethoxybenzaldehyde, to give the title compound.

$^1$H-NMR (CDCl$_3$) δ 2.64 (s, 3H) 3.94 (s, 3H) 4.17-4.30 (m, 2H) 4.72 (s, 2H) 4.72 (dt, J=47.6, 4.8 Hz, 2H) 5.46 (br.d, J=7.2

Hz, 1H) 6.84 (d, J=8.8 Hz, 2H) 6.92 (d, J=2.0 Hz, 1H) 7.03 (d, J=2.0 Hz, 1H) 7.99 (d, J=8.8 Hz, 2H)

(223c) (R) and (S)-4-{[[4-(2-Fluoroethyl)-8-methoxy-3-oxo-3,4-dihydro-2H-benzo[1,4]oxazin-6-yl]-(5-oxo-1-pyrimidin-2-yl-4,5-dihydro-1H-[1,2,4]triazol-3-yl)methyl]amino}benzamidine acetate

[Chemical Formula 565]

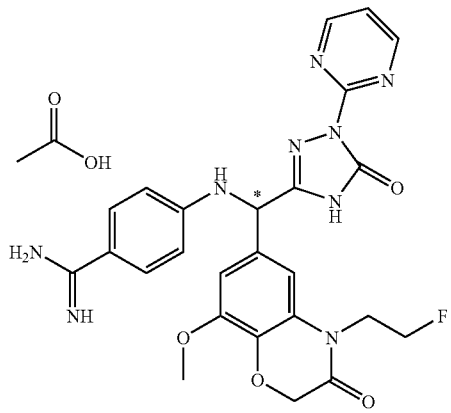

The same procedure was carried out as in Examples (10c) to (10e), except that [4-(2-fluoroethyl)-8-methoxy-3-oxo-3,4-dihydro-2H-benzo[1,4]oxazin-6-yl]-[4-(5-methyl-[1,2,4]oxadiazol-3-yl)phenylamino]acetonitrile was used instead of (3-methoxy-5-methoxymethylphenyl)-[4-(5-methyl-[1,2,4]oxadiazol-3-yl)phenylamino]acetonitrile in Example (10c), to give the first eluting enantiomer of the title compound.

¹H-NMR (CD₃OD) δ 1.92 (s, 3H) 3.78 (s, 3H) 4.08-4.32 (m, 2H) 4.40-4.65 (m, 4H) 5.67 (s, 1H) 6.88 (d, J=9.2 Hz, 2H) 7.01 (d, J=1.6 Hz, 1H) 7.04 (d, J=1.6 Hz, 1H) 7.31 (t, J=4.8 Hz, 1H) 7.60 (d, J=9.2 Hz, 2H) 8.78 (d, J=4.8 Hz, 2H)
HPLC retention time: 18 min Example 224

4-{[(2-Fluoro-3-hydroxy-5-methoxyphenyl)-(5-oxo-1-pyrimidin-2-yl-4,5-dihydro-1H-[1,2,4]triazol-3-yl)methyl]amino}benzamidine acetate

[Chemical Formula 566]

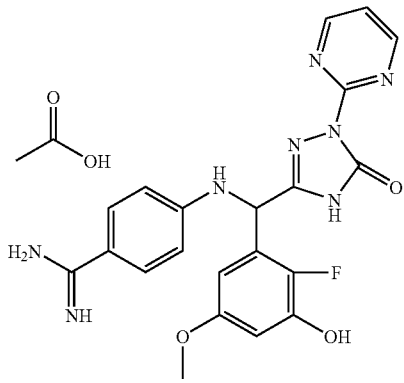

The same procedure was carried out as in Example (10d), except that [2-(2-fluoro-3-hydroxy-5-methoxyphenyl)-2-[4-(5-methyl-[1,2,4]oxadiazol-3-yl)phenylimino]-1-methylsulfanylethylidene]carbamic acid methyl ester (Example (3d)) was used instead of {2-(3-methoxy-5-methoxymethylphenyl)-2-[4-(5-methyl-[1,2,4]oxadiazol-3-yl)phenylimino]-1-methylsulfanylethylidene}carbamic acid methyl ester, to give the title compound.

¹H-NMR (CD₃OD) δ 1.94 (s, 3H) 3.68 (s, 3H) 5.95 (s, 1H) 6.40-6.58 (m, 2H) 6.87 (d, J=8.8 Hz, 2H) 7.34 (t, J=4.8 Hz, 1H) 7.62 (d, J=8.8 Hz, 2H) 8.77 (d, J=4.8 Hz, 2H)

Example 225

(R) and (S)-4-({(3,5-Dimethoxyphenyl)-[1-(3-methylpyridin-2-yl)-5-oxo-4,5-dihydro-1H-[1,2,4]triazol-3-yl]methyl}amino)benzamidine acetate (225a) {2-(3,5-Dimethoxyphenyl)-2-[4-(5-methyl-[1,2,4]oxadiazol-3-yl)phenylimino]-1-methylsulfanylethylidene}carbamic acid methyl ester

[Chemical Formula 567]

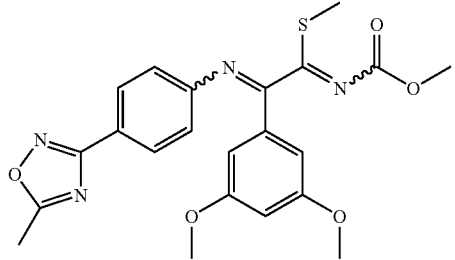

The same procedure was carried out as in Examples (21d) to (21h), except that 3,5-dimethoxybenzaldehyde was used instead of 8-methoxy-4H-benzo[1,3]dioxine-6-carboaldehyde in Example (21d), to give the first eluting enantiomer of the title compound.

(225b) (R) and (S)-4-({(3,5-Dimethoxyphenyl)-[1-(3-methylpyridin-2-yl)-5-oxo-4,5-dihydro-1H-[1,2,4]triazol-3-yl]methyl}amino)benzamidine acetate

[Chemical Formula 568]

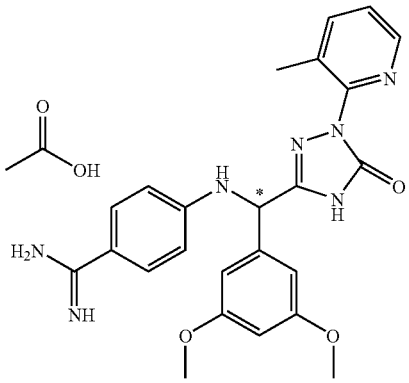

The same procedure was carried out as in Examples (10d) to (10e), except that {2-(3,5-dimethoxyphenyl)-2-[4-(5-methyl-[1,2,4]oxadiazol-3-yl)phenylimino]-1-methylsulfanylethylidene}carbamic acid methyl ester and (6-methylpyridin-2-yl)hydrazine [CAS No. 5315-24-2] were used instead of respectively {2-(3-methoxy-5-methoxymethylphenyl)-2-[4-(5-methyl-[1,2,4]oxadiazol-3-yl)phenylimino]-1-methylsulfanylethylidene}carbamic acid methyl ester and 2-hydrazinopyrimidine in Example (10d), to give the first eluting enantiomer of the title compound.

$^1$H-NMR (CD$_3$OD) δ 1.90 (s, 3H) 2.26 (s, 3H) 3.76 (s, 6H) 5.57 (s, 1H) 6.42 (t, J=2.4 Hz, 1H) 6.71 (d, J=2.4 Hz, 2H) 6.85 (d, J=8.8 Hz, 2H) 7.40 (dd, J=4.8, 7.6 Hz, 1H) 7.60 (d, J=8.8 Hz, 2H) 7.84 (dd, J=1.2, 7.6 Hz, 1H) 8.35 (dd, J=1.2, 4.8 Hz, 1H)

HPLC retention time: 10 min (Column name: SUMICHIRAL OA-2500, 30 mmφ×25 cm, Manufacturer: Sumika Chemical Analysis Service, Ltd., Mobile phase: 0.05 M ammonium acetate-methanol solution, Elution rate: 15 ml/min)

Example 226

3-{3-[(R) and (S)-(4-Carbamimidoylphenylamino)-(8-methoxy-4H-benzo[1,3]dioxin-6-yl)methyl]-5-oxo-4,5-dihydro-[1,2,4]triazol-1-yl}thiophene-2-carboxylic acid

[Chemical Formula 569]

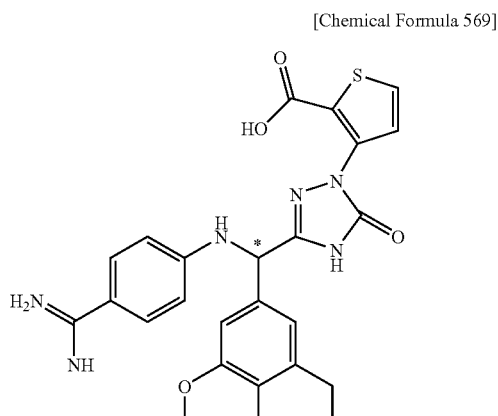

The same procedure was carried out as in Example (155), except that {2-(8-methoxy-4H-benzo[1,3]dioxin-6-yl)-2-[4-(5-methyl-[1,2,4]oxadiazol-3-yl)phenylimino]-1-methylsulfanylethylidene}carbamic acid methyl ester (Example (21h)) was used instead of {2-(3,4-dimethoxyphenyl)-2-[4-(5-methyl-[1,2,4]oxadiazol-3-yl)phenylimino]-1-methylsulfanylethylidene}carbamic acid methyl ester, to give the first eluting enantiomer of the title compound.

$^1$H-NMR (CD$_3$OD) δ 3.84 (s, 3H) 4.83-4.93 (m, 2H) 5.24 (s, 2H) 5.54 (s, 1H) 6.80 (d, J=1.6 Hz, 1H) 6.85 (d, J=8.8 Hz, 2H) 7.04 (d, J=1.6 Hz, 1H) 7.08 (d, J=5.2 Hz, 1H) 7.44 (d, J=5.2 Hz, 1H) 7.61 (d, J=8.8 Hz, 2H)

HPLC retention time: 15 min (Column name: SUMICHIRAL OA-2500, 30 mmφ×25 cm, Manufacturer: Sumika Chemical Analysis Service, Ltd., Mobile phase: 0.05 M ammonium acetate-methanol solution, Elution rate: 30 ml/min)

Example 227

3-{3-[(R) and (S)-(4-Carbamimidoylphenylamino)-(3,4,5-trimethoxyphenyl)methyl]-5-oxo-4,5-dihydro-[1,2,4]triazol-1-yl}thiophene-2-carboxylic acid (227a) [2-[4-(5-Methyl-[1,2,4]oxadiazol-3-yl)phenylimino]-1-methylsulfanyl-2-(3,4,5-trimethoxyphenyl)ethylidene]carbamic acid methyl ester

[Chemical Formula 570]

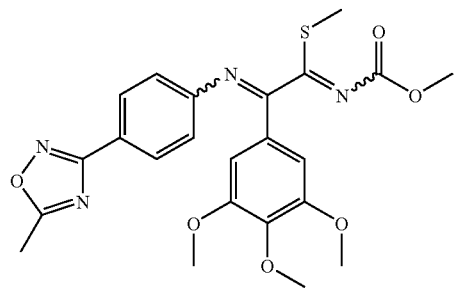

The same procedure was carried out as in Examples (1a) to (1d), except that 3,4,5-trimethoxybenzaldehyde was used instead of 2-fluoro-4,5-dimethoxybenzaldehyde in Example (1a), to give the title compound.

(227b) 3-{3-[(R) and (S)-(4-Carbamimidoylphenylamino)-(3,4,5-trimethoxyphenyl)methyl]-5-oxo-4,5-dihydro-[1,2,4]triazol-1-yl}thiophene-2-carboxylic acid

[Chemical Formula 571]

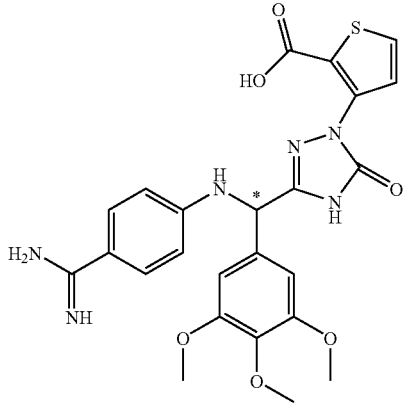

The same procedure was carried out as in Example (155), except that [2-[4-(5-methyl-[1,2,4]oxadiazol-3-yl)phenylimino]-1-methylsulfanyl-2-(3,4,5-trimethoxyphenyl)ethylidene]carbamic acid methyl ester was used instead of {2-(3,4-dimethoxyphenyl)-2-[4-(5-methyl-[1,2,4]oxadiazol-3-yl)phenylimino]-1-methylsulfanylethylidene}carbamic acid methyl ester, to give the first eluting enantiomer of the title compound.

Mass spectrum (ESI) m/z: 525 (M+H)$^+$ (data for racemic mixture)

HPLC retention time: 17 min (Column name: SUMICHIRAL OA-2500, 30 mmφ×25 cm, Manufacturer: Sumika Chemical Analysis Service, Ltd., Mobile phase: 0.05 M ammonium acetate-methanol solution, Elution rate: 20 ml/min)

Example 228

(R) and (S)-3-(3-{(4-Carbamimidoylphenylamino)-[2-fluoro-3-(2-hydroxyethoxy)-5-methoxyphenyl]methyl}-5-oxo-4,5-dihydro[1,2,4]triazol-1-yl)thiophene-2-carboxylic acid

[Chemical Formula 572]

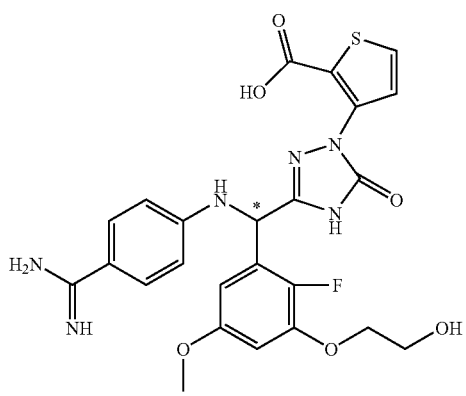

The same procedure was carried out as in Example 167, except that 3-hydrazinothiophene-2-carboxylic acid methyl ester was used instead of 4-hydrazinothiazole-5-carboxylic acid methyl ester, to give the first eluting enantiomer of the title compound.

Mass spectrum (ESI) m/z: 543 (M+H)$^+$ (data for racemic mixture)

HPLC retention time: 16 min (Column name: SUMICHIRAL OA-2500, 30 mmφ×25 cm, Manufacturer: Sumika Chemical Analysis Service, Ltd., Mobile phase: 0.05 M ammonium acetate-methanol solution, Elution rate: 20 ml/min)

Example 229

(R) and (S)-4-{[[2-Fluoro-3-(3-hydroxypropoxy)-5-methoxyphenyl]-(5-oxo-1-pyrimidin-2-yl-4,5-dihydro-1H-[1,2,4]triazol-3-yl)methyl]amino}benzamidine acetate

[Chemical Formula 573]

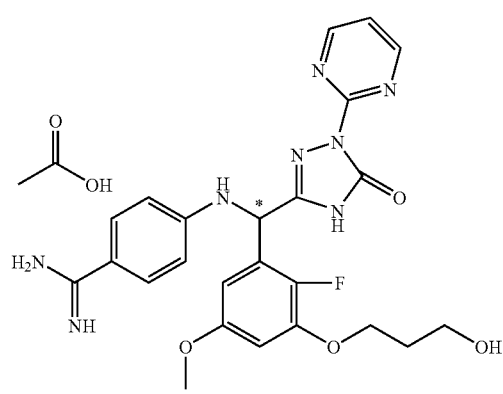

The same procedure was carried out as in Examples (153a) to (153b), except that (3-bromopropoxy)-t-butyldimethylsilane was used instead of 2-(2-bromoethoxy)tetrahydro-2H-pyran in Example (153a), to give the first eluting enantiomer of the title compound.

$^1$H-NMR (CD$_3$OD) δ 1.86-2.10 (m, 5H) 3.69 (s, 3H) 3.73 (t, J=6.0 Hz, 2H) 4.02-4.18 (m, 2H) 5.96 (br.s, 1H) 6.50-6.70 (m, 2H) 6.84 (d, J=8.4 Hz, 2H) 7.31 (br.s, 1H) 7.60 (d, J=8.4 Hz, 2H) 8.76 (br.s, 2H)

HPLC retention time: 7 min (Column name: SUMICHIRAL OA-2500, 30 mmφ×25 cm, Manufacturer: Sumika Chemical Analysis Service, Ltd., Mobile phase: 0.05 M ammonium acetate-methanol solution, Elution rate: 40 ml/min)

Example 230

(R) and (S)-3-(3-{(4-Carbamimidoylphenylamino)-[3-(2-hydroxyethoxy)-4,5-dimethoxyphenyl]methyl}-5-oxo-4,5-dihydro-[1,2,4]triazol-1-yl)thiophene-2-carboxylic acid

[Chemical Formula 574]

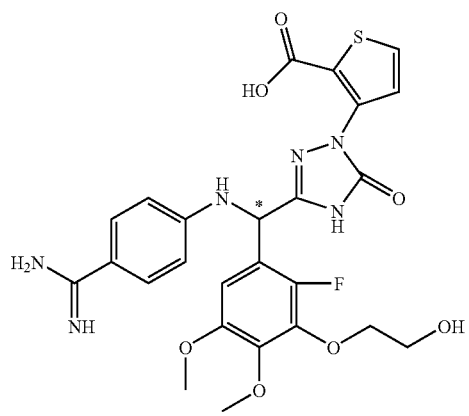

The same procedure was carried out as in Example 167, except that {2-(3-hydroxy-4,5-dimethoxyphenyl)-2-[4-(5-methyl-[1,2,4]oxadiazol-3-yl)phenylimino]-1-methylsulfanylethylidene}carbamic acid methyl ester (Example (159a)) and 3-hydrazinothiophene-2-carboxylic acid methyl ester were used instead of respectively the [2-(2-fluoro-3-hydroxy-5-methoxyphenyl)-2-[4-(5-methyl-[1,2,4]oxadiazol-3-yl)phenylimino]-1-methylsulfanylethylidene]carbamic acid methyl ester and 4-hydrazinothiazole-5-carboxylic acid methyl ester, to give the first eluting enantiomer of the title compound.

$^1$H-NMR (CD$_3$OD) δ 3.78 (s, 3H) 3.82-3.90 (m, 5H) 4.03-4.15 (m, 2H) 5.56 (s, 1H) 6.82-6.92 (m, 4H) 7.08 (d, J=5.6 Hz, 1H) 7.43 (d, J=5.6 Hz, 1H) 7.60 (d, J=9.2 Hz, 2H)

HPLC retention time: 16 min (Column name: SUMICHIRAL OA-2500, 30 mmφ×25 cm, Manufacturer: Sumika Chemical Analysis Service, Ltd., Mobile phase: 0.05 M ammonium acetate-methanol solution, Elution rate: 20 ml/min)

Example 231

(R) and (S)-3-{3-[(4-Carbamimidoyl-3-fluorophenylamino)-(5-fluoro-8-methoxy-2,3-dihydrobenzo[1,4]dioxin-6-yl)methyl]-5-oxo-4,5-dihydro-[1,2,4]triazol-1-yl}thiophene-2-carboxylic acid

[Chemical Formula 575]

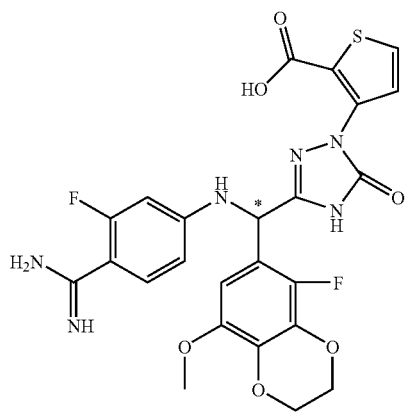

The same procedure was carried out as in Examples (168a) to (168d), except that 2-fluoro-4-aminobenzonitrile [CAS No. 53312-80-4] was used instead of 4-aminobenzonitrile in Example (168a), to give the first eluting enantiomer of the title compound.

$^1$H-NMR (CD$_3$OD) δ 3.76 (s, 3H) 4.29 (s, 4H) 5.86 (s, 1H) 6.57 (dd, J=14.0, 2.4 Hz, 1H) 6.65 (d, J=6.4 Hz, 1H) 6.67 (dd, J=8.8, 2.4 Hz, 1H) 7.09 (d, J=5.2 Hz, 1H) 7.42 (d, J=5.2 Hz, 1H) 7.47 (t, J=8.8 Hz, 1H)

HPLC retention time: 19 min (Column name: SUMICHIRAL OA-2500, 30 mmφ×25 cm, Manufacturer: Sumika Chemical Analysis Service, Ltd., Mobile phase: 0.5 mM ammonium acetate-methanol solution, Elution rate: 40 ml/min)

Example 232

(R) and (S)-4-{3-[(4-Carbamimidoylphenylamino)-(3,5-dimethoxyphenyl)methyl]-5-oxo-4,5-dihydro-[1,2,4]triazol-1-yl}thiazole-5-carboxylic acid

[Chemical Formula 576]

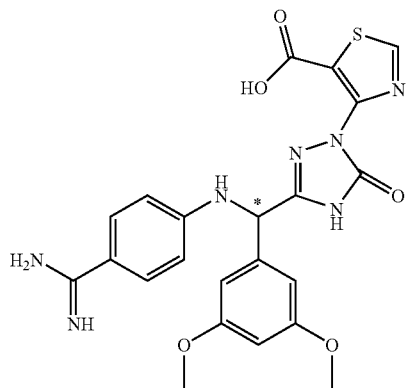

The same procedure was carried out as in Examples (166a) to (166c), except that {2-(3,5-dimethoxyphenyl)-2-[4-(5-methyl-[1,2,4]oxadiazol-3-yl)phenylimino]-1-methylsulfanylethylidene}carbamic acid methyl ester (Example (225a)) was used instead of [2-(8-methoxy-4H-benzo[1,3]dioxin-6-yl)-2-[4-(5-methyl-[1,2,4]oxadiazol-3-yl)phenylimino]-1-methylsulfanylethylidene]carbamic acid methyl ester in Example (166a), to give the first eluting enantiomer of the title compound.

$^1$H-NMR (CD$_3$OD) δ 3.77 (s, 6H) 5.57 (s, 1H) 6.45 (t, J=2.0 Hz, 1H) 6.71 (d, J=2.0 Hz, 2H) 6.85 (d, J=8.8 Hz, 2H) 7.60 (d, J=8.8 Hz, 2H) 8.92 (s, 1H)

HPLC retention time: 18 min (Column name: SUMICHIRAL OA-2500, 30 mmφ×25 cm, Manufacturer: Sumika Chemical Analysis Service, Ltd., Mobile phase: 0.5 mM ammonium acetate-methanol solution, Elution rate: 30 ml/min)

Example 233

(R) and (S)-4-(3-{(4-Carbamimidoylphenylamino)-[3-(2-hydroxyethoxy)-4,5-dimethoxyphenyl]methyl}-5-oxo-4,5-dihydro-[1,2,4]triazol-1-yl)thiazole-5-carboxylic acid

[Chemical Formula 577]

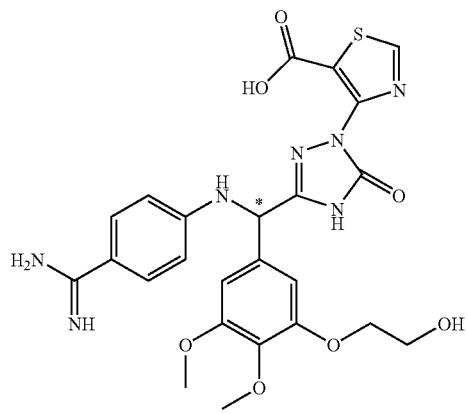

The same procedure was carried out as in Example 167, except that {2-(3-hydroxy-4,5-dimethoxyphenyl)-2-[4-(5-methyl-[1,2,4]oxadiazol-3-yl)phenylimino]-1-methylsulfanylethylidene}carbamic acid methyl ester (Example (159a)) was used instead of [2-(2-fluoro-3-hydroxy-5-methoxyphenyl)-2-[4-(5-methyl-[1,2,4]oxadiazol-3-yl)phenylimino]-1-methylsulfanylethylidene]carbamic acid methyl ester, to give the first eluting enantiomer of the title compound.

$^1$H-NMR (CD$_3$OD) δ 3.80 (s, 3H) 3.82-3.92 (m, 5H) 4.04-4.16 (m, 2H) 5.63 (s, 1H) 6.80-6.94 (m, 4H) 7.63 (d, J=8.8 Hz, 2H) 9.03 (s, 1H)

HPLC retention time: 19 min (Column name: SUMICHIRAL OA-2500, 30 mmφ×25 cm, Manufacturer: Sumika Chemical Analysis Service, Ltd., Mobile phase: 0.5 mM ammonium acetate-methanol solution, Elution rate: 25 ml/min)

Example 234

(R) and (S)-4-{[(5,6-Dimethoxypyridin-3-yl)-(5-oxo-1-pyrimidin-2-yl-4,5-dihydro-1H-[1,2,4]triazol-3-yl)methyl]amino}benzamidine acetate

[Chemical Formula 578]

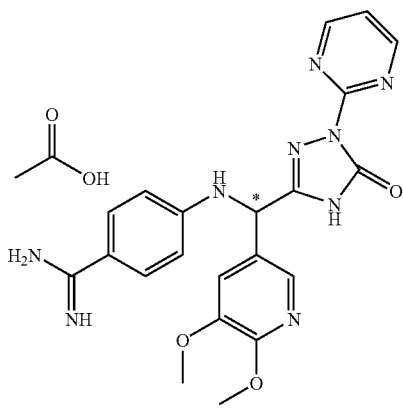

The same procedure was carried out as in Example (160b), except that {2-(5,6-dimethoxypyridin-3-yl)-2-[4-(5-methyl-[1,2,4]oxadiazol-3-yl)phenylimino]-1-methylsulfanylethylidene}carbamic acid methyl ester (Example (169a)) was used instead of {2-(5-ethoxy-6-methoxypyridin-3-yl)-2-[4-(5-methyl-[1,2,4]oxadiazol-3-yl)phenylimino]-1-methylsulfanylethylidene}carbamic acid methyl ester, to give the first eluting enantiomer of the title compound.

$^1$H-NMR (CD$_3$OD) δ 1.92 (s, 3H) 3.82 (s, 3H) 3.92 (s, 3H) 5.67 (s, 1H) 6.88 (d, J=9.2 Hz, 2H) 7.30 (t, J=4.8 Hz, 1H) 7.41 (d, J=2.0 Hz, 1H) 7.61 (d, J=9.2 Hz, 2H) 7.85 (d, J=2.0 Hz, 1H) 8.77 (d, J=4.8 Hz, 2H)

HPLC retention time: 13 min (Column name: SUMICHIRAL OA-2500, 30 mmφ×25 cm, Manufacturer: Sumika Chemical Analysis Service, Ltd., Mobile phase: 0.05 M ammonium acetate-methanol solution, Elution rate: 30 ml/min)

Example 235

(R) and (S)-3-{3-[(4-Carbamimidoylphenylamino)-(5-ethoxy-6-methoxypyridin-3-yl)methyl]-5-oxo-4,5-dihydro-[1,2,4]triazol-1-yl}thiophene-2-carboxylic acid

[Chemical Formula 579]

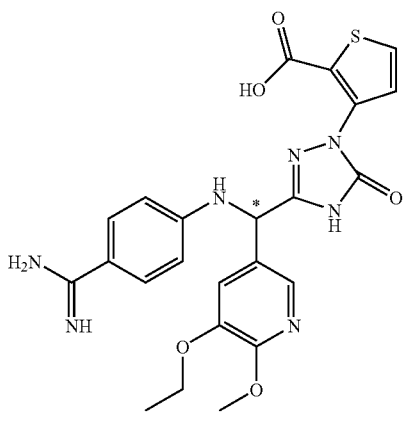

The same procedure was carried out as in Example (169b), except that {2-(5-ethoxy-6-methoxypyridin-3-yl)-2-[4-(5-methyl-[1,2,4]oxadiazol-3-yl)phenylimino]-1-methylsulfanylethylidene}carbamic acid methyl ester (Example (160a)) was used instead of {2-(5,6-dimethoxypyridin-3-yl)-2-[4-(5-methyl-[1,2,4]oxadiazol-3-yl)phenylimino]-1-methylsulfanylethylidene}carbamic acid methyl ester, to give the first eluting enantiomer of the title compound.

$^1$H-NMR (CD$_3$OD) δ 1.36 (t, J=7.2 Hz, 3H) 3.92 (s, 3H) 3.97-4.13 (m, 2H) 5.65 (s, 1H) 6.87 (d, J=9.2 Hz, 2H) 7.07 (d, J=5.2 Hz, 1H) 7.37 (d, J=2.0 Hz, 1H) 7.43 (d, J=5.2 Hz, 1H) 7.59 (d, J=9.2 Hz, 2H) 7.81 (d, J=2.0 Hz, 1H)

HPLC retention time: 14 min (Column name: SUMICHIRAL OA-2500, 30 mmφ×25 cm, Manufacturer: Sumika Chemical Analysis Service, Ltd., Mobile phase: 0.05 M ammonium acetate-methanol solution, Elution rate: 25 ml/min)

Example 236

3-Fluoro-4-{[(R) and (S)-(2-fluoro-4,5-dimethoxyphenyl)-(5-oxo-1-pyrimidin-2-yl-4,5-dihydro-1H-[1,2,4]triazol-3-yl)methyl]amino}benzamidine acetate (236a) 4-{[Cyano-(2-fluoro-4,5-dimethoxyphenyl)methyl]amino}-3-fluorobenzonitrile

[Chemical Formula 580]

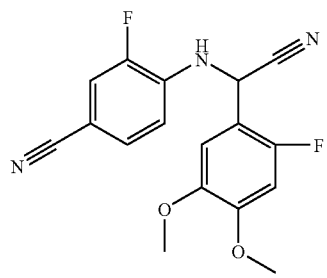

To 20 ml of a THF solution containing 1.9 g of 2-fluoro-4,5-dimethoxybenzaldehyde, 1.47 g of 4-amino-3-fluorobenzonitrile [CAS No. 63069-50-1], 6 g of MS3A, 640 mg of Yb(OTf)$_3$, and 4 ml of trimethylsilyl cyanide were added under a nitrogen atmosphere. The resulting mixture was stirred at room temperature overnight and then filtered through celite. The filtrate was concentrated under reduced pressure, and ethyl acetate and water were added to the residue. The mixture was extracted with ethyl acetate. The organic layer was washed with saturated brine and then dried over anhydrous magnesium sulfate. The desiccating agent was removed by filtration, and the filtrate was concentrated under reduced pressure. The residue was crudely purified by silica gel column chromatography (ethyl acetate-heptane) and then filtered through NH silica gel to give the title compound (1.0 g) as a light yellow solid.

$^1$H-NMR (CDCl$_3$) δ 3.91 (s, 3H) 3.93 (s, 3H) 4.71-4.74 (m, 1H) 5.61 (d, 5 J=7.2 Hz, 1H) 6.74 (d, J=11.2 Hz, 1H) 6.95 (t, J=8.4 Hz, 1H) 7.04 (d, J=6.8 Hz, 1H) 7.33 (dd, J=2.0, 11.2 Hz, 1H) 7.44-7.47 (m, 1H)

451

(236b) [2-(4-Cyano-2-fluorophenylimino)-2-(2-fluoro-4,5-dimethoxyphenyl)-1-methylsulfanylethylidene]carbamic acid methyl ester

[Chemical Formula 581]

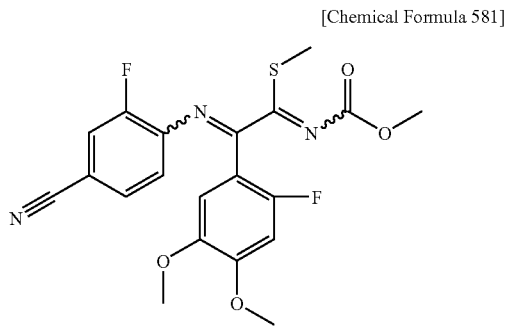

To 100 ml of an ethanol:THF=2:1 mixed solvent solution containing 1.0 g of 4-{[cyano-(2-fluoro-4,5-dimethoxyphenyl)methyl]amino}-3-fluorobenzonitrile, 5.5 ml of a 20% ammonium sulfide aqueous solution was added. The resulting mixture was stirred at room temperature for 2 hours, and then water was added thereto. The mixture was extracted with ethyl acetate. The organic layer was washed with saturated brine and then dried over anhydrous magnesium sulfate. The desiccating agent was removed by filtration, and the filtrate was concentrated under reduced pressure.

To 20 ml of an acetonitrile solution containing the residue obtained, 500 mg of $Me_3O^+BF_4^-$ was added. The resulting mixture was stirred at room temperature for 50 minutes, and then a saturated sodium hydrogen carbonate aqueous solution was added thereto. The mixture was extracted with ethyl acetate. The organic layer was washed with saturated brine and then dried over anhydrous magnesium sulfate. The desiccating agent was removed by filtration, and the filtrate was concentrated under reduced pressure.

To 20 ml of an ethyl acetate solution containing the residue obtained, 4.8 g of manganese dioxide was added, and the resulting mixture was stirred at room temperature for 19 hours. The reaction mixture was filtered through celite, and the filtrate was concentrated under reduced pressure.

To 30 ml of a toluene solution containing the residue obtained, 1.48 ml of 2,4,6-collidine and 0.74 ml of methyl chloroformate were added. The resulting mixture was stirred at 85° C. for 7 hours under a nitrogen atmosphere. The reaction mixture was cooled, and then 0.1 N hydrochloric acid was added thereto. The mixture was extracted with ethyl acetate. The organic layer was washed with a saturated sodium hydrogen carbonate aqueous solution, water, and saturated brine and then dried over anhydrous magnesium sulfate. The desiccating agent was removed by filtration, and the filtrate was concentrated under reduced pressure. The residue was purified by silica gel column chromatography (ethyl acetate-heptane) to give the title compound.

Mass spectrum (ESI) m/z: 456 (M+Na)$^+$

452

(236c) 3-Fluoro-4-{[(R) and (S)-(2-fluoro-4,5-dimethoxyphenyl)-(5-oxo-1-pyrimidin-2-yl-4,5-dihydro-1H-[1,2,4]triazol-3-yl)methyl]amino}benzamidine acetate

[Chemical Formula 582]

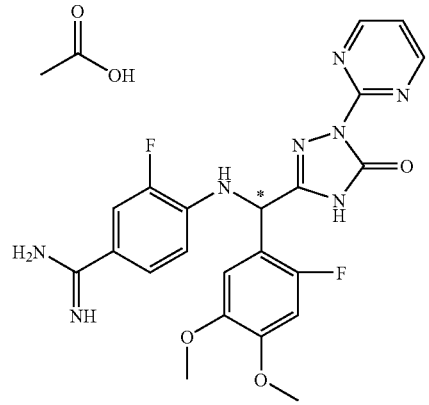

To 3 ml of a DMF solution containing 503 mg of [2-(4-cyano-2-fluorophenylimino)-2-(2-fluoro-4,5-dimethoxyphenyl)-1-methylsulfanylethylidene]carbamic acid methyl ester, 79 mg of 2-hydrazinopyrimidine and 0.15 ml of triethylamine were added. The resulting mixture was stirred at room temperature for 1 hour under a nitrogen atmosphere and then at 85° C. for 14 hours and 45 minutes. Then, the reaction mixture was concentrated.

The residue obtained was dissolved in 6.2 ml of a methanol:THF:acetic acid=20:10:1 mixed solvent, and 220 mg of sodium cyanotrihydroborate was added thereto. The resulting mixture was stirred at room temperature for 4 hours. Then, 200 mg of sodium cyanotrihydroborate, 1 ml of methanol, 1 ml of THF, and 0.2 ml of acetic acid were further added to the reaction mixture. The mixture was stirred at the same temperature for 16 hours, and then water was added thereto. The mixture was extracted with ethyl acetate. The insoluble matter was removed by filtration, and the filtrate was washed with saturated brine and then dried over anhydrous magnesium sulfate. The desiccating agent was removed by filtration, and the filtrate was concentrated under reduced pressure. The residue was crudely purified by NAM silica gel column chromatography (methanol-ethyl acetate) to give a crude product of 3-fluoro-4-{[(2-fluoro-4,5-dimethoxyphenyl)-(5-oxo-1-pyrimidin-2-yl-4,5-dihydro-1H-[1,2,4]triazol-3-yl)methyl]amino}benzonitrile.

To 2 ml of a pyridine solution containing this crude product, 0.255 ml of triethylamine and 1.57 ml of a 20% ammonium sulfide aqueous solution were added. The resulting mixture was stirred at 70° C. for 5 hours under a nitrogen atmosphere. The reaction mixture was made acidic with acetic acid, and water was added thereto. The mixture was concentrated, and the residue was purified by reverse-phase high performance liquid chromatography (acetonitrile-water, 0.1% acetic acid) to give 3-fluoro-4-{[(2-fluoro-4,5-dimethoxyphenyl)-(5-oxo-1-pyrimidin-2-yl-4,5-dihydro-1H-[1,2,4]triazol-3-yl)methyl]amino}thiobenzamide.

Mass spectrum (ESI) m/z: 500 (M+H)$^+$

This compound (40 mg) was suspended in 15 ml of acetonitrile, and 16 mg of $Me_3O^+BF_4^-$ was added thereto. The resulting mixture was stirred at room temperature for 1 hour and a quarter and then concentrated.

To the residue obtained, 1.5 ml of acetonitrile, 1.5 ml of isopropanol, and 0.021 ml of 1,1,3,3-tetramethyldisilazane were added. The resulting mixture was stirred at 70° C. for 28 and a quarter hours and then concentrated. The residue was purified by reverse-phase high performance liquid chromatography (acetonitrile-water, 0.1% acetic acid) to give 3-fluoro-4-{[(2-fluoro-4,5-dimethoxyphenyl)-(5-oxo-1-pyrimidin-2-yl-4,5-dihydro-1H-[1,2,4]triazol-3-yl)methyl]amino}benzamidine acetate.

Mass spectrum (ESI) m/z: 483 (M+H)$^+$

This compound (13.7 g) was optically resolved using a SUMICHIRAL OA-2500 column, and the first eluting enantiomer (5.67 mg) of the title compound was obtained as a white solid.

$^1$H-NMR (CD$_3$OD) δ 1.92 (s, 3H) 3.76 (s, 3H) 3.81 (s, 3H) 5.99 (s, 1H) 6.82 (d, J=11.6 Hz, 1H) 6.93 (t, J=8.4 Hz, 1H) 7.13 (d, J=6.8 Hz, 1H) 7.29 (t, J=4.8 Hz, 1H) 7.48-7.54 (m, 2H), 8.75 (d, J=4.8 Hz, 2H)

HPLC retention time: 10 min (Column name: SUMICHIRAL OA-2500, 30 mmφ×25 cm, Manufacturer: Sumika Chemical Analysis Service, Ltd., Mobile phase: 0.05 M ammonium acetate-methanol solution, Elution rate: 40 ml/min)

Example 237

3-(3-{(R) and (S)-(4-Carbamimidoylphenylamino)-[2-fluoro-4-(2-hydroxyethoxy)-5-methoxyphenyl]methyl}-5-oxo-4,5-dihydro-[1,2,4]triazol-1-yl)thiophene-2-carboxylic acid

[Chemical Formula 583]

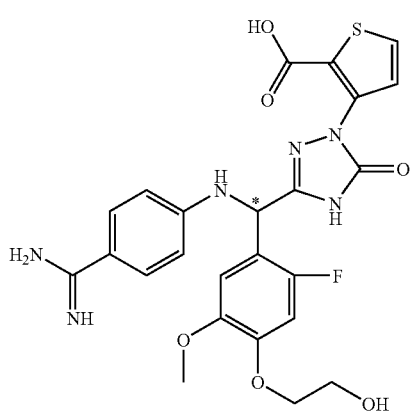

To 3 ml of a DMF solution containing 308 mg of (2-{4-[2-(t-butyldimethylsilanyloxy)ethoxy]-2-fluoro-5-methoxyphenyl}-2-[4-(5-methyl-[1,2,4]oxadiazol-3-yl)phenylimino]-1-methylsulfanylethylidene)carbamic acid methyl ester (Example (178c)), 86 mg of 3-hydrazinothiophene-2-carboxylic acid methyl ester and 0.104 ml of triethylamine were added. The resulting mixture was stirred at 85° C. for 13 and a half hours under a nitrogen atmosphere and then concentrated.

The residue obtained was dissolved in 3 ml of methanol, 1 ml of THF, and 0.3 ml of acetic acid, and then 200 mg of sodium cyanotrihydroborate was added thereto. The mixture was stirred at room temperature for 2 hours and 20 minutes, and then 100 mg of sodium cyanotrihydroborate was further added thereto. The mixture was stirred at room temperature for 1 hour and 40 minutes. Water and ethyl acetate were added to the reaction mixture. The resulting mixture was extracted with ethyl acetate twice. The organic layers were combined, washed with saturated brine, and dried over anhydrous magnesium sulfate. The desiccating agent was removed by filtration, and the filtrate was concentrated under reduced pressure.

To 5 ml of a methanol solution containing the residue obtained, 3 ml of a 5 N sodium hydroxide aqueous solution was added. The mixture was stirred at room temperature for 11 hours. The pH of the reaction mixture was adjusted to approximately 3 with 5 N hydrochloric acid. The mixture was extracted with ethyl acetate. The organic layer was washed with saturated brine and dried over anhydrous magnesium sulfate. The desiccating agent was removed by filtration, and the filtrate was concentrated under reduced pressure. The residue was crudely purified by reverse-phase high performance liquid chromatography (acetonitrile-water, 0.1% trifluoroacetic acid) to give a crude product of 3-(3-{[2-fluoro-4-(2-hydroxyethoxy)-5-methoxyphenyl]-4-(5-methyl-[1,2,4]oxadiazol-3-yl)phenylamino}methyl)-5-oxo-4,5-dihydro-[1,2,4]triazol-1-yl)thiophene-2-carboxylic acid.

Iron powder (150 mg) was added to 4.5 ml of a methanol:water:acetic acid=1:1:1 mixed solvent solution containing the crude product obtained. The mixture was stirred at 70° C. for 4 hours under a nitrogen atmosphere. After the addition of 1 ml of acetic acid, the mixture was further stirred at the same temperature for 1 hour. The reaction mixture was filtered and then crudely purified by reverse-phase high performance liquid chromatography (acetonitrile-water, 0.1% trifluoroacetic acid) to give 3-(3-{(4-carbamimidoylphenylamino)-[2-fluoro-4-(2-hydroxyethoxy)-5-methoxyphenyl]methyl}-5-oxo-4,5-dihydro-[1,2,4]triazol-1-yl)thiophene-2-carboxylic acid.

Mass spectrum (ESI) m/z: 543 (M+H)$^+$

The crude product obtained was optically resolved using a SUMICHIRAL OA-2500 column, and the first eluting enantiomer (9.22 mg) of the title compound was obtained as a white solid.

$^1$H-NMR (CD$_3$OD) δ 3.77-3.80 (m, 2H) 3.83 (s, 3H) 3.94-4.06 (m, 2H) 5.87 (s, 1H) 6.82 (d, J=5.6 Hz, 1H) 6.85 (d, J=8.8 Hz, 2H) 7.07 (d, J=5.6 Hz, 1H) 7.12 (d, J=7.2 Hz, 1H) 7.43 (d, J=5.6 Hz, 1H) 7.59 (d, J=8.8 Hz, 2H)

HPLC retention time: 16 min (Column name: SUMICHIRAL OA-2500, 30 mmφ×25 cm, Manufacturer: Sumika Chemical Analysis Service, Ltd., Mobile phase: 0.05 M ammonium acetate-methanol solution, Elution rate: 20 ml/min)

Example 238

4-{[(R) and (S)-(2-Fluoro-4-(2-hydroxyethoxy)-5-methoxyphenyl]-(5-oxo-1-pyrimidin-2-yl-4,5-dihydro-1H-[1,2,4]triazol-3-yl)methyl]amino}benzamidine acetate

[Chemical Formula 584]

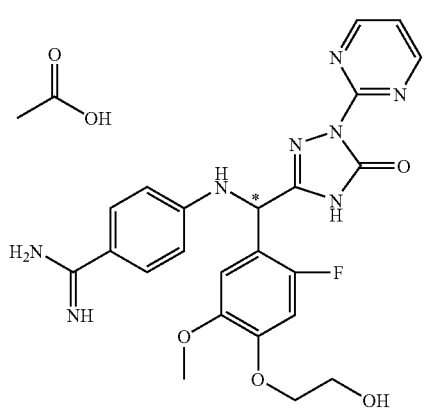

The same procedure was carried out as in Examples (3f) to (3h), except that (2-{4-[2-(t-butyldimethylsilanyloxy)ethoxy]-2-fluoro-5-methoxyphenyl}-2-[4-(5-methyl-[1,2,4]oxadiazol-3-yl)phenylimino]-1-methylsulfanylethylidene)carbamic acid methyl ester (Example (178c)) was used instead of {2-[2-fluoro-3-(2-fluoroethoxy)-5-methoxyphenyl]-2-[4-(5-methyl-[1,2,4]oxadiazol-3-yl)phenylimino]-1-methylsulfanylethylidene}carbamic acid methyl ester in Example (3f), to give the first eluting enantiomer of the title compound.

$^1$H-NMR (CD$_3$OD) δ 1.92 (s, 3H) 3.76-3.79 (m, 2H) 3.82 (s, 3H) 3.93-3.96 (m, 2H) 5.91 (s, 1H) 6.83 (d, J=11.6 Hz, 1H) 6.85 (d, J=8.8 Hz, 2H) 7.12 (d, J=7.2 Hz, 1H) 7.31 (t, J=4.8 Hz, 1H) 7.60 (d, J=8.8 Hz, 2H) 8.75 (d, J=4.8 Hz, 2H)

HPLC retention time: 16 min (Column name: SUMICHIRAL OA-2500, 30 mmφ×25 cm, Manufacturer: Sumika Chemical Analysis Service, Ltd., Mobile phase: 0.05 M ammonium acetate-methanol solution, Elution rate: 20 ml/min)

The following compounds were produced by the general production processes for the compounds of this invention and by similar processes as in the examples described above. Unless otherwise specified, the data for the following example compounds having two optical isomers listed are the data for the first eluting enantiomer.

Example X-1

2-{4-[(4-carbamimidoylphenylamino)-(5-oxo-1-pyrimidin-2-yl-4,5-dihydro-1H-[1,2,4]triazol-3-yl)methyl]-2-ethoxyphenoxy}-N,N-dimethylacetamide acetate

[Chemical Formula 585]

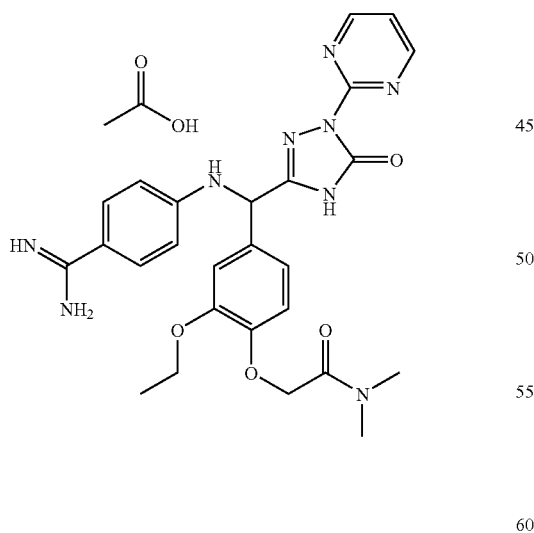

$^1$H-NMR (CD$_3$OD) δ 1.36 (t, J=6.8 Hz, 3H) 1.94 (s, 3H) 2.94 (s, 3H) 3.08 (s, 3H) 4.04 (q, J=6.8 Hz, 2H) 4.79 (s, 2H) 5.64 (s, 1H) 6.86 (d, J=8.4 Hz, 2H) 6.92 (d, J=8.0 Hz, 1H) 7.05 (d, J=8.0 Hz, 1H) 7.17 (s, 1H) 7.35 (t, J=4.8 Hz, 1H) 7.61 (d, J=8.4 Hz, 2H) 8.78 (d, J=4.8 Hz, 2H)

Mass spectrum (ESI) m/z: 532 (M+H)$^+$

Example X-2

2-(4-{(4-carbamimidoylphenylamino)-[1-(2-methoxyphenyl)-5-oxo-4,5-dihydro-1H-[1,2,4]triazol-3-yl]methyl}-2,6-dimethoxyphenoxy)-N,N-dimethylacetamide acetate

[Chemical Formula 586]

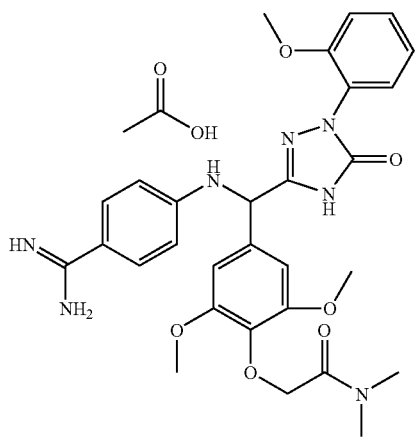

$^1$H-NMR (CD$_3$OD) δ 1.93 (s, 3H) 2.96 (s, 3H) 3.14 (s, 3H) 3.80 (s, 3H) 3.83 (s, 6H) 4.59 (s, 2H) 5.63 (s, 1H) 6.84-6.91 (m, 4H) 7.03 (ddd, J=1.2, 7.6, 7.6 Hz, 1H) 7.15 (dd, J=1.2, 8.4 Hz, 1H) 7.31 (dd, J=1.6, 7.6 Hz, 1H) 7.44 (ddd, J=1.6, 7.6, 8.4 Hz, 1H) 7.64 (d, J=8.8 Hz, 2H)

Example X-3

4-{[(R) and (S)-(3-cyanomethoxy-5-ethylphenyl)-(5-oxo-1-pyrimidin-2-yl-4,5-dihydro-1H-[1,2,4]triazol-3-yl)methyl]amino}benzamidine acetate

[Chemical Formula 587]

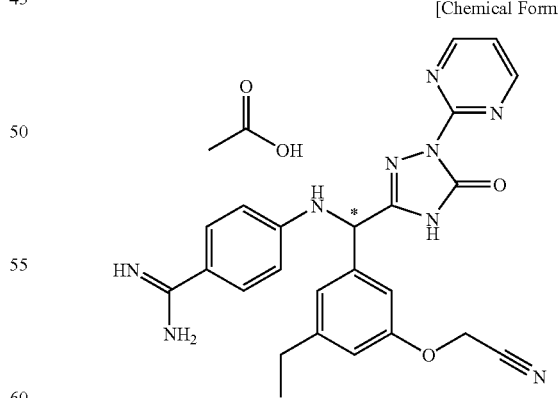

$^1$H-NMR (CD$_3$OD) δ 1.21 (t, J=7.6 Hz, 3H) 1.93 (s, 3H) 2.65 (q, J=7.6 Hz, 2H) 4.96 (s, 2H) 5.64 (s, 1H) 6.82-6.92 (m, 3H) 7.07 (s, 1H) 7.13 (s, 1H) 7.31 (br.s, 1H) 7.60 (d, J=9.2 Hz, 2H) 8.78 (br.s, 2H)

HPLC retention time: 11 min

Example X-4

4-{[(R) and (S)-(3-allyloxyphenyl)-(5-oxo-1-pyrimidin-2-yl-4,5-dihydro-1H-[1,2,4]triazol-3-yl)methyl]amino}benzamidine acetate

[Chemical Formula 588]

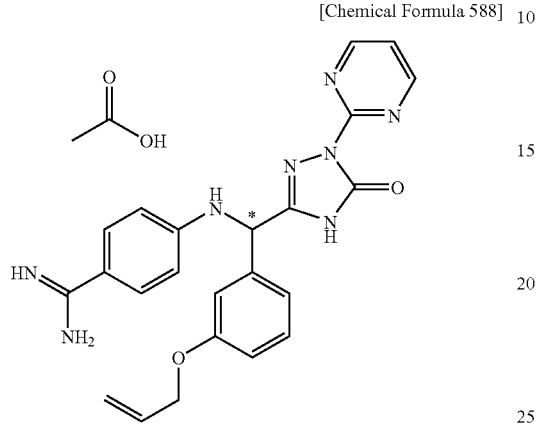

¹H-NMR (CD$_3$OD) δ 1.92 (s, 3H) 4.53 (ddd, J=1.6, 1.6, 5.2 Hz, 2H) 5.20 (tdd, J=1.6, 1.6, 10.8 Hz, 1H) 5.36 (tdd, J=1.6, 1.6, 17.2 Hz, 1H) 6.01 (tdd, J=5.2, 10.8, 17.2 Hz, 1H) 6.81-6.91 (m, 3H) 7.08-7.18 (m, 2H) 7.28 (t, J=8.0 Hz, 1H) 7.30 (t, J=4.8 Hz, 1H) 7.60 (d, J=8.8 Hz, 2H) 8.77 (d, J=4.8 Hz, 2H)

HPLC retention time: 11 min

Example X-5

4-{[(R) and (S)-(3-fluoromethyl-5-methoxyphenyl)-(5-oxo-1-pyrimidin-2-yl-4,5-dihydro-1H-[1,2,4]triazol-3-yl)methyl]amino}benzamidine trifluoroacetate

[Chemical Formula 589]

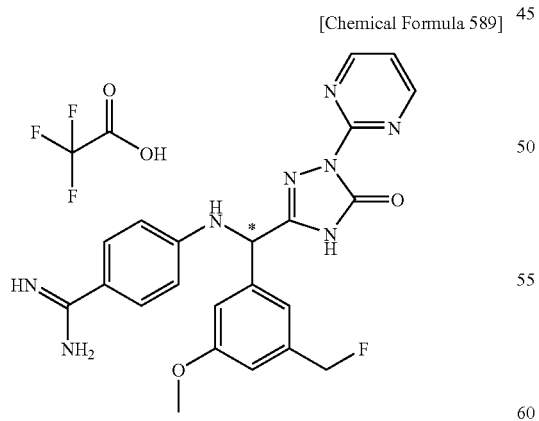

¹H-NMR (CD$_3$OD) δ 3.82 (s, 3H) 5.36 (d, J=47.6 Hz, 2H) 5.74 (s, 1H) 6.88 (d, J=8.8 Hz, 2H) 6.96 (s, 1H) 7.13 (s, 1H) 7.16 (s, 1H) 7.38 (t, J=4.8 Hz, 1H) 7.62 (d, J=8.8 Hz, 2H) 8.80 (d, J=4.8 Hz, 2H)

HPLC retention time: 13 min

Example X-6

4-{[(3-ethoxy-5-hydroxymethylphenyl)-(5-oxo-1-pyrimidin-2-yl-4,5-dihydro-1H-[1,2,4]triazol-3-yl)methyl]amino}benzamidine trifluoroacetate

[Chemical Formula 590]

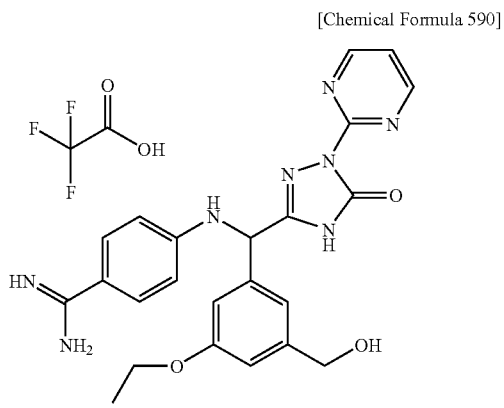

¹H-NMR (CD$_3$OD) δ 1.37 (t, J=7.2 Hz, 3H) 4.05 (q, J=7.2 Hz, 2H) 4.59 (s, 2H) 5.70 (s, 1H) 6.88 (d, J=8.8 Hz, 2H) 6.92 (s, 1H) 7.01 (br.s, 1H) 7.11 (s, 1H) 7.38 (t, J=4.8 Hz, 1H) 7.62 (d, J=8.8 Hz, 2H) 8.79 (d, J=4.8 Hz, 2H)

HPLC retention time: 11 min

Example X-7

4-{[(R) and (S)-(3,5-diethoxy-2-fluorophenyl)-(5-oxo-1-pyrimidin-2-yl-4,5-dihydro-1H-[1,2,4]triazol-3-yl)methyl]amino}benzamidine trifluoroacetate

[Chemical Formula 591]

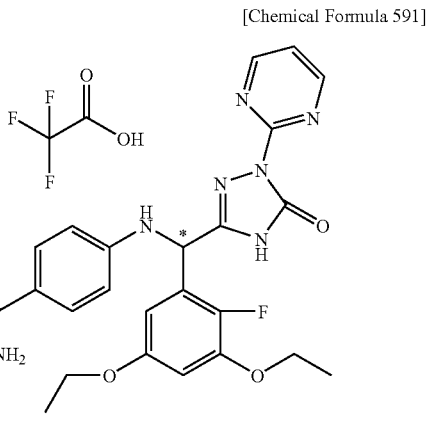

¹H-NMR (CD$_3$OD) δ 1.31 (t, J=6.8 Hz, 3H) 1.40 (t, J=6.8 Hz, 3H) 3.86-4.01 (m, 2H) 4.06 (q, J=6.8 Hz, 2H) 6.00 (s, 1H) 6.52-6.63 (m, 2H) 6.86 (d, J=8.8 Hz, 2H) 7.36 (t, J=4.8 Hz, 1H) 7.63 (d, J=8.8 Hz, 2H) 8.76 (d, J=4.8 Hz, 2H)

HPLC retention time: 12 min

Example X-8

4-{[(R) and (S)-(3-ethoxy-5-fluoromethylphenyl)-(5-oxo-1-pyrimidin-2-yl-4,5-dihydro-1H-[1,2,4]triazol-3-yl)methyl]amino}benzamidine trifluoroacetate

[Chemical Formula 592]

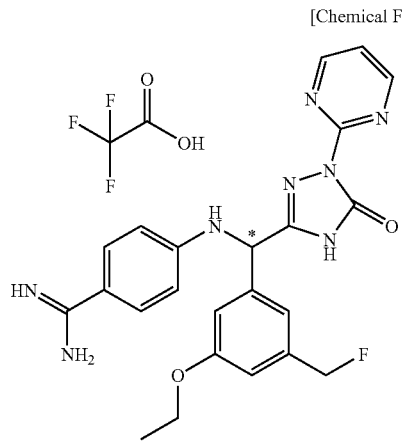

$^1$H-NMR (CD$_3$OD) δ 1.38 (t, J=6.8 Hz, 3H) 4.06 (q, J=6.8 Hz, 2H) 5.35 (d, J=47.6 Hz, 2H) 5.73 (s, 1H) 6.88 (d, J=8.8 Hz, 2H) 6.94 (s, 1H) 7.10 (s, 1H) 7.15 (s, 1H) 7.38 (t, J=4.8 Hz, 1H) 7.62 (d, J=8.8 Hz, 2H) 8.80 (d, J=4.8 Hz, 2H)

HPLC retention time: 12 min

Example X-9

4-{[[4-(2-dimethylaminoethoxy)-3,5-dimethoxyphenyl]-(5-oxo-1-pyrimidin-2-yl-4,5-dihydro-1H-[1,2,4]triazol-3-yl)methyl]amino}benzamidine diacetate

[Chemical Formula 593]

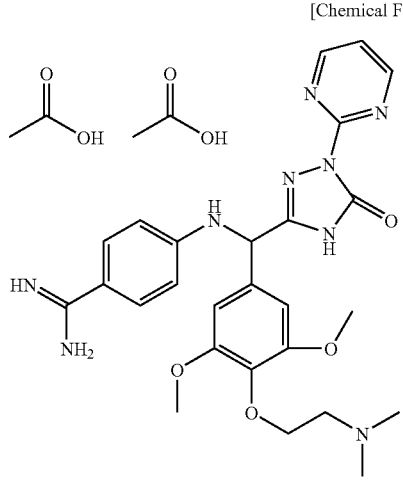

$^1$H-NMR (CD$_3$OD) δ 1.98 (br.s, 6H) 2.75 (br.s, 6H) 3.14 (br.s, 2H) 3.84 (br.s, 6H) 4.09 (br.s, 2H) 5.53 (br.s, 1H) 6.86 (br.s, 2H) 6.93 (br.s, 2H) 7.26 (br.s, 1H) 7.60 (br.s, 2H) 8.74 (br.s, 2H)

Mass spectrum (ESI) m/z: 534 (M+H)$^+$

Example X-10

4-{[(R) and (S)-(3-ethoxy-5-methoxymethylphenyl)-(5-oxo-1-pyrimidin-2-yl-4,5-dihydro-1H-[1,2,4]triazol-3-yl)methyl]amino}benzamidine trifluoroacetate

[Chemical Formula 594]

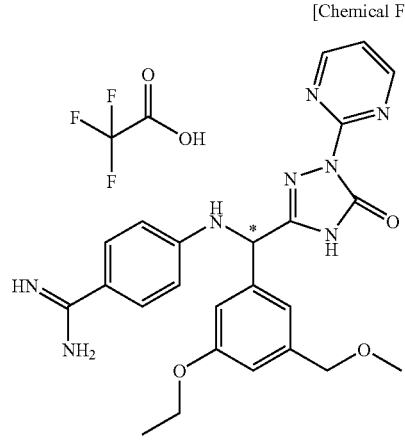

$^1$H-NMR (CD$_3$OD) δ 1.37 (t, J=6.8 Hz, 3H) 3.37 (s, 3H) 4.04 (q, J=6.8 Hz, 2H) 4.43 (s, 2H) 5.70 (s, 1H) 6.83-6.96 (m, 3H) 7.01-7.08 (m, 1H) 7.10 (s, 1H) 7.38 (t, J=4.8 Hz, 1H) 7.62 (d, J=9.2 Hz, 2H) 8.80 (d, J=4.8 Hz, 2H)

HPLC retention time: 12 min

Example X-11

4-{[(R) and (S)-(3-ethoxyphenyl)-(5-oxo-1-pyrimidin-2-yl-4,5-dihydro-1H-[1,2,4]triazol-3-yl)methyl]amino}benzamidine acetate

[Chemical Formula 595]

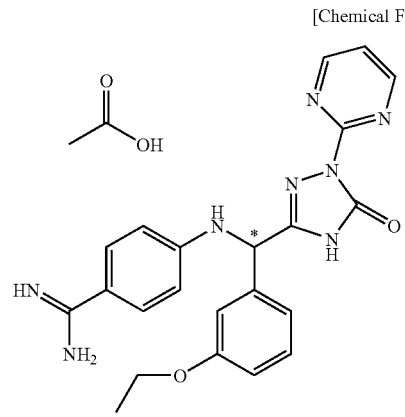

$^1$H-NMR (CD$_3$OD) δ 1.34 (t, J=7.2 Hz, 3H) 1.91 (s, 3H) 4.01 (q, J=7.2 Hz, 2H) 5.64 (s, 1H) 6.80-6.92 (m, 3H) 7.05-7.14 (m, 2H) 7.27 (dd, J=8.0, 8.4 Hz, 1H) 7.32 (t, J=4.8 Hz, 1H) 7.60 (d, J=9.2 Hz, 2H) 8.77 (d, J=4.8 Hz, 2H)

HPLC retention time: 11 min

Example X-12

4-{[(R) and (S)-[3-ethoxy-5-(2-methoxyethoxy)phenyl]-(5-oxo-1-pyrimidin-2-yl-4,5-dihydro-1H-[1,2,4]triazol-3-yl)methyl]amino}benzamidine acetate

[Chemical Formula 596]

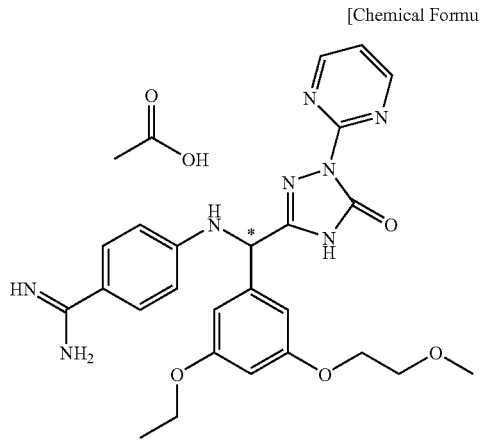

$^1$H-NMR (CD$_3$OD) δ 1.32 (q, J=6.8 Hz, 3H) 1.91 (s, 3H) 3.37 (s, 3H) 3.62-3.74 (m, 2H) 3.97 (q, J=6.8 Hz, 2H) 4.00-4.10 (m, 2H) 5.56 (s, 1H) 6.41 (dd, J=2.0, 2.4 Hz, 1H) 6.65-6.78 (m, 2H) 6.85 (d, J=8.8 Hz, 2H) 7.28 (t, J=4.8 Hz, 1H) 7.59 (d, J=8.8 Hz, 2H) 8.76 (d, J=4.8 Hz, 2H)

HPLC retention time: 13 min

Example X-13

4-{[(R) and (S)-(5-oxo-1-pyrimidin-2-yl-4,5-dihydro-1H-[1,2,4]triazol-3-yl)-(3,4,5-trimethoxyphenyl)methyl]amino}benzamidine acetate

[Chemical Formula 597]

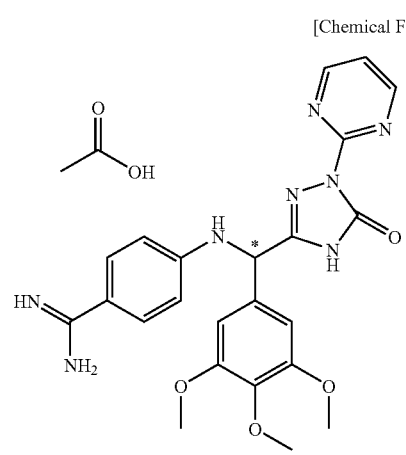

$^1$H-NMR (CD$_3$OD) δ 1.95 (br.s, 3H) 3.74 (br.s, 3H) 3.83 (br.s, 6H) 5.63 (br.s, 1H) 6.75-7.00 (m, 4H) 7.35 (br.s, 1H) 7.62 (br.d, J=8.0 Hz, 2H) 8.79 (br.s, 2H)

HPLC retention time: 13 min

Example X-14

4-{[(R) and (S)-[3-(3-fluoropropoxy)-5-methoxyphenyl]-(5-oxo-1-pyrimidin-2-yl-4,5-dihydro-1H-[1,2,4]triazol-3-yl)methyl]amino}benzamidine acetate

[Chemical Formula 598]

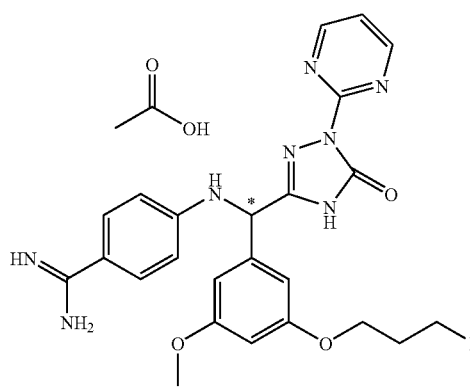

$^1$H-NMR (CD$_3$OD) δ 1.91 (s, 3H) 2.09 (quint.d, J=6.0, 25.6 Hz, 2H) 3.75 (s, 3H) 4.05 (t, J=6.0 Hz, 2H) 4.57 (td, J=6.0, 47.6 Hz, 2H) 5.57 (s, 1H) 6.42 (t, J=2.0 Hz, 1H) 6.74 (br.s, 2H) 6.86 (d, J=8.8 Hz, 2H) 7.30 (br.s, 1H) 7.60 (d, J=8.8 Hz, 2H) 8.77 (br.d, J=4.0 Hz, 2H)

HPLC retention time: 13 min

Example X-15

4-{[(3-ethoxy-2-fluoro-5-methoxyphenyl)-(5-oxo-1-pyrimidin-2-yl-4,5-dihydro-1H-[1,2,4]triazol-3-yl)methyl]amino}benzamidine acetate

[Chemical Formula 599]

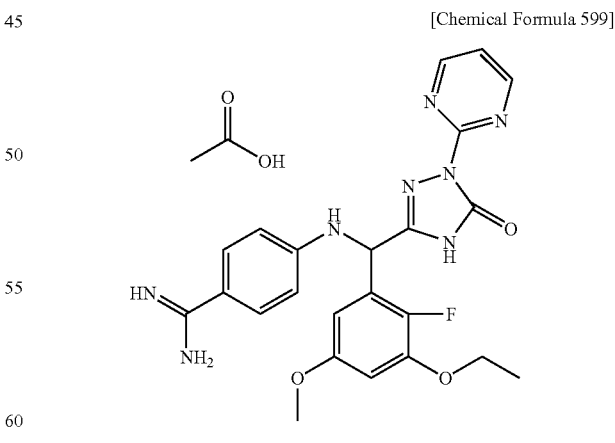

$^1$H-NMR (CD$_3$OD) δ 1.40 (t, J=6.8 Hz, 3H) 1.92 (s, 3H) 3.71 (s, 3H) 4.07 (q, J=6.8 Hz, 2H) 5.96 (s, 1H) 6.53-6.67 (m, 2H) 6.86 (d, J=8.8 Hz, 2H) 7.31 (t, J=4.8 Hz, 1H) 7.62 (d, J=8.8 Hz, 2H) 8.77 (d, J=4.8 Hz, 2H)

Mass spectrum (ESI) m/z: 479 (M+H)$^+$

Example X-16

4-{[(3-ethyl-4,5-dimethoxyphenyl)-(5-oxo-1-pyrimidin-2-yl-4,5-dihydro-1H-[1,2,4]triazol-3-yl)methyl]amino}benzamidine acetate

[Chemical Formula 600]

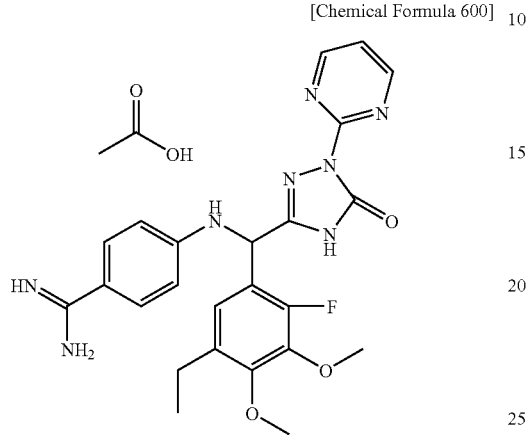

$^1$H-NMR (CD$_3$OD) δ 1.16 (t, J=7.6 Hz, 3H) 1.93 (s, 3H) 2.62 (q, J=7.6 Hz, 2H) 3.76 (s, 3H) 3.83 (s, 3H) 5.61 (s, 1H) 6.87 (d, J=8.8 Hz, 2H) 6.99 (d, J=2.0 Hz, 1H) 7.07 (d, J=2.0 Hz, 1H) 7.33 (t, J=4.8 Hz, 1H) 7.61 (d, J=8.8 Hz, 2H) 8.77 (d, J=4.8 Hz, 2H)

Mass spectrum (ESI) m/z: 475 (M+H)$^+$

Example X-17

4-{[(R) and (S)-(3-methoxy-5-(2-methoxyethyl)phenyl)-(5-oxo-1-pyrimidin-2-yl-4,5-dihydro-1H-[1,2,4]triazol-3-yl)methyl]amino}benzamidine acetate

[Chemical Formula 601]

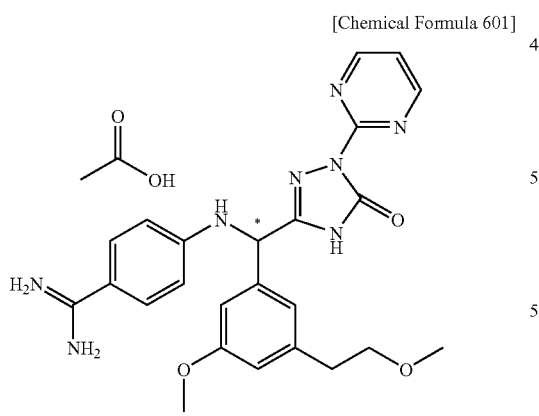

$^1$H-NMR (CD$_3$OD) δ 1.91 (s, 3H) 2.82 (t, J=6.8 Hz, 2H) 3.29 (s, 3H) 3.59 (t, J=6.8 Hz, 2H) 3.76 (s, 3H) 5.59 (s, 1H) 6.76 (s, 1H) 6.86 (d J=8.8 Hz, 2H) 6.94-7.00 (m, 1H) 7.02 (s, 1H) 7.30 (t, J=4.8 Hz, 1H) 7.60 (d, J=8.8 Hz, 2H) 8.77 (d, J=4.8 Hz, 2H)

HPLC retention time: 12 min

Example X-18

4-{[(R) and (S)-(8-methoxy-4-methyl-3-oxo-3,4-dihydro-2H-benzo[1,4]oxazin-6-yl)-(5-oxo-1-pyrimidin-2-yl-4,5-dihydro-1H-[1,2,4]triazol-3-yl)methyl]amino}benzamidine acetate

[Chemical Formula 602]

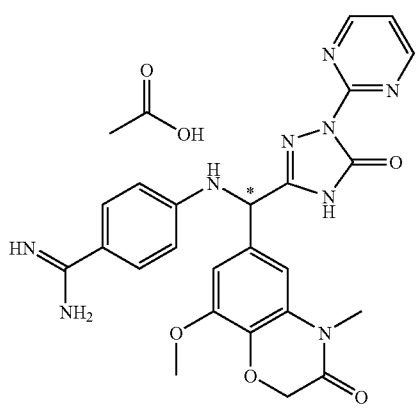

$^1$H-NMR (CD$_3$OD) δ 1.92 (s, 3H) 3.27 (s, 3H) 3.79 (s, 3H) 4.56 (s, 2H) 5.67 (s, 1H) 6.89 (d J=8.8 Hz, 2H) 6.99 (d, J=2.0 Hz, 1H) 7.01 (d, J=2.0 Hz, 1H) 7.31 (t, J=4.8 Hz, 1H) 7.60 (d, J=8.8 Hz, 2H) 8.78 (d, J=4.8 Hz, 2H)

HPLC retention time: 21 min

Example X-19

2-{[[1-(2-methoxyphenyl)-5-oxo-4,5-dihydro-1H-[1,2,4]triazol-3-yl]-(3,4,5-trimethoxyphenyl)methyl]amino}benzamidine acetate

[Chemical Formula 603]

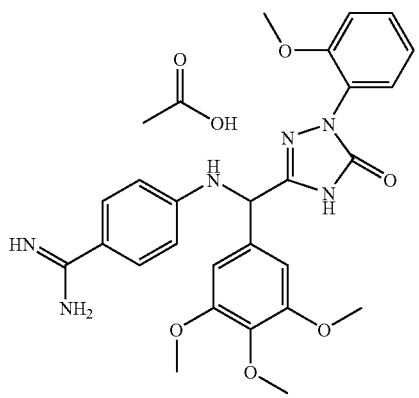

$^1$H-NMR (CD$_3$OD) δ 1.93 (s, 3H) 3.76 (s, 3H) 3.81 (s, 3H) 3.84 (s, 6H) 5.62 (s, 1H) 6.86 (s, 2H) 6.87 (d, J=8.8 Hz, 2H) 7.03 (ddd, J=1.2, 7.6, 7.6 Hz, 1H) 7.14 (dd, J=1.2, 8.4 Hz, 1H) 7.31 (dd, J=1.6, 7.6 Hz, 1H) 7.44 (ddd, J=1.6, 8.4 Hz, 1H) 7.64 (d, J=8.8 Hz, 2H)

Mass spectrum (ESI) m/z: 505 (M+H)$^+$

Example X-20

4-{[[3-(2-fluoroethoxy)-4,5-dimethoxyphenyl]-(5-oxo-1-pyrimidin-2-yl-4,5-dihydro-1H-[1,2,4]triazol-3-yl)methyl]amino}benzamidine acetate

[Chemical Formula 604]

$^1$H-NMR (CD$_3$OD) δ 1.93 (s, 3H) 3.76 (s, 3H) 3.80 (s, 3H) 4.10-4.30 (m, 2H) 4.67 (td, J=4.0, 48.0 Hz, 2H) 5.65 (s, 1H) 6.88 (d, J=8.8 Hz, 2H) 6.90 (s, 1H) 6.92 (s, 1H) 7.33 (t, J=4.4 Hz, 1H) 7.61 (d, J=8.8 Hz, 2H) 8.78 (d, J=4.4 Hz, 2H)

Mass spectrum (ESI) m/z: 509 (M+H)$^+$

Example X-21

4-{[(3-cyanomethoxy-2-fluoro-5-methoxyphenyl)-(5-oxo-1-pyrimidin-2-yl-4,5-dihydro-1H-[1,2,4]triazol-3-yl)methyl]amino}benzamidine acetate

[Chemical Formula 605]

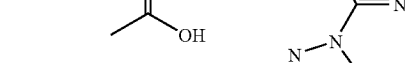

$^1$H-NMR (CD$_3$OD) δ 1.92 (s, 3H) 3.74 (s, 3H) 5.05 (s, 2H) 5.95 (s, 1H) 6.72-6.83 (m, 2H) 6.85 (d, J=8.4 Hz, 2H) 7.29 (t, J=4.4 Hz, 1H) 7.61 (d, J=8.4 Hz, 2H) 8.76 (d, J=4.4 Hz, 2H)

Mass spectrum (ESI) m/z: 490 (M+H)$^+$

Example X-22

4-{[(3-cyanomethoxy-5-methoxyphenyl)-(5-oxo-1-pyrimidin-2-yl-4,5-dihydro-1H-[1,2,4]triazol-3-yl)methyl]amino}benzamidine acetate

[Chemical Formula 606]

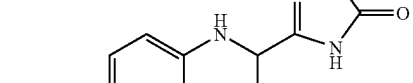

$^1$H-NMR (CD$_3$OD) δ 1.92 (s, 3H) 3.78 (s, 3H) 4.96 (s, 2H) 5.62 (s, 1H) 6.56 (dd, J=2.0, 2.4 Hz, 1H) 6.80-6.93 (m, 4H) 7.31 (t, J=4.8 Hz, 1H) 7.60 (d, J=9.2 Hz, 2H) 8.78 (d, J=4.8 Hz, 2H)

Mass spectrum (ESI) m/z: 472 (M+H)$^+$

Example X-23

4-{[[3-ethoxy-4-(2-fluoroethoxy)phenyl]-(5-oxo-1-pyrimidin-2-yl-4,5-dihydro-1H-[1,2,4]triazol-3-yl)methyl]amino}benzamidine acetate

[Chemical Formula 607]

$^1$H-NMR (CD$_3$OD) δ 1.36 (t, J=6.8 Hz, 3H) 1.95 (s, 3H) 4.05 (q, J=6.8 Hz, 2H) 4.14-4.30 (m, 2H) 4.60-4.80 (m, 2H) 5.65 (s, 1H) 6.87 (d, J=8.8 Hz, 2H) 6.97 (d, J=8.0 Hz, 1H) 7.07 (dd, J=2.0, 8.0 Hz, 1H) 7.17 (d, J=2.0 Hz, 1H) 7.34 (t, J=4.8 Hz, 1H) 7.60 (d, J=8.8 Hz, 2H) 8.78 (d, J=4.8 Hz, 2H)

Mass spectrum (ESI) m/z: 493 (M+H)$^+$

Example X-24

4-{[(3-allyloxy-5-hydroxymethylphenyl)-(5-oxo-1-pyrimidin-2-yl-4,5-dihydro-1H-[1,2,4]triazol-3-yl)methyl]amino}benzamidine acetate

[Chemical Formula 608]

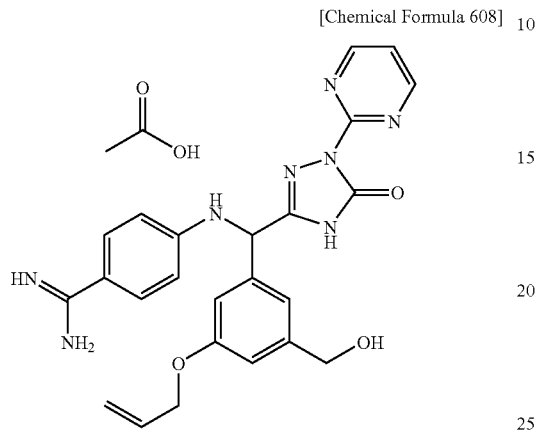

$^1$H-NMR (CD$_3$OD) δ 1.92 (s, 3H) 4.51 (ddd, J=1.6, 1.6, 5.2 Hz, 2H) 4.55 (s, 2H) 5.19 (tdd, J=1.6, 1.6, 10.4 Hz, 1H) 5.34 (tdd, J=1.6, 1.6, 17.2 Hz, 1H) 5.66 (s, 1H) 6.00 (tdd, J=5.2, 10.4, 17.2 Hz, 1H) 6.86 (d, J=9.2 Hz, 2H) 6.89 (br.s, 1H) 7.04 (t, J=2.0 Hz, 1H) 7.13 (br.s, 1H) 7.31 (t, J=4.8 Hz, 1H) 7.59 (d, J=9.2 Hz, 2H) 8.76 (d, J=4.8 Hz, 2H)

Mass spectrum (ESI) m/z: 473 (M+H)$^+$

Example X-25

4-{[(3-ethoxy-5-methoxyphenyl)-(5-oxo-1-pyrimidin-2-yl-4,5-dihydro-1H-[1,2,4]triazol-3-yl)methyl]amino}benzamidine acetate

[Chemical Formula 609]

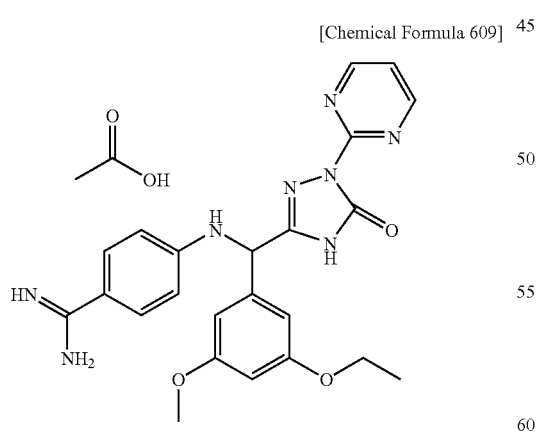

$^1$H-NMR (CD$_3$OD) δ 1.33 (t, J=6.8 Hz, 3H) 1.92 (s, 3H) 3.75 (s, 3H) 3.99 (q, J=6.8 Hz, 2H) 5.59 (s, 1H) 6.41 (dd, J=1.6, 2.4 Hz, 1H) 6.71 (br.s, 2H) 6.86 (d, J=8.8 Hz, 2H) 7.33 (t, J=4.8 Hz, 1H) 7.60 (d, J=8.8 Hz, 2H) 8.78 (d, J=4.8 Hz, 2H)

Mass spectrum (ESI) m/z: 461 (M+H)$^+$

Example X-26

4-{[(3-ethyl-5-methoxymethylphenyl)-(5-oxo-1-pyrimidin-2-yl-4,5-dihydro-1H-[1,2,4]triazol-3-yl)methyl]amino}benzamidine acetate

[Chemical Formula 610]

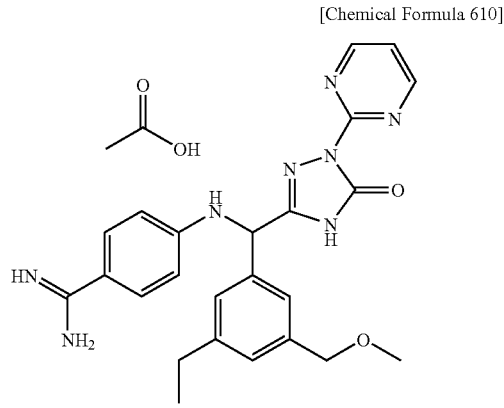

$^1$H-NMR (CD$_3$OD) δ 1.22 (t, J=7.6 Hz, 3H) 1.95 (s, 3H) 2.66 (q, J=7.6 Hz, 2H) 3.36 (s, 3H) 4.43 (s, 2H) 5.69 (s, 1H) 6.87 (d, J=8.8 Hz, 2H) 7.14 (s, 1H) 7.34 (br.s, 3H) 7.61 (d, J=8.8 Hz, 2H) 8.78 (d, J=5.2 Hz, 2H)

Mass spectrum (ESI) m/z: 459 (M+H)$^+$

Example X-27

4-{[[4-(2-dimethylaminoethoxy)-2-fluoro-5-methoxyphenyl]-(5-oxo-1-pyrimidin-2-yl-4,5-dihydro-1H-[1,2,4]triazol-3-yl)methyl]amino}benzamidine diacetate

[Chemical Formula 611]

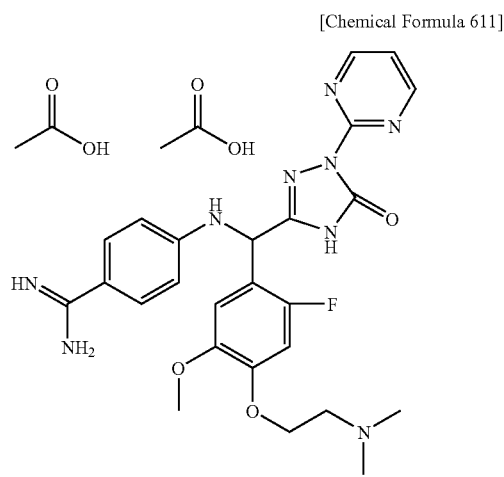

$^1$H-NMR (CD$_3$OD) δ 1.93 (br.s, 6H) 2.76 (br.s, 6H) 3.25 (br.s, 2H) 3.84 (br.s, 3H) 4.18 (br.s, 2H) 5.91 (br.s, 1H) 6.70-7.00 (m, 3H) 7.20 (br.s, 1H) 7.32 (br.s, 1H) 7.61 (br.s, 2H) 8.77 (br.s, 2H)

Mass spectrum (ESI) m/z: 522 (M+H)$^+$

Example X-28

4-{[[2-fluoro-3-(2-fluoroethoxy)-4,5-dimethoxyphenyl]-(5-oxo-1-pyrimidin-2-yl-4,5-dihydro-1H-[1,2,4]triazol-3-yl)methyl]amino}benzamidine acetate

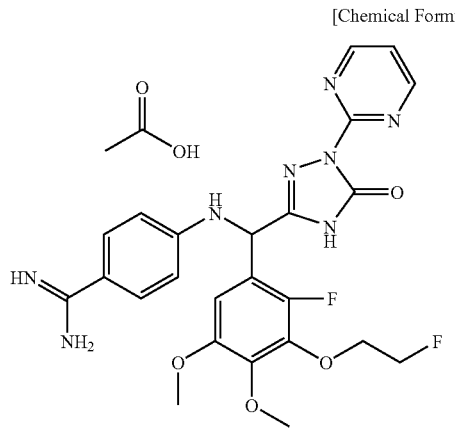

[Chemical Formula 612]

$^1$H-NMR (CD$_3$OD) δ 1.94 (s, 3H) 3.74 (s, 3H) 3.83 (s, 3H) 4.25-4.39 (m, 2H) 4.56-4.76 (m, 2H) 5.97 (s, 1H) 6.87 (d, J=8.8 Hz, 2H) 6.92 (d, J=6.4 Hz, 1H) 7.33 (t, J=4.8 Hz, 1H) 7.62 (d, J=8.8 Hz, 2H) 8.77 (d, J=4.8 Hz, 2H)

Mass spectrum (ESI) m/z: 527 (M+H)$^+$

Example X-29

4-{[[5-ethoxy-2-fluoro-3-(3-fluoropropoxy)phenyl]-(5-oxo-1-pyrimidin-2-yl-4,5-dihydro-1H-[1,2,4]triazol-3-yl)methyl]amino}benzamidine acetate

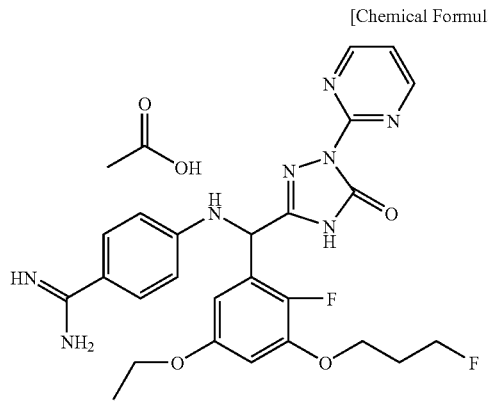

[Chemical Formula 613]

$^1$H-NMR (CD$_3$OD) δ 1.30 (t, J=6.8 Hz, 3H) 1.94 (s, 3H) 2.16 (quint.d, J=6.0, 25.2 Hz, 2H) 3.93 (q, J=6.8 Hz, 2H) 4.14 (t, J=6.0 Hz, 2H) 4.62 (td, J=6.0, 47.2 Hz, 2H) 5.97 (s, 1H) 6.55-6.69 (m, 2H) 6.86 (d, J=8.8 Hz, 2H) 7.33 (t, J=4.8 Hz, 1H) 7.61 (d, J=8.8 Hz, 2H) 8.76 (d, J=4.8 Hz, 2H)

Mass spectrum (ESI) m/z: 525 (M+H)$^+$

Example X-30

4-{[(3-ethoxy-4,5-dimethoxyphenyl)-(5-oxo-1-pyrimidin-2-yl-4,5-dihydro-1H-[1,2,4]triazol-3-yl)methyl]amino}benzamidine acetate

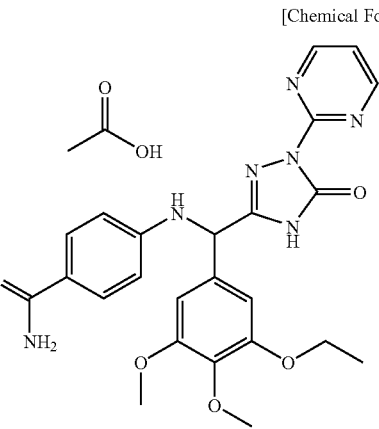

[Chemical Formula 614]

$^1$H-NMR (CD$_3$OD) δ 1.35 (t, J=6.8 Hz, 3H) 1.93 (s, 3H) 3.74 (s, 3H) 3.81 (s, 3H) 3.94-4.12 (m, 2H) 5.61 (s, 1H) 6.78-6.98 (m, 4H) 7.33 (t, J=4.8 Hz, 1H) 7.61 (d, J=8.4 Hz, 2H) 8.78 (d, J=4.8 Hz, 2H)

Mass spectrum (ESI) m/z: 491 (M+H)$^+$

Example X-31

4-{[[2-fluoro-4-(2-fluoroethoxy)-5-methoxyphenyl]-(5-oxo-1-pyrimidin-2-yl-4,5-dihydro-1H-[1,2,4]triazol-3-yl)methyl]amino}benzamidine acetate

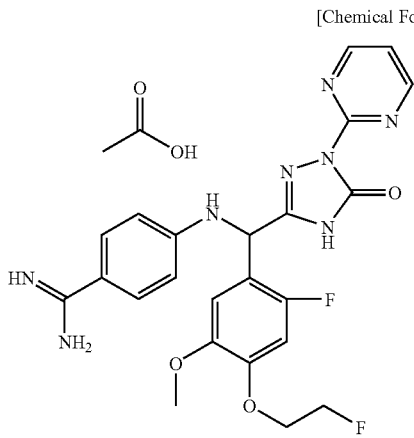

[Chemical Formula 615]

$^1$H-NMR (CD$_3$OD) δ 1.95 (s, 3H) 3.83 (s, 3H) 4.03-4.24 (m, 2H) 4.63 (td, J=4.0, 47.6 Hz, 2H) 5.94 (s, 1H) 6.78-6.94 (m, 3H) 7.12 (d, J=7.2 Hz, 1H) 7.34 (t, J=4.8 Hz, 1H) 7.61 (d, J=8.8 Hz, 2H) 8.76 (d, J=4.8 Hz, 2H)

Mass spectrum (ESI) m/z: 497 (M+H)$^+$

Example X-32

4-{[[2-fluoro-5-methoxy-3-(1-methylpyrrolidin-3-yloxy)phenyl]-(5-oxo-1-pyridin-2-yl-4,5-dihydro-1H-[1,2,4]triazol-3-yl)methyl]amino}benzamidine acetate

[Chemical Formula 616]

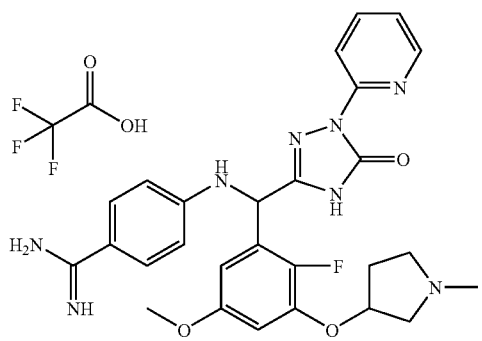

Mass spectrum (ESI) m/z: 533 (M+H)$^+$

Example X-33

2-(3-{(4-carbamimidoylphenylamino)-[1-(2-fluorophenyl)-5-oxo-4,5-dihydro-1H-[1,2,4]triazol-3-yl]methyl}-2-fluoro-5-methoxyphenoxy)-N,N-dimethylacetamide trifluoroacetate

[Chemical Formula 617]

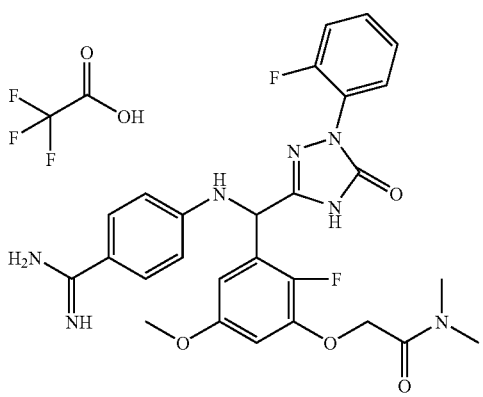

$^1$H-NMR (CD$_3$OD) δ 2.96 (s, 3H) 3.08 (s, 3H) 3.72 (s, 3H) 4.90 (s, 2H) 6.00 (s, 1H) 6.60-6.63 (m, 2H) 6.86 (d, J=8.4 Hz, 2H) 7.27 (t, J=8.0 Hz, 2H) 7.42-7.48 (m, 2H) 7.63 (d, J=8.4 Hz, 2H)

Mass spectrum (ESI) m/z: 552 (M+H)$^+$

Example X-34

2-{3-[(4-carbamimidoylphenylamino)-(5-oxo-1-pyridin-2-yl-4,5-dihydro-1H-[1,2,4]triazol-3-yl)methyl]-2-fluoro-5-methoxyphenoxy}-N,N-dimethylacetamide trifluoroacetate

[Chemical Formula 618]

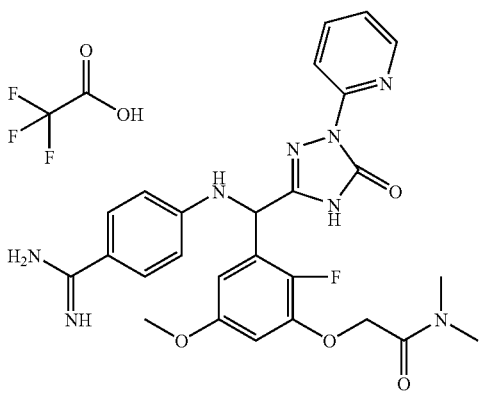

$^1$H-NMR (CD$_3$OD) δ 2.97 (s, 3H) 3.08 (s, 3H) 3.70 (s, 3H) 4.90 (s, 2H) 6.03 (s, 1H) 6.58-6.64 (m, 2H) 6.86 (d, J=8.4 Hz, 2H) 7.35 (dd, J=6.0, 6.4 Hz, 1H) 7.63 (d, J=8.4 Hz, 2H) 8.02 (dt, J=1.6, 8.0 Hz, 1H) 8.13 (d, J=8.0 Hz, 1H) 8.43 (d, J=4.8 Hz, 1H)

Mass spectrum (ESI) m/z: 535 (M+H)$^+$

Example X-35

2-(3-{(R) and (S)-(4-carbamimidoylphenylamino)-[1-(2-methoxyphenyl)-5-oxo-4,5-dihydro-1H-[1,2,4]triazol-3-yl]methyl}-2-fluoro-5-methoxyphenoxy)-N,N-dimethylacetamide acetate

[Chemical Formula 619]

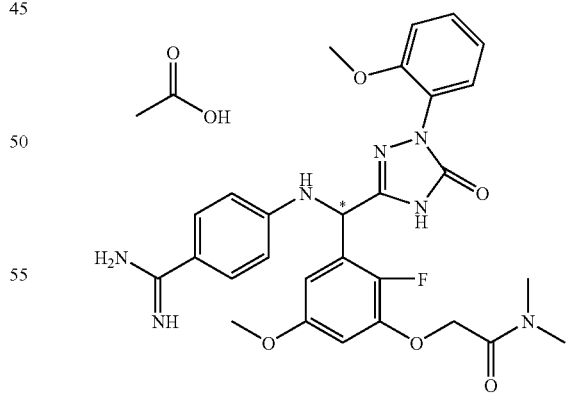

$^1$H-NMR (CD$_3$OD) δ 1.90 (s, 3H) 2.97 (s, 3H) 3.09 (s, 3H) 3.71 (s, 3H) 3.80 (s, 3H) 5.94 (s, 1H) 6.60 (dd, J=2.8, 6.8 Hz, 1H) 6.66 (dd, J=2.8, 4.4 Hz, 1H) 6.84 (d, J=8.8 Hz, 2H) 7.01 (dt, J=1.2, 7.6 Hz, 1H) 7.12 (dd, J=0.8, 8.4 Hz, 1H) 7.29 (dd, J=1.6, 7.6 Hz, 1H) 7.39-7.43 (m, 1H) 7.62 (d, J=8.8 Hz, 2H)

HPLC retention time: 7 min

Example X-36

4-({(3-ethoxy-2-fluoro-5-methylphenyl)-[1-(2-methoxyphenyl)-5-oxo-4,5-dihydro-1H-[1,2,4]triazol-3-yl]methyl}amino)benzamidine trifluoroacetate

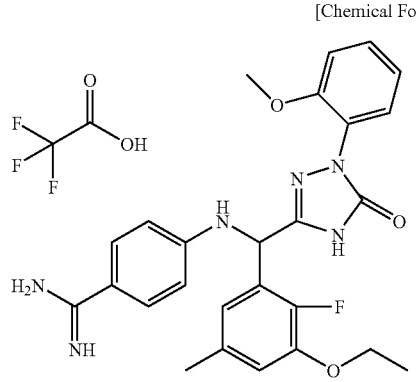

[Chemical Formula 620]

$^1$H-NMR (CD$_3$OD) δ 1.41 (t, J=6.8 Hz, 3H) 2.29 (s, 3H) 3.81 (s, 3H) 4.09 (q, J=6.8 Hz, 2H) 5.95 (s, 1H) 6.83-6.87 (m, 3H) 6.91 (dd, J=1.6, 8.0 Hz, 1H) 7.02 (dt, J=1.2, 7.6 Hz, 1H) 7.13 (dd, J=1.2, 8.4 Hz, 1H) 7.30 (dd, J=1.6, 7.6 Hz, 1H) 7.43 (ddd, J=1.6, 7.6, 8.4 Hz, 1H) 7.62-7.65 (m, 2H)

Mass spectrum (ESI) m/z: 491 (M+H)$^+$

Example X-37

4-{[(3-ethoxy-2-fluoro-5-methylphenyl)-(5-oxo-1-pyrimidin-2-yl-4,5-dihydro-1H-[1,2,4]triazol-3-yl)methyl]amino}benzamidine trifluoroacetate

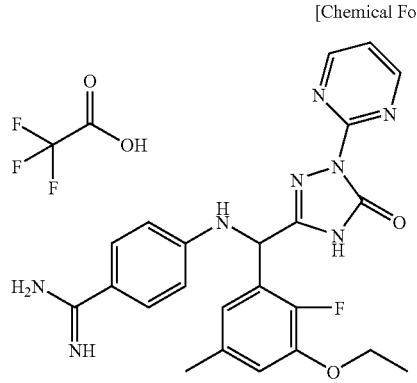

[Chemical Formula 621]

$^1$H-NMR (CD$_3$OD) δ 1.39 (t, J=6.8 Hz, 3H) 2.25 (s, 3H) 4.06 (q, J=6.8 Hz, 2H) 5.98 (s, 1H) 6.81-6.88 (m, 4H) 7.35 (br.s, 1H) 7.62 (d, J=8.4 Hz, 2H) 8.76 (br.s, 2H)

Mass spectrum (ESI) m/z: 463 (M+H)$^+$

Example X-38

4-{[(R) and (S)-[2-fluoro-3-(2-fluoroethoxy)-5-methylphenyl]-(5-oxo-1-pyrimidin-2-yl-4,5-dihydro-1H-[1,2,4]triazol-3-yl)methyl]amino}benzamidine acetate

[Chemical Formula 622]

$^1$H-NMR (CD$_3$OD) δ 1.92 (s, 3H) 2.25 (s, 3H) 4.21-4.31 (m, 2H) 4.64-4.79 (m, 2H) 5.94 (s, 1H) 6.84 (d, J=8.8 Hz, 2H) 6.88-6.93 (m, 2H) 7.29 (t, J=4.8 Hz, 1H) 7.60 (d, J=8.8 Hz, 2H) 8.75 (d, J=4.8 Hz, 2H)

HPLC retention time: 12 min

Example X-39

4-{[[2-fluoro-5-(2-fluoroethoxy)-3-(2-methoxyethoxy)phenyl]-(5-oxo-1-pyrimidin-2-yl-4,5-dihydro-1H-[1,2,4]triazol-3-yl)methyl]amino}benzamidine acetate

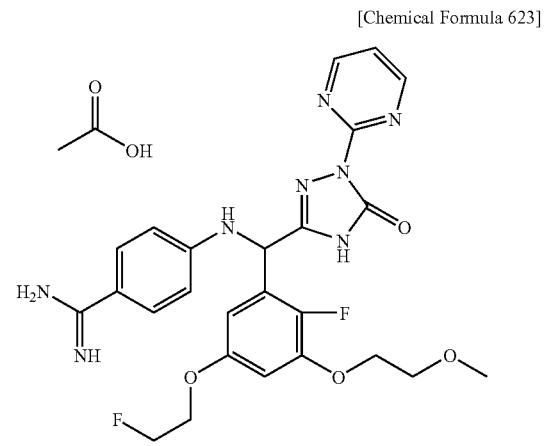

[Chemical Formula 623]

$^1$H-NMR (CD$_3$OD) δ 1.97 (s, 3H) 3.42 (s, 3H) 3.74-3.76 (m, 2H) 4.09-4.18 (m, 4H) 4.57-4.73 (m, 2H) 6.01 (s, 1H) 6.64-6.72 (m, 2H) 6.87 (d, J=8.0 Hz, 2H) 7.36 (t, J=4.8 Hz, 1H) 7.63 (d, J=8.0 Hz, 2H) 8.77 (d, J=4.8 Hz, 2H)

Mass spectrum (ESI) m/z: 541 (M+H)$^+$

Example X-40

4-{[(R) and (S)-(3-ethoxy-5-methylphenyl)-(5-oxo-1-pyrimidin-2-yl-4,5-dihydro-1H-[1,2,4]triazol-3-yl)methyl]amino}benzamidine acetate

[Chemical Formula 624]

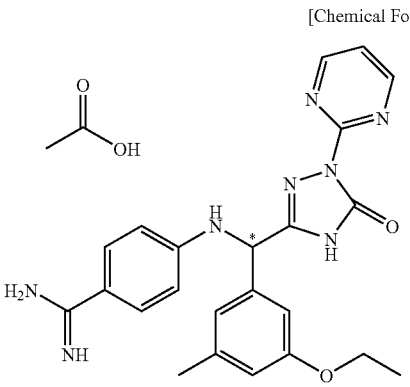

¹H-NMR (CD₃OD) δ 1.33 (t, J=6.8 Hz, 3H) 1.91 (s, 3H) 2.29 (s, 3H) 3.99 (q, J=6.8 Hz, 2H) 5.55 (s, 1H) 6.67 (s, 1H) 6.85 (d, J=9.2 Hz, 2H) 6.90 (s, 1H) 6.94 (s, 1H) 7.29 (t, J=4.8 Hz, 1H) 7.59 (d, J=9.2 Hz, 2H) 8.76 (d, J=4.8 Hz, 2H)

HPLC retention time: 12 min

Example X-41

4-{[(R) and (S)-[3-(2-fluoroethoxy)-5-methylphenyl]-(5-oxo-1-pyrimidin-2-yl-4,5-dihydro-1H-[1,2,4]triazol-3-yl)methyl]amino}benzamidine acetate

[Chemical Formula 625]

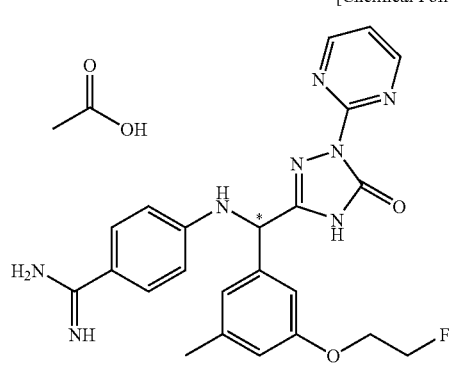

¹H-NMR (CD₃OD) δ 1.91 (s, 3H) 2.29 (s, 3H) 4.11-4.21 (m, 2H) 4.59-4.73 (m, 2H) 5.57 (s, 1H) 6.72 (s, 1H) 6.85 (d, J=8.8 Hz, 2H) 6.95 (s, 1H) 6.98 (s, 1H) 7.28 (t, J=4.8 Hz, 1H) 7.59 (d, J=8.8 Hz, 2H) 8.76 (d, J=4.8 Hz, 2H)

HPLC retention time: 12 min

Example X-42

4-{[(R) and (S)-[2-fluoro-5-(2-fluoroethoxy)phenyl]-(5-oxo-1-pyrimidin-2-yl-4,5-dihydro-1H-[1,2,4]triazol-3-yl)methyl]amino}benzamidine acetate

[Chemical Formula 626]

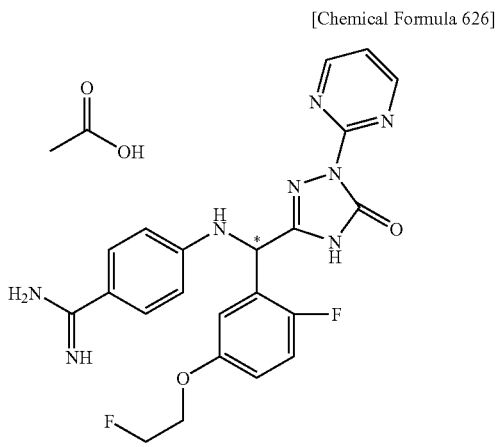

¹H-NMR (CD₃OD) δ 1.93 (s, 3H) 4.10-4.20 (m, 2H) 4.57-4.72 (m, 2H) 5.95 (s, 1H) 6.86 (d, J=8.8 Hz, 2H) 6.91-6.95 (td, J=3.6, 9.2 Hz, 1H) 7.07 (t, J=5.2 Hz, 1H) 7.14 (dd, J=2.8, 5.6 Hz, 1H) 7.31 (t, J=4.8 Hz, 1H) 7.61 (d, J=8.8 Hz, 2H) 8.76 (d, J=4.8 Hz, 2H)

HPLC retention time: 13 min

Example X-43

4-{[(R) and (S)-[3-ethoxy-2-fluoro-5-(2-fluoroethoxy)phenyl]-(5-oxo-1-pyrimidin-2-yl-4,5-dihydro-1H-[1,2,4]triazol-3-yl)methyl]amino}benzamidine acetate

[Chemical Formula 627]

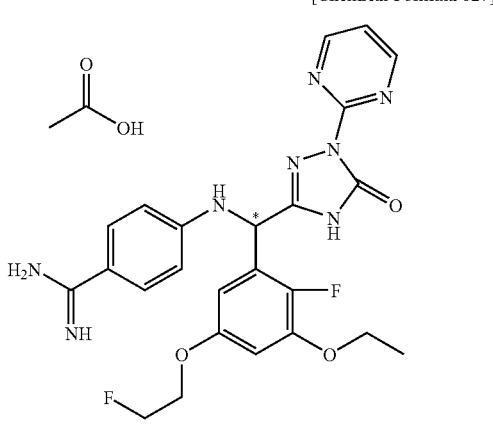

¹H-NMR (CD₃OD) δ 1.40 (t, J=6.8 Hz, 3H) 1.91 (s, 3H) 4.05-4.16 (m, 4H) 4.56-4.71 (m, 2H) 5.94 (s, 1H) 6.63-6.66 (m, 2H) 6.86 (d, J=8.8 Hz, 2H) 7.30 (t, J=4.8 Hz, 1H) 7.61 (d, J=8.8 Hz, 2H) 8.76 (d, J=4.8 Hz, 2H)

HPLC retention time: 13 min

Example X-44

4-{[[2-fluoro-3-(2-fluoroethoxy)-5-methoxyphenyl]-(1-(3-fluoropyridin-2-yl)-5-oxo-4,5-dihydro-1H-[1,2,4]triazol-3-yl)methyl]amino}benzamidine acetate

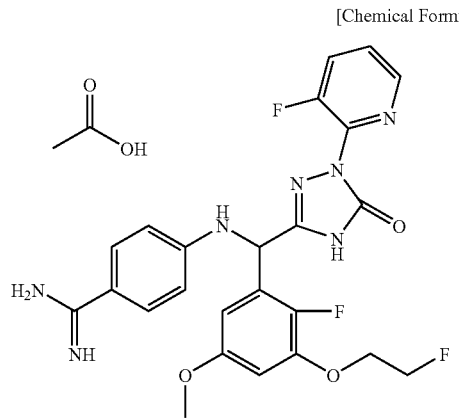

[Chemical Formula 628]

$^1$H-NMR (CD$_3$OD) δ 1.95 (s, 3H) 3.73 (s, 3H) 4.23-4.32 (m, 2H) 4.65-4.80 (m, 2H) 6.01 (s, 1H) 6.63-6.69 (m, 2H) 6.87 (d, J=8.8 Hz, 2H) 7.56 (quintet, J=4.4 Hz, 1H) 7.64 (d, J=8.8 Hz, 2H) 7.83 (t, J=8.4 Hz, 1H) 8.37 (d, J=4.4 Hz, 1H)

Mass spectrum (ESI) m/z: 514 (M+H)$^+$

Example X-45

4-{[(R) and (S)-(2-fluoro-3-methoxy-5-methylphenyl)-(5-oxo-1-pyrimidin-2-yl-4,5-dihydro-1H-[1,2,4]triazol-3-yl)methyl]amino}benzamidine acetate

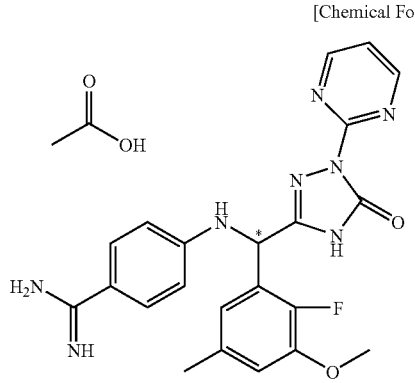

[Chemical Formula 629]

$^1$H-NMR (CD$_3$OD) δ 1.91 (s, 3H) 2.21 (s, 3H) 3.80 (s, 3H) 5.93 (s, 1H) 6.81-6.86 (m, 2H) 6.82 (d, J=9.2 Hz, 2H) 7.28 (t, J=4.8 Hz, 1H) 7.59 (d, J=9.2 Hz, 2H) 8.72 (d, J=4.8 Hz, 2H)

HPLC retention time: 12 min

Example X-46

4-{[(R) and (S)-(3-ethoxy-4-methoxyphenyl)-(5-oxo-1-pyrazin-2-yl-4,5-dihydro-1H-[1,2,4]triazol-3-yl)methyl]amino}benzamidine acetate

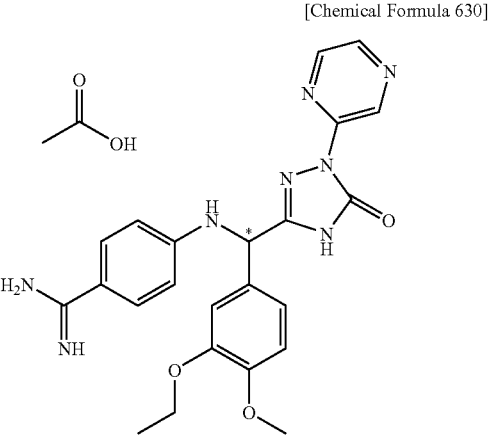

[Chemical Formula 630]

$^1$H-NMR (CD$_3$OD) δ 1.36 (t, J=6.8 Hz, 3H) 1.92 (s, 3H) 3.81 (s, 3H) 4.04 (q, J=6.8 Hz, 2H) 5.58 (s, 1H) 6.83-6.87 (m, 2H) 6.94 (d, J=8.4 Hz, 1H) 7.08 (dd, J=1.6, 8.0 Hz, 1H) 7.14 (d, J=2.4 Hz, 1H) 7.57-7.61 (m, 2H) 8.40 (d, J=2.4 Hz, 1H) 8.47 (br.s, 1H) 9.42 (d, J=1.2 Hz, 1H)

HPLC retention time: 13 min

Example X-47

4-{[(R) and (S)-(8-fluoromethoxy-4H-benzo[1,3]dioxin-6-yl)-(5-oxo-1-pyrimidin-2-yl-4,5-dihydro-1H-[1,2,4]triazol-3-yl)methyl]amino}benzamidine acetate

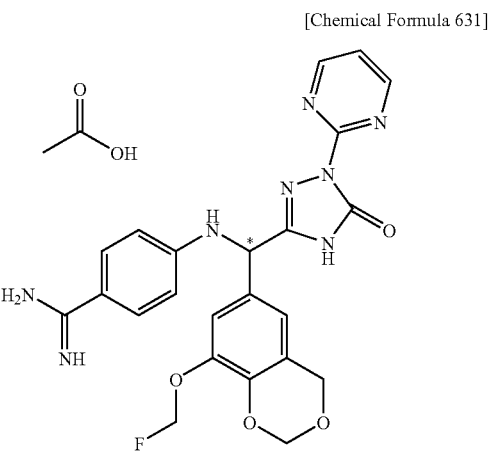

[Chemical Formula 631]

$^1$H-NMR (CD$_3$OD) δ 1.91 (s, 3H) 4.87 (s, 2H) 5.24 (s, 2H) 5.59 (s, 1H) 5.68 (d, J=54.0 Hz, 2H) 6.85 (d, J=8.8 Hz, 2H) 7.01 (d, J=1.2 Hz, 1H) 7.23 (d, J=1.2 Hz, 1H) 7.31 (t, J=4.8 Hz, 1H) 7.60 (d, J=8.8 Hz, 2H) 8.77 (d, J=4.8 Hz, 2H)

HPLC retention time: 16 min

Example X-48

2-{4-[(4-carbamimidoylphenylamino)-(5-oxo-1-pyrimidin-2-yl-4,5-dihydro-1H-[1,2,4]triazol-3-yl)methyl]-2-methoxyphenoxy}-N,N-dimethylacetamide trifluoroacetate

[Chemical Formula 632]

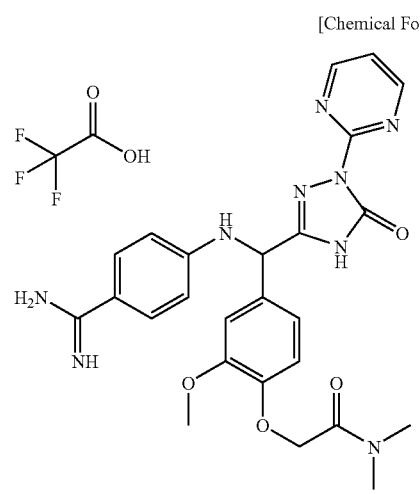

$^1$H-NMR (CD$_3$OD) δ 2.96 (s, 3H) 3.08 (s, 3H) 3.86 (s, 3H) 4.81 (s, 2H) 5.67 (s, 1H) 6.87 (d, J=8.8 Hz, 2H) 6.93 (d, J=8.4 Hz, 1H) 7.06 (dd, J=8.4, 2.0 Hz, 1H) 7.19 (d, J=2.0 Hz, 1H) 7.38 (t, J=4.8 Hz, 1H) 7.62 (d, J=8.8 Hz, 2H) 8.79 (d, J=4.8 Hz, 2H)

Mass spectrum (ESI) m/z: 518 (M+H)$^+$

Example X-49

2-(3-{(4-carbamimidoylphenylamino)-[3-(3-dimethylamino-2,2-dimethylpropoxy)-5-ethyl-2-fluorophenyl]methyl}-5-oxo-4,5-dihydro-1H-[1,2,4]triazol-1-yl)benzamide bistrifluoroacetate

[Chemical Formula 633]

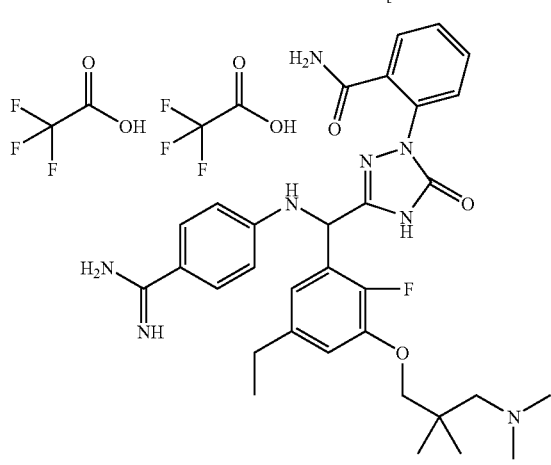

Mass spectrum (ESI) m/z: 603 (M+H)$^+$

Example X-50

(R) and (S)-2-{3-[(4-carbamimidoylphenylamino)-(3-ethoxy-4-methoxyphenyl)methyl]-5-oxo-4,5-dihydro-[1,2,4]triazol-1-yl}benzoic acid acetate

[Chemical Formula 634]

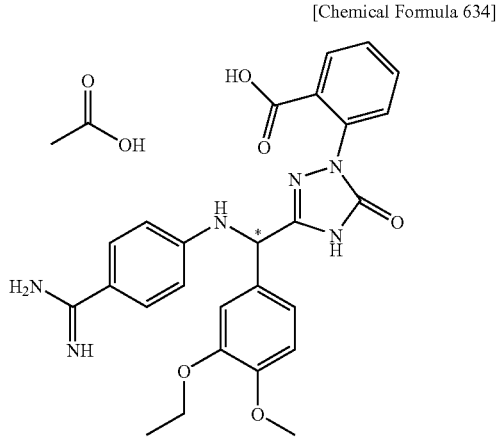

$^1$H-NMR (d6-DMSO) δ 1.31 (br.s, 3H) 3.74 (s, 3H) 4.01 (br.s, 2H) 5.36 (s, 1H) 6.84 (br.d, J=6.0 Hz, 2H) 6.95 (br.d, J=8.4 Hz, 1H) 7.05 (br.d, J=6.4 Hz, 1H) 7.21-7.33 (m, 3H) 7.52 (br.d, J=7.6 Hz, 2H) 7.68 (br.d, J=6.4 Hz, 1H) 8.36 (br.s, 1H) (data for racemic mixture)

Mass spectrum (ESI) m/z: 503 (M+H)$^+$ (data for racemic mixture)

HPLC retention time: 12 min

Example X-51

4-({[3-methoxy-4-(2-methoxy-1-methylethoxy)phenyl]-[1-(2-methoxyphenyl)-5-oxo-4,5-dihydro-1H-[1,2,4]triazol-3-yl]methyl}amino)benzamidine trifluoroacetate

[Chemical Formula 635]

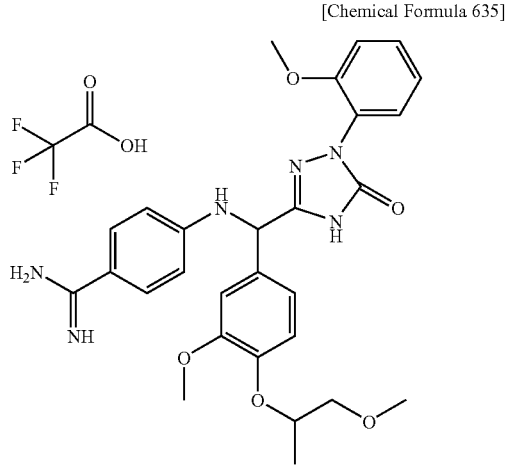

Mass spectrum (ESI) m/z: 533 (M+H)$^+$

Example X-52

2-(3-{(4-carbamimidoylphenylamino)-[4-(2-dimethylamino-1-methyl-ethoxy)-3-ethoxyphenyl]methyl}-5-oxo-4,5-dihydro-[1,2,4]triazol-1-yl)benzamide bistrifluoroacetate

[Chemical Formula 636]

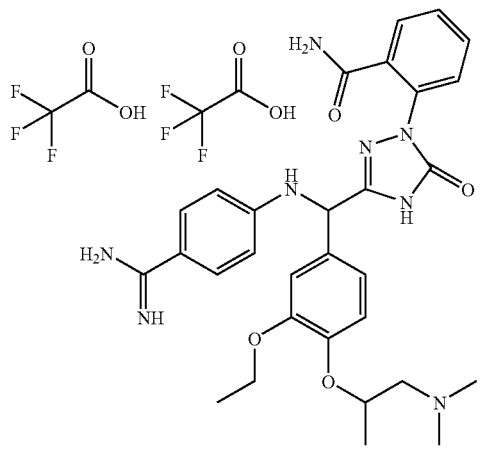

Mass spectrum (ESI) m/z: 573 (M+H)⁺

Example X-53

2-{3-[(4-carbamimidoylphenylamino)-(2-fluoro-5-methoxyphenyl)methyl]-5-oxo-4,5-dihydro-[1,2,4]triazol-1-yl}benzoic acid trifluoroacetate

[Chemical Formula 637]

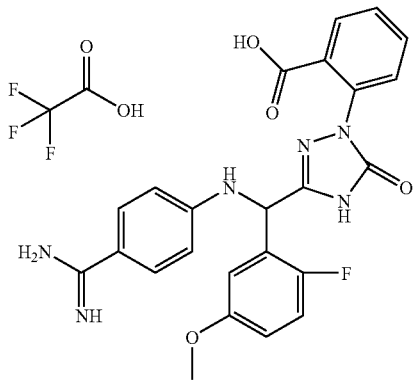

¹H-NMR (CD₃OD) δ 3.77 (s, 3H) 5.98 (s, 1H) 6.86 (d, J=8.8 Hz, 2H) 6.93 (m, 1H) 7.05 (dd, J=6.0, 3.2 Hz, 1H) 7.11 (t, J=9.2 Hz, 1H) 7.47-7.66 (m, 3H) 7.65 (d, J=8.8 Hz, 2H) 7.96 (dd, J=7.6, 1.2 Hz, 1H)
Mass spectrum (ESI) m/z: 477 (M+H)⁺

Example X-54

2-(3-{(4-carbamimidoylphenylamino)-[3-methoxy-4-(tetrahydrofuran-3-yloxy)-phenyl]methyl}-5-oxo-4,5-dihydro-[1,2,4]triazol-1-yl)benzamide trifluoroacetate

[Chemical Formula 638]

Mass spectrum (ESI) m/z: 544 (M+H)⁺

Example X-55

(R) and (S)-4-{[(4-cyanomethoxy-3-fluoro-5-methoxyphenyl)-(5-oxo-1-pyrimidin-2-yl-4,5-dihydro-1H-[1,2,4]triazol-3-yl)methyl]amino}benzamidine acetate

[Chemical Formula 639]

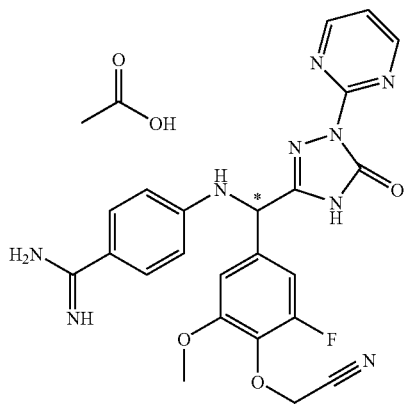

Mass spectrum (ESI) m/z: 490 (M+H)⁺ (data for racemic mixture)
HPLC retention time: 13 min

Example X-56

2-{3-[(4-carbamimidoylphenylamino)-(2-fluoro-4-methoxyphenyl)methyl]-5-oxo-4,5-dihydro-[1,2,4]triazol-1-yl}benzoic acid trifluoroacetate

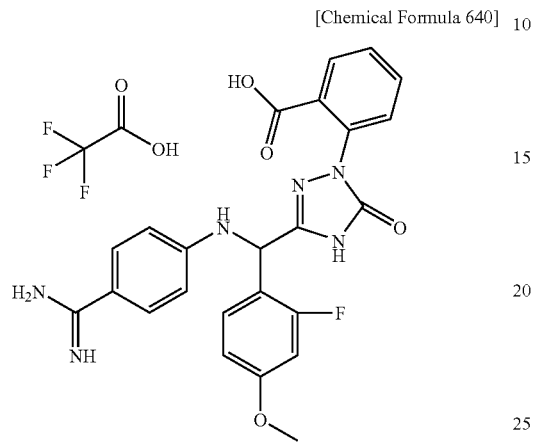

[Chemical Formula 640]

¹H-NMR (CD₃OD) δ 3.81 (s, 3H) 5.92 (s, 1H) 6.80 (m, 2H) 6.86 (d, J=8.8 Hz, 2H) 7.38-7.66 (m, 4H) 7.63 (d, J=8.8 Hz, 2H) 7.96 (dd, J=7.2, 1.6 Hz, 1H)

Mass spectrum (ESI) m/z: 477 (M+H)⁺

Example X-57

2-{3-[(4-carbamimidoylphenylamino)-(2-fluoro-4,5-dimethoxyphenyl)methyl]-5-oxo-4,5-dihydro-[1,2,4]triazol-1-yl}phenyl)carbamic acid methyl ester trifluoroacetate

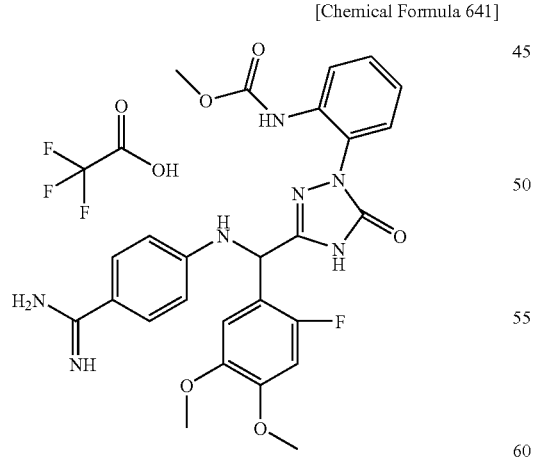

[Chemical Formula 641]

¹H-NMR (CD₃OD) δ 3.67 (s, 3H) 3.77 (s, 3H) 3.84 (s, 3H) 5.98 (s, 1H) 6.86 (m, 1H) 6.88 (d, J=8.8 Hz, 2H) 7.05 (d, J=7.2 Hz, 1H) 7.02 (m, 1H) 7.03 (m, 1H) 7.44 (dd, J=8.0, 1.6 Hz, 1H) 7.64 (d, J=8.8 Hz, 2H) 8.80 (m, 1H)

Mass spectrum (ESI) m/z: 536 (M+H)⁺

Example X-58

4-{[[3-methoxy-4-(2-methoxyethoxy)phenyl)-(5-oxo-1-pyrimidin-2-yl-4,5-dihydro-1H-[1,2,4]triazol-3-yl)methyl]amino}benzamidine trifluoroacetate

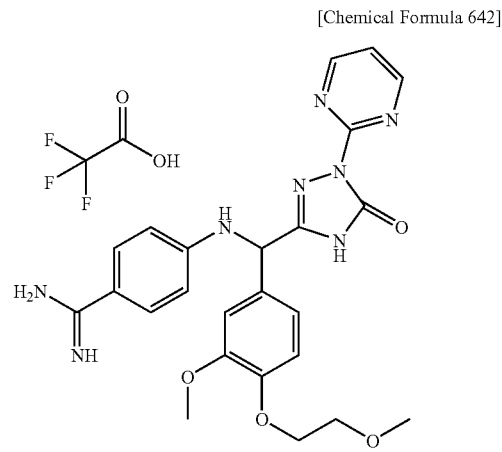

[Chemical Formula 642]

¹H-NMR (CD₃OD) δ 3.41 (s, 3H) 3.73 (m, 2H) 3.84 (s, 3H) 4.12 (m, 2H) 5.67 (s, 1H) 6.87 (d, J=8.8 Hz, 2H) 6.99 (d, J=8.0 Hz, 1H) 7.08 (dd, J=8.0, 2.0 Hz, 1H) 7.16 (d, J=2.0 Hz, 1H) 7.38 (t, J=4.8 Hz, 1H) 7.62 (d, J=8.8 Hz, 2H) 8.79 (d, J=4.8 Hz, 2H)

Mass spectrum (ESI) m/z: 491 (M+H)⁺

Example X-59

4-{[[3-allyloxy-2-fluoro-5-methoxyphenyl)-(5-oxo-1-pyrimidin-2-yl-4,5-dihydro-1H-[1,2,4]triazol-3-yl)methyl]amino}benzamidine acetate

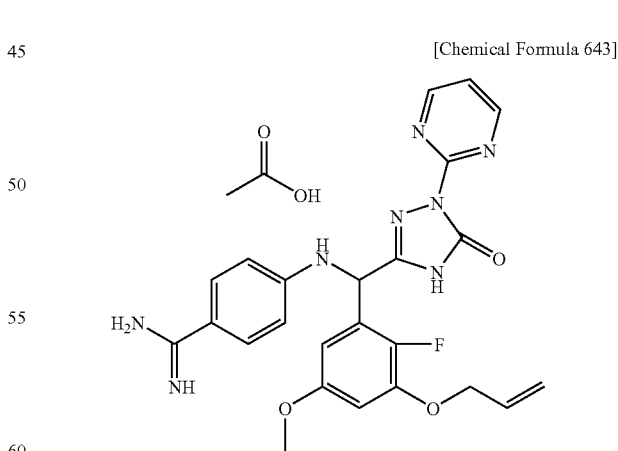

[Chemical Formula 643]

¹H-NMR (CD₃OD) δ 1.94 (br.s, 3H) 3.76 (br.s, 3H) 4.60 (br.s, 2H) 5.24 (br.d, J=10 Hz, 1H) 5.45 (br.d, J=17 Hz, 1H) 5.97 (br.s, 1H) 6.03 (m, 1H) 6.62 (br.s, 2H) 6.84 (br.s, 2H) 7.35 (br.s, 1H) 7.61 (br.s, 2H) 8.81 (br.s, 2H)

Mass spectrum (ESI) m/z: 491 (M+H)⁺

Example X-60

(R) and (S)-4-{[[3-fluoromethoxy-4-methoxyphenyl)-(5-oxo-1-pyrimidin-2-yl-4,5-dihydro-1H-[1,2,4]triazol-3-yl)methyl]amino}benzamidine acetate

[Chemical Formula 644]

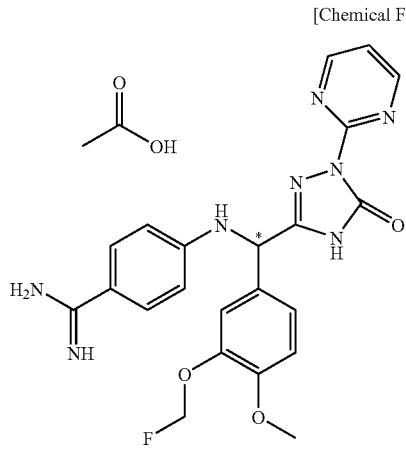

$^1$H-NMR (CD$_3$OD) δ 1.93 (s, 3H) 3.83 (s, 3H) 5.64 (s, 1H) 5.66 (d, J=54 Hz, 2H) 6.87 (d, J=8.8 Hz, 2H) 7.04 (d, J=8.4 Hz, 1H) 7.28 (br.d, J=8.4 Hz, 1H) 7.32 (m, 2H) 7.61 (d, J=8.8 Hz, 2H) 8.78 (d, J=4.8 Hz, 2H) (data for racemic mixture)

Mass spectrum (ESI) m/z: 465 (M+H)$^+$ (data for racemic mixture)

HPLC retention time: 13 min

Example X-61

4-{[(3-ethoxy-5-fluoro-4-methoxyphenyl)-(5-oxo-1-pyrimidin-2-yl-4,5-dihydro-1H-[1,2,4]triazol-3-yl)methyl]amino}benzamidine acetate

[Chemical Formula 645]

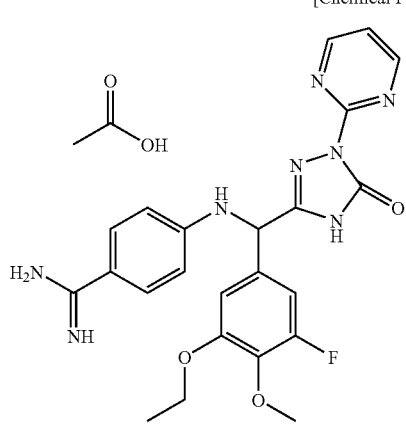

$^1$H-NMR (CD$_3$OD) δ 1.36 (t, J=7.2 Hz, 3H) 1.93 (s, 3H) 3.82 (s, 3H) 4.04 (q, J=7.2 Hz, 2H) 5.64 (s, 1H) 6.86 (d, J=8.8 Hz, 2H) 6.95 (dd, J=10.8, 1.6 Hz, 1H) 7.03 (br.s, 1H) 7.32 (t, J=4.8 Hz, 1H) 7.61 (d, J=8.8 Hz, 2H) 8.78 (d, J=4.8 Hz, 2H)

Mass spectrum (ESI) m/z: 479 (M+H)$^+$

Example X-62

(R) and (S)-4-{[[3,4-dimethoxy-5-(2-methoxyethyl)phenyl]-(5-oxo-1-pyridazin-3-yl-4,5-dihydro-1H-[1,2,4]triazol-3-yl)methyl]amino}benzamidine acetate

[Chemical Formula 646]

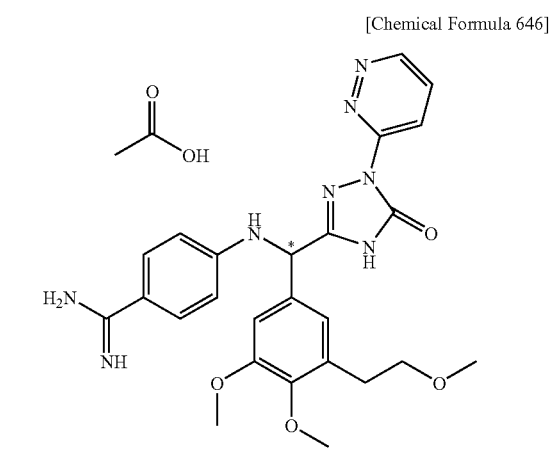

$^1$H-NMR (CD$_3$OD) δ 1.94 (s, 3H) 2.84 (t, J=6.8 Hz, 2H) 3.54 (t, J=6.8 Hz, 2H) 3.77 (s, 3H) 3.82 (s, 3H) 5.64 (s, 1H) 6.87 (d, J=8.8 Hz, 2H) 7.03 (d, J=2.0 Hz, 1H) 7.13 (d, J=2.0 Hz, 1H) 7.60 (d, J=8.8 Hz, 2H) 7.77 (dd, J=8.8, 4.8 Hz, 1H) 8.50 (dd, J=8.8, 1.2 Hz, 1H) 9.03 (dd, J=4.8, 1.2 Hz, 1H) (data for racemic mixture)

Mass spectrum (ESI) m/z: 505 (M+H)$^+$ (data for racemic mixture)

HPLC retention time: 9 min

Example X-63

2-(3-{(4-carbamimidoylphenylamino)-[3-(2-dimethylaminopropoxy)-5-ethyl-2-fluorophenyl]methyl}-5-oxo-4,5-dihydro-[1,2,4]triazol-1-yl)benzamide bistrifluoroacetate

[Chemical Formula 647]

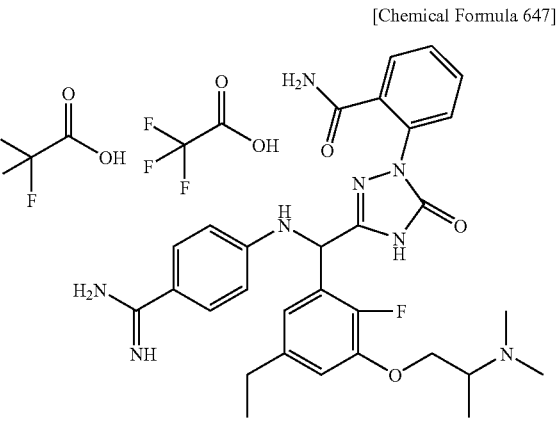

Mass spectrum (ESI) m/z: 575 (M+H)$^+$

Example X-64

2-(3-{(4-carbamimidoylphenylamino)-[3-(2-dimethylamino-1-methylethoxy)-5-ethyl-2-fluorophenyl]methyl}-5-oxo-4,5-dihydro-[1,2,4]triazol-1-yl)benzamide bistrifluoroacetate

[Chemical Formula 648]

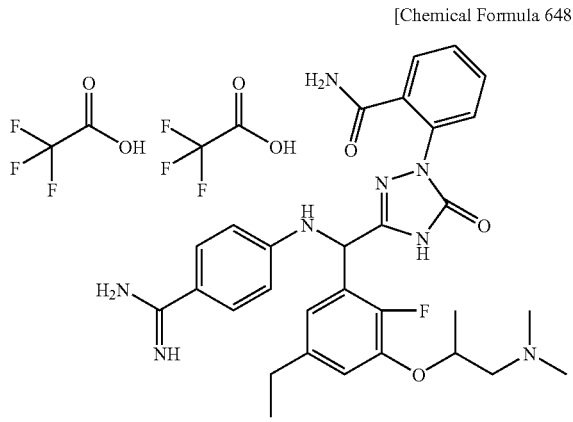

Mass spectrum (ESI) m/z: 575 (M+H)$^+$

Example X-65

(R) and (S)-4-{[[4 fluoro-3-(2-fluoroethoxy)-5-methoxyphenyl]-(5-oxo-1-pyrimidin-2-yl-4,5-dihydro-1H-[1,2,4]triazol-3-yl)methyl]amino}benzamidine acetate

[Chemical Formula 649]

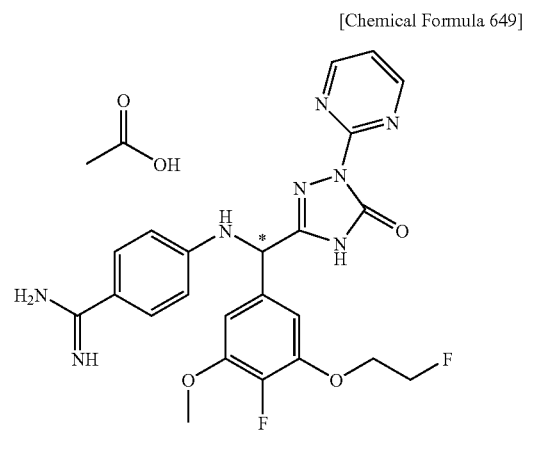

Mass spectrum (ESI) m/z: 497 (M+H)$^+$ (data for racemic mixture)

HPLC retention time: 13 min

Example X-66

4-{[(4-methoxy-3,5-dimethylphenyl)-(5-oxo-1-pyrimidin-2-yl-4,5-dihydro-1H-[1,2,4]triazol-3-yl)methyl]amino}benzamidine acetate

[Chemical Formula 650]

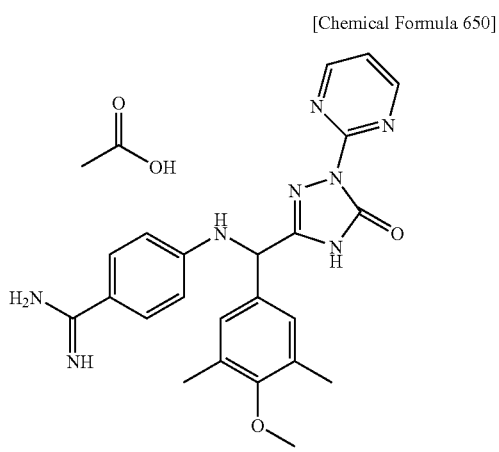

$^1$H-NMR (CD$_3$OD) δ 1.92 (s, 3H) 2.25 (s, 6H) 3.68 (s, 3H) 5.55 (s, 1H) 6.85 (d, J=8.8 Hz, 2H) 7.02 (s, 2H) 7.32 (t, J=4.4 Hz, 1H) 7.60 (d, J=8.8 Hz, 2H) 8.78 (d, J=4.4 Hz, 2H)

Mass spectrum (ESI) m/z: 445 (M+H)$^+$

Example X-67

4-{[(4-methoxy-3-methylphenyl)-[1-(2-methoxyphenyl)-5-oxo-4,5-dihydro-1H-[1,2,4]triazol-3-yl)methyl]amino}benzamidine acetate

[Chemical Formula 651]

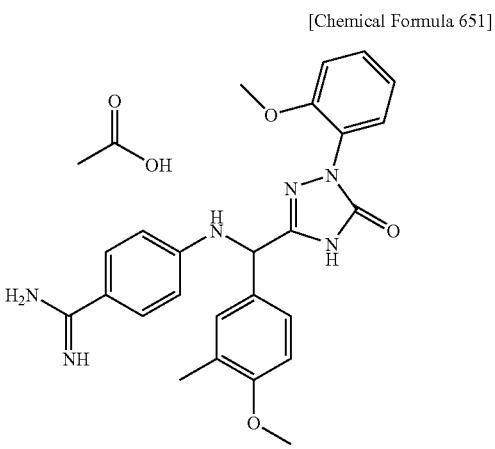

$^1$H-NMR (CD$_3$OD) δ 1.93 (s, 3H) 2.21 (s, 3H) 3.81 (s, 3H) 3.83 (s, 3H) 5.57 (s, 1H) 6.85 (d, J=8.4 Hz, 2H) 6.94 (d, J=8.0 Hz, 1H) 7.03 (t, J=7.6 Hz, 1H) 7.14 (d, J=8.4 Hz, 1H) 7.30 (m, 3H) 7.44 (t, J=8.0 Hz, 1H) 7.62 (d, J=8.4 Hz, 2H)

Mass spectrum (ESI) m/z: 459 (M+H)$^+$

Example X-68

4-{[(4-difluoromethoxy-3-methoxyphenyl)-(5-oxo-1-pyrimidin-2-yl-4,5-dihydro-1H-[1,2,4]triazol-3-yl)methyl]amino}benzamidine trifluoroacetate

[Chemical Formula 652]

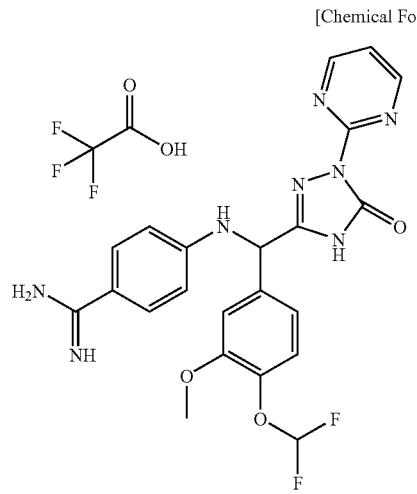

¹H-NMR (CD₃OD) δ 3.88 (s, 3H) 5.76 (s, 1H) 6.70 (t, J=75.2 Hz, 1H) 6.88 (d, J=8.8 Hz, 2H) 7.15 (m, 2H) 7.32 (s, 1H) 7.38 (br.s, 1H) 7.62 (d, J=8.8 Hz, 2H) 8.80 (br.s, 2H)

Mass spectrum (ESI) m/z: 483 (M+H)⁺

Example X-69

4-({(2-fluoro-4,5-dimethoxyphenyl)-[1-(2-hydroxymethylphenyl)-5-oxo-4,5-dihydro-1H-[1,2,4]triazol-3-yl)methyl]amino}benzamidine trifluoroacetate

[Chemical Formula 653]

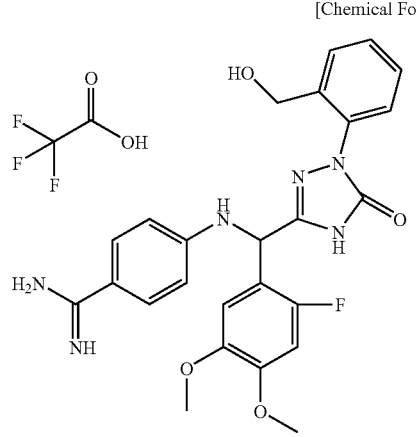

¹H-NMR (d6-DMSO) δ 3.77 (s, 3H) 3.82 (s, 3H) 4.54 (d, J=3.2 Hz, 2H) 5.96 (s, 1H) 6.85 (d, J=11.6 Hz, 1H) 6.86 (d, J=8.8 Hz, 2H) 7.02 (d, J=6.8 Hz, 1H) 7.34-7.64 (m, 4H) 7.64 (d, J=8.8 Hz, 2H)

Mass spectrum (ESI) m/z: 493 (M+H)⁺

Example X-70

4-{[(4-fluoro-3,5-dimethoxyphenyl)-(5-oxo-1-pyrimidin-2-yl-4,5-dihydro-1H-[1,2,4]triazol-3-yl)methyl]amino}benzamidine acetate

[Chemical Formula 654]

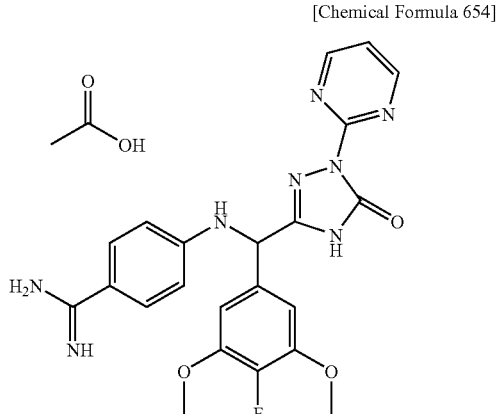

Mass spectrum (ESI) m/z: 465 (M+H)⁺

Example X-71

4-{[(3-cyanomethoxy-4-methoxyphenyl)-(5-oxo-1-pyrimidin-2-yl-4,5-dihydro-1H-[1,2,4]triazol-3-yl)methyl]amino}benzamidine trifluoroacetate

[Chemical Formula 655]

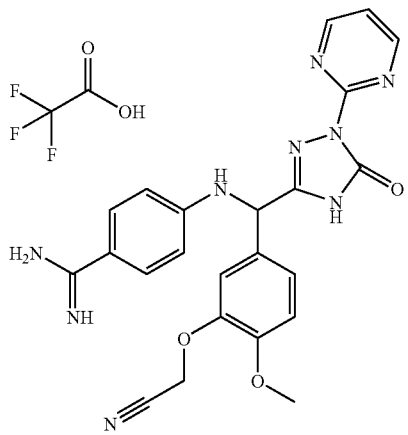

¹H-NMR (CD₃OD) δ 3.75 (s, 3H) 4.85 (s, 2H) 5.96 (s, 1H) 6.70 (d, J=8.8 Hz, 2H) 6.97 (d, J=8.4 Hz, 1H) 7.17 (m, 2H) 7.26 (t, J=4.8 Hz, 1H) 7.50 (d, J=8.8 Hz, 2H) 8.68 (d, J=4.8 Hz, 2H)

Mass spectrum (ESI) m/z: 472 (M+H)⁺

Example X-72

(R) and (S)-4-{[(3,4-dimethoxy-5-methoxymethylphenyl)-(5-oxo-1-pyridazin-3-yl-4,5-dihydro-1H-[1,2,4]triazol-3-yl)methyl]amino}benzamidine acetate

[Chemical Formula 656]

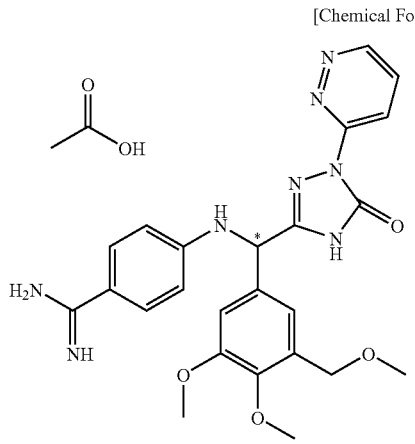

$^1$H-NMR (CD$_3$OD) δ 1.94 (s, 3H) 3.35 (s, 3H) 3.77 (s, 3H) 3.84 (s, 3H) 4.44 (s, 2H) 5.67 (s, 1H) 6.87 (d, J=9.2 Hz, 2H) 7.18 (d, J=2.0 Hz, 1H) 7.21 (d, J=2.0 Hz, 1H) 7.60 (d, J=9.2 Hz, 2H) 7.77 (dd, J=9.2, 4.8 Hz, 1H) 8.50 (dd, J=8.8, 1.2 Hz, 1H) 9.03 (dd, J=4.8, 1.2 Hz, 1H) (data for racemic mixture)
HPLC retention time: 9 min

Example X-73

(R) and (S)-4-({(2-fluoro-4,5-dimethoxyphenyl)-[1-(3-hydroxypyridin-2-yl)-5-oxo-4,5-dihydro-1H-[1,2,4]triazol-3-yl)methyl]amino}benzamidine acetate

[Chemical Formula 657]

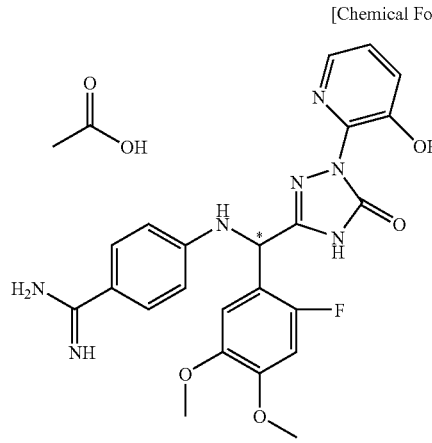

$^1$H-NMR (CD$_3$OD) δ 1.95 (s, 3H) 3.74 (s, 3H) 3.81 (s, 3H) 5.92 (s, 1H) 6.83 (d, J=11.6 Hz, 1H) 6.85 (d, J=8.8 Hz, 2H) 7.09 (d, J=7.2 Hz, 1H) 7.28 (dd, J=8.4, 4.8 Hz, 1H) 7.40 (dd, J=8.0, 1.2 Hz, 1H) 7.60 (d, J=8.8 Hz, 2H) 7.99 (dd, J=4.8, 1.2 Hz, 1H) (data for racemic mixture)
Mass spectrum (ESI) m/z: 480 (M+H)$^+$ (data for racemic mixture)
HPLC retention time: 12 min

Example X-74

(R) and (S)-4-{[(2-methoxy-6-methylpyridin-4-yl)-(5-oxo-1-pyridazin-3-yl-4,5-dihydro-1H-[1,2,4]triazol-3-yl)methyl]amino}benzamidine acetate

[Chemical Formula 658]

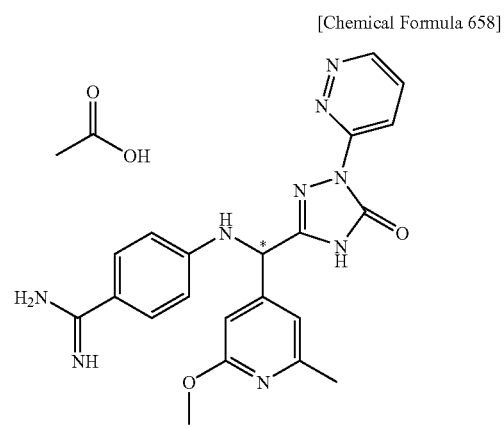

$^1$H-NMR (CD$_3$OD) δ 1.95 (s, 3H) 2.39 (s, 3H) 3.85 (s, 3H) 5.67 (s, 1H) 6.78 (s, 1H) 6.85 (d, J=8.8 Hz, 2H) 6.99 (s, 1H) 7.60 (d, J=8.8 Hz, 2H) 7.77 (dd, J=9.2, 4.4 Hz, 1H) 8.50 (d, J=9.2 Hz, 1H) 9.03 (dd, J=4.8, 1.2 Hz, 1H) (data for racemic mixture)
Mass spectrum (ESI) m/z: 432 (M+H)$^+$ (data for racemic mixture)
HPLC retention time: 12 min

Example X-75

(R) and (S)-4-{[(2,6-dimethoxypyridin-4-yl)-(5-oxo-1-pyridazin-3-yl-4,5-dihydro-1H-[1,2,4]triazol-3-yl)methyl]amino}benzamidine acetate

[Chemical Formula 659]

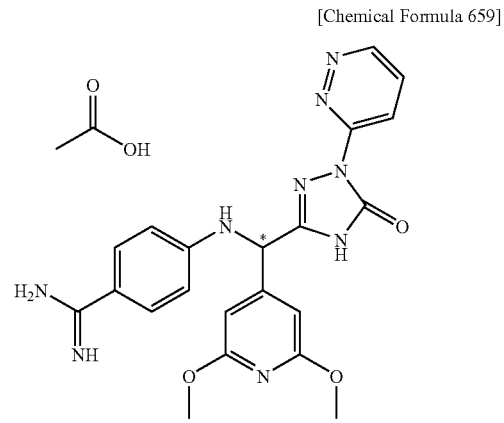

$^1$H-NMR (CD$_3$OD) δ 1.93 (s, 3H) 3.86 (s, 6H) 5.59 (s, 1H) 6.52 (s, 2H) 6.85 (d, J=9.2 Hz, 2H) 7.61 (d, J=9.2 Hz, 2H) 7.75 (dd, J=9.2, 4.8 Hz, 1H) 8.56 (d, J=9.2 Hz, 1H) 9.00 (dd, J=4.8, 1.2 Hz, 1H) (data for racemic mixture)
Mass spectrum (ESI) m/z: 448 (M+H)$^+$ (data for racemic mixture)
HPLC retention time: 14 min

Example X-76

4-{[(2,6-dimethoxypyridin-4-yl)-(5-oxo-1-pyrazin-2-yl-4,5-dihydro-1H-[1,2,4]triazol-3-yl)methyl]amino}benzamidine acetate

[Chemical Formula 660]

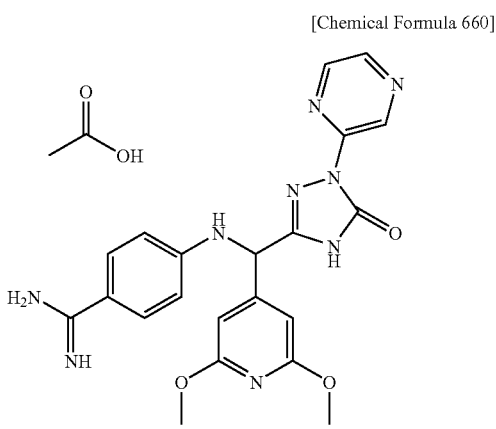

$^1$H-NMR (CD$_3$OD) δ 1.95 (s, 3H) 3.87 (s, 6H) 5.60 (s, 1H) 6.50 (s, 2H) 6.84 (d, J=8.4 Hz, 2H) 7.60 (d, J=8.4 Hz, 2H) 8.41 (br.s, 1H) 8.48 (br.s, 1H) 9.42 (br.s, 1H)

Mass spectrum (ESI) m/z: 448 (M+H)$^+$

Example X-77

(R) and (S)-4-({[3-ethoxy-4-(2-methoxyethoxy)phenyl]-[1-(3-methoxypyridin-2-yl)-5-oxo-4,5-dihydro-1H-[1,2,4]triazol-3-yl]methyl}amino)benzamidine acetate

[Chemical Formula 661]

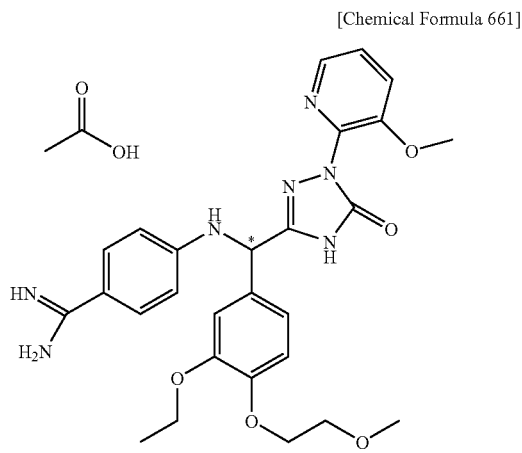

$^1$H-NMR (CD$_3$OD) δ 1.38 (t, J=7.2 Hz, 3H) 1.91 (s, 3H) 3.42 (s, 3H) 3.72-3.75 (m, 2H) 3.87 (s, 3H) 4.03-4.12 (m, 2H) 4.13-4.14 (m, 2H) 5.60 (s, 1H) 6.86 (d, J=9.2 Hz, 2H) 7.00 (d, J=8.0 Hz, 1H) 7.06 (dd, J=2.0, 8.4 Hz, 1H) 7.13 (d, J=2.4 Hz, 1H) 7.52 (dd, J=4.4, 8.4 Hz, 1H) 7.62 (d, J=9.2 Hz, 2H) 7.67 (dd, J=1.6, 8.4 Hz, 1H) 8.10 (dd, J=1.2, 4.8 Hz, 1H) (data for racemic mixture)

Mass spectrum (ESI) m/z: 534 (M+H)$^+$

HPLC retention time: 10 min (column: CHIRALPAK™ AD, 2 cmφ×25 cmL, Manufacturer: Daicel Chemical Industries, Ltd., Mobile phase: 2-propanol/hexane=1/2, 0.1% trifluoroacetic acid, Elution rate; 9 ml/min)

Example X-78

(R) and (S)-4-({[3-methoxy-4-(2-methoxyethoxy)phenyl]-[1-(2-methoxyphenyl)-5-oxo-4,5-dihydro-1H-[1,2,4]triazol-3-yl]methyl}amino)benzamidine acetate

[Chemical Formula 662]

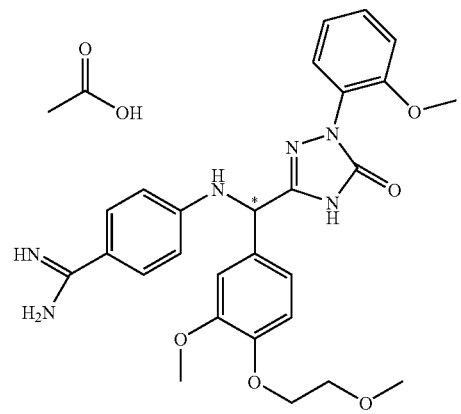

$^1$H-NMR (CD$_3$OD) δ 1.91 (s, 3H) 3.41 (s, 3H) 3.72-3.75 (m, 2H) 3.80 (s, 3H) 3.84 (s, 3H) 4.12-4.14 (m, 2H) 5.61 (s, 1H) 6.86 (d, J=8.8 Hz, 2H) 7.00 (d, J=8.4 Hz, 1H) 7.03 (dd, J=1.6, 4.0 Hz, 1H) 7.05 (dd, J=2.4, 5.2 Hz, 1H) 7.13-7.15 (m, 2H) 7.31 (dd, J=2.0, 7.6 Hz, 1H) 7.43 (ddd, J=1.6, 7.6, 9.2 Hz, 2H) 7.63 (d, J=8.8 Hz, 1H)

Mass spectrum (ESI) m/z: 519 (M+H)$^+$

HPLC retention time: 12 min (Column: CHIRALPAK™ AD, 2 cmφ×25 cmL, Manufacturer: Daicel Chemical Industries, Ltd., Mobile phase: 2-propanol/hexane=2/3, 0.1% trifluoroacetic acid, Elution rate: 9 ml/min)

Example X-79

(R) and (S)-3-{3-[(4-carbamimidoyl-3-fluorophenylamino)-(3,4-dimethoxyphenyl)methyl]-5-oxo-4,5-dihydro[1,2,4]triazol-1-yl}thiophene-2-carboxylic acid acetate

[Chemical Formula 663]

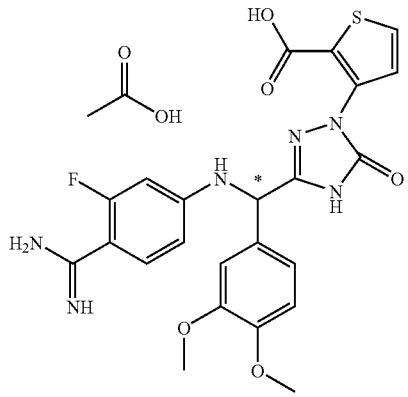

[1550]

$^1$H-NMR (CD$_3$OD) δ 1.95 (s, 3H) 3.82 (s, 3H) 3.84 (s, 3H) 5.56 (s, 1H) 6.60 (dd, J=14.4, 2.0 Hz, 1H) 6.69 (dd, J=8.8, 2.0 Hz, 1H) 6.97 (d, J=8.8 Hz, 1H) 7.06-7.09 (m, 2H) 7.13 (d, J=2.0 Hz, 1H) 7.43 (d, J=5.6 Hz, 1H) 7.47 (t, J=8.8 Hz, 1H)

HPLC retention time: 16 min (Column name: SUMICHIRAL OA-2500, 30 mmφ×25 cm, Manufacturer: Sumika Chemical Analysis Service, Ltd., Mobile phase: 0.05 M ammonium acetate-methanol solution, Elution rate: 25 ml/min)

Example X-80

(R) and (S)-4-{[(5-methoxychroman-7-yl)-(5-oxo-1-pyrimidin-2-yl-4,5-dihydro-1H-[1,2,4]triazol-3-yl)methyl]amino}benzamidine acetate

[Chemical Formula 664]

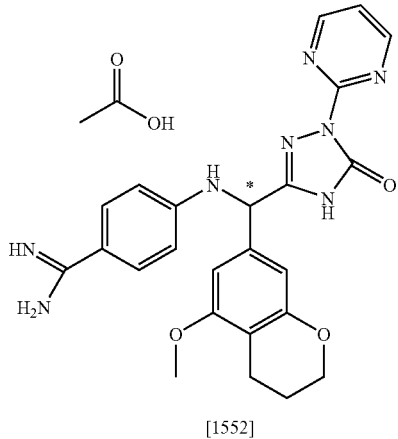

[1552]

¹H-NMR (CD₃OD) δ 1.87-1.94 (m, 5H) 2.58 (t, J=6.4 Hz, 2H) 3.78 (s, 3H) 4.06 (t, J=4.8 Hz, 2H) 5.52 (s, 1H) 6.58 (d, J=1.2 Hz, 1H) 6.66 (d, J=1.2 Hz, 1H) 6.84 (d, J=8.8 Hz, 2H) 7.29 (t, J=4.8 Hz, 1H) 7.59 (d, J=8.8 Hz, 2H) 8.76 (d, J=4.8 Hz, 2H)

Mass spectrum (ESI) m/z: 473 (M+H)⁺ (data for racemic mixture)

HPLC retention time: 12 min

Example X-81

4-({(2-fluoro-4,5-dimethoxyphenyl)-[1-(3-methylpyridin-2-yl)-5-oxo-4,5-dihydro-1H-[1,2,4]triazol-3-yl]methyl}amino)benzamidine acetate

[Chemical Formula 665]

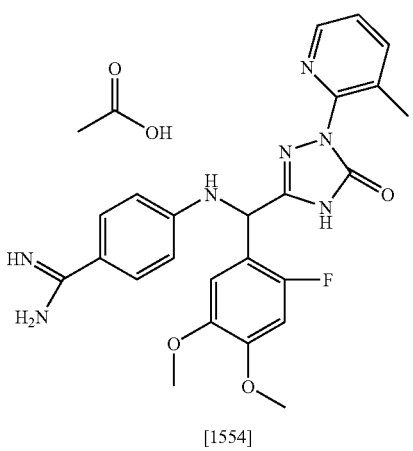

[1554]

¹H-NMR (CD₃OD) δ 1.97 (s, 3H) 2.27 (s, 3H) 3.77 (s, 3H) 3.83 (s, 3H) 5.96 (s, 1H) 6.86 (d, J=5.6 Hz, 1H) 6.87 (d, J=8.8 Hz, 2H) 7.05 (d, J=6.8 Hz, 1H) 7.44 (dd, J=4.8, 8.0 Hz, 1H) 7.64 (d, J=8.8 Hz, 2H) 7.86 (dd, J=1.2, 7.6 Hz, 1H) 8.37 (d, J=4.0 Hz, 1H)

Mass spectrum (ESI) m/z: 478 (M+H)⁺ (data for racemic mixture)

Example X-82

(R) and (S)-4-{[(9-methoxy-2,3-dihydro-5H-benzo[e][1,4]dioxepin-7-yl)-(5-oxo-1-pyrimidin-2-yl-4,5-dihydro-1H-[1,2,4]triazol-3-yl)methyl]amino}benzamidine acetate

[Chemical Formula 666]

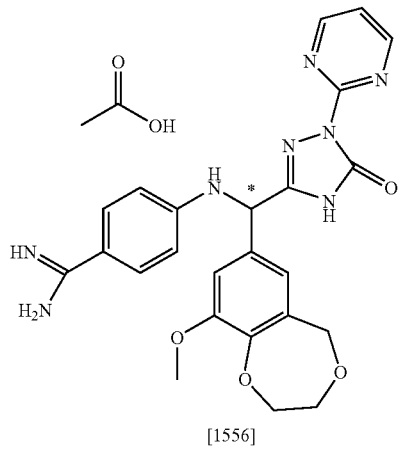

[1556]

¹H-NMR (CD₃OD) δ 1.93 (s, 3H) 3.83 (s, 3H) 3.96-4.05 (m, 4H) 4.64 (s, 2H) 5.62 (s, 1H) 6.86 (d, J=8.8 Hz, 2H) 7.02 (d, J=2.4 Hz, 1H) 7.19 (d, J=2.4 Hz, 1H) 7.32 (t, J=4.8 Hz, 1H) 7.61 (d, J=8.8 Hz, 2H) 8.78 (d, J=4.8 Hz, 2H)

Mass spectrum (ESI) m/z: 489 (M+H)⁺ (data for racemic mixture)

Example X-83

(R) and (S)-4-{[(8-fluoromethyl-4H-benzo[1,3]dioxin-6-yl)-(5-oxo-1-pyrimidin-2-yl-4,5-dihydro-1H-[1,2,4]triazol-3-yl)methyl]amino}benzamidine acetate

[Chemical Formula 667]

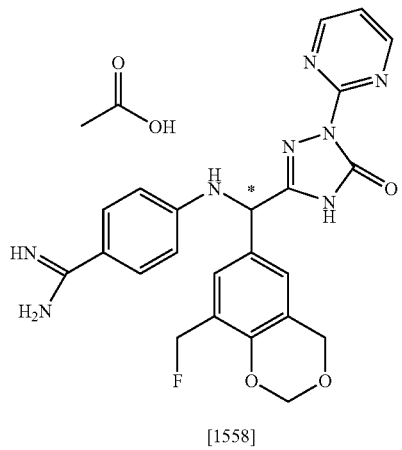

[1558]

¹H-NMR (CD₃OD) δ 1.92 (s, 3H) 4.88 (m, 2H) 5.26 (s, 2H) 5.30 (s, 1H) 5.42 (s, 1H) 5.58 (s, 1H) 6.84 (d, J=8.8 Hz, 2H) 7.24 (br.s, 1H) 7.28 (t, J=4.8 Hz, 1H) 7.45 (br.s, 1H) 7.59 (d, J=8.8 Hz, 2H) 8.75 (d, J=4.8 Hz, 2H)

Mass spectrum (ESI) m/z: 477 (M+H)+ (data for racemic mixture)
HPLC retention time: 14 min

Example X-84

2-{4-[(4-carbamimidoylphenylamino)-(5-oxo-1-o-tolyl-4,5-dihydro-1H-[1,2,4]triazol-3-yl)methyl]-2-ethoxyphenoxy}-N-methylacetamide acetate

[Chemical Formula 668]

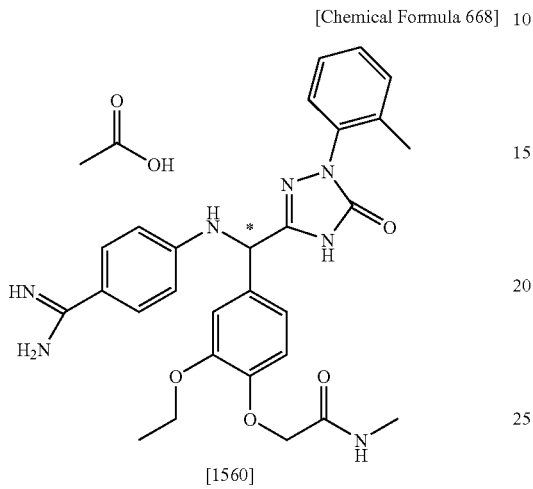

[1560]

¹H-NMR (CD₃OD) δ 1.41 (t, J=6.8 Hz, 3H) 1.96 (s, 3H) 2.19 (s, 3H) 2.81 (s, 3H) 4.11 (q, J=6.8 Hz, 2H) 4.51 (s, 2H) 5.68 (s, 1H) 6.87 (d, J=8.8 Hz, 2H) 7.03 (d, J=8.4 Hz, 1H) 7.07 (dd, J=2.0, 8.4 Hz, 1H) 7.19 (d, J=1.6 Hz, 1H) 7.26-7.28 (m, 2H) 7.32-7.35 (m, 2H) 7.63 (d, J=8.8 Hz, 2H)
Mass spectrum (ESI) m/z: 530 (M+H)+

Example X-85

(R) and (S)-4-{[[8-(2-fluoroethoxy)-4H-benzo[1,3]dioxin-6-yl]-(5-oxo-1-pyrimidin-2-yl-4,5-dihydro-1H-[1,2,4]triazol-3-yl)methyl]amino}benzamidine acetate

[Chemical Formula 669]

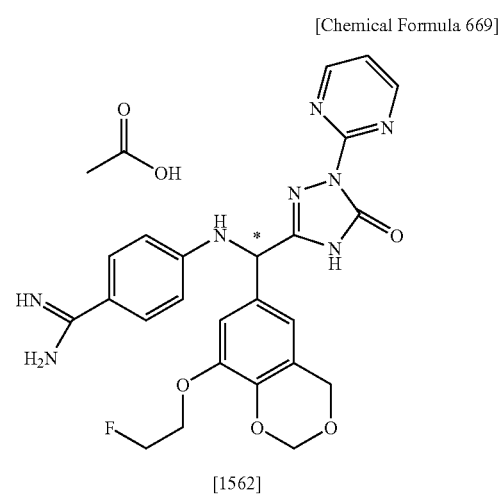

[1562]

¹H-NMR (CD₃OD) δ 1.92 (s, 3H) 4.20 (q, J=4.0 Hz, 1H) 4.27 (q, J=4.0 Hz, 1H) 4.62 (t, J=7.6 Hz, 1H) 4.74 (t, J=4.4 Hz, 1H) 4.86 (m, 2H) 5.24 (s, 2H) 5.52 (s, 1H) 6.84 (d, J=8.8 Hz, 2H) 6.85-6.88 (m, 1H) 7.07 (d, J=1.6 Hz, 1H) 7.29 (t, J=4.8 Hz, 1H) 7.59 (d, J=8.8 Hz, 2H) 8.77 (d, J=4.8 Hz, 2H)
Mass spectrum (ESI) m/z: 507 (M+H)+ (data for racemic mixture)
HPLC retention time: 17 min

Example X-86

(R) and (S)-4-{[(4-fluoro-3-methoxy-5-methoxymethylphenyl)-(5-oxo-1-pyrimidin-2-yl-4,5-dihydro-1H-[1,2,4]triazol-3-yl)methyl]amino}benzamidine acetate

[Chemical Formula 670]

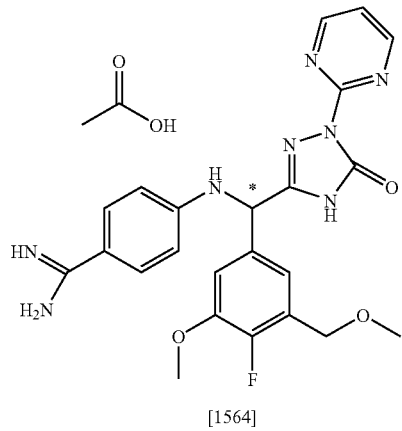

[1564]

¹H-NMR (CD₃OD) δ 1.91 (s, 3H) 3.34 (s, 3H) 3.86 (s, 3H) 4.47 (s, 2H) 5.60 (s, 1H) 6.85 (d, J=8.8 Hz, 2H) 7.18 (d, J=5.6 Hz, 1H) 7.26-7.29 (m, 2H) 7.59 (d, J=8.8 Hz, 2H) 8.75 (d, J=5.2 Hz, 2H)
Mass spectrum (ESI) m/z: 479 (M+H)+ (data for racemic mixture)
HPLC retention time: 12 min

Example X-87

(R) and (S)-4-{[(8-allyloxy-4H-benzo[1,3]dioxin-6-yl)-(5-oxo-1-pyrimidin-2-yl-4,5-dihydro-1H-[1,2,4]triazol-3-yl)methyl]amino}benzamidine acetate

[Chemical Formula 671]

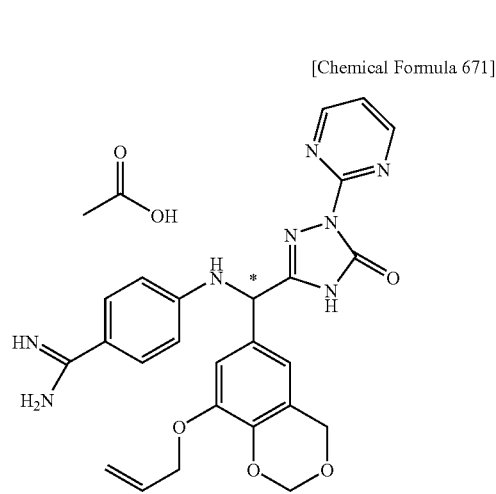

[1566]

¹H-NMR (CD₃OD) δ 1.93 (s, 3H) 4.52 (d, J=4.4 Hz, 2H) 4.83 (m, 2H) 5.16 (d, J=10.4 Hz, 1H) 5.22 (s, 2H) 5.33 (d, J=16.8 Hz, 1H) 5.56 (s, 1H) 5.94-6.03 (m, 1H) 6.78-6.90 (m, 3H) 7.03 (s, 1H) 7.31 (br.s, 1H) 7.59 (d, J=7.6 Hz, 2H) 8.76 (d, J=4.4 Hz, 2H) (data for racemic mixture)

Mass spectrum (ESI) m/z: 501 (M+H)+ (data for racemic mixture)
HPLC retention time: 17 min

Example X-88

(R) and (S)-4-{[(3-acetyl-4,5-dimethoxyphenyl)-(5-oxo-1-pyrimidin-2-yl-4,5-dihydro-1H-[1,2,4]triazol-3-yl)methyl]amino}benzamidine acetate

[Chemical Formula 672]

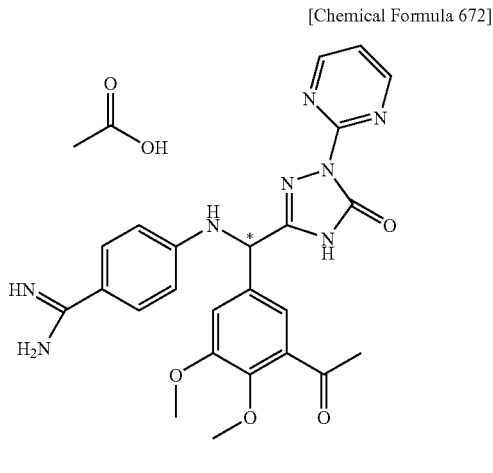

$^1$H-NMR (CD$_3$OD) δ 1.91 (s, 3H) 2.56 (s, 3H) 3.86 (s, 3H) 3.88 (s, 3H) 5.62 (s, 1H) 6.85 (d, J=8.8 Hz, 2H) 7.27 (t, J=4.8 Hz, 1H) 7.38 (d, J=2.0 Hz, 1H) 7.42 (d, J=2.0 Hz, 1H) 7.59 (d, J=8.8 Hz, 2H) 8.75 (d, J=4.8 Hz, 2H)
Mass spectrum (ESI) m/z: 489 (M+H)+ (data for racemic mixture)
HPLC retention time: 13 min

Example X-89

(R) and (S)-4-{[(8-methoxy-4-methyl-4H-benzo[1,3]dioxin-6-yl)-(5-oxo-1-pyrimidin-2-yl-4,5-dihydro-1H-[1,2,4]triazol-3-yl)methyl]amino}benzamidine acetate

[Chemical Formula 673]

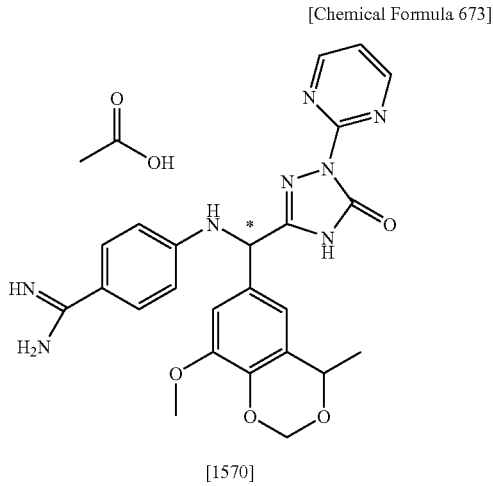

[1570]

$^1$H-NMR (CD$_3$OD) δ 1.47, 1.52 (each d, J=6.8 Hz, total 3H) 1.92 (s, 3H) 3.81, 3.82 (each s, total 3H) 5.03 (q, J=6.4 Hz, 1H) 5.15 (d, J=6.0 Hz, 1H) 5.29 (d, J=5.6 Hz, 1H) 5.57 (s, 1H) 6.86 (d, J=8.8 Hz, 2H) 6.92 (s, 1H) 7.07 (s, 1H) 7.32 (t, J=4.8 Hz, 1H) 7.61 (d, J=9.2 Hz, 2H) 8.78 (d, J=4.8 Hz, 2H)
Mass spectrum (ESI) m/z: 489 (M+H)+ (data for racemic mixture)
HPLC retention time: 15 min

Example X-90

2-{4-[(4-carbamimidoylphenylamino)-(5-oxo-1-pyrimidin-2-yl-4,5-dihydro-1H-[1,2,4]triazol-3-yl)methyl]-2-ethoxyphenoxy}-N-methylacetamide acetate

[Chemical Formula 674]

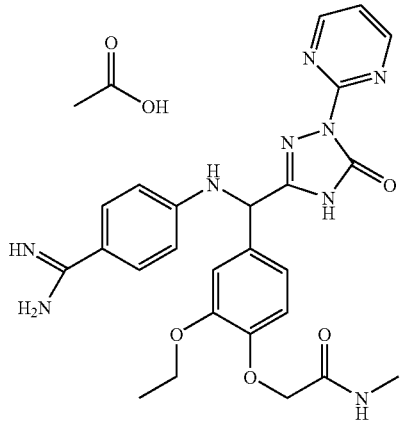

$^1$H-NMR (CD$_3$OD) δ 1.40 (t, J=6.8 Hz, 3H) 1.97 (s, 3H) 2.81 (s, 3H) 4.06-4.14 (m, 2H) 4.50 (s, 2H) 5.67 (s, 1H) 6.87 (d, J=8.8 Hz, 2H) 7.02 (d, J=8.4 Hz, 1H) 7.10 (br.d, J=8.4 Hz, 1H) 7.22 (br.s, 1H) 7.37 (t, J=4.8 Hz, 1H) δ 7.62 (d, J=8.8 Hz, 2H) 8.80 (d, J=4.8 Hz, 2H)
Mass spectrum (ESI) m/z: 518 (M+H)+

Example X-91

4-{[(3-fluoromethyl-4,5-dimethoxyphenyl)-(5-oxo-1-pyrimidin-2-yl-4,5-dihydro-1H-[1,2,4]triazol-3-yl)methyl]amino}benzamidine acetate

[Chemical Formula 675]

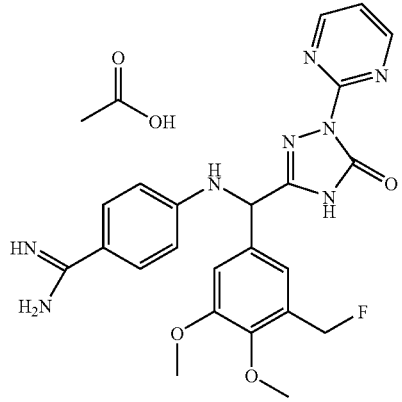

$^1$H-NMR (CD$_3$OD) δ 1.92 (s, 3H) 3.80 (s, 3H) 3.86 (s, 3H) 5.31 (s, 1H) 5.43 (s, 1H) 5.61 (s, 1H) 6.86 (d, J=8.0 Hz, 2H) 7.19 (s, 1H) 7.28 (s, 2H) 7.60 (d, J=8.0 Hz, 2H) 8.77 (br.s, 2H)
Mass spectrum (ESI) m/z: 479 (M+H)+

Example X-92

(R) and (S)-4-{[(8-acetoxy-4H-benzo[1,3]dioxin-6-yl)-(5-oxo-1-pyrimidin-2-yl-4,5-dihydro-1H-[1,2,4]triazol-3-yl)methyl]amino}benzamidine acetate

[Chemical Formula 676]

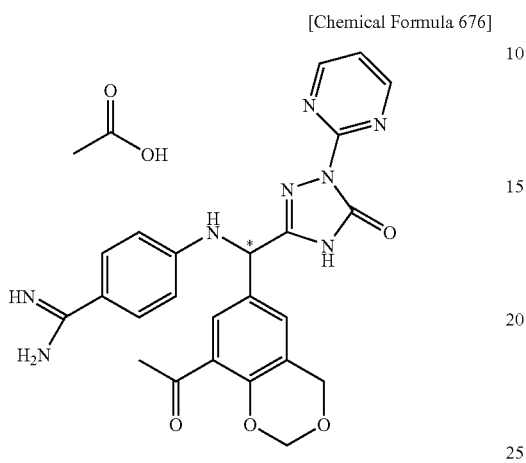

$^1$H-NMR (CD$_3$OD) δ 1.92 (s, 3H) 2.58 (s, 3H) 4.93 (m, 2H) 5.34 (s, 2H) 5.62 (s, 1H) 6.84 (d, J=8.8 Hz, 2H) 7.28 (t, J=4.8 Hz, 1H) 7.41 (br.s, 1H) 7.59 (d, J=8.8 Hz, 2H) 7.79 (br.s, 1H) 8.75 (d, J=4.8 Hz, 2H)

Mass spectrum (ESI) m/z: 487 (M+H)$^+$ (data for racemic mixture)

HPLC retention time: 16 min

Example X-93

2-{3-[(4-carbamimidoylphenylamino)-(3-ethoxy-4-methylcarbamoylmethoxyphenyl)methyl]-5-oxo-4,5-dihydro-1H-[1,2,4]triazol-1-yl}benzamidine acetate

[Chemical Formula 677]

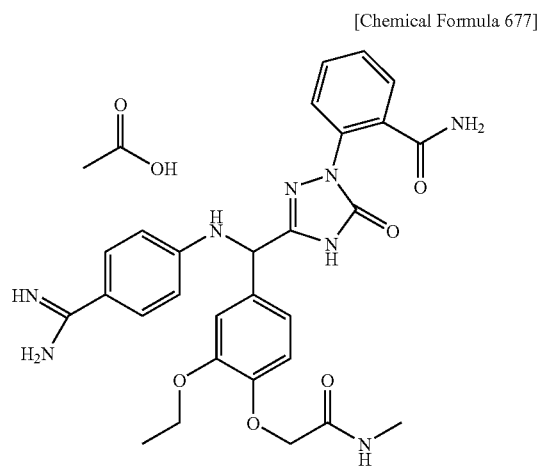

$^1$H-NMR (CD$_3$OD) δ 1.41 (t, J=7.2 Hz, 3H) 1.93 (s, 3H) 2.82 (s, 3H) 4.10-4.15 (m, 2H) 4.50 (s, 2H) 5.63 (s, 1H) 6.87 (d, J=8.8 Hz, 2H) 7.03 (d, J=8.4 Hz, 1H) 7.08 (dd, J=1.6, 8.0 Hz, 1H) 7.19 (d, J=2.0 Hz, 1H) 7.46 (dt, J=1.6, 7.2 Hz, 2H) 7.52 (dd, J=1.2, 8.0 Hz, 1H) 7.57 (ddd, J=1.6, 7.2, 8.0 Hz, 1H) 7.63 (d, J=8.8 Hz, 2H) 7.66 (dd, J=1.6, 8.0 Hz, 1H)

Mass spectrum (ESI) m/z: 559 (M+H)$^+$

Example X-94

4-{[(8-bromo-2,3-dihydrobenzo[1,4]dioxin-6-yl)-(5-oxo-1-pyrimidin-2-yl-4,5-dihydro-1H-[1,2,4]triazol-3-yl)methyl]amino}benzamidine acetate

[Chemical Formula 678]

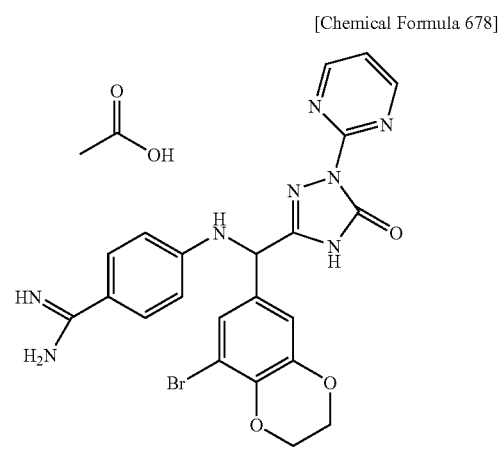

$^1$H-NMR (CD$_3$OD+CD$_3$CO$_2$D) δ 4.26 (t, J=2.8 Hz, 2H) 4.34 (t, J=3.6 Hz, 2H) 5.67 (s, 1H) 6.88 (d, J=8.8 Hz, 2H) 7.06 (d, J=2.0 Hz, 1H) 7.32 (d, J=2.0 Hz, 1H) 7.40 (t, J=4.4 Hz, 1H) 7.65 (d, J=8.8 Hz, 2H) 8.82 (d, J=4.4 Hz, 2H)

Mass spectrum (ESI) m/z: 523 (M+H)$^+$

Example X-95

4-({(2-fluoro-4,5-dimethoxyphenyl)-[5-oxo-1-(3-trifluoromethylpyridin-2-yl)-4,5-dihydro-1H-[1,2,4]triazol-3-yl]methyl}amino)benzamidine acetate

[Chemical Formula 679]

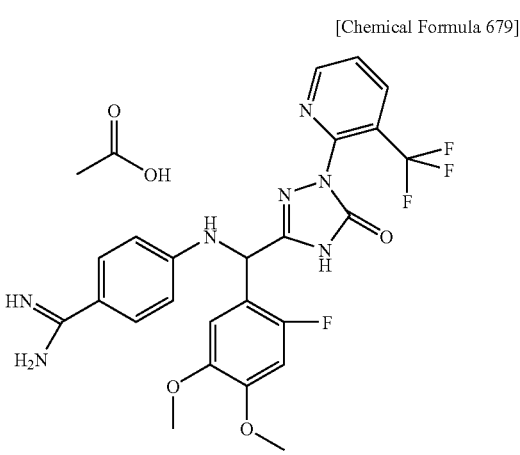

$^1$H-NMR (CD$_3$OD) δ 1.91 (s, 3H) 3.75 (s, 3H) 3.82 (s, 3H) 5.90 (s, 1H) 6.84 (d, J=12.0 Hz, 1H) 6.85 (d, J=9.2 Hz, 2H) 7.05 (d, J=7.2 Hz, 1H) 7.62 (d, J=9.2 Hz, 2H) 7.72 (ddd, J=0.4, 4.4, 8.0 Hz, 1H) 8.34 (dd, J=1.2, 8.0 Hz, 1H) 8.79 (dd, J=1.6, 5.2 Hz, 1H)

Mass spectrum (ESI) m/z: 532 (M+H)$^+$

Example X-96

4-{[(8-methoxymethyl-2,3-dihydrobenzo[1,4]dioxin-6-yl)-(5-oxo-1-pyrimidin-2-yl-4,5-dihydro-1H-[1,2,4]triazol-3-yl)methyl]amino}benzamidine acetate

[Chemical Formula 680]

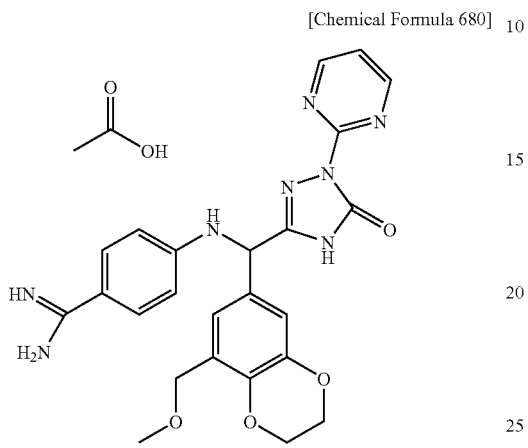

$^{1}$H-NMR (CD$_3$CO$_2$D) δ 3.41 (s, 3H) 4.22-4.32 (m, 4H) 4.51 (s, 2H) 5.77 (s, 1H) 6.92 (d, J=8.8 Hz, 2H) 7.06 (d, J=2.0 Hz, 1H) 7.18 (d, J=2.0 Hz, 1H) 7.42 (t, J=4.8 Hz, 1H) 7.71 (d, J=8.8 Hz, 2H) 8.92 (d, J=4.8 Hz, 2H)

Mass spectrum (ESI) m/z: 489 (M+H)$^+$

Example X-97

4-{[(2-fluoro-4,5-dimethoxyphenyl)-(5-oxo-1-thiazol-2-yl-4,5-dihydro-1H-[1,2,4]triazol-3-yl)methyl]amino}benzamidine acetate

[Chemical Formula 681]

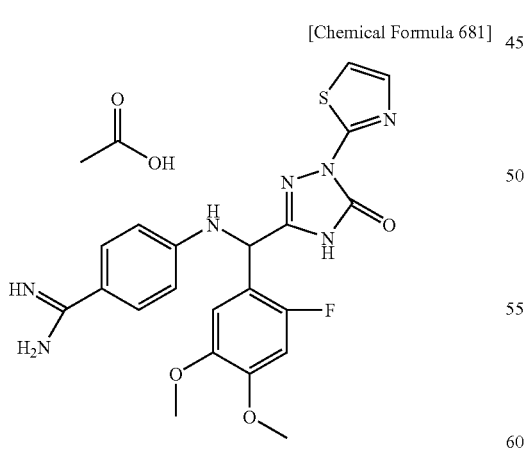

$^{1}$H-NMR (CD$_3$OD) δ 1.93 (s, 3H) 3.72 (s, 3H) 3.79 (s, 3H) 5.89 (s, 1H) 6.79 (d, J=10.4 Hz, 1H) 6.84 (d, J=8.8 Hz, 2H) 7.10 (d, J=6.8 Hz, 1H) 7.23 (d, J=3.6 Hz, 1H) 7.49 (d, J=3.6 Hz, 1H) 7.58 (d, J=8.8 Hz, 2H)

Mass spectrum (ESI) m/z: 470 (M+H)$^+$

Example X-98

4-{[(7-methoxybenzo[1,3]dioxol-5-yl)-(5-oxo-1-pyrimidin-2-yl-4,5-dihydro-1H-[1,2,4]triazol-3-yl)methyl]amino}benzamidine acetate

[Chemical Formula 682]

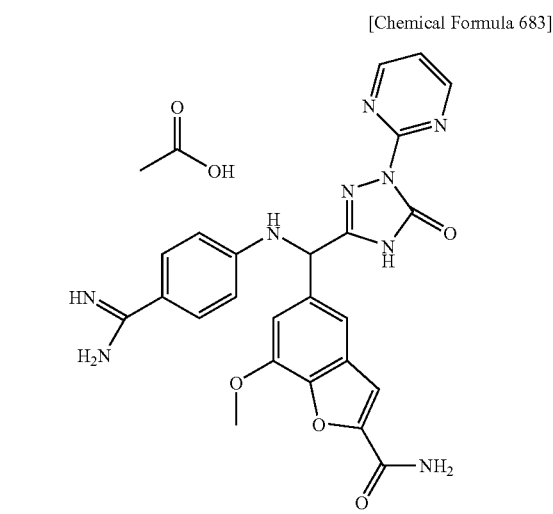

$^{1}$H-NMR (CD$_3$OD) δ 1.94 (s, 3H) 3.86 (s, 3H) 5.58 (br.s, 1H) 5.92 (s, 2H) 6.73 (br.s, 1H) 6.78-6.82 (m, 3H) 7.34 (br.s, 1H) 7.62 (br.s, 2H) 8.78 (br.s, 2H)

Mass spectrum (ESI) m/z: 461 (M+H)$^+$

Example X-99

5-[(4-carbamimidoylphenylamino)-(5-oxo-1-1-pyrimidin-2-yl-4,5-dihydro-1H-[1,2,4]triazol-3-yl)methyl]-7-methoxybenzofuran-2-carboxylic acid amide acetate

[Chemical Formula 683]

$^{1}$H-NMR (CD$_3$OD) δ 1.89 (s, 3H) 3.98 (s, 3H) 5.65 (s, 1H) 6.86 (d, J=9.2 Hz, 2H) 7.23 (t, J=4.8 Hz, 1H) 7.27 (d, J=1.2 Hz, 1H) 7.43 (s, 1H) 7.47 (br.s, 1H) 7.57 (d, J=8.8 Hz, 2H) 8.74 (d, J=4.8 Hz, 2H)

Mass spectrum (ESI) m/z: 500 (M+H)$^+$

Example X-100

4-{[(7-methoxy-2-methoxymethylbenzofuran-5-yl)-(5-oxo-1-pyrimidin-2-yl-4,5-dihydro-1H-[1,2,4]triazol-3-yl]methyl]amino}benzamidine acetate

[Chemical Formula 684]

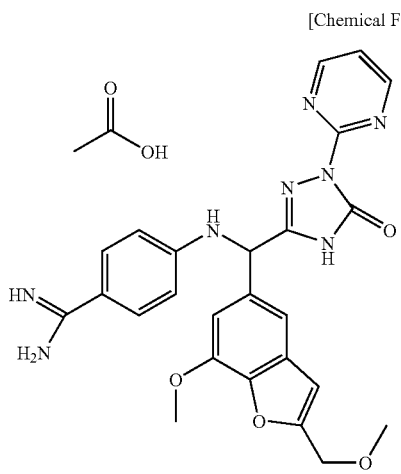

$^1$H-NMR (CD$_3$OD) δ 1.90 (s, 3H) 3.36 (s, 3H) 3.91 (s, 3H) 4.49 (s, 2H) 5.67 (s, 1H) 6.68 (s, 1H) 6.84 (d, J=8.8 Hz, 2H) 7.09 (s, 1H) 7.23 (br.s, 1H) 7.33 (s, 1H) 7.55 (d, J=8.8 Hz, 2H) 8.73 (d, J=4.0 Hz, 2H)

Mass spectrum (ESI) m/z: 501 (M+H)$^+$

Example X-101 methanesulfonic acid 6-[(R) and (S)-(4-carbamimidoylphenylamino)-(5-oxo-1-pyrimidin-2-yl-4,5-dihydro-1H-[1,2,4]triazol-3-yl)methyl]-4H-benzo[1,3]dioxin-8-yl ester acetate

[Chemical Formula 685]

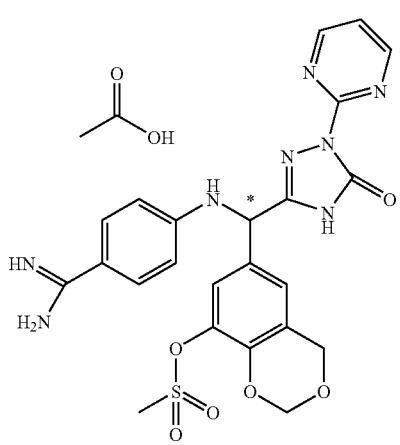

$^1$H-NMR (CD$_3$OD) δ 1.93 (s, 3H) 3.23 (s, 3H) 4.91 (m, 2H) 5.30 (s, 2H) 5.60 (s, 1H) 6.85 (d, J=8.8 Hz, 2H) 7.23 (d, J=1.6 Hz, 1H) 7.29 (d, J=4.4 Hz, 1H) 7.39 (d, J=2.4 Hz, 1H) 7.60 (d, J=8.8 Hz, 2H) 8.76 (d, J=4.8 Hz, 2H)

Mass spectrum (ESI) m/z: 539 (M+H)$^+$ (data for racemic mixture)

HPLC retention time: 16 min

Example X-102

4-{[(7-methoxy-3-oxo-2,3-dihydrobenzofuran-5-yl)-(5-oxo-1-pyrimidin-2-yl-4,5-dihydro-1H-[1,2,4]triazol-3-yl)methyl]amino}benzamidine acetate

[Chemical Formula 686]

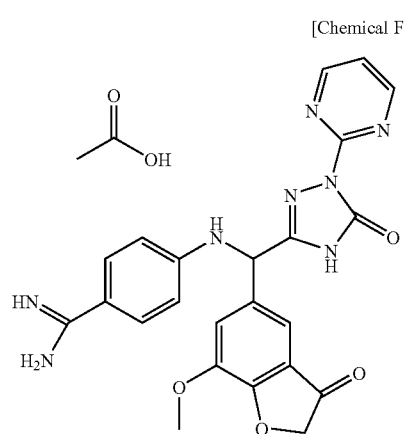

$^1$H-NMR (CD$_3$OD) δ 1.91 (s, 3H) 3.92 (s, 3H) 4.73 (s, 2H) 5.66 (s, 1H) 6.86 (d, J=8.8 Hz, 2H) 7.28 (t, J=4.8 Hz, 1H) 7.39 (s, 1H) 7.49 (s, 1H) 7.60 (d, J=8.8 Hz, 2H) 8.76 (d, J=4.8 Hz, 2H)

Mass spectrum (ESI) m/z: 473 (M+H)$^+$

Example X-103

(R) and (S)-4-{[(8-difluoromethoxy-4H-benzo[1,3]dioxin-6-yl)-(5-oxo-1-pyrimidin-2-yl-4,5-dihydro-1H-[1,2,4]triazol-3-yl)methyl]amino}benzamidine acetate

[Chemical Formula 687]

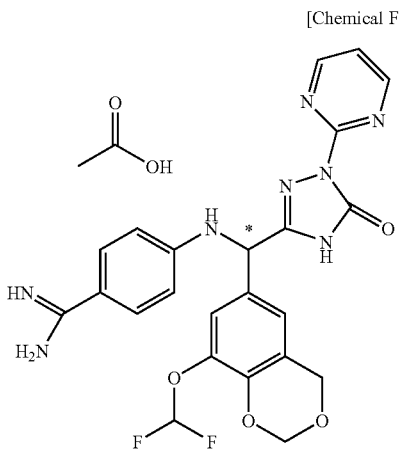

$^1$H-NMR (CD$_3$OD) δ 1.92 (s, 3H) 4.59 (br.s, 2H) 5.27 (s, 2H) 5.55 (s, 1H) 6.74 (t, J=74.8 Hz, 1H) 6.83 (d, J=8.8 Hz, 2H) 7.13 (s, 1H) 7.24 (s, 1H) 7.26 (t, J=5.2 Hz, 1H) 7.59 (d, J=8.8 Hz, 2H) 8.75-8.78 (m, 2H)

Mass spectrum (ESI) m/z: 511 (M+H)$^+$ (data for racemic mixture)

HPLC retention time: 13 min

Example X-104

4-{[(8-ethyl-2,3-dihydro-benzo[1,4]dioxin-6-yl)-(5-oxo-1-pyrimidin-2-yl-4,5-dihydro-1H-[1,2,4]triazol-3-yl)methyl]amino}benzamidine acetate

[Chemical Formula 688]

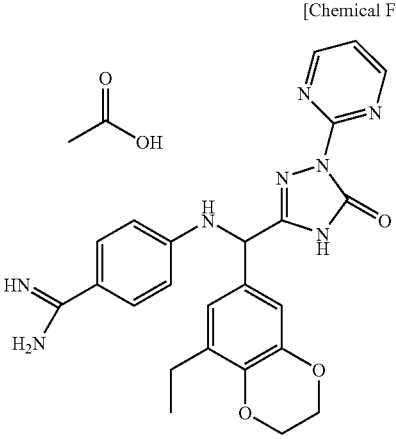

$^1$H-NMR (CD$_3$OD) δ 1.13 (t, J=7.6 Hz, 3H) 1.93 (s, 3H) 2.56 (q, J=7.6 Hz, 2H) 4.16-4.25 (m, 4H) 5.55 (s, 1H) 6.80-6.91 (m, 4H) 7.33 (t, J=4.8 Hz, 1H) 7.60 (d, J=8.8z, 2H) 8.77 (d, J=4.8 Hz, 2H)

Mass spectrum (ESI) m/z: 473 (M+H)$^+$

Example X-105

4-{[(7-methoxybenzofuran-5-yl)-(5-oxo-1-pyrimidin-2-yl-4,5-dihydro-1H-[1,2,4]triazol-3-yl)methyl]amino}benzamidine acetate

[Chemical Formula 689]

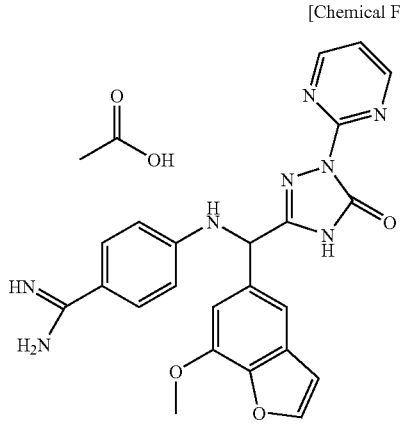

$^1$H-NMR (CD$_3$OD) δ 1.91 (s, 3H) 3.93 (s, 3H) 5.72 (s, 1H) 6.77 (s, 1H) 6.86 (br.d, J=6.4 Hz, 2H) 7.08 (br.s, 1H) 7.28 (br.s, 1H) 7.38 (br.s, 1H) 7.57 (br.d, J=6.4 Hz, 2H) 7.71 (s, 1H) 8.75 (br.s, 2H)

Mass spectrum (ESI) m/z: 457 (M+H)$^+$

Example X-106

(R) and (S)-4-{[(9-fluoromethyl-3,4-dihydro-2H-benzo[b][1,4]dioxepin-7-yl)-(5-oxo-1-pyrimidin-2-yl-4,5-dihydro-1H-[1,2,4]triazol-3-yl)methyl]amino)benzamidine acetate

[Chemical Formula 690]

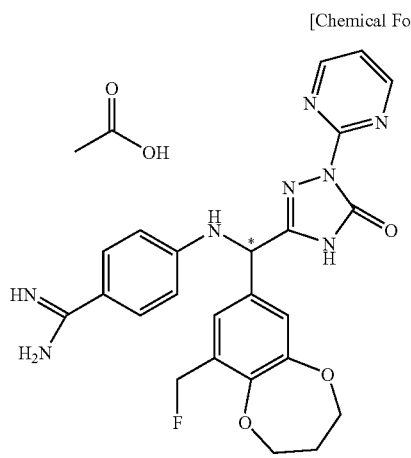

$^1$H-NMR (CD$_3$OD) δ 1.92 (s, 3H) 2.17 (quint, J=5.6 Hz, 2H) 4.19 (m, 4H) 5.31 (s, 1H) 5.43 (s, 1H) 5.57 (s, 1H) 6.84 (d, J=8.8 Hz, 2H) 7.18 (br.s, 1H) 7.25 (br.s, 1H) 7.29 (t, J=4.8 Hz, 1H) 7.59 (d, J=8.8 Hz, 2H) 8.76 (d, J=4.8 Hz, 2H)

Mass spectrum (ESI) m/z: 491 (M+H)$^+$ (data for racemic mixture)

HPLC retention time: 13 min

Example X-107

4-{[(2-chloro-4,5-dimethoxyphenyl)-(5-oxo-1-pyrimidin-2-yl-4,5-dihydro-1H-[1,2,4]triazol-3-yl)methyl]amino}benzamidine acetate

[Chemical Formula 691]

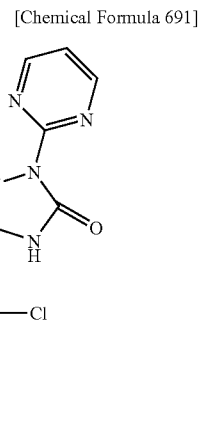

$^1$H-NMR (CD$_3$OD) δ 1.92 (s, 3H) 3.74 (s, 3H) 3.82 (s, 3H) 6.00 (s, 1H) 6.82 (d, J=8.8 Hz, 2H) 7.03 (s, 1H) 7.16 (s, 1H) 7.31 (br.s, 1H) 7.61 (d, J=8.8 Hz, 2H) 8.76 (br.s, 2H)

Mass spectrum (ESI) m/z: 481 (M+H)$^+$

Example X-108

2-{3-[(4-carbamimidoylphenylamino)-(5-oxo-1-pyrimidin-2-yl-4,5-dihydro-1H-[1,2,4]triazol-3-yl)methyl]-5-ethyl-2-fluorophenoxy}-N,N-dimethylacetamide trifluoroacetate

[Chemical Formula 692]

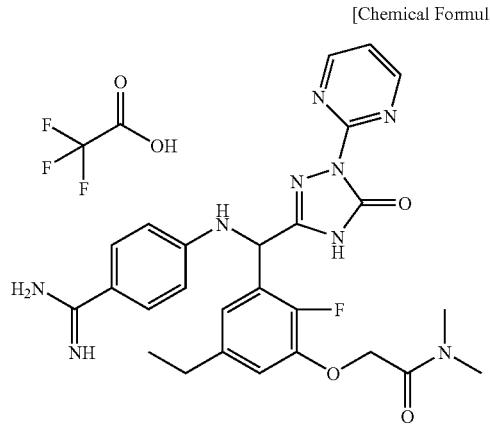

$^1$H-NMR (CD$_3$OD) δ 1.17 (t, J=7.7 Hz, 3H) 2.50 (q, J=7.7H, 2H) 2.91 (s, 3H) 3.04 (s, 3H) 4.90 (s, 2H) 6.00 (s, 1H) 6.82-6.95 (m, 4H) 7.41 (br.s, 1H) 7.59 (d, J=8.8 Hz, 2H) 8.77 (br.s, 2H)

Mass spectrum (ESI) m/z: 534 (M+H)$^+$

Example X-109

4-{[[1-(2-aminophenyl)-5-oxo-4,5-dihydro-1H-[1,2,4]triazol-3-yl]-(2-fluoro-3,5-dimethoxyphenyl)methyl)amino}benzamidine trifluoroacetate

[Chemical Formula 693]

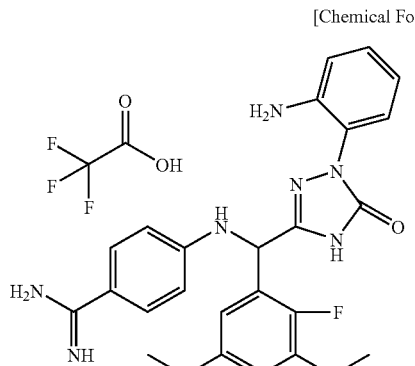

$^1$H-NMR (CD$_3$OD) δ 3.64 (s, 3H) 3.77 (s, 3H) 6.04 (s, 1H) 6.60 (dd, J=5.2, 2.6 Hz, 1H) 6.67 (dd, J=7.3, 2.6 Hz, 1H) 6.88 (d, J=8.7 Hz, 2H) 7.10 (t, J=7.6 Hz, 1H) 7.16 (d, J=7.6 Hz, 1H) 7.30 (t, J=7.6 Hz, 1H) 7.44 (d, J=7.6 Hz, 1H) 7.65 (d, J=8.7 Hz, 2H)

Example X-110

3-amino-2-(3-{(4-carbamimidoylphenylamino)-[2-fluoro-3-(2-fluoroethoxy)-5-methoxyphenyl]methyl}-5-oxo-4,5-dihydro-1H-[1,2,4]triazol-1-yl)-1-methylpyridinium bistrifluoroacetate

[Chemical Formula 694]

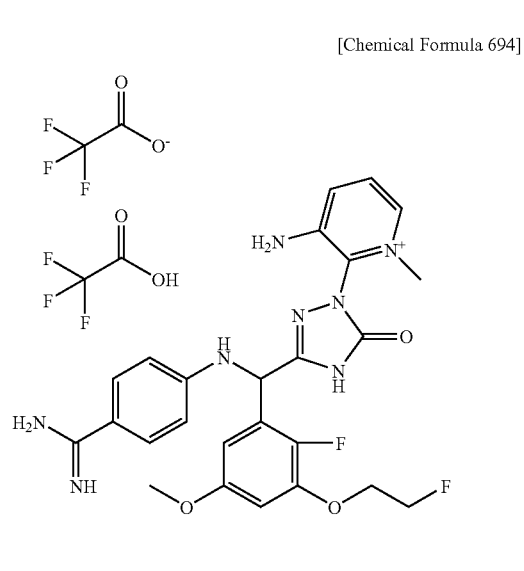

Two isomers:

$^1$H-NMR (CD$_3$OD) δ 3.73 (s, 3H) 4.03 and 4.08 (s, 3H) 4.24 (m, 1H) 4.31 (m, 1H) 4.66 (m, 1H) 4.79 (m, 1H) 6.09 and 6.10 (m, 1H) 6.62 and 6.65 (m, 1H) 6.66-6.71 (m, 1H) 6.90 (d, J=8.9 Hz, 2H) 7.65 (d, J=8.9 Hz, 2H) 7.72 and 7.74 (dd, J=8.1, 5.3 Hz, 1H) 7.90 (d, J=8.1 Hz, 1H) 8.17 and 8.20 (d, J=5.3 Hz, 1H)

Example X-111

4-{[[3-(2-dimethylaminopropoxy)-5-ethyl-2-fluorophenyl]-(5-oxo-1-pyridin-2-yl-4,5-dihydro-1H-[1,2,4]triazol-3-yl)methyl]amino}benzamidine bistrifluoroacetate

[Chemical Formula 695]

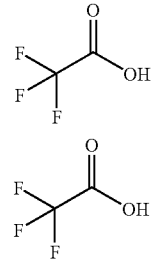

-continued

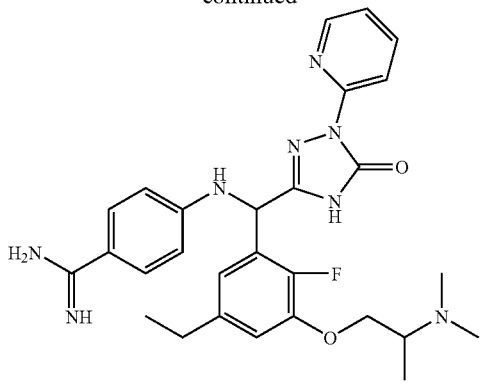

Two isomers:

¹H-NMR (CD₃OD) δ 1.20 (t, J=7.8 Hz, 3H) 1.45 and 1.47 (d, J=6.9 Hz, 3H) 2.62 (q, J=7.8 Hz, 2H) 2.95 (s, 6H) 3.83-3.93 (m, 1H) 4.30 (dd, J=11.7, 7.3 Hz, 1H) 4.39 (ddd, J=11.7, 3.9, 2.4 Hz, 1H) 6.03 (s, 1H) 6.89 (d, J=8.7 Hz, 2H) 7.06 (dd, J=5.9, 0.9 Hz, 1H) 7.09 (dd, J=7.3, 0.9 Hz, 1H) 7.32 (dd, J=7.5, 4.6 Hz, 1H) 7.65 (d, J=8.7 Hz, 2H) 7.96 (t, J=7.5 Hz, 1H) 8.06 (d, J=7.5 Hz, 1H) 8.44 (d, J=4.6 Hz, 1H)

Example X-112

4-({[1-(2-aminophenyl)-5-oxo-4,5-dihydro-1H-[1,2,4]triazol-3-yl]-[5-ethyl-2-fluoro-3-(2-fluoroethoxy)phenyl]methyl}amino)benzamidine trifluoroacetate

[Chemical Formula 696]

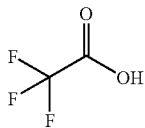

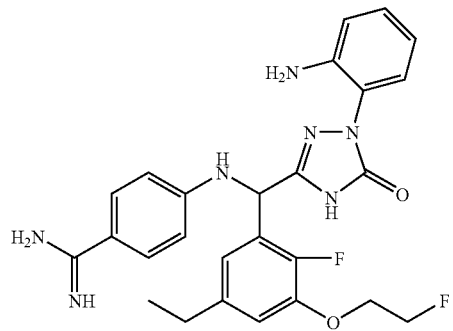

¹H-NMR (CD₃OD) δ 1.19 (t, J=7.7 Hz, 3H) 2.60 (q, J=7.7 Hz, 2H) 4.25 (m, 1H) 4.33 (m, 1H) 4.67 (m, 1H) 4.80 (m, 1H) 6.03 (s, 1H) 6.88 (d, J=8.8 Hz, 2H) 6.93 (dd, J=5.2, 2.2 Hz, 1H) 6.98 (t, J=7.6 Hz, 1H) 6.99 (d, J=6.6, 2.2 Hz, 1H) 7.06 (d, J=7.6 Hz, 1H) 7.25 (d, J=7.6 Hz, 1H) 7.35 (d, J=7.6 Hz, 1H) 7.65 (d, J=8.8 Hz, 2H)

Example X-113

N-[2-(3-{(4-carbamimidoylphenylamino)-[3-(2-dimethylaminoethoxy)-5-ethyl-2-fluorophenyl]methyl}-5-oxo-4,5-dihydro-1H-[1,2,4]triazol-1-yl)phenyl]acetamide bistrifluoroacetate

[Chemical Formula 697]

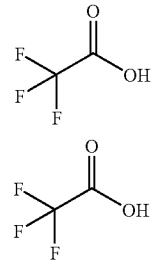

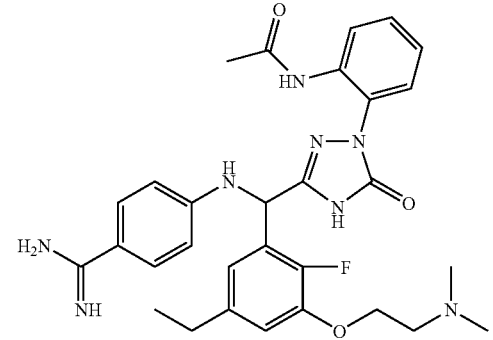

¹H-NMR (CD₃OD) δ 1.20 (t, J=7.8 Hz, 3H) 1.97 (s, 3H) 2.63 (q, J=7.8 Hz, 2H) 3.00 (s, 6H) 3.64 (t, J=5.5 Hz, 2H) 4.44 (t, J=5.5 Hz, 2H) 6.04 (s, 1H) 6.87 (d, J=8.7 Hz, 2H) 7.03 (dd, J=6.0, 1.4 Hz, 1H) 7.07 (dd, J=8.5, 1.4 Hz, 1H) 7.26 (t, J=7.5 Hz, 1H) 7.37 (t, J=7.5 Hz, 1H) 7.45 (d, J=7.5 Hz, 1H) 7.65 (d, J=8.7 Hz, 2H) 7.73 (d, J=7.5 Hz, 1H)

Example X-114

[2-(3-{(4-(carbamimidoylphenylamino)-[3-(2-dimethylaminoethoxy)-5-ethyl-2-fluorophenyl]methyl}-5-oxo-4,5-dihydro-1H-[1,2,4]triazol-1-yl)phenyl]carbamic acid methyl ester bistrifluoroacetate

[Chemical Formula 698]

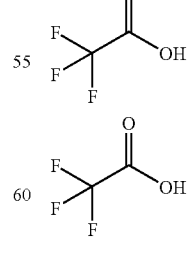

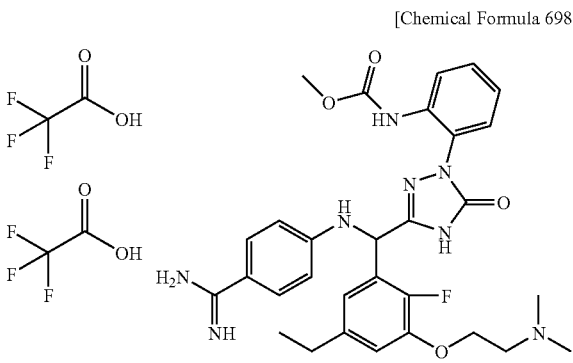

¹H-NMR (CD₃OD) δ 1.20 (t, J=7.7 Hz, 3H) 2.64 (q, J=7.7 Hz, 2H) 3.00 (s, 6H) 3.63 (t, J=5.2 Hz, 2H) 3.68 (s, 3H) 4.44

(t, J=5.2 Hz, 2H) 6.04 (s, 1H) 6.88 (d, J=8.8 Hz, 2H) 7.04 (dd, J=5.6, 1.7 Hz, 1H) 7.08 (d, J=7.8, 1.7 Hz, 1H) 7.20 (td, J=7.7, 1.5 Hz, 1H) 7.35-7.45 (m, 3H) 7.65 (d, J=8.8 Hz, 2H)

Example X-115

4-{[[3-(2-dimethylaminoethoxy)-5-ethyl-2-fluorophenyl]-(5-oxo-1-pyrimidin-2-yl-4,5-dihydro-1H-[1,2,4]triazol-3-yl)methyl]amino}benzamidine bistrifluoroacetate

[Chemical Formula 699]

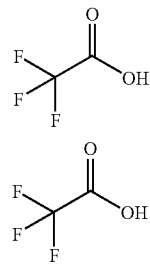

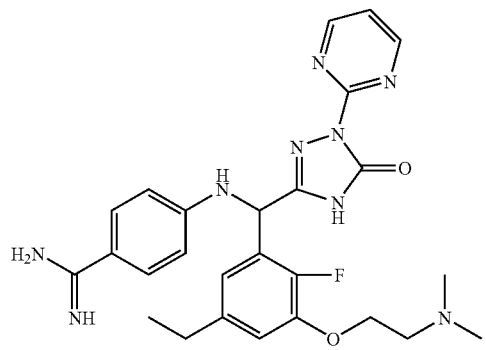

$^1$H-NMR (CD$_3$OD) δ 1.12 (t, J=7.7 Hz, 3H) 2.57 (q, J=7.7 Hz, 2H) 2.95 (s, 6H) 3.55 (m, 2H) 4.38 (m, 2H) 6.05 (br.s, 1H) 6.78-7.04 (m, 4H) 7.41 (br.s, 1H) 7.58 (d, J=8.8 Hz, 2H) 8.71 (br.s, 2H)

Mass spectrum (ESI) m/z: 520 (M+H)$^+$

Example X-116

4-{[[5-ethyl-2-fluoro-3-(2-fluoroethoxy)phenyl]-(5-oxo-1-pyrimidin-2-yl-4,5-dihydro-1H-[1,2,4]triazol-3-yl)methyl]amino}benzamidine trifluoroacetate

[Chemical Formula 700]

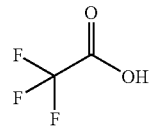

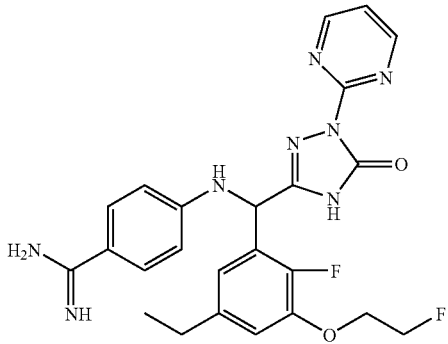

$^1$H-NMR (CD$_3$OD) δ 1.19 (t, J=7.8 Hz, 3H) 2.60 (q, J=7.8 Hz, 2H) 4.26 (m, 1H) 4.34 (m, 1H) 4.68 (m, 1H) 4.80 (m, 1H) 6.02 (s, 1H) 6.88 (d, J=8.8 Hz, 2H) 6.94 (dd, J=5.4, 1.4 Hz, 1H) 6.99 (dd, J=7.5, 1.4 Hz, 1H) 7.37 (t, J=5.1 Hz, 1H) 7.65 (d, J=8.8 Hz, 2H) 8.80 (d, J=5.1 Hz, 2H)

Example X-117

2-(3{(4-carbamimidoylphenylamino)-[3-(3-dimethylamino-2,2-dimethylpropoxy)-5-ethylphenyl]methyl}-5-oxo-4,5-dihydro-[1,2,4]triazol-1-yl}benzoic acid trifluoroacetate

[Chemical Formula 701]

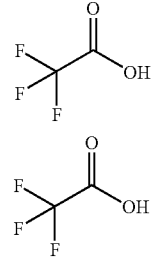

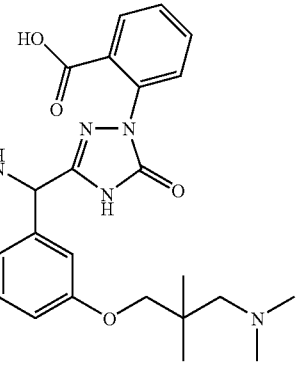

$^1$H-NMR (CD$_3$OD) δ 1.23 (s, 6H) 1.25 (t, J=7.9 Hz, 3H) 2.68 (q, J=7.9 Hz, 2H) 2.95 (s, 6H) 3.31 (s, 2H) 3.92 (s, 2H) 5.68 (s, 1H) 6.89 (s, 1H) 6.90 (d, J=8.8 Hz, 2H) 6.99 (s, 1H) 7.07 (s, 1H) 7.49-7.53 (m, 2H) 7.64-7.67 (m, 3H) 7.94 (dd, J=8.4, 1.4 Hz, 1H)

Example X-118

4-{[[1-(3-aminopyridin-1-yl)-5-oxo-4,5-dihydro-1H-[1,2,4]triazol-3-yl]-(8-methoxychroman-6-yl)methyl]amino}benzamidine trifluoroacetate

[Chemical Formula 702]

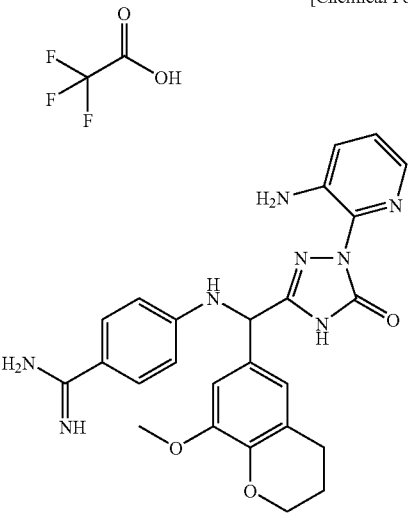

$^1$H-NMR (CD$_3$OD) δ 1.95 (m, 2H) 2.75 (m, 2H) 3.78 (s, 3H) 4.15 (m, 2H) 5.57 (s, 1H) 6.75-6.83 (m, 2H) 6.84 (d, J=8.7 Hz, 2H) 7.16-7.42 (br.s, 3H) 7.60 (d, J=8.7 Hz, 2H)

Example X-119

4-({(5-difluoromethoxy-2-fluorophenyl)-[1-(2-methoxyphenyl)-5-oxo-4,5-dihydro-1H-[1,2,4]triazol-3-yl]methyl)amino}benzamidine trifluoroacetate

[Chemical Formula 703]

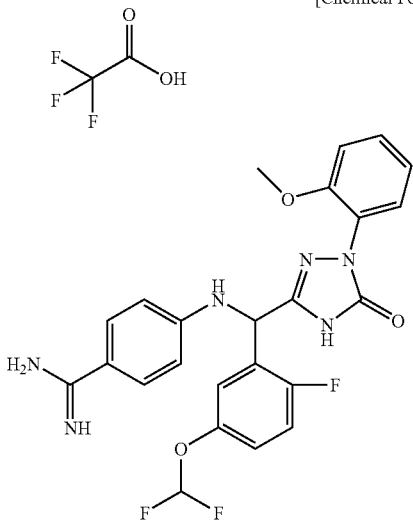

$^1$H-NMR (CD$_3$OD) δ 3.81 (s, 3H) 6.03 (s, 1H) 6.74 (t, J=73.9 Hz, 1H) 6.86 (d, J=8.7 Hz, 2H) 7.02 (td, J=5.6, 0.9 Hz, 1H) 7.13 (dd, J=5.6, 0.9 Hz, 1H) 7.17 (m, 1H) 7.22 (d, J=8.4 Hz, 1H) 7.27-7.29 (m, 2H) 7.43 (td, J=8.4, 1.2 Hz, 1H) 7.65 (d, J=8.7 Hz, 2H)

Example X-120

4-{[[1-(3-aminopyridin-2-yl)-5-oxo-4,5-dihydro-1H-[1,2,4]triazol-3-yl]-(4-ethoxy-3-methoxyphenyl)methyl]amino}benzamidine trifluoroacetate

[Chemical Formula 704]

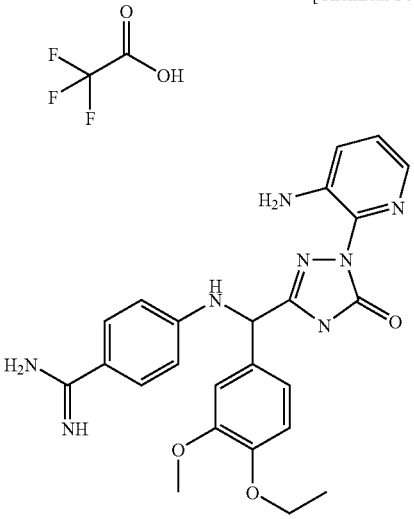

$^1$H-NMR (CD$_3$OD) δ 1.39 (t, J=7.5 Hz, 3H) 3.75 (s, 3H) 4.05 (q, J=7.5 Hz, 2H) 5.68 (s, 1H) 6.88 (d, J=8.6 Hz, 2H) 6.97 (d, J=8.2 Hz, 1H) 7.07 (dd, J=8.2, 2.2 Hz, 1H) 7.15 (d, J=2.2 Hz, 1H) 7.28 (dd, J=8.4, 4.3 Hz, 1H) 7.40 (dd, J=4.3, 1.0 Hz, 1H) 7.63 (d, J=8.6 Hz, 2H) 7.84 (dd, J=4.3, 1.0 Hz, 1H)

Example X-121

4-{[(3-allyloxy-5-fluoromethylphenyl)-(5-oxo-1-pyrimidin-2-yl-4,5-dihydro-1H-[1,2,4]triazol-3-yl)methyl]amino}benzamidine acetate

[Chemical Formula 705]

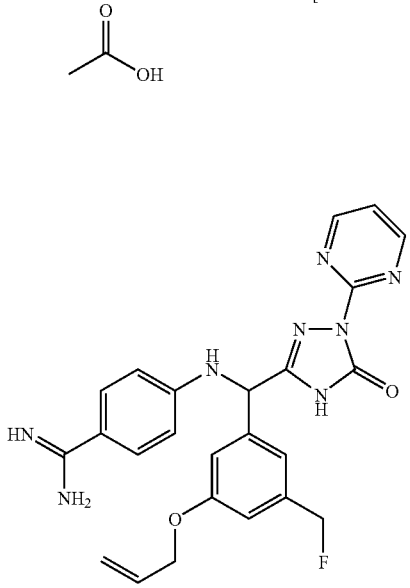

Example X-122

4-{[[4-(2-fluoroethyl)-8-methoxy-3-oxo-3,4-dihydro-2H-benzo[1,4]oxazin-6-yl]-(5-oxo-1-pyrimidin-2-yl-4,5-dihydro-1H-[1,2,4]triazol-3-yl)methyl]amino}benzamidine acetate

[Chemical Formula 706]

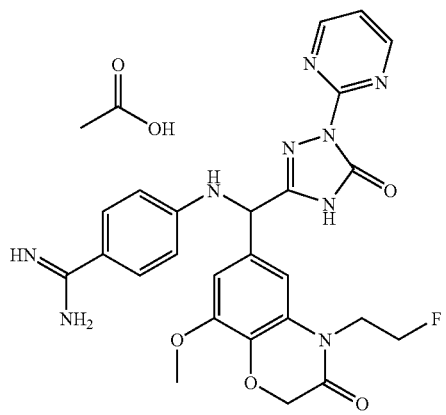

Example X-123

4-{[(3-methoxyphenyl)-(5-oxo-1-pyrimidin-2-yl-4,5-dihydro-1H-[1,2,4]triazol-3-yl)methyl]amino}benzamidine acetate

[Chemical Formula 707]

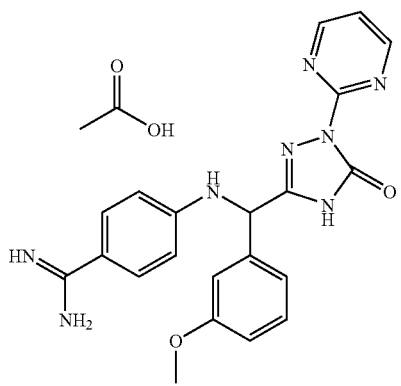

Example X-124

4-{[[3-(2-fluoroethoxy)phenyl]-(5-oxo-1-pyrimidin-2-yl-4,5-dihydro-1H-[1,2,4]triazol-3-yl)methyl]amino}benzamidine acetate

[Chemical Formula 708]

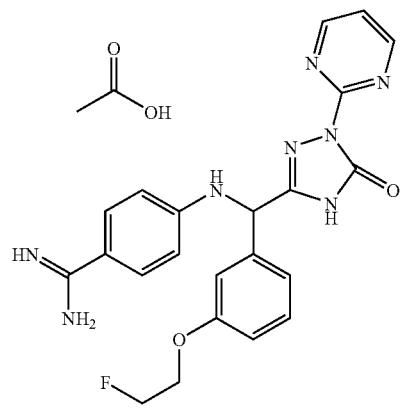

Example X-125

4-{[[3-(2-fluoroethoxy)-5-vinylphenyl]-(5-oxo-1-pyrimidin-2-yl-4,5-dihydro-1H-[1,2,4]triazol-3-yl)methyl]amino}benzamidine acetate

[Chemical Formula 709]

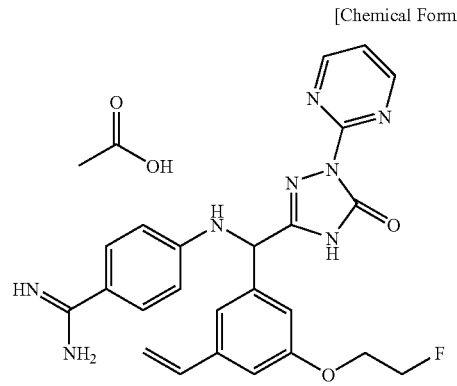

Example X-126

4-{[(3-methoxy-5-vinylphenyl)-(5-oxo-1-pyrimidin-2-yl-4,5-dihydro-1H-[1,2,4]triazol-3-yl)methyl]amino}benzamidine acetate

[Chemical Formula 710]

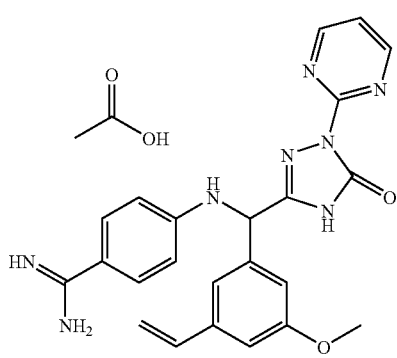

Example X-127

2-(3-{(4-carbamimidoylphenylamino)-[2-fluoro-5-methoxy-3-(1-methylpyrrolidin-3-yloxy)phenyl]methyl}-5-oxo-4,5-dihydro-[1,2,4]triazol-1-yl)benzoic acid bistrifluoroacetate

[Chemical Formula 711]

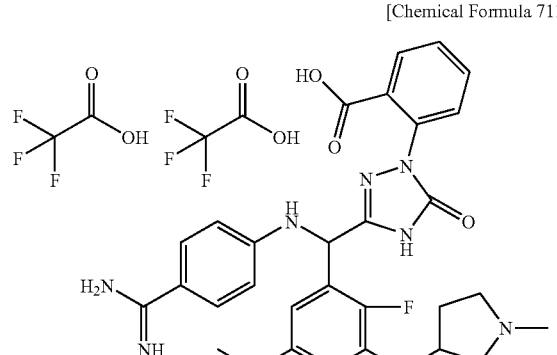

Example X-128

2-(3-{(4-carbamimidoylphenylamino)-[4-(2-dimethylamino-1-methylethoxy)-3-ethoxyphenyl]methyl}-5-oxo-4,5-dihydro-[1,2,4]triazol-1-yl)benzoic acid diacetate

[Chemical Formula 712]

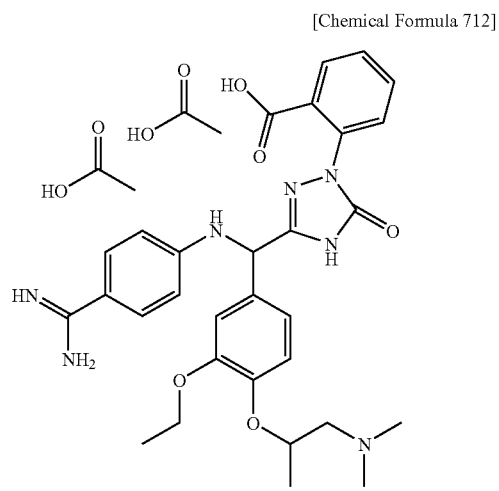

Example X-129

4-({[4-(2-dimethylamino-1-methylethoxy)-3-ethoxyphenyl]-[1-(2-methoxyphenyl)-5-oxo-4,5-dihydro-1H-[1,2,4]triazol-3-yl]methyl}amino)benzamidine diacetate

[Chemical Formula 713]

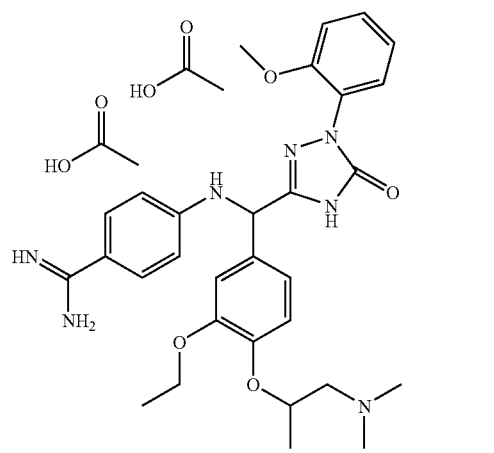

Example X-130

2-(3-{(4-carbamimidoylphenylamino)-[4-(1-dimethylcarbamoylethoxy)-3-ethoxyphenyl]methyl}-5-oxo-4,5-dihydro-[1,2,4]triazol-1-yl)benzoic acid acetate

[Chemical Formula 714]

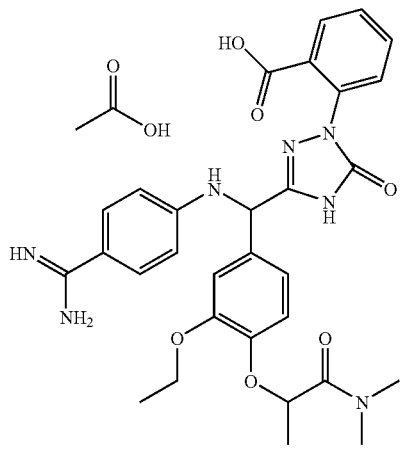

Example X-131

2-(4-{(4-carbamimidoylphenylamino)-[1-(2-methoxyphenyl)-5-oxo-4,5-dihydro-1H-[1,2,4]triazol-3-yl]methyl}-2-ethoxyphenoxy)-N,N-dimethylpropionamide acetate

[Chemical Formula 715]

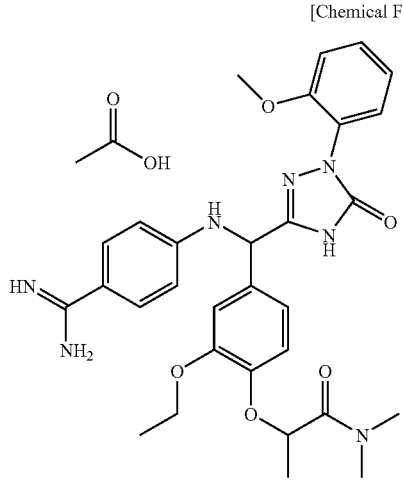

Example X-132

4-({[4-(2-dimethylamino-1-methylethoxy)-3-ethoxyphenyl]-[1-(2-fluorophenyl)-5-oxo-4,5-dihydro-1H-[1,2,4]triazol-3-yl]methyl}amino)benzamidine diacetate

[Chemical Formula 716]

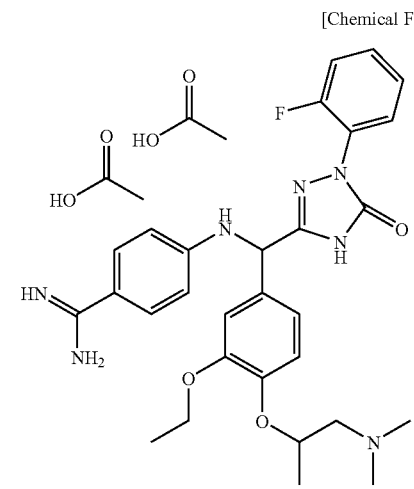

Example X-133

4-{[[3-ethoxy-4-(1-methylpyrrolidin-3-yloxy)phenyl]-(5-oxo-1-pyridin-2-yl-4,5-dihydro-1H-[1,2,4]triazol-3-yl)methyl]amino}benzamidine diacetate

[Chemical Formula 717]

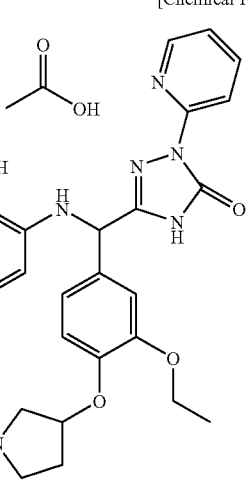

Example X-134

4-({[3-ethoxy-4-(1-methylpyrrolidin-3-yloxy)phenyl]-[1-(2-methoxyphenyl)-5-oxo-4,5-dihydro-1H-[1,2,4]triazol-3-yl]methyl}amino)benzamidine diacetate

[Chemical Formula 718]

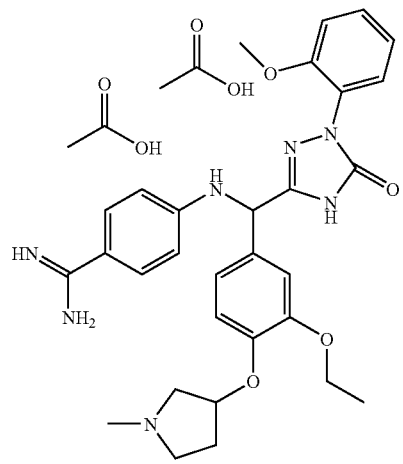

Example X-135

2-(4-{(4-carbamimidoylphenylamino)-[1-(2-fluorophenyl)-5-oxo-4,5-dihydro-1H-[1,2,4]triazol-3-yl]methyl}-2-ethoxyphenoxy)-N,N-dimethylpropionamide acetate

[Chemical Formula 719]

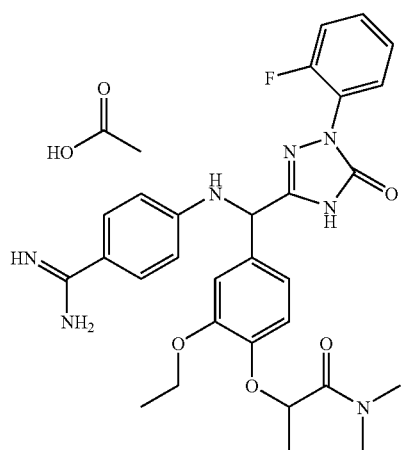

Example X-136

4-{[[4-(2-dimethylamino-1-methylethoxy)-3-ethoxyphenyl]-(5-oxo-1-pyridin-2-yl-4,5-dihydro-1H-[1,2,4]triazol-3-yl)methyl]amino}benzamidine diacetate

[Chemical Formula 720]

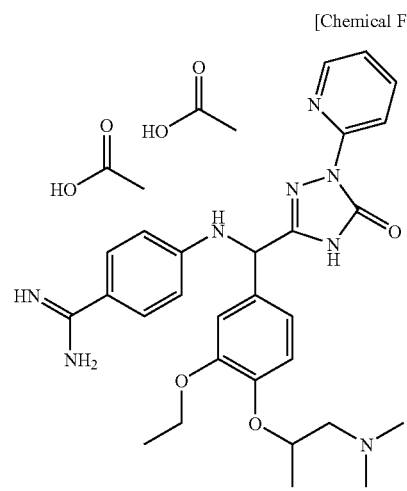

Example X-137

2-(3-{(4-carbamimidoylphenylamino)-[3-ethoxy-4-(2-methoxyethoxy)phenyl]methyl}-5-oxo-4,5-dihydro-[1,2,4]triazol-1-yl)benzoic acid acetate

[Chemical Formula 721]

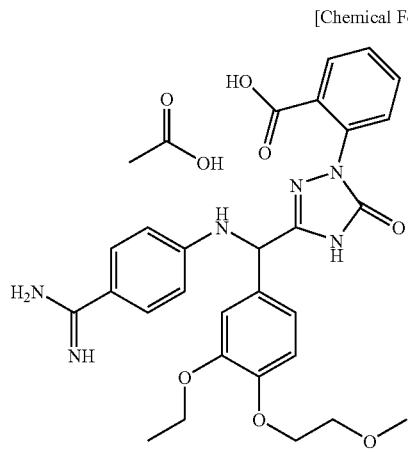

Example X-138

2-(3-{(4-carbamimidoylphenylamino)-[3-ethoxy-4-(2-methoxy-1-methylethoxy)phenyl]methyl}-5-oxo-4,5-dihydro-[1,2,4]triazol-1-yl)benzoic acid acetate

[Chemical Formula 722]

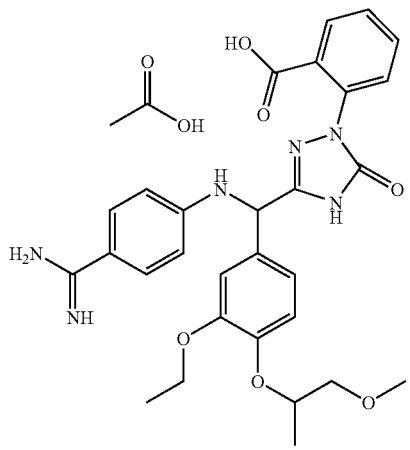

Example X-139

4-{[[4-(2-dimethylamino-1-methylethoxy)-3-ethoxyphenyl]-(5-oxo-1-pyrimidin-2-yl-4,5-dihydro-1H-[1,2,4]triazol-3-yl)methyl]amino}benzamidine diacetate

[Chemical Formula 723]

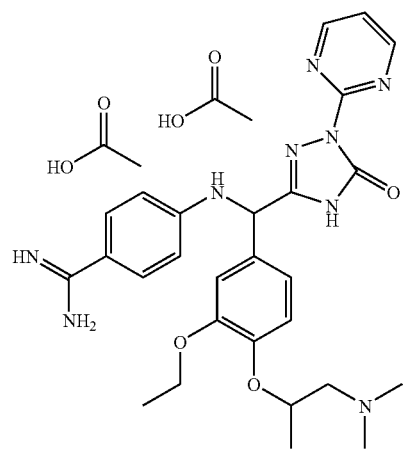

Example X-140

4-{[[3-ethoxy-4-(2-methoxyethoxy)phenyl]-(5-oxo-1-pyrimidin-2-yl-4,5-dihydro-1H-[1,2,4]triazol-3-yl)methyl]amino}benzamidine acetate

[Chemical Formula 724]

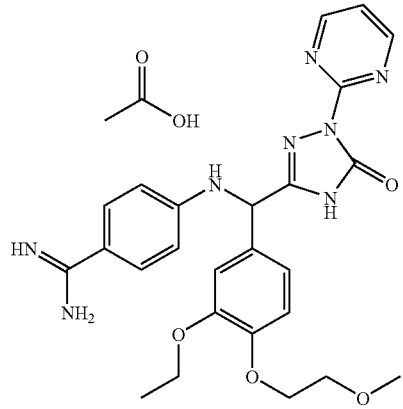

Example X-141

4-{[[3-(3-dimethylamino)-2,2-dimethylpropoxy]-2-fluoro-5-methoxyphenyl]-(5-oxo-1-pyridin-2-yl-4,5-dihydro-1H-[1,2,4]triazol-3-yl)methyl]amino}benzamidine bistrifluoroacetate

[Chemical Formula 725]

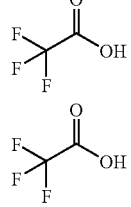

Example X-142

2-{3-{(4-carbamimidoylphenylamino)-[2-fluoro-5-methoxy-3-(1-methylpyrrolidin-3-yloxy)phenyl]methyl}-5-oxo-4,5-dihydro-[1,2,4]triazol-1-yl)benzoic acid bistrifluoroacetate

[Chemical Formula 726]

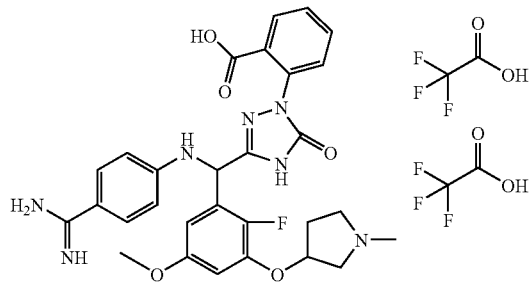

Example X-143

2-{3-{(4-carbamimidoylphenylamino)-[2-fluoro-5-methoxy-3-(1-methylpyrrolidin-3-yloxy)phenyl]methyl}-5-oxo-4,5-dihydro-[1,2,4]triazol-1-yl)benzoic acid bistrifluoroacetate

[Chemical Formula 727]

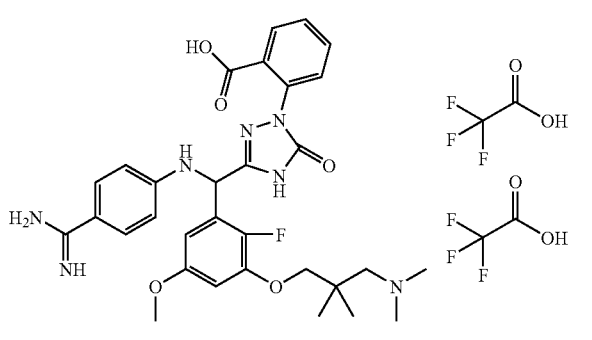

Example X-144

4-{[[2-fluoro-5-methoxy-3-(2-methoxyethoxy)phenyl]-(5-oxo-1-pyrazin-2-yl-4,5-dihydro-1H-[1,2,4]triazol-3-yl)methyl]amino}benzamidine trifluoroacetate

[Chemical Formula 728]

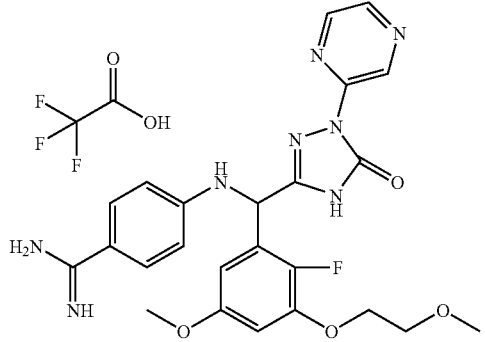

Example X-145

2-(3-{(4-carbamimidoylphenylamino)-[3-(2-dimethylamino-1-methylethoxy)-2-fluoro-5-methoxyphenyl]methyl}-5-oxo-4,5-dihydro-[1,2,4]triazol-1-yl)benzoic acid bistrifluoroacetate

[Chemical Formula 729]

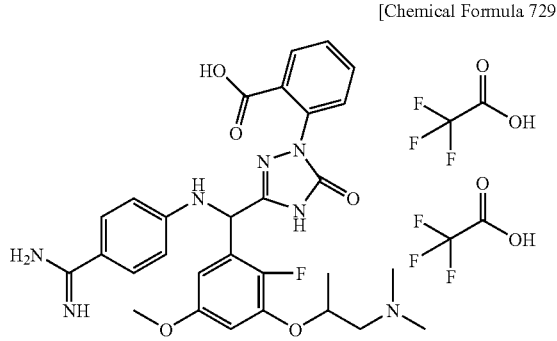

Example X-146

4-{[[3-(2-dimethylamino-1-methylethoxy)-2-fluoro-5-methoxyphenyl]-(5-oxo-1-pyrimidin-2-yl-4,5-dihydro-1H-[1,2,4]triazol-3-yl)methyl]amino}benzamidine bistrifluoroacetate

[Chemical Formula 730]

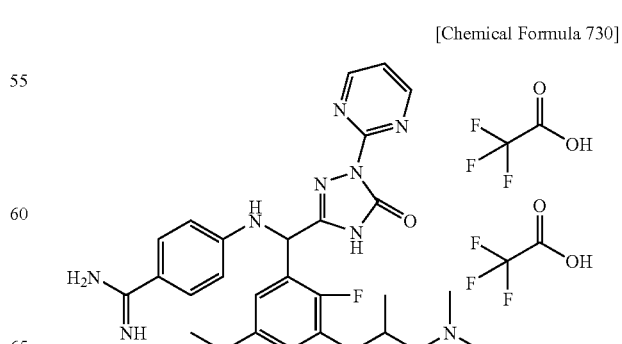

Example X-147

2-{3-[(4-carbamimidoylphenylamino)-(5-oxo-1-pyrazin-2-yl-4,5-dihydro-1H-[1,2,4]triazol-3-yl)methyl]-2-fluoro-5-methoxyphenoxy}-N,N-dimethylacetamide trifluoroacetate

[Chemical Formula 731]

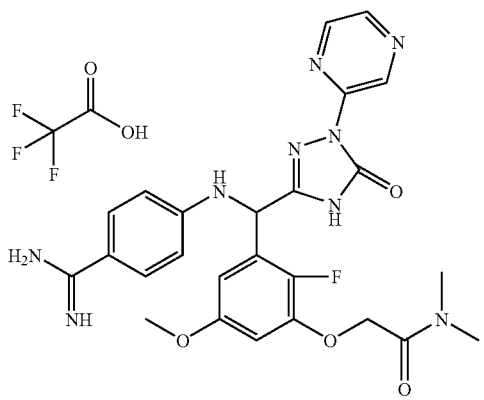

Example X-148

4-{[[2-fluoro-5-(2-hydroxyethyl)phenyl]-(5-oxo-1-pyrimidin-2-yl-4,5-dihydro-1H-[1,2,4]triazol-3-yl)methyl]amino}benzamidine acetate

[Chemical Formula 732]

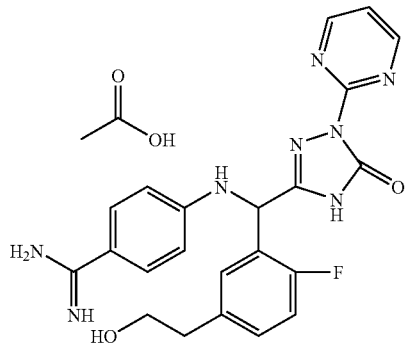

Example X-149

4-({(3-methoxy-5-methylphenyl)-[1-(2-methoxyphenyl)-5-oxo-4,5-dihydro-1H-[1,2,4]triazol-3-yl]methyl}amino)benzamidine acetate

[Chemical Formula 733]

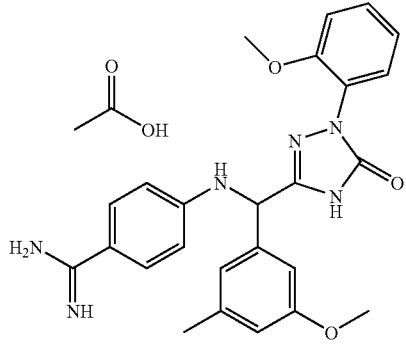

Example X-150

4-{[[2-fluoro-5-(2-fluoroethoxy)-3-methoxyphenyl]-(5-oxo-1-pyrimidin-2-yl-4,5-dihydro-1H-[1,2,4]triazol-3-yl)methyl]amino}benzamidine acetate

[Chemical Formula 734]

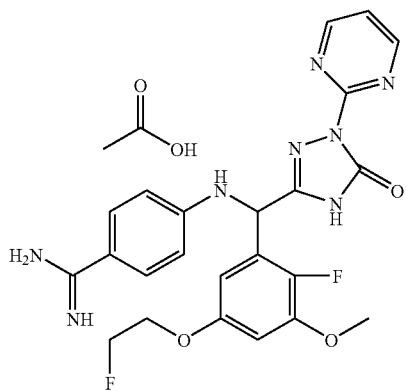

Example X-151

4-{[(R) and (S)-[2-fluoro-3-(2-methoxyethoxy)-5-methylphenyl]-(5-oxo-1-pyrimidin-2-yl-4,5-dihydro-1H-[1,2,4]triazol-3-yl)methyl]amino}benzamidine acetate

[Chemical Formula 735]

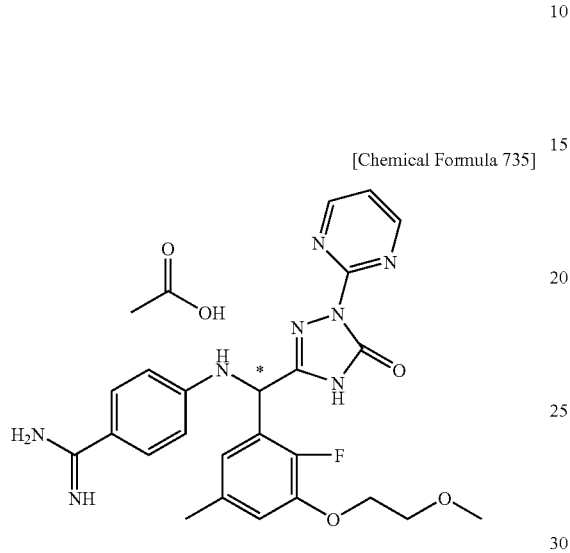

Example X-152

4-{[[3-(2,2-difluoroethoxy)-5-methoxyphenyl]-(5-oxo-1-pyrimidin-2-yl-4,5-dihydro-1H-[1,2,4]triazol-3-yl)methyl]amino}benzamidine acetate

[Chemical Formula 736]

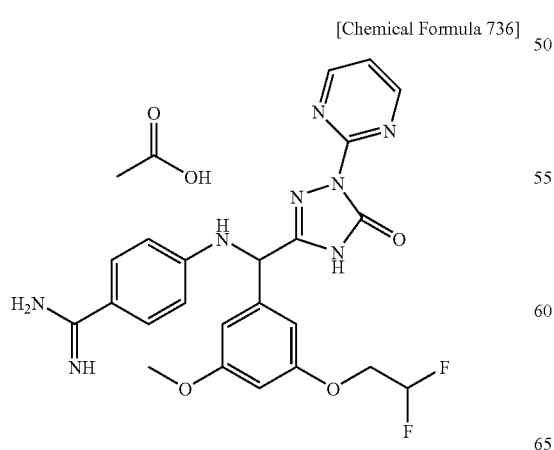

Example X-153

4-{[(4-methoxy-3-vinylphenyl)-(5-oxo-1-pyrimidin-2-yl-4,5-dihydro-1H-[1,2,4]triazol-3-yl)methyl]amino}benzamidine acetate

[Chemical Formula 737]

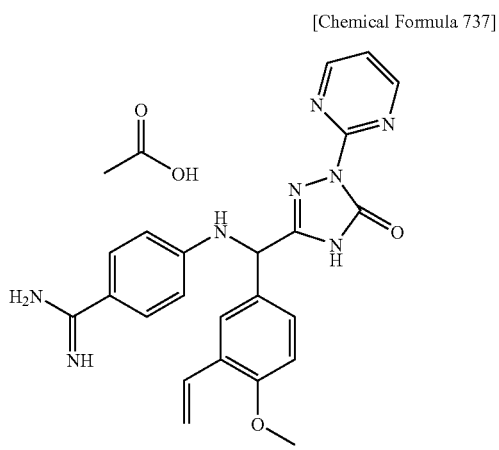

Example X-154

2-(3-{(4-carbamimidoylphenylamino)-[3-ethoxy-4-(2-methoxyethoxy)phenyl]methyl}-5-oxo-4,5-dihydro-[1,2,4]triazol-1-yl)benzamide trifluoroacetate

[Chemical Formula 738]

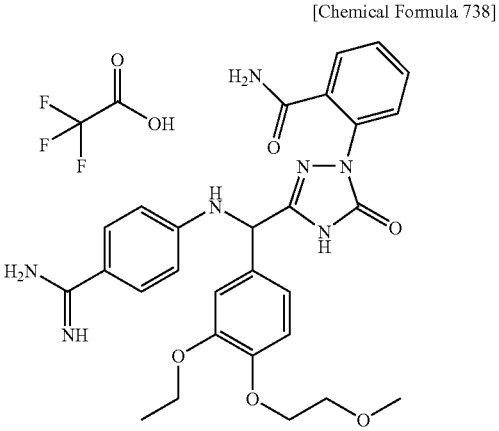

Example X-155

4-{[[1-(2-methoxyphenyl)-5-oxo-4,5-dihydro-1H-[1,2,4]triazol-3-yl]-(4-methoxy-3-vinylphenyl)methyl]amino}benzamidine acetate

Example X-156

4-{[(4-ethoxy-2-fluoro-5-methoxyphenyl)-(5-oxo-1-pyrimidin-2-yl-4,5-dihydro-1H-[1,2,4]triazol-3-yl)methyl]amino}benzamidine acetate

Example X-157

2-(3-{(4-carbamimidoylphenylamino)-[3-methoxy-4-(2-methoxyethoxy)phenyl]methyl}-5-oxo-4,5-dihydro-[1,2,4]triazol-1-yl)benzamide trifluoroacetate

Example X-158

2-(3-{(4-carbamimidoylphenylamino)-[4-(2-dimethylamino-1-methyl-ethoxy)-3-methoxyphenyl]methyl}-5-oxo-4,5-dihydro-[1,2,4]triazol-1-yl)benzoic acid bistrifluoroacetate

Example X-159

2-(3-{(4-carbamimidoylphenylamino)-[4-dimethyl-carbamoylmethoxy-3-ethoxyphenyl]methyl}-5-oxo-4,5-dihydro-[1,2,4]triazol-1-yl)benzoic acid trifluoroacetate

[Chemical Formula 743]

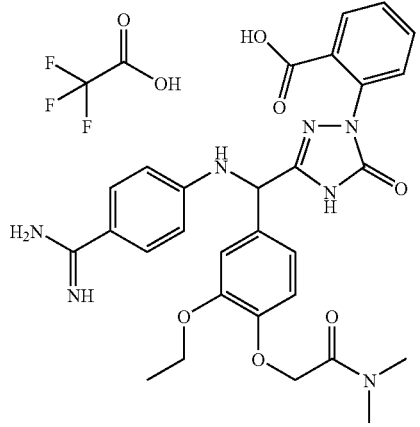

Example X-160

2-(3-{(4-carbamimidoylphenylamino)-[3-methoxy-4-(2-methoxyethoxy)phenyl]methyl}-5-oxo-4,5-dihydro-[1,2,4]triazol-1-yl)benzoic acid trifluoroacetate

[Chemical Formula 744]

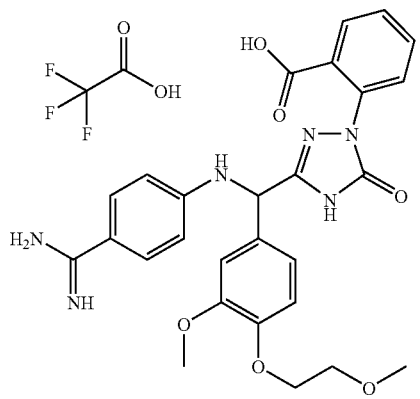

Example X-161

2-{3-[(4-carbamimidoylphenylamino)-(4-dimethyl-carbamoylmethoxyphenyl)methyl]-5-oxo-4,5-dihydro-[1,2,4]triazol-1-yl}benzoic acid trifluoroacetate

[Chemical Formula 745]

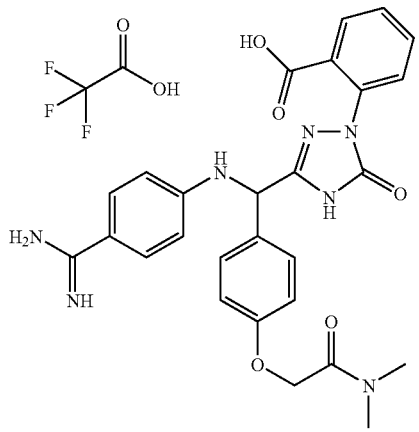

Example X-162

2-(4-{(4-carbamimidoylphenylamino)-[1-(2-methoxyphenyl)-5-oxo-4,5-dihydro-1H-[1,2,4]triazol-3-yl]methyl}-2-ethoxyphenoxy)-N,N-dimethylacetamide trifluoroacetate

[Chemical Formula 746]

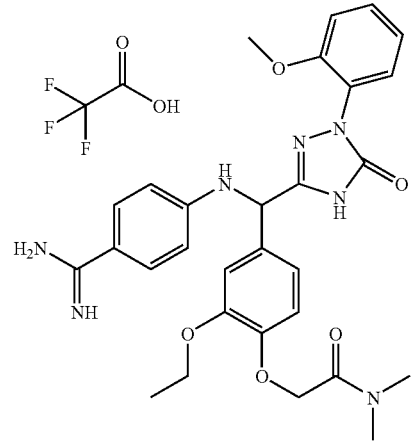

Example X-163

2-(4-{(4-carbamimidoylphenylamino)-[1-(2-methoxyphenyl)-5-oxo-4,5-dihydro-1H-[1,2,4]triazol-3-yl]methyl}-2-methoxyphenoxy)-N,N-dimethylpropionamide trifluoroacetate

[Chemical Formula 747]

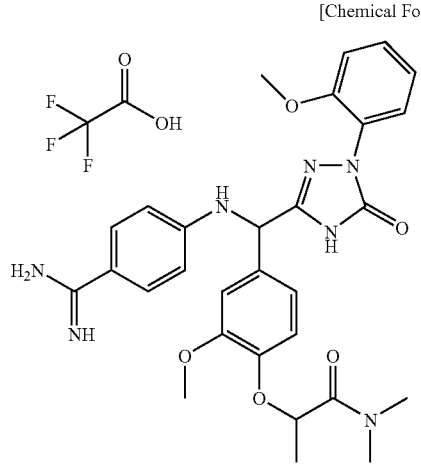

Example X-164

2-(3-{(4-carbamimidoylphenylamino)-[4-(1-dimethylcarbamoylethoxy)-3-methoxyphenyl]methyl}-5-oxo-4,5-dihydro-[1,2,4]triazol-1-yl)benzoic acid trifluoroacetate

[Chemical Formula 748]

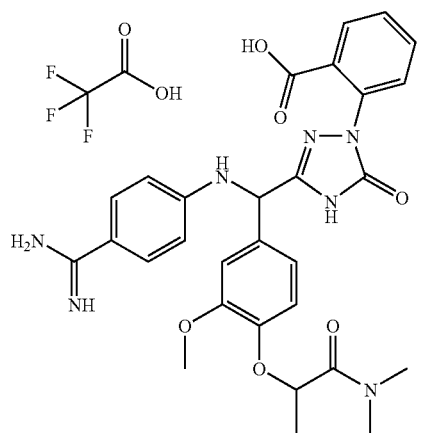

Example X-165

4-({[4-(2-dimethylamino-1-methylethoxy)-3-methoxyphenyl]-(5-oxo-1-phenyl-4,5-dihydro-1H-[1,2,4]triazol-3-yl)methyl]amino}benzamidine bistrifluoroacetate

[Chemical Formula 749]

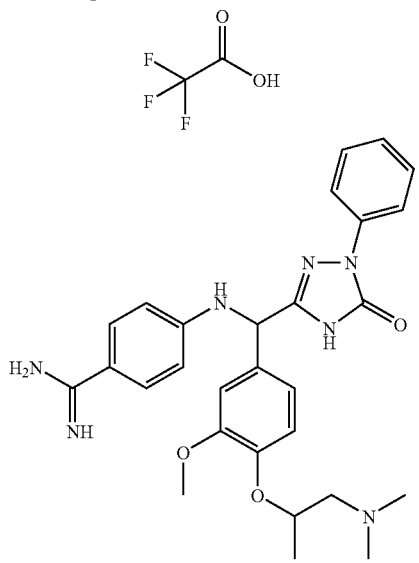

Example X-166

2-(4-{(4-carbamimidoylphenylamino)-[1-(2-chlorophenyl)-5-oxo-4,5-dihydro-1H-[1,2,4]triazol-3-yl]methyl}-2-methoxyphenoxy)-N,N-dimethylacetamide trifluoroacetate

[Chemical Formula 750]

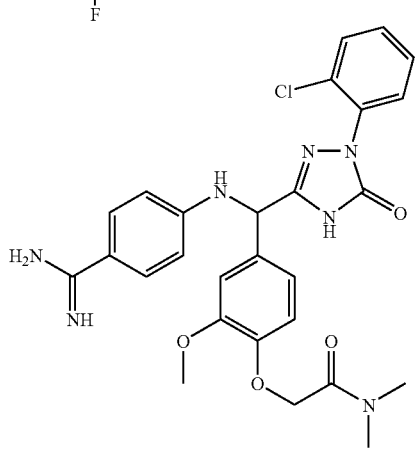

Example X-167

2-(3-{(4-carbamimidoylphenylamino)-[4-(2-dimethylamino-1-methyl-ethoxy)-3-methoxyphenyl]methyl}-5-oxo-4,5-dihydro-[1,2,4]triazol-1-yl)benzamide trifluoroacetate

[Chemical Formula 751]

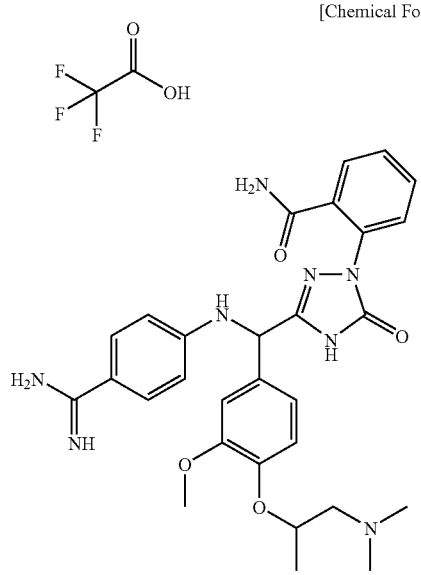

Example X-168

4-({[4-(2-dimethylamino-1-methylethoxy)-3-methoxyphenyl]-[1-(2-methoxyphenyl)-5-oxo-4,5-dihydro-1H-[1,2,4]triazol-3-yl]methyl}amino)benzamidine trifluoroacetate

[Chemical Formula 752]

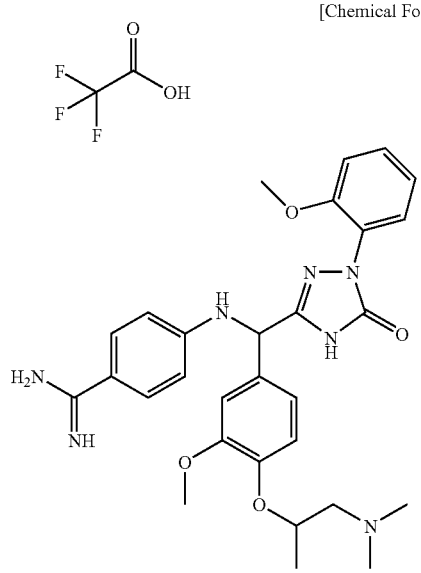

Example X-169

3-(4-{(4-carbamimidoylphenylamino)-[1-(2-methoxyphenyl)-5-oxo-4,5-dihydro-1H-[1,2,4]triazol-3-yl]methyl}-2-ethoxyphenoxy)-2,2,N,N-tetramethylpropionamide trifluoroacetate

[Chemical Formula 753]

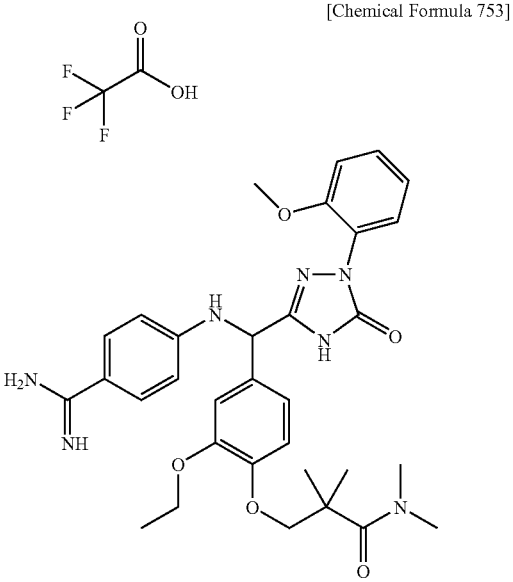

Example X-170

(R) and (S)-4-{[[3-methoxy-4-(pyridin-2-ylmethoxy)phenyl]-(5-oxo-1-pyridazin-3-yl-4,5-dihydro-1H-[1,2,4]triazol-3-yl)methyl]amino}benzamidine acetate

[Chemical Formula 754]

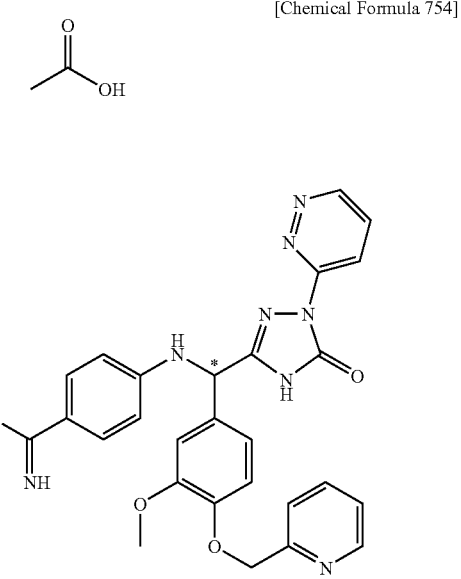

Example X-171

4-{[[4-(2-dimethylamino-1-methylethoxy)-3-methoxyphenyl]-(5-oxo-1-pyridin-2-yl-4,5-dihydro-1H-[1,2,4]triazol-3-yl)methyl]amino}benzamidine bistrifluoroacetate

[Chemical Formula 755]

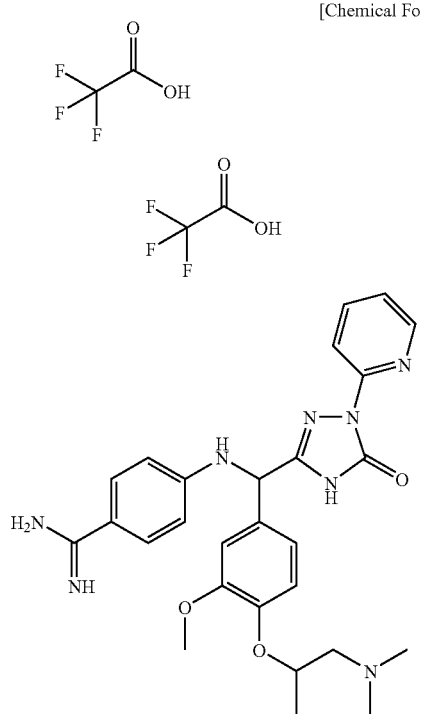

Example X-172

2-(4-{(4-carbamimidoylphenylamino)-[1-(2-methoxyphenyl)-5-oxo-4,5-dihydro-1H-[1,2,4]triazol-3-yl]methyl}-2-methoxyphenoxy)-N,N-dimethylacetamide trifluoroacetate

[Chemical Formula 756]

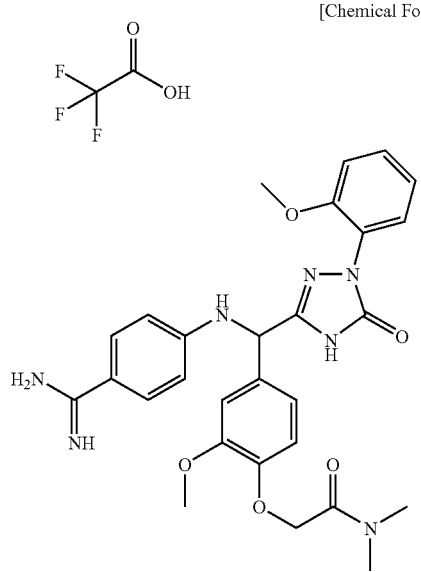

Example X-173

(R) and (S)-4-{[[3-methoxy-4-(2-methoxyethoxy)phenyl]-(5-oxo-1-pyridazin-3-yl-4,5-dihydro-1H-[1,2,4]triazol-3-yl)methyl]amino}benzamidine acetate

[Chemical Formula 757]

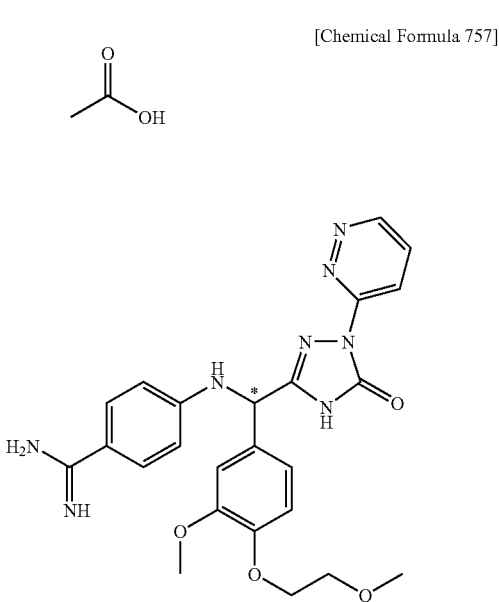

Example X-174

2-[3-((4-carbamimidoylphenylamino)-{3-methoxy-4-[2-(2-oxopyrrolidin-1-yl)ethoxy]phenyl}methyl)-5-oxo-4,5-dihydro-[1,2,4]triazol-1-yl]benzamide trifluoroacetate

[Chemical Formula 758]

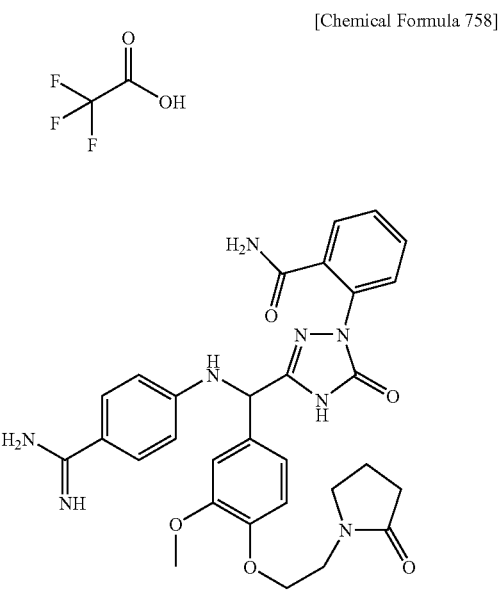

Example X-175

2-[3-{(4-carbamimidoylphenylamino)-[4-(1-dimethylcarbamoylethoxy)-3-methoxyphenyl]methyl}-5-oxo-4,5-dihydro-[1,2,4]triazol-1-yl]benzamide trifluoroacetate

[Chemical Formula 759]

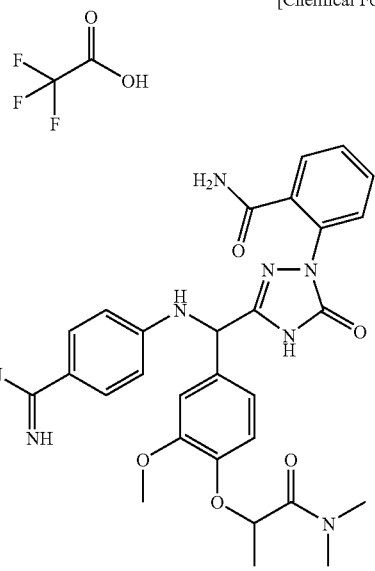

Example X-176

(R) and (S)-4-{[[3-methoxy-4-(pyridin-3-ylmethoxy)phenyl]-(5-oxo-1-pyridazin-3-yl-4,5-dihydro-1H-[1,2,4]triazol-3-yl)methyl]amino}benzamidine acetate

[Chemical Formula 760]

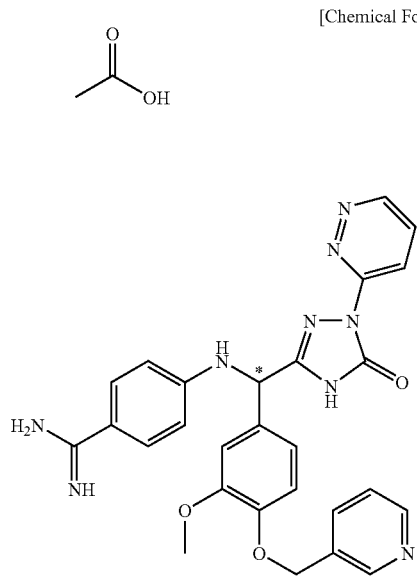

Example X-177

4-({[4-(2-dimethylaminoethoxy)-3-ethoxyphenyl]-[1-(2-methoxyphenyl)-5-oxo-4,5-dihydro-1H-[1,2,4]triazol-3-yl]methyl}amino)benzamidine bistrifluoroacetate

[Chemical Formula 761]

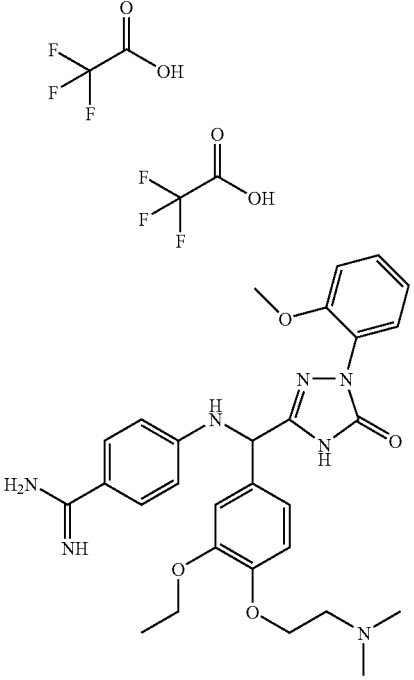

Example X-178

4-({[1-(2-methoxyphenyl)-5-oxo-4,5-dihydro-1H-[1,2,4]triazol-3-yl]-[3-methoxy-4-(2-pyrrolidin-1-ylethoxy)phenyl]methyl}amino)benzamidine diacetate

[Chemical Formula 762]

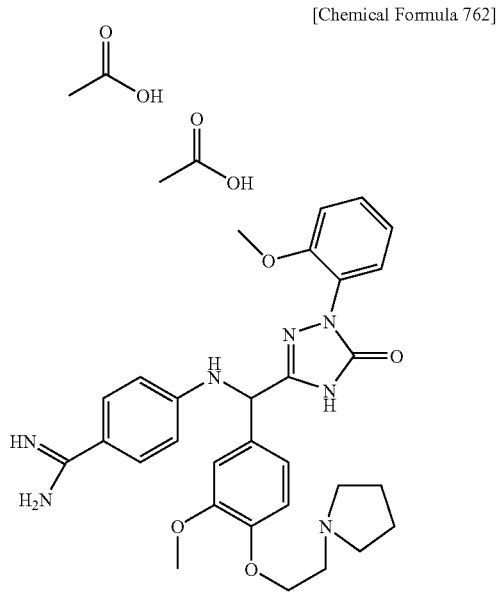

Example X-179

4-{[[3-methoxy-4-(2-pyrrolidin-1-ylethoxy)phenyl]-(5-oxo-1-pyridin-2-yl-4,5-dihydro-1H-[1,2,4]triazol-3-yl)methyl]amino}benzamidine diacetate

[Chemical Formula 763]

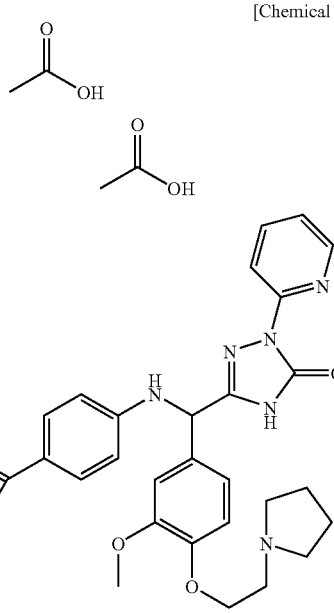

Example X-180

2-(3-{(4-carbamimidoylphenylamino)-[4-(2-dimethylcarbamoyl-2-methylpropoxy)-3-ethoxyphenyl]methyl}-5-oxo-4,5-dihydro-1H-[1,2,4]triazol-1-yl)benzoic acid acetate

[Chemical Formula 764]

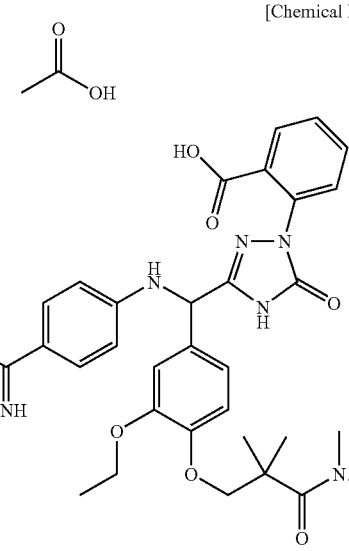

Example X-181

(R) and (S)-4-{[(2-fluoro-5-methoxy-3-propoxyphenyl)-(5-oxo-1-pyrimidin-2-yl-4,5-dihydro-1H-[1,2,4]triazol-3-yl)methyl]amino}benzamidine acetate

[Chemical Formula 765]

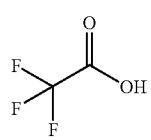

Example X-182

4-({[1-(2-aminophenyl)-5-oxo-4,5-dihydro-1H-[1,2,4]triazol-3-yl]-[2-fluoro-3-(2-fluoroethoxy)-5-methoxyphenyl]methyl}amino)benzamidine trifluoroacetate

[Chemical Formula 766]

Example X-183

N-[2-(3-{(4-carbamimidoylphenylamino)-[5-ethyl-2-fluoro-3-(2-fluoroethoxy)phenyl]methyl}-5-oxo-4,5-dihydro-1H-[1,2,4]triazol-1-yl)phenyl]acetamide trifluoroacetate

[Chemical Formula 767]

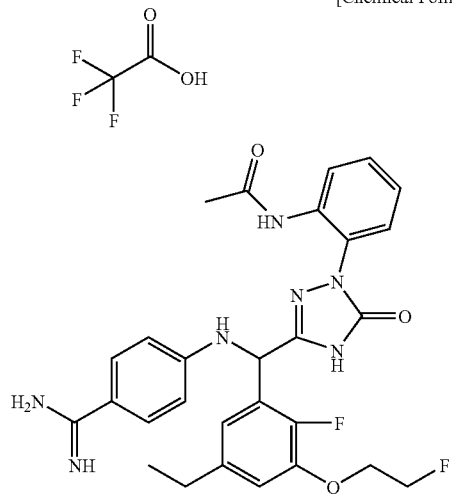

Example X-184

N-[2-(3-{(4-carbamimidoylphenylamino)-[3-(2-dimethylaminoethoxy)-5-ethyl-2-fluorophenyl]methyl}-5-oxo-4,5-dihydro-1H-[1,2,4]triazol-1-yl)phenyl]-2-hydroxyacetamide bistrifluoroacetate

[Chemical Formula 768]

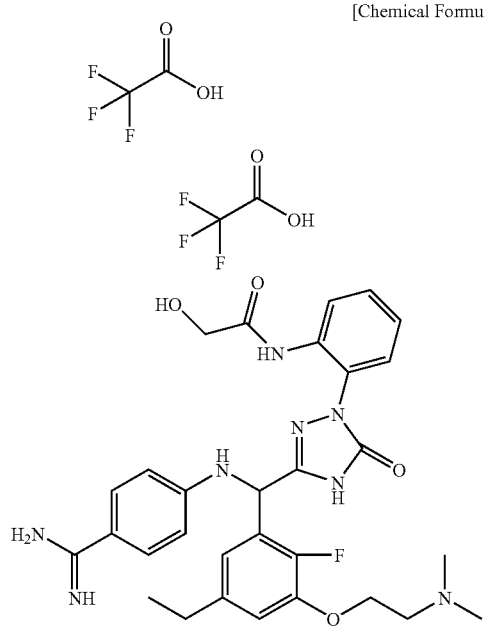

Example X-185

4-{[[1-(3-aminopyridin-2-yl)-5-oxo-4,5-dihydro-1H-[1,2,4]triazol-3-yl]-(3-allyloxy-4-methoxyphenyl)methyl]amino}benzamidine trifluoroacetate

[Chemical Formula 769]

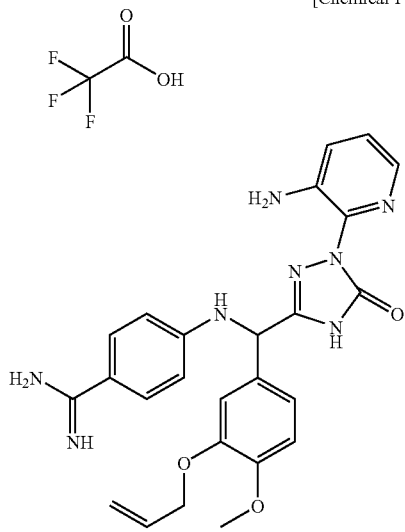

Example X-186

2-(3-{(4-carbamimidoylphenylamino)-[3-(2-dimethylaminopropoxy)-5-ethyl-2-fluorophenyl]methyl}-5-oxo-4,5-dihydro-[1,2,4]triazol-1-yl}benzoic acid bistrifluoroacetate

[Chemical Formula 770]

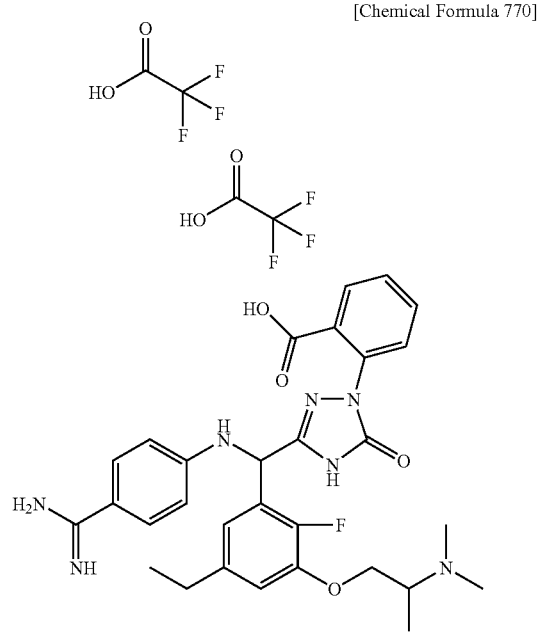

Example X-187

2-(3-{(4-carbamimidoylphenylamino)-[3-(2-dimethylamino-1-methylethoxy)-5-ethyl-2-fluorophenyl]methyl}-5-oxo-4,5-dihydro-[1,2,4]triazol-1-yl}benzoic acid bistrifluoroacetate

[Chemical Formula 771]

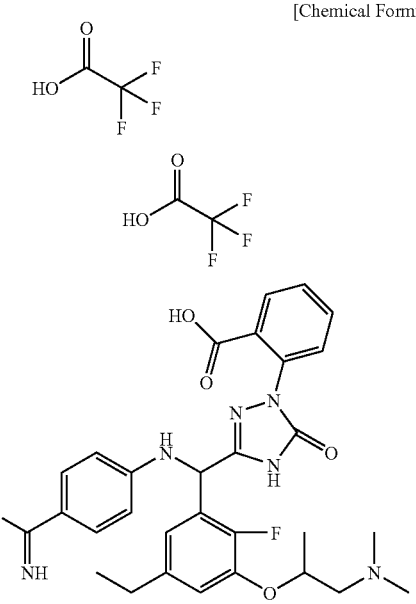

Example X-188

4-{[[3-(3-dimethylamino-2,2-dimethylpropoxy)-5-ethyl-2-fluorophenyl]-(5-oxo-1-pyridin-2-yl-4,5-dihydro-1H-[1,2,4]triazol-3-yl)methyl]amino}benzamidine bistrifluoroacetate

[Chemical Formula 772]

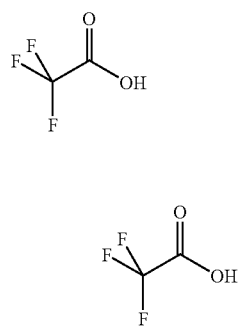

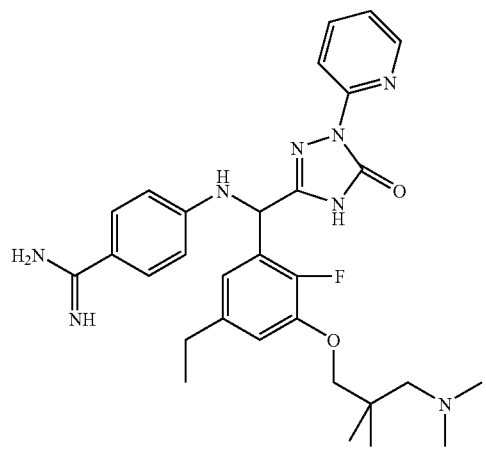

Example X-189

2-(3-{(4-carbamimidoylphenylamino)-[3-(2-dimethylaminoethoxy)-5-ethyl-2-fluorophenyl]methyl}-5-oxo-4,5-dihydro-[1,2,4]triazol-1-yl}benzoic acid bistrifluoroacetate

[Chemical Formula 773]

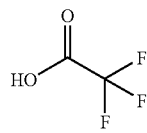

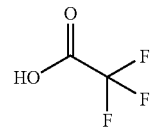

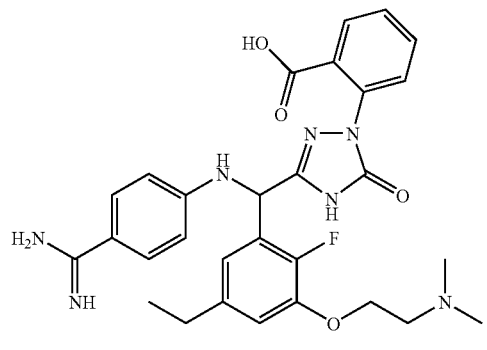

Example X-190

2-{3-[[1-(2-acetylaminophenyl)-5-oxo-4,5-dihydro-1H-[1,2,4]triazol-3-yl]-(4-carbamimidoylphenylamino)methyl]-5-ethyl-2-fluorophenoxy}-N,N-dimethylacetamide trifluoroacetate

[Chemical Formula 774]

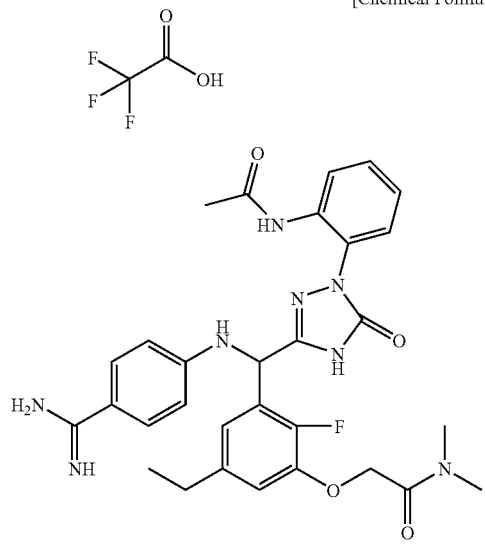

$^1$H-NMR (CD$_3$OD) δ 1.17 (t, J=7.8 Hz, 3H) 1.90 (s, 3H) 2.58 (q, J=7.8 Hz, 2H) 2.98 (s, 3H) 3.10 (s, 3H) 4.92 (s, 2H) 6.04 (s, 1H) 6.88 (d, J=8.6 Hz, 2H) 6.90-6.95 (m, 2H) 7.25 (t, J=7.4 Hz, 1H) 7.37 (t, J=7.4 Hz, 1H) 7.48 (d, J=7.4 Hz, 1H) 7.65 (d, J=8.6 Hz, 2H) 7.75 (d, J=7.4 Hz, 1H)

Example X-191

4-{3-[(R) and (S)-(4-Carbamimidoylphenylamino)-(5,6-dimethoxypyridin-3-yl)methyl]-5-oxo-4,5-dihydro-[1,2,4]triazol-1-yl}thiazole-5-carboxylic acid

[Chemical Formula 775]

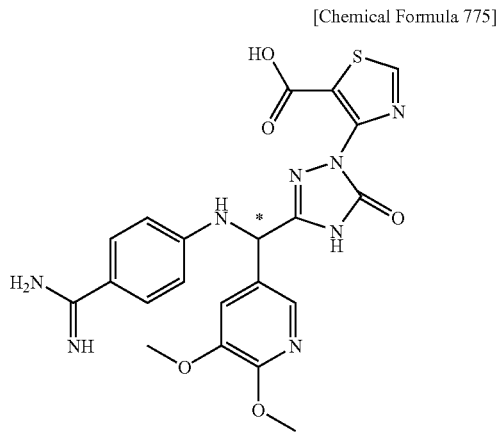

Example X-192

(R) and (S)-4-(3-{(4-Carbamimidoylphenylamino)-[3-(2-hydroxyethoxy)-5-methoxyphenyl]methyl}-5-oxo-4,5-dihydro[1,2,4]triazol-1-yl)thiazole-5-carboxylic acid

[Chemical Formula 776]

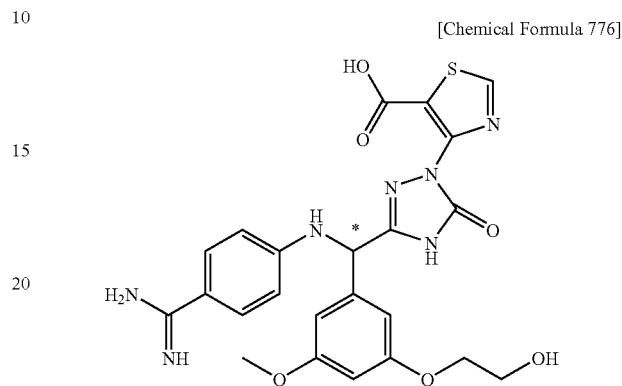

$^1$H-NMR (CD$_3$OD) δ 3.78 (s, 3H) 3.84 (t, J=4.7 Hz, 2H) 4.18 (m, 2H) 5.67 (s, 1H) 6.50 (t, J=1.8 Hz, 1H) 6.73 (t, J=1.8 Hz, 1H) 6.75 (t, J=1.8 Hz, 1H) 6.86 (d, J=9.0 Hz, 2H) 7.61 (d, J=9.0 Hz, 2H) 8.89 (s, 1H)

HPLC retention time: 17 min (Column name: SUMICHIRAL OA-2500, 30 mmφ×25 cm, Manufacturer: Sumika Chemical Analysis Service, Ltd., Mobile phase: 0.05 M ammonium acetate-methanol solution, Elution rate: 30 ml/min)

Example X-193

5-{3-[(4-Carbamimidoylphenylamino)-(3,4-dimethoxyphenyl)methyl]-5-oxo-4,5-dihydro-[1,2,4]triazol-1-yl}-1H-pyrazole-4-carboxylic acid

[Chemical Formula 777]

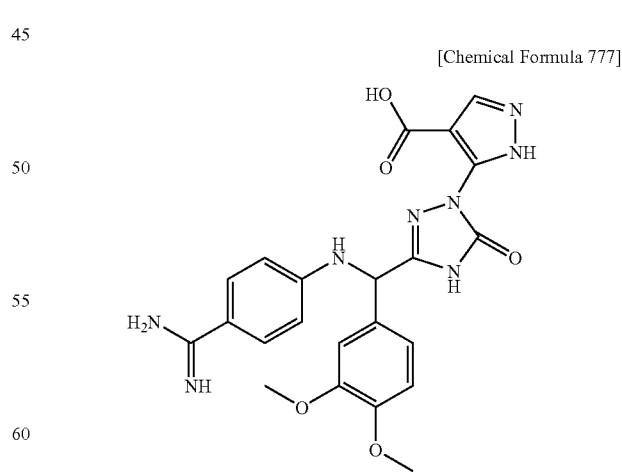

$^1$H-NMR (CD$_3$OD) δ 3.82 (s, 3H) 3.84 (s, 3H) 5.56 (s, 1H) 6.86 (d, J=9.1 Hz, 2H) 6.97 (d, J=7.9 Hz, 1H) 7.09 (d, J=7.9, 2.0 Hz, 1H) 7.15 (d, J=2.0 Hz, 1H) 7.61 (d, J=9.1 Hz, 2H) 8.01 (s, 1H)

Example X-194

5-{3-[(4-Carbamimidoylphenylamino)-(5-fluoro-8-methoxychroman-6-yl)methyl]-5-oxo-4,5-dihydro-[1,2,4]triazol-1-yl}-1H-pyrazole-4-carboxylic acid ethyl ester acetate

[Chemical Formula 778]

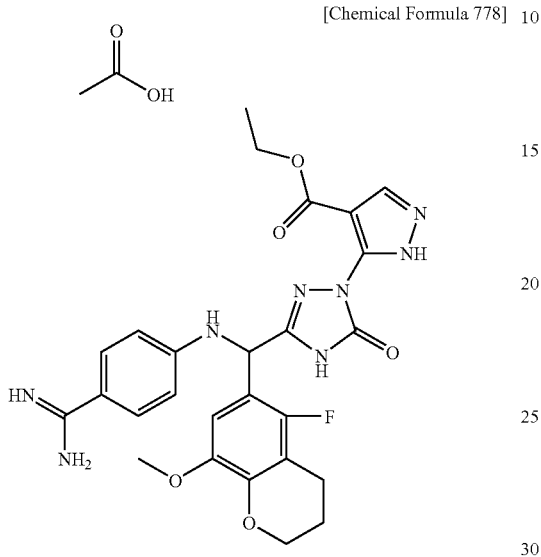

$^1$H-NMR (CD$_3$OD) δ 1.18 (t, J=7.3 Hz, 3H) 1.95 (s, 3H) 2.00 (tt, J=6.4, 5.5 Hz, 2H) 2.77 (t, J=6.4 Hz, 2H) 3.78 (s, 3H) 4.15 (m, 2H) 4.21 (t, J=5.5 Hz, 2H) 5.91 (s, 1H) 6.84 (d, J=8.8 Hz, 2H) 6.92 (d, J=6.8 Hz, 1H) 7.64 (d, J=8.8 Hz, 2H) 8.26 (s, 1H)

Example X-195

(R) and (S)-4-({(2-Fluoro-4,5-dimethoxyphenyl)-[5-oxo-1-(3-oxo-3 4-dihydropyrazin-2-yl)-4,5-dihydro-1H-[1,2,4]triazol-3-yl]methyl}amino)benzamidine acetate

[Chemical Formula 779]

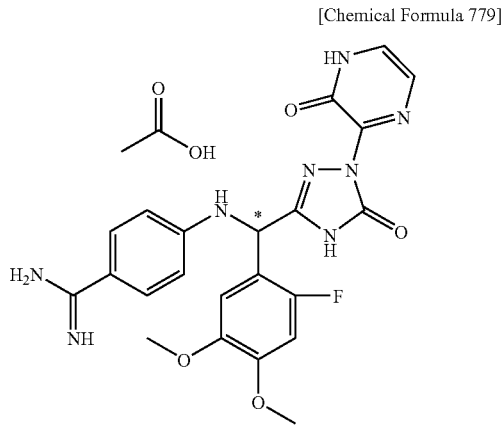

$^1$H-NMR (CD$_3$OD) δ 1.95 (s, 3H) 3.76 (s, 3H) 3.82 (s, 3H) 5.89 (s, 1H) 6.83 (d, J=11.0 Hz, 1H) 6.84 (d, J=8.7 Hz, 2H) 7.10 (d, J=6.0 Hz, 1H) 7.49 (br.s, 1H) 7.60 (d, J=8.7 Hz, 2H) 7.68 (br.s, 1H)

HPLC retention time: 15 min (Column name: SUMICHIRAL OA-2500, 20 mmφ×25 cm, Manufacturer: Sumika Chemical Analysis Service, Ltd., Mobile phase: 0.05 M ammonium acetate-methanol solution, Elution rate: 10 ml/min)

Example X-196

(R) and (S)-4-{[[1-(2-Aminopyridin-3-yl)-5-oxo-4,5-dihydro-1H-[1,2,4]triazol-3-yl]-(8-methoxy-4H-benzo[1,3]dioxin-6-yl)methyl]amino}benzamidine acetate

[Chemical Formula 780]

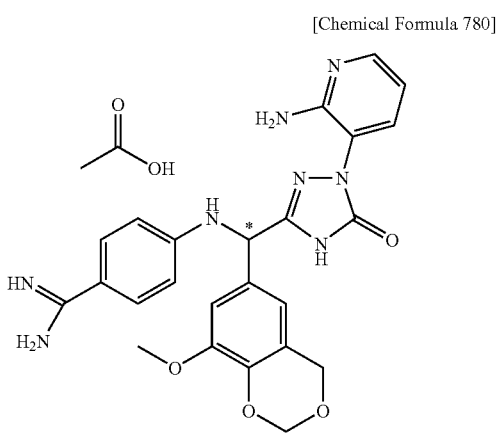

$^1$H-NMR (CD$_3$OD) δ 1.95 (s, 3H) 3.83 (s, 3H) 4.86 (s, 2H) 5.24 (s, 2H) 5.57 (s, 1H) 6.75 (dd, J=7.4, 5.2 Hz, 1H) 6.79 (d, J=1.5 Hz, 1H) 6.85 (d, J=8.9 Hz, 2H) 7.04 (d, J=1.5 Hz, 1H) 7.62 (d, J=8.9 Hz, 2H) 7.66 (dd, J=7.4, 52.2 Hz, 1H) 7.94 (dd, J=5.2, 2.2 Hz, 1H)

HPLC retention time: 10 min

Example X-197

(R) and (S)-4-{[[5-Ethyl-2-fluoro-3-(2-hydroxy-ethoxy)phenyl]-(5-oxo-1-pyrimidin-2-yl-4,5-dihydro-1H-[1,2,4]triazol-3-yl)methyl]amino}benzamidine acetate

[Chemical Formula 781]

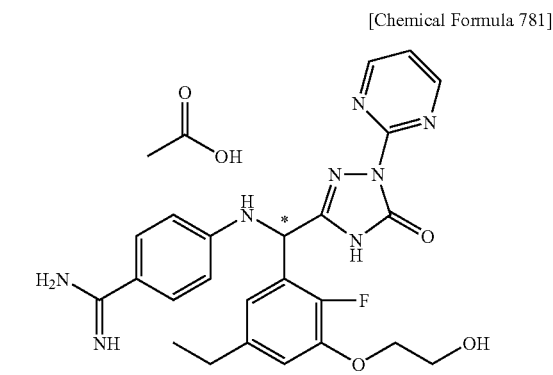

$^1$H-NMR (CD$_3$OD) δ 1.16 (t, J=7.2 Hz, 3H) 1.95 (s, 3H) 2.57 (q, J=7.2 Hz, 2H) 3.88 (t, J=4.3 Hz, 2H) 4.11 (t, J=4.3 Hz, 2H) 5.99 (s, 1H) 6.85 (d, J=8.9 Hz, 2H) 6.92-6.96 (m, 2H) 7.35 (t, J=4.3 Hz, 1H) 7.61 (d, J=8.9 Hz, 2H) 8.77 (t, J=4.3 Hz, 2H)

HPLC retention time: 7 min (Column name: SUMICHIRAL OA-2500, 30 mmϕ×25 cm, Manufacturer: Sumika Chemical Analysis Service, Ltd., Mobile phase: 0.05 M ammonium acetate-methanol solution, Elution rate: 20 ml/min)

Example X-198

(R) and (S)-5-(3-{(4-Carbamimidoylphenylamino)-[2-fluoro-3-(3-hydroxypropoxy)-5-methoxyphenyl]methyl}-5-oxo-4,5-dihydro-[1,2,4]triazol-1-yl)-3H-imidazole-4-carboxylic acid acetate

[Chemical Formula 782]

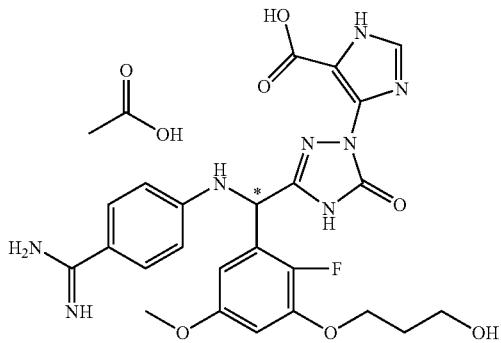

¹H-NMR (CD₃OD) δ 1.95 (s, 3H) 2.01 (quint, J=6.3 Hz, 2H) 3.73 (s, 3H) 3.75 (t, J=6.3 Hz, 2H) 4.13 (t, J=6.3 Hz, 2H) 5.91 (s, 1H) 6.61 (dd, J=4.9, 2.8 Hz, 1H) 6.64 (dd, J=7.0, 2.8 Hz, 1H) 6.83 (d, J=9.3 Hz, 2H) 7.58 (s, 1H) 7.61 (d, J=9.3 Hz, 2H)

Example X-199

(R) and (S)-4-{[[5-Ethyl-2-fluoro-3-(3-hydroxypropoxy)phenyl]-(5-oxo-1-pyrimidin-2-yl-4,5-dihydro-1H-[1,2,4]triazol-3-yl)methyl]amino}benzamidine acetate

[Chemical Formula 783]

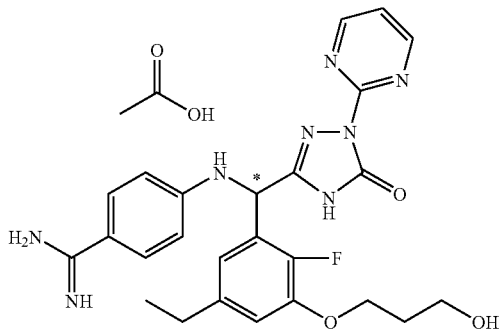

¹H-NMR (CD₃OD) δ 1.16 (t, J=7.4 Hz, 3H) 1.95 (s, 3H) 2.00 (quint, J=6.3 Hz, 2H) 2.57 (q, J=7.4 Hz, 2H) 3.74 (t, J=6.3 Hz, 2H) 4.14 (t, J=6.3 Hz, 2H) 5.98 (s, 1H) 6.86 (d, J=8.5 Hz, 2H) 6.88-6.94 (m, 2H) 7.34 (t, J=4.3 Hz, 1H) 7.61 (d, J=8.5 Hz, 2H) 8.76 (t, J=4.3 Hz, 2H)

HPLC retention time: 7 min (Column name: SUMICHIRAL OA-2500, 30 mmϕ×25 cm, Manufacturer: Sumika Chemical Analysis Service, Ltd., Mobile phase: 0.05 M ammonium acetate-methanol solution, Elution rate: 15 ml/min)

Example X-200

(R) and (S)-4-({[1-(3-Aminopyridin-2-yl)-5-oxo-4,5-dihydro-1H-[1,2,4]triazol-3-yl]-(2-fluoro-4,5-dimethoxyphenyl)methyl}amino)benzamidine acetate

[Chemical Formula 784]

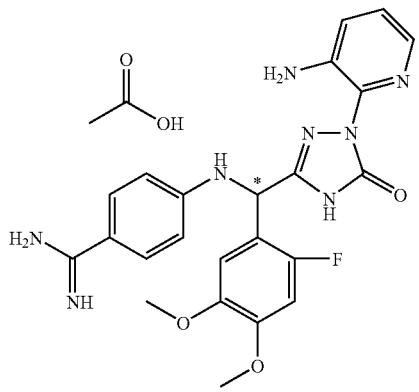

¹H-NMR (CD₃OD) δ 1.95 (s, 3H) 3.75 (s, 3H) 3.82 (s, 3H) 5.95 (s, 1H) 6.83 (d, J=11.4 Hz, 1H) 6.85 (d, J=8.6 Hz, 2H) 7.07 (d, J=7.7 Hz, 1H) 7.20 (br.s, 1H) 7.33 (br.s, 1H) 7.62 (d, J=8.6 Hz, 2H) 7.81 (br.s, 1H)

HPLC retention time: 11 min (Column name: SUMICHIRAL OA-2500, 30 mmϕ×25 cm, Manufacturer: Sumika Chemical Analysis Service, Ltd., Mobile phase: 0.05 M ammonium acetate-methanol solution, Elution rate: 15 ml/min)

Example X-201

4-({[1-(2-Aminopyridin-3-yl)-5-oxo-4,5-dihydro-1H-[1,2,4]triazol-3-yl]-(2-fluoro-4,5-dimethoxyphenyl)methyl}amino)benzamidine trifluoroacetate

[Chemical Formula 785]

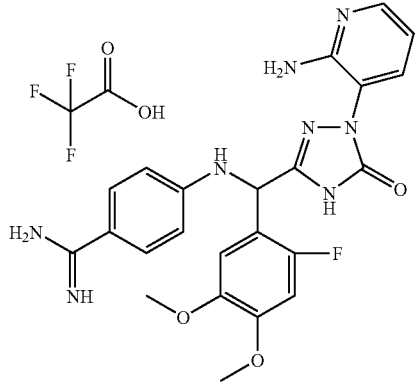

¹H-NMR (CD₃OD) δ 3.76 (s, 3H) 3.83 (s, 3H) 6.01 (s, 1H) 6.87 (d, J=11.4 Hz, 1H) 6.88 (d, J=8.7 Hz, 2H) 7.00 (dd,

J=6.9, 5.5 Hz, 1H) 7.04 (d, J=7.3 Hz, 1H) 7.65 (d, J=8.7 Hz, 2H) 7.92 (dd, J=5.5, 1.4 Hz, 1H) 8.21 (dd, J=6.9, 1.4 Hz, 1H)

Example X-202

(R) and (S)-4-({[1-(2-Aminopyridin-3-yl)-5-oxo-4,5-dihydro-1H-[1,2,4]triazol-3-yl]-(2-fluoro-3,5-dimethoxyphenyl)methyl}amino)benzamidine acetate

[Chemical Formula 786]

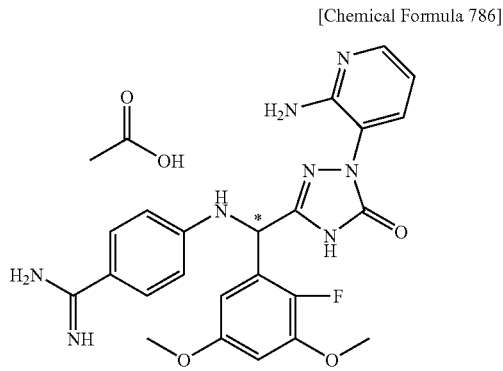

$^1$H-NMR (CD$_3$OD) δ 1.92 (s, 3H) 3.71 (s, 3H) 3.85 (s, 3H) 5.98 (s, 1H) 6.59 (dd, J=5.1, 2.6 Hz, 1H) 6.63 (dd, J=7.1, 2.6 Hz, 1H) 6.74 (dd, J=7.5, 5.3 Hz, 1H) 6.85 (d, J=8.9 Hz, 2H) 7.62 (d, J=8.9 Hz, 2H) 7.66 (dd, J=7.5, 1.6 Hz, 1H) 7.94 (dd, J=5.3, 1.6 Hz, 1H)

HPLC retention time: 12 min (Column name: SUMICHIRAL OA-2500, 30 mmϕ×25 cm, Manufacturer: Sumika Chemical Analysis Service, Ltd., Mobile phase: 0.05 M ammonium acetate-methanol solution, Elution rate: 15 ml/min)

Example X-203

(R) and (S)-4-({[1-(2-Aminophenyl)-5-oxo-4,5-dihydro-1H-[1,2,4]triazol-3-yl]-(2-fluoro-3,5-dimethoxyphenyl)methyl}amino)benzamidine acetate

[Chemical Formula 787]

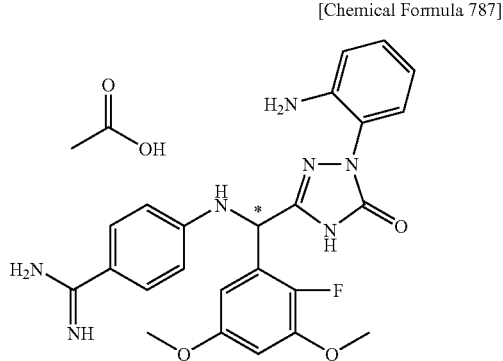

$^1$H-NMR (CD$_3$OD) δ 1.92 (s, 3H) 3.72 (s, 3H) 3.86 (s, 3H) 5.98 (s, 1H) 6.59 (dd, J=5.1, 2.6 Hz, 1H) 6.64 (dd, J=7.1, 2.6 Hz, 1H) 6.75 (td, J=7.8, 1.3 Hz, 1H) 6.85 (d, J=9.1 Hz, 2H) 6.88 (dd, J=7.8, 1.3 Hz, 1H) 7.11 (td, J=7.8, 1.3 Hz, 1H) 7.22 (dd, J=7.8, 1.3 Hz, 1H) 7.63 (d, J=9.1 Hz, 2H)

HPLC retention time: 7 min

Example X-204

4-{[[1-(3-Aminopyridin-2-yl)-5-oxo-4,5-dihydro-[1,2,4]triazol-3-yl]-(3-(4-fluoro-7-methoxy-2,3-dihydrobenzofuran-5-yl)methyl]amino)benzamidine trifluoroacetate

[Chemical Formula 788]

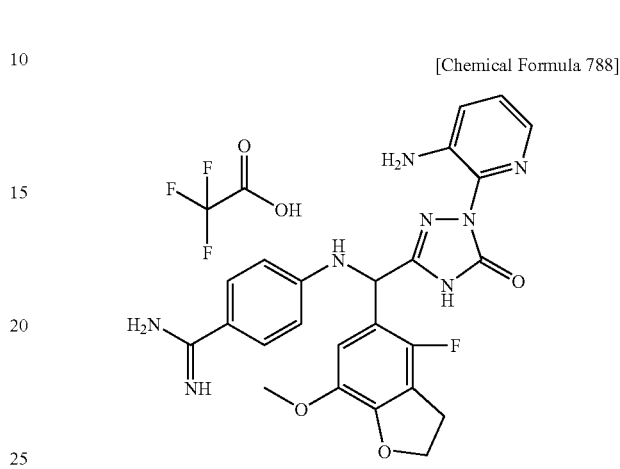

$^1$H-NMR (CD$_3$OD) δ 3.28 (t, J=8.9 Hz, 2H) 3.77 (s, 3H) 4.26 (t, J=8.9 Hz, 2H) 5.93 (s, 1H) 6.86 (d, J=8.7 Hz, 2H) 6.94 (d, J=5.4 Hz, 1H) 7.23 (dd, J=7.5, 4.1 Hz, 1H) 7.33 (d, J=7.5 Hz, 1H) 7.63 (d, J=8.7 Hz, 2H) 7.81 (d, J=4.1 Hz, 1H)

HPLC retention time: 8 min (Column name: SUMICHIRAL OA-2500, 20 mmϕ×25 cm, Manufacturer: Sumika Chemical Analysis Service, Ltd., Mobile phase: 0.05 M ammonium acetate-methanol solution, Elution rate: 10 ml/min)

Example X-205

4-({[1-(3-Aminopyridin-2-yl)-5-oxo-4,5-dihydro-[1,2,4]triazol-3-yl]-[5-ethyl-2-fluoro-3-(2-hydroxyethoxy)phenyl]methyl}amino)benzamidine acetate

[Chemical Formula 789]

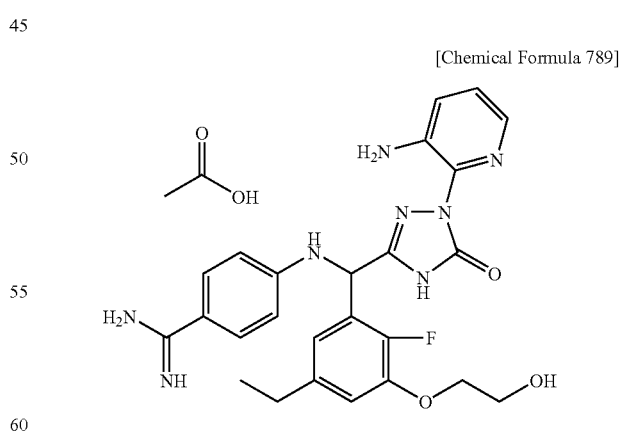

$^1$H-NMR (CD$_3$OD) δ 1.17 (t, J=7.4 Hz, 3H) 1.94 (s, 3H) 2.57 (q, J=7.4 Hz, 2H) 3.88 (t, J=4.4 Hz, 2H) 4.11 (t, J=4.4 Hz, 2H) 6.01 (s, 1H) 6.85 (d, J=9.1 Hz, 2H) 6.91 (d, J=6.2 Hz, 1H) 6.97 (d, J=7.6 Hz, 1H) 7.22 (dd, J=8.3, 4.5 Hz, 1H) 7.33 (dd, J=8.3, 1.5 Hz, 1H) 7.61 (d, J=9.1 Hz, 2H) 7.81 (dd, J=4.5, 1.5 Hz, 1H)

Example X-206

4-({(R) and (S)-[1-(3-Aminopyridin-2-yl)-5-oxo-4,5-dihydro-[1,2,4]triazol-3-yl]-[5-ethyl-2-fluoro-3-(2-hydroxyethoxy)phenyl]methyl}amino)benzamidine acetate

[Chemical Formula 790]

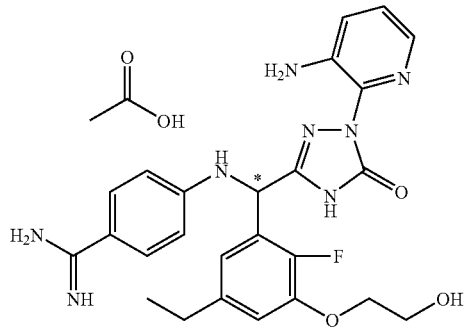

$^1$H-NMR (CD$_3$OD) δ 1.17 (t, J=7.4 Hz, 3H) 1.95 (s, 3H) 2.57 (q, J=7.4 Hz, 2H) 3.88 (t, J=4.4 Hz, 2H) 4.11 (t, J=4.4 Hz, 2H) 5.98 (s, 1H) 6.85 (d, J=9.1 Hz, 2H) 6.93-6.96 (m, 2H) 7.20 (dd, J=8.3, 4.5 Hz, 1H) 7.32 (dd, J=8.3, 1.5 Hz, 1H) 7.61 (d, J=9.1 Hz, 2H) 7.80 (dd, J=4.5, 1.5 Hz, 1H)

HPLC retention time: 12 min (Column name: SUMICHIRAL OA-2500, 30 mmφ×25 cm, Manufacturer: Sumika Chemical Analysis Service, Ltd., Mobile phase: 0.05 M ammonium acetate-methanol solution, Elution rate: 15 ml/min)

Example X-207

4-({(R) and (S)-[1-(3-Aminopyridin-2-yl)-5-oxo-4,5-dihydro-[1,2,4]triazol-3-yl]-[3-(2-hydroxyethoxy)-5-methoxyphenyl]methyl}amino)benzamidine acetate

[Chemical Formula 791]

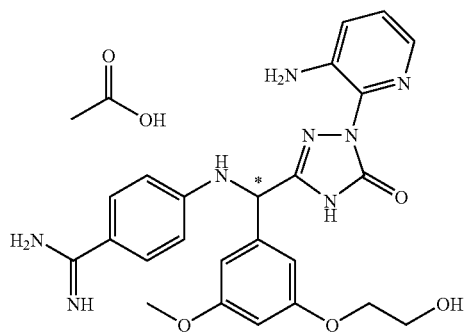

$^1$H-NMR (CD$_3$OD) δ 1.91 (s, 3H) 3.76 (s, 3H) 3.84 (t, J=4.9 Hz, 2H) 4.12 (t, J=4.9 Hz, 2H) 5.60 (s, 1H) 6.48 (t, J=1.7 Hz, 1H) 6.62-6.65 (m, 2H) 6.85 (d, J=9.1 Hz, 2H) 7.21 (dd, J=7.6, 4.7 Hz, 1H) 7.34 (dd, J=7.6, 1.7 Hz, 1H) 7.60 (d, J=9.1 Hz, 2H) 7.83 (dd, J=4.7, 1.7 Hz, 1H)

HPLC retention time: 11 min (Column name: SUMICHIRAL OA-2500, 30 mmφ×25 cm, Manufacturer: Sumika Chemical Analysis Service, Ltd., Mobile phase: 0.05 M ammonium acetate-methanol solution, Elution rate: 15 ml/min)

Example X-208

(R) and (S)-2-{3-[(4-Carbamimidoyl-3-fluorophenylamino)-(3-ethoxy-4-methoxyphenyl)methyl]-5-oxo-4,5-dihydro-[1,2,4]triazol-1-yl}benzoic acid

[Chemical Formula 792]

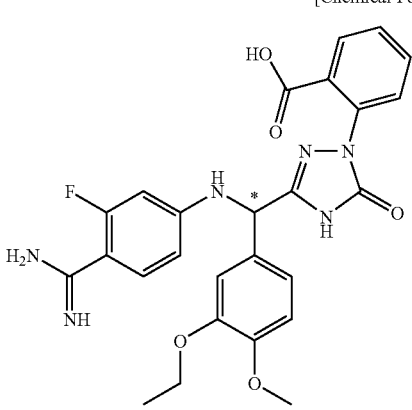

$^1$H-NMR (CD$_3$OD) δ 1.37 (t, J=7.2 Hz, 3H) 3.82 (s, 1H) 4.06 (q, J=7.2 Hz, 2H) 5.55 (s, 1H) 6.55 (dd, J=14.4, 2.4 Hz, 1H) 6.68 (dd, J=8.8, 2.4 Hz, 1H) 6.97 (d, J=8.4 Hz, 1H) 7.05-7.11 (m, 2H) 7.34-7.48 (m, 4H) 7.70 (dd, J=7.6, 1.6 Hz, 1H)

Mass spectrum (ESI) m/z: 521 (M+H)$^+$

HPLC retention time: 12 min

Example X-209

(R) and (S)-{3-[(4-Carbamimidoylphenylamino)-(5-oxo-1-pyrimidin-2-yl-4,5-dihydro-1H-[1,2,4]triazol-3-yl)methyl]2-fluoro-5-methoxyphenoxy}acetic acid methyl ester acetate

[Chemical Formula 793]

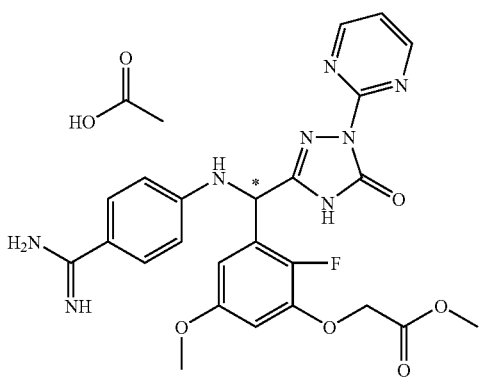

$^1$H-NMR (CD$_3$OD) δ 1.92 (s, 3H) 3.70 (s, 3H) 3.77 (s, 3H) 4.78 (s, 2H) 5.95 (s, 1H) 6.56 (dd, J=7.2, 3.2 Hz, 1H) 6.70 (m, 1H) 6.86 (d, J=8.8 Hz, 2H) 7.30 (t, J=4.8 Hz, 1H) 7.61 (d, J=8.8 Hz, 2H) 8.76 (d, J=4.8 Hz, 2H)

Mass spectrum (ESI) m/z: 523 (M+H)$^+$

HPLC retention time: 16 min (Column name: SUM-ICHIRAL OA-2500, 30 mmφ×25 cm, Manufacturer: Sumika Chemical Analysis Service, Ltd., Mobile phase: 0.05 M ammonium acetate-methanol solution, Elution rate: 25 ml/min)

Example X-210

4-(3-{(4-Carbamimidoylphenylamino)-[2-fluoro-3-(2-fluoroethoxy)-5-methoxyphenyl]methyl}-5-oxo-4,5-dihydro-1H-[1,2,4]triazol-1-yl)-thiazole-5-carboxylic acid

[Chemical Formula 794]

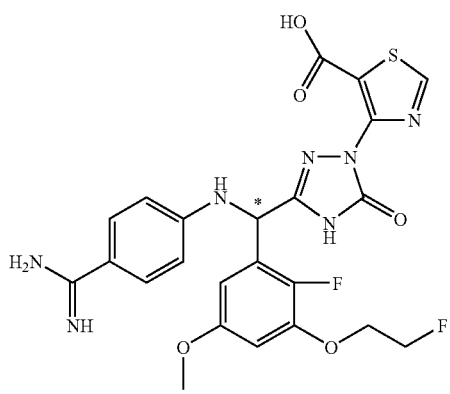

$^1$H-NMR (CD$_3$OD) δ 3.74 (s, 3H) 4.23 (m, 1H) 4.31 (m, 1H) 4.67 (m, 1H) 4.78 (m, 1H) 5.96 (s, 1H) 6.66 (m, 2H) 6.86 (d, J=9.2 Hz, 2H) 7.63 (d, J=9.2 Hz, 2H) 8.88 (s, 1H)

Mass spectrum (ESI) m/z: 546 (M+H)$^+$

HPLC retention time: 20 min (Column name: SUM-ICHIRAL OA-2500, 30 mmφ×25 cm, Manufacturer: Sumika Chemical Analysis Service, Ltd., Mobile phase: 0.5 mM ammonium acetate-methanol solution, Elution rate: 30 ml/min)

Example X-211

(R) and (S)-{3-[(4-Carbamimidoylphenylamino)-(5-oxo-1-pyridin-2-yl-4,5-dihydro-1H-[1,2,4]triazol-3-yl)methyl]-2-fluoro-5-methoxyphenoxy}acetic acid methyl ester acetate

[Chemical Formula 795]

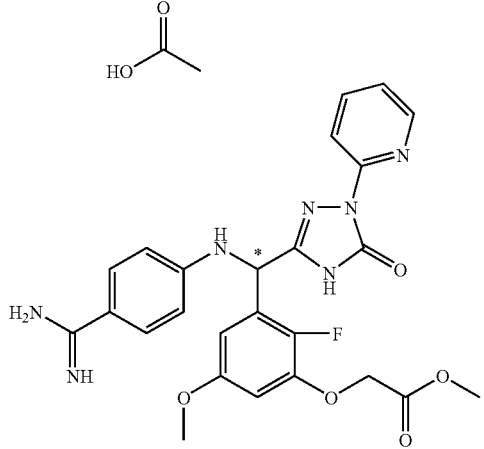

Example X-212

(R) and (S)-4-{[(3-Ethynyl-5-methoxyphenyl)-(5-oxo-1-pyrimidin-2-yl-4,5-dihydro-1H-[1,2,4]triazol-3-yl)methyl]amino}benzamidine acetate

[Chemical Formula 796]

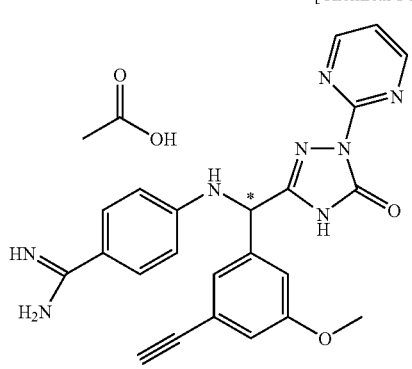

Example X-213

(R) and (S)-4-{[[3-(2-Hydroxyethoxy)-5-methoxyphenyl]-(5-oxo-1-pyrimidin-2-yl-4,5-dihydro-1H-[1,2,4]triazol-3-yl)methyl]amino}benzamidine acetate

[Chemical Formula 797]

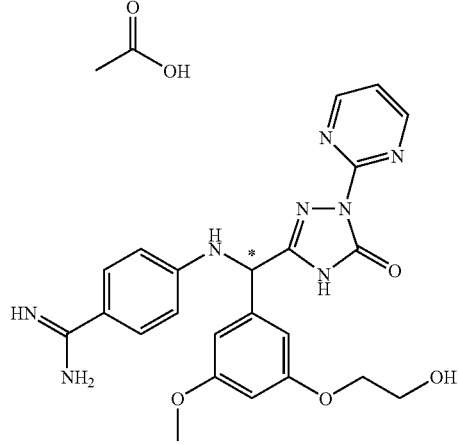

Example X-214

(R) and (S)-4-{[(8-Ethynyl-4H-benzo[1,3]dioxin-6-yl)-(5-oxo-1-pyrimidin-2-yl-4,5-dihydro-1H-[1,2,4]triazol-3-yl)methyl]amino}benzamidine acetate

[Chemical Formula 798]

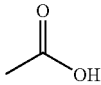

Example X-215

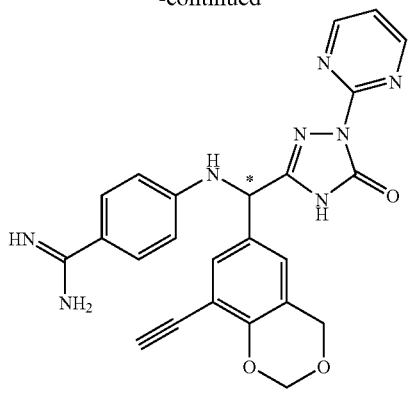

(R) and (S)-4-{[(8-Ethynylchroman-6-yl)-(5-oxo-1-pyrimidin-2-yl-4,5-dihydro-1H-[1,2,4]triazol-3-yl)methyl]amino}benzamidine acetate

[Chemical Formula 799]

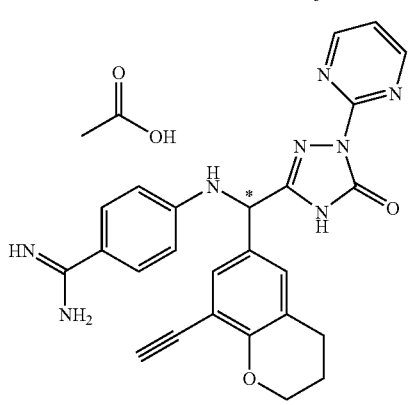

Example X-216

2-{3-[(4-Carbamimidoylphenylamino)-(5,6-dimethoxypyridin-3-yl)methyl]-5-oxo-4,5-dihydro-[1,2,4]triazol-1-yl}benzoic acid acetate

[Chemical Formula 800]

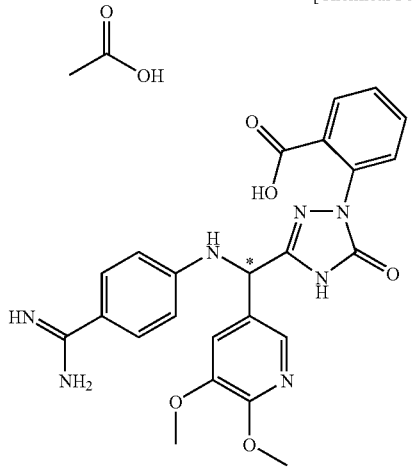

Example X-217

2-{3-[(4-Carbamimidoylphenyl-3-fluorophenylamino)-(5,6-dimethoxypyridin-3-yl)methyl]-5-oxo-4,5-dihydro-[1,2,4]triazol-1-yl}benzoic acid acetate

[Chemical Formula 801]

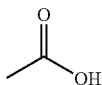

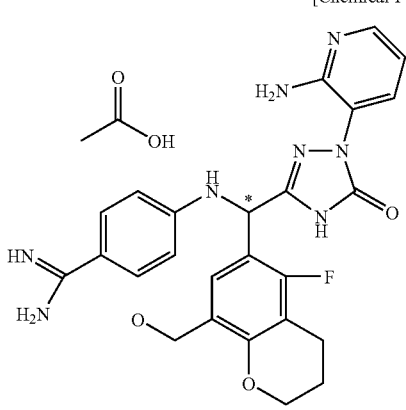

Example X-218

(R) and (S)-4-{[[1-(2-Aminopyridin-3-yl)-5-oxo-4,5-dihydro-1H-[1,2,4]triazol-3-yl]-(5-fluoro-8-methoxychroman-6-yl)methyl]amino}benzamidine acetate

[Chemical Formula 802]

Example X-219

(R) and (S)-2-Fluoro-4-{[(5-fluoro-8-methoxychroman-6-yl)-(5-oxo-1-pyrimidin-2-yl-4,5-dihydro-1H-[1,2,4]triazol-3-yl)methyl]amino}benzamidine acetate

[Chemical Formula 803]

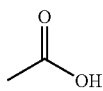

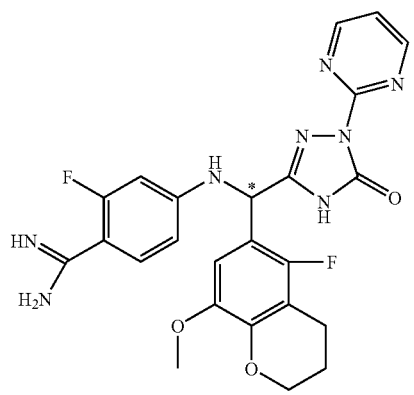

Example X-220

4-({[2-Fluoro-5-methoxy-3-(2-methoxyethoxy)phenyl]-[1-(3-hydroxypyrazin-2-yl)-5-oxo-4,5-dihydro-1H-[1,2,4]triazol-3-yl]methyl}amino)benzamidine acetate

[Chemical Formula 804]

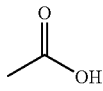

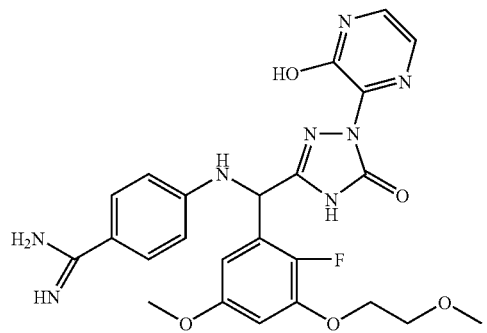

Example X-221

5-(3-{(4-Carbamimidoylphenylamino)-[2-fluoro-5-methoxy-3-(2-methoxyethoxy)phenyl]methyl}-5-oxo-4,5-dihydro-[1,2,4]triazol-1-yl)-1H-pyrazole-4-carboxylic acid ethyl ester acetate

[Chemical Formula 805]

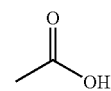

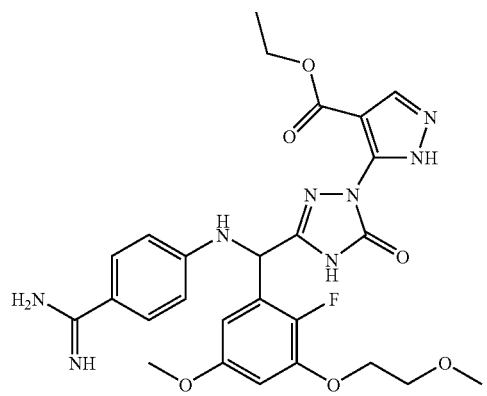

Example X-222

4-({[1-(3-Aminopyridin-2-yl)-5-oxo-4,5-dihydro-1H-[1,2,4]triazol-3-yl]-[2-fluoro-3-(3-hydroxypropoxy)-5-methoxyphenyl]methyl}amino)benzamidine acetate

[Chemical Formula 806]

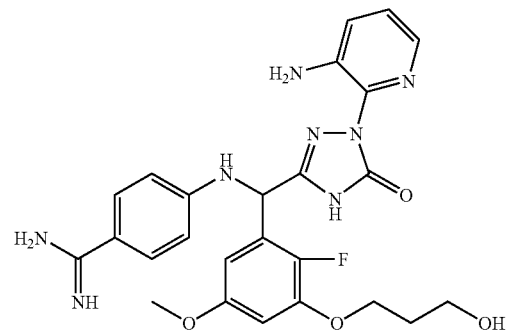

Example X-223

5-(3-{(4-Carbamimidoylphenylamino)-[2-fluoro-3-(2-hydroxyethoxy)-5-methoxyphenyl]methyl}-5-oxo-4,5-dihydro-[1,2,4]triazol-1-yl)-1H-pyrazole-4-carboxylic acid

[Chemical Formula 807]

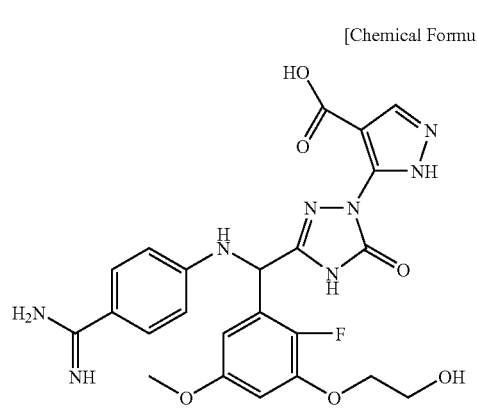

Example X-224

(R) and (S)-4-{[[2-Fluoro-3-(3-hydroxypropyl)-5-methoxyphenyl]-(5-oxo-1-pyrimidin-2-yl-4,5-dihydro-1H-[1,2,4]triazol-3-yl)methyl]amino}benzamidine acetate

[Chemical Formula 808]

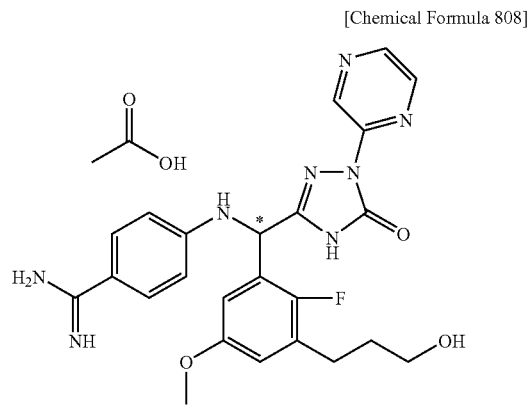

$^1$H-NMR (CD$_3$OD) δ 1.80-1.88 (m, 2H) 1.91 (s, 3H) 2.71 (t, J=6.4 Hz, 2H) 3.57 (t, J=6.4 Hz, 2H) 3.70 (s, 3H) 5.94 (s, 1H) 6.76-6.82 (m, 1H) 6.85 (d, J=8.8 Hz, 2H) 6.90-6.96 (m, 1H) 7.30 (t, J=4.8 Hz, 1H) 7.61 (d, J=8.8 Hz, 2H) 8.76 (d, J=4.8 Hz, 2H)

HPLC retention time: 7 min (Column name: SUMICHIRAL OA-2500, 4.6 mmφ×25 cm, Manufacturer: Sumika Chemical Analysis Service, Ltd., Mobile phase: 0.05 M ammonium acetate-methanol solution, Elution rate: 1 ml/min)

Example X-225

(R) and (S)-2-{3-[(4-Carbamimidoylphenyl-3-fluorophenylamino)-(8-methoxy-4H-benzo[1,3]dioxin-6-yl)methyl]-5-oxo-4,5-dihydro[1,2,4]triazol-1-yl}benzoic acid

[Chemical Formula 809]

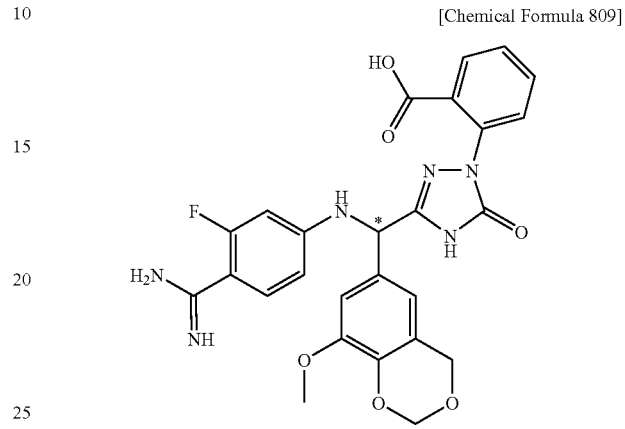

$^1$H-NMR (CD$_3$OD) δ 3.85 (s, 3H) 4.84-4.92 (m, 2H) 5.24 (s, 2H) 5.56 (s, 1H) 6.59 (d, J=14.4 Hz, 1H) 6.70 (d, J=8.8 Hz, 1H) 6.81 (s, 1H) 7.03 (s, 1H) 7.35-7.50 (m, 4H) 7.72 (d, J=8.0 Hz, 1H)

HPLC retention time: 27 min (Column name: SUMICHIRAL OA-2500, 30 mmφ×25 cm, Manufacturer: Sumika Chemical Analysis Service, Ltd., Mobile phase: 0.5 mM ammonium acetate-methanol solution, Elution rate: 20 ml/min)

Example X-226

(R) and (S)-2-Fluoro-4-{[(9-methoxy-3,4-dihydro-2H-benzo[b][1,4]dioxepin-7-yl)-(5-oxo-1-pyrimidin-2-yl-4,5-dihydro-1H-[1,2,4]triazol-3-yl)methyl]amino}benzamidine acetate

[Chemical Formula 810]

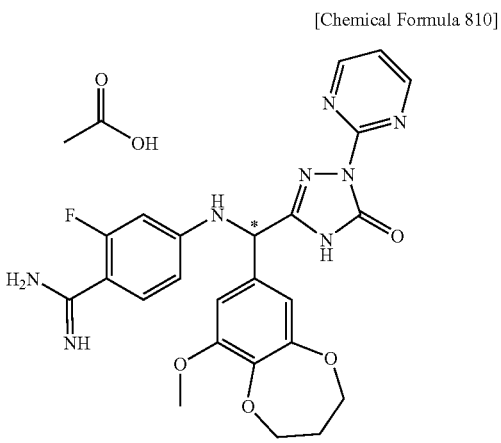

$^1$H-NMR (CD$_3$OD) δ 1.93 (s, 3H) 2.10-2.15 (m, 2H) 3.77 (s, 3H) 4.11 (t, J=4.8 Hz, 4H) 5.57 (s, 1H) 6.58 (dd, J=2.0, 14.4 Hz, 1H) 6.67 (dd, J=2.0, 8.8 Hz, 1H) 6.78 (d, J=2.0 Hz, 1H) 6.88 (d, J=2.0 Hz, 1H) 7.30 (t, J=4.8 Hz, 1H) 7.43 (t, J=8.4 Hz, 1H) 8.75 (t, J=4.8 Hz, 2H)

HPLC retention time: 26 min (Column name: SUMICHIRAL OA-2500, 30 mmφ×25 cm, Manufacturer: Sumika Chemical Analysis Service, Ltd., Mobile phase: 0.05 M ammonium acetate-methanol solution, Elution rate: 20 ml/min)

Example X-227

(R) and (S)-4-{[(9-Methoxy-2,3,4,5-tetrahydro-benzo[b]oxepin-7-yl)-(5-oxo-1-pyrimidin-2-yl-4,5-dihydro-1H-[1,2,4]triazol-3-yl)methyl]amino}benzamidine acetate

[Chemical Formula 811]

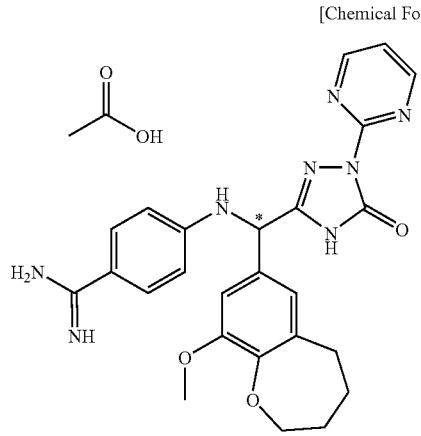

$^1$H-NMR (CD$_3$OD) δ 1.62-1.68 (m, 2H) 1.88-1.96 (m, 2H) 1.91 (s, 3H) 2.72-2.78 (m, 2H) 3.76 (s, 3H) 3.90 (t, J=4.8 Hz, 2H) 5.58 (s, 1H) 6.85 (d, J=8.8 Hz, 2H) 6.94 (d, J=2.0 Hz, 1H) 7.06 (d, J=2.0 Hz, 1H) 7.29 (t, J=4.8 Hz, 1H) 7.59 (d, J=8.8 Hz, 2H) 8.76 (d, J=4.8 Hz, 2H)

Example X-228

(R) and (S)-4-{[[2-Fluoro-3-((S)-2-hydroxypropoxy)-5-methoxyphenyl]-(5-oxo-1-pyrimidin-2-yl-4,5-dihydro-1H-[1,2,4]triazol-3-yl)methyl]amino}benzamidine acetate

[Chemical Formula 812]

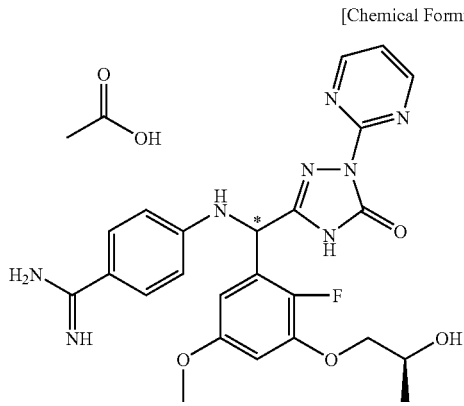

$^1$H-NMR (CD$_3$OD) δ 1.25 (d, J=6.8 Hz, 3H) 1.92 (s, 3H) 3.68 (s, 3H) 3.89 (d, J=5.6 Hz, 2H) 4.06-4.14 (m, 1H) 5.96 (s, 1H) 6.57-6.64 (m, 2H) 6.84 (d, J=8.8 Hz, 2H) 7.30 (t, J=4.8 Hz, 1H) 7.59 (d, J=8.8 Hz, 2H) 8.74 (d, J=4.8 Hz, 2H)

Example X-229

(R) and (S)-2-{3-[(4-Carbamimidoylphenylamino)-(5-fluoro-8-methoxychroman-6-yl)methyl]-5-oxo-4,5-dihydro-[1,2,4]triazol-1-yl}-benzamide acetate

[Chemical Formula 813]

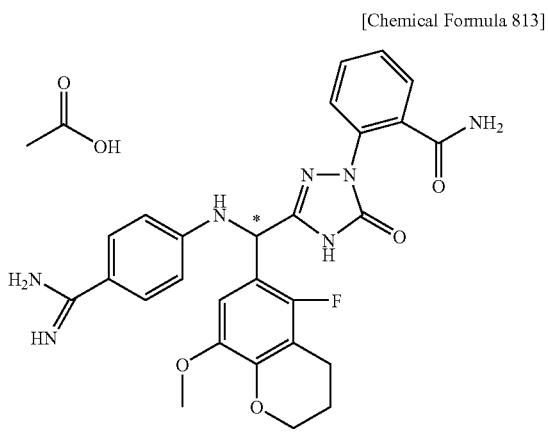

Example X-230

(R) and (S)-4-({(3,4-Dimethoxyphenyl-[1-(3-fluoropyridin-2-yl)-5-oxo-4,5-dihydro-1H-[1,2,4]triazol-3-yl]methyl}amino)-2-fluorobenzamidine acetate

[Chemical Formula 814]

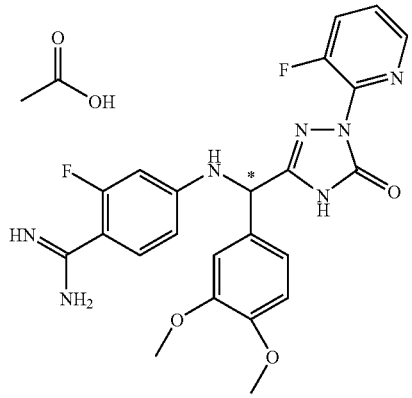

Example X-231

(R) and (S)-2-Fluoro-4-{[[1-(3-fluoropyridin-2-yl)-5-oxo-4,5-dihydro-1H-[1,2,4]triazol-3-yl]-(8-methoxy-4H-benzo[1,3]dioxin-6-yl)methyl]amino}benzamidine acetate

[Chemical Formula 815]

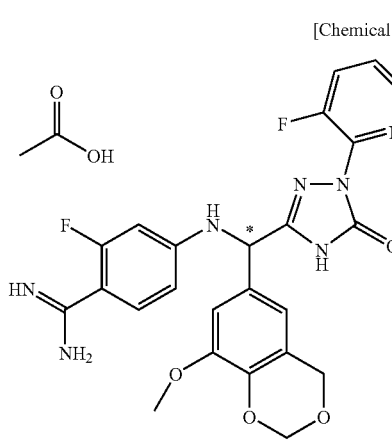

Example X-232

4-{[(3-Ethynyl-5-methoxyphenyl)-(5-oxo-1-pyrimidin-2-yl-4,5-dihydro-1H-[1,2,4]triazol-3-yl)methyl]amino}benzamidine acetate

[Chemical Formula 816]

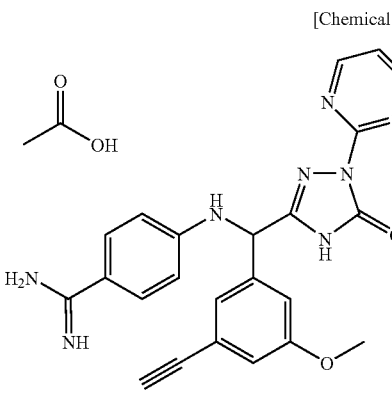

$^1$H-NMR (CD$_3$OD) δ 1.91 (s, 3H) 3.47 (s, 1H) 3.77 (s, 3H) 5.60 (s, 1H) 6.85 (d, J=8.0 Hz, 2H) 6.93 (s, 1H) 7.15 (s, 1H) 7.42-7.63 (m, 2H) 7.60 (d, J=8.0 Hz, 2H) 8.76 (d, J=3.6 Hz, 2H)

Example X-233

(R) and (S)-4-{[[3-Ethynyl-5-(2-fluoroethoxy)phenyl]-(5-oxo-1-pyrimidin-2-yl-4,5-dihydro-1H-[1,2,4]triazol-3-yl)methyl]amino}benzamidine acetate

[Chemical Formula 817]

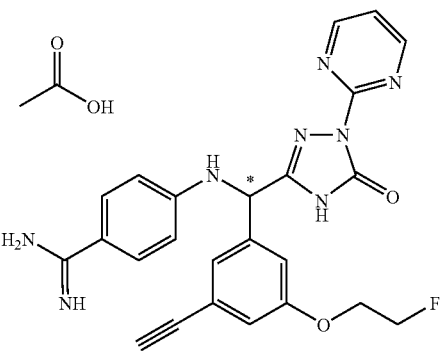

$^1$H-NMR (CD$_3$OD) δ 1.92 (s, 3H) 3.49 (s, 1H) 4.15-4.18 (m, 1H) 4.23-4.25 (m, 1H) 4.62 (t, J=4.0 Hz, 1H) 4.74 (t, J=4.0 Hz, 1H) 5.61 (s, 1H) 6.85 (d, J=8.8 Hz, 2H) 6.98 (q, J=1.2 Hz, 1H) 7.19 (t, J=2.0 Hz, 1H) 7.27-7.30 (m, 2H) 7.60 (d, J=8.8 Hz, 2H) 8.76 (d, J=5.2 Hz, 2H) HPLC retention time: 13 min

Example X-234

(R) and (S)-4-{[[3-(2-Methoxyethoxy)-5-vinylphenyl]-(5-oxo-1-pyrimidin-2-yl-4,5-dihydro-1H-[1,2,4]triazol-3-yl)methyl]amino}benzamidine acetate

[Chemical Formula 818]

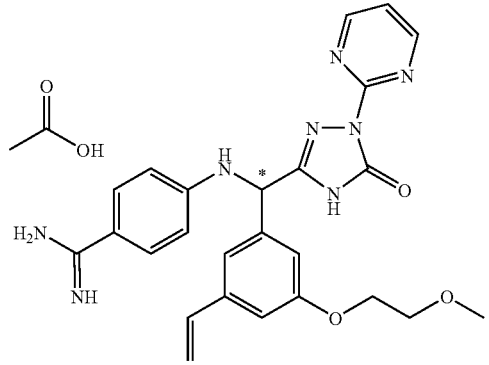

$^1$H-NMR (CD$_3$OD) δ 1.91 (s, 3H) 3.38 (s, 3H) 3.67-3.75 (m, 2H) 4.11 (dd, J=3.2, 6.0 Hz, 2H) 5.23 (d, J=10.8 Hz, 1H) 5.61 (s, 1H) 5.78 (d, J=17.6 Hz, 1H) 6.68 (dd, J=10.8, 17.6 Hz, 1H) 6.86 (d, J=8.8 Hz, 2H) 6.95 (s, 1H) 7.05 (s, 1H) 7.24 (s, 1H) 7.29 (t, J=4.4 Hz, 1H) 7.59 (t, J=8.8 Hz, 2H) 8.76 (d, J=4.4 Hz, 2H)

HPLC retention time: 13 min

Example X-235

(R) and (S)-4-{[(2-Fluoro-3-hydroxy-5-methoxyphenyl)-(5-oxo-1-pyrimidin-2-yl-4,5-dihydro-1H-[1,2,4]triazol-3-yl)methyl]amino}benzamidine acetate

[Chemical Formula 819]

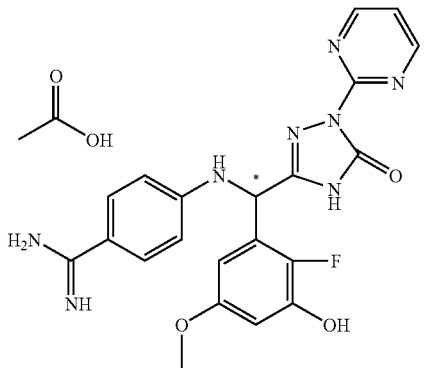

$^1$H-NMR (CD$_3$OD) δ 1.92 (s, 3H) 3.67 (s, 3H) 5.93 (s, 1H) 6.45 (dd, J=3.2, 7.2 Hz, 1H) 6.52 (dd, J=3.2, 5.2 Hz, 1H) 6.85 (d, J=8.8 Hz, 2H) 7.31 (t, J=4.8 Hz, 1H) 7.61 (d, J=8.8 Hz, 2H) 8.76 (d, J=4.8 Hz, 2H)

HPLC retention time: 11 min (Column name: SUMICHIRAL OA-2500, 30 mmφ×25 cm, Manufacturer: Sumika Chemical Analysis Service, Ltd., Mobile phase: 0.05 M ammonium acetate-methanol solution, Elution rate: 40 ml/min)

Example X-236

(R) and (S)-4-{[(8-Ethynyl-2,3-dihydrobenzo[1,4]dioxin-6-yl)-(5-oxo-1-pyrimidin-2-yl-4,5-dihydro-1H-[1,2,4]triazol-3-yl)methyl]amino}benzamidine acetate

[Chemical Formula 820]

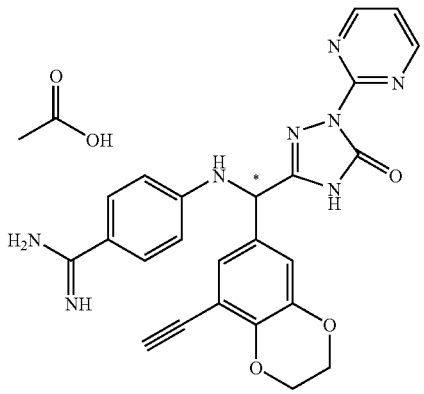

$^1$H-NMR (CD$_3$OD) δ 1.92 (s, 3H) 3.62 (s, 1H) 4.21-4.24 (m, 2H) 4.26-4.30 (m, 2H) 5.53 (s, 1H) 6.84 (d, J=8.8 Hz, 2H) 7.05 (d, J=2.0 Hz, 1H) 7.17 (d, J=2.0 Hz, 1H) 7.31 (t, J=4.8 Hz, 1H) 7.60 (d, J=8.8 Hz, 2H) 8.77 (d, J=4.8 Hz, 2H)

HPLC retention time: 10 min (Column name: SUMICHIRAL OA-2500, 30 mmφ×25 cm, Manufacturer: Sumika Chemical Analysis Service, Ltd., Mobile phase: 0.05 M ammonium acetate-methanol solution, Elution rate: 40 ml/min)

Example X-237

(R) and (S)-4-{[[3-Ethyl-5-(2-hydroxyethoxy)phenyl]-(5-oxo-1-pyrimidin-2-yl-4,5-dihydro-1H-[1,2,4]triazol-3-yl)methyl]amino}benzamidine acetate

[Chemical Formula 821]

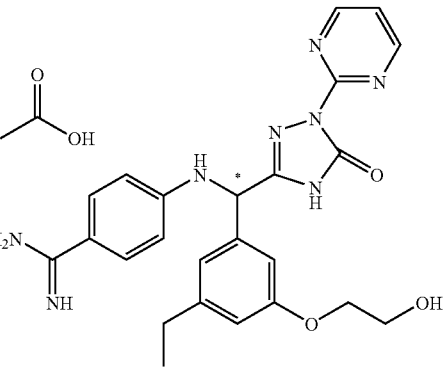

$^1$H-NMR (CD$_3$OD) δ 1.20 (t, J=7.6 Hz, 3H) 1.91 (s, 3H) 2.61 (q, J=7.6 Hz, 2H) 3.83 (t, J=4.8 Hz, 2H) 4.03 (t, J=4.8 Hz, 2H) 5.58 (s, 1H) 6.76 (s, 1H) 6.86 (d, J=8.8 Hz, 2H) 6.97 (d, J=2.0 Hz, 1H) 7.00 (s, 1H) 7.30 (t, J=4.8 Hz, 1H) 7.60 (d, J=8.8 Hz, 2H) 8.77 (d, J=4.8 Hz, 2H)

HPLC retention time: 6 min (Column name: SUMICHIRAL OA-2500, 30 mmφ×25 cm, Manufacturer: Sumika Chemical Analysis Service, Ltd., Mobile phase: 0.05 M ammonium acetate-methanol solution, Elution rate: 40 ml/min)

Example X-238

(R) and (S)-4-{[[5-Ethoxy-2-fluoro-3-(3-hydroxypropoxy)phenyl]-(5-oxo-1-pyrimidin-2-yl-4,5-dihydro-1H-[1,2,4]triazol-3-yl)methyl]amino}benzamidine acetate

[Chemical Formula 822]

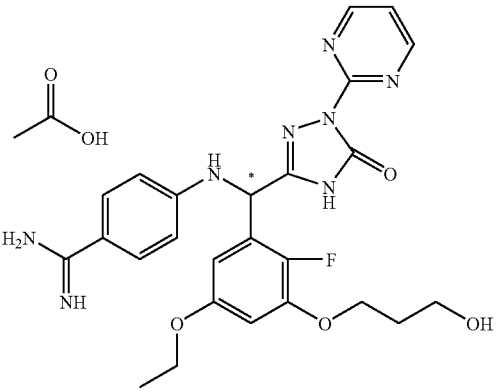

$^1$H-NMR (CD$_3$OD) δ 1.30 (t, J=7.2 Hz, 3H) 1.94 (s, 3H) 1.99 (Sept, J=6.0 Hz, 2H) 3.74 (t, J=6.0 Hz, 2H) 3.90-3.97 (m, 2H) 4.12 (t, J=6.0 Hz, 2H) 5.98 (s, 1H) 6.58 (dd, J=2.4, 4.4 Hz, 1H) 6.63 (dd, J=2.4, 6.8 Hz, 1H) 6.86 (d, J=8.8 Hz, 2H) 7.35 (t, J=4.8 Hz, 1H) 7.63 (d, J=8.8 Hz, 2H) 8.78 (d, J=4.8 Hz, 2H)

HPLC retention time: 9 min (Column name: SUMICHIRAL OA-2500, 30 mmφ×25 cm, Manufacturer: Sumika Chemical Analysis Service, Ltd., Mobile phase: 0.05 M ammonium acetate-methanol solution, Elution rate: 30 ml/min)

Example X-239

3-(3-{(R) and (S)-(4-Carbamimidoylphenylamino)-[4-(2-hydroxyethoxy)-3-methoxyphenyl]methyl}-5-oxo-4,5-dihydro-[1,2,4]triazol-1-yl)thiophene-2-carboxylic acid

[Chemical Formula 823]

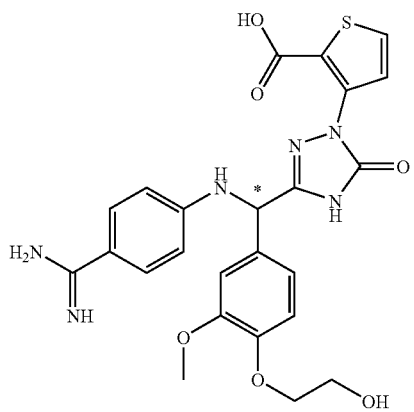

$^1$H-NMR (CD$_3$OD) δ 3.84-3.89 (m, 5H) 4.02-4.08 (m, 2H) 4.59 (br.s, 1H) 5.56 (s, 1H) 6.86 (d, J=8.8 Hz, 2H) 6.99 (d, J=8.0 Hz, 1H) 7.06-7.08 (m, 2H) 7.17 (s, 1H) 7.42 (d, J=4.8 Hz, 1H) 7.61 (d, J=8.8 Hz, 2H)

HPLC retention time: 11 min (Column name: SUMICHIRAL OA-2500, 30 mmφ×25 cm, Manufacturer: Sumika Chemical Analysis Service, Ltd., Mobile phase: 0.05 M ammonium acetate-methanol solution, Elution rate: 30 ml/min)

Example X-240

4-{[(R) and (S)-[4-(2-Hydroxyethoxy)-3-methoxyphenyl]-(5-oxo-1-pyrimidin-2-yl-4,5-dihydro-1H-[1,2,4]triazol-3-yl)methyl]amino}benzamidine acetate

[Chemical Formula 824]

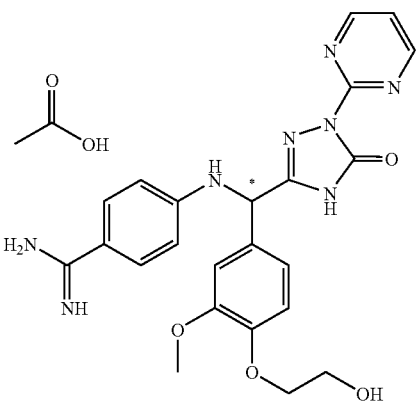

$^1$H-NMR (CD$_3$OD) δ 1.92 (s, 3H) 3.84 (s, 3H) 3.85 (t, J=4.8 Hz, 2H) 4.03 (t, J=4.8 Hz, 2H) 5.62 (s, 1H) 6.86 (d, J=8.4 Hz, 2H) 6.96 (d, J=8.4 Hz, 1H) 7.09 (d, J=8.4 Hz, 1H) 7.19 (s, 1H) 7.32 (t, J=4.8 Hz, 1H) 7.60 (d, J=8.4 Hz, 2H) 8.78 (d, J=4.8 Hz, 2H)

HPLC retention time: 8 min (Column name: SUMICHIRAL OA-2500, 30 mmφ×25 cm, Manufacturer: Sumika Chemical Analysis Service, Ltd., Mobile phase: 0.05 M ammonium acetate-methanol solution, Elution rate: 40 ml/min)

Example X-241

4-{[(R) and (S)-[4-(3-Hydroxypropoxy)-3-methoxyphenyl]-(5-oxo-1-pyrimidin-2-yl-4,5-dihydro-1H-[1,2,4]triazol-3-yl)methyl]amino}benzamidine acetate

[Chemical Formula 825]

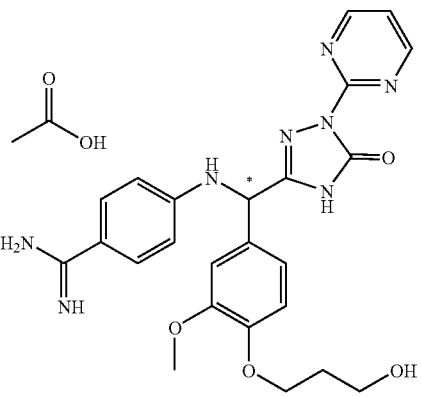

$^1$H-NMR (CD$_3$OD) δ 1.91 (s, 3H) 1.94-2.00 (m, 2H) 3.73 (t, J=6.4 Hz, 2H) 3.82 (s, 3H) 4.09 (t, J=6.4 Hz, 2H) 5.58 (s, 1H) 6.86 (d, J=8.8 Hz, 2H) 6.95 (d, J=8.4 Hz, 1H) 7.08 (d, J=8.4 Hz, 1H) 7.17 (s, 1H) 7.30 (t, 4.8 Hz, 1H) 7.60 (d, J=8.8 Hz, 2H) 8.77 (d, J=4.8 Hz, 2H)

HPLC retention time: 7 min (Column name: SUMICHIRAL OA-2500, 30 mmφ×25 cm, Manufacturer: Sumika Chemical Analysis Service, Ltd., Mobile phase: 0.05 M ammonium acetate-methanol solution, Elution rate: 40 ml/min)

Example X-242

4-(3-{(R) and (S)-(4-Carbamimidoylphenylamino)-[2-fluoro-4-(2-hydroxyethoxy)-5-methoxyphenyl]methyl}-5-oxo-4,5-dihydro-[1,2,4]triazol-1-yl)thiazole-5-carboxylic acid

[Chemical Formula 826]

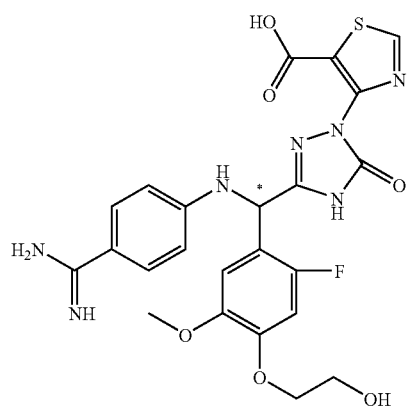

$^1$H-NMR (CD$_3$OD) δ 3.80-3.84 (m, 2H) 3.84 (s, 3H) 3.96-4.09 (m, 2H) 5.89 (s, 1H) 6.83-6.88 (m, 3H) 7.11 (d, J=7.2 Hz, 1H) 7.62 (d, J=8.4 Hz, 2H) 8.88 (s, 1H)

HPLC retention time: 17 min (Column name: SUM-ICHIRAL OA-2500, 30 mmφ×25 cm, Manufacturer: Sumika Chemical Analysis Service, Ltd., Mobile phase: 0.5 mM ammonium acetate-methanol solution, Elution rate: 30 ml/min)

Example X-243

4-{[(R) and (S)-[3-(2-Dimethylaminoethoxy)-5-methylphenyl]-(5-oxo-1-pyrimidin-2-yl-4,5-dihydro-1H-[1,2,4]triazol-3-yl)methyl]amino}benzamidine diacetate

[Chemical Formula 827]

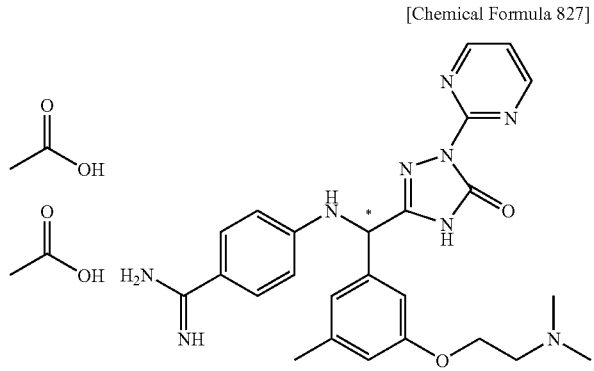

Example X-244

4-{[(R) and (S)-[3-Methyl-5-(1-methylpyrrolidin-3-yloxy)phenyl]-(5-oxo-1-pyrimidin-2-yl-4,5-dihydro-1H-[1,2,4]triazol-3-yl)methyl]amino}benzamidine diacetate

[Chemical Formula 828]

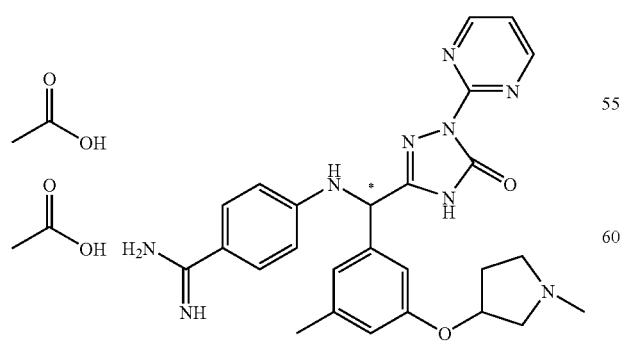

Example X-245

4-{[(R) and (S)-(2-Fluoro-5-methoxy-3-methylphenyl)-(5-oxo-1-pyrimidin-2-yl-4,5-dihydro-1H-[1,2,4]triazol-3-yl)methyl]amino}benzamidine acetate

[Chemical Formula 829]

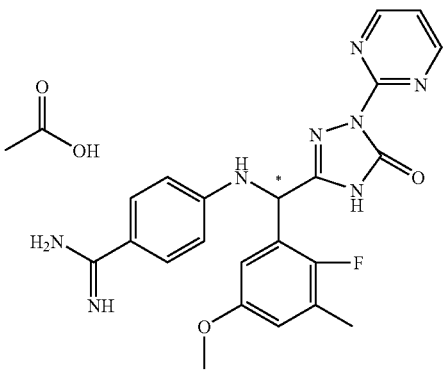

Example X-246

3-{3-[(R) and (S)-(4-Carbamimidoylphenyl-2-fluorophenylamino)-(2-fluoro-4,5-dimethoxyphenyl)methyl]-5-oxo-4,5-dihydro-[1,2,4]triazol-1-yl}thiophene-2-carboxylic acid

[Chemical Formula 830]

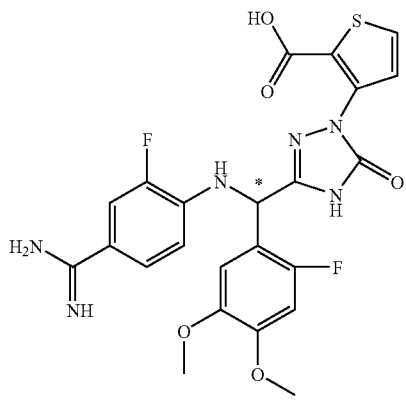

Example X-247

5-{3-[(4-Carbamimidoylphenylamino)-(5-fluoro-8-methoxy-2,3-dihydrobenzo[1,4]dioxin-6-yl)methyl]-5-oxo-4,5-dihydro-[1,2,4]triazol-1-yl}-1H-pyrazole-4-carboxylic acid trifluoroacetate

[Chemical Formula 831]

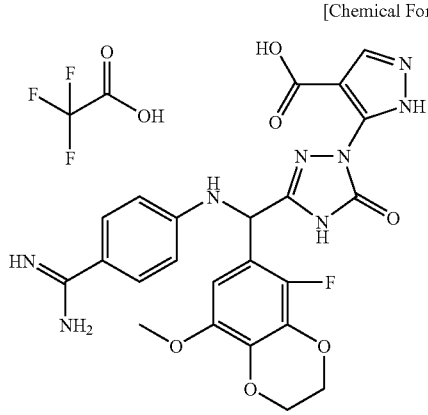

$^1$H-NMR (CD$_3$OD) δ 3.77 (s, 3H) 4.30 (s, 4H) 5.94 (s, 1H) 6.63 (d, J=6.0 Hz, 1H) 6.85 (d, J=8.5 Hz, 2H) 7.62 (d, J=8.5 Hz, 2H) 8.11 (s, 1H)

Example X-248

(R) and (S)-3-{3-[(4-Carbamimidoylphenylamino)-(2-fluoro-3,5-dimethoxyphenyl)methyl]-5-oxo-4,5-dihydro-[1,2,4]triazol-1-yl}thiophene-2-carboxylic acid

[Chemical Formula 832]

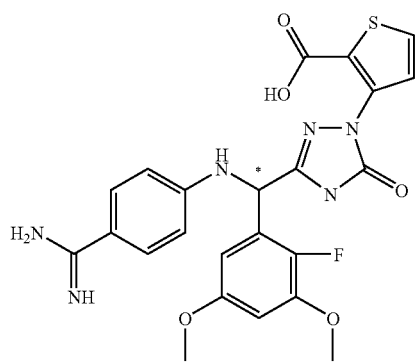

Example X-249

4-{[(R) and (S)-[2-(2-Hydroxyethoxy)-6-methylpyridin-4-yl]-(5-oxo-1-pyrimidin-2-yl-4,5-dihydro-1H-[1,2,4]triazol-3-yl)methyl]amino}benzamidine acetate

[Chemical Formula 833]

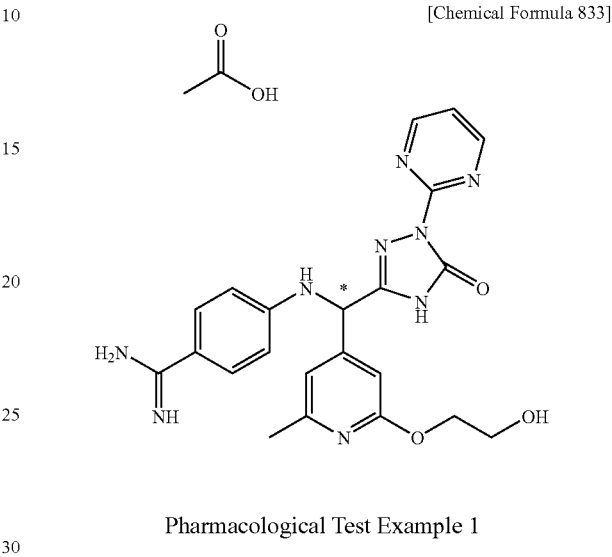

Pharmacological Test Example 1

[Inhibitory Activity Against Clotting Factor VIIa]

(1) Method

Dimethylsulfoxide (DMSO) solutions were prepared with compounds of the invention at concentration of 10 mmol/L (10 mmol/L compound solutions).

One packet of tris-hydroxymethylaminomethane-preset (hereinafter referred to as "Tris preset") (Product of Sigma Corp., Catalog No. T8293), 8.8 g of sodium chloride (NaCl) and 1 g of bovine serum albumin (hereinafter abbreviated as "BSA") were dissolved in 1 L of water to prepare a Tris-BSA buffer (100 mmol/L Tris, 0.15 mol/L NaCl, 0.1% BSA, pH 7.4).

This Tris-BSA buffer (180 μL) was added to the aforementioned 10 mmol/L compound solution (20 μL). A 10-fold dilution series was prepared for this mixture using the aforementioned Tris-BSA buffer, and solutions with the compound at concentrations of 1.0 mmol/L, 100, 10, 1, 0.1, 0.01 and 0.001 μmol/L were prepared (1.0 mmol-0.001 μmol/L compound solutions). As a control, a solution was prepared by 10-fold dilution of DMSO with the Tris-BSA buffer (hereinafter referred to as "control 10% solution").

After dissolving one packet of Tris preset, NaCl (8.8 g) and BSA (1 g) in water (about 900 mL), there were added 1 mol/L aqueous calcium chloride (CaCl$_2$) (15 mL) and 1 mg/mL aqueous cephalin (30 mL), and the total volume was brought to 1 L by adding water. To this solution there was added a human tissue factor (hereinafter, "TF") sample (product of Calbiochem, Catalog No. 612151) (450 μg) to a TF sample concentration of 10 nmol/L, and then a human clotting factor VIIa (hereinafter, "Factor VIIa") purified sample (product of Enzyme Research Laboratories, Catalog No. HFVIIa) (250 μg) was added to a Factor VIIa purified sample concentration of 5 nmol/L, to prepare an enzyme solution (100 mmol/L Tris-HCl, 0.15 mol/L NaCl, 15 mmol/L CaCl$_2$, 30 μg/mL cephalin, 1 mg/mL BSA, 10 nmol/L TF, 5 nmol/L Factor VIIa).

To 110 μL of this enzyme solution there was added 15 μL of each of the 1.0 mmol-0.001 μmol/L compound solutions, and then 25 μL of a 1.0 mmol/L synthetic chromogenic substrate solution (Spectrozyme FVIIa, product of American Diagnostica, Catalog No. 217L) was added and the mixture was allowed to stand at room temperature for 40 minutes. Next, the amount of 4-nitroanilide released into the solution was quantitated by spectrophotometry (405 nm).

A control measurement was conducted in the same manner, using the control 10% solution instead of the compound solution.

This measurement yielded the enzyme reaction inhibition in the presence of 100 μmol/L to 0.1 nmol/L of each compound of the invention.

The enzyme reaction inhibition at each compound concentration was subjected to non-linear regression analysis, and the IC50 value for inhibitory activity of each compound against clotting factor VIIa was calculated.

(2) Results

Tables 1 to 4 show the IC50 values (IC50 FVIIa (μM)) for inhibitory activity of each compound against clotting factor VIIa.

TABLE 1

|  | IC50 of FVIIa (μM) |
|---|---|
| Example 1 | 0.0075 |
| Example 2 | 0.0094 |
| Example 3 | 0.0048 |
| Example 4 | 0.003 |
| Example 5 | 0.0049 |
| Example 6 | 0.0103 |
| Example 7 | 0.0099 |
| Example 8 | 0.0226 |
| Example 9 | 0.0098 |
| Example 10 | 0.0211 |
| Example 11 | 0.0297 |
| Example 12 | 0.0338 |
| Example 13 | 0.0241 |
| Example 14 | 0.0059 |
| Example 15 | 0.0134 |
| Example 16 | 0.0115 |
| Example 17 | 0.0075 |
| Example 18 | 0.0155 |
| Example 19 | 0.0128 |
| Example 20 | 0.0097 |
| Example 21 | 0.0106 |
| Example 22 | 0.0083 |
| Example 23 | 0.0239 |
| Example 24 | 0.0074 |
| Example 25 | 0.0151 |
| Example 26 | 0.0054 |
| Example 27 | 0.0031 |
| Example 28 | 0.0089 |
| Example 29 | 0.0027 |
| Example 30 | 0.0039 |
| Example 31 | 0.0071 |
| Example 32 | 0.0116 |
| Example 33 | 0.0067 |
| Example 34 | 0.003 |
| Example 35 | 0.0068 |
| Example 36 | 0.0038 |
| Example 37 | 0.0044 |
| Example 38 | 0.0074 |
| Example 39 | 0.0206 |
| Example 40 | 0.009 |
| Example 41 | 0.0064 |
| Example 42 | 0.0036 |
| Example 43 | 0.0079 |
| Example 44 | 0.0257 |
| Example 45(1) | 0.0013 |
| Example 45(2) | 0.0015 |
| Example 46 | 0.0038 |
| Example 47 | 0.0089 |

TABLE 1-continued

|  | IC50 of FVIIa (μM) |
|---|---|
| Example 50 | 0.0032 |
| Example 51 | 0.0051 |
| Example 52 | 0.0052 |
| Example 53 | 0.0106 |
| Example 54 | 0.0187 |
| Example 55 | 0.0103 |
| Example 56 | 0.0112 |
| Example 57 | 0.0089 |
| Example 58 | 0.0034 |
| Example 59 | 0.0045 |
| Example 60 | 0.0037 |
| Example 61 | 0.0056 |
| Example 62 | 0.0244 |
| Example 63 | 0.0039 |
| Example 64 | 0.0042 |
| Example 65 | 0.0053 |
| Example 66 | 0.0079 |
| Example 67 | 0.0045 |
| Example 68 | 0.0067 |
| Example 69 | 0.0151 |
| Example 70 | 0.0049 |
| Example 71 | 0.0077 |
| Example 72 | 0.01 |
| Example 73 | 0.0112 |
| Example 74 | 0.0033 |
| Example 75 | 0.0052 |
| Example 76 | 0.0052 |
| Example 77 | 0.0088 |
| Example 78 | 0.0125 |
| Example 79 | 0.0076 |
| Example 80 | 0.0068 |
| Example 81 | 0.0186 |
| Example 82 | 0.0075 |
| Example 83 | 0.0248 |
| Example 84 | 0.0169 |
| Example 85 | 0.0153 |
| Example 86 | 0.0517 |
| Example 87 | 0.0042 |
| Example 88 | 0.0085 |
| Example 89 | 0.0092 |
| Example 90 | 0.0666 |
| Example 91 | 0.0064 |
| Example 92 | 0.0116 |
| Example 93 | 0.0303 |
| Example 94 | 0.0127 |
| Example 95 | 0.0013 |
| Example 96 | 0.017 |
| Example 97 | 0.0113 |
| Example 98 | 0.0287 |
| Example 99 | 0.0039 |
| Example 100 | 0.0053 |
| Example 101 | 0.011 |
| Example 102 | 0.0115 |
| Example 103 | 0.0089 |
| Example 104 | 0.0089 |
| Example 105 | 0.0317 |
| Example 107 | 0.0043 |
| Example 108 | 0.008 |
| Example 109 | 0.0079 |
| Example 110 | 0.0066 |
| Example 111 | 0.0113 |
| Example 112 | 0.0072 |
| Example 114 | 0.0228 |
| Example 115 | 0.0115 |
| Example 116 | 0.0119 |
| Example 117 | 0.0224 |
| Example 118 | 0.0073 |
| Example 119 | 0.007 |
| Example 120 | 0.0057 |
| Example 121 | 0.0068 |
| Example 122 | 0.002 |
| Example 123 | 0.0046 |
| Example 124 | 0.01 |
| Example 125 | 0.0103 |
| Example 126 | 0.0109 |

TABLE 2

| | IC50 of FVIIa (μM) |
|---|---|
| Example 127 | 0.0093 |
| Example 128 | 0.0099 |
| Example 129 | 0.0075 |
| Example 130 | 0.0106 |
| Example 131 | 0.0056 |
| Example 132 | 0.0024 |
| Example 133 | 0.0063 |
| Example 134 | 0.0117 |
| Example 135 | 0.0086 |
| Example 136 | 0.0051 |
| Example 137 | 0.0103 |
| Example 138 | 0.017 |
| Example 139 | 0.0038 |
| Example 140 | 0.0053 |
| Example 141 | 0.005 |
| Example 142 | 0.0047 |
| Example 143 | 0.023 |
| Example 144 | 0.0077 |
| Example 145 | 0.0087 |
| Example 146 | 0.0081 |
| Example 147 | 0.0051 |
| Example 148 | 0.0087 |
| Example 149 | 0.0092 |
| Example 150 | 0.009 |
| Example 151 | 0.0054 |
| Example 152 | 0.0012 |
| Example 153 | 0.0048 |
| Example 154 | 0.021 |
| Example 155 | 0.0023 |
| Example 156 | 0.0052 |

TABLE 3

| | IC50 of FVIIa (μM) |
|---|---|
| Example 158 | 0.0051 |
| Example 159 | 0.0117 |
| Example 160 | 0.0094 |
| Example 161 | 0.009 |
| Example 162 | 0.0165 |
| Example 163 | 0.0105 |
| Example 164 | 0.0245 |
| Example 165 | 0.0258 |
| Example 166 | 0.0187 |
| Example 167 | 0.0111 |
| Example 168 | 0.0028 |
| Example 169 | 0.0028 |
| Example 170 | 0.008 |
| Example 171 | 0.0033 |
| Example 173 | 0.0141 |
| Example 174 | 0.0018 |
| Example 175 | 0.0065 |
| Example 176 | 0.0061 |
| Example 177 | 0.0276 |
| Example 178 | 0.0143 |
| Example 179 | 0.0099 |
| Example 180 | 0.0101 |
| Example 181 | 0.0093 |
| Example 182 | 0.0417 |
| Example 183 | 0.0106 |
| Example 184 | 0.0067 |
| Example 157 | 0.0594 |
| Example 157d | 0.0069 |

TABLE 4

| | IC50 of FVIIa (μM) |
|---|---|
| Example 185 | 0.0116 |
| Example 186 | 0.0046 |
| Example 187 | 0.009 |
| Example 188 | 0.0224 |
| Example 189 | 0.0322 |
| Example 190 | 0.0079 |
| Example 191 | 0.0093 |
| Example 192 | 0.0054 |
| Example 193 | 0.0157 |
| Example 194 | 0.0745 |
| Example 195 | 0.0062 |
| Example 196 | 0.0178 |
| Example 197 | 0.0078 |
| Example 198 | 0.0196 |
| Example 199 | 0.0241 |
| Example 200 | 0.0113 |
| Example 201 | 0.0078 |
| Example 202 | 0.012 |
| Example 203 | 0.0085 |
| Example 204 | 0.0027 |
| Example 205 | 0.0023 |
| Example 206 | 0.0056 |
| Example 207 | 0.0199 |
| Example 208 | 0.0856 |
| Example 209 | 0.004 |
| Example 210 | 0.0391 |
| Example 211 | 0.0047 |
| Example 212 | 0.0057 |
| Example 213 | 0.0033 |
| Example 214 | 0.0035 |
| Example 215 | 0.0034 |
| Example 216 | 0.0134 |
| Example 217 | 0.0031 |
| Example 218 | 0.0524 |
| Example 219 | 0.0095 |
| Example 220 | 0.0072 |
| Example 221 | 0.0258 |
| Example 222 | 0.0027 |
| Example 223 | 0.0134 |
| Example 224 | 0.0488 |
| Example 225 | 0.0037 |
| Example 226 | 0.0032 |
| Example 227 | 0.0045 |
| Example 228 | 0.0026 |
| Example 229 | 0.0051 |
| Example 230 | 0.0049 |
| Example 231 | 0.0065 |
| Example 232 | 0.0237 |
| Example 233 | 0.0238 |
| Example 234 | 0.0111 |
| Example 235 | 0.0038 |
| Example 236 | 0.0118 |
| Example 237 | 0.0235 |
| Example 238 | 0.0856 |

Since the compounds of the invention have excellent suppressing effects against blood clotting, and are safer with suitable physicochemical stability, they are useful as medicaments, and especially as therapeutic and/or prophylactic agents for diseases associated with thrombus formation.

What is claimed is:

1. A compound selected from the group consisting of
4-({[2-fluoro-3-(2-hydroxyethoxy)-5-methoxyphenyl]-(5-oxo-1-pyrimidin-2-yl-4,5-dihydro-1H-[1,2,4]triazol-3-yl)methyl}amino)benzamidine:

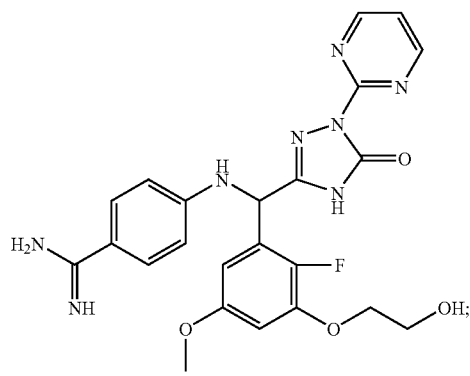

4-{3-[(4-carbamimidoylphenylamino)-(8-methoxy-4H-benzo[1,3]dioxin-6-yl)methyl]-5-oxo-4,5-dihydro-[1,2,4]triazol-1-yl}thiazole-5-carboxylic acid:

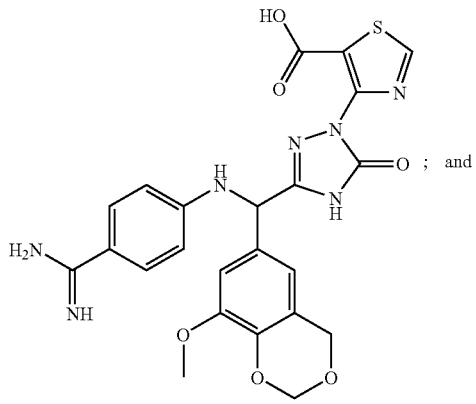

4-(3-{(4-carbamimidoylphenylamino)-[2-fluoro-3-(2-hydroxyethoxy)-5-methoxyphenyl]methy}-5-oxo-4,5-dihydro[1,2,4]triazol-1-yl)thiazole-5-carboxylic acid:

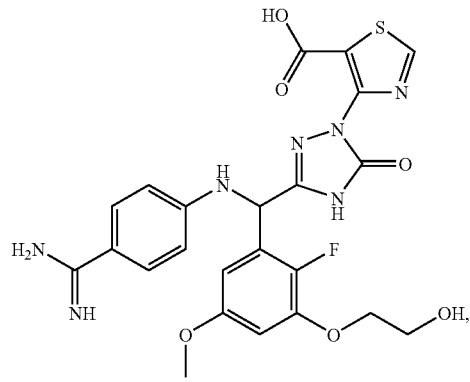

or pharmaceutically acceptable salts thereof.

2. The compound of claim 1, wherein said compound is 4-({[2-fluoro-3-(2-hydroxyethoxy)-5-methoxypheny]-(5-oxo-1-pyrimidin-2-yl-4,5-dihydro-1H-[1,2,4]triazol-3-yl)methyl}amino)benzamidine:

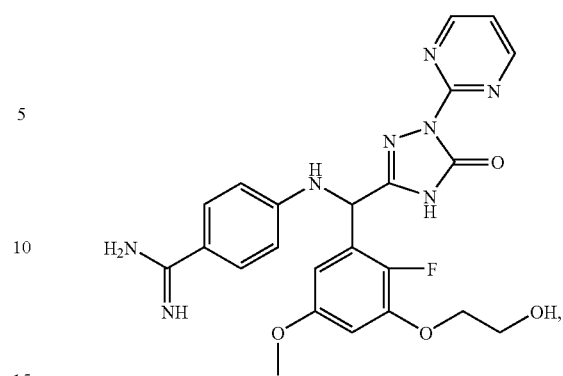

or a pharmaceutically acceptable salt thereof.

3. The compound of claim 1, wherein said compound is 4-{3-[(4-carbamimidoylphenylamino)-(8-methoxy-4H-benzo[1,3]dioxin-6-yl)methyl]-5-oxo -4,5-dihydro -[1,2,4] triazol-1-yl}thiazole-5-carboxylic acid:

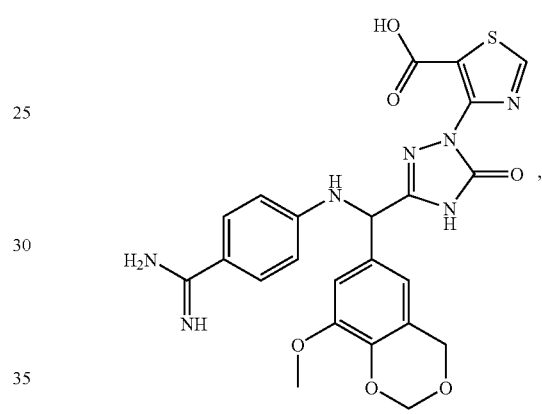

or a pharmaceutically acceptable salt thereof.

4. The compound of claim 1, wherein said compound is 4-(3-{(4-carbamimidoylphenylamino)-[2-fluoro-3-(2-hydroxyethoxy)-5methoxyphenyl]methy}-5-oxo -4,5-dihydro [1,2,4]triazol-1-yl)thiazole-5-carboxylic acid:

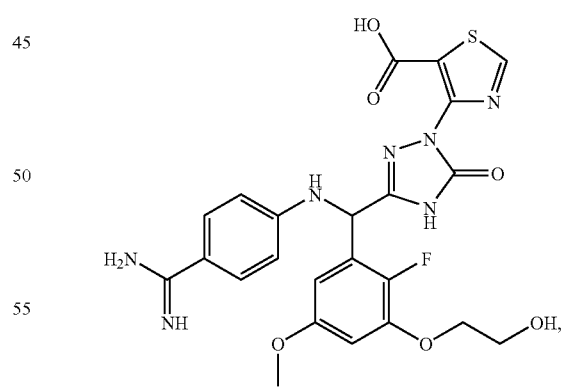

or a pharmaceutically acceptable salt thereof

5. A pharmaceutical composition comprising:
the compound according to claim 1 or pharmaceutically acceptable salt thereof; and
a pharmaceutically acceptable carrier.

* * * * *